(12) United States Patent
O'Connor et al.

(10) Patent No.: US 8,431,695 B2
(45) Date of Patent: Apr. 30, 2013

(54) PYRROLO[2,1-F][1,2,4]TRIAZIN-4-YLAMINES IGF-1R KINASE INHIBITORS FOR THE TREATMENT OF CANCER AND OTHER HYPERPROLIFERATIVE DISEASES

(75) Inventors: Stephen O'Connor, Guilford, CT (US); Jacques Dumas, Carlisle, MA (US); Wendy Lee, San Ramon, CA (US); Julie Dixon, Bethany, CT (US); David Cantin, Hamden, CT (US); David Gunn, Hamden, CT (US); Jennifer Burke, Newtown, CT (US); Barton Phillips, New Haven, CT (US); Derek Lowe, Acton, MA (US); Tatiana Shelekhin, Ridgefield, CT (US); Gan Wang, Wallingford, CT (US); Xin Ma, Haan (DE); Shihong Ying, Orange, CT (US); Andrea McClure, West Haven, CT (US); Furahi Achebe, West Haven, CT (US); Mario Lobell, Wuppertal (DE); Frederick Ehrgott, Killingworth, CT (US); Christiana Iwuagwu, Hamden, CT (US); Kyle Parcella, Wallingford, CT (US)

(73) Assignee: Bayer Intellectual Property GmbH, Monheim (DE)

( * ) Notice: Subject to any disclaimer, the term of this patent is extended or adjusted under 35 U.S.C. 154(b) by 696 days.

(21) Appl. No.: 12/084,411

(22) PCT Filed: Nov. 2, 2006

(86) PCT No.: PCT/US2006/043001
§ 371 (c)(1),
(2), (4) Date: Nov. 2, 2010

(87) PCT Pub. No.: WO2007/056170
PCT Pub. Date: May 18, 2007

(65) Prior Publication Data
US 2011/0294776 A1 Dec. 1, 2011

Related U.S. Application Data

(60) Provisional application No. 60/733,094, filed on Nov. 2, 2005.

(51) Int. Cl.
C07D 487/04 (2006.01)
C07D 413/02 (2006.01)
C07D 417/02 (2006.01)
A61K 31/53 (2006.01)
A61P 35/00 (2006.01)

(52) U.S. Cl.
USPC .......................................... 544/183; 514/243

(58) Field of Classification Search .................. 544/183; 514/243
See application file for complete search history.

(56) References Cited

FOREIGN PATENT DOCUMENTS
WO  WO 00/17203  3/2000
WO  WO 00/71129  11/2000

OTHER PUBLICATIONS

Cecil Textbook of Medicine, edited by Bennet, J.C., and Plum F., 20th edition, vol. 1, 1004-1010, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Powell et al., British Journal of Dermatology, 141: 802-810, 1999.*
Cohen et al., Current Opinion in Chemical Biology, 3,459-465, 1999.*
Golub et al., Science, 286, 531-537, 1999.*
Mass, R. D., Int. J. Radiation Oncology Bio. Phys. vol. 58(3): 932-940, 2004.*
Fabbro et al. Pharmacology & Therapeutics 93, 79-98, 2002.*

* cited by examiner

*Primary Examiner* — Venkataraman Balasubramanian

(57) ABSTRACT

This invention relates to novel compounds of formula (I). Formula (I) in which the variable groups are as defined in the specification and claims, to pharmaceutical compositions containing them, and to a method of treatment using them for treatment of cancer.

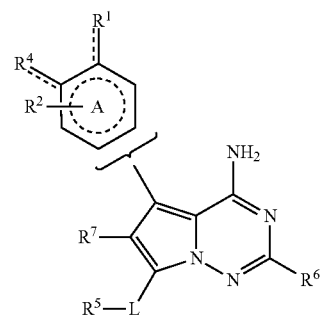

6 Claims, No Drawings

PYRROLO[2,1-F][1,2,4]TRIAZIN-4-YLAMINES IGF-1R KINASE INHIBITORS FOR THE TREATMENT OF CANCER AND OTHER HYPERPROLIFERATIVE DISEASES

This invention relates to novel compounds and processes for their preparation, and methods of treating diseases characterized by increased or deregulated proliferation, and in particular Cancer, comprising administering said compounds, and methods of making pharmaceutical compositions for the treatment or prevention of hyperproliferative disorders, and in particular Cancer.

Uncontrolled cellular proliferation, where cells fail to respond to the normal growth regulatory signals, is a hallmark of cancer. Tissue homeostasis is a balance between signals that regulate cell proliferation and those that regulate programmed cell death (apoptosis). The interplay between these processes maintains tissue stability and function. Cell proliferation and survival are complex processes and are both regulated by the interplay of extracellular and intracellular events. In the last 20 years, science has made significant advances in our understanding of these cellular processes and their underlying biochemical mechanisms. Chief amongst those advances is the elucidation of signal transduction components and pathways that regulate and coordinate cellular growth and survival.

Dysregulated signal transduction has been implicated as an underlying cause of uncontrolled cell proliferation and resistance to signals that induce apoptosis. Indeed, aberrant signal transduction from cell surface receptors or cytosolic proteins has been associated with the etiology of various cancers. Activating mutations, overexpression or aberrant receptor expression and their downregulation have been described in multiple cancers and are an underlying cause of the pathology of cancer. Specifically, the dysregulated activation of Receptor Tyrosine Kinases (RTK) has been shown to induce tumorigenesis in vivo. RTKs are membrane bound receptors with intrinsic tyrosine kinase activity that function as a nexus for extracellular stimuli to influence cell proliferation and survival. The activation of RTKs induces a cascade of signaling events that can ultimately alter cellular phenotype and genotype. The type-I Insulin-like Growth Factor-1 Receptor (IGF-1R) regulates both cell proliferation and cell survival signal transduction cascades. IGF-1R is widely expressed in both fetal and adult tissues. The receptor is activated via the binding of its cognate ligands, IGF-1 and IGF-2, resulting in receptor autophosphorylation and transactivation. Receptor activation stimulates a number of important signal transduction cascades including the Raf-MEK-ERK and the PI3K-AKT cascades.

There is substantial evidence to support a critical role for the IGF-1R not only in normal cellular proliferation, but also in carcinogenesis and tumor biology. IGF-1R is important in both neonatal and post natal growth. Mice homozygous for the targeted deletion of the IGF-1R gene die immediately after birth and exhibit severe growth deficiency (Liu et al., *Cell* 1993 Oct. 8; 75(1):59-72). Elevations in IGF-1R levels have been demonstrated in a wide variety of human tumors, including breast and colon carcinomas. Similarly, increased levels of IGF-1 ligand are associated with poor prognosis in breast and prostate cancers The forced overexpression of human IGF-1R in immortalized mouse NIH 3T3 fibroblasts induces ligand-dependent (IGF-1 or insulin) cellular transformation as evidenced by growth in soft agar and in nude mice (Kaleko et al., *Mol Cell Biol.* 1990 February; 10(2):464-73). Furthermore, the expression of functional IGF-1R is quasi-obligatory for cellular transformation and maintenance of the transformed phenotype. IGF-1R expression has been shown to be required for cellular transformation by known oncogenes including Ras, SV40 large T antigen, EGFR and PDGFR. In addition, IGF-1R cooperativity in tumor cell malignancy has been demonstrated with HER2 and c-Kit. In addition to its role in cellular transformation and its cooperativity with other oncogenes, inappropriate IGF-1R activity is associated with radiation- and chemoresistance, through its ability to regulate cell survival. Modulation of receptor levels, or receptor activity, has been demonstrated to inhibit tumor growth. Inhibition of IGF-1R function also sensitizes tumors to pro-apoptotic signals and agents, in vitro and in vivo. Several methods have been used to modulate IGF-1R activity. These include direct inhibition of its kinase activity by small molecule inhibitors and dominant-negative receptor constructs, disruption of its ligand-binding via specific antibodies, and downregulation of protein levels through the use of small interfering RNAs (siRNA) and antisense approaches. Therefore, the disruption of signaling via the IGF-1R represents a highly attractive and promising therapeutic strategy to treat a wide range of human diseases characterized by hyperproliferation, and in particular, cancer.

In one embodiment, the present invention provides a compound of formula (I)

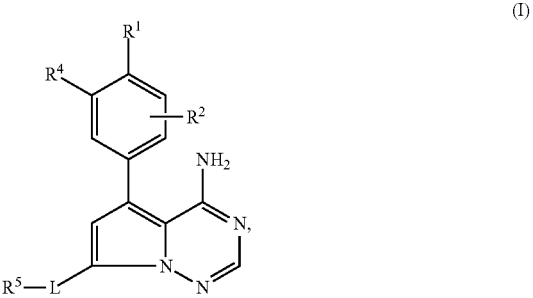

wherein
L is selected from the group consisting of a bond, alkanediyl, alkenediyl, alkynediyl, carbonyl, phenyl, alkylphenyl, phenylalkyl and pyridyl, wherein in alkanediyl one chain carbon atom can be substituted by an —NH— or —NMe-group;
$R^1$ is hydrogen or halo;
Or
—$R^1$ and $R^4$, together with the carbon atoms to which they are attached, form a pyrazole ring, wherein said pyrazole ring is substituted with benzyl, halobenzyl or alkylbenzyl;
$R^2$ is hydrogen or halo;
$R^4$ is benzyloxy, which can optionally be substituted with 1, 2 or 3 halo or alkoxy;
$R^5$ is halo, hydroxy, alkoxy, amino, alkylamino, or a nitrogen containing heterocycle or heteroaryl, wherein said heterocycle or heteroaryl can optionally be substituted with 1, 2 or 3 substituents independently selected from the group consisting of alkyl, hydroxy, hydroxyalkyl, alkoxy, alkoxyalkyl, halo, alkylsulfonyl, alkylcarbonyl, and alkyloxycarbonyl;
or a pharmaceutically acceptable salt thereof.

Depending on their structure, the compounds according to the invention can exist in stereoisomeric forms (enantiomers or diastereomers). The invention therefore relates to the enantiomers or diastereomers and to their respective mixtures.

Such mixtures of enantiomers or diastereomers can be separated into stereoisomerically unitary constituents in a known manner.

Unless otherwise stated, the following definitions apply for the technical expressions used throughout this specification and claims:

Salts for the purposes of the invention are preferably pharmaceutically acceptable salts of the compounds according to the invention. For example, see S. M. Berge, et al. "Pharmaceutical Salts," *J. Pharm. Sci.* 1977, 66, 1-19.

Pharmaceutically acceptable salts include acid addition, salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid.

Pharmaceutically acceptable salts also include salts of customary bases, such as for example and preferably alkali metal salts (for example sodium and potassium salts, alkaline earth metal salts (for example calcium and magnesium salts) and ammonium salts derived from ammonia or organic amines having 1 to 16 carbon atoms, such as illustratively and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dihydroabietylamine, arginine, lysine, ethylenediamine and methylpiperidine.

Alkyl represents a straight-chain or branched alkyl radical having generally 1 to 6, 1 to 4 or 1 to 3 carbon atoms, illustratively representing methyl, ethyl, n-propyl, isopropyl, tert-butyl, n-pentyl and n-hexyl.

Cycloalkyl means a cyclic alkane. Examples of cycloalkyl groups would be cyclopropyl, cyclobutyl, cyclopentyl, cyclohexyl, etc.

Alkanediyl, alkenediyl and alkynediyl represent terminally disubstituted alkyl, alkenyl and alkinyl radicals, respectively, such as 3-propan-1-yl or 3-prop-2-yn-1-yl. In other words, the term "alkanediyl" means a chain of $CH_2$ units, the ends of which connect to other groups. An example of alkanediyl units would be —$(CH_2)_n$— where the subscript "n" is an integer of 1-4. The term "alkenediyl" means a carbon chain consisting of $CH_2$ units and at least one double bond. Examples of alkenediyl units would be —$CH_2$—CH=CH—$CH_2$—$CH_2$— and —CH=CH—$CH_2$—. The term "alkynediyl" means a carbon chain consisting of $CH_2$ units and at least one triple bond. An example of an alkynediyl unit would be —$CH_2$C≡C—$CH_2$—$CH_2$—.

Alkoxy represents a straight-chain or branched hydrocarbon radical having 1 to 6, 1 to 4 or 1 to 3 carbon atoms and bound via an oxygen atom, illustratively representing methoxy, ethoxy, propoxy, isopropoxy, butoxy, isobutoxy, pentoxy, isopentoxy, hexoxy, isohexoxy. The terms "alkoxy" and "alkyloxy" are often used synonymously.

Alkylamino represents an alkylamino radical having one or two (independently selected) alkyl substituents, illustratively representing methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

Alkylcarbonyl represents a carbonyl radical being substituted with an alkyl radical, illustratively representing methylcarbonyl or ethylcarbonyl Alkoxycarbonyl represents a carbonyl radical being substituted with an alkoxy radical, illustratively representing methoxycarbonyl, ethoxycarbonyl, n-propoxycarbonyl, isopropoxycarbonyl, tert-butoxycarbonyl, n-pentoxycarbonyl and n-hexoxycarbonyl.

Alkylsulfonyl represents *—$S(O)_2$alkyl.

Aryl represents a mono- to tricyclic carbocyclic radical, which is aromatic at least in one ring, having generally 6 to 14 carbon atoms, illustratively representing phenyl, naphthyl and phenanthrenyl.

Alkylphenyl represents a phenyl radical being substituted with an alkyl group, such as tolyl.

Phenylalkyl represents an alkyl radical being substituted with a phenyl group, such as benzyl or Ph-$CH_2CH_2$—*.

Nitrogen containing heteroaryl represents an mono- or bicyclic radical, which is aromatic at least in one ring, said radical having 5 to 10 or 5 or 6 ring atoms and up to 4 or up to 3 hetero atoms selected from the group consisting of oxygen and sulfur, and 1, 2 or 3 nitrogen atoms. It can be attached via a ring carbon atom or a ring nitrogen atom. If it represents a bicycle, wherein one ring is aromatic and the other one is not, it can be attached at either ring. Illustrative examples are thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl and isoquinolinyl.

Nitrogen containing heterocyclyl represents a saturated or partially unsaturated mono- or bicyclic heterocyclic ring which contains 3 to 8 or 5 to 6 ring atoms and 1 to 2 heteroatoms or hetero groups selected independently from the group consisting of oxygen and sulfur, SO and $SO_2$, and 1, 2 or 3 nitrogen atoms, such as tetrahydrofuran-2-yl, pyrrolidin-2-yl, pyrrolidin-3-yl, pyrrolinyl, piperidinyl, morpholinyl, perhydroazepinyl. It can be attached via a ring carbon atom or a ring nitrogen atom.

Halo and "halogen" represent fluorine, chlorine, bromine or iodine.

A * symbol next to a bond denotes the point of attachment in the molecule.

In naming a multiunit functional group by listing the constituent units, the terminal unit is recited first, then the adjacent unit is recited, etc. An example of this style of nomenclature would be "alkylphenyl", which connotes an alkyl group located on a phenyl group, which is in turn connected to the remainder of the molecule. Conversely, the term "phenylalkyl" would connote a phenyl group located on an alkyl group which is in turn connected to the remainder of the molecule. Another example would be "cycloalkylalkyl", which connotes a cycloalkyl group connected to an alkyl group which is in turn connected to the remainder of the molecule.

When NR is indicated as being part of a heterocycle, this means that the N atom is the ring member and R is a substituent.

A wavy line across the end of a line which indicates a chemical bond extending from a chemical substructure or functional group means that the substructure or group is attached to the remainder of the molecule via that bond.

A carbonyl group is indicated as C=O in a chemical structure or substructure, or by C(O) in a typed formula.

When a phenyl or benzyl group is stated to be optionally substituted, this means that the phenyl ring may bear one or more (but typically not more than three) substituents such as halogen, $(C_1$-$C_3)$alkyl, $O(C_1$-$C_3)$alkyl, amino, mono- or di-$(C_1$-$C_3)$alkylamino, acylamino wherein the acyl group is —C(O)($C_1$-$C_3$)alkyl or —C(O)phenyl, CN, —NHC(O)$NH_2$, C(O)$NH_2$, C(O)NH($C_1$-$C_3$)alkyl, C(O)N(($C_1$-$C_3$)alkyl)$_2$, and C(O)NH-phenyl, and in these groups, alkyl and phenyl groups may be further substituted with halogen.

Throughout this document, for the sake of simplicity, the use of singular language is given preference over plural language, but is generally meant to include the plural language if not otherwise stated. E.g., the expression "A method of treating a disease in a patient, comprising administering to a patient an effective amount, of a compound of claim 1" is meant to include the simultaneous treatment of more than one disease as well as the administration of more than one compound of claim 1.

In another embodiment, the present invention provides a compound of formula (I), wherein
- L is selected from the group consisting of a bond, alkanediyl, phenyl, methylphenyl, and pyridyl, wherein in alkanediyl one chain carbon atom can be substituted by an —NH— group;
- $R^5$ is selected from the group consisting of azetidinyl, pyrrolidinyl, piperidinyl, piperazinyl, morpholinyl, imidazolyl and pyridinyl;
- or a pharmaceutically acceptable salt thereof.

In yet another embodiment, the present invention provides a compound of formula (I), wherein
- L is selected from the group consisting of a bond, propanediyl and butanediyl;
- $R^1$ and $R^4$, together with the carbon atoms to which they are attached, form a pyrazole ring, wherein said pyrazole ring is substituted with benzyl;
- $R^2$ is hydrogen;
- or a pharmaceutically acceptable salt thereof.

In yet another embodiment, the invention provides a compound of formula (I)

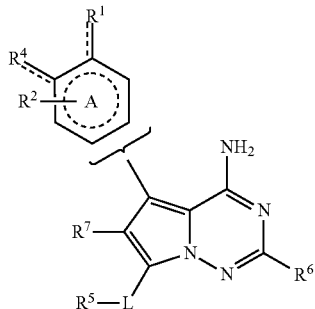

(I)

wherein
- the dotted lines between ring A and the first atoms of groups $R^1$ and $R^4$, respectively, indicate possible double bonds, if required by the structures of $R^1$ and $R^4$;
- the dotted circle in ring A indicates that ring A is aromatic;
- the bracket indicates the carbon atoms of ring A to which the pyrrolotriazine may be attached;
- $R^1$ represents H or halogen;
- $R^2$ represents H or halogen;
- $R^4$ represents
    - —C(O)—$NR^8R^9$ wherein
        - $R^8$ represents H or ($C_1$-$C_3$)alkyl; and
        - $R^9$ represents H, ($C_1$-$C_3$)alkyl, optionally substituted phenyl, or optionally substituted benzyl;
    - —$OR^{10}$ wherein
        - $R^{10}$ represents H, ($C_1$-$C_3$)alkyl, optionally substituted phenyl, or optionally substituted benzyl; or

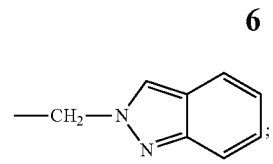

or
$R^1$ and $R^4$ may be joined, and taken together with the carbon atoms to which they are attached, form a fused heterocycle having a partial structure selected from the group consisting of

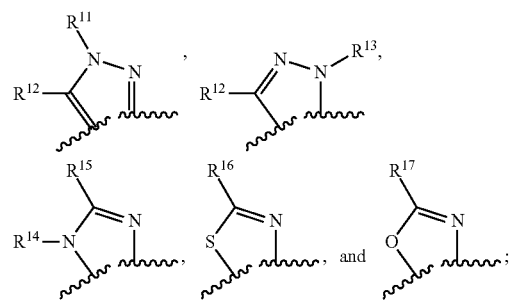

wherein
$R^{11}$ represents H, ($C_1$-$C_3$)alkyl, ($C_3$-$C_6$)cycloalkyl($C_1$-$C_3$)alkyl, pyridyl($C_1$-$C_3$)alkyl, optionally substituted phenyl, or optionally substituted benzyl;
$R^{12}$ represents
H;
($C_1$-$C_4$)alkyl;
halogen;

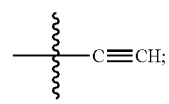

CN; or
$NR^{12a}R^{12b}$ wherein
$R^{12a}$ represents H or ($C_1$-$C_3$)alkyl; and
$R^{12b}$ represents H, ($C_1$-$C_3$)alkyl, benzyl, or —C(O)—($C_1$-$C_4$)alkyl;
$R^{13}$ represents H, ($C_1$-$C_3$)alkyl, or optionally substituted benzyl;
$R^{14}$ represents H, ($C_1$-$C_3$)alkyl, or optionally substituted benzyl;
$R^{15}$ represents H, ($C_1$-$C_3$)alkyl, or optionally substituted benzyl;
$R^{16}$ represents H, ($C_1$-$C_3$)alkyl, or optionally substituted benzyl;
$R^{17}$ represents H, ($C_1$-$C_3$)alkyl, or optionally substituted benzyl;
L represents
a bond;
($C_1$-$C_6$)alkanediyl;
($C_3$-$C_5$)alkenediyl;
($C_3$-$C_5$)alkynediyl;
a carbonyl grow;

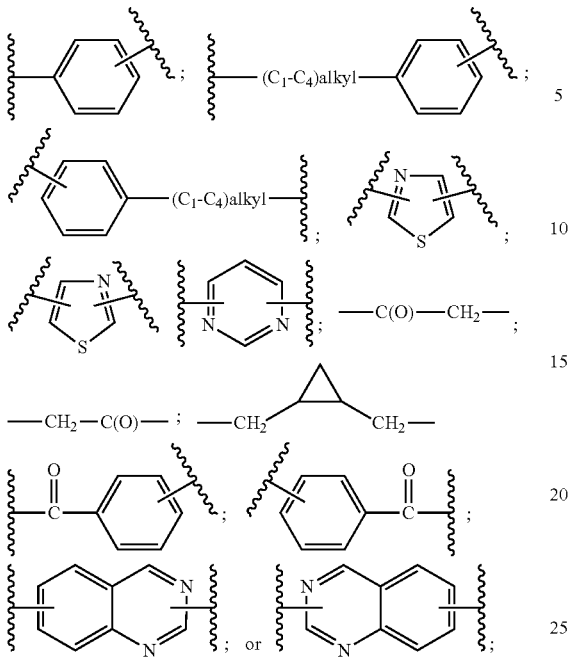

$R^5$ represents

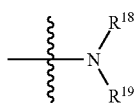

wherein
$R^{18}$ represents H or $(C_1-C_3)$alkyl;
$R^{19}$ represents
  H;
  $(C_1-C_3)$alkyl;
  $(C_3-C_7)$cycloalkyl;
  $(CH_2)_a$—$OR^{20}$ wherein
    $R^{20}$ represents H or $(C_1-C_3)$alkyl; and
    subscript "a" represents 2, 3, or 4;
  $C(O)$—$R^{21}$ wherein
    $R^{21}$ represents $(C_1-C_3)$alkyl, optionally substituted phenyl, or $NR^{22}R^{23}$ wherein
    $R^{22}$ and $R^{23}$ each independently represents H or $(C_1-C_3)$alkyl;

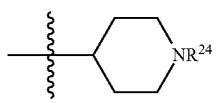

wherein
$R^{24}$ represents H, $(C_1-C_3)$alkyl, or —C(O)—O$(C_1-C_4)$alkyl;
$SO_2R^{25}$ wherein
  $R^{25}$ represents $(C_1-C_3)$alkyl or —$NR^{26}R^{27}$ wherein
  $R^{26}$ and $R^{27}$ independently represent H or $(C_1-C_3)$alkyl;

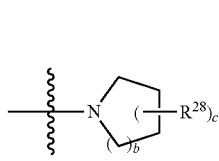

wherein
subscript "b" represents 0, 1 or 2;
subscript "c" represents 0, 1, or 2; and
$R^{28}$ represents
  H;
  $(C_1-C_4)$alkyl optionally substituted with $OR^{29}$ wherein
    $R^{29}$ represents H or $(C_1-C_3)$alkyl;
  $OR^{30}$ wherein
    $R^{30}$ represents H or $(C_1-C_3)$alkyl;
  halogen;
  —C(O)—$R^{31}$ wherein
    $R^{31}$ represents $(C_1-C_3)$alkyl;
  —$NR^{32}R^{33}$ wherein $R^{32}$ and $R^{33}$ independently represent H or $(C_1-C_3)$alkyl, or $R^{32}$ and $R^{33}$ may be joined and taken together with the N to which they are attached form a pyrrolidine or piperidine ring;
  —C(O)—$NR^{34}R^{35}$ wherein $R^{34}$ and $R^{35}$ independently represent H or $(C_1-C_3)$alkyl;

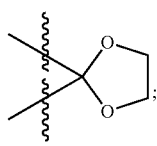 [SMILES: *C1(*)OCCO1]

or
—$CO_2R^{36}$ wherein $R^{36}$ represents $(C_1-C_4)$alkyl;

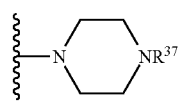

wherein
$R^{37}$ represents
  H;
  $(C_1-C_4)$alkyl;
  $(CH_2)_d$—$OR^{39}$ wherein
    subscript "d" represents 2, 3, or 4; and
    $R^{38}$ represents H or $(C_1-C_3)$alkyl;
  $(C_3-C_6)$cycloalkyl;
  $(CH_2)_e$—C(O)—$(CH_2)_f$—$NR^{39}R^{40}$ wherein
    subscript "e" represents 0 or 1;
    subscript "f" represents 0, 1, 2, or 3; and
    $R^{39}$ and $R^{40}$ independently represent H or $(C_1-C_3)$alkyl, or $R^{39}$ and $R^{40}$ may be joined and taken together with the N to which they are attached form a 6-membered heterocycle also containing O, S, or $NR^{41}$ wherein $R^{41}$ represents H or $(C_1-C_3)$alkyl;
  C(O)—$OR^{42}$ wherein
    $R^{42}$ represents H or $(C_1-C_4)$alkyl;

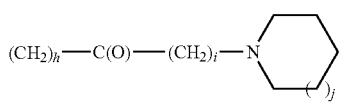

wherein the N-containing ring is
optionally substituted with halogen; and
subscript "h" represents 0 or 1;
subscript "i" represents 0, 1, 2, or 3;
subscript "j" represents 0 or 1;
$(CH_2)_k$—C(O)—$R^{43}$ wherein
subscript "k" represents 0 or 1; and
$R^{43}$ represents $(C_1\text{-}C_4)$alkyl optionally substituted with halogen, or $(C_3\text{-}C_6)$cycloalkyl optionally substituted with halogen;
$(CH_2)_m$—$SO_2R^{44}$ wherein
subscript "m" represents 1, 2, or 3; and
$R^{44}$ represents $(C_1\text{-}C_3)$alkyl, $(C_3\text{-}C_6)$cycloalkyl, or —$NR^{45}R^{46}$ wherein $R^{45}$ and $R^{46}$ independently represent H or $(C_1\text{-}C_3)$alkyl;
$(CH_2)$—CN wherein
subscript "n" represents 1, 2, or 3;

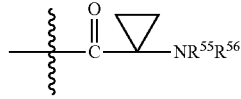

wherein
$R^{47}$ represents CN or $(C_1\text{-}C_3)$alkyl; or

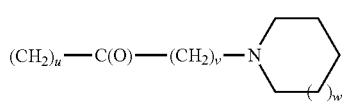

wherein
$R^{48}$ represents H or $(C_1\text{-}C_3)$alkyl;


wherein
subscript "p" represents 0, 1, or 2; and
the ring is optionally substituted on carbon with up to two substituents independently selected from halogen, hydroxyl, and $(C_1\text{-}C_3)$alkyl;
$R^{49}$ represents
H;
$(C_1\text{-}C_4)$alkyl;
$(C_{1\text{-}12})_q$—$OR^{59}$ wherein
subscript "q" represents 2, 3, or 4; and
$R^{50}$ represents H or $(C_1\text{-}C_3)$alkyl;
$(C_3\text{-}C_6)$cycloalkyl;
$(CH_2)_r$—C(O)—$(CH_2)_s$—$NR^{51}R^{52}$ wherein
subscript "r" represents 0 or 1;
subscript "s" represents 0, 1, 2, or 3; and
$R^{51}$ and $R^{52}$ independently represent H or $(C_1\text{-}C_3)$alkyl, or $R^{51}$ and $R^{52}$ may be joined and taken together with the N to which they are attached form a 6-membered heterocycle also containing O, S, or $NR^{53}$ wherein $R^{53}$ represents H or $(C_1\text{-}C_3)$alkyl;
C(O)—$(CH_2)_t$—$OR^{54}$ wherein
subscript "t" represents 0, 1, 2, or 3; and
$R^{54}$ represents H or $(C_1\text{-}C_4)$alkyl;

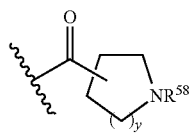

wherein
$R^{55}$ and $R^{56}$ independently represent H or $(C_1\text{-}C_3)$alkyl;

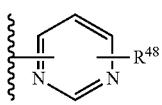

wherein
the ring is optionally substituted with halogen;
subscript "u" represents 0 or 1;
subscript "v" represents 0, 1, 2, or 3; and
subscript "w" represents 0 or 1;
$(CH_2)_x$—C(O)—$R^{57}$ wherein
subscript "x" represents 0 or 1; and
$R^{57}$ represents $(C_1\text{-}C_4)$alkyl optionally substituted with halogen, or represents $(C_3\text{-}C_6)$cycloalkyl optionally substituted with halogen;

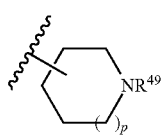

wherein
subscript "y" represents 0 or 1; and
$R^{58}$ represents H or $(C_1\text{-}C_3)$alkyl;

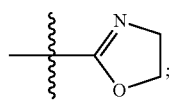 [SMILES: *C1=NCCO1]

Or
—$SO_2R^{59}$ wherein
$R^{59}$ represents $(C_1\text{-}C_3)$alkyl, $(C_3\text{-}C_6)$cycloalkyl, or —$NR^{60}R^{61}$ wherein $R^{60}$ and $R^{61}$ represent H or $(C_1\text{-}C_3)$alkyl;
—$OR^{62}$ wherein
$R^{62}$ represents H or $(C_1\text{-}C_3)$alkyl;
halogen;
CN;

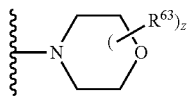

wherein
$R^{63}$ represents $(C_1-C_3)$alkyl optionally substituted with hydroxyl or halogen; and subscript "z" represents 0, 1, or 2;

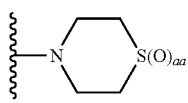

wherein
subscript "ea" represents 0, 1, or 2;

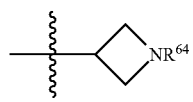

wherein
$R^{64}$ represents
 H;
 $(C_1-C_3)$alkyl optionally substituted with hydroxyl or halogen;
 —C(O)—$(CH_2)_{bb}$—$NR^{65}R^{66}$ wherein
  subscript "bb" represents 0, 1, 2, or 3;
  $R^{65}$ and $R^{66}$ are independently H or $(C_1-C_3)$alkyl, or
  $R^{65}$ and $R^{66}$ may be joined and taken together with the N to which they are attached form a pyrrolidine ring;
 —C(O)—$(C_1-C_4)$allyl;
 —C(O)—$O(C_1-C_4)$alkyl;
 —$SO_2R^{67}$ wherein
  $R^{67}$ represents $(C_1-C_3)$alkyl;

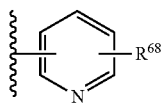

wherein
$R^{68}$ represents $(C_1-C_3)$alkyl;

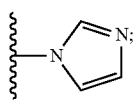

—$SO_2R^{69}$ wherein
 $R^{69}$ represents $(C_1-C_3)$alkyl;
—O—$CH_2$-phenyl;

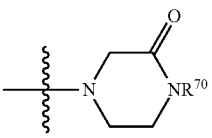

wherein
$R^{70}$ represents H or $(C_1-C_3)$alkyl;

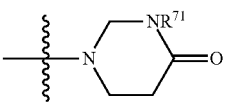

wherein
$R^{71}$ represents H or $(C_1-C_3)$alkyl;

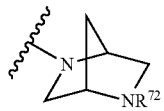

wherein
$R^{72}$ represents H, $(C_1-C_3)$alkyl, or —C(O)O(t-butyl);

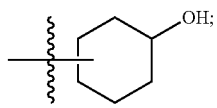

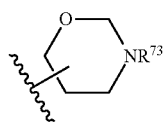

wherein
$R^{73}$ represents
 H
 $(C_1-C_3)$alkyl;

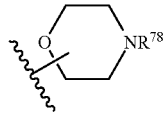

wherein
$R^{78}$ represents
 H
 $(C_1-C_3)$alkyl;
 $(C_3-C_6)$cycloalkyl;
 —$SO_2R^{78}$ wherein $R^{79}$ represents H or $(C_1-C_3)$alkyl;
 —C(O)—$(C_1-C_3)$alkyl;
 —C(O)-(optionally substituted phenyl);

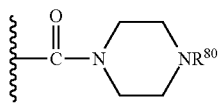

wherein $R^{80}$ represents H or $(C_1\text{-}C_3)$alkyl;
—$(CH_2)_{ee}$—C(O)—$(CH_2)_{ff}$$NR^{81}R^{82}$ wherein
subscript "ee" represents 0 or 1;
subscript "ff" represents 0, 1, 2, or 3; and
$R^{81}$ and $R^{82}$ independently represent H or $(C_1\text{-}C_3)$alkyl;

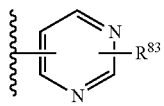

wherein
$R^{83}$ represents H or $(C_1\text{-}C_3)$alkyl;

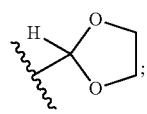

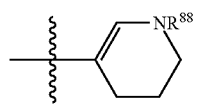

wherein
$R^{85}$ represents H, $(C_1\text{-}C_3)$alkyl, or —$(CH_2)_{ii}$—C(O)—$(CH_2)_{jj}$—$NR^{86}R^{87}$
wherein
subscript "ii" represents 0 or 1;
subscript "jj" represents 0, 1, 2, or 3; and
$R^{86}$ and $R^{87}$ independently represent H or $(C_1\text{-}C_3)$alkyl;

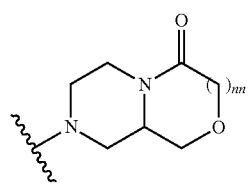

wherein
$R^{88}$ represents H, $(C_1\text{-}C_3)$alkyl, or —$(CH_2)_{kk}$—C(O)—$(CH_2)_{mm}$—$NR^{89}R^{90}$
wherein
subscript "kk" represents 0 or 1;
subscript "mm" represents 0, 1, 2, or 3; and
$R^{89}$ and $R^{90}$ independently represent H or $(C_1\text{-}C_3)$alkyl;

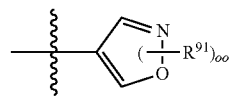

wherein subscript "nn" represents 0 or 1;

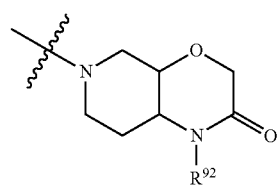

wherein
subscript "oo" represents 0, 1, or 2; and
$R^{91}$ represents $(C_1\text{-}C_3)$alkyl;

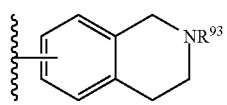

wherein $R^{92}$ represents H or $(C_1\text{-}C_3)$alkyl;

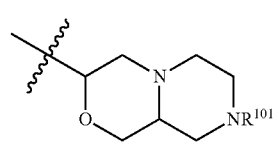

wherein
$R^{93}$ represents
H;
$(CH_2)_{pp}$—$OR^{94}$ wherein
subscript "pp" represents 2 or 3; and
$R^{94}$ represents H or $(C_1\text{-}C_3)$alkyl;
$(CH_2)_{qq}$—C(O)—$(CH_2)_{rr}$—$NR^{95}R^{96}$ wherein
subscript "qq" represents 0 or 1;
subscript "rr" represents 0 or 1; and
$R^{95}$ and $R^{96}$ independently represent H or $(C_1\text{-}C_3)$alkyl;
C(O)—$R^{97}$ wherein
$R^{97}$ represents H or $(C_1\text{-}C_3)$alkyl;
—$SO_2R^{98}$ wherein
$R^{98}$ represents H or $(C_1\text{-}C_3)$alkyl;
$(C_3\text{-}C_6)$cycloalkyl;
$(CH_2)_{ss}$—$CH(OR^{99})$—$(CH_2)_{tt}R^{100}$ wherein
subscript "ss" represents 0 or 1;
subscript "tt" represents 1, 2, or 3; and
$R^{99}$ and $R^{100}$ each independently represents H or $(C_1\text{-}C_3)$alkyl;

wherein
$R^{101}$ represents
H;
$(C_1\text{-}C_3)$alkyl;
$(C_3\text{-}C_6)$cycloalkyl;
$(CH_2)_{uu}$—$OR^{102}$ wherein
subscript "uu" represents 2 or 3; and
$R^{102}$ represents H or $(C_1\text{-}C_3)$alkyl;
$SO_2R^{103}$ wherein
$R^{103}$ represents $(C_1\text{-}C_3)$alkyl;

(CH$_2$)$_{vv}$—C(O)—(CH$_2$)$_{ww}$—NR$^{104}$R$^{105}$ wherein
subscript "vv" represents 0 or 1;
subscript "ww" represents 0 or 1; and
R$^{104}$ and R$^{105}$ independently represent H or (C$_1$-C$_3$)alkyl;
—C(O)O(t-butyl);
C(O)—R$^{106}$ wherein
R$^{106}$ represents (C$_1$-C$_3$)alkyl optionally substituted with OR$^{107}$ wherein
R$^{107}$ represents H or (C$_1$-C$_3$)alkyl;
R$^6$ represents H or (C$_1$-C$_3$)alkyl; and
R$^7$ represents H, CN, or (C$_1$-C$_3$)alkyl;
or a pharmaceutically acceptable salt or stereoisomer thereof.

In yet another embodiment, the invention provides a compound of formula (I)

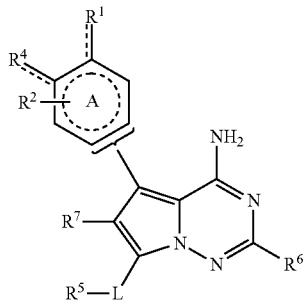

(I)

wherein
the dotted lines between ring A and the first atoms of groups R$^1$ and R$^4$, respectively, indicate possible double bonds, if required by the structures of R$^1$ and R$^4$;
the dotted circle in ring A indicates that ring A is aromatic;
the bracket Indicates the carbon atoms of ring A to which the pyrrolotriazine may be attached;
R$^1$ represents H or halogen;
R$^2$ represents H or halogen;
R$^4$ represents
OR$^{10}$ wherein
R$^{10}$ represents H, (C$_1$-C$_3$)alkyl, optionally substituted phenyl, or optionally substituted benzyl; or
or
R$^1$ and R$^4$ may be joined, and taken together with the carbon atoms to which they are attached, form a fused heterocycle having a partial structure selected from the group consisting of

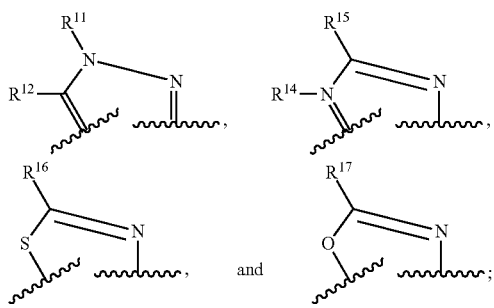

wherein
R$^{11}$ represents H, (C$_1$-C$_3$)alkyl, (C$_3$-C$_6$)cycloalkyl(C$_1$-C$_3$)alkyl, pyridyl(C$_1$-C$_3$)alkyl, optionally substituted phenyl, or optionally substituted benzyl;

R$^{12}$ represents
H;
(C$_1$-C$_4$)alkyl;
halogen;

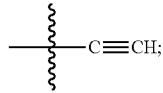

CN; or
NR$^{12a}$R$^{12b}$ wherein
R$^{12a}$ represents H or (C$_1$-C$_3$)alkyl; and
R$^{12b}$ represents H, (C$_1$-C$_3$)alkyl, benzyl, or —C(O)—(C$_1$-C$_4$)alkyl;
R$^{14}$ represents H, (C$_1$-C$_3$)alkyl, or optionally substituted benzyl;
R$^{15}$ represents H, (C$_1$-C$_3$)alkyl, or optionally substituted benzyl;
R$^{16}$ represents H, (C$_1$-C$_3$)alkyl, or optionally substituted benzyl;
R$^{17}$ represents H, (C$_1$-C$_3$)alkyl, or optionally substituted benzyl;
L represents
a bond;
—(C$_1$-C$_6$)alkanediyl;
a carbonyl group;

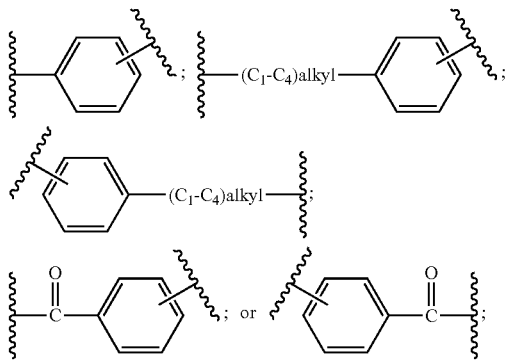

R$^5$ represents

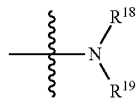

wherein
R$^{18}$ represents H or (C$_1$-C$_3$)alkyl;
R$^{19}$ represents
H;
(C$_1$-C$_3$)alkyl;
(C$_3$-C$_7$)cycloalkyl;
(CH$_2$)$_a$—OR$^{20}$ wherein
R$^{20}$ represents H or (C$_1$-C$_3$)alkyl; and
subscript "a" represents 2, 3, or 4;
C(O)—R$^{21}$ wherein
R$^{21}$ represents (C$_1$-C$_3$)alkyl, optionally substituted phenyl, or NR$^{22}$R$^{23}$ wherein
R$^{22}$ and R$^{23}$ each independently represents H or (C$_1$-C$_3$)alkyl;

$SO_2R^{25}$ wherein
  $R^{25}$ represents $(C_1-C_3)$alkyl or —$NR^{26}R^{27}$ wherein $R^{26}$ and $R^{27}$ independently represent H or $(C_1-C_3)$alkyl;

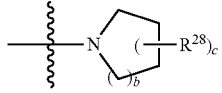

wherein
subscript "b" represents 0, 1 or 2;
subscript "c" represents 0, 1, or 2; and
$R^{28}$ represents
  H;
  $(C_1-C_4)$alkyl optionally substituted with $OR^{29}$ wherein
    $R^{29}$ represents H or $(C_1-C_3)$alkyl;
  $OR^{30}$ wherein
    $R^{30}$ represents H or $(C_1-C_3)$alkyl;
  halogen;
  —C(O)—$R^{31}$ wherein
    $R^{31}$ represents $(C_1-C_3)$alkyl;
  —C(O)—$NR^{34}R^{35}$ wherein $R^{34}$ and $R^{33}$ independently represent H or $(C_1-C_3)$alkyl; or
  —$CO_2R^{36}$ wherein $R^{36}$ represents $(C_1-C_4)$alkyl;

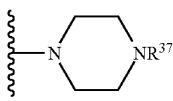

wherein
$R^{37}$ represents
  H;
  $(C_1-C_4)$alkyl;
  $(CH_2)_d$—$OR^{38}$ wherein
    subscript "d" represents 2, 3, or 4; and
    $R^{38}$ represents H or $(C_1-C_3)$alkyl;
  $(C_3-C_6)$cycloalkyl;
  $(CH_2)_e$—C(O)—$(CH_2)_f$—$NR^{36}R^{40}$ wherein
    subscript "e" represents 0 or 1;
    subscript "f" represents 0, 1, 2, or 3; and
    $R^{39}$ and $R^{40}$ independently represent H or $(C_1-C_3)$alkyl, or $R^{39}$ and $R^{40}$ may be joined and taken together with the N to which they are attached form a 6-membered heterocycle also containing O, S, or $NR^{41}$ wherein $R^{41}$ represents H or $(C_1-C_3)$alkyl;

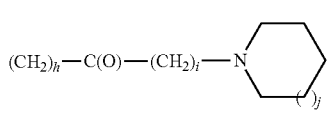

wherein the N-containing ring is
optionally substituted with halogen; and
subscript "h" represents 0 or 1;
subscript "i" represents 0, 1, 2, or 3;
subscript "j" represents 0 or 1; or
$(CH_2)_m$—$SO_2R^{44}$ wherein
  subscript "m" represents 1, 2, or 3; and
  $R^{44}$ represents $(C_1-C_3)$alkyl, $(C_3-C_6)$cycloalkyl, or —$NR^{45}R^{46}$ wherein $R^{45}$ and $R^{45}$ independently represent H or $(C_1-C_3)$alkyl;

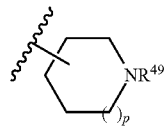

wherein
subscript "p" represents 0, 1, or 2; and
the ring is optionally substituted on carbon with up to two substituents independently selected from halogen, hydroxyl, and $(C_1-C_3)$alkyl;
$R^{49}$ represents
  H;
  $(C1-C_4)$alkyl;
  $(CH_2)_q$—$OR^{50}$ wherein
    subscript "q" represents 2, 3, or 4; and
    $R^{50}$ represents H or $(C_1-C_3)$alkyl;
  $(C_3-C_6)$cycloalkyl;
  $(CH_2)_r$—C(O)—$(CH_2)_s$—$NR^{51}R^{52}$ wherein
    subscript "r" represents 0 or 1;
    subscript "s" represents 0, 1, 2, or 3; and
    $R^{51}$ and $R^{52}$ independently represent H or $(C_1-C_3)$alkyl, or $R^{51}$ and $R^{52}$ may be joined and taken together with the N to which they are attached form a 6-membered heterocycle also containing O, S, or $NR^{53}$ wherein $R^{53}$ represents H or $(C_1-C_3)$alkyl;
  C(O)—$(CH_2)$, —$OR^{54}$ wherein
    subscript "t" represents 0, 1, 2, or 3; and
    $R^{54}$ represents H or $(C_1-C_4)$alkyl;

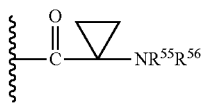

wherein
$R^{55}$ and $R^{56}$ independently represent H or $(C_1-C_3)$alkyl;

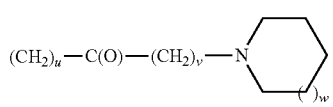

wherein
the ring is optionally substituted with halogen;
subscript "u" represents 0 or 1;
subscript "v" represents 0, 1, 2, or 3; and
subscript "w" represents 0 or 1;
$(CH_2)_x$—C(O)—$R^{57}$ wherein
  subscript "x" represents 0 or 1; and
  $R^{57}$ represents $(C_1-C_4)$alkyl optionally substituted with halogen, or represents $(C_3-C_6)$cycloalkyl optionally substituted with halogen;

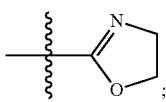

or
—SO$_2$R$^{69}$ wherein
R$^{59}$ represents (C$_1$-C$_3$)'alkyl, (C$_3$-C$_6$)cycloalkyl, or —NR$^{60}$R$^{61}$ wherein R$^{60}$ and R$^{61}$ represent H or (C$_1$-C$_3$)alkyl;
—OR$^{62}$ wherein
R$^{62}$ represents H or (C$_1$-C$_3$)alkyl;
halogen;
CN;

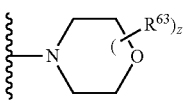

wherein
R$^{63}$ represents (C$_1$-C$_3$)alkyl optionally substituted with hydroxyl or halogen; and subscript "z" represents 0, 1, or 2;

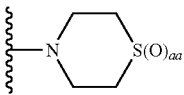

wherein
subscript "aa" represents 0, 1, or 2;

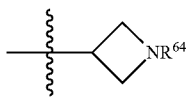

wherein
R$^{64}$ represents
H;
(C$_1$-C$_3$)alkyl optionally substituted with hydroxyl or halogen;
—C(O)—(CH$_2$)$_{bb}$—NR$^{65}$R$^{66}$ wherein
subscript "bb" represents 0, 1, 2, or 3;
R$^{65}$ and R$^{66}$ are independently H or (C$_1$-C$_3$)alkyl, or
R$^{65}$ and R$^{66}$ may be joined and taken together with the N to which they are attached form a pyrrolidine ring;
—C(O)—(C$_1$-C$_4$)alkyl;
—C(O)—O(C$_1$-C$_4$)alkyl;

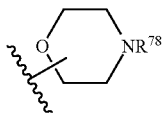

wherein
R$^{78}$ represents
H
(C$_1$-C$_3$)alkyl;
(C$_3$-C$_6$)cycloalkyl;
—SO$_2$R$^{79}$ wherein R$^{79}$ represents H or (C$_1$-C$_3$)alkyl;
—C(O)—(C$_1$-C$_3$)alkyl;
—(CH$_2$)$_{ee}$—C(O)—(CH$_2$)$_{ff}$NR$^{81}$R$^{82}$ wherein
subscript "ee" represents 0 or 1;
subscript "ff" represents 0, 1, 2, or 3; and
R$^{81}$ and R$^{82}$ independently represent H or (C$_1$-C$_3$) alkyl;

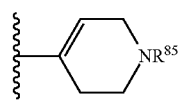

wherein
R$^{85}$ represents H, (C$_1$-C$_3$)alkyl, or —(CH$_2$)$_{ii}$—C(O)—(CH$_2$)$_{jj}$—NR$^{86}$R$^{87}$
wherein
subscript "ii" represents 0 or 1;
subscript "jj" represents 0, 1, 2, or 3; and
R$^{86}$ and R$^{87}$ independently represent H or (C$_1$-C$_3$)alkyl;

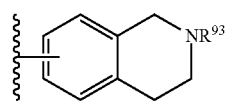

wherein
R$^{93}$ represents
H;
(CH$_2$)$_{pp}$—OR$^{94}$ wherein
subscript "pp" represents 2 or 3; and
R$^{94}$ represents H or (C$_1$-C$_3$)alkyl;
(CH$_2$)$_{qq}$—C(O)—(CH$_2$)$_{rr}$—NR$^{95}$R$^{96}$ wherein
subscript "qq" represents 0 or 1;
subscript "rr" represents 0 or 1; and
R$^{95}$ and R$^{96}$ independently represent H or (C$_1$-C$_3$) alkyl;
C(O)—R$^{97}$ wherein
R$^{97}$ represents H or (C$_1$-C$_3$)alkyl;
—SO$_2$R$^{98}$ wherein
R$^{98}$ represents H or (C$_1$-C$_3$)alkyl;

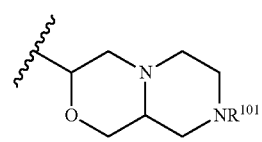

wherein
R$^{101}$ represents
H;
(C$_1$-C$_3$)alkyl;
(C$_3$-C$_6$)cycloalkyl;
(CH$_2$)$_{uu}$—OR$^{102}$ wherein
subscript "uu" represents 2 or 3; and
R$^{102}$ represents H or (C$_1$-C$_3$)alkyl;
SO$_2$R$^{103}$ wherein
R$^{103}$ represents (C$_1$-C$_3$)alkyl;
(CH$_2$)$_{vv}$—C(O)—(CH$_2$)$_{ww}$—NR$^{104}$R$^{105}$ wherein
subscript "vv" represents 0 or 1;
subscript "ww" represents 0 or 1; and $R^{104}$ and $R^{105}$ independently represent H or $(C_1\text{-}C_3)$alkyl;

C(O)—$R^{106}$ wherein
$R^{106}$ represents $(C_1\text{-}C_3)$alkyl optionally substituted with $OR^{107}$ wherein
$R^{107}$ represents H or $(C_1\text{-}C_3)$alkyl;

$R^6$ represents H or $(C_1\text{-}C_3)$alkyl; and $R^7$ represents H, CN, or $(C_1\text{-}C_3)$alkyl;

or a pharmaceutically acceptable salt or stereoisomer thereof.

In yet another embodiment, the invention provides a compound of formula (I)

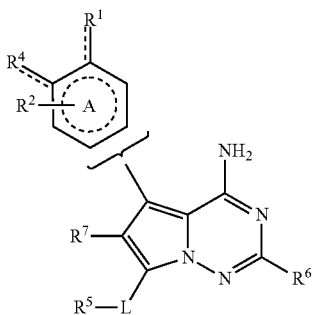

(I)

wherein
the dotted lines between ring A and the first atoms of groups $R^1$ and $R^4$, respectively, indicate possible double bonds, if required by the structures of $R^1$ and $R^4$;
the dotted circle in ring A indicates that ring A is aromatic;
the bracket indicates the carbon atoms of ring A to which the pyrrolotriazine may be attached;
$R^1$ represents H or halogen;
$R^2$ represents H or halogen;
$R^4$ represents
—$OR^{10}$ wherein
$R^{10}$ represents H, $(C_1\text{-}C_3)$alkyl, optionally substituted phenyl, or optionally substituted benzyl; or or
$R^1$ and $R^4$ may be joined, and taken together with the carbon atoms to which they are attached, form a fused heterocycle having a partial structure selected from the group consisting of

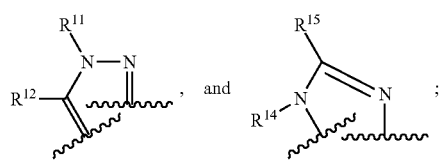

wherein
$R^{11}$ represents H, $(C_1\text{-}C_3)$alkyl, $(C_3\text{-}C_3)$cycloalkyl$(C_1\text{-}C_3)$alkyl, pyridyl$(C_1\text{-}C_3)$alkyl, optionally substituted phenyl, or optionally substituted benzyl;
$R^{12}$ represents
H;
$(C_1\text{-}C_4)$alkyl;
halogen;

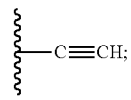 [SMILES: *C#C]

CN; or
$NR^{12a}R^{12b}$ wherein
$R^{12a}$ represents H or $(C_1\text{-}C_3)$alkyl; and
$R^{12b}$ represents H, $(C_1\text{-}C_3)$alkyl, benzyl, or —C(O)—$(C_1\text{-}C_4)$alkyl;
$R^{14}$ represents H, $(C_1\text{-}C_3)$alkyl, or optionally substituted benzyl;
$R^{15}$ represents H, $(C_1\text{-}C_3)$alkyl, or optionally substituted benzyl;
L represents
a bond; or
—$(C_1\text{-}C_6)$alkanediyl;
$R^5$ represents

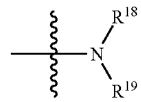

wherein
$R^{18}$ represents H or $(C_1\text{-}C_3)$alkyl;
$R^{19}$ represents
H;
$(C_1\text{-}C_3)$alkyl;
$(C_3\text{-}C_7)$cycloalkyl;
$(CH_2)_a$—$OR^{29}$ wherein
$R^{20}$ represents H or $(C_1\text{-}C_3)$alkyl; and
subscript "a" represents 2, 3, or 4;
C(O)—$R^{21}$ wherein
$R^{21}$ represents $(C_1\text{-}C_3)$alkyl, optionally substituted phenyl, or $NR^{22}R^{23}$ wherein
$R^{22}$ and $R^{23}$ each independently represents H or $(C_1\text{-}C_3)$alkyl;
$SO_2R^{25}$ wherein
$R^{25}$ represents $(C_1\text{-}C_3)$alkyl or —$NR^{26}R^{27}$ wherein
$R^{26}$ and $R^{27}$ independently represent H or $(C_1\text{-}C_3)$alkyl;

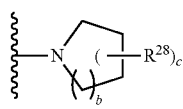

wherein
subscript "b" represents 0, 1 or 2;
subscript "c" represents 0, 1, or 2; and
$R^{28}$ represents
H;
$(C_1\text{-}C_4)$alkyl optionally substituted with $OR^{29}$ wherein
$R^{29}$ represents H or $(C_1\text{-}C_3)$alkyl;
$OR^{30}$ wherein
$R^{30}$ represents H or $(C_1\text{-}C_3)$alkyl;
halogen;
—C(O)—$R^{31}$ wherein
$R^{31}$ represents $(C_1\text{-}C_3)$alkyl;
—C(O)—$NR^{34}R^{35}$ wherein $R^{34}$ and $R^{35}$ independently represent H or $(C_1\text{-}C_3)$alkyl; or —CO$_2$R$^{36}$ wherein R$^{36}$ represents (C$_1$-C$_4$)alkyl;

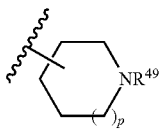

wherein
subscript "p" represents 0, 1, or 2; and
the ring is optionally substituted on carbon with up to two substituents independently selected from halogen, hydroxyl, and (C$_1$-C$_3$)alkyl;
R$^{49}$ represents
H;
(C$_1$-C$_4$)alkyl;
(CH$_2$)$_q$—OR$^{50}$ wherein
  subscript "q" represents 2, 3, or 4; and
  R$^{50}$ represents H or (C$_1$-C$_3$)alkyl;
(C$_3$-C$_6$)cycloalkyl;
(CH$_2$)$_r$—C(O)—(CH$_2$)$_s$—NR$^{51}$R$^{52}$ wherein
  subscript "r" represents 0 or 1;
  subscript "s" represents 0, 1, 2, or 3; and
  R$^{51}$ and R$^{52}$ independently represent H or (C$_1$-C$_3$) alkyl, or R$^{51}$ and R$^{52}$ may be joined and taken together with the N to which they are attached form a 6-membered heterocycle also containing O, S, or NR$^{53}$ wherein R$^{53}$ represents H or (C$_1$-C$_3$)alkyl;

wherein
R$^{55}$ and R$^{56}$ independently represent H or (C$_1$-C$_3$) alkyl;

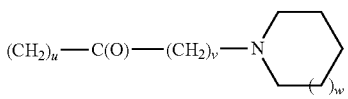

wherein
the ring is optionally substituted with halogen;
subscript "u" represents 0 or 1;
subscript "v" represents 0, 1, 2, or 3; and
subscript "w" represents 0 or 1; or
—SO$_2$R$^{59}$ wherein
  R$^{59}$ represents (C$_1$-C$_3$)alkyl, (C$_3$-C$_6$)cycloalkyl, or —NR$^{60}$R$^{61}$ wherein R$^{60}$ and R$^{61}$ represent H or (C$_1$-C$_3$)alkyl;

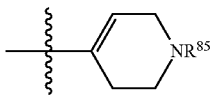

wherein
R$^{85}$ represents H, (C$_1$-C$_3$)alkyl, or —(CH$_2$)$_{ii}$—C(O)—(CH$_2$)$_{jj}$—NR$^{86}$R$^{87}$ wherein
subscript "ii" represents 0 or 1;
subscript "jj" represents 0, 1, 2, or 3; and
R$^{66}$ and R$^{67}$ independently represent H or (C$_1$-C$_3$)alkyl;

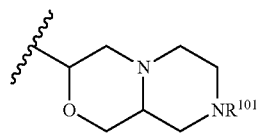

wherein
R$^{101}$ represents
H;
(C$_1$-C$_3$)alkyl;
(C$_3$-C$_6$)cycloalkyl;
(CH$_2$)$_{uu}$—OR$^{102}$ wherein
  subscript "uu" represents 2 or 3; and
  R$^{102}$ represents H or (C$_1$-C$_3$)alkyl;
SO$_2$R$^{103}$ wherein
  R$^{103}$ represents (C$_1$-C$_3$)alkyl;
(CH$_2$)$_{vv}$—C(O)—(CH$_2$)$_{ww}$—NR$^{104}$R$^{105}$ wherein
  subscript "vv" represents 0 or 1;
  subscript "ww" represents 0 or 1; and
  R$^{104}$ and R$^{105}$ independently represent H or (C$_1$-C$_3$)alkyl;
C(O)—R$^{106}$ wherein
  R$^{106}$ represents (C$_1$-C$_3$)alkyl optionally substituted with OR$^{107}$ wherein
    R$^{107}$ represents H or (C$_1$-C$_3$)alkyl;
R$^6$ represents H or (C$_1$-C$_3$)alkyl; and
R$^7$ represents H, CN, or (C$_1$-C$_3$)alkyl;
or a pharmaceutically acceptable salt or stereoisomer thereof.

It is also to be understood that starting materials are commercially available or readily prepared by standard methods well known in the art. Such methods include, but are not limited to the transformations listed herein.

If not mentioned otherwise, the reactions are usually carried out in inert organic solvents which do not change under the reaction conditions. These include ethers, such as diethyl ether, 1,4-dioxane, 1,2-dimethoxyethane or tetrahydrofuran, halogenated hydrocarbons, such as dichloromethane, trichloromethane, carbon tetrachloride, 1,2-dichloroethane, trichloroethane or tetrachloroethane, hydrocarbons, such as benzene, toluene, xylene, hexane, cyclohexane or mineral oil fractions, alcohols, such as methanol, ethanol or iso-propanol, nitromethane, dimethylformamide or acetonitrile. It is also possible to use mixtures of the solvents.

The reactions are generally carried out in a temperature range of from 0° C. to 150° C., preferably from 0° C. to 100° C. The reactions can be carried out under atmospheric, elevated or under reduced pressure (for example from 0.5 to 5 bar). Unless otherwise noted, they are carried out under atmospheric pressure of air or inert gas, typically nitrogen.

The compounds of the invention may be prepared by use of known chemical reactions and procedures. Nevertheless, the following general preparative methods are presented to aid the reader in synthesizing said compounds, with more detailed particular examples being presented below in the experimental section describing the examples. The prepara tion of a compound of the present invention can be illustrated by means of the following synthetic schemes:

General Methods of Preparation of Invention Compounds

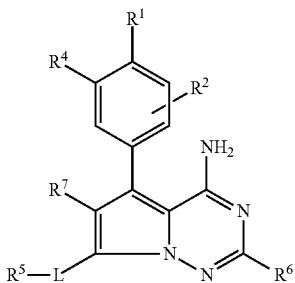

Compounds of the present invention of formula I can be prepared by straightforward means as described in the Reaction Schemes below or by means well known to those skilled in the art.

Scheme 1

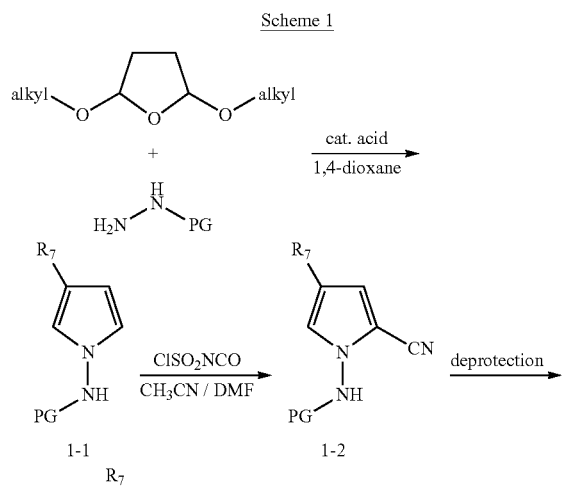

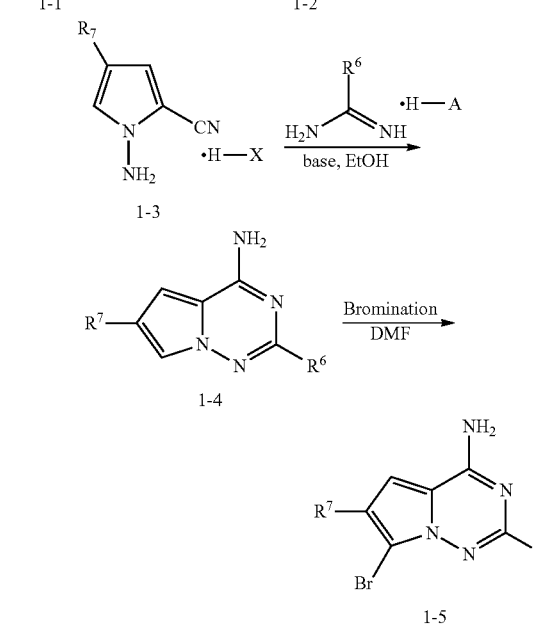

The preparation of compounds of the invention begins with the preparation of compounds of structure 1-5, as outlined in Scheme 1. Treatment of a suitably protected (e.g. a protecting group well known to those skilled in the art) hydrazine derivative with a 2,5-dialkoxy tetrahydrofuran derivative in the presence of an acid, such as HCl or the like in a solvent such as 1,4-dioxane or the like provides the protected aminopyrrole derivative 1-1. Cyanation using chlorosulfonyl isocyanate in a solvent such as acetonitrile or the like provides the 2-cyano derivative 1-2, which upon deprotection (using procedures/reagents known in the art) liberates the aminopyrrole product 1-3. Reaction of 1-3 with a formamidine reagent in the presence of a base such as potassium phosphate or the like in a solvent such as ethanol provides compounds of the type 1-4. Bromination is carried out by reacting 1-4 with an appropriate brominating reagent, such as 1,3-dibromo-5,5-dimethylhydantoin or another, appropriate agent in an appropriate solvent, such as DMF or the like, provides 1-5.

Scheme 2 outlines a similar preparation, beginning with treatment of a suitably protected (e.g. a protecting group well known to those skilled in the art) hydrazine derivative with a 2,5-dialkoxy tetrahydrofuran derivative in the presence of an acid, such as HCl or the like in a solvent such as 1,4-dioxane or the like provides the protected aminopyrrole derivative 2-1. Cyanation using chlorosulfonyl isocyanate in a solvent such as acetonitrile or the like provides the 2-cyano derivative 2-2, which upon deprotection (using procedures/reagents known in the art) liberates the aminopyrrole product 2-3. Reaction of 2-3 with a formamidine reagent in the presence of a base such as potassium phosphate or the like in a solvent such as ethanol or similar provides compounds of structure 2-4. Bromination is carried out by reacting 2-4 with an appropriate brominating reagent, such as 1,3-dibromo-5,5-dimethylhydantoin or another appropriate agent in an appropriate solvent, such as DMF or the like, and provides 2-5. The following schemes demonstrate the conversion of compounds of these types to the compounds of formula I.

Scheme 2

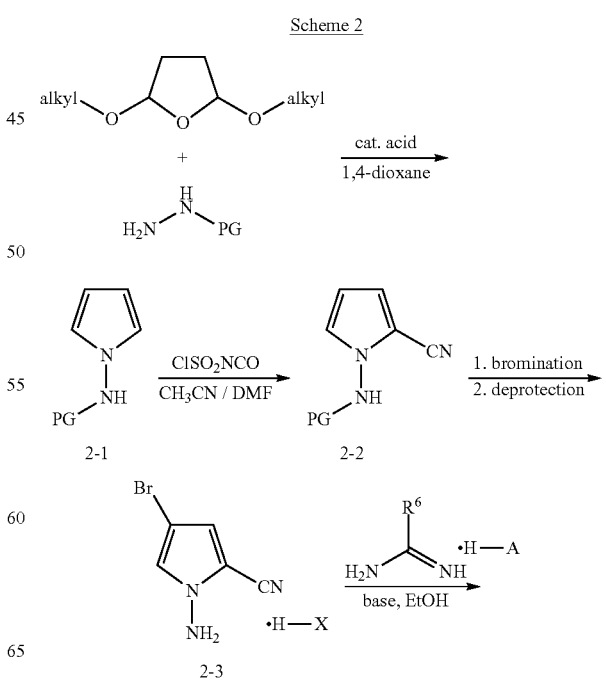

27
-continued
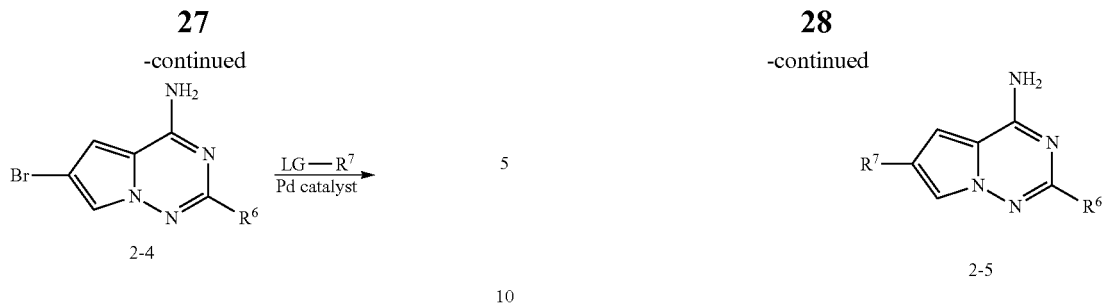
28
-continued
Scheme 3
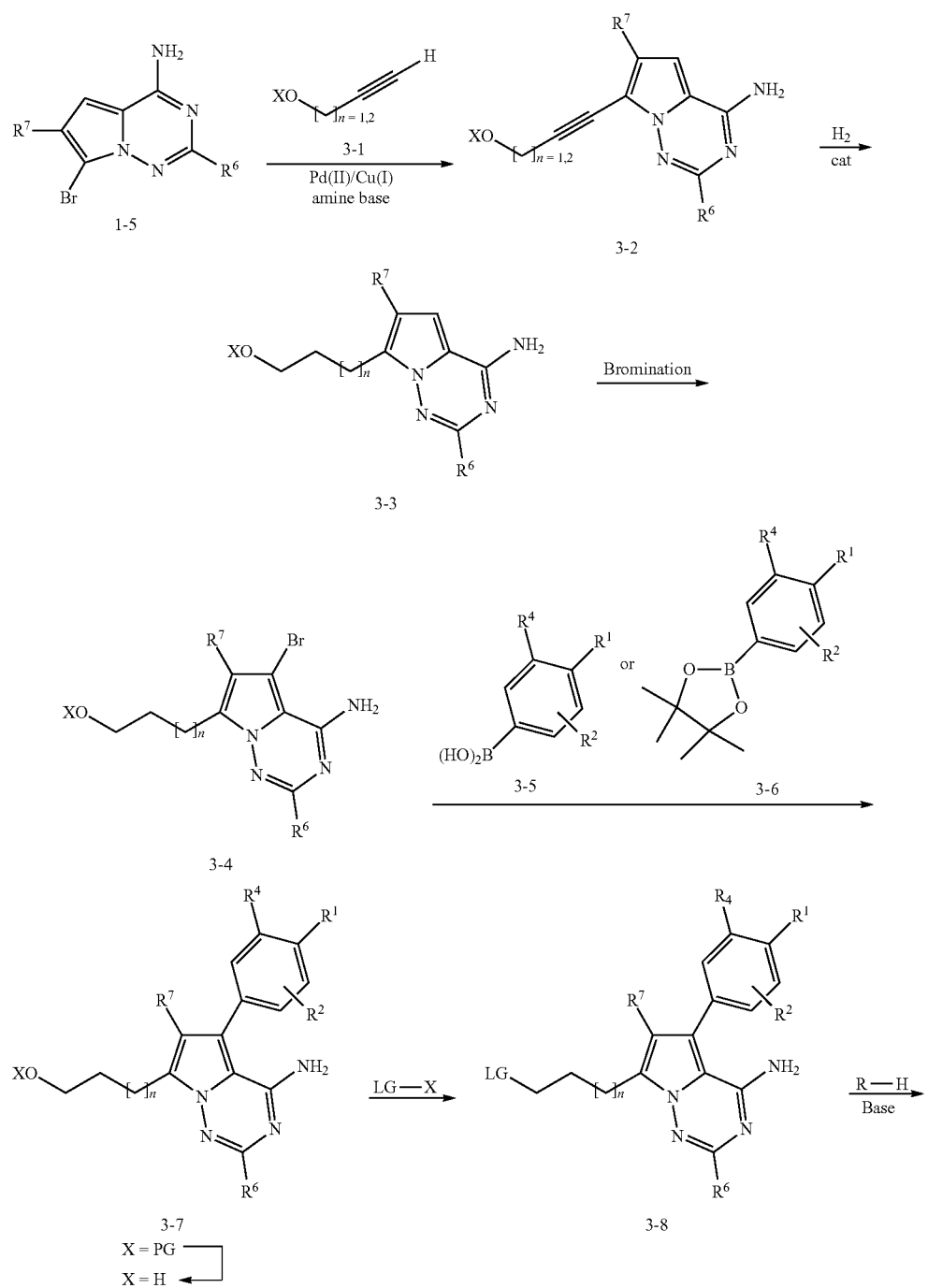

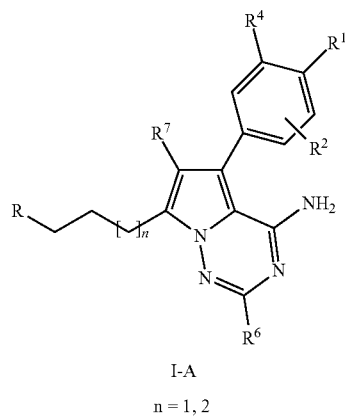

I-A n = 1, 2

The compounds of formula I-A are conveniently prepared according to reaction sequences shown in Scheme 3. Thus, reaction of compounds of formula 1-5 with an appropriate terminal acetylene of formula 3-1 (wherein X=H or a suitable protecting groups such as a trialkylsilane) in presence of a Pd(II) catalyst, a Cu(I) co-catalyst and an amine base such as pyrrolidine or triethylamine or the like, in a solvent such as DMF or the like provides compounds of formula 3-2. Reduction of the triple bond using hydrogen gas in the presence of a metal catalyst such as $PtO_2$ or the like in a solvent such as acetic acid or the like provides compounds of formula 3-3. Treatment of 3-3 with a brominating reagent such as 1,3-dibromo-5,5-dimethylhydantoin or the like in an appropriate solvent, such as DMF or the like provides 3-4. Suzuki coupling of 3-4 with a boronic acid such as 3-5 or a boronate such as 3-6 provides compounds of formula 3-7. Conversion of 3-7 to compounds of formula 3-8 (where LG is a suitable leaving group) can be carried out by methods known in the art. If necessary, a protecting group (PG) can be removed by methods known in the art prior to the conversion to 3-8. Treatment of 3-8 with a primary or secondary amine, in the presence of a suitable base such as potassium phosphate or the like or a tertiary amine, such as Hunig's Base or the like provides compounds of formula 1-A.

Scheme 4

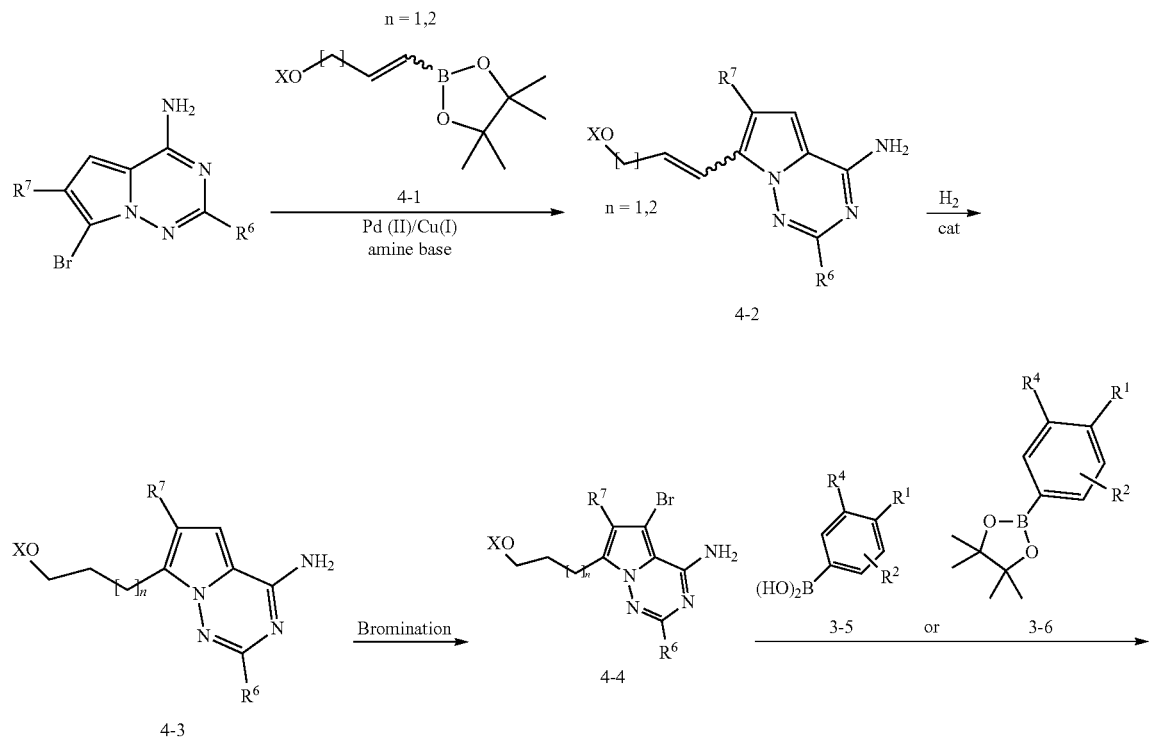

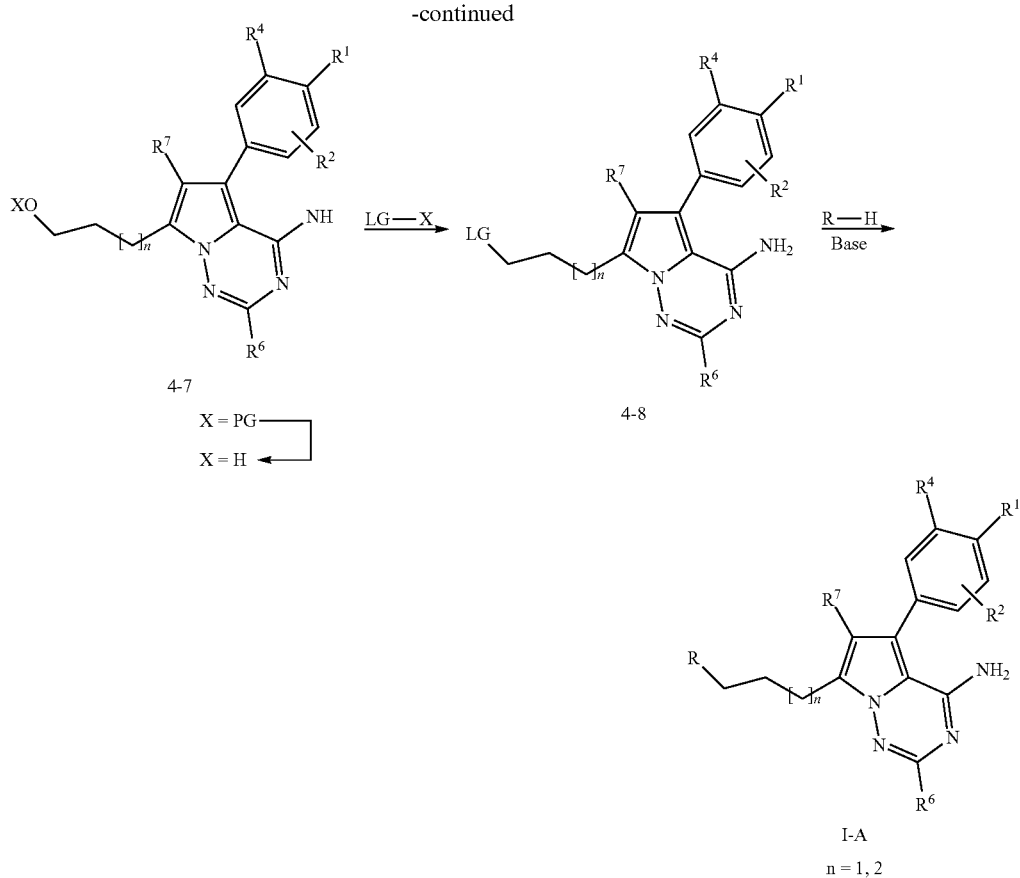

An alternative preparation of compounds of compounds of formula 1-A is shown in Scheme 4. In this sequence, compounds of formula 1-5 are converted to compounds of formula 4-2 by coupling a vinyl boronate such as compound 4-1 (wherein X=H or a suitable protecting groups such as a trialkylsilane) or the like under conditions known in the art. Conversion of compounds of formula 4-2 to compounds of formula 1-A proceeds as described above for Scheme 3. Alternatively, as should be obvious to one skilled in the art, the sequence of steps in Schemes 3 and 4, (particularly the later steps) can be altered to accommodate the preparation of other examples of compounds of formula 1-A.

Scheme 5

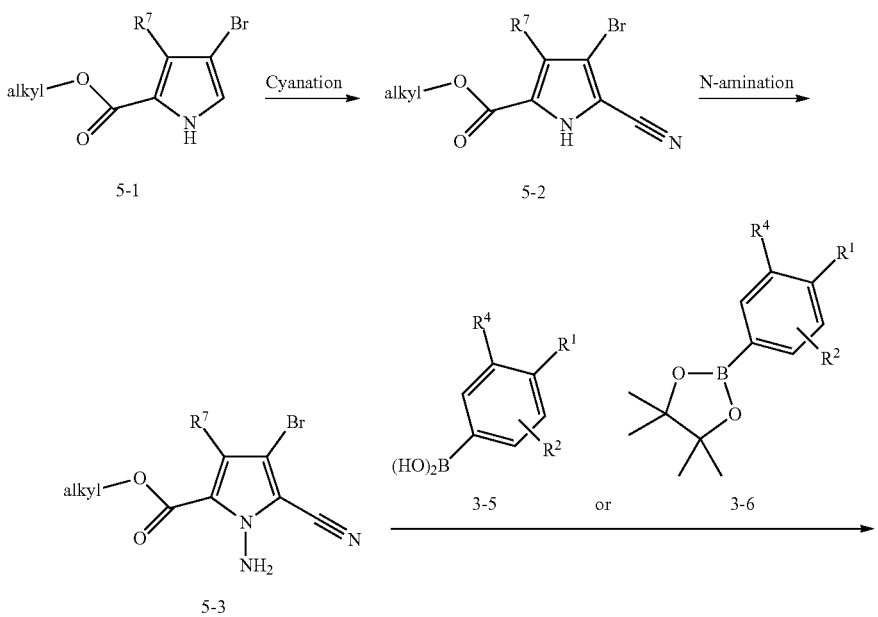

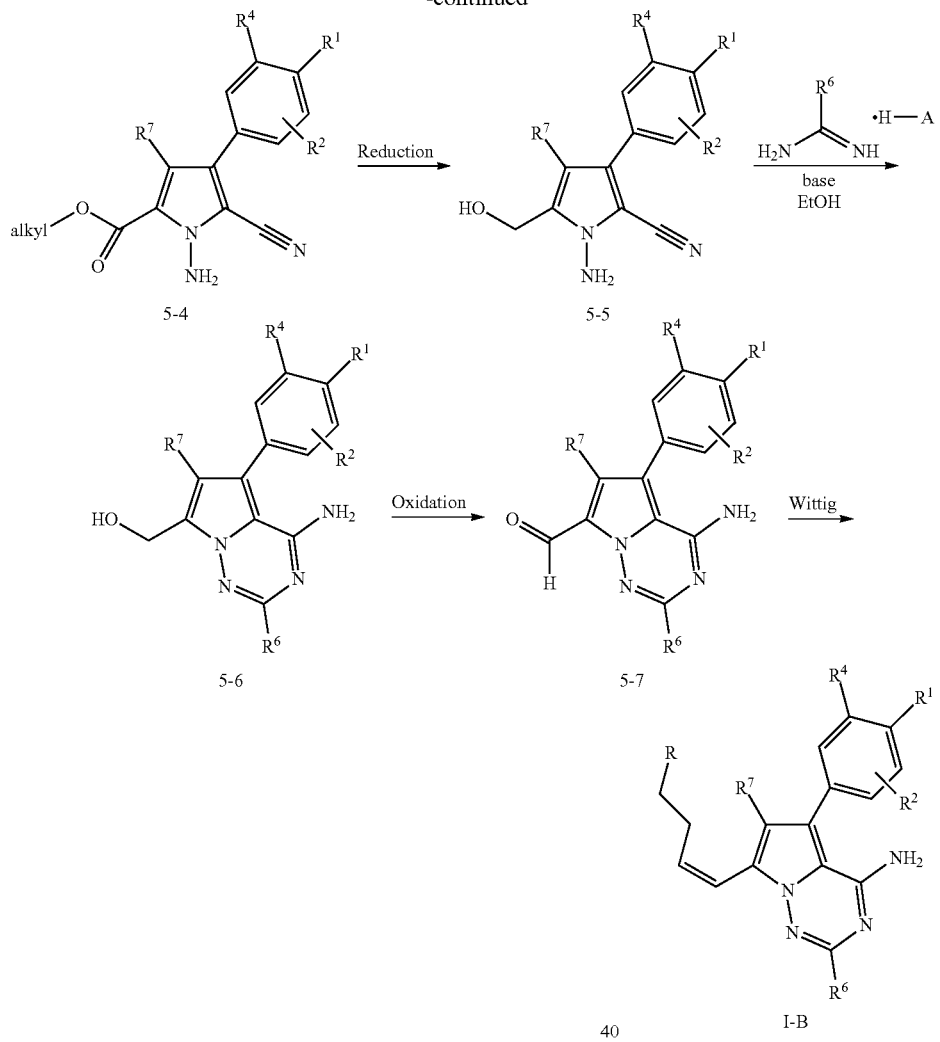

The compounds of formula I-B are prepared according to reaction sequences shown in Scheme 5. Thus, cyanation of a bromopyrrole such as 5-1 using chlorosulfonyl isocyanate or the like provides compounds of formula 5-2. N-Amination of the pyrrole using O-diphenylphosphoryl hydroxylamine or the like in the presence of a base such as sodium hydride or the like in a solvent such as DMF or similar provides the aminopyrrole 5-3. Suzuki reaction with boronic acid 3-5 or boronate 3-6 under conditions well known in the art provides compounds of formula 5-4. Reduction of the ester using sodium borohydride of the like in a solvent such as ethanol or the like provides the corresponding hydroxyl compounds of formula 5-5. Reaction of 5-5 with a formamidine reagent in the presence of a base such as potassium phosphate or the like in a solvent such as ethanol or similar provides compounds of the type 5-6. Oxidation of these to the aldehyde using Dess-Martin periodinane or the like in a solvent such as dichloromethane or the like provides compounds of formula 5-7, and subsequent Wittig reaction under conditions well known in the art provides compounds of formula 1B.

Scheme 6

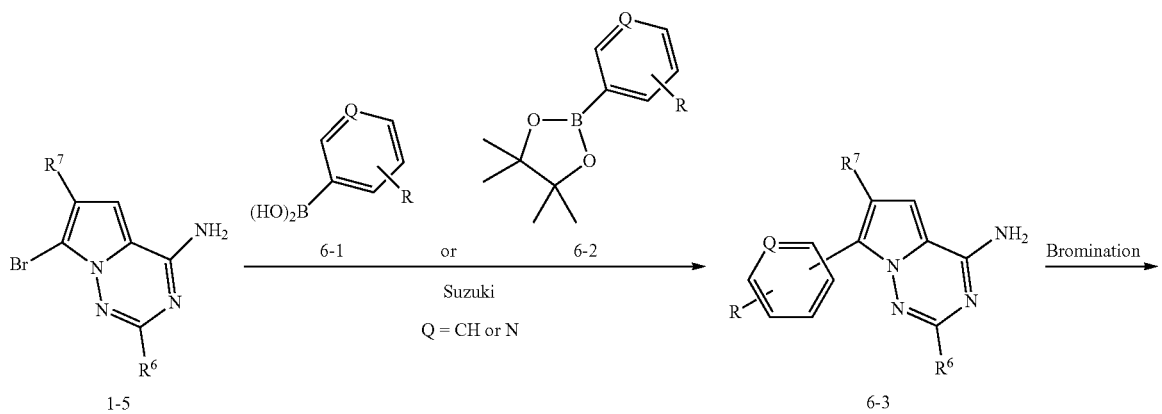

-continued

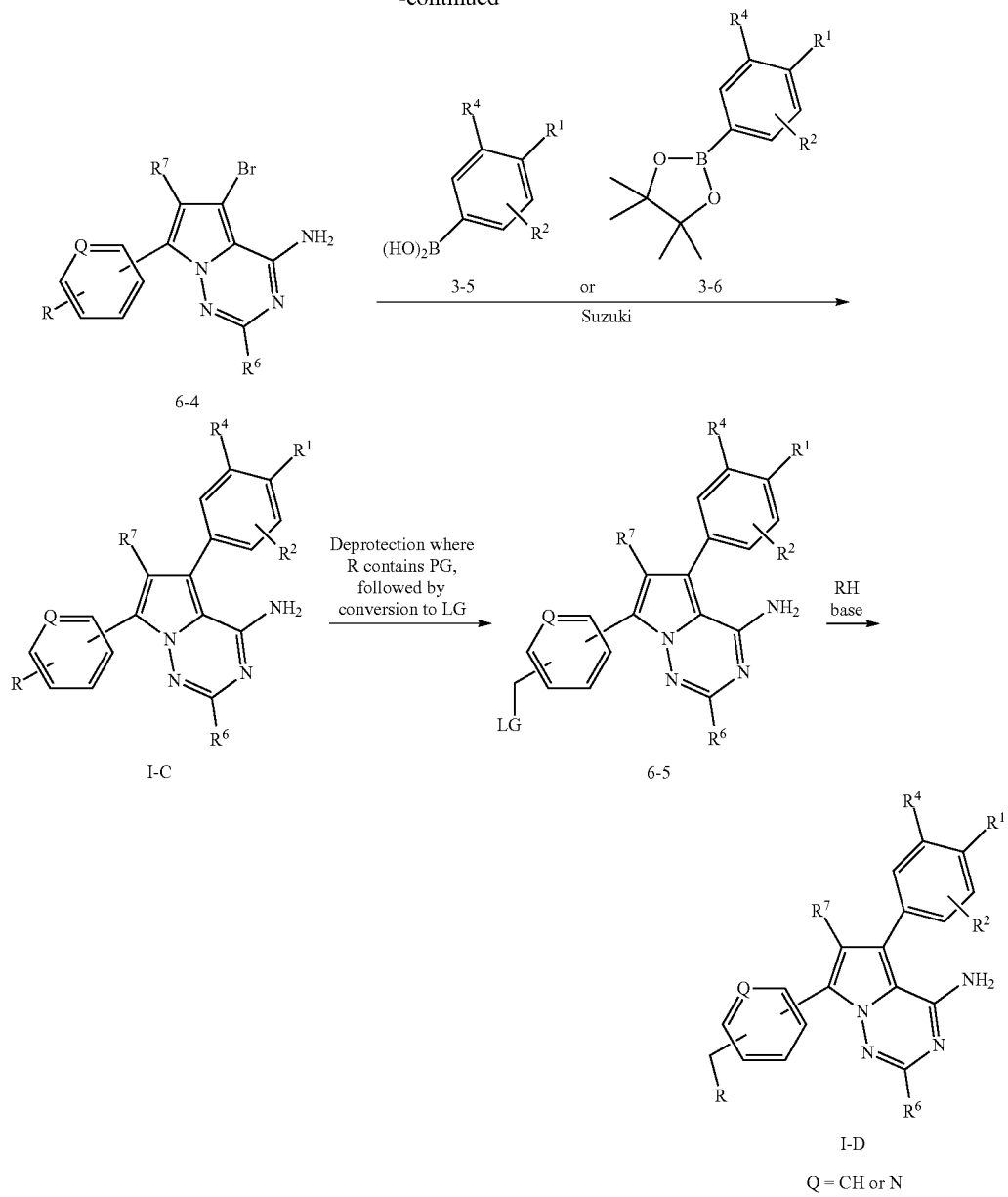

The compounds of formula I-C and formula I-D are prepared according to reaction sequences shown in Scheme 6. Treatment of compound 1-5 with an aryl boronic acid of type 6-1 or arylboronate of type 6-2 under conditions known in the art provides compounds of the formula 6-3. Bromination of 6-3 with a suitable brominating agent such as 1,3-dibromo-5,5-dimethylhydantoin or the like in a solvent such as THF or DMF or the like provides compounds of formula 6-4. Suzuki coupling of compounds of formula 6-4 with boronic acids of type 3-5 or boronates of type 3-6 using conditions well-known in the art provides compounds of the formula 1-C. Deprotection (if necessary) can be conducted by means well known in the art, followed by equally well-precedented conversion, when necessary, of the liberated hydroxyl group to an appropriate leaving group (such as halo, sulfonate, or the like) provides structures of the type 6-5. Reaction of compounds of the formula I-C with an appropriate alkylating agent such as ethylene carbonate in the presence of a suitable base such as sodium hydroxide provides compounds of the formula I-D. Compounds of formula I-D are also prepared by treatment of compounds of the formula 6-5, in cases when an amino group has been liberated by deprotection, with an aldehyde such as formaldehyde and the like and a reducing agent such as sodium triacetoxyborohydride or the like in a solvent such as 1,2-dichloroethane or the like.

Compounds of formula I-E are conveniently prepared according to reaction sequences shown in Scheme 7. Treatment of compound 1-5 with a boronate such as 7-1 under conditions well known in the art provides the appropriately protected di-dehydrocyclic amines of formula 7-3. Alternatively, such protected amines can be prepared by their conversion to a Grignard reagent, which can be carried out by reaction with an appropriate Grignard reagent such as isopropylmagnesium chloride, in the presence of a temporary protecting agent such as trimethylsilyl chloride in a solvent such as THF. This Grignard reagent formed from 1-5 is reacted with a protected piperidone of formula 7-2 to provide, after an acidic workup which eliminates the intermediate hydroxy compound, compounds of formula 7-3. Reduction of the double bond of 7-3 with hydrogen in the presence of a catalyst such as $PtO_2$ or the like in a solvent such as acetic acid or the like provides cyclic amines of formula 7-4. Bromination of 7-4 with 1,3-dibromo-5,5-dimethylhydantoin or other suitable brominating agents provides compounds of formula 7-5. Suzuki coupling of 7-5 with boronic acids such as 3-5 or boronates such as 3-6 under conditions well known in the art provides compounds of formula 7-6. Removal of the protecting group using conditions well known in the art provides compounds of formula I-E. Reaction of compounds of the formula I-E with an appropriate alkylating agent such as ethylene carbonate in the presence of a suitable base such as sodium hydroxide provides compounds of the formula I-F. Compounds of formula I-F are also prepared by treatment of compounds of the formula I-E with an aldehyde such as formaldehyde and the like and a reducing agent such as sodium triacetoxyborohydride or the like in a solvent such as 1,2-dichloroethane or the like. Compounds of formula 1-F can also be prepared by the reaction of the amines of formula 1-E with an acylating or sulfonating reagent, such as an acyl anhydride, acyl chloride, sulfonyl chloride or the like, in the presence of a suitable base such as pyridine, potassium carbonate, a tertiary amine or the like, in appropriate solvents such as THF, dichloromethane, or others.

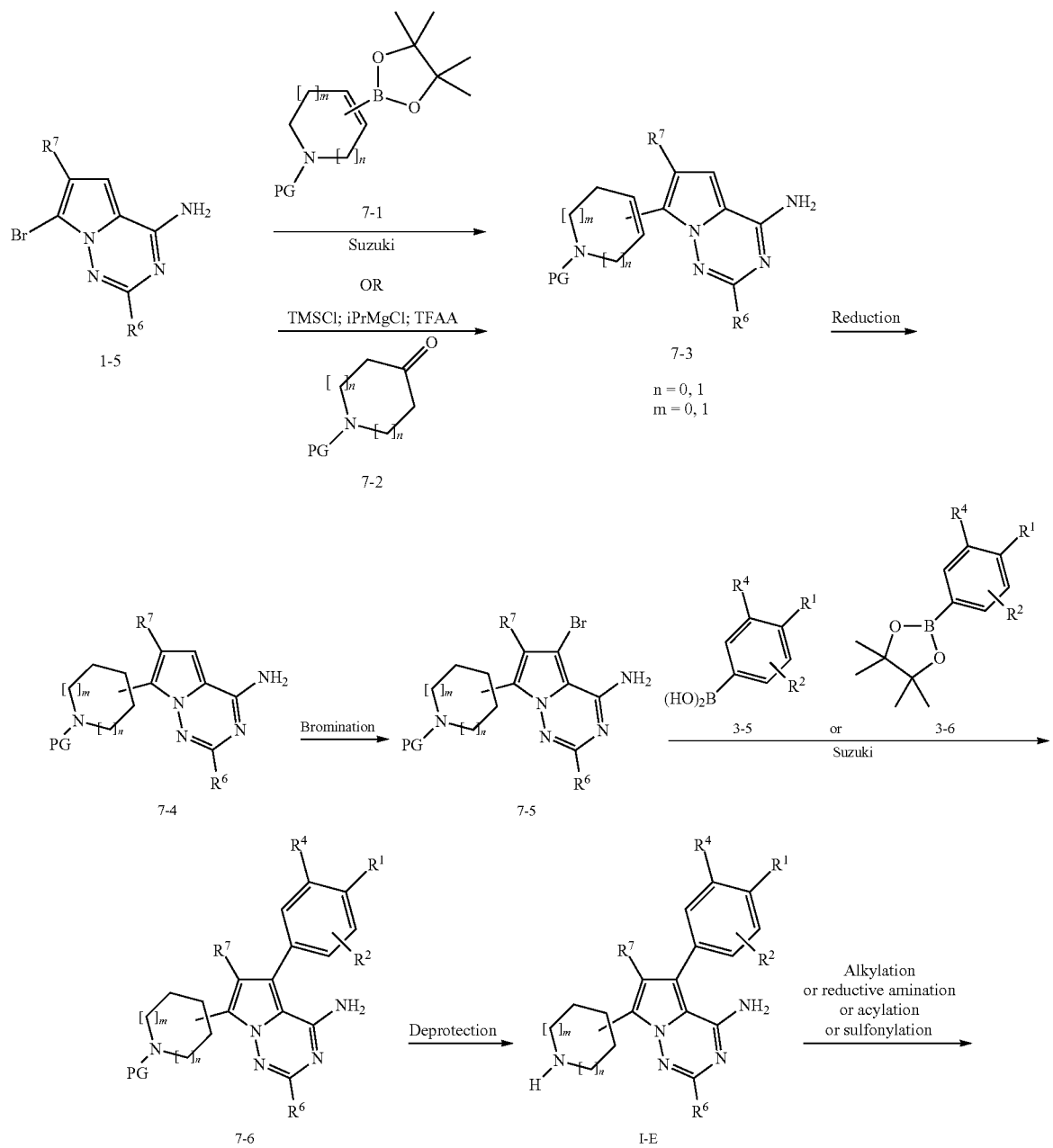

Scheme 7

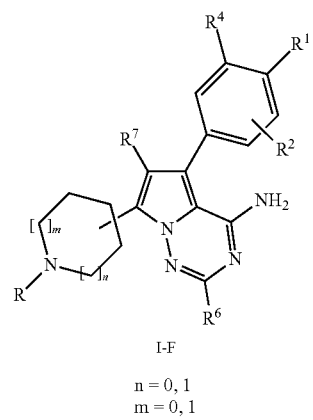

I-F n = 0, 1
m = 0, 1

The compounds of formula 1-G are conveniently prepared according to reaction sequences shown in Scheme 8. Compounds of formula 1-5 are converted to their corresponding Grignard reagents under the conditions given in Scheme 7, and reacted with protected 3-piperidones of formula 8-1 to give compounds with structures corresponding to formula 8-2. Bromination of compounds of formula 8-2 with 1,3-dibromo-5,5-dimethylhydantoin or other suitable brominating agents provides compounds of formula 8-3. Suzuki coupling of 8-3 with boronic acids such as 3-5 or boronates such as 3-6 under conditions well known in the art provides compounds of formula 8-4. Removal of the protecting group using conditions well known in the art provides compounds of formula I-G.

Scheme 8

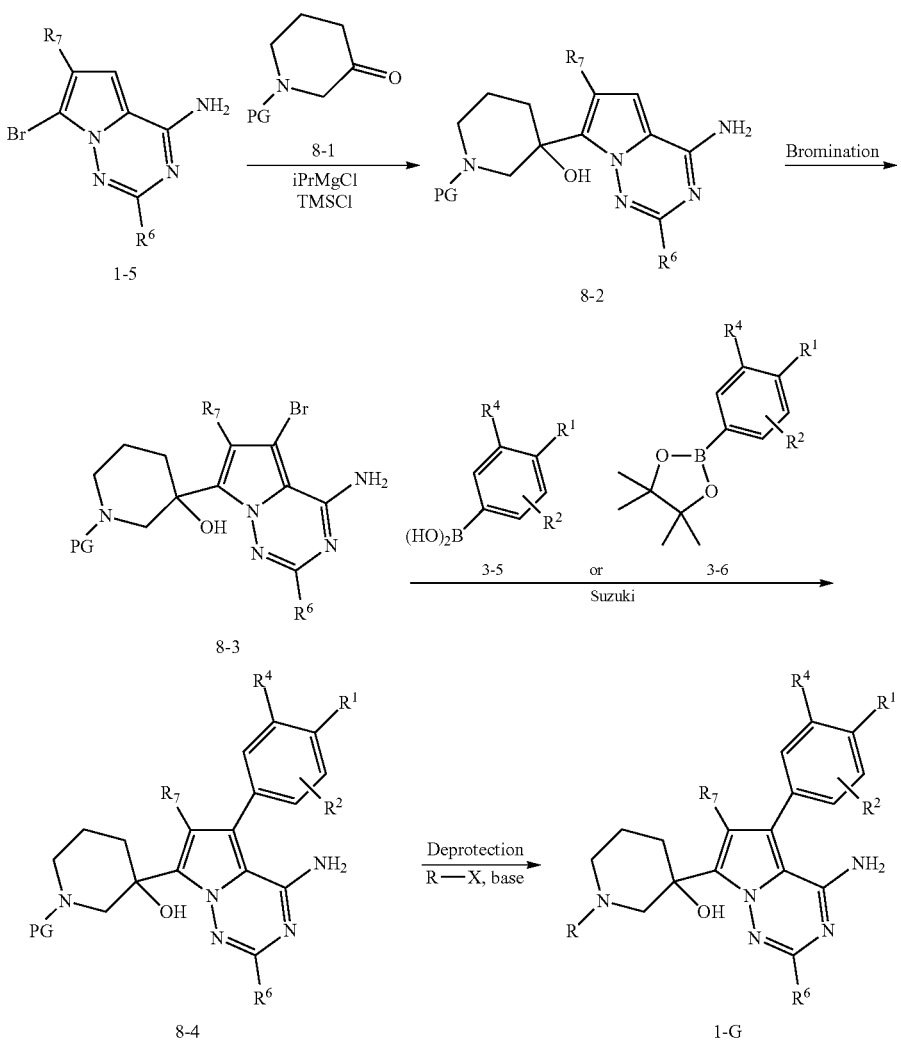

Compounds of formula I-H are conveniently prepared according to reaction sequences shown in Scheme 9. Treatment of compound 1-5 with an excess of an alkyllithium such as n-BuLi or the like in a solvent such as THF or the like at a temperature of about −78° C. followed by the addition of the corn pounds of formula 9-1 provides compounds of the formula 9-2. Bromination of compounds of formula 9-2 with 1,3-dibromo-5,5-dimethylhydantoin or the like in a solvent such as THF or DMF or the like provides compounds of formula 9-3. Suzuki reaction under conditions well known in the art using boronic acids such as 3-5 or boronates such as 3-6 provides compounds of formula 9-4.

Removal of the protecting group using conditions well known in the art provides compounds of the formula I-H (R═H). Treatment of compounds of the formula I-H with an alkylating agent such as ethyl bromide or propyl bromide or the like in solvent such as THF or the like in the presence of a base such as triethylamine or the like provides compounds of the formula I-I.

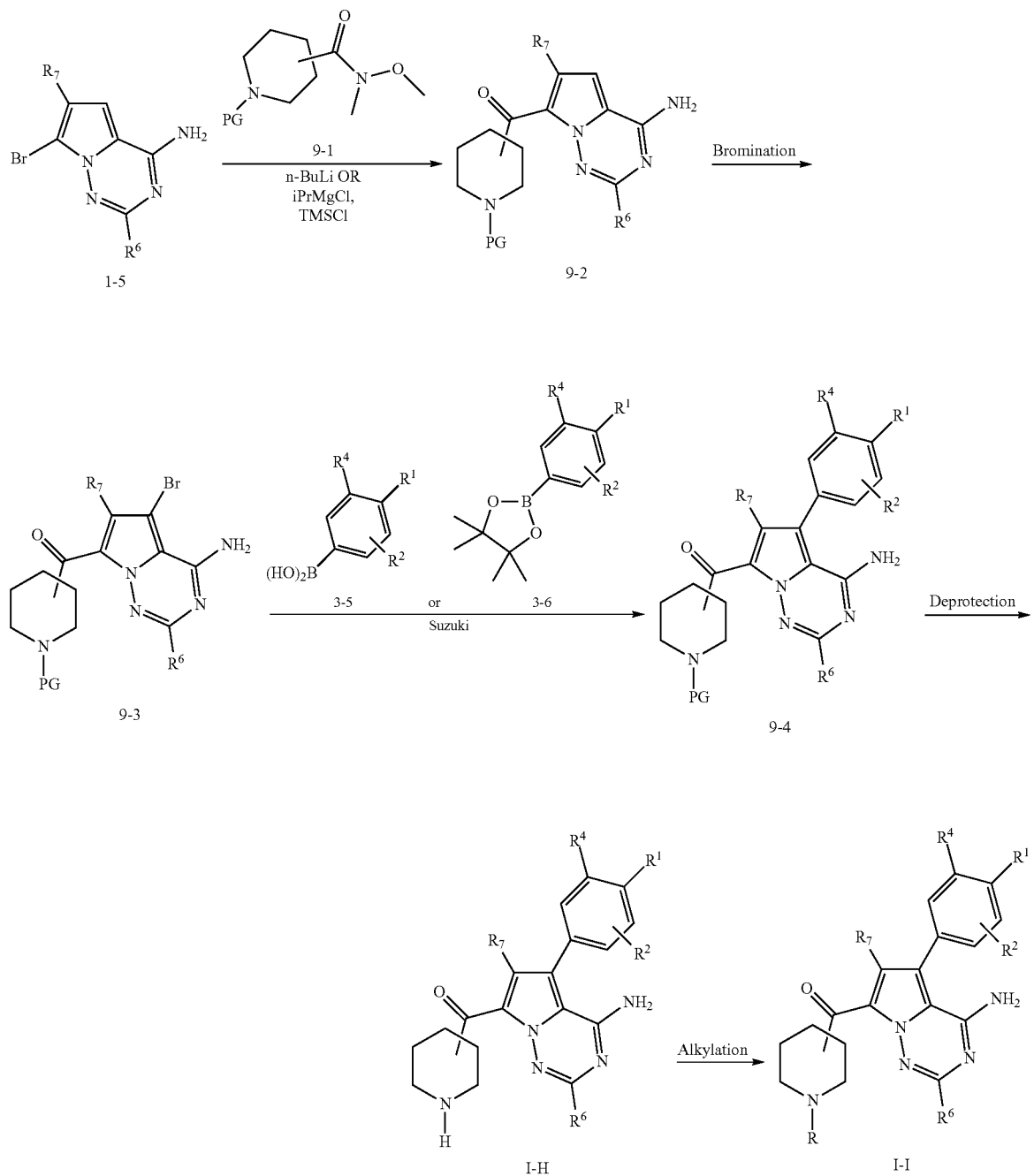

Scheme 9

The compounds of formula I-J are conveniently prepared according to reaction sequences shown in Scheme 10. Thus, treatment of compound 2-5 with an amine (R—H) such as a primary, secondary (cyclic or acyclic) amine and formaldehyde in an acidic solvent such as acetic acid or the like provides Mannich compounds of the formula 10-1. Bromination of 10-1 with 1,3-dibromo-5,5-dimethylhydantoin or the like in a solvent such as THF or the like provides compounds of the formula 10-2. Suzuki reaction of 10-2 with boronic acids of the formula 3-5 or boronates of the formula 3-6 under conditions well known in the art provides compounds of the formula I-J.

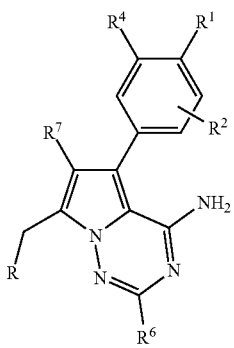

I-J

The compounds of formula 1-K are prepared according to reaction sequences shown in Scheme 11. Compounds of formula 1-5 are converted to their corresponding Grignard reagents under the conditions described in Scheme 7 and reacted with a suitable cyclopropanecarboxylate ester carboxaldehyde of formula 11-1 to give compounds of formula 11-2. These compounds are then deoxygenated under conditions well known in the art, such as the reaction with a trialkylsilane in the presence of a strong acid such as TFA, to give compounds of formula 11-3. Bromination of such compounds with 1,3-dibromo-5,5-dimethylhydantoin or other suitable brominating agents provides compounds of formula 11-4. Suzuki coupling of 11-4 with boronic acids such as 3-5 or boronates such as 3-6 under conditions well known in the art provides compounds of formula 11-5. These compounds are then reduced by standard agents such as lithium aluminum hydride, diisobutylaluminum hydride, or other suitable strong reducing agents in solvents such as THF or the like to give alcohols of formula 11-6. These are then converted to a suitable leaving group by reaction with a reagent such as a sulfonic anhydride in appropriate solvents such as THF to provide compounds of formula 11-7, which are converted to compounds of formula 1-K by reaction with the desired nucleophile, such as a primary, secondary (cyclic or acyclic) amine, in a solvent such as DMF or the like in the presence of a suitable base, such as potassium carbonate or a tertiary amine such as diisopropylethylamine.

Scheme 10

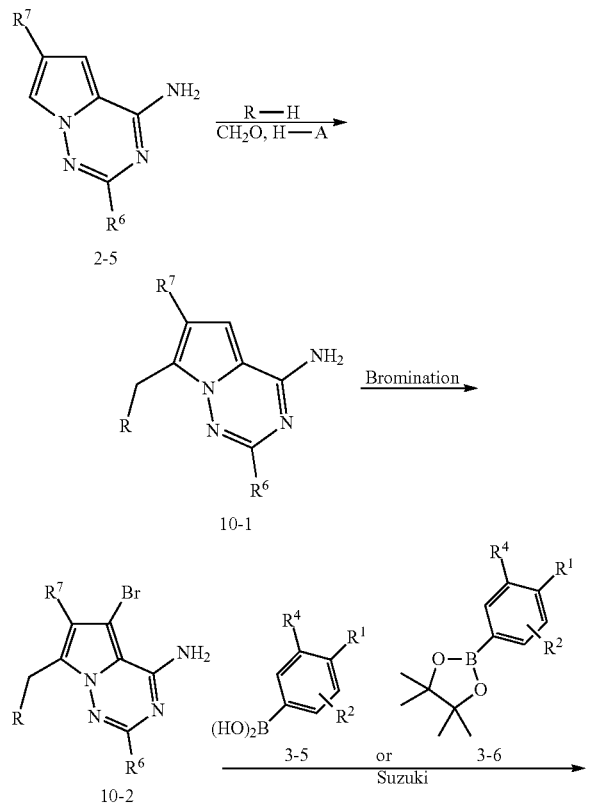

Scheme 11

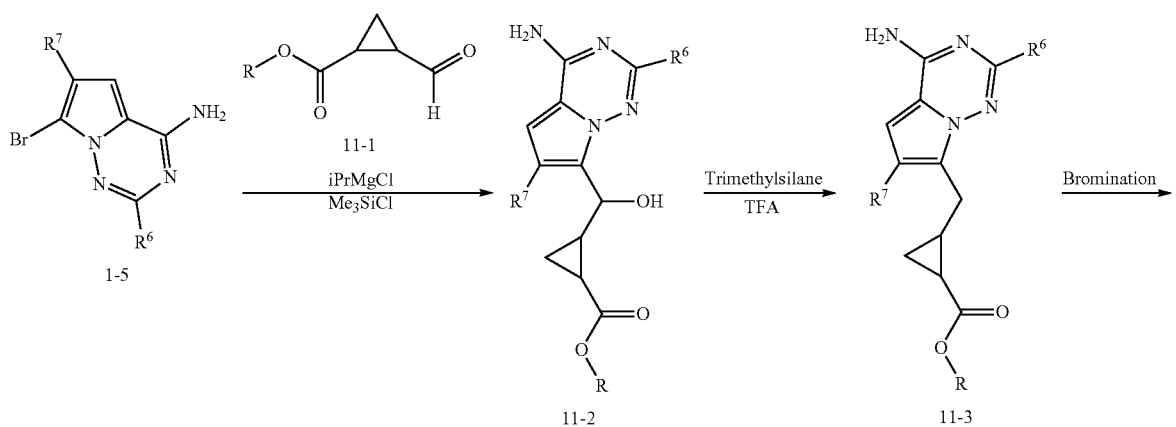

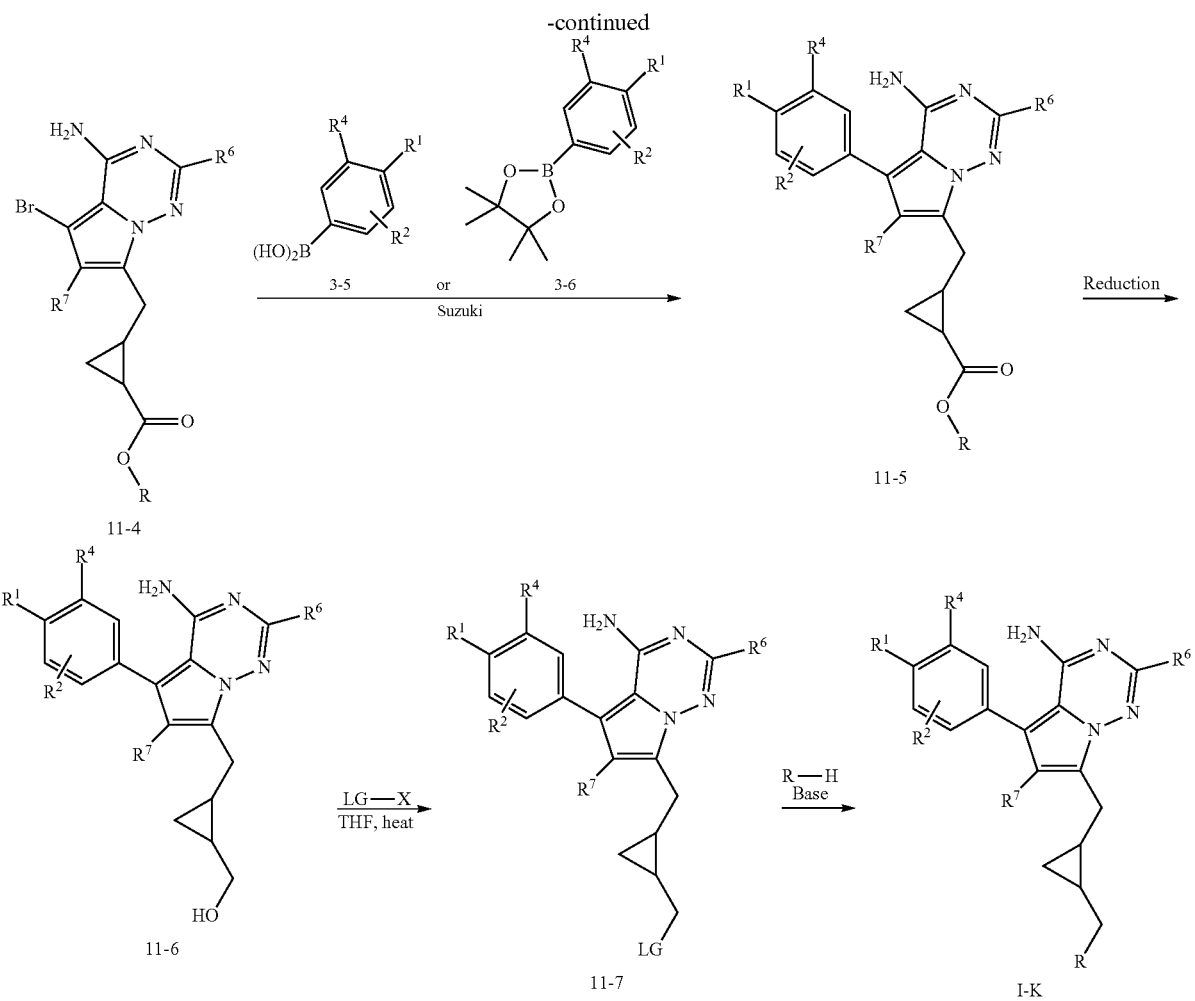

The compounds of formula 1-L are prepared according to reaction sequences shown in Scheme 12. The starting amine 11-1 is protected as its BOC carbamate 12-2 by its reaction with the anhydride in a solvent such as THF in the presence of a tertiary amine and a catalytic amount of dimethylaminopyridine. Compound 12-2 is converted to the corresponding boronate ester 12-3 using methods well known to those skilled in the art, and this compound is reacted with compounds of formula 1-5 in a further well-precedented metal-catalyzed coupling reaction to give compounds of formula 12-4. Bromination of such compounds with 1,3-dibromo-5,5-dimethylhydantoin or other suitable brominating agents provides compounds of formula 12-5. Suzuki coupling of 12-5 with boronates such as 3-6 under conditions well known in the art provides compounds of formula 12-6. Removal of the BOC group with an acid such as TFA or HCl in the presence of solvents such as dichloromethane, dioxane, or the like provides the amines of formula 12-7. Reaction of these compounds with an appropriate alkylating agent such as ethylene carbonate in the presence of a suitable base such as sodium hydroxide provides compounds of formula I-L. Compounds of formula I-L are also prepared by treatment of compounds of the formula 12-7 with an aldehyde such as formaldehyde and the like and a reducing agent such as sodium triacetoxyborohydride or the like in a solvent such as 1,2-dichloroethane or the like. Compounds of formula 1-L can also be prepared by the reaction of the amines of formula 12-7 with an acylating or sulfonating reagent, such as an acyl anhydride, acyl chloride, sulfonyl chloride or the like, in the presence of a suitable base such as pyridine, potassium carbonate, a tertiary amine or the like, in appropriate solvents such as THF, dichloromethane, or others.

Scheme 12

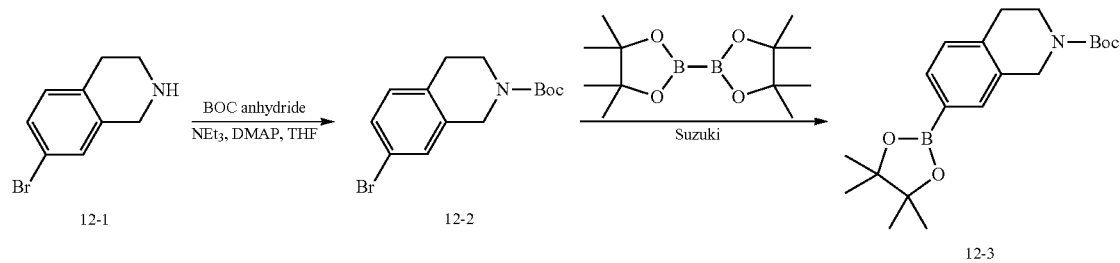

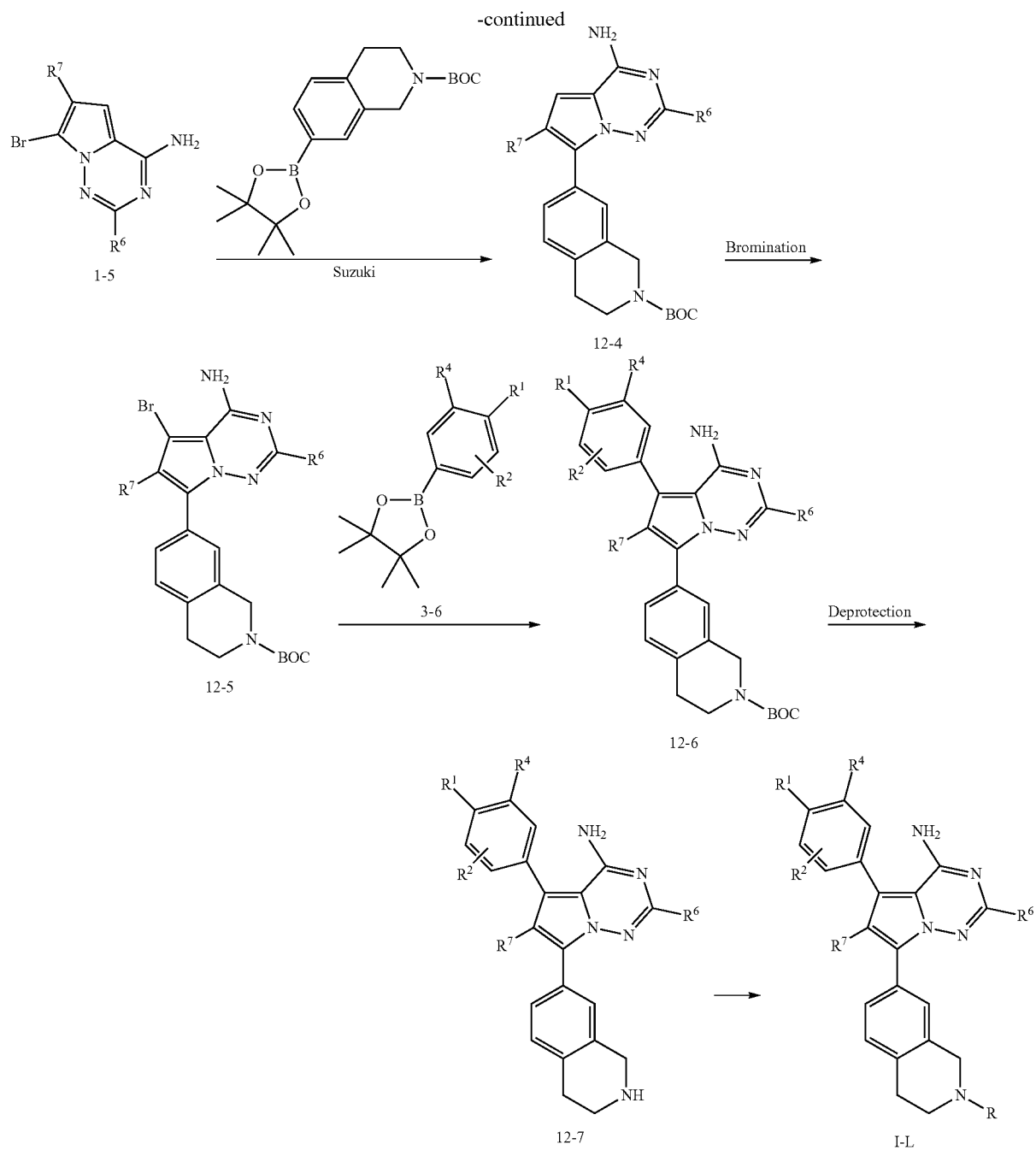
Scheme 13
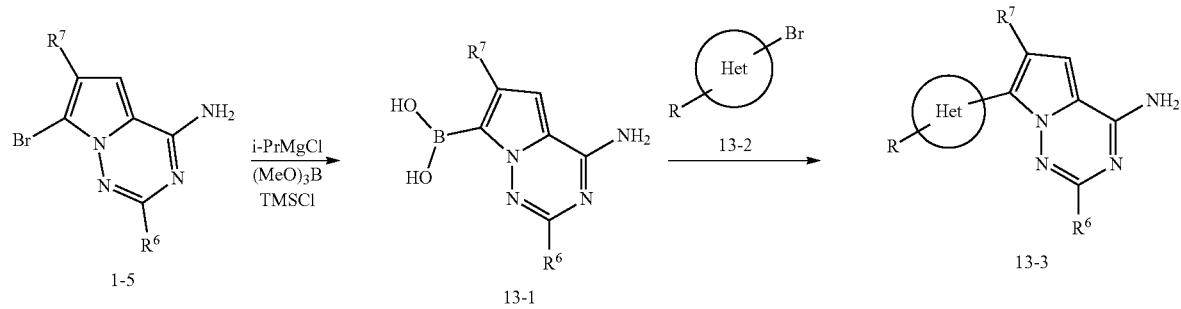

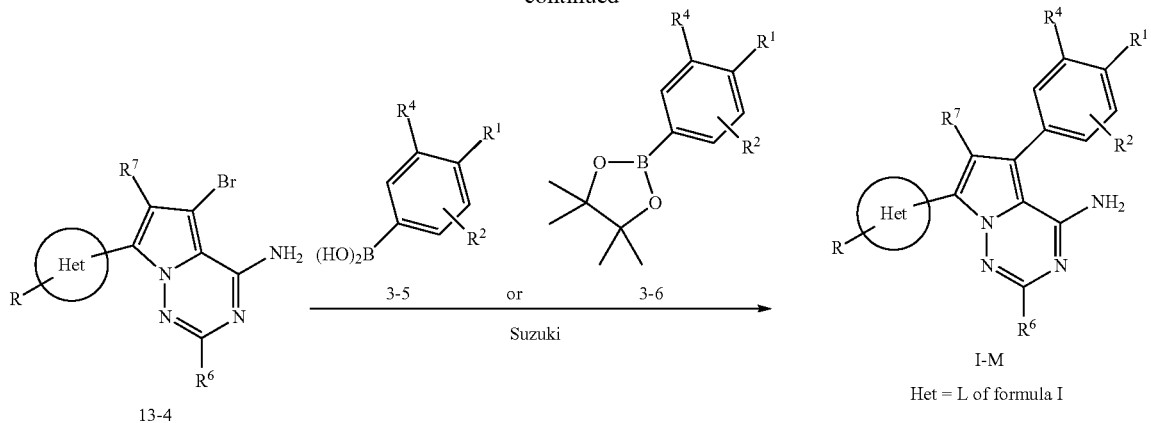

The compounds of formula I-M are conveniently prepared according to reaction sequences shown in Scheme 13. Compounds corresponding to formula 1-5 are converted to their corresponding Grignard reagents as Scheme 7, and these species are reacted with trimethyl borate in situ to give the boronic acids of formula 13-1. These compounds are reacted under well-precedented metal-catalyzed coupling conditions with the appropriate heterocyclic bromo compounds of formula 13-2 to provide compounds of formula 13-3. Suzuki coupling of 13-3 with boronic acids such as 3-5 or boronates such as 3-6 under conditions well known in the art provides compounds of formula I-M.

The compounds of formula I-N are conveniently prepared according to reaction sequences shown in Scheme 14. Compounds corresponding to formula 1-5 are converted to their corresponding Grignard reagents as Scheme 7, and these species are reacted with Weinreb esters of formula 14-1 in situ to give the compounds corresponding to formula 13-1. These are reduced to compounds of formula 14-3 by procedures well known to those skilled in the art, for example a sequence involving reaction with a suitable hydride reducing agent such as sodium borohydride in solvents such as methanol or other lower alcohols to provide the secondary hydroxyl intermediate, which is further reduced by agents such as trialkylsilanes in the presence of a strong acid such as TFA. Bromination of 14-3 with 1,3-dibromo-5,5-dimethylhydantoin or other suitable brominating agents provides compounds of formula 14-4, which are then subjected to Suzuki coupling with boronic acids such as 3-5 or boronates such as 3-6 under conditions well known in the art to provide compounds of formula 14-5. The protecting groups used until this point in the sequence can then be removed under various well-precedented procedures (acid-catalyzed removal of BOC carbamates, e.g.), and the resulting amines of formula 14-6 can be converted to compounds of formula I-N by reaction with various electrophiles. For example, with an appropriate alkylating agent in the presence of a suitable base, or by the reaction of the amines of formula 14-6 with an acylating or sulfonating reagent, such as an acyl anhydride, acyl chloride, sulfonyl chloride or the like, in the presence of a suitable base such as pyridine, potassium carbonate, a tertiary amine or the like, in appropriate solvents such as THF, dichloromethane, or others.

Scheme 14

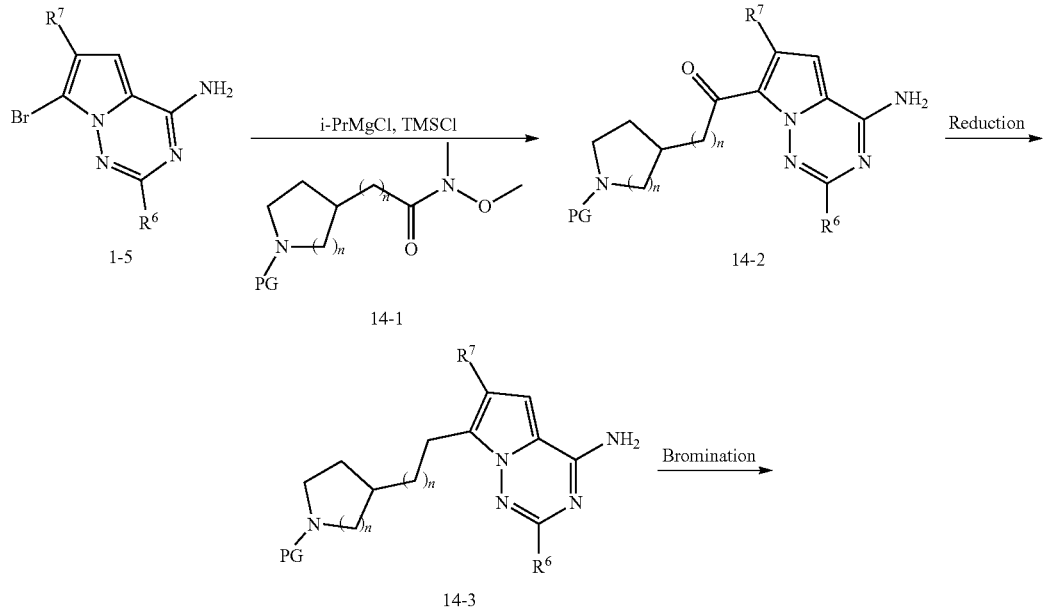

-continued
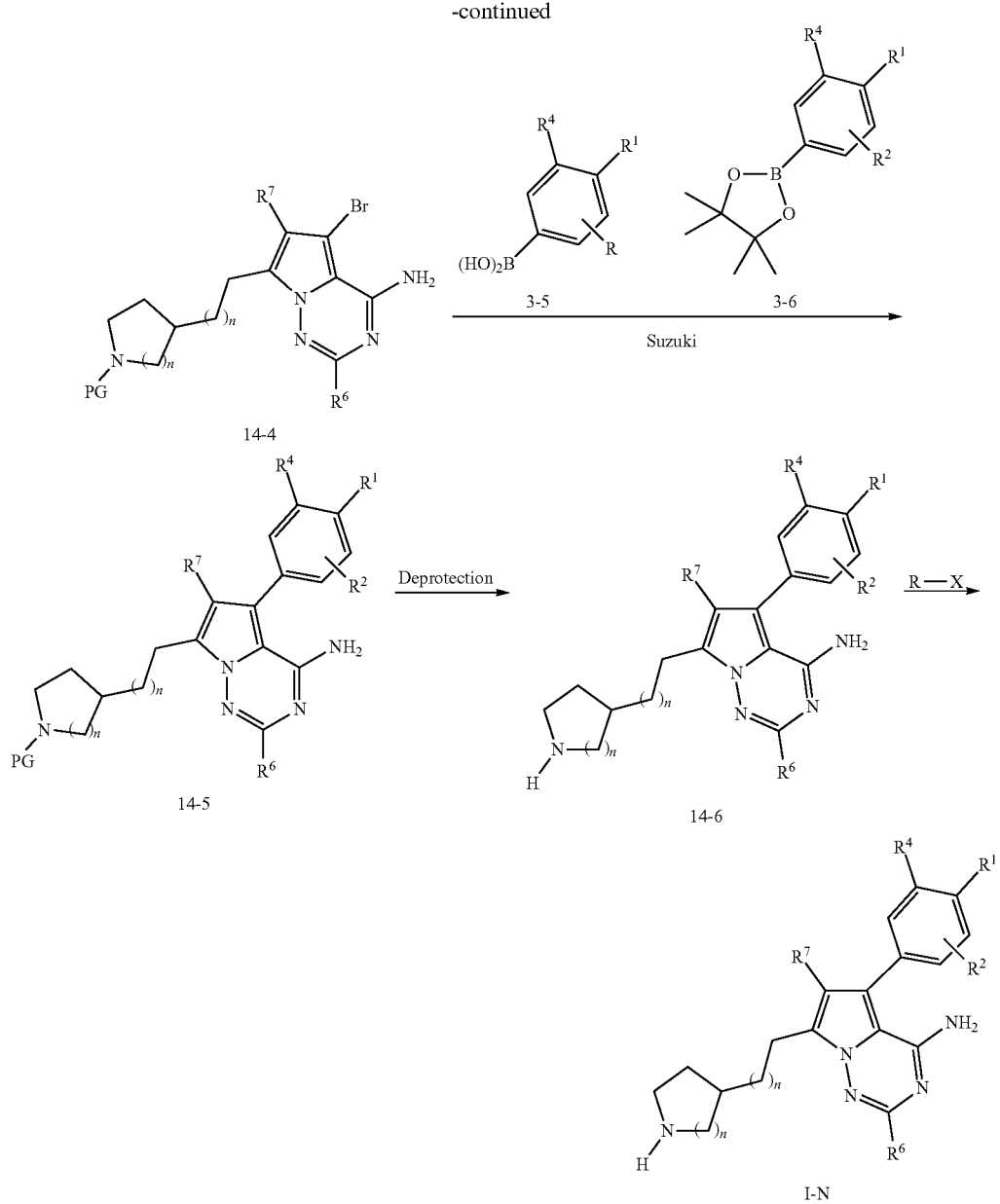
Scheme 15
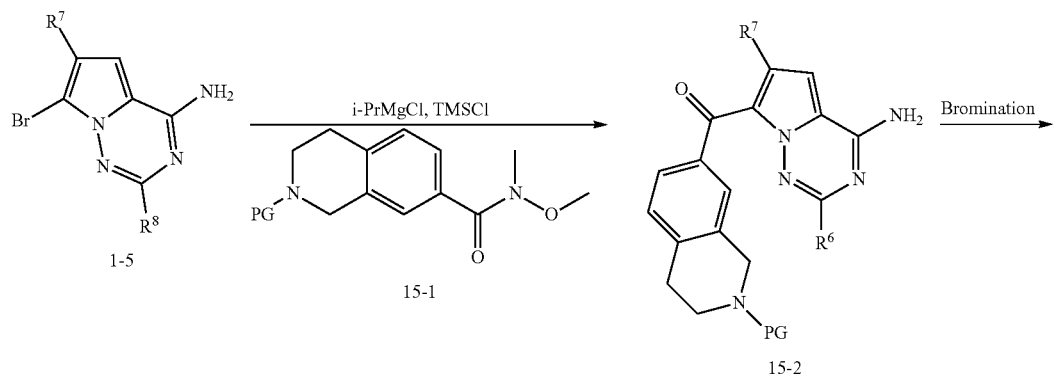

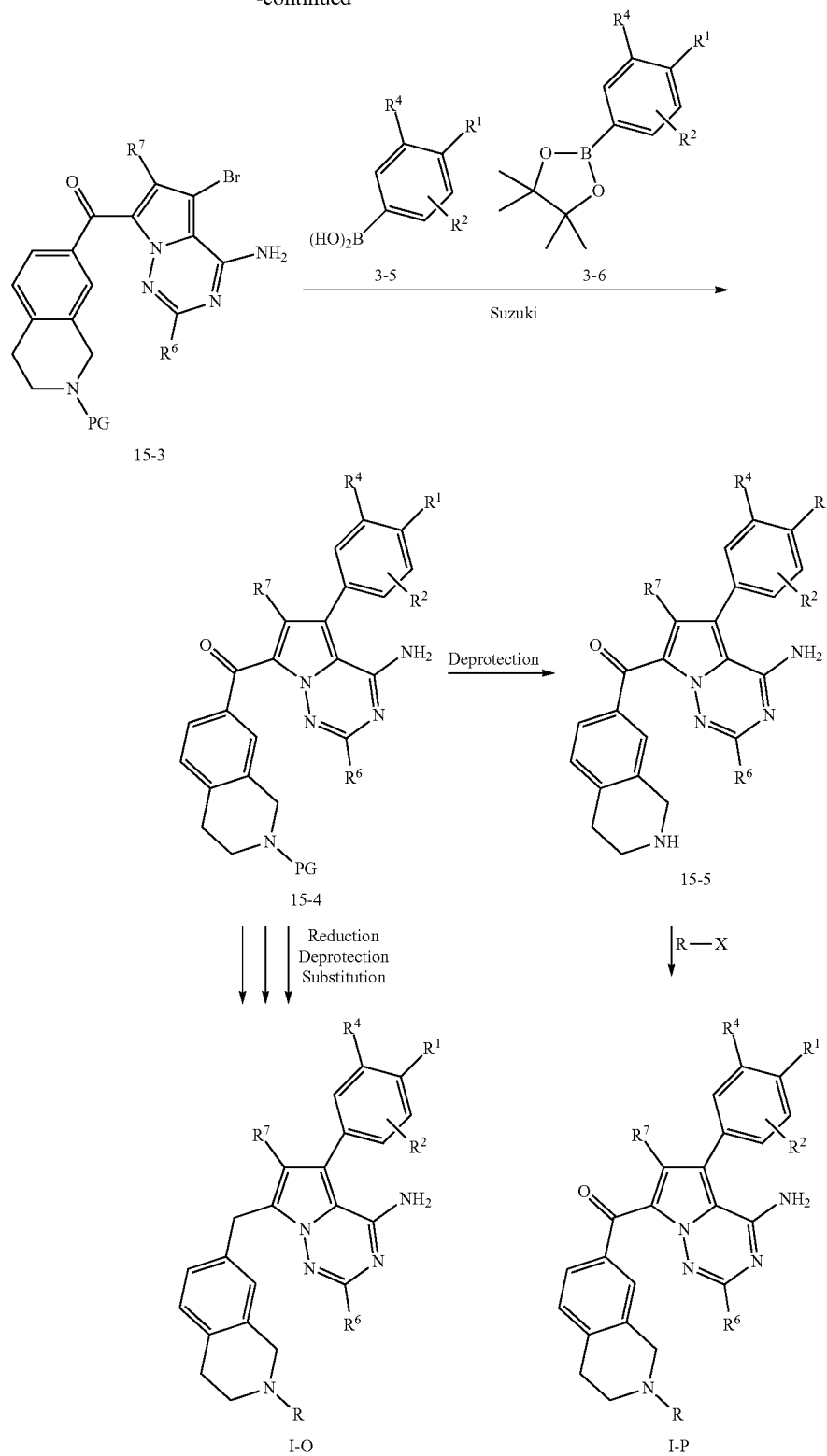

The compounds of formula I-O and I-P are conveniently prepared according to reaction sequences shown in Scheme 15. Compounds of formula 1-5 are converted to their corresponding Grignard reagents and reacted in situ with Weinreb amides in the same manner as those of Scheme 14 to furnish compounds of formula 15-2. Bromination of 15-2 with 1,3-dibromo-5,5-dimethylhydantoin or other suitable brominating agents provides compounds of formula 15-3, which are then subjected to Suzuki coupling with boronic acids such as 3-5 or boronates such as 3-6 under conditions well known in the art to provide compounds of formula 15-4. To convert structures of this type to compounds of formula I-O, the carbonyl group can be reduced in similar fashion to the procedures shown in Scheme 14 to provide the intermediate methylene compound. The protecting groups used until this point in the sequence can then be removed under various well-precedented procedures (acid-catalyzed removal of BOC carbamates, e.g.), and the resulting amines can converted to compounds of formula I-O by reaction with various electrophiles: for example, with an appropriate alkylating agent in the presence of a suitable base, or by the reaction of the amines of formula 14-6 with an acylating or sulfonating reagent, such as an acyl anhydride, acyl chloride, sulfonyl chloride or the like, in the presence of a suitable base such as pyridine, potassium carbonate, a tertiary amine or the like, in appropriate solvents such as THF, dichloromethane, or others. Alternatively, the carbonyl group can be left unaltered, in which case the deprotection of the amine, under the same well-known procedures as in the previous case, provides compounds of formula 15-5. These can be substituted in the same fashion to give compounds corresponding to formula I-P.

The compounds of formula I-Q and I-R are conveniently prepared according to reaction sequences shown in Scheme 16. Compounds of formula 1-5 are converted to their corresponding Grignard reagents and reacted in situ with protected piperazinylaryl Weinreb amides in the same manner as those of Scheme 14 to furnish compounds of formula 16-2. Bromination of 16-2 with 1,3-dibromo-5,5-dimethylhydantoin or other suitable brominating agents provides compounds of formula 16-3, which are then subjected to Suzuki coupling with boronic acids such as 3-5 or boronates such as 3-6 under conditions well known in the art to provide compounds of formula 16-4. To convert structures of this type to compounds of formula I-Q, the carbonyl group can be reduced in similar fashion to the procedures shown in Scheme 14 to provide the intermediate methylene compound. The protecting groups used until this point in the sequence can then be removed under various well-precedented procedures (acid-catalyzed removal of BOC carbamates, e.g.), and the resulting amines can converted to compounds of formula I-Q by reaction with various electrophiles: for example, with an appropriate alkylating agent in the presence of a suitable base, or by the reaction of the amines of formula 14-6 with an acylating or sulfonating reagent, such as an acyl anhydride, acyl chloride, sulfonyl chloride or the like, in the presence of a suitable base such as pyridine, potassium carbonate, a tertiary amine or the like, in appropriate solvents such as THF, dichloromethane, or others. Alternatively, the carbonyl group can be left unaltered, in which case the deprotection of the amine, under the same well-known procedures as in the previous case, provides compounds of formula 16-5. These can be substituted in the same fashion to give compounds corresponding to formula I-Q.

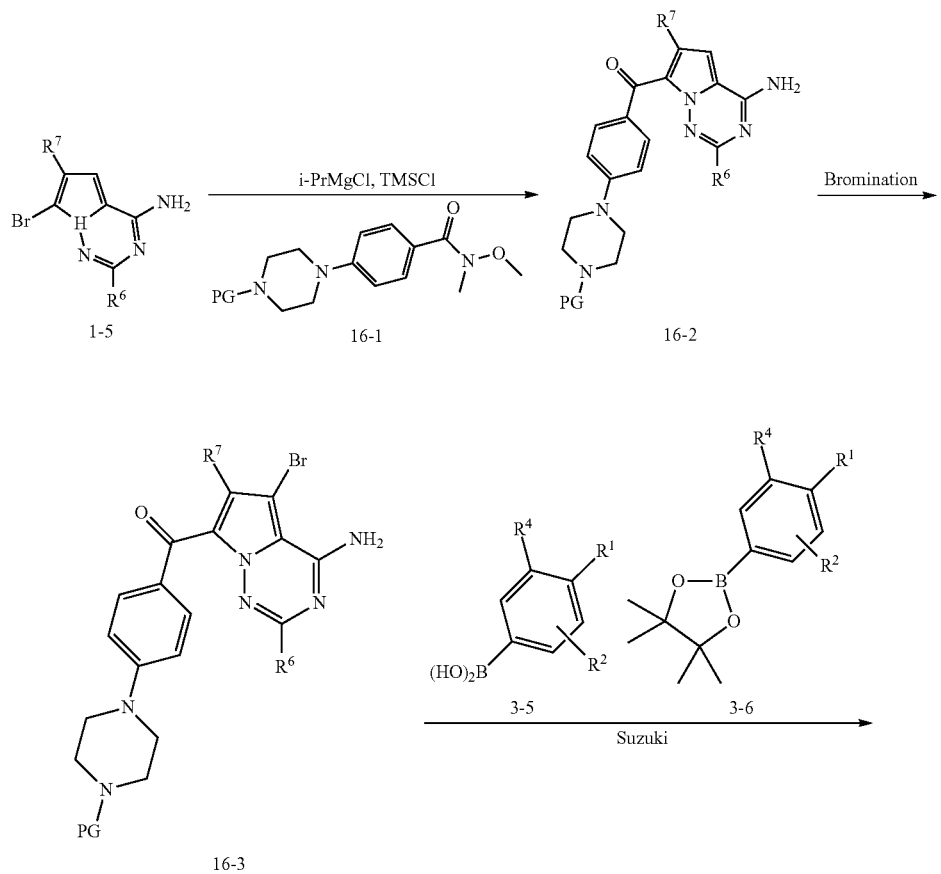

-continued

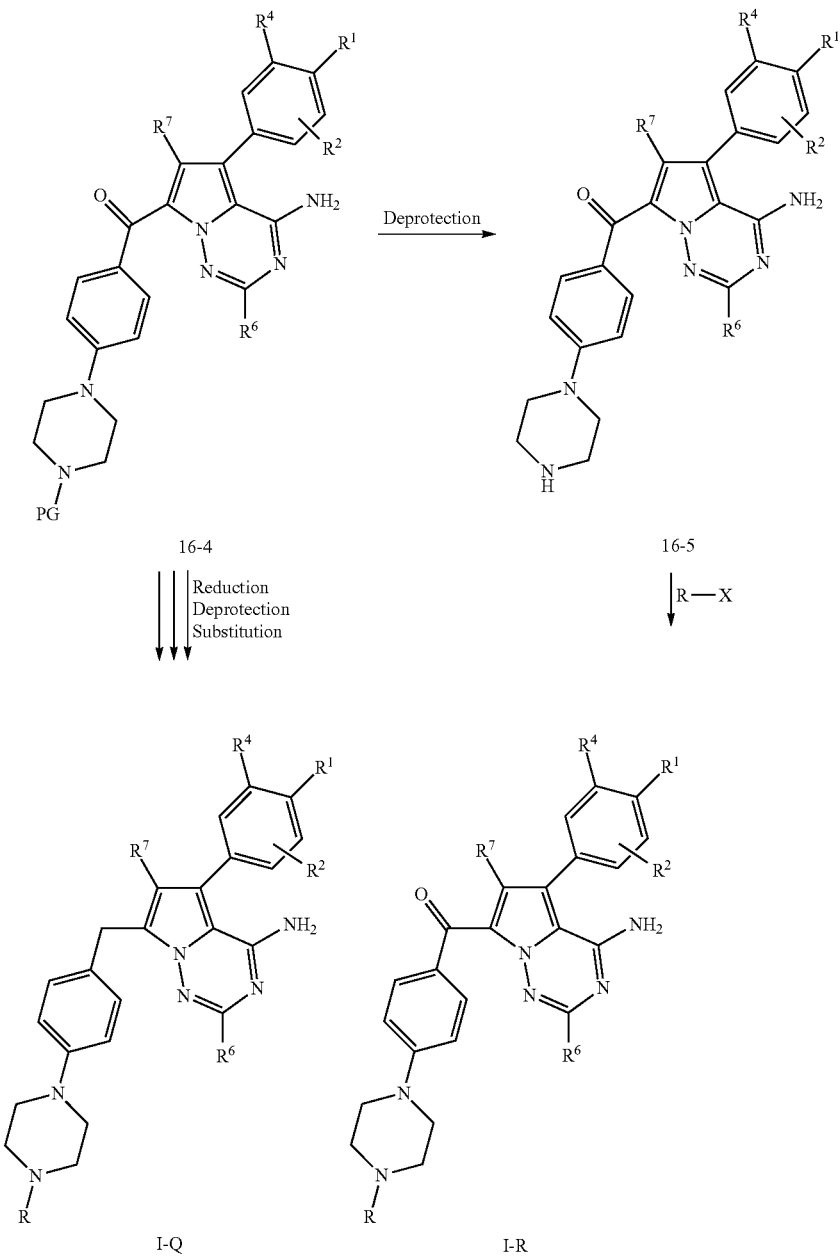

The compounds of formula I-S are conveniently prepared according to reaction sequences shown in Scheme 17. Treatment of compound 1-5 with an excess of an organometallic reagent such as IPrMgCl or the like in a solvent such as THF or the like followed by the addition of compounds of formula 17-1 provides compounds of formula 17-2. Reduction of the carbonyl using sodium borohydride or the like in a solvent such as ethanol or the like provides corresponding hydroxyl compounds of formula 17-3. Reduction to the methylene group using triethylsilane or the like with in the presence of acid such as TFA or the like provides compounds of formula 17-4. Bromination of compounds of formula 17-4 with 1,3-dibromo-5,5-dimethylhydantoin or the like in a solvent such as THF or DMF or the like provides compounds of formula 17-5. Suzuki reaction under conditions well known in the art using boronic acids such as 3-5 or boronates such as 3-6 provides compounds of formula 17-6. Removal of the protecting group using conditions well known in the art provides compounds of formula 17-7. Reaction of compounds of the formula 17-7 with an appropriate alkylating agent in the presence of a suitable base such as N,N-diisopropylethylamine or the like in a solvent such as DMF or the like provides compounds of formula I-S. Compounds of formula I-S are also prepared by treatment of compounds of the formula 17-7 with an acetal and a reducing agent such as sodium (continued)

Scheme 17
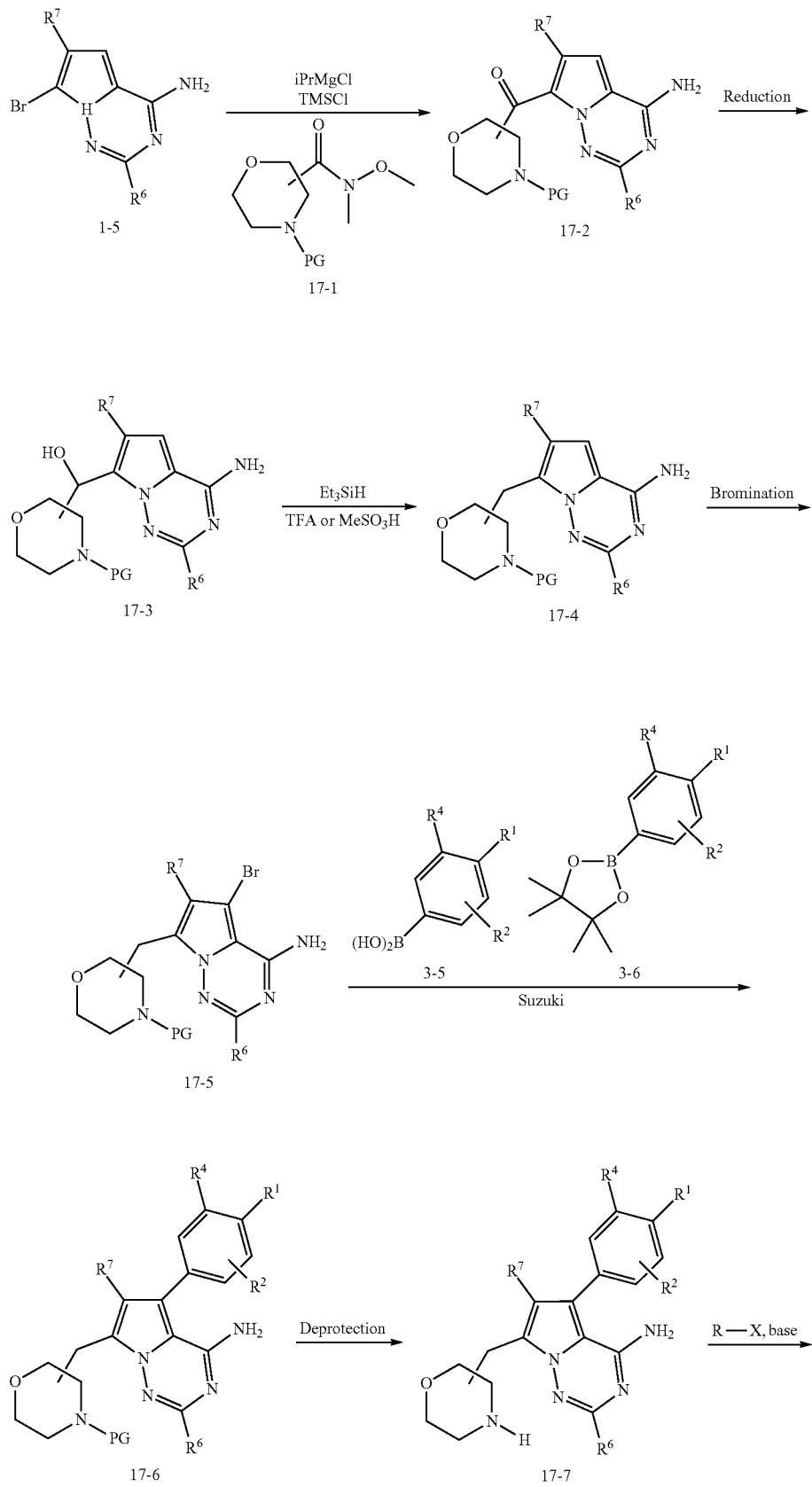

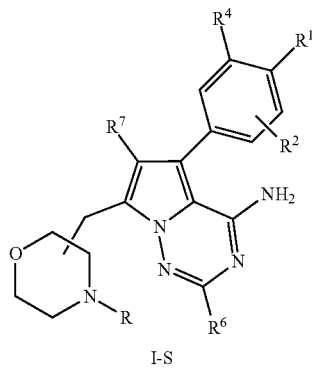

cyanoborohydride or the like in the presence of an acid such as acetic acid or the like in a solvent such as methanol or the like. Additionally, compounds of the formula I-S can be prepared through the reaction of compounds of formula 17-7 with a carboxylic acid and a coupling reagent such as EDCl or the like and a base such as N,N-diisopropylethylamine or the like in a solvent such at DMF or the like. Reaction of compounds of the formula 17-7 with an appropriate sulfonylating reagent in the presence of a base such as N,N-diisopropylethylamine or the like in a solvent such as DMF or the like provides compounds of formula I-S.

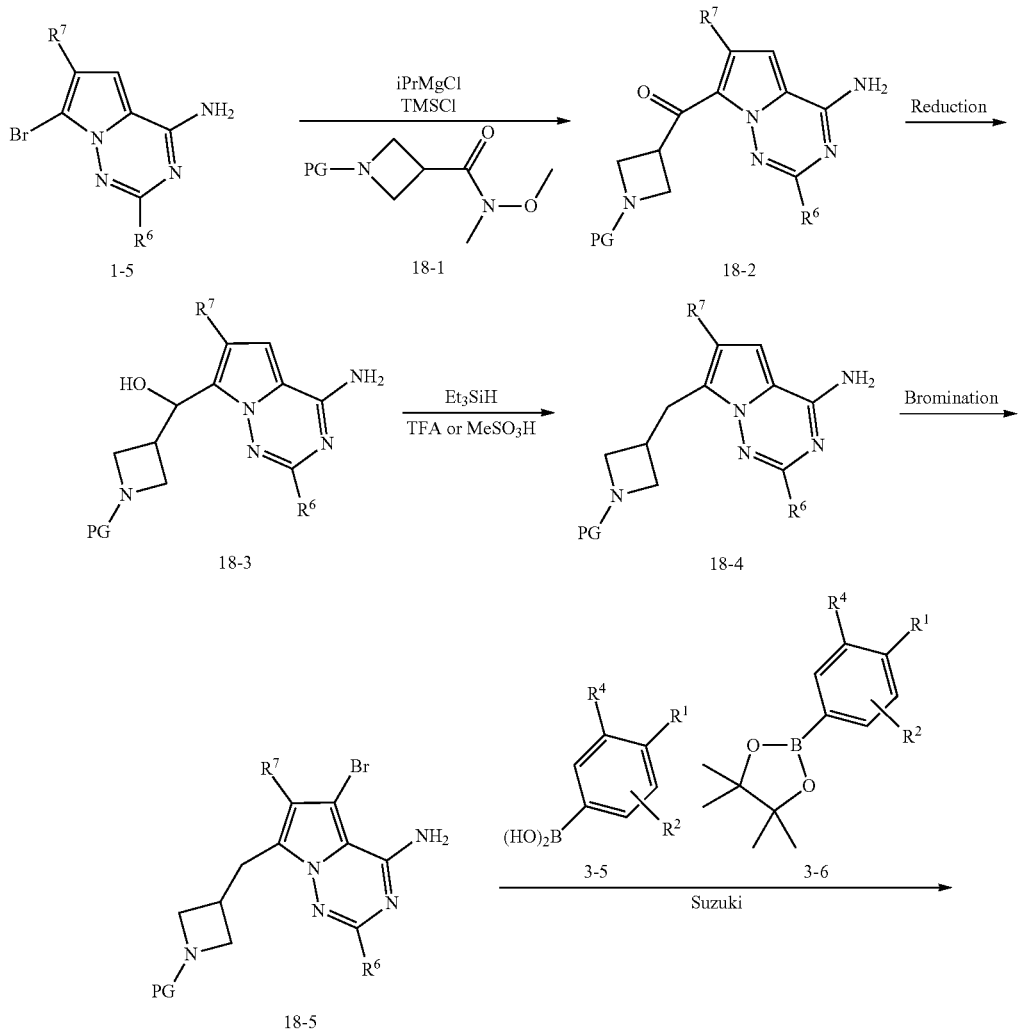

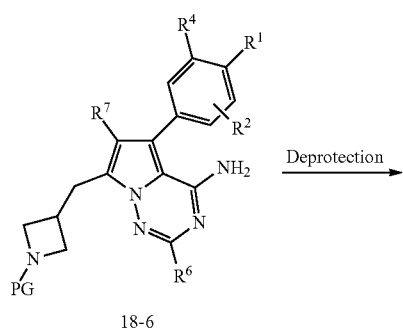
18-6

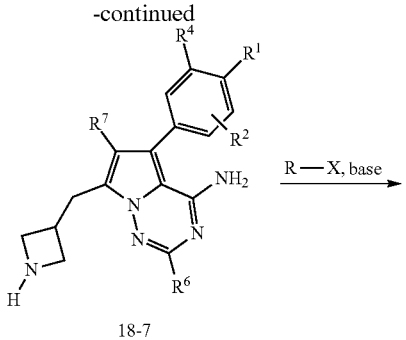
18-7

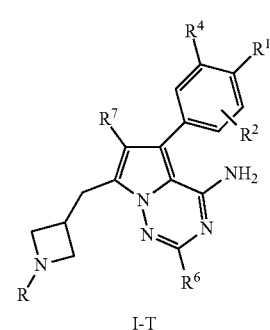
I-T

The compounds of formula I-T are conveniently prepared according to reaction sequences shown in Scheme 18. Compound 1-5 is converted to compound 18-2 by treatment with an excess of an organometallic reagent such as iPrMgCl or the like in a solvent such as THF or the like followed by the addition of compounds of formula 18-1. Conversion of a compound of formula 18-2 to compounds of formula I-T proceeds as described above for Scheme 17.

Scheme 19

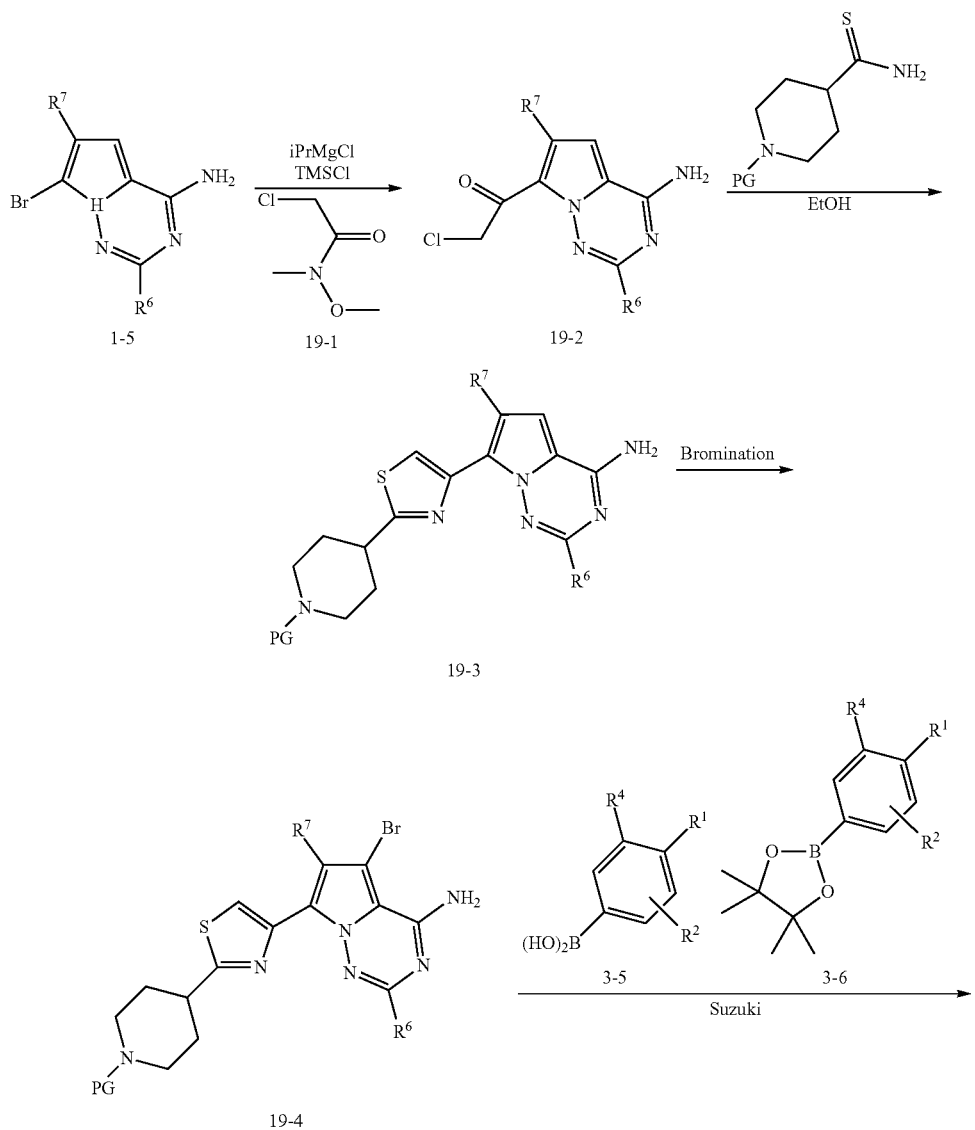

-continued

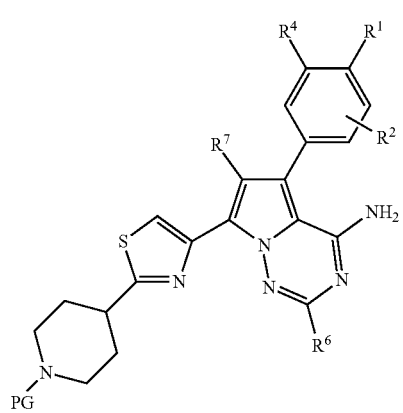

19-5

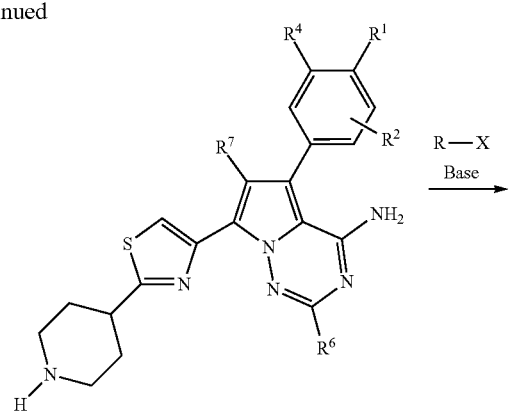

19-6

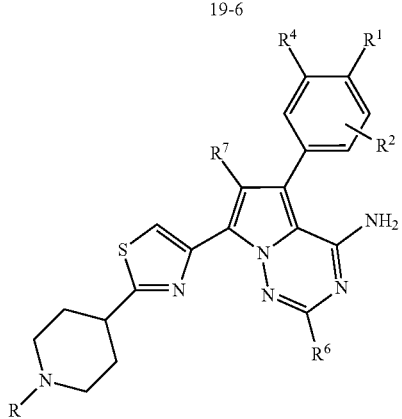

I-U

The compounds of formula I-U are conveniently prepared according to reaction sequences shown in Scheme 19. Compound 1-5 is converted to compound 18-2 by treatment with an excess of an organometallic reagent such as iPrMgCl or the like in a solvent such as THF or the like followed by the addition of compounds of formula 19-1. Treatment of compounds of formula 19-2 with thioacetamides of suitable structure in a solvent such as ethanol or the like provides thiazoles of formula 19-3. Treatment of 19-3 with a brominating reagent such as 1,3-dibromo-5,5-dimethylhydantoin or the like in an appropriate solvent, such as DMF, provides compounds of formula 19-4. Suzuki coupling of 19-4 with boronic acids such as 3-5 or boronates such as 3-6 under conditions well known in the art provides compounds of formula 19-5. Removal of the protecting group using conditions known in the art provides compounds of formula 19-6.

Conversion of 19-6 to a compound of formula I-U (where X is a suitable leaving group) can be carried out by methods known in the art. For example, reaction of compounds of the formula 19-6 with an appropriate alkylating agent, such as iodomethane in the presence of a base such as potassium carbonate or the like provides compounds of the formula I-U in which R is an alkyl group. Also, the reaction of compounds of the formula 19-6 with an appropriate sulfonylating agent, such as methansulfonyl chloride or the like provides compounds of the formula I-U in which R is an alkylsulfonyl group. Moreover, the reaction of compounds of the formula 19-6 with an appropriately functionalized carboxylic acid, a suitable coupling reagent, such as BOP or the like, and a suitable base, such as triethylamine or the like in a suitable solvent such as DMF and the like affords compounds of the formula I-U in which R is an amide.

Scheme 20

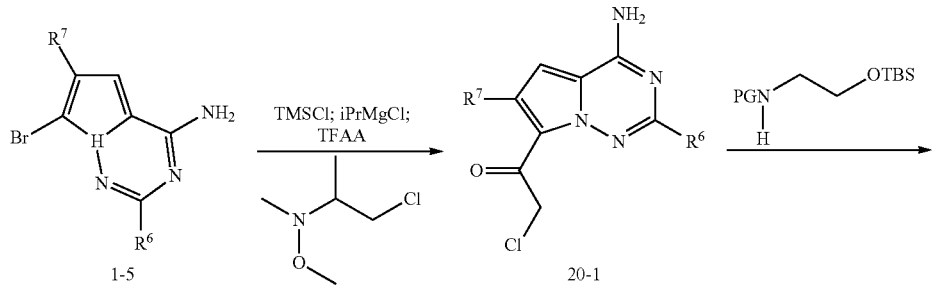

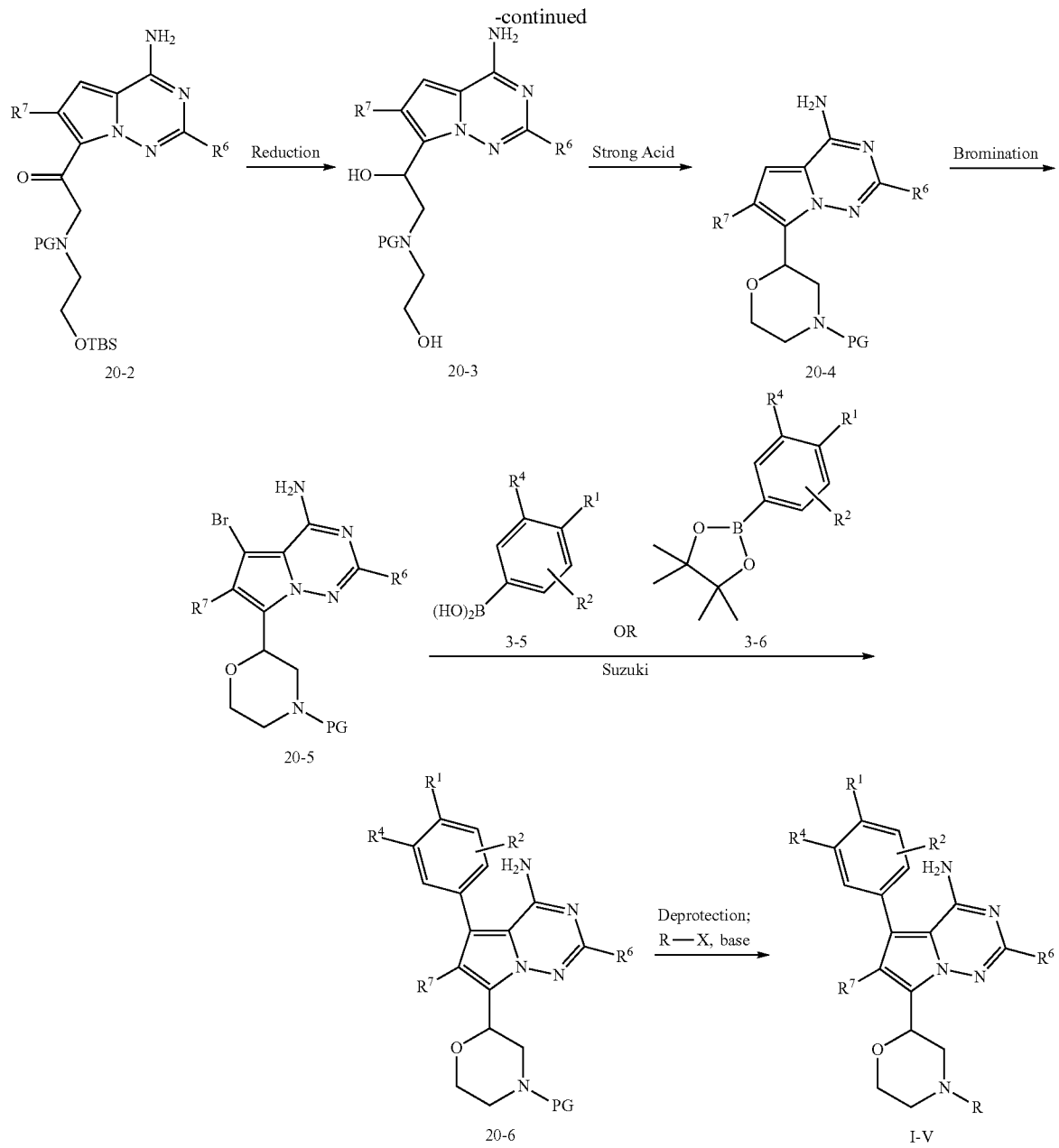

The compounds of Formula I-V are conveniently prepared according to reaction sequences shown in Scheme 20. Metallation of bromides of formula 1-5 with a Grignard reagent such as isopropylmagnesium chloride in the presence of TMS-Cl, followed by treatment with 2-chloro-N-methoxy-N-methyl-acetamide provides α-haloketones of formula 20-1. Displacement of the chloride with a suitably protected amine nucleophile in a solvent such as acetonitrile provides corresponding α-aminoketones of formula 20-2. Conversion of 20-2 to diols of formula 20-3 can be carried out with a reducing agent, preferably DIBAL-H, in a suitable solvent such as tetrahydrofuran. Treatment of 20-3 with a strong acid such as methanesulfonic acid provides cyclized compounds of formula 20-4. Treatment of 20-4 with a brominating reagent such as 1,3-dibromo-5,5-dimethylhydantoin or the like in an appropriate solvent, such as DMF, provides 20-5.

Suzuki coupling of 20-5 with a boronic acid such as 3-5 or a boronate such as 3-6 provides compounds of Formula 20-6. The protecting groups used until this point in the sequence can then be removed under various well-precedented procedures (acid-catalyzed removal of BOC carbamates, e.g.), and the resulting morpholines of formula I-V (R=H) can be converted to compounds by reaction with various electrophiles. For example, with an appropriate alkylating agent in the presence of a suitable base, or by the reaction of the amines of formula (I-V) with an acylating or sulfonating reagent, such as an acyl anhydride, acyl chloride, sulfonyl chloride or the like, in the presence of a suitable base such as pyridine, potassium carbonate, a tertiary amine or the like, in appropriate solvents such as THF, dichloromethane, or others.

Scheme 21
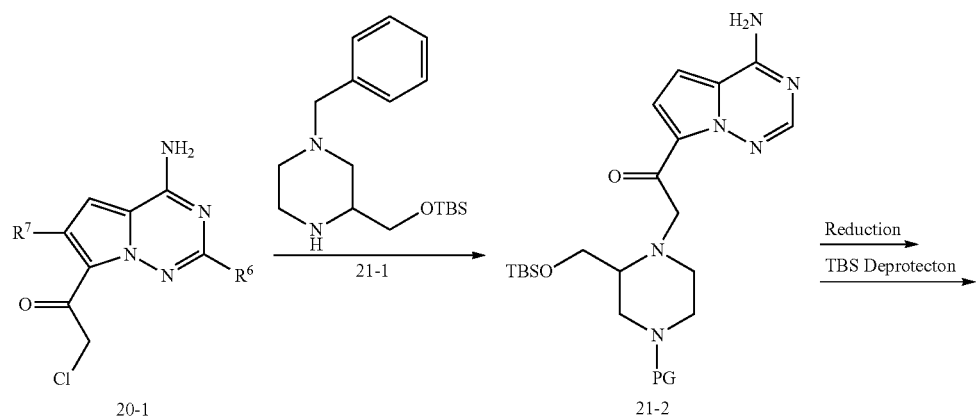
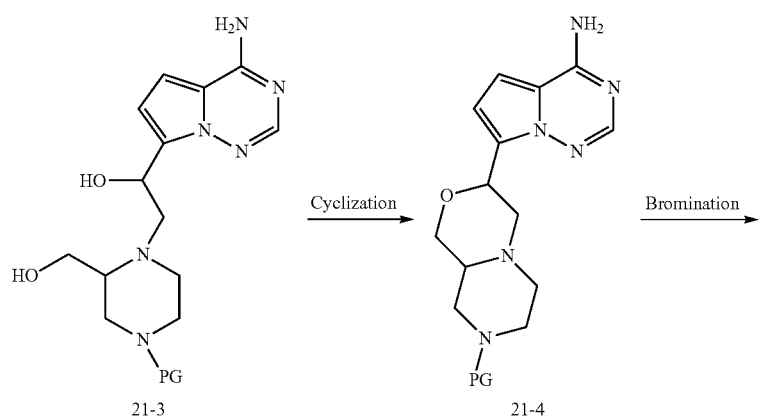
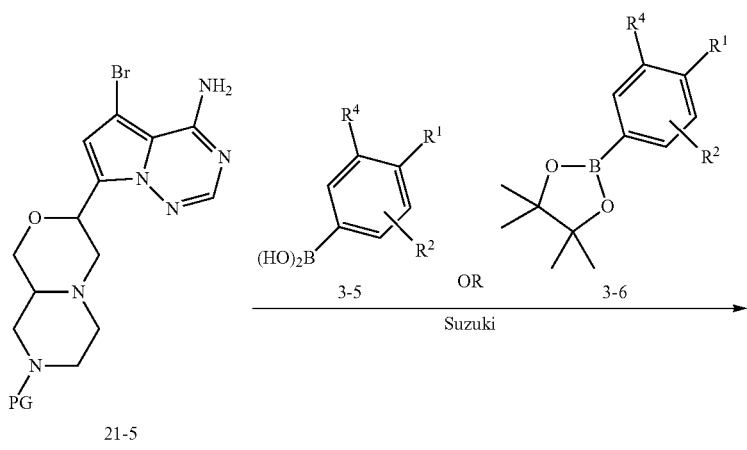

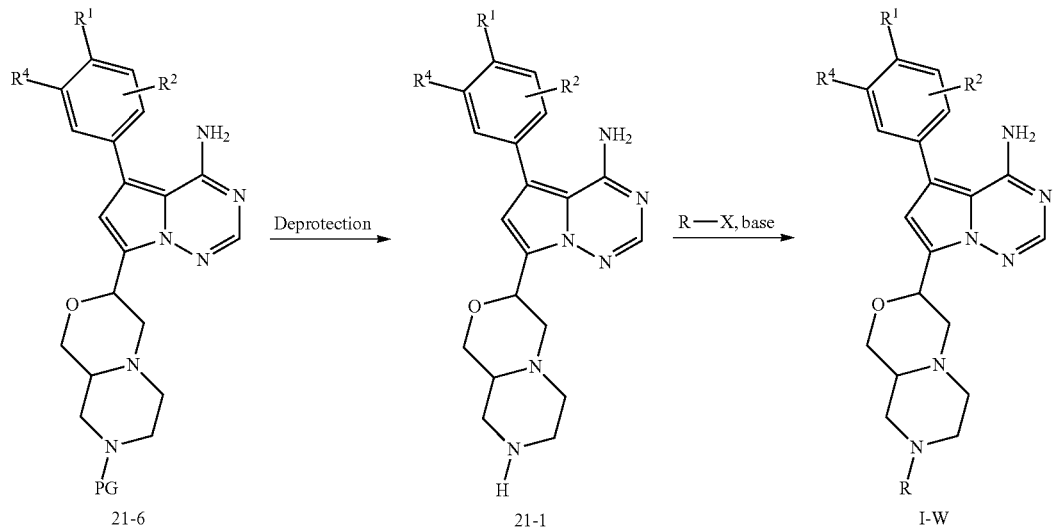

The compounds of formula I-W are prepared according to reaction sequences shown in Scheme 21. Thus, treatment of compound of formula 20-1 with a secondary amine of formula 21-1 presented in the literature (*J. Med. Chem.*, 1993, 36, 2075) in the presence of a suitable base, such as potassium carbonate, and a suitable catalyst such as potassium iodide in a solvent such as DMF or the like provides compounds with the Formula 21-2. Treatment of compounds of formula 21-2 with a suitable reducing agent, preferably DIBAL-H, in a suitable solvent, such as tetrahydrofuran, results in the reduction of the ketone and subsequent deprotection of the primary alcohol, providing diols of formula 21-3. Cyclization of 21-3 with a suitable acid, such as methanesulfonic acid or the like in a solvent such as dichloromethane or the like affords formula 21-4. Bromination of 21-4 with a suitable brominating reagent, such as 1,3-dibromo-5,5-dimethylhydantoin or the like in an appropriate solvent, such as DMF or the like provides 21-5. Suzuki coupling of 21-5 with boronic acids such as 3-5 or boronates such as 3-6 under conditions well known in the art provides compounds of formula 21-6. Removal of the protecting group using conditions known in the art provides compounds of Formula 21-7. Conversion of 21-7 to compounds of formula I-W (where X is a suitable leaving group) can be carried out by methods known in the art. For example, reaction of compounds of the formula 21-7 with an appropriate alkylating agent, such as iodomethane in the presence of a base such as potassium carbonate or the like provides compounds of the formula I-W in which R is an alkyl group. Also, the reaction of compounds of the formula 21-7 with an appropriate sulfonylating agent, such as methansulfonyl chloride or the like Scheme 22

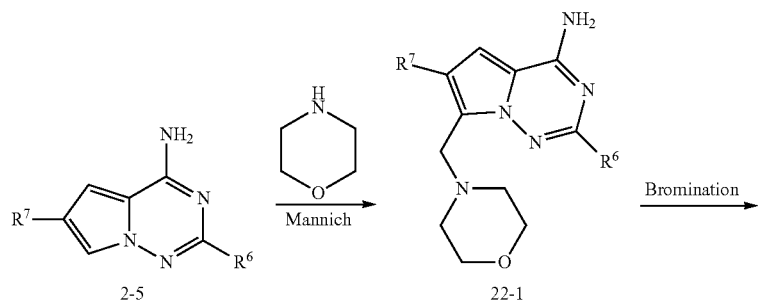

-continued

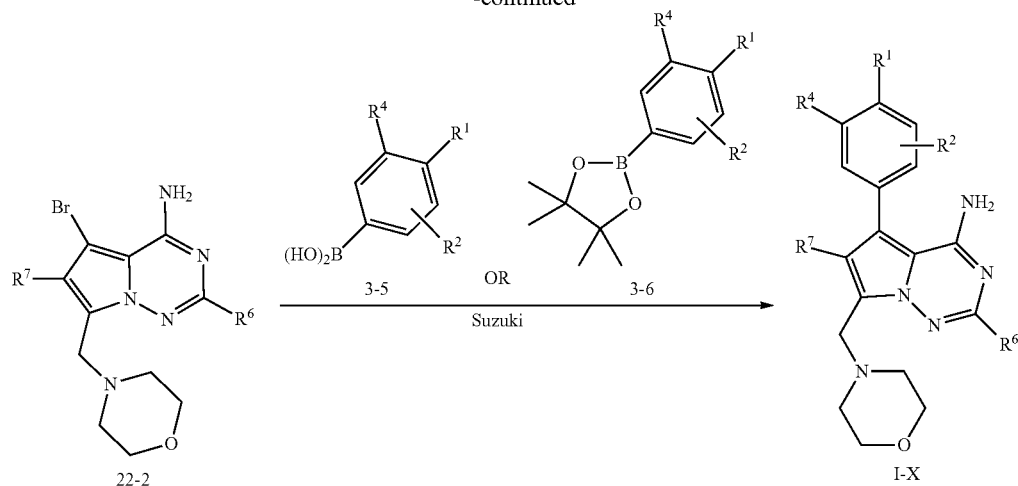

provides compounds of the formula I-W in which R is an alkylsulfonyl group. Moreover, the reaction of compounds of the formula 21-7 with an appropriately functionalized carboxylic acid, a suitable coupling reagent, such as BOP or the like, and a suitable base, such as triethylamine or the like in a suitable solvent such as DMF and the like affords compounds of the formula I-W in which R is an amide.

The compounds of formula I-X are conveniently prepared according to reaction sequences shown in Scheme 22. Thus, a compound of Formula 2-5 can be converted to 22-1 by treatment with morpholine and formaldehyde in the presence of an acid, such as acetic acid or the like. Bromination of 22-1 with a suitable brominating reagent, such as 1,3-dibromo-5,5-dimethylhydantoin or the like in an appropriate solvent, such as DMF or the like provides formula 22-2. Suzuki coupling of 22-2 with boronic acids such as 3-5 or boronates such as 3-6 under conditions well known in the art provides compounds of formula I-X.

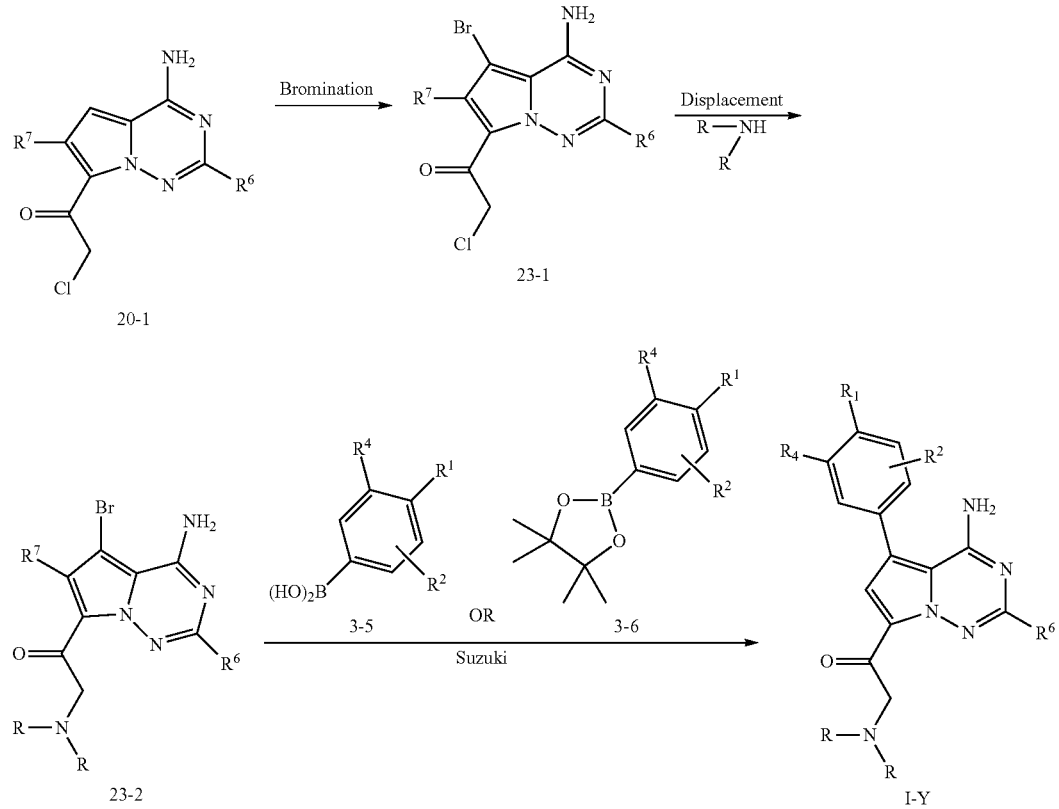

The compounds of Formula I-Y are conveniently prepared according to reaction sequences shown in Scheme 23. Thus, a compound of formula 20-1 can be treated with a suitable brominating reagent, such as 1,3-dibromo-5,5-dimethylhydantoin or the like in an appropriate solvent, such as DMF or the like to provide 23-1. Compounds of formula 23-1 can be treated with excess of an appropriate amine, such as morpholine or the like in an appropriate solvent, such as DMF or the like to provide 23-2. Suzuki coupling of compounds of formula 23-2 with boronic acids such as 3-5 or boronates such as 3-6 under conditions well known in the art provides compounds of formula I-V.

24-1 with a boronic acid such as 3-5 or a boronate such as 3-6 provides compounds of formula 24-2. Treatment of 24-2 with a brominating reagent such as 1,3-dibromo-5,5-dimethylhydantoin or the like in a suitable solvent such as DMF will provide 24-3. Suzuki coupling of 24-3 with a suitable boronate ester prepared by methods known in the literature (Eastwood, P. R., *Tetrahedron Letters,* 2000, 41, 3705) will generate compounds of formula 24-4. The protecting groups used until this point in the sequence can then be removed under various well-precedented procedures (acid-catalyzed removal of BOC carbamates, e.g.), and free amines of for-

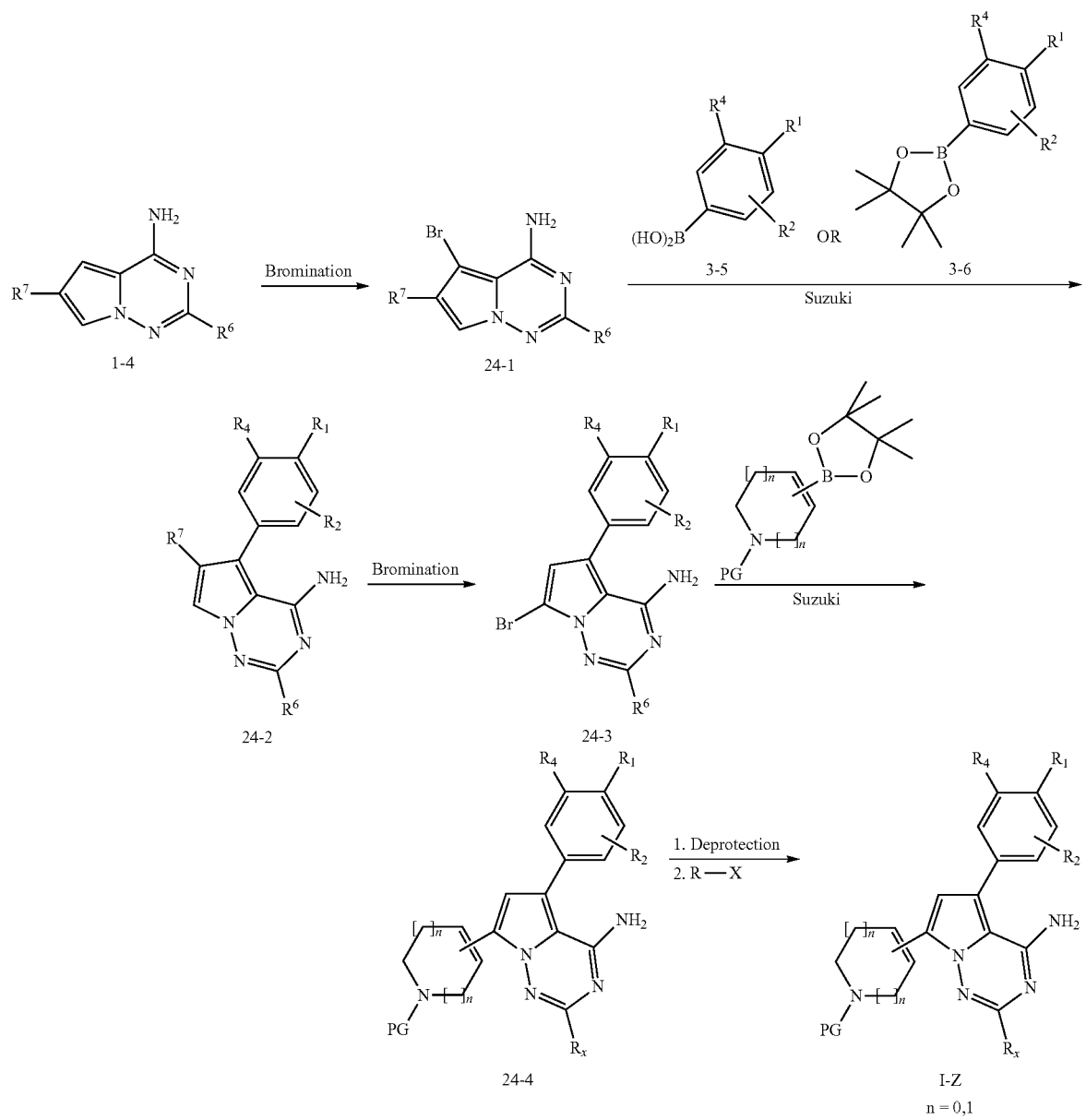

Scheme 24

Scheme 24 illustrates the preparation of compounds of formula I-Z. Treatment of compounds of formula 1-4 with a brominating reagent such as 1,3-dibromo-5,5-dimethylhydantoin or the like in a suitable solvent such as chloroform will provide compounds of formula 24-1. Suzuki coupling of mula I-Z can be converted to N-substituted compounds of formula I-Z by reaction with a suitable electrophile (where X is a suitable leaving group). For example, with an appropriate alkylating agent in the presence of a suitable base, or by the reaction with an Scheme 25
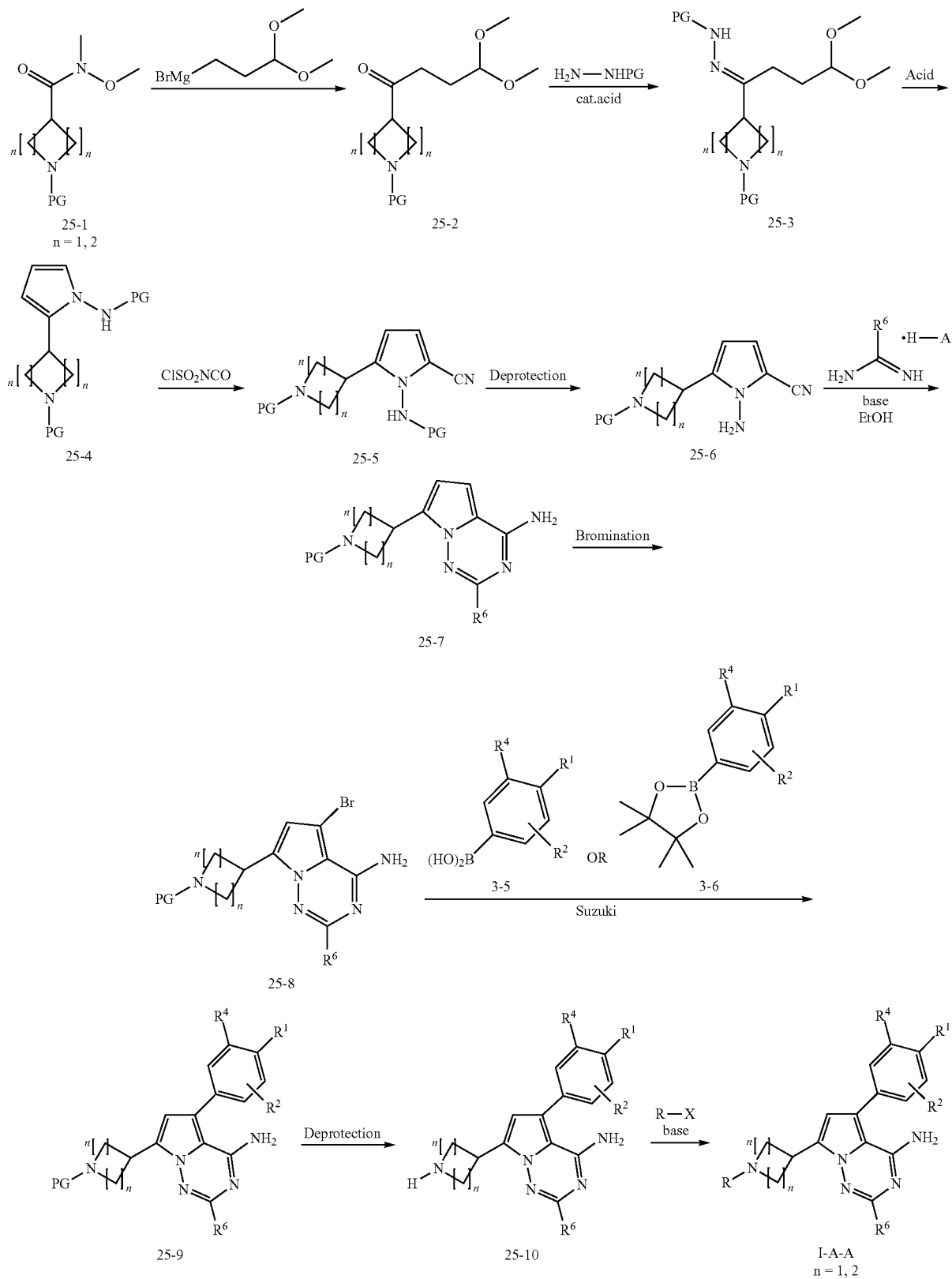

acylating or sulfonating reagent, such as an acyl anhydride, acyl chloride, sulfonyl chloride or the like, in the presence of a suitable base such as pyridine, potassium carbonate, a tertiary amine or the like, in appropriate solvents such as THF, dichloromethane, or others.

The compounds of formula 1-A-A are conveniently prepared according to reaction sequences shown in Scheme 25. Treatment of compounds of formula 25-1 with a Grignard reagent in a solvent such as THF or the like can provide compounds of formula 25-2. Treatment of compounds of formula 25-2 with a suitably protected (e.g. a protecting group well known to those skilled in the art) hydrazine derivative in the presence of an acid such as p-TsOH or the like in a solvent such as 1,4-dioxane or the like provides compounds of formula 25-3. Cyclization of compounds of formula 25-3 in the presence of acid such as acetic acid or the like provides compounds of formula 25-4. Cyanation of compounds of formula 25-4 using chlorosulfonyl isocyanate in a solvent such as acetonitrile or the like provides compounds of formula 25-5. Removal of the protecting group using conditions well known in the art provides compounds of formula 25-6. Reaction of compounds of formula 25-6 with a formamidine reagent in a solvent such as n-BuOH or the like provides compounds of formula 25-7. Bromination of compounds of formula 25-7 with 1,3-dibromo-5,5-dimethylhydantoin or the like in a solvent such as THF or DMF or the like provides compounds of formula 25-8. Suzuki reaction under conditions well known in the art using boronic acids such as 3-5 or boronates such as 3-6 provides compounds of formula 25-9. Removal of the protecting group using conditions well known in the art (acid-catalyzed removal of BOC carbamates, e.g.) provides amines of formula 25-10. The free amines of formula 25-10 can be converted to compounds of formula 1-A-A by reaction with various electrophiles. For example, with an appropriate alkylating agent in the presence of a suitable base, or by the reaction with an acylating or sulfonating reagent, such as an acyl anhydride, acyl chloride, sulfonyl chloride or the like, in the presence of a suitable base such as pyridine, potassium carbonate, a tertiary amine or the like, in appropriate solvents such as THF, dichloromethane, or others.

Scheme 26

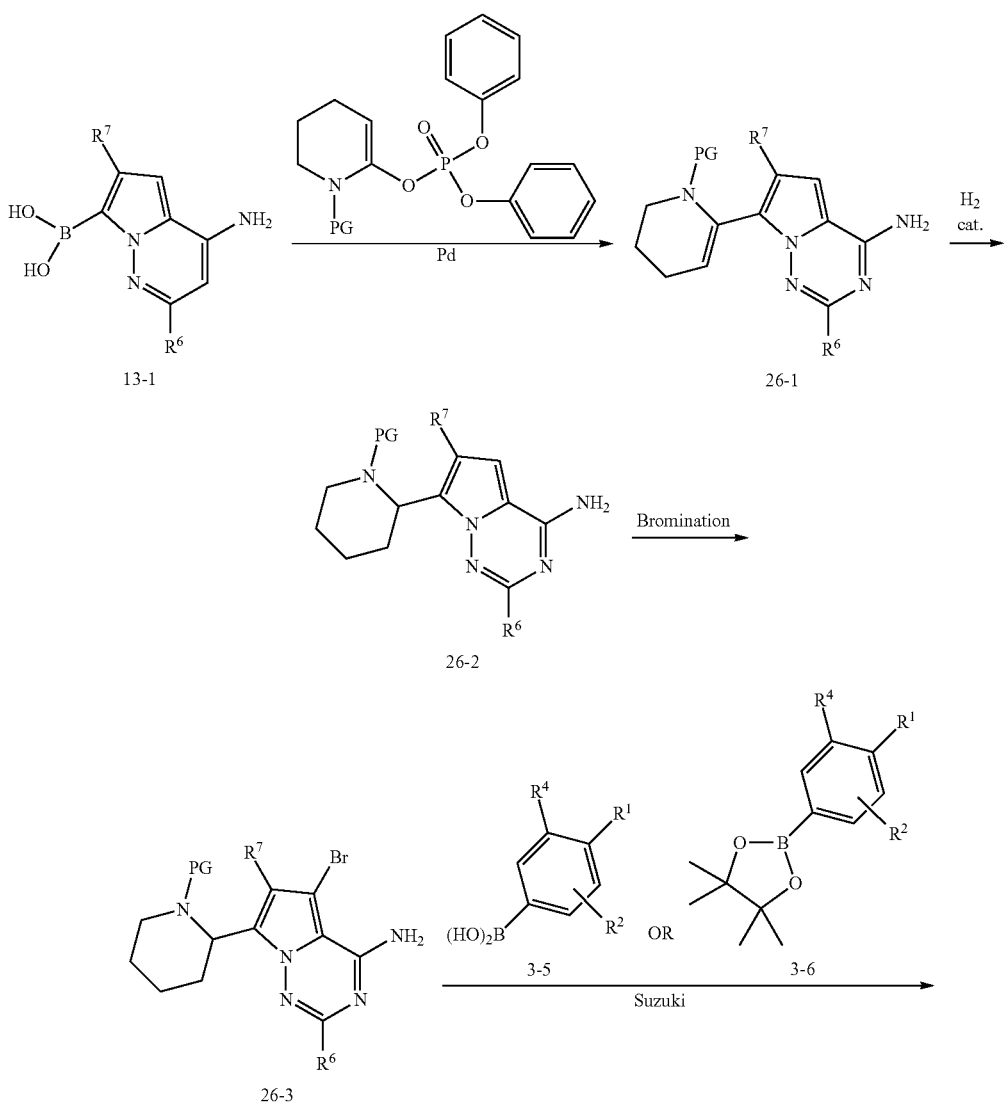

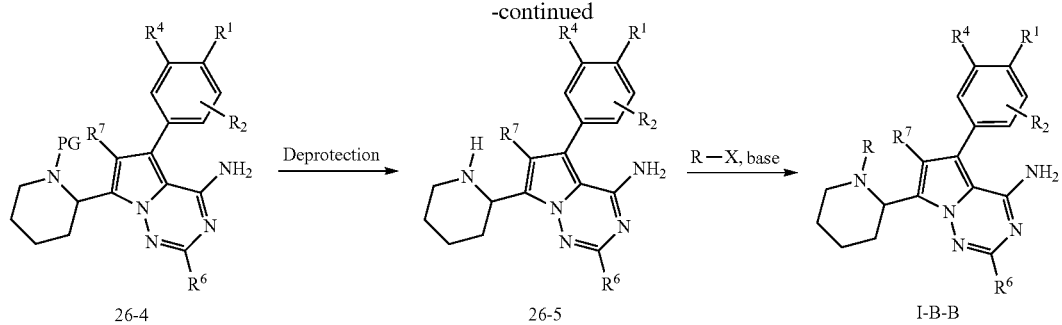

Scheme 26 illustrates the preparation of compounds of Formula I-B-B. Suzuki-Miyaura coupling of boronic acids of formula 13-1 with a suitable vinylphosphate known in the literature (method of Occhiato: *J. Org. Chem.*, 2005, 70, 7324) provides compounds of formula 26-1. Reduction of 26-1 with hydrogen and a suitable catalyst such as platinum (IV) oxide provides 26-2. Treatment of 26-2 with a brominating reagent such as 1,3-dibromo-5,5-dimethylhydantoin or the like in a solvent such as DMF will provide compounds of formula 26-3. Suzuki coupling of 26-3 with a boronic acid such as 3-5 or a boronate such as 3-6 under conditions known to those skilled in the art provides compounds of formula 26-4. The protecting group (PG) of 26-4 can be removed by methods known in the art to give free amines of formula 26-5. Conversion of 26-5 to compounds of formula I-B-B (where X is a suitable leaving group) can be carried out by methods known in the art, and described in Scheme 25.

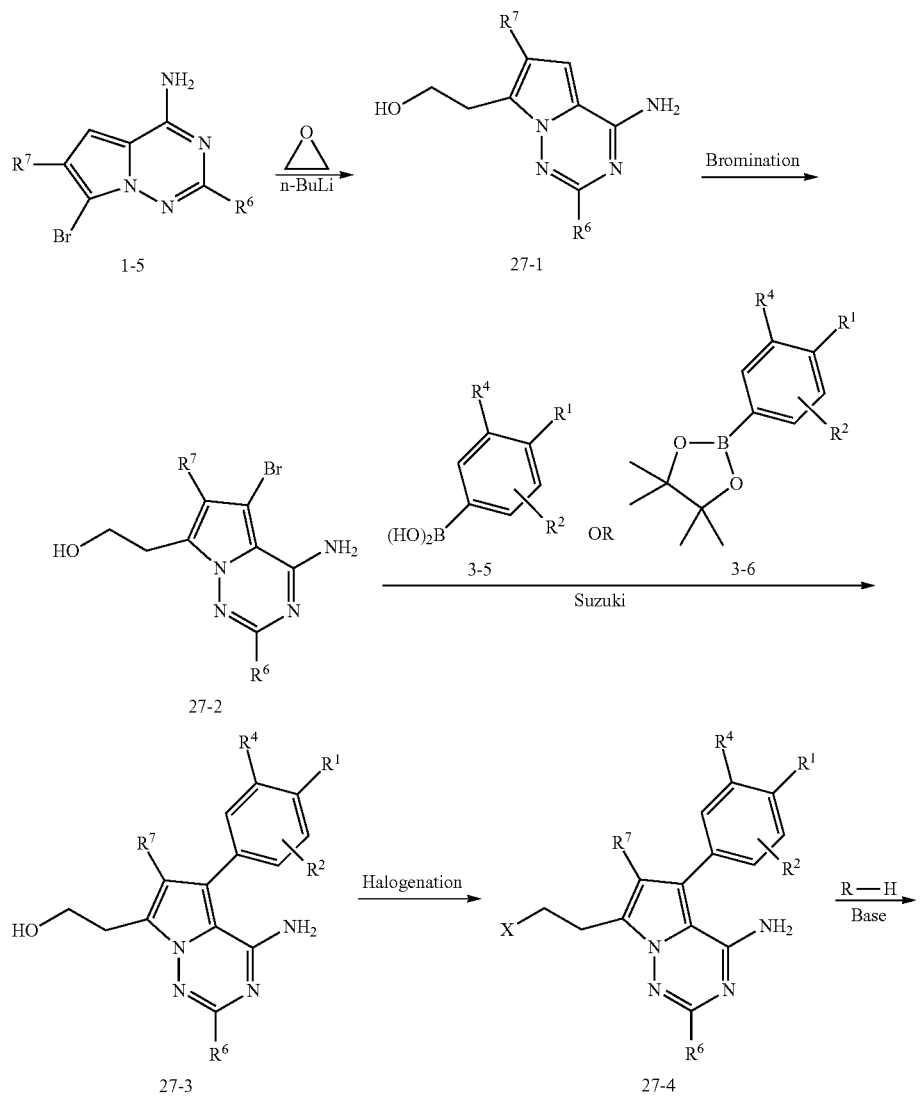

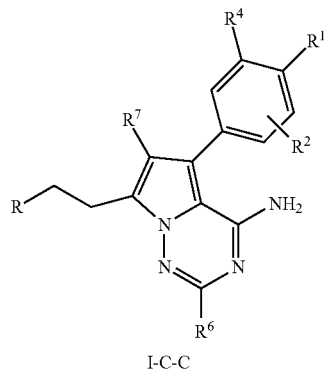

I-C-C

Scheme 27 illustrates the preparation of compounds of Formula (I-C-C). Metallation of bromides of formula 1-5 with a suitable base such as n-butyllithium, followed by treatment with ethylene oxide provides alcohols of formula 27-1. Treatment of 27-1 with a brominating reagent such as 1,3-dibromo-5,5-dimethylhydantoin or the like in a solvent such as DMF provides compounds of formula 27-2. Suzuki coupling of 27-2 with a boronic acid such as 3-5 or a boronate such as 3-6 provides compounds of formula 27-3. Conversion of alcohol 27-3 to the corresponding halogen with a reagent such as bromine in the presence of triphenylphosphine provides compounds of formula 27-4. Conversion of 27-4 to compounds of formula (I-C-C) can be carried out by treatment with an appropriately substituted amine in a suitable solvent such as DMF and in the presence of a base such as potassium carbonate.

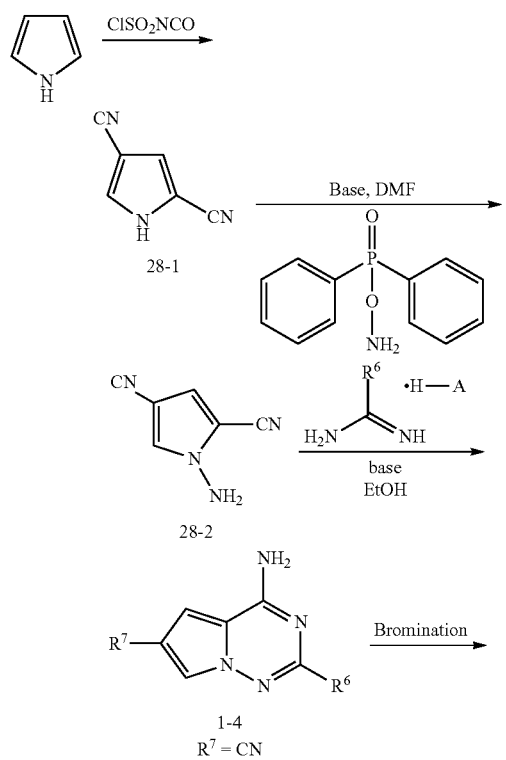

Scheme 28

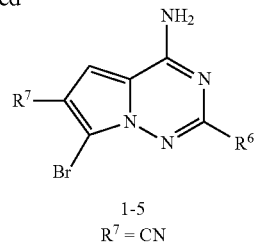

1-5
R$^7$ = CN

Scheme 28 illustrates the preparation of compounds of formula 1-5. Treatment of commercially available pyrrole with chlorosulfonylisocyanate and DMF in a suitable solvent such as dichloromethane yields the bis-cyanopyrrole of Formula 28-1. Conversion of 28-1 to 28-2 can be carried out by treatment with a base, such as sodium hydride, and an aminating reagent, preferably O-diphenylphosphinylhydroxylamine in a solvent such as DMF. Cyclization of 28-2 to heterocycles of formula 1-4 proceeds upon treatment with an appropriate formamidine derivative (in which R$^6$ is defined as above) in the presence of a base such as potassium phosphate. Conversion of 1-4 to compounds of formula 1-5 can be accomplished by treatment with a brominating reagent such as 1,3-dibromo-5,5-dimethylhydantoin or the like in a solvent such as DMF.

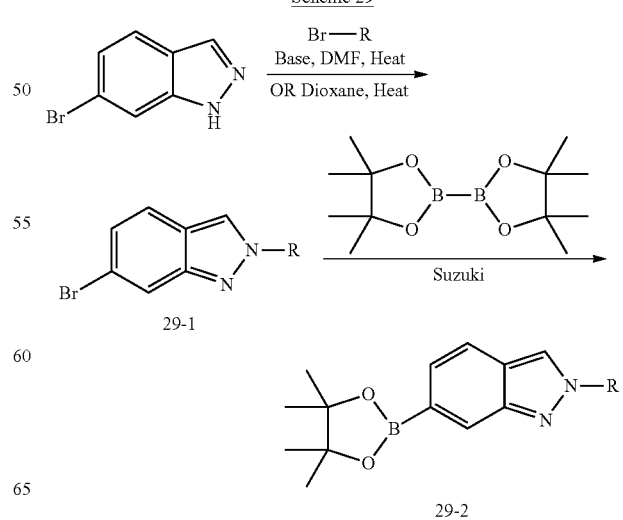

Scheme 29 illustrates the preparation of compounds of formula 29-2. Treatment of 6-bromoindazole with a suitable 1° bromide, preferably in the absence of base and in a solvent such as dioxane provides C-2 alkylated compounds of formula 29-2. Conversion of 29-1 to boronates of formula 29-2 can be carried out by treatment with bis(pinacolato)-diboron in the presence of palladium catalyst, preferably 1,1'-bis (diphenylphosphino)ferrocenepalladium(II) chloride, and with potassium acetate as a base.

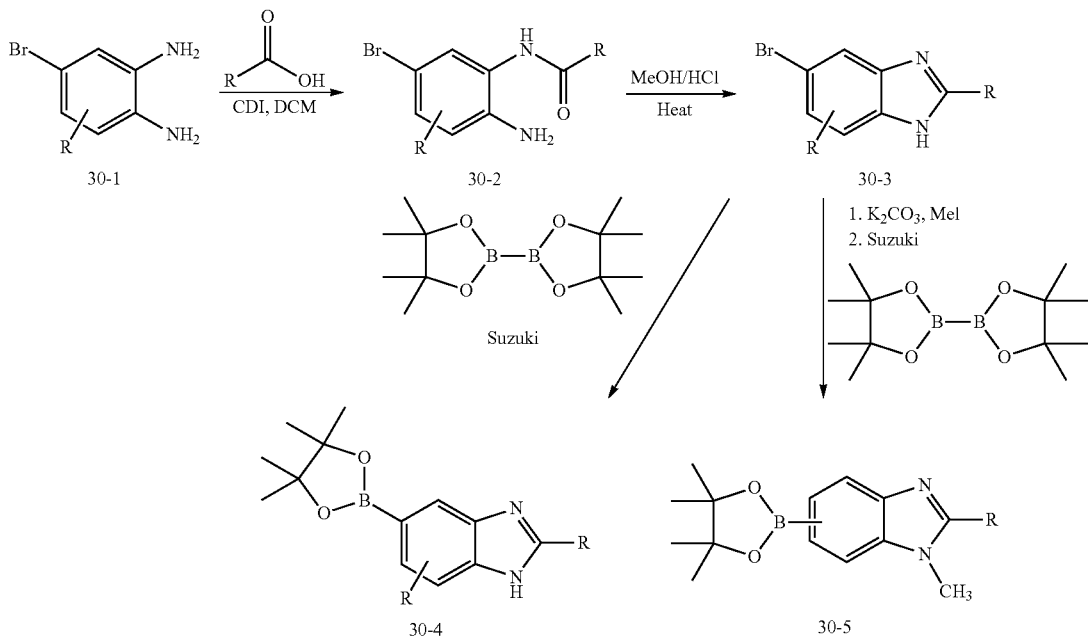

Scheme 30 illustrates the preparation of the benzimidazole compounds of formula 30-4 and formula 30-5. Treatment of compounds of formula 30-1 with an appropriate phenylacetic acid and a coupling reagent such as carbonyldiimidazole in a solvent such as dichloromethane provides amides of formula 30-2. Cyclization of 30-2 to yield benzimidazoles of formula 30-3 can be carried out by treatment with an acid such as HCl, in a solvent such as MeOH. Conversion of 30-3 to boronates of formula 30-4 can be carried out by treatment with bis (pinacolato)-diboron in the presence of palladium catalyst, preferably 1,1'-bis(diphenylphosphino)ferrocenepalladium (11) chloride, and with potassium acetate as a base. Alternatively, 30-3 can be converted to an N-methylated compounds of formula 30-5 by first treating with iodomethane in the presence of a base, preferably potassium carbonate, followed by conversion to the boronate using the same conditions used for 30-4, providing compounds of formula 30-5 as a mixture of regioisomers.

Compounds of the present invention exhibit useful pharmacological and pharmacokinetic properties. They can therefore be useful for the treatment or prevention of disorders in humans and animals, especially Cancer.

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound Of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypothalamic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

In another embodiment, the present invention provides a pharmaceutical composition comprising at least one compound according to the invention. In another embodiment, the present invention provides a pharmaceutical composition comprising at least one compound according to the invention together with one or more pharmacologically safe excipient or carrier substances. In a further embodiment, the present invention provides the use of said compound and composition for the treatment of a disease, as well as a method of treating a disease by administering to a patient a therapeutically effective amount of said compound or composition.

The active compound can act systemically, locally or both. For this purpose it can be administered in a suitable manner, such as for example by oral, parenteral, pulmonary, nasal, sublingual, lingual, buccal, rectal, dermal, transdermal, conjunctival or aural administration or in the form of an implant or stent. The active compound can be administered in forms suitable for these modes of administration.

Suitable forms of oral administration are those according to the prior art which function by releasing the active compound rapidly or in a modified or controlled manner and which contain the active compound in a crystalline, amorphous, or dissolved form, for example tablets (which can be uncoated or coated, for example with enteric coatings or coatings which dissolve after a delay in time or insoluble coatings which control the release of the active compound), tablets or films (wafers), which disintegrate rapidly in the oral cavity, films/lyophilisates, capsules (e.g. hard or soft gelatin capsules), dragées, pellets, powders, emulsions, suspensions and solutions. An overview of application forms is given in Remington's Pharmaceutical Sciences, 18$^{th}$ ed. 1990, Mack Publishing Group, Enolo.

Parenteral administration can be carried out by avoiding an absorption step (e.g. by intravenous, intraarterial, intracardial, intraspinal or intralumbar administration) or by including absorption (e.g. by intramuscular, subcutaneous, intracutaneous or intraperitoneal administration). Suitable parenteral administration forms are for example injection and infusion formulations in the form of solutions, suspensions, emulsions, lyophilisates and sterile powders. Such parenteral pharmaceutical compositions are described in Part 8, Chapter 84 of Remington's Pharmaceutical Sciences, 18$^{th}$ ed. 1990, Mack Publishing Group, Enolo.

Suitable forms of administration for the other modes of administration are for example inhalation devices (such as for example powder inhalers, nebulizers), nasal drops, solutions and sprays; tablets or films/wafers for lingual, sublingual or buccal administration or capsules, suppositories, ear and eye preparations, vaginal capsules, aqueous suspensions (lotions or shaking mixtures), lipophilic suspensions, ointments, creams, transdermal therapeutic systems, milky lotions, pastes, foams, dusting powders, implants or stents.

The active compounds can be converted into the above mentioned forms of administration in a manner known to the skilled man and in accordance with the prior art using inert, non-toxic, pharmaceutically suitable auxiliaries. The latter include for example excipients (e.g. microcrystalline cellulose, lactose, mannitol, etc.), solvents (e.g. liquid polyethylene glycols), emulsifiers and dispersants or wetting agents (e.g. sodium dodecyl sulfate, polyoxysorbitan oleate etc.), binders (e.g. polyvinyl pyrrolidone), synthetic and/or natural polymers (e.g. albumin), stabilizers (e.g. antioxidants, such as, for example, ascorbic acid), dyes (e.g. inorganic pigments such as iron oxides) or taste- and/or odor-corrective agents.

In general it has proven advantageous to administer daily quantities of approximately from 0.001 to 300 mg/kg body weight, and preferably approximately from 0.010 to 100 mg/kg mg/kg body weight in order to obtain effective results.

It may however be necessary to deviate from the above-mentioned quantities, depending on the body weight, mode of administration, the individual patient response to the active compound, the type of preparation and the time or interval of administration.

If used as active compounds, the compounds according to the invention are preferably isolated in more or less pure form, that is more or less free from residues from the synthetic procedure. The degree of purity can be determined by methods known to the chemist or pharmacist (see Remington's Pharmaceutical Sciences, 18$^{th}$ ed. 1990, Mack Publishing Group, Enolo). Preferably the compounds are greater than 99% pure (w/w), while purifies of greater than 95%, 90% or 85% can be employed if necessary.

The percentages in the tests and examples which follows are, unless otherwise stated, by weight (w/w); parts are by weight. Solvent ratios, dilution ratios and concentrations reported for liquid/liquid solutions are each based on the volume.

A. EXAMPLES

List of Abbreviations and Acronyms

ACN acetonitrile
AcOH acetic acid
aq. aqueous
atm atmosphere(s)
Biotage® silica gel chromatographic system, Biotage Inc.
Isco® silica gel chromatographic system, Isco Inc.
t-BOC tert-butoxycarbonyl
BOP benzotriazol-1-yloxy-tris(dimethylamino)phosphonium hexafluorophosphate
BSA bovine serum albumin
n-BuLi n-butyllithium
calcd calculated
Cbz carbobenzyloxy CDI carbonyl diimidazole
Celite® diatomaceous earth filter agent, Celite Corp.
conc concentrated
d doublet
dd doublet of doublets
ddd doublet of doublet of doublets
dppf (diphenylphosphino)ferrocene
DCE dichloroethane
DCM dichloromethane
Di EA N,N-diisopropylethylamine
DIBAL-H diisobutylaluminum hydride
DMF N,N-dimethylformamide
DMSO dimethylsulfoxide
DMSO-$d_6$ dimethylsulfoxide-$d_6$
DTT dithiothreitol
EDCl 1-(3-dimethylaminopropyl)-3-ethylcarbodiimide hydrochloride
EDTA ethylenediamine tetraacetic acid
EI-MS electron impact mass spectrometry
ES-MS electrospray mass spectrometry
EtN(iPr)$_2$ N,N-diisopropylethylamine
EtOAc ethyl acetate
EtOH ethanol
Et$_2$O diethyl ether
GC/MS gas chromatography/mass spectrometry
GHLF silica gel G hard layer fluorescent (TLC plates)
GST glutathione-S-transferase
h hour, hours
$^1$H NMR proton nuclear magnetic resonance
HEPES 4-(2-hydroxyethyl)-1-piperazineethanesulfonic acid
HOBt N-hydroxybenzotriazole
HPLC high performance liquid chromatography
IPA isopropyl alcohol
J coupling constant (NMR spectroscopy)
LC liquid chromatography
LC-MS liquid chromatography-mass spectrometry
m multiplet
M molar
MeCN acetonitrile
MeOH methanol
Me$_4$Si tetramethylsilane
min minute, minutes
MPLC medium-pressure liquid chromatography
MS mass spectrum, mass spectrometry
m/z mass-to-charge ratio
NBS N-bromosuccinimide
N normal
NMP N-methylpyrrolidine
OAc acetate
OMe methoxy, methoxide
$R_f$ retention factor (TLC)
RB Round bottom flask
RP-HPLC reversed-phase HPLC
RT retention time (HPLC)
rt room temperature
s singlet
SPA scintillation proximity assay
t triplet
TBDMS t-butyldimethylsilyl
THF tetrahydrofuran
TFA trifluoroacetic acid
TLC thin layer chromatography
UV ultraviolet
v/v volume per volume
w/v weight per volume
w/w weight per weight General Information Mass spectra Electron impact mass spectra (EI-MS) were obtained with a Hewlett Packard 5973 mass spectrometer equipped Hewlett Packard 6890 Gas Chromatograph with a J & W HP-5 column (0.25 uM coating; 30 m×0.32 mm, Agilent Technologies, Palo Alto, Calif., USA). The ion source was maintained at 250° C. and Spectra were scanned from 50-550 amu at 0.34 sec per scan.

HPLC—electrospray mass spectra (HPLC ES-MS) were obtained using a Hewlett-Packard 1100 HPLC (Agilent Technologies, palo Alto, Calif., USA) equipped with a quaternary pump, a variable wavelength detector set at 254 nm, a Sunfire C-18 column (2.1×30 mm, 3.5 micron, Waters Corp., Milford, Mass., USA), a Gilson autosampler (Gilson Inc., Middleton, Wis., USA) and a Finnigan LCQ ion trap mass spectrometer with electrospray ionization (Thermoelctron Corp., San Jose, Calif., USA). Spectra were scanned from 120-1200 amu using a variable ion time according to the number of ions in the source. The eluents were A: 2% acetonitrile in water with 0.02% TFA and B: 2% water in acetonitrile with 0.018% TFA. Gradient elution from 10% B to 95% over 3.5 minutes at a flowrate of 1.0 mL/min was used with an initial hold of 0.5 minutes and a final hold at 95% B of 0.5 minutes. Total run time was 6.5 minutes.

NMR Spectra

Routine one-dimensional NMR spectroscopy was performed on 300 MHz or 400 MHz Varian Mercury-plus spectrometers (Varian Inc., Palo Alto, Calif., USA). The samples were dissolved in deuterated solvents obtained from Cambridge Isotope Labs (Cambridge Mass., USA), and transferred to 5 mm ID Wilmad NMR tubes (Wilmad Glassworks, Inc., Buena, N.J., USA). The spectra were acquired at 293° K. The chemical shifts were recorded on the ppm scale and were referenced to the appropriate solvent signals, such as 2.49 ppm for DMSO-$d_6$, 1.93 ppm for CD$_3$CN, 3.30 ppm for CD$_3$OD, 5.32 ppm for CD$_2$Cl$_2$, and 7.26 ppm for CDCl$_3$ for $^1$H spectra; and 39.5 ppm for DMSO-$d_6$, 1.3 ppm for CD$_3$CN, 49.0 ppm for CD$_3$OD, 53.8 ppm for CD$_2$Cl$_2$ and 77.0 ppm for CDCl$_3$ for $^{13}$C spectra.

Flow-NMR Method 150-200 uL of a 10 mM solution of the compound in dimethyl sulfoxide (DMSO) is pipetted using a Tecan into a 96-well deep well microtiter plate. The plate is placed into a Genevac Speedvac to evaporate the compounds to dryness. Dimethyl sulfoxide-$d_6$ (DMSO-$d_6$), 500 ul, is added to each well containing dry compound. The compounds are dissolved by repetitively aspirating with a multipipettor.

All NMR spectra were acquired using the Bruker DPX400 Spectrometer operating at 400.23 MHz for $^1$H and 100.63 MHz for $^{13}$C. The spectrometer was equipped with a Gilson 215 liquid handling system and a Valvemate accessory. The NMR probe was a dual cell $^1$H, $^{13}$C 4 mm flow probe with Z gradient capabilities. Proton spectra were acquired using a double presaturation pulse sequence that included carbon decoupling. The Gilson 215 liquid handling system was set up to inject 350 ul from each well. In between sample injections, the NMR flow probe was washed with 250 ul DMSO-$d_6$. The data is processed by utilizing NMR Manager (Advanced Chemical Development, Inc (ACD)) V8.0. In some instances the signals using this method are weaker in intensity, broadened, or absent due to solvent suppression.

Preparation of Key Intermediates

Intermediate A: Preparation of Pyrrolo[2,1-f[]1,2,4]triazin-4-ylamine

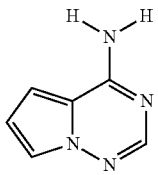

Step 1: Preparation of Pyrrol-1-yl-carbamic acid tert-butyl ester

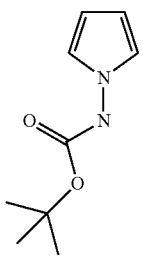

A flask (fitted with a Dean-Stark trap) containing a stirred solution of tert-butylcarbazate (100, 0.757 mol), 2,5-dimethoxytetrahydrofuran (108 g, 0.832 mol) and 2N HCl (10 mL) in 1,4-dioxane (700 mL) was heated under nitrogen at 90° C. As the reaction progressed over several hours, the solution changed from pale yellow to orange and began to reflux. The reaction was monitored by the amount of distillate collected in the D/S trap (primarily $CH_3OH$, 2 moles/1 mole reagent). As methanol collection approached the theoretical amount (50 mL) a sample was analyzed by TLC (silica gel, GHLF, 1:3 EtOAc/hexane, ninhydrin stain) to confirm reaction completion. Heating was shut off and the reaction was allowed to cool somewhat before adding saturated sodium bicarbonate solution (~25 mL) to neutralize the hydrochloric acid. The quenched mixture was filtered through a sintered-glass funnel and concentrated in vacuo to leave an orange, semi-solid residue. The residue was suspended in diethyl ether (minimum volume) and the nearly colorless solids were collected by suction filtration, washed with hexane and air-dried to afford 60.2 g (40%) of product. A second crop (yellow-tan solids) from the mother liquors was isolated: 29.0 g, (19%). Additional material which was present in the mother liquors could be recovered by silica gel chromatography to increase the yield.

$^1$H-NMR ($CD_3OD$): δ 10.23 (br s, 1H), 6.66 (t, 2H, J=2.2 Hz), 5.94 (t, 2H, J=2.2), 1.42 (s, 9H); MS: GC/MS (+esi): m/z=182.9 [MH]$^+$

Step 2: Preparation of (2-Cyano-pyrrol-1-yl)-carbamic acid, tert-butyl ester

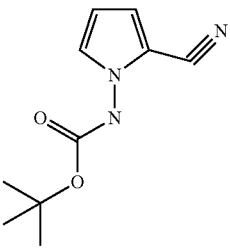

A 2 L, 3-neck RB was fitted w/stir bar, N2 inlet, rubber septum low-temp. thermometer and ice/acetone cooling bath. Pyrrol-1-yl-carbamic acid tert-butyl ester (99.0 g, 0.543 mol) was added to the reactor, dissolved w/anhydrous acetonitrile (700 mL) and the stirred solution was cooled to 0° C. Chlorosulfonyl isocyanate (49.7 mL, 0.57 mol) was added dropwise via syringe (maintaining an internal temperature below 5° C.); after ~20 minutes a suspension was observed. After 45 minutes N,N-dimethylformamide (anhydrous, 100 mL) was added dropwise via addition funnel (keeping internal temp. below 5° C.) and the reaction mixture became a solution. Stirring @ 0° C. was continued for 45 minutes, then the reaction was allowed to warm to RT; monitoring by TLC (silica gel, 1:3 ethyl acetate/hexane, UV, ninhydrin stain) of a quenched sample indicated that the reaction had progressed to completion. The mixture was poured onto ice (~2 L) and stirred with addition of EtOAc (2 L). The layers were separated and the organic layer was dried over magnesium sulfate. The dried solution was filtered through a pad of 30/40 Magnesol and the filtrate was concentrated to dryness in vacuo, then the residue was dissolved in a minimum volume of dichloromethane and chromatographed on a plug of silica gel, eluting with ethyl acetate/hexane, 0-50% ethyl acetate. The clean, product-containing fractions were combined and concentrated to dryness in vacuo, to afford the desired product as a white solid, 69.8 g (62%). A somewhat impure fraction provided additional material, 16.8 g (15%), bringing the total recovery to 86.6 g, (77%). $^1$H-NMR ($CD_3OD$): δ 7.01 (dd, 1H, J=3.0, 1.6 Hz), 6.82 (dd, 1H, J=4.4, 1.7 Hz), 6.19 (dd, 1H, J=4.2, 2.9 Hz), 4.88 (s, 1H, $H_2O$+NH–), 1.50 (br s, 9H, HN—BOC); MS: LC/MS (+esi), m/z=207.9 [M+H]

Step 3: Preparation of 1-Amino-1H-pyrrole-2-carbonitrile hydrochloride

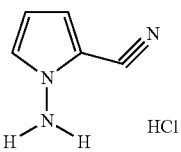

A 3 L, 3-neck RB flask was fitted with a mechanical stirrer, nitrogen inlet, thermocouple/JKEM thermocontroller, addition funnel and ice water cooling bath. (2-Cyano-pyrrol-1-yl)-carbamic acid, tert-butyl ester (85 g, 0.41 mol) was added and dissolved with 1,4-dioxane (400 mL), then the stirred orange solution was cooled to 0° C. and HCl/dioxane (4N, 820 mL, 8 eq.) was slowly added from the addition funnel, maintaining an internal temperature below 5° C. After ~30 minutes the solution became cloudy and stirring @ room temperature was continued for 5 hours; the reaction was monitored for completion by TLC (silica gel, GHLF, 1:3 EtOAc/hexane, UV; Note: the free base may be observed as a high-Rf spot and can be misinterpreted as incomplete reaction). The reaction mixture was diluted with diethyl ether (2 L) and the precipitated solids were collected by suction filtration and washed with ether (1 L). Drying (vacuum oven @ 50° C.) afforded the desired product as 50.5 g (85%) of a tan solid. $^1$H-NMR (CD$_3$OD): δ 7.05 (dd, 1H, J=2.8, 1.9 Hz), 6.75 (dd, 1H, J=1.8, 4.2 Hz), 6.13 (dd, 1H, J=2.8, 4.4 Hz), 5.08 (s, 3H, NH$_3^+$); MS: GC/MS, m/z=1082 [M+H].

Step 4: Preparation of the Title Compound

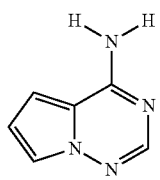

To a stirred suspension of 1-Amino-1H-pyrrole-2-carbonitrile hydrochloride (50 g, 0.35 mol) in absolute ethanol (800 mL) was added formamidine acetate (181.3 g, 1.74 mol) and potassium phosphate (370 g, 1.74 mol). The suspension was heated for 18 hours @ 78° C. (under N$_2$), then cooled, filtered and concentrated to dryness in vacuo. The residue was mixed with ice water (2 L) and the dark grayish-brown solids were collected by suction filtration. The filter cake was washed with water, sucked dry and the solids were dissolved (on the funnel) with hot ethyl acetate and filtered into a collection vessel. The dark solution was filtered through a long plug of 30/40 Magnesol and the pale yellow filtrate was concentrated to dryness In vacuo to afford a yellow-tinged solid (20.6 g, 44.1% yield). The plug was washed with ethyl acetate/ethanol and the washings were concentrated in vacuo to afford additional material, 10.7 g (23%). Extraction of the aqueous work-up filtrate with ethyl acetate followed by drying, Magnesol filtration and concentration gave another 6.3 g (14%) of clean product, bringing the total recovery to 37.6 g (81%). $^1$H-NMR (CD$_3$OD): δ 7.72 (s, 1H), 7.52 (dd, 1H, J=2.5, 1.6 Hz), 6.85 (dd, 1H, J=4.5, 1.6 Hz), 6.64 (dd, 1H, J=4.5, 2.7 Hz) LC/MS (+esi): m/z=135.1 [M+H].

Intermediate B: Preparation of 7-Bromo-pyrrolo[2,1-f][1,2,4]triazin-4-ylamine

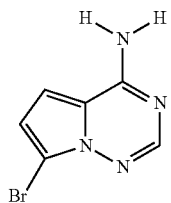

A stirred solution containing Intermediate A (21.0 g, 0.157 mol) in anhydrous DMF (200 mL) was cooled to −20° C. and 1,3-dibromo-5,5-dimethylhydantoin (22.4 g, 0.078 mol) was added portionwise over ~45 minutes. The reaction was stirred for another 45 minutes and monitored for completion by TLC (silica gel, GHLF, 5% CH$_3$OH/CH$_2$Cl$_2$). Saturated Na$_2$SO$_3$ solution (300 mL) was added, the resulting suspension was stirred and the solids were collected by suction filtration. The filter cake was washed with water, dried by suction and then partitioned between ethyl acetate (1 L) and 5% sodium carbonate solution (1 l). The layers were separated, the organic layer was washed with fresh sodium carbonate solution and dried over magnesium sulfate. The filtrate from the work-up was also extracted and combined with the main batch then filtered through a pad of Magnesol and concentrated in vacuo to afford crude mono-bromide, KRAM 206-3-1, 29.9 g, 90% yield. Trituration of a 21.5 g quantity of the crude product in hot ethyl acetate (300 mL, 70 C) provided colorless solids (12.3 g) containing only ~2% of the di-brominated side-product. $^1$H-NMR (CD$_3$OD): δ 7.84 (s, 1H), 6.95 (d, 1H, J=4.7 Hz), 6.71 (d, 1H, J=4.7 Hz), 4.89 (s, 3H, —NH$_2$+H$_2$O); MS: LC/MS (+esi), m/z=213.1 [M+H].

Intermediate C: 2-Benzyl-6-(4,4,5,5-tetramethyl-[1, 3,2]dioxaborolan-2-yl)-2H-indazole

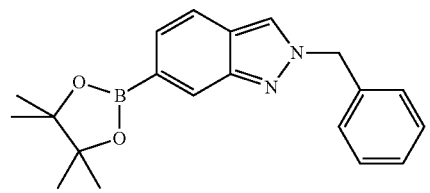 [SMILES: CC1(C)OB(c2ccc3cn(Cc4ccccc4)nc3c2)OC1(C)C]

Step 1: Preparation of 2-Benzyl-6-bromo-2H-indazole

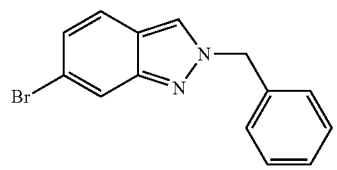 [SMILES: Brc1ccc2cn(Cc3ccccc3)nc2c1]

6-Bromoindazole (14.42 g, 73.2 mmol) was suspended in 50 mL of dioxane and the mixture was treated with benzyl bromide (10.5 mL, 88.8 mmol) and then heated in an oil bath to 120° C. with mechanical stirring overnight. The resulting thick suspension was allowed to cool to 80° C. (bath temp) and 200 mL of EtOAc was added. The mixture was vigorously stirred for 20 minutes and the precipitated orange-brown solid was collected by filtration, washed well with EtOAc and air-dried. The resulting brown solid was partitioned between sat aq. NaHCO$_3$ (100 mL) and EtOAc (300 mL) with stirring until all of the solid material had dissolved. The layers were separated and the aqueous phase was extracted with 2×100 mL of EtOAc. The combined organic phases were washed with brine, dried and filtered and concentrated in vacuo to give a brown solid. Recrystallization of the solid from 200 mL of 2:1 EtOH:water gave 12.78 g (61%) of desired product as tan needles. $^1$H-NMR (DMSO-d$_6$)

δ 8.55 (s, 1H), 7.84 (s, 1H), 7.72 (d, 1H), 7.48-7.28 (m, 5H), 7.13 (d, 1H), 5.62 (s, 2H); LC-MS [M+H]⁺=287.3, 289.0, RT=3.53 min.

Step 2: Preparation of the Title Compound

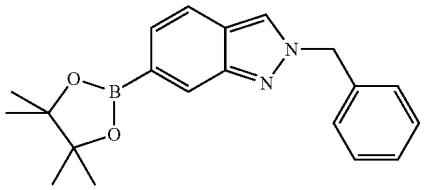 [SMILES: CC1(C)OB(c2ccc3cn(Cc4ccccc4)nc3c2)OC1(C)C]

2-Benzyl-6-bromo-2H-indazole (12.60 g, 43.9 mmol), bis(pinacolato)-diboron (12.26 g, 48.3 mmol) and K-OAc (12.92 g, 131.6 mmol) were dissolved in dioxane and degassed using a vacuum purge/N2 flll. 1,1'-Bis(diphenylphosphino)ferrocenepalledium(II) chloride-complex with CH₂Cl₂ (0.96 g, 1.3 mmol) was added and a final vacuum/N2 purge was conducted. The mixture was heated to 80° C. for 2.5 hours (TLC analysis indicated complete consumption of SM) and then allowed to cool to room temperature. The mixture was diluted with 200 mL of EtOAc and filtered through a plug of Celite® atop SiO₂ (1"×4", prewetted with EtOAc). The pad was washed with 400 mL of EtOAc and the filtrate was concentrated to dark oil. The oil was dissolved in ~75 mL of EtOAc and ~250 mL of hexanes was added dropwise over ~1.5 hours with stirring. The mixture was stirred for 10 minutes and filtered through Celite®. The pad was washed with 25% EtOAc/hexanes and the concentrated. The oil was partitioned between 250 mL of EtOAc and water (100 mL). The layers were separated and the aqueous layer extracted with 150 mL of EtOAc. The combined organic extracts were extracted with 100 mL of saturated aqueous NaHCO₃, water, brine and then dried (Na₂SO₄), filtered and concentrated in vacuo to provide a brown oily solid. The crude product was suspended in 50 mL of EtOAc and heated until solid dissolved. 50 mL of hexanes were added with swirling and the mixture was allowed to cool to room temperature and then placed in a freezer for 3 days. The solid was collected by filtration and washed with cold 1:1 EtOAc/Hexanes and dried in a vacuum oven at 40° C. to give 9.78 g of a light brown solid. The filtrate was concentrated and the residue was purified by Isco® (Redisep 120, 15%-70% EtOAc/hexanes) to give an additional 3.49 g. total yield=90%. ¹H-NMR (DMSO-d₆) δ 8.45 (s, 1H), 7.93 (s, 1H), 7.66 (d, 1H), 7.38-7.24 (m, 5H), 7.22 (d, 1H), 5.64 (s, 2H), 1.30 (s, 12H); LC-MS [M+H]⁺=335.2, RT=3.77 min.

Intermediates D-F

Using the procedure described for Intermediate C and using the appropriate benzyl bromide, Intermediates D-F were prepared.

| Intermediate & Name | Structure | ¹H-NMR | LC/MS or TLC |
|---|---|---|---|
| Intermediate D: 2-(3-fluorobenzyl)-6-(4,4,5,5-tetramethyl-1,3,2-dioxaborolan-2-yl)-2H-indazole | 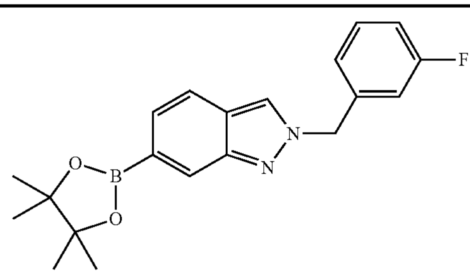 | ¹H NMR (300 MHz, DMSO-d₆) δ 8.51 (s, 1 H), 7.95 (s, 1 H), 7.69 (d, 1 H), 7.42-7.33 (m, 1 H), 7.17.26 (d, 1 H), 7.17-7.08 (m, 3 H), 5.69 (s, 2 H), 1.29 (s, 12 H) | ES-MS m/z 353.22 [M + H]⁺, HPLC RT (min) 3.63. |
| Intermediate E: 2-(3-methylbenzyl)-6-(4,4,5,5-tetramethyl-1,3,2-dioxaborolan-2-yl)-2H-indazole | 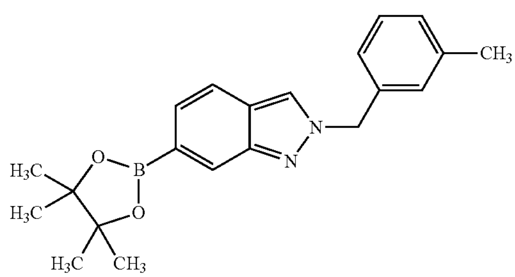 | ¹H NMR (300 MHz, DMSO-d₆) δ 8.46 (d, 1 H), 7.95-7.93 (m, 1 H), 7.67 (dd, 1 H), 7.28-7.18 (m, 2 H), 7.13-7.06 (m, 3 H), 5.61 (s, 2 H), 2.25 (s, 3 H), 1.29 (s, 12 H); | ES-MS m/z 349.19 [M + H]⁺, HPLC RT (min) 3.83. |
| Intermediate F: 2-(3-chlorobenzyl)-6-(4,4,5,5-tetramethyl-1,3,2-dioxaborolan-2-yl)-2H-indazole | 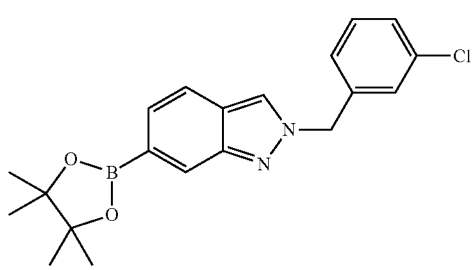 [SMILES: CC1(C)OB(c2ccc3cn(Cc4cccc(Cl)c4)nc3c2)OC1(C)C] | ¹H-NMR (DMSO-d₆) δ 8.50 (s, 1H), 7.93 (s, 1H), 7.67 (d, 1H), 7.36 to 7.34 (m, 3H), 7.26 to 7.23 (m, 2H), 5.68 (s, 2H), 1.30 (s, 12H); | TLC (15% EtOAc/Hex), R_f = 0.20. |

Intermediate G: Preparation of 6-Bromopyrrolo[2,1-f][1,2,4]triazin-4-amine

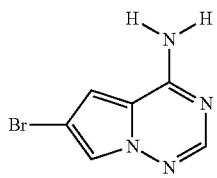 [SMILES: Nc1ncnn2cc(Br)cc12]

Step 1: Preparation of Pyrrol-1-yl-carbamic acid tert-butyl ester

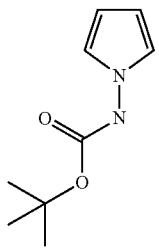

A flask (fitted with a Dean-Stark trap) containing a stirred solution of tert-butylcarbazate (100, 0.757 mol), 2,5-dimethoxytetrahydrofuran (108 g, 0.832 mol) and 2N HCl (10 mL) in 1,4-dioxane (700 mL) was heated under nitrogen at 90° C. As the reaction progressed over several hours, the solution changed from pale yellow to orange and began to reflux. The reaction was monitored by the amount of distillate collected in the Dean-Stark trap (primarily $CH_3OH$, 2 moles/1 mole reagent). As methanol collection approached the theoretical amount (50 mL), a sample was analyzed by TLC (silica gel, 1:3 EtOAc/hexane, ninhydrin stain) to confirm reaction completion. Heating was shut off and the reaction was allowed to cool somewhat before adding saturated, aq sodium bicarbonate solution (~25 mL) to neutralize the hydrochloric acid. The quenched mixture was filtered through a sintered-glass funnel and concentrated in vacuo to leave an orange, semi-solid residue. The residue was suspended in diethyl ether (minimum volume) and the nearly colorless solids were collected by suction filtration, washed with hexane and air-dried to afford 60.2 g (40%) of product. A second crop (yellow-tan solids) from the mother liquors was isolated: 29.0 g (19%). $^1$H-NMR ($CD_3OD$): $\delta$10.23 (br s, 1H), 6.66 (t, 2H, J=2.2 Hz), 5.94 (t, 2H, J=2.2), 1.42 (s, 9H); MS: GC/MS (+esi): m/z=182.9 [MH]$^+$

Step 2: Preparation of (2-Cyano-pyrrol-1-yl)-carbamic acid, tert-butyl ester

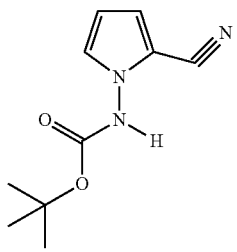

A 2 L, 3-neck flask was fitted with stir bar, $N_2$ inlet, rubber septum, thermometer and ice/acetone cooling bath. Pyrrol-1-yl-carbamic acid tert-butyl ester (99.0 g, 0.543 mol) was added to the reactor, dissolved with anhydrous acetonitrile (700 mL) and the stirred solution was cooled to 0° C. Chlorosulfonyl isocyanate (49.7 mL, 0.57 mol) was added dropwise via syringe (maintaining an internal temperature below 5° C.). After ~20 minutes a suspension was observed. After 45 minutes, N,N-dimethylformamide (anhydrous, 100 mL) was added dropwise via addition funnel (keeping internal temperature below 5° C.) and the reaction mixture became a solution. Stirring at 0° C. was continued for 45 minutes, then the reaction was allowed to warm to rt. Monitoring by TLC (silica gel, 1:3 ethyl acetate/hexane, UV, ninhydrin stain) of a quenched sample indicated that the reaction had progressed to completion. The mixture was poured onto ice (~2 L) and stirred with addition of EtOAc (2 L). The layers were separated and the organic layer was dried over magnesium sulfate. The dried solution was filtered through a pad of 30/40 Magnesol and the filtrate was concentrated to dryness in vacuo, then the residue was dissolved in a minimum volume of dichloromethane and chromatographed on a plug of silica gel, eluting with ethyl acetate/hexane, 0-50% ethyl acetate. The clean, product-containing fractions were combined and concentrated to dryness in vacuo, to afford the desired product as a white solid, 69.8 g (62%). A somewhat impure fraction provided additional material, 16.8 g (15%), bringing the total recovery to 86.6 g, (77%). $^1$H-NMR ($CD_3OD$): $\delta$ 7.01 (dd, 1H, J=3.0; 1.6 Hz), 6.82 (dd, 1H, J=4.4, 1.7 Hi), 6.19 (dd, 1H, J=4.2, 2.9 Hz), 4.88 (s, 1H), 1.50 (br s, 9H); MS: LC/MS (+esi), m/z=207.9 [M+H].

Step 3: Preparation of tert-Butyl (4-bromo-2-cyano-1H-pyrrol-1-yl)carbamate

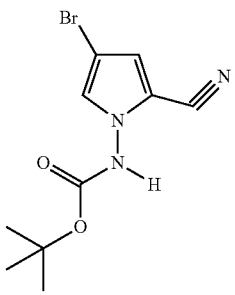 [SMILES: CC(C)(C)OC(=O)Nn1cc(Br)cc1C#N]

A 1 L, 3-neck RB flask was fitted with a mechanical stirrer, nitrogen inlet, thermocouple and thermocontroller, and dry-ice acetonitrile cooling. 2-Cyano-pyrrol-1-yl-carbamic acid, tert-butyl ester (20 g, 96.5 mmol) was added and dissolved in 350 mL acetonitrile and cooled to below −30° C. 1,3-Dibromo-5,5-dimethylhydantoin (13.79 g, 48.26 mmol) was added as a solid, and the reaction was allowed to warm to rt over 2 h. Analysis by RP-HPLC at 2 h indicated that about 10% starting material remained. The reaction was cooled again to below −30° C. and treated with additional 1,3-dibromo-5,5-dimethylhydantoin (1.3 g, 4.8 mmol). The reaction was allowed to warm slowly to rt over 3 h. The reaction was diluted with 500 mL EtOAc and transferred to a separatory funnel. The organic layer was washed with 1N aq sodium carbonate, water and brine and then dried with sodium sulfate. Filtration of the organic layer through silica gel removed much of the colored impurities. Evaporation of the solvent under vacuum provided reddish oil, which provided orange-brown crystals of the desired product upon seeding (27.16 g, 98%). $^1$H-NMR (DMSO): δ 10.95 (bs, 1H), 7.61 (d, 1H, J=2.0 Hz), 7.16 (d, 1H, J=2 Hz), 1.44 (s, 9H, J=4.4, 1.7 Hz). MS: LC/MS (+esi), m/z=[M+H].

Step 3: Preparation of
1-Amino-4-bromo-1H-pyrrole-2-carbonitrile hydrochloride

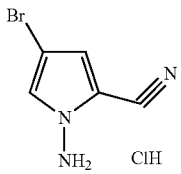

A 1 L, 3-neck flask was fitted with a mechanical stirrer, nitrogen inlet, thermocouple and thermocontroller, cooling bath and an addition funnel. tert-Butyl (4-bromo-2-cyano-1H-pyrrol-1-yl)carbamate (19 g, 66 mmol) was added and dissolved with 1,4-dioxane (50 mL), then the stirred orange solution was cooled to 0° C. and HCl/dioxane (4N, 100 mL, 8 eq.) was slowly added from the addition funnel, maintaining an internal temperature around 25° C. After 2 hours, the solution became cloudy and stirring at room temperature was continued for 7 hours. The reaction was monitored for completion by TLC (silica gel, 1:3 EtoAc/hexane, UV; Note: the free base may be observed as a high-Rf spot and can be misinterpreted as incomplete reaction). The reaction mixture was diluted with diethyl ether (150 mL) and the precipitated solids were collected by suction filtration and washed with ether (200 mL). Drying (vacuum oven at 50° C.) afforded the desired product as 10.9 g (93%) of a white solid. $^1$H-NMR (DMSO): δ 7.24 (d, 1H, J=2 Hz), 6.93 (d, 1H, J=2 Hz), 6.2 (bs, 3H, J=2.8, 4.4 Hz); MS: GC/MS, m/z=[M+H].

Step 4: Preparation of the Title Compound

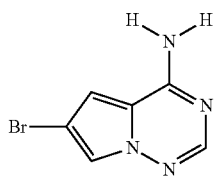 [SMILES: Nc1ncnn2cc(Br)cc12]

To a stirred suspension of 1-Amino-4-bromo-1H-pyrrole-2-carbonitrile hydrochloride (17 g, 61.1 mmol) in absolute ethanol (350 mL) was added formamidine acetate (31.8 g, 305 mmol) and potassium phosphate (64.9 g, 305 mol). The suspension was heated for 18 hours at 78° C. (under N$_2$), then cooled, filtered and concentrated to dryness in vacuo. The residue was mixed with ice water (2 L) and the dark, grayish-brown solids were collected by suction filtration. The solids were taken up in refluxing MeOH and treated with decolorizing carbon, then filtered through Celite® and concentrated dryness in vacuo. The solids were taken up in THF:DCE (1:3) and filtered through a pad of silica.

Removal of the solvent in vacuo provided a yellowish-brown solid. This material was recrystallized from THF:hexanes to provide the desired compound as a yellow solid (9.86 g, 75%). $^1$H-NMR (DMSO): δ 7.85 (bs, 2H), 7.81 (s, 1H), 7.80 (d, 1H, j=2 Hz), 6.96 (d, 1H, J=2 Hz) LC/MS (+esi): m/z=[M+H].

Intermediate H: Preparation of 4,4,5,5-tetramethyl-1,3,2-dioxaborolan-2-ol-2-benzyl-3-methyl-6-(4,4,5,5-tetramethyl-1,3,2-dioxaborolan-2-yl)-2H-indazole (1:1)

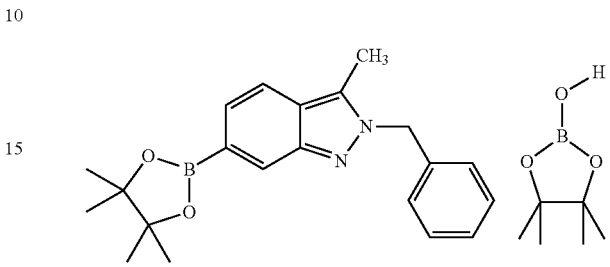

Step 1: Preparation of
2-benzyl-6-chloro-3-methyl-2H-indazole

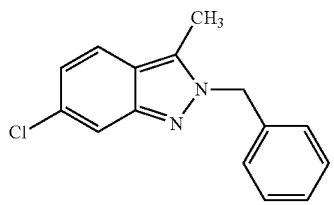

A solution of 1-(4-chloro-2-nitrophenyl)ethanone (12.5 g, 63 mmol) and benzylamine (13.7 g, 125 mmol) in 200 mL toluene was treated with titanium(IV) isopropoxide (53.5 g, 188 mmol) and heated at 60° C. for 16 h. The solvent was removed in vacuo and the residue taken up in triethylphosphite (31 g, 187 mmol) and the mixture heated cautiously to 150° C. for 2 h. The reaction was cooled to rt and diluted with 30 mL absolute ethanol. 3 mL of 4N aq NaOH was added dropwise with vigorous stirring. After 5 min, the solids were filtered off and the solution diluted with 60 mL absolute ethanol and 60 mL 1N aq NaOH. After stirring overnight, the ethanol was removed in vacuo and the residue diluted with water. Filtration gave the desired product as a dark brown solid (9.86 g, 62%) $^1$H-NMR (DMSO): δ 7.72 (dd, 1H, J=9, 1 Hz), 7.61 (dd, 1H, J=2, 1 Hz), 7.23 to 7.36 (m, 3H), 7.15 to 7.20 (m, 2H), 6.96 (dd, 1H, J=9, 2 Hz), 5.60 (s, 2H), 2.58 (s, 1H); MS: LC/MS (+esi): m/z=275.1 [MH]$^+$; LC/MS rt=3.51 min.

Step 2: Preparation of the Title Compound

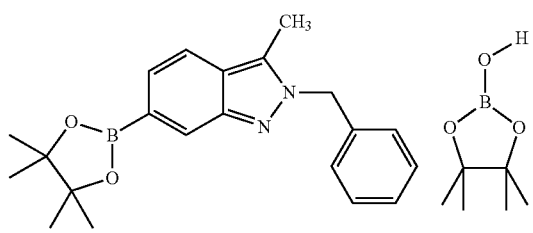

A 3-neck RB flask was charged with tris(dibenzylideneacetone)dipalladium (970 mg, 1.06 mmol) and tricyclohexylphosphine (713 mg, 2.54 mmol) and the flask flushed with $N_2$ for 5 min. Freshly degassed dioxane was added (100 mL) and the solution purged with $N_2$ for 10 min. After stirring 30 min at 25° C., bis(pinacoloto)diboron (5.92 g, 23.3 mmol), potassium acetate (6.24 g, 63.6 mmol) and 2-benzyl-6-chloro-3-methyl-2H-indazole (5.44 g, 21.2 mmol) were added, and the reaction was degassed with $N_2$. The reaction was heated to 80° C. and stirred under $N_2$ for 22 h. The reaction was cooled to rt, diluted with hexanes (600 mL) and filtered through a plug of Celite®. After removal of the solvent in vacuo, the residue was taken up in $CH_2Cl_2$ and filtered through a pad of silica. Removal of the solvent in vacuo provided a yellow oil that spontaneously crystallized (5.28 g, 72%). $^1$H-NMR ($CD_2Cl_2$): δ 8.12 (at, 1H, J=1 Hz), 7.56 (d, 1H, J=8 Hz), 7.28 to 7.36 (m, 4H), 7.11 to 7.17 (m, 2H), 5.61 (s, 2H), 2.55 (s, 3H), 1.37 (s, 6H), 1.27 (s, 6H)); MS: LC/MS (+esi), m/z=349.1 [M+H]; LC/MS rt=3.82.

Intermediate I: Preparation of tert-butyl 3-(4-amino-5-bromopyrrolo[2,1-f][1,2,4]triazin-7-yl)pyrrolidine-1-carboxylate

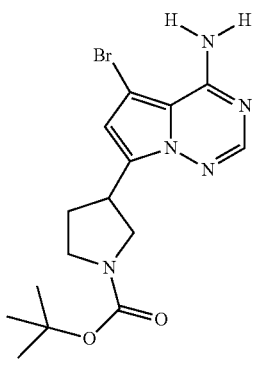 [SMILES: CC(C)(C)OC(=O)N1CCC(c2cc(Br)c3c(N)ncnn23)C1]

Step 1: Preparation of tert-butyl 3-(4-aminopyrrolo[2,1-f][1,2,4]triazin-7-yl)-2,5-dihydro-1H-pyrrole-1-carboxylate

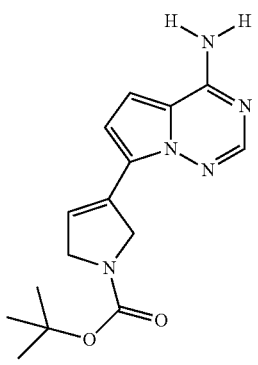 [SMILES: CC(C)(C)OC(=O)N1CC=C(c2ccc3c(N)ncnn23)C1]

A 2 L, 3-neck RB flask was fitted with a mechanical stirrer, a nitrogen inlet, thermocouple and thermocontroller, and a water cooling bath. In the flask, 7-bromopyrrolo[2,1-f][1,2,4]triazin-4-amine (18.4 g, 86.3 mmol) was suspended in tetrahydrofuran (250 mL) and treated with chlorotrimethylsilane (18.8 g, 172 mmol). The mixture was allowed to stir 16 h at rt. A solution of isopropylmagnesium bromide in THF (2M, 173 mL, 345 mmol) was added slowly over 20 min taking care that the internal temperature never rose above 40° C. After 1.5 h, a sample quenched in MeOH and analyzed by RP-HPLC indicated that the metallation was 95% complete. The water bath was replaced with an ice-acetone bath and stirring was continued until the internal temperature fell to −10° C. tert-Butyl 3-oxopyrrolidine-1-carboxylate (20 g, 108 mmol) was added as a solid, and the reaction allowed to warm to rt over 30 min. The reaction was again cooled to −10° C. and cautiously treated with trifluoroacetic anhydride (45.4 g, 216 mmol), diisopropylethylamine (33.5 g, 259 mmol) and dimethylaminopyridine (527 mg, 4.3 mmol). The reaction was warmed to rt and allowed to stir for 30 min, then treated with a 25% solution of NaOMe in MeOH (46 g, 215 mmol) and stirred for an additional 15 min. The reaction was partitioned between EtOAc and 1N aq citric acid. After 15 min stirring the organic layer was separated, washed with brine and dried with sodium sulfate. After filtering the solution through a plug of silica, the organic were removed in vacuo and the residue triturated with ethyl ether to provide the desired product as a bright yellow solid (16.8 g, 65%). $^1$H-NMR (DMSO): δ 7.72 (dd, 1H), 7.61 (dd, 1H), 7.23 to 7.36 (m, 3H), 7.15 to 7.20 (m, 2H), 6.96 (dd, 1H), 5.60 (s, 2H), 2.58 (s, 1H); MS: LC/MS (+esi): m/z=275.1 [MH]$^+$; LC/MS rt=3.51 min.

Step 2: Preparation of tert-butyl 3-(4-aminopyrrolo[2,1-f][1,2,4]triazin-7-yl)pyrrolidine-1-carboxylate

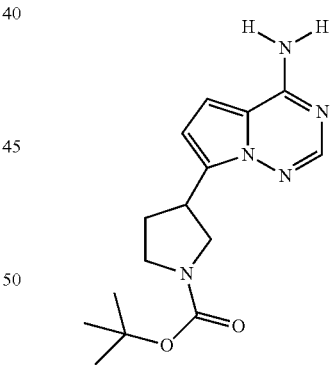

A suspension of platinum(IV) oxide (2.1 g, 9.5 mmol) and tert-butyl 3-(4-aminopyrrolo[2,1-f][1,2,4]triazin-7-yl)-2,5-dihydro-1H-pyrrole-1-carboxylate (11.4 g, 37.8 mmol) in AcOH (150 mL) was stirred for 16 h under a $H_2$ atmosphere. The reaction was purged with $N_2$ and filtered through Celite®, washing with AcOH. After removal of solvent in vacuo, the residue was dissolved in THF:EtoAc and washed with saturated, aqueous sodium carbonate solution. The organic layer was dried and concentrated in vacuo to provide the desired product as a dark solid (10.7 g, 93%). MS: LC/MS (+esi): m/z=304.1 [MH]$^+$; LC/MS rt=2.74 min.

Step 3: Preparation of the Title Compound

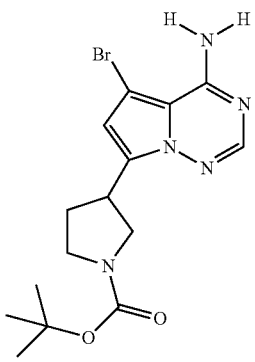 [SMILES: CC(C)(C)OC(=O)N1CCC(c2cc(Br)c3c(N)ncnn23)C1]

A solution of tert-butyl 3-(4-aminopyrrolo[2,1-f][1,2,4]triazin-7-yl)pyrrolidine-1-carboxylate (1.2 g, 3.96 mmol) in DMF (20 mL) was cooled to −40° C. and treated with 1,3-dibromo-55, dimethylhydantoin (508 mg, 1.78 mmol). The reaction was allowed to warm slowly to rt over a 2 h period and was then partitioned between EtOAc and bicarbonate solution. After concentration, the residue was triturated with EtOAc to yield the desired product (1.28 g, 85%). $^1$H-NMR (DMSO): δ 7.86 (s, 1H), 6.69 (s, 1H), 3.68 to 3.80 (m, 2H), 3.36 to 3.46 (m, 1H), 3.20 to 3.30 (m, 2H), 2.16 to 2.30 (m, 1H), 1.98 to 2.08 (m, 1H), 1.37 (s, 9H); MS: LC/MS (+esi), m/z=382.1 [M+H]; LC/MS rt=3.08.

Intermediate J: Preparation of 7-(4-benzylmorpholin-2-yl)-5-bromopyrrolo[2,1-f][1,2,4]triazin-4-amine

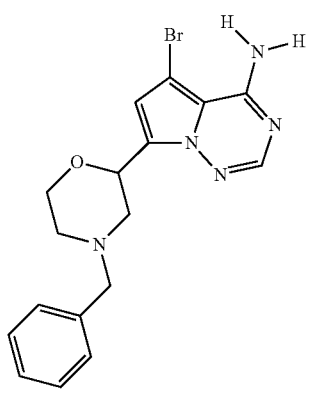 [SMILES: Nc1ncnn2c(C3CN(Cc4ccccc4)CCO3)cc(Br)c12]

Step 1: Preparation of 1-(4-aminopyrrolo[2,1-f][1,2,4]triazin-7-yl)-2-chloroethanone

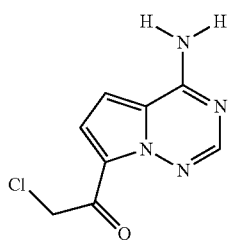 [SMILES: Nc1ncnn2c(C(=O)CCl)ccc12]

A 1 L, 3-neck RB flask was fitted with a mechanical stirrer, a nitrogen inlet, thermocouple and thermocontroller, and a water cooling bath. In the flask 7-bromopyrrolo[2,1-f][1,2,4]triazin-4-amine (175 g, 352 mmol) was suspended in tetrahydrofuran (100 mL) and treated with chlorotrimethylsilane (7.65 g, 70.4 mmol). The mixture was allowed to stir 3 h at rt. A solution of isopropylmagnesium bromide in THF (2M, 70.4 mL, 141 mmol) was added slowly over 20 min taking care that the internal temperature never rose above 40° C. After 1 h a sample quenched in MeOH and analyzed by RP-HPLC indicated that the metallation was >90% complete. The water bath was replaced with an ice-acetone bath and stirring was continued until the internal temperature fell to −10° C. 2-Chloro-N-methoxy-N-methylacetamide (7.3 g, 53 mmol) was added as a solid, and the reaction allowed to warm to rt over 30 min. The reaction was quenched with MeOH and diluted with EtOAc (200 mL) and 500 mL of citrate buffer (pH 4). The mixture was stirred for 15 min, during which time a thick tan precipitate formed. This was filtered off to provide the desired compound as a tan solid (2 g, 27%). The organic layer was separated, dried with sodium sulfate and filtered through a silica plug. Removal of the solvent in vacuo and trituration of the residue with EtOAc gave a second batch of the desired product (4.3 g, 58%). The 2 batches were combined to provide the desired product as a tan powder (6.25 g, 84%). $^1$H-NMR (DMSO): δ 7.88 (bs, 1H), 7.80 (s, 1H), 7.08 (d, 1H, J=5 Hz), 6.70 (d, 1H, J=5 Hz), 4.82 (s, 2H), 3.06 (bs, 1); MS: LC/MS (+esi): m/z=211.2 [MH]$^+$; LC/MS rt=1.69 min.

Step 2: Preparation of 1-(4-aminopyrrolo[2,1-f][1,2,4]triazin-7-yl)-2-[benzyl(2-{[tert-butyl(dimethyl)silyl]oxy}ethyl)amino]ethanone

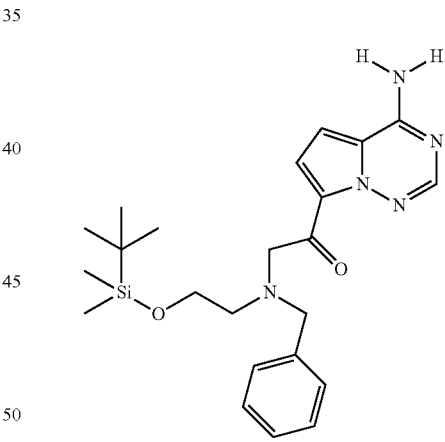

A suspension of 1-(4-aminopyrrolo[2,1-1,2,4]triazin-7-yl)-2-chloroethanone (4.0 g, 19 mmol) and N-benzyl-2-{[tert-butyl(dimethyl)silyl]oxy}ethanamine (6.05 g, 22.8 mmol) (Prepared by the method of Rosenstroem; J. Med. Chem., 2004, 47, 859-870) in DMF (40 mL) was treated with sodium carbonate (3.93 g, 28.5 mmol) and sodium iodide (315 mg, 1.9 mmol) and heated to 60° C. for 16 h. The reaction was cooled to rt and diluted with EtOAc and 1N sodium carbonate solution. The organic phase was separated, washed 2 times with water, dried with sodium sulfate and concentrated in in vacuo. The residue was taken up in DCM:THF and purified by column filtration to provide the desired compound (3.47 g, 42%); MS: LC/MS (+esi): m/z=440.9 [MH]$^+$; LC/MS rt=2.80 min.

Step 3: Preparation of 1-(4-aminopyrrolo[2,1-f][1,2,4]triazin-7-yl)-2-1-benzyl[2-hydroxyethyl)amino]ethanol

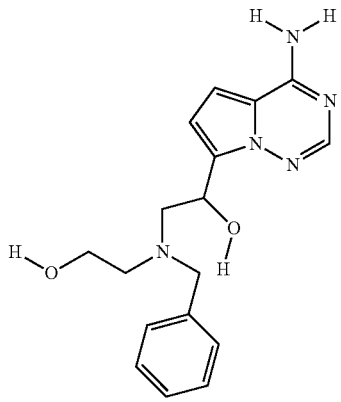 [SMILES: Nc1ncnn2c(C(O)CN(CCO)Cc3ccccc3)ccc12]

A 1 L, 3-neck RB flask was fitted with a nitrogen inlet, thermocouple and thermocontroller, and a water cooling bath. In the flask 1-(4-aminopyrrolo[2,1-f][1,2,4]triazin-7-yl)-2-[benzyl(2-{[tert-butyl(dimethyl)silyl]oxy}ethyl)amino]ethanone (6.23 g, 14.2 mmol) was dissolved in THF (150 mL) and treated with a solution of diisobutylaluminium hydride in THF (1M, 85 mL, 85 mmol). The mixture was allowed to stir 0.5 h at rt, then quenched via careful addition of MeOH. The reaction was diluted with EtOAc and an aqueous solution of Rochelle's salt. This mixture was heated to 50° C. and stirred vigorously overnight. The organic layer was separated, dried with sodium sulfate and concentrated in vacuo to provide a brown solid. Trituration with EtOAc provided the desired product as a tan powder (2.89 g, 62%); MS: LC/MS (+esi) m/z=328.3 [MH]$^+$; LC/MS rt=1.11 min.

Step 4: Preparation of 7-(4-benzylmorpholin-2-yl)pyrrolo[2,1-f][1,2,4]triazin-4-amine

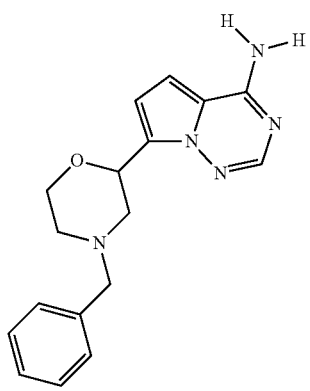 [SMILES: Nc1ncnn2c(C3CN(Cc4ccccc4)CCO3)ccc12]

A sample of 1-(4-aminopyrrolo[2,1-f][1,2,4]triazin-7-yl)-2-[benzyl(2-hydroxyethyl)amino]ethanol (3.50 g, 10.7 mmol) was suspended in methanesulfonic acid (15 mL) and stirred vigorously for 10 min. The now homogeneous solution was diluted with EtOAc and ice and made basic by dropwise addition of 2N aq NaOH. The organic layer was separated and dried with sodium sulfate. Removal of the solvent in vacuo gave the desired product as a tan solid (3.15 g, 95%). MS: LC/MS (+esi): m/z=310.4 [MH]$^+$; LC/MS rt=1.12 min.

Step 5: Preparation of the Title Compound

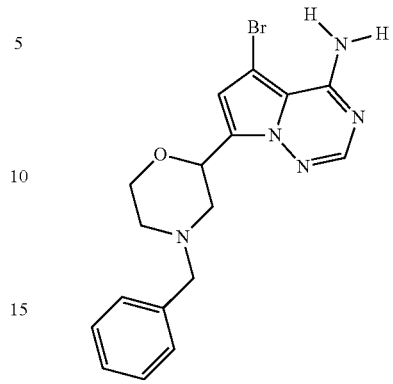

A solution of 7-(4-benzylmorpholin-2-yl)pyrrolo[2,1-f][1,2,4]triazin-4-amine (3.15 g, 9.7 mmol) in a DMF (35 mL) was cooled to below −30° C. and treated with 1,3-dibromo-5,5-dimethylhydantoin (1.38 g, 4.8 mmol). The reaction was allowed to warm slowly to rt over the next 4 h. The mixture was partitioned between EtOAc and 1N sodium carbonate solution. The organic layer was separated, washed 2 times with water and once with brine. After evaporation of the solvent, the residue was triturated with ether, and stirred vigorously for 10 min. The now homogeneous solution was diluted with EtOAc and ice and made basic by dropwise addition of 2N NaOH. The organic layer was separated and dried with sodium sulfate. Removal of the solvent in vacuo gave the desired product as a tan solid (3.15 g, 95%). $^1$H-NMR (DMSO): δ 7.84 (s, 1H), 7.30 to 7.35 (m, 4H), 7.20 to 7.28 (m, 1H), 6.76 (s, 1H), 5.02 (dd, 1H), 3.84 (d, 1H), 3.64 (ddd, 1H), 3.55 (d, 1H), 3.49 (d, 1H), 2.89 (app d, 1H), 2.64 (app d, 1H), 2.15 to 2.31 (m, 2H), (s, 1H); MS: LC/MS (+esi), m/z=320.1 [M+H]; LC/MS rt=2.23.

Intermediate K: Preparation of tert-butyl 2-[4-amino-5-(2-benzyl-2H-indazol-6-yl)pyrrolo[2,1-f][1,2,4]triazin-7-yl]morpholine-4-carboxylate

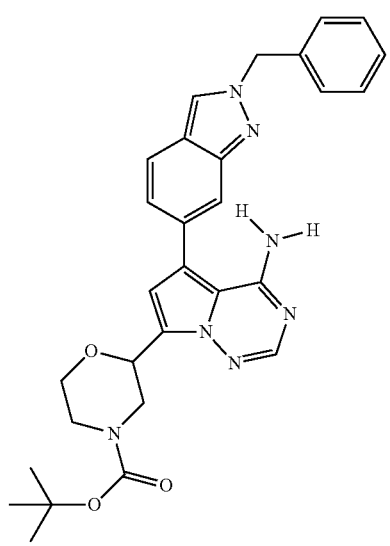 [SMILES: CC(C)(C)OC(=O)N1CCOC(c2cc(-c3ccc4cn(Cc5ccccc5)nc4c3)c3c(N)ncnn23)C1]

Step 1: Preparation of tert-butyl 2-(4-aminopyrrolo[2,1-f][1,2,4]triazin-7-yl)morpholine-4-carboxylate

A solution of 7-(4-benzylmorpholin-2-yl)pyrrolo[2,1-f][1,2,4]triazin-4-amine (1.25 g, 4.04 mmol) and 10% palladium on carbon (214 mg, 0.2 mmol) in EtOH (40 mL) was stirred under a $H_2$ atmosphere for 16 h. After purging the solution with $N_2$, the mixture was filtered through Celite® and the solvent removed in vacuo to provide 818 mg of the intermediate amine. This material was taken up in EtOH (10 mL) and cooled to 0° C. The solution was treated with triethylamine (755 mg, 7.64 mmol) and di-tert-butyl-dicarbonate (896 mg, 4.1 mmol) and warmed to rt. After 1 h the reaction was diluted with EtOAc and washed with 1N citrate buffer (pH 4) and bicarbonate. The organic layer was dried with sodium sulfate and concentrated in vacuo to provide the desired product as a semi-solid (880 mg, 84%); $^1$H-NMR (DMSO): δ 7.84 (s, 1H), 7.75 (bs, 1H), 6.84 (d, 1H, J=5 Hz), 6.63 (d, 1H, J=5 Hz), 4.87 (dd, 1H, J=11, 3 Hz), 3.95 to 4.06 (m, 1H), 3.68 to 3.92 (m, 2H), 3.50 to 3.62 (m, 1H), 3.37 to 3.46 (m, 1H), 2.80 to 3.15 (m, 2H), 1.37 (s, 9H); MS: LC/MS (+esi): m/z=320.1 [MH]$^+$; LC/MS rt=2.23 min.

Step 2: Preparation of tert-butyl 2-(4-amino-5-bromopyrrolo[2,1-f][1,2,4]triazin-7-yl)morpholine-4-carboxylate

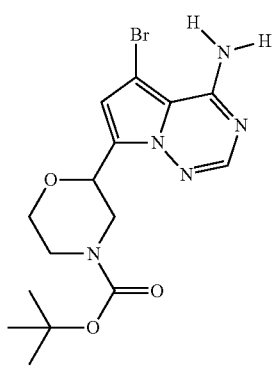 [SMILES: CC(C)(C)OC(=O)N1CCOC(c2cc(Br)c3c(N)ncnn23)C1]

A solution of tert-butyl 2-(4-aminopyrrolo[2,1-f][1,2,4]triazin-7-yl)morpholine-4-carboxylate (840 mg, 2.63 mmol) in DMF (20 mL) was cooled to −40° C. and treated with 1,3-dibromo-5,5-dimethylhydantoin (376 mg, 1.32 mmol). The reaction was warmed to rt over 3 h, and then partitioned between EtOAc and 1N sodium carbonate. The organic layer was separated and washed with water and brine. After drying with sodium sulfate and removal of the solvent in vacuo, trituration with ether provided the desired compound as a brown solid (880 mg, 84%). $^1$H-NMR (DMSO): δ 7.89 (s, 1H), 4.88 (dd, 1H, J=10, 3 Hz), 3.95 to 4.06 (m, 1H), 3.82 to 3.91 (m, 1H), 3.70 to 3.79 (m, 1H), 3.55 (ddd, 1H, J=11, 11, 3 Hz), 2.92 to 3.28 (m, 2H), 1.37 (s, 9H); MS: LC/MS (+esi): m/z=400.2 [MH]$^+$; LC/MS rt=2.76 min.

Step 3: Preparation of Title Compound

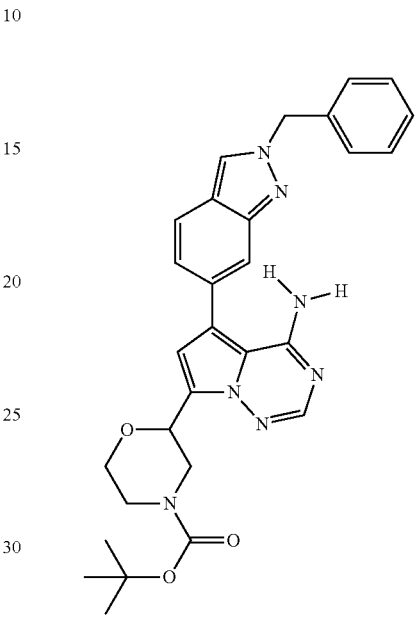

A solution of tert-butyl 2-(4-amino-5-bromopyrrolo[2,1-f][1,2,4]triazin-7-yl)morpholine-4-carboxylate (880 mg, 2.63 mmol) and tetrakis(triphenylphosphoranyl)palladium (512 mg, 0.44 mmol) in 1 mL DMF and 1 mL dioxane was degassed under vacuum and backfilled with $N_2$ 3 times. The mixture was stirred for 30 min at 100° C. The reaction mixture was then treated with 2-benzyl-6-(4,4,5,5-tetramethyl-1,3,2-dioxaborolan-2-yl)-2H-indazole (812 mg, 2.43 mmol), powdered potassium phosphate (937 mg, 4.42 mmol) and 4 drops of water. This mixture was allowed to stir at 100° C. for 30 min. The reaction was cooled to rt and diluted with EtOAc:MeOH and filtered through a silica plug. Evaporation of the solvent gave an orange semi-solid. This was dissolved in DCM and purified using an ISCO® instrument to provide the desired compound as a tan solid (380 mg, 33%); MS: LC/MS (+esi): m/z=526.2 [MI-1]$^+$; LC/MS rt=3.26 min.

Intermediate L: Preparation of tert-butyl 3-(4-amino-5-bromopyrrolo[2,1-f][1,2,4]triazin-7-yl)hexahydropyrazino[2,1-c][1,4]oxazine-8(1H)-carboxylate

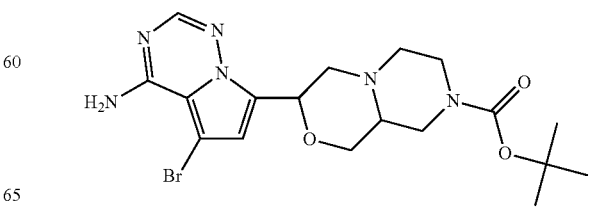

Step 1: Preparation of 1-(4-aminopyrrolo[2,1-f][1,2,4]triazin-7-yl)-2-[4-benzyl-2-({[tert-butyl(dimethyl)silyl]oxy}methyl)piperazin-1-yl]ethanone

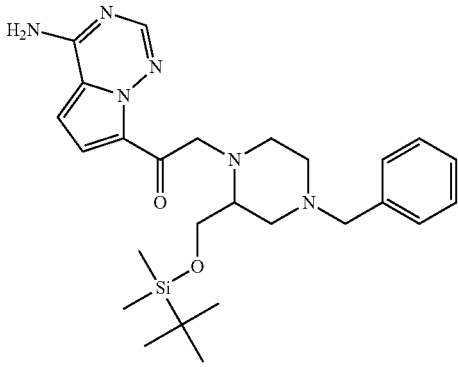 [SMILES: CC(C)(C)[Si](C)(C)OCC1CN(Cc2ccccc2)CCN1CC(=O)c1ccc2c(N)ncnn12]

To a solution of 1-(4-aminopyrrolo[2,1-f][1,2,4]triazin-7-yl)-2-chloroethanone (1.00 g, 4.75 mmol), K$_2$CO$_3$ (1.97 g, 14.2 mmol) and potassium iodide (79 mg, 0.47 mmol) in DMF (20 mL), was added 1-benzyl-3-({[tert-butyl(dimethyl)silyl]oxy}methyl)piperazine (1.53 g, 4.79 mmol, prepared by the method of Naylor et al *J. Med. Chem.* 36, 2075). The reaction was allowed to stir for 17 hours. The mixture was partitioned between ethyl acetate (200 mL) and saturated, aqueous Na$_2$CO$_3$ solution (100 mL). The layers were separated and the organic was washed with brine, dried (Na$_2$SO$_4$), and evaporated. The crude material was purified by ISCO® chromatography using a gradient elution from 50% to 100% ethyl acetate in hexanes to obtain 1.9 g (81%) of the desired product LC-MS [M+H]$^+$=495.6, RT=2.56 min.

Step 2: Preparation of 7-(8-benzyloctahydropyrazino[2,1-c][1,4]oxazin-3-yl)pyrrolo[2,1-f][1,2,4]triazin-4-amine

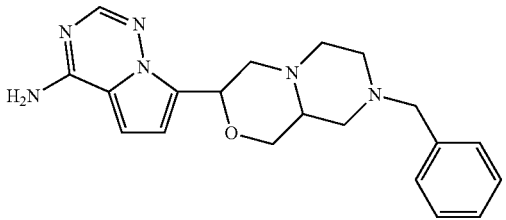 [SMILES: Nc1ncnn2c(C3CN4CCN(Cc5ccccc5)CC4CO3)ccc12]

A solution of 1-(4-aminopyrrolo[2,1-f][1,2,4]triazin-7-yl)-2-[4-benzyl-2-({[tert-butyl(dimethyl)silyl]oxy}methyl)piperazin-1-yl]ethanone (2.30 g, 4.65 mmol) in THF (10 mL) was added dropwise to a −78° C. solution of DIBAL-H (46.5 mL, 46.5 mmol, 1.0M solution in THF). The reaction was stirred for 3 hours while warming to rt. The mixture was quenched with MeOH (1.0 mL) and transferred to a stirring solution of ethyl acetate (400 mL) and saturated, aqueous sodium potassium tartrate (300 mL). The solution was warmed to 60° C. and allowed to stir for 2 hr. The layers were separated and the organic layer was washed with brine, dried (Na$_2$SO$_4$), and evaporated. The crude material (1.5 g, 84%) was dissolved in dichloromethane (10 mL) and treated with methanesulfonic acid (5 mL) and stirred for 1 hr at rt. The mixture was partitioned between ethyl acetate (300 mL) and saturated, aqueous Na$_2$CO$_3$ solution (300 mL) and allowed to stir for 30 minutes. The layers were separated and the organic was washed with brine, dried (Na$_2$SO$_4$), and concentrated to dryness. The residue was triturated with Et$_2$O to obtain 1.3 g (91%) of the desired product. $^1$H NMR (300 MHz, DMSO-d$_6$) δ 7.81 (s, 1 H), 7.69 (br s, 1 H), 7.31-7.29 (m, 5 H), 6.81 (d, J=4.5 Hz, 1 H), 6.57 (d, J=4.5 Hz, 1 H), 5.03-5.01 (m, 1 H), 3.71 (dd, J=3.0, 11.4 Hz, 1 H) 3.45 (s, 2H), 3.33-3.26 (m, 1H), 2.92 (dd, J=2.1, 11.7 Hz, 1H), 2.72-2.68 (m, 2H), 2.62-2.58 (m, 1H), 2.33 (t, J=10.8 Hz, 1H), 2.23-2.13 (m, 3H), 1.70 (t, J=10.4 Hz, 1H); LC-MS [M+H]$^+$=365, RT=0.22 min.

Step 3: Preparation of 7-(octahydropyrazino[2,1-c][1,4]oxazin-3-yl)pyrrolo[2,1-f][1,2,4]triazin-4-amine

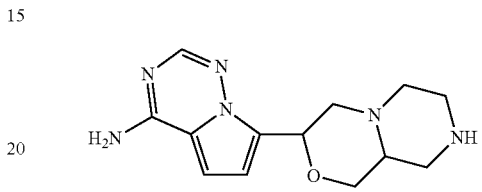

Palladium on carbon (200 mg, 10% by wt.) was placed under an inert atmosphere and suspended in AcOH (20 mL). A solution of 7-(8-benzyloctahydropyrazino[2,1-c][1,4]oxazin-3-yl)pyrrolo[2,1-f][1,2,4]triazin-4-amine (2.00 g, 5.48 mmol) dissolved in AcOH (30 mL) was added. The reaction mixture was placed under H$_2$ atmosphere (1 atmosphere) and stirred overnight. The resulting mixture was filtered through a pad of Celite® and the solvent was concentrated under reduced pressure. Trituration with Et$_2$O afforded 1.45 g (96%) of the desired product as a white solid. LC-MS [M+H]$^+$=275, RT=1.11 min.

Step 4: Preparation of the Title Compound

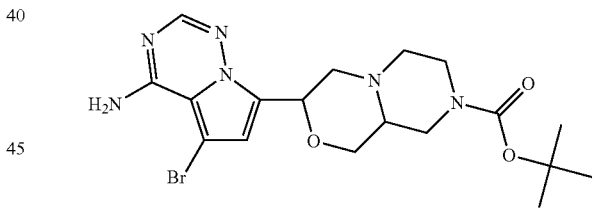

To a solution of 7-(octahydropyrazino[2,1-c][1,4]oxazin-3-yl)pyrrolo[2,1-f][1,2,4]triazin-4-amine (1.20 g, 4.37 mmol) in absolute ethanol (40 mL) was added triethylamine (1.3 mL, 9.62 mmol) followed by di-tert-butyl dicarbonate (1.05 g, 4.81 mmol). The reaction was stirred 1 hr at rt. The mixture was partitioned between ethyl acetate (200 mL) and saturated, aqueous Na$_2$CO$_3$ solution (150 mL). The layers were separated and the organic phase was washed, dried (Na$_2$SO$_4$), and concentrated to dryness. The crude material was dissolved in DMF (40 mL), cooled to −40° C., and treated with 1,3-dibromo-5,5-dimethylimidazolidine-2,4-dione (610 mg, 2.14 mmol). The reaction was allowed to stir for 30 min while warming to rt. The mixture was partitioned between ethyl acetate (300 mL) and saturated, aqueous Na$_2$CO$_3$ solution (150 mL). The layers were separated and the organic phase was washed, dried (Na$_2$SO$_4$), and concentrated to dryness. The crude material was triturated with acetonitrile to afford 1.51 g (78%) of the desired product as a pale yellow solid. LC-MS [M+H]$^+$=453, 455, RT=2.18 min.

Intermediate M: Preparation of 7-(8-benzyloctahydropyrazino[2,1-c][1,4]oxazin-3-yl)-5-bromopyrrolo[2,1-f][1,2,4]triazin-4-amine

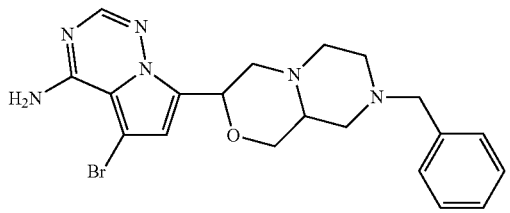 [SMILES: Nc1ncnn2c(C3CN4CCN(Cc5ccccc5)CC4CO3)cc(Br)c12]

To a solution of 7-(8-benzyloctahydropyrazino[2,1-c][1,4]oxazin-3-yl)pyrrolo[2,1-f][1,2,4]triazin-4-amine (700 mg, 1.92 mmol) in DMF (20 mL), cooled to −40° C., was added 1,3-dibromo-5,5-dimethylimidazolidine-2,4-dione (274 mg, 0.96 mmol). The reaction was allowed to stir for 30 min while warming to rt. The mixture was partitioned between ethyl acetate (200 mL) and saturated, aqueous $Na_2CO_3$ solution (150 mL). The layers were separated and the organic phase was washed with brine, dried ($Na_2SO_4$), and concentrated to dryness. The crude material was triturated with acetonitrile to afford 500 mg (59%) of the desired product as a pale yellow solid. LC-MS [M+H]$^+$=443, 445, RT=1.91 min.

Intermediate N: Preparation of 1-(4-amino-5-bromopyrrolo[2,1-f][1,2,4]triazin-7-yl)-2-morpholin-4-ylethanone

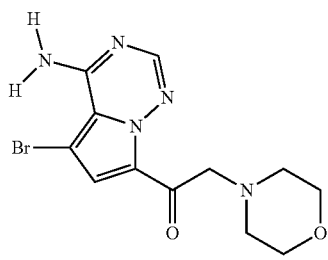 [SMILES: Nc1ncnn2c(C(=O)CN3CCOCC3)cc(Br)c12]

Step 1: Preparation of 1-(4-amino-5-bromopyrrolo[2,1-f][1,2,4]triazin-7-yl)-2-chloroethanone

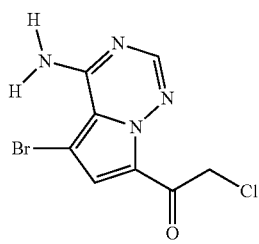

To a solution of 1-(4-aminopyrrolo[2,1-f][1,2,4]triazin-7-yl)-2-chloroethanone (500 mg, 2.37 mmol) in DMF (40 mL) at −40° C., was added 1,3-dibromo-5,5-dimethylimidazolidine-2,4-dione (339 mg, 1.19 mmol). The reaction was allowed to stir for 1 hr while warming to rt. A precipitate had formed and the reaction was filtered and the precipitate was washed With $Et_2O$ to afford 360 mg (52%) of the desired product as a white powder. $^1$H NMR (300 MHz, DMSO-$d_6$) δ 8.12 (s, 1 H), 7.53 (s, 1 H), 5.10 (s, 2H); LC-MS (m+H)$^+$= 291, RT=2.51 min.

Step 2: Preparation of the Title Compound

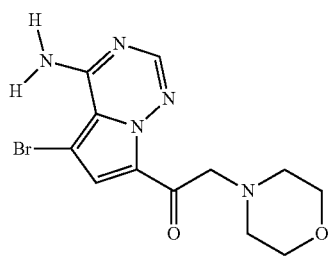 [SMILES: Nc1ncnn2c(C(=O)CN3CCOCC3)cc(Br)c12]

To a solution of 1-(4-amino-5-bromopyrrolo[2,1-f][1,2,4]triazin-7-yl)-2-chloroethanone (90 mg, 0.31 mmol) in DMF (3 mL) was added morpholine (274 μL, 3.11 mmol). The reaction was stirred 15 minutes at rt. The mixture was partitioned between ethyl acetate (20 mL) and saturated, aqueous $Na_2CO_3$ solution (15 mL). The layers were separated and the organic phase was washed with brine, dried ($Na_2SO_4$), and concentrated to dryness. Trituration with $Et_2O$ afforded 90 mg (85%) of the desired product as a white solid. LC-MS [M+H]$^+$=340,342, RT=1.11 min.

Intermediate O: Preparation of 5-bromo-6-methyl-7-(morpholin-4-ylmethyl)pyrrolo[2,1-f][1,2,4]triazin-4-amine

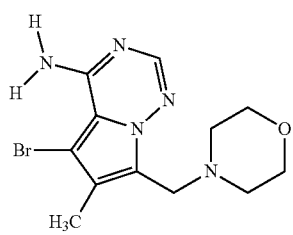 [SMILES: Cc1c(Br)c2c(N)ncnn2c1CN1CCOCC1]

Step 1: Preparation of 6-methylpyrrolo[2,1-f]1,2,4]triazin-4-amine

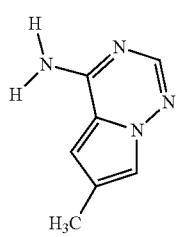

To a degassed solution of 6-bromopyrrolo[2,1-f][1,2,4]triazin-4-amine (316 mg, 1.48 mmol) in 1,4-dioxane (10 mL) and bis(diphenylphosphino)ferrocenepalladium dichloride (30 mg, 0.037 mmol), was added dimethyl zinc (2.97 mL, 5.93 mmol, 2.0 M in toluene). The reaction was allowed to stir at 90° C. for 17 hr. The reaction was quenched with MeOH (1.0 mL) and partitioned between ethyl acetate (200 mL) and potassium phosphate dibasic pH 10 buffer (100 mL). The layers were separated and the organic phase was washed with brine, dried (Na$_2$SO$_4$), and concentrated to dryness. Trituration with Et$_2$O afforded 175 mg (79%) of the desired product. LC-MS [M+H]$^+$=149, RT=1.16 min.

Step 2: Preparation of the Titled Compound

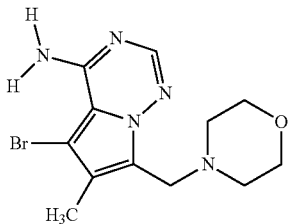 [SMILES: Cc1c(Br)c2c(N)ncnn2c1CN1CCOCC1]

To a solution of 6-methylpyrrolo[2,1-f][1,2,4]triazin-4-amine (350 mg, 2.36 mmol) in DMF (5 mL) was added 4-methylenemorpholin-4-ium chloride (750 mg, 2.84 mmol) at rt. The reaction was stirred for 17 hr, cooled to −78° C., and treated with 1,3-dibromo-5,5-dimethylimidazolidine-2,4-dione (337 mg, 1.18 mmol). The reaction was allowed to stir for 30 minutes while warming to rt. The mixture was partitioned between ethyl acetate (200 mL) and saturated, aqueous Na$_2$CO$_3$ solution (150 mL). The layers were separated and the organic phase was washed with brine, dried (Na$_2$SO$_4$), and concentrated to dryness. Trituration with acetonitrile afforded 300 mg (39%) of the desired product. LC-MS [M+H]$^+$=326, 328, RT=1.10 min.

Intermediate Q: 7-(8-benzyloctahydropyrazino[2,1-c][1,4]oxazin-3-yl)-5-(2-Phenyl-2H-indazol-6-yl)pyrrolo[2,1-f][1,2,4]triazin-4-amine

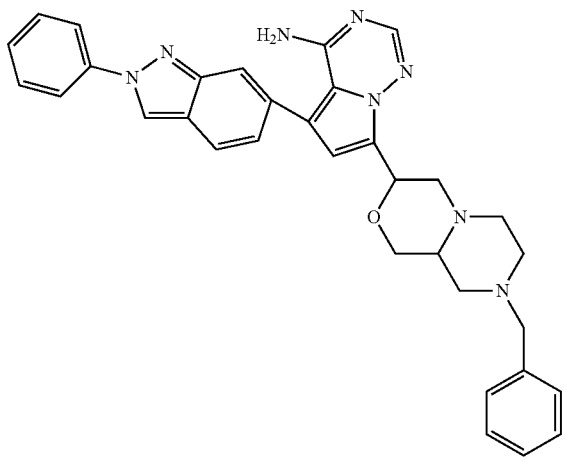 [SMILES: Nc1ncnn2c(C3CN4CCN(Cc5ccccc5)CC4CO3)cc(-c3ccc4cn(-c5ccccc5)nc4c3)c12]

In a manner similar to the procedure described for the preparation of Example 101 and using 7-(8-benzyloctahydropyrazino[2,1-c][1,4]oxazin-3-yl)-5-bromopyrrolo[2,1-f][1,2,4]triazin-4-amine and 2-phenyl-6-(4,4,55-tetramethyl-1,3,2-dioxaborolan-2-yl)-2H-indazole, 550 mg (58%) of the desired product was isolated. LC-MS [M+H]$^+$=557, RT=2.81 min.

Intermediate R: Preparation of 2-Benzyl-5-fluoro-6-(4,4,5,5-tetramethyl-[1,3,2]dioxaborolan-2-yl)-2H-indazole

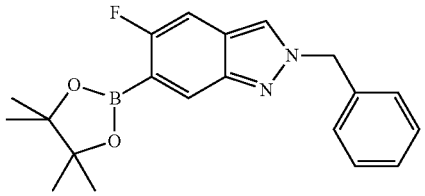 [SMILES: CC1(C)OB(c2cc3nn(Cc4ccccc4)cc3cc2F)OC1(C)C]

Step 1: Preparation of 6-Chloro-5-fluoro-1H-indazole

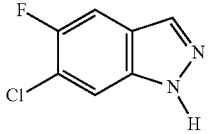 [SMILES: Fc1cc2cn[nH]c2cc1Cl]

A mixture of 4-chloro-2,5-difluorobenzaldehyde (20.6 g, 105.0 mmol) and hydrazine hydrate (77.2 mL, 1575.2 mmol, 15 eq) in n-butanol (35 mL) was stirred at 140° C. for 3 days. The mixture was cooled to room temperature and poured into ice water (750 mL). The mixture was stirred vigorously for 2 h, and the orange solid was filtered. The filtrate was extracted with EtOAc (3×250 mL), and the combined organic phases were washed with brine, dried over Na$_2$SO$_4$, filtered, and concentrated in vacuo. The residue was combined with the orange solid and then purified by MPLC (Biotage®, gradient elution 25% EtOAc/hexane) to give 2.81 g (16%) of a white solid. $^1$H-NMR (300 MHz, DMSO-d$_6$) δ 13.3 (broad s, 1H), 8.09 (s, 1H), 7.80 to 7.76 (m, 2H); ES-MS m/z 171.2/173.2 [M+H]$^+$, RT (min) 3.02.

Step 2: Preparation of 2-Benzyl-6-chloro-5-fluoro-2H-indazole

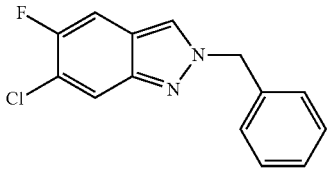 [SMILES: Fc1cc2cn(Cc3ccccc3)nc2cc1Cl]

This compound was prepared in a manner similar to the procedure described for the preparation of 2-benzyl-6-bromo-2H-indazole, using 6-chloro-5-fluoro-1H-indazole in place of 6-bromoindazole. $^1$H-NMR (300 MHz, DMSO-d$_6$) δ 8.54 (s, 1H), 7.90 (d, 1H), 7.71 (d, 1H), 7.36 to 7.29 (m, 5H), 5.64 (s, 2H); ES-MS m/z 261.0 [M+H]$^+$, RT (min) 3.56.

Step 3: Preparation of the Title Compound

To the microwave vial was added 2-benzyl-6-chloro-5-fluoro-2H-indazole (500 mg, 1.92 mmol), bis-pinacoldiborane (535.7 mg, 2.11 mmol, 1.1 eq), tris(dibenzylideneacetone) dipalladium (53.7 mg, 0.06 mmol, 0.03 mmol), tricyclohexylphosphine (38.7 mg, 0.14 mmol, 0.07 eq), and potassium acetate (564.7 mg, 5.75 mmol, 3.0 eq). Degassed anhydrous DMF (12 mL) was added. The vial was capped and the reaction was irradiated in a microwave reactor at 180° C. for 20 min. The mixture was cooled to room temperature and poured into EtOAc. The organic layer was washed with 50% aqueous brine (3×), dried over Na$_2$SO$_4$, filtered, and concentrated in vacuo. The residue was purified by MPLC (Biotage®, gradient elution 10 to 25% EtOAc/hexane) to give the product (337.3 mg, 50%) as an oil. $^1$H-NMR (300 MHz, CD$_3$OD) δ 8.24 (s, 1H), 8.04 (d, 1H), 7.36 to 7.30 (m, 5H), 7.26 (d, 1H), 5.64 (s, 2H), 1.37 (s, 12H); ES-MS m/z 247.2 [M+H]$^+$, RT (min) 1.07.

Intermediate S: 2-Phenyl-6-(4,4,5,5-tetramethyl-[1,3,2]dioxaborolan-2-yl)-2H-indazol-3-ylamine

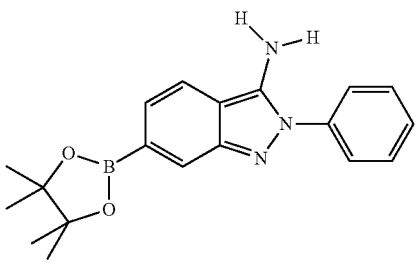 [SMILES: CC1(C)OB(c2ccc3c(N)n(-c4ccccc4)nc3c2)OC1(C)C]

Step 1: Preparation of 6-Bromo-2-phenyl-2H-indazol-3-ylamine

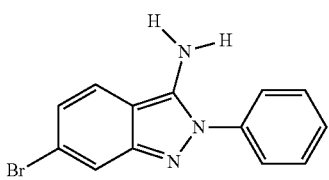 [SMILES: Nc1c2ccc(Br)cc2nn1-c1ccccc1]

To a dried flask charged with 4-bromo-2-fluorobenzonitrile (4.0 g, 18.0 mmol) in n-butanol (60 mL) was added a solution of phenylhydrazine hydrochloride (10.4 g, 72.0 mmol, 4.0 eq) and diisopropylethylamine (13.2 mL, 75.6 mmol, 4.2 eq) in n-butanol (35 mL). The reaction mixture was stirred at 140° C. under N$_2$ for 3 days. The mixture was cooled to rt and partitioned between EtOAc and water. The organic layer was washed with water and brine, dried over Na$_2$SO$_4$, filtered, and concentrated in vacuo. The crude product was purified using an ISCO® instrument (gradient 10 to 65% EtOAc/hexane) and the product containing fractions were concentrated. Crystallization from DCM-hexane afforded 1.33 g (26%) of the title compound as beige solid. $^1$H NMR (300 MHz, DMSO-d$_6$) δ 7.71 (d, 1H), 7.69 to 7.66 (m, 2H), 7.58 to 7.54 (m, 2H), 7.47 to 7.44 (m, 2H), 6.78 (dd, 1H), 6.50 (s, 2H); ES-MS m/z 288.1/290.1 [M+H]$^+$, RT (min) 2.28.

Step 2: Preparation of the Title Compound

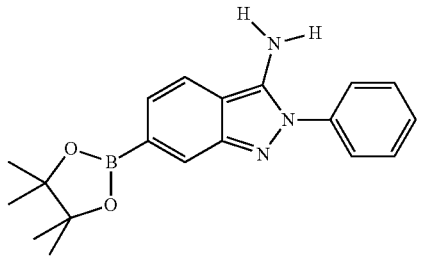 [SMILES: CC1(C)OB(c2ccc3c(N)n(-c4ccccc4)nc3c2)OC1(C)C]

This compound was prepared in a manner similar to the procedure described for the preparation of 2-benzyl-6-(4,4,5,5-tetramethyl-{1,3,2]dioxaborolan-2-yl)-2H-indazole (Intermediate C, step 2), using 6-bromo-2-phenyl-2H-indazol-3-ylamine in place of 2-benzyl-6-bromo-2H-indazole. $^1$H-NMR (300 MHz, DMSO-d$_6$) δ 7.72 to 7.69 (m, 3H), 7.64 (s, 1H), 7.56 (t, 2H), 7.44 (t, 1H), 6.93 (d, 1H), 6.25 (s, 2H), 1.30 (s, 12H); ES-MS m/z 336.2 [M+H]$^+$, RT (min) 2.51.

Intermediate T: Preparation of piperazine-1-carboxylic acid methylamide

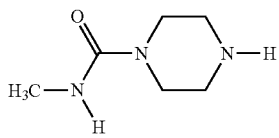

Step 1: Preparation of 4-Benzyl-piperazine-1-carboxylic acid methylamide

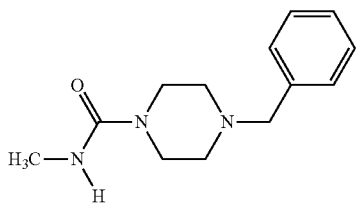

To a suspension of 1-benzyl-piperazine (1.28 g, 7.3 mmol) in anhydrous DCE (36 mL) was added N-methylisocyanate (0.50 g, 8.76 mmol, 1.2 eq.), and the reaction mixture was stirred at 50° C. under N$_2$ for 6 h. The reaction was cooled to rt and MeOH (10 mL) was added to quench the reaction. The solvent was evaporated at reduced pressure. Trituration with DCM-ether gave 1.58 g (92%) of the desired product as an off-white solid. $^1$H-NMR (300 MHz, DMSO-d$_6$) δ 7.33 to 7.23 (m, 5H), 6.37 (broad d, 1H), 3.45 (s, 2H), 3.23 (t, 4H), 2.52 (d, 3H), 2.27 (t, 4H); ES-MS m/z 234.1 [M+H]$^+$, RT (min) 1.08.

Step 2: Preparation of the Title Compound

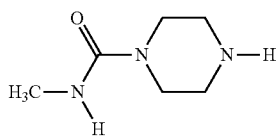

Palladium on carbon (300 mg, 10% by wt.) was placed under an inert atmosphere and suspended in EtOH (10 mL). A solution of 4-benzyl-piperazine-1-carboxylic acid methylamide (1.50 g, 6.43 mmol) dissolved in 2:1 v/v EtOH/THF (96 mL) was added. The reaction mixture was placed under $H_2$ atmosphere (1 atmosphere pressure) and stirred overnight. The resulting mixture was filtered through a pad of Celite® and the solvent was concentrated in vacuo to give 916 mg (99%) of the title compound as clear oil. $^1$H-NMR (300 MHz, DMSO-$d_6$) δ 6.30 (broad d, 1H), 3.15 to 3.12 (m, 5H), 2.59 to 2.55 (m, 4H), 2.53 (d, 3H).

Intermediate T: Preparation of piperazin-2-yl-methanol

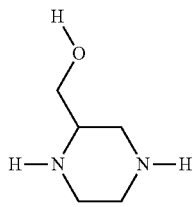

Palladium on carbon (40 mg, 10% by wt.) was placed under an inert atmosphere and suspended in EtOH (10 mL). A solution of (4-benzyl-piperazin-2-yl)methanol (200 mg, 0.970 mmol) dissolved in EtOH (9.6 mL) was added. The reaction mixture was placed under $H_2$ atmosphere (1 atmosphere pressure) and stirred overnight. The resulting mixture was filtered through a pad of Celite® and the solvent was concentrated In vacuo. Crystallization from ether-hexane gave 112.4 mg (99%) of the title compound as a white solid. $^1$H-NMR (300 MHz, CDCl$_3$) δ 3.62 to 3.57 (m, 1H), 3.48 to 3.45 (m, 1H), 3.03 to 2.99 (m, 1H), 2.94 to 2.89 (m, 2H), 2.86 to 2.79 (m, 2H), 2.76 to 2.70 (m, 1H), 2.56 to 2.50 (m, 1H), 1.89 to 1.86 (broad s, 31-1).

Intermediate U: Preparation of Azetidin-3-ol

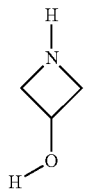

To a stirred mixture of N-boc-3-hydroxyazetidine (500 mg, 2.89 mmol) in DCM (14 mL) was added trifluoroacetic acid (2.9 mL). The mixture was stirred at room temperature for 1 h and concentrated in vacuo to give crude product. This material was mixed with DMF to make a 1 M stock solution and used as is.

Intermediate V: Preparation of Hexahydro-pyrazino 2,1-c[]1,4 oxazin-4-one

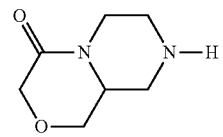 [SMILES: O=C1COCC2CNCCN12]

Step 1: Preparation of 1-(4-Benzyl-2-hydroxymethyl-piperazin-1-yl)-2-chloro-ethanone

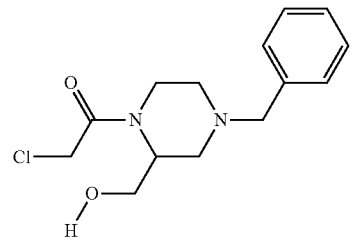 [SMILES: O=C(CCl)N1CCN(Cc2ccccc2)CC1CO]

To a stirred solution of (4-benzyl-piperazin-2-yl)methanol (500 mg, 2.42 mmol) and sodium acetate (397.6 mg, 4.85 mmol, 2.0 eq) in acetone (9.7 mL) and water (24.2 mL) under $N_2$ at 0° C. was added dropwise chloroacetyl chloride (0.20 mL, 2.54 mmol, 1.05 eq) over 5 minutes. The mixture was stirred at 0° C. for 5 min and at rt for 1 h. The mixture was diluted with EtOAc (150 mL) and the organic phase was washed with water, aqueous saturated NaHCO$_3$ solution, and brine. The organic layer was dried over Na$_2$SO$_4$, filtered, and concentrated in vacuo to give 680 mg (99%) of the desired product as an oil. $^1$H-NMR (300 MHz, CD$_3$OD) δ 7.32 to 7.23 (m, 5H), 4.51 (d, 1H), 4.32 to 3.98 (m, 4H), 3.82 to 3.73 (m, 1H), 3.62 to 3.42 (m, 3H), 3.06 to 3.00 (m, 1H), 2.91 to 2.82 (m, 2H), 2.25 to 1.98 (m, 2H).

Step 2: Preparation of 8-Benzyl-hexahydro-pyrazino [2,1-c][1,4]oxazin-4-one

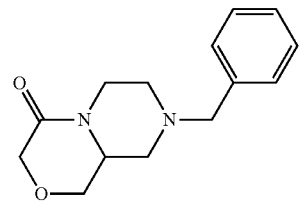 [SMILES: O=C1COCC2CN(Cc3ccccc3)CCN12]

To a stirred mixture of 1-(4-Benzyl-2-hydroxymethyl-piperazin-1-yl)-2-chloro-ethanone (425 mg, 1.50 mmol) in anhydrous THF (10 mL) under $N_2$ was added 60% sodium hydride (240.5 mg, 6.0 mmol, 4.0 eq). The mixture was stirred at rtT for 6 h and quenched with aqueous, saturated NH$_4$Cl solution. The mixture was poured into EtOAc, and the organic layer was washed with 50% aqueous brine (3×), dried over Na$_2$SO$_4$, filtered, and concentrated in vacuo. The residue was purified by MPLC (Biotage®, gradient elution 75 to 100% EtOAc/hexane) to give the product (265 mg, 72%) as clear oil. ¹H-NMR (300 MHz, DMSO-d₆) δ 7.34 to 7.24 (m, 5H), 4.34 to 4.29 (m, 1H), 3.99 (s, 2H), 2.92 (dd, 1H), 3.57 to 3.52 (m, 1H), 3.49 (d, 2H), 3.47 to 3.42 (dd, 1H), 2.82 to 2.74 (m, 2H), 2.69 (dt, 1H), 1.89 (dt, 1H), 1.77 (t, 1H); ES-MS m/z 247.2 [M+H]⁺, RT (min) 1.07.

Step 3: Preparation of the Title Compound

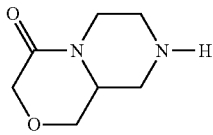

10% Palladium on carbon (53 mg, 20% by wt.) was placed under an inert atmosphere and suspended in EtOH (2 mL). A solution of 8-benzyl-hexahydro-pyrazino[2,1-c][1,4]oxazin-4-one (265 mg, 1.08 mmol) dissolved in EtOH (10 mL) was added. The reaction mixture was placed under H₂ atmosphere (1 atmosphere pressure) and stirred overnight. The resulting mixture was filtered through a pad of Celite® and the solvent was concentrated in vacuo to give 168 mg (99.9%) of the title compound as clear oil. ¹H-NMR (300 MHz, CD₃OD) δ 4.45 (dt, 1H), 4.11 (broad s, 2H), 4.02 to 3.96 (m, 1H), 3.60 to 3.50 (m, 2H), 3.03 to 2.92 (m, 2H), 2.75 to 2.59 (m, 2H), 2.55 to 2.47 (m, 1H).

Intermediate W: Preparation of Hexahydro-oxazolo[3,4-a]pyrazin-3-one

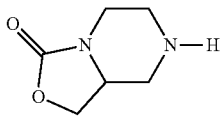

Step 1: Preparation of 7-Benzyl-hexahydro-oxazolo[3,4-a]pyrazin-3-one

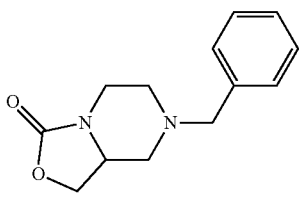

To a stirred solution of (4-benzyl-piperazin-2-yl)methanol (250 mg, 1.21 mmol) in anhydrous DCE (8.0 mL) was added triphosgene (133 mg, 0.45 mmol, 0.37 eq) followed by diisopropylethylamine (0.25 mL, 1.45 mmol, 1.2 eq). The mixture was stirred at 50° C. under N₂ for 16 h. The mixture was cooled to rt, quenched with aqueous, saturated NH₄Cl solution (2.0 mL), and poured into EtOAc. The organic phase was washed with water and brine, dried over Na₂SO₄, filtered, and concentrated in vacuo. The residue was purified by MPLC (Biotage®, gradient elution 80 to 100% EtOAc/hexane) to give the product (91.2 mg, 32%) as a clear oil, ¹H-NMR (300 MHz, CD₃OD) δ 7.35 to 7.24 (m, 5H), 4.38 (t, 1H), 3.96 to 3.87 (m, 2H), 3.71 to 3.66 (m, 1H), 3.57 (q, 2H), 3.14 to 3.07 (m, 1H), 2.97 to 2.93 (m, 2H), 2.04 (dt, 1H), 1.93 (t, 1H); ES-MS m/z 233.2 [M+H]⁺, RT (min) 0.29.

Step 2: Preparation of the Title Compound

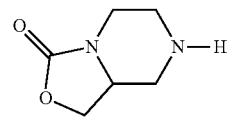

10% Palladium on carbon (18 mg, 20% by wt.) was placed under an inert atmosphere and suspended in EtOH (1 mL). A solution of 7-benzyl-hexahydro-oxazolo[3,4-a]pyrazin-3-one (90 mg, 0.39 mmol) dissolved in EtOH (3.8 mL) was added. The reaction mixture was placed under H₂ atmosphere (1 atmosphere pressure) and stirred overnight. The resulting mixture was filtered through a pad of Celite® and the solvent was concentrated in vacuo to give 53.6 mg (97%) of the title compound as clear oil. ¹H-NMR (300 MHz, CD₃Cl) δ 4.36 (t, 1H), 3.89 to 3.81 (m, 1H), 3.79 to 3.69 (m, 2H), 3.10 to 2.88 (m, 3H), 2.67 to 2.50 (m, 2H), 2.00 to 1.90 (m, 1H).

Intermediate X: Preparation of Hexahydro-pyrido[4,3-b][1,4]oxazin-3-one

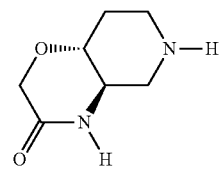 [SMILES: O=C1CO[C@@H]2CCNC[C@H]2N1]

The title compound was prepared following the method described in PCT/US2004/043169. ¹H-NMR (300 MHz, CDCl₃) δ 7.13 (broad s, 1H), 4.27 (q, 2H), 3.31 to 3.22 (m, 3H), 3.09 to 3.03 (m, 1H), 2.66 to 2.53 (m, 2H), 1.90 to 1.85 (m, 1H), 1.81 to 1.72 (broad s, 1H), 1.54 to 1.43 (m, 1H).

Intermediate Y: Preparation of Cyclopropyl-piperazin-1-yl-methanone

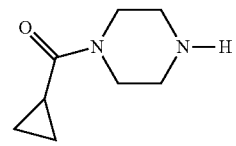 [SMILES: O=C(C1CC1)N1CCNCC1]

Step 1: Preparation of (4-Benzyl-piperazin-1-yl)-cyclopropyl-methanone

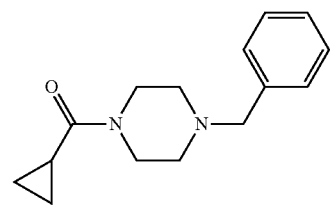 [SMILES: O=C(C1CC1)N1CCN(Cc2ccccc2)CC1]

To a mixture of 1-benzyl-piperazine (1.20 g, 6.81 mmol) in anhydrous DCE (23 mL) was added cyclopropane carboxylic acid chloride (854 mg, 8.17 mmol, 1.2 eq) followed by diisopropylethylamine (1.3 mL, 7.49 mmol, 1.1 eq), and the reaction mixture was stirred at 50° C. under N₂ for 15 h. The mixture was cooled to rt and poured into EtOAc. The organic phase was washed with water and brine, dried over Na₂SO₄, filtered, and concentrated in vacuo. The residue was purified by MPLC (Biotage®, gradient elution 75% EtOAc/hexane) to give the product (1.65 g, 99%) as a brown oil. ¹H-NMR (300 MHz, DMSO-$d_6$) δ 7.34 to 7.23 (m, 5H), 3.64 (broad s, 2H), 3.48 (s, 2H), 3.44 (broad s, 2H), 2.37 (broad s, 2H), 2.28 (broad s, 2H), 1.95 to 1.91 (m, 1H), 0.70 to 0.65 (m, 4H); ES-MS m/z 245.2 [M+H]⁺, RT (min) 1.12.

Step 2: Preparation of the Title Compound

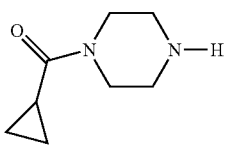 [SMILES: O=C(C1CC1)N1CCNCC1]

10% Palladium on carbon (175 mg, 10% by wt.) was placed under an inert atmosphere and suspended in EtOH (5 mL). A solution of (4-benzyl-piperazin-1-yl)-cyclopropyl-methanone (1.75 g, 7.16 mmol) dissolved in EtOH (25 mL) was added. The reaction mixture was placed under H₂ atmosphere (1 atmosphere pressure) and stirred overnight. The resulting mixture was filtered through a pad of Celite® and the solvent was concentrated in vacuo to give 1.07 g (97%) of the title compound as a clear oil. ¹H-NMR (300 MHz, CD₃OD) δ 3.74 (broad s, 2H), 3.57 (broad s, 2H), 2.87 (broad s, 2H), 2.80 (broad s, 2H), 1.97 to 1.91 (m, 1H), 0.89 to 0.78 (m, 4H); ES-MS m/z 154.9 [M+H]⁺, RT (min) 1.02.

Intermediate Z: Preparation of N-Methyl-2-piperazin-1-yl-acetamide

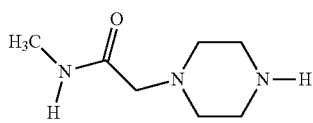

Step 1: Preparation of 2-(4-Benzyl-piperazin-1-yl)-N-methyl-acetamide

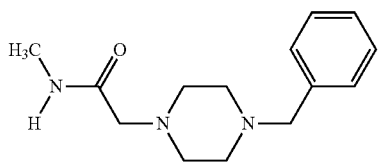

A mixture of 1-benzyl-piperazine (1.0 g, 5.67 mmol), 2-chloro-N-methylacetamide (671.2 mg, 6.24 mmol, 1.1 eq.), and potassium carbonate (941 mg, 6.81 mmol, 1.2 eq.) in anhydrous THF (23 mL) was stirred at 60° C. under N₂ for 18 h. The mixture was cooled to rt and poured into EtOAc. The organic phase was washed with water and brine, dried over Na₂SO₄, filtered, and concentrated in vacuo. The residue was purified by MPLC (Biotage®, gradient elution 1:4:5 v/v MeOH:Acetone:DCM) to give 1.16 g (83%) of the product as a white solid. ¹H-NMR (300 MHz, DMSO-$d_6$) δ 7.62 to 7.56 (broad d, 1H), 7.33 to 7.20 (m, 5H), 3.45 (s, 2H), 2.85 (s, 2H), 2.58 (d, 3H), 2.44 to 2.33 (broad s, 8H); ES-MS m/z 248.2 [M+H]⁺, RT (min) 0.33.

Step 2: Preparation of the Title Compound

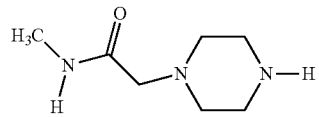

10% Palladium on carbon (115 mg, 10% by wt.) was placed under an inert atmosphere and suspended in EtOH (5 mL). A solution of 2-(4-benzyl-piperazin-1-yl)-N-methyl-acetamide (1.15 g, 4.65 mmol) dissolved in EtOH (18 mL) was added. The reaction mixture was placed under H₂ atmosphere (1 Atm pressure) and stirred overnight. The resulting mixture was filtered through a pad of Celite® and the solvent was concentrated in vacuo to give 723 mg (98.9%) of the title compound as a white solid. ¹H-NMR (300 MHz, DMSO-$d_6$) δ 7.61 (broad s, 1H), 2.80 (s, 2H), 2.68 (t, 4H), 2.59 (d, 3H), 2.31 to 2.26 (m, 4H); ES-MS m/z 158.0 [M+H]⁺, RT (min) 1.13.

Intermediate A A: Preparation of 2-methylpyrrolo[2,1-f][1,2,4]triazin-4-amine

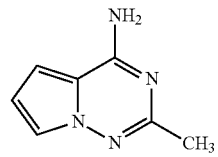

A mixture of 1-amino-1H-pyrrole-2-carbonitrile hydrochloride (2.77 g, 19.3 mmol), potassium phosphate (21.11 g, 96.5 mmol), acetamidine hydrochloride (9.6 g, 96.5 mmol) and 1-butanol (166 mmol) was refluxed under nitrogen atmosphere. After 166.5 h of reflux, the mixture was allowed to cool to rt, and was then partitioned between ethyl acetate and water. The phases were separated, and the organic phase was extracted with 1N aqueous hydrochloric acid. The acid extracts were made basic (pH>7) and extracted with ethyl acetate. After washing the organic layers with water and brine, drying (anhydrous sodium sulfate) and concentration afforded 1.63 g (57%) of solid. ¹H-NMR (CD₂Cl₂): δ 7.51 (m, 1 H), 6.40 (m, 2 H), 6.72 (br s, 2 H), 2.32 (s, 3 H). MS: LC/MS (+esi), m/z=149 [M+H]. RT=1.12 min.

Intermediate B B: Preparation of 5-bromo-2-methylpyrrolo[2,1,][1,2.4]triazin-4-amine

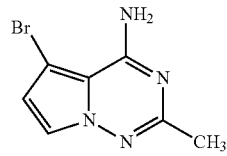

A stirred solution of 2-methylpyrrolo[2,1-f][1,2,4]triazin-4-amine (54 mg, 0.34 mmol) in dichloromethane (10 mL) was cooled under nitrogen atmosphere below −70° C., and a solution of 1,3-dibromo-5,5-dimethylimidazolidine-2,4-dione (49 mg, 0.17 mmol) in dichloromethane (10 mL) added dropwise over a 1 h. After stirring overnight at room temperature, 10% aqueous sodium thiosulfate solution was added, and the mixture was stirred vigorously for a few minutes. The phases were separated, and the dichloromethane phase was washed with water, then brine, before drying (anhydrous sodium sulfate). The extracts were filtered and concentrated in vacuo, and the solid purified via MPLC (hexanes/ethyl acetate gradient) to afford 19 mg (25%) of sand-colored solid. $^1$H-NMR (CD$_2$Cl$_2$): δ 6.68 (s, 2 H), 5.51 (br s, 2 H), 2.41 (s, 3 H). MS: LC/MS (+esi), m/z=227 [M+H]. RT=1.25 min.

Intermediate C C: Preparation of 7-bromo-2-methylpyrrolo[2,1-f][1,2,4]triazin-4-amine

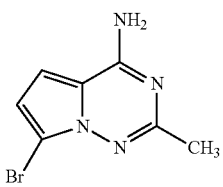

The above experiment also afforded 17 mg (22%) of the title compound as a colorless solid. $^1$H-NMR (CD$_3$CN): δ 7.44 (d, 1 H), 6.64 (d, 1 H), 6.27 (br s, 2 H), 2.23 (s, 3 H). MS: LC/MS (+esi), m/z=227 [M+H]. RT=1.28 min.

Intermediate E E: Preparation of 5-bromopyrrolo[2,1-f][1,2,4]triazin-4-ylamine

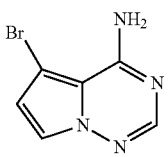

A suspension of pyrrolo[2,1-f][1,2,4]triazin-4-amine (0.5 g, 0.004 mol) in dichloromethane (100 mL) was stirred and cooled between −10° C. and −14° C. under nitrogen atmosphere. A solution of 1,3-dibromo-5,5-dimethylimidazolidine-2,4-dione (544 mg, 0.002 mol) in dichloromethane (100 mL) added dropwise over a 1 h. After 4 h, 100 mL of 10% aqueous sodium thiosulfate solution was added, and the mixture was stirred vigorously for a few minutes. The phases were separated, the dichloromethane phase washed with water, then brine, dried (anhydrous sodium sulfate), filtered and concentrated in vacuo. The residue was purified by MPLC (dichloromethane/ethyl acetate gradient). Purified material was triturated with dichloromethane, filtered, washed and dried under vacuum to afford 289 mg (36%) of colorless, fluffy solid. $^1$H-NMR (DMSO-d$_6$): δ 8.01 (br s, 1 H), 7.82 (s, 1 H), 7.70 (d, 1 H), 6.78 (d, br s, 2 H). MS: LC/MS (+esi), m/z=212.5, 213.1 [M+H]. RT=1.34 min. Calc. for C$_6$H$_5$BrN$_4$: C, 33.83; H, 2.37; Br, 37.50; N, 26.3. Found: C, 33.85; H, 2.24; Br, 38.24; N, 26.21.

Intermediate F F: Preparation of tert-butyl 4-(4-amino-2-methylpyrrolo[2,1-f][1,2,4]triazin-7-yl)-3,6-dihydropyridine-1(2H)-carboxylate

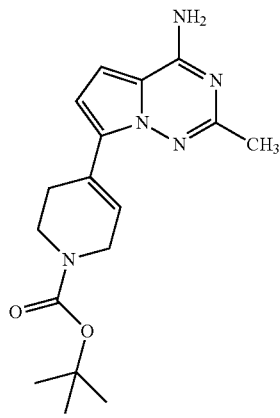 [SMILES: Cc1nc(N)c2ccc(C3=CCN(C(=O)OC(C)(C)C)CC3)n2n1]

The title compound was prepared in the same manner described for the preparation of tert-butyl 4-(4-aminopyrrolo[2,1-f][1,2,4]triazin-7-yl)-3,6-dihydropyridine-1(2H)-carboxylate and substituting 7-bromo-2-methylpyrrolo[2,1-f][1,2,4]triazin-4-amine for 7-bromopyrrolo[2,1-f][1,2,4]triazin-4-amine. $^1$H-NMR (CD$_3$OD): δ 7.02 (s, 1 H), 6.83 (d, 1 H), 6.62 (d, 1 H), 4.13 (s, 2 H), 3.64 (s, 2 H), 2.62 (d, 2 H), 2.33 (s, 3 H), 1.49 (s, 9 H). MS: LC/MS (+esi), m/z=330 [M+H]. RT=2.47 min.

Intermediate G G: tert-butyl 4-(4-amino-2-methylpyrrolo[2,1-f][1,2,4]triazin-7-yl)piperidine-1-carboxylate

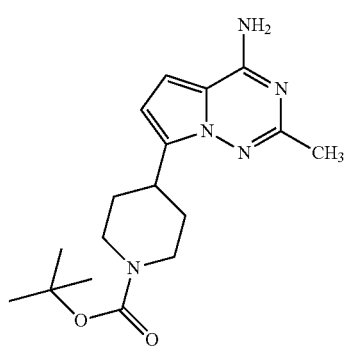 [SMILES: Cc1nc(N)c2ccc(C3CCN(C(=O)OC(C)(C)C)CC3)n2n1]

The title compound was prepared in the same manner described for the preparation of tert-butyl 4-(4-aminopyrrolo[2,1-f][1,2,4]triazin-7-yl)piperidine-1-carboxylate and substituting tert-butyl 4-(4-amino-2-methylpyrrolo[2,1-f][1,2,4]triazin-7-yl)-3,6-dihydropyridine-1(2H)-carboxylate for tert-butyl 4-(4-aminopyrrolo[2,1-f][1,2,4]triazin-7-yl)-3,6-dihydropyridine-1(2H)-carboxylate. $^1$H-NMR (CD2 Cl$_2$): δ 6.59 (d, 1 H), 6.41 (d, 1 H), 5.53 (br s, 2 H), 4.18 (m, 2 H), 3.33 (m, 1 H), 2.89 (m, 2 H), 2.36 (s, 3 H), 2.03 (m, 2 H), 1.58 (m, 2 H), 1.45 (s, 9 H). MS: LC/MS (+esi), m/z=332 [M+H]. RT=2.39 min.

Intermediate H H: tert-butyl 5-bromo-4-(4-amino-2-methylpyrrolo[2,1-f][1,2,4]triazin-7-yl)Piperidine-1-carboxylate

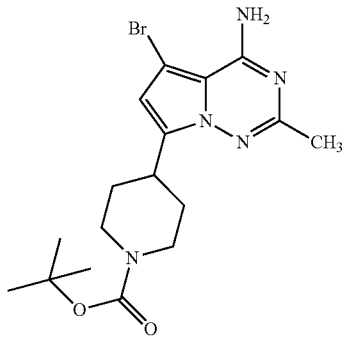 [SMILES: Cc1nc(N)c2c(Br)cc(C3CCN(C(=O)OC(C)(C)C)CC3)n2n1]

The title compound was prepared in the same manner described for the preparation of tert-butyl 4-(4-amino-5-bromopyrrolo[2,1-f][1,2,4]triazin-7-yl)piperidine-1-carboxylate and substituting tert-butyl 4-(4-amino-2-methylpyrrolo[2,1-f]]1,2,4]triazin-7-yl)piperidine-1-carboxylate for tert-butyl 4-(4-aminopyrrolo[2,1-f][1,2,4]triazin-7-yl)piperidine-1-carboxylate. $^1$H-NMR (CD$_2$Cl$_2$): δ 6.44 (d, 1 H), 6.26 (br s, 2 H), 4.19 (m, 2 H), 3.33 (m, 1 H), 2.86 (m, 2 H), 2.34 (s, 3 H), 2.0 (m, 2 H), 1.56 (m, 2 H), 1.45 (s, 9 H). MS: LC/MS (+esi), m/z=410 [M+H]. RT=2.82 min.

Intermediate I I: Preparation of 2-pyrrolidin-1-ylethanol

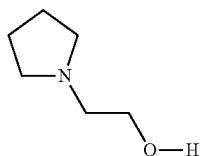

A solution of 2-chloroethanol (3.5 mL, 0.05 mol) in acetonitrile (25 mL) was added dropwise to a stirred, refluxing mixture of pyrrolidine (4.5 mL, 0.053 mol) and anhydrous, powdered potassium carbonate (6.0 g, 0.043 mol) in acetonitrile (75 mL) under nitrogen atmosphere. After 19 h of refluxing, the mixture was allowed to cool to rt and the solids were filtered off and washed with ethyl acetate. The filtrate was concentrated in vacuo, the residual oil taken up in diethyl ether, and the solution filtered through Celite®. Concentration of the filtrate in vacuo afforded 6.24 g of yellow oil, which was used as is in the next step.

Intermediate J J: Preparation of 3-pyrrolidin-1-ylpropan-1-ol

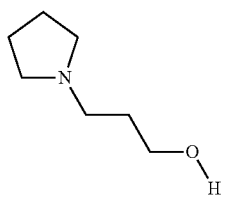

The title compound was prepared in the same manner described for intermediate I I substituting 3-chloropropanol for 2-chloroethanol. $^1$H-NMR (CD$_2$Cl$_2$): δ 3.72 (t, 2 H), 2.7 (m, 2 H), 2.54 (m, 4 H), 2.81 (m, 2 H), 1.76-1.65 (m, 6 H).

Intermediate K K: Preparation of 1-(2-chloroethyl)pyrrolidine hydrochloride

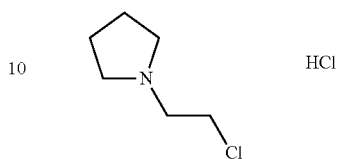

2-pyrrolidin-1-ylethanol (6.24 g, 0.05 mol) was stirred while cautiously adding thionyl chloride (40 mL, 0.54 mol). The stirred mixture was refluxed for 1 hour under nitrogen atmosphere, then concentrated in vacuo. The residue was triturated with diethyl ether to give a solid, and the liquid decanted; this process was repeated several times, until the decantate was almost colorless. The flask containing solid was evaporated to give a free-flowing, cocoa-colored solid (4.21 g, 46%). $^1$H-NMR (CD$_2$Cl$_2$): δ 13.1 (br s, 1 H), 3.97 (t, 3 H), 3.7 (m, 2 H), 3.33 (dd, 2 H), 2.81 (m, 2 H), 2.14-1.95 (m, 3 H).

Intermediate L L: Preparation of 1-(3-chloropropyl)pyrrolidine hydrochloride The title compound was prepared in the same manner described for intermediate K K and substituting 3-pyrrolidin-1-ylpropan-1-ol for 2-pyrrolidin-1-ylethanol. $^1$H-NMR (CD$_2$Cl$_2$): δ 12.69 (br s, 1 H), 3.74-3.69 (m, 4 H), 33.21-3.16 (m, 2 H), 2.80-2.76 (m, 2 H), 2.42-2.37 (m, 2 H), 2.18-2.06 (m, 4 H).

Intermediate M M: Preparation of 2-benzyl-5-bromo-1,3-benzoxazole

Phenylacetyl chloride (1.43 mL, 10.6 mmol) was added to a stirred suspension of 2-amino-4-bromophenol (1.99 g, 10.6 mmol) in toluene (60 mL), and the mixture refluxed into a Dean-Stark trap under nitrogen atmosphere. After 30 min of reflux, the mixture was allowed to cool, and p-toluenesulfonic acid monohydrate (119 mg, 0.63 mmol) was added. After 2.5 h of refluxing, the mixture was allowed to cool, then was concentrated in vacuo to give a solid. Purification by silica gel chromatography (hexanes/dichloromethane gradient) afforded 2.74 g (89%) of nearly colorless solid. $^1$H-NMR (CD₃CN): δ 7.83 (t, 1 H), 7.47 (d, 2 H), 7.37-7.27 (m, 5 H), 4.28 (s, 2 H). MS: LC/MS (+esi), m/z=287.5, 288.5 [M+H]. RT=3.83 min.

Intermediate N N: Preparation of 2-benzyl-6-chloro-1,3-benzoxazole

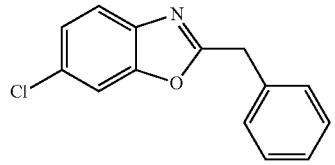 [SMILES: Clc1ccc2nc(Cc3ccccc3)oc2c1]

The title compound was prepared in the same manner described for the preparation of 2-benzyl-5-bromo-1,3-benzoxazole and substituting 2-amino-5-chlorophenol for 2-amino-4-bromophenol. ¹H-NMR (CD₃CN): δ 7.61 (s, 1 H), 7.60 (d, 1 H), 7.36-7.29 (m, 6 H), 4.27 (s, 2 H). MS: LC/MS (+esi), m/z=244 [M+H]. RT=3.67 min.

Intermediate O O: Preparation of 2-benzyl-6-(4,4,5,5-tetramethyl-1,3,2-dioxaborolan-2-yl)-1,3-benzoxazole

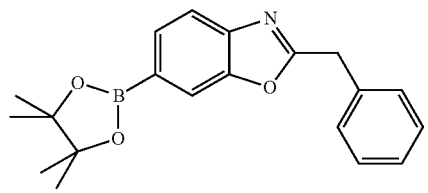 [SMILES: CC1(C)OB(c2ccc3nc(Cc4ccccc4)oc3c2)OC1(C)C]

The title compound was prepared in the same manner described for intermediate R R and substituting 2-benzyl-6-chloro-1,3-benzoxazole for 2-benzyl-7-chloroimidazo[1,2-a]pyridine. ¹H-NMR (CD₂Cl₂): δ 7.88 (s, 1 H), 7.72 (dd, 1 H), 7.65 (dd, 1 H), 7.40-7.29 (m, 5 H), 4.30 (s, 2 H), 1.34 (s, 12 H). MS: LC/MS (+esi), m/z=336 [M+H]. RT=4.03 min.

Intermediate P P: Preparation of 2-benzyl-5-(4,4,5,5-tetramethyl-1,3,2-dioxaborolan-2-yl)-1,3-benzoxazole

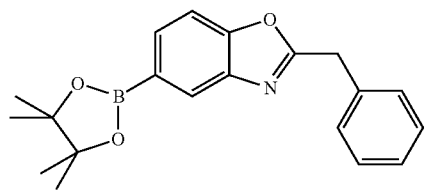 [SMILES: CC1(C)OB(c2ccc3oc(Cc4ccccc4)nc3c2)OC1(C)C]

The title compound was prepared in the same manner described for step 2 of intermediate C and substituting 2-benzyl-5-bromo-1,3-benzoxazole for 2-benzyl-6-bromo-2H-indazole. ¹H-NMR (CD₂Cl₂): δ 8.04 (s, 1 H), 7.72 (dd, 1 H), 7.47 (dd, 1 H), 7.39-7.27 (m, 5 H), 4.28 (s, 2 H), 1.34 (s, 12 H). MS: LC/MS (+esi), m/z=336 [M+H]. RT=4.09 min.

Intermediate S S: Preparation of 5-(2-benzyl-2H-indazol-6-yl)-7-piperidin-3-ylpyrrolo[2,1-f][1,2,4]triazin-4-amine hydrochloride

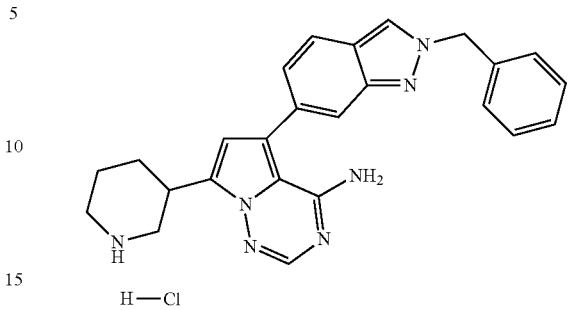

Step 1: Preparation of tert-butyl 3-(4-aminopyrrolo[2,1-f][1,2,4]triazin-7-yl)-3-hydroxypiperidine-1-carboxylate

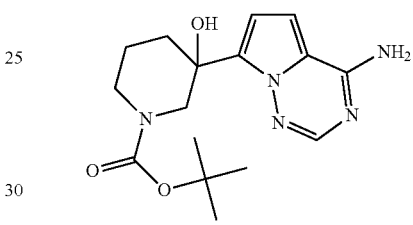

To a stirred suspension of Intermediate B (2.50 g, 9.39 mmol) in THF (50 mL) was added chlorotrimethylsilane (2.98 mL, 23.47 mmol), dropwise. The mixture was stirred at rt for 3 h and 2-propylmagnesium chloride (2M in THF; 24.64 mL, 49.29 mmol) was added dropwise. The suspension immediately went into solution. The mixture was stirred at rt for 3 h and 1-Boc-3-piperidone (3.51 g, 17.60 mmol) was added in one portion. The reaction was stirred at it for 16 h. The reaction was poured over a mixture of ice and saturated, aqueous ammonium chloride (250 mL). The mixture was allowed to warm to rt and was extracted with EtOAc (3×100 mL). The combined organic layers were washed with brine, dried (Na₂SO₄), and concentrated to dryness. The crude residue was purified by ISCO® chromatography using a gradient of 50 to 75% ethyl acetate in hexanes to afford 2.77 g (71%) of the desired product. ES-MS m/z 334.08 [M+H]⁺, HPLC RT (min) 0.97.

Step 2: Preparation of tert-butyl 5-(4-aminopyrrolo[2,1-f][1,2,4]triazin-7-yl)-3,4-dihydropyridine-1(2H)-carboxylate,

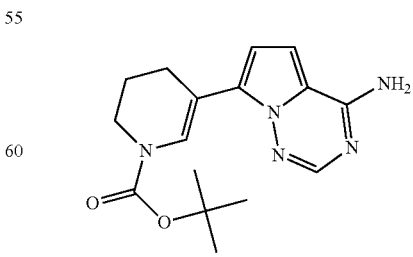

To a cooled (0° C.) solution of tert-butyl 3-(4-aminopyrrolo[2,1-f][1,2,4]triazin-7-yl)-3-hydroxypiperidine-1-carboxylate (2.77 g, 8.31 mmol) in pyridine (55 mL) was added trifluoroacetic anhydride (2.35 mL, 14.1 mmol), dropwise. The ice bath was removed and the mixture was stirred at rt for 17 h. The mixture was concentrated to dryness. The crude solid was triturated with 3:1 EtOAc/hexanes then with MeOH to afford 2.09 g (76%) of the desired product. ES-MS m/z 316.04 [M+H]+, HPLC RT (min) 2.50.

Step 3: Preparation of tert-butyl 3-(4-aminopyrrolo[2,1-f][1,2,4]triazin-7-yl)piperidine-1-carboxylate

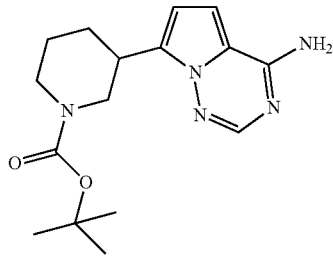 [SMILES: CC(C)(C)OC(=O)N1CCCC(c2ccc3c(N)ncnn23)C1]

To a dry flask purged with N₂ was added platinum (IV) oxide (150 mg, 0.66 mmol) followed by tert-butyl 5-(4-aminopyrrolo[2,1-f][1,2,4]triazin-7-yl)-3,4-dihydropyridine-1(2H)-carboxylate (2.09 mg, 6.63 mmol) as a solution in acetic acid (60 mL). The mixture was stirred under an H₂ atmosphere for 64 h. The mixture was filtered through a pad of Celite® rinsing with acetic acid and EtOH. The solvent was evaporated under reduced pressure and the residue was dissolved in ethyl acetate (200 mL). The organic mixture was washed with saturated, aqueous NaHCO₃ (200 mL) followed by brine, and was dried (Na₂SO₄) and concentrated to dryness to afford 1.60 g (76%) of the desired product. ES-MS m/z 318.22 [M+H]+, HPLC RT (min) 2.43.

Step 4: Preparation of tert-butyl 3-(4-amino-5-bromopyrrolo[2,1-f][1,2,4]triazin-7-yl)piperidine-1-carboxylate

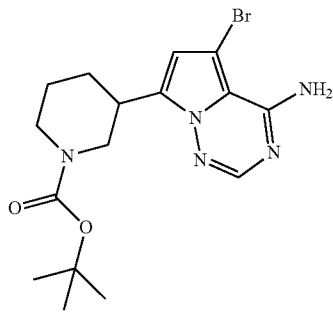 [SMILES: CC(C)(C)OC(=O)N1CCCC(c2cc(Br)c3c(N)ncnn23)C1]

To a cooled (−20° C.) solution tert-butyl 3-(4-aminopyrrolo[2,1-f][1,2,4]triazin-7-yl)piperidine-1-carboxylate (891 mg, 2.81 mmol) in DMF (8.7 mL) and acetic acid (7.0 mL) was added 1,3-dibromo-5,5-dimethylhydantoin (401 mg, 1.40 mmol) in 3 portions over 10 min. The mixture was allowed to stir at −20° C. for 90 min. The reaction was quenched with the addition 5% aqueous K₂CO₃ (20 mL) and was allowed to warm to rt. The mixture was extracted with ethyl acetate (3×20 mL). The combined organics were washed with brine, dried (Na₂SO₄) and evaporated to provide 1.07 g (96%) of the desired product. ES-MS m/z 396.06 [M+H]+, HPLC RT (min) 3.05.

Step 5: Preparation of tert-butyl 3-[4-amino-5-(2-benzyl-2H-indazol-6-yl)pyrrolo[2,1-f][1,2,4]triazin-7-yl]piperidine-1-carboxylate

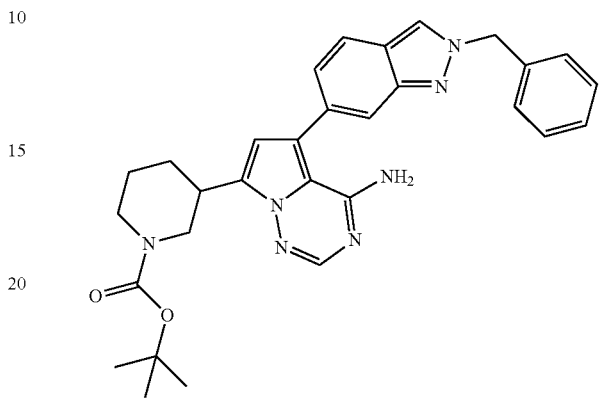

To a stirred, degassed mixture of tert-butyl 3-(4-amino-5-bromopyrrolo[2,1-f]]1,2,4]triazin-7-yl)piperidine-1-carboxylate (1.20 g, 3.03 mmol), Intermediate C (1.52 g, 4.54 mmol), Na₂CO₃ (963 mg, 9.08 mmol) and H₂O (4.5 mL) in DMF (27 mL) was added tetrakis(triphenylphosphine)palladium(0) (350 mg, 0.30 mmol). The reaction was heated (110° C.) for 17 h and then cooled to rt. The mixture was partitioned between ethyl acetate (75 mL) and H₂O (75 mL). The layers were separated and the aqueous was further extracted with ethyl acetate (1×75 mL). The combined organic layers were washed with brine, dried (Na₂SO₄), and concentrated to dryness. The crude material was purified via ISCO® chromatography using a gradient of 50 to 75% ethyl acetate in hexanes to afford 1.4 g (75%) of the desired product, which contained trace impurities. ES-MS m/z 524.26 [M+H]+, HPLC RT (min) 3.16.

Step 6: Preparation of the Title Compound

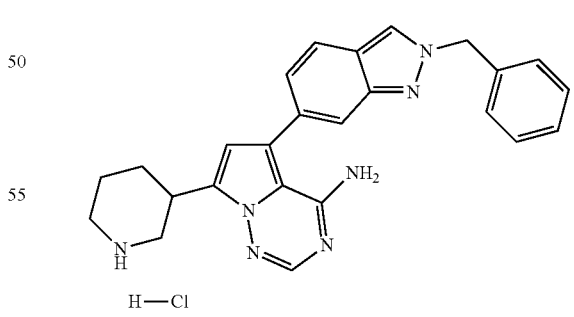

To a suspension of tert-butyl 3-[4-amino-5-(2-benzyl-2H-indazol-6-yl)pyrrolo[2,1-f][1,2,4]triazin-7-yl]piperidine-1-carboxylate in MeOH (8 mL) was added 4M HCl in dioxane (4 mL). The mixture was stirred at rt for 17 h. The mixture was concentrated to dryness to afford 1.5 g (100%) of the desired product. ES-MS m/z 424.21 [M+H]+, HPLC RT (min) 2.21.

Intermediate T T: Preparation of 7-azepan-4-yl-5-(2-benzyl-2H-indazol-6-yl)pyrrolo[2,1-f][1,2,4]triazin-4-amine hydrochloride

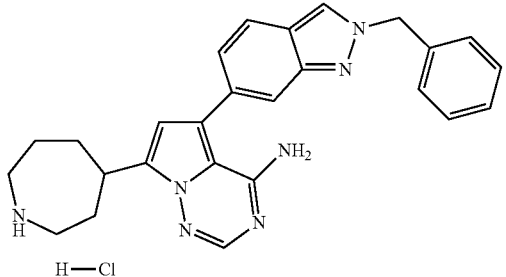

Step 1: Preparation of tert-butyl 4-(4-aminopyrrolo[2,1-f][1,2,4]triazin-7-yl)-4-hydroxyazepane-1-carboxylate

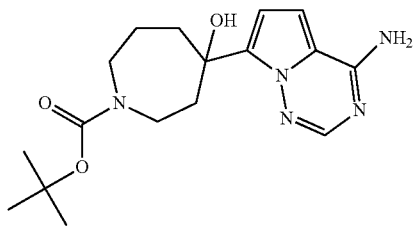 [SMILES: CC(C)(C)OC(=O)N1CCCC(O)(c2ccc3c(N)ncnn23)CC1]

To a stirred suspension of Intermediate B (2.00 g, 9.39 mmol) in THF (40 mL) was added chlorotrimethylsilane (2.38 mL, 18.78 mmol), dropwise. The mixture was stirred at rt for 2 h. The mixture was placed in an ice bath and 2-propylmagnesium chloride (2M in THF; 19.71 mL, 39.43 mmol) was added dropwise. The suspension immediately went into solution. The ice bath was removed and the mixture was stirred at rt for 2 h. The mixture was placed in an ice bath and 4-oxazepane-1-carboxylic acid tert-butyl ester (3.00 g, 14.1 mmol) was added in one portion. The ice bath was once again removed and the reaction was stirred at rt for 16 h. The reaction was poured over a mixture of ice and saturated, aqueous ammonium chloride (200 mL). The mixture was allowed to warm to rt and was extracted with EtOAc (4×50 mL). The combined organics were washed with brine, dried (Na$_2$SO$_4$), and concentrated to dryness. The crude residue was purified by ISCO® chromatography using a gradient of 50 to 75% ethyl acetate in hexanes to afford 2.55 g (78%) of the desired product. ES-MS m/z 348.32 [M+H]$^+$, HPLC RT (min) 2.18.

Step 2: Preparation of tert-butyl 5-(4-aminopyrrolo[2,1-f][1,2,4]triazin-7-yl)-2,3,4,7-tetrahydro-1H-azepine-1-carboxylate

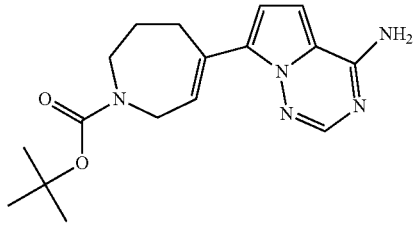 [SMILES: CC(C)(C)OC(=O)N1CC=C(c2ccc3c(N)ncnn23)CCC1]

To a cooled (0° C.) solution of tert-butyl 4-(4-aminopyrrolo[2,1-f][1,2,4]triazin-7-yl)-4-hydroxyazepane-1-carboxylate (2.45 g, 7.05 mmol) and triethylamine (2.95 mL, 21.2 mmol) in CH$_2$Cl$_2$ (49 mL) was added trifluoroacetic anhydride (1.99 mL, 14.1 mmol), dropwise. The ice bath was removed and the mixture was stirred at rt for 3 h. The reaction was quenched with H$_2$O (40 mL) and the layers were separated. The organic phase was washed with brine, dried (Na$_2$SO$_4$), and concentrated to dryness. The crude residue was purified by ISCO® chromatography using 1:1 ethyl acetate/hexanes to afford 1.66 g (72%) of the desired product. ES-MS m/z 330.11 [M+H]$^+$, HPLC RT (min) 2.47.

Step 3: Preparation of tert-butyl 4-(4-aminopyrrolo[2,1-f][1,2,4]triazin-7-yl)azepane-1-carboxylate

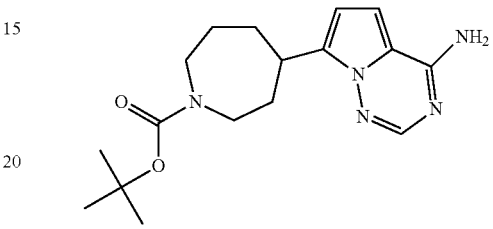

To a dry flask purged with N$_2$ was added platinum (IV) oxide (114 mg, 0.50 mmol) followed by tert-butyl 5-(4-aminopyrrolo[2,1-f][1,2,4]triazin-7-yl)-2,3,4,7-tetrahydro-1H-azepine-1-carboxylate (1.66 mg, 5.04 mmol) as a solution in acetic acid (25 mL). The mixture was stirred under an H$_2$ atmosphere for 16 h. Additional platinum (IV) oxide (114 mg, 0.50 mmol) was added and the reaction continued to stir under an H$_2$ atmosphere for 20 h. The mixture was filtered through a pad of Celite® rinsing with acetic acid. The filtrate was concentrated under reduced pressure and the residue was dissolved in ethyl acetate (200 mL). The organic mixture was washed with saturated, aqueous NaHCO$_3$ (1×200 mL) and the aqueous mixture was back extracted with ethyl acetate (2×75 mL). The combined organic layers were washed with brine, dried (Na$_2$SO$_4$) and concentrated to dryness to afford 1.44 g (86%) of the desired product. ES-MS m/z 332.11 [M+H]$^+$, HPLC RT (min) 2:46.

Step 4: Preparation of tert-butyl 4-(4-amino-5-bromopyrrolo[2,1-f][1,2,4]triazin-7-yl)azepane-1-carboxylate

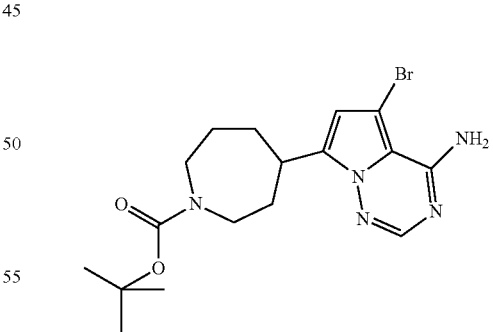

To a cooled (−20° C.) solution tert-butyl 4-(4-aminopyrrolo[2,1-f][1,2,4]triazin-7-yl)azepane-1-carboxylate (1.44 g, 4.35 mmol) in tetrahydrofuran (22 mL) was added 1,3-dibromo-5,5-dimethylhydantoin (621 mg, 2.17 mmol) in 4 portions over 15 min. The mixture was allowed to stir (−20° C.) for 4 h. The reaction was quenched with the addition 5% aqueous K$_2$CO$_3$ (20 mL) and was allowed to warm to rt. The mixture was extracted with ethyl acetate (3×20 mL). The combined organic layers were washed with 5% aqueous K$_2$CO$_3$ (25 mL), brine, dried (Na$_2$SO$_4$) and evaporated to provide 1.74 g (98%) of the desired product, which contained trace impurities. ES-MS m/z 411.91 [M+H]$^+$, HPLC RT (min) 2.92.

Step 5: Preparation of tert-butyl 4-[4-amino-5-(2-benzyl-2H-indazol-6-yl)pyrrolo[2,1-f][1,2,4]triazin-7-yl]azepane-1-carboxylate

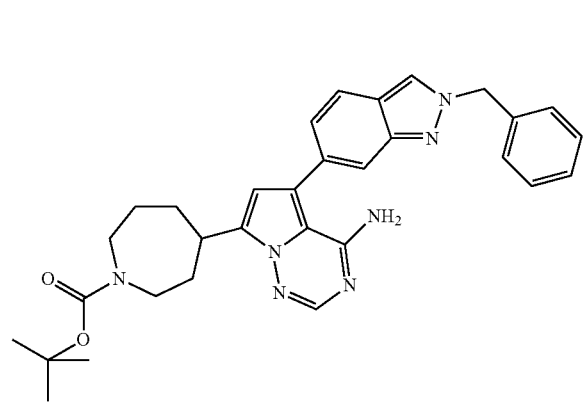 [SMILES: CC(C)(C)OC(=O)N1CCCC(c2cc(-c3ccc4cn(Cc5ccccc5)nc4c3)c3c(N)ncnn23)CC1]

To a stirred, degassed mixture tert-butyl 4-(4-amino-5-bromopyrrolo[2,1-f][1,2,4]triazin-7-yl)cycloheptanecarboxylate (740 mg, 1.80 mmol), Intermediate C (904 mg, 2.71 mmol), Na$_2$CO$_3$ (573 mg, 5.41 mmol) and H$_2$O (2.7 mL) in DMF (14 mL) was added tetrakis(triphenylphosphine)palladium(0) (208 mg, 0.18 mmol). The reaction was heated (110° C.) for 17 h and then cooled to rt. The mixture was partitioned between ethyl acetate (100 mL) and H$_2$O (100 mL). The layers were separated and the aqueous was further extracted with ethyl acetate (1×75 mL). The combined organic layers were washed with brine, dried (Na$_2$SO$_4$), and concentrated to dryness. The crude material was purified via ISCO® chromatography using a gradient of 50 to 75% ethyl acetate in hexanes to afford 882 mg (91%) of the desired product, which contained trace impurities. ES-MS m/z 537.67 [M+H]$^+$, HPLC RT (min) 3.32.

Step 6: Preparation of the Title Compound

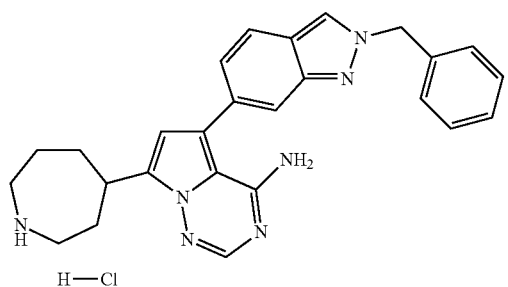

To a solution of tert-butyl 4-[4-amino-5-(2-benzyl-2H-indazol-6-yl)pyrrolo[2,1-f][1,2,4]triazin-7-yl]azepane-1-carboxylate in MeOH (10 mL) was added 4M HCl in dioxane (5 mL). The mixture was stirred at rt for 5 h. The mixture was concentrated to dryness to afford 924 mg (100%) of the desired product, which contained trace impurities. LC-MS [M+H]$^+$=438.28, RT=2.10 min.

Intermediate U U: Preparation of 5-(2-benzyl-2H-indazol-6-yl)-7-(2-piperidin-4-yl-1,3-thiazol-4-yl)pyrrolo[2,1-f][1,2,4]triazin-4-amine hydrochloride

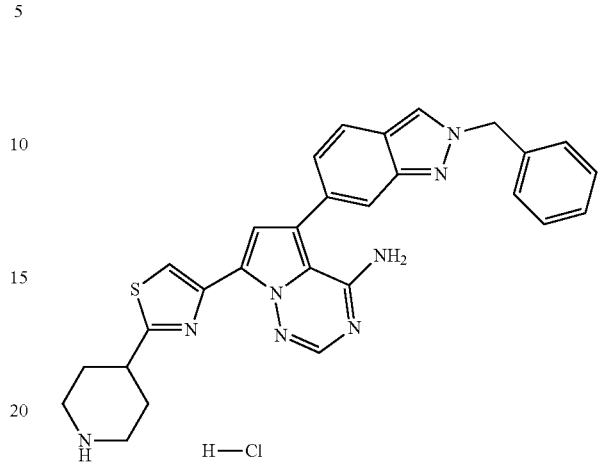

Step 1: Preparation of 1-(4-aminopyrrolo[2,1-f][1,2,4]triazin-7-yl)-2-chloroethanone

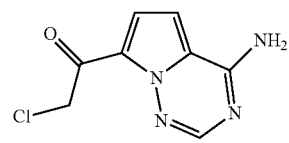 [SMILES: Nc1ncnn2c(C(=O)CCl)ccc12]

To a stirred suspension of Intermediate B (3.00 g, 14.08 mmol) in THF (50 mL) was added chlorotrimethylsilane (3.57 mL, 28.16 mmol). The mixture was stirred at rt for 3 h. The mixture was placed in a water ice bath and 2-propylmagnesium chloride (2M in THF; 29.6 mL, 59.14 mmol) was added dropwise. The suspension immediately went into solution. The ice bath was removed and the mixture was stirred at rt for 3 h. The mixture was placed in an ice bath and 2-chloro-N-methoxy-N-methylacetamide (2.91 g, 21.12 mmol) was added in one portion. The ice bath was once again removed and the reaction was stirred at rt for 16 h. The reaction was poured over a mixture of ice and saturated, aqueous ammonium chloride (250 mL). The mixture was allowed to warm to rt and EtOAc (200 mL) was added. The undissolved solid was collected by filtration to afford 636 mg (21%) of the desired product. The layers of the filtrate were separated and the aqueous phase was extracted with EtOAc (2×100 mL). The combined organic layers were washed with brine, dried (Na$_2$SO$_4$), and concentrated to dryness. The crude solid was triturated with EtOAc to provide an additional 1.62 g (55%) of the desired product, for a combined yield of 2.26 g (76%). ES-MS m/z 211.47 [M+H]$^+$, HPLC RT (min) 1.67.

Step 2: Preparation of tert-butyl 4-[4-(4-aminopyrrolo[2,1-f][1,2,4]triazin-7-yl)-1,3-thiazol-2-yl]piperidine-1-carboxylate

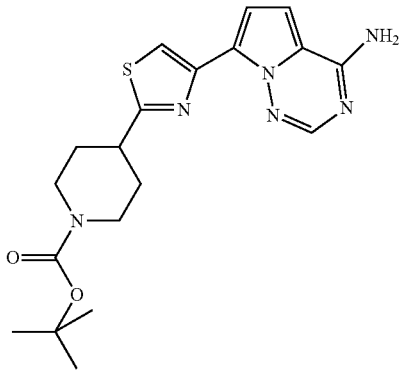 [SMILES: CC(C)(C)OC(=O)N1CCC(c2nc(-c3ccc4c(N)ncnn34)cs2)CC1]

To a mixture of 1-(4-aminopyrrolo[2,1-f][1,2,4]triazin-7-yl)-2-chloroethanone (500 mg, 2.37 mmol) in EtOH (12.5 mL) was added tert-butyl 4-aminocarbothioyl)tetrahydropyridine-1(2H)-carboxylate (580 mg, 2.37 mmol). The mixture was stirred at 78° C. for 4.5 h, then allowed to cool to rt and stir overnight. The mixture was partitioned between saturated, aqueous NaHCO$_3$ (50 mL) and EtOAc (50 mL). The layers were separated and the aqueous phase was extracted with EtOAc (50 mL). The combined organic layers were washed with brine, dried (Na$_2$SO$_4$), and concentrated to dryness to provide 914 mg (96%) of the desired product, which contained trace impurities. ES-MS m/z 400.94 [M+H]$^+$, HPLC RT (min) 3.12.

Step 3: Preparation of tert-butyl 4-[4-(4-amino-5-bromopyrrolo[2,1-f][1,2,4]triazin-7-yl)-1,3-thiazol-2-yl]piperidine-1-carboxylate

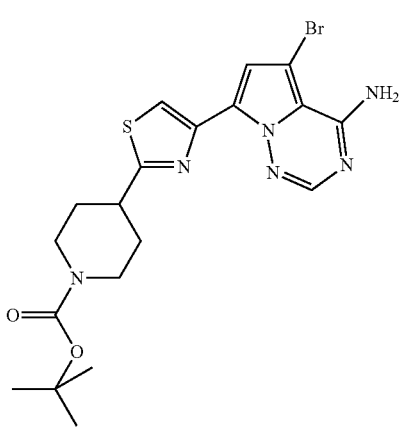 [SMILES: CC(C)(C)OC(=O)N1CCC(c2nc(-c3cc(Br)c4c(N)ncnn34)cs2)CC1]

To a cooled (−20° C.) solution of tert-butyl 4-[4-(4-aminopyrrolo[2,1-f][1,2,4]triazin-7-yl)-1,3-thiazol-2-yl]piperidine-1-carboxylate (914 mg. 2.28 mmol) in DMF (12.6 mL) and AcOH (5 mL) was added 1,3-dibromo-5,5-dimethylhydantoin (326 mg, 1.14 mmol) in 3 portions over 10 minutes. The mixture was stirred at 0° C. for 3 h. The reaction was quenched with the addition 5% aqueous K$_2$CO$_3$ (50 mL) and was allowed to warm to rt. The mixture was extracted with ethyl acetate (3×50 mL). The combined organics were washed with brine, dried (Na$_2$SO$_4$) and evaporated. The crude material was purified by ISCO® chromatography using a gradient of 50% to 75% ethyl acetate in hexanes to afford 596 mg (54%) of the desired product. ES-MS m/z 480.85 [M+H]$^+$, HPLC RT (min) 3.45.

Step 4: Preparation of tert-butyl 4-{4-[4-amino-5-(2-benzyl-2H-indazol-6-yl)pyrrolo[2,1-f][1,2,4]triazin-7-yl]-1,3-thiazol-2-yl}piperidine-1-carboxylate

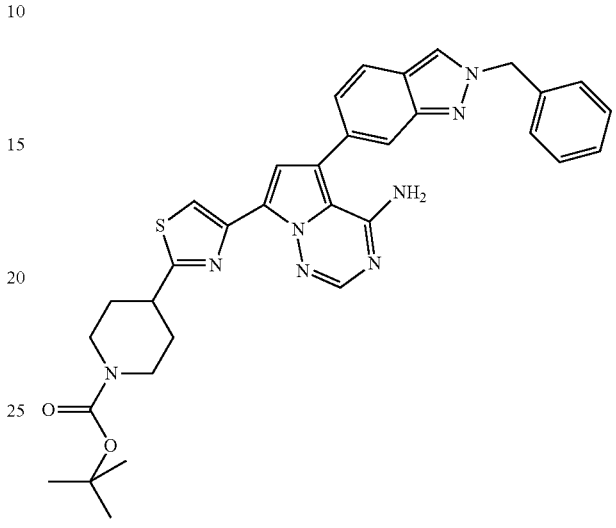

To a stirred, degassed mixture of tort-butyl 4-[4-(4-amino-5-bromopyrrolo[2,1-f][1,2,4]triazin-7-yl)-1,3-thiazol-2-yl]piperidine-1-carboxylate (596 mg, 1.24 mmol), Intermediate C (623 mg, 1.87 mmol), Na$_2$CO$_3$ (395 mg, 3.73 mmol) and H$_2$O (1.9 mL) in DMF (10.5 mL) was added tetrakis(triphenylphosphine)palladium(0) (143 mg, 0.12 mmol). The reaction was heated (110° C.) for 17 h and then cooled to rt. The mixture was partitioned between ethyl acetate (50 mL) and H$_2$O (50 mL). The layers were separated and the aqueous was further extracted with ethyl acetate (50 mL). The combined organic layers were washed with brine, dried (Na$_2$SO$_4$), and concentrated to dryness. The crude material was purified via ISCO® chromatography using a gradient of 50 to 75% ethyl acetate in hexanes to afford 586 mg (78%) of the desired product, which contained trace impurities. ES-MS m/z 607.00 [M+H]$^+$, HPLC RT (min) 3.50.

Step 5: Preparation of the Title Compound

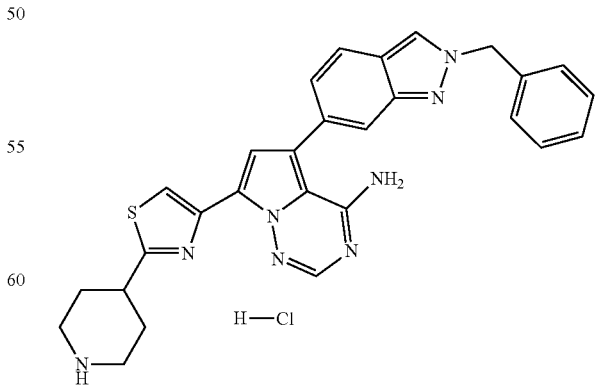

To a solution of tert-butyl 4-{4-[4-amino-5-(2-benzyl-2H-indazol-6-yl)pyrrolo[2,1-f][1,2,4]triazin-7-yl]-1,3-thiazol- 2-yl}piperidine-1-carboxylate (586 mg, 0.97 mmol) in MeOH (4 mL) was added 4M HCl in dioxane (2 mL). The mixture was stirred at rt for 16 h. The mixture was concentrated to afford 577 mg (100%) of, the desired product, which was used without further characterization.

Intermediate V V: Preparation of 7-(azetidin-3-ylmethyl)-5-(2-benzyl-2H-indazol-6-yl)pyrrolo[2,1-f][1,2,4]triazin-4-amine hydrochloride

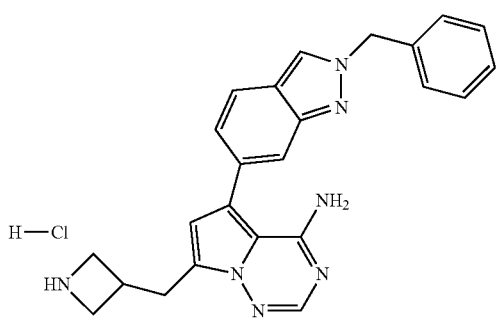

Step 1: Preparation of tert-butyl 3-[methoxy(methyl)carbamoyl]azetidine-1-carboxylate

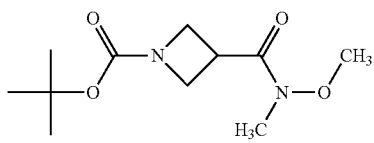

To a solution of 1-(tert-butoxycarbonyl)azetidine-3-carboxylic acid (2.00 g, 9.94 mmol) in THF (50 mL) was added EDCl (2.10 g, 10.93 mmol), HOBt (1.48 g, 10.93 mmol), and N,N-diisopropylethylamine (5.19 mL, 29.82 mmol). The mixture was stirred at rt for 15 min. N,O-dimethylhydroxylamine hydrochloride (1.16 g, 11.93 mmol), was added and stirring continued for 64 h. The crude reaction was purified via ISCO® chromatography using 3:1 ethyl/hexanes to afford 2.4 g (99%) of the desired product, which was used without further characterization.

Step 2: Preparation of tert-butyl 3-[(4-aminopyrrolo[2,1-f][1,2,4]triazin-7-yl)carbonyl]azetidine-1-carboxylate

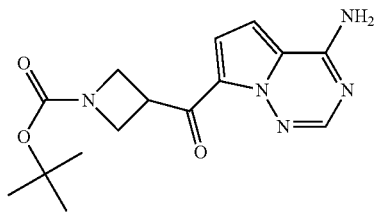 [SMILES: CC(C)(C)OC(=O)N1CC(C(=O)c2ccc3c(N)ncnn23)C1]

To a stirred suspension of Intermediate B (1.30 g, 6.08 mmol) in THF (31 mL) was added chlorotrimethylsilane (1.54 mL, 12.15 mmol), dropwise. The mixture was stirred at rt for 3 h and 2-propylmagnesium chloride (2M in THF; 12.76 mL, 25.52 mmol) was added dropwise. The suspension immediately went into solution. The mixture was stirred at rt for 2 h and tert-butyl 3-[methoxy(methyl)carbamoyl]azetidine-1-carboxylate (1.93 g, 7.90 mmol) was added in one portion. The reaction was stirred at rt for 16 h. The reaction was poured over a mixture of ice and saturated, aqueous ammonium chloride (200 mL). The mixture was allowed to warm to rt and was extracted with EtOAc (3×100 mL). The combined organics were washed with brine, dried (Na$_2$SO$_4$), and concentrated to dryness. The crude residue was purified by ISCO® chromatography using a gradient of 50 to 75% ethyl acetate in hexanes to afford 1.6 g (83%) of the desired product. ES-MS m/z 318.14 [M+H]$^+$, HPLC RT (min) 2.58.

Step 3: Preparation of tert-butyl 3-[(4-aminopyrrolo[2,1-f][1,2,4]triazin-7-yl)(hydroxy)methyl]azetidine-1-carboxylate

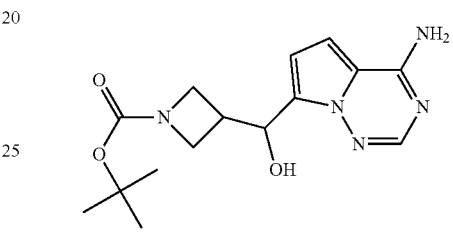

To a solution of tert-butyl 3-[(4-aminopyrrolo[2,1-f][1,2,4]triazin-7-yl)carbonyl]azetidine-1-carboxylate (1.35 g, 4.25 mmol) in EtOH (25 mL) was added sodium borohydride (644 mg, 17.01 mmol). The mixture was stirred at 78° C. for 2 h. The reaction was quenched with the addition of H$_2$O (20 mL). The resulting solid was removed by filtration and the filtrate was extracted with EtOAc (3×20 mL). The combined organics were washed with brine, dried (Na$_2$SO$_4$), and concentrated to dryness to afford 1.0 g (74%) of the desired product. ES-MS m/z 320.16 [M+H]$^+$, HPLC RT (min) 2.02.

Step 4: Preparation of tert-butyl 3-[(4-aminopyrrolo[2,1-f][1,2,4]triazin-7-yl)methyl]azetidine-1-carboxylate

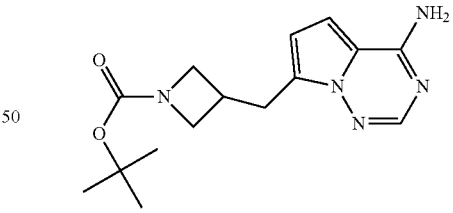

To a cooled (0° C.) solution of tert-butyl 3-[(4-aminopyrrolo[2,1-f][1,2,4]triazin-7-yl)(hydroxy)methyl]azetidine-1-carboxylate (1.35 g, 4.25 mmol) in CH$_2$Cl$_2$ (12 mL) was added TFA (3.7 mL, 47.54 mmol) followed by triethylsilane (3.80 mL, 23.77 mmol), dropwise. The mixture was stirred at rt for 17 h. Additional TFA (1.8 mL) and triethylsilane (1.9 mL) were added and the mixture continued to stir at rt for 22 h. The reaction was concentrated to dryness. To a solution of the residue in THF (10 mL) was added 2M aqueous Na$_2$CO$_3$ (36 mL, 71.32 mmol) and di-tert-butyl carbonate (713 mg, 3.27 mmol). The mixture was stirred at rt for 17 h. The mixture was partitioned between EtOAc (50 mL) and H$_2$O (25 mL) and the solid was removed by filtration. The layers of the filtrate were separated and the aqueous was further extracted with EtOAc (2×50 mL). The combined organics were washed with brine, dried (Na₂SO₄), and concentrated to dryness. The crude residue was purified by ISCO® chromatography using a gradient of 50 to 75% ethyl acetate in hexanes to afford 259 mg (29%) of the desired product. ES-MS m/z 304.02 [M+H]⁺, HPLC RT (min) 2.35.

Step 5: Preparation of tert-butyl 3-[(4-amino-5-bromopyrrolo[2,1-f][1,2,4]triazin-7-yl)methyl]azetidine-1-carboxylate

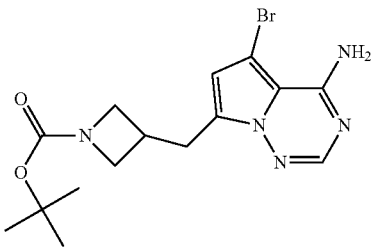 [SMILES: CC(C)(C)OC(=O)N1CC(Cc2cc(Br)c3c(N)ncnn23)C1]

To a cooled (−20° C.) solution of tert-butyl 3-[(4-aminopyrrolo[2,1-f][1,2,4]triazin-7-yl)methyl]azetidine-1-carboxylate (325 mg, 1.07 mmol) in DMF (5 mL) and AcOH (1 mL) was added 1,3-dibromo-5,5-dimethylhydantoin (153 mg, 0.54 mmol) in 3 portions over 10 min. The mixture was stirred at −20° C. for 3 h. Aqueous K₂CO₃ (5%, 20 mL) was added and the mixture was allowed to warm to rt. The mixture was extracted with ethyl acetate (3×20 mL). The combined organic layers were washed with brine, dried (Na₂SO₄) and evaporated to provide 397 mg (97%) of the desired product, which contained minor impurities. ES-MS m/z 382.08 [M+H]⁺, HPLC RT (min) 3.05.

Step 6: Preparation of tert-butyl 3-{[4-amino-5-(2-benzyl-2H-indazol-6-yl)pyrrolo[2,1-f][1,2,4]triazin-7-yl]methyl}azetidine-1-carboxylate

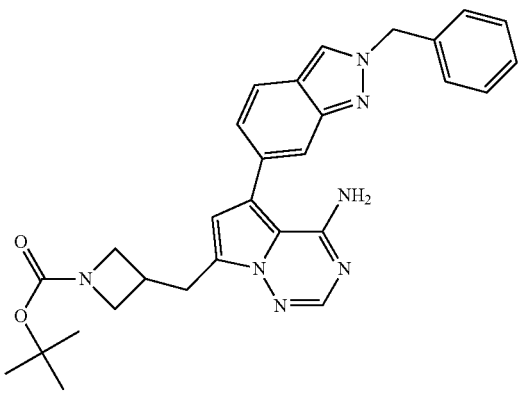 [SMILES: CC(C)(C)OC(=O)N1CC(Cc2cc(-c3ccc4cn(Cc5ccccc5)nc4c3)c3c(N)ncnn23)C1]

To a stirred, degassed mixture tert-butyl 3-[(4-amino-5-bromopyrrolo[2,1-f][1,2,4]triazin-7-yl)methyl]azetidine-1-carboxylate (397 mg, 1.04 mmol), Intermediate C (521 mg, 1.56 mmol), Na₂CO₃ (330 mg, 3.12 mmol) and H₂O (1.6 mL) in DMF (10 mL) was added tetrakis(triphenylphosphine)palladium(0) (120 mg, 0.10 mmol). The reaction was heated (110° C.) for 17 h and then cooled to rt. The mixture was partitioned between ethyl acetate (50 mL) and H₂O (50 mL). The layers were separated and the aqueous was further extracted with ethyl acetate (1×50 mL). The combined organic layers were washed with brine, dried (Na₂SO₄), and concentrated to dryness. The crude material was purified via ISCO® chromatography using a gradient of 50 to 75% ethyl acetate in hexanes to afford 500 mg (80%) of the desired product, which contained trace impurities.

ES-MS m/z 510.19 [M+H]⁺, HPLC RT (min) 3.16.

Step 7: Preparation of Title Compound

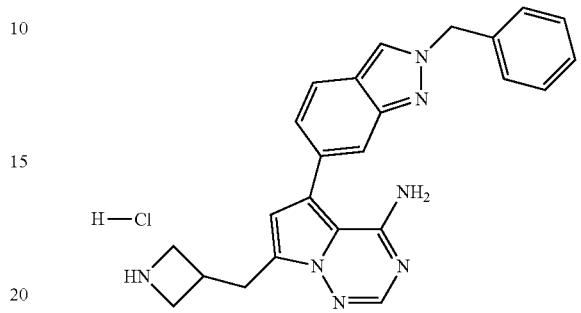

To a suspension of tert-butyl 3-[4-amino-5-(2-benzyl-2H-indazol-6-yl)pyrrolo[2,1-f][1,2,4]triazin-7-yl]piperidine-1-carboxylate (500 mg, 0.98 mmol) in MeOH (3 mL) was added 4M HCl in dioxane (1.5 mL). The mixture was stirred at rt for 2.5 h. Additional 4M HCl in dioxane (1.5 mL) was added and the mixture was stirred at rt for 2 h. The mixture was concentrated to dryness to afford 481 mg (100%) of the desired product, which contained trace impurities ES-MS Fritz 410.27 [M+H]⁺, HPLC RT (min) 2.05.

Intermediate W W: Preparation of 6-bromo-2-(2-fluorobenzyl)-2H-indazol-3-amine

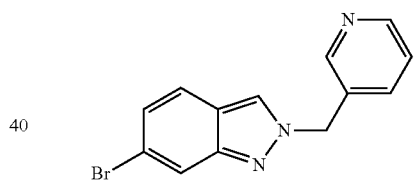

To a mixture 6-bromo-1H-Indazole (2 g, 10.15 mmol) and 3-(bromomethyl)pyridine hydrobromide (5.29 g, 20.31 mmol) in DMF (15 mL) was added a solution of triethylamine (2.83 mL, 20.30 mmol) in DMF (5 mL) and the mixture was stirred at rt for 18 h. The mixture was then heated at 150° C. for 3 days. The light pink slurry was diluted with ethyl acetate and filtered. The filtrate was concentrated and the resulting pink foamy residue was purified using an ISCO® instrument using 35-100% ethyl acetate hexanes. LC-MS [M+H]⁺= 288.3, 290.1, RT=1.47 min.

Intermediate X X: 2-benzyl-6-bromo-4-fluoro-2H-indazole

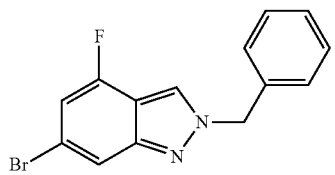 [SMILES: Fc1cc(Br)cc2nn(Cc3ccccc3)cc12]

A mixture of 6-bromo-4-fluoro-1H-indazole (0.5 g, 2.26 mmol) and benzyl bromide (0.55 g, 3.16 mmol) in 1,4-dioxane (10 mL) was stirred at reflux for 18 h. DMF (5 mL) and NaHCO$_3$ (0.95 g, 11.28 mmol) were added to the mixture and heating continued at 100° C. for 18 h. The mixture was diluted with ethyl acetate and subsequently washed with water and brine, dried over MgSO$_4$ and concentrated. The product (0.25 g, 36%) was isolated using an ISCO® instrument using 0-10% ethyl acetate in hexanes. LC-MS [M+H]$^+$=305.4, 307.0, RT=3.81 min.

Intermediate Y Y: Preparation of 6-Bromo-2-(cyclohexylmethyl)-2H-indazole

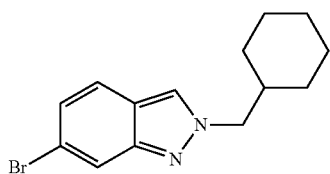

To a mixture of 6-bromo-4-fluoro-1H-indazole (2.0 g, 10.15 mmol) and K$_2$CO$_3$ (7.01 g, 50.75 mmol) in DMF (16 mL) was added cyclohexylmethyl bromide (3.67 g, 20.30 mmol) and the mixture was stirred at rt for 18 h. The mixture was diluted with ethyl acetate and washed successively with water and saturated, aqueous NaHCO$_3$, then dried over MgSO$_4$ and concentrated. The product (0.97 g, 32%) was isolated using an ISCO® instrument using 0-15% ethyl acetate in hexanes. LC-MS [M+H]$^+$=293.3, 295.1, RT=4.04 min.

Preparation of 2-(pyridin-3-ylmethyl)-6-(4,4,5,5-tetramethyl-1,3,2-dioxaborolan-2-yl)-2H-indazole

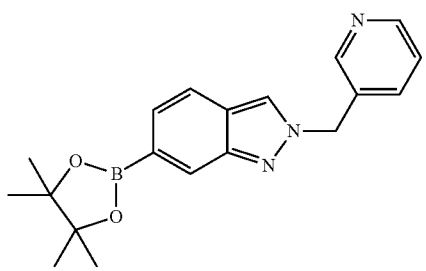 [SMILES: CC1(C)OB(c2ccc3cn(Cc4cccnc4)nc3c2)OC1(C)C]

A solution of 6-bromo-2-(pyridin-3-ylmethyl)-2H-Indazole (1.07 g, 3.71 mmol), bis(pinacolato)-diboron (1.41 g, 5.57 mmol) and KOAc (1.09 g, 11.14 mmol) in 1,4-dioxane (20 mL) was degassed for 5 min, then 1,1'-bis(diphenylphosphino)ferrocenepalladium(II) chloride-complex with CH$_2$Cl$_2$ (0.09 g, 0.111 mmol) was added and the mixture further degassed for 5 min. The mixture was heated to 85° C. for 3 h and then cooled to rt. The mixture was diluted with ethyl acetate and filtered through Celite® and concentrated. The residue was purified using an ISCO® instrument using 50-100% ethyl acetate in hexanes. The desired fractions were concentrated to give the product as a yellow solid (0.89 g, 72%). LC-MS [M+H]$^+$=336.2, RT=2.39 min.

Intermediate Z Z: Preparation of 2-benzyl-4-fluoro-6-(4,4,5,5-tetramethyl-1,3,2-dioxaborolan-2-yl)-2H-indazole

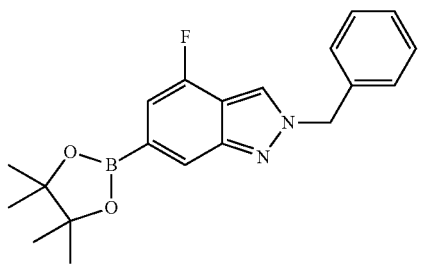 [SMILES: CC1(C)OB(c2cc(F)c3cn(Cc4ccccc4)nc3c2)OC1(C)C]

A solution of 2-benzyl-6-bromo-4-fluoro-2H-indazole (0.25 g, 819 mmol), bis(pinacolato)-diboron (0.312 g, 1.23 mmol) and KOAc (0.482 g, 4.92 mmol) in DMSO (8 mL) was degassed for 5 min, then 1,1'-bis(diphenylphosphino)ferrocenepalladium(11) chloride-complex with CH$_2$Cl$_2$ (0.02 g, 0.025 mmol) was added and the mixture further degassed for 5 min. The mixture was heated to 85° C. for 3 h and then cooled to rt. The mixture was diluted with ethyl acetate and filtered through Celite® and concentrated. The residue was poured into water (200 mL) and stirred for 10 min and the mixture filtered through Celite®. The residue was purified using an ISCO® instrument using 0-40% ethyl acetate in hexanes. The desired fractions were concentrated to give the product (0.26 g, 90%). LC-MS [M+H]$^+$=353.3, RT=3.99 min.

Intermediate A A A: Preparation of 2-(cyclohexylmethyl)-6-(4,4,5,5-tetramethyl-1,3,2-dioxaborolan-2-yl)-2H-indazole

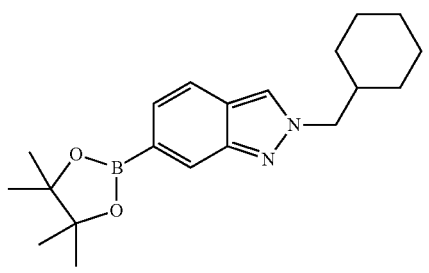 [SMILES: CC1(C)OB(c2ccc3cn(CC4CCCCC4)nc3c2)OC1(C)C]

A solution of 6-bromo-2-(cyclohexylmethyl)-2H-indazole (1.08 g, 3.67 mmol), bis(pinacolato)-diboron (1.40 g, 5.51 mmol) and KOAc (1.08 g, 11.02 mmol) in 1,4-dioxane (15 mL) was degassed for 5 min, then 1,1'-bis(diphenylphosphino)ferrocenepalladium(II) chloride-complex with CH$_2$Cl$_2$ (0.09 g, 0.11 mmol) was added and the mixture further degassed for 5 min. The mixture was heated to 85° C. for 3 h and cooled to rt. The mixture was diluted with ethyl acetate and filtered through Celite® and concentrated. The residue was passed through a pad of silica gel and eluted with 25% ethyl acetate in hexanes. The desired fractions were concentrated to give the product as a white waxy solid (1.15 g, 92%). LC-MS [M+H]$^+$=341.3, RT=3.82 min.

Intermediate BBB: Preparation of 2-Benzyl-6-(4,4,5,5-tetramethyl-[1,3,2]dioxaborolan-2-yl)-2H-indazol-3-ylamine

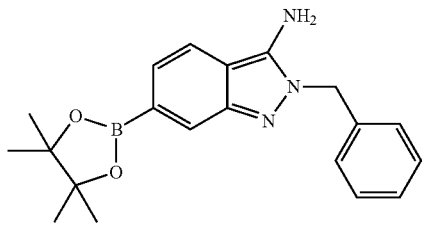 [SMILES: CC1(C)OB(c2ccc3c(N)n(Cc4ccccc4)nc3c2)OC1(C)C]

Step 1: Preparation of
2-Benzyl-6-bromo-2H-indazol-3-ylamine

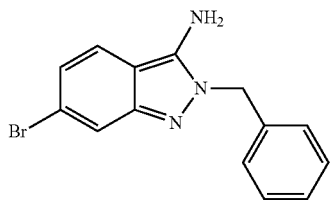 [SMILES: Nc1c2ccc(Br)cc2nn1Cc1ccccc1]

To a dried flask charged with 4-bromo-2-fluorobenzonitrile (5.0 g, 22.5 mmol) in n-butanol (60 mL) was added a solution of benzylhydrazine hydrochloride (17.56 g, 90 mmol, 4.0 eq) and diisopropylethylamine (32.1 mL, 184.48 mmol, 8.2 eq). The reaction mixture was stirred at 140° C. under $N_2$ for 3 days. The mixture was cooled to rt and partitioned between EtOAc and water. The organic layer was washed with saturated aqueous $NaHCO_3$, water, brine, dried over $Na_2SO_4$, filtered, and concentrated in vacuo. The crude product was purified using an ISCO® instrument (gradient 5 to 60% EtOH/DCM) and the product containing fractions were concentrated to give 3.4 g (50%) of the title compound as beige solid. $^1$H NMR (300 MHz, $CD_2Cl_2$) δ 7.63 (dd, 1H), 7.37 to 7.30 (m, 4H), 7.20 to 7.16 (m, 2H), 6.94 (dd, 1H), 5.44 (s, 2H), 4.02 (broad s, 2H); ES-MS m/z 302.3/304.3 [M+H]$^+$, RT (min) 2.34.

Step 2: Preparation of the Title Compound

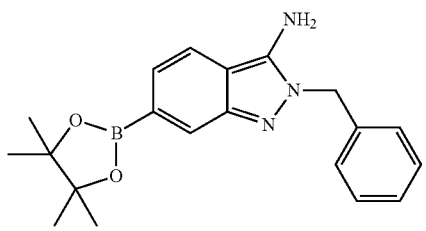 [SMILES: CC1(C)OB(c2ccc3c(N)n(Cc4ccccc4)nc3c2)OC1(C)C]

This compound was prepared in a manner similar to the procedure described for the preparation of 2-benzyl-6-(4,4,5,5-tetramethyl-{1,3,2]dioxaborolan-2-yl)-2H-indazole (Intermediate C, step 2), using 2-benzyl-6-bromo-2H-indazol-3-ylamine in place of 2-benzyl-6-bromo-2H-indazole.
$^1$H-NMR (300 MHz, $CD_2Cl_2$) δ 7.95 (s, 1H), 7.44 (dd, 1H), 7.63 to 7.29 (m, 3H), 7.29 to 7.17 (m, 3H), 5.51 (s, 2H), 3.88 (broad s, 2H), 1.36 (s, 12H).

Intermediate C C C: 2-Phenyl-6-(4,4,5,5-tetramethyl-[1,3,2]dioxaborolan-2-yl)-2H-indazole

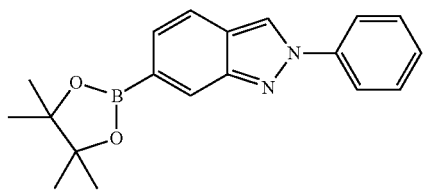 [SMILES: CC1(C)OB(c2ccc3cn(-c4ccccc4)nc3c2)OC1(C)C]

Step 1: Preparation of
6-Chloro-2-phenyl-2H-Indazole

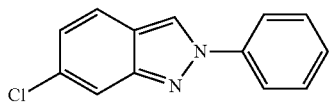 [SMILES: Clc1ccc2cn(-c3ccccc3)nc2c1]

4-Chloro-2-nitrobenzaldehyde (1.86 g, 10.0 mmol) was suspended in 5 mL of ethanol and aniline (0.91 mL, 10.0 mmol) was added. A solution quickly formed and the mixture was heated to reflux for 30 minutes and the mixture was allowed to cool with gentle stirring. When crystallization started, the stirring was stopped and the mixture allowed to cool to room temperature. It was then placed in a 0° C. refrigerator for 2 hours. The yellow crystalline solid was collected by filtration, washed with cold ethanol and dried in vacuo for 1 hour to give 2.42 g (93%) of the imine as a' yellow, crystalline solid. This material was mixed with triethylphosphite (5.1 mL, 30 mmol) and heated under an $N_2$ atmosphere to 150° C. for 2 hours and cooled to rt. The mixture was poured into 40 mL of ethanol and 10 mL of 4N NaOH was added carefully and the mixture was stirred overnight. The resulting brown mixture was diluted with ~150 mL of water and stirred for 10 minutes. The precipitated solids were collected by filtration and washed with water until the filtrate was clear. The collected solid was dried in vacuo (40° C.) for 1.5 h to provide 1.76 grams of a tan solid that was used without further purification. $^1$H NMR (300 MHz, DMSO-$d_6$) δ 9.12 (s, 1H), 8.07 (d, 2H), 7.83 (d, 2H), 7.60 (m, 2H), 7.44 (m, 1H), 7.10 (m, 1H). ES-MS m/z 229.2, 231.1 [M+H]$^+$, HPLC RT (min) 3.62.

Step 2: Preparation of the Title Compound

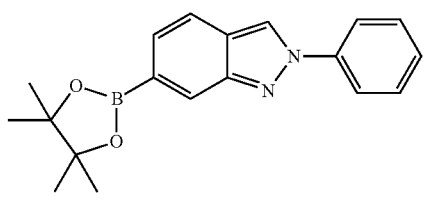 [SMILES: CC1(C)OB(c2ccc3cn(-c4ccccc4)nc3c2)OC1(C)C]

100 mL 3N flask was charged with the product from step 1 (641 mg, 2.80 mmol) and flushed with $N_2$. Dioxane (14 mL) was added and the mixture degassed by a vacuum purge/$N_2$ flush process. This procedure was repeated 2 more times.

Tris(dibenzylideneacetone) dipalladium (77 mg, 0.084 mmol) and tricyclhexylphosphine (56 mg, 0.20 mmol) were added and the mixture was stirred for 30 minutes. KOAc (825 mg, 8.41 mmol) and bispinacolatodiborane (783 mg, 3.08 mmol) were sequentially added. The mixture was placed in an oil bath preheated to 80° C. and stirring continued for 4 h. The mixture was removed from the oil bath and allowed to cool to room temperature. The reaction was diluted with 50 mL of hexanes and stirred vigorously for 5 minutes and then filtered through a pad of Celite®. The Celite® pad was washed with hexanes until the filtrate remained colorless (~100 mL). The filtrate was concentrated in vacuo to a thick, brown oil. This oil was taken up in ~10 mL of hexanes and gently warmed in a 40° C. water bath until a solution was obtained. The mixture was allowed to stand at rt and crystals began to form in the bottom of the flask. It was allowed to stand overnight. The flask was placed in a freezer for 6 hours and the resulting crystals were collected by filtration and washed with cold hexanes and air dried to give 620 mg of the title compound as a brown, crystalline solid. $^1$H NMR (300 MHz, DMSO-$d_6$) δ 9.12 (s, 1H), 8.08 (d, 2H), 8.04 (s, 1H), 7.76 (d, 1H), 7.60 (m, 2H), 7.45 (m, 1H), 7.31 (d, 1H), 1.26 (s, 12H). ES-MS m/z 321.5, 231.1 [M+H]$^+$, HPLC RT (min) 3.92.

Intermediate D D D: (R)3-(4-Amino-5-bromo-pyrrolo[2,1-f][1,2,4]triazin-7-yl)-piperidine-1-carboxylic acid benzyl ester

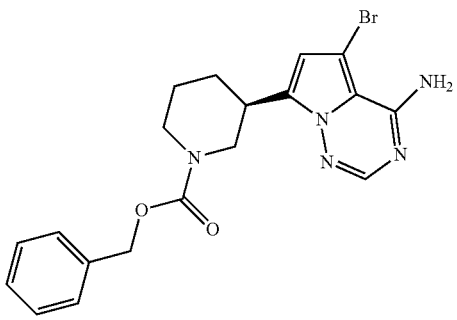 [SMILES: Nc1ncnn2c([C@@H]3CCCN(C(=O)OCc4ccccc4)C3)cc(Br)c12]

Step 1: Preparation of 3-(4,4-Dimethoxybutyryl)-piperidine-1-carboxylic acid benzyl ester

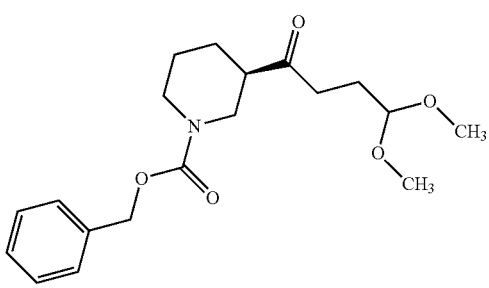 [SMILES: COC(CCC(=O)[C@@H]1CCCN(C(=O)OCc2ccccc2)C1)OC]

Magnesium turnings (2.27 g, 93.4 mmol) were placed in a 500 mL 3-N flask and stirred vigorously while an $N_2$ stream was passed over them for 1.5 hours. The turnings were suspended in 10 mL of THF and ~1.0 mL of 3-bromoprionaldehyde dimethylacetal (previously filtered through a plug of activated alumina) was added. The reaction initiated within ~2 minutes. The remaining bromide in 40 mL of THF was added drop wise over ~1 h. The reaction was mildly exothermic during the addition and the flask remained warm for 15 minutes past completion of the addition of bromide, whereupon the mixture was placed in an oil bath and heated to 40° C. for 1.5 h and then cooled in an ice bath. (R)-3-(Methoxymethyl-carbamoyl)-piperidine-1-carboxylic acid benzyl ester (WO200246157) in 40 mL of THF (+10 mL rinse) was added drop wise over 30 minutes and stirred overnight during which time the ice bath melted. The mixture was re-cooled to <10° C. in an Ice bath and quenched by the addition of 50 mL cold 1M aqueous $H_3PO_4$ such that the internal temp<25° C. The mixture was partitioned between 50 mL of 1M aqueous $H_3PO_4$ and 100 mL of EtOAc and the layers were separated. The aqueous layer was extracted with 1×50 mL of EtOAc and the combined organic phases were washed with water and brine, dried over $Na_2SO_4$, filtered and concentrated in vacuo to give a clear oil that was used without further purification (20.40 g). $^1$H NMR (300 MHz, DMSO-$d_6$) δ 7.40-7.28 (m, 5H), 5.05 (s, 2H), 4.28 (m, 1H), 3.96 (bs, 1H), 3.80 (m, 1H), 3.19 (s, 3H), 3.18 (s, 3H), 3.04 (m, 1H), 2.87 (m, 2H), 2.54, (m, 2H), 1.91 (m, 1H), 1.71-1.59 (m, 3H), 1.50-1.24 (m, 2H). ES-MS m/z 372.2 [M+Na]$^+$, HPLC RT (min) 3.26

Step 2: Preparation of (R)3-[1-(tert-Butoxycarbonylhydrazono)-4,4-dimethoxy-butyl]-piperidine-1-carboxylic acid benzyl ester

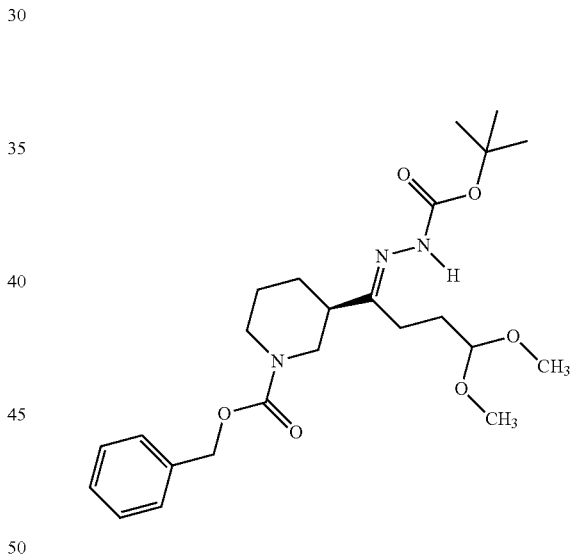

The product from step 1 (16.32 g, 46.70 mmol) was dissolved in 100 mL of $CH_2Cl_2$ and treated with tert-butylcarbazate (6.48 g, 49.04 mmol) followed by para-toluensulfonic acid monohydrate (0.44 g, 2.33 mmol) and the mixture was stirred 4 h. The mixture was poured into a separatory funnel and extracted with 50 mL 2M aq. $Na_2CO_3$. The aqueous phase was extracted with 50 mL of $CH_2Cl_2$ and the combined organic phases were dried ($Na_2SO_4$), filtered and concentrated in vacuo. The residue was purified using an ISCO® instrument (Red-Sep 330, 30%-100% EtOAc hexanes) to give 20.40 g of a clear oil. $^1$H NMR (300 MHz, DMSO-$d_6$) δ 9.48 (bs, 1H), 7.40-7.28 (m, 5H), 5.04 (s, 2H), 4.32 (m, 1H), 4.05 (bd, 1H), 3.96 (bd, 1H), 3.20 (m, 6H), 2.88-2.63 (m, 2H), 2.31-2.11 (m, 1H), 1.87 (m, 1H), 1.66, (m, 1H), 1.59 (m, 1H), 1.42 (s, 9H), 1.40-1.24 (m, 5H). ES-MS m/z 463.9 [M+Na]$^+$, HPLC RT (min) 3.67

Step 3: Preparation of (R)3-(1-tert-Butoxycarbonylamino-1H-pyrrol-2-yl)-piperidine-1-carboxylic acid benzyl ester

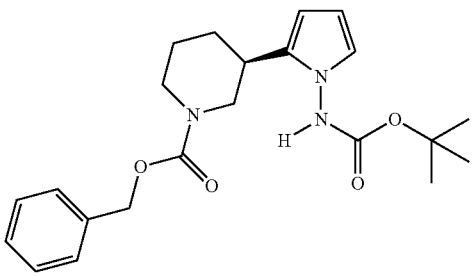 [SMILES: CC(C)(C)OC(=O)Nn1cccc1[C@@H]1CCCN(C(=O)OCc2ccccc2)C1]

The product from step 2 (20.25 g, 43.68 mmol) was dissolved in 125 mL of AcOH and stirred at 40° C. for 8 h and then concentrated in vacuo. The residue was dissolved in EtOAc (200 mL) and extracted with 50 mL of water, 2×100 mL 2M aq. $Na_2CO_3$, brine, dried over $Na_2SO_2$. The mixture was filtered through a 1"×4" pad of $SiO_2$ (pre-wetted with EtOAc) and the pad was washed with 300 mL of EtOAc and the filtrate concentrated in vacuo to give the title compounds as a light, brown syrup that was used without further purification. $^1$H NMR (300 MHz, DMSO-$d_6$) δ 10.14 (bs, 1H), 7.40-7.24 (m, 5H), 6.59 (d, 1H), 5.90 (dd, 1H), 5.78 (d, 1H), 5.15-4.92 (m, 2H), 4.13 (bd, 1H), 3.99 (bd, 1H), 2.91-2.60 (m, 3H), 1.91 (m, 1H), 1.74-1.62, (m, 1H), 1.42 (s, 12H). ES-MS m/z 400.0 [M+H]$^+$, HPLC RT (min) 3.93

Step 4: Preparation of (R)3-(1-tert-Butoxycarbonylamino-5-cyano-1H-pyrrol-2-yl)-piperidine-1-carboxylic acid benzyl ester

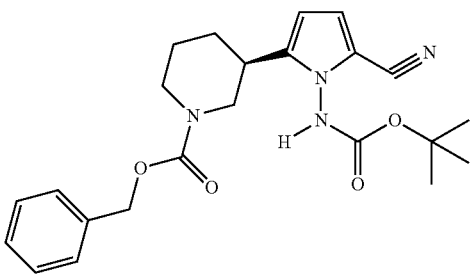 [SMILES: CC(C)(C)OC(=O)Nn1c(C#N)ccc1[C@@H]1CCCN(C(=O)OCc2ccccc2)C1]

The product from step 3 (12.00 g, 30.04 mmol) was dissolved in 90 mL acetonitrile and cooled in an ice/isopropanol/dry ice bath to ~−10° C. A solution of chlorosulfonylisocyanate (2.87 mL, 33.04 mL) in 10 mL of acetonitrile was added drop wise keeping the internal temp<−10° C. (~30 minutes). A precipitate formed and the slurry was stirred for 4 h and then DMF was added drop wise (keeping the internal temp<−10° C.) and stirring continued for 2 hours during which time the reaction warmed to 0° C. (the precipitate dissolved) and then to ambient temperature. The mixture was poured onto crushed ice (500 g) and 2M aq. $Na_2CO_3$ (25 mL) and EtOAc (300 mL) and stirred for 20 minutes. The layers were separated and the aq. layer extracted with 1×100 mL of EtOAc. The combined organic phases were washed with water (2×) and brine, dried ($Na_2SO_4$), filtered and concentrated in vacuo to give a yellow, foamy solid (12.20 g). The solid was purified using an ISCO® instrument (RediSep 120, 35-100% EtOAc/hexanes, 2 batches). The product containing fractions were combined and concentrated to give 7.13 g of the title compound as a white foamy solid (45% ee). This material was further purified by chiral HPLC (using a 2 inch by 250 mm column packed with OJ bulk phase; 5% (3-1 MeOH-EtOH), 95% Hexane and 0.1% TFA) to provide 4.64 g of the title compound (>98% ee). $^1$H NMR (300 MHz, $CD_3OD$) δ 7.42-7.24 (m, 5H), 6.80 (d, 1H), 6.05 (d, 1H), 5.13 (dd, 2H), 4.12-4.03 (m, 2H), 2.96 (m, 2H), 2.72 (m, 1H), 2.00 (m, 1H), 1.77, (m, 1H), 1.74 (m, 1H) 1.60-1.29 (m, 10H). ES-MS m/z 424.8 [M+H]$^+$, HPLC RT (min) 3.78

Step 5: Preparation of (R)3-(1-Amino-5-cyano-1H-pyrrol-2-yl)-piperidine-1-carboxylic acid benzyl ester

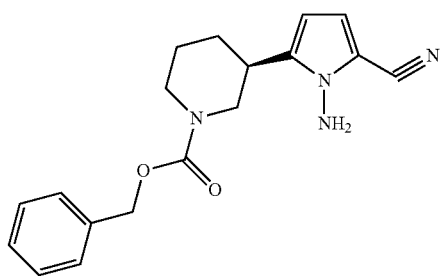 [SMILES: N#Cc1ccc([C@@H]2CCCN(C(=O)OCc3ccccc3)C2)n1N]

The product from step 4 (4.64 g, 10.93 mmol) was dissolved in 20 mL of MeOH and cooled to 0° C. 4M HCl in dioxane (27 mL, 109.3 mmol) was added drop wise and the mixture was stirred for 30 min. The bath was removed and the mixture was stirred for 4 h and then concentrated in vacuo. The residue was dissolved in 100 mL of EtOAc and washed with 2M aq. $Na_2CO_3$, water and brine (50 mL each), dried over $Na_2SO_4$, filtered and concentrated in vacuo to give an oil that was dried in a vacuum oven at 40° C. overnight to provide the title compound (3.57 g) as a partially solidified glass. This material was used without further purification. $^1$H NMR (300 MHz, $CD_3OD$) δ 7.42-7.28 (m, 5H), 6.71 (d, 1H), 6.09 (s, 2H), 5.92 (d, 1H), 5.08 (bs, 2H), 4.11 (d, 1H), 3.97 (d, 1H), 3.00-2.75 (m, 3H), 1.98 (m, 1H), 1.69, (m, 1H), 1.43 (m, 2H). ES-MS m/z 325.1 [M+H]$^+$, HPLC RT (min) 2.45.

Step 6: Preparation of (R)3-(4-Amino-pyrrolo[2,1-f][1,2,4]triazin-7-yl)-piperidine-1-carboxylic acid benzyl ester

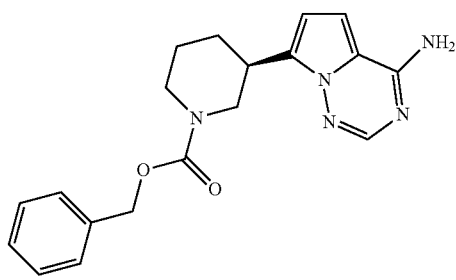 [SMILES: Nc1ncnn2c([C@@H]3CCCN(C(=O)OCc4ccccc4)C3)ccc12]

The product from step 5 (3.57 g, 11.00 mmol) was dissolved in 40 mL of n-BuOH and treated with formamidine acetate (11.48 g, 110.0 mmol). The mixture was heated to reflux for 8 h whereupon an additional 2.75 g (26.4 mmol) of formamidine acetate was added. Heating continued for 1.5 h and then the reaction was allowed to cool to rt overnight. The black reaction mixture was filtered through Celite® and the Celite® pad was washed with 100 mL of EtOH. The filtrate was concentrated in vacuo and the residue was partitioned between water (100 mL) and 3×75 mL of EtOAc. The combined organic extracts were washed with water, 2M aq. Na₂CO₃, brine, dried over Na₂SO₄ and filtered through a 1" (d) by 4" (w) pad of SiO₂ (pre-wetted with EtOAc) and the pad was washed with ~500 mL of EtOAc. The filtrate was concentrated in vacuo and the residue dried in a vacuum oven at 40° C. for 2 h to give the title compound as a yellowish brown solid (3.60 g). ¹H NMR (300 MHz, CD₃OD) δ 7.82 (s, 1H), 7.64 (bs, 2H), 7.42-7.24 (m, 5H), 6.81 (d, 1H), 6.44 (d, 1H), 5.08 (bs, 2H), 4.2 (d, 1H), 3.96 (d, 1H), 3.23 (m, 1H), 3.16-2.84 (m, 2H), 2.03, (m, 1H), 1.79-1.62 (m, 2H), 1.46 (m, 1H). ES-MS m/z 352.2 [M+H]⁺, HPLC RT (min) 2.49.

Step 7: Preparation of the Title Compound

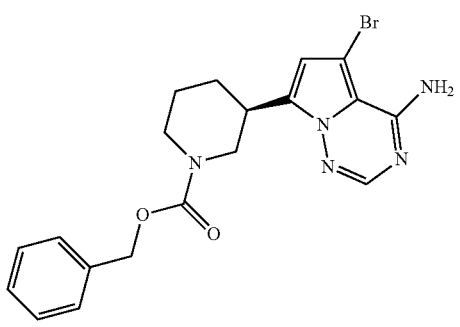 [SMILES: Nc1ncnn2c([C@@H]3CCCN(C(=O)OCc4ccccc4)C3)cc(Br)c12]

The product of step 6 (3.59 g, 10.22 mmoL) was dissolved in 40 mL of DMF and cooled in an Ice/isopropanol/dry ice bath to −20° C. and 1,3-dibromo-5,5-dimethylhydantoin (1.46 g, 5.11 mmol) was added in 4 equal portions 15 minutes apart. The mixture was stirred for 10 minutes past the last addition and quenched by addition to a mixture of ice (400 g), saturated, aqueous Na₂SO₃ (20 mL) and 2M aq. Na₂CO₃ (20 mL) and the mixture was allowed to reach rt and vigorously stirred for 30 minutes. The solid was collected by filtration dried in a vacuum oven until a constant weight was obtained. The title compound (4.28 g) was obtained as a freely flowing solid. ¹H NMR (300 MHz, CD₃OD) δ 7.83 (s, 1H), 7.40-7.25 (m, 5H), 6.66 (s, 1H), 5.06 (bs, 2H), 4.19 (d, 1H), 3.92 (m, 1H), 3.22 (m, 1H), 3.12-2.83 (m, 3H), 1.99, (m, 1H), 1.78-1.62 (m, 2H), 1.48 (m, 1H). ES-MS m/z 430.1, 432.0 [M+H]⁺, HPLC RT (min) 2.98.

Intermediate E E E: (S)-3-(4-Amino-5-bromo-pyrrolo[2,1-f][1,2,4]triazin-7-yl)-piperidine-1-carboxylic acid benzyl ester

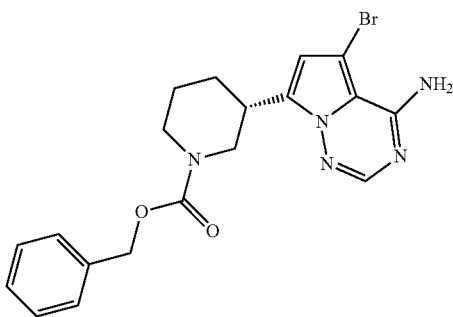 [SMILES: Nc1ncnn2c([C@H]3CCCN(C(=O)OCc4ccccc4)C3)cc(Br)c12]

Using the same conditions as those used in the preparation of Intermediate D D D, except starting with (S)-3-(methoxymethyl-carbamoyl)-piperidine-1-carboxylic acid benzyl ester (WO0246157), the title compound was prepared. The ¹H NMR, ES-MS spectrum and the HPLC RT were identical in all respects to the corresponding (R)-isomer.

Intermediate F F F: Preparation of 2-benzyl-1-methyl-6-(4,4,5,5-tetramethyl-1,3,2-dioxaborolan-2-yl)-1H-benzimidazole

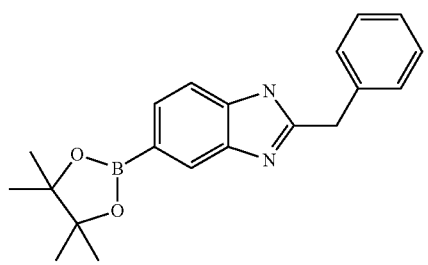 [SMILES: CC1(C)OB(c2ccc3[nH]c(Cc4ccccc4)nc3c2)OC1(C)C]

Step 1: Preparation of N-(2-amino-5-bromophenyl)-2-phenylacetamide

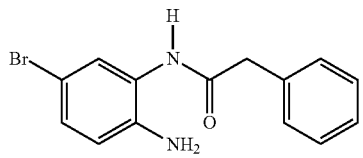 [SMILES: Nc1ccc(Br)cc1NC(=O)Cc1ccccc1]

A mixture of 4-bromo-o-phenyldiamine (4.18 g, 22.35 mmol) phenyl acetic acid (3.04 g, 22.35 mmol) and 1,1'-carbonyldiimidazole (3.99 g, 24.58 mmol) in DCM (60 mL) was stirred at room temperature for 18 h. The reaction mixture was concentrated and the product (3.64 g, 53%) was isolated by column chromatography (33% ethyl acetate in hexanes). LC-MS [M+H]⁺=306.1, RT=3.66 min Step 2: Preparation of 2-benzyl-5-bromo-1H-benzimidazole

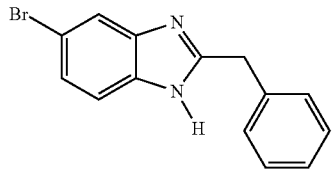 [SMILES: Brc1ccc2[nH]c(Cc3ccccc3)nc2c1]

Concentrated hydrochloric acid (12 drops) was added to a solution of N-(2-amino-5-bromophenyl)-2-phenylacetamide (4.10 g, 13.44 mmol) in methanol (80 mL) and the mixture was stirred at room temperature for 2.5 days. The reaction mixture was concentrated and taken up in DCM. Solid sodium bicarbonate was added in portions to the suspension and the mixture stirred for 30 min. and water (20 mL) was added. The organic layer was isolated and dried over Na₂SO₄. The product (3.2 g, 82%) was Isolated by purified by column chromatography (50% hexanes in ethyl acetate). LC-MS [M+H]⁺=288.5, RT=2.11 min Step 3: Preparation of 2-benzyl-1-methyl-6-(4,4,5,5-tetramethyl-1,3,2-dioxaborolan-2-yl)-1H-benzimidazole

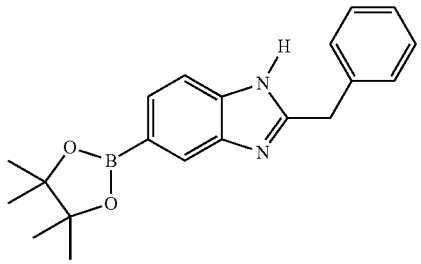 [SMILES: CC1(C)OB(c2ccc3[nH]c(Cc4ccccc4)nc3c2)OC1(C)C]

In a manner similar to the procedure described for step 1 of the preparation 5-(2-ethyl-2H-Indazol-6-yl)-7-piperidin-4-ylpyrrolo[2,1-f][1,2,4]triazin-4-amine and using 2-benzyl-5-bromo-1H-benzimidazole (120 mg).

Intermediate G G G: Preparation of 2-benzyl-1-methyl-6-(4,4,5,5-tetramethyl-1,3,2-dioxaborolan-2-yl)-1H-benzimidazole

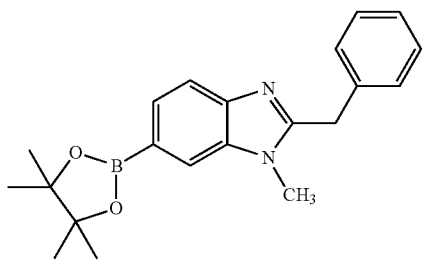 [SMILES: Cn1c(Cc2ccccc2)nc2ccc(B3OC(C)(C)C(C)(C)O3)cc21]

Step 1: Preparation of 2-benzyl-6-bromo-1-methyl-1H-benzimidazole

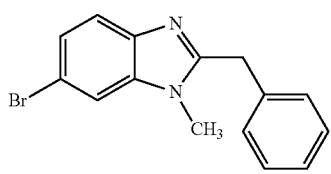 [SMILES: Cn1c(Cc2ccccc2)nc2ccc(Br)cc21]

Powdered KOH (5.25 g, 93.50 mmol) was added to a stirred solution of 2-benzyl-5-bromo-1H-benzimidazole (5.37 g, 8.70 mmol) in acetone (100 mL), after 10 min, iodomethane (1.28 mL, 20.57 mmol) was added and the mixture was stirred for 1 h and diluted with DCM. The mixture was washed with water and brine, then dried over $Na_2SO_4$ and concentrated. The residue was taken up in DCM and hexanes and the resulting suspension filtered. The filtrate was concentrated and the oily residue taken up in hexanes and stirred for about 1 h. The resulting solid was filtered and the filter cake washed with hexanes and dried (2.0 g, 34%). LC-MS $[M+H]^+ = 302.1$, RT=2.47 min.

Step 2: Preparation of 2-benzyl-1-methyl-6-(4,4,5,5-tetramethyl-1,3,2-dioxaborolan-2-yl)-1H-benzimidazole

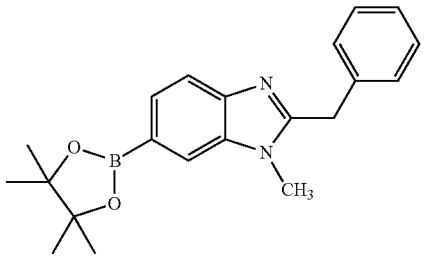 [SMILES: Cn1c(Cc2ccccc2)nc2ccc(B3OC(C)(C)C(C)(C)O3)cc21]

In a manner similar to the procedure described for step 1 of the preparation 5-(2-ethyl-2H-indazol-6-yl)-7-piperidin-4-ylpyrrolo[2,1-f][1,2,4]triazin-4-amine and using 2-benzyl-6-bromo-1-methyl-1H-benzimidazole, 270 mg, (42%) of the desired product was isolated.

Intermediate H H H: Preparation of 2-benzyl-1-methyl-5-(4,4,5,5-tetramethyl-1,3,2-dioxaborolan-2-yl)-1H-benzimidazole

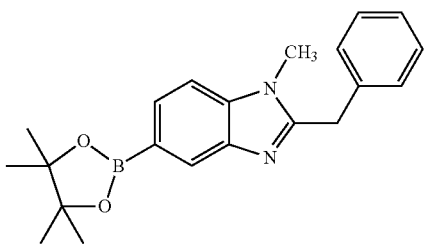 [SMILES: Cn1c(Cc2ccccc2)nc2cc(B3OC(C)(C)C(C)(C)O3)ccc21]

Step 1: Preparation of 2-benzyl-5-bromo-1-methyl-1H-benzimidazole

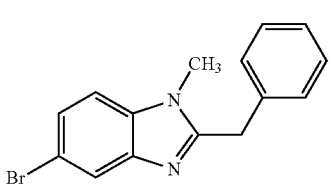 [SMILES: Cn1c(Cc2ccccc2)nc2cc(Br)ccc21]

Powdered KOH (5.25 g, 93.50 mmol) was added to a stirred solution of 2-benzyl-5-bromo-1H-benzimidazole (5.37 g, 18.70 mmol) in acetone (100 mL), after 10 min, methyl iodide (1.28 mL, 20.57 mmol) was added and the mixture was stirred for 1 h and diluted with DCM. The mixture was washed with water and brine, then dried over $Na_2SO_4$ and concentrated. The residue was taken up in DCM and hexanes and the resulting suspension filtered. The filter cake was washed with hexanes and dried on a high vacuum pump to give an off-white solid (2.07 g, 37%). LC-MS $[M+H]^+ = 302.1$, RT=2.47 min Step 2: Preparation of 2-benzyl-1-methyl-5-(4,4,5,5-tetramethyl-1,3,2-dioxaborolan-2-yl)-1H-benzimidazole

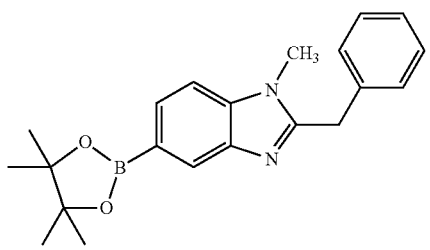 [SMILES: Cn1c(Cc2ccccc2)nc2cc(B3OC(C)(C)C(C)(C)O3)ccc21]

In a manner similar to the procedure described for step 1 of the preparation 5-(2-ethyl-2H-indazol-6-yl)-7-piperidin-4-ylpyrrolo[2,1-f][1,2,4]triazin-4-amine and using 2-benzyl-5-bromo-1-methyl-1H-benzimidazole, 1.83 g, (77%) of the desired product was isolated. LC-MS [M+H]$^+$=349.3, RT=2.62 min.

Intermediate I I I: Preparation of {3-[4-Amino-5-(2-benzyl-2H-indazol-6-yl)-pyrrolo[2,1-f][1,2,4]triazin-7-yl]-benzyl}-carbamic acid tert-butyl ester

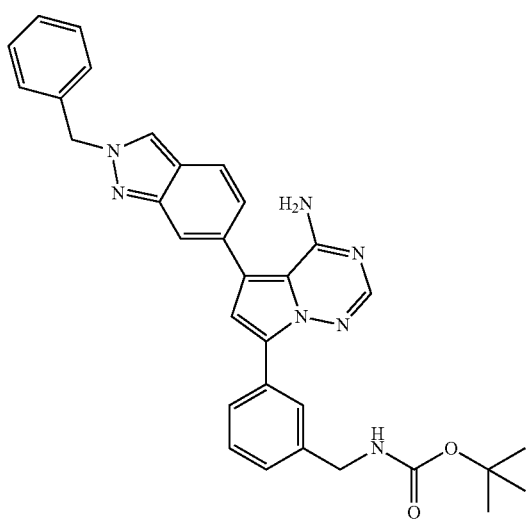 [SMILES: CC(C)(C)OC(=O)NCc1cccc(-c2cc(-c3ccc4cn(Cc5ccccc5)nc4c3)c3c(N)ncnn23)c1]

Step 1. Preparation of [3-(4-Amino-pyrrolo[2,1-f][1,2,4]triazin-7-yl)-benzyl]-carbamic acid tert-butyl ester

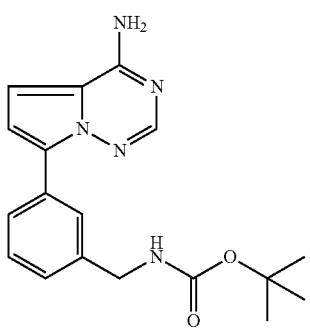 [SMILES: CC(C)(C)OC(=O)NCc1cccc(-c2ccc3c(N)ncnn23)c1]

To a solution of [3-(4,4,5,5-tetramethyl-[1,3,2]dioxaborolan-2-yl)-benzyl]-carbamic acid tert-butyl ester (7 g, 21 mmol) in DME (100 mL), 7-bromo-pyrrolo[2,1-f][1,2,4]triazin-4-ylamine (2.5 g, 11.7 mmol), PdCl$_2$(dppf) complexed with CH$_2$Cl$_2$ (850 mg, 1.2 mmol) and 2 N Na$_2$CO$_3$ (12 mL) were added. The mixture was degassed for 20 min and was then heated to 80° C. for 23 hours. After cooling, the mixture was partitioned between EtOAc and H$_2$O, and the organic layer was separated and dried. Biotage® chromatography (50-100% EtOAc) provided the title product as off white solid 2.6 g (76%). $^1$H NMR (300 MHz, DMSO-d$_6$) δ 7.80-7.50 (m, 6 H), 7.20-7.0 (m, 3 H), 4.80 (s, 2 H), 1.30 (s, 9 H); ES-MS m/z 339 [M+H]$^+$, HPLC RT (min) 2.41.

Step 2. Preparation of [3-(4-Amino-5-bromo-pyrrolo[2,1-f][1,2,4]triazin-7-yl)-benzyl]-carbamic acid tert-butyl ester

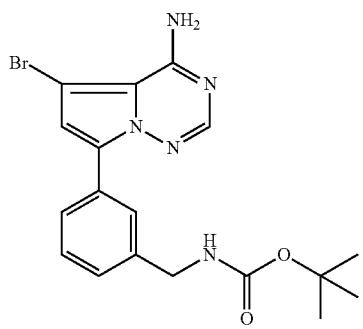 [SMILES: CC(C)(C)OC(=O)NCc1cccc(-c2cc(Br)c3c(N)ncnn23)c1]

To a solution of [3-(4-amino-pyrrolo[2,1-f][1,2,4]triazin-7-yl)-benzyl]-carbamic acid tert-butyl ester (3.3 g, 9.7 mmol) in THF (73 mL) cooled to −20° C. (isopropanol/ice/CO$_2$), 2,5-dibromo-4,4-dimethyl-cyclopentane-1,3-dione (1.4 g, 4.9 mmol) was added in four portions over 15 mins. The mixture was allowed to stir at −20° C. for 2 hours. The mixture was quenched with sodium thiosulfate solution (20 mL). The organic layer was separated and the aqueous layer was extracted with ethyl acetate (100 mL). The combined organic layer was washed with water, brine, dried by Na$_2$SO$_4$, filtered and concentrated. The residue was purified by Biatage® to give desired product 3 g (72%). NMR (300 MHz, DMSO-d$_5$) δ 7.80-7.7 (m, 3 H), 7.5 (m, 2 H), 7.2 (m, 2 H), 4.0 (m, 2 H), 1.5 (s, 9 H); ES-MS m/z 420 [M+H]$^+$, HPLC RT (min) 2.91.

Step 3. Preparation of {3-[4-Amino-5-(2-benzyl-2H-indazol-6-yl)-pyrrolo[2,1-f][1,2,4]triazin-7-yl]-benzyl}-carbamic acid tert-butyl ester

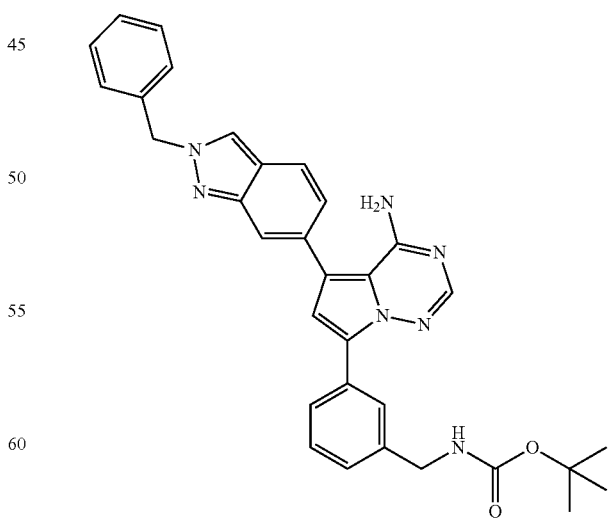

To a solution of [3-(4-amino-5-bromo-pyrrolo[2,1-f][1,2,4]triazin-7-yl)-benzyl]-carbamic acid tert-butyl ester (2.65 g, 6.1 mmol) in DMF (20 mL), 2-benzyl-6-(4,4,5,5-tetramethyl-[1,3,2]dioxaborolan-2-yl)-2H-indazole (3.26 g, 9.8 mmol), Pd(PPh₃)₄ (700 mg, 0.6 mmol) and 2 N Na₂CO₃ (12 mL) were added. The mixture was degassed for 20 min and was then heated to 150° C. in microwave reactor for 10 min. After cooling, the mixture was partitioned between EtoAc/H₂O and the organic layer was separated and dried. Biotage® chromatography (50-100% EtOAc) provided the title product as off white solid 2.6 g (76%). NMR (300 MHz, DMSO-d₆) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.10 (d, 2 H), 0.9 (s, 9 H); ES-MS m/z 561.34 [M+H]⁺, HPLC RT (min) 4.06.

Example 1

Preparation of 5-(2-benzyl-2H-indazol-8-yl)-7-piperidin-4-ylpyrrolo[2,1-f][1,2,4]triazin-4-amine

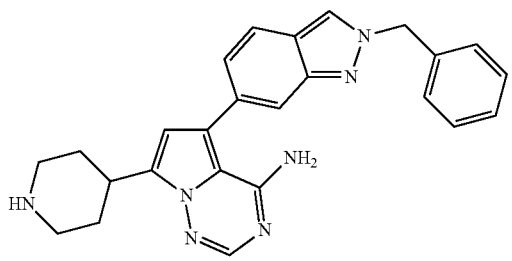 [SMILES: Nc1ncnn2c(C3CCNCC3)cc(-c3ccc4cn(Cc5ccccc5)nc4c3)c12]

Step 1: Preparation of tert-butyl 4-(4-aminopyrrolo[2,1-f][1,2,4]triazin-7-yl)-3,6-dihydropyridine-1(2H)-carboxylate

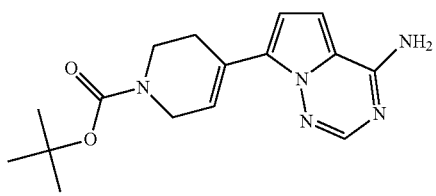 [SMILES: CC(C)(C)OC(=O)N1CC=C(c2ccc3c(N)ncnn23)CC1]

To a stirred suspension of Intermediate B (523 mg, 2.46 mmol), tert-butyl 4-(4,4,5,5-tetramethyl-1,3,2-dioxaborolan-2-yl)-3,6-dihydropyridine-1(2H)-carboxylate (Eastwood, P. R. *Tetrahedron Lett.* 2000, 41, 3705) (950 mg, 3.07 mmol), and 1,1'-bis(diphenylphosphino)-ferrocene]dichloro palladium(11)-complex with dichloromethane (180 mg, 025 mmol) in degassed DME (18 mL) was added aqueous Na₂CO₃ solution (2 M, 3.7 mL). The reaction was heated (80° C.) for 17 h and then cooled to rt. The mixture was partitioned between ethyl acetate (50 mL) and H₂O (50 mL). The layers were separated and the organic layer was washed with brine (25 mL), dried (Na₂SO₄), and concentrated to dryness. The crude residue was purified by ISCO® chromatography using a gradient of 50 to 75% ethyl acetate in hexanes to afford 584 mg (75%) of the desired product as an off-white solid, which contained trace impurities. ¹H NMR (300 MHz, DMSO-d₆) δ 7.85 (s, 1 H), 7.68 (br s, 2 H), 6.97 (br s, 1 H), 6.87 (d, 1 H), 6.66 (d, 1H), 4.07-4.00 (m, 2 H), 3.53 (t, 2 H), 2.56-2.50 (m, 2 H), 1.42 (s, 9 H); ES-MS m/z 316.1 [M+H]⁺, HPLC RT (min) 2.31.

Alternate synthesis of tert-butyl 4-(4-aminopyrrolo[2,1-f][1,2,4]triazin-7-yl)-3,6-dihydropyridine-1(2H)-carboxylate Step A: Preparation of tert-Butyl 4-(4-aminopyrrolo[2,1-f][1,2,4]triazin-7-yl)-4-hydroxypiperidine-1-carboxylate

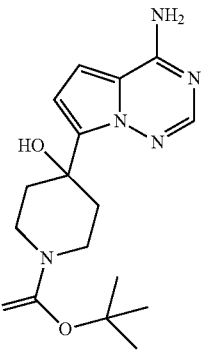

Chlorotrimethylsilane (89 mL, 0.70 mol) was added drop wise to a stirred solution of 7-bromopyrrolo[2,1-f][1,2,4]triazin-4-amine in tetrahydrofuran (1.6 L, anhydrous) and stirring was continued for 3 h. The solution was cooled to 0° C. and 2-propyl magnesium chloride solution (2M in THF, 740 mL, 1.48 mol) was slowly added. The reaction was warmed to 25° C. and stirring continued for 2 h, then cooled back down to −5° C. and a solution of N-tert-butoxycarbonyl piperidine (91.0 g, 0.68 mol) in THF (1 L) was added drop wise. The reaction was continued for 18 h at 25° C., then the mixture was, poured into vigorously-stirred ice water (8 L). The aqueous mixture was extracted with ethyl acetate (3×3 L) and the combined organic portions were dried over magnesium sulfate. Filtration and concentration in vacuo gave a dark-orange oil which was dissolved in a minimal volume of dichloromethane and crystallization induced. After cooling (−10° C.) the mixture for several hours, the crystalline product was collected by suction filtration, washed with diethyl ether and dried to give a colorless solid (61 g, 52%). Purification of the filtrate by silica gel chromatography (5% methanol/dichloromethane) yielded additional product (37 g, 32%). ¹H-NMR (DMSO-d₆) δ 7.77 (s, 1H), 7.69 (br s, 2H), 6.80 (d, 1H), 6.55 (d, 1H), 5.74 (s, 1H), 3.77 (m, 2H), 3.15 (br m, 2H), 2.48 (m, 2H), 1.70 (d, 2H), 1.40 (s, 9H). ES-MS m/z=334.1 [M+H]⁺, RT (min) 2.15.

Step B: Preparation of tert-butyl 4-(4-aminopyrrolo[2,1-f][1,2,4]triazin-7-yl)-3,6-dihydropyridine-1(2H)-carboxylate

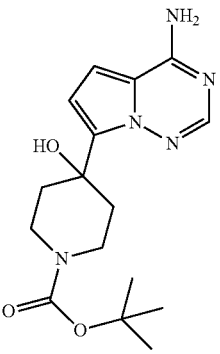 [SMILES: CC(C)(C)OC(=O)N1CCC(O)(c2ccc3c(N)ncnn23)CC1]

Trifluoroacetic anhydride (9 mL, 63 mmol) was added dropwise to a cold (0° C.), stirred mixture containing tert-butyl 4-(4-aminopyrrolo[2,1-f][1,2,4]triazin-7-yl)-4-hydroxy piperidine-1-carboxylate (21 g, 63 mmol) and N,N-diisopropylethylamine (16.5 mL, 94 mmol) in dichloromethane (420 mL). The reaction was stirred for 18 h at 25° C., then the mixture was washed with 10% acetic acid followed by water. The organic solution was dried over magnesium sulfate, filtered and concentrated to give a gummy, dark-orange oil. The residue was dissolved in methanol (350 mL) and excess potassium hydroxide solution was added. The mixture was stirred at 25° C. for 18 h. The mixture was concentrated and the precipitated product was collected by suction filtration. The dried yellow-orange solids (19.4 g, 98%) were used without additional purification. $^1$H-NMR (DMSO-d$_6$) δ 7.91 (s, 1H), 7.74 (br s, 2H), 7.03 (br s, 1H), 6.93 (d, 1H), 6.71 (d, 1H), 4.08 (br s, 2H), 3.57 (m, 2H), 2.57 (m, 2H), 1.45 (s, 9H). ES-MS m/z=316.0 [M+H]$^+$, RT (min) 2.44.

Step 2: Preparation of tert-butyl 4-(4-aminopyrrolo[2,1-f][1,2,4]triazin-7-yl)piperidine-1-carboxylate

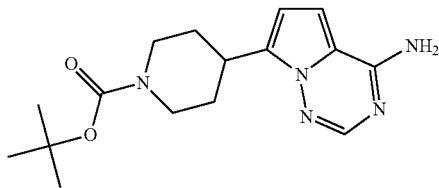 [SMILES: CC(C)(C)OC(=O)N1CCC(c2ccc3c(N)ncnn23)CC1]

To a dry flask purged with N$_2$ was added platinum(IV) oxide (127 mg, 0.56 mmol) followed by tert-butyl 4-(4-aminopyrrolo[2,1-f][1,2,4]triazin-7-yl)-3,6-dihydropyridine-1(2H)-carboxylate (587 mg, 1.86 mmol) as a solution in acetic acid (19 mL). The mixture was stirred under an H$_2$ atmosphere for 16 h. The mixture was filtered through a pad of Celite® rinsing with acetic acid and ethanol. The solvent was evaporated under reduced pressure and the residue was dissolved in ethyl acetate (100 mL). The organic was washed with saturated aqueous NaHCO$_3$ (2×75 mL) and the aqueous mixture was back extracted with ethyl acetate (3×50 mL). The combined organics were washed with brine, dried (Na$_2$SO$_4$) and concentrated to dryness to afford 610 mg (100%) of the desired product as a gray solid. $^1$H NMR (300 MHz, DMSO-d$_6$) δ 7.78 (s, 1 H), 7.57 (br s, 2 H), 6.78 (d, 1 H), 6.42 (d, 1 H), 4.08-3.97 (m, 2H), 3.28-3.18 (m, 1 H), 1.94 (d, 2 H), 1.55-1.42 (m, 2 H), 1.41 (s, 9 H); ES-MS m/z 318.1 [M+H]$^+$, HPLC RT (min) 2.21.

Step 3: Preparation of tert-butyl 4-(4-amino-5-bromopyrrolo[2,1-f][1,2,4]triazin-7-yl)piperidine-1-carboxylate

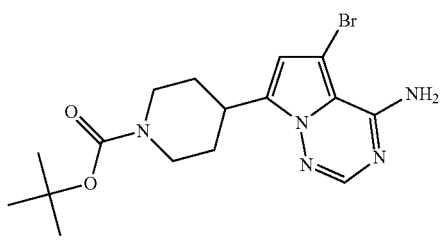 [SMILES: CC(C)(C)OC(=O)N1CCC(c2cc(Br)c3c(N)ncnn23)CC1]

To a cooled (−20° C.) solution of tert-butyl 4-(4-aminopyrrolo[2,1-f][1,2,4]triazin-7-yl)piperidine-1-carboxylate (660 mg, 2.08 mmol) in tetrahydrofuran (10 mL) was added 1,3-dibromo-5,5-dimethylhydantoin (297 mg, 1.04 mmol) in 3 portions over 10 min. The mixture was allowed to stir (−20° C.) for 1 h. The reaction was quenched with the addition saturated aqueous Na$_2$SO$_3$ (10 mL) and was allowed to warm to rt. The mixture was extracted with ethyl acetate (3×20 mL). The combined organics were washed with brine (25 mL), dried (Na$_2$SO$_4$) and evaporated. The crude material was purified by ISCO® chromatography using a gradient of 75 to 100% ethyl acetate in hexanes to afford 494 mg (60%) of the desired product. $^1$H NMR (300 MHz, DMSO-d$_6$) δ 7.83 (s, 1 H), 6.64 (s, 1 H), 4.10-3.96 (m, 2H), 3.29-3.19 (m, 1 H), 1.90 (d, 2 H), 1.55-1.42 (m, 2 H), 1.41 (s, 9 H); ES-MS m/z 396.1 [M+H]$^+$, HPLC RT (min) 2.79.

Step 4: Preparation of tert-butyl 4-[4-amino-5-(2-benzyl-2H-indazol-6-yl)pyrrolo[2,1-f][1,2,4]triazin-7-yl]piperidine-1-carboxylate

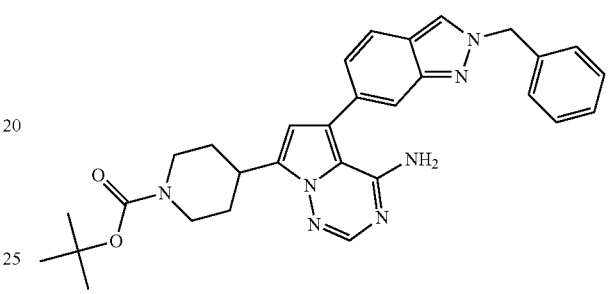

To a stirred solution of tert-butyl 4-(4-amino-5-bromopyrrolo[2,1-f][1,2,4]triazin-7-yl)piperidine-1-carboxylate (494 mg, 1.25 mmol), Intermediate C (1.04 g, 1.87 mmol), and tetrakis(triphenylphosphine)palladium(0) (144 mg, 0.13 mmol) in degassed DME (5.5 mL) was added aqueous Na$_2$CO$_3$ solution (2 M, 1.87 mL). The reaction was heated (80° C.) for 17 h and then cooled to rt. The mixture was partitioned between ethyl acetate (50 mL) and H$_2$O (50 mL). The layers were separated and the aqueous layer was back extracted with ethyl acetate (50 mL). The combined organics were washed with brine, dried (Na$_2$SO$_4$), and concentrated to dryness. The crude material was purified ISCO® chromatography using a gradient of 25 to 75% ethyl acetate in hexanes to afford 378 mg (58%) of the desired product, which contained trace impurities. $^1$H NMR (300 MHz, DMSO-d$_6$) δ 8.52 (s, 1 H), 7.88 (s, 1 H), 7.78 (d, 1 H), 7.57 (s, 1 H), 7.36-7.31 (m, 5 H), 7.13 (d, 1 H), 6.61 (s, 1 H), 5.64 (s, 2 H), 4.13-3.98 (m, 2 H), 3.35-3.25 (m, 1 H), 2.05-1.96 (m, 2 H), 1.63-1.1.50 (m, 2 H), 1.41 (s, 9 H); ES-MS m/z 524.2 [M+H]$^+$, HPLC RT (min) 3.08.

Step 5: Preparation of the Title Compound

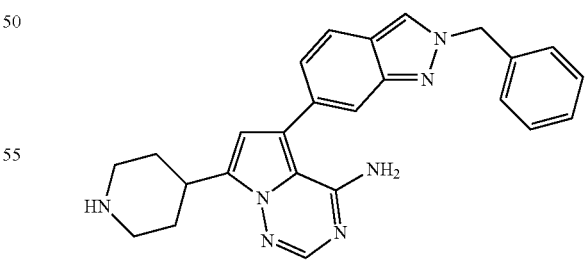

To a solution of tert-butyl 4-[4-amino-5-(2-benzyl-2H-indazol-6-yl)pyrrolo[2,1-f][1,2,4]triazin-7-yl]piperidine-1-carboxylate (325 mg, 0.62 mmol) in dichloromethane (3 mL) was added trifluoroacetic acid (1 mL). The reaction was stirred (rt) for 17 h. The mixture was made basic (pH 9) with the addition of saturated aqueous NaHCO$_3$ and the layers were separated. The aqueous phase was back extracted with dichloromethane (2×10 mL) and the combined organics were washed with brine, dried (Na₂SO₄), and evaporated to afford 299 mg (100%) of the desired product, which contained trace impurities. ¹H NMR (300 MHz, DMSO-d₆) δ 8.53 (s, 1 H), 7.87 (s, 1 H), 7.78 (d, 1 H), 7.57 (s, 1 H), 7.36-7.30 (m, 5 H), 7.13 (d, 1 H), 6.55 (s, 1 H), 5.64 (s, 2 H), 3.41 (br s, 1 H), 3.30-3.18 (m, 1 H), 3.07 (d, 2 H), 2.75-2.64 (m, 2H), 1.97 (d, 2 H), 1.68-1.53 (m, 2 H); ES-MS m/z 424.3 [M+H]⁺, HPLC RT (min) 0.78.

Example 2

Preparation of 5-(2-benzyl-2H-indazol-6-yl)-7-(1-methylpiperidin-4-yl)pyrrolo[2,1-f][1,2,4]triazin-4-amine

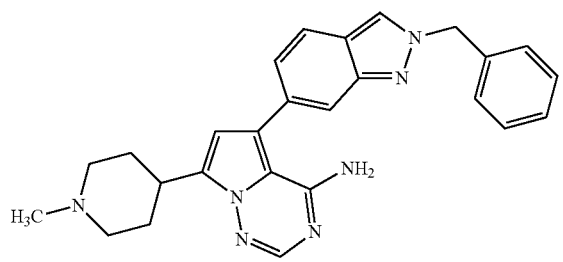 [SMILES: CN1CCC(c2cc(-c3ccc4cn(Cc5ccccc5)nc4c3)c3c(N)ncnn23)CC1]

To a solution of 5-(2-benzyl-2H-indazol-6-yl)-7-piperidin-4-ylpyrrolo[2,1-f][1,2,4]triazin-4-amine (75 mg, 0.18 mmol) in dichloromethane (2 mL) was added formaldehyde (37% solution in water) (80 μL, 1.06 mmol) and sodium triacetoxyborohydride (113 mg, 0.53 mmol). The reaction was stirred (rt) for 17 h. The mixture was diluted with dichloromethane and was washed with H₂O (1×10 mL). The organic phase was washed with brine, and was dried (Na₂SO₄) and concentrated. The residue was purified by preparative HPLC using a gradient elution from 15% to 50% acetonitrile in water to obtain 13 mg (17%) of the desired product. ¹H NMR (300 MHz, DMSO-d₆) δ 8.54 (s, 1 H), 7.88 (s, 1 H), 7.79 (d, 1 H), 7.58 (s, 1 H), 7.37-7.28 (m, 5 H), 7.14 (dd, 1 H), 6.58 (s, 1 H), 5.65 (s, 2 H), 3.11-2.97 (m, 1 H), 2.85 (d, 2 H), 2.18 (s, 3 H), 2.04-1.94 (m, 4H), 1.77-1.61 (m, 2 H); ES-MS m/z 438.3 [M+H]⁺, HPLC RT (min) 2.11.

Example 3

Preparation of 2-{4-[4-amino-5-(2-benzyl-2H-indazol-6-yl)pyrrolo[2,1-f][1,2,4]triazin-7-yl]piperidin-1-yl}ethanol

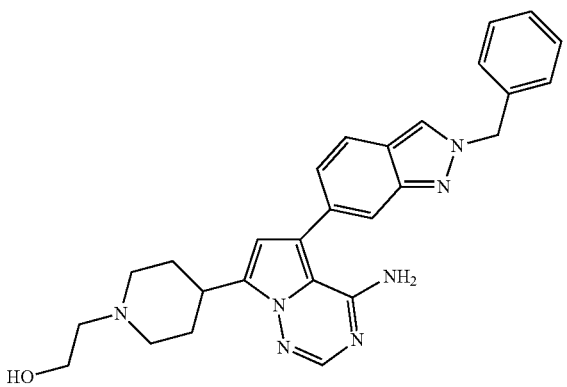 [SMILES: Nc1ncnn2c(C3CCN(CCO)CC3)cc(-c3ccc4cn(Cc5ccccc5)nc4c3)c12]

Step 1: Preparation of 5-(2-benzyl-2H-indazol-6-yl)-7-[1-(2-{[tert-butyl(dimethyl)silyl]oxy}ethyl)piperidin-4-yl]pyrrolo[2,1-f][1,2,4]triazin-4-amine

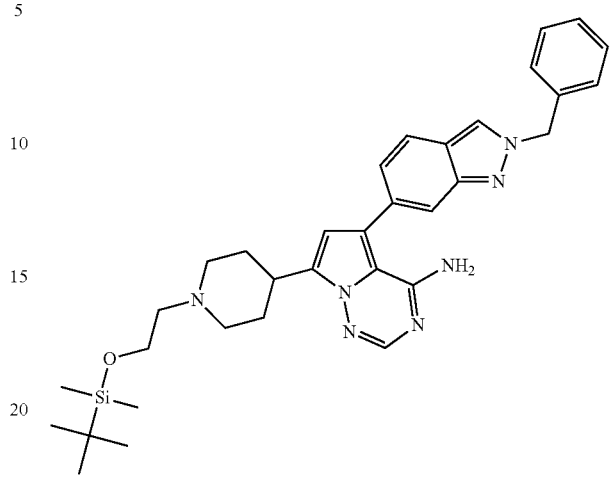

To a solution of 5-(2-benzyl-2H-indazol-6-yl)-7-piperidin-4-ylpyrrolo[2,1-f][1,2,4]triazin-4-amine (96 mg, 0.23 mmol) in DMF (1.5 mL) was added (2-bromoethoxy)-tert-butyldimethylsilane (53 μL, 0.25 mmol), triethylamine (95 μl, 0.68 mmol), and sodium iodide (3.4 mg, 0.023 mmol). The reaction was heated (55° C.) for 17 h and then cooled to rt. The mixture was partitioned between ethyl acetate (25 mL) and H₂O (25 mL). The layers were separated and the organic was washed with H₂O (20 mL). The combined aqueous was back extracted with ethyl acetate (20 mL). The combined organics were washed with brine, dried (Na₂SO₄), and evaporated. The crude material was purified by ISCO® chromatography using 100% ethyl acetate to afford 39 mg (29%) of the desired product. ¹H NMR (300 MHz, DMSO-d₅) δ 8.50 (s, 1 H), 7.90 (s, 1 H), 7.85 (d, 1 H), 7.54 (s, 1 H), 7.38-7.23 (m, 5 H), 7.10 (d, 1 H), 6.54 (s, 1 H), 5.61 (s, 2 H), 3.65 (t, 2 H), 3.09-2.98 (m, 1 H), 2.98-2.88 (m, 2 H), 2.44-2.36 (m, 2 H), 2.09 (t, 2H), 1.99-2.02 (m, 2 H), 1.73-1.56 (m, 2 H), 0.82 (s, 9 H), 0.00 (s, 6 H); ES-MS m/z 582.3 [M+H]⁺, HPLC RT (min) 2.87.

Step 2: Preparation of the Title Compound,

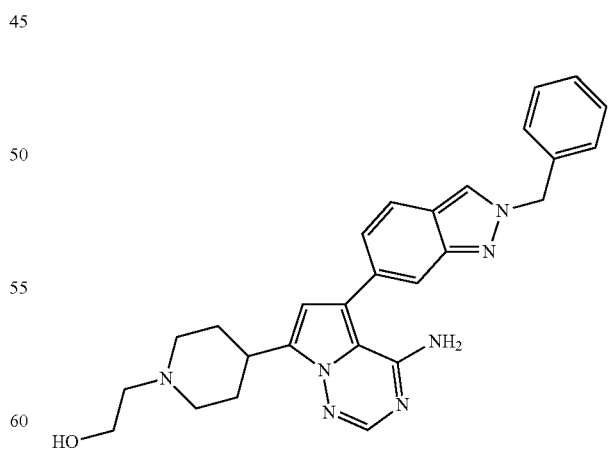

To a solution of 5-(2-benzyl-2H-indazol-6-yl)-7-[1-(2-{[tert-butyl(dimethyl)silyl]oxy}ethyl)piperidin-4-yl]pyrrolo[2,1-f][1,2,4]triazin-4-amine (38 mg, 0.065 mmol) in 95% aqueous ethanol (300 μL) was added concentrated hydrochloric acid (6 μL). The reaction was stirred (rt) for 48 h. The mixture was basified (pH 9) with, the addition of saturated aqueous NaHCO₃ solution and was evaporated to remove volatiles. The aqueous mixture was extracted with ethyl acetate (3×20 mL) and the combined organics were washed with brine, dried (Na₂SO₄) and concentrated. The crude material was triturated with Et₂O to afford 18 mg (61%) of the desired product as a pale yellow solid. ¹H NMR (300 MHz, DMSO-d₆) δ 8.60 (s, 1 H), 7.94 (s, 1 H), 7.85 (d, 1 H), 7.64 (s, 1H), 7.54 (s, 1 H), 7.46-7.33 (m, 5 H), 7.20 (d, 1 H), 6.63 (s, 1 H), 5.70 (s, 2 H), 3.60-3.51 (m, 2 H), 3.18-3.08 (m, 1 H), 3.06-2.98 (m, 2 H), 2.46 (t, 2 H), 2.14 (t, 2H), 2.02 (d, 2 H), 1.82-1.68 (m, 2 H); ES-MS m/z 468.34 [M+H]⁺, HPLC RT (min) 0.82.

Example 4

Preparation of 5-(2-benzyl-2H-indazol-6-yl)-7-(4-piperazin-1-ylphenyl)pyrrolo[2,1-f][1,2,4]triazin-4-amine

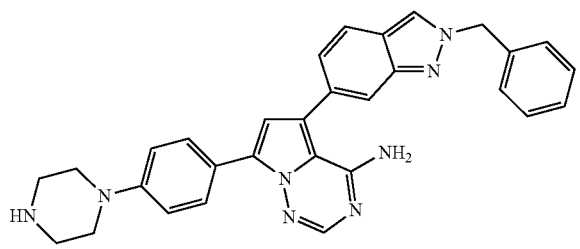 [SMILES: Nc1ncnn2c(-c3ccc(N4CCNCC4)cc3)cc(-c3ccc4cn(Cc5ccccc5)nc4c3)c12]

Step 1: Preparation of tert-butyl 4-[4-(4-aminopyrrolo[2,1-f][1,2,4]triazin-7-yl)-phenyl]piperazine-1-carboxylate

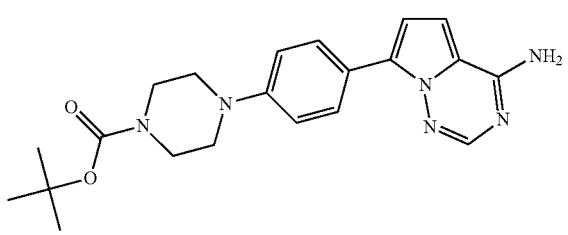 [SMILES: CC(C)(C)OC(=O)N1CCN(c2ccc(-c3ccc4c(N)ncnn34)cc2)CC1]

To a stirred suspension of 7-bromopyrrolo[2,1-f][1,2,4]triazin-4-amine (801 mg, 3.76 mmol), tert-butyl 4-[4-(4,4,5,5-tetramethyl-1,3,2-dioxaborolan-2-yl)phenyl]tetrahydro-1(2H)-pyrazinecarboxylate (2.19 g, 5.64 mmol), and [1,1'-bis(diphenylphosphino)-ferrocene]dichloro palladium(II)-complex with dichloromethane (275 mg, 0.38 mmol) in degassed DME (25 mL) was added aqueous Na₂CO₃ solution (2 M, 5.6 mL). The reaction was heated (80° C.) for 17 h and then cooled to rt. The mixture was filtered through a pad of Celite® using ethyl acetate to rinse. The filtrate was washed with water (75 mL), dried (Na₂SO₄), and concentrated. The crude material was purified by ISCO® chromatography using a gradient of 50 to 75% ethyl acetate in hexanes to afford 1.22 g (74%) of the desired product as an off-white solid, which contained trace impurities. ¹H NMR (300 MHz, DMSO-d₆) δ 7.94-7.88 (m, 2 H), 7.86 (s, 1 H), 7.65 (br s, 2 H), 7.03-6.97 (m, 1 H), 6.94 (d, 1H), 6.89 (d, 1 H), 3.51-3.42 (m, 4 H), 3.19-3.11 (m, 4 H), 1.42 (s, 9 H); ES-MS m/z 395.1 [M+H]⁺, HPLC RT (min) 2.52.

Step 2: Preparation of tert-butyl 4-[4-(4-amino-5-bromopyrrolo[2,1-f][1,2,4]triazin-7-yl)phenyl]piperazine-1-carboxylate

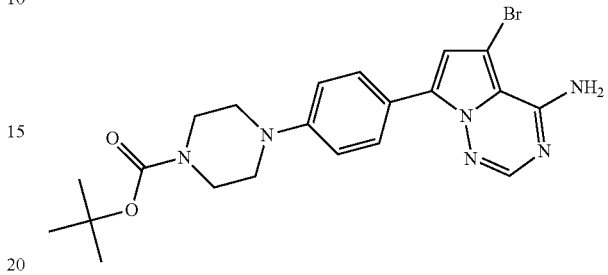

To a cooled (−20° C.) solution of tert-butyl 4-[4-(4-aminopyrrolo[2,1-f][1,2,4]triazin-7-yl)phenyl]piperazine-1-carboxylate (1.20 g, 3.04 mmol) in tetrahydrofuran (15 mL) was added 1,3-dibromo-5,5-dimethylhydantoin (435 mg, 1.21 mmol) in four portions over 15 min. The mixture was allowed to stir (−20° C.) for 3 h. The reaction was quenched with the addition saturated aqueous Na₂SO₃ (20 mL) and was allowed to warm to rt. The mixture was extracted with ethyl acetate (2×25 mL). The combined organics were dried (Na₂SO₄) and concentrated. The crude material was purified by ISCO® chromatography using a gradient of 25 to 75% ethyl acetate in hexanes. ¹H-NMR indicated the presence of residual hydantoin side product, thus the material was partitioned between ethyl acetate (50 mL) and 5% aqueous K₂CO₃ (50 mL). The layers were separated and the organic layer was further washed with 5% aqueous K₂CO₃ (2×25 mL). The combined aqueous was back extracted with ethyl acetate (2×25 mL) and the combined organics were washed with brine, dried (Na₂SO₄) and concentrated to afford 340 mg (23%) of the desired product as a white solid. ¹H NMR (300 MHz, DMSO-d₆) δ 7.91-7.83 (m, 3 H), 7.09 (s, 1 H), 7.00 (d, 2H), 3.50-3.42 (m, 4 H), 3.20-3.14 (m, 4 H), 1.42 (s, 9 H); ES-MS m/z 473.0 [M+H]⁺, HPLC RT (min) 3.25.

Step 3: Preparation of tert-butyl 4-{4-[4-amino-5-(2-benzyl-2H-indazol-6-yl)pyrrolo[2,1-f][1,2,4]triazin-7-yl]phenyl}piperazine-1-carboxylate

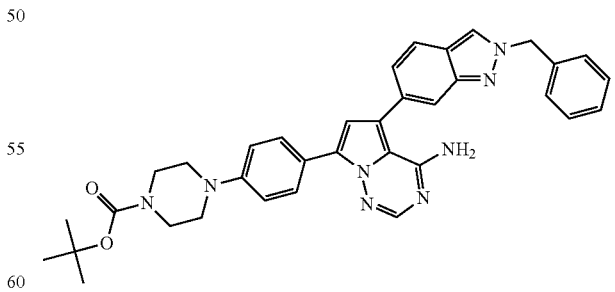

To a stirred solution of tert-butyl 4-[4-(4-amino-5-bromopyrrolo[2,1-f][1,2,4]triazin-7-yl)phenyl]piperazine-1-carboxylate (4 mg, 1.25 mmol), 2-benzyl-6-(4,4,5,5-tetramethyl-1,3,2-dioxaborolan-2-yl)-2H-Indazole (1.04 g, 1.87 mmol), and tetrakis(triphenylphosphine)palladium(0) (144 mg, 0.13 mmol) in degassed DME (5.5 mL) was added aqueous Na$_2$CO$_3$ solution (2 M, 1.87 mL). The reaction was heated (80° C.) for 17 h and then cooled to rt. The mixture was partitioned between ethyl acetate (25 mL) and H$_2$O (25 mL). The layers were separated and the aqueous phase was back extracted with ethyl acetate. The combined organics were washed with brine, dried (Na$_2$SO$_4$), and concentrated to dryness. The crude material was purified by ISCO® chromatography using a gradient of 25 to 75% ethyl acetate in hexanes to afford 378 mg (58%) of the desired product, which contained trace impurities. $^1$H NMR (300 MHz, DMSO-d$_6$) δ 8.52 (s, 1 H), 7.88 (s, 1 H), 7.78 (d, 1 H), 7.57 (s, 1 H), 7.36-7.31 (m, 5 H), 7.13 (d, 1 H), 6.61 (s, 1 H), 5.64 (s, 2 H), 4.13-3.98 (m, 2 H), 3.35-3.25 (m, 1 H), 2.05-1.96 (m, 2 H), 1.63-1.50 (m, 2 H), 1.41 (s, 9 H); ES-MS m/z 524.2 [M+H]$^+$, HPLC RT (min) 3.08.

Step 4: Preparation of the Title Compound

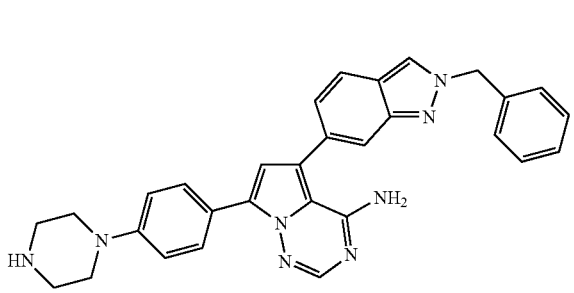 [SMILES: Nc1ncnn2c(-c3ccc(N4CCNCC4)cc3)cc(-c3ccc4cn(Cc5ccccc5)nc4c3)c12]

To a suspension of tert-butyl 4-{4-[4-amino-5-(2-benzyl-2H-indazol-6-yl)pyrrolo[2,1-f][1,2,4]triazin-7-yl]phenyl}piperazine-1-carboxylate (610 mg, 1.02 mmol) in dichloromethane (6 mL) was added trifluoroacetic acid (2 mL). The reaction was stirred (rt) for 17 h. The mixture was evaporated to dryness and saturated aqueous NaHCO$_3$ was added to the residue. The resulting solid was collected by filtration and was dried in vacuo to afford 489 mg (96%) of the desired product. $^1$H NMR (300 MHz, DMSO-d$_6$) δ 8.54 (s, 1 H), 7.99-7.91 (m, 3 H), 7.81 (d, 1 H), 7.65 (s, 1 H), 7.41-7.25 (m, 5 H), 7.19 (d, 1 H), 7.06-6.96 (m, 3 H), 5.65 (s, 2 H), 3.14 (s, 4 H), 2.89 (s, 4 H); ES-MS m/z 501.4 HPLC RT (min) 2.25.

Example 5

Preparation of 5-(2-benzyl-2H-indazol-6-yl)-7-[4-(4-propylpiperazin-1-yl)phenyl]pyrrolo[2,1-f][1,2,4]triazin-4-amine

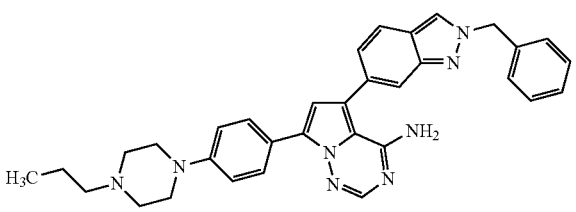 [SMILES: CCCN1CCN(c2ccc(-c3cc(-c4ccc5cn(Cc6ccccc6)nc5c4)c4c(N)ncnn34)cc2)CC1]

To a solution of 5-(2-benzyl-2H-indazol-6-yl)-7-(4-piperazin-1-ylphenyl)pyrrolo[2,1-f][1,2,4]triazin-4-amine (75 mg, 0.15 mmol) and 1-iodopropane (31 mg, 0.18 mmol) in DMF (2 mL) was added potassium carbonate (37 mg, 0.27 mmol). The reaction was heated (50° C.) for 17 h. The reaction was cooled to rt and was partitioned between ethyl acetate (25 mL) and H$_2$O (25 mL). The layers were separated and the organic was washed with brine, dried (Na$_2$SO$_4$) and concentrated. The residue was purified by preparative HPLC using a gradient elution from 15% to 50% acetonitrile in water followed by trituration with Et$_2$O to obtain 21 mg (25%) of the desired product. $^1$H NMR (300 MHz, DMSO-d$_6$) δ 8.55 (s, 1 H), 7.97-7.91 (m, 3 H), 7.81 (d, 1 H), 7.65 (s, 1 H), 7.37-7.26 (m, 5H), 7.19 (d, 1 H), 7.04-6.96 (m, 3 H), 5.66 (s, 2 H), 325-3.15 (m, 4 H), 2.51-2.48 (m, 4 H), 2.32-2.24 (m, 2 H), 1.53-1.42 (m, 2 H), 0.88 (t, 3 H), 2.89 (s, 4 H); ES-MS m/z 543.4 [M+H]$^+$, HPLC RT (min) 2.40.

Example 6

Preparation of 7-[4-(4-acetylpiperazin-1-yl)phenyl]-5-(2-benzyl-2H-indazol-6-yl)pyrrolo[2,1-f][1,2,4]triazin-4-amine

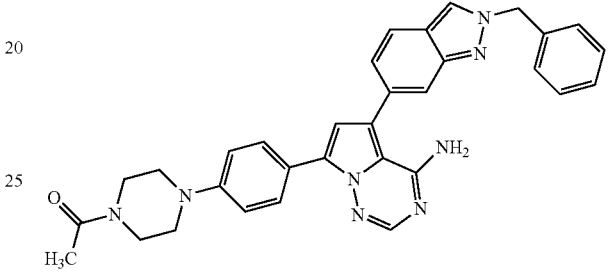

To a solution of 5-(2-benzyl-2H-indazol-6-yl)-7-(4-piperazin-1-ylphenyl)pyrrolo[2,1-f][1,2,4]triazin-4-amine (100 mg, 0.20 mmol) in dichloromethane (2 mL) was added pyridine (23 µL, 0.28 mmol) followed by acetyl chloride (17 µL, 0.24 mmol). The mixture was stirred (rt) overnight. The mixture was diluted with dichloromethane (25 mL) and was washed with H$_2$O (20 mL), brine, and was dried (Na$_2$SO$_4$) and concentrated. The residue was purified by preparative HPLC using a gradient elution from 15% to 50% acetonitrile in water to obtain 28 mg (26%) of the desired product. $^1$H NMR (300 MHz, DMSO-d$_6$) δ 8.56 (s, 1 H), 7.97 (d, 2 H), 7.94 (s, 1 H), 7.81 (d, 1 H), 7.66-7.64 (m, 1 H), 7.36-7.26 (m, 5 H), 7.19 (dd, 1 H), 7.06-7.01 (m, 3 H), 5.66 (s, 2. H), 3.62-3.55 (m, 4 H), 3.26-3.21 (m, 2 H), 3.20-3.14 (m, 2 H), 2.05 (s, 3 H); ES-MS m/z 543.33 [M+H]$^+$, HPLC RT (min) 2.65.

Example 7

Preparation of 5-(2-benzyl-2H-indazol-6-yl)-7-[4-(4-methylpiperazin-1-yl)phenyl]pyrrolo[2,1-f][1,2,4]triazin-4-amine

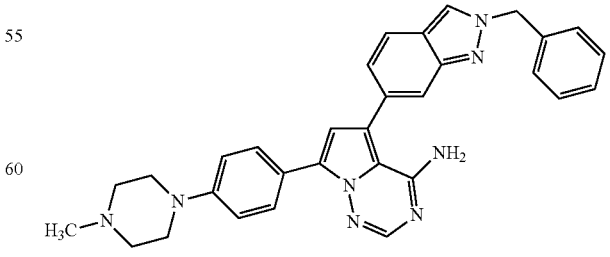

To a solution of 5-(2-benzyl-2H-indazol-6-yl)-7-(4-piperazin-1-ylphenyl)pyrrolo[2,1-f][1,2,4]triazin-4-amine (89 mg, 0.18 mmol) in dichloromethane (3 mL) was added formaldehyde (37% in water) (80 μL, 1.06 mmol) and sodium triacetoxyborohydride (113 mg, 0.53 mmol). The reaction was stirred (rt) for 17 h. The mixture was diluted with dichloromethane (25 mL) and was washed with H₂O (1×20 mL), brine, and was dried (Na₂SO₄) and evaporated. The residue was purified by preparative HPLC using a gradient elution from 5% to 30% acetonitrile in water to obtain 53 mg (58%) of the desired product. ¹H NMR (300 MHz, DMSO-d₆) δ 8.57 (s, 1 H), 7.99-7.91 (m, 3 H), 7.86-7.79 (m, 1 H), 7.69-7.63 (m, 1 H), 7.39-7.26 (m, 5 H), 7.23-7.17 (m, 1 H), 7.06-6.98 (m, 3 H), 5.66 (s, 2 H), 3.27-3.14 (m, 4 H), 2.47-2.40 (m, 4 H), 2.22 (s, 3 H); ES-MS m/z 515.32 [M+H]⁺, HPLC RT (min) 2.36.

Example 8

Preparation of 5-(2-benzyl-2H-indazol-6-yl)-7-[2-(4-methylpiperazin-1-yl)pyridin-4-yl]pyrrolo[2,1-f][1,2,4]triazin-4-amine

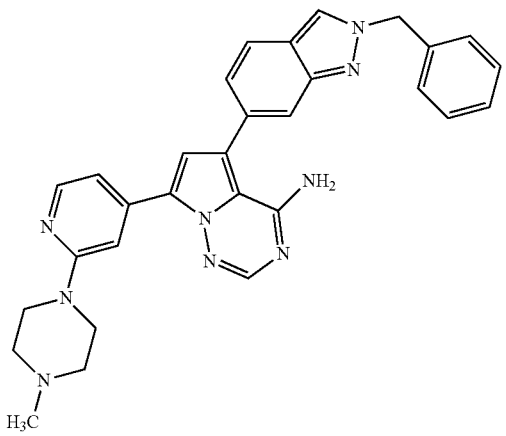 [SMILES: CN1CCN(c2cc(-c3cc(-c4ccc5cn(Cc6ccccc6)nc5c4)c4c(N)ncnn34)ccn2)CC1]

Step 1: Preparation of 7-[2-(4-methylpiperazin-1-yl)pyridin-4-yl]pyrrolo[2,1-f][1,2,4]triazin-4-amine

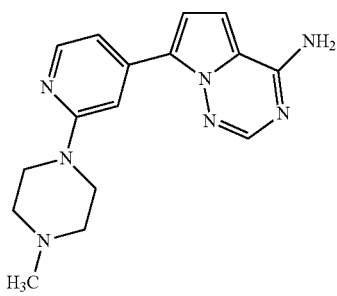 [SMILES: CN1CCN(c2cc(-c3ccc4c(N)ncnn34)ccn2)CC1]

To a stirred suspension of 7-bromopyrrolo[2,1-f][1,2,4]triazin-4-amine (937 mg, 4.40 mmol), 1-methyl-4-[4,4,5,5-tetramethyl-1,3,2-dioxaborolan-2-yl)pyridine-2-yl]piperazine (2.00 g, 6.60 mmol), and [1,1'-bis(diphenylphosphino)-ferrocene]dichloro palladium(II)-complex with dichloromethane (322 mg, 0.44 mmol) in degassed DME (33 mL) was added aqueous Na₂CO₃ solution (2 M, 6.6 mL). The reaction was heated (80° C.) for 17 h and then cooled to rt. The mixture was filtered through a pad of Celite® using ethyl acetate to rinse. The filtrate was washed with water (75 mL), dried (Na₂SO₄), and concentrated to dryness to afford 1.0 g (74%) of the desired product as a tan solid, which was used in the next reaction without further purification. ES-MS m/z 310.15 [M+H]⁺, HPLC RT (min) 1.08.

Step 2: Preparation of 5-bromo-7-[2-(4-methylpiperazin-1-yl)pyridin-4-yl]pyrrolo[2,1-f][1,2,4]triazin-4-amine

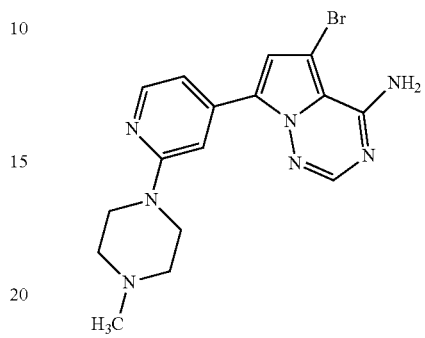

To a cooled (−20° C.) solution 7-[2-(4-methylpiperazin-1-yl)pyridin-4-yl]pyrrolo[2,1-f][1,2,4]triazin-4-amine (250 mg, 0.81 mmol) in tetrahydrofuran (5 mL) was added 1,3-dibromo-5,5-dimethylhydantoin (115 mg, 0.40 mmol) in four portions over 15 min. The mixture was allowed to stir (−20° C.) for 4 h. The reaction was quenched with the addition saturated aqueous Na₂SO₃ (10 mL) and was allowed to warm to rt. The mixture was extracted with ethyl acetate (2×20 mL). The combined organics were filtered to remove a fine precipitate and the filtrate was washed with brine, dried (Na₂SO₄) and concentrated. The residue was purified by preparative HPLC using a gradient elution from 0% to 25% acetonitrile in water to obtain 60 mg (19%) of the desired product as a yellow foam. ¹H NMR (300 MHz, DMSO-d₆) δ 8.70 (d, 1 H), 8.14 (dd, 1 H), 7.89 (s, 1 H), 7.14 (s, 1 H), 6.90 (d, 1 H), 3.55-3.50 (m, 4 H), 2.40-2.34 (m, 4 H), 2.20 (s, 3 H); ES-MS m/z 388.12 [M+H]⁺, HPLC RT (min) 1.38.

Step 3: Preparation of 5-(2-benzyl-2H-indazol-6-yl)-7-[2-(4-methylpiperazin-1-yl)pyridin-4-yl]pyrrolo[2,1-f][1,2,4]triazin-4-amine

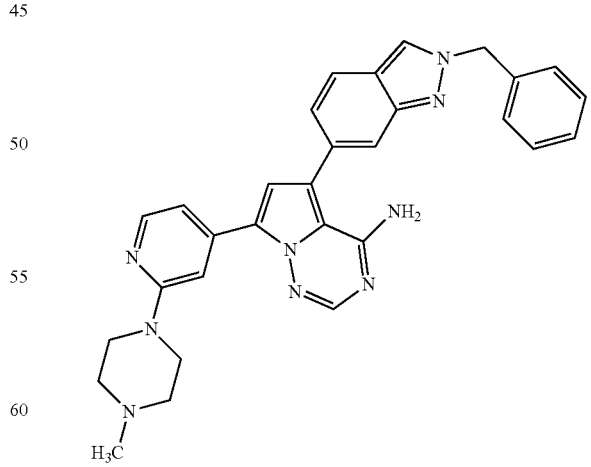

To a stirred solution of 5-bromo-7-[2-(4-methylpiperazin-1-yl)pyrrolo[2,1-f][1,2,4]triazin-4-amine (60 mg, 0.16 mmol), 2-benzyl-6-(4,4,5,5-tetramethyl-1,3,2-dioxaborolan-2-yl)-2H-indazole (103 mg, 0.31 mmol), and

[1,1'-bis(diphenylphosphino)-ferrocene]dichloro palladium (II) complex with dichloromethane (5.6 mg, 0.008 mmol) in degassed DME (1.2 mL) was added aqueous sodium carbonate solution (2 M, 232 □L). The reaction was heated (80° C.) for 17 h and then cooled to rt. The mixture was partitioned between ethyl acetate (25 mL) and H₂O (25 mL) and the layers were separated. The organic phase was washed with brine (25 mL), dried (Na₂SO₄), and concentrated. The crude material was purified by preparative HPLC using a gradient elution from 5% to 35% acetonitrile in water to obtain 17 mg (21%) of the desired product. ¹H NMR (300 MHz, DMSO-d₆) δ 8.81-8.79 (m, 1 H), 8.58 (s, 1 H), 8.28-8.21 (s, 1 H), 7.98-7.94 (m, 1 H), 7.87-7.81 (m, 1 H), 7.68 (s, 1H), 7.41-7.29 (m, 5 H), 7.24-7.19 (m, 1H), 7.12-7.08 (m, 1 H), 6.97-6.91 (m, 1 H), 5.67 (s, 2 H), 3.58-3.52 (m, 4 H), 2.44-2.37 (m, 4 H), 2.22 (s, 3 H); ES-MS m/z 516.24 [M+H]⁺, HPLC RT (min) 2.28.

Example 9

Preparation of 5-[3-(benzyloxy)phenyl]-7-(4-pyrrolidin-1-ylbutyl)pyrrolo[2,1-f][1,2,4]triazin-4-amine

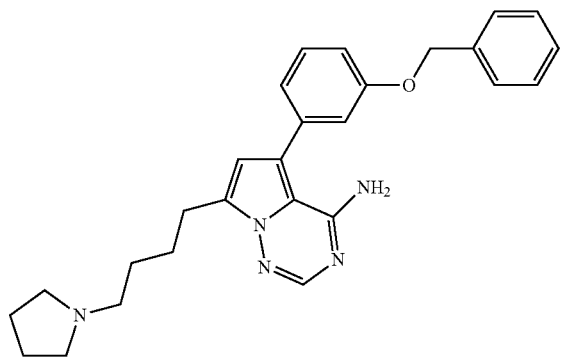 [SMILES: Nc1ncnn2c(CCCCN3CCCC3)cc(-c3cccc(OCc4ccccc4)c3)c12]

Step 1: Preparation of 4-(4-aminopyrrolo[2,1-f][1,2,4]triazin-7-yl)but-3-yn-1-ol

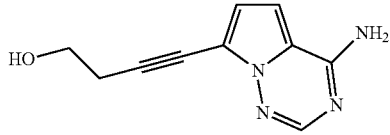 [SMILES: Nc1ncnn2c(C#CCCO)ccc12]

To a solution of 7-bromopyrrolo[2,1-f][1,2,4]triazin-4-amine (2.25 g, 10.6 mmol), tetrakis(triphenylphosphine)palladium(0) (610 mg, 0.53 mmol), and copper(I) iodide (500 mg, 2.64 mmol) in degassed pyrrolidine (45 mL) was added 3-butyn-1-ol (1.6 mL, 21.1 mmol), dropwise. The reaction was heated (50° C.) for 17 h. After cooling to rt, saturated aqueous ammonium chloride solution was added (50 mL) and the mixture was extracted first with ethyl acetate (4×50 mL) then with 3:1 chloroform/isopropanol (5×100 mL). The organics were separately dried (Na₂SO₄) and the solvent was evaporated. The combined crude oils were purified via flash chromatography on silica gel eluting with 100% ethyl acetate, followed by trituration with ethyl acetate to obtain 1.3 g (61%) of the desired product. ¹H NMR (300 MHz, DMSO-d₆) δ 7.85 (s, 1 H), 7.81 (br s, 2 H), 6.82 (d, 1 H), 6.75 (s, 1 H), 4.91 (t, 1 H), 3.58 (q, 2 H), 2.63 (t, 2 H); ES-MS m/z 203.2 [M+H]⁺, HPLC RT (min) 1.05.

Step 2: Preparation of 4-(4-aminopyrrolo[2,1-f][1,2,4]triazin-7-yl)butan-1-ol

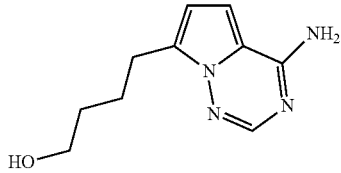 [SMILES: Nc1ncnn2c(CCCCO)ccc12]

To a dry flask purged with N₂ was added platinum(IV) oxide (440 mg, 1.93 mmol) followed by 4-(4-aminopyrrolo[2,1-f][1,2,4]triazin-7-yl)but-3-yn-1-ol (1.30 g, 6.43 mmol) as a solution in acetic acid (50 mL). The mixture was stirred under an H₂ atmosphere for 16 h. The mixture was filtered through a pad of Celite®, rinsing with acetic acid and ethanol. The solvent was evaporated under reduced pressure and the residue was taken up in EtOAc (100 mL). The organic was washed with saturated aqueous NaHCO₃ (1×100 mL) and the aqueous phase was back extracted with ethyl acetate (3×50 mL). The combined organics were washed with brine, dried (Na₂SO₄) and concentrated to dryness to afford the 1.2 g (91%) of the desired product. ¹H NMR (300 MHz, DMSO-d₆) δ 7.77 (s, 1 H), 7.52 (br s, 2 H), 6.78 (d, 1 H), 6.39 (d, 1 H), 4.36 (br s, 1 H), 3.39 (t, 2 H), 2.81 (t, 2H), 1.72-1.61 (m, 2 H), 1.50-1.41 (m, 2 H); ES-MS m/z 207.2 [M+H]⁺, HPLC RT (min) 1.11.

Step 3: Preparation of 4-(4-amino-5-bromopyrrolo[2,1-f][1,2,4]triazin-7-yl)butan-1-ol

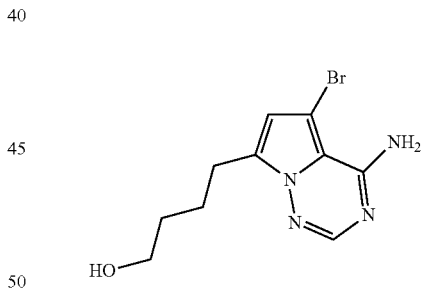

To a cooled (−20° C.) solution of 4-(4-aminopyrrolo[2,1-f][1,2,4]triazin-7-yl)butan-1-ol (1.20 g, 5.82 mmol) in tetrahydrofuran (30 mL) was added 1,3-dibromo-5,5-dimethylhydantoin (832 mg, 2.91 mmol) in 4 portions over 10 min. The mixture was allowed to stir (−20° C.) for 3 h. The reaction was quenched with the addition saturated aqueous Na₂SO₃ (30 mL) and was allowed to warm to rt. The mixture was extracted with ethyl acetate (3×25 mL). The combined organics were washed with brine, dried (Na₂SO₄) and concentrated. The crude material was purified by ISCO® chromatography using a gradient of 75% to 100% ethyl acetate in hexanes to afford 1.2 g (72%) of the desired product. ¹H NMR (300 MHz, DMSO-d₆) δ 7.81 (s, 1 H), 6.60 (s, 1 H), 4.37 (t, 1H), 3.39 (q, 2 H), 2.80 (t, 2 H), 1.70-1.60 (m, 2 H), 1.48-1.39 (m, 2 H); ES-MS m/z 285.1 [M+H]⁺, HPLC RT (min) 1.55.

Step 4: Preparation of 4-{4-amino-5-[3-benzyloxy) phenyl]pyrrolo[2,1-f][1,2,4]triazin-7-yl}butan-1-ol

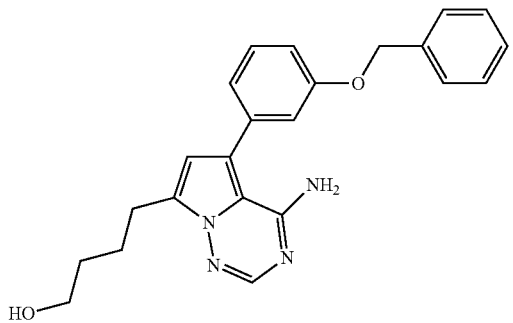

To a stirred solution of 4-(4-amino-5-bromopyrrolo[2,1-f][1,2,4]triazin-7-yl)butan-1-ol (500 mg, 1.75 mmol), 4-benzyloxybenzeneboronic add (1.20 g, 5.26 mmol), and tetrakis(triphenylphosphine)palladium(0) (203 mg, 0.18 mmol) in degassed DME (13 mL) was added aqueous Na$_2$CO$_3$ solution (2 M, 2.63 mL). The reaction was heated (80° C.) for 17 h and then cooled to rt. The mixture was partitioned between ethyl acetate (25 mL) and H$_2$O (25 mL). The layers were separated and the aqueous phase was back extracted with ethyl acetate. The combined organics were washed with brine, dried (Na$_2$SO$_4$), and concentrated. The crude material was purified by ISCO® chromatography eluting with 3:1 ethyl acetate/hexanes to afford 489 mg (72%) of the desired product, which contained trace impurities. $^1$H NMR (300 MHz, DMSO-d$_6$) δ7.87 (s, 1 H), 7.47-7.42 (m, 2 H), 7.41-7.28 (m, 4 H), 7.08-7.05 (m, 1 H), 7.03-6.97 (m, 2 H), 6.55 (s, 1 H), 5.14 (s, 2 H), 4.39 (t, 1H), 3.42 (q, 2 H), 2.87 (t, 2 H), 1.78-1.66 (m, 2 H), 1.56-1.44 (m, 2 H)); ES-MS m/z 389.2 [M+H]$^+$, HPLC RT (min) 2.59.

Step 5: Preparation of 5-[3-(benzyloxy)phenyl]-7-(4-bromobutyl)pyrrolo[2,1-f][1,2,4]triazin-4-amine

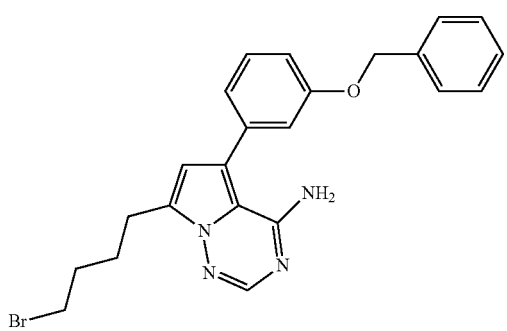 [SMILES: Nc1ncnn2c(CCCCBr)cc(-c3cccc(OCc4ccccc4)c3)c12]

To a cooled (0° C.) solution of 4{4-amino-5-[3-(benzyloxy)phenyl]pyrrolo[2,1-f][1,2,4]triazin-7-yl}butan-1-ol (489 mg, 1.26 mmol) and triphenylphosphine (495 mg, 1.89 mmol) in tetrahydrofuran (8 mL) was added carbon tetrabromide (501 mg, 1.51 mmol). The reaction was stirred (0° C.) for 2 h and was then warmed to rt and stirred an additional 17 h. Water (25 mL) was added and the mixture was extracted with ethyl acetate (2×20 mL). The combined organics were washed with brine, dried (Na$_2$SO$_4$) and evaporated. The crude material was purified via ISCO® chromatography using a gradient of 25 to 50% ethyl acetate in hexanes to afford 484 mg (85%) of the desired product. $^1$H NMR (300 MHz, DMSO-d$_6$) δ7.88 (s, 1 H), 7.46-7.42 (m, 2 H), 7.41-7.28 (m, 4 H), 7.08-7.05 (m, 1 H), 7.03-6.97 (m, 2 H), 6.57 (s, 1 H), 5.14 (s, 2 H), 3.57 (t, 2 H), 2.90 (t, 2 H), 1.92-1.77 (m, 4 H); ES-MS m/z 451.1 [M+H]$^+$, HPLC RT (min) 3.22.

Step 6: Preparation of the Title Compound

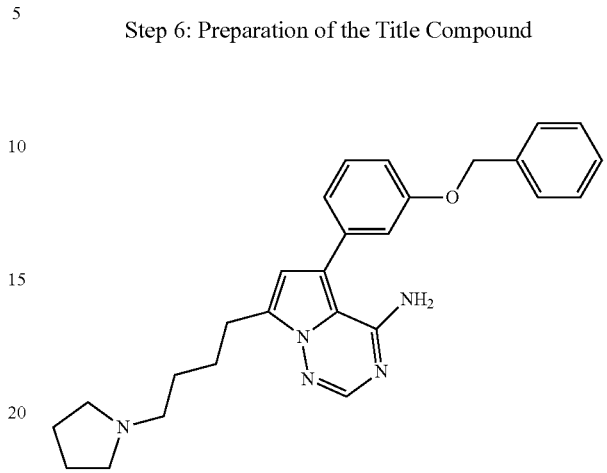

To a solution of 5-[3-(benzyloxy)phenyl]-7-(4-bromobutyl)pyrrolo[2,1-f][1,2,4]triazin-4-amine (129 mg, 0.29 mmol) in DMF (1.5 mL) was added pyrrolidine (26 μL, 0.31 mmol), triethylamine (120 μl, 0.86 mmol), and sodium iodide (0.4 mg, 0.003 mmol). The reaction was heated (55° C.) for 17 h and then cooled to rt. The mixture was partitioned between ethyl acetate (25 mL) and water (25 mL). The layers were separated and the organic was washed with water (2×20 mL), brine, dried (Na$_2$SO$_4$) and evaporated to afford 121 mg (96%) of the desired product. $^1$H NMR (300 MHz, DMSO-d$_6$) δ7.87 (s, 1 H), 7.46-7.41 (m, 2 H), 7.41-7.28 (m, 4 H), 7.08-7.04 (m, 1 H), 7.02-6.97 (m, 2 H), 6.55 (s, 1 H), 5.14 (s, 2H), 2.87 (t, 2 H), 2.42-2.33 (m, 6 H), 1.76-1.66 (m, 2 H), 1.67-1.60 (m, 4 H), 1.56-1.46 (m, 2 H); ES-MS m/z 442.2 [M+H]$^+$, HPLC RT (min) 2.30.

Example 10

5-[3-(benzyloxy)phenyl]-7-[4-(dimethylamino)butyl]pyrrolo-[2,1-f][1,2,4]triazin-4-amine

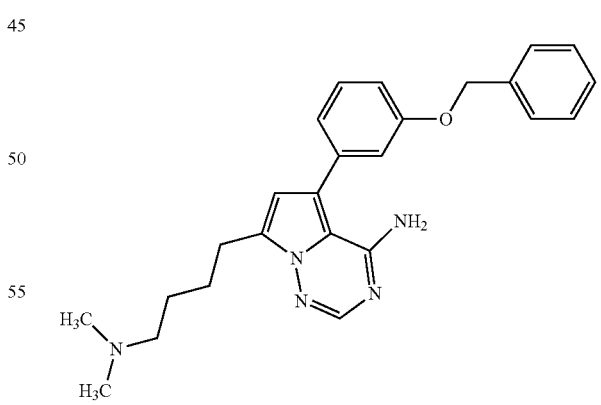

In a manner similar to the procedure described for the preparation of Example 9, using 5-[3-(benzyloxy)phenyl]-7-(4-bromobutyl)pyrrolo[2,1-f][1,2,4]triazin-4-amine as starting material, 30 mg (44%) of the desired product was isolated. $^1$H NMR (300 MHz, DMSO-d$_6$) δ 7.87 (s, 1 H), 7.46-7.41 (m, 2 H), 7.41-7.27 (m, 4 H), 7.08-7.03 (m, 1 H), 7.03-6.95 (m, 2 H), 6.54 (s, 1 H), 5.14 (s, 2 H), 2.87 (t, 2 H), 2.20 (t, 2 H), 2.09

(s, 6 H), 1.74-1.64 (m, 2 H), 1.53-1.41 (m, 2 H); ES-MS m/z 416.2 [M+H]+, HPLC RT (min) 2.23.

Example 11

Preparation of 5-[3-(benzyloxy)phenyl]-7-[4-(diethylamino)-butyl]-pyrrolo[2,1-f][1,2,4]triazin-4-amine

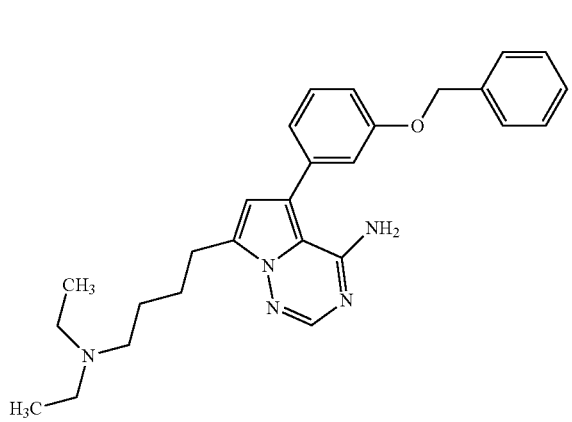 [SMILES: CCN(CC)CCCCc1cc(-c2cccc(OCc3ccccc3)c2)c2c(N)ncnn12]

In a manner similar to the procedure described for the preparation of Example 9, using 5-[3-(benzyloxy)phenyl]-7-(4-bromobutyl)pyrrolo[2,1-f][1,2,4]triazin-4-amine as starting material, 31 mg (42%) of the desired product was isolated. $^1$H NMR (300 MHz, DMSO-$d_6$) δ 7.87 (s, 1 H), 7.47-7.41 (m, 2 H), 7.41-7.28 (m, 4 H), 7.07-7.04 (m, 1 H), 7.03-6.96 (m, 2 H), 6.54 (s, 1 H), 5.14 (s, 2 H), 2.87 (t, 2 H), 2.44-2.34 (m, 6 H), 1.74-1.63 (m, 2 H), 1.50-1.39 (m, 2 H), 0.92 (t, 6 H); ES-MS m/z 444.2 [M+H]+, HPLC RT (min) 2.27.

Example 12

Preparation of 7-(4-azetidin-1-ylbutyl)-5-[3-(benzyloxy)phenyl]pyrrolo[2,1-f][1,2,4]triazin-4-amine

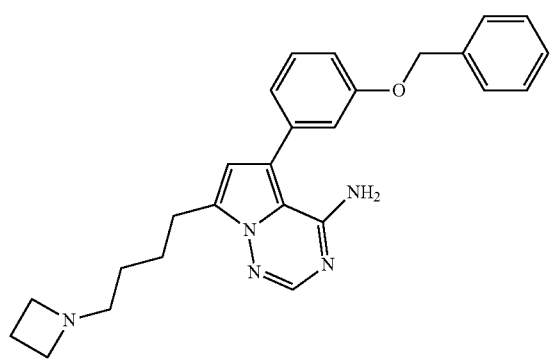 [SMILES: Nc1ncnn2c(CCCCN3CCC3)cc(-c3cccc(OCc4ccccc4)c3)c12]

In a manner similar to the procedure described for the preparation of Example 9, using 5-[3-(benzyloxy)phenyl]-7-(4-bromobutyl)pyrrolo[2,1-f][1,2,4]triazin-4-amine as starting material, 40 mg (56%) of the desired product was isolated. $^1$H NMR (300 MHz, DMSO-$d_6$) δ 7.87 (s, 1 H), 7.47-7.41 (m, 2 H), 7.41-7.27 (m, 4 H), 7.08-7.04 (m, 1 H), 7.03-6.96 (m, 2 H), 6.54 (s, 1 H), 5.14 (s, 2 H), 3.01 (t, 4 H), 2.84 (t, 2 H), 2.31 (t, 2 H), 1.95-1.85 (m, 2 H), 1.73-1.61 (m, 2 H), 1.36-1.26 (m, 2 H); ES-MS m/z 428.2 [M+H]+, HPLC RT (min) 2.27.

Example 13

Preparation of 5-[3-(benzyloxy)phenyl]-7-{4-[(2R)-2-(methoxymethyl)pyrrolidin-1-l]butyl}pyrrolo[2,1-f][1,2,4]triazin-4-amine

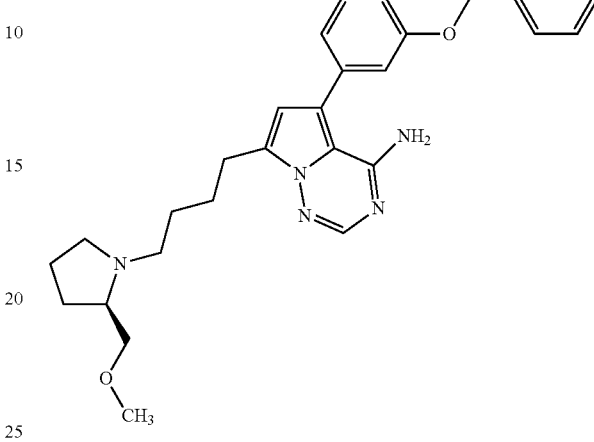

In a manner similar to the procedure described for the preparation of Example 9, using 5-[3-(benzyloxy)phenyl]-7-(4-bromobutyl)pyrrolo[2,1-f][1,2,4]triazin-4-amine as starting material, 64 mg (79%) of the desired product was isolated. $^1$H NMR (300 MHz, DMSO-$d_6$) δ 7.87 (s, 1 H), 7.48-7.42 (m, 2 H), 7.41-7.27 (m, 4 H), 7.08-7.04 (m, 1 H), 7.03-6.96 (m, 2 H), 6.54 (s, 1 H), 5.14 (s, 2 H), 3.36-3.27 (m, 4 H), 3.17-3.06 (m, 1 H), 3.01-2.94 (m, 1 H), 2.91-2.84 (t, 2 H), 2.84-2.74 (m, 1 H), 2.28-2.18 (m, 1 H), 2.13-2.00 (m, 1 H), 1.85-1.55 (m, 5 H), 1.55-1.38 (m, 4 H); ES-MS m/z 486.2 [M+H]+, HPLC RT (min) 2.35.

Example 14

Preparation of 5-[3-(benzyloxy)phenyl]-7-(4-piperidin-1-ylbutyl)pyrrolo[2,1-f][1,2,4]triazin-4-amine

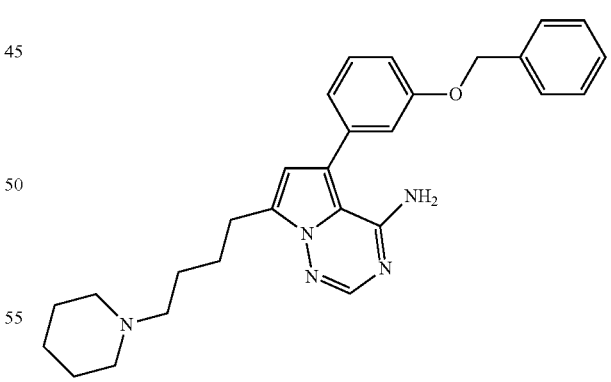

To a cooled (0° C.) solution of 4-{4-amino-5-[3-(benzyloxy)phenyl]pyrrolo[2,1-f][1,2,4]triazin-7-yl}butan-1-ol (80 mg, 0.21 mmol) in dichloromethane (1 mL) was added triethylamine (32 μL, 0.23 mmol) and methanesulfonyl chloride (17 μL, 0.22 mmol). The reaction was stirred (0° C.) for 4 h and then warmed to rt. The mixture was quenched with the addition of ice water (1 mL). The layers were separated and the organic layer was dried (Na$_2$SO$_4$) and evaporated. The residue was dissolved in DMF (1 mL) and potassium carbonate (85 mg, 0.62 mmol) and piperidine (18 µL, 0.22 mol) were added to the mixture. The reaction was stirred (60° C.) for 17 h and then cooled to rt. The mixture was partitioned between ethyl acetate (15 mL) and water (15 mL). The layers were separated and the aqueous was further extracted with ethyl acetate (2×10 mL). The combined organics were dried (Na$_2$SO$_4$) and evaporated. The residue was purified by preparative HPLC using a gradient elution from 15% to 45% acetonitrile in water to obtain 4 mg (5%) of the desired product. $^1$H NMR (300 MHz, CD$_3$CN) δ 7.86 (s, 1 H), 7.51-7.46 (m, 2 H), 7.45-7.32 (m, 4 H), 7.12-7.09 (m, 1 H), 7.09-7.06 (m, 1 H), 7.04-7.00 (s, 1 H), 6.56 (s, 1 H), 5.17 (s, 2 H), 2.96 (t, 2 H), 2.47-2.27 (m, 6 H), 1.83-1.73 (m, 2 H), 1.63-1.1.51 (m, 6 H), 1.48-1.40 (m, 2 H); ES-MS m/z 456.3 [M+H]$^+$, HPLC RT (min) 2.29.

Example 15

Preparation of 5-[3-(benzyloxy)phenyl]-7-[4-(4-methyl piperazin-1-yl)butyl]pyrrolo[2,1-f][1,2,4]triazin-4-amine

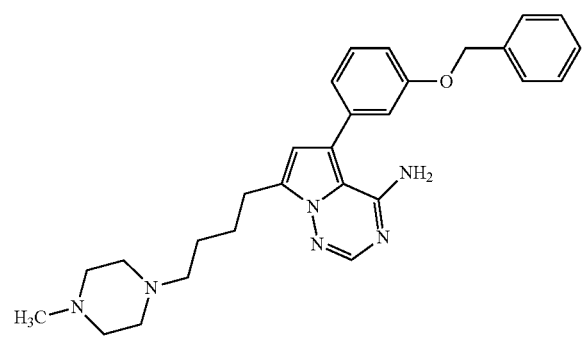 [SMILES: CN1CCN(CCCCc2cc(-c3cccc(OCc4ccccc4)c3)c3c(N)ncnn23)CC1]

In a manner similar to the procedure described for the preparation of Example 14, 4-{4-amino-5-[3-(benzyloxy)phenyl]pyrrolo[2,1-f][1,2,4]triazin-7-yl}butan-1-ol as starting material, 11 mg (11%) of the desired product was isolated. $^1$H NMR (300 MHz, CD$_3$CN) δ 7.86 (s, 1 H), 7.51-7.45 (m, 2 H), 7.45-7.32 (m, 4 H), 7.12-7.05 (m, 1 H), 7.05-6.99 (m, 2H), 6.55 (s, 1 H), 5.17 (s, 2 H), 2.95 (t, 2 H), 2.48-2.29 (m, 11 H), 2.01-1.94 (m, 2 H), 1.83-1.73 (m, 2 H), 1.61-1.51 (m, 2 H); ES-MS m/z 471.3 [M+H]$^+$, HPLC RT (min) 2.04.

Example 16

Preparation of 5-{3-[(3,5-dimethoxybenzyl)oxy]phenyl}-7-(4-pyrrolidin-1-ylbutyl)pyrrolo[2,1-f][1,2,4]triazin-4-amine

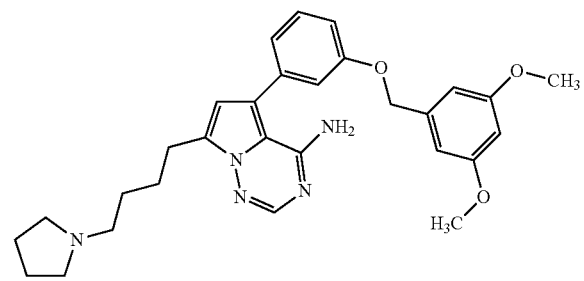 [SMILES: COc1cc(COc2cccc(-c3cc(CCCCN4CCCC4)n4ncnc(N)c34)c2)cc(OC)c1]

Step 1: Preparation of 5-bromo-7-(4-bromobutyl)pyrrolo[2,1-f][1,2,4]triazin-4-amine

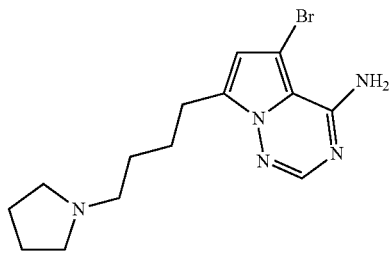 [SMILES: Nc1ncnn2c(CCCCN3CCCC3)cc(Br)c12]

To a cooled (0° C.) solution of 4-(4-amino-5-bromopyrrolo[2,1-f][1,2,4]triazin-7-yl)butan-1-ol (600 mg, 2.10 mmol) and triphenylphosphine (828 mg, 3.16 mmol) in tetrahydrofuran (15 mL) was added carbon tetrabromide (837 mg, 2.53 mmol). The reaction was stirred (0° C.) for 90 min and then was warmed to rt and stirred an additional 1 h. Water (25 mL) was added and the mixture was extracted with ethyl acetate (2×25 mL). The combined organics were dried (Na$_2$SO$_4$) and evaporated. The crude material was purified via ISCO® chromatography using a gradient of 25 to 50% ethyl acetate in hexanes to afford 597 mg (82%) of the desired product. $^1$H NMR (300 MHz, DMSO-d$_6$) δ 7.82 (s, 1 H), 6.62 (s, 1 H), 3.54 (t, 2 H), 2.84 (t, 2 H), 1.86-1.70 (m, 4 H); ES-MS m/z 347.2 [M+H]$^+$, HPLC RT (min) 2.58.

Step 2: Preparation of 5-bromo-7-(4-pyrrolidin-1-ylbutyl)pyrrolo[2,1-f][1,2,4]triazin-4-amine To a solution of 5-bromo-7-(4-bromobutyl)pyrrolo[2,1-f][1,2,4]triazin-4-amine (597 mg, 1.72 mmol) in DMF (10 mL) was added pyrrolidine (158 µL, 1.89 mmol), triethylamine (717 µL, 5.15 mmol), and sodium iodide (26 mg, 0.17 mmol). The reaction was heated (55° C.) for 22 h and then cooled to rt. The mixture was partitioned between ethyl acetate (50 mL) and water (50 mL). The layers were separated and the aqueous phase was further extracted with ethyl acetate (3×50 mL). The combined organics were washed with water (1×50 mL), brine, dried (Na$_2$SO$_4$) and evaporated to afford 467 mg (80%) of the desired product. $^1$H NMR (300 MHz, DMSO-d$_6$) δ 7.81 (s, 1 H), 6.60 (s, 1 H), 2.81 (t, 2 H), 2.40-2.31 (m, 6 H), 1.70-1.59 (m, 6 H), 1.50-1.40 (m, 2 H); ES-MS m/z 338.1 [M+H]$^+$, HPLC RT (min) 1.12.

175

Step 3: Preparation of the Title Compound

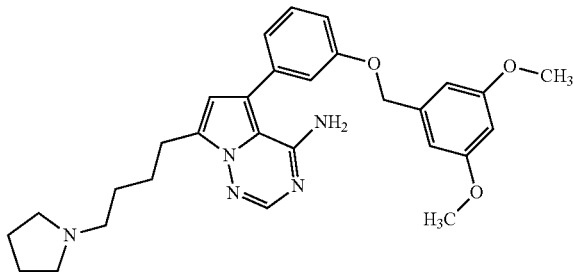 [SMILES: COc1cc(COc2cccc(-c3cc(CCCCN4CCCC4)n4ncnc(N)c34)c2)cc(OC)c1]

To a stirred solution of 5-bromo-7-(4-pyrrolidin-1-ylbutyl) pyrrolo[2,1-f][1,2,4]triazin-4-amine (70 mg, 0.21 mmol), 3-(3,5-dimethoxybenzyloxy)phenyl boronic acid (179 mg, 0.62 mmol), and tetrakis(triphenylphosphine)palladium(0) (23 mg, 0.021 mmol) in degassed DME (1.5 mL) was added aqueous $Na_2CO_3$ solution (2 M, 310 µL). The reaction was heated (80° C.) for 17 h and then cooled to rt. The mixture was partitioned between ethyl acetate (25 mL) and water (25 mL). The layers were separated and the organic phase was washed dried ($Na_2SO_4$) and concentrated to dryness. The residue was purified by preparative HPLC using a gradient elution from 20% to 70% acetonitrile followed by preparative TLC eluting with 9:1 ethyl acetate/methanol (with 1% concentrated ammonium hydroxide) to obtain 29 mg (28%) of the desired product. $^1$H NMR (300 MHz, DMSO-$d_6$) δ 7.88 (s, 1 H), 7.36 (t, 1 H), 7.07-7.04 (m, 1 H), 7.03-6.96 (m, 2 H), 6.60 (d, 2 H), 6.55 (s, 1 H), 6.43 (t, 1 H), 5.07 (s, 2 H), 3.73 (s, s H), 2.88 (t, 2 h), 2.56-2.48 (m, 6 H), 1.78-1.65 (m, 6 H), 1.60-1.49 (m, 2 H); ES-MS m/z 502.2 [M+H]$^+$, HPLC RT (min) 2.27.

Example 17

Preparation of 5-(2-benzyl-2H-indazol-6-yl)-7-(4-pyrrolidin-1-ylbutyl)pyrrolo[2,1-f][1,2,4]triazin-4-amine

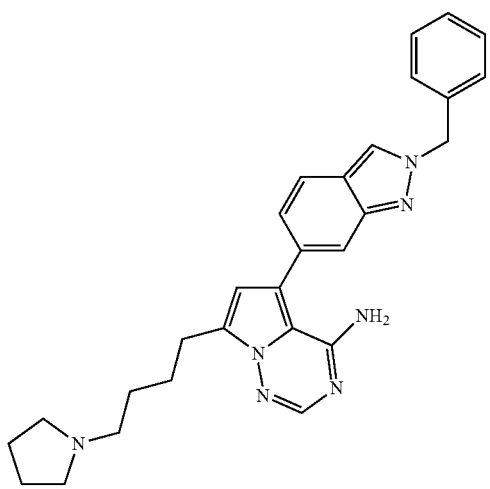 [SMILES: Nc1ncnn2c(CCCCN3CCCC3)cc(-c3ccc4cn(Cc5ccccc5)nc4c3)c12]

176

Step 1: Preparation of 7-((1E)-4-{[tert-butyl(dimethyl)silyl]oxy}but-1-en-1-yl)pyrrolo[2,1-f][1,2,4]triazin-4-amine

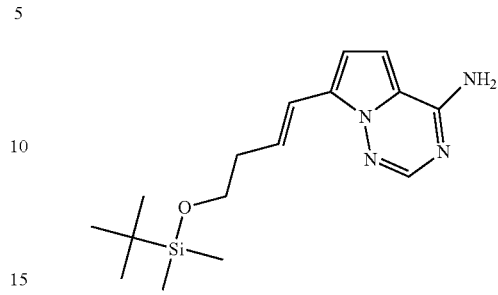

To a stirred suspension of 7-bromopyrrolo[2,1-f][1,2,4]triazin-4-amine (5.0 g, 23.5 mmol), trans-1-buten-1-yl-(4-tert-butylsimethylsiloxy-4',4',5',5'-tetramethyl-(1',3',2')-dioxaborolane (14.6 g, 46.9 mmol), and [1,1'-bis(diphenylphosphino)-ferrocene]dichloro palladium(II) complex with dichloromethane (1.72 g, 2.35 mmol) in degassed DME (175 mL) was added aqueous $Na_2CO_3$ solution (2 M, 35.2 mL). The reaction was heated (80° C.) for 17 h and then cooled to rt. The mixture was partitioned between ethyl acetate (200 mL) and water (200 mL) and the layers were separated. The organic phase was further washed with water (200 mL), brine, dried ($Na_2SO_4$), and concentrated. The crude material was purified by ISCO® chromatography using a gradient of 50 to 75% ethyl acetate in hexanes to afford 5.35 g (72%) of the desired product as a pale yellow solid. $^1$H NMR (300 MHz, DMSO-$d_6$) δ 7.76 (s, 1 H), 7.59 (br s, 2 H), 6.81-6.78 (m, 1 H), 6.76-6.67 (m, 2 H), 6.38-6.29 (m, 1 H), 3.65 (t, 2 H), 2.35 (q, 2 H), 0.82 (s, 9 H) 0.00 (s, 6 H); ES-MS m/z 319.3 [M+H]$^+$, HPLC RT (min) 3.01.

Step 2: Preparation of 7-(4-{[tert-butyl(dimethyl)silyl]oxy}butyl)pyrrolo[2,1-f][1,2,4]triazin-4-amine

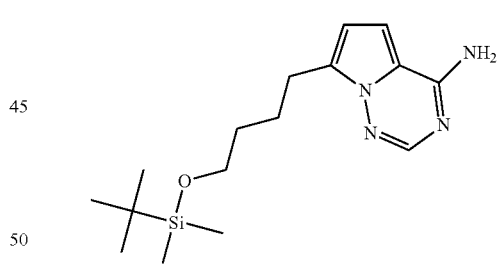

To a dry flask purged with $N_2$ was added platinum(IV) oxide (635 mg, 2.80 mmol) followed by 7-((1E)-4-{[tert-butyl(dimethyl)silyl]oxy}but-1-en-1-yl)pyrrolo[2,1-f][1,2,4]triazin-4-amine (6.35 g, 19.9 mmol) as a solution in acetic acid (100 mL). The mixture was stirred under an $H_2$ atmosphere for 16 h. The mixture was filtered through a pad of Celite® rinsing with acetic acid. The solvent was evaporated under reduced pressure and the residue was made basic with saturated aqueous $NaHCO_3$ solution. The resulting solid was collected by filtration and dried in vacuo to afford 5.6 g (88%) of the desired product. $^1$H NMR (300 MHz, DMSO-$d_6$) δ 7.76 (s, 1 H), 7.52 (br s, 2 H), 6.77 (d, 1 H), 6.38 (d, 2 H), 3.57 (t, 2 H), 2.82 (t, 2 H), 1.74-1.62 (m, 2 H), 1.54-1.43 (m, 2 H), 0.83 (s, 9 H), 0.00 (s, 6 H); ES-MS m/z 321.2 [M+H]$^+$, HPLC RT (min) 3.11.

Step 3: Preparation of 5-bromo-7-(4-{[tert-butyl(dimethyl)silyl]oxy}butyl)pyrrolo[2,1-f][1,2,4]triazin-4-amine

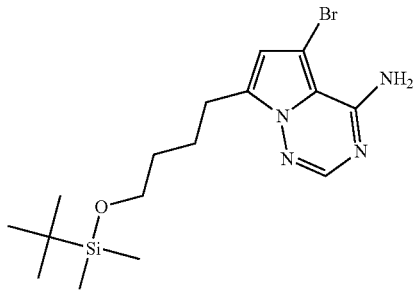 [SMILES: CC(C)(C)[Si](C)(C)OCCCCc1cc(Br)c2c(N)ncnn12]

To a cooled (−20° C.) solution of 7-(4-{[tert-butyl(dimethyl)silyl]oxy}butyl)pyrrolo[2,1-f][1,2,4]triazin-4-amine (5.60 g, 17.5 mmol) in tetrahydrofuran (85 mL) was added 1,3, dibromo-5,5-dimethylhydantoin (2.50 g, 8.74 mmol) in four portions over 15 min. The mixture was allowed to stir (−20° C.) for 2 h. The reaction was quenched with the addition saturated aqueous $Na_2SO_3$ solution and was allowed to warm to rt. The mixture was extracted with ethyl acetate (3×75 mL). The combined organics were washed with brine, dried ($Na_2SO_4$) and concentrated to dryness. The crude material was purified by ISCO® chromatography using a gradient of 50% to 75% ethyl acetate in hexanes to afford 6.29 g (90%) of the desired product. $^1$H NMR (300 MHz, DMSO-$d_6$) δ 7.80 (s, 1 H), 6.58 (s, 1 H), 3.56 (t, 2 H), 2.81 (t, 2 H), 1.72-1.61 (m, 2 H), 1.51-1.42 (m, 2 H), 0.83 (s, 9 H), 0.00 (s, 6 H); ES-MS m/z 399.2 HPLC RT (min) 3.72.

Step 4: Preparation of 5-(2-benzyl-2H-indazol-6-yl)-7-(4-{[tert-butyl(dimethyl)silyl]oxy}butyl)pyrrolo[2,1-f][1,2,4]triazin-4-amine

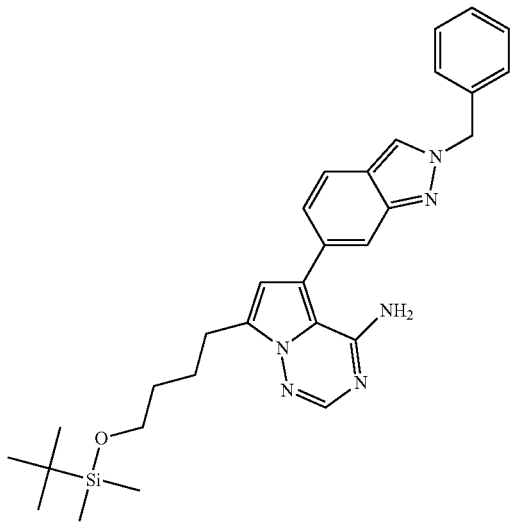 [SMILES: CC(C)(C)[Si](C)(C)OCCCCc1cc(-c2ccc3cn(Cc4ccccc4)nc3c2)c2c(N)ncnn12]

To a stirred suspension of 5-bromo-7-(4-{[tert-butyl(dimethyl)silyl]oxy}butyl)pyrrolo[2,1-f][1,2,4]triazin-4-amine (3.00 g, 7.51 mmol), 2-benzyl-6-(4,4,5,5-tetramethyl-1,3,2-dioxaborolan-2-yl)-2H-indazole (3.77 g, 11.3 mmol), and [1,1'-bis(diphenylphosphino)-ferrocene]dichloro palladium (II) dichloromethane adduct (550 mg, 0.75 mmol) in degassed DME (50 mL) was added aqueous $Na_2CO_3$ solution (2 M, 11.3 mL). The reaction was heated (80° C.) for 17 h and then cooled to rt. The mixture was partitioned between ethyl acetate (75 mL) and water (75 mL) and the layers were separated. The aqueous phase was further extracted with ethyl acetate (2×75 mL). The combined organics were filtered to remove a fine precipitate, dried ($Na_2SO_4$), and concentrated. The crude material was purified by ISCO® chromatography using a gradient of 25 to 75% ethyl acetate in hexanes to afford 1.9 g (48%) of the desired product. $^1$H NMR (300 MHz, DMSO-$d_6$) δ 8.51 (s, 1 H), 7.85 (s, 1 H), 7.77 (dd, 1 H), 7.57-7.54 (m, 1 H), 7.35-7.25 (m, 5 H), 7.11 (dd, 1 H), 6.55 (s, 1 H), 5.63 (s, 2 H), 3.59 (t, 2 H), 2.88 (t, 2 H), 1.79-1.68 (m, 2 H), 1.58-1.48 (m, 2 H), 0.83 (s, 9 H), 0.00 (s, 6 H); ES-MS m/z 527.3 [M+H]$^+$, HPLC RT (min) 3.62.

Step 5: Preparation of 4-[4-amino-5-(2-benzyl-2H-indazol-6-yl)pyrrolo[2,1-f][1,2,4]triazin-7-yl]butan-1-ol

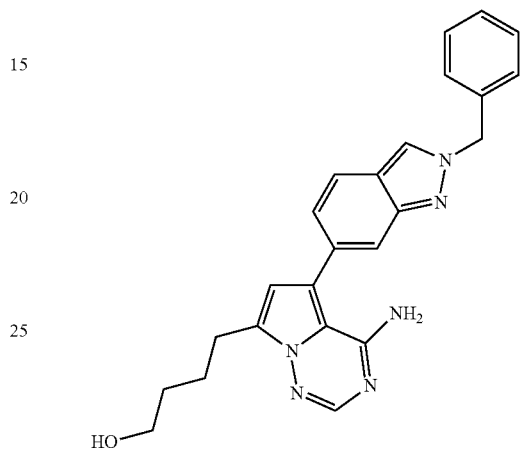

To a solution of 5-(2-benzyl-2H-indazol-6-yl)-7-(4-{[tert-butyl(dimethyl)silyl]oxy}butyl)pyrrolo[2,1-f][1,2,4]triazin-4-amine (3.00 g, 5.70 mmol) in 95% aqueous ethanol (30 mL) was added concentrated hydrochloric acid (500 μL). The reaction was stirred (rt) for 1 h. The mixture was basified (pH 8) with the addition of saturated aqueous $NaHCO_3$ solution and was evaporated to remove volatiles. The aqueous mixture was extracted with ethyl acetate (3×25 mL) and the combined organics were washed with brine, dried ($Na_2SO_4$) and concentrated to afford 2.54 g (97%) of the desired product, which contained minor impurities. $^1$H NMR (300 MHz, DMSO-$d_6$) δ 8.57 (s, 1 H), 7.91 (s, 1 H), 7.82 (d, 1 H), 7.61 (s, 1 H), 7.40-7.29 (m, 5 H), 7.17 (dd, 1 H), 6.62 (s, 1 H), 5.68 (s, 2 H), 4.43 (t, 1 H), 3.46 (q, 2 H), 2.92 (t, 2 H), 1.82-1.71 (m, 2 H), 1.60-1.50 (m, 2 H); ES-MS m/z 413.4 [M+H]$^+$, HPLC RT (min) 2.50.

Step 6: Preparation of 5-(2-benzyl-2H-indazol-6-yl)-7-(4-bromobutyl)pyrrolo[2,1-f][1,2,4]triazin-4-amine

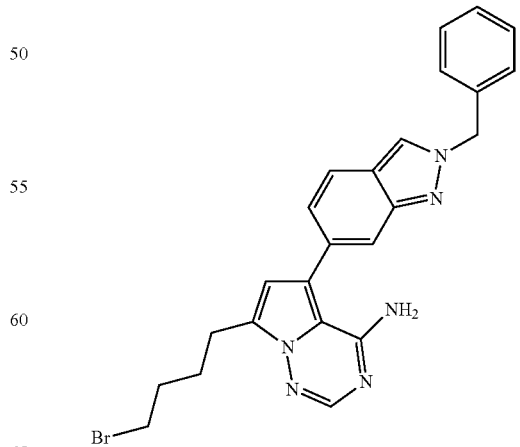

To a cooled (0° C.) solution of 4-(4-amino-5-(2-benzyl-2H-indazol-6-yl)pyrrolo[2,1-f][1,2,4]triazin-7-yl]butan-1-ol (2.54 g, 6.16 mmol) and triphenylphosphine (2.42 g, 9.24 mmol) in tetrahydrofuran (30 mL) was added carbon tetrabromide (2.45 g, 7.39 mmol).

The reaction was stirred (0° C.) for 2 h and then was warmed to rt and stirred an additional 17 h. The mixture was partitioned between water (50 mL) and ethyl acetate (50 mL). The layers were separated and the aqueous was further extracted with ethyl acetate (2×50 mL). The combined organics were washed with brine, dried ($Na_2SO_4$), and evaporated. The crude material was purified via ISCO® chromatography using a gradient of 50 to 75% ethyl acetate in hexanes followed by trituration with ethyl acetate to afford 2.0 g (68%) of the desired product. $^1$H NMR (300 MHz, DMSO-$d_5$) δ 8.52 (s, 1 H), 7.88 (s, 1 H), 7.78 (d, 1 H), 7.57 (s, 1 H), 7.37-7.26 (m, 5 H), 7.13 (dd, 1 H), 6.60 (s, 1 H), 5.64 (s, 2 H), 3.57 (t, 2 H), 2.92 (t, 2 H), 1.95-1.78 (m, 4 H).

Step 7: Preparation of the Title Compound

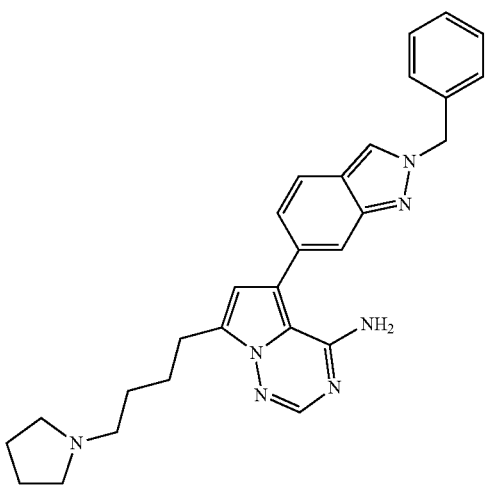 [SMILES: Nc1ncnn2c(CCCCN3CCCC3)cc(-c3ccc4cn(Cc5ccccc5)nc4c3)c12]

To a solution of 5-(2-benzyl-2H-indazol-6-yl)-7-(4-bromobutyl)pyrrolo[2,1-f][1,2,4]triazin-4-amine (440 mg, 0.93 mmol) in DMF (5.0 mL) was added pyrrolidine (155 μL, 1.86 mmol), triethylamine (387 μl, 2.78 mmol), and sodium iodide (1.4 mg, 0.009 mmol). The reaction was heated (55° C.) for 17 h and then cooled to rt. The mixture was partitioned between ethyl acetate (25 mL) and water (25 mL). The layers were separated and the organic was washed with water (2×20 mL), brine, dried ($Na_2SO_4$) and evaporated to afford 360 mg (84%) of the desired product. $^1$H NMR (300 MHz, DMSO-$d_6$) δ 8.53 (s, 1 H), 7.87 (s, 1 H), 7.78 (d, 1 H), 7.56 (s, 1 H), 7.36-7.26 (m, 5 H), 7.13 (dd, 1 H), 6.57 (s, 1 H), 5.64 (s, 2 H), 2.88 (t, 2 H), 2.42-2.33 (m, 6 H), 1.78-1.66 (m, 2 H), 1.67-1.60 (m, 4 H), 1.57-1.46 (m, 2H); ES-MS m/z 466.3 [M+H]$^+$, HPLC RT (min) 2.20.

Example 18

Preparation of 1-{4-[4-amino-5-(2-benzyl-2H-indazol-6-yl)pyrrolo[2,1-f][1,2,4]triazin-7-yl]butyl}pyrrolidin-3-ol

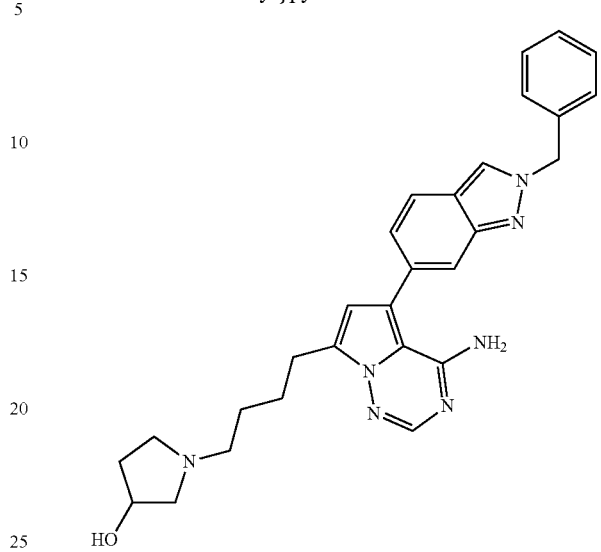

In a manner similar to the procedure described for the preparation of Example 17, using 5-(2-benzyl-2H-indazol-6-yl)-7-(4-bromobutyl)pyrrolo[2,1-f][1,2,4]triazin-4-amine as starting material, 22 mg (44%) of the desired product was isolated. $^1$H NMR (300 MHz, DMSO-$d_6$) δ 8.53 (s, 1 H), 7.87 (s, 1 H), 7.78 (d, 1 H), 7.56 (s, 1 H), 7.36-7.24 (m, 5 H), 7.13 (dd, 1 H), 6.57 (s, 1 H), 5.64 (s, 2 H), 4.65 (d, 1 H), 4.17-4.09 (m, 1 H), 2.88 (t, 2 H), 2.68-2.61 (m, 1 H), 2.43-2.32 (m, 3 H), 2.30-2.21 (m, 1 H), 2.00-1.88 (m, 1 H), 1.77-1.66 (m, 2 H), 1.55-1.43 (m, 2 H); ES-MS m/z 428.27 [M+H]$^+$, HPLC RT (min) 2.05.

Example 19

Preparation of 5-(2-benzyl-2H-indazol-6-yl)-7-[4-3,3-difluoropyrrolidin-1-yl)butyl]pyrrolo[2,1-f][1,2,4]triazin-4-amine

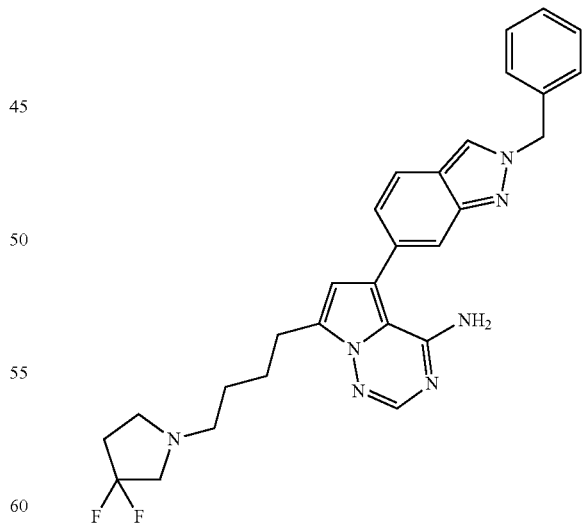

In a manner similar to the procedure described for the preparation of Example 17, using 5-(2-benzyl-2H-Indazol-6-yl)-7-(4-bromobutyl)pyrrolo[2,1-f][1,2,4]triazin-4-amine as starting material, 27 mg (26%) of the desired product was isolated. $^1$H NMR (300 MHz, DMSO-$d_6$) δ 8.51 (s, 1 H); 7.86 (s, 1 H), 7.77 (d, 1 H), 7.56 (s, 1 H), 7.38-7.24 (m, 5 H), 7.12 (dd, 1 H), 6.57 (s, 1 H), 5.63 (s, 2 H), 2.88 (t, 2 H), 2.81 (t, 2

H), 2.62 (t, 2 H), 2.42 (t, 2 H), 2.25-2.11 (m, 2 H), 1.76-1.65 (m, 2 H), 1.55-1.44 (m, 2 H); ES-MS m/z 502.30 [M+H]+, HPLC RT (min) 2.66.

Example 20

Preparation of 5-(2-benzyl-2H-Indazol-6-yl)-7-(4-morpholin-4-ylbutyl)pyrrolo[2,1-f][1,2,4]triazin-4-amine

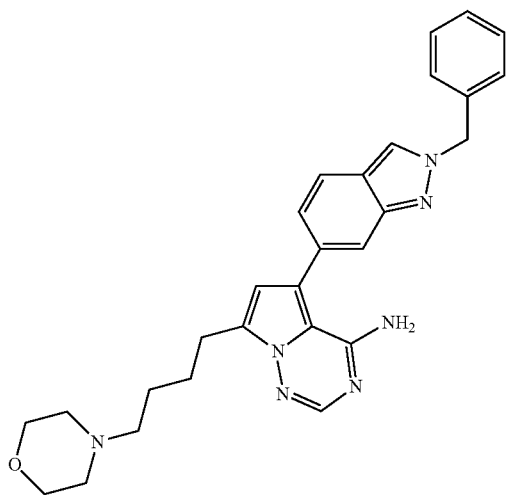 [SMILES: Nc1ncnn2c(CCCCN3CCOCC3)cc(-c3ccc4cn(Cc5ccccc5)nc4c3)c12]

In a manner similar to the procedure described for the preparation of Example 17, using 5-(2-benzyl-2H-indazol-6-yl)-7-(4-bromobutyl)pyrrolo[2,1-f]]1,2,4]triazin-4-amine as starting material, 17 mg (17%) of the desired product was isolated. $^1$H NMR (300 MHz, DMSO-d$_6$) δ 8.52 (s, 1 H), 7.87 (s, 1 H), 7.78 (d, 1 H), 7.56 (s, 1 H), 7.37-7.23 (m, 5 H), 7.12 (dd, 1 H), 6.58 (s, 1 H), 5.64 (s, 2 H), 3.53 (t, 4 H), 2.89 (t, 2 H), 2.37-2.21 (m, 6 H), 1.78-1.66 (m, 2 H), 1.57-1.45 (m, 2 H); ES-MS m/z 482.25 [M+H]+, HPLC RT (min) 2.15.

Example 21

Preparation of 5-(2-benzyl-2H-indazol-6-yl)-7-[4-(4-methylpiperazin-1-yl)butyl]pyrrolo[2,1-f][1,2,4]triazin-4-amine

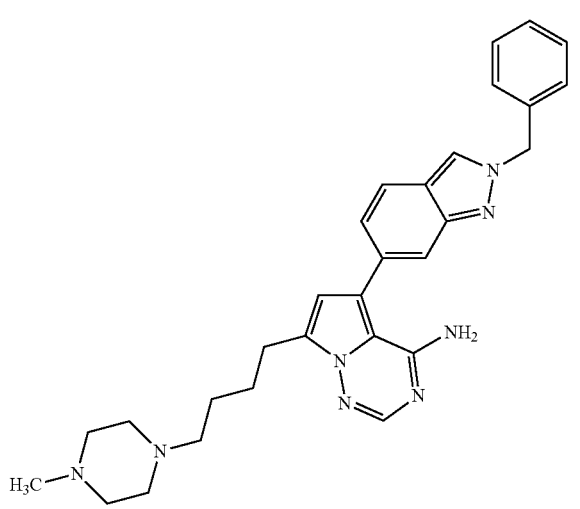 [SMILES: CN1CCN(CCCCc2cc(-c3ccc4cn(Cc5ccccc5)nc4c3)c3c(N)ncnn23)CC1]

In a manner similar to the procedure described for the preparation of Example 17, using 5-(2-benzyl-2H-indazol-6-yl)-7-(4-bromobutyl)pyrrolo[2,1-f][1,2,4]triazin-4-amine as starting material, 68 mg (66%) of the desired product was isolated. $^1$H NMR (300 MHz, DMSO-d$_6$) δ 8.52 (s, 1 H), 7.87 (s, 1 H), 7.78 (d, 1 H), 7.56 (s, 1 H), 7.36-7.24 (m, 5 H), 7.13 (dd, 1 H), 6.57 (s, 1 H), 5.64 (s, 2 H), 2.88 (t, 2 H), 2.45-2.20 (m, 10 H), 2.11 (s, 3 H), 1.75-1.64 (m, 2 H), 1.54-1.43 (m, 2 H); ES-MS m/z 495.27 [M+H]+, HPLC RT (min) 1.90.

Example 22

Preparation of 5-[4-(2H-indazol-2-ylmethyl)phenyl]-7-(4-pyrrolidin-1-ylbutyl)pyrrolo[2,1-f][1,2,4]triazin-4-amine

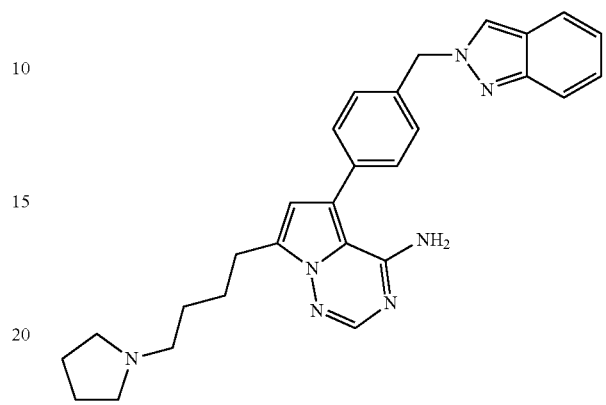

To a stirred solution of 5-bromo-7-(4-pyrrolidin-1-ylbutyl)pyrrolo[2,1-1,2,4]triazin-4-amine (100 mg, 0.30 mmol), 2-[4-(4,4,5,5-tetramethyl-1,3,2-dioxaborolan-2-yl)benzyl]-2H-indazole (153 mg, 0.46 mmol), and [1,1'-bis(diphenylphosphino)-ferrocene]dichloro palladium(II) dichloromethane adduct (34 mg, 0.030 mmol) in degassed DME (2.3 mL) was added aqueous Na$_2$CO$_3$ solution (2 M, 443 μL). The reaction was heated (80° C.) for 17 h and then cooled to rt. The mixture was partitioned between ethyl acetate (25 mL) and water (25 mL). The layers were separated and the organic phase was washed with brine, dried (Na$_2$SO$_4$), and concentrated. The residue was purified by preparative HPLC using a gradient elution from 15% to 50% acetonitrile to obtain 77 mg (56%) of the desired product. $^1$H NMR (300 MHz, DMSO-d$_6$) δ 8.52 (d, 1 H), 7.88 (s, 1 H), 7.73-7.69 (m, 1 H), 7.62-7.58 (m, 1 H), 7.46-7.39 (m, 4 H), 7.25-7.19 (m, 1 H), 7.06-7.00 (m, 1 H), 6.52 (s, 1 H), 5.69 (s, 2 H), 2.86 (t, 2 H), 2.42-2.33 (m, 6 H), 1.74-1.60 (m, 6 H), 1.54-1.44 (m, 2 H); ES-MS m/z 466.23 [M+H]+, HPLC RT (min) 2.21.

Example 23

Preparation of 5-[2-(3-chlorobenzyl)-2H-indazol-6-yl]-7-(4-pyrrolidin-1-ylbutyl)pyrrolo[2,1-f][1,2,4]triazin-4-amine

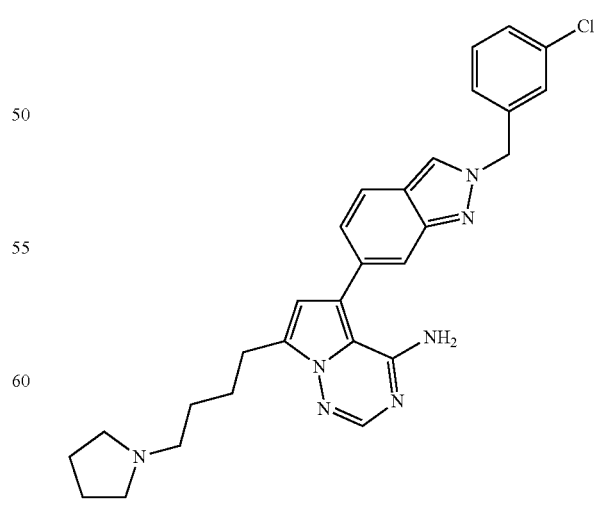

In a manner similar to the procedure described for the preparation of Example 22, using 5-bromo-7-(4-pyrrolidin-1-ylbutyl)pyrrolo[2,1-f][1,2,4]triazin-4-amine as starting material, 15 mg (30%) of the desired product was isolated. $^1$H NMR (300 MHz, DMSO-d$_6$) δ 8.58 (s, 1 H), 7.88 (s, 1 H), 7.80 (d, 1 H), 7.58 (s, 1 H), 7.43 (s, 1 H), 7.39-7.37 (m, 3 H), 7.33-7.28 (m, 1 H), 7.14 (dd, 1 H), 6.58 (s, 1 H), 5.67 (s, 2 H), 2.87 (t, 2 H), 2.41-2.32 (m, 6 H), 1.76-1.59 (m, 6 H), 1.55-1.46 (m, 2 H); ES-MS m/z 500.20 [M+H]$^+$, HPLC RT (min) 2.37.

Example 24

Preparation of 5-[2-(3-fluorobenzyl)-2H-indazol-6-yl]-7-(4-pyrrolidin-1-ylbutyl)pyrrolo[2,1-f][1,2,4]triazin-4-amine

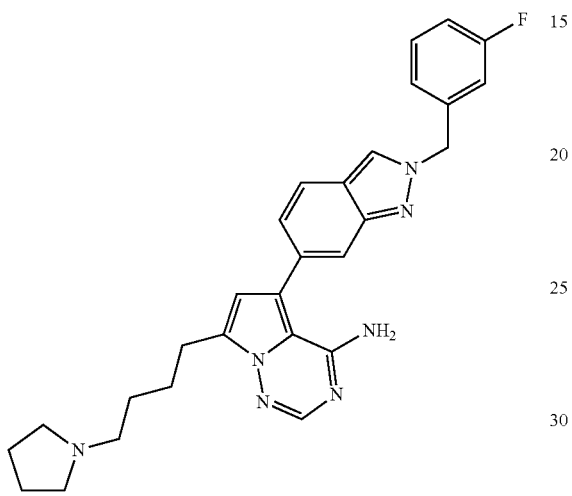

In a manner similar to the procedure described for the preparation of Example 22, using 5-bromo-7-(4-pyrrolidin-1-ylbutyl)pyrrolo[2,1-f][1,2,4]triazin-4-amine as starting material, 21 mg (20%) of the desired product was isolated. $^1$H NMR (300 MHz, DMSO-d$_6$) δ 8.57 (s, 1 H), 7.88 (s, 1H), 7.80 (d, 1 H), 7.58 (s, 1 H), 7.43-7.36 (m, 1 H), 7.20-7.11 (m, 4 H), 6.59 (s, 1 H), 5.68 (s, 2 H), 2.88 (t, 2 H), 2.44-2.34 (m, 6 H), 1.76-1.60 (m, 6 H), 1.56-1.46 (m, 2 H); ES-MS m/z 484.25 [M+H]$^+$, HPLC RT (min) 2.29.

Example 25

Preparation of 5-[2-(3-methylbenzyl)-2H-indazol-6-yl]-7-(4-pyrolidin-1-ylbutyl)pyrrolo[2,1-f][1,2,4]triazin-4-amine

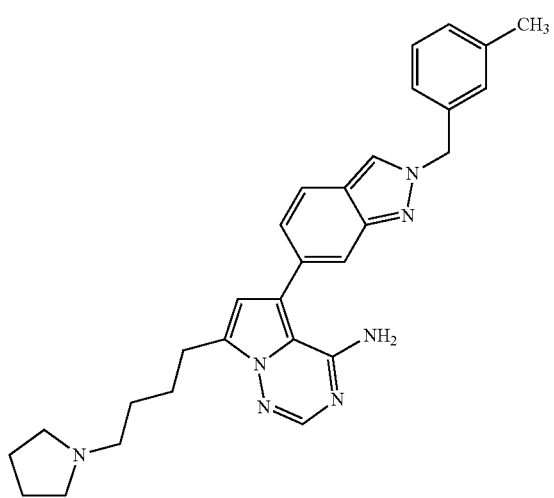 [SMILES: Cc1cccc(Cn2cc3ccc(-c4cc(CCCCN5CCCC5)n5ncnc(N)c45)cc3n2)c1]

In a manner similar to the procedure described for the preparation of Example 22, using 5-bromo-7-(4-pyrrolidin-1-ylbutyl)pyrrolo[2,1-f][1,2,4]triazin-4-amine as starting material, 27 mg (26%) of the desired product was isolated. $^1$H NMR (300 MHz, DMSO-d$_6$) δ 8.58 (s, 1 H), 7.94 (s, 1H), 7.85 (d, 1 H), 7.63 (s, 1 H), 7.32-7.14 (m, 5 H), 6.64 (s, 1 H), 5.65 (s, 2 H), 2.94 (t, 2 H), 2.49-2.39 (m, 6 H), 2.33 (s, 3 H), 1.82-1.63 (m, 6 H), 1.62-1.51 (m, 2 H); ES-MS m/z 480.26 [M+H]$^+$, HPLC RT (min) 2.36.

Example 26

Preparation of 3-[4-Amino-5-(2-benzyl-2H-indazol-6-yl)-pyrrolo[2,1-f][1,2,4]-triazin-7-yl]-propan-1-ol

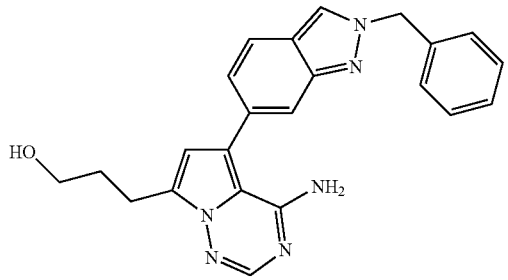 [SMILES: Nc1ncnn2c(CCCO)cc(-c3ccc4cn(Cc5ccccc5)nc4c3)c12]

Step 1: Preparation of 3-(4-Aminopyrrolo[2,1-f][1,2,4]triazin-7-yl)-prop-2-yn-1-ol

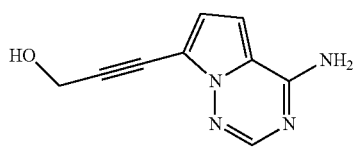 [SMILES: Nc1ncnn2c(C#CCO)ccc12]

To a degassed solution of 7-bromopyrrolo[2,1-f][1,2,4]trazin-4-ylamine (10.0 g, 46.9 mmol) in anhydrous DMF (78 mL) and triethylamine (47 mL) was added tetrakis(triphenylphosphine)palladium(0) (2.17 g, 1.88 mmol, 0.04 eq) and copper (I) bromide dimethylsulfide complex (0.77 g, 3.75 mmol, 0.08 eq). After degassing with N$_2$ for 5 min., propargyl alcohol (8.2 mL, 140.8 mmol, 3.0 eq) was added, and the reaction mixture was stirred at 90° C. for 6 h. The reaction was quenched with 5% aq. NH$_3$ in saturated aq. NH$_4$Cl. The aqeuous layer was washed with EtOAc (1×) followed by 25% iPrOH in DCM (3×). The combined organic layers were dried over MgSO$_4$, filtered through a pad of Celite®, and concentrated at reduced pressure. The crude product was purified by MPLC eluted with 5% EtOH/DCM. Trituration from EtOAc afforded 4.75 g (53.8%) of the desired product as a yellow solid. $^1$H-NMR (DMSO-d$_6$) δ 7.89 (s, 1H), 7.88 (broad s, 2H), 6.85 (dd, 2H), 5.39 (t, 1H), 4.36 (d, 2H); LC-MS [M+H]$^+$ =189, RT=1.08 min.

Step 2: Preparation of 3-(4-Aminopyrrolo[2,1-f][1,2,4]triazin-7-yl)-propan-1-ol

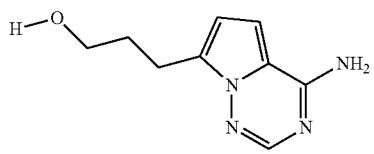 [SMILES: Nc1ncnn2c(CCCO)ccc12]

Palladium on carbon (474 mg, 10% by wt.) was placed under an Inert atmosphere and suspended in EtOH (15 mL). A solution of 3-(4-aminopyrrolo[2,1-f][1,2,4]trazin-7-yl)-prop-2-yn-1-ol (4.74 g, 25.2 mmol) dissolved in 2:1 v/v EtOH/THF was added. The reaction mixture was placed under H₂ atmosphere (1 Atm pressure) and stirred overnight. The resulting mixture was filtered through a pad of Celite® and the solvent was concentrated under reduced pressure. Trituration from EtOAc/hexane afforded 4.64 g (95.8%) of the desired product as an off-white solid. ¹H-NMR (DMSO-d₆) δ 7.77 (s, 1H), 7.54 (broad s, 2H), 6.78 (d, 1H), 6.39 (d, 1H), 4.50 (t, 1H), 3.43 (q, 2H), 2.84 (t, 2H), 1.74 to 1.82 (m, 2H); LC-MS [M+H]⁺=193, RT=1.06 min.

Step 3: Preparation of 3-(4-Amino-5-bromopyrrolo [2,1-f][1,2,4]triazin-7-yl)-propan-1-ol

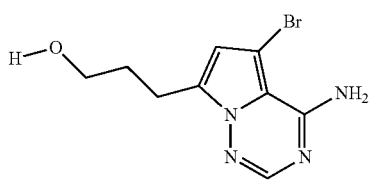 [SMILES: Nc1ncnn2c(CCCO)cc(Br)c12]

To a solution of 3-(4-aminopyrrolo[2,1-f][1,2,4]triazin-7-yl)-propan-1-ol (5.40 g, 28.09 mmol) in anhydrous DMF (56 mL) was added 1,3-dibromo-5,5-dimethylhydantoin (3.96 g, 13.9 mmol, 0.50 eq) proportionwise at −50° C. The reaction mixture was warmed to 0° C. and stirred at 0° C. for 2 h. The reaction mixture was quenched with water and poured into EtOAc. The organic layer was washed with water and brine, dried over Na₂SO₄, filtered, and concentrated at reduced pressure. Crystallization from DCM afforded 6.54 g (85.9%) of the desired product as a beige solid. ¹H-NMR (DMSO-d₆) δ 7.83 (s, 1H), 6.61 (s, 1H), 4.52 (broad s, 1H), 3.41 (t, 2H), 2.83 (t, 2H), 1.75 to 1.77 (m, 2H); LC-MS [M+H]⁺=271/273, RT=1.40 min.

Step 4: Preparation of the Title Compound

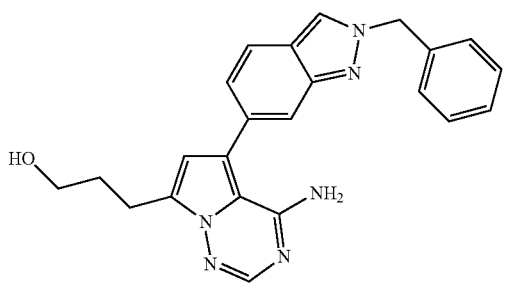 [SMILES: Nc1ncnn2c(CCCO)cc(-c3ccc4cn(Cc5ccccc5)nc4c3)c12]

3-(4-Amino-5-bromopyrrolo[2,1-f][1,2,4]triazin-7-yl)-propan-1-ol (4.0 g, 14.75 mmol) and 2-benzyl-6-(4,4,5,5-tetramethyl-[1,3,2]dioxaborolan-2-yl)-2H-indazole (6.66 g, 19.9 mmol, 1.35 eq) were dissolved in 1:1 v/v EtOH-toluene and degassed with nitrogen. After 30 minutes [1,1'-bis(diphenylphosphino)ferrocene]dichloropalladium (II) complex with dichloromethane (1.20 g, 1.47 mmol, 0.1 eq) followed by 2M sodium carbonate solution (22 mL, 44.26 mmol, 3.0 eq) were added. The reaction mixture was stirred at 80° C. for 6 h. The reaction mixture was partitioned between EtOAc and water and filtered through a pad of Celite® to rid of excess palladium salts. The organic layer was washed with water and brine, dried over Na₂SO₄, filtered, and concentrated at reduced pressure. The crude product was purified by MPLC eluted with 10% MeOH/DCM with 1% Et₃N to give the desired product as white foam (3.41 g, 58%). ¹H-NMR (DMSO-d₆) δ 8.53 (s, 1H), 7.87 (s, 1H), 7.78 (d, 1H), 7.57 (s, 1H), 7.28 to 7.35 (m, 5H), 7.13 (d, 1H), 6.58 (s, 1H), 5.64 (s, 2H), 4.53 (t, 1H), 3.47 (q, 2H), 2.91 (t, 2H), 1.82 to 1.86 (m, 2H); LC-MS [M+H]P=399, RT=2.41 min.

Example 27

Preparation of 3-{4-Amino-5-[2-(3-chlorobenzyl)-2H-indazol-6-yl]-pyrrolo[2,1-f][1,2,4]triazin-7-yl}-propan-1-ol

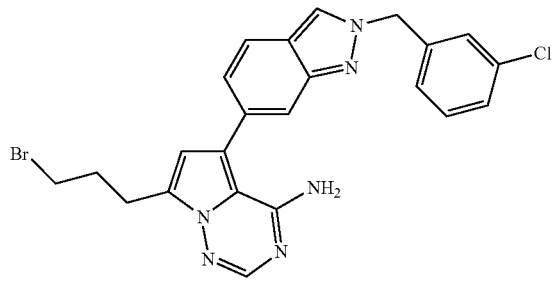 [SMILES: Nc1ncnn2c(CCCBr)cc(-c3ccc4cn(Cc5cccc(Cl)c5)nc4c3)c12]

The title compound was prepared in the same manner described for example 26, step 4, substituting 2-(3-chlorobenzyl)-6-(4,4,5,5-tetra-methyl-[1,3,2]dioxaborolan-2-yl)-2H-indazole for 2-benzyl-6-(4,4,5,5-tetramethyl-[1,3,2]dioxaborolan-2-yl)-2H-indazole. ¹H-NMR (DMSO-d₆) δ 8.57 (s, 1H), 7.88 (s, 1H), 7.80 (d, 1H), 7.59 (s, 1H), 7.44 (s, 1H), 7.40 to 7.37 (m, 2H), 7.31 (t, 1H), 7.15 (d, 1H), 6.59 (s, 1H), 5.67 (s, 2H), 4.53 (t, 1H), 3.48 to 3.46 (m, 2H), 2.93 to 2.89 (m, 2H), 1.86 to 1.82 (m, 2H); LC-MS [M+H]⁺=433, RT=2.96 min.

Example 28

Preparation of 5-(2-Benzyl-2H-indazol-6-yl)-7-(3-pyrrolidin-1-yl-propyl)-pyrrolo[2,1-f][1,2,4]triazin-4-ylamine

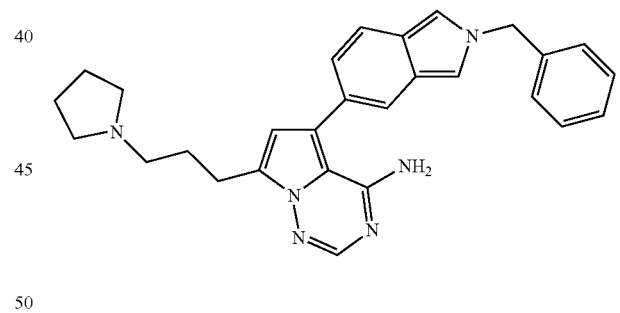

Step 1: Preparation of 5-(2-Benzyl-2H-indazol-6-yl)-7-(3-bromopropyl)pyrrolo[2,1-f][1,2,4]triazin-4-ylamine

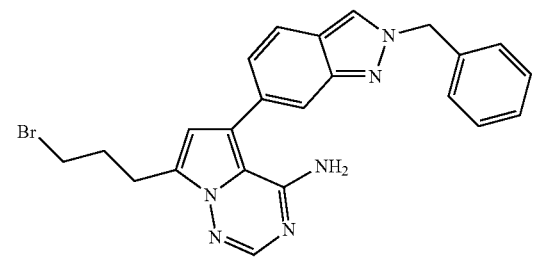

To a solution of 3-[4-amino-5-(2-benzyl-2H-indazol-6-yl) pyrrolo[2,1-f][1,2,4]triazin-7-yl]propan-1-ol (step 4, example 24, 3.40 g, 8.53 mmol) in anhydrous THF (85 mL) at 0° C. was added carbon tetrabromide (3.68 g, 11.0 mmol, 1.3 eq) and triphenylphosphine (2.46 g, 9.4 mmol, 1.1 eq), and the reaction mixture was stirred at RT for 16 h. The reaction was poured into EtOAc. The organic layer was washed with water and brine, dried over Na$_2$SO$_4$, filtered, and concentrated at reduced pressure. The crude product was purified by MPLC eluted with 15% acetone/DCM to give 2.45 g (62.4%) of desired product as a white solid. $^1$H-NMR (DMSO-d$_6$) δ 8.52 (s, 1H), 7.89 (s, 1H), 7.78 (d, 1H), 7.57 (s, 1H), 7.15 to 7.35 (m, 5H), 7.13 (d, 1H), 6.62 (s, 1H), 5.74 (s, 2H), 3.61 (t, 2H), 3.03 (t, 2H), 2.22 to 2.26 (m, 2H); LC-MS [M+H]$^+$=461/463, RT=3.16 min.

Step 2: Preparation of the Title Compound

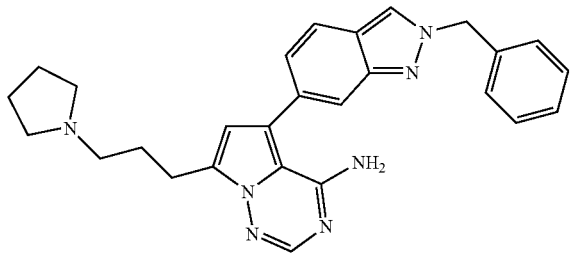 [SMILES: Nc1ncnn2c(CCCN3CCCC3)cc(-c3ccc4cn(Cc5ccccc5)cc4c3)c12]

A solution of 5-(2-benzyl-2H-indazol-6-yl)-7-(3-bromopropyl)pyrrolo[2,1-f][1,2,4]-triazin-4-ylamine (2.62 g, 5.68 mmol), pyrrolidine (808 mg, 11.36 mmol, 2.0 eq), triethylamine (575 mg, 5.68 mmol, 1.0 eq); and sodium iodide (85 mg, 0.56 mmol, 0.1 eq) in anhydrous DMF (28 mL) was stirred at 55° C. for 17 h. The reaction mixture was partitioned between EtOAc and water, and the organic layer was washed with 50% aq. brine (3×), dried over Na$_2$SO$_4$, filtered, and concentrated at reduced pressure. The crude was triturated from MeOH, filtered, and washed with cold MeOH and ether to provide 2.16 g (84.2%) of the desired product as a white solid. $^1$H-NMR (DMSO-d$_6$) δ 8.54 (s, 1H), 7.89 (s, 1H), 7.80 (d, 1H), 7.58 (s, 1H), 7.36 to 7.30 (m, 5H), 7.14 (d, 1H), 6.59 (s, 1H), 5.65 (s, 2H), 2.90 (t, 2H), 2.48 to 2.39 (m, 6H), 1.87 to 1.83 (m, 2H), 1.67 to 1.64 (m, 4H); LC-MS [M+H]$^+$=452, RT=2.14 min.

Example 29

Preparation of 5-(2-Benzyl-2H-indazol-6-yl)-7-(3-chloro-propyl)-pyrrolo[2,1-f][1,2,4]triazin-4-ylamine

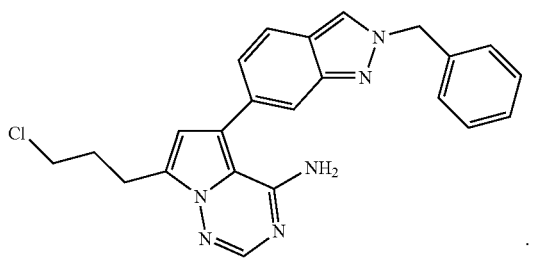 [SMILES: Nc1ncnn2c(CCCCl)cc(-c3ccc4cn(Cc5ccccc5)nc4c3)c12 ; "."]

A solution of 5-(2-benzyl-2H-indazol-6-yl)-7-(3-bromopropyl)pyrrolo[2,1-f][1,2,4]-triazin-4-ylamine (50 mg, 0.108 mmol), 3,3-difluoropyrrolidine hydrochloride (78 mg, 0.54 mmol, 5.0 eq), triethylamine (77 mg, 0.76 mmol, 7.0 eq), and sodium iodide (3.3 mg, 0.022 mmol, 0.2 eq) in anhydrous DMF (1.0 mL) was stirred at 50° C. for 6 h. The reaction mixture was partitioned between EtOAc and water, and the organic layer was washed with 50% aq. brine (3×), dried over Na$_2$SO$_4$, filtered, and concentrated under reduced pressure. The crude product was dissolved in MeOH (3 mL) and purified using HPLC (RT=10.16 min) to give a colorless oil. Crystallization from DCM/hexane afforded 9.4 mg (20.8%) of the byproduct as a white solid. $^1$H-NMR (CD$_3$OD) δ 8.35 (s, 1H), 7.82 (s, 1H), 7.81 (d, 1H), 7.64 (s, 1H), 7.36 to 7.30 (m, 5H), 7.23 (d, 1H), 6.62 (s, 1H), 5.66 (s, 2H), 3.64 (t, 2H), 3.14 (t, 2H), 226 to 2.22 (m, 2H); LC-MS [M+H]$^+$=417/419, RT=2.91 min.

Example 30

Preparation of 5-(3-Benzyloxyphenyl)-7-{3-[2-methoxyethyl)methylamino]propyl}-pyrrolo[2,1-f][1,2,4]triazin-4-ylamine dihydrochloride

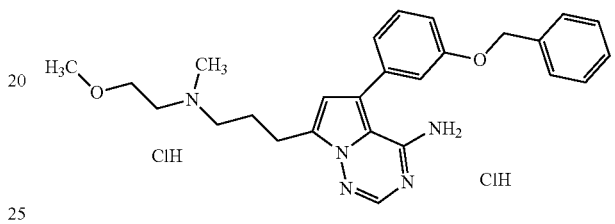

Step 1: Preparation of 3-[4-Amino-5-(3-benzyloxyphenyl)-pyrrolo[2,1-f][1,2,4]triazin-7-yl]-propan-1-ol

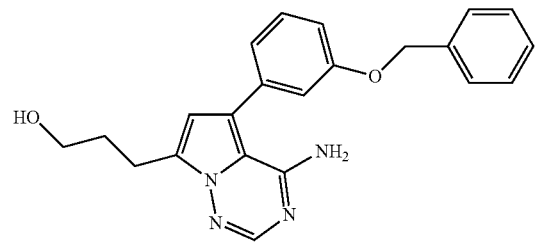 [SMILES: Nc1ncnn2c(CCCO)cc(-c3cccc(OCc4ccccc4)c3)c12]

The title compound was prepared in the same manner described for example 25, step 4, substituting 3-benzyloxyphenyl boronic acid for 2-benzyl-6-(4,4,5,5-tetramethyl-[1,3,2]dioxaborolan-2-yl)-2H-indazole. $^1$H-NMR (DMSO-d$_6$) δ 7.87 (s, 1H), 7.45 to 7.29 (m, 6H), 7.07 (t, 1H), 7.02 to 6.98 (m, 2H), 6.55 (s, 1H), 5.14 (s, 2H), 4.53 (t, 1H), 3.47 (q, 2H), 2.89 (t, 2H), 1.87 to 1.80 (m, 2H); LC-MS [M+H]$^+$=375, RT=2.55 min; TLC (100% EtOAc), R$_f$=0.29.

Step 2: Preparation of 5-(3-Benzyloxyphenyl-7-(3-bromopropyl)-pyrrolo[2,1-f][1,2,4]triazin-4-ylamine

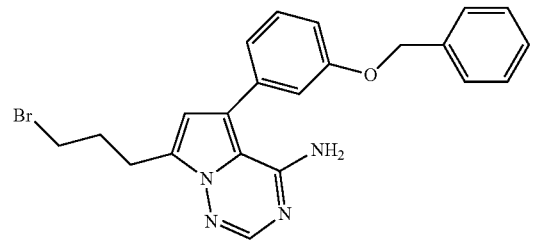 [SMILES: Nc1ncnn2c(CCCBr)cc(-c3cccc(OCc4ccccc4)c3)c12]

The title compound was prepared in the same manner described in the same manner described for example 25, step 5, substituting 3-[4-amino-5-(3-benzyloxyphenyl)-pyrrolo[2,1-f][1,2,4]triazin-7-yl]-propan-1-ol for 3-[4-amino-5-(2-benzyl-2H-indazol-6-yl)-pyrrolo[2,1-f][1,2,4]triazin-7-yl]-propan-1-ol. $^1$H-NMR (DMSO-d$_6$) δ 7.89 (s, 1H), 7.45 to 7.29 (m, 6H), 7.08 (s, 1H), 7.07 to 6.99 (m, 2H), 6.59 (s, 1H), 5.14 (s, 2H), 3.60 (t, 2H), 3.02 (t, 2H), 2.27 to 2.19 (m, 2H); LC-MS [M+H]$^+$=437/439, RT=3.11 min; TLC (50% EtOAc/hexane), R$_f$=0.28.

Step 3: Preparation of the Title Compound

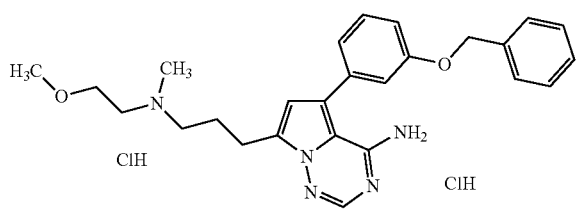 [SMILES: COCCN(C)CCCc1cc(-c2cccc(OCc3ccccc3)c2)c2c(N)ncnn12 ; Cl ; Cl]

A solution of 5-(3-benzyloxyphenyl)-7-(3-bromopropyl)pyrrolo[2,1-f][1,2,4]triazin-4-ylamine (40 mg, 0.09 mmol), N-methyl(methoxyethyl)amine (41 mg, 0.45 mmol, 5.0 eq), diisopropylethylamine (28 mg, 0.27 mmol, 3.0 eq), and sodium iodide (1.3 mg, 0.01 mmol, 0.1 eq) in anhydrous THF (0.50 mL) was stirred at 55° C. for 17 h. The volatile solvent was evaporated at reduced pressure. The crude product was dissolved in MeOH (3 mL) and purified using HPLC (RT=7.62 min) to give a colorless oil. The oil was redissolved in anydrous THF (1.0 mL) and 1.0M HCl in ether (0.45 mL, 5.0 eq) was added dropwise until a precipitate was seen. The precipitate was collected by filtration and washed with cold THF to give 25 mg (52.7%) of the dihydrochloride salt as a white solid. $^1$H-NMR (DMSO-d$_6$) δ 9.83 (broad s, 1H), 8.06 (s, 1H), 7.46 to 7.30 (m, 6H), 7.09 (s, 1H), 7.05 (t, 2H), 6.77 (s, 1H), 5.14 (s, 2H), 3.64 (t, 2H), 3.39 to 3.28 (m, 1H), 3.27 (s, 3H), 3.26 to 3.17 (m, 2H), 3.14 to 3.05 (m, 1H), 2.95 (t, 2H), 2.76 (d, 3H), 2.15 to 2.06 (m, 2H); LC-MS [M+H]$^+$=446, RT=2.65 min.

Examples 31-39 were prepared as described above using example 30 by choosing the appropriate amine starting materials that are readily available and/or the synthesis of which is taught herein, and using the processes of method described above or other standard chemical processes known in the art.

Example 31

Preparation of 5-(3-Benzyloxyphenyl)-7-(3-pyrrolidin-1-yl-propyl)-pyrrolo[2,1-f][1,2,4]triazin-4-ylamine

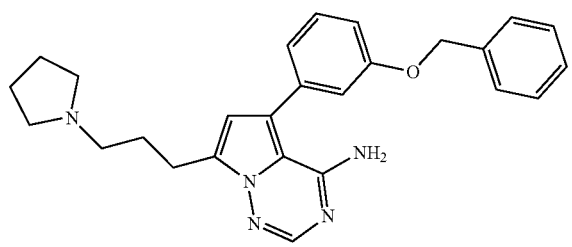 [SMILES: Nc1ncnn2c(CCCN3CCCC3)cc(-c3cccc(OCc4ccccc4)c3)c12]

$^1$H-NMR (CD$_3$OD) δ 7.79 (s, 1H), 7.43 (d, 2H), 7.38 to 7.33 (m, 3H), 7.31 to 7.27 (m, 1H), 7.07 to 7.00 (m, 3H), 6.53 (s, 1H), 5.13 (s, 2H), 2.97 (t, 2H), 2.60 to 2.55 (m, 6H), 2.04 to 1.98 (m, 2H), 1.85 to 1.77 (m, 4H); LC-MS [M+H]$^+$=428, RT=2.23 min.

Example 32

Preparation of 5-(3-Benzyloxyphenyl)-7-[3-(2-(S)-methoxymethyl-pyrrolidin-1-yl)-propyl]pyrrolo[2,1-f][1,2,4]triazin-4-ylamine dihydrochloride

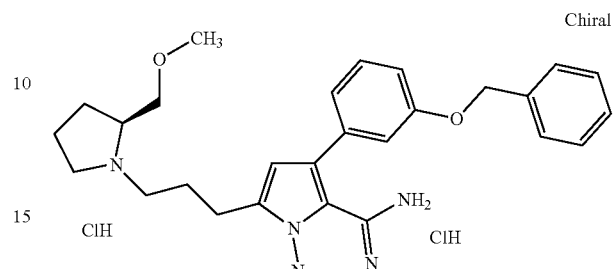

$^1$H-NMR of free-base (CD$_3$OD) δ 7.80 (s, 1H), 7.45 to 7.28 (m, 6H), 7.08 to 7.07 (m, 1H), 7.06 to 7.02 (m, 2H), 6.55 (s, 1H), 5.15 (s, 2H), 3.41 (dd, 1H), 3.34 (dd, 1H), 3.29 (s, 3H), 3.21 to 3.16 (m, 1H), 3.09 to 3.03 (m, 1H), 2.98 (t, 2H), 2.70 (broad s, 1H), 2.45 to 2.37 (m, 1H), 2.33 to 2.27 (m, 1H), 2.05 to 1.90 (m, 3H), 1.81 to 1.74 (m, 2H), 1.63 to 1.54 (m, 1H); LC-MS [M+H]$^+$=472, RT=2.25 min; HPLC RT=7.73 min.

Example 33

Preparation of 5-(3-Benzyloxyphenyl)-7-[3-(2-(R)-methoxymethyl-pyrrolidin-1-yl)propoyl]pyrrolo[2,1-f][1,2,4]triazin-4-ylamine dihydrochloride

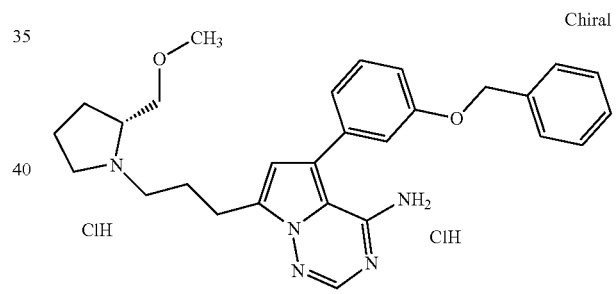

LC-MS [M+H]$^+$=472, RT=2.42 min; HPLC RT=7.90 min.

Example 34

Preparation of 5-(3-Benzyloxyphenyl)-7-(3-morpholin-4-yl-propyl)-pyrrolo[2,1-f][1,2,4]triazin-4-ylamine

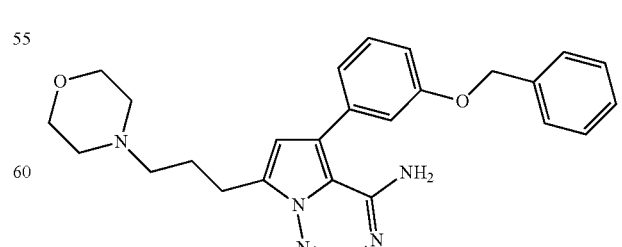

$^1$H-NMR (DMSO-d$_6$) δ 7.87 (s, 1H), 7.45 to 7.42 (m, 2H), 7.40 to 7.28 (m, 4H), 7.05 (t, 1H), 7.01 to 6.98 (m, 2H), 6.55

(s, 1H), 5.14 (s, 2H), 3.54 (t, 4H), 2.88 (t, 2H), 2.36 to 2.32 (m, 6H), 1.88 to 1.80 (m, 2H); LC-MS [M+H]+=442, RT=2.32 min.

Example 35

Preparation of 5-(3-Benzyloxyphenyl)-7-(3-piperidin-1-yl-propyl)-pyrrolo-[2,1-f][1,2,4]triazin-4-ylamine

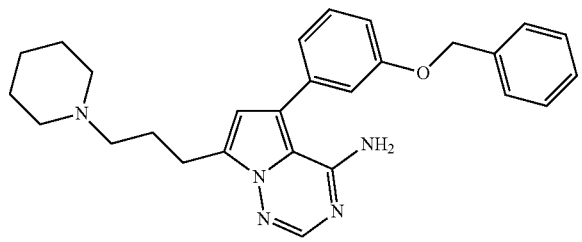 [SMILES: Nc1ncnn2c(CCCN3CCCCC3)cc(-c3cccc(OCc4ccccc4)c3)c12]

$^1$H-NMR (CD$_3$OD) δ 7.79 (s, 1H), 7.45 to 7.42 (m, 2H), 7.40 to 728 (m, 4H), 7.07 to 7.01 (m, 3H), 6.54 (s, 1H), 5.14 (s, 2H), 2.97 (t, 2H), 2.50 to 2.45 (m, 6H), 2.04 to 1.97 (m, 2H), 1.65 to 1.60 (m, 4H), 1.50 to 1.48 (m, 2H); LC-MS [M+H]+=442, RT=2.32 min.

Example 36

Preparation of 5-(3-Benzyloxyphenyl)-7-[3-(4-methyl-piperazin-1-yl)-propyl]-pyrrolo[2,1-f][1,2,4]triazin-4-ylamine

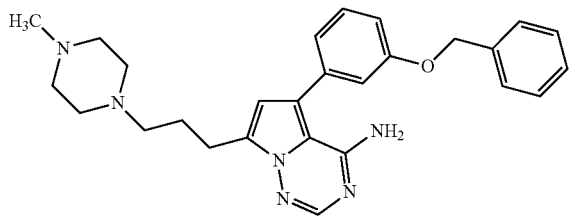 [SMILES: CN1CCN(CCCc2cc(-c3cccc(OCc4ccccc4)c3)c3c(N)ncnn23)CC1]

$^1$H-NMR (CD$_3$OD) δ 7.79 (s, 1H), 7.45 to 7.42 (m, 2H), 7.40 to 7.29 (m, 4H), 7.06 to 7.00 (m, 3H), 6.53 (s, 1H), 5.14 (s, 2H), 2.98 (t, 2H), 2.55 to 2.46 (m, 10H), 2.31 (s, 3H), 2.00 to 1.29 (m, 2H); LC-MS [M+H]+=457, RT=2.07 min.

Example 37

Preparation of (3-(3-Benzyloxyphenyl)-2-methyl-5-{3-[(pyridin-2-ylmethyl)-amino]propyl}-pyrrol-1-yl)ethylidene-amine

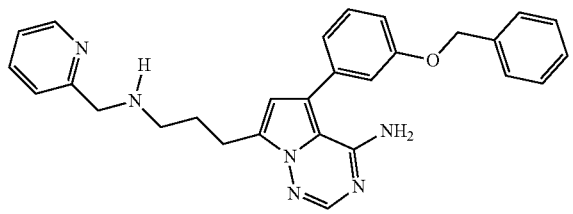 [SMILES: Nc1ncnn2c(CCCNCc3ccccn3)cc(-c3cccc(OCc4ccccc4)c3)c12]

$^1$H-NMR (CD$_3$OD) δ 8.45 (d, 1H), 7.78 (s, 1H), 7.77 to 7.73 (m, 1H), 7.45 to 724 (m, 8H), 7.05 to 7.01 (m, 3H), 6.51 (s, 1H), 5.15 (s, 2H), 3.90 (s, 2H), 3.02 (t, 2H), 2.69 (t, 2H), 2.04 to 2.00 (m, 2H); LC-MS [M+H]+=465, RT=2.24 min.

Example 38

Preparation of 5-(3-Benzyloxyphenyl)-7-(3-imidazol-1-yl-propyl)pyrrolo[2,1-f][1,2,4]triazin-4-ylamine

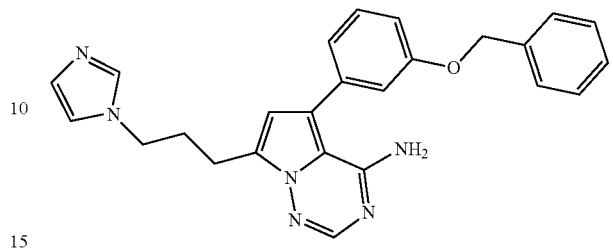

$^1$H-NMR (DMSO-d$_6$) δ 7.88 (s, 1H), 7.63 (s, 1H), 7.45 to 7.31 (m, 6H), 7.20 (s, 1H), 7.08 to 7.01 (m, 3H), 6.87 (s, 1H), 6.59 (s, 1H), 5.14 (s, 2H), 4.04 (t, 2H), 2.82 (t, 2H), 2.17 to 2.12 (m, 2H); LC-MS [M+H]+=425, RT=2.24 min.

Example 39

Preparation of 1-{3-[4-Amino-5-(3-benzyloxyphenyl)pyrrolo[2,1-f][1,2,4]triazin-7-yl]-propyl}-pyrrolidin-3-ol

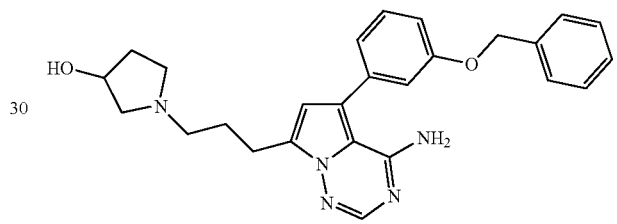

$^1$H-NMR (CD$_3$OD) δ 7.80 (s, 1H), 7.45 to 7.42 (m, 2H), 7.39 to 7.29 (m, 4H), 7.06 (t, 1H), 7.05 to 7.01 (m, 2H), 6.54 (s, 1H), 5.14 (s, 2H), 4.40 to 4.35 (m, 1H), 3.00 (t, 2H), 2.94 (dd, 1H), 2.89 to 2.84 (m, 1H), 2.75 to 2.62 (m, 4H), 2.17 to 2.12 (m, 1H), 2.05 to 1.99 (m, 3H), 1.79 to 1.75 (m, 1H); LC-MS [M+H]+=444, RT=2.12 min.

Examples 40-79 were prepared as described above using example 28 by choosing the appropriate amine starting materials that are readily available and/or the synthesis of which is taught herein, and using the processes of method described above or other standard chemical processes known in the art.

Example 40

Preparation of 5-(2-Benzyl-2H-indazol-6-yl)-7-[3-(3,3-difluoro-pyrrolidin-1-yl)-propyl]pyrrolo[2,1-f][1,2,4]triazin-4-ylamine

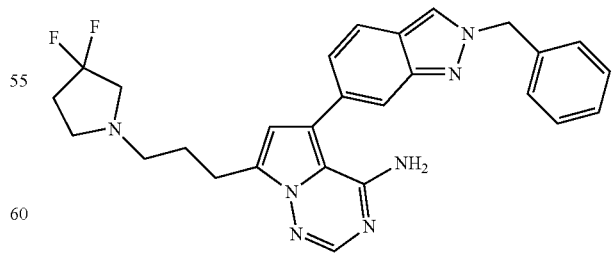

$^1$H-NMR (CD$_3$OD) δ 8.36 (s, 1H), 7.81 (s, 1H), 7.81 (d, 1H), 7.64 (s, 1H), 7.36 to 7.30 (m, 5H), 7.23 (dd, 1H), 6.62 (s, 1H), 5.66 (s, 2H), 3.03 (t, 2H), 2.93 (t, 2H), 2.78 (t, 2H), 2.59 (t, 2H), 2.32 to 2.23 (m, 2H), 2.02 to 1.96 (m, 2H); LC-MS [M+H]+=488, RT=1.69 min.

Example 41

Preparation of 1-{3-[4-Amino-5-(2-benzyl-2H-indazol-6-yl)-pyrrolo[2,1-f][1,2,4]-triazin-7-yl]propyl}-pyrrolidin-3-ol

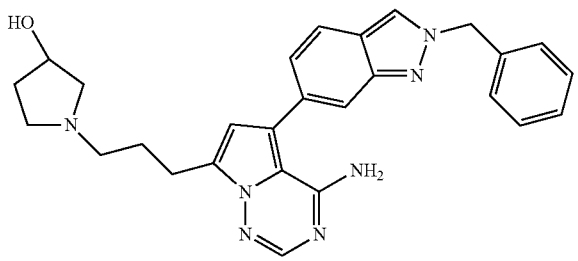 [SMILES: Nc1ncnn2c(CCCN3CCC(O)C3)cc(-c3ccc4cn(Cc5ccccc5)nc4c3)c12]

¹H-NMR (CD₃OD) δ 8.36 (s, 1H), 7.82 to 7.80 (m, 2H), 7.64 (s, 1H), 7.37 to 7.30 (m, 5H), 7.23 (d, 1H), 6.63 (s, 1H), 5.65 (s, 2H), 4.36 (broad s, 1H), 3.03 (t, 2H), 2.95 (dd, 1H), 2.88 (t, 1H), 2.76 to 2.64 (m, 5H), 2.18 to 2.12 (m, 1H), 2.04 (t, 2H), 1.80 to 1.75 (m, 1H); LC-MS [M+H]⁺=468, RT=1.21 min.

Example 42

Preparation of 1-{3-[4-Amino-5-(2-benzyl-2H-indazol-6-yl)-pyrrolo[2,1-f][1,2,4]-triazin-7-yl]-propyl}-pyrrolidin-3-(S)-ol

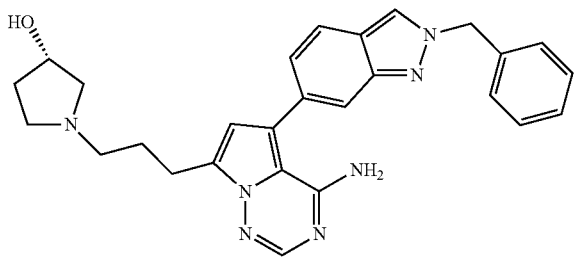 [SMILES: Nc1ncnn2c(CCCN3CC[C@H](O)C3)cc(-c3ccc4cn(Cc5ccccc5)nc4c3)c12]

¹H-NMR (DMSO-d₆) δ 8.54 (s, 1H), 7.88 (s, 1H), 7.80 (d, 1H), 7.58 (s, 1H), 7.36 to 7.29 (m, 5H), 7.14 (dd, 1H), 6.59 (s, 1H), 5.65 (s, 2H), 4.65 (d, 1H), 4.16 (broad s, 1H), 2.89 (t, 2H), 2.67 (dd, 1H), 2.56 to 2.37 (m, 4H), 2.26 (dd, 1H), 2.00 to 1.90 (m, 1H), 1.87 to 1.79 (m, 2H), 1.54 to 1.46 (m, 1H); LC-MS [M+H]⁺=468, RT=2.13 min.

Example 43

Preparation of 1-{3-[4-Amino-5-(2-benzyl-2H-indazol-6-yl)-pyrrolo[2,1-f][1,2,4]-triazin-7-yl]-propyl}-pyrrolidin-3-(R)-ol

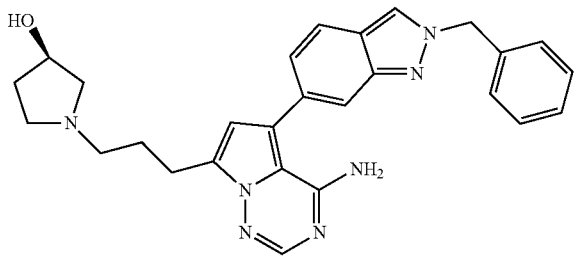 [SMILES: Nc1ncnn2c(CCCN3CC[C@@H](O)C3)cc(-c3ccc4cn(Cc5ccccc5)nc4c3)c12]

¹H-NMR (DMSO-d₆) δ 8.54 (s, 1H), 7.88 (s, 1H), 7.80 (d, 1H), 7.58 (s, 1H), 7.36 to 7.29 (m, 5H), 7.14 (dd, 1H), 6.59 (s, 1H), 5.65 (s, 2H), 4.65 (d, 1H), 4.16 (broad s, 1H), 2.89 (t, 2H), 2.68 (dd, 1H), 2.53 to 2.32 (m, 4H), 2.27 (dd, 1H), 2.00 to 1.90 (m, 1H), 1.87 to 1.79 (m, 2H), 1.54 to 1.46 (m, 1H); LC-MS [M+H]⁺=468, RT=2.13 min.

Example 44

Preparation of 5-(2-Benzyl-2H-indazol-6-yl)-7-[3-(3-methanesulfonyl-pyrrolidin-1-yl)-propyl]-pyrrolo[2,1-f][1,2,4]triazin-4-ylamine

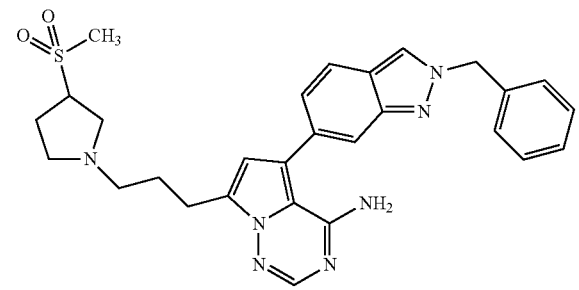 [SMILES: CS(=O)(=O)C1CCN(CCCc2cc(-c3ccc4cn(Cc5ccccc5)nc4c3)c3c(N)ncnn23)C1]

¹H-NMR (DMSO-d₆) δ 8.53 (s, 1H), 7.87 (s, 1H), 7.78 (d, 1H), 7.57 (s, 1H), 7.35 to 7.29 (m, 5H), 7.13 (dd, 1H), 6.59 (s, 1H), 5.64 (s, 2H), 3.73 (broad s, 1H), 2.91 to 2.87 (m, 5H), 2.79 (d, 2H), 2.56 to 2.43 (m, 4H), 2.08 to 2.04 (m, 2H), 1.86 to 1.83 (m, 2H); LC-MS [M+H]⁺=530, RT=2.10 min.

Example 45

Preparation of 5-(2-Benzyl-2H-indazol-6-yl)-7-[3-(4-methyl-piperazin-1-yl)-propyl]-pyrrolo[2,1-f][1,2,4]triazin-4-ylamine

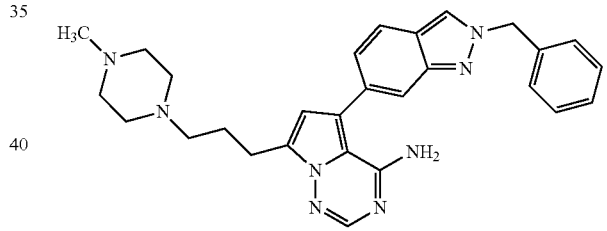

¹H-NMR (DMSO-d₆) δ 8.55 (s, 1H), 7.89 (s, 1H), 7.80 (d, 1H), 7.59 (s, 1H), 7.37 to 7.30 (m, 5H), 7.15 (d, 1H), 6.60 (s, 1H), 5.65 (s, 2H), 2.88 (t, 2H), 2.35 to 2.25 (m, 10H), 2.12 (s, 3H), 1.84 (t, 2H); LC-MS [M+H]⁺=481, RT=2.05 min.

Example 46

Preparation of 5-(2-Benzyl-2H-indazol-6-yl)-7-(3-morpholin-4-yl-propyl)-pyrrolo[2,1-f][1,2,4]triazin-4-ylamine

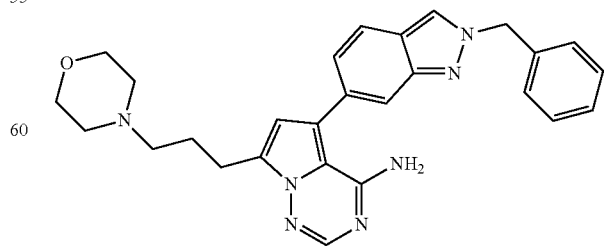

¹H-NMR (DMSO-d₆) δ 8.54 (s, 1H), 7.94 (s, 1H), 7.80 (d, 1H), 7.58 (s, 1H), 7.34 to 7.29 (m, 5H), 7.14 (d, 1H), 6.60 (s,

1H), 5.65 (s, 2H), 3.55 (1,4H), 2.89 (t, 2H), 2.37 to 2.33 (m, 6H), 1.89 to 1.82 (m, 2H); LC-MS [M+H]⁺=468, RT=2.16 min.

Example 47

Preparation of 542-Benzyl-2H-Indazol-6-yl)-7-(3-piperazin-1-yl-propyl)pyrrolo-[2,1-f][1,2,4]triazin-4-ylamine

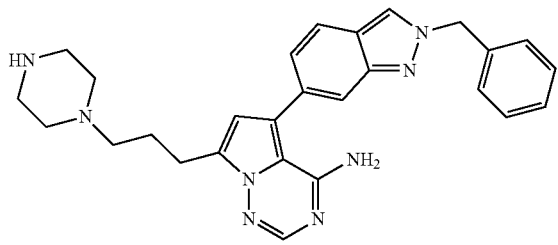 [SMILES: Nc1ncnn2c(CCCN3CCNCC3)cc(-c3ccc4cn(Cc5ccccc5)nc4c3)c12]

¹H-NMR (DMSO-d₆) δ 8.55 (s, 1H), 7.89 (s, 1H), 7.80 (d, 1H), 7.59 (s, 1H), 7.36 to 7.30 (m, 5H), 7.15 (d, 1H), 6.60 (s, 1H), 5.65 (s, 2H), 3.35 to 3.26 (m, 4H), 2.89 (t, 2H), 2.65 (broad s, 2H), 2.40 to 2.26 (m, 5H), 1.86 to 1.82 (m, 2H); LC-MS [M+H]⁺=467, RT=1.97 min.

Example 48

Preparation of 5-(2-Benzyl-2H-indazol-6-yl)-7-{3-[(pyridin-2-ylmethyl)-amino]-propyl}-pyrrolo[2,1-f][1,2,4]triazin-4-ylamine

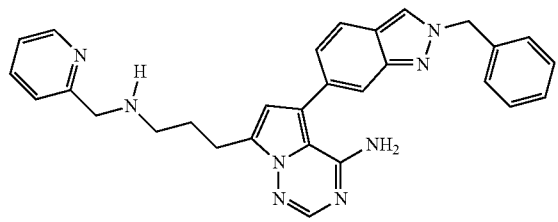 [SMILES: Nc1ncnn2c(CCCNCc3ccccn3)cc(-c3ccc4cn(Cc5ccccc5)nc4c3)c12]

¹H-NMR (DMSO-d₆) δ 8.53 (s, 1H), 8.44 (d, 1H), 7.87 (s, 1H), 7.78 (d, 1H), 7.69 (t, 1H), 7.55 (s, 1H), 7.39 (d, 1H), 7.35 to 7.28 (m, 5H), 7.19 (dd, 1H), 7.11 (d, 1H), 6.56 (s, 1H), 5.64 (s, 2H), 3.79 (s, 2H), 2.93 (t, 2H), 2.60 (t, 2H), 1.90 to 1.84 (m, 2H); LC-MS [M+H]⁺=489, RT=1.15 min.

Example 49

Preparation of 5-(2-Benzyl-2H-indazol-6-yl)-7-{3-[(3-methyl-pyridin-2-ylmethyl)-amino]-propyl}-pyrrolo[2,1-f][1,2,4]triazin-4-ylamine

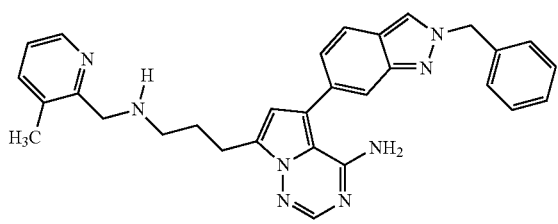 [SMILES: Cc1cccnc1CNCCCc1cc(-c2ccc3cn(Cc4ccccc4)nc3c2)c2c(N)ncnn12]

¹H-NMR (DMSO-d₆) δ 9.13 (broad s, 1H), 8.56 (s, 1H), 8.42 (d, 1H), 8.00 (s, 1H), 7.81 (d, 1H), 7.66 (d, 1H), 7.61 (s, 1H), 7.35 to 7.29 (m, 5H), 7.14 (d, 1H), 6.73 (s, 1H), 5.64 (s, 2H), 4.35 (s, 2H), 3.14 to 3.07 (m, 2H), 3.00 (t, 2H), 225 (s, 3H), 2.20 to 2.13 (m, 2H); LC-MS [M+H]⁺=503, RT=2.30 min.

Example 50

Preparation of 5-[2-(3-Chlorobenzyl)-2H-indazol-6-yl]-7-(3-pyrrolidin-1-yl-propyl)-pyrrolo[2,1-f][1,2,4]triazin-4-ylamine

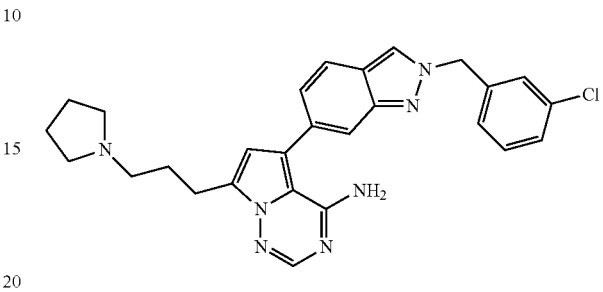

¹H-NMR (DMSO-d₃) δ 8.58 (s, 1H), 7.89 (s, 1H), 7.81 (d, 1H), 7.59 (s, 1H), 7.44 (S, 1H), 7.40 to 7.38 (m, 2H), 7.33 to 7.30 (m, 1H), 7.16 (d, 1H), 6.60 (s, 1H), 5.67 (s, 2H), 2.90 (t, 2H), 2.48 to 2.39 (m, 6H), 1.89 to 1.82 (m, 2H), 1.68 to 1.63 (m, 4H); LC-MS [M+H]⁺=486, RT=2.35 min.

Example 51

Preparation of 5-[2-(3-Chlorobenzyl)-2H-indazol-6-yl]-7-[3-(4-methyl-piperazin-1-yl)-propyl]-pyrrolo[2,1-f][1,2,4]triazin-4-ylamine

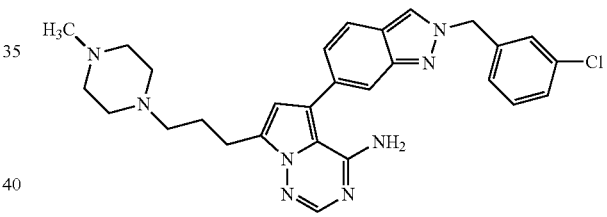

¹H-NMR (DMSO-dₛ) δ 8.58 (s, 1H), 7.89 (s, 1H), 7.81 (d, 1H), 7.59 (s, 1H), 7.44 (s, 1H), 7.42 to 7.38 (m, 2H), 7.33 to 7.31 (m, 1H), 7.16 (d, 1H), 6.60 (s, 1H), 5.68 (s, 2H), 2.88 (t, 2H), 2.35 to 2.16 (m, 10H), 2.12 (s, 3H), 1.86 to 1.82 (t, 2H); LC-MS [M+H]⁺=515, RT=2.18 min.

Example 52

Preparation of 5-(2-Benzyl-2H-indazol-6-yl)-7-{3-[(2-methoxy-ethyl)-methyl-amino]-propyl}-pyrrolo[2,1-f][1,2,4]triazin-4-ylamine

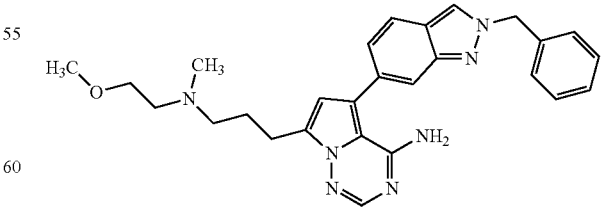

¹H-NMR (300 MHz, CD₃OD) δ 8.32 (s, 1H), 7.80 (s, 1H), 7.77 (d, 1H), 7.64 (s, 1H), 7.35 to 7.28 (m, 5H), 7.20 (dd, 1H), 6.59 (s, 1H), 5.65 (s, 2H), 3.46 (t, 2H), 3.28 (s, 3H), 2.94 (t, 2H), 2.58 (t, 2H), 2.50 (dd, 2H), 2.26 (s, 3H), 1.98 to 1.92 (m, 2H); ES-MS m/z 470.0 [M+H]⁺, RT (min) 2.07.

Example 53

Preparation of 2-({3-[4-Amino-5-(2-benzyl-2H-indazol-6-yl)-pyrrolo[2,1-f][1,2,4]triazin-7-yl]-propyl}-methyl-amino)-ethanol

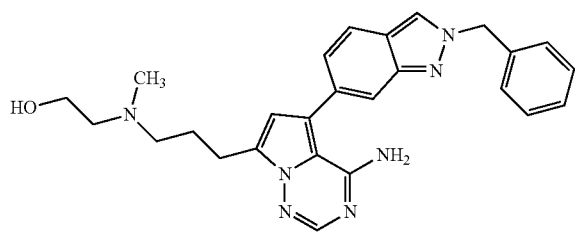 [SMILES: CN(CCO)CCCc1cc(-c2ccc3cn(Cc4ccccc4)nc3c2)c2c(N)ncnn12]

$^1$H-NMR (300 MHz, DMSO-d$_6$) δ 8.54 (s, 1H), 7.88 (s, 1H), 7.79 (d, 1H), 7.54 (s, 1H), 7.35 to 7.28 (m, 5H), 7.13 (d, 1H), 6.59 (s, 1H), 5.64 (s, 2H), 3.47 to 3.42 (m, 2H), 3.14 (d, 1H), 2.87 (t, 2H), 2.40 to 2.38 (m, 4H), 2.17 (s, 3H), 1.86 to 1.80 (m, 2H); ES-MS m/z 456.2 [M+H]$^+$, RT (min) 1.98.

Example 54

Preparation of (4-{3-[4-Amino-5-(2-benzyl-2H-indazol-6-yl)-pyrrolo[2,1-f][1,2,4]triazin-7-yl]-propyl}-morpholin-2-yl)-methanol

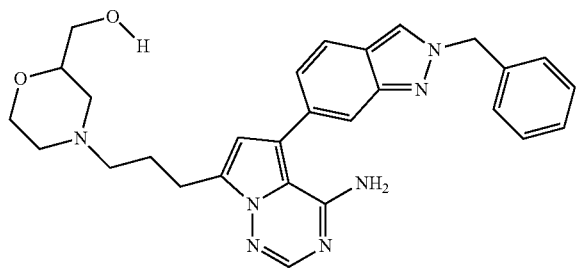 [SMILES: Nc1ncnn2c(CCCN3CCOC(CO)C3)cc(-c3ccc4cn(Cc5ccccc5)nc4c3)c12]

$^1$H NMR (300 MHz, DMSO-d$_6$) δ 8.54 (s, 1H), 7.89 (s, 1H), 7.79 (d, 1H), 7.58 (s, 1H), 7.36 to 7.29 (m, 5H), 7.14 (d, 1H), 6.60 (s, 1H), 5.65 (s, 2H), 4.64 to 4.62 (m, 1H), 3.73 (d, 1H), 3.48 to 3.35 (m, 4H), 3.29 to 3.25 (m, 1H), 2.89 (t, 2H), 2.81 (d, 1H), 2.66 (d, 1H), 2.34 (t, 2H), 1.95 (t, 1H), 1.87 to 1.82 (m, 2H); ES-MS m/z 498.2 [M+H]$^+$, RT (min) 2.16.

Example 55

Preparation of 4-{3-[4-Amino-5-(2-benzyl-2H-indazol-6-yl)-pyrrolo[2,1-f][1,2,4]triazin-7-yl]-propyl}-piperazine-1-carboxylic acid dimethylamide

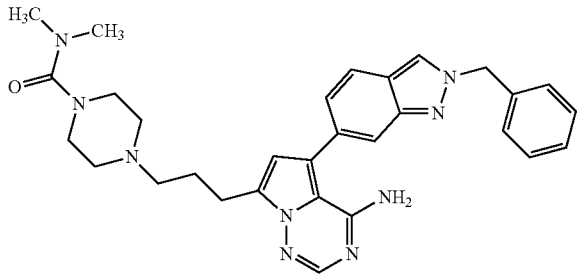 [SMILES: CN(C)C(=O)N1CCN(CCCc2cc(-c3ccc4cn(Cc5ccccc5)nc4c3)c3c(N)ncnn23)CC1]

$^1$H NMR (300 MHz, DMSO-d$_6$) δ 8.54 (s, 1H), 7.89 (s, 1H), 7.79 (d, 1H), 7.58 (s, 1H), 7.36 to 7.30 (m, 5H), 7.14 (d, 1H), 6.60 (s, 1H), 5.65 (s, 2H), 3.15 (d, 2H), 3.07 (t, 4H), 2.89 (t, 2H), 2.70 (s, 6H), 2.38 to 2.34 (m, 4H), 1.88 to 1.84 (m, 2H); ES-MS m/z 538.3 [M+H]$^+$, RT (min) 2.05.

Example 56

(4-{3-[4-Amino-5-(2-benzyl-2H-indazol-6-yl)-pyrrolo[2,1-f][1,2,4]triazin-7-yl]-propyl}-piperazin-1-yl)-morpholin-4-yl-methanone

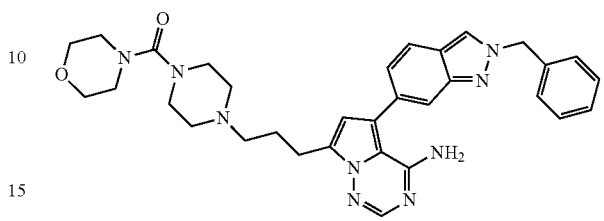

$^1$H NMR (300 MHz, DMSO-d$_s$) δ 8.54 (s, 1H), 7.89 (s, 1H), 7.79 (d, 1H), 7.58 (s, 1H), 7.36 to 7.30 (m, 5H), 7.14 (dd, 1H), 6.60 (s, 1H), 5.65 (s, 2H), 3.53 (t, 4H), 3.14 to 3.12 (m, 4H), 3.10 to 3.07 (m, 4H), 2.89 (t, 2H), 2.38 to 2.32 (m, 6H), 1.88 to 1.84 (m, 2H); ES-MS m/z 580.3 [M+H]$^+$, RT (min) 2.28.

Example 57

(4-{3-[4-Amino-5-(2-benzyl-2H-Indazol-6-yl)-pyrrolo[2,1-f][1,2,4]triazin-7-yl]-propyl}-piperazin-1-yl)-pyrrolidin-1-yl-methanone

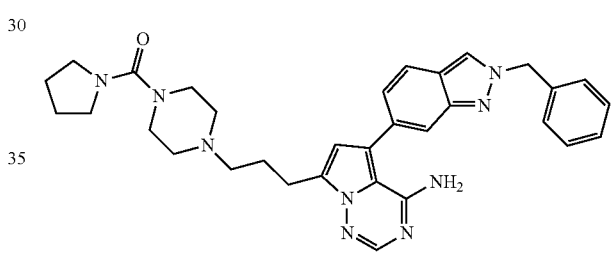

$^1$H NMR (300 MHz, DMSO-d$_6$) δ 8.54 (s, 1H), 7.89 (s, 1H), 7.79 (d, 1H), 7.57 (s, 1H), 7.35 to 7.29 (m, 5H), 7.13 (dd, 1H), 6.59 (s, 1H), 5.64 (s, 2H), 3.23 to 3.19 (m, 4H), 3.12 to 3.10 (m, 4H), 2.88 (t, 2H), 2.37 to 2.31 (m, 6H), 1.87 to 1.83 (m, 2H), 1.72 to 1.68 (m, 4H); ES-MS m/z 564.4 [M+H]$^+$, RT (min) 2.20.

Example 58

2-(4-{3-[4-Amino-5-(2-benzyl-2H-indazol-6-yl)-pyrrolo[2,1-f][1,2,4]triazin-7-yl]-propyl}-piperazin-1-yl)-1-pyrrolidin-1-yl-ethanone

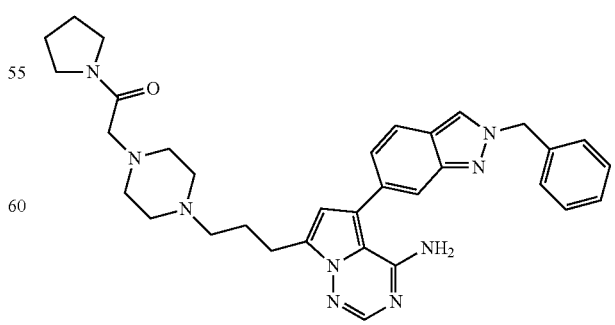

$^1$H NMR (300 MHz, DMSO-d$_6$) δ 8.54 (s, 1H), 7.87 (s, 1H), 7.78 (d, 1H), 7.57 (s, 1H), 7.34 to 7.27 (m, 5H), 7.14 (d,

1H), 6.58 (s, 1H), 5.62 (s, 2H), 3.47 to 3.42 (m, 4H), 3.26 to 3.22 (m, 4H), 3.02 (s, 2H), 2.87 (t, 2H), 2.43 to 2.25 (m, 6H), 1.83 to 1.71 (m, 6H); ES-MS m/z 578.4 [M+H]⁺, RT (min) 2.12.

Example 59

4-{3-[4-Amino-5-(2-benzyl-2H-indazol-6-yl)-pyrrolo[2,1-f][1,2,4]triazin-7-yl]-propyl}-piperazine-1-carboxylic acid tert-butyl ester

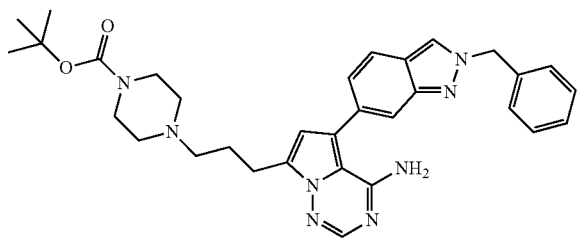 [SMILES: CC(C)(C)OC(=O)N1CCN(CCCc2cc(-c3ccc4cn(Cc5ccccc5)nc4c3)c3c(N)ncnn23)CC1]

$^1$H NMR (300 MHz, DMSO-d$_6$) δ 8.54 (s, 1H), 7.89 (s, 1H), 7.79 (d, 1H), 7.58 (s, 1H), 7.36 to 7.30 (m, 5H), 7.14 (dd, 1H), 6.60 (s, 1H), 5.65 (s, 2H), 3.29 to 3.25 (m, 4H), 2.88 (t, 2H), 2.36 (t, 2H), 2.29 (t, 4H), 1.88 to 1.84 (m, 2H), 1.37 (s, 9H); ES-MS m/z 567.2 [M+H]⁺, RT (min) 2.34.

Example 60

2-(4-{3-[4-Amino-5-(2-benzyl-2H-indazol-6-yl)-pyrrolo[2,1-f][1,2,4]triazin-7-yl]-propyl}-piperazin-1-yl)-ethanol

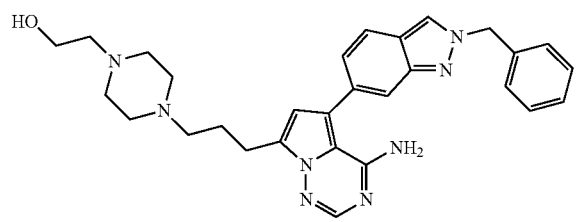 [SMILES: Nc1ncnn2c(CCCN3CCN(CCO)CC3)cc(-c3ccc4cn(Cc5ccccc5)nc4c3)c12]

$^1$H NMR (300 MHz, DMSO-d$_6$) δ 8.54 (s, 1H), 7.88 (s, 1H), 7.79 (d, 1H), 7.58 (s, 1H), 7.36 to 7.28 (m, 5H), 7.14 (dd, 1H), 6.60 (s, 1H), 5.65 (s, 2H), 4.35 (broad s, 1H), 3.46 to 3.44 (m, 2H), 2.87 (t, 2H), 2.37 to 2.28 (m, 12H), 1.85 to 1.81 (m, 2H); ES-MS m/z 511.3 [M+H]⁺, RT (min) 1.91.

Example 61

4-{3-[4-Amino-5-(2-benzyl-2H-indazol-6-yl)-pyrrolo[2,1-f][1,2,4]triazin-7-yl]-propyl}-piperazin-2-one

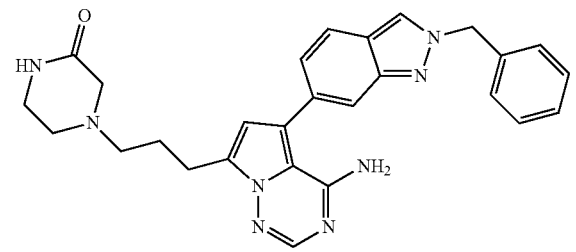 [SMILES: Nc1ncnn2c(CCCN3CCNC(=O)C3)cc(-c3ccc4cn(Cc5ccccc5)nc4c3)c12]

$^1$H NMR (300 MHz, DMSO-d$_6$) δ 8.54 (s, 1H), 7.88 (s, 1H), 7.79 (d, 1H), 7.72 (broad s, 1H), 7.58 (s, 1H), 7.35 to 7.28 (m, 5H), 7.14 (dd, 1H), 6.61 (s, 1H), 5.65 (s, 2H), 3.14 to 3.11 (m, 2H), 2.91 to 2.87 (m, 4H), 2.53 (t, 2H), 2.42 (t, 2H), 1.88 to 1.84 (m, 2H); ES-MS m/z 481.2 [M+H]⁺, RT (min) 1.99.

Example 62

5-(2-Benzyl-2H-indazol-6-yl)-7-[3-(4-pyridin-2-yl-piperazin-1-yl)-propyl]-pyrrolo[2,1-f][1,2,4]triazin-4-ylamine

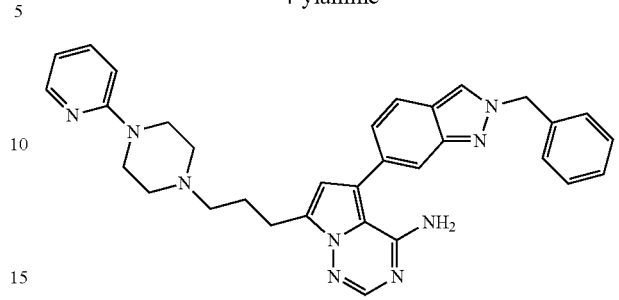

$^1$H NMR (300 MHz, DMSO-d$_6$) δ 8.54 (s, 1H), 8.08 (dd, 1H), 7.90 (s, 1H), 7.80 (d, 1H), 7.58 (s, 1H), 7.49 (ddd, 1H), 7.36 to 7.30 (m, 5H), 7.15 (dd, 1H), 6.78 (d, 1H), 6.62 (s, 1H), 6.60 (dd, 1H), 5.65 (s, 2H), 3.44 (t, 4H), 2.92 (t, 2H), 2.46 to 2.38 (m, 4H), 1.92 to 1.88 (m, 2H); ES-MS m/z 544.2 [M+H]⁺, RT (min) 2.17.

Example 63

5-(2-Benzyl-2H-indazol-6-yl)-7-{3-[4-(4-methyl-pyridin-2-yl)-piperazin-1-yl]-propyl}-pyrrolo[2,1-f][1,2,4]triazin-4-ylamine

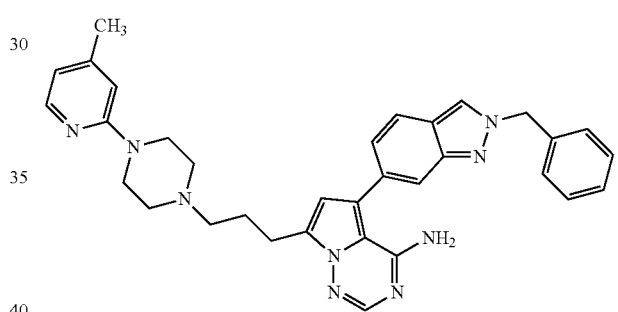

$^1$H NMR (300 MHz, DMSO-d$_6$) δ 8.54 (s, 1H), 7.93 (d, 1H), 7.89 (s, 1H), 7.79 (d, 1H), 7.58 (s, 1H), 7.36 to 7.28 (m, 5H), 7.14 (dd, 1H), 6.62 (s, 2H), 6.46 (d, 1H), 5.65 (s, 2H), 3.42 (t, 4H), 2.91 (t, 2H), 2.51 to 2.36 (m, 6H), 2.18 (s, 3H), 1.94 to 1.86 (m, 2H); ES-MS m/z 558.2 [M+H]⁺, RT (min) 2.07.

Example 64

5-(2-Benzyl-2H-indazol-6-yl)-7-{3-[4-(3-methyl-pyridin-2-yl)-piperazin-1-yl]-propyl}-pyrrolo[2,1-f][1,2,4]triazin-4-ylamine

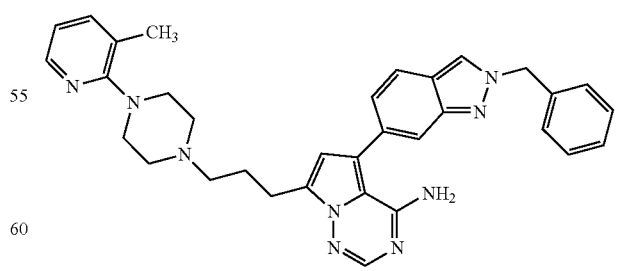

$^1$H NMR (300 MHz, DMSO-d$_6$) δ 8.54 (s, 1H), 7.89 (s, 1H), 7.79 (d, 1H), 7.58 (s, 1H), 7.40 to 7.29 (m, 6H), 7.14 (dd, 1H), 6.62 (s, 1H), 6.56 (d, 1H), 6.47 (d, 1H), 5.65 (s, 2H), 3.42 (t, 4H), 2.91 (t, 2H), 2.45 to 2.37 (m, 6H), 2.27 (s, 3H), 1.92 to 1.87 (m, 2H); ES-MS m/z 558.2 [M+H]⁺, RT (min) 2.10.

Example 65

2-(4-{3-[4-Amino-5-(2-benzyl-2H-indazol-6-yl)-pyrrolo[2,1-f][1,2,4]triazin-7-yl]-propyl}-piperazin-1-yl)-nicotinonitrile

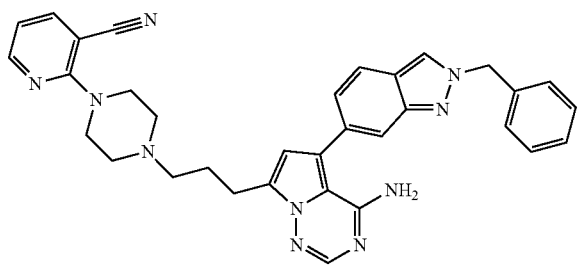 [SMILES: N#Cc1cccnc1N1CCN(CCCc2cc(-c3ccc4cn(Cc5ccccc5)nc4c3)c3c(N)ncnn23)CC1]

$^1$H NMR (300 MHz, DMSO-d$_6$) δ 8.54 (s, 1H), 8.39 to 8.37 (m, 1H), 8.03 (dd, 1H), 7.89 (s, 1H), 7.79 (d, 1H), 7.58 (s, 1H), 7.35 to 7.29 (m, 5H), 7.14 (d, 1H), 6.88 (dd, 1H), 6.62 (s, 1H), 5.64 (s, 2H), 3.61 to 3.57 (m, 4H), 2.91 (t, 2H), 2.52 to 2.48 (obscured by DMSO peak, 4H), 2.42 (t, 2H), 1.92 to 1.87 (m, 2H); ES-MS m/z 569.3 [M+H]$^+$, RT (min) 2.23.

Example 66

3-(4-{3-[4-Amino-5-(2-benzyl-2H-indazol-6-yl)-pyrrolo[2,1-f][1,2,4]triazin-7-yl]-propyl}-piperazin-1-yl)-propionitrile

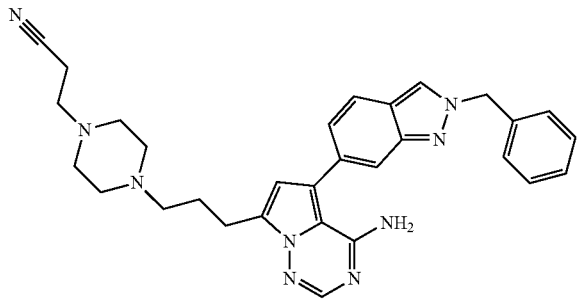 [SMILES: N#CCCN1CCN(CCCc2cc(-c3ccc4cn(Cc5ccccc5)nc4c3)c3c(N)ncnn23)CC1]

$^1$H NMR (300 MHz, MeOD) δ 8.34 (s, 1H), 7.83 to 7.80 (m, 2H), 7.66 (s, 1H), 7.36 to 7.31 (m, 5H), 7.24 (d, 1H), 6.62 (s, 1H), 5.65 (s, 2H), 3.0 (t, 2H), 2.69 to 2.46 (m, 14H), 2.02 to 1.97 (m, 2H); ES-MS m/z 520.3 [M+H]$^+$, RT (min) 2.06.

Example 67

5-(2-Benzyl-2H-indazol-6-yl)-7-[3-(4-methanesulfonyl-piperazin-1-yl)-propyl]-pyrrolo[2,1-f][1,2,4]triazin-4-ylamine

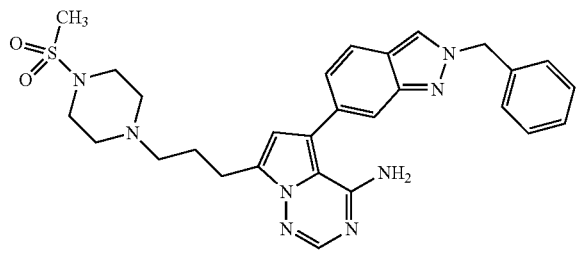 [SMILES: CS(=O)(=O)N1CCN(CCCc2cc(-c3ccc4cn(Cc5ccccc5)nc4c3)c3c(N)ncnn23)CC1]

$^1$H NMR (300 MHz, DMSO-d$_5$) δ 8.54 (s, 1H), 7.88 (s, 1H), 7.79 (d, 1H), 7.57 (s, 1H), 7.35 to 7.29 (m, 5H), 7.13 (d, 1H), 6.59 (s, 1H), 5.64 (s, 2H), 3.06 (t, 4H), 2.89 (t, 2H), 2.83 (s, 3H), 2.44 to 2.38 (m, 6H), 1.88 to 1.83 (m, 2H); ES-MS m/z 545.3 [M+H]$^+$, RT (min) 2.08.

Example 68

1-{3-[4-Amino-5-(2-benzyl-2H-indazol-6-yl)-pyrrolo[2,1-f][1,2,4]triazin-7-yl]propyl}-piperidin-4-ol

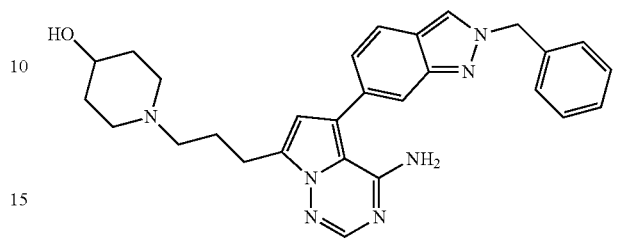

$^1$H NMR (300 MHz, DMSO-d$_5$) δ 8.54 (s, 1H), 7.88 (s, 1H), 7.79 (d, 1H), 7.57 (s, 1H), 7.35 to 7.29 (m, 5H), 7.13 (d, 1H), 6.58 (s, 1H), 5.64 (s, 2H), 4.52 (s, 1H), 3.39 to 3.34 (m, 1H), 2.85 (t, 2H), 2.69 to 2.66 (m, 2H), 2.30 (t, 2H), 1.93 (t, 2H), 1.86 to 1.78 (m, 2H), 1.68 to 1.65 (m, 2H), 1.37 to 1.29 (m, 2H); ES-MS m/z 482.3 [M+H]$^+$, RT (min) 0.86.

Example 69

1-{3-[4-Amino-5-(2-benzyl-2H-indazol-6-pyrrolo[2,1-f][1,2,4]triazin-7-yl]-propyl}-azetidin-3-ol

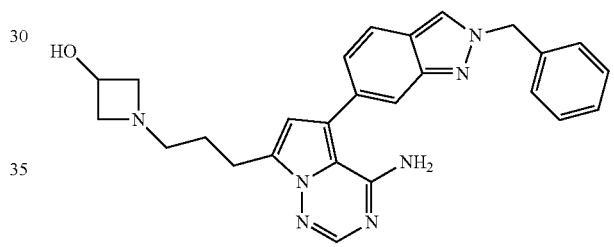

$^1$H NMR (300 MHz, DMSO-d$_6$) δ 8.54 (s, 1H), 7.88 (s, 1H), 7.79 (d, 1H), 7.57 (s, 1H), 7.35 to 7.29 (m, 5H), 7.13 (d, 1H), 6.58 (s, 1H), 5.64 (s, 2H), 4.59 to 4.50 (m, 1H), 4.15 to 4.06 (m, 1H), 3.49 (t, 2H), 2.87 to 2.83 (m, 2H), 2.61 (t, 2H), 2.42 to 2.38 (m, 2H), 2.32 to 2.25 (m, 0.5H), 1.84 to 1.79 (m, 0.5H), 1.69 to 1.67 (m, 1H); ES-MS m/z 454.2 [M+H]$^+$, RT (min) 2.17.

Example 70

3-({3-[4-Amino-5-(2-benzyl-2H-indazol-6-yl)-pyrrolo[2,1-f][1,2,4]triazin-7-yl]-propylamino}-methyl)-azetidine-1-carboxylic acid tert-butyl ester

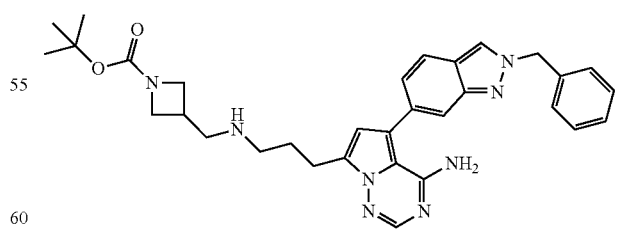

$^1$H NMR (300 MHz, DMSO-d$_6$) δ 8.54 (s, 1H), 7.88 (s, 1H), 7.79 (d, 1H), 7.57 (s, 1H), 7.35 to 7.28 (m, 5H), 7.13 (dd, 1H), 6.59 (s, 1H), 5.64 (s, 2H), 3.83 (broad s, 2H), 3.50 (broad s, 2H), 2.91 (t, 2H), 2.74 (d, 2H), 2.65 to 2.58 (m, 3H), 2.51 to 2.49 (m, 1H), 1.86 to 1.82 (m, 2H), 1.34 (s, 9H); ES-MS m/z 5672 [M+H]$^+$, RT (min) 2.79.

Example 71

4-{3-[4-Amino-5-(2-benzyl-2H-indazol-6-yl)-pyrrolo[2,1-f][1,2,4]triazin-7-yl]-propylamino}-piperidine-1-carboxylic acid ethyl ester

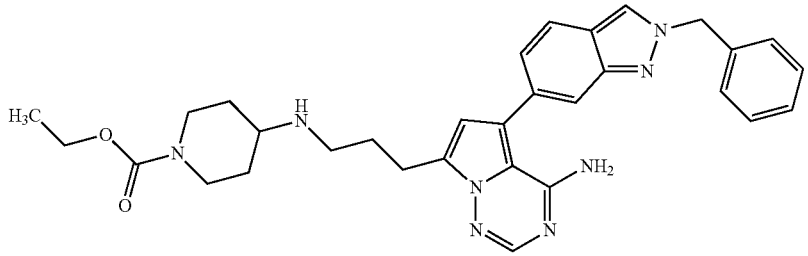 [SMILES: CCOC(=O)N1CCC(NCCCc2cc(-c3ccc4cn(Cc5ccccc5)nc4c3)c3c(N)ncnn23)CC1]

¹H NMR (300 MHz, DMSO-d₆) δ 8.54 (s, 1H), 7.88 (s, 1H), 7.79 (d, 1H), 7.57 (s, 1H), 7.35 to 7.28 (m, 5H), 7.13 (dd, 1H), 6.58 (s, 1H), 5.64 (s, 2H), 3.98 (q, 2H), 3.80 (broad d, 2H), 2.90 (t, 2H), 2.83 (broad s, 2H), 2.58 to 2.54 (m, 2H), 1.81 to 1.71 (m, 4H), 1.57 (s, 1H), 1.14 (t, 3H), 1.09 to 1.05 (m, 2H); ES-MS m/z 553.3 [M+H]⁺, RT (min) 1.67.

Example 72

4-{3-[4-Amino-5-(2-benzyl-2H-indazol-6-yl)-pyrrolo[2,1-f][1,2,4]triazin-7-yl]-propyl}-piperazine-1-carboxylic acid methylamide

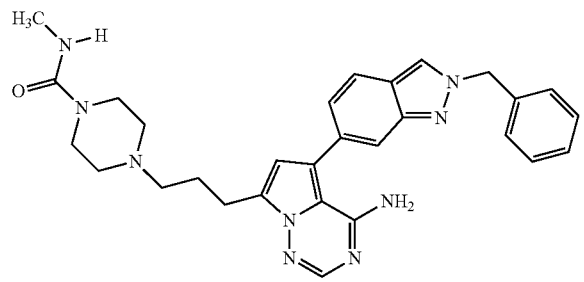 [SMILES: CNC(=O)N1CCN(CCCc2cc(-c3ccc4cn(Cc5ccccc5)nc4c3)c3c(N)ncnn23)CC1]

¹H NMR (300 MHz, DMSO-d₆) δ 8.54 (s, 1H), 7.88 (s, 1H), 7.79 (d, 1H), 7.58 (s, 1H), 7.36 to 7.29 (m, 5H), 7.14 (dd, 1H), 6.60 (s, 1H), 6.39 to 6.36 (m, 1H), 5.65 (s, 2H), 3.22 (t, 4H), 2.89 (t, 2H), 2.52 (d, 3H), 2.35 (t, 2H), 2.28 (t, 4H), 1.89 to 1.84 (m, 2H); ES-MS m/z 524.2 [M+H]⁺, RT (min) 2.08.

Example 73

(4-{3-[4-Amino-5-(2-benzyl-2H-indazol-6-yl)-pyrrolo[2,1-f][1,2,4]triazin-7-yl]-propyl}-piperazin-2-yl)-methanol

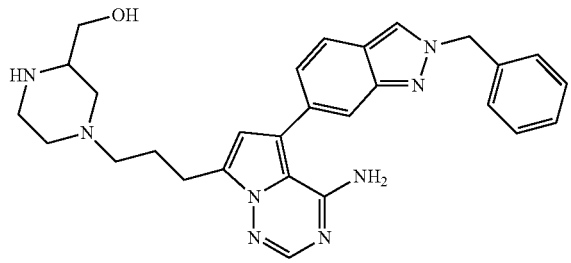 [SMILES: Nc1ncnn2c(CCCN3CCNC(CO)C3)cc(-c3ccc4cn(Cc5ccccc5)nc4c3)c12]

¹H NMR (300 MHz, DMSO-d₆) δ 8.55 (s, 1H), 7.89 (s, 1H), 7.79 (d, 1H), 7.35 to 7.30 (m, 5H), 7.13 (d, 1H), 6.60 (s, 1H), 5.65 (s, 2H), 5.04 (broad s, 1H), 3.42 to 3.28 (m, 8H), 2.95 to 2.79 (m, 5H), 2.39 (broad s, 1H), 1.86 to 1.84 (m, 2H); ES-MS m/z 497.2 [M+H]⁺, RT (min) 1.93.

Example 74

8-{3-[4-Amino-5-(2-benzyl-2H-indazol-6-yl)-pyrrolo[2,1-f][1,2,4]triazin-7-yl]-propyl}-hexahydro-pyrazino[2,1-c][1,4]oxazin-4-one

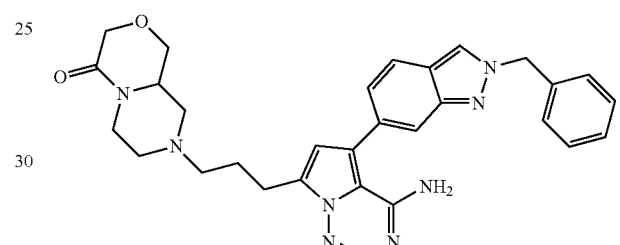

¹H NMR (300 MHz, DMSO-d₅) δ 8.55 (s, 1H), 7.89 (s, 1H), 7.80 (d, 1H), 7.58 (s, 1H), 7.41 to 7.29 (m, 5H), 7.14 (d, 1H), 6.61 (s, 1H), 5.65 (s, 2H), 4.30 (d, 1H), 3.99 to 3.93 (m, 3H), 3.52 to 3.43 (m, 2H), 2.92 to 2.85 (m, 4H), 2.66 (t, 2H), 2.41 to 2.37 (m, 2H), 1.89 to 1.83 (m, 2H), 1.68 (t, 1H); ES-MS m/z 537.2 [M+H]⁺, RT (min) 2.10.

Example 75

7-{3-[4-Amino-5-(2-benzyl-2H-indazol-6-yl)-pyrrolo[2,1-f][1,2,4]triazin-7-yl]-propyl}-hexahydro-oxazolo[3,4-a]pyrazin-3-one

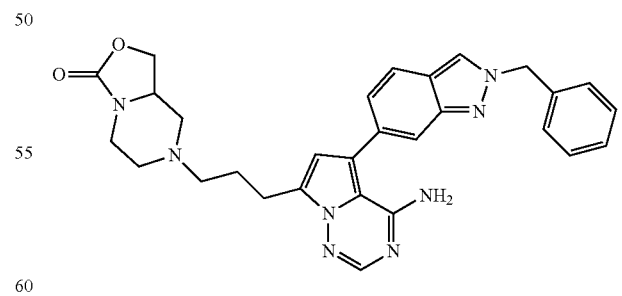

¹H NMR (300 MHz, CD₃OD) δ 8.38 (s, 1H), 7.84 to 7.82 (m, 2H), 7.65 (s, 1H), 7.38 to 7.33 (m, 5H), 7.24 (dd, 1H), 6.63 (s, 1H), 5.66 (s, 2H), 4.41 (t, 1H), 3.98 (dd, 1H), 3.92 to 3.86 (m, 1H), 3.72 to 3.69 (m, 1H), 3.14 to 2.99 (m, 5H), 2.92 to 2.86 (m, 1H), 2.52 (dt, 2H), 2.05 to 1.96 (m, 3H); ES-MS m/z 523.3 [M+H]⁺, RT (min) 2.11.

Example 76

6-{3-[4-Amino-5-(2-benzyl-2H-indazol-6-yl)-pyrrolo[2,1-f][1,2,4]triazin-7-yl]-propyl}-hexahydro-pyrido[3,4-b][1,4]oxazin-2-one

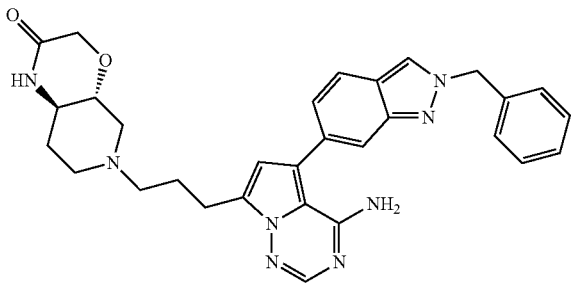 [SMILES: Nc1ncnn2c(CCCN3CC[C@H]4NC(=O)CO[C@@H]4C3)cc(-c3ccc4cn(Cc5ccccc5)nc4c3)c12]

$^1$H NMR (300 MHz, DMSO-$d_6$) δ 8.54 (s, 1H), 8.22 (s, 1H), 7.88 (d, 1H), 7.79 (d, 1H), 7.58 (s, 1H), 7.39 to 7.30 (m, 5H), 7.14 (d, 1H), 6.60 (s, 1H), 5.66 (s, 2H), 4.02 (s, 2H), 3.29 to 3.22 (m, 1H), 3.01 to 2.94 (m, 2H), 2.87 to 2.79 (m, 3H), 2.46 to 2.38 (m, 2H), 1.96 to 1.75 (m, 4H), 1.30 to 1.23 (m, 2H); ES-MS m/z 537.3 [M+H]$^+$, RT (min) 2.15.

Example 77

(4-{3-[4-Amino-5-(2-benzyl-2H-Indazol-6-yl)-pyrrolo[2,1-f][1,2,4]triazin-7-yl]-propyl}-piperazin-1-yl)-cyclopropyl-methasone

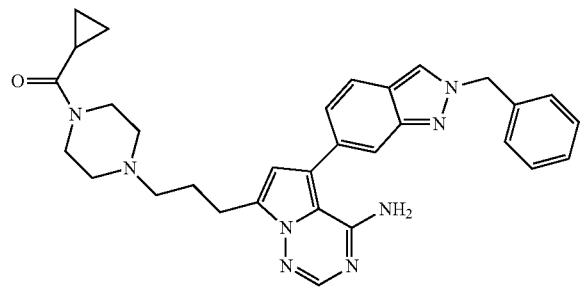 [SMILES: Nc1ncnn2c(CCCN3CCN(C(=O)C4CC4)CC3)cc(-c3ccc4cn(Cc5ccccc5)nc4c3)c12]

$^1$H NMR (300 MHz, DMSO-$d_x$) δ 8.55 (s, 1H), 7.89 (s, 1H), 7.80 (s, 1H), 7.58 (s, 1H), 7.36 to 7.30 (m, 5H), 7.14 (dd, 1H), 6.61 (s, 1H), 5.65 (s, 2H), 3.63 (broad s, 2H), 3.42 (broad s, 2H), 2.90 (t, 2H), 2.38 (t, 4H), 2.29 (broad s, 2H), 1.94 to 1.85 (m, 3H), 0.70 to 0.64 (m, 4H); ES-MS m/z 535.3 [M+H]$^+$, RT (min) 1.18.

Example 78

2-(4-{3-[4-Amino-5-(2-benzyl-2H-indazol-6-yl)-pyrrolo[2,1-f][1,2,4]triazin-7-yl]-propyl}-piperazin-1-yl)-N-methyl-acetamide

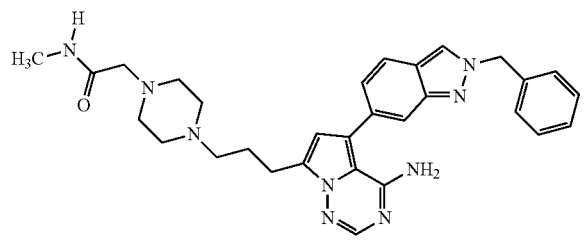 [SMILES: CNC(=O)CN1CCN(CCCc2cc(-c3ccc4cn(Cc5ccccc5)nc4c3)c3c(N)ncnn23)CC1]

$^1$H NMR (300 MHz, DMSO-$d_6$) δ 8.55 (s, 1H), 7.88 (s, 1H), 7.79 (d, 1H), 7.60 to 7.57 (m, 2H), 7.36 to 7.30 (m, 5H), 7.14 (dd, 1H), 6.59 (s, 1H), 5.65 (s, 2H), 3.15 (d, 2H), 2.90 to 2.84 (m, 4H), 2.58 (d, 3H), 2.44 to 2.33 (m, 8H), 1.87 to 1.82 (m, 2H); ES-MS m/z 538.3 [M+H]$^+$, RT (min) 0.82.

Example 79

Preparation of 1-(4-{3-[4-Amino-5-(2-benzyl-2H-indazol-6-yl)-pyrrolo[2,1-f][1,2,4]triazin-7-yl]-propyl}-piperazin-1-yl)-ethanone

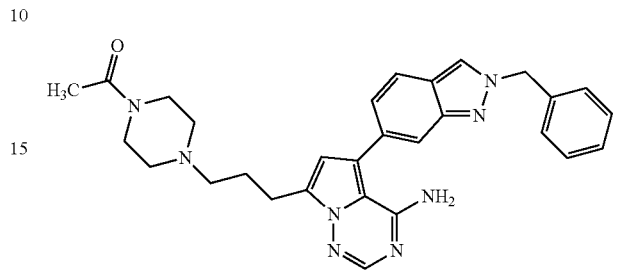

$^1$H NMR (300 MHz, DMSO-$d_6$) δ 8.55 (s, 1H), 7.89 (s, 1H), 7.79 (d, 1H), 7.58 (s, 1H), 7.36 to 7.30 (m, 5H), 7.14 (dd, 1H), 6.60 (s, 1H), 5.65 (s, 2H), 3.41 to 3.36 (m, 4H), 2.89 (t, 2H), 2.38 to 2.31 (m, 4H), 2.28 (t, 2H), 1.95 (s, 3H), 1.91 to 1.83 (m, 2H); ES-MS m/z 509.3 [M+H]$^+$, RT (min) 2.17.

Example 80

Preparation of {3-[4-Amino-5-(2-benzyl-2H-indazol-6-yl)-pyrrolo[2,1-f][1,2,4]triazin-7-yl]-phenyl}-methanol

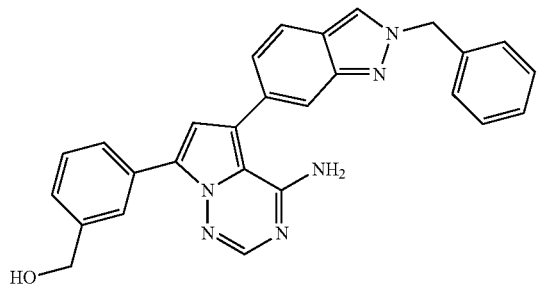 [SMILES: Nc1ncnn2c(-c3cccc(CO)c3)cc(-c3ccc4cn(Cc5ccccc5)nc4c3)c12]

Step 1: Preparation of [3-(4-Amino-pyrrolo[2,1-f][1,2,4]triazin-7-yl)-phenyl]-methanol

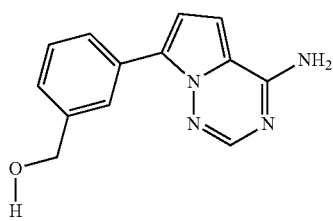 [SMILES: Nc1ncnn2c(-c3cccc(CO)c3)ccc12]

Intermediate B (3.00 g, 14.1 mmol) and 3-hydroxymethylphenyl boronic acid (2.57 g, 16.9 mmol) were suspended in 36 mL of 8:1 to toluene:dioxane and degassed via a vacuum/N$_2$ purge (3 cycles). 1,1'-Bis(diphenylphosphino)ferrocene-palladium(II) chloride-complex with CH$_2$Cl$_2$ (0.52 g, 0.7 mmol) was added followed by 21 mL of 2M aqueous sodium carbonate and the mixture was heated with stirring to 75° C. overnight. The mixture was allowed to cool to room temp (solid mass formed) and diluted with water and EtOAc. The mixture was filtered through Celite® and the pad washed well with EtOAc followed by MeOH. The filtrate was poured into a separatory funnel and the layers were separated. The organic phase was washed with brine, dried (Na$_2$SO$_4$), filtered and concentrated in vacuo. The residue was purified by Isco® (Red-Sep 120, eluting with 75%-100% EtOAc, hexanes) to provide 1.54 g (45%) of the title compound as an off white solid. $^1$H-NMR (DMSO-d$_6$) δ 7.98 (s, 1H), 7.91 (m, 2H), 7.22 (bs, 2H), 7.38 (t, 1H), 7.24 (d, 1H), 6.99 (s, 2H), 5.25 (t, 12H), 4.55 (d, 2H); LC-MS [M+H]$^+$=241.3, RT=1.51 min.

Step 2: Preparation of [3-(4-Amino-5-bromo-pyrrolo[2,1-f][1,2,4]triazin-7-yl)-phenyl]methanol 2.86 (m, 1H), 2.52 (dt, 2H), 2.05 to 1.96 (m, 3H); ES-MS m/z 523.3 [M+H]$^+$, RT (min) 2.11.

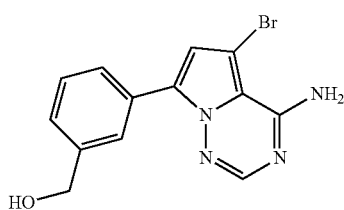 [SMILES: Nc1ncnn2c(-c3cccc(CO)c3)cc(Br)c12]

The product from step 1 (1.54 g, 6.4 mmol) was dissolved in 18 mL of 1:1 DMF:THF. The mixture was cooled to −20° C. (internal temperature) and 1,3-dibromo-5,5-dimethylhydantoin (0.92 g, 3.2 mmol) was added in 4 equal portions over 40 minutes. The mixture was stirred for an additional 1 hour during which the internal temp rose to −5° C. A solid mass formed, which was diluted with a mixture of 15 mL of 2M Na$_2$CO$_3$, 10 mL of sat. Na$_2$SO$_3$ and 60 mL of water and the mixture was stirred for an additional 30 minutes. The solid was collected by filtration, washed with water and dried in a vacuum oven at 40° C. to give 1.96 g (95%) of the title compound as a tan solid. $^1$H-NMR (DMSO-d$_6$) δ 8.10 (bs, 1H), 7.94 (s, 2H), 7.86 (d, 1H), 7.40 (t, 1H), 7.29 (d, 1H), 7.17 (s, 1H), 6.84 (bs, 1H), 5.22 (t, 1H), 4.56 (d, 2H); LC-MS [M+H]$^+$=319.3, 321.1, RT=2.29 min.

Step 3: Preparation of 5-Bromo-7-[3-(tert-butyl-dimethyl-silanyloxymethyl)-phenyl]-pyrrolo[2,1-f][1,2,4]triazin-4-ylamine

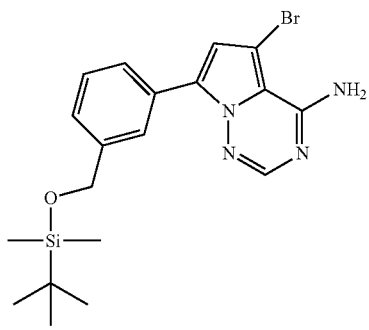 [SMILES: CC(C)(C)[Si](C)(C)OCc1cccc(-c2cc(Br)c3c(N)ncnn23)c1]

The product from step 2 (1.96 g, 6.1 mmol) was dissolved in 6 mL of DMF and imidazole (0.92 g, 13.5 mmol) was added. To the resulting solution was added a THF solution of TBDMS chloride (6.8 mL of a 1.0M solution) was added dropwise over 2 minutes. The mixture was stirred for 6 hours at rt and heated to 50° C. overnight. TLC analysis indicated only ~50% conversion. An additional 6.8 mL of 1M TBDMSCl in THF was added at 50° C. (carefully due to mild exotherm) and stirring was continued for an additional hour at 50° C. The mixture was cooled to rt and partitioned between 100 mL of water and 3×50 mL of EtOAc. The combined organic phases were washed with water and brine, dried (Na$_2$SO$_4$), filtered and concentrated in vacuo to give a brown solid. The solid was triturated with hexanes, collected by filtration, washed with hexanes and dried in a vacuum oven at 40° C. to give 2.19 g (82%) of the title compound as a tan solid. $^1$H NMR (DMSO-d$_6$) δ 8.08 (bs, 1H), 7.90 (s, 1H), 7.80 (s, 1H), 7.74 (d, 1H), 7.40 (t, 1H), 7.18 (d, 1H), 7.07 (s, 1H), 6.77 (bs, 1H), 4.63 (s, 2H), 0.81 (s, 9H), 0.02 (s, 6H); LC-MS [M+H]$^+$=433.4, 435.2, RT=4.06 min.

Step 4: Preparation of 5-(2-Benzyl-2H-indazol-6-yl)-7-[3-(tert-butyl-dimethyl-silanyloxymethyl)-phenyl]-pyrrolo[2,1-f][1,2,4]triazin-4-ylamine

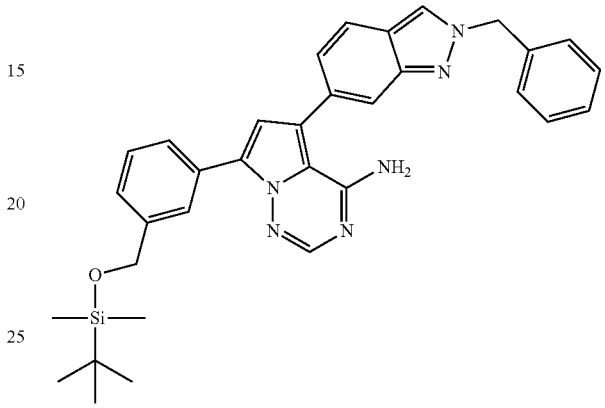

Pd(OAc)$_2$ (11 mg, 0.05 mmol) was suspended in a degassed mixture of 3:2 toluene:dioxane and PPh$_3$ (52 mg, 0.20 mmol) was added. The mixture was stirred for 10 minutes and then the product from step 3 (433 mg, 1.00 mmol) and Intermediate C (434 mg, 1.30 mmol) were added followed by 2.5 mL of 2M aqueous Na$_2$CO$_3$ solution. The mixture was heated to 90° C. overnight. The reaction was allowed to cool to rt and partitioned between water and EtOAc. The layers were separated and the aqueous layer was extracted with EtOAc. The combined organic phases were washed with brine, dried (Na$_2$SO$_4$), filtered and concentrated in vacuo. The residue was purified by Isco® (Redi-sep 40, eluting with 75-100% EtOAc/Hexanes) to provide 368 mg (66%) of the title compound as an off-white solid. $^1$H-NMR (DMSO-d$_6$) δ 8.44 (s, 1H), 7.98 (s, 1H), 7.84 (s, 1H), 7.82 (m, 1H), 7.74 (d, 1H), 7.56 (s, 1H), 7.50-7.39 (m, 2H), 7.31 (t, 1H), 7.26-7.12 (m, 5H), 7.08 (d, 1H), 7.00, (s, 1H), 5.57 (s, 2H), 4.64 (s, 2H) 0.82 (s, 9H), 0.01 (s, 6H); LC-MS [M+H]$^+$=561.5, RT=3.65 min.

Step 5: Preparation of the Title Compound

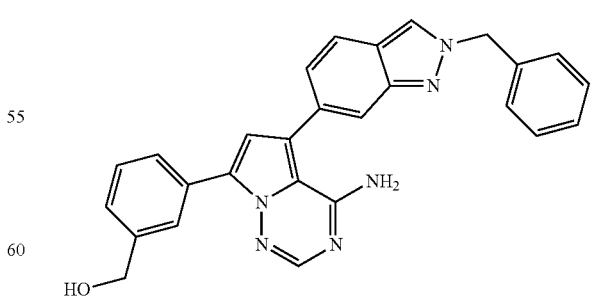

The product from step 4 (367 mg, 0.65 mmol) was dissolved in 4 mL of 1:1 EtOH:THF and 0.5 mL of water was added followed by the addition of 1 drop of concentrated aqueous HCl. The mixture was stirred for 1 hour (ppt formed) and the solid was collected by filtration, washed with THF and air dried overnight to give 286 mg (98%) of the title compound as a white solid. $^1$H-NMR (DMSO-$d_6$) δ 9.00 (bs, 1H), 8.63 (s, 1H), 8.26 (s, 1H), 8.02, (s, 1H) 7.96-7.86 (m, 2H) 7.80 (s, 1H), 7.49 (t, 1H), 7.46-7.30 (m, 6H), 7.28 (d, 1H), 7.26 (bs, 1H), 5.72 (s, 2H), 4.60 (s, 2H); LC-MS [M+H]$^+$= 447.3, RT=2.72 min.

Example 81

Preparation of 5-(2-Benzyl-2H-indazol-6-yl)-7-(3-pyrrolidin-1-ylmethyl-phenyl)-pyrrolo[2,1-f][1,2,4]triazin-4-ylamine

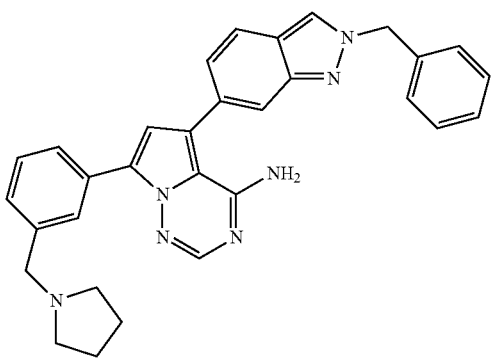 [SMILES: Nc1ncnn2c(-c3cccc(CN4CCCC4)c3)cc(-c3ccc4cn(Cc5ccccc5)nc4c3)c12]

Step 1: Preparation of 5-(2-Benzyl-2H-indazol-6-yl)-7-(3-chloromethyl-phenyl)-pyrrolo[2,1-f][1,2,4]triazin-4-ylamine

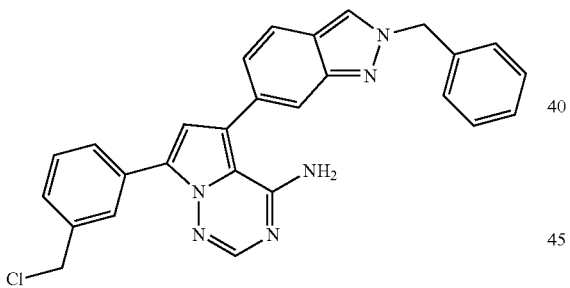

{3-[4-Amino-5-(2-benzyl-2H-indazol-6-yl)-pyrrolo[2,1-f][1,2,4]triazin-7-yl]-phenyl}-methanol (254 mg, 0.57 mmol) was suspended in 2 mL of dioxane and SOCl$_2$ (83 μL, 1:1 mmol) was added followed by the dropwise addition of pyridine (0.14 mL, 1.7 mmol). The mixture was stirred for 1.5 hours and carefully quenched by the addition of 2M aqueous Na$_2$CO$_3$. The mixture was diluted with water and extracted with 3×10 mL of 10% MeOH/EtOAc. The combined organic fractions were washed with 1M aqueous H$_3$PO$_4$, brine, dried (Na$_2$SO$_4$), filtered and concentrated. The residue was purified by ISCO® Redi-sep 12, 80% to 100% EtOAc/hexanes to provide 65 mg (24%) of the title compound as a crusty solid. $^1$H-NMR (DMSO-$d_6$) δ 8.55 (s, 1H), 8.19 (s, 1H), 8.08, (d, 1H) 7.99 (s, 1H) 7.83 (d, 1H) 7.70 (s, 1H), 7.46 (t, 1H), 7.40 (t, 1H), 7.38-7.26 (m, 4H), 7.24 (d, 1H), 7.22 (s, 1H), 5.72 (s, 2H), 4.60 (s, 2H); LC-MS [M+H]$^+$=465.3, 467.2, RT=3.24 min.

Step 2: Preparation the Title Compound

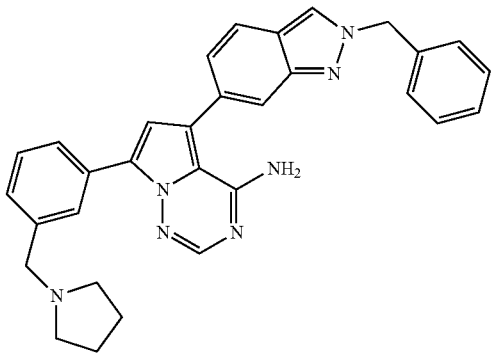 [SMILES: Nc1ncnn2c(-c3cccc(CN4CCCC4)c3)cc(-c3ccc4cn(Cc5ccccc5)nc4c3)c12]

The product from step 1 (60 mg, 0.13 mmol) was dissolved in 1 mL of DMF and K$_3$PO$_4$ (33 mg, 0.16 mmol) was added. The mixture was treated with pyrrolidine (0.15 mL, 1.55 mmol) and stirred for 1 hour. The mixture was diluted with water (10 mL) and stirred for 10 minutes. The precipitate was collected and purified by preparative HPLC eluting with 10%-90% acetonitrile/water (0.1% TFA) to provide 29 mg (54%) of the title compound.

$^1$H-NMR (DMSO-$d_6$) δ 8.56 (s, 1H), 8.02-7.93 (m, 3H), 7.84, (d, 1H) 7.69 (s, 1H) 7.40 (t, 1H) 7.37-7.34 (m, 6H), 7.22 (d, 1H), 7.13 (s, 1H), 5.64 (s, 2H), 3.63 (s, 2H), 2.42 (bs, 4H), 1.70 (bs, 4H); LC-MS [M+H]$^+$=500.2, RT=2.42 min.

Example 82

Preparation of 5-(2-Benzyl-2H-indazol-6-yl)-7-(3-piperazin-1-yl-phenyl)-pyrrolo[2,1-f][1,2,4]triazin-4-ylamine

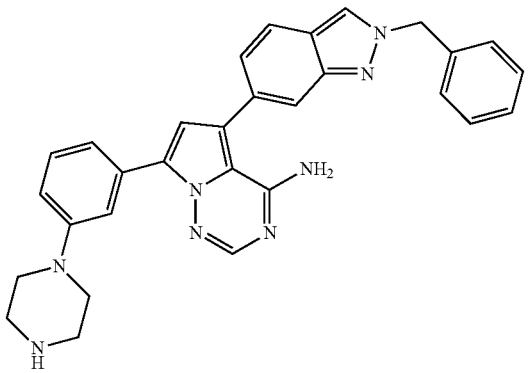 [SMILES: Nc1ncnn2c(-c3cccc(N4CCNCC4)c3)cc(-c3ccc4cn(Cc5ccccc5)nc4c3)c12]

Step 1: Preparation of 4-(3-Bromo-phenyl)-piperazine-1-carboxylic acid tert-butyl ester

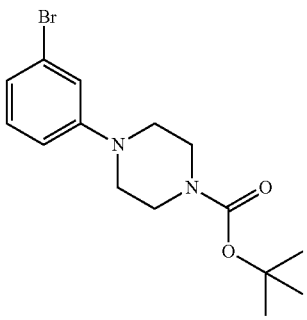 [SMILES: CC(C)(C)OC(=O)N1CCN(c2cccc(Br)c2)CC1]

N-3-Bromophenylpiperazine (2.41 g, 10.0 mmol) was dissolved in 10 mL of CH$_2$CL$_2$ and a solution of di-tert-butyldicarbonate (2.18 g, 10.0 mmol) in 10 mL of CH$_2$Cl$_2$ was added dropwise over ~10 minutes (vigorous gas evolution). The mixture was stirred at rt for 1 hour past the cessation of the gas evolution and then concentrated in vacuo and dried in a vacuum oven at 30° C. for 3 hours to provide the product. $^1$H-NMR (CD$_2$Cl$_2$) δ 7.14 (t, 1H), 7.08 (m, 1H), 6.97, (dd, 1H) 6.84 (dd, 1H) 7.40 (t, 1H) 3.55 (m, 4H), 3.16 (m, 4H), 1.48 (s, 9H); LC-MS [M+H]$^+$=343.0, RT=4.03 min.

Step 2: Preparation of 4-(4-tert-butoxycarbonyl-1-piperzalnyl)-phenylboronic acid

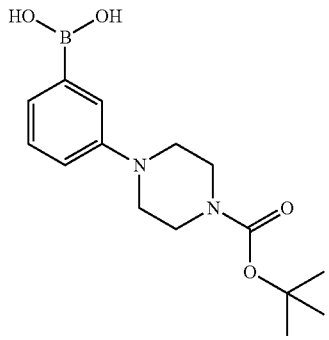 [SMILES: CC(C)(C)OC(=O)N1CCN(c2cccc(B(O)O)c2)CC1]

The product from step 1 (682 mg, 2.00 mmol) was dissolved in 8 mL of THF and cooled to −70° C. In a dry ice/isopropanol bath. n-BuLi (0.88 mL of a 2.5M solution in hexanes, 2.20 mmol) was added dropwise over 10 minutes. The mixture was stirred for 1 hour at −70° C. and triisopropyl borate (0.56 mL, 2.40 mmol) was added the mixture allowed to reach rt overnight. The mixture was quenched with water and 1 mL of 4M aqueous NaOH was added and stirring continued for 1 hour. The reaction mixture was poured into water and extracted with 2 portions of Et$_2$O. The Et$_2$O layer was back extracted with water and the pH of the combined aqueous phases was adjusted to 6 with 1M aqueous H$_3$PO$_4$. The organic phase was extracted with 2 portions of EtOAc and the combined EtOAc layers were washed with brine, dried (Na$_2$SO$_4$), filtered and concentrated in vacuo to give 406 mg of a white sticky solid. LC-MS [M+H]$^+$=343.0, RT=4.03 min.

Step 3: Preparation of 4-[3-(4-Amino-pyrrolo[2,1-f][1,2,4]triazin-7-yl)-phenyl]-piperazine-1-carboxylic acid tert-butyl ester

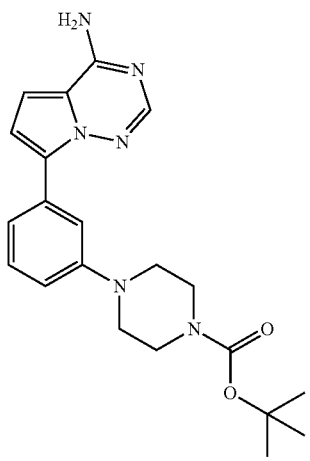 [SMILES: CC(C)(C)OC(=O)N1CCN(c2cccc(-c3ccc4c(N)ncnn34)c2)CC1]

Intermediate B (230 mg, 1.08 mmol) and the product from step 2 (396 mg, 1.30 mmol) were dissolved in 5 mL of 3:2 dioxane:toluene and degassed via a vacuum/N$_2$ purge (3 cycles). 1,1'-Bis(diphenylphosphino)ferrocenepalladium(II) chloride-dichloromethnane complex (39 mg, 0.05 mmol) was added followed by 2.2 mL of 2M aqueous Na$_2$CO$_3$ and the mixture was heated with stirring to 85° C. overnight. The dark green reaction mixture was cooled to room temp, filtered through a Celite® pad and the pad washed well with EtOAc. The organic phase was washed with water, 2M aqueous Na$_2$CO$_3$, water and brine, dried over Na$_2$SO$_4$, filtered and concentrated. The residue was purified by Isoc Red-Sep 40, 80%—100% EtOAc/hexanes to give 173 mg (41%) of the title compound. $^1$H-NMR (DMSO-d$_6$) δ 7.90 (s, 1H), 7.75 (bs, 2H), 7.61, (s, 1H), 7.53 (d, 1H), 7.28 (t, 1H), 7.02 (d, 1H), 6.97 (d, 1H), 6.83 (dd, 1H) 3.45 (m, 4H), 3.16 (m, 4H), 1.43 (s, 9H); LC-MS [M+H]$^+$=395.10, RT=2.71 min.

Step 4 Preparation of 4-[3-(4-Amino-5-bromo-pyrrolo[2,1-f][1,2,4]triazin-7-yl)-phenyl]-piperazine-1-carboxylic acid tert-butyl ester

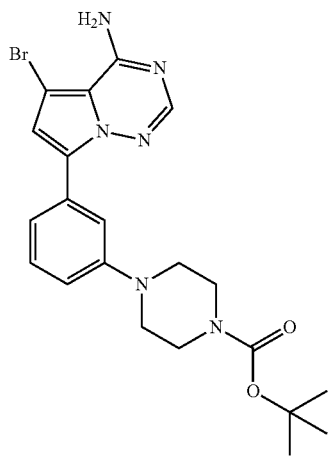 [SMILES: CC(C)(C)OC(=O)N1CCN(c2cccc(-c3cc(Br)c4c(N)ncnn34)c2)CC1]

The product from step 3 (160 mg. 0.40 mmol) was dissolved in 1 mL of DMF and 1 mL of THF was added. The mixture was cooled to −20° C. (isopropanol/ice/dry ice bath) and 1,3-dibromo-5,5-dimethyl hydantoin (58 mg, 0.20 mmol) was added in 4 portions over 40 minutes. The mixture was stirred for an additional 1 hour during which the internal temp rose to −5° C. It was diluted with a mixture of 1 mL of 2M Na$_2$CO$_3$, 1 mL of sat. Na$_2$SO$_3$ and 6 mL of water and the mixture stirred for 5 minutes. EtOAc (10 mL) was added and the layers were separated. The aqueous layer was extracted with 15 mL of EtOAc and the combined organic fractions were washed with 2M aqueous Na$_2$CO$_3$, water, brine, dried (Na$_2$SO$_4$), filtered and concentrated in vacuo. The residue was purified by Isco®(Red-sep 12, eluting with 60-100% hexanes/EtOAc) to provide 157 mg (82%) of the title compound as a foamy solid. $^1$H-NMR (DMSO-d$_6$) δ 7.98-7.64 (bs, 2H), 7.61 (s, 1H), 7.797 (s, 1H), 7.52 (d, 1H), 7.03 (d, 1H), 7.00-6.93 (m, 2H), (d, 1H), 6.71 (d, 1H), 3.43 (m, 4H), 3.13 (m, 4H), 1.40 (s, 9H); LC-MS [M+H]$^+$=473, 475, RT=2.80 min.

Step 5: Preparation of 4-{3-[4-Amino-5-(2-benzyl-2H-indazol-6-yl)-pyrrolo[2,1-f][1,2,4]triazin-7-yl]-phenyl}-piperazine-1-carboxylic acid tert-butyl ester

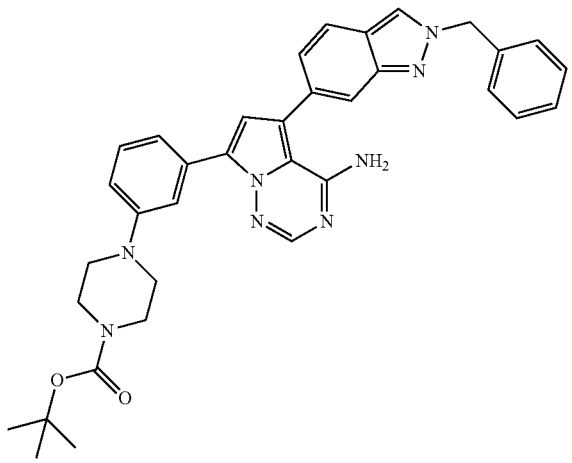 [SMILES: CC(C)(C)OC(=O)N1CCN(c2cccc(-c3cc(-c4ccc5cn(Cc6ccccc6)nc5c4)c4c(N)ncnn34)c2)CC1]

The product from step 4 (150 mg, 0.32 mmol) and Intermediate C (138 mg, 0.41 mmol) were dissolved in 2 mL of 1:1-toluene:dioxane and degassed with a vacuum/N₂ purge sequence (3×). 1,1'-Bis(diphenylphosphino)ferrocenepalladium(II) chloride-complex with methylene chloride (12 mg, 0.02 mmol) was added followed by 1 mL of 2M aqueous Na₂CO₃ solution and the mixture heated to 80° C. overnight. The heating bath was removed and the mixture diluted with water and EtOAc (5 mL each). The layers were separated and the aqueous phase was extracted with EtOAc and the combined organic phases were washed with water and brine, dried (Na₂SO₄), filtered and concentrated in, vacuo. The residue was purified by Isco® (Red-sep 12 eluting with 70%—100% EtOAc/hexanes) to give 77 mg (40%) of the title compound as a tan solid. $^1$H-NMR (DMSO-d$_6$) δ 8.33 (s, 1H), 7.61 (s, 1H), 7.57 (bs, 2H), 7.40-7.24 (m, 7H), 7.22 (s, 1H), 7.08, (d, 1H), 7.06 (s, 1H), 6.77 (d, 1H), 6.58 (d, 1H), 6.25 (d, 1H), 5.55 (s, 2H), 3.47 (m, 4H), 3.18 (m, 4H), 1.42 (s, 9H); LC-MS [M+H]$^+$=601.3, RT=3.12 min.

Step 6: Preparation of the Title Compound

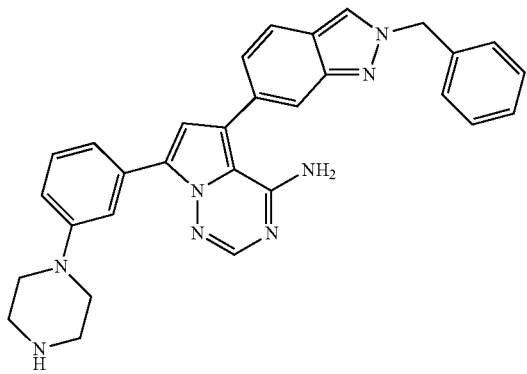 [SMILES: Nc1ncnn2c(-c3cccc(N4CCNCC4)c3)cc(-c3ccc4cn(Cc5ccccc5)nc4c3)c12]

The product from step 5 (55 mg, (0.09 mmol) was dissolved in 1 mL of CH₂Cl₂ and 1 mL of TFA was added dropwise. The mixture stirred for 1 hour and then concentrated to dryness. The residue was dissolved in acetonitrile and water was added and the pH was adjusted to 9 by the addition of aqueous K₃PO₄. The mixture was concentrated in vacuo and the solids obtained were extracted with MeOH, and then concentrated in vacuo again. The solid residue obtained was re-extracted with MeOH, filtered and the filtrate purified by preparative HPLC to provide 14 mg (30%) of the title compound. $^1$H-NMR (DMSO-d$_6$) δ 8.35 (s, 1H), 7.61 (s, 1H), 7.58 (bs, 2H), 7.39-7.24 (m, 7H), 7.22 (s, 1H), 7.11-7.01, (m, 2H), 6.77 (d, 1H), 6.57 (d, 1H), 6.26 (d, 1H), 5.57 (s, 2H), 3.10 (m, 4H), 2.84 (m, 4H); LC-MS [M+H]$^+$=501.2, RT=2.24 min.

Example 83

Preparation of 5-(2-Benzyl-2H-indazole-6-yl)-7-(4-methyl-piperazine-1-ylmethyl)-pyrrololo[2,1-f][1,2,4]triazin-4-ylamine

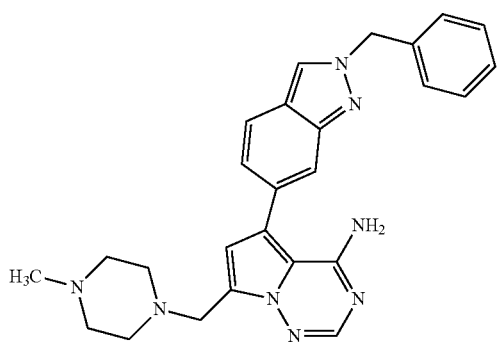 [SMILES: CN1CCN(Cc2cc(-c3ccc4cn(Cc5ccccc5)nc4c3)c3c(N)ncnn23)CC1]

Step 1: Preparation of 7-(4-methyl-piperazine-1-ylmethyl)-pyrrolo[2,1-f][1,2,4]triazin-4-ylamine synthesis

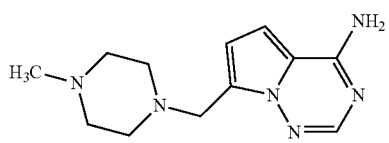 [SMILES: CN1CCN(Cc2ccc3c(N)ncnn23)CC1]

A mixture of Intermediate A (150 mg, 1.1 mmol), N-methylpiperazine (0.13 mL, 1.2 mmol) and aqueous formaldehyde (0.09 mL, 1.2 mmol) was dissolved into acetic acid (3 mL). The resulting mixture was stirred for 3 hours at 60° C. and then concentrated in vacuo. The resulting residue was purified by preparative HPLC to provide the title compound. $^1$H NMR (CD3OD) δ 2.20 (s, 3H), 2.40-2.80 (br, 8H). 4.00 (s, 2H), 6.60 (d, 1H), 6.90 (d, 1H), 7.80 (s, 1H).

Step 2: Preparation of 5-Bromo-7-(4-methyl-piperazine-1-ylmethyl)-pyrrololo[2,1-f][1,2,4]triazin-4-ylamine

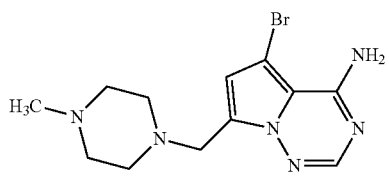 [SMILES: CN1CCN(Cc2cc(Br)c3c(N)ncnn23)CC1]

The product from step 1 (350 mg, 1.2 mmol) was dissolved into THF. The temperature was lowered to −40° C., and 1,3-dibromo-5,5-dimethyl hydantoin (203 mg, 0.6 mmol) was added into the solution as solid in 3 portions. The resulting mixture was stirred for 2 h. The mixture was diluted with ethyl acetate, and washed with aqueous sodium carbonate. The organic layer was dried over sodium sulfate and concentrated in vacuo. The residue was purified by Biotage®. ¹H NMR (CD₂Cl₂) δ 2.20 (s, 3H), 2.40-2.80 (m, 8H), 3.80 (s, 2H), 6.20 (br, 2H), 6.60 (s, 1H), 7.80 (s, 1H). LC-MS M+1 325.1, 1.02 min.

Step 3: Preparation of the Title Compound

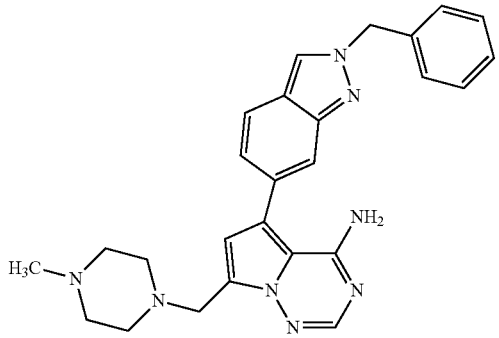 [SMILES: CN1CCN(Cc2cc(-c3ccc4cn(Cc5ccccc5)nc4c3)c3c(N)ncnn23)CC1]

The product from step 2 (50 mg, 0.15 mmol), Intermediate C (51 mg, 0.15 mmol), and PdCl₂(dppf)-complex with dichloromethane (5 mg, 0.015 mmol) were dissolved in 1:1 toluene/dioxane (10 mL) solution and 2M Na₂CO₃ (5 mL) was added. The resulting mixture was degassed and stirred under N₂ at 80° C. for 2 hours. The organic layer was separated from the resulting mixture, and concentrated in vacuo. The residue was purified by silica gel column (CH₂Cl₂/MeOH 6/4) to provide 14 mg (20%) of the title compound. ¹H NMR (CD3OD) δ 2.20 (s, 3H), 2.40-2.80 (m, 8H), 4.00 (s, 2H), 5.70 (s, 2H), 6.80 (s, 2H), 7.20 (d, 1H), 7.30 (m, 5H), 7.60 (s, 1H), 7.80 (m, 2H), 8.40 (s, 1H); LC-MS [M+H]⁺=453.0, RT=2.12 min.

Example 84

Preparation of 5-(3-Benzyloxy-phenyl)-7-(4-methyl-piperazin-1-ylmethyl)-pyrrolo[2,1-f][1,2,4]triazin-4-ylamine

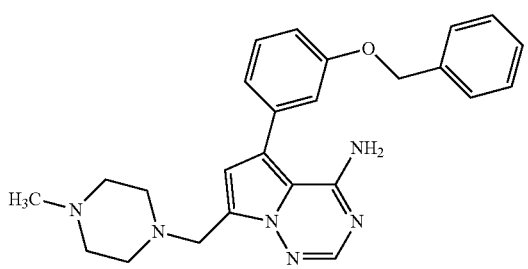 [SMILES: CN1CCN(Cc2cc(-c3cccc(OCc4ccccc4)c3)c3c(N)ncnn23)CC1]

Using the procedure described in Step 3 of Example 83, and substituting 3-benzyloxyphenylboronic acid for Intermediate C, the title compound was prepared. ¹H NMR (CD₃OD) δ 7.89 (s, 1H), 7.47 (m, 1H), 7.45 (bs, 1H), 7.43-7.32 (m, 4H), 7.10-7.06 (m, 2H), 7.01 (m, 1H), 6.64 (s, 1H), 5.37 (bs, 2H), 5.34, (m, 2H), 5.15 (s, 2H), 2.76-2.29 (m, 4H), 2.24 (s, 3H), LC-MS [M+H]⁺=428.9, RT=2.17 min.

Example 85

Preparation of 5-(2-Benzyl-2H-indazol-6-yl)-7-morpholin-4-ylmethyl-pyrrolo[2,1-f][1,2,4]triazin-4-ylamine

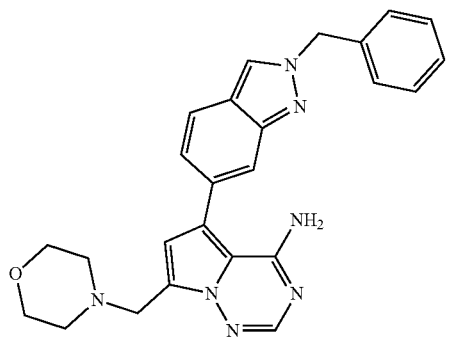 [SMILES: Nc1ncnn2c(CN3CCOCC3)cc(-c3ccc4cn(Cc5ccccc5)nc4c3)c12]

Using the procedures described in Example 83 and substituting morpholine for N-methylpiperazine, Intermediate A was converted to the title compound. ¹H NMR (DMSO d₆) δ 8.04 (s, 1H), 7.92 (s, 1H), 7.76 (d, 1H), 7.74 (s, 1H), 7.40-7.29 (m, 5H), 7.23 (d, 1H), 6.73 (s, 1H), 5.62 (s, 2H), 5.33 (s, 2H), 3.96 (bs, 2H), 3.70 (m, 6H), LC-MS [M+H]⁺=439.9, RT=1.08 min.

Example 86

Preparation of 4-[4-Amino-5-(2-benzyl-2H-indazol-6-yl)-pyrrolo[2,1-f][1,2,4]triazine-7-carbonyl]-piperidine-1-carboxylic acid tert-butyl ester

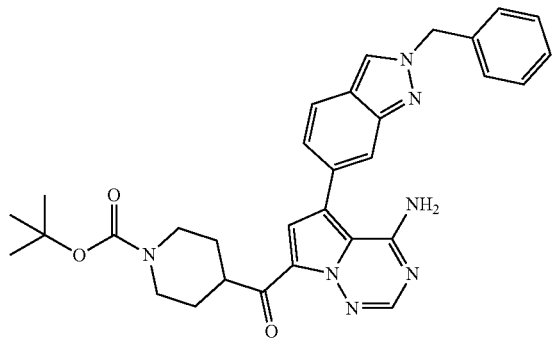 [SMILES: CC(C)(C)OC(=O)N1CCC(C(=O)c2cc(-c3ccc4cn(Cc5ccccc5)nc4c3)c3c(N)ncnn23)CC1]

Step 1: Preparation of 4-(Methoxy-methyl-carbamoyl)-piperidine-1-carboxylic acid tert-butyl ester

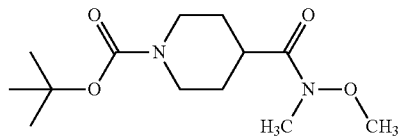

N-BOC-piperidine-4-carboxylic acid (3.00 g, 13.08 mmol) was dissolved in THF and CDI (4.00 g, 24.7 mmol)

was added in portions. The mixture was stirred for 2 h and N,O-dimethylhydroxylamine hydrochloride (4.00 g, 41 mmol) was added and stirring continued for 12 hours. The mixture was diluted with EtOAc and extracted 3 times with brine, dried over Na$_2$SO$_4$, filtered and concentrated in vacuo. The residue was purified Biotage® to provide the title compound. $^1$H NMR (CD2Cl2) δ 4.12 (d,2H), 3.71 (s, 3H), 3.15 (s, 3H), 2.83 (m, 1H), 2.76 (t, 2H), 1.70 (dd, 2H), 1.59 (m, 2H), 1.45 (s, 9H).

Step 2: 4-(4-Amino-pyrrolo[2,1-f][1,24]triazine-7-carbonyl)-piperidine-1-carboxylic acid tert-butylester synthesis

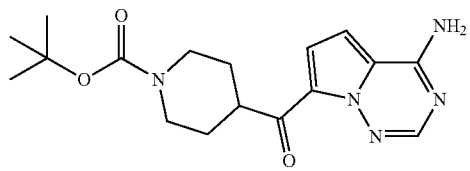 [SMILES: CC(C)(C)OC(=O)N1CCC(C(=O)c2ccc3c(N)ncnn23)CC1]

A solution of Intermediate B (524 mg, 2.46 mmol) in 5 mL of THF was cooled to −78° C., and n-BuLi (3.7 mL of a 2.5M solution in hexanes, 9.84 mmol) was added. The resulting mixture was stirred at −78° C., for 2 h and a solution of the product from step 1 (1.00 g, 3.6 mmol) in 5 mL of THF was added slowly. The resulting mixture was stirred for 4 hours at −78° C., and 1 h at room temperature. To the resulting mixture, NH$_4$Cl aqueous solution was added, and ethyl acetate was used to extract the product. The organic layer was separated and concentrated in vacuo. The residue was purified by Biotage® to provide 350 mg (41%) of the title compound. $^1$H NMR (CD3OD) δ 1.50 (s, 9H), 1.60-2.00 (m, 3H), 2.80 (m, 2H), 3.80 (t, 1H), 4.10 (m, 3H), 6.80 (d, 1H), 7.40 (d, 1H), 8.00 (s, 1H); LC-MS [M+Na]$^+$=368, RT=2.53 min.

Step 3: Preparation of 4-(4-Amino-5-bromo-pyrrolo[2,1-f][1,2,4]triazine-7-carbonyl)-piperidine-1-carboxylic acid tert-butyl ester

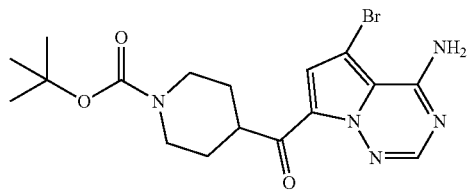 [SMILES: CC(C)(C)OC(=O)N1CCC(C(=O)c2cc(Br)c3c(N)ncnn23)CC1]

The product from step 2 (280 mg, 0.810 mmol) was dissolved in THF. The solution was cooled to −30° C. 1,3-Dibromo-6,5-dimethyl hydantoin (139 mg, 0.49 mmol) was added into the solution. The resulting mixture was stirred for 2 h. The mixture was diluted with ethyl acetate, and washed with aqueous sodium carbonate. The organic layer was dried over sodium sulfate and concentrated under reduced vacuum. The residue was purified by Biotage® to provide the title compound. LC-MS [M+H]$^+$=425.82, RT=3.16 min.

Step 4: Preparation of the Title Compound

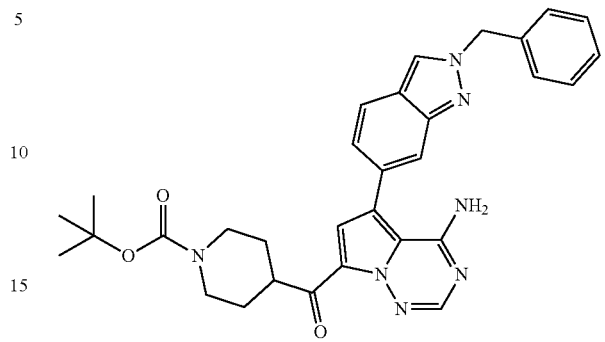

The product from step 3 (330 mg, 0.78 mmol) and Intermediate C (337 mg, 1.01 mmol), were dissolved in 7 mL dioxane:ethanol (5:2) and the mixture was treated with 2 M sodium carbonate (7 mL) and 1,1'-bis(diphenylphosphinoferrocenyl)palladium dichloride (27 mg) was added. The mixture was heated to 80° C. with stirring for 4 h. The mixture was allowed to cool and filtered through Celite®. Ethyl acetate was added and the product was extracted from the aqueous solution. The organic layer was dried over Na$_2$SO$_4$ and concentrated in vacuo. The resulting residue purified by Biotage® to provide the title compound. $^1$H NMR (CD$_2$Cl$_2$) δ 1.50 (s, 9H), 1.60-2.00 (m, 3H), 2.80 (m, 2H), 3.80 (t, 1H), 4.10 (m, 3H), 5.60 (s, 2H), 7.20 (d, 1H), 7.40 (m, 6H), 7.80 (dd, 2H), 8.10 (m, 2H). LC-MS [M+H]$^+$=574.1, RT=3.36 min.

Example 87

Preparation of [4-Amino-5-(2-benzyl-2H-indazol-6-yl)-pyrrolo[2,1-f[]1,2,4]triazin-7-yl]-piperidin-4-yl-methanone

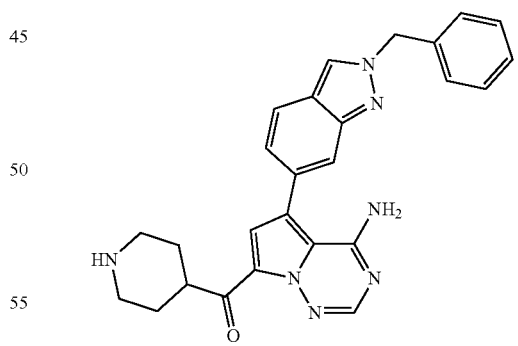

The product from step 4 of example 86 (25 mg, 0.045 mmol) was dissolved in 1 mL of 1:1 TFA:CH$_2$Cl$_2$, and stirred for 3 h. The mixture was concentrated in vacuo and the residue was dissolved in methanol and purified by preparative HPLC to provide the title compound. $^1$H NMR (CD$_3$OD) δ 1.80-220 (m, 4H), 3.20 (m, 2H), 3.50 (m, 2H), 4.00 (m, 1H), 5.70 (s, 2H), 7.20 (d, 1H), 7.40 (m, 6H), 7.50 (s, 1H), 7.70 (s, 1H), 7.80 (d, 1H), 8.10 (s, 1H), 8.40 (s, 1H); LC-MS [M+H]$^+$=453.1, RT=2.15 min.

Example 88

Preparation of 4-Amino-5-(2-benzyl-2H-indazol-6-yl)-pyrrolo[2,1-f][1,2,4]triazin-7-yl]-piperidin-3-yl-methanone

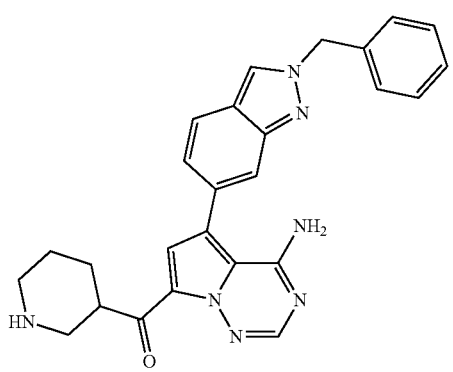 [SMILES: Nc1ncnn2c(C(=O)C3CCCNC3)cc(-c3ccc4cn(Cc5ccccc5)nc4c3)c12]

Using the procedure described in Steps 1-4 of Example 86 and Example 87 and substituting N'-BOC piperidine 3-carboxylic acid for N-BOC-piperidine-4-carboxylic acid, the title compound was prepared. $^1$H NMR (CD$_3$OD) δ 8.50 (s, 1H), 8.26 (s, 1H), 7.94 (d, 1H), 7.78 (s, 1H), 7.59 (s, 1H), 7.35 (s, 5H), 7.30 (m, 1H), 5.70 (s, 2H), 3.72 (m, 1H), 3.45 (m, 2H), 3.14 (m, 1H), 2.28 (m, 1H), 1.98-1.73 (m, 3H); LC-MS [M+H]$^+$=453.1, RT=2.25 min.

Example 89

Preparation of [4-Amino-5-(2-benzyl-2H-indazol-6-yl)-pyrrolo[2,1-f][1,2,4]triazin-7-yl]-(1-propyl-piperidin-3-yl)-methanone

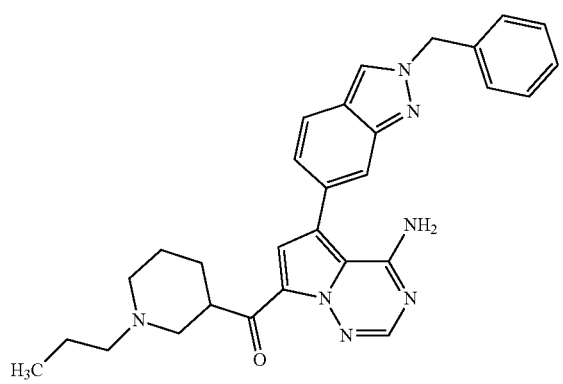 [SMILES: CCCN1CCCC(C(=O)c2cc(-c3ccc4cn(Cc5ccccc5)nc4c3)c3c(N)ncnn23)C1]

Example 88 (30 mg, 0.066 mmol) was dissolved in 3 mL of acetone and triethylamine (1 mL) was added followed by 1-bromopropane (7 μL. 0.079 mmol). The mixture was stirred for 1 and the mixture was concentrated in vacuo. The residue was purified by preparative HPLC to provide the title compound. $^1$H NMR (CD$_3$OD) δ 8.41 (s, 1H), 8.11 (d, 1H), 7.88 (m, 1H), 7.70 (m, 1H), 7.39-7.28 (m, 6H), 7.22 (m, 1H), 5.68 (s, 2H), 4.52 (m, 1H), 3.26-2.94 (m, 6H), 2.40-1.56 (m, 6H), 1.41 (t, 3H); LC-MS [M+H]$^+$=494.3, RT=2.83 min.

Example 90

Preparation of [4-Amino-5-(2-benzyl-2H-indazol-6-yl)-pyrrolo[2,1-f][1,2,4]triazin-7-yl]-(1-ethyl-piperidin-3-yl)-methanone

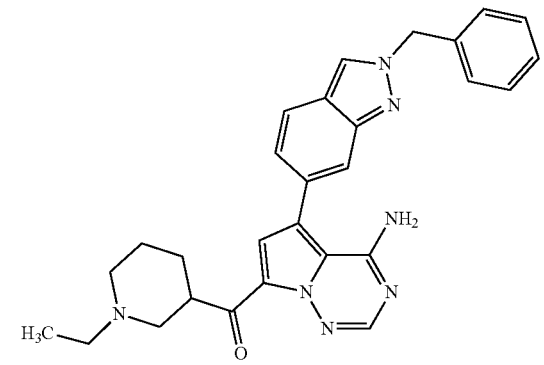 [SMILES: CCN1CCCC(C(=O)c2cc(-c3ccc4cn(Cc5ccccc5)nc4c3)c3c(N)ncnn23)C1]

Using the procedure described in Example 89 and substituting 1-bromoethane for 1-bromopropane, Example 88 was converted to the title compound. $^1$H NMR (CD$_3$OD) δ 8.42 (s, 1H), 8.10 (d, 1H), 7.87 (m, 1H), 7.70 (m, 1H), 7.39-7.29 (m, 6H), 7.23 (m, 1H), 5.68 (s, 2H), 4.52 (m, 1H), 3.26-2.94 (m, 6H), 2.40-1.56 (m, 4H), 1.40 (t, 3H); LC-MS [M+H]$^+$=480.3, RT=2.27 min.

Example 91

5-(2-Benzyl-2H-indazol-6-yl)-7-(3-piperidin-4-yl-phenyl)-pyrrolo[2,1-f][1,2,4]triazin-4-ylamine

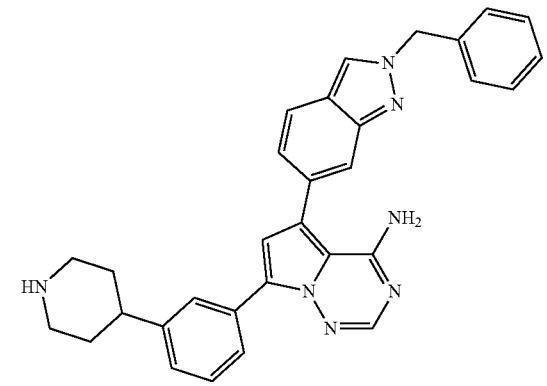 [SMILES: Nc1ncnn2c(-c3cccc(C4CCNCC4)c3)cc(-c3ccc4cn(Cc5ccccc5)nc4c3)c12]

Step 1: Preparation of 4-[3-(4,4,5,5-Tetramethyl-[1,3,2]dioxaborolan-2-yl)-phenyl]-piperidine-1-carboxylic acid tert-butyl ester

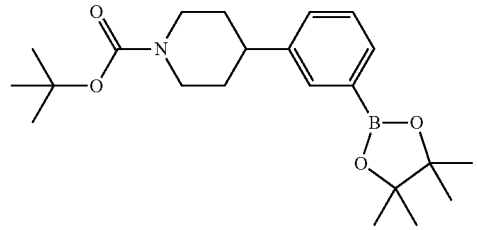 [SMILES: CC(C)(C)OC(=O)N1CCC(c2cccc(B3OC(C)(C)C(C)(C)O3)c2)CC1]

Using the procedure described for the preparation of Intermediate C, 4-(3-bromo-phenyl)-piperidine-1-carboxylic acid Pert-butyl ester was converted to the title compound. ¹H NMR (CD₃OD) δ 7.63 (bs, 1H), 7.60 (m, 1H), 7.32 (m, 1H), 7.31 (m, 1H), 4.23 (m, 2H), 2.83-2.62 (m, 3H), 1.80 (m, 2H), 1.62 (ddd, 2H), 1.47 (s, 6H), 1.33 (s, 3H), 1.24 (s, 9H).

Step 2: Preparation of 4-[3-(4-Amino-pyrrolo[2,1-f][1,2,4]triazin-7-phenyl]-piperidine-1-carboxylic acid tert-butyl ester

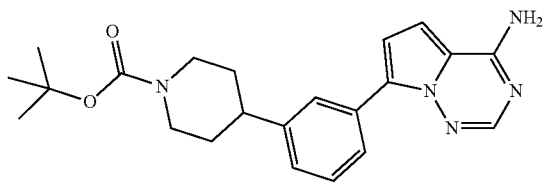 [SMILES: CC(C)(C)OC(=O)N1CCC(c2cccc(-c3ccc4c(N)ncnn34)c2)CC1]

Using the procedure described In step 1 of Example 80, the product from step 1 above, and Intermediate B were converted to the title compound. ¹H NMR (CD₂Cl₂) δ 1.50 (s, 9H), 1.60 (m, 1H), 1.80 (m, 2H), 2.80 (m, 3H), 4.10-4.30 (m, 3H), 5.50 (br, 2H), 6.80 (m, 1H), 7.00 (d, 1H), 7.20 (d, 1H), 7.40 (m, 1H), 7.80 (m, 2H), 8.10 (s, 1H); LC-MS [M+H]⁺= 393.9, RT=2.87 min.

Step 3: Preparation of 4-[3-(4-Amino-5-bromo-pyrrolo[2,1-f][1,2,4]triazin-7-yl)-phenyl]-piperidine-1-carboxylic acid tert-butyl ester

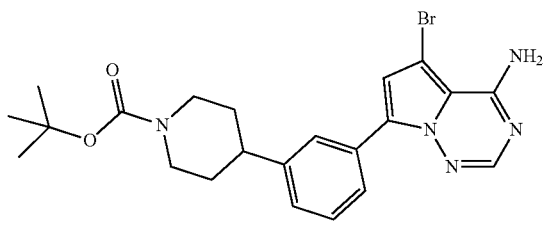 [SMILES: CC(C)(C)OC(=O)N1CCC(c2cccc(-c3cc(Br)c4c(N)ncnn34)c2)CC1]

Using the procedure described in step 2 of Example 80, the product from step 2 above was converted to the title compound. ¹H NMR (CD2Cl2) δ 1.50 (s, 9H), 1.60 (m, 1H), 1.80 (m, 2H), 2.80 (m, 3H), 4.10-4.30 (m, 3H), 5.50 (br, 2H), 6.80 (m, 1H), 7.00 (d, 1H), 7.20 (d, 1H), 7.80 (m, 2H), 8.10 (s, 11-1); LC-MS [M+H]⁺=473.8, RT=3.52 min.

Step 4: Preparation of 4-{3-[4-Amino-5-(2-benzyl-2H-indazol-6-yl)-pyrrolo[2,1-f][1,2,4]triazin-7-yl]-phenyl}-piperidine-1-carboxylic acid tert-butyl ester

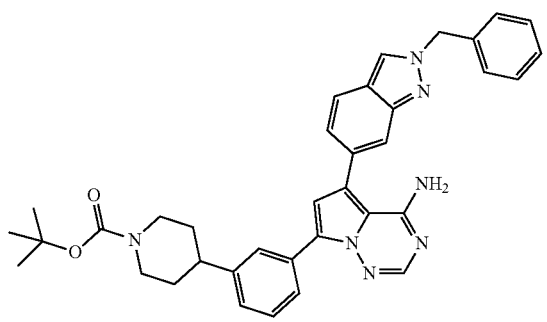 [SMILES: CC(C)(C)OC(=O)N1CCC(c2cccc(-c3cc(-c4ccc5cn(Cc6ccccc6)nc5c4)c4c(N)ncnn34)c2)CC1]

Using the procedure described in step 4 of Example 80, the product from step 3 above and Intermediate C were converted to the title compound. ¹H NMR (CD₂Cl₂) 1.50 (s, 9H), 1.60 (m, 1H), 1.80 (m, 2H), 2.80 (m, 3H), 4.10-4.30 (m, 3H), 5.60 (s, 2H), 5.80 (br, 2H), 7.00 (s, 1H), 7.10-7.50 (m, 9H), 7.80 (m, 2H), 7.90 (m, 2H), 7.95 (s, 1H), 8.10 (s, 1H); LC-MS [M+H]⁺=600.1, RT=3.55 min.

Step 5: Preparation of the Title Compound

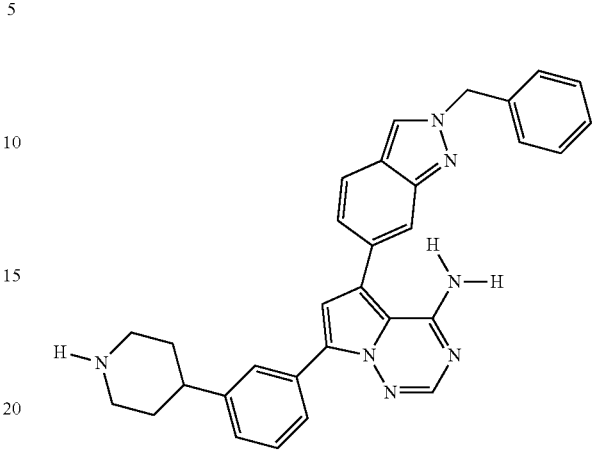

The product from step 4 was dissolved in 5 mL of 4M HCl in dioxane and the mixture was stirred for 4 h. Ethyl acetate (10 mL) was added into the resulting mixture and washed with 2M Na₂CO₂ (2 mL). The resulting organic solution was dried over Na₂SO₄ and concentrated in vacuo. The residue was purified by preparative TLC. (CH₂Cl₂/MeOH). δ ¹H NMR (CD₂Cl₂) 1.60 (m, 1H), 1.80 (m, 2H), 2.80 (m, 3H), 4.10-4.30 (m, 3H), 5.60 (s, 2H), 5.80 (br, 2H), 7.00 (s, 1H), 7.10-7.50 (m, 9H), 7.80 (m, 2H), 7.90 (m, 2H), 7.95 (s, 1H), 8.10 (s, 1H); LC-MS [M+H]⁺=500.2, RT=2.39 min.

Example 92

5-[3-(benzyloxy)phenyl]-7-[(1Z)-4-pyrrolidin-1-ylbut-1-en-1-yl]pyrrolo[2,1-f][1,2,4]triazin-4-amine

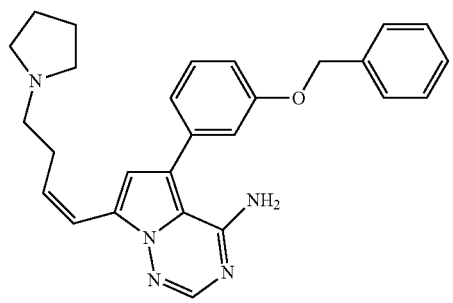 [SMILES: Nc1ncnn2c(/C=C\CCN3CCCC3)cc(-c3cccc(OCc4ccccc4)c3)c12]

Step 1: Preparation of Ethyl 4-bromo-5-cyano-1H-pyrrole-2-carboxylate

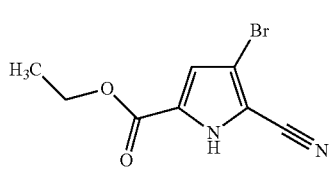

To a cooled (0° C.) solution of ethyl 4-bromo-1H-pyrrole-2-carboxylate (Belanger, P. *Tetrahedron Lett.* 1979, 20, 2505) (9.50 g, 43.6 mmol) in acetonitrile (200 mL) was added chlorosulfonyl isocyanate (3.87 mL, 43.6 mmol), drop wise.

The reaction was allowed to warm to rt and stir for 17 h. The reaction was quenched with the addition of DMF (17 mL) and the reaction was heated (50° C.) for 2 h then cooled to rt and stirred an additional 2 h. The mixture was poured over ice water (500 mL) and was extracted with ethyl acetate (3×250 mL). The combined organics were washed with brine, dried (Na$_2$SO$_4$) and concentrated. The crude material was purified via flash chromatography on silica gel eluting with 10% to 25% ethyl acetate in hexanes to afford 7.88 g (74%) of the desired product. $^1$H NMR (300 MHz, DMSO-d$_6$) δ 13.77 (br s, 1 H), 7.01 (s, 1 H), 4.28 (q, 2 H), 1.29 (t, 3 H).

Step 2: Preparation of Ethyl 1-amino-4-bromo-5-cyano-1H-pyrrole-2-carboxylate

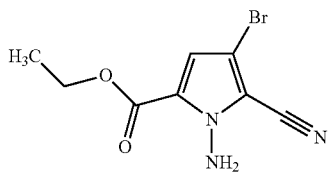

To a solution of ethyl 4-bromo-5-cyano-1H-pyrrole-2-carboxylate (2.70 g, 11.1 mmol) in DMF (75 mL) was added 95% sodium hydride powder (323 mg, 12.8 mmol). The mixture was stirred (rt) for 20 min, then (aminooxy)(diphenyl)phosphine oxide (3.89 g, 16.7 mmol) was added in one portion. After 15 min, the reaction mixture became thick and additional DMF (25 mL) was added. The reaction was heated (50° C.) for 3 h and was allowed to cool to rt and stir for 17 h. The reaction was poured into saturated aqueous NaHCO$_3$ solution (200 mL) and was extracted with ethyl acetate (3×100 mL). The combined organics were washed with water (2×100 mL), dried (Na$_2$SO$_4$) and were concentrated to dryness to afford 2.8 g (100%) of the desired product, which contained minor impurities. $^1$H NMR (300 MHz, DMSO-d$_6$) δ 6.95 (s, 1 H), 6.57 (s, 2 H), 4.28 (q, 2 H), 1.29 (t, 3 H).

Step 3: Preparation of Ethyl 1-amino-4-[3-(benzyloxy)phenyl]-5-cyano-1H-pyrrole-2-carboxylate

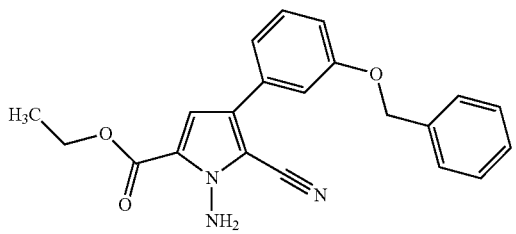 [SMILES: CCOC(=O)c1cc(-c2cccc(OCc3ccccc3)c2)c(C#N)n1N]

To a stirred solution of ethyl 1-amino-4-bromo-5-cyano-1H-pyrrole-2-carboxylate (1.43 g, 5.55 mmol), 4-benzyloxybenzeneboronic acid (3.80 g, 16.7 mmol), and [1,1'-bis(diphenylphosphino)-ferrocene]dichloro palladium(II) complex with dichloromethane (453 mg, 0.56 mmol) in degassed DME (41 mL) was added aqueous Na$_2$CO$_3$ solution (2 M, 8.3 mL). The reaction was heated (80° C.) for 17 h and then cooled to rt. The reaction was filtered through a pad of Celite® and the filter cake was rinsed well with ethyl acetate. The filtrate was partitioned between ethyl acetate (100 mL) and water (100 mL) and the layers were separated. The organic phase was further washed with water (75 mL), brine, was dried (Na$_2$SO$_4$), and concentrated. The crude material was purified by flash chromatography on silica gel using a gradient of 10 to 20% ethyl acetate in hexanes to afford 1.0 g (50%) of the desired product. $^1$H NMR (300 MHz, DMSO-d$_6$) δ 7.47-7.43 (m, 2 H), 7.41-7.25 (m, 6 H), 7.18 (s, 1 H), 7.02-6.97 (m, 1 H), 6.55 (s, 2 H), 5.15 (s, 2 H), 4.31 (q, 2 H), 1.33 (t, 3 H); ES-MS m/z 362.02 [M+H]$^+$, HPLC RT (min) 3.38.

Step 4: Preparation of 1-amino-3-[3-(benzyloxy)phenyl]-5-(hydroxymethyl)-1H-pyrrole-2-carbonitrile

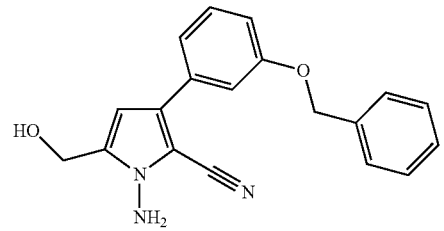 [SMILES: N#Cc1c(-c2cccc(OCc3ccccc3)c2)cc(CO)n1N]

To a solution of ethyl 1-amino-4-[3-(benzyloxy)phenyl]-5-cyano-1H-pyrrole-2-carboxylate (1.00 g, 2.77 mmol) in ethanol (24 mL) was added sodium borohydride (523 mg, 13.8 mmol). The mixture was heated (80° C.) for 17 h and then cooled to rt. The reaction was quenched with the addition of water (25 mL) and the mixture was extracted with ethyl acetate (2×25 mL). The combined organics were washed with brine, dried (Na$_2$SO$_4$) and concentrated to dryness to obtain 883 mg (100%) of the desired product. $^1$H NMR (300 MHz, DMSO-d$_6$) δ 7.48-7.42 (m, 2 H), 7.41-7.28 (m, 4 H), 7.25-7.19 (m, 2 H), 6.97-6.93 (m, 1 H), 6.41 (s, 1 H), 6.07 (s, 2 H), 5.23 (t, 1 H), 5.13 (s, 2 H), 4.49 (d, 2 H).

Step 5: Preparation of {4-amino-5-[3-(benzyloxy)phenyl]pyrrolo[2,1-f][]1,2,4]triazin-7-yl}methanol

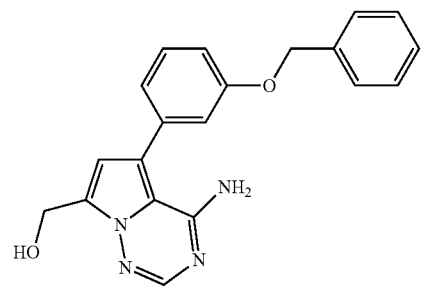 [SMILES: Nc1ncnn2c(CO)cc(-c3cccc(OCc4ccccc4)c3)c12]

To a solution of 1-amino-3-[3-(benzyloxy)phenyl]-5-(hydroxymethyl)-1H-pyrrole-2-carbonitrile (883 mg, 2.77 mmol) in ethanol (20 mL) was added formamidine acetate (3.81 g, 36.6 mmol). The mixture was heated (80° C.) for 2 h and then potassium carbonate (5.89 g, 42.6 mmol) was added. The mixture continued to heat (80° C.) for additional 4 h and then cooled to rt. The mixture was partitioned between ethyl acetate (50 mL) and water (50 mL). The layers were separated and the aqueous phase was further extracted with ethyl acetate (2×25 mL). The combined organics were washed with brine, dried (Na$_2$SO$_4$) and concentrated. The crude material was purified by ISCO® chromatography using a gradient of 50 to 75% ethyl acetate in hexanes to obtain 330 mg (31%) of the desired product. $^1$H NMR (300 MHz, DMSO-d$_6$) δ 7.89 (s, 1 H), 7.48-7.42 (m, 2 H), 7.41-7.28 (m, 4 H), 7.07-7.05 (m, 2 H), 7.04-6.99 (m, 2H), 6.67 (s, 1 H), 5.19 (t, 1 H), 5.15 (s, 2 H), 4.74 (d, 2 H); ES-MS m/z 347.2 [M+H]$^+$, HPLC RT (min) 2.40.

Step 6: Preparation of 4-amino-5-[3-(benzyloxy) phenyl]pyrrolo[2,1-f][1,2,4]triazine-7-carbaldehyde

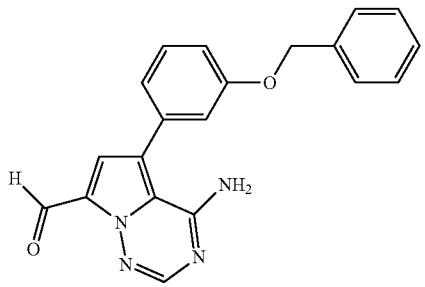 [SMILES: Nc1ncnn2c(C=O)cc(-c3cccc(OCc4ccccc4)c3)c12]

To a solution of {4-amino-5-[3-(benzyloxy)phenyl]pyrrolo[2,1-f][1,2,4]triazin-7-yl}methanol (300 mg, 0.87 mmol) in dichloromethane (5 mL) was added Dess-Martin Periodinane (492 mg, 1.13 mmol). The mixture was stirred (rt) for 4 h. The reaction was quenched with the addition of a 1:1 mixture of saturated, aqueous NaHCO$_3$ and saturated aqueous Na$_2$S$_2$O$_3$ solutions (5 mL) and the mixture was allowed to stir at it for 1 h. The mixture was extracted with dichloromethane (3×5 mL) and the combined organics were washed with brine, dried (Na$_2$SO$_4$) and concentrated to afford 105 mg (35%) of the desired product, which was used without further purification. ES-MS m/z 345.2 [M+H]$^+$, HPLC RT (min) 3.12.

Step 7: Preparation of the Title Compound

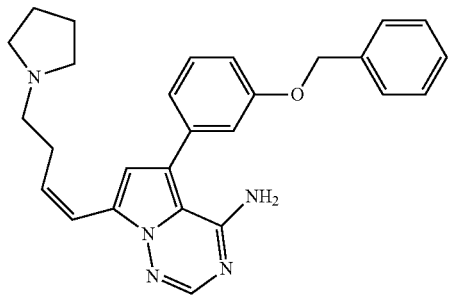 [SMILES: Nc1ncnn2c(/C=C\CCN3CCCC3)cc(-c3cccc(OCc4ccccc4)c3)c12]

To a suspension of triphenyl(3-pyrrolidin-1-ylpropyl)phosphonium bromide (660 mg, 1.45 mmol) in tetrahydrofuran (9.7 mL) was added 2.5 M n-BuLi in hexanes (700 µL, 1.74 mmol), dropwise. The mixture was stirred at rt for 1 h and then 4-amino-5-[3-(benzyloxy)phenyl]pyrrolo[2,1-f][1,2,4]triazine-7-carbaldehyde (100 mg, 0.29 mmol) was added. The mixture continued to stir at rt for an additional 17 h. The reaction was quenched with the addition of saturated aqueous NaHCO$_3$ solution (5 mL) and the mixture was extracted with ethyl acetate (2×10 mL). The combined organics were washed with brine, dried (Na$_2$SO$_4$) and concentrated. The crude material was purified via preparative TLC eluting with 9:1 ethyl acetate/methanol (containing 1% concentrated ammonium hydroxide) to afford 1.4 mg (1%) of the desired product. $^1$H NMR (300 MHz, CD$_3$OD) δ 7.83 (s, 1 H), 7.48-7.28 (m, 6 H), 7.14-7.04 (m, 3 H), 6.98 (d, 1 H), 6.86 (s, 1 H), 5.84-5.75 (m, 1 H), 5.16 (s, 2H), 2.91-2.73 (m, 8 H), 1.94-1.85 (m, 4 H); ES-MS m/z 440.3 [M+H]$^+$, HPLC RT (min) 2.54.

Example 93

Preparation of 5-(2-benzyl-2H-indazol-6-yl)-7-morpholin-2-ylpyrrolo[2,1-f][1,2,4]triazin-4-amine

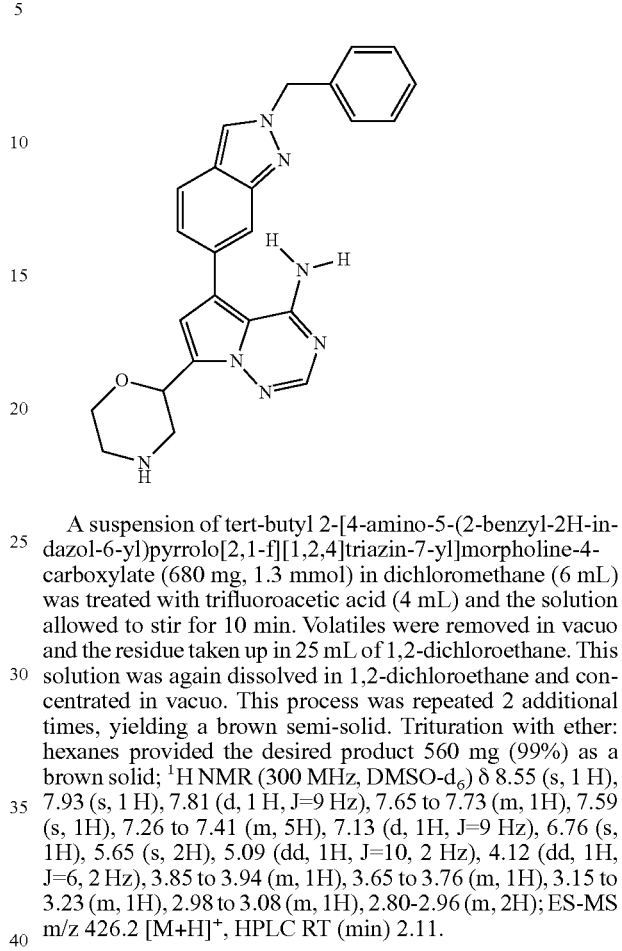

A suspension of tert-butyl 2-[4-amino-5-(2-benzyl-2H-indazol-6-yl)pyrrolo[2,1-f][1,2,4]triazin-7-yl]morpholine-4-carboxylate (680 mg, 1.3 mmol) in dichloromethane (6 mL) was treated with trifluoroacetic acid (4 mL) and the solution allowed to stir for 10 min. Volatiles were removed in vacuo and the residue taken up in 25 mL of 1,2-dichloroethane. This solution was again dissolved in 1,2-dichloroethane and concentrated in vacuo. This process was repeated 2 additional times, yielding a brown semi-solid. Trituration with ether:hexanes provided the desired product 560 mg (99%) as a brown solid; $^1$H NMR (300 MHz, DMSO-d$_6$) δ 8.55 (s, 1 H), 7.93 (s, 1 H), 7.81 (d, 1 H, J=9 Hz), 7.65 to 7.73 (m, 1H), 7.59 (s, 1H), 7.26 to 7.41 (m, 5H), 7.13 (d, 1H, J=9 Hz), 6.76 (s, 1H), 5.65 (s, 2H), 5.09 (dd, 1H, J=10, 2 Hz), 4.12 (dd, 1H, J=6, 2 Hz), 3.85 to 3.94 (m, 1H), 3.65 to 3.76 (m, 1H), 3.15 to 3.23 (m, 1H), 2.98 to 3.08 (m, 1H), 2.80-2.96 (m, 2H); ES-MS m/z 426.2 [M+H]$^+$, HPLC RT (min) 2.11.

Example 94

Preparation of 5-(2-benzyl-2H-indazol-6-yl)-7-{4-[(dimethylamino)acetyl]morpholin-2-yl}pyrrolo[2,1-f][1,2,4]triazin-4-amine

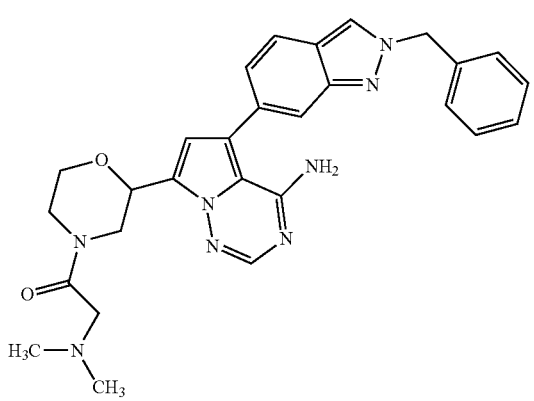 [SMILES: CN(C)CC(=O)N1CCOC(c2cc(-c3ccc4cn(Cc5ccccc5)nc4c3)c3c(N)ncnn23)C1]

A solution in THF (1 mL) containing 5-(2-benzyl-2H-indazol-6-yl)-7-morpholin-2-ylpyrrolo[2,1-f][1,2,4]triazin- 4-amine (170 mg, 0.315 mmol), (1H-benzotriazol-1-yloxy)[tris(dimethylamino)]phosphonium hexafluorophosphate (209 mg, 0.47 mmol), N-methylmorpholine (111 mg, 1.1 mmol) and N,N-dimethylglycine hydrochloride (65.9 mg, 0.47 mmol) was stirred at rt for one hour. The reaction was diluted with 1 mL MeOH and treated with 25% sodium methoxide solution in MeOH (100 uL, 2 mmol). After an additional 30 min stirring at rt, the reaction was partitioned between EtOAc and 2N sodium carbonate solution. The organic phase was separated, dried with sodium sulfate and concentrated in vacuo to provide a dark orange solid. This material was taken up in 9.5 mL $CH_2Cl_2$ and 0.5 mL 7N $NH_3$ in MeOH. The resulting solution was filtered through a silica plug (pretreated with NH3) and the volatiles removed in vacuo. Trituration of the resulting solid with ether provided 114 mg (71%) of the desired product as a tan solid. $^1$H NMR (300 MHz, DMSO-$d_6$) δ 8.55 (s, 1 H), 7.98 (d, 1 H, J=4 Hz)), 7.60 (s, 1 H), 7.50-7.60 (m, 2H), 7.14 (d, 1H, J=7 Hz), 6.80 (s, 1H), 7.27-7.41 (m, 5H), 5.65 (s, 2H), 4.89-5.06 (m, 1H), 4.18-4.52 (m, 2H), 3.86-4.04 (m, 2H), 3.21-3.65 (m, 2H), 3.30 (s, 2H), 2.19 (s, 3H), 2.15 (s, 3H); ES-MS m/z 511.3 [M+H]$^+$, HPLC RT (min) 2.12 min.

Example 95

Preparation of 5-(2-benzyl-2H-indazol-6-yl)-7-{4-[(4-methylpiperazin-1-yl)carbonyl]morpholin-2-yl}pyrrolo[2,1-f][1,2,4]triazin-4-amine

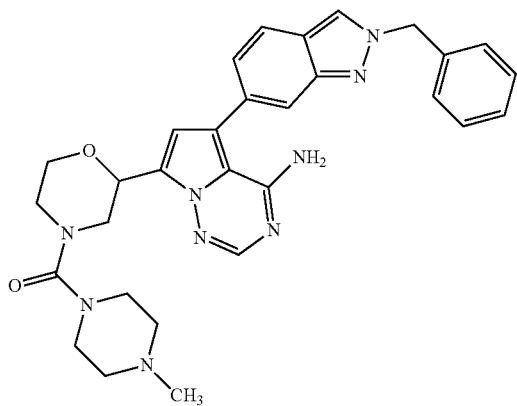 [SMILES: CN1CCN(C(=O)N2CCOC(c3cc(-c4ccc5cn(Cc6ccccc6)nc5c4)c4c(N)ncnn34)C2)CC1]

A solution of 5-(2-benzyl-2H-indazol-6-yl)-7-morpholin-2-ylpyrrolo[2,1-f][1,2,4]triazin-4-amine (59.1 mg, 0.11 mmol) in dichloromethane (1 mL) was cooled to 0° C. and treated with 4-methylpiperazine-1-carbonyl chloride (18 mg, 0.11 mmol) and N-methylmorpholine (28 mg, 0.28 mmol). After stirring for 1 h at rt, the reaction was diluted with 1 mL MeOH and diluted with EtOAc and 1N sodium carbonate solution. The organic layer was dried with sodium sulfate and concentrated in vacuo. The residue was triturated with acetonitrile to provide 41 mg (67%) of the desired product as an off-white solid. $^1$H NMR (300 MHz, DMSO-$d_6$) δ 8.55 (s, 1 H), 7.95 (d, 1 H, J=3 Hz), 7.81 (d, 1 H, J=9 Hz), 7.61 (s, 1 H), 7.27-7.40 (m, 5H), 7.14 (d, 1H, J=9 Hz), 6.81 (d, 1 H, J=4 Hz), 5.65 (s, 2 H), 5.10-5.15 (m, 1H), 4.45-4.55 (m, 1 H), 3.95-4.25 (m, 3H), 3.65-3.85 (m, 3H), 3.49-3.60 (m, 1H), 3.30 (s, 3H), 3.35-3.25 (m, 1H), 3.14-3.25 (m, 1H); ES-MS Ink 552.1 [M+H]$^+$, HPLC RT (min) 2.21.

Example 96

Preparation of 5-(2-benzyl-2H-indazol-6-yl)-7-(4-methylmorpholin-2-yl)pyrrolo[2,1-f][1,2,4]triazin-4-amine

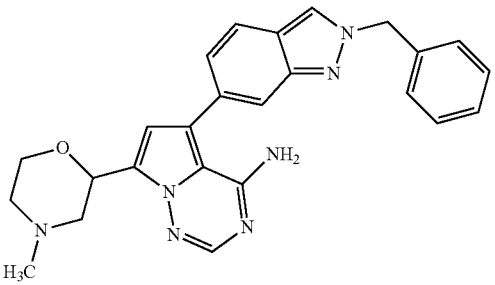 [SMILES: CN1CCOC(c2cc(-c3ccc4cn(Cc5ccccc5)nc4c3)c3c(N)ncnn23)C1]

A solution of 5-(2-benzyl-2H-indazol-6-yl)-7-morpholin-2-ylpyrrolo[2,1-f][1,2,4]triazin-4-amine (65 mg, 0.12 mmol) in DMF (2 mL) was cooled to −40° C. and treated with methyl iodide (20.5 mg, 0.145 mmol) as a solution in DMF (1 mL) and potassium carbonate (33 mg, 0.24 mmol). The reaction was allowed to warm slowly to rt over 1 h. The reaction was diluted with EtOAc and washed 3 times with water. The organic layer was dried with sodium sulfate and concentrated in vacuo. The residue was purified by silica gel chromatography eluting with $CH_2Cl_2$:MeOH:$NH_3$ to provide 17.9 mg (34%) of the desired product. $^1$H NMR (300 MHz, DMSO-$d_6$) δ 8.55 (s, 1 H), 7.89 (s, 1 H), 7.79 (d, 1 H, J=9 Hz), 7.65 to 7.73 (m, 1H), 7.59 (s, 1H), 7.26 to 7.41 (m, 5H), 7.13 (d, 1 H, J=9 Hz), 6.76 (s, 1H), 5.65 (s, 2H), 4.98 (dd, 1H, J=11, 2 Hz), 4.08 (dd, 1H, J=6, 2 Hz), 3.85 to 3.94 (m, 1H), 3.15 to 3.23 (m, 1H), 2.98 to 3.08 (m, 1H), 2.80-2.96 (m, 2H), 2.11 (s, 3H); ES-MS m/z 440.4 [M+H]$^+$, HPLC RT (min) 2.07.

Example 97

Preparation of 2-{2-[4-amino-5-(2-benzyl-2H-indazol-6-yl)pyrrolo[2,1-f][1,2,4]triazin-7-yl]morpholin-4-yl}-N,N-dimethylacetamide

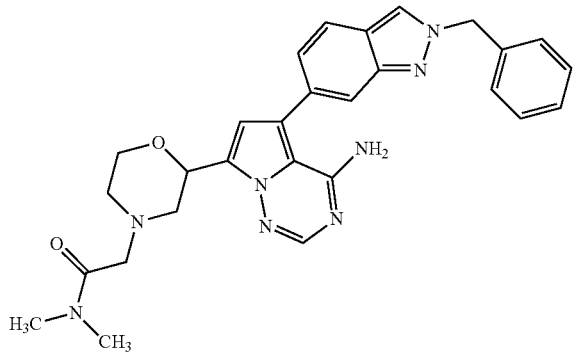 [SMILES: CN(C)C(=O)CN1CCOC(c2cc(-c3ccc4cn(Cc5ccccc5)nc4c3)c3c(N)ncnn23)C1]

A solution of 5-(2-benzyl-2H-indazol-6-yl)-7-morpholin-2-ylpyrrolo[2,1-f][1,2,4]triazin-4-amine (247 mg, 0.521 mmol) in DMF (5 mL) was treated with 2-chloro-N,N-dimethylacetamide (115 mg, 0.94 mmol), potassium carbonate (658 mg, 4.8 mmol) and potassium iodide (19 mg, 0.12 mmol) and the mixture vigorously stirred at 60° C. for 18 h. Basic, aqueous workup and purification by column chromatography ($CH_2Cl_2$:MeOH:$NH_3$) gave 312 mg (50%) of the desired compound. $^1$H NMR (300 MHz, DMSO-$d_6$) δ 7.89 (s, 1 H), 7.76 (dd, 1 H, J=9, 1 Hz), 7.53 (s, 1H), 7.25 to 7.36 (m, 3H), 7.18-7.23 (m, 2H), 7.09 (d, 1 H, J=9 Hz), 6.60 (s, 1H), 5.63 (s, 2H), 3.14 (s, 2H), 3.03 (s, 3H), 2.89-2.94 (m, 2H), 2.80 (s, 3H), 2.62 (s, 3H), 2.12-2.24 (m, 2H), 1.93-2.03 (m, 2H), 1.63-1.79 (m, 2H); ES-MS m/z 523.2 [M+H]$^+$, HPLC RT (min) 2.21.

Example 98

Preparation of 5-(2H-indazol-6-yl)-7-morpholin-2-ylpyrrolo[2,1-f][1,2,4]triazin-4-amine

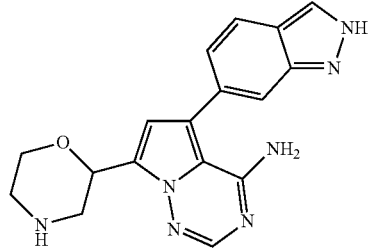 [SMILES: Nc1ncnn2c(C3CNCCO3)cc(-c3ccc4c[nH]nc4c3)c12]

Step 1: Preparation of 5-(2-benzyl-2H-indazol-6-yl)-7-(4-benzylmorpholin-2-yl)pyrrolo[2,1-f][1,2,4]triazin-4-amine

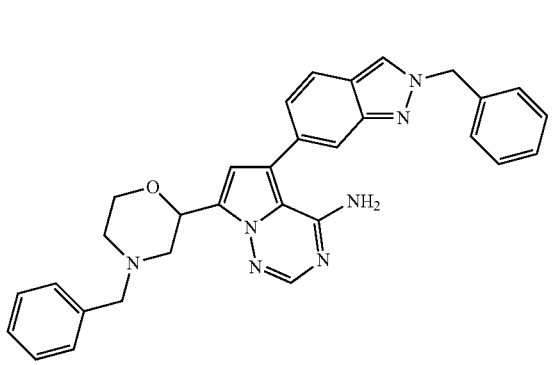 [SMILES: Nc1ncnn2c(C3CN(Cc4ccccc4)CCO3)cc(-c3ccc4cn(Cc5ccccc5)nc4c3)c12]

A stirred, degassed mixture of 7-(4-benzylmorpholin-2-yl)-5-bromopyrrolo[2,1-f][1,2,4]triazin-4-amine (701 mg, 1.81 mmol) and tetrakis(triphenylphosphine)palladium(0) (350 mg, 0.30 mmol) in DMF (2 mL) was stirred under N$_2$ for 30 min at 80 C, then treated with 2-benzyl-6-(4,4,5,5-tetramethyl-[1,3,2]dioxaborolan-2-yl)-2H-indazole (754 mg, 2.26 mmol), K$_3$PO$_4$ (765 mg, 3.61 mmol) and H$_2$O (165 mg, 9 mmol). The reaction was heated (100° C.) for 1 h and then cooled to rt. The mixture was partitioned between ethyl acetate (25 mL) and MeOH (2.5 mL) and the mixture filtered through a long silica plug. After removal of the volatiles in vacuo, the residue was purified by ISCO® chromatography using a gradient of 1% to 10% MeOH in CH$_2$Cl$_2$ to afford 401 mg (43%) of the desired product. $^1$H NMR (300 MHz, DMSO-d$_6$) δ 8.54 (s, 1 H), 7.90 (s, 1 H), 7.79 (d, 1 H, J=9 Hz), 7.57 (s, 1 H), 7.21-7.38 (m, 5 H), 7:12 (d, 1 H, J=9 Hz), 6.73 (s, 1 H), 5.65 (s, 2 H), 5.10 (dd, 1H, J=10, 2Hz), 3.88 (d, 1H, J=12 Hz), 3.69 (dd, 1H, J=10, 9 Hz), 3.57 (d, 1H, J=13 Hz), 3.51 (d, 1H, J=13 Hz), 2.97 (d, 1H, J=12 Hz), 2.17-2.28 (m, 1H), 2.67 (d, 1H, J=11 Hz), 2.36 (t, 1H, J=11 Hz); ES-MS m/z 516.3 [M+H]$^+$, HPLC RT (min) 2.80.

Step 2: Preparation of Final Compound

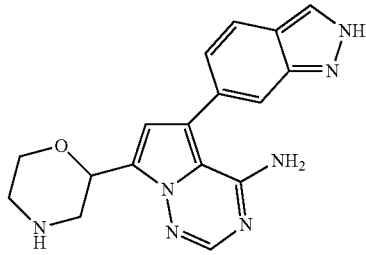 [SMILES: Nc1ncnn2c(C3CNCCO3)cc(-c3ccc4c[nH]nc4c3)c12]

A solution of 5-(2-benzyl-2H-indazol-6-yl)-7-(4-benzylmorpholin-2-yl)pyrrolo[2,1-f][1,2,4]triazin-4-amine (200 mg, 0.388 mmol) and 25 mg 10% by wt. palladium on carbon in acetic acid (5 mL) was stirred under an atmosphere of hydrogen for 52 h. The reaction was filtered through Celite® and concentrated in vacuo. The residue was purified by preparative RP-HPLC to provide 35.1 mg (27%) of the desired product. $^1$H NMR (300 MHz, DMSO-d$_6$) δ 8.10 (s, 1 H), 7.92 (s, 1 H), 7.83 (d, 1 H, J=8 Hz), 7.52 (s, 1 H), 7.19 (d, 1 H, J=8 Hz), 6.73 (s, 1 H), 4.98 (dd, 1 H, J=10, 2 Hz) (m, 1 H), 3.81 (d, 1H, J=11 Hz), 3.55-3.66 (m, 2H), 3.31 (bs, 3H), 3.05 (dd, 1H, J=12, 3 Hz), 2.86 (dd, 1H, J=12, 10 Hz), 2.71-2.78 (m, 2H); ES-MS m/z 336.4 [M+H]$^+$, HPLC RT (min) 1.10.

Example 99

Preparation of 5-(2-benzyl-2H-indazol-6-yl)-6-methyl-7-(morpholin-4-ylmethyl)pyrrolo[2,1-f][1,2,4]-triazin-4-amine

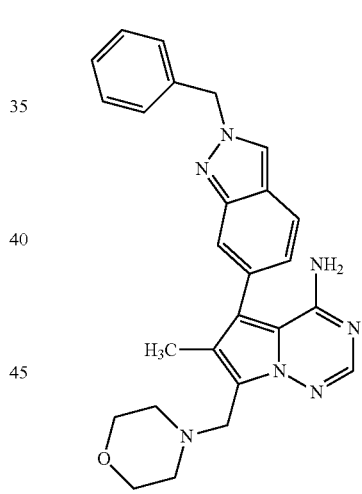

To a stirred solution of 5-bromo-6-methyl-7-(morpholin-4-ylmethyl)pyrrolo[2,1-f][1,2,4]triazin-4-amine (150 mg, 0.46 mmol) and tetrakis(triphenylphosphine)palladium(0) (159 mg, 0.14 mmol), in degassed DMF (3.0 mL) was added 2-benzyl-6-(4,4,5,5-tetramethyl-1,3,2-dioxaborolan-2-yl)-2H-indazole (184 mg, 0.55 mmol), K$_2$CO$_3$ (153 mg, 1.10 mmol), and H$_2$O (0.5 mL). The mixture was degassed and heated (100° C.) for 17 h and then cooled to rt. The mixture was partitioned between ethyl acetate (25 mL) and saturated aqueous Na$_2$CO$_3$ solution (25 mL). The layers were separated and the organic phase was washed, dried (Na$_2$SO$_4$), and concentrated to dryness. The residue was purified by preparative HPLC using a gradient elution from 10% to 70% acetonitrile to obtain 15 mg (7%) of the desired product. $^1$H-NMR (DMSO-d$_6$) δ 8.56 (s, 1H), 7.85 (s, 1H), 7.80 (d, 1H), 7.54 (s, 1H), 7.32-7.38 (m, 5H), 7.02 (d, 1H), 5.65 (s, 2H), 3.81 (s, 2H), 2.53-2.50 (m, 4H), 2.43-2.40 (m, 4H), 2.10 (s, 3H); LC-MS [M+H]$^+$=454, RT=2.30 min.

Example 100

Preparation of 1-[4-amino-5-(2-benzyl-2H-indazol-6-yl)pyrrolo[2,1-f][1,2,4]triazin-7-yl]-2-morpholin-4-ylethanone

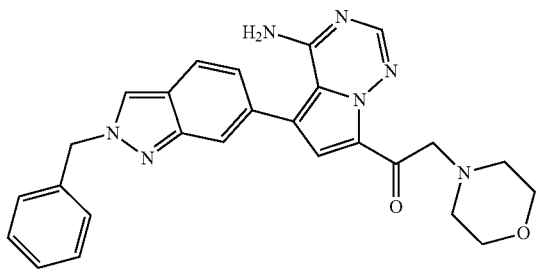 [SMILES: Nc1ncnn2c(C(=O)CN3CCOCC3)cc(-c3ccc4cn(Cc5ccccc5)nc4c3)c12]

To a stirred solution of 1-(4-amino-5-bromopyrrolo[2,1-f][1,2,4]triazin-7-yl)-2-morpholin-4-ylethanone (90 mg, 0.27 mmol) and tetrakis(triphenylphosphine)palladium(0) (61 mg, 0.05 mmol), in degassed 1,4-dioxane (1.0 mL) and DMF (2.0 mL) was added 2-benzyl-6-(4,4,5,5-tetramethyl-1,3,2-dioxaborolan-2-yl)-2H-indazole (97 mg, 0.29 mmol), $K_2CO_3$ (80 mg, 0.58 mmol), and $H_2O$ (0.3 mL). The mixture was degassed and heated (100° C.) for 17 h and then cooled to rt. The mixture was partitioned between ethyl acetate (25 mL) and saturated aqueous $K_2CO_3$ solution (25 mL). The layers were separated and the organic phase was washed, dried ($Na_2SO_4$), and concentrated to dryness. The residue was purified by preparative HPLC using a gradient elution from 10% to 70% acetonitrile to obtain 20 mg (16%) of the desired product. $^1$H-NMR (DMSO-$d_6$) δ 8.57 (s, 1H), 8.13 (s, 1H), 7.82 (d, 1H), 7.65 (s, 1H), 7.39 (s, 1H), 7.36-7.28 (m, 5H), 7.14 (d, 1H), 5.65 (s, 2H), 3.93 (s, 2H), 3.58-3.56 (m, 4H), 2.56-2.53 (m, 4H); LC-MS [M+H]$^+$=468, RT=2.27 min.

Example 101

Preparation of tert-butyl 3-[4-amino-5-(2-benzyl-2H-indazol-6-yl)pyrrolo[2,1-f][1,2,4]triazin-7-yl]hexahydropyrazino[2,1-c][1,4]oxazine-8(1H)-carboxylate

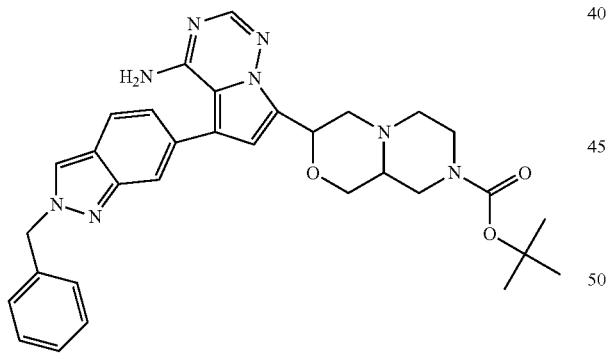

To a stirred solution of tert-butyl 3-(4-amino-5-bromopyrrolo[2,1-f][1,2,4]triazin-7-yl)hexahydropyrazino[2,1-c][1,4]oxazine-8(1H)-carboxylate (1.50 g, 3.31 mmol) and tetrakis(triphenylphosphine)palladium(0) (764 mg, 0.66 mmol), in degassed 1,4-dioxane (15 mL) and DMF (15 mL) was added 2-benzyl-6-(4,4,5,5-tetramethyl-1,3,2-dioxaborolan-2-yl)-2H-indazole (1.33 g, 3.97 mmol), $K_2CO_3$ (1.10 g, 7.94 mmol), and $H_2O$ (3.9 mL). The mixture was degassed and heated (100° C.) for 17 h and then cooled to rt. The mixture was partitioned between ethyl acetate (250 mL) and saturated aqueous $K_2CO_3$ solution (200 mL). The layers were separated and the organic phase was washed, dried ($Na_2SO_4$), and concentrated to dryness. The residue was purified by recrystallization from acetonitrile to obtain 750 mg (39%) of the desired product. $^1$H-NMR (DMSO-$d_6$) δ 8.53 (s, 1H), 7.91 (s, 1H), 7.79 (d, 1H), 7.57 (s, 1H), 7.35-7.28 (m, 5H), 7.11 (d, 1H), 6.71 (s, 1H), 5.64 (s, 2H), 5.14-5.10 (m, 1H), 3.88-3.71 (m, 3H), 3.33-3.26 (m, 2H), 3.03-2.99 (m, 1H), 2.89-2.69 (m, 2H), 2.42-2.38 (m, 1H), 2.12-2.08 (m, 2H), 1.38 (s, 9H); LC-MS [M+H]$^+$=581, RT=2.57 min.

Example 102

Preparation of 5-(2-benzyl-2H-indazol-6-yl)-7-(octahydropyrazino[2,1-c][1,4]oxazin-3yl)pyrrolo[2,1-f][1,2,4]triazin-4-amine

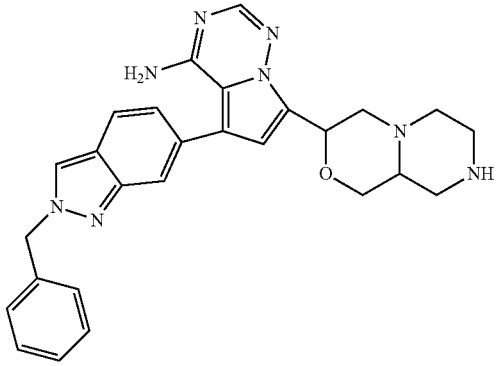 [SMILES: Nc1ncnn2c(C3CN4CCNCC4CO3)cc(-c3ccc4cn(Cc5ccccc5)nc4c3)c12]

To a stirred solution of tert-butyl 3-[4-amino-5-(2-benzyl-2H-indazol-6-yl)pyrrolo[2,1-f][1,2,4]triazin-7-yl]hexahydropyrazino[2,1-c][1,4]oxazine-8(1H)-carboxylate (75 mg, 0.13 mmol) in dichloromethane (5 mL), trifluoroacetic acid (1 mL) was added. The reaction was allowed to stir for 30 minutes and concentrated. The mixture was partitioned between ethyl acetate (30 mL) and pH 14 saturated aqueous NaCl (10 mL). The layers were separated and the organic phase was washed, dried ($Na_2SO_4$), and concentrated to dryness. The residue was triturated with $Et_2O$ to obtain 50 mg (80%) of the desired product. $^1$H-NMR (DMSO-$d_6$) δ 8.53 (s, 1H), 7.90 (s, 1H), 7.78 (d, 1H), 7.57 (s, 1H), 7.35-7.28 (m, 5H), 7.11 (d, 1H), 6.70 (s, 1H), 5.64 (s, 2H), 5.11 (d, 1H), 3.71 (dd, 1H), 3.33-3.26 (m, 1H), 2.91 (d, 1H), 2.74-2.58 (m, 4H), 2.39 (t, 1H), 2.21-2.00 (m, 4H); LC-MS [M+H]$^+$=481, RT=2.00 min.

Example 103

Preparation of 5-(2-benzyl-2H-indazol-6-yl)-7-(8-methyloctahydro-pyrazino[2,1-c][1,4]oxazin-3-yl)pyrrolo[2,1-f][1,2,4]triazin-4-amine

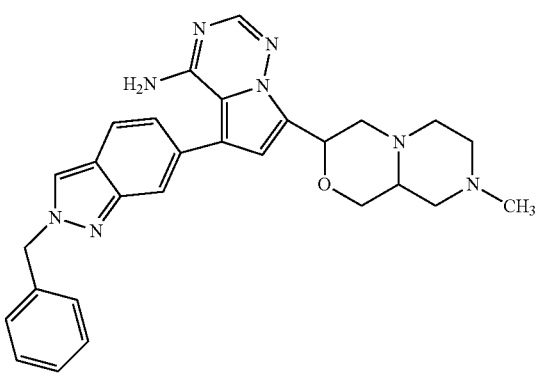 [SMILES: CN1CCN2CC(c3cc(-c4ccc5cn(Cc6ccccc6)nc5c4)c4c(N)ncnn34)OCC2C1]

To a stirred solution of 5-(2-benzyl-2H-indazol-6-yl)-7-(octahydropyrazino[2,1-c][1,4]oxazin-3-yl)pyrrolo[2,1-f][1, 2,4]triazin-4-amine (85 mg, 0.18 mmol) and triethylamine (49 µL, 0.35 mmol) in DMF (1 mL) at −78° C., iodomethane (177 µL, 0.17 mmol, 1.0M in DMF) was added. The reaction was allowed to stir for 1 h while warming to rt. The mixture was partitioned between ethyl acetate (30 mL) and pH 14 saturated aqueous NaCl (10 mL). The layers were separated and the organic phase was washed, dried (Na$_2$SO$_4$), and concentrated to dryness. The residue was triturated with Et$_2$O to obtain 30 mg (34%) of the desired product. $^1$H-NMR (DMSO-d$_6$) δ 8.53 (s, 1H), 7.90 (s, 1H), 7.78 (d, 1H), 7.57 (s, 1H), 7.35-7.28 (m, 5H), 7.11 (d, 1H), 6.70 (s, 1H), 5.64 (s, 2H), 5.11 (dd, 1 H), 3.75 (dd, 1 H), 3.37-3.26 (m, 1H), 2.98 (dd, 1H), 2.70-2.65 (m, 2H), 2.56-2.50 (m, 1H), 2.47-2.30 (m, 1H), 2.26-2.18 (m, 2H), 2.14 (s, 3H), 2.11-2.01 (m, 1H), 1.61 (t, J=10.5 Hz, 1H); LC-MS [M+H]$^+$=495, RT=2.10 min.

Example 104

Preparation of 2-{3-[4-amino-5-(2-benzyl-2H-indazol-6-yl)pyrrolo[2,1-f][1,2,4]triazin-7-yl]hexahydropyrazino[2,1,4]oxazin-8(1H)-yl}ethanol

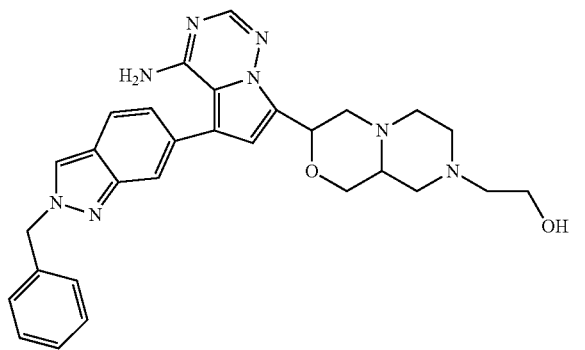 [SMILES: Nc1ncnn2c(C3CN4CCN(CCO)CC4CO3)cc(-c3ccc4cn(Cc5ccccc5)nc4c3)c12]

To a stirred solution of 5-(2-benzyl-2H-indazol-6-yl)-7-(octahydropyrazino[2,1-c][1,4]oxazin-3-yl)pyrrolo[2,1-f][1,2,4]triazin-4-amine (50 mg, 0.10 mmol) and triethylamine (29 µL, 0.21 mmol) in DMF (1 mL), (2-bromoethoxy)(tert-butyl)dimethylsilane (25 µL, 0.11 mmol) was added at rt. The reaction was heated to 65° C. and allowed to stir for 4 hours. The mixture was allowed to cool and partitioned between ethyl acetate (50 mL) and saturated aqueous K$_2$CO$_3$ solution (30 mL). The layers were separated and the organic phase was washed, dried (Na$_2$SO$_4$), and concentrated to dryness. The crude residue was dissolved in tetrahydrofuran (5 mL) and treated with tetrabutylammonium fluoride (104 µL, 0.10 mmol, 1.0M in THF). The mixture was allowed to stir for 15 minutes and partitioned between ethyl acetate (30 mL) and pH 14 saturated aqueous NaCl (10 mL). The layers were separated and the organic phase was washed, dried (Na$_2$SO$_4$), and concentrated to dryness. The residue was triturated with Et$_2$O to obtain 26 mg (47%) of the desired product. $^1$H-NMR (DMSO-d$_6$) δ 8.59 (s, 1H), 7.97 (s, 1H), 7.85 (d, 1H), 7.64 (s, 1H), 7.42-7.35 (m, 5H), 7.18 (dd, 1H), 6.78 (s, 1H), 5.70 (s, 2H), 7.14 (dd, 1H), 4.44 (br s, 1H), 3.83 (dd, 1H), 3.56-3.50 (m, 2H), 3.45-3.34 (m, 1H), 3.04 (dd, 1H), 2.86-2.82 (m, 1H), 2.77-2.73 (m, 2H), 2.49-2.40 (m, 2H), 2.31-2.20 (m, 3H), 1.77 (t, 1H), 0.98 (t, 1H); LC-MS [M+H]$^+$=525, RT=2.08 min.

Example 105

Preparation of 2-{3-[4-amino-5-(2-benzyl-2H-indazol-6-yl)pyrrolo[2,1-f][1,2,4]triazin-7-yl]hexahydropyrazino[2,1-c][1,4]oxazin-8(1H)-yl}-N,N-dimethylacetamide

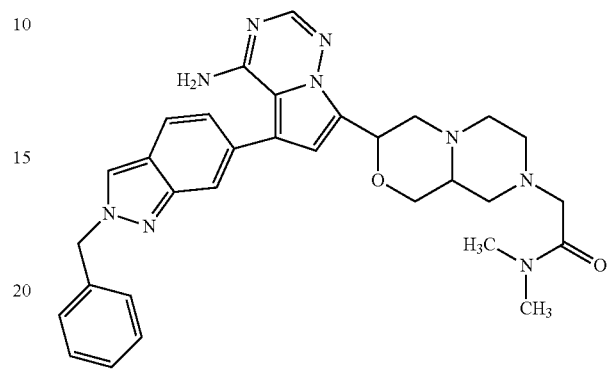

To a stirred solution of 5-(2-benzyl-2H-indazol-6-yl)-7-(octahydropyrazino[2,1-c][1,4]oxazin-3-yl)pyrrolo[2,1-f][1,2,4]triazin-4-amine (50 mg, 0.10 mmol), K$_2$CO$_3$ (28 mg, 0.21 mmol), and potassium iodide (19 mg, 0.11 mmol) in DMF (1 mL), 2-chloro-N,N-dimethylacetamide (14 mg, 0.11 mmol) was added at rt. The reaction was heated to 65° C. and allowed to stir for 2 hours. The mixture was allowed to cool and partitioned between ethyl acetate (50 mL) and saturated aqueous K$_2$CO$_3$ solution (30 mL). The layers were separated and the organic phase was washed, dried (Na$_2$SO$_4$), and concentrated to dryness. The residue was purified by preparative HPLC using a gradient elution from 10% to 70% acetonitrile to obtain 5 mg (9%) of the desired product. $^1$H-NMR (DMSO-d$_6$) δ 8.53 (s, 1H), 7.90 (s, 1H), 7.78 (d, 1H), 7.57 (s, 1H), 7.36 to 7.30 (m, 5H), 7.12 (dd, 1H), 6.71 (s, 1H), 5.64 (s, 2H), 5.09 (dd, 1H), 3.76 (dd, 1H), 3.36-3.27 (m, 1H), 3.11 (d, 2H), 2.99-2.93 (m, 4H), 2.78-2.63 (m, 6H), 2.48-2.36 (m, 1H), 2.24-2.21 (m, 3H), 1.80 (t, 1H); LC-MS [M+H]$^+$=566, RT=2.07 min.

Example 106

Preparation of 2-{3-[4-amino-5-(2-benzyl-2H-indazol-6-yl)pyrrolo[2,1-f][1,2,4]triazin-7-yl]hexahydropyrazino[2,1-c][1,4]oxazin-8(1H)-yl}-2-oxoethanol

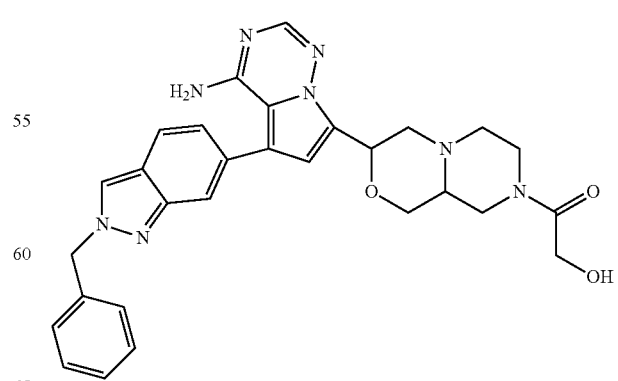

To a stirred solution of 5-(2-benzyl-2H-indazol-6-yl)-7-(octahydropyrazino[2,1-c][1,4]oxazin-3-yl)pyrrolo[2,1-f][1, 2,4]triazin-4-amine (50 mg, 0.10 mmol), triethylamine (43 µL, 0.31 mmol), and glycolic acid (8 mg, 0.10 mmol) in DMF (1 mL), benzotriazol-1-yloxytris(dimethylamino)-phosphonium hexafluorophosphate (51 mg, 0.11 mmol) was added at 0° C. The reaction was allowed to stir for 30 minutes while warming to rt. The mixture was partitioned between ethyl acetate (30 mL) and saturated aqueous K$_2$CO$_3$ solution (10 mL). The layers were separated and the organic phase was washed, dried (Na$_2$SO$_4$), and concentrated to dryness. The residue was triturated with Et$_2$O to obtain 20 mg (36%) of the desired product. $^1$H-NMR (DMSO-d$_6$) δ 8.53 (s, 1H), 7.91 (s, 1H), 7.78 (d, 1H), 7.57 (s, 1H), 7.35 to 7.27 (m, 5H), 7.11 (dd, 1H), 6.71 (s, 1H), 5.64 (s, 2H), 5.16-5.12 (m, 1H), 4.35-3.96 (m, 3H), 3.88-3.85 (m, 1H), 3.67-3.55 (m, 1H), 3.36-3.27 (m, 1H), 3.12-3.01 (m, 1H), 2.79-2.64 (m, 2H), 2.55-2.41 (m, 3H), 2.19-2.10 (m, 2H); LC-MS [M+H]$^+$=539, RT=2.19 min.

Example 107

Preparation of 7-(8-acetyloctahydropyrazino[2,1-c][1,4]oxazin-3-yl)-5-(2-benzyl-2H-indazol-6-yl)pyrrolo[2,1-f][1,2,4]triazin-4-amine

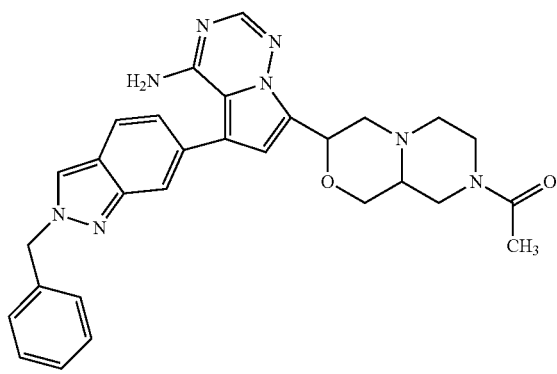 [SMILES: CC(=O)N1CCN2CC(c3cc(-c4ccc5cn(Cc6ccccc6)nc5c4)c4c(N)ncnn34)OCC2C1]

To a stirred solution of 5-(2-benzyl-2H-indazol-6-yl)-7-(octahydropyrazino[2,1-c][1,4]oxazin-3-yl)pyrrolo[2,1-f][1,2,4]triazin-4-amine (50 mg, 0.10 mmol), triethylamine (29 µL, 0.21 mmol), in DMF (1 mL) at 0° C., acetic anhydride (11 µL, 0.11 mmol) was added. The reaction was allowed to stir for 20 minutes while warming to rt. The mixture was partitioned between ethyl acetate (30 mL) and saturated aqueous K$_2$CO$_3$ solution (10 mL). The layers were separated and the organic phase was washed, dried (Na$_2$SO$_4$), and concentrated to dryness. The residue was triturated with Et$_2$O to obtain 19 mg (35%) of the desired product. $^1$H-NMR (DMSO-d$_6$) δ 8.53 (s, 1H), 7.91 (s, 1H), 7.78 (d, 1H), 7.57 (s, 1H), 7.35-7.28 (m, 5H), 7.10 (dd, 1H), 6.71 (s, 1H), 5.64 (s, 2H), 5.14 (dd, 1 H), 4.33-4.21 (m, 1H), 3.91-3.84 (m, 1H), 3.79-3.68 (m, 1H), 3.39-3.27 (m, 2H), 3.06-3.00 (m, 1H), 2.76-2.64 (m, 2H), 2.41-2.37 (m, 1H), 223-2.11 (m, 1H), 2.07-1.95 (m, 1H), 1.99 (s, 3H); LC-MS [M+H]$^+$=523, RT=2.24 min.

Example 108

Preparation of 5-(2-benzyl-2H-indazol-6-yl)-7-{8-[(dimethylamino)acetyl]-octahydropyrazino[2,1-c][1,4]oxazin-3-yl}pyrrolo[2,1-f][1,2,4]triazin-4-amine

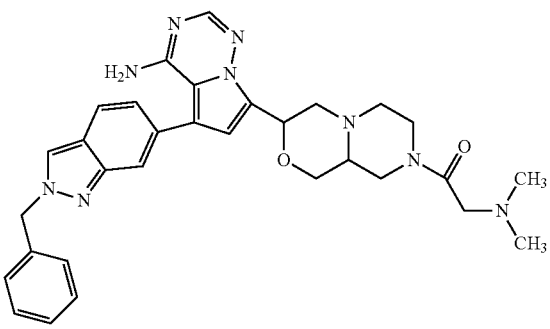 [SMILES: CN(C)CC(=O)N1CCN2CC(c3cc(-c4ccc5cn(Cc6ccccc6)nc5c4)c4c(N)ncnn34)OCC2C1]

In a manner similar to the procedure described for the preparation of Example 106 and using N,N-dimethylglycine hydrochloride in place of glycolic acid, 14 mg (24%) of the desired product was isolated. $^1$H NMR (300 MHz, DMSO-d$_6$) δ 8.53 (s, 1 H), 7.91 (s, 1 H), 7.78 (d, 1 H), 7.57 (s, 1 H), 7.35-7.30 (m, 5 H), 7.11 (dd, 1H), 6.71 (s, 1 H), 5.64 (s, 2 H), 5.13 (dd, 1H), 4.32-4.19 (m, 1H), 4.05-3.83 (m, 2H), 3.40-3.23 (m, 1H), 3.16-2.94 (m, 4H), 2.79-2.65 (m, 2H), 2.24-1.96 (m, 9H); LC-MS [M+H]$^+$=566, RT=1.94 min.

Example 109

Preparation of 3-[4-amino-5-(2-benzyl-2H-indazol-6-yl)pyrrolo[2,1-f][1,2,4]-triazin-7-yl]-N,N-dimethylhexahydropyrazino[2,1-c][1,4]oxazine-8(1H)-carboxamide

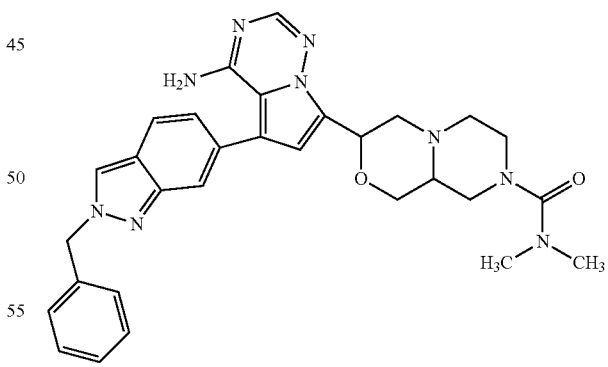

In a manner similar to the procedure described for the preparation of Example 107 and using dimethylcarbamic chloride in place of acetic anhydride, 27 mg (47%) of the desired product was isolated. $^1$H NMR (300 MHz, DMSO-d$_6$) δ 8.53 (s, 1 H), 7.90 (s, 1 H), 7.78 (d, 1 H), 7.57 (s, 1 H), 7.38-7.24 (m, 5 H), 7.2 (d, 1 H), 6.71 (s, 1 H), 5.63 (s, 2 H), 5.12 (d, 1H), 3.87-3.83 (m, 1H), 3.47-3.29 (m, 4H), 3.00 (d, 1H), 2.89-2.81 (m, 1H), 2.71 (s, 6H), 2.43-2.38 (m, 2H), 2.21-2.15 (m, 2H); LC-MS [M+H]$^+$=552, RT=2.57 min.

Example 110

Preparation of 5-(2-benzyl-2H-indazol-6-yl)-7-[8-(methylsulfonyl)octa-hydropyrazino[2,1-c][1,4]oxazin-3-yl]pyrrolo[2,1-f][1,2,4]triazin-4-amine

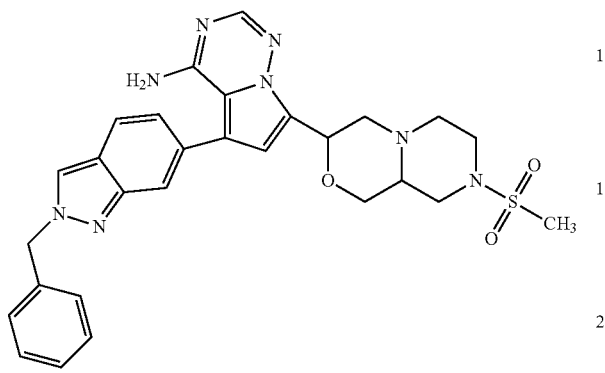

In a manner similar to the procedure described for the preparation of Example 107 and using methanesulfonyl chloride in place of acetic anhydride, 18 mg (31%) of the desired product was isolated. $^1$H-NMR (DMSO-d$_6$) δ 8.53 (s, 1H), 7.91 (s, 1H), 7.79 (d, 1H), 7.57 (s, 1H), 7.35-7.28 (m, 5H), 7.12 (dd, 1H), 6.73 (s, 1H), 5.64 (s, 2H), 5.12 (dd, 1H), 3.91 (dd, 1 H), 3.48-3.30 (m, 3H), 3.04 (dd, 1H), 2.90-2.84 (m, 5H), 2.52-2.42 (m, 2H), 2.30-2.24 (m, 2H); LC-MS [M+H]$^+$= 559, RT=2.47 min.

Example 111

Preparation of 5-(2-benzyl-2H-indazol-6-yl)-7-(8-cyclopropyloctahydro-pyrazino[2,1-c][1,4]oxazin-3-yl)pyrrolo[2,1-f][1,2,4]triazin-4-amine

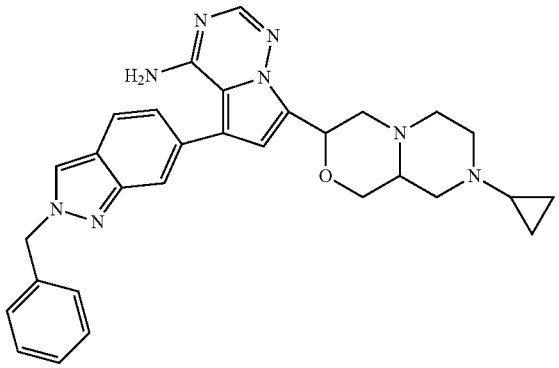 [SMILES: Nc1ncnn2c(C3CN4CCN(C5CC5)CC4CO3)cc(-c3ccc4cn(Cc5ccccc5)nc4c3)c12]

To a stirred solution of 5-(2-benzyl-2H-indazol-6-yl)-7-(octahydropyrazino[2,1-c][4]oxazin-3-yl)pyrrolo[2,1-f][1,2,4]triazin-4-amine (75 mg, 0.16 mmol), in ethanol (1 mL) containing freshly activated powdered 3 Å molecular sieves, acetic acid (0.16 mL, 1.56 mmol), [(1-ethoxycyclopropyl)oxy](trimethyl)silane (163 mg, 0.94 mmol) and sodium cyanoborohydride (27 mg, 0.62 mmol) were added at rt. The reaction was heated to 60° C. allowed to stir for 2 h. The mixture was allowed to cool and partitioned between ethyl acetate (30 mL) and 1N NaOH (10 mL). The layers were separated and the organic phase was washed, dried (Na$_2$SO$_4$), and concentrated to dryness. The residue was purified by column chromatography using a 10% methanol in dichloromethane as the eluent to obtain 13 mg (15%) of the desired product. $^1$H NMR (300 MHz, DMSO-d$_6$) δ 8.25 (s, 1 H), 7.63 (s, 1 H), 7.51 (d, 1H), 7.30 (s, 1 H), 7.08-7.01 (m, 5 H), 6.84 (dd, 1 H), 6.43 (s, 1 H), 5.36 (s, 2 H), 4.83 (dd, 1H), 3.51 (dd, 1H), 3.11-3.00 (m, 1H), 2.71 (dd, 1H), 2.52-2.39 (m, 3H), 2.14-2.05 (m, 2H), 1.90-1.82 (m, 2H), 1.67 (t, 1H), 1.33-1.30 (m, 1H), 0.12-0.09 (m, 2H), 0.09 to −0.02 (m, 2H); LC-MS [M+H]$^+$=521, RT=2.08 min.

Example 112

Preparation of 7-(octahydropyrazino[2,1-c][1,4]oxazin-3-yl)-5-(2-phenyl-2H-indazol-6-yl)pyrrolo[2,1-f][1,2,4]triazin-4-amine

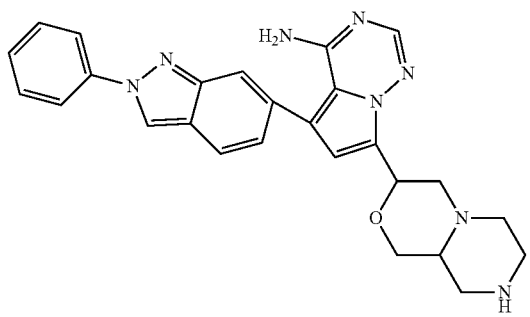 [SMILES: Nc1ncnn2c(C3CN4CCNCC4CO3)cc(-c3ccc4cn(-c5ccccc5)nc4c3)c12]

Palladium on carbon (60 mg, 10% by wt.) was placed under an inert atmosphere and suspended in AcOH (5 mL). A solution of 7-(8-benzyloctahydropyrazino[2,1-c][1,4]oxazin-3-yl)-5-(2-phenyl-2H-indazol-6-yl)pyrrolo[2,1-f][1,2,4]triazin-4-amine (600 mg, 1.08 mmol) in AcOH (6 mL) was added. The reaction mixture was placed under H$_2$ atmosphere (1 Atm pressure) and stirred overnight. Additional amounts of palladium on carbon (10% by wt.) were added as needed until the reaction was complete as observed by HPLC. The resulting mixture was filtered through a pad of Celite® and the solvent was concentrated under reduced pressure. Trituration with Et$_2$O afforded 150 mg (29%) of the desired product as an off-white solid. $^1$H NMR (300 MHz, DMSO-d$_6$) δ 9.16 (s, 1 H), 8.10 (d, 2 H), 7.94 (s, 1 H), 7.85 (d, 1 H), 7.68 (s, 1 H), 7.58 (t, 2 H), 7.44 (t, 1 H), 7.21 (dd, 1H), 6.78 (s, 1H), 5.14 (dd, 1H), 3.74 (dd, 1H), 3.49-3.28 (m, 1H), 2.94 (dd, 1H), 2.75-2.60 (m, 5H), 2.46-2.38 (m, 1H), 2.26-2.08 (m, 3H); LC-MS [M+H]$^+$=467, RT=0.91 min.

Example 113

Preparation of 7-(8-methyloctahydropyrazino[2,1-c][1,4]oxazin-3-yl)-5-(2-phenyl-2H-indazol-6-yl)pyrrolo[2,1-f][1,2,4]triazin-4-amine

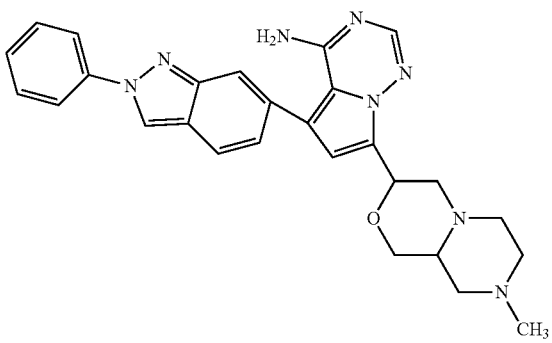 [SMILES: CN1CCN2CC(c3cc(-c4ccc5cn(-c6ccccc6)nc5c4)c4c(N)ncnn34)OCC2C1]

In a manner similar to the procedure described for the preparation of Example 103 and using 7-(octahydropyrazino[2,1-c][1,4]oxazin-3-yl)-5-(2-phenyl-2H-indazol-6-yl)pyrrolo[2,1-f][1,2,4]triazin-4-amine and iodomethane as the starting materials, 27 mg (52%) of the desired product was isolated. $^1$H NMR (300 MHz, DMSO-d$_6$) δ 9.16 (s, 1 H), 8.10 (d, 2 H), 7.94 (s, 1 H), 7.85 (d, 1 H), 7.68 (s, 1 H), 7.59 (t, 2 H), 7.44 (t, 1 H), 7.21 (dd, 1H), 6.78 (s, 1H), 5.12 (dd, 1H), 3.78 (dd, 1H), 3.39-3.30 (m, 1H), 3.00 (dd, 1H), 2.71-2.67 (m, 2H), 2.61-2.54 (m, 1H), 2.48-2.38 (m, 1H), 2.27-2.19 (m, 2H), 2.15 (s, 3H), 2.10-2.02 (m, 1H), 1.63 (t, 1H); LC-MS [M+H]$^+$=481, RT=1.08 min.

Example 114

Preparation of 5-(2-benzyl-3-methyl-2H-indazol-6-yl)-7-(octahydro-pyrazino[2,1-c][1,4]oxazin-3-yl)pyrrolo[2,1-f][1,2,4]triazin-4-amine

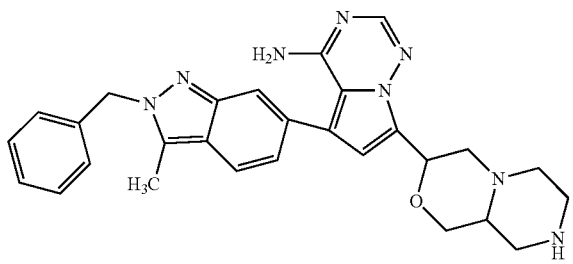 [SMILES: Cc1c2ccc(-c3cc(C4CN5CCNCC5CO4)n4ncnc(N)c34)cc2nn1Cc1ccccc1]

To a stirred solution of tert-butyl 3-(4-amino-5-bromopyrrolo[2,1-f][1,2,4]triazin-7-yl)hexahydropyrazino[2,1-c][1,4]oxazine-8(1H)-carboxylate (300 mg, 0.66 mmol) and tetrakis(triphenylphosphine)palladium(0) (114 mg, 0.099 mmol) in degassed 1,4-dioxane (5 mL) and DMF (5 mL) were added 2-benzyl-3-methyl-6-(4,4,5,5-tetramethyl-1,3,2-dioxaborolan-2-yl)-2H-indazole (345 mg, 0.99 mmol), K$_2$CO$_3$ (274 mg, 1.99 mmol), and H$_2$O (1.0 mL). The reaction was degassed and heated (100° C.) for 17 h and then cooled to rt. The mixture was partitioned between ethyl acetate (250 mL) and saturated aqueous K$_2$CO$_3$ solution (200 mL). The layers were separated and the organic phase was washed, dried (Na$_2$SO$_4$), and concentrated to dryness. The crude residue was dissolved in dichloromethane (20 mL) and treated with trifluoroacetic acid (5 mL). The solution was allowed to stir for 30 minutes and concentrated. The mixture was partitioned between ethyl acetate (75 mL) and H$_2$O (50 mL). The layers were separated and the organic phase was washed with 1N HCl (50 mL). The combined aqueous phase was transferred to a stirring mixture of ethyl acetate and pH 14 brine and allowed to stir for 30 minutes, keeping the pH above 12 with additional NaOH pellets as needed. The layers were partitioned and aqueous layer was extracted 2× with ethyl acetate (75 mL ea.). The combined organic phase was washed with brine, dried (Na$_2$SO$_4$), and concentrated to dryness. The residue was triturated with Et$_2$O to obtain 135 mg (42%) of the desired product. $^1$H NMR (300 MHz, DMSO-d$_6$) δ 7.91 (s, 1 H), 7.78 (d, 1 H), 7.52 (s, 1 H), 7.34-7.19 (m, 5 H), 7.21 (dd, 1H), 6.72 (s, 1H), 5.63 (s, 2H), 5.12 (dd, 1H), 3.73 (dd, 1H), 3.30-3.23 (m, 1H), 2.92 (dd, 1H), 2.75-2.64 (m, 4H), 2.61 (s, 3H), 2.41 (t, 1H), 2.25-2.06 (m, 4H); LC-MS [M+H]$^+$=495, RT=2.17 min.

Example 115

Preparation of 5-(2-benzyl-3-methyl-2H-indazol-6-yl)-7-(8-methylocta-hydropyrazino[2,1-c][1,4]oxazin-3-yl)pyrrolo[2,1-f][1,2,4]triazin-4-amine

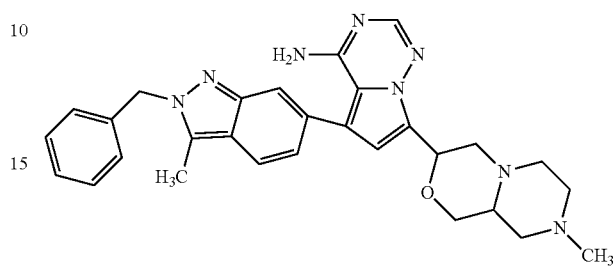

In a manner similar to the procedure described for the preparation of Example 103 and using 5-(2-benzyl-3-methyl-2H-indazol-6-yl)-7-(octahydropyrazino[2,1-c][1,4]oxazin-3-yl)pyrrolo[2,1-f][1,2,4]triazin-4-amine and iodomethane as the starting materials, 18 mg (27%) of the desired product was isolated. $^1$H NMR (300 MHz, DMSO-d$_6$) δ 7.91 (s, 1 H), 7.75 (d, 1 H), 7.52 (s, 1 H), 7.34-7.19 (m, 5 H), 7.06 (dd, 1H), 6.72 (s, 1H), 5.63 (s, 2H), 5.14-5.10 (m, 1H), 3.73 (dd, 1H), 3.37-3.30 (m, 1H), 2.93 (dd; 1H), 2.75-2.63 (m, 4H), 2.61 (s, 3H), 2.41 (t, 1H), 2.25-2.06 (m, 3H), 1.57 (s, 3H); LC-MS [M+H]$^+$=509, RT=0.28 min.

Example 116

Preparation of 5-(2-benzyl-3-fluoro-2H-indazol-6-yl)-7-(octahydro-pyrazino[2,1-c][1,4]oxazin-3-yl)pyrrolo[2,1-f][1,2,4]triazin-4-amine

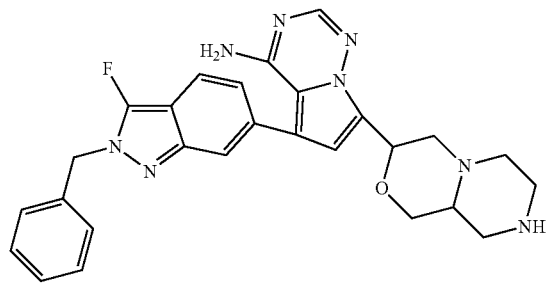 [SMILES: Nc1ncnn2c(C3CN4CCNCC4CO3)cc(-c3ccc4c(F)n(Cc5ccccc5)nc4c3)c12]

In a manner similar to the procedure described for the preparation of Example 114 and using 2-benzyl-3-fluoro-6-(4,4,5,5-tetramethyl-1,3,2-dioxaborolan-2-yl)-2H-indazole in place of 2-benzyl-3-methyl-6-(4,4,5,5-tetramethyl-1,3,2-dioxaborolan-2-yl)-2H-indazole, 140 mg (22%) of the desired product was isolated. $^1$H NMR (300 MHz, DMSO-d$_6$) δ 7.91 (s, 1 H), 7.68 (d, 1H), 7.46-7.45 (m, 1H), 7.37-7.30 (m, 5H), 7.13 (dd, 1H), 6.73 (s, 1H), 5.58 (s, 2H), 5.12 (dd, 1H), 3.72 (dd, 1H), 3.33-3.26 (m, 1H), 2.92 (dd, 1H), 2.75-2.59 (m, 5H), 2.39 (t, 1H), 2.21 (t, 1H), 2.14-2.06 (m, 2H); LC-MS [M+H]$^+$=499, RT=1.33 min.

Example 117

Preparation of 5-(2-benzyl-2H-indazol-6-yl)-7-pyrrolidin-3-ylpyrrolo[2,1-f][1,2,4]triazin-4-amine

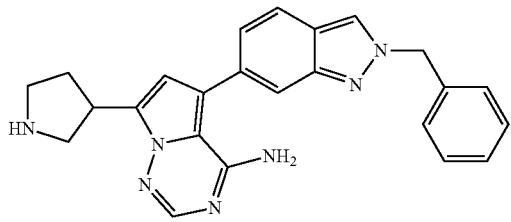 [SMILES: Nc1ncnn2c(C3CCNC3)cc(-c3ccc4cn(Cc5ccccc5)nc4c3)c12]

Step 1: Preparation of tert-butyl 3-[4-amino-5(2-benzyl-2H-indazol-6-yl)pyrrolo[2,1-f][1,2,4]triazin-7-yl]pyrrolidine-1-carboxylate

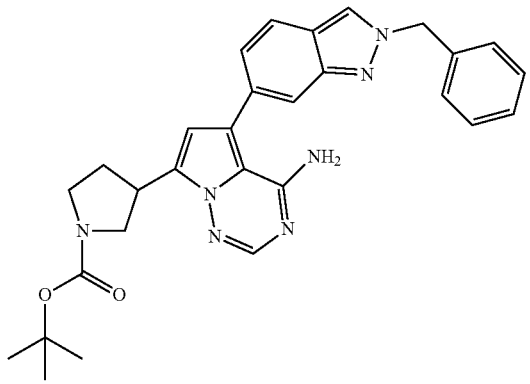 [SMILES: CC(C)(C)OC(=O)N1CCC(c2cc(-c3ccc4cn(Cc5ccccc5)nc4c3)c3c(N)ncnn23)C1]

To a stirred suspension of Intermediate C (2.62 g mg, 7.85 mmol) and tert-butyl 3-(4-amino-5-bromopyrrolo[2,1-f][1,2,4]triazin-7-yl)pyrrolidine-1-carboxylate (2.50 g, 6.54 mmol) in degassed DMF (6.7 mL) was added solid potassium phosphate (4.16 g, 19.62 mmol) followed by water (833 uL, 49 mmol). The reaction mixture was taken through three purge-fill cycles using nitrogen and vacuum. The reaction was then heated (100° C.) for 1 h and then cooled to rt. The mixture was partitioned between ethyl acetate (200 mL) and H$_2$O (100 mL). The layers were separated and the organic layer was washed 6 times with brine to remove DMF (50 mL each), dried (Na$_2$SO$_4$), and concentrated to dryness. The crude residue was purified by ISCO® chromatography using a gradient of 50 to 100% ethyl acetate in dichloromethane to afford 1.27 g (38%) of the desired product as an off-white solid. $^1$H NMR (300 MHz, DMSO-d$_6$) δ 8.53 (s, 1 H), 7.93 (s, 1 H), 7.80 (d, 1 H), 7.59 (s, 1 H), 7.35-7.30 (m, 4H), 7.15 (d, 1 H), 6.66 (s, 1H), 5.64 (s, 2 H), 3.9-3.7 (m, 1 H), 3.50-3.30 (m, 4H), 2.42 (m, 1H), 2.13 (m, 1H), 1.38 (s, 9H); ES-MS m/z 510.3 [M+H]$^+$, HPLC RT (min) 3.16.

Step 2: Preparation of (5-(2-benzyl-2H-indazol-6-yl)-7-pyrrolidin-3-ylpyrrolo[2,1-f][1,2,4]triazin-4-amine

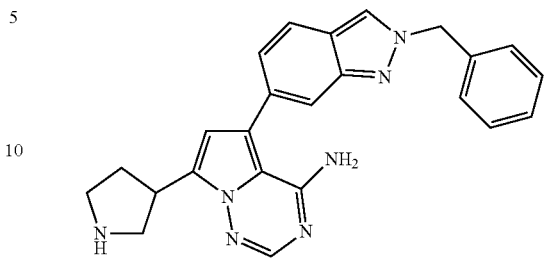

To a dry flask was added tert-butyl 3-[4-amino-5-(2-benzyl-2H-indazol-6-yl)pyrrolo[2,1-f][1,2,4]triazin-7-yl]pyrrolidine-1-carboxylate (420 mg, 0.824 mmol) followed by a solution of 1:1 trifluoroacetic acid in dichloromethane (3 mL). The mixture was stirred under N$_2$ atmosphere for 1.5 h. The reaction was then partitioned between dichloromethane (150 mL) and 10% aqueous potassium carbonate. The aqueous layer was back extracted with dichloromethane (2×25 mL). The combined organic layer was washed with brine (50 mL) then dried with sodium sulfate. The solvent was evaporated under reduced pressure to yield 320 mg (95%) of the desired product as a tan solid. $^1$H NMR (300 MHz, DMSO-d$_6$) δ 8.53 (s, 1 H), 7.89 (s, 1 H), 7.78 (d, 1 H), 7.58 (s, 1 H), 7.50-7.30 (m, 4H), 7.14 (d, 1 H), 6.58 (s, 1 H), 5.64 (s, 2 H), 3.98 (m, 1 H), 3.35-3.25 (m, 3 H), 2.10 (m, 1 H), 1.92 (m, 1 H); ES-MS m/z 410.4 [M+H]$^+$, HPLC RT (min) 2.00.

Example 118

Preparation of (−)-5-(2-benzyl-2H-indazol-6-yl)-7-pyrrolidin-3-ylpyrrolo[2,1-f][1,2,4]triazin-4-amine

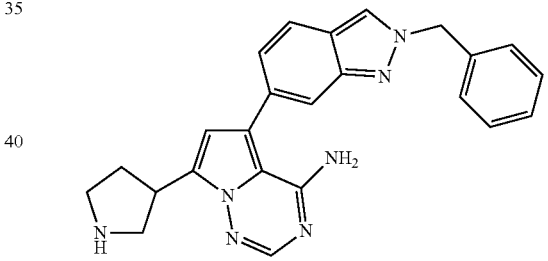

Step 1: Preparation of optically pure, tert-butyl 3-[4-amino-5-(2-benzyl-2H-indazol-6-yl)pyrrolo[2,1f][1,2,4]triazin-7-yl]pyrrolidine-1-carboxylate

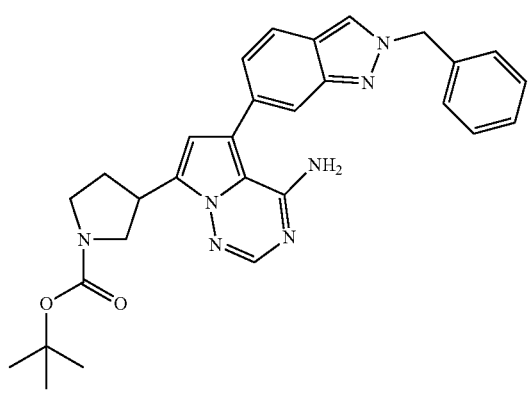 [SMILES: CC(C)(C)OC(=O)N1CCC(c2cc(-c3ccc4cn(Cc5ccccc5)nc4c3)c3c(N)ncnn23)C1]

Tert-butyl-3-[4-amino-5-(2-benzyl-2H-indazol-6-yl)pyrrolo[2,1-f][1,2,4]triazin-7-yl]pyrrolidine-1-carboxylate (200 mg, 0.392 mmol) was subjected to chiral separation using a Daicel Chiralpak AD-H column (20×250 mm). Eluent was 4:1 isopropanol-methanol at 10 mL/min. The racemic material separated into two optically pure fractions. Fraction A eluted first from the column. The eluent was removed by rotary evaporation to yield 50 mg of an off white solid product (rotation: −0.46 at 1 mg/mL in methanol). Fraction B (Muted second from the column. The eluent was removed by rotary evaporation to yield 65 mg an off white solid product (rotation: +0.45).

Step 2: Preparation of (−)(5-(2-benzyl-2H-indazol-6-yl)-7-pyrrolidin-3-ylpyrrolo[2,1-f][1,2,4]triazin-4-amine

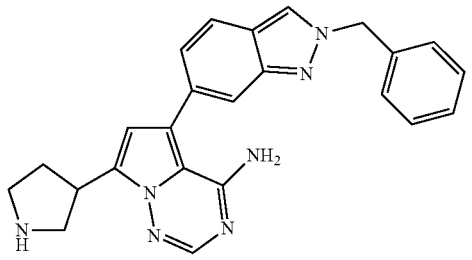 [SMILES: Nc1ncnn2c(C3CCNC3)cc(-c3ccc4cn(Cc5ccccc5)nc4c3)c12]

The optically pure tert-butyl 3-[4-amino-5-(2-benzyl-2H-indazol-6-yl)pyrrolo[2,1-f][1,2,4]triazin-7-yl]pyrrolidine-1-carboxylate (Fraction A from step 1, 50 mg) was treated in the same manner as described for the deprotection of racemic tert-butyl 3-[4-amino-5-(2-benzyl-2H-indazol-6-yl)pyrrolo[2,1-f][1,2,4]triazin-7-yl]pyrrolidine-1-carboxylate to yield 20 mg, (50%) of the title compound. $^1$H NMR (300 MHz, dichloromethane-d$_2$) δ 7.96 (s, 1 H), 7.80 (s, 1 H), 7.70-7.64 (m, 2 H), 7.29-7.24 (m, 4 H), 7.10 (d, 1H), 6.59 (s, 1 H), 5.75 (br s, 1 H), 5.53 (s, 2 H), 4.00 (q, H) 3.75, (m, 1 H), 3.70-3.40 (m, 3H) 2.52 (m, 1H), 2.30 (m, 1H); ES-MS m/z 410.4 [M+H]$^+$, HPLC RT (min) 2.00.

Example 119

Preparation of (+)-5-(2-benzyl-2H-indazol-6-yl)-7-pyrrolidin-3-ylpyrrolo[2,1-f][1,2,4]triazin-4-amine

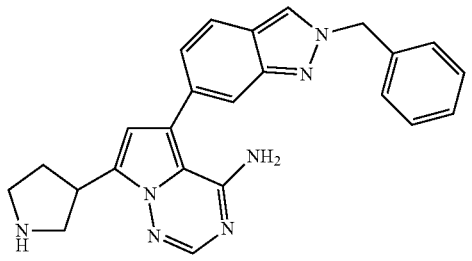 [SMILES: Nc1ncnn2c(C3CCNC3)cc(-c3ccc4cn(Cc5ccccc5)nc4c3)c12]

The optically pure tert-butyl 3-[4-amino-5-(2-benzyl-2H-indazol-6-yl)pyrrolo[2,1-f][1,2,4]triazin-7-yl]pyrrolidine-1-carboxylate (Fraction B from step 1, 61 mg) was treated in the same manner as described for the deprotection of racemic tert-butyl 3-[4-amino-5-(2-benzyl-2H-indazol-6-yl)pyrrolo[2,1-f][1,2,4]triazin-7-yl]pyrrolidine-1-carboxylate to yield 23 mg, (47%) of the title compound. $^1$H NMR (300 MHz, methanol-d$_4$) δ 8.05 (s, 1 H), 7.99 (s, 1 H), 7.78-7.73 (m, 2 H), 7.38-7.37 (m, 4 H), 7.35 (d, 1H), 6.63 (s, 1 H), 5.62 (s, 2 H), 4.00 (q, H), 3.60 (m, 1 H), 3.47-3.20 (m, 3H), 2.25 (m, 1H), 2.10 (m, 1H); ES-MS m/z 410.2 [M+H]$^+$, HPLC RT (min) 2.07.

Example 120

Preparation of 7-[1-(azetidin-3-ylcarbonyl)pyrrolidin-3-yl]-5-(2-benzyl-2H-indazol-6-yl)pyrrolo[2,1-f][1,2,4]triazin-4-amine

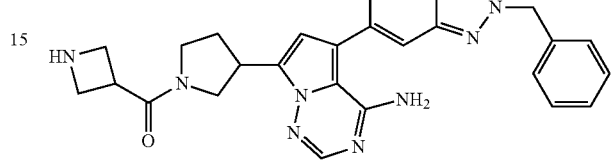

Step 1: Preparation of tert-butyl 3-({3-[4-amino-5-(2-benzyl-2H-indazol-6-yl)pyrrolo[2,1-f][1,2,4]triazin-7-yl]pyrrolidin-1-yl}carbonyl)azetidine-1-carboxylate

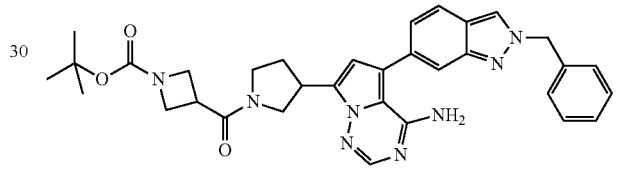

To a solution of (5-(2-benzyl-2H-indazol-6-yl)-7-pyrrolidin-3-ylpyrrolo[2,1-f][1,2,4]triazin-4-amine (100 mg, 0.244 mmol) in DMF (1.5 mL) was added 1-(tert-butoxycarbonyl)azetidine-3-carboxylic acid (50.6 mg, 0.252 mmol), triethylamine (102 µl, 0.733 mmol), and (BOP) benzoltriazolyloxy-tris(dimethylamino)phosphonium-hexafluorophosphate (140 mg, 0.317 mmol). The reaction was stirred at rt overnight. The mixture was partitioned between ethyl acetate (25 mL) and H$_2$O (25 mL). The layers were separated and the organic was washed with H$_2$O (20 mL). The combined aqueous layers were extracted with ethyl acetate (20 mL). The combined organics were washed with water (5×20 mL) to remove DMF, dried (Na$_2$SO$_4$), and evaporated. The crude material was purified by trituration with ether to yield 50 mg (35%) of the desired product. $^1$H NMR (300 MHz, Methanol-d$_6$) δ 8.36 (s, 1 H), 7.85-7.81 (m, 2 H), 7.65 (s, 1 H), 7.40-7.20 (m, 4 H), 7.23 (d, 1 H), 6.67 (d, 1 H), 5.85 (s, 2 H), 4.20-3.90 (m, 3 H), 3.80-3.40 (m, 2 H), 3.30-3.10 (m, 4 H), 2.60-2.10 (m, 2 H), 1.33 (d, 9H); ES-MS m/z 579.0 [M+H]$^+$, HPLC RT (min) 2.46.

Step 2: Preparation of the Title Compound

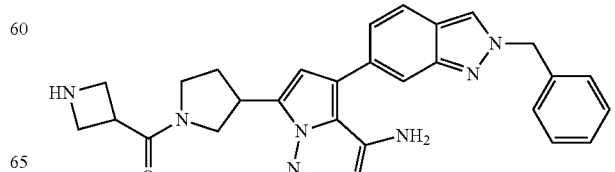

Tert-butyl-3-({3-[4-amino-5-(2-benzyl-2H-indazol-6-yl)pyrrolo[2,1-f][1,2,4]triazin-7-yl]pyrrolidin-1-yl}carbonyl)azetidine-1-carboxylate (33 mg, 0.056 mmol) was deprotected in the same manner as step 6 of the preparation of Intermediate S S to yield 27 mg (99%) of desired product. $^1$H NMR (300 MHz, Methanol-d$_4$) δ 8.27 (s, 1 H), 7.85 (s, 1 H), 7.79 (d, 1 H), 7.68 (s, 1 H), 7.40-7.30 (m, 4 H), 6.62 (d, 1 H), 4.10-3.50 (m, 7 H), 3.40-3.25 (m, 1 H), 2.27-2.10; ES-MS m/z 493.2[M+H]$^+$, HPLC RT (min) 2.10.

Example 121

Preparation of 5-(2-benzyl-2H-indazol-6-yl)-7-(1-{[(dimethylamino)oxy]carbonyl}pyrrolidin-3-yl)pyrrolo[2,1-f][1,2,4]triazin-4-amine

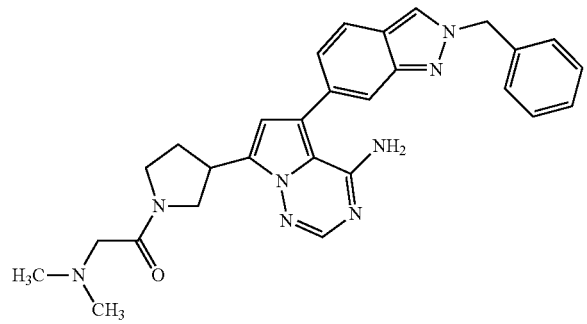 [SMILES: CN(C)CC(=O)N1CCC(c2cc(-c3ccc4cn(Cc5ccccc5)nc4c3)c3c(N)ncnn23)C1]

5-(2-benzyl-2H-indazol-6-yl)-7-pyrrolidin-3-ylpyrrolo[2,1-f][1,2,4]triazin-4-amine (75 mg, 0.183 mmol) was coupled to N,N-dimethylglycine hydrochloride (33 mg, 0.238 mmol) following the procedure described in Example 120. The material was then subjected to HPLC purification using a Sunfire Prep C18 OBD 5 micron, 30×75 mm column. The compound was eluted using a gradient 10-70% acetonitrile/water with 0.1% TFA over 20 minutes to yield (14 mg, 15%) desired product. $^1$H NMR (300 MHz, DMSO-d$_5$) δ 8.54 (s, 1 H), 7.92 (s, 1 H), 7.80 (d, 1 H), 7.50 (s, 1 H), 7.36-7.34 (m, 4 H), 7.15 (d, 1 H), 5.64 (s, 2 H), 4.10-3.30 (m, 5H), 3.04 (m, 2 H), 2.45-2.05 (m, 2H), 2.20 (d, 6 H); ES-MS m/z 495.2 [M+H]$^+$, HPLC RT (min) 2.11.

Example 122

Preparation of 5-(2-benzyl-2H-indazol-6-yl)pyrrolo[2,1-f][1,2,4]triazin-4-amine

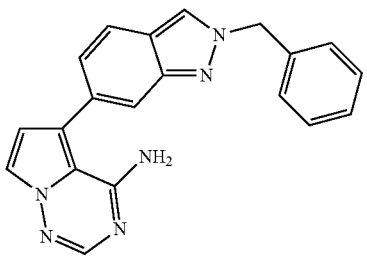 [SMILES: Nc1ncnn2ccc(-c3ccc4cn(Cc5ccccc5)nc4c3)c12]

This material was isolated as an impurity during the chromatography of 5-(2-benzyl-2H-indazol-6-yl)-7-(1-{[((dimethylamino)oxy]carbonyl}pyrrolidin-3-yl)pyrrolo[2,1-f][1,2,4]triazin-4-amine. $^1$H NMR (300 MHz, Methanol-d$_4$) δ 8.48 (s, 1 H), 8.27 (s, 1 H), 7.86 (s, 1 H), 7.73 (d, 1 H), 7.67 (d, 1 H), 7.34 (m, 4 H), 7.04 (m, 2H) 5.64 (s, 2 H); ES-MS m/z 341.5 [M+H]$^+$, HPLC RT (min) 2.51.

Example 123

Preparation of 2-{3-[4-amino-5-(2-benzyl-2H-indazol-6-yl)pyrrolo[2,1-f][1,2,4]triazin-7-yl]pyrrolidin-1-yl]-2-oxoethanol

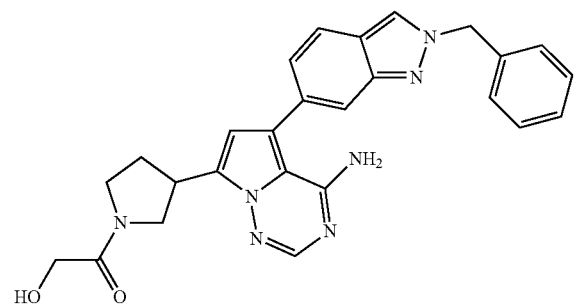 [SMILES: Nc1ncnn2c(C3CCN(C(=O)CO)C3)cc(-c3ccc4cn(Cc5ccccc5)nc4c3)c12]

(5-(2-benzyl-2H-indazol-6-yl)-7-pyrrolidin-3-ylpyrrolo[2,1-f][1,2,4]triazin-4-amine (50 mg, 0.122 mmol) was suspended in dichloromethane (1 mL). Glycolyic acid (10 mg, 0.134 mmol) was then added, followed by triethylamine (37 mg, 37 mmol), dimethylaminopyridine (4 mg, 0.031 mmol), and EDCl (26 mg, 0.134 mmol). The suspension was stirred at rt overnight. The material was then purified via column chromatography. The compound was eluted using a gradient 1-10% (2N NH$_3$ in methanol)/dichloromethane to yield desired product (15 mg, 26%). $^1$H NMR (300 MHz, dichloromethane-d$_2$) δ 8.05 (s, 1 H), 7.91 (s, 1 H), 7.78-7.73 (m, 3 H), 7.60-7.45 (m, 4 H), 7.33 (d, 2 H), 6.60 (s, 1 H), 5.33 (s, 2 H), 4.15-3.39 (m, 7H), 2.60-2.20 (m, 2H); ES-MS m/z 468.2 [M+H]$^+$, HPLC RT (min) 2.36.

Example 124

Preparation of trifluoromethyl 3-[4-amino-5-(2-benzyl-2H-indazol-6-yl)pyrrolo[2,1-f][1,2,4]triazin-7-yl]pyrrolidine-1-carboxylate

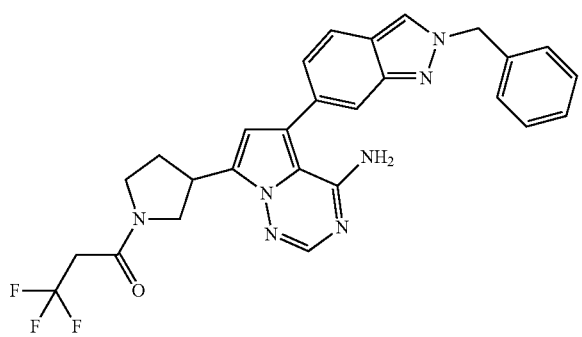 [SMILES: Nc1ncnn2c(C3CCN(C(=O)CC(F)(F)F)C3)cc(-c3ccc4cn(Cc5ccccc5)nc4c3)c12]

(5-(2-benzyl-2H-indazol-6-yl)-7-pyrrolidin-3-ylpyrrolo[2,1-f][1,2,4]triazin-4-amine (50 mg, 0.122 mmol) was coupled with 3,3,3-trifluoropropanoic acid (17 mg, 0.134 mmol) using the procedure described in Example 123. The material was then subjected to column chromatography. The compound was eluted using a gradient 0-6% (2N NH$_3$ in methanol)/dichloromethane to yield desired product (13 mg, 20%). $^1$H NMR (300 MHz, DMSO-d$_6$) δ 8.53 (s, 1 H), 7.92 (s, 1 H), 7.80 (d, 1 H), 7.70-7.60 (m, 2 H), 7.55-7.34 (m, 4 H), 7.20 (d, 1 H), 5.64 (s, 2 H), 4.05-3.60 (m, 7H), 2.65-2.00 (m, 2H); ES-MS m/z 520.2 [M+h]+, HPLC RT (min) 2.70.

Example 125

Preparation of 5-(2-benzyl-2H-indazol-6-yl)-7-[1-(cyclopropylcarbonyl)pyrrolidin-3-yl]pyrrolo[2,1-f][1,2,4]triazin-4-amine

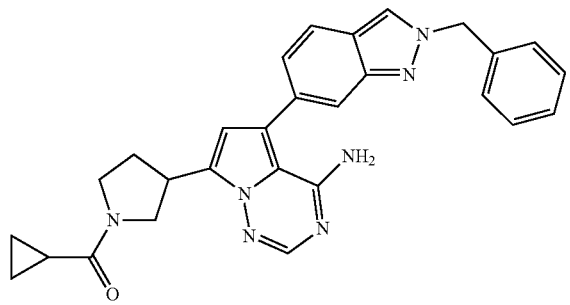 [SMILES: Nc1ncnn2c(C3CCN(C(=O)C4CC4)C3)cc(-c3ccc4cn(Cc5ccccc5)nc4c3)c12]

(5-(2-benzyl-2H-indazol-6-0)-7-pyrrolidin-3-ylpyrrolo[2,1-f][1,2,4]triazin-4-amine (75 mg, 0.183 mmol) was coupled with cyclopropanecarboxylic acid (16 mg, 0.183 mmol) using the procedure of Example 123. The material was then purified via column chromatography. The compound was eluted using a gradient 0-6% (2N $NH_3$ in methanol)/dichloromethane to yield desired product (69 mg, 79%). $^1$H NMR (300 MHz, DMSO-$d_6$) δ 8.53 (s, 1 H), 7.92 (d, 1 H), 7.80 (d, 1 H), 7.75-7.50 (m, 3 H), 7.35-7.30 (m, 4 H), 7.14 (d, 1 H), 6.70 (d, 1 H), 5.65 (d, 2H), 3.95-2.40 (m, 5H), 2.50-2.00 (m, 2H), 1.8-1.1 (m, 5 H); ES-MS m/z 478.4 [M+H]+, HPLC RT (min) 2.53.

Example 126

Preparation of 5-(2-benzyl-2H-indazol-6-yl)-7-[1-(morpholin-4-ylcarbonyl)pyrrolidin-3-yl]pyrrolo[2,1-f][1,2,4]triazin-4-amine

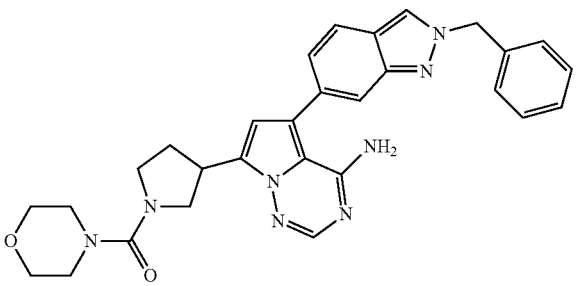 [SMILES: Nc1ncnn2c(C3CCN(C(=O)N4CCOCC4)C3)cc(-c3ccc4cn(Cc5ccccc5)nc4c3)c12]

(5-(2-benzyl-2H-indazol-6-yl)-7-pyrrolidin-3-ylpyrrolo[2,1-f][1,2,4]triazin-4-amine (75 mg, 0.183 mmol) was dissolved in tetrahydrofuran (2 mL). Morpholine-4-carbonyl chloride (27 mg, 0.183 mmol) was added to the reaction mixture followed by triethylamine (51 uL, 0.366 mmol). The suspension was stirred at rt overnight. The reaction was concentrated under vacuum. The compound was triturated with 1:1 ether-hexanes to yield desired product (70 mg, 73%). $^1$H NMR (300 MHz, DMSO-$d_6$) δ 8.53 (s, 1 H), 7.92 (s, 1 H), 7.79 (d, 1 H), 7.58 (m, 3 H), 7.35-7.32 (m, 4 H), 7.13 (d, 1 H), 6.67 (s, 1 H), 5.64 (s, 2 H), 3.90-2.50 (m, 13 H), 2.50-2.10 (m, 2 H); ES-MS m/z 523.3 [M+H]+, HPLC RT (min) 2.47.

Example 127

Preparation of 3-[4-amino-5-(2-benzyl-2H-indazol-6-yl)pyrrolo[2,1-f][1,2,4]triazin-7-yl]-N,N-dimethylpyrrolidine-1-carboxamide (5-(2-benzyl-2H-indazol-6-yl)-7-pyrrolidin-3-ylpyrrolo[2,1-f][1,2,4]triazin-4-amine (75 mg, 0.183 mmol) was reacted with dimethylcarbamoyl chloride (14 uL, 0.192 mmol), according to the procedure of Example 126. The crude product was triturated with 1:1 ether-hexanes to yield (30 mg, 34%) desired product. $^1$H NMR (300 MHz, DMSO-$d_6$) δ 8.53 (s, 1 H), 7.91 (s, 1 H), 7.81 (d, 1 H), 7.59 (s, 1H), 7.45-7.32 (m, 6 H), 7.13 (d, 1 H), 6.65 (s, 1 H), 5.64 (s, 2 H), 3.76 (m, 2 H), 3.42 (m, 3 H), 3.29 (m, 1 H), 2.73 (s, 6 H), 2.31-1.95 (m, 2 H); ES-MS m/z 481.2 [M+H]+, HPLC RT (min) 2.57.

Example 128

Preparation of 3-[4-amino-5-(2-benzyl-2H-indazol-6-yl)pyrrolo[2,1-f][1,2,4]triazin-7-yl]-N,N-dimethylpyrrolidine-1-sulfonamide (5-(2-benzyl-2H-indazol-6-yl)-7-pyrrolidin-3-ylpyrrolo[2,1-f][1,2,4]triazin-4-amine (50 mg, 0.122 mmol) was dissolved in tetrahydrofuran (2 mL). Dimethylsulfamoyl chloride (18 mg, 0.122 mmol) was added to the reaction mixture followed by triethylamine (34 uL, 0.244 mmol). The suspension was stirred at rt overnight. The reaction was concentrated under vacuum. The compound was triturated with 1:1 ether-hexanes to yield desired product (22 mg, 35%). $^1$H NMR (300 MHz, DMSO-$d_6$) δ 8.54 (s, 1 H), 7.92 (1s, 1 H), 7.80 (d, 1 H), 7.59 (s, 1 H), 7.20 (m, 3H), 7.35-7.25 (m, 4 H), 7.12 (d, 1 H), 5.64 (s, 2 H), 3.90-3.20 (m, 5H), 2.70-2.05 (m, 8H).

Example 129

Preparation of 5-(2-benzyl-2H-indazol-6-yl)-7-[1-(methylsulfonyl)pyrrolidin-3-yl]pyrrolo[2,1-f][1,2,4]triazin-4-amine

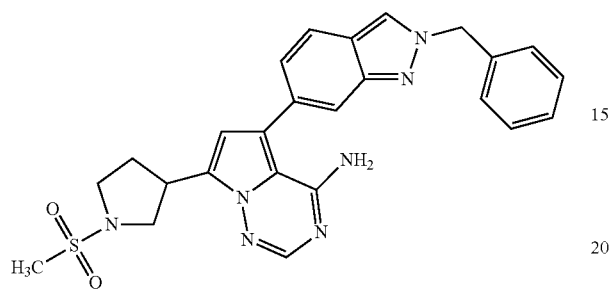

(5-(2-benzyl-2H-indazol-6-yl)-7-pyrrolidin-3-ylpyrrolo[2,1-f][1,2,4]triazin-4-amine (40 mg, 0.098 mmol) was dissolved in tetrahydrofuran (2 mL). Methanesulfonyl chloride (18 mg, 0.127 mmol) was added to the reaction mixture followed by triethylamine (136 uL, 0.977 mmol). The suspension was stirred at rt overnight. The compound was triturated with 1:1 ether-hexanes to yield desired product (14 mg, 29%). $^1$H NMR (300 MHz, dichloromethane-d$_2$) δ 7.95 (1d, 1 H), 7.80 (1s, 1 H), 7.69-7.97.64 (m, 3 H), 7.27-7.25 (m, 4 H), 7.13 (d, 1 H), 6.54 (s, 1 H) 5.61 (bs, 2 H), 5.61 (bs, 2 H), 5.52 (s, 2H), 4.05-3.90 (m, 2H), 3.60-3.35 (m, 3 H), 2.75 (s, 3 H), 2.45 (m, 1 H), 2.20 (m, 1 H); ES-MS m/z 488.3 [M+H]$^+$, HPLC RT (min) 2.72.

Example 130

Preparation of 5-(2-benzyl-2H-indazol-6-yl)-7-(1-cyclopropylpyrrolidin-3-yl)pyrrolo[2,1-f][1,2,4]triazin-4-amine

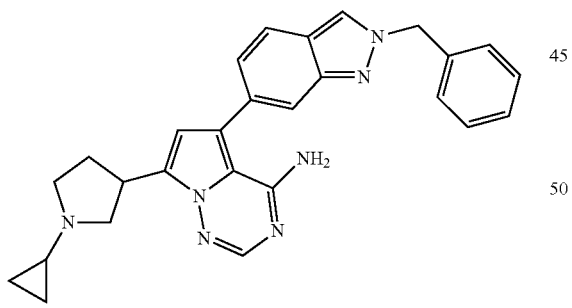

(5-(2-benzyl-2H-indazol-6-yl)-7-pyrrolidin-3-ylpyrrolo[2,1-f][1,2,4]triazin-4-amine (100 mg, 0.244 mmol) was dissolved in methanol (3.5 mL). Acetic acid (140 uL, 2.44 mmol) was added followed by a small scoop of activated molecular sieves. [(1-ethoxycyclopropyl)oxy](trimethyl)silane (255 mg, 1.47 mmol) was added to the flask via syringe. Solid sodium cyanoborohydride was added (61 mg, 0.977 mmol) to the reaction which was then heated under nitrogen overnight. The mixture was partitioned between ethyl acetate (100 mL) and sodium bicarbonate (50 mL). The aqueous layer was extracted with ethyl acetate (20 mL). The combined organic layer was washed with brine and then dried with sodium sulfate. The product was purified using column chromatography, eluent 2-3% (7N NH$_3$ in Methanol)/dichloromethane to afford 32 mg (29%) of desired product. $^1$H NMR (300 MHz, dichloromethane-d$_2$) δ 8.04 (s, 1 H), 7.89 (s, 1 H), 7.78-7.73 (m, 3 H), 7.60-7.40 (m, 4 H), 7.25 (d, 1 H), 6.63 (s, 1H), 5.62 (s, 2 H), 5.52 (bs, 2 H), 3.90 (m, 1H), 3.40 (m, 1H), 2.80 (m, 3 H), 2.40 (m, 1 H), 1.95 (m, 1 H), 1.75 (m, 1 H), 1.40-0.90 (m, 3 H); ES-MS m/z 450.2 [M+H]$^+$, HPLC RT (min) 2.17.

Example 131

Preparation of 7-(1-acetylpyrrolidin-3-yl)-5-(2-benzyl-2H-indazol-6-yl)pyrrolo[2,1-f][1,2,4]triazin-4-amine

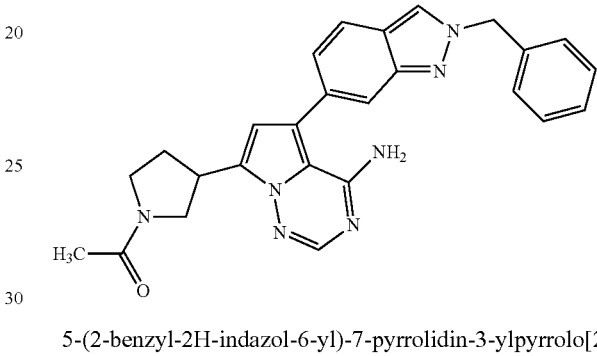

5-(2-benzyl-2H-indazol-6-yl)-7-pyrrolidin-3-ylpyrrolo[2,1-f][1,2,4]triazin-4-amine (40 mg, 0.098 mmol) was reacted with acetic anhydride (13 mg, 0.127 mmol) following the procedure of Example 107. The product was chromatographed on an ISCO® instrument (4 g column). The eluent was 0-6% (2N NH$_3$ in methanol)/dichloromethane to yield 18 mg (41%) of desired product. $^1$H NMR (300 MHz, DMSO-d$_6$) δ 8.62 (s, 1 H), 8.00-7.75 (m, 4 H), 7.60-7.40 (m, 4H), 7.23 (d, 1 H), 6.77 (d, 1 H), 5.72 (s, 2 H), 4.10-3.20 (m, 5H), 2.52-2.15 (m, 2H), 2.05 (s, 3 H); ES-MS m/z 452.4 [M+H]$^+$, HPLC RT (min) 2.36.

Example 132

Preparation of 5-(2-benzyl-2H-indazol-6-yl)-7-{1-[(pyrrolidin-1-yloxy)carbonyl]pyrrolidin-3-yl}pyrrolo[2,1-f][1,2,4]triazin-4-amine

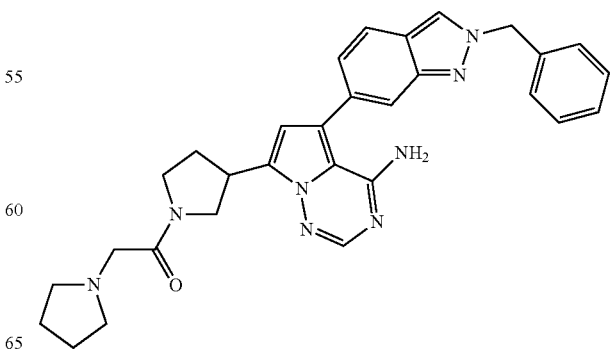

Step 1: Preparation of 5-(2-benzyl-2H-indazol-6-yl)-7-[1-(chloroacetyl)pyrrolidin-3-yl]pyrrolo[2,1-f][1,2,4]triazin-4-amine

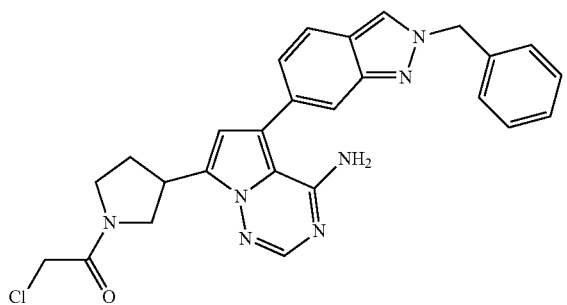 [SMILES: Nc1ncnn2c(C3CCN(C(=O)CCl)C3)cc(-c3ccc4cn(Cc5ccccc5)nc4c3)c12]

5-(2-benzyl-2H-indazol-6-yl)-7-pyrrolidin-3-ylpyrrolo[2,1-f][1,2,4]triazin-4-amine (600 mg, 1.47 mmol) was dissolved in THF (6 mL). The solution was cooled to −78° C. under nitrogen. Triethylamine (613 uL, 4.39 mmol) was added via syringe followed by chloroacetylchloride (165 mg, 1.47 mmol). The reaction was stirred at −78° C. for 30 min then warmed to rt. The solution was diluted to 12 mL with anhydrous DMF then divided in 6-2 mL portions for use in the next steps.

Step 2: Preparation of the Title Compound

To a solution of 5-(2-benzyl-2H-indazol-6-yl)-7-[1-(chloroacetyl)pyrrolidin-3-yl]pyrrolo[2,1-f][1,2,4]triazin-4-amine (100 mg, 0.206 mmol) in 2 mL of 1:1 DMF-THF, triethylamine was added (86 uL, 0.617 mmol), followed by pyrrolidine (34 uL, 0.412 mmol). A spatula tip of potassium iodide was added and the reaction was heated at 60° C. overnight. The reaction was cooled and partitioned between EtOAc (50 mL) and water (25 mL). The layers were separated and the organic layer was washed with water (5×15 mL) to remove DMF. The organic layer was the dried with $Na_2SO_4$ and concentrated to yield an off-white solid. The solid was triturated with 1:1 ether hexanes to yield 45 mg (42%) of the title compound. $^1$H NMR (300 MHz, DMSO-$d_6$) δ 8.52 (s, 1 H), 7.91 (s, 1 H), 7.80 (d 1 H), 7.65 (m, 3 H), 7.40 (m, 4 H), 7.21 (d, 1 H), 6.63 (d, 1 H), 5.64 (s, 2 H), 3.97-3.00 (m, 11H), 2.52-2.00 (m, 6H); ES-MS m/z 521.2 [M+H]$^+$, HPLC RT (min) 2.15.

Example 133

Preparation of 5-(2-benzyl-2H-indazol-6-yl)-7-{1-[(3,3-difluoropyrrolidin-1-yl)acetyl]pyrrolidin-3-yl}pyrrolo[2,1-f][1,2,4]triazin-4-amine

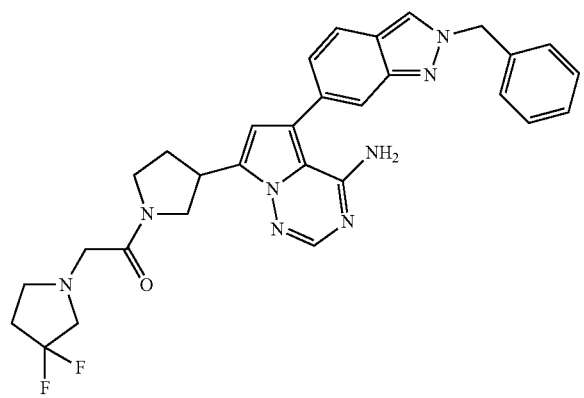 [SMILES: Nc1ncnn2c(C3CCN(C(=O)CN4CCC(F)(F)C4)C3)cc(-c3ccc4cn(Cc5ccccc5)nc4c3)c12]

5-(2-benzyl-2H-indazol-6-yl)-7-[1-(chloroacetyl)pyrrolidin-3-yl]pyrrolo[2,1-f][1,2,4]triazin-4-amine (100 mg, 0.206 mmol) was reacted with 3,3-difluoropyrrolidine (44 mg, 0.412 mmol) using the procedure of Example 132 to yield 100 mg (87%) of title compound. $^1$H NMR (300 MHz, DMSO-$d_6$) δ 8.53 (s, 1 H), 7.91 (s, 1 H), 7.80 (d 1 H), 7.67 (m, 3 H), 7.38 (m, 4 H), 7.11 (d, 1 H), 6.63 (d, 1H), 5.63 (s, 2 H), 3.95-3.10 (m, 11 H), 3.05-2.60 (m, 4 H), 2.50-2.05 (m, 2 H); ES-MS m/z 557.3 [M+H]$^+$, HPLC RT (min) 2.56.

Example 134

Preparation of 5-(2-benzyl-2H-indazol-6-yl)-7-[1-(morpholin-4-ylacetyl)pyrrolidin-3-yl]pyrrolo[2,1-f][1,2,4]triazin-4-amine

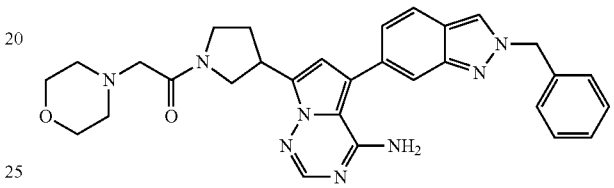

5-(2-benzyl-2H-indazol-6-yl)-7-[1-(chloroacetyl)pyrrolidin-3-yl]pyrrolo[2,1-f][1,2,4]triazin-4-amine (100 mg, 0.206 mmol) was reacted with 3,3-morpholine (36 uL, 0.412 mmol) using the procedure of Example 132 to yield 70 mg (63%) of title compound. $^1$H NMR (300 MHz, DMSO-$d_6$) δ 8.53 (s, 1 H), 7.91 (s, 1 H), 7.80 (d 1 H), 7.66 (m, 3 H), 7.40 (m, 4 H) 7.22 (d, 1 H), 6.65 (d, 1 H) 5.64 (s, 2 H), 4.10-3.30 (m, 7 H), 3.25-2.95 (m, 2 H), 2.50-2.05 (m, 6 H); ES-MS m/z 537.4 [M+H]$^+$, HPLC RT (min) 2.03.

Example 135

Preparation of 5-(2-benzyl-2H-indazol-6-yl)-7-{1-[(4-methylpiperazin-1-yl)acetyl]pyrrolidin-3-yl}pyrrolo[2,1-f][1,2,4]triazin-4-amine

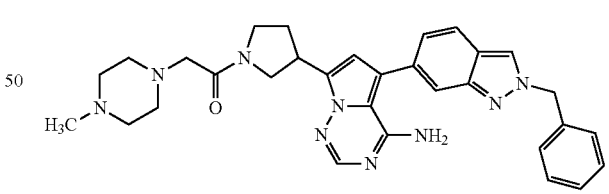

5-(2-benzyl-2H-indazol-6-yl)-7-[1-(chloroacetyl)pyrrolidin-3-yl]pyrrolo[2,1-f][1,2,4]triazin-4-amine (100 mg, 0.206 mmol) was reacted with 4-methylpiperazine (46 uL, 0.412 mmol) using the procedure of Example 132 to yield 52 mg (46%) of title compound. $^1$H NMR (300 MHz, methanol-$d_4$) δ 8.04 (s, 1 H), 7.92 (s, 1 H), 7.78 (m, 3 H), 7.41 (m, 4 H), 7.22 (d, 1 H), 6.63 (d, 1 H), 5.46 (s, 2 H), 4.15-3.95 (m, 2 H), 3.90-3.40 (m, 4 H), 3.12 (m, 2 H), 2.60-2.10 (d, 13 H); ES-MS m/z 550.2 [M+H]$^+$, HPLC RT (min) 2.10.

Example 136

Preparation of 5-(2-benzyl-2H-indazol-6-yl)-7-[1-(2-methoxyethyl)pyrrolidin-3-yl]pyrrolo[2,1-f][1,2,4]triazin-4-amine

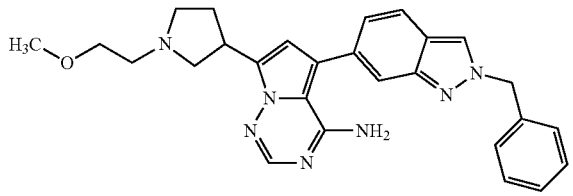 [SMILES: COCCN1CCC(c2cc(-c3ccc4cn(Cc5ccccc5)nc4c3)c3c(N)ncnn23)C1]

To a solution of 5-(2-benzyl-2H-indazol-6-yl)-7-pyrrolidin-3-ylpyrrolo[2,1-f][1,2,4]triazin-4-amine (50 mg, 0.122 mmol) in 2 mL of DMF, triethylamine is added (34 uL, 0.244 mmol) followed by 1-bromo-2-methoxyethane (36 uL, 0.256 mmol). A spatula tip of potassium iodide was added and the reaction heated at 60° C. for 48 hours. The reaction was cooled and then partitioned between EtOAc (50 mL) and water (25 mL). The organic layer was washed with water (5×15 mL) to remove DMF. The EtOAc layer was the dried with Na$_2$SO$_4$ and then concentrated to yield an off-white solid. The solid was recrystallized from EtOAc-hexanes to yield 11 mg (19%) of title compound. $^1$H NMR (300 MHz, DMSO-d$_6$) δ 8.53 (s, 1 H), 7.88 (s, 1 H), 7.80 (d 1 H), 7.58 (s, 1 H), 7.35 (m, 5 H), 7.15 (d, 1 H), 6.66 (s, 1 H), 5.64 (s, 2 H), 3.80 (m, 2H), 3.45 (t, 2H), 3.30-3.05 (m, 6 H), 2.70-2.50 (m, 2 H), 2.25 (m, 1 H), 1.97 (m, 1H); ES-MS m/z 468.2 [M+H]$^+$, HPLC RT (min) 2.17.

Example 137

Preparation of 2-{3-[4-amino-5-(2-benzyl-2H-indazol-6-pyrrolo[2,1-f][1,2,4]triazin-7-yl]pyrrolidin-4-yl}ethanol

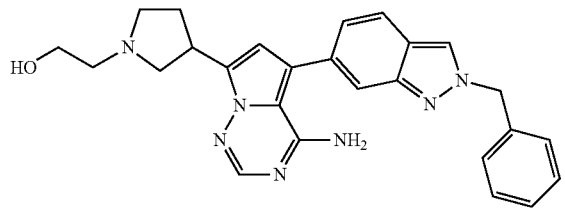 [SMILES: Nc1ncnn2c(C3CCN(CCO)C3)cc(-c3ccc4cn(Cc5ccccc5)nc4c3)c12]

Step 1: Preparation of 5-(2-benzyl-2H-indazol-6-yl)-7-[1-(2-{[tert-butyl(dimethyl)-silyl]oxy}ethyl)pyrrolidin-3-yl]pyrrolo[2,1-f][1,2,4]triazin-4-amine

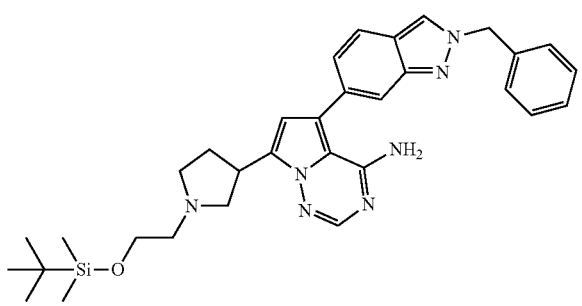 [SMILES: CC(C)(C)[Si](C)(C)OCCN1CCC(c2cc(-c3ccc4cn(Cc5ccccc5)nc4c3)c3c(N)ncnn23)C1]

5-(2-benzyl-2H-indazol-6-yl)-7-pyrrolidin-3-ylpyrrolo[2,1-f][1,2,4]triazin-4-amine (50 mg, 0.122 mmol) was reacted with (2-bromoethoxy)(tert-butyl)dimethylsilane (60 mg, 0.254 mmol), following the procedure of Example 136. The product was triturated with ether-hexanes to yield 36 mg (52%) of pure product. $^1$H NMR (300 MHz, DMSO-d$_6$) δ 8.52 (s, 1 H), 7.87 (s, 1 H), 7.79 (d 1 H), 7.56 (m, 2 H), 7.33 (m, 4 H) 7.15 (d, 1 H), 6.67 (s, 1 H), 5.63 (s, 2 H) 4.10-3.2 (m, 7 H), 3.00-1.75 (m, 4 H), 0.85 (m, 9 H), 0.05 (s, 6 H); ES-MS m/z 568.3 [M+H]$^+$, HPLC RT (min) 3.11.

Step 2: Preparation of the Title Compound 5-(2-benzyl-2H-indazol-6-yl)-7-[1-(2-{[tert-butyl(dimethyl)silyl]oxy}ethyl)pyrrolidin-3-yl]pyrrolo[2,1-f][1,2,4]triazin-4-amine (36 mg, 0.063 mmol) was dissolved in 1N tert-butyl ammonium fluoride in THF (1 mL). The reaction was stirred at rt for 15 minutes. The reaction was then partitioned between EtOAc (50 mL) and 10% aqueous potassium carbonate (20 mL). The aqueous layer was extracted with EtOAc (20 mL). The combined organic layer was washed with brine and then dried with sodium sulfate. The residue was triturated with ether to yield 13 mg (45%) of title compound. $^1$H NMR (300 MHz, dichloromethane-d$_4$) δ 8.04 (s, 1 H), 7.90 (s, 1 H), 7.78-7.73 (m, 2 H), 7.39-7.36 (m, 5 H), 7.23 (d, 1 H), 6.64 (s, 1 H), 5.62 (s, 2 H), 5.43 (bs, 2 H), 4.00 (m, 1H), 3.62 (m, 2H), 3.43 (m, 1 H), 3.25 (m, 3 H), 2.80-2.60 (m, 2 H), 2.40 (m, 1 H), 2.15 (m, 1H); ES-MS m/z 454.2 [M+H]$^+$, HPLC RT (min) 2.06.

Example 128

Preparation of 2-{3-[4-amino-5-(2-benzyl-2H-indazol-6-yl)pyrrolo[2,1-f][1,2,4]triazin-7-yl]pyrrolidin-1-yl}-N,N-dimethylacetamide

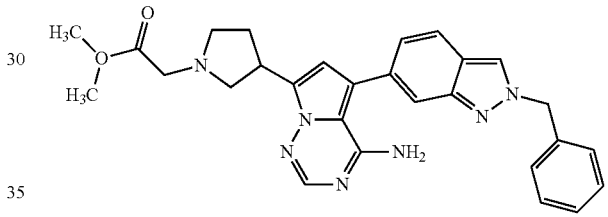

5-(2-benzyl-2H-indazol-6-yl)-7-pyrrolidin-3-ylpyrrolo[2,1-f][1,2,4]triazin-4-amine (100 mg, 0.244 mmol) was reacted with 2-chloro-N,N-dimethylacetamide (33 mg, 0.269 mmol) following the procedure of Example 136. The product was then chromatographed using 0-6% (2N NH$_3$ in methanol)/dichloromethane to yield 56 mg (46%) of product. $^1$H NMR (300 MHz, dichloromethane-d$_2$) δ 8.04 (s, 1 H), 7.89 (s, 1 H), 7.80 (d 1 H), 7.77-7.73 (m, 2 H), 7.36 (m, 5 H), 7.23 (d, 1 H), 6.66 (s, 1 H), 5.62 (s, 2 H), 5.43 (bs, 2 H), 4.00 (m, 1 H), 3.45 (m, 1 H), 3.35 (t, 1H), 3.18 (s, 2 H) 2.75-26.60 (m, 8 H), 2.45 (m, 1 H), 2.00 (m, 1 H); ES-MS m/z 495.2 [M+H]$^+$, HPLC RT (min) 2.13.

Example 139

Preparation of 5-(2-benzyl-2H-indazol-6-yl)-7-{1-[(4-methylpiperazin-1-yl)carbonyl]pyrrolidin-3-yl}pyrrolo[2,1-f][1,2,4]triazin-4-amine

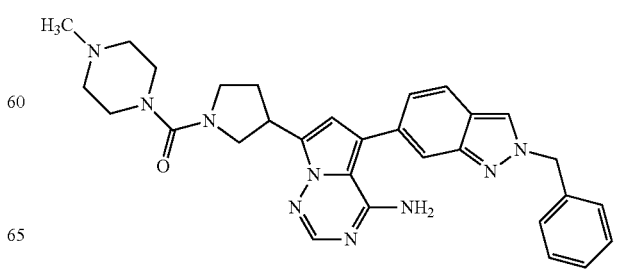

Step 1: Preparation of 4-methylpiperazine-1-carbonyl chloride

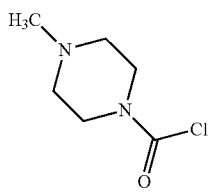

To solution of methyl piperazine (166 uL, 1.50 mmol) In anhydrous dichloromethane (2 mL), diisopropyl ethyl amine (300 uL, 1.72 mmol) was added. The reaction was cooled to 0° C. under $N_2$. Triphosgene (240 mg, 0.809 mmol) was added and the reaction was allowed to warm to rt. The chloride was used immediately without purification.

Step 2: Preparation of title compound

To a solution of 5-(2-benzyl-2H-indazol-6-yl)-7-pyrrolidin-3-ylpyrrolo[2,1-f][1,2,4]triazin-4-amine (60 mg, 0.147 mmol) in $CH_2Cl_2$ (2 mL), the solution made in Step 1 of 4-methylpiperazine-1-carbonyl chloride (62 mg, 0.163 mmol) was added. The reaction mixture was stirred at rt overnight. The reaction was then partitioned between EtOAc (50 mL) and 10% aqueous potassium carbonate. (20 mL). The aqueous layer was extracted with EtOAc (20 mL). The combined organic layers were washed with brine, dried with sodium sulfate and concentrated under vacuum. The residue was triturated with ether to yield 16 mg (20%) of product. $^1$H NMR (300 MHz, DMSO-$d_6$) δ 8.54 (s, 1 H), 7.91 (s, 1 H), 7.78 (d 1 H), 7.58 (s, 1 H), 7.33 (m, 5 H), 7.13 (d, 1 H), 6.66 (s, 1 H), 5.64 (s, 2 H), 3.90 (m, 1 H), 3.60-3.30 (m, 8 H), 2.50-2.00 (m, 9 H); ES-MS m/z 536.3 [M+H]$^+$, HPLC RT (min) 2.13.

Example 140

Preparation of 5-(2-benzyl-2H-indazol-6-yl)-7-{1-[3-(dimethylamino)propanoyl]pyrrolidin-3-yl}pyrrolo[2,1-f][1,2,4]triazin-4-amine

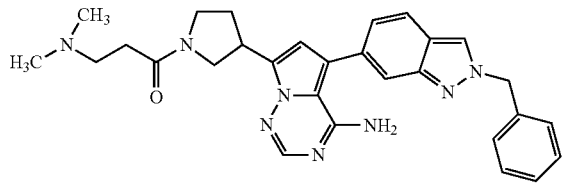 [SMILES: CN(C)CCC(=O)N1CCC(c2cc(-c3ccc4cn(Cc5ccccc5)nc4c3)c3c(N)ncnn23)C1]

5-(2-benzyl-2H-indazol-6-yl)-7-pyrrolidin-3-ylpyrrolo[2,1-f][1,2,4]triazin-4-amine (75 mg, 0.183 mmol) was coupled to N,N-dimethyl-beta-alanine hydrochloride (29 mg, 0.189 mmol) following the procedure described in step 1 of Example 120. The product was purified via HPLC using a Sunfire Prep C18 OBD 5 micron, 30×75 mm column. The compound was eluted using a gradient 10-70% acetonitrile/water with 0.1% TFA over 20 minutes to yield (17 mg, 18%) title compound. $^1$H NMR (300 MHz, DMSO-$d_6$) δ 8.53 (s, 1 H), 7.92 (s, 1 H), 7.79 (d, 1 H), 7.58 (s, 1 H), 7.36-7.32 (m, 4 H), 7.14 (d, 1 H), 6.68 (d, 1 H), 5.64 (s, 2 H), 4.00-3.30 (m, 9 H), 2.45-2.05 (m, 2H), 2.07 (s, 6 H); ES-MS m/z 509.2 [M+H]+, HPLC RT (min) 2.11.

Example 141

Preparation of 2-{4-[4-Amino-5-(2-benzyl-2H-indazol-6-yl)-pyrrolo[2,1-f][1,2,4]triazin-7-yl]-benzylamino}-ethanol

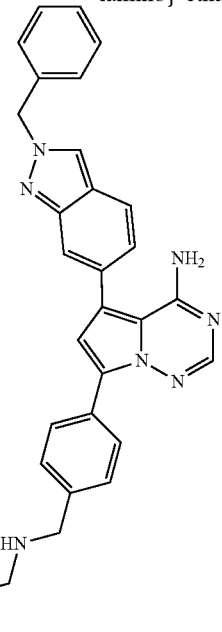

Using a procedure similar to that of Example 5 and Example 104, step 2,7-(4-amino methyl-phenyl)-5-(2-benzyl-2H-indazol-6-yl)-pyrrolo[2,1-f][1,2,4]triazin-4-ylamine and (2-bromo-ethoxy)-tert-butyl-dimethyl-silane as the starting material, 23.4 mg (11%) of the desired product was isolated. $^1$ NMR (300 MHz, DMSO-$d_6$) δ 8.80 (s, 1 H), 8.05 (d, 2H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.50 (t, 1 H), 3.80 (s, 2 H), 3.50 (t, 2 H), 2.60 (t, 2H); ES-MS m/z 490.27 [M+H]$^+$, HPLC RT (min) 2.68.

Example 142

Preparation of 5-(2-Benzyl-2H-indazol-6-yl)-7-(4-diethylaminomethyl-phenyl)-pyrrolo[2,1-f][1,2,4]triazin-4-ylamine

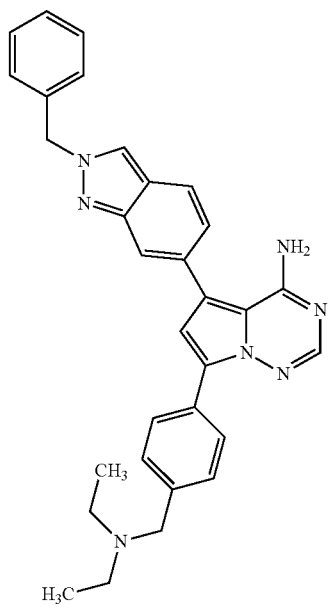 [SMILES: CCN(CC)Cc1ccc(-c2cc(-c3ccc4cn(Cc5ccccc5)nc4c3)c3c(N)ncnn23)cc1]

Using a procedure similar to that of Example 5 with 7-(4-aminomethyl-phenyl)-5-(2-benzyl-2H-indazol-6-yl)-pyrrolo[2,1-f][1,2,4]triazin-4-ylamine and iodoethane as the starting materials, 44.1 mg (26%) of the desired product was isolated. $^1$H NMR (300 MHz, DMSO-d$_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.60 (s, 2 H), 2.45 (q, 4 H), 1.00 (t, 6 H); ES-MS m/z 502.01 [M+H]$^+$, HPLC RT (min) 2.73.

Example 143

Preparation of 7-(4-Aminomethyl-phenyl)-5-(2-benzyl-2H-indazol-6-yl)-pyrrolo[2,1-f][1,2,4]triazin-4-ylamine

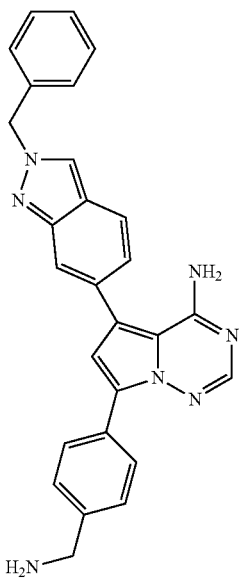 [SMILES: NCc1ccc(-c2cc(-c3ccc4cn(Cc5ccccc5)nc4c3)c3c(N)ncnn23)cc1]

Using a procedure similar to that of Example 93 with {4-[4-amino-5-(2-benzyl-2H-indazol-6-yl)-pyrrolo[2,1-f][1,2,4]triazin-7-yl]-benzyl}-carbamic acid tert-butyl ester (see intermediate 111) as starting material, 900 mg (85%) of the desired product was isolated. $^1$H NMR (300 MHz, DMSO-d$_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.75 (s, 2 H); ES-MS m/z 446.23 [M+H]$^+$, HPLC RT (min) 2.37.

Example 144

Preparation of 5-(2-Benzyl-2H-indazol-6-yl)-7-(4-cyclopentylaminomethyl-phenyl)-pyrrolo[2,1-f][1,2,4]triazin-4-ylamine

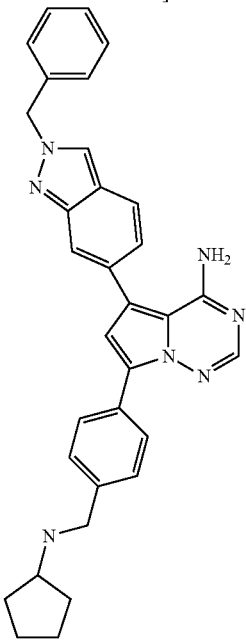

Using a procedure similar to that of Example 111 with 7-(4-Aminomethyl-phenyl)-5-(2-benzyl-2H-indazol-6-yl)-pyrrolo[2,1-f][1,2,4]triazin-4-ylamine and cyclopentanone as starting materials, 29.3 mg (12%) of the desired product was isolated. $^1$H NMR (300 MHz, DMSO-d$_6$) δ 8.80 (s, 1 H), 8.05 (d, 2H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.75 (s, 2 H) 3.00 (m, 1 H), 2.80-2.70 (m, 4 H), 2.50-2.40 (m, 4H); ES-MS m/z 514.16 [M+H]$^+$, HPLC RT (min) 2.62.

Example 145

Preparation of 5-(2-Benzyl-2H-indazol-6-yl)-7-(4-cyclohexylaminomethyl-phenyl)-pyrrolo[2,1-f][1,2,4]triazin-4-ylamine

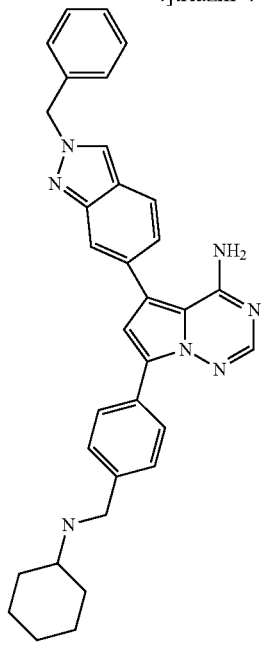

Using a procedure similar to that of Example 111 with 7-(4-Aminomethyl-phenyl)-5-(2-benzyl-2H-indazol-6-yl)-pyrrolo[2,1-f][1,2,4]triazin-4-ylamine and cyclohexanone as starting materials, 27 mg (23%) of the desired product was isolated. $^1$H NMR (300 MHz, DMSO-d$_6$) δ 8.80 (s, 1 H), 8.05 (d, 2H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.80 (s, 2 H) 2.4 (m, 1 H), 1.80 (m, 2 H), 1.60 (m, 2 H), 1.20-1.10 (m, 6 H); ES-MS m/z 528.06 [M+H]$^+$, HPLC RT (min) 2.72.

Example 146

Preparation of 5-(2-Benzyl-2H-indazol-6-yl)-7-(4-piperidin-1-ylmethyl-phenyl)-pyrrolo[2,1-f][1,2,4]triazin-4-ylamine

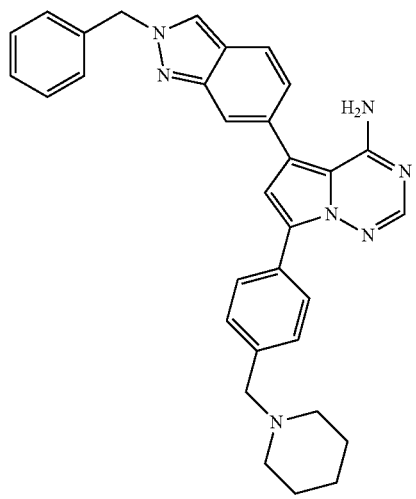 [SMILES: Nc1ncnn2c(-c3ccc(CN4CCCCC4)cc3)cc(-c3ccc4cn(Cc5ccccc5)nc4c3)c12]

Using a procedure similar to that of Example 282 (step 2) with 5-(2-benzyl-2H-indazol-6-yl)-7-(4-bromomethyl-phenyl)-pyrrolo[2,1-f][1,2,4]triazin-4-ylamine and piperidine as starting materials, 12 mg (5%) of the desired product was isolated. $^1$H NMR (300 MHz, DMSO-d$_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.50 (s, 2 H) 2.30 (m, 4 H), 1.80 (m, 2 H), 1.55 (m, 4 H), 1.40 (m, 2 H); ES-MS m/z 514.04 [M+H]$^+$, HPLC RT (min) 2.34.

Example 147

Preparation of 1-{4-[4-Amino-5-(2-benzyl-2H-indazol-6-yl)-pyrrolo[2,1-f][1,2,4]triazin-7-yl]-benzyl}-piperidin-4-ol

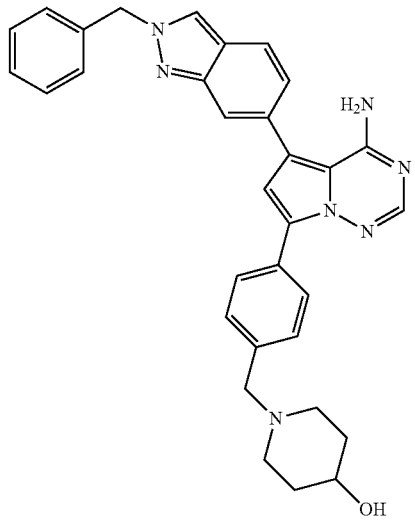 [SMILES: Nc1ncnn2c(-c3ccc(CN4CCC(O)CC4)cc3)cc(-c3ccc4cn(Cc5ccccc5)nc4c3)c12]

Using a procedure similar to that of Example 282 (step 2) with 5-(2-benzyl-2H-indazol-6-yl)-7-(4-bromomethyl-phenyl)-pyrrolo[2,1-f][1,2,4]triazin-4-ylamine and 4-amino-cyclohexanol as starting materials, 11.5 mg (5%) of the desired product was isolated. $^1$H NMR (300 MHz, DMSO-d$_6$) δ 8.80 (s, 1 H), 8.05 (d, 2H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.50 (s, 1 H), 3.60 (s, 1 H), 3.40 (m, 2 H), 2.80 (m, 2 H), 2.0 (m, 2 H), 1.70 (m, 2 H), 1.40 (m, 2 H); ES-MS m/z 530.03 [M+H]$^+$, HPLC RT (min) 2.24.

Example 148

Preparation of 1-{4-[4-Amino-5-(2-benzyl-2H-indazol-6-yl)-pyrrolo[2,1-f][1,2,4]triazin-7-yl]-benzyl}-pyrrolidin-3-ol

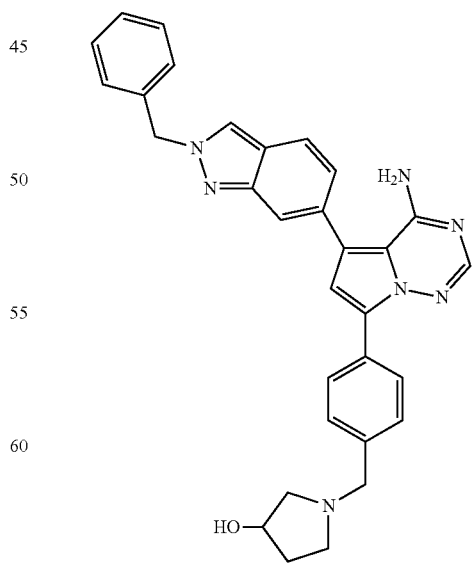

Using a procedure similar to that of Example 282 (step 2) with 5-(2-benzyl-2H-indazol-6-yl)-7-(4-bromomethyl-phe nyl)-pyrrolo[2,1-f][1,2,4]triazin-4-ylamine and 3-amino-cyclopentanol as starting materials, 8.7 mg (4%) of the desired product was isolated. $^1$H NMR (300 MHz, DMSO-d$_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.65 (s, 1 H), 3.60 (m, 2 H), 2.85-2.20 (m, 6 H); ES-MS m/z 515.99 [M+H]$^+$, HPLC RT (min) 2.24.

Example 149

Preparation of 5-(2-Benzyl-2H-indazol-6-yl)-7-(3-cyclobutylaminomethyl-phenyl)-pyrrolo[2,1-f][1,2,4]triazin-4-ylamine

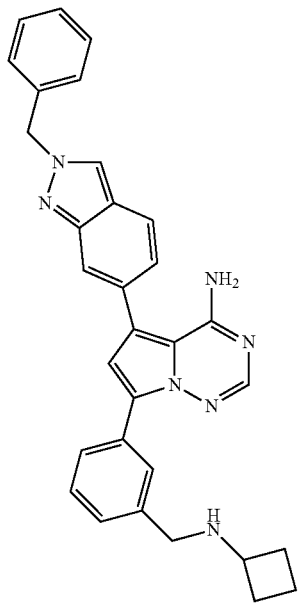 [SMILES: Nc1ncnn2c(-c3cccc(CNC4CCC4)c3)cc(-c3ccc4cn(Cc5ccccc5)nc4c3)c12]

Using a procedure similar to that of Example 111 with 7-(3-aminomethyl-phenyl)-5-(2-benzyl-2H-indazol-6-yl)-pyrrolo[2,1-f][1,2,4]triazin-4-ylamine and cyclobutanone as starting materials, 39 mg (17%) of the desired product was isolated. $^1$H NMR (300 MHz, DMSO-d$_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.80 (m, 2 H), 2.10 (m, 1 H), 2.00 (m, 2 H), 1.70-1.40 (m, 4 H); ES-MS m/z 500.2 [M+H]$^+$, HPLC RT (min) 2.46.

Example 150

Preparation of 5-(2-Benzyl-2H-indazol-6-yl)-7-(3-cyclohexylaminomethyl-phenyl)-pyrrolo[2,1-f][1,2,4]triazin-4-ylamine

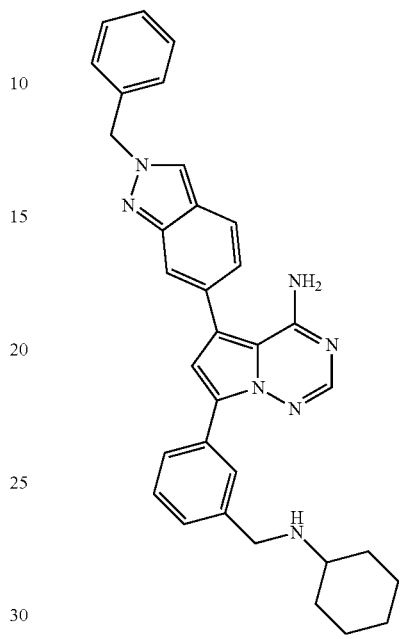

Using a procedure similar to that of Example 111 with 7-(3-aminomethyl-phenyl)-5-(2-benzyl-2H-indazol-6-yl)-pyrrolo[2,1-f][1,2,4]triazin-4-ylamine and cyclohexanone as starting materials, 40 mg (11%) of the desired product was isolated. $^1$H NMR (300 MHz, DMSO-d$_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.80 (m, 2 H), 3.60 (t, 1 H), 1.90 (m, 4 H), 1.70 (m, 2 H), 1.10 (m, 4 H); ES-MS m/z 528.18 [M+H]$^+$, HPLC RT (min) 2.51.

Example 151

Preparation of 7-(3-Aminomethyl-phenyl)-5-(2-benzyl-2H-indazol-6-yl)-pyrrolo[2,1-f][1,2,4]triazin-4-ylamine

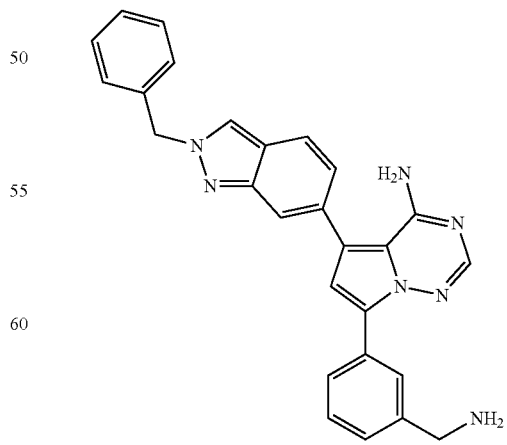

Using a procedure similar to that Example 93, {3-[4-amino-5-(2-benzyl-2H-indazol-6-yl)-pyrrolo[2,1-f][1,2,4]

triazin-7-yl]-benzyl}-carbamic acid tert-butyl ester (intermediate 111) as starting material. 2 g (81%) of the desired product was isolated. $^1$H NMR (300 MHz, DMSO-d$_6$) δ 8.80 (s, 1 H), 8.05 (d, 2 H), 8.00 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.10 (s, 2 H); ES-MS m/z 446.18 [M+H]$^+$, HPLC RT (min) 2.32.

Example 152

Preparation of 5-(2-Benzyl-2H-indazol-6-yl)-7-(3-cyclopentylaminomethyl-phenyl)-pyrrolo[2,1-f][1,2,4]triazin-4-ylamine

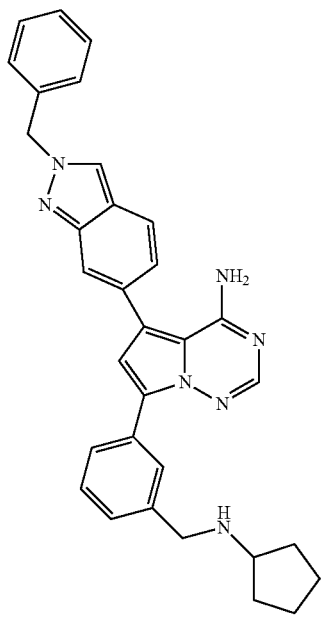 [SMILES: Nc1ncnn2c(-c3cccc(CNC4CCCC4)c3)cc(-c3ccc4cn(Cc5ccccc5)nc4c3)c12]

Using a procedure similar to that of Example 111 with 7-(3-aminomethyl-phenyl)-5-(2-benzyl-2H-indazol-6-yl)-pyrrolo[2,1-f][1,2,4]triazin-4-ylamine and cyclopentanone as starting materials, 66 mg (28%) of the desired product was isolated. $^1$H NMR (300 MHz, DMSO-d$_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.70 (s, 2 H), 3.00 (m, 1 H), 1.80-1.60 (m, 4 H), 1.30-1.20 (m, 4 H); ES-MS m/z 514.16 [M+H]$^+$, HPLC RT (min) 2.45.

Example 153

Preparation of 5-(2-Benzyl-2H-indazol-6-yl)-7-(4-pyrrolidin-1-ylmethyl-phenyl)-pyrrolo[2,1-f][1,2,4]triazin-4-ylamine

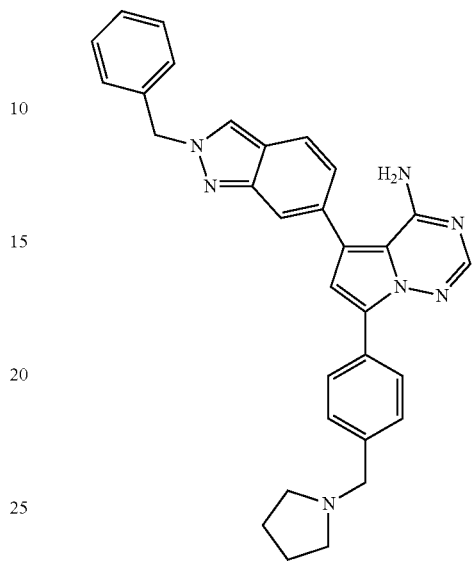

Using a procedure similar to that of Example 282 (step 2) with 5-(2-benzyl-2H-indazol-6-yl)-7-(4-bromomethyl-phenyl)-pyrrolo[2,1-f][1,2,4]triazin-4-ylamine and pyrrolidine as starting materials, 17 mg (8%) of the desired product was isolated. $^1$H NMR (300 MHz, DMSO-d$_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.70 (m, 2 H), 3.40 (s, 2 H), 2.60 (m, 2 H), 1.70 (m, 4 H); ES-MS m/z 500.03 [M+H]$^+$, HPLC RT (min) 2.30.

Example 154

Preparation of 5-(2-Benzyl-2H-indazol-6-yl)-7-(3-diethylaminomethyl-phenyl)pyrrolo[2,1-f][1,2,4]triazin-4-ylamine

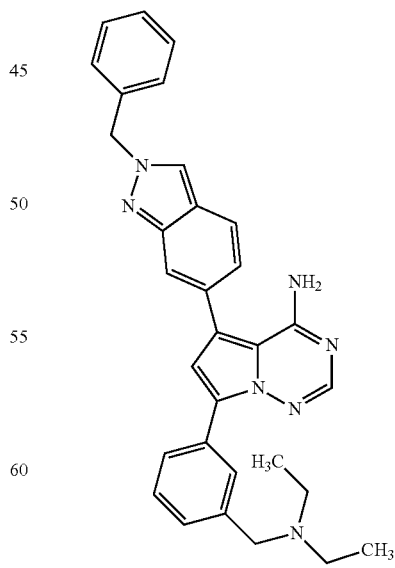

Using a procedure similar to that of Example 5 and 7-(3-aminomethyl-phenyl)-5-(2-benzyl-2H-indazol-6-yl)-pyrrolo[2,1-f][1,2,4]triazin-4-ylamine and iodoethane as starting materials, 42 mg (18%) of the desired product was isolated. $^1$H NMR (300 MHz, DMSO-d$_6$) δ 8.80 (s, 1 H), 8.05 (d, 2 H), 8.00 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.60 (m, 2 H), 2.40 (q, 4 H), 1.00 (t, 6H); ES-MS m/z 502.16 [M+H]$^+$, HPLC RT (min) 2.45.

Example 155

Preparation of N-{3-[4-Amino-5-(2-benzyl-2H-indazol-6-yl)-pyrrolo[2,1-f][1,2,4]triazin-7-yl]-benzyl}-methanesulfonamide

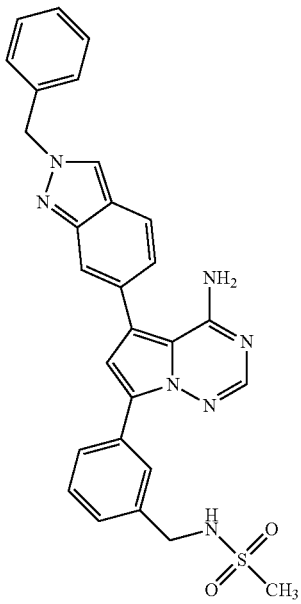 [SMILES: CS(=O)(=O)NCc1cccc(-c2cc(-c3ccc4cn(Cc5ccccc5)nc4c3)c3c(N)ncnn23)c1]

Using a procedure similar to that of Example 5 and 7-(3-aminomethyl-phenyl)-5-(2-benzyl-2H-indazol-6-yl)-pyrrolo[2,1-f][1,2,4]triazin-4-ylamine and methanesulfonyl chloride as starting materials, 18 mg (8%) of the desired product was isolated. $^1$H NMR (300 MHz, DMSO-d$_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.20 (s, 2 H), 2.90 (s, 2 H), 2.80 (s, 3 H); ES-MS m/z 524.3 [M+H]$^+$, HPLC RT (min) 2.84.

Example 156

Preparation of 5-(2-Benzyl-2H-indazol-6-yl)-7-[4-(4-methyl-piperazin-1-ylmethyl)-phenyl]-pyrrolo[2,1-f][1,2,4]triazin-4-ylamine

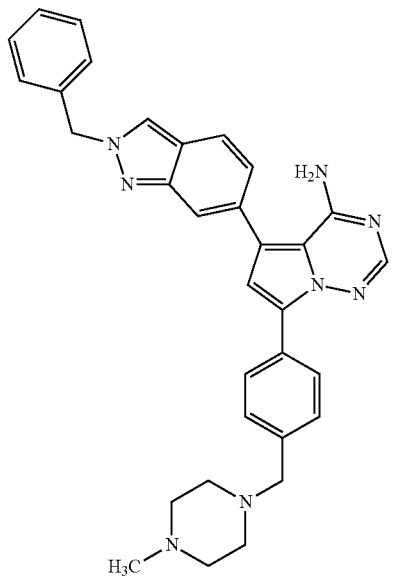 [SMILES: CN1CCN(Cc2ccc(-c3cc(-c4ccc5cn(Cc6ccccc6)nc5c4)c4c(N)ncnn34)cc2)CC1]

Using a procedure similar to that of Example 282 (step 2) with 5-(2-benzyl-2H-indazol-6-yl)-7-(4-bromomethyl-phenyl)-pyrrolo[2,1-f][1,2,4]triazin-4-ylamine and 1-methyl-piperazine as starting materials, 25 mg (10%) of the desired product was isolated. $^1$H NMR (300 MHz, DMSO-d$_6$) δ 8.80 (s, 1 H), 8.05 (d, 2 H), 8.00 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.50 (s, 2 H), 2.50 (m, 4 H), 2.30 (s, 4 H), 2.10 (s, 3 H); ES-MS m/z 529.05 [M+H]$^+$, HPLC RT (min) 2.27.

Example 157

Preparation of 5-(2-Benzyl-2H-indazol-6-yl)-7-(3-cycloheptylaminomethyl-phenyl)-pyrrolo[2,1-f][1,2,4]triazin-4-ylamine

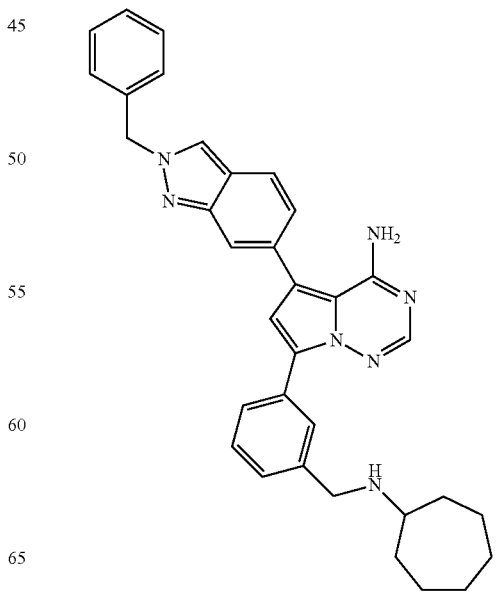

Using a procedure similar to that of Example 111 with 7-(3-aminomethyl-phenyl)-5-(2-benzyl-2H-indazol-6-yl)-pyrrolo[2,1-f][1,2,4]triazin-4-ylamine and cycloheptanone as starting materials, 136 mg (56%) of the desired product was isolated. $^1$H NMR (300 MHz, DMSO-$d_6$) δ 8.80 (s, 1 H), 8.05 (d, 2 H), 8.00 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.70 (s, 2 H), 2.50 (m, 1 H), 1.80-1.30 (m, 12 H); ES-MS m/z 5542.21 [M+H]$^+$, HPLC RT (min) 2.58.

Example 158

Preparation of N-{4-[4-Amino-5-(2-benzyl-2H-indazol-6-yl)-pyrrolo[2,1-f][1,2,4]triazin-7-yl]-benzyl}-acetamide

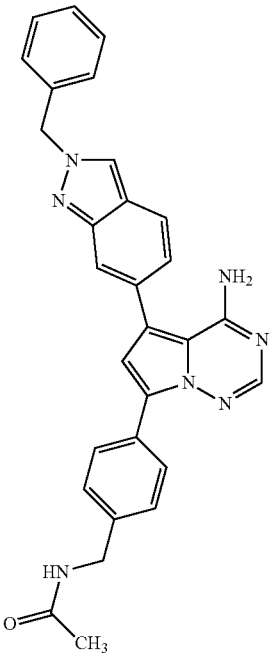 [SMILES: CC(=O)NCc1ccc(-c2cc(-c3ccc4cn(Cc5ccccc5)nc4c3)c3c(N)ncnn23)cc1]

Using a procedure similar to that of Example 5 with 5-(2-benzyl-2H-indazol-6-yl)-7-(4-bromomethyl-phenyl)-pyrrolo[2,1-f][1,2,4]triazin-4-ylamine and acetyl chloride as starting materials, 43.5 mg (26%) of the desired product was isolated. $^1$H NMR (300 MHz, DMSO-$d_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.20 (s, 2 H), 1.90 (s, 3 FI); ES-MS m/z 488.35 [M+H]$^+$, HPLC RT (min) 2.65.

Example 159

Preparation of 5-(2-Benzyl-2H-indazol-6-yl)-7-[4-(4-ethyl-piperazin-1-ylmethyl)-phenyl]-pyrrolo[2,1-f][1,2,4]triazin-4-ylamine

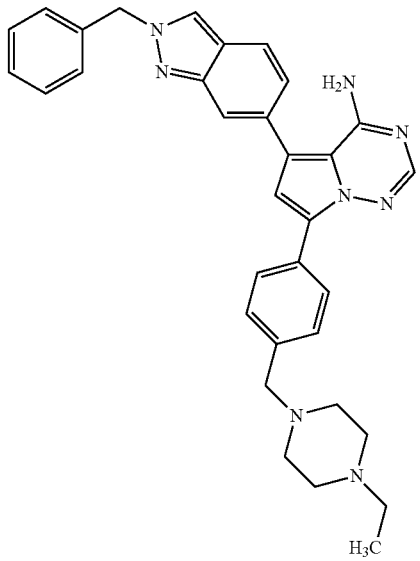 [SMILES: CCN1CCN(Cc2ccc(-c3cc(-c4ccc5cn(Cc6ccccc6)nc5c4)c4c(N)ncnn34)cc2)CC1]

Using a procedure similar to that of Example 282, step 2, with 5-(2-benzyl-2H-indazol-6-yl)-7-(4-bromomethyl-phenyl)-pyrrolo[2,1-f][1,2,4]triazin-4-ylamine and 1-ethyl-piperazine as starting materials, 3.4 mg (1.2%) of the desired product was isolated. $^1$H NMR (300 MHz, DMSO-$d_6$) δ 8.80 (s, 1 H), 8.05 (d, 2 H), 8.00 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.50 (s, 2 H), 2.40-2.20 (m, 10), 1.0 (t, 3 H); ES-MS m/z 543.01 [M+H]$^+$, HPLC RT (min) 2.28.

Example 160

Preparation of 4-[4-Amino-5-(2-benzyl-2H-indazol-6-yl)-pyrrolo[2,1-f][1,2,4]triazin-7-yl]-2-methoxy-phenol

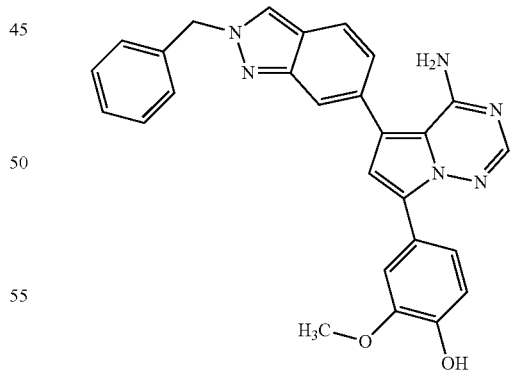

Using a procedure similar to that of Example 4 with 4-(4-Amino-5-bromo-pyrrolo[2,1-f][1,2,4]triazin-7-yl)-2-methoxy-phenol and 2-benzyl-6-(4,4,5,5-tetramethyl-[1,3,2]dioxaborolan-2-yl)-2H-indazole as starting materials, 21.5 mg (9%) of the desired product was isolated. $^1$H NMR (300 MHz, DMSO-$d_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.80 (s, 3 H); ES-MS m/z 463.49 [M+H]$^+$, HPLC RT (min) 2.99.

Example 161

Preparation of 5-(2-Benzyl-2H-indazol-6-yl)-7-[4-(3,3-difluoro-pyrrolidin-1-ylmethyl)-phenyl]-pyrrolo[2,1-f][1,2,4]triazin-4-ylamine

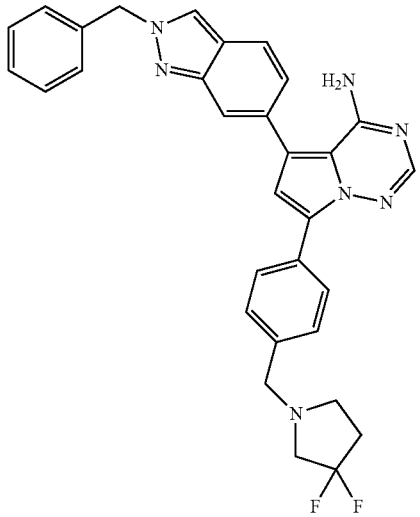 [SMILES: Nc1ncnn2c(-c3ccc(CN4CCC(F)(F)C4)cc3)cc(-c3ccc4cn(Cc5ccccc5)nc4c3)c12]

Using a procedure similar to that of Example 282, step 2, with 5-(2-benzyl-2H-indazol-6-yl)-7-(4-bromomethyl-phenyl)-pyrrolo[2,1-f][1,2,4]triazin-4-ylamine and 3,3-difluoropyrrolidine as starting materials, 6.3 mg (2.4%) of the desired product was isolated. $^1$H NMR (300 MHz, DMSO-$d_6$) δ 8.80 (s, 1 H), 8.05 (d, 2 H), 8.0 (s, 1 H), 7.90 (d, 1 H), 7.70 (s, 1 H), 7.60-7.40 (m, 7 H), 725 (d, 1 H), 7.20 (s, 1 H), 5.70 (s, 2 H), 3.70 (s, 2 H), 3.2 (m, 2 H), 2.70 (m, 2 H), 2.20 (s, 2 H); ES-MS m/z 536.22 [M+H]$^+$, HPLC RT (min) 2.52.

Example 162

Preparation of 5-(2-Benzyl-2H-indazol-6-yl)-7-[4-(1,1-dioxo-1lambda-6-thlomorpholin-4-ylmethyl)-phenyl]-pyrrolo[2,1-f][1,2,4]triazin-4-ylamine

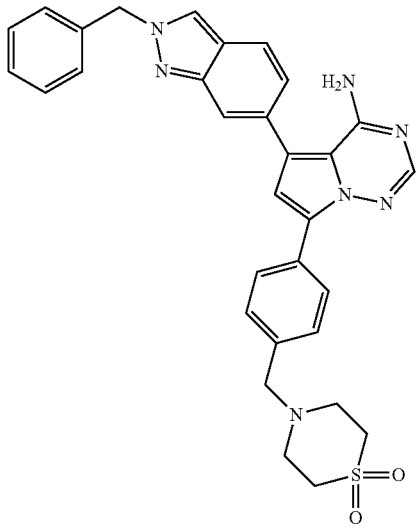 [SMILES: Nc1ncnn2c(-c3ccc(CN4CCS(=O)(=O)CC4)cc3)cc(-c3ccc4cn(Cc5ccccc5)nc4c3)c12]

Using a procedure similar to that of Example 282, step 2, with 5-(2-benzyl-2H-indazol-6-yl)-7-(4-bromomethyl-phenyl)-pyrrolo[2,1-f][1,2,4]triazin-4-ylamine and thiomorpholine 1,1-dioxide as starting materials, 9 mg (2.7%) of the desired product was isolated. $^1$H NMR (300 MHz, DMSO-$d_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.70 (s, 2 H), 3.1 (t, 4 H), 2.90 (t, 4 H); ES-MS m/z 564.29 [M+H]$^+$, HPLC RT (min) 2.57.

Example 163

Preparation of 1-{4-[4-Amino-5-(2-benzyl-2H-indazol-6-yl)-pyrrolo[2,1-f][1,2,4]triazin-7-yl]-benzyl}-tetrahydro-pyrimidin-4-one

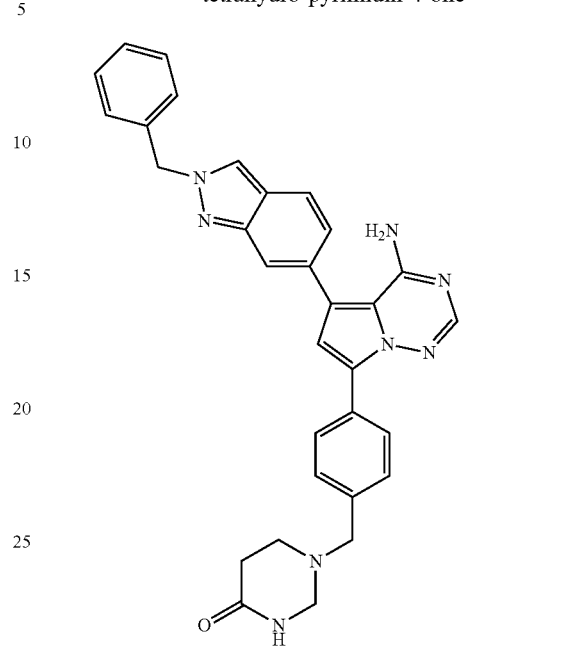

Using a procedure similar to that of Example 282, step 2, with 5-(2-benzyl-2H-indazol-6-yl)-7-(4-bromomethyl-phenyl)-pyrrolo[2,1-f][1,2,4]triazin-4-ylamine and tetrahydropyrimidin-4-one as starting materials, 14 mg (4.5%) of the desired product was isolated. $^1$H NMR (300 MHz, DMSO-$d_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.60 (s, 2 H), 3.20 (t, 2 H), 2.95 (s, 2 H), 2.60 (t, 2 H); ES-MS m/z 529.29 [M+H]$^+$, HPLC RT (min) 2.24.

Example 164

Preparation of 5-(2-Benzyl-2H-indazol-6-yl)-7-(4-morpholin-4-ylmethyl-phenyl)-pyrrolo[2,1-f][1,2,4]triazin-4-ylamine

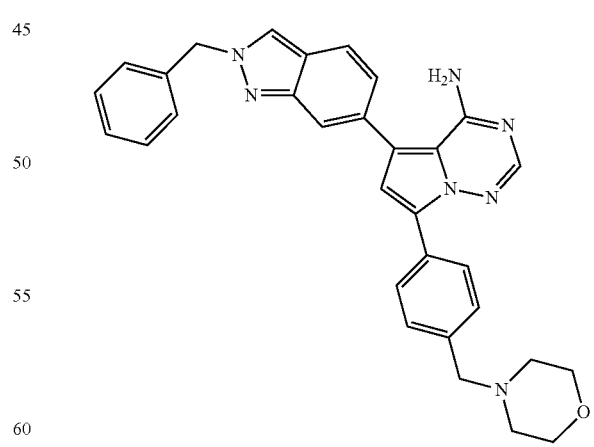

Using a procedure similar to that of Example 282, step 2, with 5-(2-benzyl-2H-indazol-6-yl)-7-(4-bromomethyl-phenyl)-pyrrolo[2,1-f][1,2,4]triazin-4-ylamine and morpholine as starting material, 55 mg (28%) of the desired product was isolated. $^1$H NMR (300 MHz, DMSO-$d_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.60 (t, 4 H), 3.50 (s 2 H), 2.405 (t, 4 H); ES-MS m/z 516.25 [M+H]+, HPLC RT (min) 2.61.

Example 165

Preparation of 3-{3-[4-Amino-5-(2-benzyl-2H-indazol-6-yl)-pyrrolo[2,1-f][1,2,4]triazin-7-yl]-benzyl}-1,1-dimethyl-urea

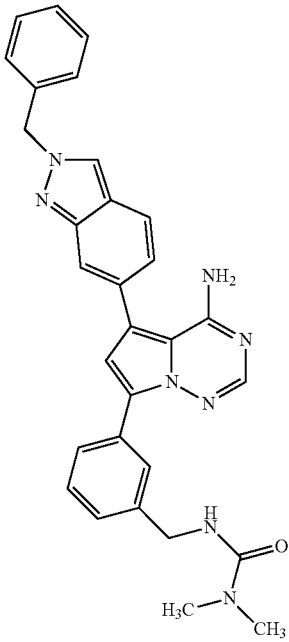 [SMILES: CN(C)C(=O)NCc1cccc(-c2cc(-c3ccc4cn(Cc5ccccc5)nc4c3)c3c(N)ncnn23)c1]

Using a procedure similar to that of Example 5 with 7-(3-aminomethyl-phenyl)-5-(2-benzyl-2H-indazol-6-yl)-pyrrolo[2,1-f][1,2,4]triazin-4-ylamine and dimethylcarbamyl chloride as starting materials, 32 mg (14%) of the desired product was isolated. $^1$H NMR (300 MHz, DMSO-d$_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.3 (d, 2 H), 2.8 (s, 6 H); ES-MS m/z 517.3 [M+H]+, HPLC RT (min) 2.75.

Example 166

Preparation of 3-{3-[4-Amino-5-(2-benzyl-2H-indazol-6-yl)-pyrrolo[2,1-f][1,2,4]triazin-7-yl]-phenyl}-1,1-dimethyl-urea

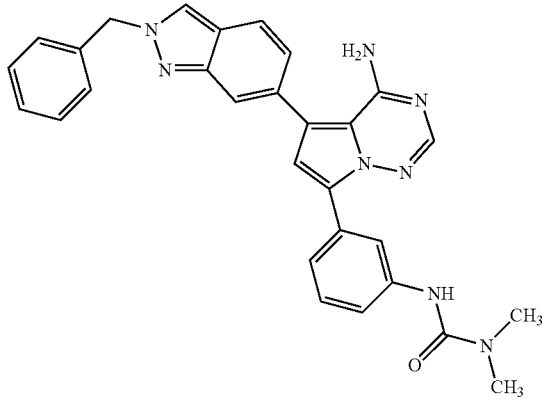 [SMILES: CN(C)C(=O)Nc1cccc(-c2cc(-c3ccc4cn(Cc5ccccc5)nc4c3)c3c(N)ncnn23)c1]

Using a procedure similar to that of Example 5 with 7-(3-amino-phenyl)-5-(2-benzyl-2H-indazol-6-yl)-pyrrolo[2,1-f][1,2,4]triazin-4-ylamine and dimethylcarbamyl chloride as starting materials, 26 mg (9%) of the desired product was isolated. $^1$H NMR (300 MHz, DMSO-d$_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.0 (s, 6 H); ES-MS m/z 503.26 [M+H]+, HPLC RT (min) 2.66.

Example 167

Preparation of 3-{3-[4-Amino-5-(2-benzyl-2H-indazol-6-yl)-pyrrolo[2,1-f][1,2,4]triazin-7-yl]-phenyl}-1,1-dimethyl-sulfonylurea

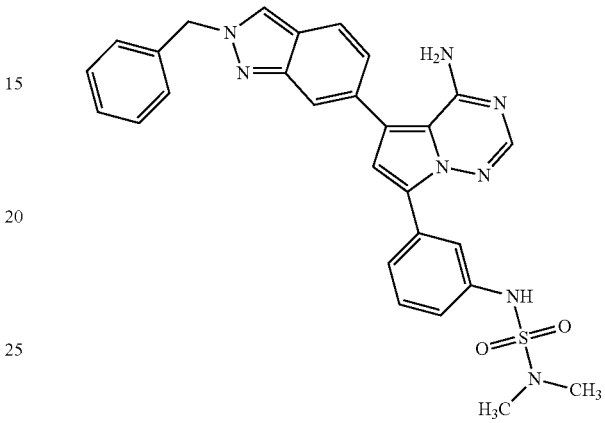

Using a procedure similar to that of Example 5 with 7-(3-amino-phenyl)-5-(2-benzyl-2H-indazol-6-yl)-pyrrolo[2,1-f][1,2,4]triazin-4-ylamine and dimethylsulfamoyl chloride as starting materials, 97 mg (32%) of the desired product was isolated. $^1$H NMR (300 MHz, DMSO-d$_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.4 (s, 6 H); ES-MS m/z 539.22 [M+H]+, HPLC RT (min) 2.97.

Example 168

Preparation of N-{4-[4-Amino-5-(2-benzyl-2H-indazol-6-yl)-pyrrolo[2,1-f][1,2,4]triazin-7-yl]-phenyl}-acetamide

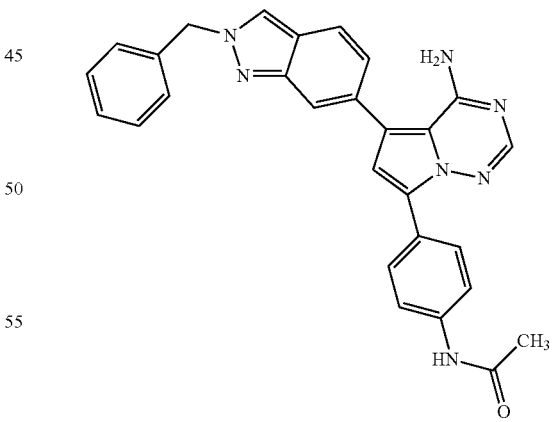

Using a procedure similar to that of Example 5 with 7-(4-amino-phenyl)-5-(2-benzyl-2H-indazol-6-yl)-pyrrolo[2,1-f][1,2,4]triazin-4-ylamine and acetyl chloride as starting materials, 17 mg (10%) of the desired product was isolated. $^1$H NMR (300 MHz, DMSO-d$_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 2.1 (s, 3 H); ES-MS m/z 474.23 [M+H]+, HPLC RT (min) 3.01.

Example 169

Preparation of N-{4-[4-Amino-5-(2-benzyl-2H-indazol-6-yl)-pyrrolo[2,1-f][1,2,4]triazin-7-yl]-benzyl}-methanesulfonamide

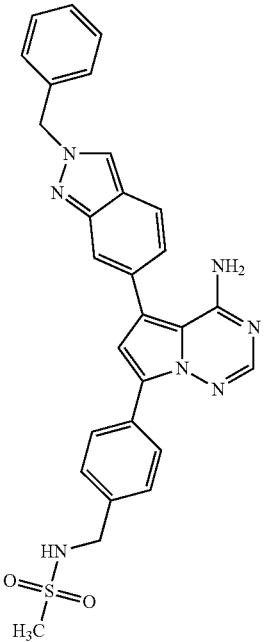 [SMILES: CS(=O)(=O)NCc1ccc(-c2cc(-c3ccc4cn(Cc5ccccc5)nc4c3)c3c(N)ncnn23)cc1]

Using a procedure similar to that of Example 5 with 5-bromo-7-(4-aminomethyl-phenyl)-pyrrolo[2,1-f][1,2,4]triazin-4-ylamine and methylsulfonyl chloride as starting materials, 47 mg (26%) of the desired product was isolated. $^1$H NMR (300 MHz, DMSO-d$_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1H), 7.20 (s, 1 H), 5.70 (s, 2 H), 4.10 (d, 2 H), 3.10 (s, 3 H); ES-MS m/z 524.35 [M+H]$^+$, HPLC RT (min) 2.80.

Example 170

Preparation of N-{3-[4-Amino-5-(2-benzyl-2H-indazol-6-yl)-pyrrolo[2,1-f][1,2,4]triazin-7-yl]-benzyl}-acetamide

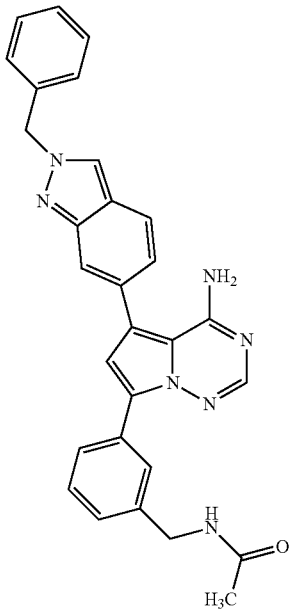 [SMILES: CC(=O)NCc1cccc(-c2cc(-c3ccc4cn(Cc5ccccc5)nc4c3)c3c(N)ncnn23)c1]

Using a procedure similar to that of Example 5 with 7-(3-aminomethyl-phenyl)-5-(2-benzyl-2H-indazol-6-yl)-pyrrolo[2,1-f][1,2,4]triazin-4-ylamine and acetyl chloride as starting materials, 13 mg (6%) of the desired product was isolated. $^1$H NMR (300 MHz, DMSO-d$_5$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.10 (d, 2 H), 1.90 (s, 3 H); ES-MS m/z 488.4 [M+H]$^+$, HPLC RT (min) 2.69.

Example 171

Preparation of N-{3-[4-Amino-5-(2-benzyl-2H-indazol-6-yl)-pyrrolo[2,1-f][1,2,4]triazin-7-yl]-phenyl}-acetamide

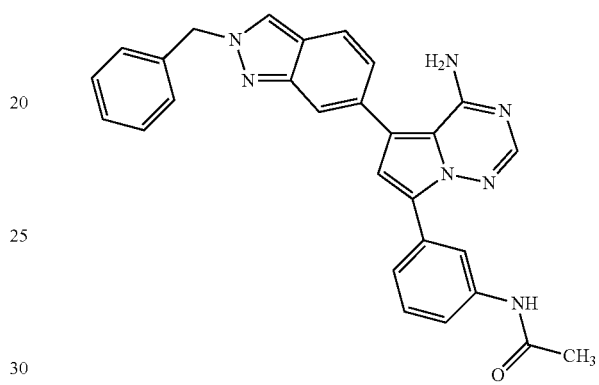

Using a procedure similar to that of Example 5 with 7-(3-amino-phenyl)-5-(2-benzyl-2H-indazol-6-yl)-pyrrolo[2,1-f][1,2,4]triazin-4-ylamine and acetyl chloride as starting materials, 75 mg (28%) of the desired product was isolated. $^1$H NMR (300 MHz, DMSO-d$_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 2.10 (s, 3 H); ES-MS m/z 474.41 [M+H]$^+$, HPLC RT (min) 3.04.

Example 172

Preparation of 5-(2-Benzyl-2H-indazol-6-yl)-7-(2-chloro-pyridin-4-yl)-pyrrolo[2,1-f][1,2,4]triazin-4-ylamine

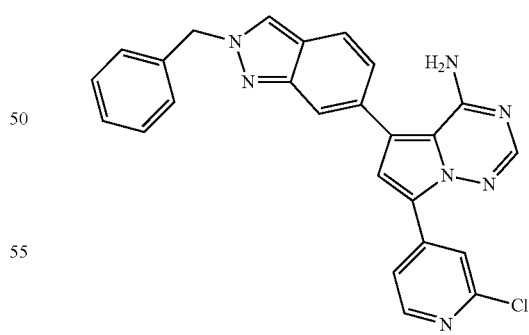

Using a procedure similar to that of Example 4 with 5-bromo-7-(2-chloro-pyridin-4-yl)-pyrrolo[2,1-f][1,2,4]triazin-4-ylamine and 2-benzyl-6-(4,4,5,5-tetramethyl-[1,3,2]dioxa-borolan-2-yl)-2H-indazole as starting materials, 60 mg (28%) of the desired product was isolated. $^1$H NMR (300 MHz, DMSO-d$_6$) δ 8.60 (s, 1 H), 8.5 (d, 2 H), 8.0 (m, 2 H), 7.90 (d, 1 H), 7.70 (s, 1 H), 7.60-7.40 (m, 3 H), 7.25-7.15 (m, 4 H), 7.20 (s, 1 H), 5.70 (s, 2 H); ES-MS m/z 45224 [M+H]$^+$, HPLC RT (min) 3.33.

Example 173

Preparation of Preparation of 3-{3-[4-Amino-5-(2-benzyl-2H-indazol-6-yl)-pyrrolo[2,1-f][1,2,4]triazin-7-yl]-benzyl}-1,1-dimethyl-sulfonylurea

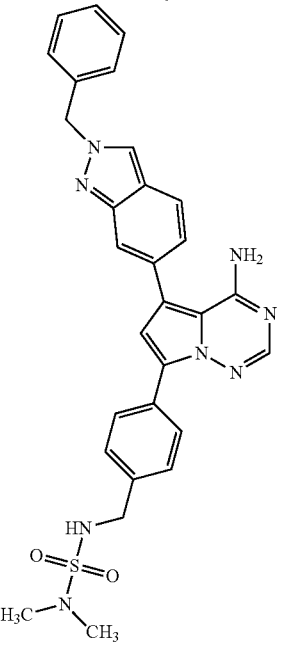 [SMILES: CN(C)S(=O)(=O)NCc1ccc(-c2cc(-c3ccc4cn(Cc5ccccc5)nc4c3)c3c(N)ncnn23)cc1]

Using a procedure similar to that of Example 5 with 5-bromo-7-(4-aminomethyl-phenyl)-pyrrolo[2,1-f][1,2,4]triazin-4-ylamine and dimethylsulfamoyl chloride as starting materials, 38 mg (20%) of the desired product was isolated. $^1$H NMR (300 MHz, DMSO-d$_6$) δ 8.80 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.10 (d, 2 H), 2.60 (s, 6 H); ES-MS m/z 533.29 [M+H]$^+$, HPLC RT (min) 2.96.

Example 174

Preparation of Ethanesulfonic acid 4-[4-amino-5-(2-benzyl-2H-indazol-6-yl)-pyrrolo[2,1-f][1,2,4]triazin-7-yl]-benzylamide

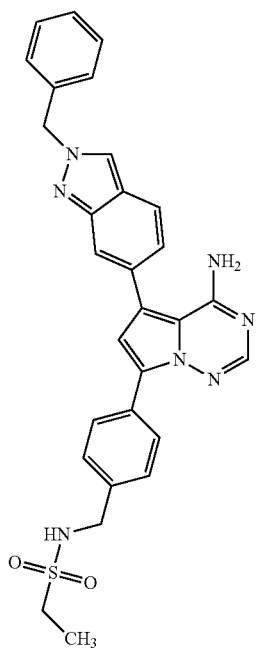 [SMILES: CCS(=O)(=O)NCc1ccc(-c2cc(-c3ccc4cn(Cc5ccccc5)nc4c3)c3c(N)ncnn23)cc1]

Using a procedure similar to that of Example 5 with 5-bromo-7-(4-aminomethyl-phenyl)-pyrrolo[2,1-f][1,2,4]triazin-4-ylamine and ethanesulfonyl chloride as starting materials, 7.4 mg (6%) of the desired product was Isolated. $^1$H NMR (300 MHz, DMSO-d$_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.10 (d, 2 H), 3.0 (t, 2 H), 1.2 (q, 3 H); ES-MS m/z 538.33 [M+H]$^+$, HPLC RT (min) 2.87.

Example 175

Preparation of 7-(4-Amino-phenyl)-5-(2-benzyl-2H-indazol-6-yl)-pyrrolo[2,1-f][1,2,4]triazin-4-ylamine

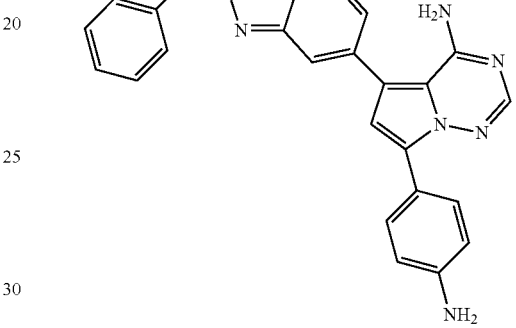

Using a procedure similar to that of Example 93 with {4-[4-amino-5-(2-benzyl-2H-indazol-6-yl)-pyrrolo[2,1-f][1,2,4]triazin-7-yl]-phenyl}-carbamic acid tert-butyl ester (intermediate III) as starting material, 300 mg (74%) of the desired product was isolated. $^1$H NMR (300 MHz, DMSO-d$_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H); ES-MS m/z 432.24 [M+H]$^+$, HPLC RT (min) 2.51.

Example 176

Preparation of 7-(3-Amino-phenyl)-5-(2-benzyl-2H-indazol-6-yl)-pyrrolo[2,1-f][1,2,4]triazin-4-ylamine

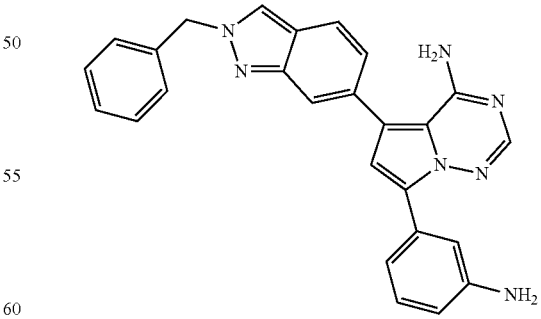

Using a procedure similar to that of Example 93 with {3-[4-amino-5-(2-benzyl-2H-indazol-6-yl)-pyrrolo[2,1-f][1,2,4]triazin-7-yl]phenyl}-carbamic acid tert-butyl ester (intermediate III) as starting material, 700 mg (86%) of the desired product was isolated. $^1$H NMR (300 MHz, DMSO-d$_6$) δ 8.60 (s, 1 H), 8.05 (d, 2 H), 8.0 (s, 1 H), 7.90 (d, 1 H), 7.70

(s, 1 H), 7.60-7.40 (m, 7 H), 7.25 (d, 1 H), 6.60 (s, 1 H), 5.70 (s, 2 H); ES-MS m/z 432.24 [M+H]+, HPLC RT (min) 2.49.

Example 177

Preparation of 5-(2-Benzyl-2H-indazol-6-yl)-7-(4-thiomorpholin-4-ylmethyl-phenyl)-pyrrolo[2,1-f][1,2,4]triazin-4-ylamine

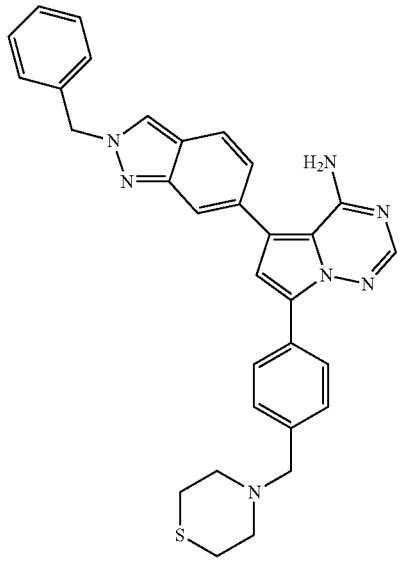 [SMILES: Nc1ncnn2c(-c3ccc(CN4CCSCC4)cc3)cc(-c3ccc4cn(Cc5ccccc5)nc4c3)c12]

Using a procedure similar to that of Example 282, step 2, with 5-(2-benzyl-2H-indazol-6-yl)-7-(4-bromomethyl-phenyl)-pyrrolo[2,1-f][1,2,4]triazin-4-ylamine and thiomorpholine as starting materials, 19 mg (6%) of the desired product was isolated. $^1$H NMR (300 MHz, DMSO-d$_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.60 (d, 2 H), 2.6 (t, 8 H); ES-MS m/z 532.07 [M+H]+, HPLC RT (min) 2.34.

Example 178

Preparation of 3-[4-Amino-5-(2-benzyl-2H-indazol-6-yl)-pyrrolo[2,1-f][1,2,4]triazin-7-yl]-N,N-dimethyl-benzamide

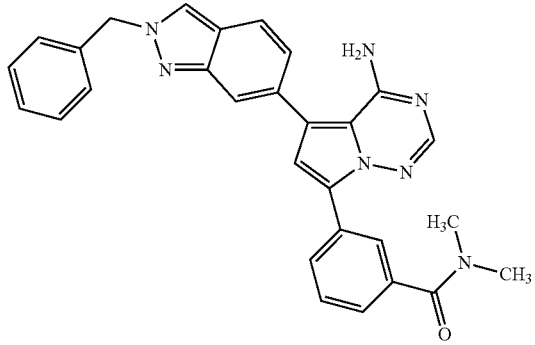 [SMILES: CN(C)C(=O)c1cccc(-c2cc(-c3ccc4cn(Cc5ccccc5)nc4c3)c3c(N)ncnn23)c1]

Using a procedure similar to that of Example 4 with 3-(4-amino-5-bromo-pyrrolo[2,1-f][1,2,4]triazin-7-yl)-N,N-dimethyl-benzamides and 2-benzyl-6-(4,4,5,5-tetramethyl-[1,3,2]dioxaborolan-2-yl)-2H-indazole as starting materials, 4.6 mg (6%) of the desired product was isolated. $^1$H NMR (300 MHz, DMSO-d$_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.05-3.00 (s, 6H); ES-MS m/z 488.44 [M+H]+, HPLC RT (min) 2.80.

Example 179

Preparation of N-{4-[4-Amino-5-(2-benzyl-2H-indazol-6-yl)-pyrrolo[2,1-f][1,2,4]triazin-7-yl]-phenyl}-methanesulfonamide

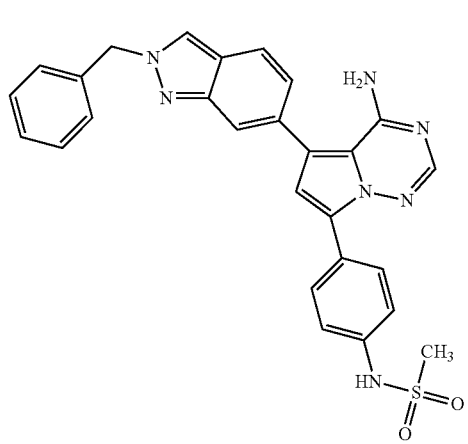 [SMILES: CS(=O)(=O)Nc1ccc(-c2cc(-c3ccc4cn(Cc5ccccc5)nc4c3)c3c(N)ncnn23)cc1]

Using a procedure similar to that of Example 5, with 7-(4-amino-phenyl)-5-(2-benzyl-2H-indazol-6-yl)-pyrrolo[2,1-f][1,2,4]triazin-4-ylamine and methanesulfonyl chloride as starting materials, 30 mg (16%) of the desired product was isolated. $^1$H NMR (300 MHz, DMSO-d$_6$) δ 9.80 (s, 1 H), 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.10 (s, 3H); ES-MS m/z 510.17 [M+H]+, HPLC RT (min) 3.07.

Example 180

Preparation of N-{3-[4-Amino-5-(2-benzyl-2H-indazol-6-yl)-pyrrolo[2,1-f][1,2,4]triazin-7-yl]-phenyl}-methanesulfonamide

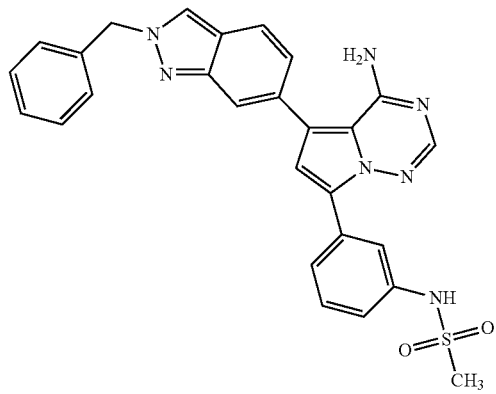 [SMILES: CS(=O)(=O)Nc1cccc(-c2cc(-c3ccc4cn(Cc5ccccc5)nc4c3)c3c(N)ncnn23)c1]

Using a procedure similar to that of Example 5 with 7-(3-amino-phenyl)-5-(2-benzyl-2H-Indazol-6-yl)-pyrrolo[2,1-f][1,2,4]triazin-4-ylamine and methanesulfonyl chloride as starting materials, 19 mg (1%) of the desired product was isolated. $^1$H NMR (300 MHz, DMSO-d$_6$) δ 9.90 (s, 1 H), 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.10 (s, 3H); ES-MS m/z 510.27 [M+H]+, HPLC RT (min) 2.85.

Example 181

Preparation of 3-{4-[4-Amino-5-(2-benzyl-2H-indazol-6-yl)-pyrrolo[2,1-f][1,2,4]triazin-7-yl]-benzyl}-1,1-dimethyl-urea

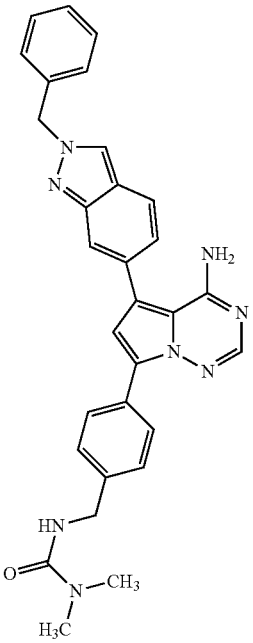 [SMILES: CN(C)C(=O)NCc1ccc(-c2cc(-c3ccc4cn(Cc5ccccc5)nc4c3)c3c(N)ncnn23)cc1]

Using a procedure similar to that of Example 5 with 5-bromo-7-(4-aminomethyl-phenyl)-pyrrolo[2,1-f][1,2,4]triazin-4-ylamine and dimethylcarbamyl chloride as starting materials, 72 mg (42%) of the desired product was isolated. $^1$H NMR (300 MHz, DMSO-$d_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.25 (d, 2 H), 2.80 (s, 6H), 2.10 (s, 1 H); ES-MS m/z 517.33 [M+H]$^+$, HPLC RT (min) 2.70.

Example 182

Preparation of N-{3-[4-Amino-5-(2-benzyl-2H-indazol-6-yl)-pyrrolo[2,1-f][1,2,4]triazin-7-yl]-benzyl}-1,1-dimethyl-sulfonylurea

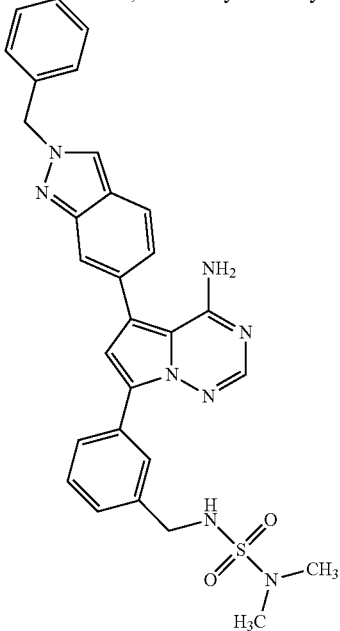 [SMILES: CN(C)S(=O)(=O)NCc1cccc(-c2cc(-c3ccc4cn(Cc5ccccc5)nc4c3)c3c(N)ncnn23)c1]

Using a procedure similar to that of Example 5 with 7-(3-aminomethyl-phenyl)-5-(2-benzyl-2H-indazol-6-yl)-pyrrolo[2,1-f][1,2,4]triazin-4-ylamine and dimethylsulfamoyl chloride as starting materials, 30 mg (12%) of the desired product was isolated. $^1$H NMR (300 MHz, DMSO-$d_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.25 (d, 2 H), 2.80 (s, 6H), 1.95 (s, 1 H); ES-MS m/z 553.3 [M+H]$^+$, HPLC RT (min) 3.00.

Example 183

Preparation of 5-(2-benzyl-2H-indazol-6-yl)-7-{[2-(pyrrolidin-1-ylmethyl)-cyclopropyl]methyl}pyrrolo[2,1-f][1,2,4]triazin-4-amine (trans)

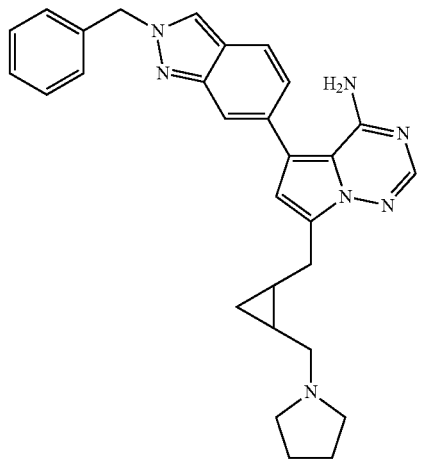 [SMILES: Nc1ncnn2c(CC3CC3CN3CCCC3)cc(-c3ccc4cn(Cc5ccccc5)nc4c3)c12]

Step 1: Preparation of 2-[(4-Amino-pyrrolo[2,1-f][1,2,4]triazin-7-yl)-hydroxy-methyl]-cyclopropanecarboxylic acid ethyl ester (Trans)

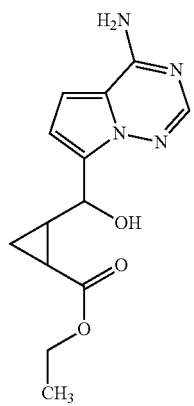 [SMILES: CCOC(=O)C1CC1C(O)c1ccc2c(N)ncnn12]

To a stirred solution of 7-bromo-pyrrolo[2,1-f][1,2,4]triazin-4-ylamine (5.27 g, 24.7 mmol) in anhydrous THF (40 mL) was added chlorotrimethylsilane (5.9 g, 54.4 mmol) at rt. The reaction mixture was stirred at rt for 2 hours and cooled in an ice water bath. 2-propylmagnesium chloride in THF (52 mL, 104 mmol, 2.0 M) was added dropwise, and the reaction mixture was allowed stirred at rt for 2 hours. The reaction was cooled to 0° C. with an ice bath, and 2-formyl-cyclopropanecarboxylic acid ethyl ester (4.6 g, 32 mmol) was added. The reaction mixture was stirred at rt for 1 hour. The mixture was quenched with saturated, aqueous ammonium chloride (20 mL) In ice water bath. The organic layer was separated and the aqueous layer was extracted with ethyl acetate (100 mL). The combined organic layer was washed with water, brine, dried by Na₂SO₄, filtered and concentrated. The crude product was separated by column (30% EtOAc/70% Hexane) to give 2.0 g (30%) of product. $^1$H NMR (300 MHz, DMSO-$d_6$) δ 8.80 (s, 1 H), 8.75 (bs, 2 H), 6.80 (s, 1 H), 6.60 (m, 1 H), 5.40 (s, 1 H), 5.0-4.8 (m, 1 H), 4.0 (m, 2 H), 1.9-1.8 (m, 2 H), 1.2 (t, 3 H), 1.0 (m, 2 H); ES-MS m/z 277.34 [M+H]$^+$, HPLC RT (min) 1.51.

Step 2: Preparation of 2-(4-Amino-pyrrolo[2,1-f][1,2,4]triazin-7-ylmethyl)-cyclopropanecarboxylic acid ethyl ester (trans)

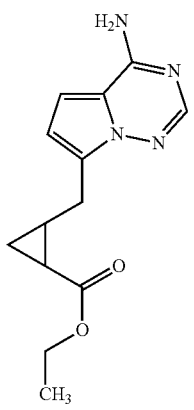 [SMILES: CCOC(=O)C1CC1Cc1ccc2c(N)ncnn12]

A solution of 2-[(4-amino-pyrrolo[2,1-f][1,2,4]triazin-7-yl)-hydroxy-methyl]-cyclopropanecarboxylic acid ethyl ester (1.75 g, 6.3 mmol) in dichloromethane (17.5 mL) was added dropwise into a mixture of triethylsilane (3 g, 25 mmol) and TFA (17.5 mL) in ice water bath. It was stirred at rt for overnight. 2N sodium carbonate solution (10 mL) was added and organic layer was separated, dried and concentrated. The residue was purified by Biotage® to give desired product 0.43 g (26). $^1$H NMR (300 MHz, DMSO-$d_6$) δ 8.80 (s, 1 H), 8.75 (bs, 2 H), 6.80 (s, 1 H), 6.60 (m, 1 H), 4.0 (m, 2 H), 2.9 (d, 2 H), 1.5 (m, 2 H), 1.2 (t, 3 H), 1.0 (m, 2 H); ES-MS m/z 261.07 [M+H]$^+$, HPLC RT (min) 2.03.

Step 3: Preparation of 2-(4-Amino-5-bromo-pyrrolo[2,1-f][1,2,4]triazin-7-ylmethyl)-cyclopropanecarboxylic acid ethyl ester (trans)

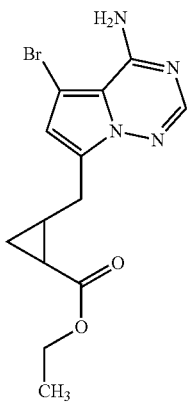 [SMILES: CCOC(=O)C1CC1Cc1cc(Br)c2c(N)ncnn12]

To a solution of 2-(4-amino-pyrrolo[2,1-f][1,2,4]triazin-7-ylmethyl)-cyclopropanecarboxylic acid ethyl ester (4.5 g, 17.2 mmol) in THF (73 mL) cooled to −20° C. was added 2,5-dibromo-4,4-dimethyl-cyclopentane-1,3-dione (2.4 g, 8.6 mmol) in four portions over 15 mins. The mixture was allowed to stir at −20° C. for 2 hours. The mixture was quenched with sodium thiosulfate solution (20 mL). The organic layer was separated and the aqueous layer was extracted with ethyl acetate (100 mL). The combined organic layer was washed with water, brine, dried by Na₂SO₄, filtered and concentrated. The residue was purified by Biotage® to give 3.0 g (51%) of the desired product. $^1$H NMR (300 MHz, DMSO-$d_6$) δ 7.80 (s, 1 H), 8.75 (bs, 2 H), 6.60 (s, 1 H), 4.0 (m, 2 H), 2.9 (d, 2 H), 1.5 (m, 2 H), 1.2 (t, 3 H), 1.0 (m, 2 H); ES-MS m/z 339.19 [M+H]$^+$, HPLC RT (min) 2.58.

Step 4: Preparation of 2-[4-Amino-5-(2-benzyl-2H-indazol-6-yl)-pyrrolo[2,1-f][1,2,4]triazin-7-ylmethyl]-cyclopropanecarboxylic acid ethyl ester (trans)

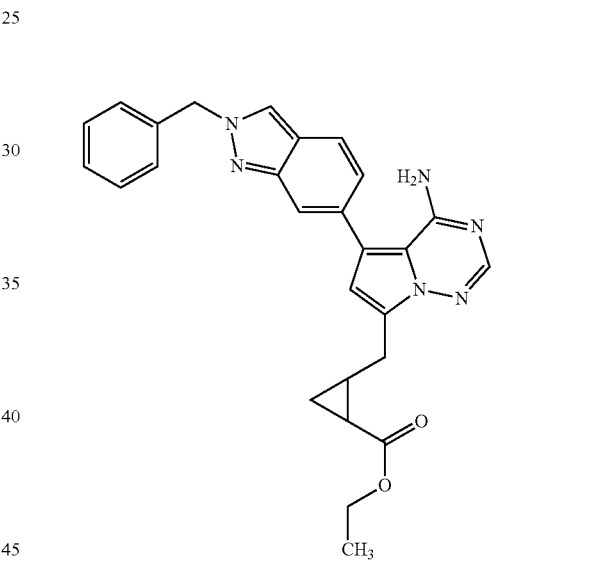

To a solution of 2-(4-amino-5-bromo-pyrrolo[2,1-f][1,2,4]triazin-7-ylmethyl)-cyclopropanecarboxylic acid ethyl ester (1.33 g, 4 mmol) in degassed DMF (6.6 mL) was added 2-benzyl-6-(4,4,5,5-tetramethyl-[1,3,2]dioxaborolan-2-yl)-2H-indazole (2.1 g, 6.3 mmol), Pd(PPh₃)₄, and 2N Na₂CO₃ solution (5.3 mL). The reaction was irradiated in a microwave reactor at 150° C. for 10 min. After cooling the mixture was partitioned between EtOAc and H₂O. The organic phase was separated and dried over Na₂SO₄, filtered, and evaporated in vacuo. The crude was purified by Biotage® (50-100% EtOAc/hexane) to give the title product as an off white solid, 1.0 g (yield 54%). $^1$H NMR (300 MHz, DMSO-$d_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.0 (m, 2 H), 3.0 (m, 2 H), 1.70 (m, 2 H), 1.2-1.0 (m, 5 H); ES-MS m/z 5467.27 [M+H]$^+$, HPLC RT (min) 2.79.

Step 5: Preparation of {2-[4-Amino-5-(2-benzyl-2H-indazol-6-yl)-pyrrolo[2,1-f][1,2,4]triazin-7-ylmethyl]-cyclopropyl}-methanol (trans)

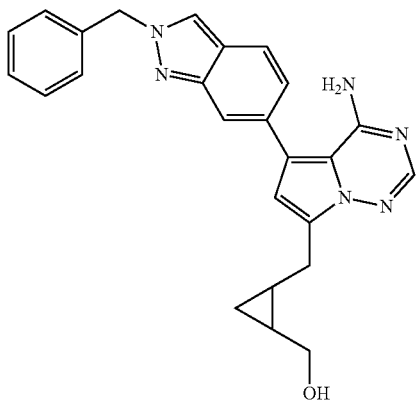 [SMILES: Nc1ncnn2c(CC3CC3CO)cc(-c3ccc4cn(Cc5ccccc5)nc4c3)c12]

To a solution of 2-[4-amino-5-(2-benzyl-2H-indazol-6-yl)-pyrrolo[2,1-f][1,2,4]triazin-7-ylmethyl]-cyclopropanecarboxylic acid ethyl ester (3.55 g, 7.6 mmol) in THF (106 mL) at 0° C. was added DIBAL (4.3 g, 30 mmol). The reaction mixture was stirred at rt for 1.5 hour. TLC analysis showed starting material, and 20 mL of DIBAL was added. The reaction mixture was stirred at rt for another 3 hours until no starting material was detected by TLC analysis. The reaction was quenched by saturated, aqueous NH$_4$Cl. The organic layer was separated, dried and concentrated in vacuo. The residue was purified by Biotage® (gradient 50%—100% EtOAc/hexane to 5% MeOH/EtOAc) to give the title product as an off-white solid, 2.5 g (yield 77%). $^1$H NMR (300 MHz, DMSO-d$_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.6 (m, 2 H), 3.4 (m, 2 H), 2.90 (m, 2 H), 1.2-1.0 (m, 2 H); ES-MS m/z 425.33 [M+H]$^+$, HPLC RT (min) 2.93.

Step 6: Preparation of (2-{[4-amino-5-(2-benzyl-2H-indazol-6-pyrrolo[2,1f][1,2,4]triazin-7-ylmethyl}cyclopropyl)methyl methanesulfonate

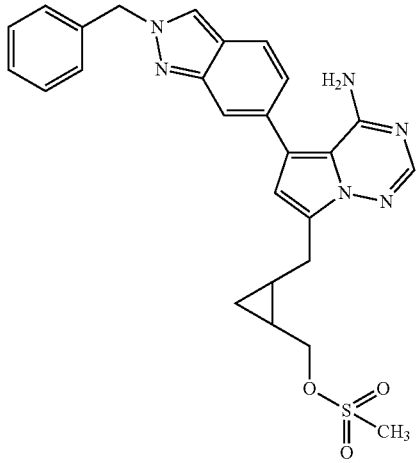 [SMILES: CS(=O)(=O)OCC1CC1Cc1cc(-c2ccc3cn(Cc4ccccc4)nc3c2)c2c(N)ncnn12]

To a solution of {2-[4-amino-5-(2-benzyl-2H-indazol-6-yl)-pyrrolo[2,1-f][1,2,4]triazin-7-ylmethyl]-cyclopropyl}-methanol (0.6 g, 1.4 mmol) in anhydrous DCM (15 mL) was added methanesulfonic anhydride (492 mg, 2.8 mmol) and pyridine (223 mg, 2.8 mmol), and the reaction mixture was heated to 50° C. for 2 hours. LC-MS showed the reaction conversion is about 50%, the solvent was evaporated and the product was used as is for the next step without purification.

Step 7: Preparation of 5-(2-benzyl-2H-indazol-6-yl)-7-{[2-(pyrrolidin-1-ylmethyl) cyclopropyl] methyl}pyrrolo[2,1-f][1,2,4]triazin-4-amine (Trans)

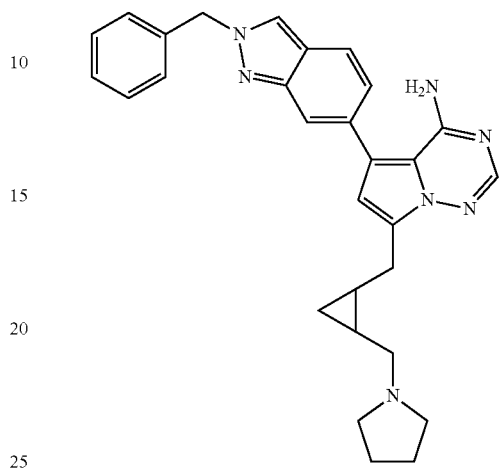

To a solution of (2-{[4-amino-5-(2-benzyl-2H-indazol-6-yl)pyrrolo[2,1-f][1,2,4]triazin-7-yl]methyl}cyclopropyl) methyl methanesulfonate (0.2 g, 0.4 mmol) in DMF (2 mL) was added pyrrolidine (84 mg, 1.2 mmol) and DIEA (102 mg, 0.8 mmol), and the mixture was heated to 80° C. for 3 hours. The mixture was concentrated in vacuo and the residue was dissolved in methanol and purified by preparative HPLC to provide 11 mg (6%) of the title compound. $^1$H NMR (300 MHz, DMSO-d$_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 720 (s, 1 H), 5.70 (s, 2 H), 2.9-2.8 (m, 2 H), 2.4-2.2 (m, 6 H), 1.7 (m, 4 H), 1.1-0.9 (m, 2 H), 0.5-0.4 (m, 2 H); ES-MS m/z 478.2 [M+H]P, HPLC RT (min) 2.29.

Example 184

Preparation of 5-(2-Benzyl-2H-indazol-6-yl)-7-(2-morpholin-4-ylmethyl-cyclopropylmethyl)-pyrrolo[2,1-f][1,2,4]triazin-4-ylamine (trans)

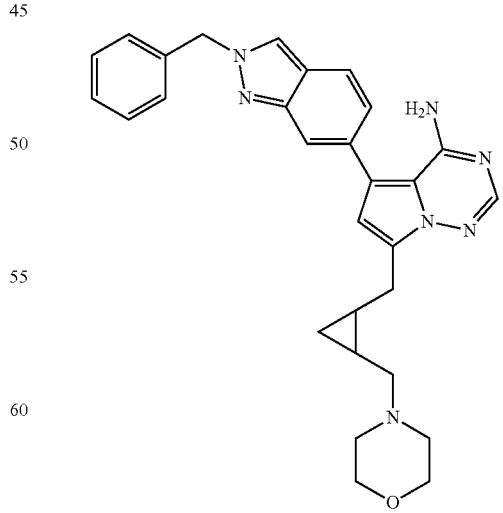

Using a procedure similar to that of Example 183 with morpholine as starting material, 30 mg (16%) of the desired product was isolated. $^1$H NMR (300 MHz, DMSO-d$_6$) δ 8.60

(s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.5 (m, 4 H), 3.0-2.8 (m, 2 H), 2.5-2.1 (m, 5 H), 1.6 (M, 1 H), 1.0 (m, 2 H), 0.6-0.5 (M, 2 H); ES-MS m/z 494.35 [M+H]$^+$, HPLC RT (min) 2.13.

Example 185

Preparation of 7-[4-Amino-5-(2-benzyl-2H-indazol-6-yl)-pyrrolo[2,1-f][1,2,4]triazin-7-yl]-3,4-dihydro-1H-isoquinoline-2-carboxylic acid dimethylamide

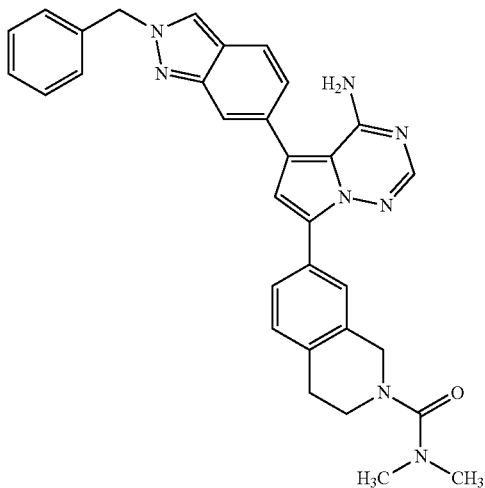 [SMILES: CN(C)C(=O)N1CCc2ccc(-c3cc(-c4ccc5cn(Cc6ccccc6)nc5c4)c4c(N)ncnn34)cc2C1]

Step 1: Preparation of 7-Bromo-3,4-dihydro-1H-Isoquinoline-2-carboxylic acid tert-butyl ester

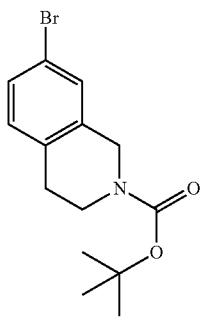 [SMILES: CC(C)(C)OC(=O)N1CCc2ccc(Br)cc2C1]

To a solution of 7-bromo-1,2,3,4-tetrahydro-isoquinoline (5.0 g, 23.5 mmol) in methanol (50 mL) was added BOC anhydride 6.1 g, 28 mmol) and 2 N Na$_2$CO$_9$ solution (70 mL), and the reaction mixture was stirred at rt overnight. The solvent was concentrated in vacuo to give the desired product, 4 g (80%). $^1$H NMR (300 MHz, DMSO-d$_6$) δ 7.4 (s, H), 7.35 (d, 1 H), 7.1 (d, 1 H), 4.5 (s, 2 H), 3.5 (t, 2 H), 2.8 (t, 2 H) 1.4 (s, 9 H).

Step 2: Preparation of 7-(4,4,5,5-Tetramethyl-[1,3,2]dioxaborolan-2-yl)-3,4-dihydro-1H-isoquinoline-2-carboxylic acid tert-butylester

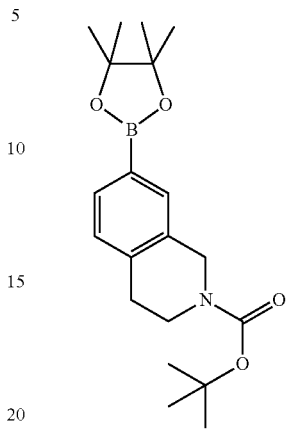

To a solution of 7-bromo-3,4-dihydro-1H-isoquinoline-2-carboxylic acid tert-butyl ester (5 g, 16 mmol) in dioxane (250 mL) was added bis(pinacolato)-diboron (4.5 g, 17.6 mmol) and KOAc (4.7 g, 48 mmol). The reaction mixture was degassed with N$_2$ for 30 min and Pd(dppf)Cl$_2$ (1.3 g, 1.6 mmol) was added. It was heated to 80° C. for 2 h. The reaction was cooled to rt and filtered through a pad of Celite®. The filtrate was concentrated in vacuo, and the crude was purified by column chromatography (20-50% EtOAc/Hexane) to provide 4.0 g (70%) of product as an off white solid. $^1$H NMR (300 MHz, DMSO-d$_6$) δ 7.4 (s, H), 7.35 (d, 1 H), 7.1 (d, 1 H), 4.5 (s, 2 H), 3.5 (t, 2 H), 2.8 (t, 2 H), 1.4 (s, 9 H), 1.2 (s, 12 H).

Step 3: Preparation of 7-(4-Amino-pyrrolo[2,1-f][1,2,4]triazin-7-yl)-3,4-dihydro-1H-isoquinoline-2-carboxylic acid tert-butyl ester

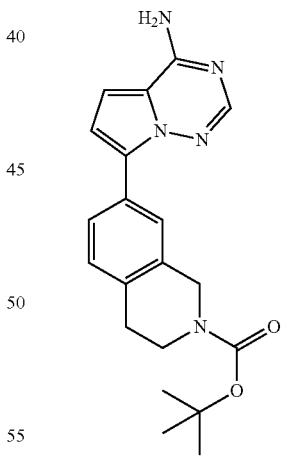

To a solution of 7-(4,4,5,5-tetramethyl-[1,3,2]dioxaborolan-2-yl)-3,4-dihydro-1H-isoquinoline-2-carboxylic acid tert-butylester (4 g, 11 mmol) and 7-bromo-pyrrolo[2,1-f][1,2,4]triazin-4-ylamine (1.3 g, 6.1 mmol) in DME (133 mL) and 2 N Na$_2$CO$_3$ solution (26 mL) was added Pd(dppf)Cl$_2$ (452 mg, 0.6 mmol). The reaction mixture was degassed with N$_2$ for 15 min. The mixture was heated to 80° C. for 23 h. The reaction mixture was filtered through a pad of Celite® and the filtrate was concentrated in vacuo. The crude residue was purified by Biotage® to provide 2.20 g (55%) of the desired product. $^1$H NMR (300 MHz, DMSO-d$_6$) δ 7.9 (m, 2 H), 7.85

(d, 1 H), 7.2 (d, 1 H), 7.0 (d, 2 H), 4.5 (s, 2 H), 3.5 (t, 2 H), 2.8 (t, 2 H) 1.4 (s, 9 H); ES-MS m/z 366.05 [M+H]+, HPLC RT (min) 2.64.

Step 4: Preparation of 7-(4-Amino-5-bromo-pyrrolo[2,1-f][1,2,4]triazin-7-yl)-3,4-dihydro-1H-isoquinoline-2-carboxylic acid tert-butyl ester

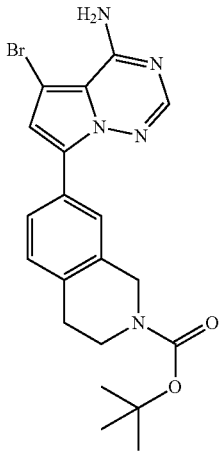 [SMILES: CC(C)(C)OC(=O)N1CCc2ccc(-c3cc(Br)c4c(N)ncnn34)cc2C1]

To a solution of 7-(4-amino-pyrrolo[2,1-f][1,2,4]triazin-7-yl)-3,4-dihydro-1H-isoquinoline-2-carboxylic acid tert-butyl ester (2.2 g, 6.1 mmol) in THF (30 mL) at −20° C. was added 1,3-dibromo-5,5-dimethyl-imidazolidine-2,4-dione (884 mg, 3 mmol) in four portions. The reaction mixture was allowed to stir at −20° C. for 2 h. The solvent was evaporated and the residue was purified by column chromatography (10-50% EtOAc/Hexane) to provide 2 g (72%) of the desired product. $^1$H NMR (300 MHz, DMSO-d$_6$) δ 7.9 (s, 1 H), 7.85 (d, 2 H), 7.2 (d, 2 H), 4.5 (s, 2 H), 3.5 (t, 2 H), 2.8 (t, 2 H), 1.4 (s, 9 H); ES-MS m/z 444.08 [M+H]+, HPLC RT (min) 3.24.

Step 5: Preparation of 7-[4-Amino-5-(2-benzyl-2H-indazol-6-yl)-pyrrolo[2,1-f][1,2,4]triazin-7-yl]-3,4-dihydro-1H-isoquinoline-2-carboxylic acid tert-butyl ester

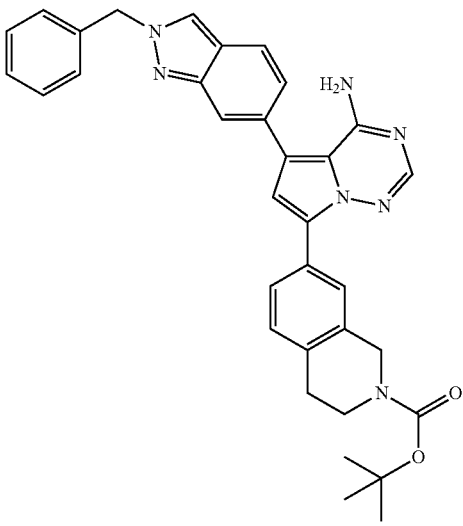 [SMILES: CC(C)(C)OC(=O)N1CCc2ccc(-c3cc(-c4ccc5cn(Cc6ccccc6)nc5c4)c4c(N)ncnn34)cc2C1]

To a solution of 7-(4-amino-5-bromo-pyrrolo[2,1-f][1,2,4]triazin-7-yl)-3,4-dihydro-1H-isoquinoline-2-carboxylic acid tert-butyl ester (1.2 g, 2.7 mmol) in DMF (20 mL), 2-benzyl-was added 6-(4,4,5,5-tetramethyl-[1,3,2]dioxaborolan-2-yl)-2H-indazole (1.4 g, 4.3 mmol), Pd(dppf)Cl$_2$ (311 mg, 0.27 mmol) and 2 N Na$_2$CO$_3$ solution (12 mL). The mixture was degassed with N$_2$ for 20 min. The reaction was irradiated in a microwave reactor at 150° C. for 10 min. After cooling, the mixture was partitioned between EtOAc and H$_2$O, The organic layer was separated and dried over Na$_2$SO$_4$. Biotage® chromatography (50-100% EtOAc/hexane) provided the title product as off white solid, 1.1 g (71%). $^1$H NMR (300 MHz, DMSO-d$_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.6 (m, 2 H), 3.6 (m, 2 H), 2.80 (m, 2 H), 1.4 (m, 9 H); ES-MS m/z 572.24 [M+H]+, HPLC RT (min) 3.44.

Step 6: Preparation of 5-(2-Benzyl-2H-indazol-6-yl)-7-(1,2,3,4-tetrahydro-isoquinolin-7-yl)-pyrrolo[2,1-f][1,2,4]triazin-4-ylamine

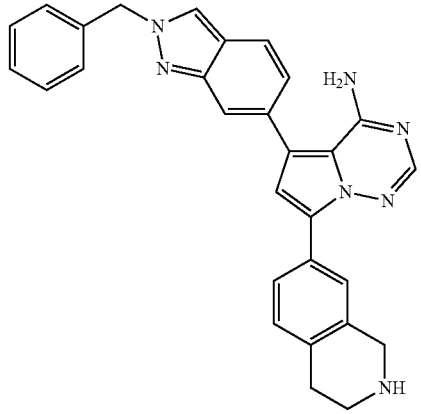 [SMILES: Nc1ncnn2c(-c3ccc4c(c3)CNCC4)cc(-c3ccc4cn(Cc5ccccc5)nc4c3)c12]

To a suspension of 7-[4-amino-5-(2-benzyl-2H-indazol-6-yl)-pyrrolo[2,1-f][1,2,4]triazin-7-yl]-3,4-dihydro-1H-isoquinoline-2-carboxylic acid tert-butyl ester (2.7 g, 4.7 mmol) in DCM (17 mL) was added TFA (8.6 mL), and the reaction mixture was stirred at rt overnight. The reaction mixture was concentrated and ethyl acetate was added. Saturated, aqueous NaHCO$_3$ was added until the pH was basic. Yellow gum formed in the wall of glass, it was dried in vacuum oven overnight and the title product was obtained as light yellow solid, 2.2 g (98%). $^1$H NMR (300 MHz, DMSO-d$_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.1 (m, 2 H), 3.2 (m, 2 H), 2.80 (m, 2 H); ES-MS m/z 472.29 [M+H]+, HPLC RT (min) 2.22.

Step 7: Preparation of 7-[4-Amino-5-(2-benzyl-2H-indazol-6-yl)-pyrrolo[2,1-f][1,2,4]triazin-7-yl]-3,4-dihydro-1H-isoquinoline-2-carboxylic acid dimethylamide

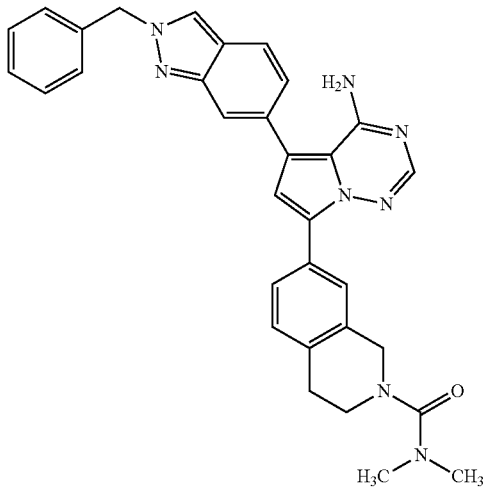 [SMILES: CN(C)C(=O)N1CCc2ccc(-c3cc(-c4ccc5cn(Cc6ccccc6)nc5c4)c4c(N)ncnn34)cc2C1]

To a solution of 5-(2-benzyl-2H-indazol-6-yl)-7-(1,2,3,4-tetrahydro-isoquinolin-7-yl)-pyrrolo[2,1-f][1,2,4]triazin-4-ylamine (150 mg, 0.3 mmol) in THF (2 mL) was added dimethylcarbamyl chloride (44 mg, 0.4 mmol) and triethylamine (64 mg), and the mixture was heated to 40° C. for 4 hours. The mixture was concentrated in vacuo and the residue was dissolved in methanol and purified by preparative HPLC to provide the title compound, 53 mg (31%). $^1$H NMR (300 MHz, DMSO-d$_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.4 (m, 2 H), 3.5 (m, 2 H), 2.9 (m, 2 H), 2.8 (s, 6 H); ES-MS m/z 543.47 [M+H]$^+$, HPLC RT (min) 3.16.

Example 186

Preparation of 5-(2-Benzyl-2H-indazol-6-yl)-7-(2-methanesulfonyl-1,2,3,4-tetrahydro-isoquinolin-7-yl)-pyrrolo[2,1-f][1,2,4]triazin-4-ylamine

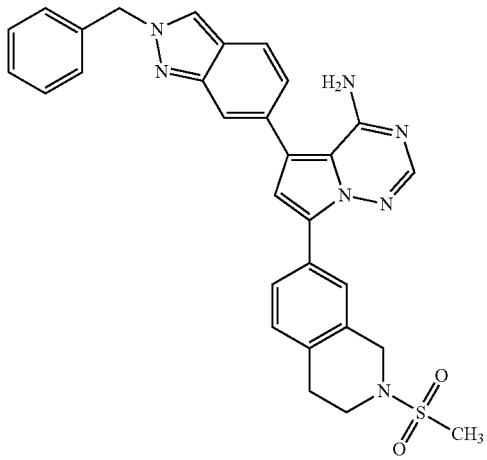 [SMILES: CS(=O)(=O)N1CCc2ccc(-c3cc(-c4ccc5cn(Cc6ccccc6)nc5c4)c4c(N)ncnn34)cc2C1]

Using a procedure similar to that of Example 185 with methanesulfonyl chloride as starting material, 17 mg (16%) of the desired product was isolated. $^1$H NMR (300 MHz, DMSO-d$_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.5 (m, 2 H), 3.5 (m, 2 H), 3.0 (m, 5 H); ES-MS m/z 550.35 [M+H]$^+$, HPLC RT (min) 3.13.

Example 187

Preparation of 1-{7-[4-Amino-5-(2-benzyl-2H-indazol-6-yl)-pyrrolo[2,1-f][1,2,4]triazin-7-yl]-3,4-dihydro-1H-isoquinolin-2-yl}-propan-1-one

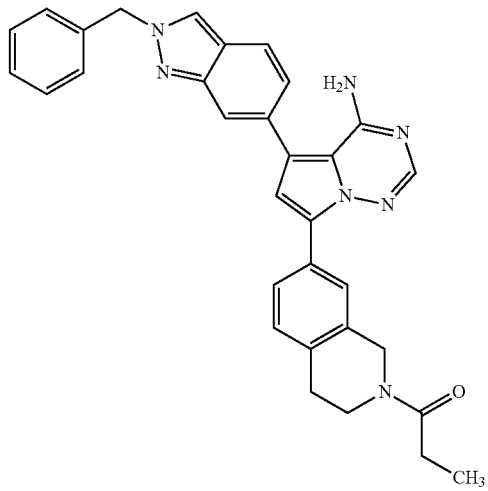 [SMILES: CCC(=O)N1CCc2ccc(-c3cc(-c4ccc5cn(Cc6ccccc6)nc5c4)c4c(N)ncnn34)cc2C1]

Using a procedure similar to that of Example 185 with propionyl chloride as starting material, 33 mg (33%) of the desired product was isolated. $^1$H NMR (300 MHz, DMSO-d$_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.7 (d, 2 H), 3.7 (m, 2 H), 3.0 (m, 2 H), 2.9 (s, 2 H), 2.5 (M, 2 H), 1.05 (t, 3 H); ES-MS m/z 528.4 [M+H]$^+$, HPLC RT (min) 2.92.

Example 188

Preparation of 5-(2-Benzyl-2H-indazol-6-yl)-7-[2-(2-methoxy-ethyl)-1,2,3,4-tetrahydro-isoquinolin-7-yl]-pyrrolo[2,1-f][1,2,4]triazin-4-ylamine

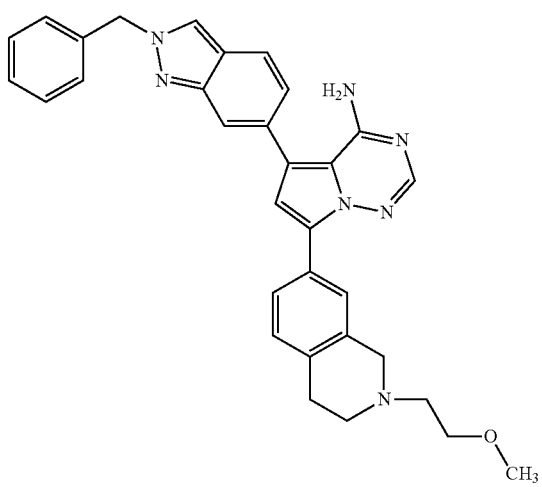 [SMILES: COCCN1CCc2ccc(-c3cc(-c4ccc5cn(Cc6ccccc6)nc5c4)c4c(N)ncnn34)cc2C1]

Using a procedure similar to that of Example 185 with 1-bromo-2-methoxy-ethane as starting material, 20 mg (18%) of the desired product was isolated. $^1$H NMR (300 MHz, DMSO-d$_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.65 (s, 2 H), 3.5 (t, 2 H), 3.3 (s, 3 H), 2.8 (m, 2 H), 2.7 (m, 2 H), 2.7 (m, 2 H); ES-MS m/z 529.97 [M+H]+, HPLC RT (min) 2.29.

Example 189

Preparation of 1-{7-[4-Amino-5-(2-benzyl-2H-indazol-6-yl)-pyrrolo[2,1-f][1,2,4]triazin-7yl]-3,4-dihydro-1H-isoquinolin-2-yl}-ethanone

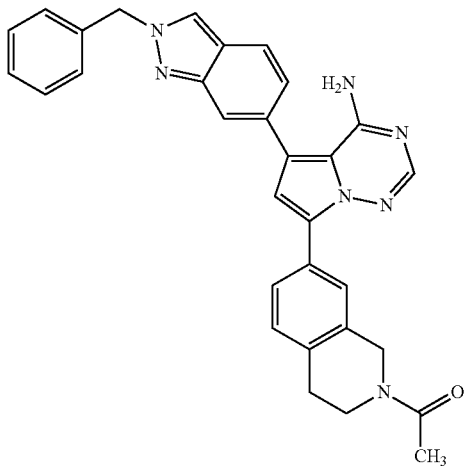 [SMILES: CC(=O)N1CCc2ccc(-c3cc(-c4ccc5cn(Cc6ccccc6)nc5c4)c4c(N)ncnn34)cc2C1]

Using a procedure similar to that of Example 185 with acetyl chloride as starting material, 22 mg (14%) of the desired product was isolated. $^1$H NMR (300 MHz, DMSO-$d_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.7 (d, 2 H), 3.7 (m, 2 H), 3.0-2.8 (m, 2 H), 2.1 (s, 2 H); ES-MS m/z 514.46 [M+H]+, HPLC RT (min) 3.06.

Example 190

Preparation of 2-{7-[4-Amino-5-(2-benzyl-2H-indazol-6-yl)-pyrrolo[2,1-f][1,2,4]triazin-7-yl]-3,4-dihydro-1H-isoquinolin-2-yl}-N,N-dimethyl-acetamide

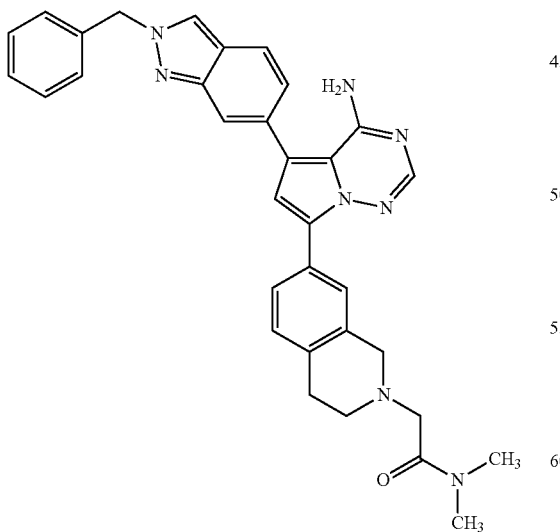

Using a procedure similar to that of Example 185 with 2-chloro-N,N-dimethyl-acetamide as starting materials, 32 mg (18%) of the desired product was isolated. $^1$H NMR (300 MHz, DMSO-$d_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.4 (d, 2 H), 3.7 (s, 2 H), 3.5 (m, 2 H), 3.1 (s, 2 H), 2.9 (s, 6 H), 2.8 (m, 2 H); ES-MS m/z 557.26 [M+H]+, HPLC RT (min) 2.63.

Example 191

Preparation of 2-{7-[4-Amino-5-(2-benzyl-2H-indazol-6-yl)-pyrrolo[2,1-f][1,2,4]triazin-7-yl]-3,4-dihydro-1H-isoquinolin-2-yl}-ethanol hydrochloride

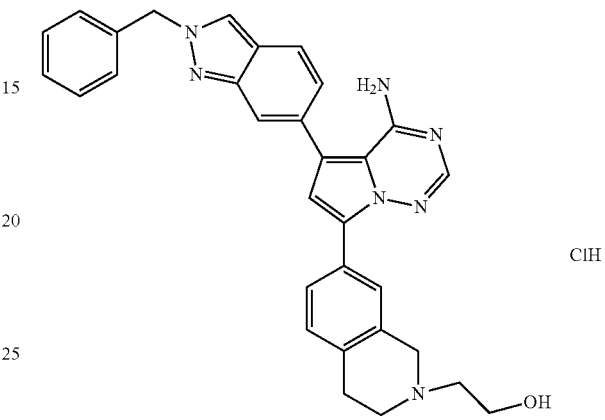

Using a procedure similar to that of Example 185 with hydroxyethyl bromide as starting material, followed by one equivalent of conc. HCl in ethanol and water, 600 mg (57%) of the desired product was Isolated. $^1$H NMR (300 MHz, DMSO-$d_6$) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.6 (d, 2 H), 4.4 (M, 2 H), 3.9 (bs, 2 H)<3.8 (m, 2 H), 3.6-3.4 (m, 4 H); ES-MS m/z 516.28 [M+H]+, HPLC RT (min) 1.03.

Example 192

Preparation of 3-{7-[4-Amino-5-(2-benzyl-2H-indazol-6-yl)-pyrrolo[2,1-f][1,2,4]triazin-7-yl]-3,4-dihydro-1H-isoquinolin-2-yl}-propan-1-ol

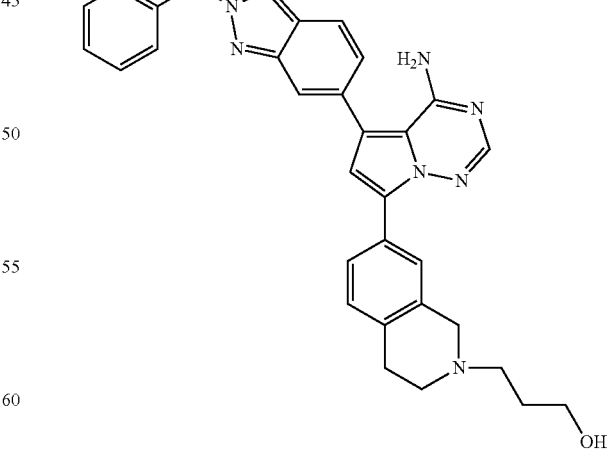

Using a procedure similar to that of Example 185 and Example 104, step 2, with (2-bromo-ethoxy)-tert-butyl-dimethyl-silane as the starting material, 20 mg (18%) of the desired product was isolated. $^1$H NMR (300 MHz, DMSO-$d_6$) δ 8.60 (s, 1 H), 8.05 (d, 2 H), 8.0 (s, 1 H), 7.90 (d, 1 H), 7.70

(s, 1 H), 7.60-7.40 (m, 7 H), 7.25 (d, 1 H), 7.20 (s, 1 H), 5.70 (s, 2 H), 4.2 (m, 2 H), 3.6 (bs, 2 H), 3.5 (m, 2 H), 2.9 (m, 2 H), 2.7 (m, 2 H), 1.7 (m, 2 H); ES-MS m/z 529.98 [m+H]⁺, HPLC RT (min) 2.24.

Example 193

Preparation of 3-{7-[4-Amino-5-(2-benzyl-2H-indazol-6-yl)-pyrrolo[2,1-f][1,2,4]triazin-7-yl]-3,4-dihydro-1H-isoquinolin-2-yl}-propionic acid

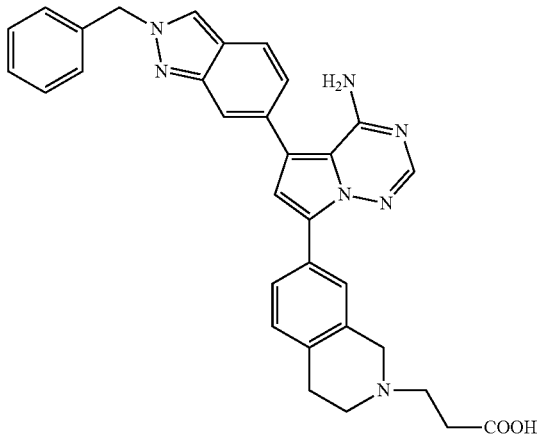 [SMILES: Nc1ncnn2c(-c3ccc4c(c3)CN(CCC(=O)O)CC4)cc(-c3ccc4cn(Cc5ccccc5)nc4c3)c12]

Using a procedure similar to that of Example 185 with 3-bromo-propionic acid as starting material, 44 mg (27%) of the desired product was isolated. ¹H NMR (300 MHz, DMSO-d₆) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 3.5 (m, 2 H), 2.9 (m, 2 H), 2.7 (m, 4 H), 2.0 (m, 2 H); ES-MS m/z 543.91 [M+H]⁺, HPLC RT (min) 2.24.

Example 194

Preparation of 2-{7-[4-Amino-5-(2-benzyl-2H-indazol-6-yl-pyrrolo[2,1-f][1,2,4]triazin-7-yl]-3,4-dihydro-1H-isoquinolin-2-yl}-ethanol

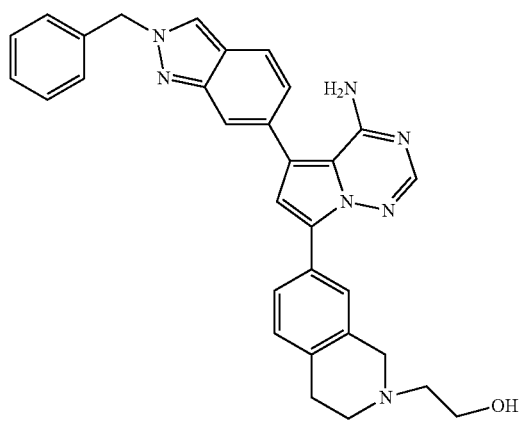 [SMILES: Nc1ncnn2c(-c3ccc4c(c3)CN(CCO)CC4)cc(-c3ccc4cn(Cc5ccccc5)nc4c3)c12]

Using a procedure similar to that of Example 185 with 5-(2-benzyl-2H-indazol-6-yl)-7-(1,2,3,4-tetrahydro-isoquinolin-7-yl)-pyrrolo[2,1-f][1,2,4]triazin-4-ylamine and hydroxyethyl bromide as starting materials, 41 mg (4%) of the desired product was isolated. ¹H NMR (300 MHz, DMSO-d₆) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.6 (d, 2 H), 4.4 (M, 2 H), 3.9 (bs, 2 H), 3.8 (m, 2 H), 3.6-3.4 (m, 4 H); ES-MS m/z 516.28 [M+H]⁺, HPLC RT (min) 2.25.

Example 195

Preparation of 3-{7-[4-Amino-5-(2-benzyl-2H-indazol-6-yl)-pyrrolo[2,1-f][1,2,4]triazin-7-yl]-3,4-dihydro-1H-isoquinolin-2-yl}-propane-1,2-diol

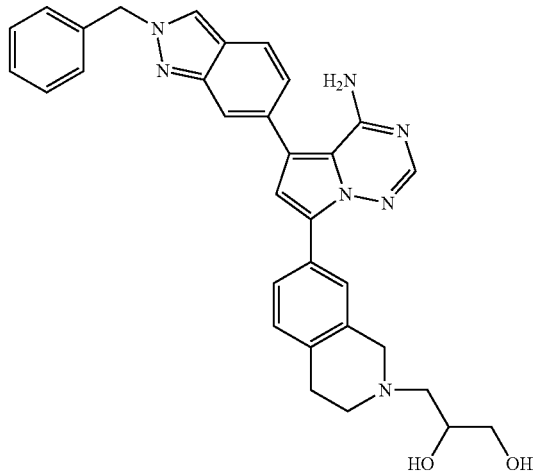 [SMILES: Nc1ncnn2c(-c3ccc4c(c3)CN(CC(O)CO)CC4)cc(-c3ccc4cn(Cc5ccccc5)nc4c3)c12]

Using a procedure similar to that of Example 185 with 3-bromo-propane-1,2-diol as the starting material, 15 mg (8%) of the desired product was isolated. ¹H NMR (300 MHz, DMSO-d₆) δ 8.60 (s, 1 H), 8.05 (d, 2 H), 8.0 (s, 1 H), 7.90 (d, 1 H), 7.70 (s, 1 H), 7.60-7.40 (m, 7 H), 7.25 (d, 1 H), 7.20 (s, 1 H), 5.70 (s, 2 H), 4.6 (d, 2 H), 3.7 (m, 2 H), 3.3 (m, 1 H), 2.9-2.6 (m, 6 H); ES-MS m/z 545.95 HPLC RT (min) 2.24.

Example 196

Preparation of [4-Amino-5-(2-benzyl-2H-indazol-6-yl)-pyrrolo[2,1-f][1,2,4]triazin-7-yl]-pyrrolidin-3-yl-methanone

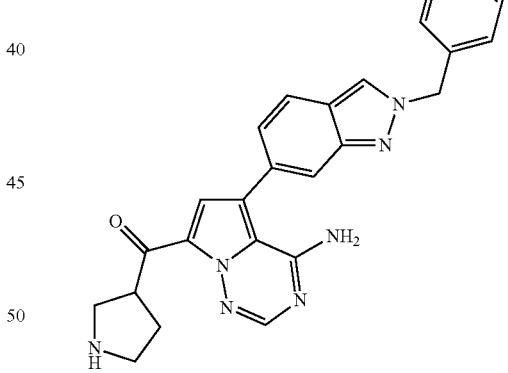

Step 1: Preparation of 3-(4-Amino-pyrrolo[2,1-f][1,2,4]triazine-7-carbonyl)-pyrrolidine-1-carboxylic acid tert-butyl ester

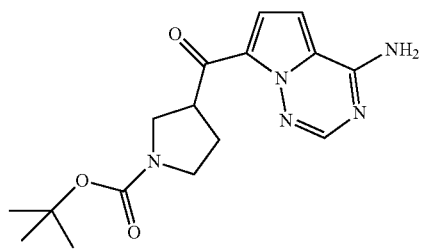 [SMILES: CC(C)(C)OC(=O)N1CCC(C(=O)c2ccc3c(N)ncnn23)C1]

To a suspension of Intermediate B (1.30 g, 6.10 mmol) in THF (30 mL) was added trimethylsilylchloride (1.49 g, 13.4 mmol) and the resulting mixture was stirred for 2.5 h. Isopropylmagnesium chloride (2M in THF) (12.81 mL, 25.63 mmol) was added dropwise.

The mixture was stirred for 2 h at rt and then cooled in an ice-bath. A cold solution of 3-(methoxy-methyl-carbamoyl)-pyrrolidine-1-carboxylic acid tert-butyl ester (2.05 g, 7.93 mmol) in THF (10 mL) was added and the mixture was stirred cold for 1 h and allowed to warm up to rt. The mixture was quenched with cold saturated NH$_4$Cl and stirred for 20 min and the layers were separated. The aqueous layer was extracted with THF. The combined extracts were dried over Na$_2$SO$_4$, filtered and concentrated. The crude product was purified by Biotage® chromatography eluting with 50-75% gradient EtOAc/hexanes to afford 1.31 g (65% yield) of the desired product. $^1$H NMR (300 MHz, CD$_3$OD-d$_4$) δ 8.00 (s, 1 H), 7.45 (d, 1 H), 6.94 (d, 1 H), 4.44-4.32 (m, 1 H), 3.63 (dd, 2 H), 3.47-3.38 (m, 2 H), 2.31-2.11 (m, 2 H), 1.45 (s, 9 H); LC-MS [M+H]$^+$=331.7, RT=2.48 min.

Step 2: Preparation of 3-(4-Amino-5-bromo-pyrrolo[2,1-f][1,2,4]triazine-7-carbonyl)-pyrrolidine-1-carboxylic acid tert-butyl ester

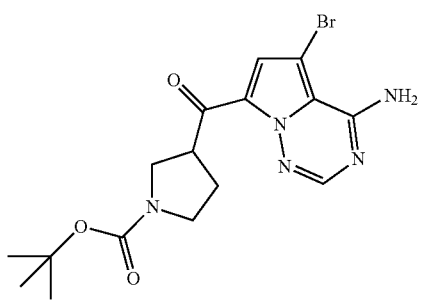 [SMILES: CC(C)(C)OC(=O)N1CCC(C(=O)c2cc(Br)c3c(N)ncnn23)C1]

To a cooled (−20° C.) solution of 3-(4-amino-pyrrolo[2,1-f][1,2,4]triazine-7-carbonyl)-pyrrolidine-1-carboxylic acid tert-butyl ester (1.19 g, 3.59 mmol) in tetrahydrofuran (35 mL) was added THF solution of 1,3-dibromo-5,5-dimethyl-hydantoin (0.56 g, 1.97 mmol). The mixture was allowed to stir (−20° C.) for 2 h and then allowed to warm to rt. The reaction was quenched with the addition of 10% aqueous Na$_2$S$_2$O$_3$ solution. The mixture was extracted with ethyl acetate (3×75 mL). The combined organics were washed with brine, dried (Na$_2$SO$_4$) and concentrated to dryness. The crude material was purified by Biotage® chromatography using a gradient of 50% to 75% ethyl acetate in hexanes to afford 1.33 g (90%) of the desired product. $^1$H NMR (300 MHz, CD$_3$OD-d$_4$) δ 8.00 (s, 1 H), 7.45 (d, 1 H), 6.94 (d, 1 H), 4.44-4.32 (m, 1 H), 3.65-3.59 (m, 2 H), 3.47-3.38 (m, 2 H), 2.31-2.11 (m, 2 H), 1.45 (s, 9 H); LC-MS [M+H]$^+$=411.7, RT=2.98 min.

Step 3: Preparation of 3-[4-Amino-5-(2-benzyl-2H-indazol-6-yl)-pyrrolo[2,1-f][1,2,4]triazine-7-carbonyl]-pyrrolidine-1-carboxylic acid tert-butyl ester

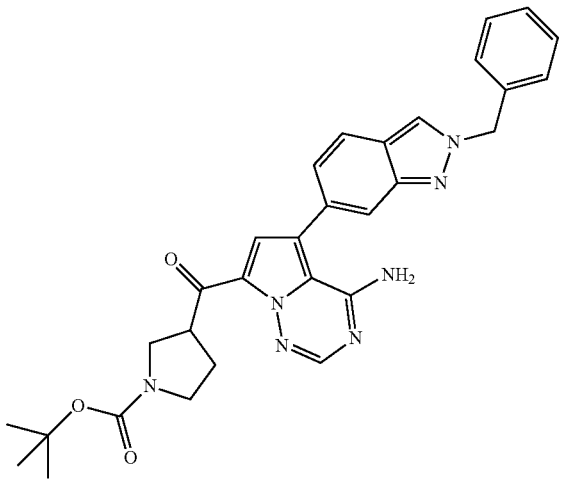 [SMILES: CC(C)(C)OC(=O)N1CCC(C(=O)c2cc(-c3ccc4cn(Cc5ccccc5)nc4c3)c3c(N)ncnn23)C1]

To a stirred solution 3-(4-amino-5-bromo-pyrrolo[2,1-f][1,2,4]triazine-7-carbonyl)-pyrrolidine-1-carboxylic acid tert-butyl ester (1.33 g, 3.24 mmol), intermediate C (1.63 g, 4.86 mmol), and tetrakis(triphenylphosphine)palladium(0) (0.37 g, 0.32 mmol) in degassed DMF (35 mL) was added aqueous Na$_2$CO$_3$ (2M, 5.34 mL). The resulting mixture was heated at 110° C. for 3 h and then cooled to rt. The reaction mixture was diluted with EtOAc and filtered through a Celite® pad. The organic layer was separated and concentrated in vacuo. The residue was purified by silica-gel column using a gradient of 50 to 100% EtOAc in hexanes to afford 1.16 g (66%) of the desired product. $^1$H-NMR (CD$_3$OD-d$_4$) δ 8.39 (s, 1H), 8.05 (s, 1H), 7.87 (dd, 1H), 7.70 (s, 1H), 7.50 (s, 1H), 7.37-7.29, (m, 5 H), 7.24 (dd, 1 H), 5.67 (s, 1 H), 4.47-4.39 (m, 2 H), 3.71-3.59 (m, 2 H), 2.34-2.12 (m, 2 H), 1.45 (s, 1H); LC-MS [M+H]$^+$=537.9, RT=3.36 min.

Step 4: Preparation of the Title Compound

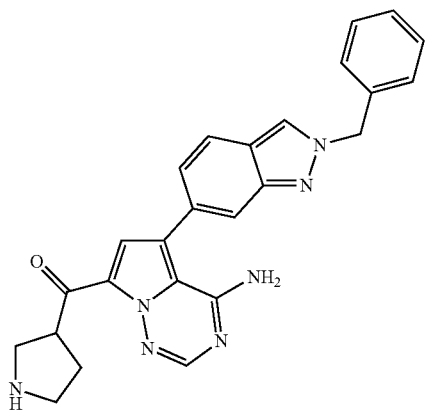 [SMILES: Nc1ncnn2c(C(=O)C3CCNC3)cc(-c3ccc4cn(Cc5ccccc5)nc4c3)c12]

The product from Step 3 (0.51 g, 0.94 mmol) was dissolved in THF (15 mL) and HCl in dioxane (4N, 2.34 mL) was added. The mixture was stirred for 12 hours and then concentrated. The residue was suspended in EtOAc, sonicated for 10 min and the white solid was filtered. The solid was partitioned between NaHCO₃ saturated solution and i-PrOH/CHCl₃ (1:2) mixture. The organic layer was separated and washed with brine, dried over Na₂SO₄ filtered and concentrated to provide 320 mg (78%) of the title compound. ¹H-NMR (CD₃OD-d₄) δ 8.41-8.39 (m, 1H), 8.05 (s, 1H), 7.87 (dd, 1H), 7.71-7.69 (m, 1H), 7.70 (s, 1H), 7.37-7.29, (m, 5 H), 7.24 (dd, 1 H), 5.67 (s, 1 H), 4.39-4.31 (m, 1 H), 3.28-3.21 (m, 2 H), 3.12-2.96 (m, 2 H), 2.25-2.07 (m, 2 H); LC-MS [M+H]⁺=438.4, RT=2.52 min.

Example 197

Preparation of 1-{3-[4-Amino-5-(2-benzyl-2H-indazol-6-yl)-pyrrolo[2,1-f][1,2,4]triazine-7-carbonyl]-pyrrolidin-1-yl}-ethanone

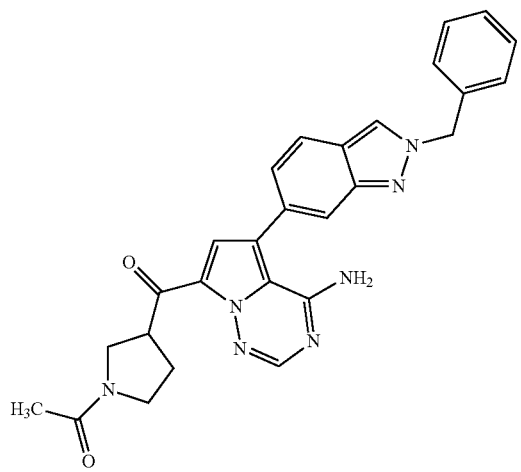 [SMILES: CC(=O)N1CCC(C(=O)c2cc(-c3ccc4cn(Cc5ccccc5)nc4c3)c3c(N)ncnn23)C1]

[4-Amino-5-(2-benzyl-2H-indazol-6-yl)-pyrrolo[2,1-f][1,2,4]triazin-7-yl]-pyrrolidin-3-yl-methanone hydrochloride salt (80 mg, 0.17 mmol) was dissolved in CH₃CN/MeOH (1:1, 2 mL) and 2N Na₂CO₃ (0.84 mL, 1.68 mmol) was added, followed by acetyl chloride (0.013 mL, 0.19 mmol). The resulting mixture was stirred at rt for 12 h. The mixture was concentrated, diluted with EtOAc and layers were separated. The organic layer was washed with brine and concentrated. The residue was purified by short silica-gel column eluting with EtOAc, then 10% MeOH in EtOAc to give 39 mg (48%) of the desired product. ¹H-NMR (CD₃OD-d₄) δ 8.39-8.35 (m, 1H), 8.03 (d, 1H), 7.81 (dt, 1H), 7.69-7.67 (m, 1 H), 7.47 (d, 1H), 7.37-7.27, (m, 5 H), 7.19 (fit, 1 H), 5.64 (s, 1 H), 4.53-4.38 (m, 1 H), 3.92-3.72 (m, 2 H), 3.62 (t, 1H), 3.52 (t, 1 H), 2.38-2.07 (m, 2 H), 2.10 (d, 3 H); LC-MS [M+H]⁺= 480.1, RT=2.64 min.

Example 198

Preparation of 1-{3-[4-Amino-5-(2-benzyl-2H-indazol-6-yl)-pyrrolo[2,1-f][1,2,4]triazine-7-carbonyl]-pyrrolidin-1-yl}-3-methyl-butan-1-one

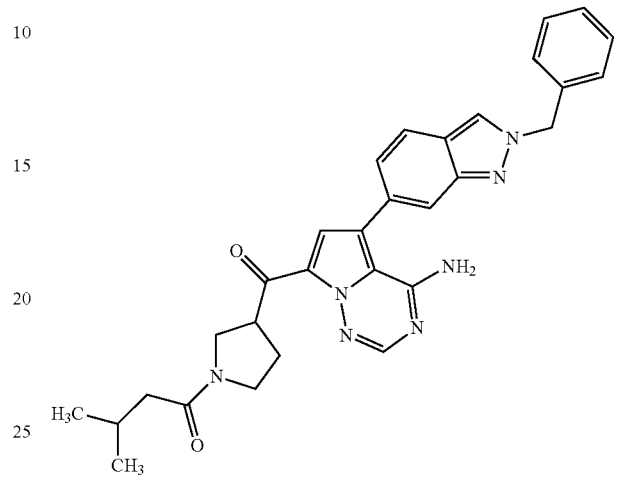

The title compound was prepared in the same manner described for the preparation of Example 197 substituting isovaleryl chloride for acetyl chloride. ¹H-NMR (CD₃OD-d₄) δ 8.39-8.35 (m, 1H), 8.03 (s, 1H), 7.81 (dt, 1H), 7.71-7.67 (m, 1 H), 7.47 (d, 1H), 7.37-7.27, (m, 5 H), 7.19 (dt, 1 H), 5.64 (s, 1 H), 4.53-4.38 (m, 1 H), 3.92-3.72 (m, 2 H), 3.62 (t, 1H), 3.52 (t, 1 H), 2:38-2.07 (m, 2 H), 0.99-0.92 (m, 6 H); LC-MS [M+H]⁺=522.2, RT=3.13 min.

Example 199

Preparation of 1-{3-[4-Amino-5-(2-benzyl-2H-indazol-6-yl)-pyrrolo[2,1-f][1,2,4]triazine-7-carbonyl]-pyrrolidin-1-yl}-2-methoxy-ethanone

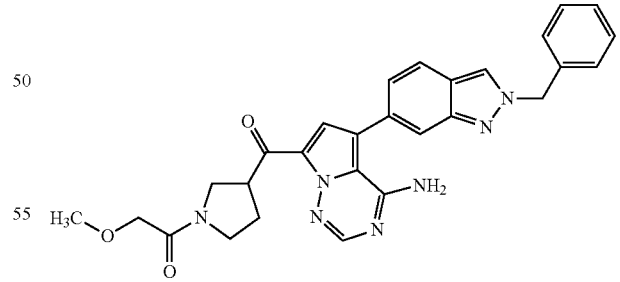

The title compound was prepared in the same manner described for the preparation of Example 197 substituting methoxyacetyl chloride for acetyl chloride. ¹H-NMR (CD₃OD-d₄) δ 8.40-8.39 (m, 1H), 8.06 (d, 1H), 7.85 (d, 1H), 7.71-7.67 (m, 1 H), 7.47 (d, 1H), 7.37-7.27, (m, 5 H), 723 (dd, 1 H), 5.64 (s, 1 H), 4.53-4.38 (m, 1 H), 4.11 (d, 2 H), 3.88-3.74 (m, 2H), 3.62-3.53 (m, 2 H), 3.40 (d, 3 H); LC-MS [M+H]⁺= 510.3, RT=2.74 min.

Example 200

Preparation of 1-{3-[4-Amino-5-(2-benzyl-2H-indazol-6-yl)-pyrrolo[2,1-f][1,2,4]triazine-7-carbonyl]-pyrrolidin-1-yl}-propan-1-one

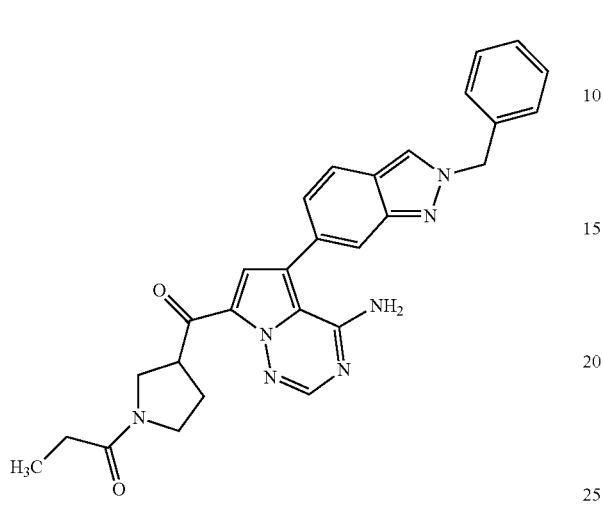

The title compound was prepared in the same manner described for the preparation of Example 197 substituting propionyl chloride for acetyl chloride. $^1$H-NMR (CD$_3$OD-d$_4$) δ 8.39-8.35 (m, 1H), 8.03 (d, 1H), 7.81 (dt, 1H), 7.69-7.67 (m, 1 H), 7.47 (d, 1H), 7.37-7.27, (m, 5 H), 7.27 (dd, 1 H), 5.64 (s, 1 H), 4.53-4.38 (m, 1 H), 3.90-3.74 (m, 2 H), 3.62 (t, 1H), 3.52 (t, 1 H), 2.42-2.29 (m, 4 H), 1.15-1.09 (m, 3 H); LC-MS [M+H]$^+$=494.2, RT=2.77 min.

Example 201

Preparation of [4-Amino-5-(2-benzyl-2H-indazol-6-yl)-pyrrolo[2,1-f][1,2,4]triazin-7-yl]-(1-cyclopropanecarbonyl-pyrrolidin-3-yl)-methanone

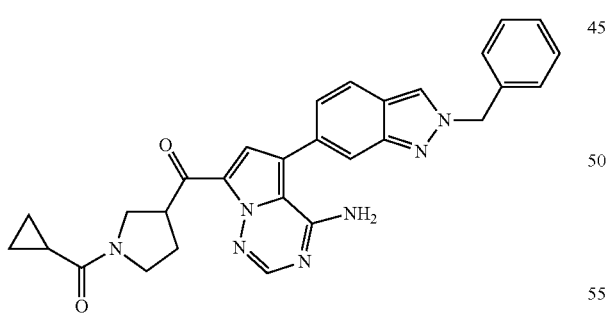

The title compound was prepared in the same manner described for the preparation of Example 197 substituting cyclopropyl chloride for acetyl chloride. $^1$H-NMR (CD$_3$OD-d$_4$) δ 8.39-8.35 (m, 1H), 8.03 (d, 1H), 7.81 (dt, 1H), 7.69-7.67 (m, 1 H), 7.47 (d, 1H), 7.37-7.27, (m, 5 H), 7.23 (dd, 1 H), 5.64 (s, 1 H), 4.53-4.38 (m, 1 H), 4.10-3.95 (m, 1 H), 3.85-3.74 (m, 2 H), 3.54 (t, 1 H), 2.42-2.13 (m, 2 H), 1.85-1.77 (m, 1 H), 0.93-0.79 (m, 4 H); LC-MS [M+H]$^+$=506.2, RT=2.95 min.

Example 202

Preparation of 3-[4-Amino-5-(2-benzyl-2H-indazol-6-yl)-pyrrolo[2,1-f][1,2,4]triazine-7-carbonyl]-pyrrolidine-1-carboxylic acid dimethylamide

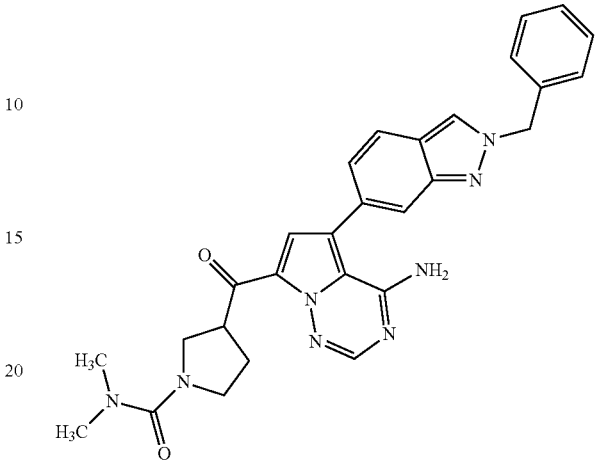

The title compound was prepared in the same manner described for the preparation of Example 197 substituting N,N-dimethylcarbamoyl chloride for acetyl chloride.
$^1$H-NMR (CD$_3$OD-d$_4$) δ 8.41-8.39 (m, 1H), 8.06 (s, 1H), 7.87 (dd, 1 H), 7.71-7.69 (m, 1 H), 7.51 (s, 1H), 7.37-7.29, (m, 5 H), 7.24 (dd, 1 H), 5.67 (s, 1 H), 4.44-4.35 (m, 1 H), 3.77-3.69 (m, 2 H), 3.55-3.45 (m, 2 H), 2.87 (s, 6 H), 2.33-2.15 (m, 2 H); LC-MS [M+H]$^+$=509.1, RT=2.78 min.

Example 203

Preparation of [4-Amino-5-(2-benzyl-2H-indazol-6-yl)-pyrrolo[2,1-f][1,2,4]triazin-7-yl]-(1-methanesulfonyl-pyrrolidin-3-yl)-methanone

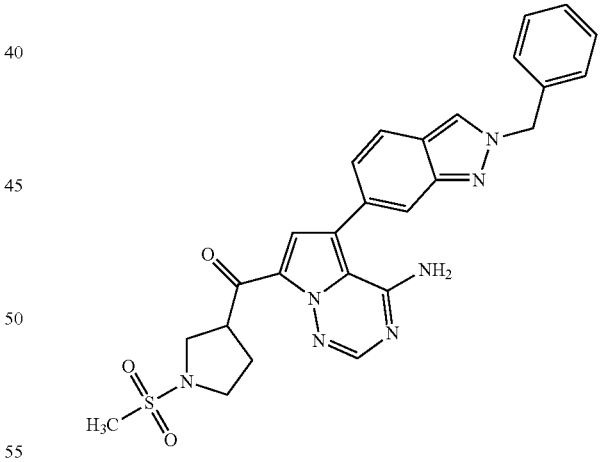

[4-Amino-5-(2-benzyl-2H-indazol-6-yl)-pyrrolo[2,1-f][1,2,4]triazin-7-yl]-pyrrolidin-3-yl-methanone hydrochloride salt (89 mg, 0.19 mmol) was dissolved in dichloromethane (1 mL) and triethylamine (0.079 mL, 0.56 mmol) was added, followed by methanesulfonyl chloride (0.022 mL, 0.28 mmol). The mixture was stirred at it for 18 h and then at 50° C. overnight. The mixture was concentrated, diluted with MeOH, filtered and the filtrate purified by HPLC eluting with 20-95% gradient acetonitrile/water to afford 24 mg (25%) of the title compound. $^1$H-NMR (CD$_2$Cl$_2$-d$_2$) δ 8.13-8.06 (m, 2 H), 7.81 (dt, 1H), 7.77-7.76 (m, 1 H), 7.43 (s, 1H), 7.42-7.33, (m, 5 H), 7.19 (dd, 1 H), 5.64 (s, 1 H), 4.61-4.53 (m, 1 H), 3.74-3.65 (m, 2 H), 3.54-3.44 (m, 1 H), 3.39-3.31 (m, 1 H), 2.89 (s, 1 H), 2.46-2.28 (m, 2 H); LC-MS [M+H]$^+$=516.2, RT=2.88 min.

Example 204

Preparation of [4-Amino-5-(2-benzyl-2H-indazol-6-yl)-pyrrolo[2,1-f][1,2,4]triazin-7-yl]-(1-cyclopropanesulfonyl-pyrrolidin-3-yl)-methanone

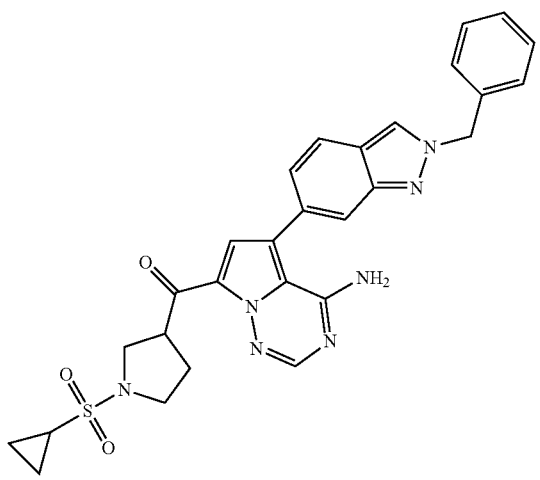 [SMILES: Nc1ncnn2c(C(=O)C3CCN(S(=O)(=O)C4CC4)C3)cc(-c3ccc4cn(Cc5ccccc5)nc4c3)c12]

The title compound was prepared in the same manner described for the preparation of Example 203 substituting cyclopropanesulfonyl chloride for methanesulfonyl chloride.
$^1$H-NMR (CD$_3$OD-d$_4$) δ 8.42-8.30 (m, 1 H), 8.08 (s, 1 H), 7.87 (d, 1H), 7.74-7.70 (m, 1 H), 7.52 (s, 1H), 7.38-7.31, (m, 5 H), 7.24 (dd, 1 H), 5.65 (s, 1 H), 4.58-4.49 (m, 1 H), 3.80-3.71 (m, 2 H), 3.54-3.44 (m, 2 H), 2.64-2.58 (m, 1H), 2.43-2.24 (m, 2 H), 1.26-0.99 (m, 4H); LC-MS [M+H]$^+$= 542.2, RT=3.12 min.

Example 205

Preparation of 3-[4-Amino-5-(2-benzyl-2H-indazol-6-yl)-pyrrolo[2,1-f][1,2,4]triazine-7-carbonyl]-pyrrolidine-1-sulfonic acid dimethylamide

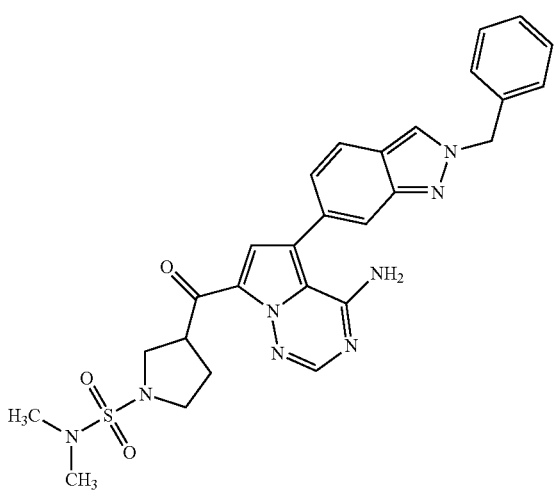 [SMILES: CN(C)S(=O)(=O)N1CCC(C(=O)c2cc(-c3ccc4cn(Cc5ccccc5)nc4c3)c3c(N)ncnn23)C1]

The title compound was prepared in the same manner described for the preparation of Example 203 substituting dimethylsulfamoyl chloride for methanesulfonyl chloride.
$^1$H-NMR (CD$_3$OD-d$_4$) δ 8.41 (s, 1 H), 8.07 (s, 1 H), 7.86 (d, 1H), 7.71 (s, 1 H), 7.50 (s, 1H), 7.38-7.30, (m, 5 H), 7.23 (d, 1 H), 5.65 (s, 1 H), 4.54-4.45 (m, 1 H), 3.66 (d, 2 H), 3.44 (t, 2 H), 2.82 (s, 6 H), 2.39-2.21 (m, 2 H); LC-MS [M+H]$^+$= 545.3, RT=3.18 min.

Example 206

Preparation of [4-Amino-5-(2-benzyl-2H-indazol-6-yl)-pyrrolo[2,1-f][1,2,4]triazin-7-yl]-(1-ethanesulfonyl-pyrrolidin-3-yl)-methanone

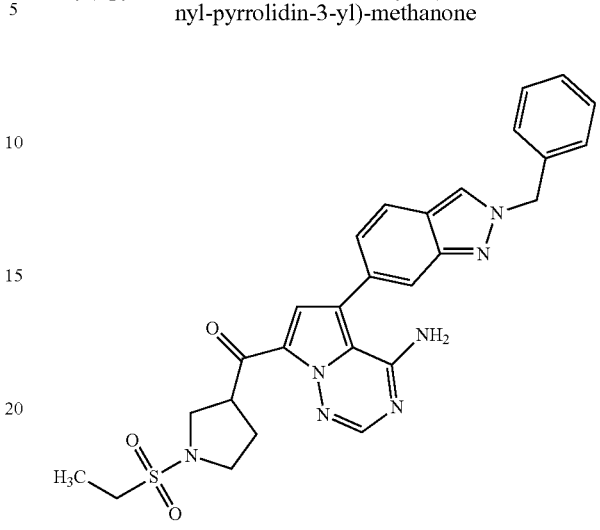

The title compound was prepared in the same manner described for the preparation of Example 203 substituting ethanesulfonyl chloride for methanesulfonyl chloride.
$^1$H-NMR (CD$_3$OD-d$_4$) δ 8.41-8.40 (m, 1 H), 8.07 (s, 1H), 7.86 (dd, 1 H), 7.72-7.70 (m, 1 H), 7.51 (s, 1H), 7.38-7.30, (m, 5 H), 7.23 (d, 1 H), 5.65 (s, 1 H), 4.57-4.50 (m, 1 H), 3.75-3.68 (m, 2 H), 3.51-3.41 (m, 2 H), 3.18-3.11 (m, 2 H), 2.43-2.21 (m, 2 H), 1.35 (t, 3 H); LC-MS [M+H]$^+$=530.2, RT=3.08 min.

Example 207

Preparation of [4-Amino-5-(2-benzyl-2H-indazol-6-yl)-pyrrolo[2,1-f][1,2,4]triazin-7-yl]-[1-(propane-2-sulfonyl)-pyrrolidin-3-yl]-methanone

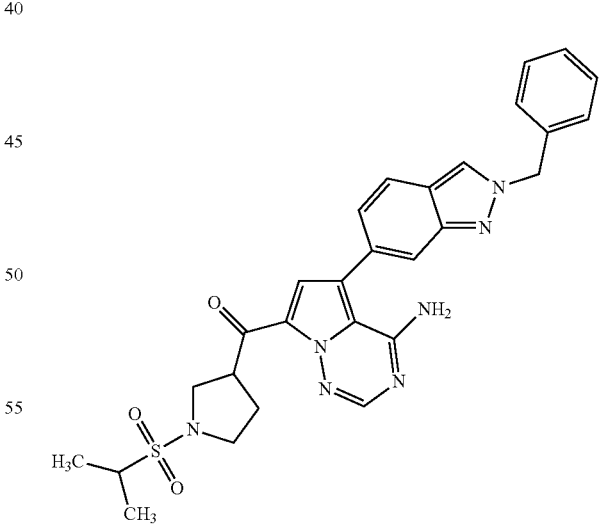

The title compound was prepared in the same manner described for the preparation of Example 203 substituting isopropanesulfonyl chloride for methanesulfonyl chloride.
$^1$H-NMR (CD$_3$OD-d$_4$) δ 8.41-8.38 (m, 1 H), 8.07 (s, 1 H), 7.86 (dd, 1H), 7.72-7.70 (m, 1 H), 7.51 (s, 1H), 7.38-7.30, (m, 5 H), 7.23 (d, 1 H), 5.65 (s, 1 H), 4.57-4.45 (m, 1 H), 3.79-3.68 (m, 2 H), 3.58-3.45 (m, 2 H), 3.41-3.32 (m, 1 H), 2.43-2.21

(m, 2 H), 1.34 (d, 3 H); LC-MS [M+H]⁺=544.3, RT=3.11 min.

Example 208

Preparation of 2-{3-(4-Amino-5-(2-benzyl-2H-indazol-6-yl)-pyrrolo[2,1-f][1,2,4]triazine-7-carbon-1-yl}-N,N-dimeth 1-acetamide

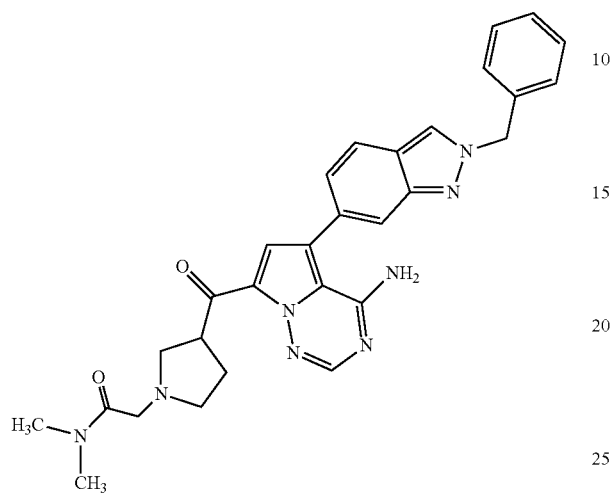

[4-Amino-5-(2-benzyl-2H-indazol-6-yl)-pyrrolo[2,1-f][1,2,4]triazin-7-yl]-pyrrolidin-3-yl-methanone hydrochloride salt (66 mg, 0.14 mmol) was dissolved in methanol (2 mL) and 2-chloro-N,N-dimethyl-acetamide (0.019 mL, 0.18 mmol) was added followed by diisopropylethylamine (0.10 mL, 0.55 mmol). The mixture was stirred at rt for 18 h and then heated at 60° C. for 3 h. The mixture was concentrated, diluted with EtOAc and layers were separated. The organic layer was washed with brine and concentrated. The residue purified by preparative HPLC using 20-95% gradient acetonitrile/water to afford 63 mg (86%) of the title compound. ¹H-NMR (CD₃OD-d₄) δ 8.41-8.40 (m, 1 H), 8.07 (s, 1 H), 7.86 (dd, 1H), 7.72-7.70 (m, 1 H), 7.54 (s, 1H), 7.38-7.30, (m, 5 H), 7.23 (d, 1 H), 5.65 (s, 1 H), 4.32-4.22 (m, 1 H), 3.54-3.32 (m, 2 H), 3.08-2.96 (m, 6 H), 2.92 (s, 2 H), 2.82-2.71 (m, 2 H), 2.29-2.13 (m, 2 H); LC-MS [M+H]⁺=523.2, RT=2.20 min.

Example 209

Preparation of 1-[4-Amino-5-(2-benzyl-2H-indazol-6-yl)-pyrrolo[2,1-f][1,2,4]triazin-7-yl]-2-[1-(2-hydroxy-ethyl)-piperidin-4-yl]-ethanone

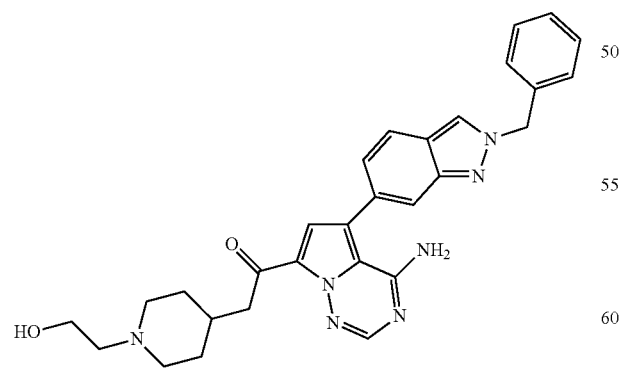

The title compound was prepared in the same manner described for the preparation of Example 196 and substituting 4-[(methoxy-methyl-carbamoyl)-methyl]-piperidine-1-carboxylic acid tert-butyl ester for 3-(methoxy-methyl-carbamoyl)-pyrrolidine-1-carboxylic acid tert-butyl ester and then using procedure described for Example 218. ¹H-NMR (CD₃OD-d₄) δ 8.41-8.39 (m, 1 H), 8.07 (s, 1 H), 7.86 (dd, 1H), 7.72-7.70 (m, 1 H), 7.45 (s, 1H), 7.38-7.30, (m, 5 H), 7.23 (d, 1 H), 5.65 (s, 1 H), 3.68 (t, 2 H), 3.11 (d, 2 H), 3.08-2.96 (m, 2 H), 2.57 (t, 2 H), 2.22-2.12 (m, 2 H), 2.09-1.98 (m, 2 H), 1.85-1.76 (m, 2 H), 1.50-1.35 (m, 2 H); LC-MS [M+H]⁺=510.2, RT=2.33 min.

Example 210

Preparation of 2-(1-Acetyl-piperidin-4-yl)-1-[4-amino-5-(2-benzyl-2H-indazol-6-yl)-pyrrolo[2,1-f][1,2,4]triazin-7-yl]-ethanone

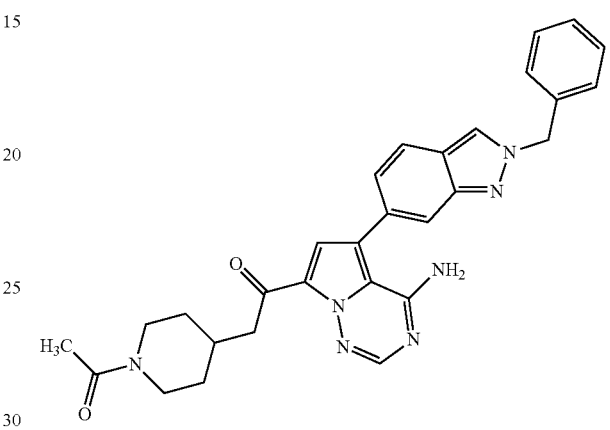

The title compound was prepared in the same manner described for the preparation of Examples 196 and 197 and substituting 4-[(methoxy-methyl-carbamoyl)-methyl]-piperidine-1-carboxylic acid tert-butyl ester for 3-(methoxy-methyl-carbamoyl)-pyrrolidine-1-carboxylic acid tert-butyl ester. ¹H-NMR (CD₃OD-d₄) δ 8.41-8.39 (m, 1 H), 8.07 (s, 1 H), 7.86 (dd, 1H), 7.72-7.70 (m, 1 H), 7.45 (s, 1H), 7.38-7.30, (m, 5 H), 7.23 (d, 1 H), 5.65 (s, 1 H), 4.54-4.46 (m, 1 H), 3.19-3.07 (m, 3 H), 2.72-2.59 (m, 1 H), 2.33-2.21 (m, 1 H), 2.08 (s, 3 H), 1.93-1.78 (m, 2 H), 1.38-1.16 (m, 2 H); LC-MS [M+H]⁺=508.2, RT=2.85 min.

Example 211

Preparation of 1-[4-Amino-5-(2-benzyl-2H-indazol-6-yl)-pyrrolo[2,1-f][1,2,4]triazin-7-yl]-2-(1-methanesulfonyl-piperidin-4-yl)-ethanone

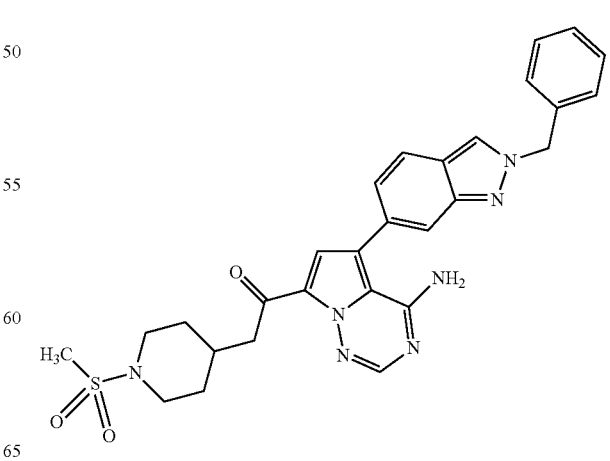

The title compound was prepared in the same manner described for the preparation of Examples 196 and 203 and substituting 4[(methoxy-methyl-carbamoyl)-methyl]-piperidine-1-carboxylic acid tert-butyl ester for 3-(methoxy-methyl-carbamoyl)-pyrrolidine-1-carboxylic acid tert-butyl ester. $^1$H-NMR (DMSO-d$_6$) δ 8.56 (s, 1 H), 8.14 (s, 1 H), 8.05 (s, 2 H), 7.82 (dd, 1H), 7.65 (s, 1 H), 7.41 (s, 1H), 7.38-7.30, (m, 5 H), 7.14 (dd, 1 H), 5.65 (s, 1 H), 3.51 (d, 2 H), 3.09 (d, 2 H), 2.82 (s, 3 H), 2.75-2.64 (m, 2 H), 2.06-1.94 (m, 1 H), 1.79 (d, 2 H), 1.35-1.21 (m, 2 H); LC-MS [M+H]$^+$= 544.4, RT=3.23 min.

Example 212

Preparation of 5-(2-Benzyl-2H-indazol-6-yl)-7-pyrrolidin-3-ylmethyl-pyrrolo[2,1-f][1,2,4]triazin-4-ylamine

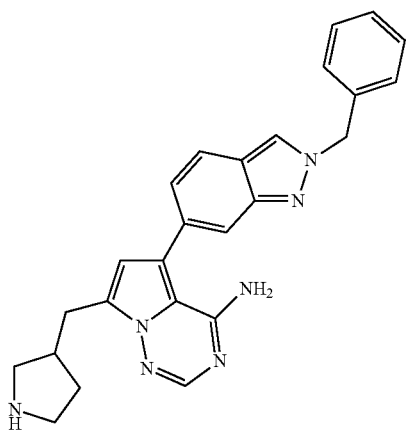 [SMILES: Nc1ncnn2c(CC3CCNC3)cc(-c3ccc4cn(Cc5ccccc5)nc4c3)c12]

Step 1: Preparation of 3-[(4-Amino-pyrrolo[2,1-f][1,2,4]triazin-7-yl)-hydroxy-methyl]-pyrrolidine-1-carboxylic acid tert-butyl ester

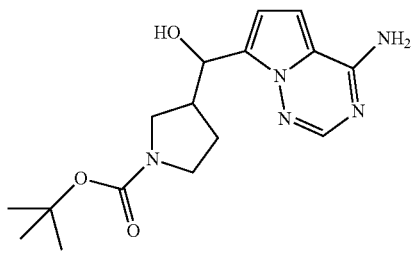 [SMILES: CC(C)(C)OC(=O)N1CCC(C(O)c2ccc3c(N)ncnn23)C1]

The product from Step 1 of the preparation of Example 196 (0.50 mg, 1.51 mmol) was dissolved in MeOH (10 mL) and NaBH$_4$ (0.09 mg, 2.26 mmol) was added. The resulting mixture was stirred for 2 h at rt. The mixture was concentrated, and partitioned between DCM/water. The organic layer was washed with brine, dried and concentrated to give 0.50 g (99%) of desired product. $^1$H NMR (300 MHz, CD$_3$OD-d$_4$) δ 7.77 (s, 1 H), 6.88-6.84 (m, 1 H), 6.68 (d, 1 H), 5.16 (d, 1 H), 3.60-3.35 (m, 2 H), 3.32-3.12 (m, 2 H), 3.06-2.80 (m, 2 H), 2.16-1.90 (m, 1 H), 1.75-1.55 (m, 1 H), 1.49-1.35 (m, 9 H); LC-MS [M+H]$^+$=333.9, RT=2.08 min.

Step 2: Preparation of 3-(4-Amino-pyrrolo[2,1-f][1,2,4]triazin-7-methyl)pyrrolidine-1-carboxylic acid tert-butyl ester

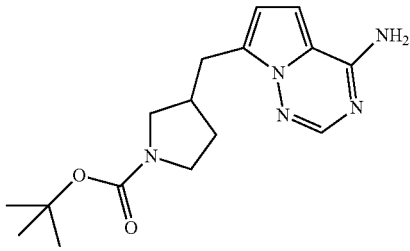 [SMILES: CC(C)(C)OC(=O)N1CCC(Cc2ccc3c(N)ncnn23)C1]

Triethylsilane (3.40 mL, 20.24 mmol) was mixed with TFA (4 mL) and cooled to 0° C. A solution of 3-[(4-amino-pyrrolo[2,1-f][1,2,4]triazin-7-yl)-hydroxy-methyl]-pyrrolidine-1-carboxylic acid tert-butyl ester (0.85 mg, 2.53 mmol) in DCM (4 mL) was added dropwise and the resulting mixture was stirred at rt overnight. Volatiles were evaporated and dried under high vacuum for 2 h. The residue was dissolved in MeOH and di-tert-butyl dicarbonate (0.69 mg, 2.78 mmol) was added followed by aqueous Na$_2$CO$_3$ (2N, 7.60 ml). The reaction mixture was stirred for 2 h, diluted with dichloromethane and organic layer was separated, dried over Na$_2$SO$_4$, filtered and concentrated. The residue was purified by Biotage® chromatography eluting with 10% MeOH in EtOAc to afford 0.61 mg (75%) of the desired product. $^1$H NMR (300 MHz, CD$_3$OD-d$_4$) δ 7.77 (s, 1 H), 6.83 (d, 1 H), 6.49 (d, 1 H), 3.46-3.35 (m, 2 H), 3.29-3.20 (m, 2 H), 3.06-2.95 (m, 3 H), 2.73-2.61 (m, 1 H), 2.02-1.91 (m, 1 H), 1.44 (s, 9 H); LC-MS [M+H−100]$^+$=218.2, RT=2.25 min.

Step 3: Preparation of 3-(4-Amino-5-bromo-pyrrolo[2,1-f][1,2,4]triazin-7-ylmethyl)-pyrrolidine-1-carboxylic acid tart-butyl ester

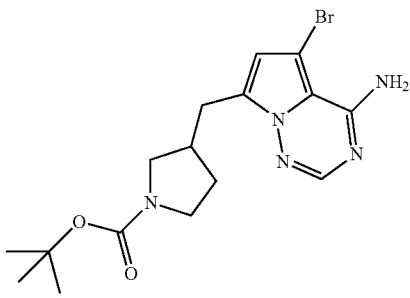 [SMILES: CC(C)(C)OC(=O)N1CCC(Cc2cc(Br)c3c(N)ncnn23)C1]

To a cooled (−20° C.) solution of 3-(4-amino-pyrrolo[2,1-f][1,2,4]triazin-7-ylmethyl)-pyrrolidine-1-carboxylic acid tert-butyl ester (0.60 g, 1.91 mmol) in tetrahydrofuran (10 mL) was added THF solution of 1,3-dibromo-5,5-dimethyl-hydantoin (0.27 g, 0.95 mmol). The mixture was allowed to stir (−20° C.) for 2 h and then allowed to warm to rt. The reaction was quenched with the addition of 10% aqueous Na$_2$S$_2$O$_3$ solution. The mixture was extracted with ethyl acetate (3×50 mL). The combined organics were washed with brine, dried (Na$_2$SO$_4$) and concentrated to dryness. The crude material was purified by Biotage® chromatography using a gradient of 50% to 75% ethyl acetate in hexanes to afford 0.51 g (67%) of the desired product. $^1$H NMR (300 MHz, CD$_3$OD-d$_4$) δ 7.77 (s, 1 H), 6.83 (s, 1 H), 3.46-3.35 (m, 2 H), 3.29-3.20 (m, 2 H), 3.06-2.95 (m, 3 H), 2.73-2.61 (m, 1 H), 2.02-1.91 (m, 1 H), 1.44 (s, 9 H); LC-MS [M+H]$^+$=395.9, RT=2.80 min.

307

Step 4: Preparation of 3-[4-Amino-5-(2-benzyl-2H-indazol-6-yl)-pyrrolo[2,1-f][1,2,4]triazin-7-ylmethyl]-pyrrolidine-1-carboxylic acid tert-butyl ester

To a stirred solution 3-(4-Amino-5-bromo-pyrrolo[2,1-f][1,2,4]triazin-7-ylmethyl)-pyrrolidine-1-carboxylic acid tert-butyl ester (0.49 g, 1.24 mmol), Intermediate C (0.62 g, 1.86 mmol), and tetrakis(triphenylphosphine)palladium(0) (0.37 g, 0.32 mmol) in degassed DMF (8 mL) was added aqueous Na$_2$CO$_3$ (2M, 2.00 mL). The resulting mixture was heated at 110° C. for 3 h and then cooled to rt. The reaction mixture was diluted with EtOAc and filtered through a Celite® pad. The organic layer was separated and concentrated in vacuo. The residue was purified by silica-gel column using a gradient of 50% to 100% EtOAc in hexanes to afford 0.30 g (46%) of the product. LC-MS [M+H]$^+$=524.1, RT=3.19 min.

Step 5: Preparation of the Title Compound

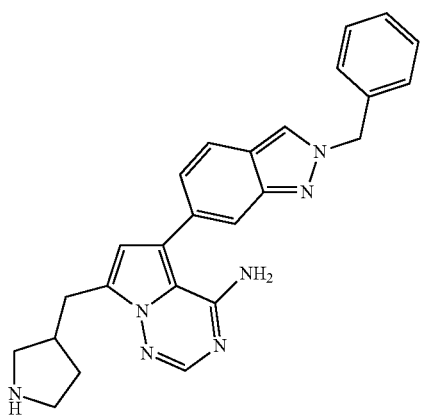 [SMILES: Nc1ncnn2c(CC3CCNC3)cc(-c3ccc4cn(Cc5ccccc5)nc4c3)c12]

The product from Step 4 (0.10 g, 0.19 mmol) was dissolved in dichloromethane (3 mL) and TFA (0.14 mL, 1.95 mmol) was added. The mixture was stirred for 18 hours and concentrated. The residue was purified by preparative HPLC using 10-90% gradient of acetonitrile/water to provide 25 mg (31%) of the title compound. $^1$H-NMR (CD$_3$OD-d$_4$) 8.30-8.35 (m, 1H), 7.85-7.80 (m, 2 H), 7.67-7.64 (m, 1H), 7.40-7.22 (m, 5 H), 7.24 (dd, 1 H), 6.64 (s, 1 H), 5.67 (s, 2 H), 3.17-2.94 (m, 3 H), 2.77-2.68 (m, 2 H), 2.08-1.98 (m, 1 H), 1.70-1.59 (m, 1 H); LC-MS [M+H]$^+$=424.2, RT=2.03 min.

308

Example 213

Preparation of 1-{3-[4-Amino-5-(2-benzyl-2H-indazol-6-yl)-pyrrolo[2,1-f][1,2,4]triazin-7-ylmethyl]-pyrrolidin-1-yl}-ethanone

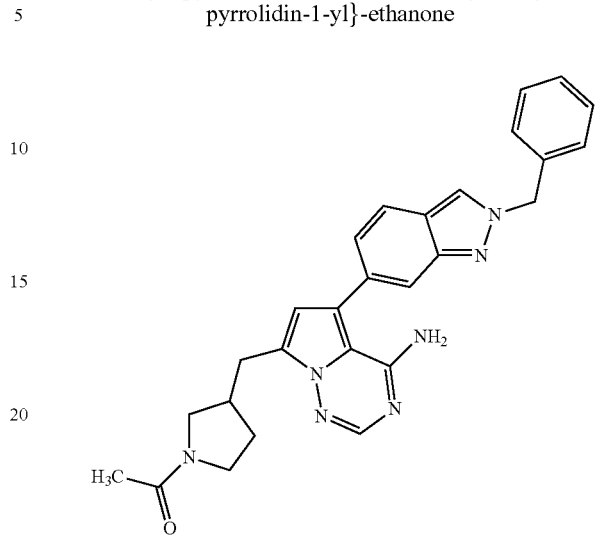

The title compound was prepared in the same manner described for the preparation of Example 197 and using 5-(2-benzyl-2H-indazol-6-yl)-7-pyrrolidin-3-ylmethyl-pyrrolo[2,1-f][1,2,4]triazin-4-ylamine as a starting material. $^1$H-NMR (CD$_3$OD-d$_4$) δ 8.39-8.35 (m, 1 H), 7.85-7.80 (m, 2 H), 7.67-7.64 (m, 1 H), 7.40-7.23 (m, 5 H), 6.64 (d, 1 H), 5.65 (s, 2 H), 3.69-3.45 (m, 3 H), 3.28-3.25 (m, 1 H), 320-3.05 (m, 2 H), 2.88-2.68 (m, 1 H), 2.18-2.04 (m, 1 H), 2.02 (d, 3 H), 1.87-1.67 (m, 1 H); LC-MS [M+H]$^+$=508.2, RT=2.85 min.

Example 214

Preparation of 5-(2-Benzyl-2H-indazol-6-yl)-7-(3-piperidin-3-yl-propyl)-pyrrolo[2,1-f][1,2,4]triazin-4-ylamine

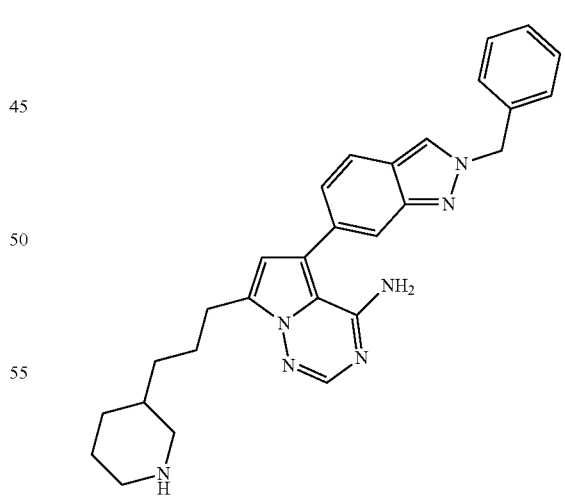

The title compound was prepared in the same manner described for the preparation of Example 212 and using 3-[2-(methoxy-methyl-carbamoyl)-ethyl]-piperidine-1-carboxylic acid Pert-butyl ester as a starting material. $^1$H-NMR (CD$_3$OD-d$_4$) δ 8.39-8.35 (m, 1 H), 7.85-7.80 (m, 2 H), 7.67-7.64 (m, 1 H), 7.40-7.30 (m, 5 H), 7.23 (dd, 1 H), 6.59 (s, 1 H), 5.65 (s, 1 H), 3.17-2.91 (m, 4H), 2.67-2.53 (m, 1 H), 2.37-

2.23 (m, 1 H), 1.94-1.65 (m, 4 H), 1.62-1.48 (m, 2 H), 1.38-1.26 (m, 2 H), 1.16-1.09 (m, 1 H); LC-MS [M+H]⁺=466.3, RT=2.36 min.

Example 215

Preparation of [4-Amino-5-(2-benzyl-2H-indazol-6-yl)-pyrrolo[2,1-f][1,2,4]triazin-7-yl]-(1,2,3,4-tetrahydro-isoquinolin-7-yl)-methanone

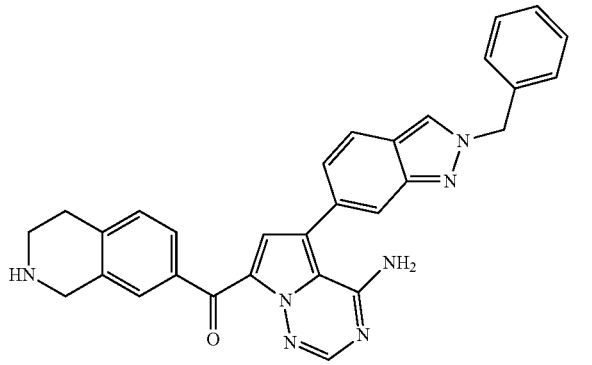 [SMILES: Nc1ncnn2c(C(=O)c3ccc4c(c3)CNCC4)cc(-c3ccc4cn(Cc5ccccc5)nc4c3)c12]

The title Compound was prepared in the same manner described for the preparation of Example 196 and using 7-(methoxy-methyl-carbamoyl)-3,4-dihydro-1H-isoquinoline-2-carboxylic acid tert-butyl ester as a starting material. $^1$H-NMR (CD$_3$OD-d$_4$) δ 8.39-8.35 (m, 1 H), 8.00 (s, 1 H), 7.85 (dd, 1 H), 7.73-7.71 (m, 1 H), 7.68 (dd, 1 H), 7.63-7.60 (m, 1 H), 7.38-7.22 (m, 7 H), 7.13 (s, 1 H), 5.65 (s, 2 H), 4.04 (s, 2 H), 3.12 (t, 2 H), 2.93 (t, 2 H); LC-MS [M+H]⁺=500.3, RT=2.41 min.

Example 216

Preparation of 5-(2-Benzyl-2H-indazol-6-yl)-7-(1,2,3,4-tetrahydro-isoquinolin-7-ylmethyl)-pyrrolo[2,1-f][1,2,4]triazin-4-ylamine

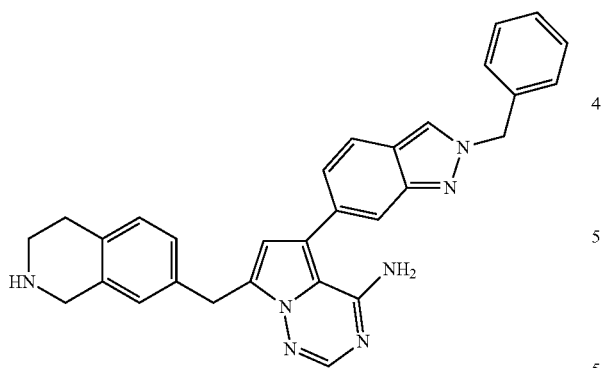

[4-Amino-5-(2-benzyl-2H-indazol-6-yl)-pyrrolo[2,1-f][1,2,4]triazin-7-yl]-(1,2,3,4-tetrahydro-isoquinolin-7-yl)-methanone (0.050 g, 0.01 mmol) was dissolved in dichloromethane (1 mL) and methanesulfonic acid (0.104 mL, 1.61 mmol) was added followed by Et$_3$SIH (0.128 mL, 0.80 mmol). The resulting mixture was stirred at rt overnight. The mixture was diluted with dichloromethane and washed with saturated aqueous NaHCO$_3$, water and brine. The organic layer was concentrated, suspended in MeOH and filtered to give a desired product as white solid (30 mg, 62%). $^1$H-NMR (CD$_3$OD-d$_4$) δ 8.28-8.24 (m, 1 H), 7.78 (s, 1 H), 7.70 (dd, 1H), 7.59-7.56 (m, 1 H), 7.33-7.23 (m, 5 H), 7.11 (dd, 1 H), 7.07-6.89 (m, 3 H), 6.39 (s, 1 H), 5.57 (s, 2 H), 4.16 (s, 2 H), 3.82 (s, 2 H), 2.96 (t, 2 H), 2.71 (t, 2 H); LC-MS [M+H]⁺= 486.3, RT=2.30 min.

Example 217

Preparation of 5-(2-Benzyl-2H-indazol-6-yl)-7-(2-cyclopropyl-1,2,3,4-tetrahydro-isoquinolin-7-ylmethyl)-pyrrolo[2,1-f][1,2,4]triazin-4-ylamine

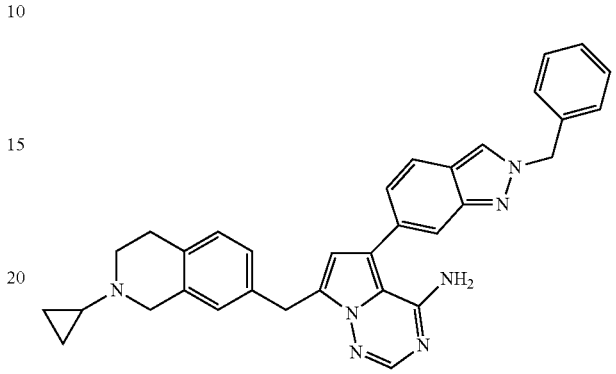

5-(2-Benzyl-2H-indazol-6-yl)-7-(1,2,3,4-tetrahydro-isoquinolin-7-ylmethyl)-pyrrolo[2,1-f][1,2,4]triazin-4-ylamine (0.100 g, 0.21 mmol) was dissolved in MeOH (1 mL) and (1-ethoxy-cyclopropoxy)-trimethyl-silane (0.22 g, 1.24 mmol) was added followed by acetic acid (0.118 mL, 2.05 mmol) and sodium cyanoborohydride (0.058 g, 0.92 mmol). The resulting mixture was refluxed overnight and then allowed to cool. The mixture was filtered, concentrated and the residue was purified by preparative HPLC to give 55 mg (50%) of the title compound. $^1$H-NMR (CD$_3$OD-d$_4$) δ 8.36-8.23 (m, 1 H), 7.81 (s, 1 H), 7.78 (dd, 1H), 7.38-7.29 (m, 4 H), 7.19 (dd, 1 H), 7.10-6.99 (m, 2 H), 6.44 (s, 1 H), 5.63 (s, 2 H), 4.23 (s, 2 H), 3.72 (s, 2 H), 2.96-2.81 (m, 4 H), 1.86-1.79 (m, 1 H), 0.57-0.75 (m, 4 H); LC-MS [M+H]⁺=426.3, RT=2.32 min.

Example 218

Preparation of 2-{7-[4-Amino-5-(2-benzyl-2H-indazol-6-yl)-pyrrolo[2,1-f][1,2,4]triazin-7-ylmethyl]-3,4-dihydro-1H-isoquinolin-2-yl}-ethanol

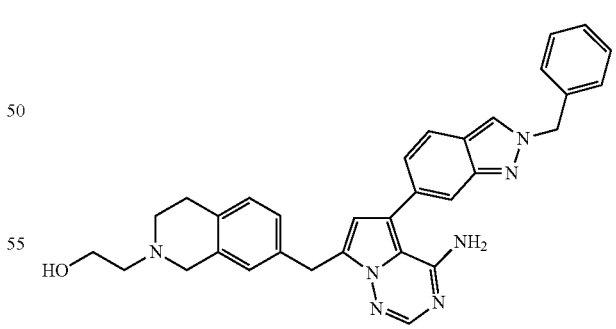

5-(2-Benzyl-2H-indazol-6-yl)-7-(1,2,3,4-tetrahydro-isoquinolin-7-ylmethyl)-pyrrolo[2,1-f][1,2,4]triazin-4-ylamine (200 mg, 0.41 mmol) was dissolved in DMF (4 mL) and (2-bromo-ethoxy)-tert-butyl-dimethyl-silane (0.15 g, 0.62 mmol) was added followed by triethylamine (0.17 mL, 1.26 mmol) and sodium iodide (0.006 g, 0.004 mmol). The resulting mixture was stirred at 50° C. overnight. The mixture was concentrated, dried using a vacuum pump for 2 hours. The residue was dissolved in 2 mL dichloromethane and TFA (0.30 mL) was added and the resulting solution was stirred overnight, concentrated and purified by preparative HPLC to afford 32 mg (15%) of the title compound. $^1$H-NMR (CD$_3$OD-d$_4$) δ 8.36-8.33 (m, 1 H), 7.81 (s, 1 H), 7.76 (dd, 1H), 7.63-7.61 (m, 1 H), 7.38-7.29 (m, 5 H), 7.19 (dd, 1 H), 7.11-6.98 (m, 3 H), 6.46 (s, 1 H), 5.65 (s, 2 H), 4.24 (s, 2 H), 3.76 (t, 2 H), 3.67 (s, 2 H), 2.93-2.79 (m, 4 H), 2.69 (t, 2 H); LC-MS [M+H]$^+$=530.3, RT=2.36 min.

Example 219

Preparation of 2-{7-[4-Amino-5-(2-benzyl-2H-indazol-6-yl)-pyrrolo[2,1-f][1,2,4]triazin-7-ylmethyl]-3,4-dihydro-1H-isoquinolin-2-yl}-N,N-dimethyl-acetamide

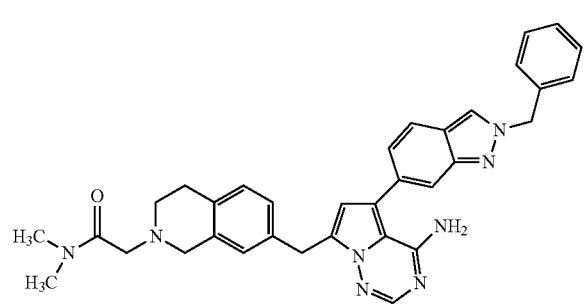 [SMILES: CN(C)C(=O)CN1CCc2ccc(Cc3cc(-c4ccc5cn(Cc6ccccc6)nc5c4)c4c(N)ncnn34)cc2C1]

The title compound was prepared in the same manner described for the preparation of Example 208 and using (2-benzyl-2H-indazol-6-yl)-7-(1,2,3,4-tetrahydro-isoquinolin-7-ylmethyl)-pyrrolo[2,1-f][1,2,4]triazin-4-ylamine as a starting material. $^1$H-NMR (CD$_3$OD-d$_4$) δ 8.36-8.33 (m, 1 H), 7.81 (s, 1 H), 7.76 (dd, 1H), 7.63-7.61 (m, 1 H), 7.38-729 (m, 5 H), 7.19 (dd, 1 H), 7.09-6.93 (m, 3 H), 6.46 (s, 1 H), 5.63 (s, 2 H), 4.21 (s, 2 H), 3.65 (s, 2 H), 3.06 (s, 3 H), 3.92 (s, 3 H), 2.88-2.75 (m, 4 H), 2.69 (t, 2 H); LC-MS [M+H]$^+$=571.2, RT=2.33 min.

Example 220

Preparation of [4-Amino-5-(2-benzyl-2H-indazol-6-yl)-pyrrolo[2,1-f][1,2,4]triazin-7-yl]-(4-piperidin-3-yl-phenyl)-methanone

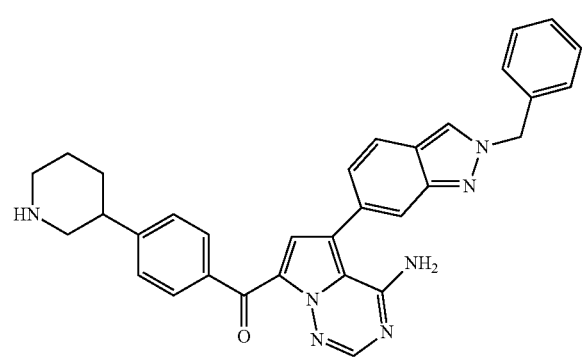 [SMILES: Nc1ncnn2c(C(=O)c3ccc(C4CCCNC4)cc3)cc(-c3ccc4cn(Cc5ccccc5)nc4c3)c12]

The title compound was prepared in the same manner described for the preparation of Example 196 and using 3-[4-(methoxy-methyl-carbamoyl)-phenyl]-piperidine-1-carboxylic acid tert-butyl ester as a starting material. $^1$H-NMR (CD$_3$OD-d$_4$) δ 8.38-8.35 (m, 1 H), 8.01 (s, 1 H), 7.84-7.68 (m, 4 H), 7.55-7.41 (m, 2 H), 7.35-7.29 (m, 4 H), 7.21 (dd, 1 H), 7.09 (s, 1 H), 3.21-3.13 (m, 2 H), 2.84-2.75 (m, 3 H), 1.93-1.81 (m, 2 H), 1.78-1.62 (m, 2 H); LC-MS [M+H]$^+$=528.1, RT=2.42 min.

Example 221

Preparation of 2-(3-{4-[4-Amino-5-(2-benzyl-2H-indazol-6-yl)-pyrrolo[2,1-f][1,2,4]triazine-7-carbonyl]-phenyl}-piperidin-1-yl)-N,N-dimethyl-acetamide

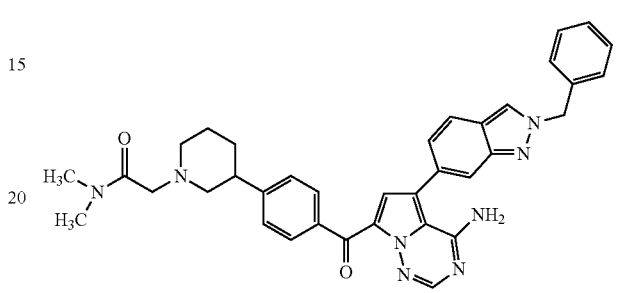

The title compound was prepared in the same manner described for the preparation of Example 208 and using 4-amino-5-(2-benzyl-2H-indazol-6-yl)-pyrrolo[2,1-f][1,2,4]triazin-7-yl]-(4-piperidin-3-yl-phenyl)-methanone as starting material. $^1$H-NMR (CD$_3$OD-d$_4$) δ 8.38-8.35 (m, 1 H), 8.01 (s, 1 H), 7.84 (dd, 2 H), 7.79-7.69 (m, 3 H), 7.55-7.41 (m, 2 H), 7.35-7.29 (m, 5 H), 7.24 (dd, 1 H), 7.11 (s, 1 H), 5.65 (s, 2 H), 3.31-3.29 (m, 2 H), 3.10-3.03 (m, 4 H), 2.92 (s, 3 H), 2.70-2.58 (m, 1 H), 1.88-1.81 (m, 4 H), 1.78-1.62 (m, 2 H); LC-MS [M+H]$^+$=613.4, RT=2.46 min.

Example 222

Preparation of 5-(2-Benzyl-2H-indazol-6-yl)-7-(4-piperidin-3-yl-benzyl)-pyrrolo[2,1-f][1,2,4]triazin-4-ylamine

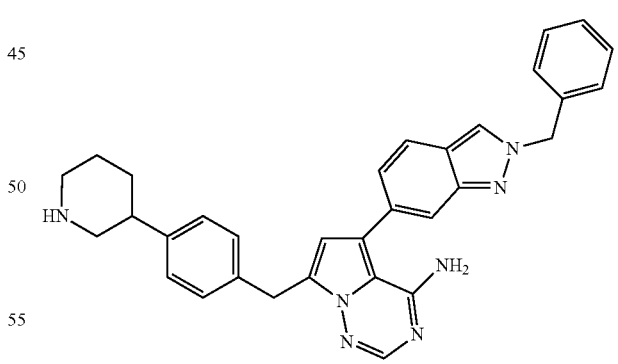

The title compound was prepared in the same manner described for the preparation of Example 216 and using [4-amino-5-(2-benzyl-2H-indazol-6-yl)-pyrrolo[2,1-f][1,2,4]triazin-7-yl]-(4-piperidin-3-yl-phenyl)-methanone as a starting material. $^1$H-NMR (CD$_3$OD-d$_4$) δ 8.38-8.35 (m, 1 H), 7.81 (s, 1 H), 7.84 (dd, 2 H), 7.64-7.60 (m, 1 H), 7.35-7.29 (m, 5 H), 7.24-7.18 (m, 3 H), 7.16-7.05 (m, 2 H), 6.47 (s, 1 H), 5.65 (s, 2 H), 4.28 (s, 2 H), 3.17-3.10 (m, 2 H), 2.78-2.59 (m, 3 H), 1.84-1.59 (m, 4 H); LC-MS [M+H]$^+$=514.4, RT=2.37 min.

Example 223

Preparation of 2-(3-{4-[4-Amino-5-(2-benzyl-2H-indazol-6-yl)-pyrrolo[2,1-f][1,2,4]triazin-7-ylmethyl]-phenyl}-piperidin-1-yl)-N,N-dimethyl-acetamide

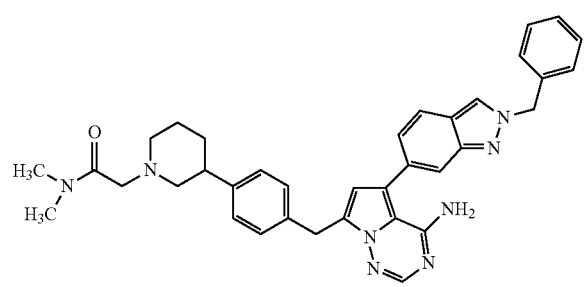 [SMILES: CN(C)C(=O)CN1CCCC(c2ccc(Cc3cc(-c4ccc5cn(Cc6ccccc6)nc5c4)c4c(N)ncnn34)cc2)C1]

The title compound was prepared in the same manner described for the preparation of Example 208 and using 5-(2-benzyl-2H-indazol-6-yl)-7-(4-piperidin-3-yl-benzyl)-pyrrolo[2,1-f][1,2,4]triazin-4-ylamine a starting material. $^1$H-NMR (CD$_3$OD-d$_4$) δ 8.38-8.35 (m, 1 H), 7.81 (s, 1 H), 7.84 (dd, 2 H), 7.64-7.60 (m, 1 H), 7.35-7.29 (m, 5 H), 7.24-7.18 (m, 3 H), 7.16-7.05 (m, 2 H), 6.47 (s, 1 H), 5.65 (s, 2 H), 4.28 (s, 2 H), 3.23 (s, 2 H), 3.08 (s, 3 H), 3.01 (d, 2 H), 2.92 (s, 3 H), 2.51-2.42 (m, 1 H), 2.23-2.13 (m, 2 H), 1.81-1.71 (m, 4 H); LC-MS [M+H]$^+$=599.3, RT=2.48 min.

Example 224

Preparation of 1-(3-{4-[4-Amino-5-(2-benzyl-2H-indazol-6-yl)-pyrrolo[2,1-f][1,2,4]triazin-7-ylmethyl]-phenyl}-piperidin-1-yl)-ethanone

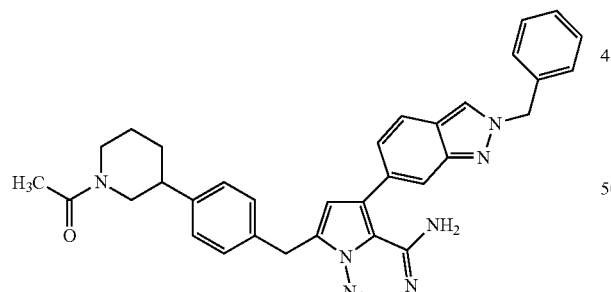

The title compound was prepared in the same manner described for the preparation of Example 197 and using 5-(2-benzyl-2H-indazol-6-yl)-7-(4-piperidin-3-yl-benzyl)-pyrrolo[2,1-f][1,2,4]triazin-4-ylamine a starting material. $^1$H-NMR (CD$_3$OD-d$_4$) δ 8.33-8.31 (m, 1 H), 7.81 (s, 1 H), 7.76 (dd, 1 H), 7.64-7.60 (m, 1 H), 7.35-7.29 (m, 5 H), 7.24-7.02 (m, 5 H), 6.47 (s, 1 H), 5.65 (s, 2 H), 4.65-4.57 (m, 1 H), 4.25 (s, 2 H), 3.99-3.95 (m, 1 H), 3.19-3.10 (m, 1 H), 2.76-2.59 (m, 2 H), 2.08 (s, 3 H), 1.87-1.85 (m, 2 H), 1.67-1.45 (m, 2 H); LC-MS [M+H]$^+$=556.1, RT=2.92 min.

Example 225

Preparation of 5-(2-Benzyl-2H-indazol-6-yl)-7-[4-(1-methanesulfonyl-piperidin-3-yl)-benzyl]-pyrrolo[2,1-f][1,2,4]triazin-4-ylamine

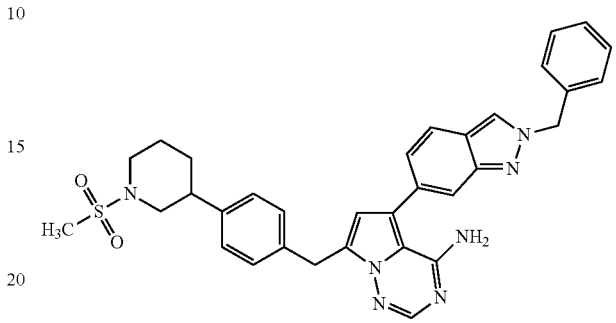

The title compound was prepared in the same manner described for the preparation of Example 203 and using 5-(2-benzyl-2H-indazol-6-yl)-7-(4-piperidin-3-yl-benzyl)-pyrrolo[2,1-f][1,2,4]triazin-4-ylamine as a starting material. $^1$H-NMR (CD$_3$OD-d$_4$) δ 8.33-8.31 (m, 1 H), 7.81 (s, 1 H), 7.76 (dd, 1 H), 7.64-7.60 (m, 1 H), 7.35-7.29 (m, 5 H), 7.24-7.02 (m, 5 H), 6.47 (s, 1 H), 5.65 (s, 2 H), 4.28 (s, 2 H), 3.82-3.77 (m, 2 H), 2.86-2.76 (m, 5 H), 2.67-2.57 (m, 1 H), 1.93-1.86 (m, 2 H), 1.81-1.69 (m, 2 H); LC-MS [M+H]$^+$= 592.4, RT=3.12 min.

Example 226

Preparation of 5-(2-Benzyl-2H-indazol-6-yl)-7-(4-piperazin-1-yl-benzyl)-pyrrolo[2,1-f][1,2,4]triazin-4-ylamine

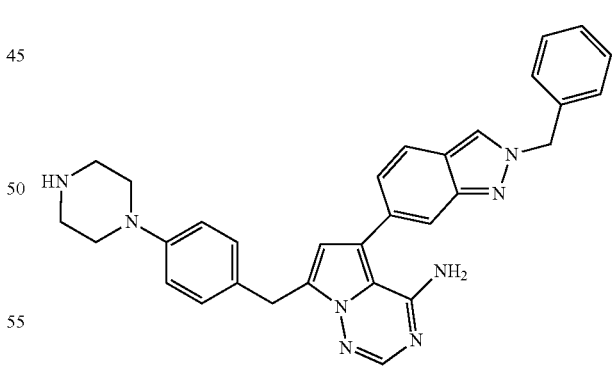

The title compound was prepared in the same manner described for the preparation of Example 216 and using 4-[4-(methoxy-methyl-carbamoyl)-phenyl]-piperazine-1-carboxylic acid tert-butyl ester as a starting material. $^1$H-NMR (CD$_3$OD-d$_4$) δ 8.33-8.31 (m, 1 H), 7.81 (s, 1 H), 7.76 (dd, 1 H), 7.64-7.60 (m, 1 H), 7.38-7.29 (m, 6 H), 7.21-7.15 (m, 3 H), 6.94-6.88 (m, 2 H), 6.47 (s, 1 H), 5.65 (s, 2 H), 4.20 (s, 2 H), 3.12-3.06 (m, 4 H), 3.00-2.92 (m, 4 H); LC-MS [M+H]$^+$= 515.2, RT=2.37 min.

Example 227

Preparation of 5-(2-Benzyl-2H-indazol-6-yl)-7-(3,5-dimethyl-isoxazol-4-ylmethyl)-pyrrolo[2,1-f][1,2,4]triazin-4-ylamine

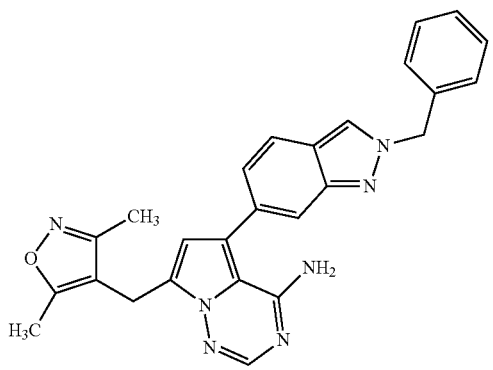 [SMILES: Cc1noc(C)c1Cc1cc(-c2ccc3cn(Cc4ccccc4)nc3c2)c2c(N)ncnn12]

The title compound was prepared in the same manner described for the preparation of Example 196 and using 3,5-dimethyl-Isoxazole-4-carbaldehyde as a starting material. $^1$H-NMR (CD$_3$OD-d$_4$) δ 8.38 (s, 1 H), 7.87-7.27 (m, 2 H), 7.65-7.60 (m, 1 H), 7.38-7.28 (m, 5 H), 7.22-7.16 (m, 1 H), 6.50 (s, 1 H), 5.64 (s, 2 H), 4.02 (s, 2 H), 2.35 (s, 3 H), 2.18 (s, 3 H); LC-MS [M+H]$^+$=450.4, RT=2.67 min.

Example 228

Preparation of 5-(2-Benzyl-2H-indazol-6-yl)-7-(2-piperazin-1-yl-pyrimidin-5-yl)-pyrrolo[2,1-f][1,2,4]triazin-4-ylamine

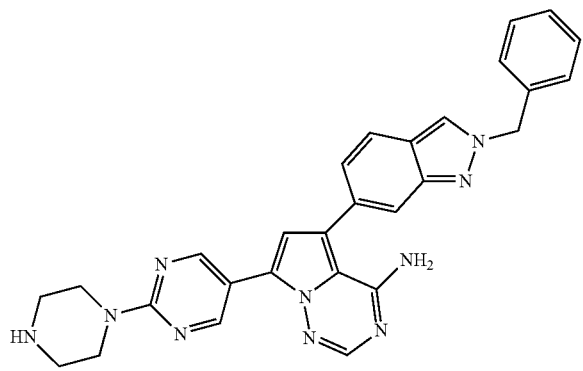 [SMILES: Nc1ncnn2c(-c3cnc(N4CCNCC4)nc3)cc(-c3ccc4cn(Cc5ccccc5)nc4c3)c12]

Step 1: Preparation of Pyrrolo[2,1-f][1,2,4]triazin-4-ylamine-7-boronic acid

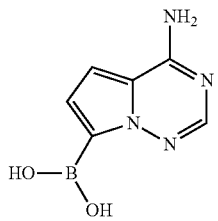 [SMILES: Nc1ncnn2c(B(O)O)ccc12]

To a suspension of Intermediate B (9.00 g, 42.25 mmol) in THF (100 mL) was added trimethylsilychloride (10.01 g, 92.93 mmol) and the resulting mixture was stirred for 2.5 h. Isopropylmagnesium chloride (2M in THF) (105 mL, 211.3 mmol) was added dropwise. The mixture was stirred for 2 h at rt and then cooled on ice-bath. Trimethyl borate (9.47 mL, 84.49 mmol) was added and the mixture was stirred cold for 1 h and allowed to warm to rt. The mixture was quenched with cold, saturated NH$_4$Cl stirred for 20 min and the layers were separated. The aqueous layer was extracted with THF. The combined extracts were dried over Na$_2$SO$_4$, filtered and concentrated. The crude product was purified by silica-gel chromatography, eluting with 20% MeOH in EtOAc to afford a brown solid, which was suspended in 5 mL methanol and filtered to give a desired product as an off-white solid (3.6 g, 46%). NMR (300 MHz, DMSO-d$_6$) δ 8.31 (s, 2 H), 8.07-7.88 (m, 3 H), 7.05 (d, 1 H), 6.87 (d, 1 H); LC-MS [M+H]$^+$=179.1, RT=1.04 min.

Step 2: Preparation of 4-[5-(4-Amino-pyrrolo[2,1-f][1,2,4]triazin-7-pyrimidin-2-yl]-piperazine-1-carboxylic acid tert-butyl ester

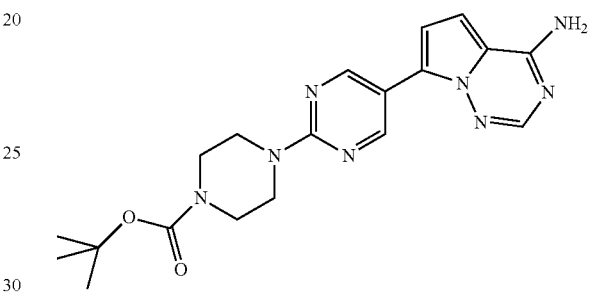

To a stirred solution of the product from Step 1 (0.20 g, 1.12 mmol), 4-(5-bromo-pyrimidin-2-yl)-piperazine-1-carboxylic acid tert-butyl ester (0.50 g, 1.46 mmol), and tetrakis(triphenylphosphine)palladium(0) (0.13 g, 0.12 mmol) in degassed DMF (2.5 mL) was added aqueous Na$_2$CO$_3$ (2M, 1.85 mL). The resulting mixture was heated at 160° C. for 11 min in a microwave reactor and then cooled to rt. The reaction mixture was diluted with EtOAc and filtered through a Celite® pad. The organic layer was separated and concentrated in vacuo. The residue was purified by Biotage® chromatography using a gradient of 50 to 100% EtOAc in hexanes to afford 0.093 g (21%) of the desired product. $^1$H NMR (300 MHz, DMSO-d$_6$) δ 8.98 (s, 2 H), 7.88 (s, 1 H), 6.97 (dd, 2 H), 3.80-3.72 (m, 4 H), 3.44-3.37 (m, 4 H), 1.41 (s, 9 H); LC-MS [M+H]$^+$=397.3, RT=2.50 min.

Step 3: Preparation of 4-[5-(4-Amino-5-bromo-pyrrolo[2,1-f][1,2,4]triazin-7-yl)-pyrimidin-2-yl]-piperazine-1-carboxylic acid tert-butyl ester

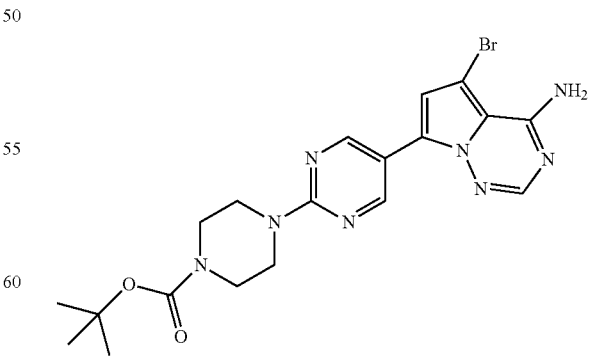

To a cooled (−20° C.) solution of the product from Step 1 (0.080 g, 0.21 mmol) in tetrahydrofuran (3 mL) was added a THF solution of 1,3-dibromo-5,5-dimethylhydantoin (0.030 g, 0.11 mmol). The mixture was stirred at −20° C. for 2 h and then warmed to rt. The reaction was quenched with the addition of 10% aqueous Na₂S₂O₃ solution. The mixture was extracted with dichloromethane (3×15 mL). The combined organic layers were washed with brine, dried (Na₂SO₄) and concentrated to dryness to afford 91 mg of the desired product. The crude material was used in the next step without purification. LC-MS [M+H]⁺=475.0, RT=3.19 min.

Step 4: Preparation of the Title Compound

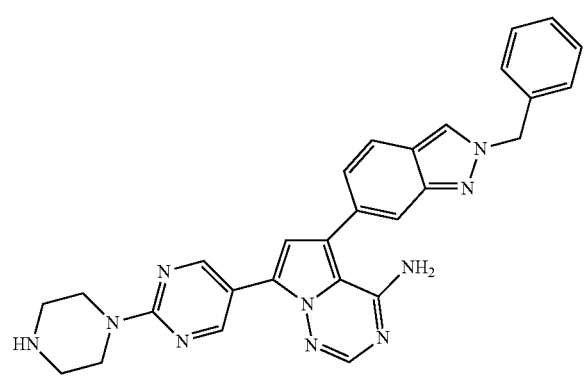 [SMILES: Nc1ncnn2c(-c3cnc(N4CCNCC4)nc3)cc(-c3ccc4cn(Cc5ccccc5)nc4c3)c12]

To a stirred solution of the product from Step 3 (0.090 g, 0.19 mmol), Intermediate C (0.100 g, 0.29 mmol), and tetrakis(triphenylphosphine)palladium(0) (0.020 g, 0.02 mmol) in degassed DMF (1.5 mL) was added aqueous Na₂CO₃ (2M, 0.30 mL). The resulting mixture was heated at 160° C. for 11 min in a microwave reactor and then cooled to rt. The reaction mixture was diluted with EtOAc and filtered through a Celite® pad. The organic layer was separated and concentrated in vacuo. The residue was purified using a short silica-gel column and a gradient of 50 to 100% EtOAc in hexanes to afford 0.090 g of a brown solid. The solid was dissolved in dichloromethane (3 mL) and TFA (0.30 mL) was added. The reaction mixture was stirred overnight, concentrated and purified by preparative HPLC to give 60 mg of the desired product. ¹H-NMR (CD₃OD-d₄) δ 9.01 (s, 2 H), 8.40-8.36 (m, 1 H), 7.88 (s, 1 H), 7.84 (d, 1 H), 7.72-7.70 (m, 1 H), 7.38-7.29 (m, 5 H), 7.28 (dd, 1 H), 7.03 (s, 1 H), 5.65 (s, 2 H), 3.88-3.80 (m, 4 H), 2.92-2.84 (m, 4 H); LC-MS [M+H]⁺= 503.2, RT=2.27 min.

Example 229

Preparation of 5-(2-Benzyl-2H-indazol-6-yl)-7-(2-pyrrolidin-1-yl-pyrimidin-5-yl)-pyrrolo[2,1-f][1,2,4]triazin-4-ylamine

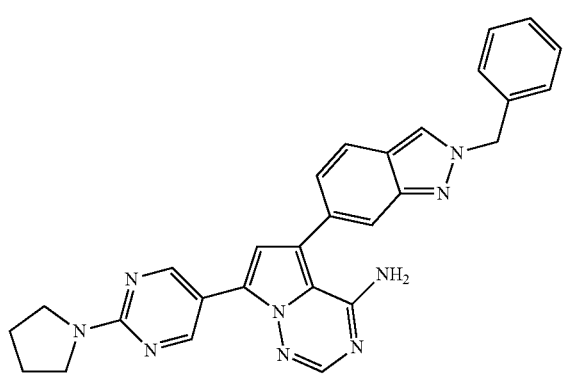 [SMILES: Nc1ncnn2c(-c3cnc(N4CCCC4)nc3)cc(-c3ccc4cn(Cc5ccccc5)nc4c3)c12]

The title compound was prepared in the same manner described for the preparation of Example 228 and using 5-bromo-2-pyrrolidin-1-yl-pyrimidine as a starting material.
¹H-NMR (CD₃OD-d₄) δ 9.01-8.98 (m, 2 H), 8.40-8.36 (m, 1 H), 7.90-7.82 (m, 2 H), 7.75-7.71 (m, 1 H), 7.38-7.29 (m, 6 H), 7.04-7.02 (m, 1 H), 5.65 (s, 2 H), 3.64-3.58 (m, 4 H), 2.09-1.98 (m, 4 H); LC-MS [M+H]⁺=488.2.2, RT=2.86 min.

Example 23

Preparation of 2-{6-[4-Amino-5-(2-benzyl-2H-indazol-6-yl)-pyrrolo[2,1-f][1,2,4]triazin-7-yl]-quinazolin-4-ylamino}-ethanol

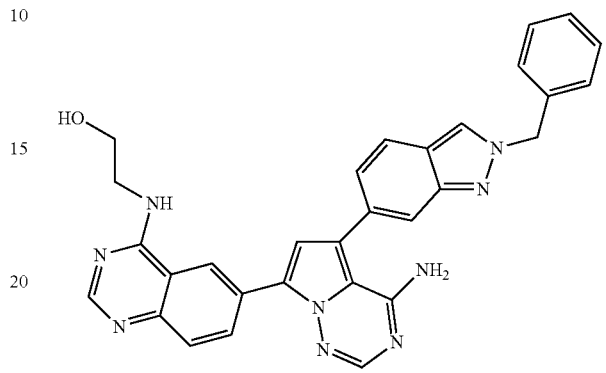

The title compound was prepared in the same manner described for the preparation of Example 228 and using 2-(6-bromo-quinazolin-4-ylamino)-ethanol as a starting material.
¹H-NMR (CD₃OD-d₄) δ 8.76 (d, 1 H), 8.62 (dd, 1 H), 8.43 (s, 1 H), 8.38 (d, 1 H), 7.95 (s, 1 H), 7.85 (dd, 1 H), 7.77-7.22 (m, 2 H), 7.38-7.28 (m, 6 H), 7.24 (s, 1 H), 5:67 (s, 2 H), 3.87-3.82 (m, 2 H), 3.80-3.82 (m, 2 H); LC-MS [M-1-H]⁺= 528.3, RT=2.66 min.

Example 231

Preparation of 7-(1-acetylpiperidin-4-yl)-5-(2-benzyl-2H-indazol-6-yl)pyrrolo[2,1-f][1,2,4]triazin-4-amine

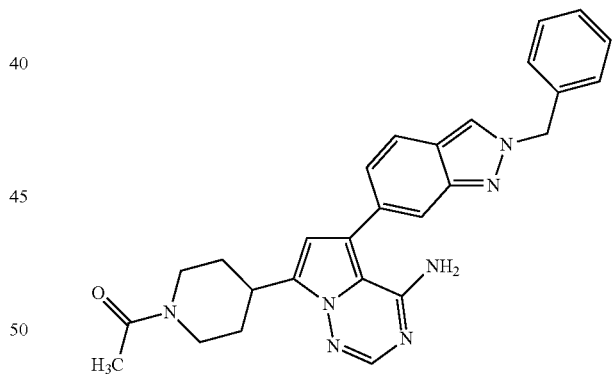

To a solution of 5-(2-benzyl-2H-indazol-6-yl)-7-piperidin-4-ylpyrrolo[2,1-f][1,2,4]triazin-4-amine (150 mg, 0.33 mmol) in THF (1.88 mL) was added acetyl chloride (26 μL, 0.36 mmol) and N,N-diisopropylethylamine (170 μL, 0.98 mmol). The reaction was stirred at rt for 17 h. The mixture was partitioned between EtOAc (25 mL) and H₂O (25 mL). The layers were separated and the organic phase was washed with H₂O (20 mL), brine, dried (Na₂SO₄) and concentrated. The crude material was purified by ISCO® chromatography using a gradient of 0 to 10% MeOH in EtOAc. The isolated compound was crystallized from EtOAc/hexanes to afford 64 mg (42%) of the desired product. ¹H NMR (400 MHz, DMSO-d₆) δ 8.54 (s, 1 H), 7.90 (s, 1 H), 7.79 (d, 1 H), 7.58 (s, 1 H), 7.28-7.38 (m, 5 H), 7.13 (dd, 1 H), 6.59 (s, 1 H), 5.64 (s, 2 H), 4.48 (d, 1 H) 3.89 (s, 1 H), 3.32-3.41 (m, 3 H), 3.19 (s, 1 H), 2.67 (d, 1 H), 1.98-2.07 (m, 3 H), 1.66 (d, 1 H), 1.51 (s, 1 H); ES-MS m/z 466.4 [M+H]⁺, HPLC RT (min) 2.49.

Example 232

Preparation of 5-(2-benzyl-2H-indazol-6-yl)-7-{1-[(dimethylamino)acetyl]-piperidin-4-yl}pyrrolo[2,1-f][1,2,4]triazin-4-amine

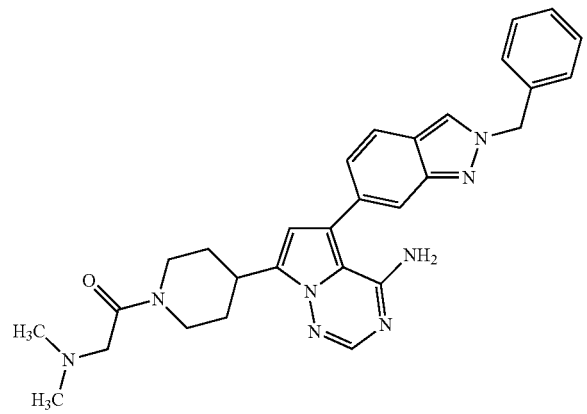

A mixture of 5-(2-benzyl-2H-indazol-6-yl)-7-piperidin-4-ylpyrrolo[2,1-f][1,2,4]triazin-4-amine (150 mg, 0.33 mmol), N,N-dimethylglycine (40 mg, 0.39 mmol), EDCl (69 mg, 0.36 mmol), HOBt (48 mg, 0.36 mmol), and N,N-diisopropylethylamine (227 µL, 1.30 mmol) in DMF (2 mL) was stirred at rt for 6 h. An additional 0.5 eq. of N,N-dimethylglycine was added and the mixture continued to stir at rt for 16 hr. The crude reaction mixture was purified via preparative HPLC using a gradient elution from 15% to 40% acetonitrile in water to provide 39 mg (24%) of the desired product. ¹H NMR (400 MHz, DMSO-d₆) δ 8.56 (s, 1 H), 7.92 (s, 1 H), 7.81 (d, 1 H), 7.66 (s, 1 H), 7.28-7.39 (m, 5 H), 7.15 (dd, 1 H), 6.60 (s, 1 H), 5.67 (s, 2 H), 4.32 (dd, 1 H) 3.33-3.46 (m, 1 H), 3.01-3.20 (m, 4 H), 2.66-2.78 (m, 1 H), 2.19 (s, 6 H), 2.05 (d, 2 H), 1.44-1.75 (m, 2 H); ES-MS m/z 509.23 [M+H]⁺, HPLC RT (min) 2.12.

Example 233

Preparation of 5-(2-benzyl-2H-indazol-6-yl)-7-(1-cyclopropylpiperidin-4-yl)pyrrolo[2,1-f][1,2,4]triazin-4-amine

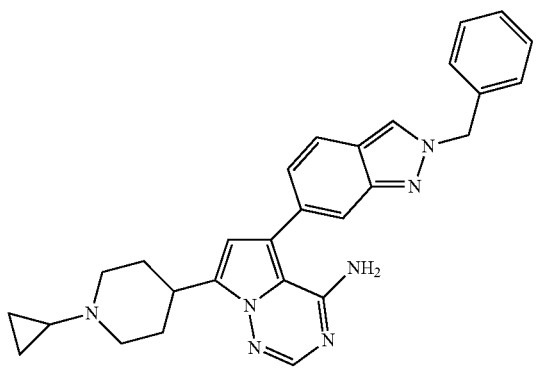 [SMILES: Nc1ncnn2c(C3CCN(C4CC4)CC3)cc(-c3ccc4cn(Cc5ccccc5)nc4c3)c12]

To a solution of 5-(2-benzyl-2H-indazol-6-yl)-7-piperidin-4-ylpyrrolo[2,1-f][1,2,4]triazin-4-amine (85 mg, 0.20 mmol) in MeOH (2.25 mL) containing 3 Å molecular sieves was added AcOH (114 µL, 2.00 mmol), [(1-ethoxycyclopropyl)oxy]trimethylsilane (241 µL, 1.20 mmol) and sodium cyanoborohydride (57 mg, 0.90 mmol). The reaction was stirred at 60° C. for 17 h. The mixture was quenched with the addition of saturated, aqueous NaHCO₃ (10 mL) and was extracted with EtOAc (3×15 mL). The combined organic layers were washed with brine, dried (Na₂SO₄) and concentrated. The residue was purified by preparative HPLC using a gradient elution from 15% to 45% acetonitrile in water followed by filtration through an acidic resin, washing with MeOH. The product was eluted with 2M NH₃ in MeOH and the filtrate was concentrated to provide 47 mg (51%) of the desired product. ¹H NMR (400 MHz, DMSO-d₆) δ 825 (s, 1 H), 7.60 (s, 1 H), 7.50 (d, 1 H), 7.28 (s, 1 H), 6.98-7.08 (m, 5 H), 6.84 (dd, 1 H), 6.27 (s, 1 H), 5.35 (s, 2 H), 3.04 (s, 2 H), 2.72 (s, 2 H), 1.99 (s, 2 H), 1.66 (s, 2 H), 1.27-1.38 (m, 2 H), 0.13 (s, 1 H), 0.11 (d, 1 H), −0.03-0.03 (m, 2 H); ES-MS m/z 464.32 [M+H]⁺, HPLC RT (min) 1.24.

Example 234

Preparation of 4-[4-amino-5-(2-benzyl-2H-indazol-6-yl)pyrrolo[2,1-f][1,2,4]triazin-7-yl]-N,N-dimethylpiperidine-1-carboxamide

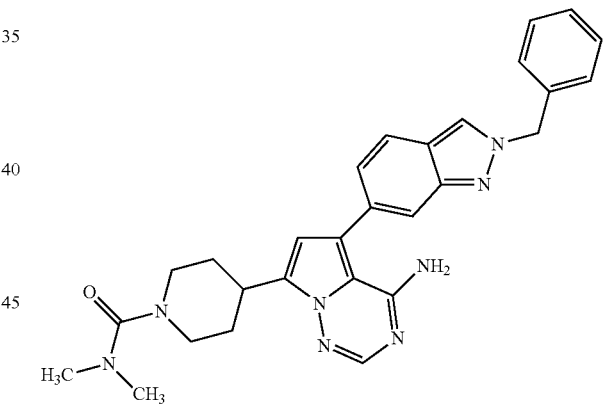

To a suspension of 5-(2-benzyl-2H-indazol-6-yl)-7-piperidin-4-ylpyrrolo[2,1-f][1,2,4]triazin-4-amine (80 mg, 0.17 mmol) in dichloromethane (1 mL) was added N,N-dimethylcarbamoyl chloride (18 µL, 0.19 mmol) and triethylamine (73 µL, 0.52 mmol). The reaction was stirred at 40° C. for 17 h. The crude mixture was purified by preparative HPLC using a gradient elution from 15% to 50% acetonitrile in water followed by filtration through an acidic resin, washing with MeOH. The product was eluted with 2M NH₃ in MeOH and the filtrate was concentrated to provide 40 mg (46%) of the desired product. ¹H NMR (400 MHz, DMSO-d₆) δ 8.54 (d, 1 H), 7.87-7.97 (m, 1 H), 7.79 (dd, 1 H), 7.59 (d, 1 H), 7.28-7.39 (m, 5 H), 7.14 (dd, 1 H), 6.58-6.65 (m, 1 H), 5.65 (d, 2 H), 3.63 (s, 2 H), 3.32-3.40 (m, 1 H), 2.85 (s, 2 H), 2.74 (d, 6 H), 1.99 (s, 2 H), 1.66 (s, 2 H); ES-MS m/z 495.20 [M+H]⁺, HPLC RT (min) 2.69.

Example 235

Preparation of 5-(2-benzyl-2H-indazol-6-yl)-7-[1-(methylsulfonyl)piperidin-4-yl]pyrrolo[2,1-f][1,2,4]triazin-4-amine

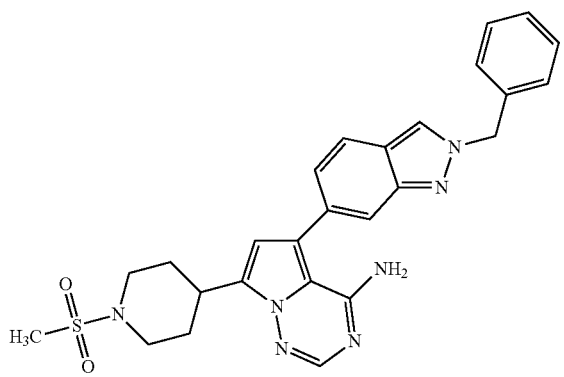 [SMILES: CS(=O)(=O)N1CCC(c2cc(-c3ccc4cn(Cc5ccccc5)nc4c3)c3c(N)ncnn23)CC1]

To a suspension of 5-(2-benzyl-2H-indazol-6-yl)-7-piperidin-4-ylpyrrolo[2,1-f][1,2,4]triazin-4-amine (80 mg, 0.17 mmol) in dichloromethane (1 mL) was added methanesulfonyl chloride (15 μL, 0.19 mmol) and triethylamine (73 μL, 0.52 mmol). The reaction was stirred at 40° C. for 17 h. The crude mixture was purified by preparative HPLC using a gradient elution from 15% to 50% acetonitrile in water followed by filtration through an acidic resin, washing with MeOH. The product was eluted with 2M $NH_3$ in MeOH and the filtrate was concentrated to provide 22 mg (25%) of the desired product. $^1$H NMR (400 MHz, DMSO-$d_6$) δ 8.54 (s, 1 H), 7.90 (s, 1 H), 7.80 (d, 1 H), 7.59 (s, 1 H), 7.28-7.39 (m, 5 H), 7.15 (d, 1 H), 6.64 (s, 1 H), 5.65 (s, 2 H), 3.66 (d, 2 H), 3.19-3.30 (m, 1 H), 2.85-2.95 (m, 5 H), 2.11 (d, 2 H), 1.69-1.80 (m, 2 H); ES-MS m/z 502.31 [M+H]$^+$, HPLC RT (min) 2.73.

Example 236

Preparation of 4-[4-amino-5-(2-benzyl-2H-indazol-6-yl)pyrrolo[2,1-f][1,2,4]triazin-7-yl]-N,N-dimethylpiperidine-1-sulfonamide

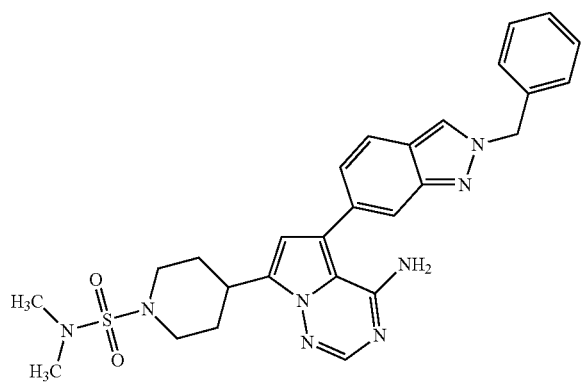 [SMILES: CN(C)S(=O)(=O)N1CCC(c2cc(-c3ccc4cn(Cc5ccccc5)nc4c3)c3c(N)ncnn23)CC1]

To a suspension of 5-(2-benzyl-2H-indazol-6-yl)-7-piperidin-4-ylpyrrolo[2,1-f][1,2,4]triazin-4-amine (80 mg, 0.17 mmol) in toluene (1 mL) was added N,N-dimethylsulfamoyl chloride (27 mg, 0.19 mmol) and triethylamine (73 μL, 0.52 mmol). The reaction was stirred at rt for 17 h. Additional N,N-dimethylsulfamoyl chloride (27 mg, 0.19 mmol) and triethylamine (73 μL, 0.52 mmol) were added and the reaction continued to stir at rt for 6 h. The mixture was partitioned between EtOAc (20 mL) and $H_2O$ (20 mL). The layers were separated and the organic phase was washed with saturated, aqueous $NaHCO_3$ (20 mL), brine, dried ($Na_2SO_4$) and concentrated. The resulting solid was triturated with $Et_2O$ and was collected by vacuum filtration to afford 92 mg (99%) of the desired product. $^1$H NMR (400 MHz, DMSO-$d_6$) δ ppm 8.55 (s, 1 H), 7.90 (s, 1 H), 7.80 (d, 1 H), 7.59 (s, 1 H), 7.28-7.37 (m, 5 H), 7.14 (d, 1 H), 6.63 (s, 1 H), 5.65 (s, 2 H), 3.67 (d, 2 H), 3.22-3.33 (m, 1 H), 3.01 (t, 2 H), 2.77 (s, 6 H), 2.07 (d, 2 H), 1.62-1.77 (m, 2 H); ES-MS m/z 531.26 [M+H]$^+$, HPLC RT (min) 2.75.

Example 237

Preparation of 7-(1-{[1-(aminomethyl)cyclopropyl]carbonyl}piperidin-4-yl)-5-(2-benzyl-2H-indazol-6-yl)pyrrolo[2,1-f][1,2,4]triazin-4-amine

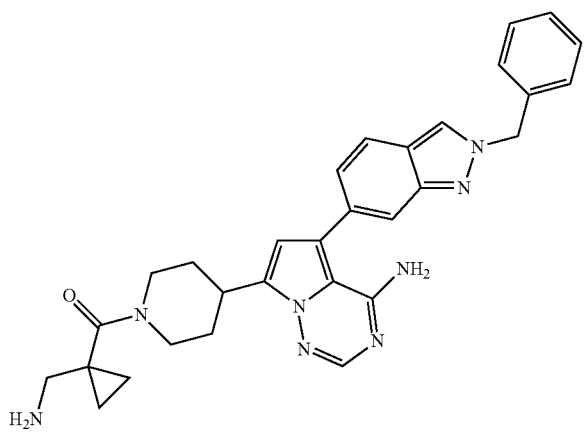 [SMILES: NCC1(C(=O)N2CCC(c3cc(-c4ccc5cn(Cc6ccccc6)nc5c4)c4c(N)ncnn34)CC2)CC1]

A mixture of 5-(2-benzyl-2,1-indazol-6-yl)-7-piperidin-4-ylpyrrolo[2,1-f][1,2,4]triazin-4-amine (120 mg, 0.28 mmol), 1-(Boc-aminomethyl)-cyclopropyl-1-carboxylic acid (73 mg, 0.34 mmol), EDCl (60 mg, 0.31 mmol), HOBt (42 mg, 0.31 mmol), and N,N-diisopropylethylamine (148 μL, 0.85 mmol) in DMF (1.8 mL) was stirred at rt for 64 h. Additional 1-(Boc-aminomethyl)-cyclopropyl-1-carboxylic acid (37 mg), EDCl (30 mg), HOBt (21 mg) and N,N-diisopropylethylamine (74 μL) were added and the mixture continued to stir at rt for 16 hr. The crude mixture was purified by preparative HPLC using a gradient elution from 15% to 45% acetonitrile in water followed by filtration through an acidic resin, washing with MeOH. The product was eluted with 2M $NH_3$ in MeOH and the filtrate was concentrated. To a solution of the residue in MeOH (1 mL) was added 4M HCl in dioxane (500 μL). The mixture was stirred at rt for 64 h. The mixture was concentrated and the residue was dissolved in 3:1 $CHCl_3$/isopropanol (15 mL). The mixture was washed with saturated, aqueous $NaHCO_3$ (15 mL), brine, dried ($Na_2SO_4$) and concentrated to dryness to afford 40 mg (27%) of the desired product. $^1$H NMR (400 MHz, DMSO-$d_6$) δ 8.54 (s, 1 H), 7.91 (s, 1 H), 7.81 (d, 1 H), 7.58 (s, 1 H), 7.23-7.34 (m, 5 H), 7.14 (d, 1 H), 6.63 (s, 1 H), 5.65 (s, 2 H), 4.37 (d, 2 H), 3.35-3.45 (m, 1 H), 2.84-3.03 (br s, 4 H), 2.72 (s, 2 H), 2.04 (d, 2 H), 1.48-1.72 (m, 2 H), 0.62-0.78 (m, 4 H); ES-MS m/z 521.37 [M+H]$^+$, HPLC RT (min) 2.06.

Example 238

Preparation of 7-{1-[(1-aminocyclopropyl)carbonyl]piperidin-4-yl}-5-(2-benzyl-2H-indazol-6-yl)pyrrolo[2,1-f][1,2,4]triazin-4-amine

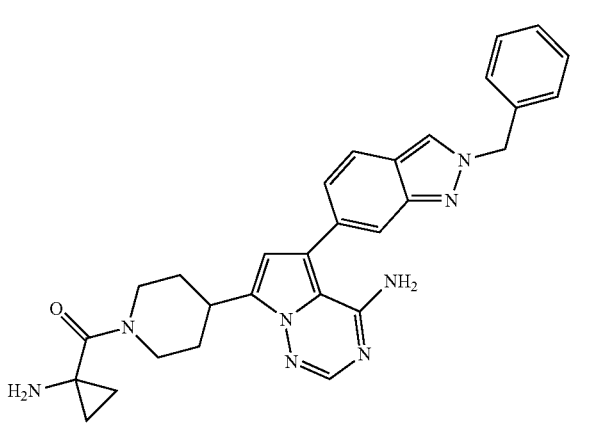 [SMILES: Nc1ncnn2c(C3CCN(C(=O)C4(N)CC4)CC3)cc(-c3ccc4cn(Cc5ccccc5)nc4c3)c12]

In a manner similar to the procedure described for the preparation of Example 237 and substituting 1-[(tert-butoxycarbonyl)amino]cyclopropanecarboxylic acid for 1-(Boc-aminomethyl)-cyclopropyl-1-carboxylic acid, 11 mg (7%) of the desired product was isolated. $^1$H NMR (400 MHz, DMSO-d$_6$) δ 8.54 (s, 1 H), 7.91 (s, 1 H), 7.79 (d, 1 H), 7.58 (s, 1 H), 7.24-7.38 (m, 5 H), 7.14 (d, 1 H), 6.61 (s, 1 H), 5.65 (s, 2 H), 4.43 (d, 2 H), 3.35-3.47 (m, 1 H), 2.74-3.13 (br s, 3 H), 2.29 (s, 2 H), 2.03 (d, 2 H), 1.53-1.71 (m, 1 H), 0.78-0.90 (m, 2 H), 0.57-0.69 (m, 2 H); ES-MS m/z 507.18 HPLC RT (min) 2.14.

Example 239

Preparation of 7-[1-(azetidin-3-ylcarbonyl)piperidin-4-yl]-5-(2-benzyl-2H-indazol-6-yl)pyrrolo[2,1-f][1,2,4]triazin-4-amine

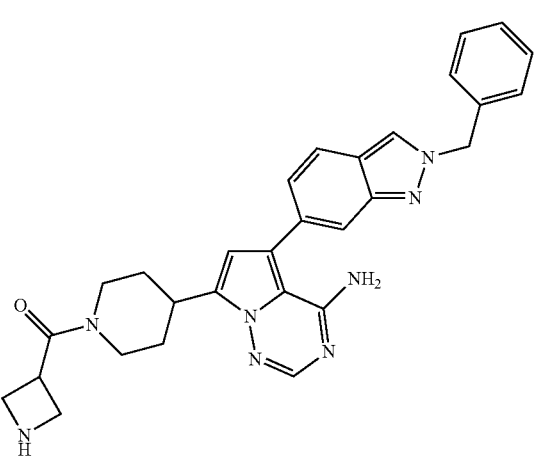 [SMILES: Nc1ncnn2c(C3CCN(C(=O)C4CNC4)CC3)cc(-c3ccc4cn(Cc5ccccc5)nc4c3)c12]

In a manner similar to the procedure described for the preparation of Example 237 and substituting 1-(tert-butoxycarbonyl)azetidine-3-carboxylic acid for 1-(Boc-aminomethyl)-cyclopropyl-1-carboxylic acid, 38 mg (27%) of the desired product was isolated. $^1$H NMR (400 MHz, DMSO-d$_a$) δ 8.54 (s, 1 H), 7.90 (s, 1 H), 7.79 (d, 1 H), 7.58 (s, 1 H), 727-7.39 (m, 5 H), 7.13 (d, 1 H), 6.59 (s, 1 H), 5.65 (s, 2 H), 4.49 (d, 1 H), 3.03-3.92 (m, 9 H), 2.68-2.81 (m, 1 H), 2.03 (m, 2 H), 1.43-1.65 (m, 1 H); ES-MS m/z 507.40 [M+H]$^+$, HPLC RT (min) 2.00.

Example 240

Preparation of 5-[3-amino-2-(2-fluorobenzyl)-2H-indazol-6-yl]-7-piperidin-4-ylpyrrolo[2,1-f][1,2,4]triazin-4-amine

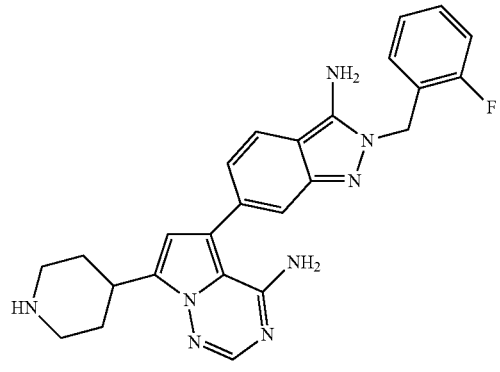 [SMILES: Nc1ncnn2c(C3CCNCC3)cc(-c3ccc4c(N)n(Cc5ccccc5F)nc4c3)c12]

Using the procedure described in steps 1-5 of the preparation of Example 1 and substituting 2-(2-fluorobenzyl)-6-(4,4,5,5-tetramethyl-1,3,2-dioxaborolan-2-yl)-2H-indazol-3-amine for Intermediate C, the title compound was prepared. $^1$H NMR (400 MHz, DMSO-d$_6$) δ 7.86 (s, 1 H), 7.72 (d, 1 H), 7.28-7.38 (m, 1 H), 7.17-7.27 (m, 1 H), 7.06-7.16 (m, 2 H), 6.83-6.90 (m, 1 H), 6.73-6.89 (m, 1 H), 6.51 (s, 1 H), 6.42 (s, 2 H), 5.44 (s, 2 H), 3.13-3.25 (m, 1 H), 2.97-3.07 (m, 2 H), 2.56-2.70 (m, 2 H), 1.87-1.98 (m, 2 H), 1.48-1.64 (m, 2 H); ES-MS m/z 457.18 [M+H]$^+$, HPLC RT (min) 1.37.

Example 241

Preparation of 5-[3-amino-2-(2-fluorobenzyl)-2H-indazol-6-yl]-7-(1-cyclopropylpiperidin-4-yl)pyrrolo[2,1,2,4]triazin-4-amine

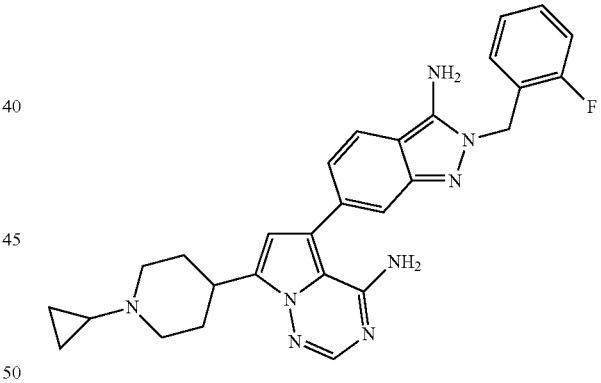

To a solution of 5-[3-amino-2-(2-fluorobenzyl)-2H-indazol-6-yl]-7-piperidin-4-ylpyrrolo[2,1-f][1,2,4]triazin-4-amine (75 mg, 0.16 mmol) in MeOH (1.5 mL) containing 3 Å molecular sieves was added AcOH (94 μL, 2.00 mmol), [(1-ethoxycyclopropyl)oxy]trimethylsilane (1.14 mL, 0.99 mmol) and sodium cyanoborohydride (46 mg, 0.74 mmol). The reaction was stirred at 60° C. for 17 h. The mixture was quenched with the addition of saturated, aqueous NaHCO$_3$ (10 mL) and was extracted with EtOAc (3×15 mL). The combined organic layers were washed with brine, dried (Na$_2$SO$_4$) and concentrated. The residue was purified by preparative HPLC using a gradient elution from 15% to 45% acetonitrile in water followed by filtration through an acidic resin, washing with MeOH. The product was eluted with 2M NH$_3$ in MeOH and the filtrate was concentrated to provide 13 mg (15%) of the desired product. $^1$H NMR (400 MHz, DMSO-d$_6$) δ 7.58 (s, 1 H), 7.42-7.51 (m, 1 H), 7.00-7.10 (m, 1 H), 6.88-6.98 (m, 1 H), 6.81-6.87 (m, 2 H), 6.55-6.61 (m, 1

H), 6.46 (dd, 1 H), 6.23 (s, 1 H), 6.13 (s, 2 H), 5.15 (s, 2 H), 2.75-2.85 (m, 3 H), 1.95-2.04 (m, 2 H), 1.66 (d, 2 H), 1.27-1.38 (m, 3 H), 0.06-0.15 (m, 2 H), −0.02-0.06 (m, 2 H); ES-MS m/z 497.31 [M+H]⁺, HPLC RT (min) 0.27.

Example 242

Preparation of 5-(2-phenyl-2H-indazol-6-yl)-7-piperidin-4-ylpyrrolo[2,1-f][1,2,4]triazin-4-amine

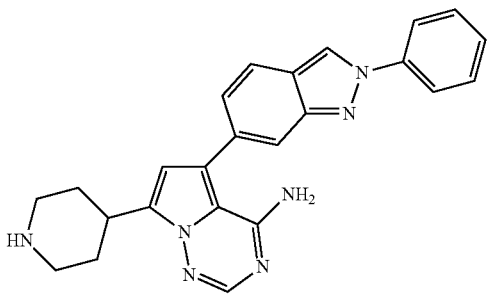 [SMILES: Nc1ncnn2c(C3CCNCC3)cc(-c3ccc4cn(-c5ccccc5)nc4c3)c12]

Using the procedure described in Steps 1-5 of Example 1 and substituting 2-phenyl-6-(4,4,5,5-tetramethyl-1,3,2-dioxaborolan-2-yl)-2H-indazole for Intermediate C, the title compound was prepared. ¹H NMR (400 MHz, DMSO-d₆) δ 9.16 (s, 1 H), 8.11 (d, 2 H), 7.90 (s, 1 H), 7.85 (d, 1 H), 7.69 (s, 1 H), 7.53-7.63 (m, 2 H), 7.40-7.49 (m, 1 H), 7.23 (dd, 1 H), 6.62 (s, 1 H), 3.11-3.27 (m, 1 H), 2.96-3.06 (m, 2 H), 2.56-2.68 (m, 2 H), 1.88-1.99 (m, 2 H), 1.49-1.65 (m, 2 H); ES-MS m/z 410.44 [M+H]⁺, HPLC RT (min) 1.96.

Example 243

Preparation of 7-{1-[(dimethylamino)acetyl]piperidin-4-yl}-5-(2-phenyl-2H-indazol-6-yl)pyrrolo[2,1-f][1,2,4]triazin-4-amine

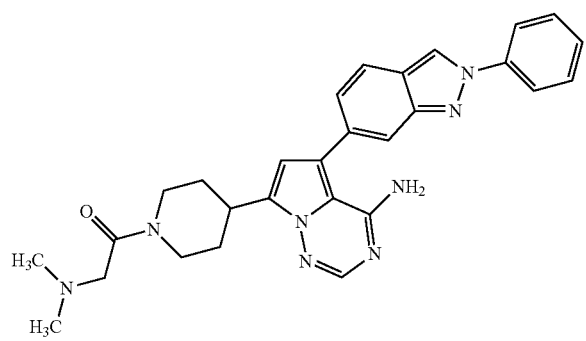 [SMILES: CN(C)CC(=O)N1CCC(c2cc(-c3ccc4cn(-c5ccccc5)nc4c3)c3c(N)ncnn23)CC1]

A mixture 5-(2-phenyl-2H-indazol-6-yl)-7-piperidin-4-ylpyrrolo[2,1-f][1,2,4]triazin-4-amine (80 mg, 0.20 mmol), N,N-dimethylglycine (22 mg, 0.22 mmol), EDCl (41 mg, 022 mmol), HOBt (29 mg, 0.22 mmol), and N,N-diisopropylethylamine (102 μL, 0.59 mmol) in DMF (1 mL) was stirred at rt for 17 h. The residue was purified by preparative HPLC using a gradient elution from 15% to 45% acetonitrile in water followed by filtration through an acidic resin, washing with MeOH. The product was eluted with 2M NH₃ in MeOH and the filtrate was concentrated to provide 22 mg (23%) of the desired product. ¹H NMR (400 MHz, DMSO-d₆) δ 9.16 (s, 1 H), 8.11 (d, 2 H), 7.93 (s, 1 H), 7.85 (d, 1 H), 7.69 (s, 1 H), 7.56-7.62 (m, 2 H), 7.45 (t, 1 H), 7.23 (dd, 1 H), 6.66 (s, 1 H), 4.31 (dd, 1 H), 3.36-3.51 (m, 1 H), 3.08-3.24 (m, 2 H), 3.01-3.06 (m, 1 H), 2.63-2.80 (m, 1 H), 2.18 (s, 6 H), 1.99-2.12 (s, 2 H), 1.44-1.77 (m, 1 H); ES-MS m/z 495.18 [M+H]⁺, HPLC RT (min) 2.13.

Example 244

Preparation of 7-{1-[(1-aminocyclopropyl)carbonyl]piperidin-4-yl}-5-(2-phenyl-2H-indazol-6-yl)pyrrolo[2,1-f][1,2,4]triazin-4-amine

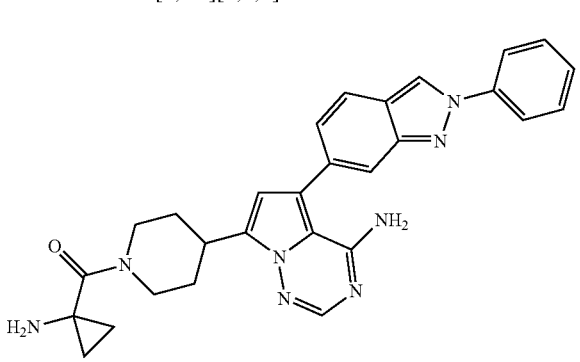

A mixture 5-(2-phenyl-2H-indazol-6-yl)-7-piperidin-4-ylpyrrolo[2,1-f][1,2,4]triazin-4-amine (120 mg, 0.29 mmol), 1-(Boc-amino)-cyclopropyl-1-carboxylic acid (65 mg, 0.32 mmol), EDCl (62 mg, 0.32 mmol), HOBt (44 mg, 0.32 mmol), and N,N-diisopropylethylamine (115 μL, 0.85 mmol) in DMF (1.5 mL) was stirred at rt for 16 h. The crude mixture was purified by preparative HPLC using a gradient elution from 15% to 45% acetonitrile in water followed by filtration through an acidic resin, washing with MeOH. The product was eluted with 2M NH₃ in MeOH and the filtrate was concentrated. To a solution of the residue in MeOH (1 mL) was added 4M HCl in dioxane (500 μL). The mixture was stirred at rt for 16 h. The mixture was concentrated and the residue was dissolved in 3:1 CHCl₃/isopropanol (15 mL). The mixture was washed with saturated aqueous NaHCO₃ (15 mL), brine, dried (Na₂SO₄) and concentrated to dryness. The crude mixture was purified by preparative HPLC using a gradient elution from 15% to 45% acetonitrile in water followed by filtration through an acidic resin, washing with MeOH. The product was eluted with 2M NH₃ in MeOH and the filtrate was concentrated to afford 11 mg (8%) of the desired product. ¹H NMR (400 MHz, DMSO-d₆) δ 9.16 (s, 1 H), 8.10 (d, 2 H), 7.93 (s, 1 H), 7.84 (d, 1 H), 7.69 (s, 1 H), 7.54-7.64 (m, 2 H), 7.45 (t, 1 H), 7.22 (dd, 1 H), 6.68 (s, 1 H), 3.36-3.51 (m, 1 H), 3.01-3.06 (m, 2 H), 2.21-2.37 (m, 2 H), 1.98-2.09 (m, 2 H), 1.51-1.72 (m, 2 H), 0.77-0.88 (m, 2 H), 0.59-0.74 (m, 2 H); ES-MS m/z 493.36 [M+H]⁺, HPLC RT (min) 2.07.

Example 245

Preparation of 7-[1-(methylsulfonyl)piperidin-4-yl]-5-(2-phenyl-2H-indazol-6-yl)pyrrolo[2,1-f][1,2,4]triazin-4-amine

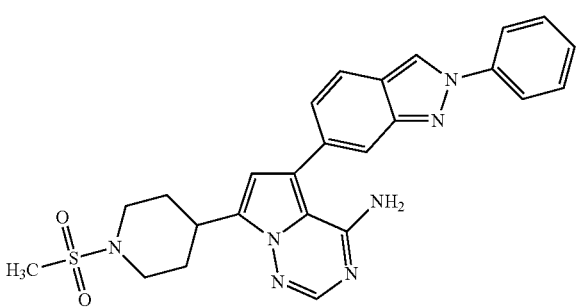 [SMILES: CS(=O)(=O)N1CCC(c2cc(-c3ccc4cn(-c5ccccc5)nc4c3)c3c(N)ncnn23)CC1]

To a suspension of 5-(2-phenyl-2H-indazol-6-yl)-7-piperidin-4-ylpyrrolo[2,1-f][1,2,4]triazin-4-amine (80 mg, 0.20 mmol) in DMF (1 mL) was added methanesulfonyl chloride (17 μL, 0.22 mmol) and N,N-diisopropylethylamine (68 μL, 0.39 mmol). The reaction was stirred at rt for 17 h. The crude mixture was purified by preparative HPLC using a gradient elution from 15% to 45% acetonitrile in water followed by filtration through an acidic resin, washing with MeOH. The product was eluted with 2M NH₃ in MeOH and the filtrate was concentrated to provide 28 mg (29%) of the desired product. $^1$H NMR (400 MHz, DMSO-$d_6$) δ 9.16 (s, 1 H), 8.10 (d, 2 H), 7.93 (s, 1 H), 7.85 (d, 1 H), 7.69 (s, 1 H), 7.55-7.63 (m, 2 H), 7.41-7.48 (m, 1 H), 7.22 (dd, 1 H), 6.68 (s, 1 H), 3.63-3.73 (m, 2 H), 3.21-3.32 (m, 1 H), 2.86-2.98 (m, 5 H), 2.10-2.21 (m, 2 H), 1.69-1.86 (m, 2 H); ES-MS m/z 488.23 [M+H]⁺, HPLC RT (min) 2.72.

Example 246

5-(2-benzyl-2H-indazol-6-yl)-7-(1,2,3,6-tetrahydropyridin-4-yl)pyrrolo[2,1-f][1,2,4]triazin-4-amine

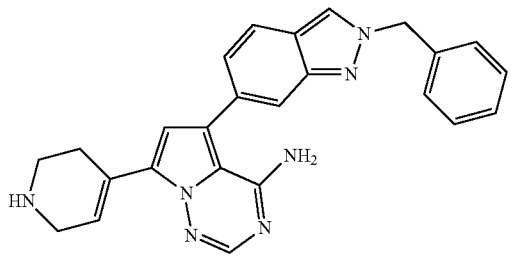 [SMILES: Nc1ncnn2c(C3=CCNCC3)cc(-c3ccc4cn(Cc5ccccc5)nc4c3)c12]

Step 1: Preparation of 5-(2-benzyl-2H-indazol-6-yl)pyrrolo[2,1-f][1,2,4]triazin-4-amine

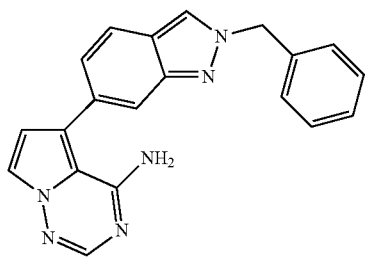 [SMILES: Nc1ncnn2ccc(-c3ccc4cn(Cc5ccccc5)nc4c3)c12]

To a stirred degassed mixture 5-bromopyrrolo[2,1-f][1,2,4]triazin-4-amine (500 mg, 2.35 mmol), Intermediate C (1.18 g, 3.52 mmol), Na₂CO₃ (746 mg, 7.04 mmol) and H₂O (3.5 mL) in DMF (18 mL) was added tetrakis(triphenylphosphine)palladium(0) (271 mg, 0.24 mmol). The reaction was heated at 110° C. for 17 h and then cooled to rt. The mixture was partitioned between ethyl acetate (50 mL) and H₂O (50 mL). The layers were separated and the aqueous was further extracted with ethyl acetate (1×50 mL). The combined organic layers were washed with brine, dried (Na₂SO₄), and concentrated to dryness. The crude material was purified via ISCO® chromatography using 3:1 ethyl acetate/hexanes to afford 600 mg (75%) of the desired product, which contained trace impurities. ES-MS ink 341.23 [M+H]⁺, HPLC RT (min) 2.91.

Step 2: Preparation of 5-(2-benzyl-2H-indazol-6-yl)-7-bromopyrrolo[2,1-f][1,2,4]triazin-4-amine

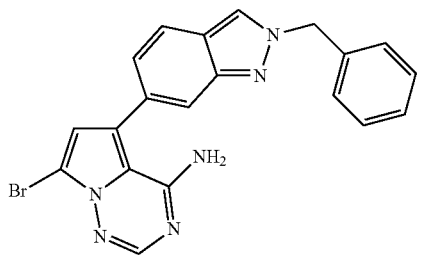 [SMILES: Nc1ncnn2c(Br)cc(-c3ccc4cn(Cc5ccccc5)nc4c3)c12]

To a cooled (−20° C.) solution 5-(2-benzyl-2H-indazol-6-yl)pyrrolo[2,1-f][1,2,4]triazin-4-amine (600 mg, 1.76 mmol) in THF (18 mL) was added 1,3-dibromo-5,5-dimethylhydantoin (252 mg, 0.88 mmol) in 3 portions over 10 min. The mixture was stirred at −20° C. for 2 h. Saturated, aqueous Na₂SO₃ (20 mL) was added and the mixture warmed to rt. The mixture was extracted with ethyl acetate (2×20 mL). The combined organics were washed with 5% aqueous K₂CO₃ (2×20 mL), brine, dried (Na₂SO₄) and evaporated to provide 660 mg (89%) of the desired product, which contained trace impurities. ES-MS m/z 419.12 [M+H]⁺, HPLC RT (min) 3.00.

Step 3: Preparation of tert-butyl 4-[4-amino-5-(2-benzyl-2H-indazol-6-yl)pyrrolo[2,1-f][1,2,4]triazin-7-yl]-3,6-dihydropyridine-1(2H)-carboxylate

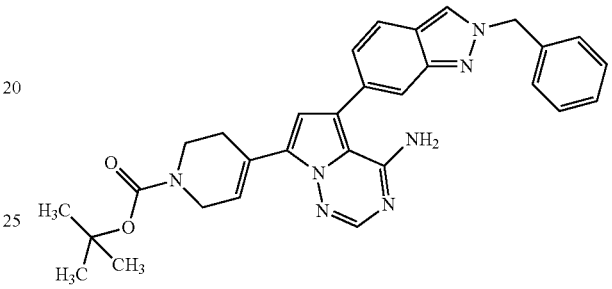

To a stirred suspension of 5-(2-benzyl-2H-indazol-6-yl)-7-bromopyrrolo[2,1-f][1,2,4]triazin-4-amine (660 mg, 1.57 mmol), tert-butyl 4-(4,4,5,5-tetramethyl-1,3,2-dioxaborolan-2-yl)-3,6-dihydropyridine-1(2H)-carboxylate (see Eastwood, P. R. *Tetrahedron Lett* 2000, 41, 3705 for preparation) (730 mg, 2.36 mmol), and 1,1'-bis(diphenylphosphino)-ferrocene]dichloro palladium(II)-complex with dichloromethane (115 mg, 0.16 mmol) in degassed DME (12 mL) was added aqueous Na₂CO₃ solution (2 M, 2.4 mL). The reaction was heated (75° C.) for 17 h and was then cooled to rt. The mixture was partitioned between ethyl acetate (25 mL) and H₂O (25 mL). The layers were separated and the organic layer was washed with brine, dried (Na₂SO₄), and concentrated to dryness. The crude residue was purified by ISCO® chromatography using a gradient of 50 to 75% ethyl acetate in hexanes to afford 564 mg (69%) of the desired product, which was approximately 50% pure. ES-MS m/z 522.12 [M+H]⁺, HPLC RT (min) 3.20.

Step 4: Preparation of the Title Compound

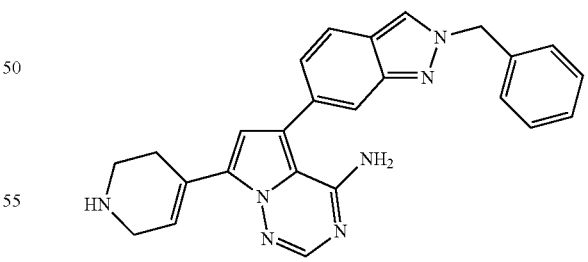

To a solution of tert-butyl 4-[4-amino-5-(2-benzyl-2H-indazol-6-yl)pyrrolo[2,1-f][1,2,4]triazin-7-yl]-3,6-dihydropyridine-1(2H)-carboxylate (564 mg, 1.08 mmol) in MeOH (4 mL) was added 4M HCl in dioxane (2 mL). The mixture was stirred at rt for 41 h. The mixture was concentrated and the residue was dissolved in 3:1 CHCl₃/isopropanol (25 mL). The mixture was washed with saturated, aqueous NaHCO₃ (25 mL), brine, dried (Na₂SO₄) and concentrated to dryness to afford 510 mg (96%) of the desired product, which contained trace impurities. $^1$H NMR (400 MHz, DMSO-$d_6$) δ

8.54-8.58 (s, 1 H), 7.92 (s, 1 H), 7.80 (d, 1 H), 7.61 (s, 1 H), 7.27-7.37 (m, 5 H), 7.14 (dd, 1 H), 7.01-7.06 (m, 1 H), 6.75 (s, 1 H), 5.65 (s, 2 H), 3.40-3.48 (m, 2 H), 2.92 (t, 1 H), 2.42-2.49 (m, 2 H); ES-MS m/z 422.06 [M+H]$^+$, HPLC RT (min) 1.03 min.

Example 247

Preparation of 5-(2-benzyl-2H-indazol-6-yl)-7-{1-[(dimethylamino)acetyl]-1,2,3,6-tetrahydropyridin-4-yl}pyrrolo[2,1-f][1,2,4]triazin-4-amine

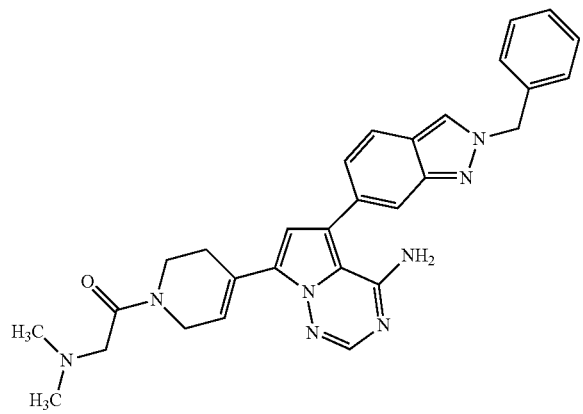 [SMILES: CN(C)CC(=O)N1CC=C(c2cc(-c3ccc4cn(Cc5ccccc5)nc4c3)c3c(N)ncnn23)CC1]

A mixture of 5-(2-benzyl-2H-indazol-6-yl)-7-(1,2,3,6-tetrahydropyridin-4-yl)pyrrolo[2,1-f][1,2,4]triazin-4-amine (100 mg, 0.24 mmol), N,N-dimethylglycine (27 mg, 0.26 mmol), EDCl (50 mg, 0.26 mmol), HOBt (35 mg, 026 mmol), and N,N-diisopropylethylamine (124 µL, 0.71 mmol) in DMF (1.5 mL) was stirred at rt for 16 h. The crude mixture was purified by preparative HPLC using a gradient elution from 15% to 45% acetonitrile in water followed by filtration through an acidic resin, washing with MeOH. The product was eluted with 2M NH$_3$ in MeOH and the filtrate was concentrated to provide 24 mg (20%) of the desired product. $^1$H NMR (400 MHz, DMSO-d$_6$) δ 8.55 (s, 1 H), 7.96 (s, 1 H), 7.81 (d, 1 H), 7.61 (s, 1 H), 7.27-7.37 (m, 5 H), 7.14 (dd, 1 H), 7.03-7.10 (m, 1 H), 6.80-6.84 (m, 1 H), 5.65 (s, 2 H), 4.25 (d, 2 H), 3.69 (dt, 2 H), 3.13 (d, 2 H), 2.63-2.70 (m, 1 H), 2.53-2.60 (m, 1 H), 2.17 (m, 6 H); ES-MS m/z 507.17 [M+H]$^+$, HPLC RT (min) 1.36.

Example 248

Preparation of 5-(2-benzyl-2H-indazol-6-yl)-7-piperidin-3-ylpyrrolo[2,1-f][1,2,4]triazin-4-amine

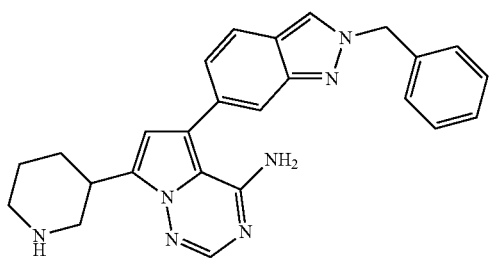 [SMILES: Nc1ncnn2c(C3CCCNC3)cc(-c3ccc4cn(Cc5ccccc5)nc4c3)c12]

Crude 5-(2-benzyl-2H-indazol-6-yl)-7-piperidin-3-ylpyrrolo[2,1-f][1,2,4]triazin-4-amine hydrochloride (120 mg, 0.26 mmol) was purified via preparative HPLC using a gradient elution from 15% to 45% acetonitrile in water followed by filtration through an acidic resin, washing with MeOH. The product was eluted with 2M NH$_3$ in MeOH and the filtrate was concentrated to provide 29 mg (26%) of the desired product. $^1$H NMR (400 MHz, CD$_3$OD) δ 8.37 (s, 1 H), 7.79-7.86 (m, 2 H), 7.64 (s, 1 H), 7.30-7.38 (m, 5 H), 7.23 (dd, 1 H), 6.61 (s, 1 H), 5.65 (s, 2 H), 3.41-3.57 (m, 2 H), 3.09-3.19 (m, 1 H), 2.68-2.80 (m, 2 H), 2.15-2.26 (m, 1 H), 1.70-1.92 (m, 3 H); ES-MS m/z 424.22 [M+H]$^+$, HPLC RT (min) 2.12.

Example 249

Preparation of 5-(2-benzyl-2H-indazol-6-yl)-7-[1-(methylsulfonyl)piperidin-3-yl]pyrrolo[2,1-f][1,2,4]triazin-4-amine

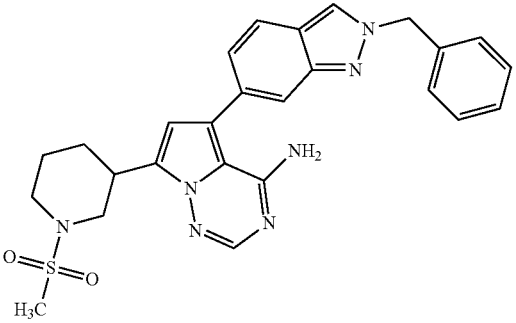 [SMILES: CS(=O)(=O)N1CCCC(c2cc(-c3ccc4cn(Cc5ccccc5)nc4c3)c3c(N)ncnn23)C1]

To a solution of 5-(2-benzyl-2H-indazol-6-yl)-7-piperidin-3-ylpyrrolo[2,1-f][1,2,4]triazin-4-amine hydrochloride (100 mg, 0.22 mmol) in DMF (1.5 mL) was added methanesulfonyl chloride (19 µL, 0.24 mmol) and N,N-diisopropylethylamine (114 µL, 0.65 mmol). The reaction was stirred at rt for 17 h. The crude mixture was purified by preparative HPLC using a gradient elution from 20% to 50% acetonitrile in water followed by filtration through an acidic resin, washing with MeOH. The product was eluted with 2M NH$_3$ in MeOH and the filtrate was concentrated to provide 25 mg (23%) of the desired product. $^1$H NMR (400 MHz, DMSO-d$_6$) δ 8.54 (s, 1 H), 7.93 (s, 1 H), 7.80 (d, 1 H), 7.58 (s, 1 H), 7.27-7.37 (m, 5 H), 7.13 (dd, 1 H), 6.70 (s, 1 H), 5.64 (s, 2 H), 3.82-3.88 (m, 1 H), 3.55 (d, 1 H), 3.34-3.46 (m, 1 H), 2.86 (s, 3 H), 2.74-2.85 (m, 2 H), 2.03-2.13 (m, 1 H), 1.78-1.89 (m, 1 H), 1.57-1.77 (m, 2 H); ES-MS m/z 502.47 [M+H]$^+$, HPLC RT (min) 3.04.

Example 250

Preparation of 5-(2-benzyl-2H-indazol-6-yl)-7-{1-[(dimethylamino)acetyl]piperidin-3-yl}pyrrolo[2,1-f][1,2,4]triazin-4-amine

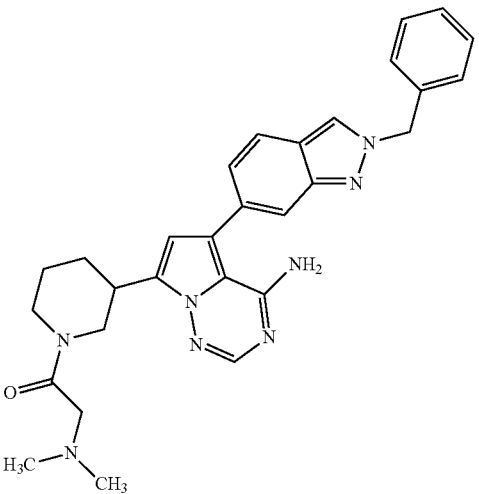 [SMILES: CN(C)CC(=O)N1CCCC(c2cc(-c3ccc4cn(Cc5ccccc5)nc4c3)c3c(N)ncnn23)C1]

A mixture of 5-(2-benzyl-2H-indazol-6-yl)-7-piperidin-4-ylpyrrolo[2,1-f][1,2,4]triazin-4-amine (100 mg, 0.24 mmol), N,N-dimethylglycine (29 mg, 0.28 mmol), EDCl (50 mg, 0.26 mmol), HOBt (35 mg, 0.26 mmol), and N,N-diisopropylethylamine (123 μL, 0.71 mmol) in DMF (1.5 mL) was stirred at rt for 16 h. The Prude mixture was purified by preparative HPLC using a gradient elution from 15% to 45% acetonitrile in water followed by filtration through an acidic resin, washing with MeOH. The product was eluted with 2M NH$_3$ in MeOH and the filtrate was concentrated to provide 24 mg (20%) of the desired product $^1$H NMR (400 MHz, DMSO-d$_6$) δ 8.54 (s, 1 H), 7.91 (d, 1 H), 7.80 (d, 1 H), 7.58 (s, 1 H), 7.26-7.41 (m, 5 H), 7.13 (d, 1 H), 6.64 (d, 1 H), 5.65 (s, 2 H), 4.44 (dd, 1 H), 4.13 (dd, 1 H), 2.61-3.68 (m, 5 H), 2.22 (s, 3 H), 2.16 (s, 3 H), 1.68-1.94 (m, 1 H), 1.39-1.65 (m, 1 H); ES-MS m/z 509.36 [M+H]$^+$, HPLC RT (min) 2.54.

Example 251

Preparation of 7-(1-{[1-(aminomethyl)cyclopropyl]carbonyl}piperidin-3-yl)-5-(2-benzyl-2H-indazol-6-yl)pyrrolo[2,1-f][1,2,4]triazin-4-amine

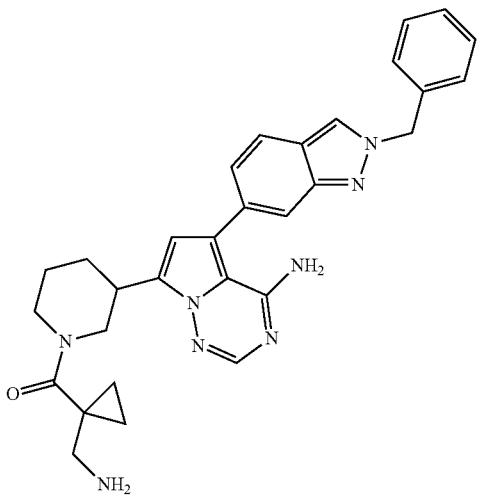 [SMILES: NCC1(C(=O)N2CCCC(c3cc(-c4ccc5cn(Cc6ccccc6)nc5c4)c4c(N)ncnn34)C2)CC1]

A mixture of 5-(2-benzyl-2H-indazol-6-yl)-7-piperidin-4-ylpyrrolo[2,1-f][1,2,4]triazin-4-amine (100 mg, 0.24 mmol), 1-(Boc-aminomethyl)-cyclopropyl-1-carboxylic acid (61 mg, 0.28 mmol), EDCl (50 mg, 0.26 mmol), HOBt (35 mg, 0.26 mmol), and N, diisopropylethylamine (123 μL, 0.71 mmol) in DMF (1.5 mL) was stirred at rt for 17 h. Additional 1-(Boc-aminomethyl)-cyclopropyl-1-carboxylic acid (30 mg), EDCl (25 mg), HOBt (18 mg) and N,N-diisopropylethylamine (62 μL) were added and the mixture continued to stir at rt for 16 hr. The crude mixture was purified by preparative HPLC using a gradient elution from 15% to 45% acetonitrile in water followed by filtration through an acidic resin, washing with MeOH. The product was eluted with 2M NH$_3$ in MeOH and the filtrate was concentrated. To a solution of the residue in MeOH (1 mL) was added 4M HCl in dioxane (500 μL). The mixture was stirred at rt for 64 h. The mixture was concentrated and the residue was dissolved in 3:1 CHCl$_3$/isopropanol (15 mL). The mixture was washed with saturated, aqueous NaHCO$_3$ (15 mL), brine, dried (Na$_2$SO$_4$) and concentrated to dryness to afford 9 mg (8%) of the desired product. $^1$H NMR (400 MHz, CD$_3$OD) δ 8.36 (s, 1 H), 7.78-7.88 (m, 2 H), 7.65 (s, 1 H), 7.29-7.37 (m, 5 H), 7.22 (dd, 1 H), 6.66 (s, 1 H), 5.65 (s, 2 H), 4.69-4.82 (m, 1 H), 4.44 (br s, 1 H), 3.37-3.51 (m, 1 H), 3.05 (dd, 1 H), 2.94 (br s, 2 H), 2.75 (d, 1 H), 2.21 (d, 1 H), 1.83-2.03 (m, 2 H), 1.60-1.75 (m, 1 H), 0.72-1.06 (m, 4 H); ES-MS m/z 521.21 [M+H]$^+$, HPLC RT (min) 2.30.

Example 252

Preparation of 7-{1-[(1-aminocyclopropyl)carbonyl]piperidin-3-yl}-5-(2-benzyl-2H-indazol-6-yl)pyrrolo[2,1-f][1,2,4]triazin-4-amine

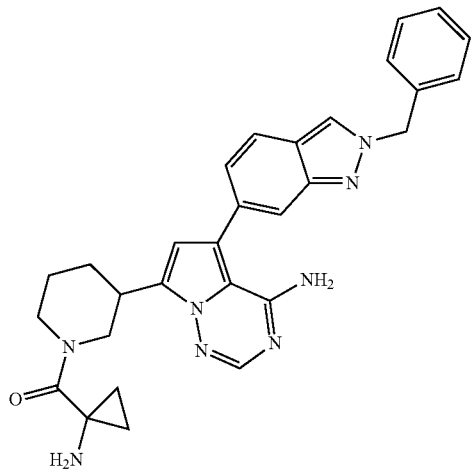 [SMILES: Nc1ncnn2c(C3CCCN(C(=O)C4(N)CC4)C3)cc(-c3ccc4cn(Cc5ccccc5)nc4c3)c12]

In a manner similar to the procedure described for the preparation of Example 251 and substituting 1-[(tert-butoxycarbonyl)amino]cyclopropanecarboxylic acid for 1-(Boc-aminomethyl)-cyclopropyl-1-carboxylic acid, 24 mg (20%) of the desired product was isolated. $^1$H NMR (400 MHz, DMSO-d$_6$) δ 8.54 (s, 1 H), 7.89 (s, 1 H), 7.79 (d, 1 H), 7.59 (s, 1 H), 7.28-7.39 (m, 5 H), 7.15 (d, 1 H), 6.66 (s, 1 H), 5.65 (s, 2 H), 4.62 (br s, 1 H), 4.34 (d, 1 H), 2.84-3.05 (m, 1 H), 2.01-2.21 (m, 1 H), 1.70-1.94 (m, 1 H), 1.43-1.64 (m, 1 H), 1.19-1.31 (m, 1 H), 0.53-0.92 (m, 4 H); ES-MS m/z 507.34 [M+H]$^+$, HPLC RT (min) 2.29.

Example 253

Preparation of 7-[1-(azetidin-3-ylcarbonyl)piperidin-3-yl]-5-(2-benzyl-2H-indazol-6-yl)pyrrolo[2,1,2,4]triazin-4-amine

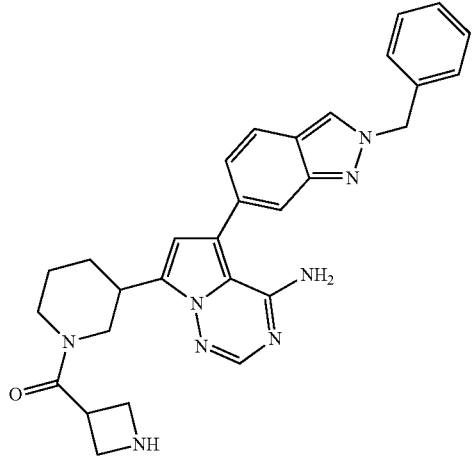 [SMILES: Nc1ncnn2c(C3CCCN(C(=O)C4CNC4)C3)cc(-c3ccc4cn(Cc5ccccc5)nc4c3)c12]

In a manner similar to the procedure described for the preparation of Example 251 and substituting 1-(tert-butoxycarbonyl)azetidine-3-carboxylic acid for 1-(Boc-aminomethyl)-cyclopropyl-1-carboxylic acid, 18 mg (15%) of the desired product was isolated. $^1$H NMR (400 MHz, DMSO-d$_6$) δ 8.54 (s, 1 H), 7.85-7.95 (m, 1 H), 7.79 (d, 1 H), 7.58 (s, 1 H), 7.28-7.39 (m, 5 H), 7.13 (d, 1 H), 6.64 (s, 1 H), 5.64 (s, 2 H), 4.19-4.66 (m, 1 H), 2.93-3.96 (m, 8 H), 2.60-2.79 (m, 1 H), 1.98-2.19 (m, 1 H), 1.61-1.96 (m, 2 H), 1.33-1.61 (m, 1 H); ES-MS m/z 507.36 [M+H]$^+$, HPLC RT (min) 2.27.

Example 254

Preparation of 2-{3-[4-amino-5-(2-benzyl-2H-indazol-6-yl)pyrrolo[2,1-f][1,2,4]triazin-7-yl]piperidin-1-yl}ethanol

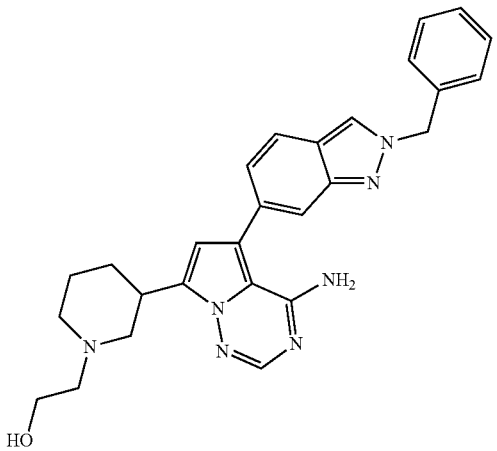 [SMILES: Nc1ncnn2c(C3CCCN(CCO)C3)cc(-c3ccc4cn(Cc5ccccc5)nc4c3)c12]

To a solution of 5-(2-benzyl-2H-indazol-6-yl)-7-piperidin-4-ylpyrrolo[2,1-f][1,2,4]triazin-4-amine (100 mg, 0.22 mmol) in THF (1.5 mL) was added (2-bromoethoxy)-tert-butyldimethylsilane (51 µL, 0.24 mmol) and N,N-diisopropylethylamine (114 µl, 0.65 mmol). The reaction was heated at 60° C. for 17 h and then cooled to rt. Additional (2-bromoethoxy)-tert-butyldimethylsilane (51 µL) and N,N-diisopropylethylamine (114 µl) were added and the mixture continued to stir at 60° C. for 64 h. The crude mixture was purified by preparative HPLC using a gradient elution from 20% to 50% acetonitrile in water followed by filtration through an acidic resin, washing with MeOH. The product was eluted with 2M NH$_3$ in MeOH and the filtrate was concentrated. A solution of the residue in 1% HCl in 95:5 EtOH/H$_2$O (4 mL) was stirred at rt for 16 h. The mixture was basified (pH 9) with the addition of saturated, aqueous NaHCO$_3$ solution and was evaporated to remove volatiles. The aqueous mixture was extracted with ethyl acetate (3×15 mL) and the combined organic layers were washed with brine, dried (Na$_2$SO$_4$) and concentrated.

The compound was crystallized from EtOAc/hexanes to afford 24 mg (23%) of the desired product. $^1$H NMR (400 MHz, DMSO-d$_6$) δ 8.53 (s; 1 H), 7.89 (s, 1 H), 7.79 (d, 1 H), 7.57 (s, 1 H), 7.28-7.39 (m, 5 H), 7.13 (d, 1 H), 6.62 (s, 1 H), 5.64 (s, 1 H), 4.40 (br s, 1 H), 3.50 (d, 2 H), 3.37 (s, 1 H), 3.09 (s, 1 H), 2.86 (s, 1 H), 2.41 (s, 2 H), 1.89-2.05 (m, 2 H), 1.43-1.77 (m, 4H); ES-MS m/z 468.26 [M+H]$^+$, HPLC RT (min) 2.19.

Example 255

Preparation of 2-{3-[4-amino-5-(2-benzyl-2H-indazol-6-yl)pyrrolo[2,1-f][1,2,4]triazin-7-yl]piperidin-1-yl}-N,N-dimethylacetamide

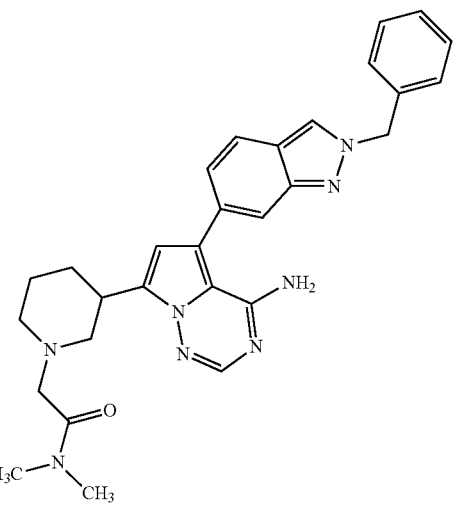

To a solution of 5-(2-benzyl-2H-indazol-6-yl)-7-piperidin-4-ylpyrrolo[2,1-f][1,2,4]triazin-4-amine (100 mg, 0.24 mmol) in DMF (1.5 mL) was added 2-chloro-N,N-dimethylacetamide (32 mg, 0.26 mmol) and N,N-diisopropylethylamine (123 µL, 0.71 mmol). The reaction was stirred at 60° C. for 17 h. The crude mixture was purified via ISCO® chromatography using 9:1 CH$_2$Cl$_2$ to afford 23 mg (19%) of the desired product. $^1$H NMR (400 MHz, DMSO-d$_6$) δ 8.54 (s, 1 H), 7.89 (s, 1 H), 7.78 (d, 1 H), 7.57 (s, 1 H), 7.25-7.45 (m, 5 H), 7.09-7.19 (m, 1 H), 6.63 (s, 1 H), 5.65 (s, 2 H), 3.34-3.52 (m, 2 H), 2.97-3.16 (m, 6H), 2.72-2.91 (m, 4 H), 2.09-2.43 (m, 2 H), 1.85-2.06 (m, 1 H), 1.44-1.89 (m, 2 H); ES-MS m/z 509.30 HPLC RT (min) 2.42.

Example 256

Preparation of 5-(2-benzyl-2H-indazol-6-yl)-7-(1-cyclopropylpiperidin-3-yl)pyrrolo[2,1-f][1,2,4]triazin-4-amine

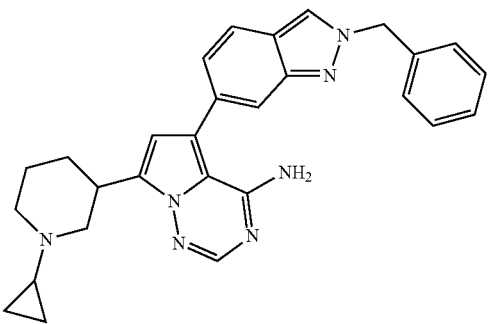 [SMILES: Nc1ncnn2c(C3CCCN(C4CC4)C3)cc(-c3ccc4cn(Cc5ccccc5)nc4c3)c12]

To a solution of 5-(2-benzyl-2H-indazol-6-yl)-7-piperidin-4-ylpyrrolo[2,1-f][1,2,4]triazin-4-amine (85 mg, 0.20 mmol) in MeOH (2.3 mL) containing 3 Å molecular sieves was added AcOH (114 µL, 2.00 mmol), [(1-ethoxycyclopropyl)oxy]trimethylsilane (241 μL, 1.20 mmol) and sodium cyanoborohydride (57 mg, 0.90 mmol). The reaction was stirred at 60° C. for 17 h. Aqueous NaOH (1N, 15 mL) was added and the mixture was extracted with EtOAc (3×15 mL). The combined organic layers were washed with brine, dried (Na$_2$SO$_4$) and concentrated. The residue was purified by preparative HPLC using a gradient elution from 15% to 45% acetonitrile in water followed by filtration through an acidic resin, washing with MeOH. The product was eluted with 2M NH$_3$ in MeOH and the filtrate was concentrated to provide 37 mg (40%) of the desired product. $^1$H NMR (400 MHz, DMSO-d$_6$) δ 8.24 (s, 1 H), 7.60 (s, 1 H), 7.50 (d, 1 H), 7.29 (s, 1 H), 6.98-7.08 (m, 5 H), 6.84 (dd, 1 H), 6.31 (s, 1 H), 5.35 (s, 2 H), 2.96-3.05 (m, 1 H), 2.88 (d, 1 H), 2.60 (d, 1 H), 2.01 (t, 1 H), 1.93 (t, 1 H), 1.62-1.71 (m, 1 H), 1.12-1.41 (m, 4 H), −0.04-0.16 (m, 4 H); ES-MS m/z 463.31 [M+H]$^+$, HPLC RT (min) 1.48.

Example 257

Preparation of 5-(2-benzyl-3-methyl-2H-indazol-6-yl)-7-piperidin-3-ylpyrrolo[2,1-f][1,2,4]triazin-4-amine

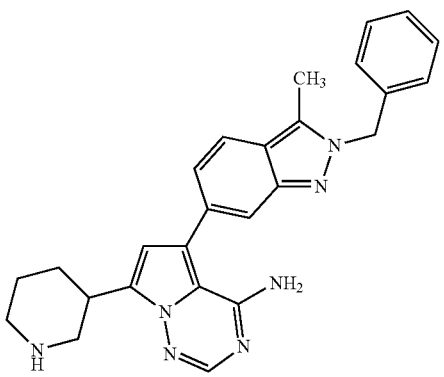 [SMILES: Cc1c2ccc(-c3cc(C4CCCNC4)n4ncnc(N)c34)cc2nn1Cc1ccccc1]

Using the procedures described in Steps 1-6 of Intermediate SS and substituting 4,4,5,5-tetramethyl-1,3,2-dioxaborolan-2-ol-2-benzyl-3-methyl-6-(4,4,5,5-tetramethyl-1,3,2-dioxaborolan-2-yl)-2H-indazole (1:1) for Intermediate C, 5-(2-benzyl-3-methyl-2H-indazol-6-yl)-7-piperidin-3-ylpyrrolo[2,1-f][1,2,4]triazin-4-amine hydrochloride was prepared. The salt was dissolved in 3:1 CHCl$_3$/isopropanol (25 mL). The mixture was washed with saturated, aqueous NaHCO$_3$ (25 mL), brine, dried (Na$_2$SO$_4$) and concentrated to dryness to afford the title compound. $^1$H NMR (400 MHz, DMSO-d$_6$) δ 7.89 (s, 1 H), 7.76 (d, 1 H), 7.53 (s, 1 H), 7.24-7.38 (m, 3 H), 7.21 (d, 2 H), 7.08 (dd, 1 H), 6.58 (s, 1 H), 5.64 (s, 2 H), 3.14-3.30 (m, 3H,) 2.93 (d, 1 H), 2.62 (s, 3 H), 2.50-2.59 (m, 1 H), 2.01-2.11 (m, 1 H), 1.43-1.70 (m, 3 H); ES-MS m/z 438.39 [M+H]$^+$, HPLC RT (min) 2.10.

Example 258

Preparation of 5-(2-benzyl-3-methyl-2H-indazol-6-yl)-7-{1-[(dimethylamino)acetyl]piperidin-3-yl}pyrrolo[2,1-f][1,2,4]triazin-4-amine

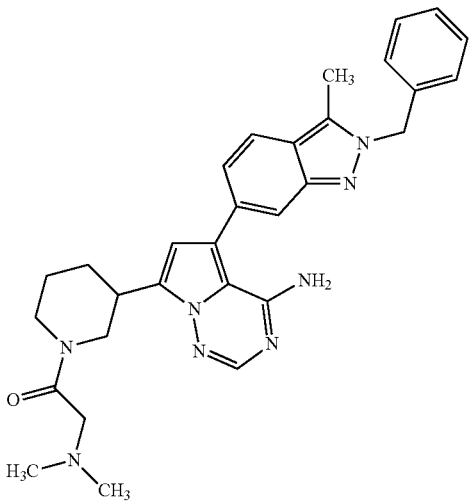 [SMILES: Cc1c2ccc(-c3cc(C4CCCN(C(=O)CN(C)C)C4)n4ncnc(N)c34)cc2nn1Cc1ccccc1]

A mixture of 5-(2-benzyl-3-methyl-2H-indazol-6-yl)-7-piperidin-3-ylpyrrolo[2,1-f][1,2,4]triazin-4-amine (100 mg, 0.23 mmol), N,N-dimethylglycine (28 mg, 0.27 mmol), EDCl (48 mg, 0.25 mmol), HOBt (34 mg, 0.25 mmol), and N,N-diisopropylethylamine (119 μL, 0.69 mmol) in DMF (1.5 mL) was stirred at rt for 16 h. The crude mixture was purified by preparative HPLC using a gradient elution from 15% to 45% acetonitrile in water followed by filtration through an acidic resin, washing with MeOH. The product was eluted with 2M NH$_3$ in MeOH and the filtrate was concentrated to provide 19 mg (16%) of the desired product. $^1$H NMR (400 MHz, DMSO-d$_6$) δ 7.92 (d, 1 H), 7.76 (d, 1 H), 7.53 (s, 1 H), 7.25-7.38 (m, 3 H), 7.21 (d, 2 H), 7.08 (d, 1 H), 6.63-6.68 (m, 1 H), 5.63 (s, 2 H), 3.96-4.95 (m, 2 H), 2.83-3.34 (m, 5 H), 2.57-2.77 (m, 4 H), 2.06-2.23 (m, 6 H), 1.69-1.92 (m, 2 H), 1.39-1.64 (m, 1 H); ES-MS m/z 523.41 [M+H]$^+$, HPLC RT (min) 2.20.

Example 259

Preparation of 5-(2-phenyl-2H-indazol-6-yl)-7-piperidin-3-ylpyrrolo[2,1-f][1,2,4]triazin-4-amine

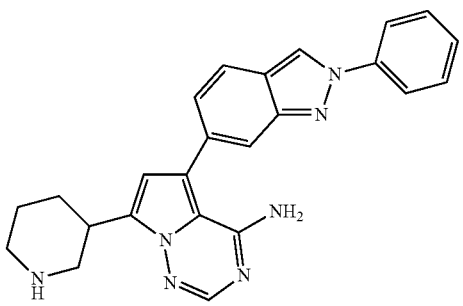 [SMILES: Nc1ncnn2c(C3CCCNC3)cc(-c3ccc4cn(-c5ccccc5)nc4c3)c12]

Using the procedures described in Steps 1-6 of Intermediate SS and substituting 2-phenyl-6-(4,4,5,5-tetramethyl-1,3,2-dioxaborolan-2-yl)-2H-Indazole for Intermediate C, 5-(2-phenyl-2H-indazol-6-yl)-7-piperidin-3-ylpyrrolo[2,1-f][1,2,4]triazin-4-amine hydrochloride was prepared. The salt was dissolved in 3:1 CHCl$_3$/isopropanol (25 mL). The mixture was washed with saturated, aqueous NaHCO$_3$ (25 mL), brine, dried (Na$_2$SO$_4$) and concentrated to dryness to afford the title compound. $^1$H NMR (400 MHz, DMSO-d$_6$) δ 9.19 (s, 1 H), 8.12 (d, 2 H), 7.80-8.02 (m, 2 H), 7.71 (s, 1 H), 7.54-7.79 (m, 2 H), 7.39-7.54 (m, 1 H), 7.25 (d, 1 H), 6.67 (s, 1 H), 3.19-3.48 (m, 3 H), 2.93-3.05 (m, 1 H), 2.48-2.73 (m, 2 H), 2.01-2.17 (m, 1 H), 1.46-1.82 (m, 2 H); ES-MS m/z 410.36 [M+H]$^+$, HPLC RT (min) 2.05.

Example 260

Preparation of 7-{1-[(dimethylamino)acetyl]piperidin-3-yl}-5-(2-phenyl-2H-indazol-6-yl)pyrrolo[2,1-f][1,2,4]triazin-4-amine

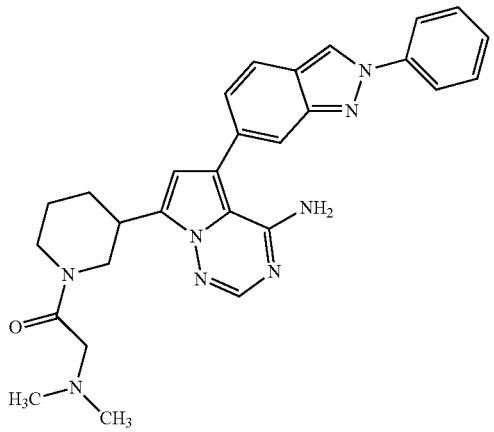 [SMILES: CN(C)CC(=O)N1CCCC(c2cc(-c3ccc4cn(-c5ccccc5)nc4c3)c3c(N)ncnn23)C1]

A mixture of 5-(2-phenyl-2H-indazol-6-yl)-7-piperidin-3-ylpyrrolo[2,1-f][1,2,4]triazin-4-amine (120 mg, 0.27 mmol), N,N-dimethylglycine (31 mg, 0.30 mmol), EDCl (62 mg, 0.32 mmol), HOBt (44 mg, 0.32 mmol), and N,N-diisopropylethylamine (187 µL, 1.08 mmol) in DMF (2 mL) was stirred at rt for 16 h. The crude mixture was purified by preparative HPLC using a gradient elution from 15% to 45% acetonitrile in water followed by filtration through an acidic resin, washing with MeOH. The product was eluted with 2M NH$_3$ in MeOH and the filtrate was concentrated to provide 19 mg (16%) of the desired product. $^1$H NMR (400 MHz, DMSO-d$_6$) δ 9.16 (s, 1 H), 8.10 (d, 2 H), 7.94 (d, 1 H), 7.85 (d, 1 H), 7.69 (s, 1 H), 7.53-7.63 (m, 2 H), 7.39-7.48 (m, 1 H), 722 (s, 1 H), 6.67-6.73 (m, 1 H), 3.98-4.57 (m, 2 H), 2.84-3.38 (m, 5 H), 2.58-2.81 (m, 1 H), 2.08-2.29 (m, 6 H), 1.68-1.91 (m, 2 H), 1.39-1.66 (m, 1 H); ES-MS m/z 495.15 [M+H]$^+$, HPLC RT (min) 2.27.

Example 261

Preparation of 5-(2-benzyl-2H-indazol-6-yl)-7-Piperidin-2-ylpyrrolo[2,1-f][1,2,4]triazin-4-amine

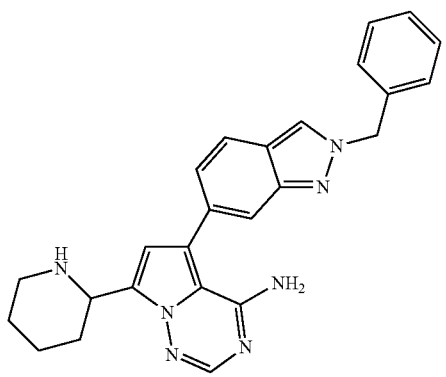 [SMILES: Nc1ncnn2c(C3CCCCN3)cc(-c3ccc4cn(Cc5ccccc5)nc4c3)c12]

Step 1: Preparation of benzyl 2-oxopiperidine-1-carboxylate

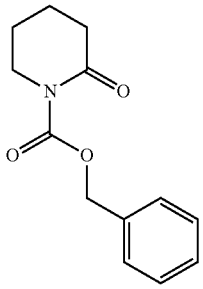 [SMILES: O=C1CCCCN1C(=O)OCc1ccccc1]

n-Butyllithium (2.5 M in hexanes; 12.11 mL, 30.26 mmol) was added dropwise to a cooled (−78° C.) solution of piperidin-2-one (2.50 g, 25.22 mmol) in THF (100 mL). The mixture was stirred at −78° C. for 2.5 h. A solution of benzyl chloroformate (7.20 mL, 50.44 mmol) in THF (30 mL) was added dropwise. The mixture was stirred at −78 PC for 2 h and then was allowed to warm to rt. Water was added (200 and the mixture was extracted with EtOAc (3×100 mL). The combined organics were washed with brine, dried (Na$_2$SO$_4$), and concentrated to dryness to afford 4.13 g (70%) of the desired product. ES-MS m/z 233.91 [M+H]$^+$, HPLC RT (min) 2.76.

Step 2: Preparation of benz 6-[(diphenoxyphosphoryl)oxy]-3,4-dihydropyridine-1(2H)-carboxylate

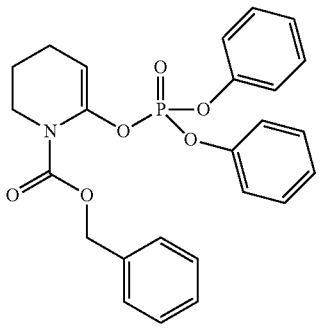 [SMILES: O=C(OCc1ccccc1)N1CCCC=C1OP(=O)(Oc1ccccc1)Oc1ccccc1]

n-Butyllithium (2.5M in hexanes; 2.23 mL, 5.57 mmol) was added dropwise to a cooled (0° C.) solution of diisopropylamine (781 µL, 5.57 mmol) in THF (3 mL). The mixture was stirred at 0° C. for 1 h. This mixture was then added dropwise to a cooled (−78° C.) solution of benzyl 2-oxopiperidine-1-carboxylate (1.00 g, 4.29 mmol) and 1,2-bis(dimethylamino)ethane (809 µL, 5.36 mmol) in THF (15 mL). The mixture was stirred at −78° C. for 2 h. A solution of diphenyl chlorophosphate (1.07 mL, 5.14 mmol) in THF (5 mL) was added to the reaction dropwise. The mixture was stirred at −78° C. for 1 h and was then allowed to warm to rt. Aqueous NaOH (1N, 50 mL) was added and the mixture was extracted with EtOAc (3×50 mL). The combined organic layers were washed with brine, dried (Na$_2$SO$_4$), and concentrated to dryness to afford 1.61 g (81%) of the desired product. ES-MS m/z 488.16 [M+Na]$^+$, HPLC RT (min) 3.69.

Step 3: Preparation of (4-aminopyrrolo[2,1-f][1,2,4]triazin-7-yl)boronic acid

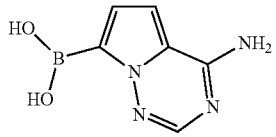 [SMILES: Nc1ncnn2c(B(O)O)ccc12]

To a stirred suspension of Intermediate B (1.00 g, 4.69 mmol) in THF (15 mL) was added chlorotrimethylsilane (1.31 mL, 10.33 mmol), dropwise. The mixture was stirred at rt for 90 min and 2-propyl magnesium chloride (2M in THF; 10.56 mL, 21.12 mmol) was added dropwise. The suspension immediately became a solution. The mixture was stirred at rt for 2 h. The mixture was placed in an ice bath and a solution of trimethyl borate (1.05 mL, 9.39 mmol) in THF (5 mL) was added dropwise. The ice bath was removed and the reaction was stirred at rt for 1 h. The reaction mixture was poured over ice and saturated, aqueous ammonium chloride (200 mL). The mixture was allowed to warm to rt and was extracted with EtOAc (3×75 mL). The combined organic layers were washed with brine, dried (Na$_2$SO$_4$), and concentrated to dryness. The crude residue was purified by ISCO® chromatography using a gradient of 0 to 20% methanol in ethyl acetate to afford 462 mg (55%) of the desired product. ES-MS m/z 179.14 [M+H]$^+$, HPLC RT (min) 1.02.

Step 4: Preparation of benzyl 6-(4-aminopyrrolo[2,1-f][1,2,4]triazin-7-yl)-3,4-dihydropyridine-1(2H)-carboxylate

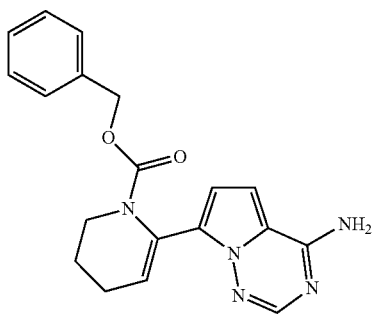 [SMILES: Nc1ncnn2c(C3=CCCCN3C(=O)OCc3ccccc3)ccc12]

Using the procedure described in Step 1 of Example 1 and substituting benzyl 6-(diphenoxyphosphoryl)oxy]-3,4-dihydropyridine-1(2H)-carboxylate for tert-butyl 4-(4,4,5,5-tetramethyl-1,3,2-dioxaborolan-2-yl)-3,6-dihydropyridine-1(2H)-carboxylate and employing 4-aminopyrrolo[2,1-f][1,2,4]triazin-7-yl)boronic acid, the desired compound was obtained from the coupling reaction. ES-MS m/z 350.45 [M+H]$^+$, HPLC RT (min) 2.46.

Step 5: Preparation of tert-butyl 2-(4-aminopyrrolo[2,1-f][1,2,4]triazin-7-yl)piperidine-1-carboxylate

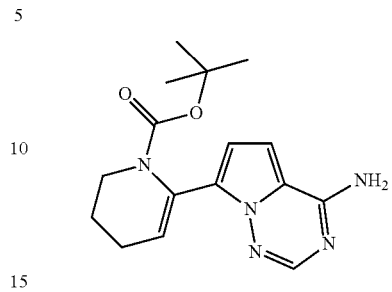

To a dry flask purged with N$_2$ was added platinum(IV) oxide (32 mg, 0.14 mmol) followed by benzyl 6-(4-aminopyrrolo[2,1-f][1,2,4]triazin-7-yl)-3,4-dihydropyridine-1(2H)-carboxylate (480 mg, 1.37 mmol) as a solution in acetic acid (15 mL). The mixture was stirred under an H$_2$ atmosphere for 6 h. Additional platinum(IV) oxide (32 mg) was added and the mixture continued to stir under an H$_2$ atmosphere for an additional 16 h. The mixture was filtered through a pad of Celite®, eluting with acetic acid. The solvent was evaporated under reduced pressure. To a solution of the residue in THF (6 mL) was added 2N aqueous NaOH (6.9 mL, 13.7 mmol) and di-tert-butyl carbonate (314 mg, 1.44 mmol). The solvent was evaporated under reduced pressure and the aqueous mixture was extracted with ethyl acetate (3×15 mL). The organic layers were washed with brine, dried (Na$_2$SO$_4$) and concentrated to dryness to afford 440 mg (100%) of the desired product. ES-MS m/z 318.08 [M+H]$^+$, HPLC RT (min) 2.45.

Step 6: Preparation of the Title Compound

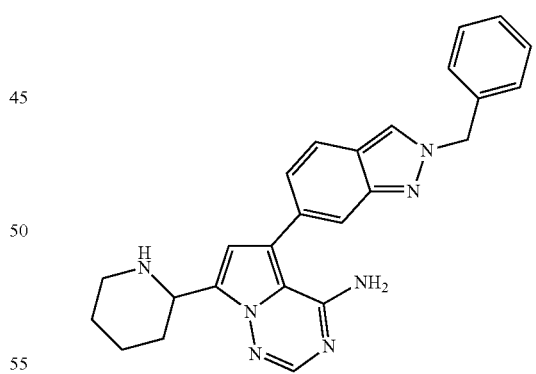

Following the procedure described in Steps 3-5 (bromination, coupling, deprotection) of Example 1, the title compound was prepared using tert-butyl 2-(4-aminopyrrolo[2,1-f][1,2,4]triazin-7-yl)piperidine-1-carboxylate and Intermediate C. $^1$H NMR (400 MHz, CD$_3$OD) δ 8.36 (s, 1 H), 7.85 (s, 1 H), 7.81 (d, 1 H), 7.64 (s, 1 H), 7.27-7.41 (m, 5 H), 7.22 (dd, 1 H), 6.73 (s, 1 H), 5.65 (s, 2 H), 4.27 (dd, 1 H), 3.08-3.18 (m, 1 H), 2.79-2.90 (m, 1 H), 1.51-2.14 (m, 6 H); ES-MS m/z 424.42 [M+H]$^+$, HPLC RT (min) 2.14.

Example 262

Preparation of 5-(2-benzyl-2H-indazol-6-yl)-7-{1-[(dimethylamino)acetyl]piperidin-2-yl}pyrrolo[2,1-f][1,2,4]triazin-4-amine

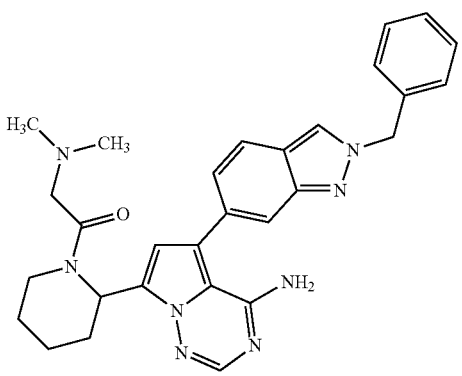 [SMILES: CN(C)CC(=O)N1CCCCC1c1cc(-c2ccc3cn(Cc4ccccc4)nc3c2)c2c(N)ncnn12]

A mixture of 5-(2-benzyl-2H-indazol-6-yl)-7-piperidin-2-ylpyrrolo[2,1-f][1,2,4]triazin-4-amine (100 mg, 0.22 mmol), N,N-dimethylglycine (27 mg, 0.26 mmol), EDCl (46 mg, 0.24 mmol), HOBt (32 mg, 0.24 mmol), and N,N-diisopropylethylamine (114 µL, 0.65 mmol) in DMF (1.5 mL) was stirred at it for 16 h. The crude mixture was purified by preparative HPLC using a gradient elution from 15% to 45% acetonitrile in water followed by filtration through an acidic resin, washing with MeOH. The product was eluted with 2M $NH_3$ in MeOH and the filtrate was concentrated to provide 11 mg (10%) of the desired product. NMR (400 MHz, $CD_3OD$) δ 8.54 (s, 1 H), 7.90 (s, 1 H), 7.80 (d, 1 H), 7.55-7.68 (m, 1 H), 7.25-7.42 (m, 5 H), 7.16 (s, 1 H), 6.08 (d, 1 H), 5.65 (s, 2 H), 3.59-4.46 (m, 2 H), 2.99-3.26 (m, 1 H), 2.63-2.85 (m, 1 H), 2.25-2.42 (m, 1 H), 1.97 (s, 6 H), 1.54-1.82 (m, 3 H), 1.29-1.53 (m, 1 H), 1.22 (s, 2 H); ES-MS m/z 509.26 [M+H]$^+$, HPLC RT (min) 2.16.

Example 263

Preparation of 3-[4-amino-5-(2-benzyl-2H-indazol-6-yl)pyrrolo[2,1-f][1,2,4]triazin-7-yl]piperidin-3-ol

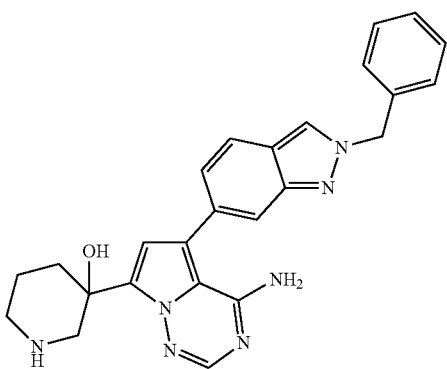 [SMILES: Nc1ncnn2c(C3(O)CCCNC3)cc(-c3ccc4cn(Cc5ccccc5)nc4c3)c12]

Step 1: Preparation of tert-butyl 3-(4-amino-5-bromopyrrolo[2,1-f][1,2,4]triazin-7-yl)-3-hydroxypiperidine-1-carboxylate

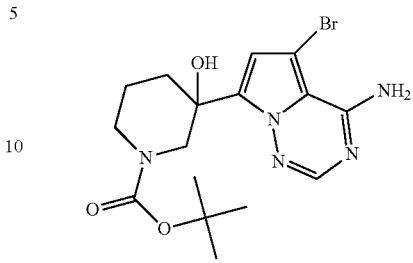

To a cooled (−20° C.) solution tert-butyl 3-(4-aminopyrrolo[2,1-f][1,2,4]triazin-7-yl)-3-hydroxypiperidine-1-carboxylate (1.00 g, 3.00 mmol) in THF (16 mL) was added 1,3-dibromo-5,5-dimethylhydantoin (429 mg, 1.50 mmol) in 3 portions over 10 min. The mixture was allowed warm to 0° C. and stirred for 2 h. The mixture was then stirred at rt for 64 h. Saturated, aqueous $Na_2SO_3$ (50 mL) was added and the mixture was warmed to rt. The mixture was extracted with ethyl acetate (3×50 mL). The combined organic layers were washed with brine, dried ($Na_2SO_4$) and evaporated. The crude mixture was purified via ISCO® chromatography using a gradient of 50 to 75% ethyl acetate in hexanes to afford 892 mg (72%) of the desired product. ES-MS m/z 412.26 [M+H]$^+$, HPLC RT (min) 2.62.

Step 2: Preparation of tert-butyl 3-[4-amino-5-(2-benzyl-2H-indazol-6-yl)pyrrolo[2,1-f][1,2,4]triazin-7-yl]-3-hydroxypiperidine-1-carboxylate

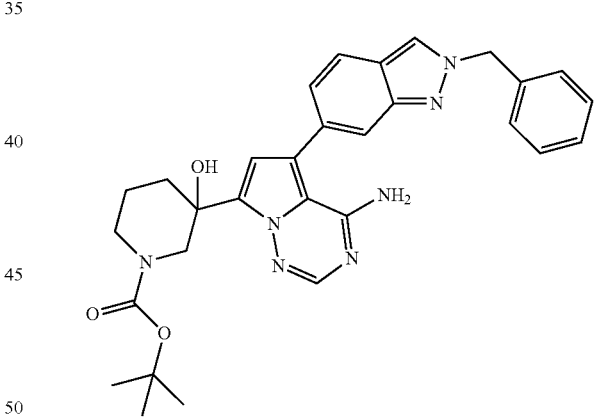

To a stirred, degassed mixture tert-butyl 3-(4-amino-5-bromopyrrolo[2,1-f][1,2,4]triazin-7-yl)-3-hydroxypiperidine-1-carboxylate (292 mg, 0.71 mmol), Intermediate C (355 mg, 1.06 mmol), $Na_2CO_3$ (225 mg, 2.13 mmol) and $H_2O$ (1 mL) in DMF (6 mL) was added tetrakis(triphenylphosphine)palladium(0) (82 mg, 0.071 mmol). The reaction was heated (110° C.) for 17 h and then cooled to rt. The mixture was partitioned between ethyl acetate (50 mL) and $H_2O$ (50 mL). The layers were separated and the aqueous layer was further extracted with ethyl acetate (1×50 mL). The combined organic layers were washed with brine, dried ($Na_2SO_4$), and concentrated to dryness. The crude material was purified via ISCO® chromatography using a gradient of 50 to 75% ethyl acetate in hexanes to afford 270 mg (71%) of the desired product, which contained trace impurities. ES-MS m/z 540.30 [M+H]$^+$, HPLC RT (min) 2.91.

343

Step 3: Preparation of the Title Compound

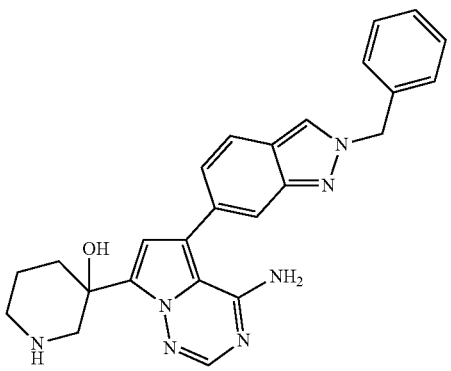 [SMILES: Nc1ncnn2c(C3(O)CCCNC3)cc(-c3ccc4cn(Cc5ccccc5)nc4c3)c12]

To a solution of tert-butyl 3-[4-amino-5-(2-benzyl-2H-indazol-6-yl)pyrrolo[2,1-f][1,2,4]triazin-7-yl]-3-hydroxypiperidine-1-carboxylate (270 mg, 0.500 mmol) in MeOH (2.5 mL) was added 4M HCl in dioxane (1.25 mL). The mixture was stirred at rt for 17 h. The mixture was concentrated and the residue was dissolved in 3:1 CHCl$_3$/isopropanol (25 mL). The mixture was washed with saturated, aqueous NaHCO$_3$ (25 mL), brine, dried (Na$_2$SO$_4$) and concentrated to dryness to afford 211 mg (96%) of the desired product, which was approximately 50% pure. ES-MS m/z 440.19 [M+H]$^+$, HPLC RT (min) 1.97. 50 mg of material was purified by preparative HPLC using a gradient elution from 15% to 40% acetonitrile in water followed by filtration through an acidic resin, washing with MeOH. The product was eluted with 2M NH$_3$ in MeOH and the filtrate was concentrated to provide 28 mg of pure desired product. $^1$H NMR (400 MHz, DMSO-d$_6$) δ 8.54 (s, 1 H), 7.89 (s, 1 H), 7.80 (d, 1 H), 7.58 (s, 1 H), 7.27-7.37 (m, 5 H), 7.13 (dd, 1.36 Hz, 1 H), 6.69 (s, 1 H), 5.64 (s, 2 H), 5.19 (s, 1 H), 2.77-2.93 (m, 2 H), 2.43-2.54 (m, 3 H), 2.12 (br s, 1 H), 1.68-1.88 (m, 2 H), 1.33-1.46 (m, 1 H); ES-MS m/z 439.92 [M+H]$^+$, HPLC RT (min) 2.06.

Example 264

Preparation of 5-(2-benzyl-2H-indazol-6-yl)-7-{1-[(dimethylamino)acetyl]-1,4,5,6-tetrahydropyridin-3-yl}pyrrolo[2,1-f][1,2,4]triazin-4-amine

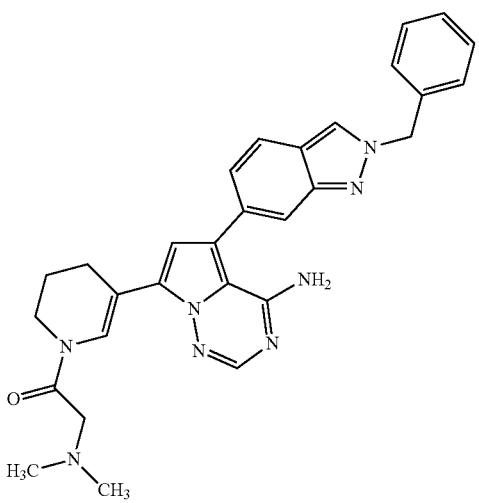 [SMILES: CN(C)CC(=O)N1C=C(c2cc(-c3ccc4cn(Cc5ccccc5)nc4c3)c3c(N)ncnn23)CCC1]

344

Step 1: Preparation of 3-[4-amino-5-(2-benzyl-2H-indazol-6-yl)pyrrolo[2,1-f][1,2,4]triazin-7-yl]-1-(N,N-dimethylglycyl)piperidin-3-ol

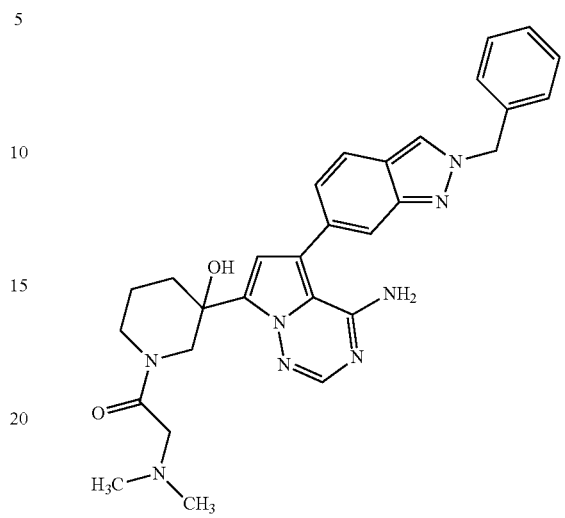

A mixture of 3-[4-amino-5-(2-benzyl-2H-indazol-6-yl)pyrrolo[2,1-f][1,2,4]triazin-7-yl]piperidin-3-ol (154 mg, 0.35 mmol), N,N-dimethylglycine (43 mg, 0.42 mmol), EDCI (74 mg, 0.39 mmol), HOBt (52 mg, 0.39 mmol), and N,N-diisopropylethylamine (183 µL, 1.05 mmol) in DMF (3.0 mL) was stirred at rt for 80 h. The crude mixture was purified by preparative HPLC using a gradient elution from 15% to 45% acetonitrile in water followed by filtration through an acidic resin, washing with MeOH. The product was eluted with 2M NH$_3$ in MeOH and the filtrate was concentrated to provide 61 mg (33%) of the desired product. ES-MS m/z 525.52 [M+H]$^+$, HPLC RT (min) 2.04.

Step 2: Preparation of Title Compound

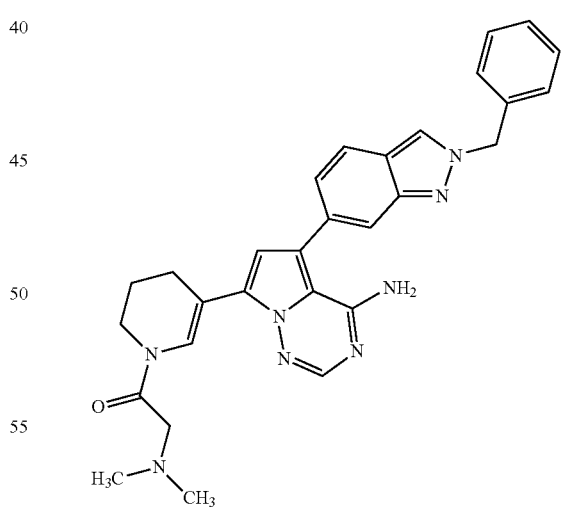

To a cooled (0° C.) mixture of 3-[4-amino-5-(2-benzyl-2H-indazol-6-yl)pyrrolo[2,1-f][1,2,4]triazin-7-yl]-1-(N,N-dimethylglycyl)piperidin-3-ol (58 mg, 0.11 mmol) and N,N-diisopropylethylamine (58 µL, 0.33 mmol) in CH$_2$Cl$_2$ (2 mL) was added trifluoroacetic anhydride (31 µL, 0.22 mmol), dropwise. The ice bath was removed and the mixture was stirred at rt for 2 h. The reaction was cooled (0° C.) and additional N,N-diisopropylethylamine (58 µL) and trifluoroacetic anhydride (31 µL) was added. The ice bath was removed and the reaction was stirred at rt for 5 h. Water (5 mL) was added and the layers were separated. The aqueous phase was extracted with CH$_2$Cl$_2$ (2×5 mL) and the combined organic layers were washed with brine, dried (Na$_2$SO$_4$) and concentrated. To a solution of the residue in EtOH (3 mL) was added NaOH (66 mg, 1.66 mmol). The mixture was stirred at rt for 17 h. The mixture was partitioned between EtOAc (10 mL) and H$_2$O (10 mL). The layers were separated and the organic phase was washed with H$_2$O (10 mL), brine, dried (Na$_2$SO$_4$) and concentrated. The material was crystallized from EtOAc/hexanes to afford 41 mg (73%) of the desired product. $^1$H NMR (400 MHz, DMSO-d$_6$) δ 8.66-8.70 (m, 1H,) 8.55 (s, 1 H), 7.94-7.98 (m, 1 H), 7.81 (d, 1 H), 7.61 (s, 1 H), 7.27-7.36 (m, 5 H), 7.15 (dd, 1 H), 6.76-6.80 (m, 1 H), 5.65 (s, 2 H), 3.56-3.79 (m, 2 H), 3.22-3.28 (m, 2 H), 2.48-2.59 (m, 2 H), 2.17-2.25 (m, 6 H), 1.85-1.94 (m, 2 H); ES-MS m/z 507.13 [M+H]$^+$, HPLC RT (min) 2.31.

Example 265

Preparation of 7-azepan-4-yl-5-(2-benzyl-2H-indazol-6-yl)pyrrolo[2,1-f][1,2,4]triazin-4-amine

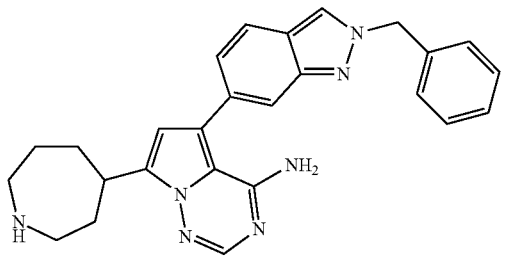 [SMILES: Nc1ncnn2c(C3CCCNCC3)cc(-c3ccc4cn(Cc5ccccc5)nc4c3)c12]

7-Azepan-4-yl-5-(2-benzyl-2H-indazol-6-yl)pyrrolo[2,1-f][1,2,4]triazin-4-amine hydrochloride (50 mg, 0.11 mmol) was purified via preparative HPLC using a gradient elution from 15% to 40% acetonitrile in water followed by filtration through an acidic resin, washing with MeOH. The product was eluted with 2M NH$_3$ in MeOH and the filtrate was concentrated to provide 11 mg (24%) of the desired product. $^1$H NMR (400 MHz, Methanol-d$_4$) δ 8.35 (s, 1 H), 7.75-7.82 (m, 2 H), 7.64 (d, 1 H), 7.29-7.37 (m, 5 H), 7.22 (dd, 1 H), 6.60 (s, 1 H), 5.64 (m, 2 H), 3.47-3.56 (m, 1 H), 2.93-3.18 (m, 4 H), 2.15-2.27 (m, 2 H), 1.77-2.03 (m, 4 H); ES-MS m/z 438.26 [M+H]$^+$, HPLC RT (min) 2.12.

Example 266

Preparation of 5-(2-benzyl-2H-indazol-6-yl)-7-[1-(methylsulfonyl)azepan-4-yl]pyrrolo[2,1-f][1,2,4]triazin-4-amine

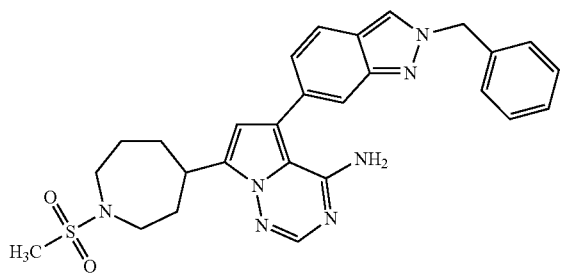 [SMILES: CS(=O)(=O)N1CCCC(c2cc(-c3ccc4cn(Cc5ccccc5)nc4c3)c3c(N)ncnn23)CC1]

To a solution of 7-azepan-4-yl-5-(2-benzyl-2H-indazol-6-yl)pyrrolo[2,1-f][1,2,4]triazin-4-amine (100 mg, 0.20 mmol) in DMF (1.5 mL) was added methanesulfonyl chloride (17 pt, 0.22 mmol) and N,N-diisopropylethylamine (136 μL, 0.78 mmol). The reaction was stirred at rt for 17 h. The crude mixture was purified by preparative HPLC using a gradient elution from 15% to 40% acetonitrile in water followed by filtration through an acidic resin, washing with MeOH. The product was eluted with 2M NH$_3$ in MeOH and the filtrate was concentrated to provide 21 mg (21%) of the desired product. $^1$H NMR (400 MHz, DMSO-d$_6$) δ 8.53 (s, 1 H), 7.90 (s, 1 H), 7.78 (dd, 1 H), 7.58 (s, 1 H), 7.28-7.38 (m, 5 H), 7.14 (dd, 1 H), 6.61 (s, 1 H), 5.64 (s, 2 H), 3.19-3.56 (m, 4 H), 2.90 (s, 3 H), 1.66-2.20 (m, 7 H); ES-MS m/z 516.30 [M+H]$^+$, HPLC RT (min) 3.07.

Example 267

Preparation of 5-(2-benzyl-2H-indazol-6-yl)-7-(1-cyclopropylazepan-4-yl)pyrrolo[2,1-f][1,2,4]triazin-4-amine

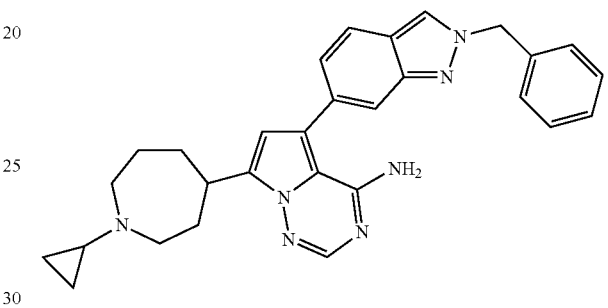

To a solution of 7-azepan-4-yl-5-(2-benzyl-2H-indazol-6-yl)pyrrolo[2,1-f][1,2,4]triazin-4-amine (100 mg, 0.20 mmol) in MeOH (2 mL) containing 3 Å molecular sieves was added AcOH (112 μL, 2.00 mmol), [(1-ethoxycyclopropyl)oxy]trimethylsilane (236 μL, 1.18 mmol) and sodium cyanoborohydride (55 mg, 0.88 mmol). The reaction was stirred at 60° C. for 17 h. Aqueous NaOH (1N, 15 mL) was added and the mixture was extracted with EtOAc (3×15 mL). The combined organics were washed with brine, dried (Na$_2$SO$_4$) and concentrated. The residue was purified by preparative HPLC using a gradient elution from 15% to 40% acetonitrile in water followed by filtration through an acidic resin, washing with MeOH. The product was eluted with 2M NH$_3$ in MeOH and the filtrate was concentrated to provide 47 mg (50%) of the desired product. $^1$H NMR (400 MHz, DMSO-d$_6$) δ 8.23 (s, 1 H), 7.58 (s, 1 H), 7.48 (d, 1 H), 7.28 (s, 1 H), 6.97-7.07 (m, 5 H), 6.84 (dd, 1 H), 6.27 (s, 1 H), 5.34 (s, 2 H), 3.04-3.15 (m, 1 H), 2.56-2.64 (m, 1 H), 2.44-2.53 (m, 2 H), 1.27-1.77 (m, 6 H), 0.07-0.14 (m, 2 H), −0.03-0.05 (m, 2 H); ES-MS m/z 478.33 [M+H]$^+$, HPLC RT (min) 2.10.

Example 268

Preparation of 5-(2-benzyl-2H-indazol-6-yl)-7-(4-piperazin-1-ylphenyl)pyrrolo[2,1-f][1,2,4]triazin-4-amine

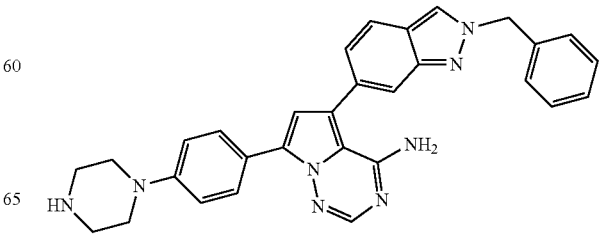

Step 1: Preparation of tert-butyl 4-[4-(4-aminopyrrolo[2,1-f][1,2,4]triazin-7-yl)phenyl]piperazine-1-carboxylate

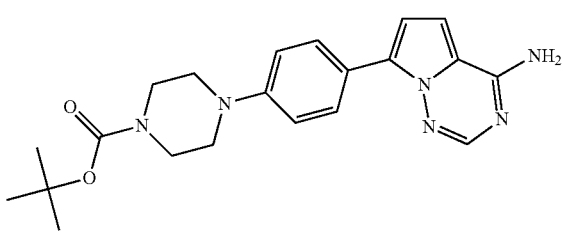 [SMILES: CC(C)(C)OC(=O)N1CCN(c2ccc(-c3ccc4c(N)ncnn34)cc2)CC1]

To a stirred suspension of 7-bromopyrrolo[2,1-f][1,2,4]triazin-4-amine (801 mg, 3.76 mmol), tert-butyl 4-[4-(4,4,5,5-tetramethyl-1,3,2-dioxaborolan-2-yl)phenyl]tetrahydro-1(2H)-pyrazinecarboxylate (2.19 g, 5.64 mmol), and [1,1'-bis(diphenylphosphino)-ferrocene]dichloro palladium(II)-complex with dichloromethane (275 mg, 0.38 mmol) in degassed DME (25 mL) was added aqueous $Na_2CO_3$ solution (2 M, 5.6 mL). The reaction was heated at 80° C. for 17 h and then cooled to rt. The mixture was filtered through a pad of Celite® using ethyl acetate. The filtrate was washed with water (75 mL), dried ($Na_2SO_4$), and concentrated. The crude material was purified by ISCO® chromatography using a gradient of 50 to 75% ethyl acetate in hexanes to afford 1.22 g (74%) of the desired product as an off-white solid, which contained trace impurities. $^1$H NMR (300 MHz, DMSO-$d_6$) δ 7.94-7.88 (m, 2 H), 7.86 (s, 1 H), 7.65 (br s, 2 H), 7.03-6.97 (m, 1 H), 6.94 (d, 1 H), 6.89 (d, 1 H), 3.51-3.42 (m, 4 H), 3.19-3.11 (m, 4 H), 1.42 (s, 9 H); ES-MS m/z 395.1 [M+H]$^+$, HPLC RT (min) 2.52.

Step 2: Preparation of tert-butyl 4-[4-(4-amino-5-bromopyrrolo[2,1-f][1,2,4]triazin-7-yl) phenyl]piperazine-1-carboxylate

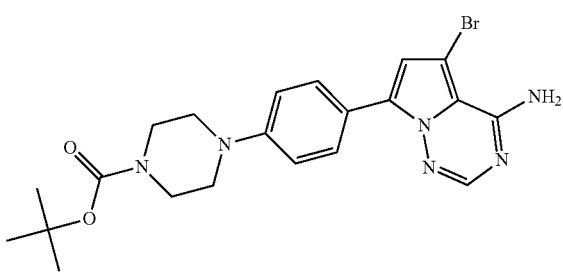 [SMILES: CC(C)(C)OC(=O)N1CCN(c2ccc(-c3cc(Br)c4c(N)ncnn34)cc2)CC1]

To a cooled (−20° C.) solution of tert-butyl 4-[4-(4-aminopyrrolo[2,1-f][1,2,4]triazin-7-yl)phenyl]piperazine-1-carboxylate (1.20 g, 3.04 mmol) in tetrahydrofuran (15 mL) was added 1,3-dibromo-5,5-dimethylhydantoin (435 mg, 1.21 mmol) in four portions over 15 min. The mixture stirred at −20° C. for 3 h. Saturated, aqueous $Na_2SO_3$ (20 mL) was added and the mixture was allowed to warm to rt. The mixture was extracted with ethyl acetate (2×25 mL). The combined organic layers were dried ($Na_2SO_4$) and concentrated. The crude material was purified by ISCO® chromatography using a gradient of 25 to 75% ethyl acetate in hexanes. $^1$H-NMR indicated the presence of residual hydantoin side product, thus the material was partitioned between ethyl acetate (50 mL) and 5% aqueous $K_2CO_3$ (50 mL). The layers were separated and the organic layer was further washed with 5% aqueous $K_2CO_3$ (2×25 mL). The combined aqueous layer was extracted with ethyl acetate (2×25 mL) and the combined organic layers were washed with brine, dried ($Na_2SO_4$) and concentrated to afford 340 mg (23%) of the desired product as a white solid. $^1$H NMR (300 MHz, DMSO-$d_6$) δ 7.91-7.83 (m, 3 H), 7.09 (s, 1 H), 7.00 (d, 2 H), 3.50-3.42 (m, 4 H), 3.20-3.14 (m, 4 H), 1.42 (s, 9 H); ES-MS m/z 473.0 [M+H]$^+$, HPLC RT (min) 3.25.

Step 3: Preparation of tert-butyl 4-{4-[4-amino-5-(2-benzyl-2H-indazol-6-yl) pyrrolo[2,1-f][1,2,4]triazin-7-yl]phenyl}piperazine-1-carboxylate

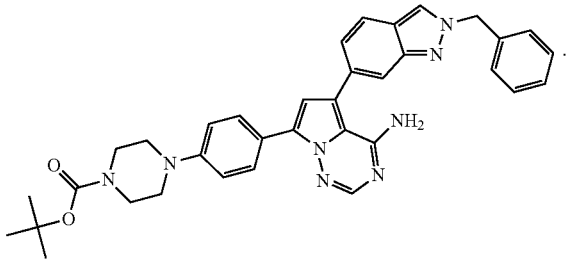 [SMILES: CC(C)(C)OC(=O)N1CCN(c2ccc(-c3cc(-c4ccc5cn(Cc6ccccc6)nc5c4)c4c(N)ncnn34)cc2)CC1]

To a stirred solution of tert-butyl 4-[4-(4-amino-5-bromopyrrolo[2,1-f][1,2,4]triazin-7-yl)phenyl]piperazine-1-carboxylate (4 mg, 1.25 mmol), 2-benzyl-6-(4,4,5,5-tetramethyl-1,3,2-dioxaborolan-2-yl)-2H-indazole (1.04 g, 1.87 mmol), and tetrakis(triphenylphosphine)palladium(0) (144 mg, 0.13 mmol) in degassed DME (5.5 mL) was added aqueous $Na_2CO_3$ solution (2 M, 1.87 mL). The reaction was heated at 80° C. for 17 h and then cooled to rt. The mixture was partitioned between ethyl acetate (25 mL) and $H_2O$ (25 mL). The layers were separated and the aqueous phase was extracted with ethyl acetate. The combined organic layers were washed with brine, dried ($Na_2SO_4$), and concentrated to dryness. The crude material was purified by ISCO® chromatography using a gradient of 25 to 75% ethyl acetate in hexanes to afford 378 mg (58%) of the desired product, which contained trace impurities. $^1$H NMR (300 MHz, DMSO-$d_6$) δ 8.52 (s, 1 H), 7.88 (s, 1 H), 7.78 (d, 1 H), 7.57 (s, 1 H), 7.36-7.31 (m, 5 H), 7.13 (d, 1 H), 6.61 (s, 1 H), 5.64 (s, 2 H), 4.13-3.98 (m, 2 H), 3.35-3.25 (m, 1 H), 2.05-1.96 (m, 2 H), 1.63-1.50 (m, 2 H), 1.41 (s, 9 H); ES-MS m/z 524.2 [M+H]$^+$, HPLC RT (min) 3.08.

Step 4: Preparation of the Title Compound

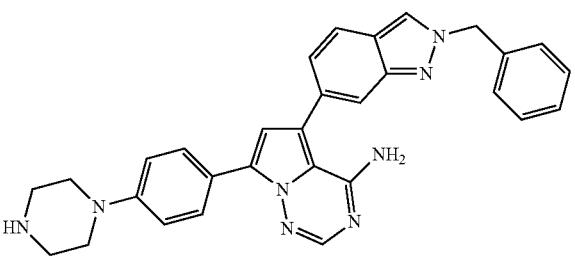 [SMILES: Nc1ncnn2c(-c3ccc(N4CCNCC4)cc3)cc(-c3ccc4cn(Cc5ccccc5)nc4c3)c12]

To a suspension of tert-butyl 4-{4-[4-amino-5-(2-benzyl-2H-indazol-6-yl)pyrrolo[2,1-f][1,2,4]triazin-7-yl]phenyl}piperazine-1-carboxylate (610 mg, 1.02 mmol) in dichloromethane (6 mL) was added trifluoroacetic acid (2 mL). The reaction was stirred at rt for 17 h. The mixture was evaporated to dryness and saturated, aqueous $NaHCO_3$ was added to the residue. The resulting solid was collected by filtration and was dried in vacuo to afford 489 mg (96%) of the desired product. $^1$H NMR (300 MHz, DMSO-$d_6$) δ 8.54 (s, 1 H), 7.99-7.91 (m, 3 H), 7.81 (d, 1 H), 7.65 (s, 1 H), 7.41-7.25 (m, 5 H), 7.19 (d, 1 H), 7.06-6.96 (m, 3 H), 5.65 (s, 2 H), 3.14 (s, 4 H), 2.89 (s, 4 H); ES-MS m/z 501.4 [M+H]$^+$, HPLC RT (min) 2.25.

Example 269

5-[3-(benzyloxyl)phenyl]-7-(4-morpholin-4-ylbutyl)pyrrolo[2,1-f][1,2,4]triazin-4-amine

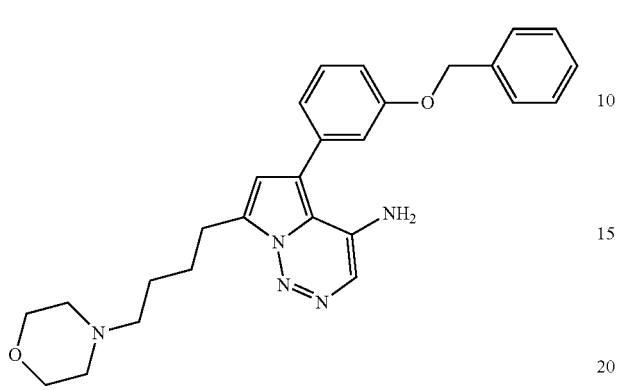

In a manner similar to the procedure described for the preparation of Example 9 and substituting morpholine for pyrrolidine, 62 mg (53%) of the desired product was isolated. $^1$H NMR (400 MHz, DMSO-$d_6$) δ 7.87 (s, 1 H), 7.25-7.48 (m, 6 H), 7.08-7.04 (m, 1 H), 7.03-6.96 (m, 2 H), 6.55 (s, 1 H), 5.14 (s, 2 H), 3.60-3.48 (m, 4 H), 2.88 (t, 2 H), 2.42-2.20 (m, 6 H), 1.76-1.63 (m, 2 H), 1.58-1.44 (m, 2 H); ES-MS m/z 458.2 [M+H]$^+$, HPLC RT (min) 2.23.

Example 270

Preparation of 5-(2-benzyl-2H-indazol-6-yl)-7-[4-(1,1-dioxidothiomorpholin-4-yl)butyl]pyrrolo[2,1-f][1,2,4]triazin-4-amine

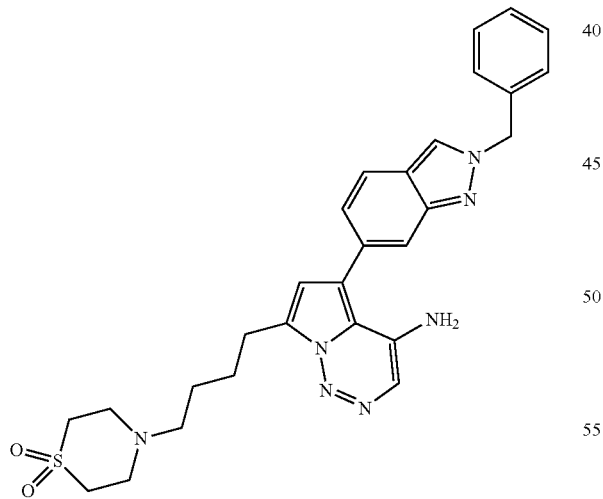

In a manner similar to the procedure described for the preparation of Example 17 and substituting thiomorpholine 1,1,-dioxide for pyrrolidine, 27 mg (30%) of the desired product was isolated. $^1$H NMR (400 MHz, DMSO-$d_6$) δ 8.56 (s, 1 H), 7.89 (s, 1 H), 7.81 (d, 1 H), 7.59 (s, 1 H), 7.29-7.39 (m, 5 H), 7.14 (d, 1 H), 6.60 (s, 1 H), 5.66 (s, 2 H), 3.01-3.07 (m, 5 H), 2.81-2.92 (m, 7 H), 1.65-1.79 (m, 2 H), 1.45-1.56 (m, 2 H); ES-MS m/z 530.47 [M+H]$^+$, HPLC RT (min) 2.72.

Example 271

Preparation of 7-[4-(4-acetylpiperazin-1-yl)butyl]-5-(2-benzyl-2H-indazol-6-yl)pyrrolo[2,1-f][1,2,4]triazin-4-amine

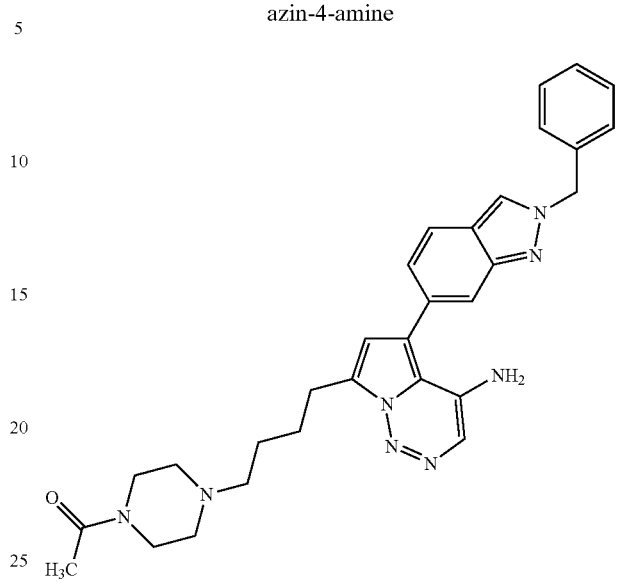

In a manner similar to the procedure described for the preparation of Example 17 and substituting 1-acetylpiperazine for pyrrolidine, 44 mg (67%) of the desired product was isolated. $^1$H NMR (400 MHz, DMSO-$d_6$) δ 8.58 (s, 1 H), 7.92 (s, 1 H), 7.82 (d, 1 H), 7.61 (s, 1 H), 7.30-7.42 (m, 5 H), 7.17 (d, 1 H), 6.63 (s, 1 H), 5.68 (s, 2 H), 3.37-3.45 (m, 4 H), 2.89-2.96 (m, 2 H), 2.25-2.39 (m, 6 H), 1.98 (s, 3 H), 1.69-1.80 (m, 2 H), 1.49-1.60 (m, 2 H); ES-MS m/z 523.33 [M+H]$^+$, HPLC RT (min) 2.16.

Example 272

Preparation of 4-{4-[4-amino-5-(2-benzyl-2H-indazol-6-yl)pyrrolo[2,1-f][1,2,4]triazin-7-yl]butyl}piperazin-2-one

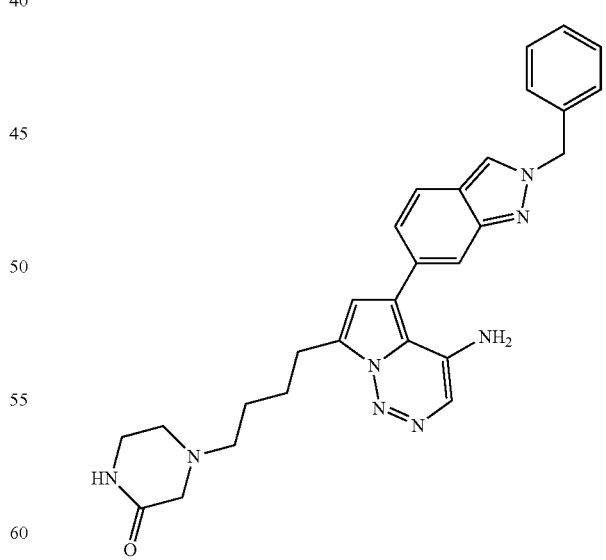

In a manner similar to the procedure described for the preparation of Example 17 and substituting 2-oxopiperazine for pyrrolidine, 37 mg (44%) of the desired product was isolated. $^1$H NMR (400 MHz, DMSO-$d_6$) δ 8.54 (d, 1 H), 7.88 (d, 1 H), 7.79 (dd, 1 H), 7.69 (s, 1 H), 7.58 (s, 1 H), 7.28-7.38 (m, 5 H), 7.15 (d, 1 H), 6.59 (d, 1 H), 5.64 (d, 2 H), 3.33 (d, 2

H), 3.07-3.16 (m, 2 H), 2.83-2.92 (m, 4 H), 2.30-2.39 (m, 2 H), 1.65-1.76 (m, 2 H), 1.45-1.56 (m, 2 H); ES-MS m/z 495.54 [M+H]$^+$, HPLC RT (min) 2.00.

Example 273

Preparation of 1-{4-[4-amino-5-(2-benzyl-2H-indazol-6-yl)pyrrolo[2,1-f][1,2,4]triazin-7-yl]butyl}piperidin-4-ol

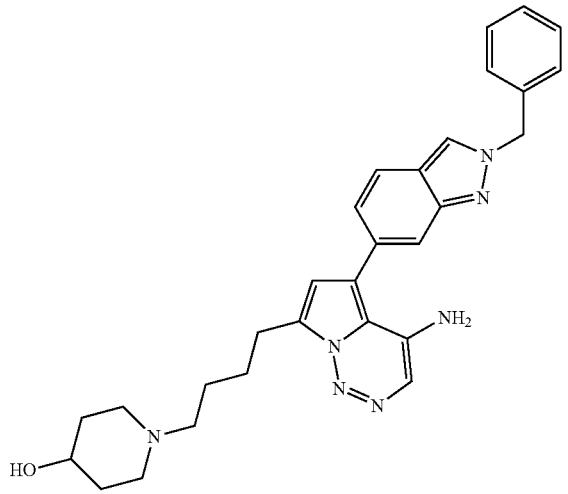 [SMILES: Nc1cnnn2c(CCCCN3CCC(O)CC3)cc(-c3ccc4cn(Cc5ccccc5)nc4c3)c12]

In a manner similar to the procedure described for the preparation of Example 17 and substituting 4-hydroxypiperidine for pyrrolidine, 63 mg (81%) of the desired product was isolated. $^1$H NMR (400 MHz, DMSO-d$_6$) δ 8.54 (s, 1 H), 7.88 (d, 1 H), 7.79 (d, 1 H), 7.57 (s, 1 H), 7.26-7.38 (m, 5 H), 7.13 (d, 1 H), 6.58 (d, 1 H), 5.64 (d, 2 H), 4.49 (d, 1 H), 3.31-3.41 (m, 1 H), 2.82-2.91 (m, 2 H), 2.60-2.68 (m, 2 H), 2.18-2.28 (m, 2 H), 1.84-1.96 (m, 2 H) 0.60-1.74 (m, 4 H), 1.40-1.53 (m, 2 H), 1.25-1.38 (m, 2 H); ES-MS m/z 496.27 [M+H]$^+$, HPLC RT (min) 2.17.

Example 274

Preparation of 4-{4-[4-amino-5-(2-benzyl-2H-indazol-6-yl)pyrrolo[2,1-f][1,2,4]triazin-7-yl]butyl}-N-methylpiperazine-1-carboxamide

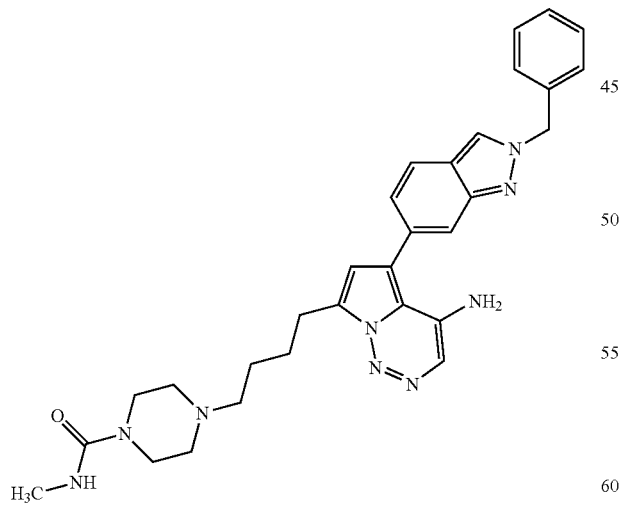

In a manner similar to the procedure described for the preparation of Example 17 and substituting N-methylpiperazine-1-carboxamide for pyrrolidine, 32 mg (38%) of the desired product was isolated. $^1$H NMR (400 MHz, DMSO-d$_6$) δ 8.54 (s, 1 H), 7.88 (s, 1 H), 7.79 (d, 1 H), 7.57 (s, 1 H), 7.26-7.39 (m, 5 H), 7.13 (d, 1 H), 6.58 (s, 1 H), 6.37 (s, 1 H), 5.65 (s, 2 H), 3.15-3.26 (m, 4 H), 2.83-2.93 (m, 2 H), 2.49- 2.58 (m, 3 H), 2.17-2.35 (m, 6 H), 1.61-1.78 (m, 2 H), 1.43-1.58 (m, 2 H); ES-MS m/z 538.21 [M+H]$^+$, HPLC RT (min) 2.17.

Example 275

Preparation of 4-{4-[4-amino-5-(2-benzyl-2H-indazol-6-yl)pyrrolo[2,1-f][1,2,4]triazin-7-yl]butyl}-N,N-dimethylpiperazine-1-carboxamide

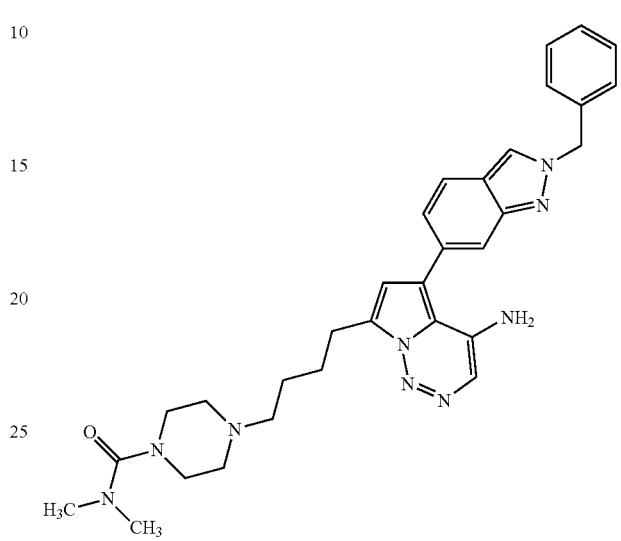

In a manner similar to the procedure described for the preparation of Example 17 and substituting piperazine-1-carboxylic acid dimethylamide for pyrrolidine, 48 mg (52%) of the desired product was isolated. $^1$H NMR (400 MHz, DMSO-d$_6$) δ 8.54 (s, 1 H), 7.88 (s, 1 H), 7.79 (d, 1 H), 7.58 (s, 1 H), 7.27-7.36 (m, 5 H), 7.13 (dd, 1 H), 6.58 (s, 1 H), 5.64 (s, 2 H), 3.01-3.09 (m, 4 H), 2.88 (t, 2 H), 2.68 (s, 6 H), 2.26-2.32 (m, 6 H), 1.64-1.76 (m, 2 H), 1.45-1.54 (m, 2 H); ES-MS m/z 552.33 [M+H]$^+$, HPLC RT (min) 2.20.

Example 276

Preparation of 5-(2-benzyl-2H-indazol-6-yl)-7-{4-[4-(methylsulfonyl)piperazin-1-yl]butyl}pyrrolo[2,1-f][1,2,4]triazin-4-amine

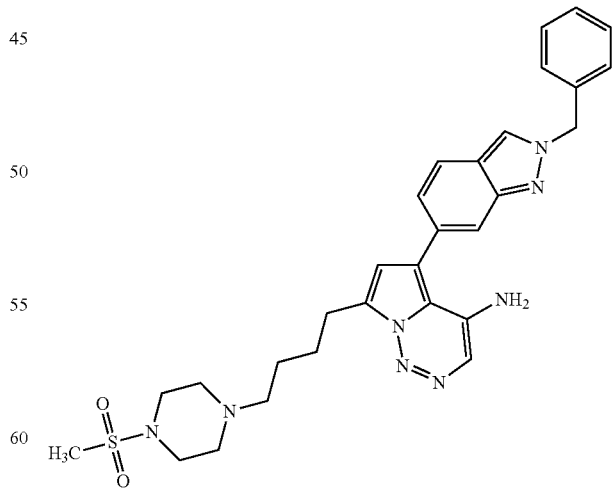

In a manner similar to the procedure described for the preparation of Example 17 and substituting 1-methanesulfonylpiperazine for pyrrolidine, 41 mg (44%) of the desired product was isolated. $^1$H NMR (400 MHz, DMSO-d$_6$) δ 8.54 (d, 1 H), 7.88 (s, 1 H), 7.79 (d, 1 H), 7.58 (d, 1 H), 7.27-7.37

(m, 5 H), 7.14 (dd, 1 H), 6.58 (s, 1 H), 5.64 (s, 2 H), 2.99-3.09 (m, 4 H), 2.88 (t, 2 H), 2.89 (t, 2 H), 2.83 (s, 3 H), 2.31-2.44 (m, 4 H), 1.65-1.75 (m, 2 H), 1.46-1.55 (m, 2 H); ES-MS m/z 559.24[M+H]$^+$, HPLC RT (min) 2.28.

Example 277

Preparation of 4-{4-[4-amino-5-(2-benzyl-2H-indazol-6-yl)pyrrolo[2,1-f][1,2,4]triazin-7-yl]butyl}-N,N-dimethylpiperazine-1-sulfonamide

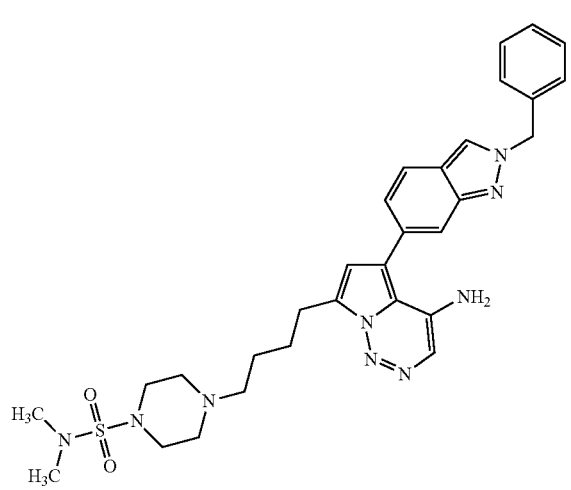 [SMILES: CN(C)S(=O)(=O)N1CCN(CCCCc2cc(-c3ccc4cn(Cc5ccccc5)nc4c3)c3c(N)cnnn23)CC1]

In a manner similar to the procedure described for the preparation of Example 17 and substituting piperazine-1-sulfonic acid dimethylamide for pyrrolidine, 67 mg (68%) of the desired product was isolated. $^1$H NMR (400 MHz, DMSO-d$_6$) δ 8.54 (s, 1 H), 7.88 (s, 1 H), 7.79 (d, 1 H), 7.57 (s, 1 H), 7.28-7.38 (m, 5 H), 7.10-7.17 (m, 1 H), 6.59 (s, 1 H), 5.64 (s, 2 H), 3.32 (s, 6 H), 2.88 (t, 2 H), 2.72 (s, 6 H), 2.29-2.39 (m, 6 H), 1.66-1.75 (m, 2 H), 1.45-1.54 (m, 2 H); ES-MS m/z 588.23 HPLC RT (min) 2.36.

Example 278

Preparation of 2-(4-{4-[4-amino-5-(2-benzyl-2H-indazol-6-yl)pyrrolo[2,1-f][1,2,4]triazin-7-yl]butyl}piperazin-1-yl)-N,N-dimethylacetamide

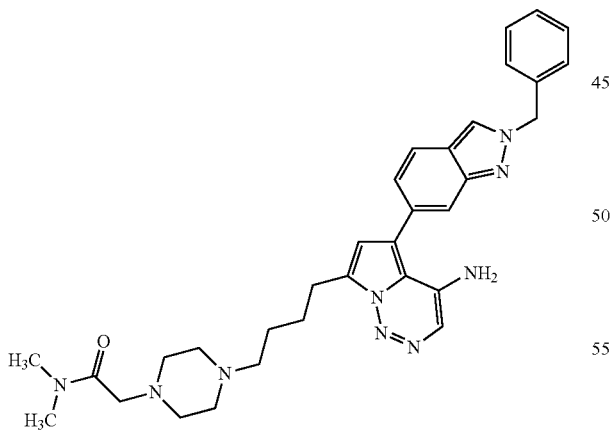

In a manner similar to the procedure described for the preparation of Example 17 and substituting N,N-dimethyl-2-piperazin-1-yl-acetamide for pyrrolidine, 38 mg (40%) of the desired product was Isolated. $^1$H NMR (400 MHz, DMSO-d$_6$) δ 8.53 (s, 1 H), 7.88 (s, 1 H), 7.79 (d, 1 H), 7.57 (s, 1 H), 7.27-7.37 (m, 5 H), 7.13 (dd, 1 H), 6.58 (s, 1 H), 5.64 (s, 2 H), 3.04 (s, 2 H), 2.97 (s, 3 H), 2.87 (t, 2 H), 2.77 (s, 3 H), 2.21-2.45 (m, 10 H), 1.64-1.74 (m, 2 H), 1.42-1.54 (m, 2 H); ES-MS m/z 466.35 [M+H]$^+$, HPLC RT (min) 2.12.

Example 279

Preparation of tert-butyl (1S,4S)-5-{4-[4-amino-5-(2-benzyl-2H-indazol-6-yl)pyrrolo[2,1-f][1,2,4]triazin-7-yl]butyl}-2,5-diazabicyclo[2.2.1]heptane-2-carboxylate

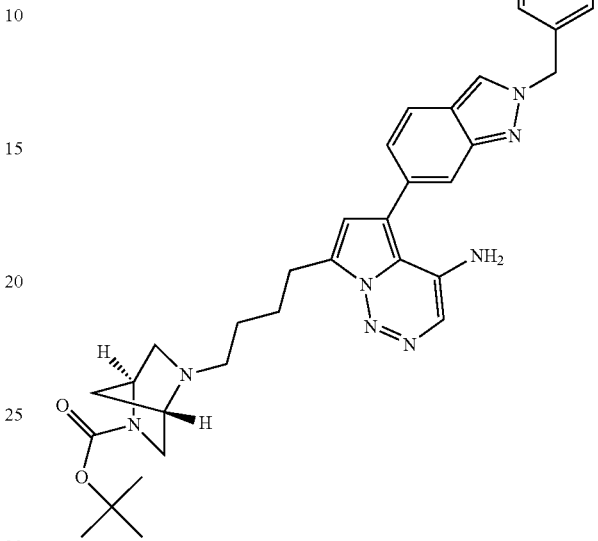

In a manner similar to the procedure described for the preparation of Example 17 and substituting N-BOC-2,5-diaza-bicyclo[2.2.1]heptane for pyrrolidine, 100 mg (67%) of the desired product was isolated. $^1$H NMR (400 MHz, DMSO-d$_6$) δ 8.51-8.57 (m, 1 H), 7.84-7.95 (m, 1 H), 7.76-7.84 (m, 1 H), 7.58 (s, 1 H), 7.28-7.39 (m, 5 H), 7.09-7.18 (m, 1 H), 6.58 (s, 1 H), 5.65 (d, 2 H), 4.09 (d, 1 H), 3.25-3.34 (m, 4 H), 2.95-3.08 (m, 1 H), 2.81-2.92 (m, 2 H), 2.69-2.79 (m, 1 H), 2.29-2.45 (m, 1 H), 1.37-1.77 (m, 6 H), 1.37 (s, 9 H); ES-MS m/z 593.13 [M+H]$^+$, HPLC RT (min) 2.48.

Example 280

Preparation 5-(2-benzyl-2H-indazol-6-yl)-7-{4-[(1S,4S)-2,5-diazabicyclo[2.2.1]hept-2-yl]butyl}pyrrolo[2,1-f][1,2,4]triazin-4-amine

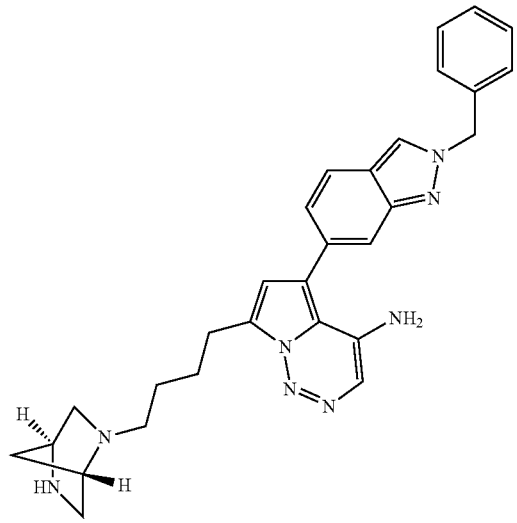 [SMILES: Nc1cnnn2c(CCCCN3C[C@@H]4C[C@H]3CN4)cc(-c3ccc4cn(Cc5ccccc5)nc4c3)c12]

To a solution of tert-butyl (1S,4S)-5-{-4-[4-amino-5-(2-benzyl-2H-indazol-6-yl)pyrrolo[2,1-f][1,2,4]triazin-7-yl]butyl}-2,5-diazabicyclo[2.2.1]heptane-2-carboxylate in MeOH (1 mL) was added 4M HCl in dioxane (0.5 mL). The mixture was stirred at rt for 2 h. Additional 4M HCl in dioxane (0.5 mL) was added and the mixture continued to stir at rt for 16 h. The mixture was concentrated and the residue was partitioned between saturated, aqueous NaHCO$_3$ (20 mL) and EtOAc (20 mL). The layers were separated and the organic phase was washed with brine, dried (Na$_2$SO$_4$) and concentrated. The residue was purified by preparative HPLC using a gradient elution from 15% to 50% acetonitrile in water to obtain 36 mg (62%) of the desired product. $^1$H NMR (400 MHz, DMSO-d$_6$) δ 8.54 (s, 1 H), 7.88 (s, 1 H), 7.79 (d, 1 H), 7.57 (s, 1 H), 7.28-7.39 (m, 5 H), 7.13 (d, 1 H), 6.58 (s, 1 H), 5.64 (s, 2 H), 3.51 (s, 1 H), 3.25-3.47 (m, 2 H), 2.97 (d, 1 H), 2.87 (t, 2 H), 2.73 (dd, 1 H), 2.66 (dd, 2 H), 2.37-2.45 (m, 1 H), 2.33 (d, 1 H), 1.59-1.77 (m, 3 H), 1.35-1.52 (m, 3 H); ES-MS m/z 493.27 [M+H]$^+$, HPLC RT (min) 1.89.

Example 281

Preparation of 5-(2-phenyl-2/4-indazol-6-yl)-7-(4-pyrrolidin-1-ylbutyl)pyrrolo[2,1-f][1,2,4]triazin-4-amine

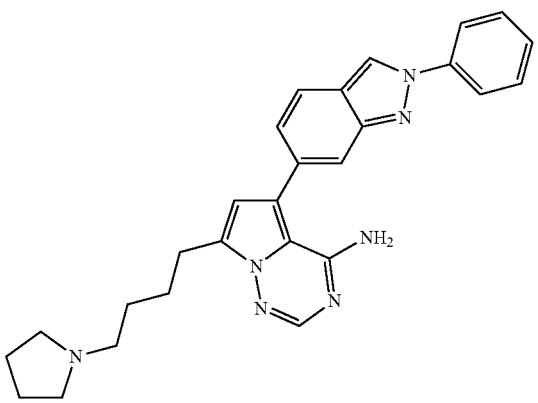 [SMILES: Nc1ncnn2c(CCCCN3CCCC3)cc(-c3ccc4cn(-c5ccccc5)nc4c3)c12]

In a manner similar to the procedure described for the preparation of Example 22 and substituting 2-phenyl-6-(4,4,5,5-tetramethyl-1,3,2-dioxaborolan-2-yl)-2H-indazole for 2-[4-(4,4,5,5-tetramethyl-1,3,2-dioxaborolan-2-yl)benzyl]-2H-indazole, 16 mg (17%) of the desired product was isolated. $^1$H NMR (400 MHz, DMSO-d$_6$) δ 9.20 (s, 1 H), 8.28 (s, 1 H), 8.11 (d, 2 H), 7.92 (d, 1 H), 7.83 (s, 1 H), 7.60 (t, 2 H), 7.46 (t, 1 H), 7.23 (dd, 1 H), 6.95 (s, 1 H), 3.47-3.57 (m, 2 H), 3.13-3.22 (m, 2 H), 2.93-3.03 (m, 4 H), 1.93-2.03 (m, 2 H), 1.65-1.91 (m, 6 H); ES-MS m/z 452.25 [M+H]$^+$, HPLC RT (min) 2.31.

Example 282

Preparation of 1-{3-[4-amino-5-(2-benzyl-2H-indazol-6-yl)pyrrolo[2,1-f][1,2,4]triazin-7-yl]benzyl}pyrrolidin-3-ol

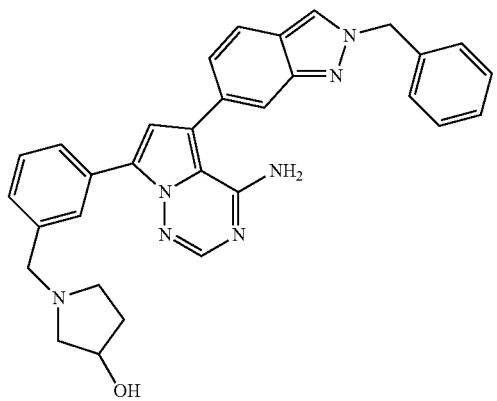 [SMILES: Nc1ncnn2c(-c3cccc(CN4CCC(O)C4)c3)cc(-c3ccc4cn(Cc5ccccc5)nc4c3)c12]

Step 1: Preparation of 5-(2-benzyl-2H-indazol-6-yl)-7-[3-(bromomethyl)phenyl]pyrrolo[2,1-f][1,2,4]triazin-4-amine

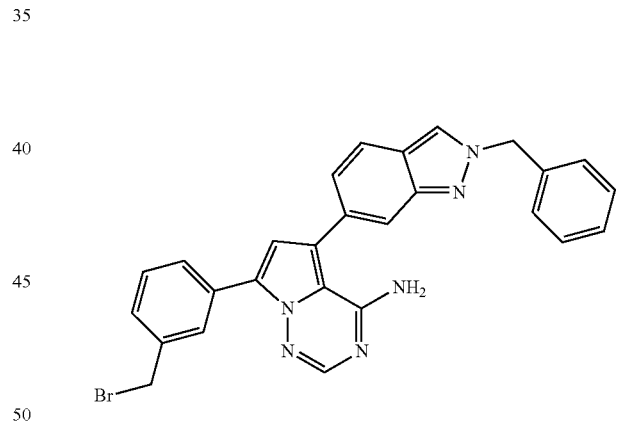

To a solution of {3-[4-amino-5-(2-benzyl-2H-indazol-6-yl)pyrrolo[2,1-f][1,2,4]triazin-7-yl]phenyl}methanol (575 mg, 1.29 mmol) and triphenylphosphine (507 mg, 1.93 mmol) in tetrahydrofuran (10 mL) was added carbon tetrabromide (512 mg, 1.55 mmol). The reaction was stirred at rt for 17 h. The mixture was partitioned between water (50 mL) and CH$_2$Cl$_2$ (50 mL). The layers were separated and the organic phase was washed with brine, dried (Na$_2$SO$_4$), and evaporated. The crude material was purified via ISCO® chromatography using a gradient of 50 to 75% ethyl acetate in hexanes to afford 592 mg (90%) of the desired product, which contained a minor impurity. ES-MS m/z 509.41 [M+H]$^+$, HPLC RT (min) 3.31 min.

357

Step 2: Preparation the Title Compound

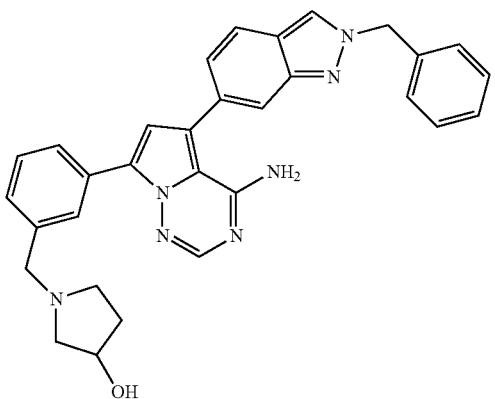 [SMILES: Nc1ncnn2c(-c3cccc(CN4CCC(O)C4)c3)cc(-c3ccc4cn(Cc5ccccc5)nc4c3)c12]

To a solution of 5-(2-benzyl-2H-indazol-6-yl)-7-[3-(bromomethyl)phenyl]pyrrolo[2,1-f][1,2,4]triazin-4-amine (125 mg, 025 mmol) in DMF (1 mL) was added 3-pyrrolidinol (26 µL, 0.27 mmol), triethylamine (103 µl, 0.74 mmol), and sodium iodide (0.4 mg, 0.002 mmol). The reaction was heated (55° C.) for 17 h and then cooled to rt. The crude reaction mixture was purified via preparative HPLC using a gradient elution from 15% to 50% acetonitrile in water followed by filtration through an acidic resin, washing with MeOH. The product was eluted with 2M NH₃ in MeOH and the filtrate was concentrated to provide 28 mg (22%) of the desired product. $^1$H NMR (400 MHz, DMSO-d$_6$) δ 8.57 (s, 1 H), 7.92-8.00 (m, 3 H), 7.83 (d, 1 H), 7.69 (d, 1 H), 7.25-7.44 (m, 7 H), 7.22 (dd, 1 H), 7.14 (s, 1 H), 5.67 (s, 2 H), 4.68 (d, 1 H), 4.09-4.21 (m, 1 H), 3.60 (q, 2 H), 2.65-2.72 (m, 1 H), 2.58 (q, 1 H), 2.37-2.46 (m, 1 H), 2.32 (dd, 1 H), 1.93-2.03 (m, 1 H), 1.48-1.59 (m, 1 H); ES-MS m/z 516.20 [M+H]$^+$, HPLC RT (min) 2.53.

Example 283

Preparation of 5-(2-benzyl-2H-indazol-6-yl)-7-{3-[(4-methylpiperazin-1-yl)methyl]phenyl}pyrrolo[2,1-f][1,2,4]triazin-4-amine

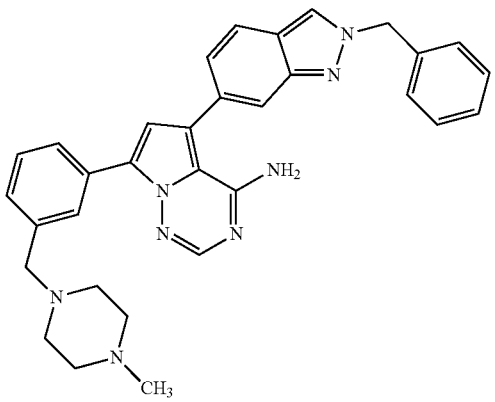 [SMILES: CN1CCN(Cc2cccc(-c3cc(-c4ccc5cn(Cc6ccccc6)nc5c4)c4c(N)ncnn34)c2)CC1]

In a manner similar to the procedure described for the preparation of Example 282 and substituting 1-methylpiperazine for 3-pyrrolidinol, 36 mg (29%) of the desired product was isolated. $^1$H NMR (400 MHz, DMSO-d$_6$) δ 8.57 (s, 1H), 7.96-8.01 (m, 3 H), 7.83 (d, 1 H), 7.69 (s, 1 H), 7.20-7.45 (m,

358

8 H), 7.14 (s, 1 H), 5.66 (s, 2 H), 3.50 (s, 2 H), 2.20-2.47 (m, 8 H), 2.12 (s, 3 H); ES-MS m/z 529.24 [M+H]$^+$, HPLC RT (min) 2.50.

Example 284

Preparation of 1-{3-[4-amino-5-(2-benzyl-2H-indazol-6-yl)pyrrolo[2,1-f][1,2,4]triazin-7-yl]benzyl}piperidin-4-ol

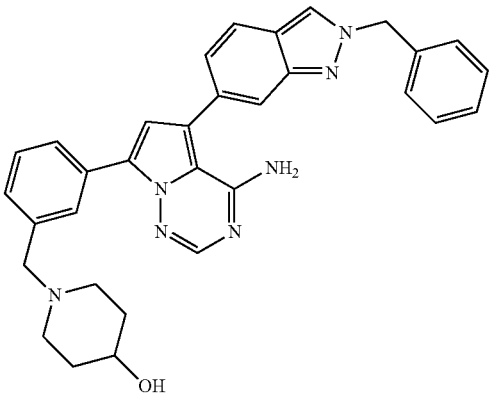 [SMILES: Nc1ncnn2c(-c3cccc(CN4CCC(O)CC4)c3)cc(-c3ccc4cn(Cc5ccccc5)nc4c3)c12]

In a manner similar to the procedure described for the preparation of Example 282 and 282 and substituting 4-piperidinol for 3-pyrrolidinol, 52 mg (41%) of the desired product was isolated. $^1$H NMR (400 MHz, DMSO-d$_6$) δ 8.58 (s, 1 H), 7.95-8.02 (m, 3 H), 7.84 (d, 1 H), 7.69 (d, 1 H), 7.19-7.45 (m, 8 H), 7.14 (s, 1 H), 5.67 (s, 2 H), 4.54 (d, 1 H), 3.48 (s, 2 H), 3.38-3.48 (m, 1 H), 2.63-2.73 (m, 2 H), 1.98-2.09 (m, 2 H), 1.63-1.74 (m, 2 H), 1.30-1.44 (m, 2 H); ES-MS m/z 530.24 [M+H]$^+$, HPLC RT (min) 2.54.

Example 285

Preparation of 5-(2-benzyl-2H-indazol-6-yl)-7-(2-piperidin-4-yl-1,3-thiazol-4-yl)pyrrolo[2,1-f][1,2,4]triazin-4-amine

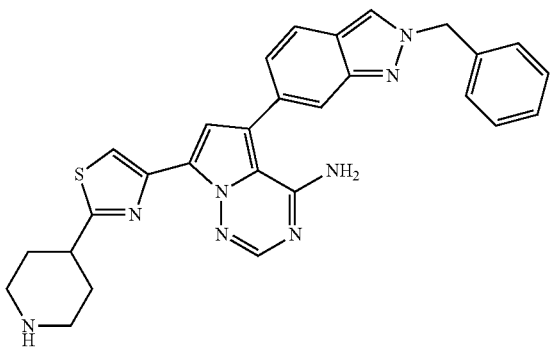 [SMILES: Nc1ncnn2c(-c3csc(C4CCNCC4)n3)cc(-c3ccc4cn(Cc5ccccc5)nc4c3)c12]

To a solution of tert-butyl 4-{4-[4-amino-5-(2-benzyl-2H-indazol-6-yl)pyrrolo[2,1-f][1,2,4]triazin-7-yl]-1,3-thiazol-2-yl}piperidine-1-carboxylate (81 mg, 0.13 mmol) in MeOH (600 µL) was added 4M HCl in dioxane (300 µL). The mixture was stirred at rt for 16 h. The mixture was concentrated and the residue was purified by preparative HPLC using a gradient elution from 15% to 45% acetonitrile in water followed by filtration through an acidic resin, washing with MeOH. The product was eluted with 2M NH₃ in MeOH and the filtrate was concentrated to provide 5 mg (7%) of the desired product. $^1$H NMR (400 MHz, DMSO-d$_6$) δ 8.80 (s, 1 H), 8.64 (s, 1 H), 8.59 (s, 1 H), 8.07 (d, 1 H), 7.98 (s, 1 H), 7.46-7.61 (m, 6H), 7.40 (dd, 1 H), 5.86 (s, 2 H), 3.51-3.69 (m, 3 H), 3.25 (t, 2 H), 2.39-2.50 (m, 2 H), 2.12 (q, 2 H); LC-MS [M+H]+=507.30, RT=2.69 min.

Example 286

Preparation of 5-(2-benzyl-2H-indazol-6-yl)-7-{2-[1-(methylsulfonyl)piperidin-4-yl]-1,3-thiazol-4-yl}pyrrolo[2,1-f][1,2,4]triazin-4-amine

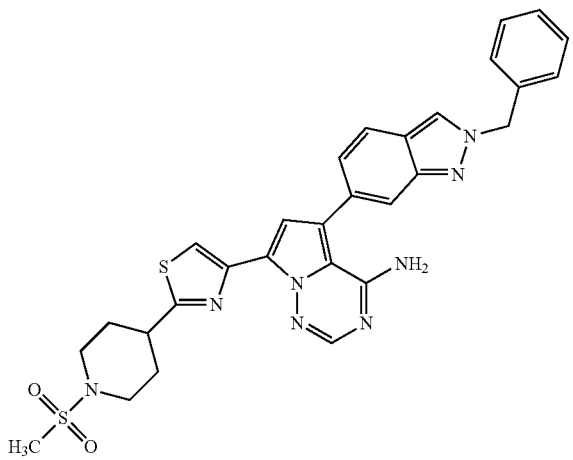 [SMILES: CS(=O)(=O)N1CCC(c2nc(-c3cc(-c4ccc5cn(Cc6ccccc6)nc5c4)c4c(N)ncnn34)cs2)CC1]

To a solution of 5-(2-benzyl-2H-indazol-6-yl)-7-(2-piperidin-4-yl-1,3-thiazol-4-yl)pyrrolo[2,1-f][1,2,4]triazin-4-amine hydrochloride (100 mg, 0.17 mmol) in DMF (1.5 mL) was added methanesulfonyl chloride (15 µL, 0.19 mmol) and N,N-diisopropylethylamine (120 µL, 0.69 mmol). The reaction was stirred at rt for 17 h. The crude mixture was purified by preparative HPLC using a gradient elution from 15% to 45% acetonitrile to provide 28 mg (28%) of the desired product. $^1$H NMR (400 MHz, DMSO-$d_6$) δ 8.56 (s, 1 H), 8.38 (s, 1 H), 8.10 (s, 1 H), 7.83 (d, 1 H), 7.67 (s, 1 H), 7.27-7.40 (m, 5H), 7.17-7.24 (m, 2 H), 5.66 (s, 2 H), 3.59-3.69 (m, 2 H), 3.16-3.28 (m, 1 H), 2.85-2.95 (m, 5H), 2.20 (d, 2 H), 1.78 (q, 2 H); ES-MS m/z 585.21 [M+H]+, HPLC RT (min) 2.97.

Example 287

Preparation of 5-(2-benzyl-2H-indazol-6-yl)-7-(2-{1-[(dimethylamino)acetyl]piperidin-4-yl}-1,3-thiazol-4-yl)pyrrolo[2,1-f][1,2,4]triazin-4-amine

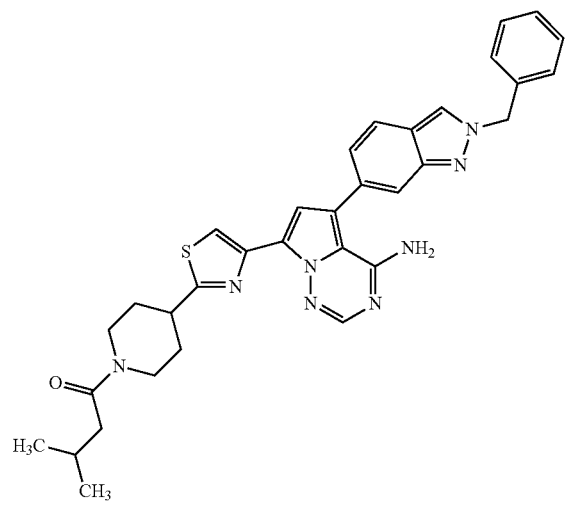 [SMILES: CC(C)CC(=O)N1CCC(c2nc(-c3cc(-c4ccc5cn(Cc6ccccc6)nc5c4)c4c(N)ncnn34)cs2)CC1]

A mixture of 5-(2-benzyl-2H-indazol-6-yl)-7-(2-piperidin-4-yl-1,3-thiazol-4-yl)pyrrolo[2,1-f][1,2,4]triazin-4-amine hydrochloride (100 mg, 0.17 mmol), N,N-dimethylglycine (19 mg, 0.18 mmol), EDCl (36 mg, 0.19 mmol), HOBt (26 mg, 0.19 mmol), and N,N-diisopropylethylamine (90 µL, 0.52 mmol) in DMF (1.5 mL) was stirred at rt for 16 h. The crude mixture was purified by preparative HPLC using a gradient elution from 15% to 45% acetonitrile in water followed by filtration through an acidic resin, washing with MeOH. The product was eluted with 2M NH$_3$ in MeOH and the filtrate was concentrated to provide 20 mg (20%) of the desired product. $^1$H NMR (400 MHz, DMSO-$d_6$) δ 8.56 (s, 1 H), 8.37 (s, 1 H), 8.09 (s, 1 H), 7.82 (d, 1 H), 7.67 (s, 1 H), 7.26-7.39 (m, 5H), 7.16-7.23 (m, 2 H), 5.66 (s, 2 H), 4.40 (d, 1 H), 4.10 (d, 1 H), 3.01-3.23 (m, 3 H), 2.75 (t, 1 H), 2.18 (s, 6H), 2.06-2.15 (m, 3 H), 1.70 (q, 1 H), 1.53 (q, 1 H); ES-MS m/z 592.16 HPLC RT (min) 2.39.

Example 288

Preparation of 5-(2-benzyl-2H-indazol-6-yl)-7-[2-(1-cyclopropylpiperidin-4-yl)-1,3-thiazol-4-yl]pyrrolo[2,1-f][1,2,4]triazin-4-amine

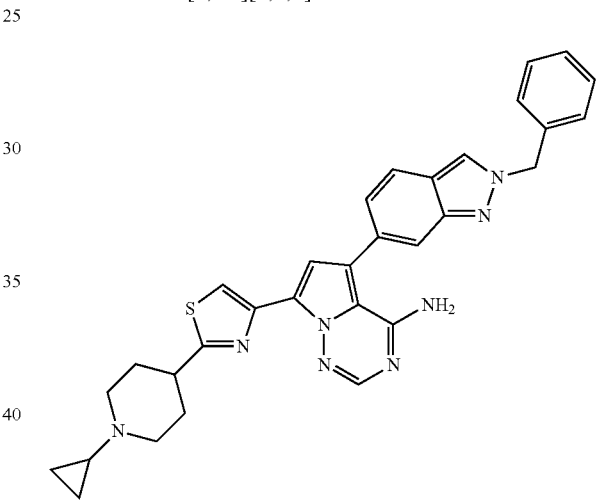

To a solution of 5-(2-benzyl-2H-indazol-6-yl)-7-(2-piperidin-4-yl-1,3-thiazol-4-yl)pyrrolo[2,1-f][1,2,4]triazin-4-amine hydrochloride (100 mg, 0.17 mmol) in MeOH (2 mL) containing 3 Å molecular sieves was added AcOH (99 µL, 1.73 mmol), [(1-ethoxycyclopropyl)oxy]trimethylsilane (180 mg, 1.04 mmol) and sodium cyanoborohydride (49 mg, 0.78 mmol). The reaction was stirred at 60° C. for 17 h. Aqueous NaOH (1N, 5 mL) was added and the mixture was extracted with EtOAc (2×10 mL). The combined organic layers were washed with brine, dried (Na$_2$SO$_4$) and concentrated. The residue was purified by preparative HPLC using a gradient elution from 15% to 45% acetonitrile in water followed by filtration through an acidic resin, washing with MeOH. The product was eluted with 2M NH$_3$ in MeOH and the filtrate was concentrated to provide 19 mg (21%) of the desired product. $^1$H NMR (400 MHz, DMSO-$d_6$) δ 8.57 (s, 1 H), 8.35 (s, 1 H), 8.09 (s, 1 H), 7.83 (d, 1 H), 7.67 (s, 1 H), 7.28-7.41 (m, 5H), 7.18-7.23 (m, 2 H), 5.67 (s, 2 H), 2.95-3.09 (m, 3 H), 2.30 (t, 2 H), 2.05 (d, 2 H), 1.57-1:72 (m, 3 H), 0.37-0.45 (m, 2 H), 0.25-0.34 (m, 2 H); ES-MS m/z 547.21 HPLC RT (min) 2.39.

Example 289

5-(2-benzyl-2H-indazol-6-yl)-7-{1-[(dimethylamino)acetyl]azetidin-3-yl}pyrrolo[2,1-f][1,2,4]triazin-4-amine

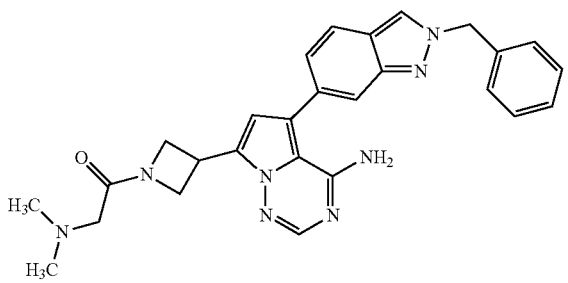 [SMILES: CN(C)CC(=O)N1CC(c2cc(-c3ccc4cn(Cc5ccccc5)nc4c3)c3c(N)ncnn23)C1]

Step 1: Preparation of 1-[(benzyloxy)carbonyl]azetidine-3-carboxylic acid

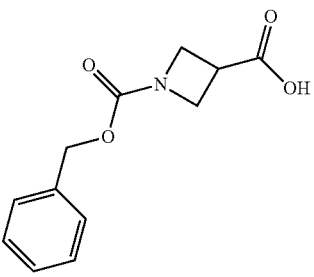 [SMILES: O=C(O)C1CN(C(=O)OCc2ccccc2)C1]

To a solution of 1-(tert-butoxycarbonyl)azetidine-3-carboxylic acid (3.00 g, 14.9 mmol) in MeOH (12.5 mL) was added 4M HCl in 1,4-dioxane (12.5 mL). The reaction was stirred at rt for 16 h. The mixture was evaporated to dryness. To a cooled (0° C.) solution of the residue in 1,4-dioxane (15 mL) and 2N aqueous NaOH (75 mL) was added benzyl chloroformate (2.67 g, 15.7 mmol), dropwise. The reaction was warmed to rt and was allowed to stir for 4 h. The mixture was washed with ethyl acetate (75 mL) and the aqueous layer was acidified (pH 5) with the addition of conc HCl. The mixture was extracted with ethyl acetate (3×75 mL) and the combined organic layers were washed with brine, dried (Na$_2$SO$_4$) and evaporated to give 2.10 g (60%) of the desired product. ES-MS m/z 235.90 [M+H]$^+$, HPLC RT (min) 2.53.

Step 2: Preparation of benzyl 3-[methoxy(methyl)carbamoyl]azetidine-1-carboxylate

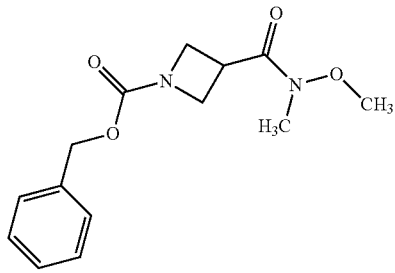 [SMILES: CON(C)C(=O)C1CN(C(=O)OCc2ccccc2)C1]

To a solution of 1-[(benzyloxy)carbonyl]azetidine-3-carboxylic acid (2.30 g, 9.78 mmol) and N,O-dimethylhydroxylamine hydrochloride (1.14 g, 11.73 mmol) in THF (45 mL) was added EDCl (2.06 g, 10.76 mmol), HOBt (1.45 g, 10.76 mmol), N,N-diisopropylethylamine (5.11 mL, 29.33 mmol). The reaction was stirred at rt for 16 h. The mixture was partitioned between ethyl acetate (75 mL) and H$_2$O (75 mL). The layers were separated and the aqueous phase was extracted with ethyl acetate (2 50 mL). The combined organic layers were washed with brine, dried (Na$_2$SO$_4$), and concentrated. The crude material was filtered through a plug of silica gel, eluting with 3:1 ethyl acetate/hexanes to afford 1.66 g (61%) of the desired product after concentration of the filtrate. ES-MS m/z 279.03 [M+H]$^+$, HPLC RT (min) 3.07.

Step 3: Preparation of benzyl 3-(4,4-dimethoxybutanoyl)azetidine-1-carboxylate

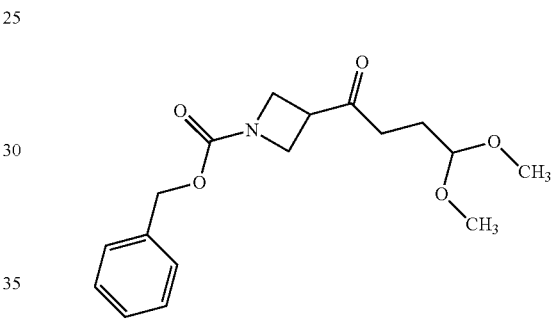

Magnesium turnings (319 mg, 13.12 mmol) were placed in a 50 mL 3-N flask and stirred vigorously while an N$_2$ stream was passed over the turnings for 2.5 h. The turnings were suspended in THF (3 mL) and 3-bromoprionaldehyde dimethylacetal (300 uL) (previously filtered through a plug of activated alumina) was added. The reaction initiated within ~5 minutes. 3-Bromoprionaldehyde dimethylacetal (1.5 mL) in TI-IF (6 mL) was added dropwise over 20 m. The reaction was mildly exothermic during the addition and the flask remained warm for 15 minutes past completion of the addition of bromide. The reaction mixture was placed in an oil bath and heated to 50° C. for 2 h, and then was cooled to rt. The preformed Grignard reagent was added dropwise to a cooled (0° C.) solution of benzyl 3-(4,4-dimethoxybutanoyl)azetidine-1-carboxylate (1.66 g, 5.97 mmol) in THF (10 mL) over 15 m. The mixture was stirred at 0° C. for 3 h. Water (20 mL) was added and the mixture was warmed to rt. The mixture was partitioned between ethyl acetate (50 mL) and H$_2$O (50 mL). The layers were separated and the aqueous phase was extracted with ethyl acetate (3×50 mL). The combined organic layers were washed with brine, dried (Na$_2$SO$_4$), and concentrated to afford 1.91 g (99%) of the desired product. ES-MS m/z 275.99 [M+H]$^+$, HPLC RT (min) 3.21.

Step 4: Preparation of benzyl 3-[(1E)-N-(tert-butoxycarbonyl)-4,4-dimethoxybutane-hydrazonoyl]azetidine-1-carboxylate

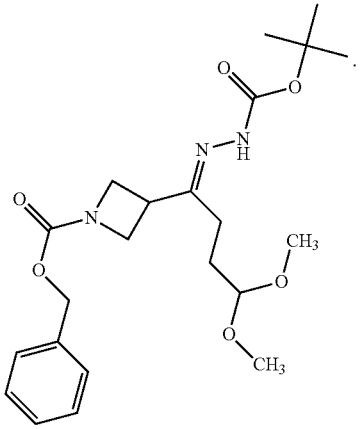 [SMILES: COC(CC/C(=N\NC(=O)OC(C)(C)C)C1CN(C(=O)OCc2ccccc2)C1)OC]

A solution of benzyl 3-(4,4-dimethoxybutanoyl)azetidine-1-carboxylate (1.91 g, 5.94 mmol) in CH$_2$Cl$_2$ (30 mL) was treated with Pert-butylcarbazate (824 mg, 6.24 mmol) followed by para-toluensulfonic acid monohydrate (170 mg, 0.89 mmol). The reaction was stirred at rt for 16 h. The mixture was washed with H$_2$O (25 mL), saturated aqueous NaHCO$_3$ (25 mL), and brine. The organic phase was dried (Na$_2$SO$_4$), filtered and concentrated to afford 2.47 (95%) of the desired product. ES-MS m/z 458.47 [M+Na]$^+$, HPLC RT (min) 3.32.

Step 5: Preparation of benzyl 3-{1-[(tert-butoxycarbonyl)amino]-1H-pyrrol-2-yl}azetidine-1-carboxylate

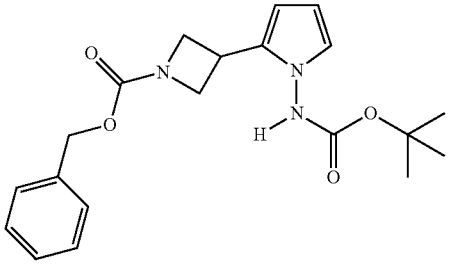 [SMILES: CC(C)(C)OC(=O)Nn1cccc1C1CN(C(=O)OCc2ccccc2)C1]

A solution of benzyl 3-[(1E)-N-(tert-butoxycarbonyl)-4,4-dimethoxybutanehydrazonoyl]azetidine-1-carboxylate (2.47 g, 5.67 mmol) and AcOH (30 mL) was stirred (40° C.) for 18 h. The mixture was concentrated and the residue was dissolved in EtOAc (75 mL) and washed with saturated, aqueous NaHCO$_3$ (75 mL). The aqueous layer was extracted with EtOAc (2×50 mL) and the combined organic layers were washed with brine, dried (Na$_2$SO$_4$) and concentrated to afford the desired product (2.1 g) which was used without further purification. ES-MS m/z 272.01 [M+H]$^+$, HPLC RT (min) 3.50.

Step 6: Preparation of benzyl 3-{1-[(tert-butoxycarbonyl)amino]-5-cyano-1H pyrrol-2-yl}azetidine-1-carboxylate

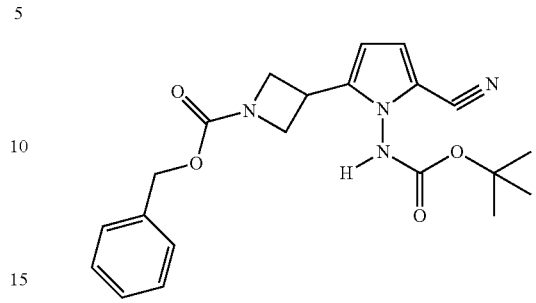

A solution of chlorosulfonylisocyanate (541 µL, 6.22 mmol) in acetonitrile (5 mL) was added dropwise to a cooled (0° C.) solution of benzyl 3-{1-[(tert-butoxycarbonyl)amino]-1H-pyrrol-2-yl}azetidine-1-carboxylate (2.10 g, 5.65 mmol) in acetonitrile (15 mL). The mixture was stirred at 0° C. for 30 min and was warmed to rt. After 1 h, the mixture was recooled (0° C.) and DMF was added dropwise. The reaction was allowed to warm to rt. After 30 min, the mixture was poured onto crushed ice (100 g) and was allowed to warm to rt. The aqueous mixture was extracted with EtOAc (3×75 mL) and the combined organic layers were washed with brine, dried (Na$_2$SO$_4$), and concentrated. The crude material was purified by ISCO® chromatography using a gradient of 50 to 75% ethyl acetate in hexanes to obtain 800 mg (36%) of the desired product, which was used without further characterization.

Step 7: Preparation of benzyl 3-(1-amino-5-cyano-1H-pyrrol-2-yl)azetidine-1-carboxylate

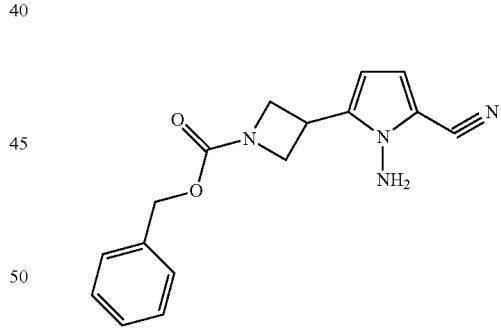

To a cooled (0° C.) solution of benzyl 3-{1-[(tert-butoxycarbonyl)amino]-5-cyano-1H-pyrrol-2-yl}azetidine-1-carboxylate (800 mg, 2.02 mmol) in methanol (2.5 mL) was added a solution of 4 M HCL in dioxane (2.5 mL). The reaction was stirred (0° C.) for 15 min, then was allowed to warm to rt. After 4 h, the reaction was recooled (0° C.) and the mixture was made basic (pH 9) with slow addition of 2M aqueous Na$_2$CO$_3$. The mixture was allowed to warm to rt and was extracted with EtOAc (3×20 mL). The combined organics were washed with brine, dried (Na$_2$SO$_4$), and evaporated to afford 575 mg (96%) of the desired product, which was used without further characterization.

Step 8: Preparation of benzyl 3-(4-aminopyrrolo[2,1-f][1,2,4]triazin-7-yl)azetidine-1-carboxylate

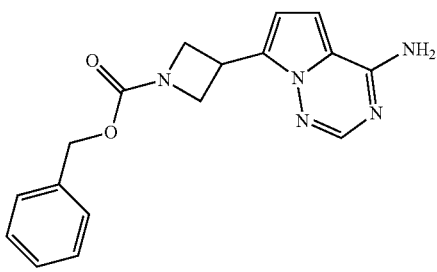 [SMILES: Nc1ncnn2c(C3CN(C(=O)OCc4ccccc4)C3)ccc12]

A solution of benzyl 3-(1-amino-5-cyano-1H-pyrrol-2-yl)azetidine-1-carboxylate (575 mg, 1.94 mmoL) and formamidine acetate (2.02 g, 19.4 mmol) in 1-butanol (8 mL) was stirred at 120° C. for 4 hours. The mixture was then cooled to rt and was partitioned between EtOAc (25 mL) and H$_2$O (25 mL). The layers were separated and the aqueous layer was further extracted with EtOAc (2×25 mL). The combined organic layers were washed with brine, dried (Na$_2$SO$_4$) and concentrated. The crude material was purified by ISCO® chromatography using 3:1 ethyl acetate/hexanes to obtain 250 mg (40%) of the desired product. ES-MS m/z 324.34 [M+H]$^+$, HPLC RT (min) 2.30.

Step 9: Preparation of benzyl 3-(4-amino-5-bromopyrrolo[2,1-f][1,2,4]triazin-7-yl)azetidine-1-carboxylate

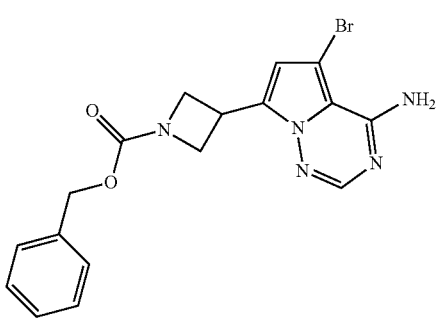 [SMILES: Nc1ncnn2c(C3CN(C(=O)OCc4ccccc4)C3)cc(Br)c12]

To a cooled (−20° C.) solution of benzyl 3-(4-aminopyrrolo[2,1-f][1,2,4]triazin-7-yl)azetidine-1-carboxylate (250 mg, 0.84 mmol) in tetrahydrofuran (4 mL) and DMF (1.5 mL) was added 1,3-dibromo-5,5-dimethylhydantoin (120 mg, 0.42 mmol) in 3 portions over 10 min. The mixture stirred at −20° C. for 1 h. Saturated, aqueous Na$_2$SO$_3$ (10 mL) was added and the mixture was allowed to warm to rt. The mixture was extracted with ethyl acetate (3×20 mL). The combined organic layers were washed with 5% aqueous K$_2$CO$_3$ (25 mL), brine, dried (Na$_2$SO$_4$) and evaporated to afford 371 mg (100%) of the desired product, which contained minor impurities. ES-MS m/z 402.01 [M+H]$^+$, HPLC RT (min) 2.84.

Step 10: Preparation of benzyl 3-[4-amino-5-(2-benzyl-2H-indazol-6-yl)pyrrolo[2,1-f][1,2,4]triazin-7-yl]azetidine-1-carboxylate

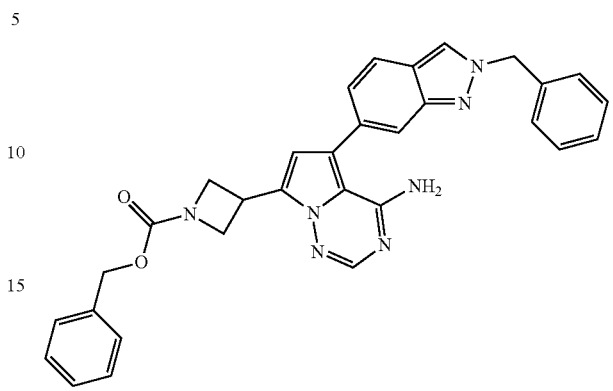

To a stirred degassed mixture of benzyl 3-(4-amino-5-bromopyrrolo[2,1-1,2,4]triazin-7-yl)azetidine-1-carboxylate (371 mg, 0.92 mmol), Intermediate C (462 mg, 1.38 mmol), Na$_2$CO$_3$ (293 mg, 2.77 mmol) and H$_2$O (1.4 mL) in DMF (7 mL) was added aqueous tetrakis(triphenylphosphine)palladium(0) (144 mg, 0.13 mmol). The reaction was heated at 110° C. for 17 h and then cooled to rt. The mixture was partitioned between ethyl acetate (50 mL) and H$_2$O (50 mL). The layers were separated and organic layer was washed with brine, dried (Na$_2$SO$_4$), and concentrated to dryness. The crude material was purified via ISCO® chromatography using 3:1 ethyl/hexanes to afford 304 mg (62%) of the desired product, which contained trace impurities. $^1$H NMR (400 MHz, DMSO-d$_3$) δ 8.54 (s, 1 H), 7.87 (s, 1 H), 7.80 (d, 1 H), 7.60 (s, 1 H), 7.26-7.38 (m, 10 H), 7.15 (d, 1 H), 6.88 (s, 1 H), 5.65 (s, 2 H), 5.05 (s, 2 H), 4.04-4.45 (m, 5 H); ES-MS m/z 530.21 [M+H]$^+$, HPLC RT (min) 3.26.

Step 11: Preparation of 7-azetidin-3-yl-5-(2-benzyl-2H-indazol-6-yl)-pyrrolo[2,1-f][1,2,4]triazin-4-amine

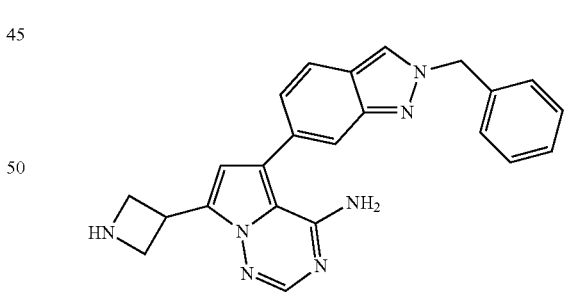

A mixture of benzyl 3-[4-amino-5-(2-benzyl-2H-indazol-6-yl)pyrrolo[2,1-f][1,2,4]triazin-7-yl]azetidine-1-carboxylate (304 mg, 0.57 mmol) and 6N aqueous HCl (10 mL) were stirred at 100° C. for 1 h. The mixture was concentrated to dryness. The residue was purified by preparative HPLC using a gradient elution from 15% to 50% acetonitrile in water followed by filtration through an acidic resin, washing with MeOH. The product was eluted with 2M NH$_3$ in MeOH and the filtrate was concentrated to provide 26 mg (11%) of the desired product, which was approximately 70% pure. ES-MS m/z 396.42 [M+H]$^+$, HPLC RT (min) 2.04.

Step 12: Preparation of the Title Compound

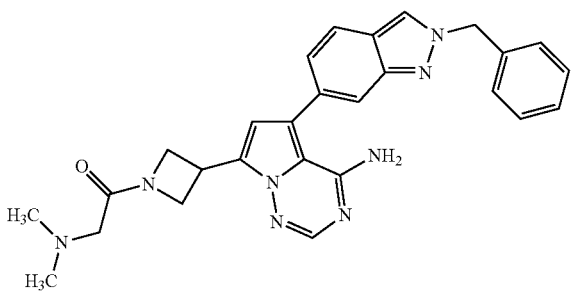 [SMILES: CN(C)CC(=O)N1CC(c2cc(-c3ccc4cn(Cc5ccccc5)nc4c3)c3c(N)ncnn23)C1]

A mixture of 7-azetidin-3-yl-5-(2-benzyl-2H-indazol-6-yl)pyrrolo[2,1-f][1,2,4]triazin-4-amine (20 mg, 0.051 mmol), N,N-dimethylglycine (5.7 mg, 0.056 mmol), EDCl (11.6 mg, 0.061 mmol), HOBt (8.2 mg, 0.061 mmol), and N,N-diisopropylethylamine (26 µL, 0.15 mmol) in DMF (1 mL) was stirred at rt for 16 h. The crude reaction mixture was purified via preparative HPLC using a gradient elution from 15% to 45% acetonitrile in water followed by filtration through an acidic resin, washing with MeOH. The product was eluted with 2M NH$_3$ in MeOH and the filtrate was concentrated to provide 5 mg (21%) of the desired product. $^1$H NMR (400 MHz, CD$_3$OD) δ 8.37 (s, 1 H), 7.79-7.85 (m, 2 H), 7.67 (s, 1 H), 7.29-7.37 (m, 5 H), 7.25 (d, 1 H), 6.81 (s, 1 H), 5.65 (s, 2 H), 4.70 (t, 1 H), 4.25-4.54 (m, 4 H), 3.18 (s, 2 H), 2.38 (s, 6 H); ES-MS m/z 481.10 [M+H]$^+$, HPLC RT (min) 2.07.

Example 290

Preparation of 5-(2-benzyl-2H-indazol-6-yl)-7-{(3R)-1-[(dimethylamino)acetyl]piperidin-3-yl}pyrrolo[2,1-f][1,2,4]triazin-4-amine

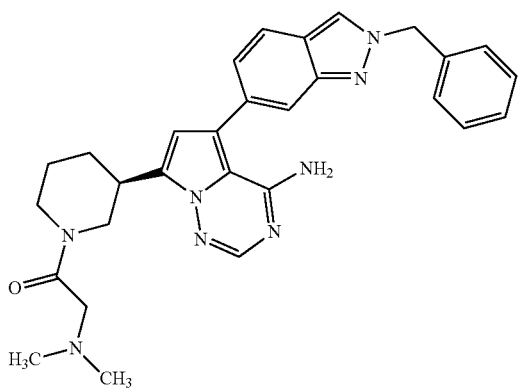 [SMILES: CN(C)CC(=O)N1CCC[C@@H](c2cc(-c3ccc4cn(Cc5ccccc5)nc4c3)c3c(N)ncnn23)C1]

A mixture of 5-(2-benzyl-2H-indazol-6-yl)-7-[(3R)-piperidin-3-yl]pyrrolo[2,1-f][1,2,4]triazin-4-amine (107 mg, 0.25 mmol), N,N-dimethylglycine (31 mg, 0.30 mmol), EDCl (53 mg, 0.28 mmol), HOBt (38 mg, 0.28 mmol), and N,N-diisopropylethylamine (132 µL, 0.76 mmol) in DMF (2.3 mL) was stirred at rt for 16 h. The crude reaction mixture was purified via preparative HPLC using a gradient elution from 15% to 45% acetonitrile in water followed by filtration through an acidic resin, washing with MeOH. The product was eluted with 2M NH$_3$ in MeOH and the filtrate was concentrated to provide 35 mg (27%) of the desired product. $^1$H NMR (400 MHz, DMSO-d$_6$) δ 8.54 (s, 1 H), 7.92 (d, 1 H), 7.80 (d, 1 H), 7.59 (s, 1 H), 7.27-7.39 (m, 5 H), 7.14 (d, 1 H), 6.64 (d, 1 H), 5.65 (s, 2 H), 3.95-4.97(m, 2 H), 2.62-3.32 (m, 5 H), 2.03-2.23 (m, 7 H), 1.68-1.91 (m, 2 H), 1.37-1.64 (m, 1 H); ES-MS m/z 509.15 [M+H]$^+$, HPLC RT (min) 2.22.

Example 291

Preparation of 5-(2-benzyl-2H-indazol-6-yl)-7{(3S)-1-[(dimethylamino)acetyl]piperidin-3-yl}pyrrolo[2,1-f][1,2,4]triazin-4-amine

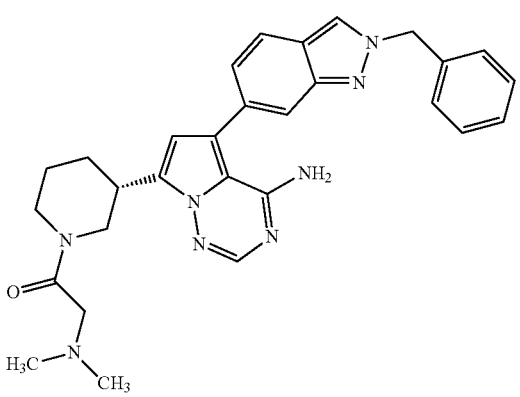 [SMILES: CN(C)CC(=O)N1CCC[C@H](c2cc(-c3ccc4cn(Cc5ccccc5)nc4c3)c3c(N)ncnn23)C1]

A mixture of 5-(2-benzyl-2H-indazol-6-yl)-7-[(3S)-piperidin-3-yl]pyrrolo[2,1-f][1,2,4]triazin-4-amine (95 mg, 0.22 mmol), N,N-dimethylglycine (28 mg, 0.27 mmol), EDCl (47 mg, 0.25 mmol), HOBt (33 mg, 0.25 mmol), and N,N-diisopropylethylamine (117 µL, 0.67 mmol) in DMF (2 mL) was stirred at rt for 16 h. The crude reaction mixture was purified via preparative HPLC using a gradient elution from 15% to 45% acetonitrile in water followed by filtration through an acidic resin, washing with MeOH. The product was eluted with 2M NH$_3$ in MOON and the filtrate was concentrated to provide 35 mg (27%) of the desired product. $^1$H NMR (400 MHz, DMSO-d$_6$) δ 8.55 (s, 1 H), 7.92 (d, 1 H), 7.80 (d, 1 H), 7.59 (s, 1 H), 7.27-7.39 (m, 5 H), 7.14 (d, 1 H), 6.61-6.67 (m, 1 H), 5.65 (s, 2 H); 3.95-4.94 (m, 2 H), 2.62-3.32 (m, 5 H), 2.05-2.23 (m, 7 H), 1.70-1.91 (m, 2 H), 1.40-1.64 (m, 1 H); ES-MS m/z 509.18 [M+H]$^+$, HPLC RT (min) 2.23.

Example 292

Preparation of 7-(azetidin-3-ylmethyl)-5-(2-benzyl-2H-indazol-6-yl)pyrrolo[2,1-f[]1,2,4]triazin-4-amine

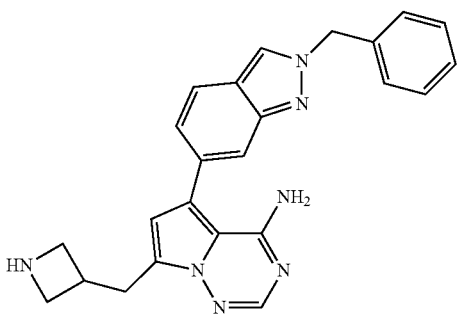 [SMILES: Nc1ncnn2c(CC3CNC3)cc(-c3ccc4cn(Cc5ccccc5)nc4c3)c12]

A solution of 7-(azetidin-3-ylmethyl)-5-(2-benzyl-2H-indazol-6-yl)pyrrolo[2,1-f][1,2,4]triazin-4-amine hydrochloride was partitioned between 3:1 CHCl$_3$/isopropanol (25 mL)

and saturated, aqueous NaHCO₃ (25 mL). The layers were separated and the organic layer was washed with brine, dried (Na₂SO₄) and concentrated to dryness to provide 7-(azetidin-3-ylmethyl)-5-(2-benzyl-2H-indazol-6-yl)pyrrolo[2,1-f][1,2,4]triazin-4-amine which was used without purification. A pure sample was obtained by preparative HPLC using a gradient elution from 15% to 40% acetonitrile in water followed by filtration through an acidic resin, washing with MeOH. The product was eluted with 2M NH₃ in MeOH and the filtrate was concentrated to provide 28 mg (from 90 mg) of desired product. $^1$H NMR (400 MHz, DMSO-d₆) δ 8.54 (s, 1 H), 7.88 (s, 1 H), 7.79 (d, 1 H), 7.57 (s, 1 H), 7.26-7.36 (m, 5 H), 7.13 (d, 1 H), 6.53 (s, 1 H), 5.64 (s, 2 H), 3.09-3.62 (m, 7 H); ES-MS m/z 46439.92 [M+H]⁺, HPLC RT (min) 2.06.

Example 293

Preparation of 2-(3-{[4-amino-5-(2-benzyl-2H-indazol-6-yl)pyrrolo[2,1-f][1,2,4]triazin-7-yl]methyl}azetidin-1-yl)ethanol

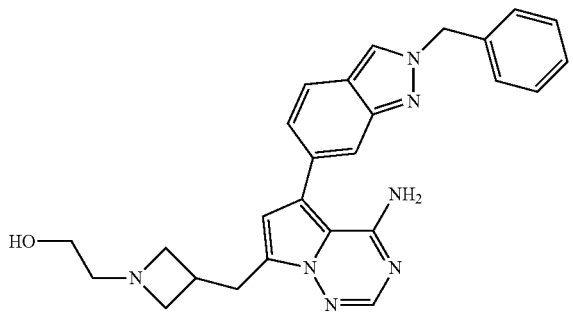 [SMILES: Nc1ncnn2c(CC3CN(CCO)C3)cc(-c3ccc4cn(Cc5ccccc5)nc4c3)c12]

To a solution of 7-(azetidin-3-ylmethyl)-5-(2-benzyl-2H-indazol-6-yl)pyrrolo[2,1-f][1,2,4]triazin-4-amine hydrochloride (100 mg, 0.22 mmol) in THF (1.5 mL) was added (2-bromoethoxy)-tert-butyldimethylsilane (53 µL, 0.25 mmol) and N,N-diisopropylethylamine (117 µl, 0.67 mmol). The reaction was heated (60° C.) for 17 h and then cooled to rt. The crude mixture was purified by preparative HPLC using a gradient elution from 20% to 50% acetonitrile in water followed by filtration through an acidic resin, washing with MeOH. The product was eluted with 2M NH₃ in MeOH and the filtrate was concentrated. A solution of the residue in 1% HCl in 95:5 EtOH/H₂O (4 mL) was stirred at rt for 16 h. The mixture was basified (pH 9) with the addition of saturated, aqueous NaHCO₃ solution and was evaporated to remove volatiles. The remaining aqueous mixture was extracted with ethyl acetate (3×15 mL) and the combined organic layers were washed with brine, dried (Na₂SO₄) and concentrated. The residue was triturated with Et₂O to afford 6 mg (6%) of the desired product. $^1$H NMR (400 MHz, DMSO-d₆) δ 8.58 (s, 1 H), 8.17 (s, 1 H), 7.83 (d, 1 H), 7.67 (s, 1 H), 7.26-7.39 (m, 5 H), 7.14 (d, 1 H), 6.77 (d, 1 H), 5.66 (s, 2 H), 4.11-4.27 (m, 2 H), 3.89-4.02 (m, 3 H), 3.53-3.63 (m, 2 H), 3.33-3.42 (m, 1 H), 3.10-3.30 (m, 4 H); ES-MS m/z 454.46 [M+H]⁺, HPLC RT (min) 1.96.

Example 294

Preparation of 5-(2-benzyl-2H-indazol-6-yl)-7-({1-[(dimethylamino)acetyl]azetidin-3-yl}methyl)pyrrolo[2,1-f][1,2,4]triazin-4-amine

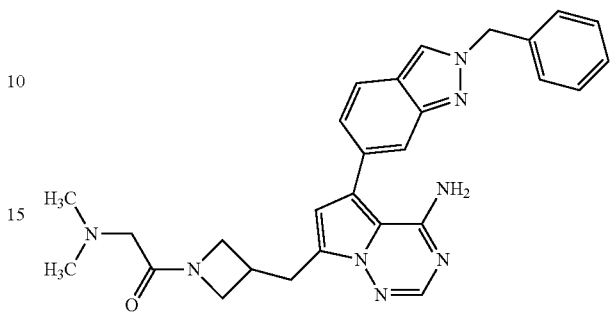

A mixture of 7-(azetidin-3-ylmethyl)-5-(2-benzyl-2H-indazol-6-yl)pyrrolo[2,1-f][1,2,4]triazin-4-amine (80 mg, 0.20 mmol), N,N-dimethylglycine (24 mg, 0.23 mmol), EDCI (41 mg, 0.22 mmol), HOBt (29 mg, 0.22 mmol), and N,N-diisopropylethylamine (102 µL, 0.59 mmol) in DMF (1.8 mL) was stirred at rt for 16 h. The crude mixture was purified by preparative HPLC using a gradient elution from 15% to 30% acetonitrile in water followed by filtration through an acidic resin, washing with MeOH. The product was eluted with 2M NH₃ in MeOH and the filtrate was concentrated to provide 21 mg (22%) of the desired product. $^1$H NMR (400 MHz, DMSO-d₆) δ 8.54 (s, 1 H), 7.90 (s, 1 H), 7.79 (d, 1 H), 7.58 (s, 1 H), 7.26-7.39 (m, 5 H), 7.13 (dd, 1 H), 6.62 (s, 1 H), 5.65 (s, 2 H), 4.26 (t, 1 H), 4.00 (t, 1 H), 3.90 (dd, 1 H), 3.66 (dd, 1 H), 3.31-3.21 (m, 4 H), 2.99-3.11 (m, 1 H), 2.30 (s, 6 H); ES-MS m/z 495.47 [M+H]⁺, HPLC RT (min) 2.03.

Example 295

Preparation of 5-(2-benzyl-2H-indazol-6-yl)-7-{[1-(methylsulfonyl)azetidin-3-yl]methyl}pyrrolo[2,1-f][1,2,4]triazin-4-amine

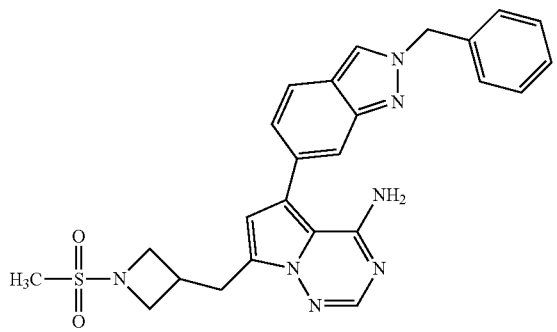 [SMILES: CS(=O)(=O)N1CC(Cc2cc(-c3ccc4cn(Cc5ccccc5)nc4c3)c3c(N)ncnn23)C1]

To a solution 7-(azetidin-3-ylmethyl)-5-(2-benzyl-2H-indazol-6-yl)pyrrolo[2,1-f][1,2,4]triazin-4-amine hydrochloride (100 mg, 0.22 mmol) in DMF (1.5 mL) was added methanesulfonyl chloride (19 µL, 0.25 mmol) and N,N-diisopropylethylamine (117 µL, 0.67 mmol). The reaction was stirred at rt for 17 h. The crude mixture was purified by preparative HPLC using a gradient elution from 15% to 45% acetonitrile in water followed by filtration through an acidic resin, washing with MeOH. The product was eluted with 2M NH₃ in MeOH and the filtrate was concentrated to provide 19 mg (17%) of the desired product. $^1$H NMR (400 MHz, DMSO-d₆) δ 8.54 (s, 1 H), 7.90 (s, 1 H), 7.79 (d, 1 H), 7.58 (s, 1 H), 7.25-7.37 (m, 5 H), 7.13 (dd, 1 H), 6.66 (s, 1 H), 5.64 (s, 2 H), 3.97 (t, 2 H), 3.69 (dd, 2 H), 3.14-3.19 (m, 2 H), 2.97-3.98 (m, 1 H), 2.96 (s, 3 H); ES-MS m/z 5488.38 [M+H]⁺, HPLC RT (min) 2.98.

Example 296

Preparation of 5-(2-benzyl-2H-indazol-6-yl)-7-(morpholin-2-ylmethyl)pyrrolo[2,1-f][1,2,4]triazin-4-amine

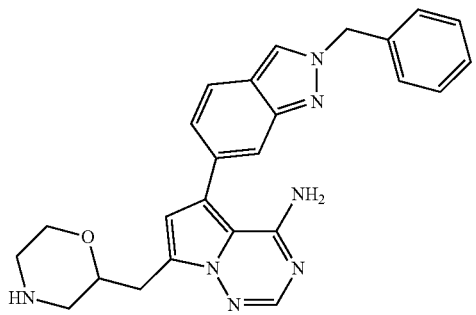 [SMILES: Nc1ncnn2c(CC3CNCCO3)cc(-c3ccc4cn(Cc5ccccc5)nc4c3)c12]

Using the procedure described in Steps 1-7 of intermediate V V and substituting 4-Boc-2-morpholinecarboxylic acid for 1-(tert-butoxycarbonyl)azetidine-3-carboxylic acid and the title compound was prepared as an HCl salt. The salt was free-based following the method of Example 301 to afford the title compound. ¹H NMR (400 MHz, DMSO-$d_5$) δ 8.54 (s, 1 H), 7.89 (s, 1 H), 7.79 (d, 1 H), 7.57 (s, 1 H), 7.27-7.37 (m, 5 H), 7.13 (dd, 1 H), 6.61 (s, 1 H), 5.65 (s, 2 H), 3.65-3.79 (m, 2 H), 3.25-3.45 (m, 1 H), 2.90-3.05 (m, 2 H), 2.72-2.79 (m, 1 H), 2.60-2.68 (m, 2 H), 2.40-2.47 (m, 1 H); LC-MS=440.25, RT=2.15 min.

Example 297

Preparation of 5-(2-benzyl-2H-indazol-6-yl)-7-{[4-(methylsulfonyl)morpholin-2-yl]methyl}pyrrolo[2,1-f][1,2,4]triazin-4-amine

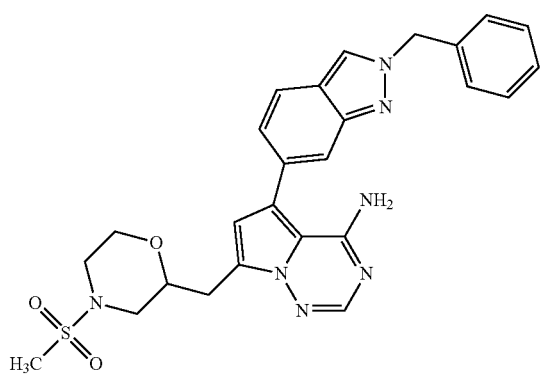 [SMILES: CS(=O)(=O)N1CCOC(Cc2cc(-c3ccc4cn(Cc5ccccc5)nc4c3)c3c(N)ncnn23)C1]

To a solution 5-(2-benzyl-2H-indazol-6-yl)-7-(morpholin-2-ylmethyl)pyrrolo[2,1-f][1,2,4]triazin-4-amine (80 mg, 0182 mmol) in DMF (1.5 mL) was added methanesulfonyl chloride (15 µL, 0.20 mmol) and N,N-diisopropylethylamine (95 µL, 0.55 mmol). The reaction was stirred at rt for 17 h. The crude mixture was purified by preparative HPLC using a gradient elution from 15% to 45% acetonitrile in water followed by filtration through an acidic resin, washing with MeOH. The product was eluted with 2M NH₃ in MeOH and the filtrate was concentrated to provide 20 mg (21%) of the desired product. ¹H NMR (400 MHz, DMSO-$d_6$) δ 8.54 (s, 1 H), 7.91 (s, 1 H), 7.80 (d, 1 H), 7.59 (s, 1 H), 7.26-7.41 (m, 5 H), 7.14 (d, 1 H), 6.68 (s, 1 H), 5.74 (s, 1 H), 5.65 (s, 2 H), 3.86-3.95 (m, 2 H), 3.51 (t, 1 H), 3.40 (d, 1 H), 3.04-3.17 (m, 2 H), 2.88 (s, 3H), 2.78-2.88 (m, 1 H), 2.62-2.71 (m, 1 H); ES-MS m/z 518.40 [M+H]⁺, HPLC RT (min) 2.51.

Example 298

Preparation 2-(2-{[4-amino-5-(2-benzyl-2H-indazol-6-yl)pyrrolo[2,1-f][1,2,4]triazin-7-yl]methyl}morpholin-4-yl)-N,N-dimethylacetamide

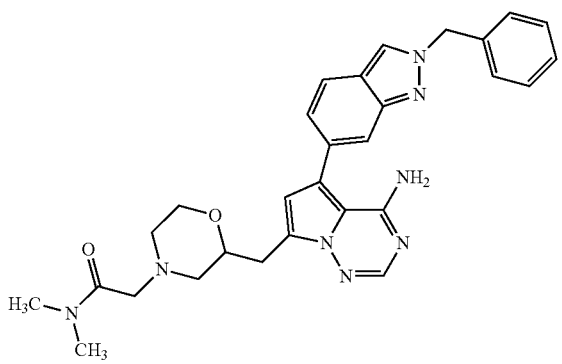 [SMILES: CN(C)C(=O)CN1CCOC(Cc2cc(-c3ccc4cn(Cc5ccccc5)nc4c3)c3c(N)ncnn23)C1]

To a solution of 5-(2-benzyl-2H-indazol-6-yl)-7-(morpholin-2-ylmethyl)pyrrolo[2,1-f][1,2,4]triazin-4-amine (80 mg, 0.18 mmol) in MeOH (1.5 mL) was added 2-chloro-N,N-dimethylacetamide (24 mg, 0.20 mmol) and N,N-diisopropylethylamine (95 µL, 0.55 mmol). The reaction was stirred at 60° C. for 17 h. The crude mixture was purified by preparative HPLC using a gradient elution from 15% to 45% acetonitrile in water followed by filtration through an acidic resin, washing with MeOH. The product was eluted with 2M NH₃ in MeOH and the filtrate was concentrated to provide 49 mg (52%) of the desired product. ¹H NMR (400 MHz, DMSO-$d_6$) δ 8.51-8.57 (m, 1H), 7.86-7.93 (m, 1 H), 7.76-7.84 (m, 1 H), 7.55-7.62 (m, 1 H), 7.26-7.41 (m, 5 H), 7.09-7.18 (m, 1 H), 6.58-6.66 (m, 1 H), 5.71-5.77 (m, 1 H), 5.62-5.68 (m, 2 H), 3.79-3.91 (m, 1 H), 3.68-3.79 (m, 1 H), 3.39-3.53 (m, 1 H), 2.90-3.20 (m, 7H), 2.69-2.82 (m, 4 H), 2.62 (d, 1 H), 2.11-2.24 (m, 1 H), 1.96-2.09 (m, 1 H); ES-MS m/z 525.38 [M+H]⁺, HPLC RT (min) 2.03.

Example 299

Preparation of 5-(2-benzyl-2H-indazol-6-yl)-7-(morpholin-3-ylmethyl)pyrrolo[2,1-f][1,2,4]triazin-4-amine

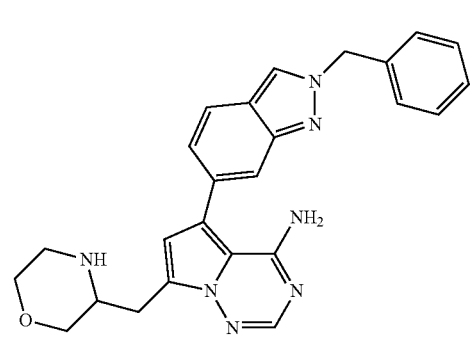 [SMILES: Nc1ncnn2c(CC3COCCN3)cc(-c3ccc4cn(Cc5ccccc5)nc4c3)c12]

Using the procedure described in Steps 1-7 of intermediate V V and substituting 4-N-Boc-3-morpholinecarboxylic acid for 1-(tert-butoxycarbonyl)azetidine-3-carboxylic acid, the title compound was prepared as an HCl salt. The salt was free-based following the method of Example 301 to afford the title compound. $^1$H NMR (400 MHz, CD$_3$OD) δ 8.35 (s, 1 H), 7.83 (s, 1 H), 7.79 (d, 1 H), 7.66 (s, 1 H), 7.28-7.39 (m, 5 H), 7.23 (dd, 1 H), 6.63 (s, 1 H), 5.64 (s, 2 H), 3.70-3.81 (m, 2 H), 3.45-3.56 (m, 1 H), 3.19-3.36 (m, 2 H), 2.93-3.07 (m, 2 H), 2.79-2.89 (m, 2 H); LC-MS [M+H]$^+$=440.18, RT=2.07 min.

Example 300

Preparation of 5-(2-benzyl-2H-indazol-6-yl)-7-({4-[(dimethylamino)acetyl]morpholin-3-yl}methyl)pyrrolo[2,1-f][1,2,4]triazin-4-amine

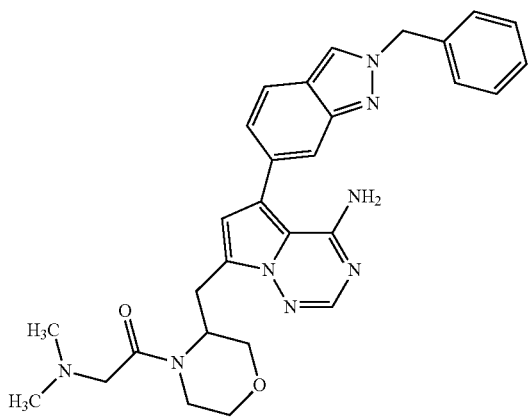 [SMILES: CN(C)CC(=O)N1CCOCC1Cc1cc(-c2ccc3cn(Cc4ccccc4)nc3c2)c2c(N)ncnn12]

A mixture of 5-(2-benzyl-2H-indazol-6-yl)-7-(morpholin-3-ylmethyl)pyrrolo[2,1-f][1,2,4]triazin-4-amine (100 mg, 0.23 mmol), N,N-dimethylglycine (25 mg, 0.24 mmol), EDCl (48 mg, 0.25 mmol), HOBt (34 mg, 0.25 mmol), and N,N-diisopropylethylamine (119 μL, 0.68 mmol) in DMF (1.2 mL) was stirred at rt for 16 h. The crude mixture was purified by preparative HPLC using a gradient elution from 15% to 45% acetonitrile in water followed by filtration through an acidic resin, washing with MeOH. The product was eluted with 2M NH$_3$ in MeOH and the filtrate was concentrated to provide 50 mg (42%) of the desired product. $^1$H NMR (400 MHz, DMSO-d$_6$) δ 8.52-8.57 (m, 1 H), 7.88-7.96 (m, 1H), 7.76-7.84 (m, 1 H), 7.48-7.55 (m, 1 H), 7.26-7.39 (m, 5 H), 7.04-7.11 (m, 1 H), 6.58-6.63 (m, 1 H), 5.64 (s, 2 H), 4.43-4.89 (m, 1 H), 3.69-4.12 (m, 3 H), 3.24-3.57 (m, 4 H), 3.09-3.23 (m, 1 H), 2.72-2.99 (m, 1 H), 2.15-2.27 (m, 1 H), 1.88-1.99 (m, 6H); ES-MS m/z 525.15 [M+H]$^+$, HPLC RT (min) 2.17.

Example 301

Preparation of 5-(2-benzyl-2H-indazol-6-yl)-7-[(4-cyclopropylmorpholin-3-yl)methyl]pyrrolo[2,1-f][1,2,4]triazin-4-amine

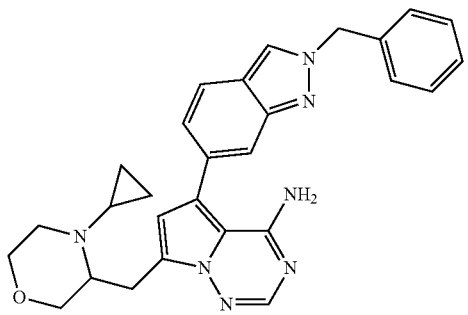 [SMILES: Nc1ncnn2c(CC3COCCN3C3CC3)cc(-c3ccc4cn(Cc5ccccc5)nc4c3)c12]

To a solution of 5-(2-benzyl-2H-indazol-6-yl)-7-(morpholin-3-ylmethyl)pyrrolo[2,1-f][1,2,4]triazin-4-amine (100 mg, 0.23 mmol) in MeOH (2.0 mL) containing 3 Å molecular sieves was added AcOH (130 μL, 2.28 mmol), [(1-ethoxycyclopropyl)oxy]trimethylsilane (238 mg, 1.37 mmol) and sodium cyanoborohydride (64 mg, 1.02 mmol). The reaction was stirred at 60° C. for 17 h. Aqueous NaOH (1N, 15 mL) was added and the mixture was extracted with EtOAc (3×15 mL). The combined organic layers were washed with brine, dried (Na$_2$SO$_4$) and concentrated. The residue was purified by preparative HPLC using a gradient elution from 15% to 45% acetonitrile in water followed by filtration through an acidic resin, washing with MeOH. The product was eluted with 2M NH$_3$ in MeOH and the filtrate was concentrated to provide 48 mg (44%) of the desired product. $^1$H NMR (400 MHz, DMSO-d$_6$) δ 8.54 (s, 1 H), 7.91 (s, 1 H), 7.79 (d, 1 H), 7.59 (s, 1 H), 7.26-7.41 (m, 5 H), 7.14 (d, 1 H), 6.63 (s, 1 H), 5.65 (s, 2 H), 3.55-3.65 (m, 2 H), 3.44-3.52 (m, 1 H), 3.30-3.41 (m, 1 H), 3.19-3.28 (m, 1 H), 2.80-2.96 (m, 3 H), 2.34-2.44 (m, 1 H), 1.77-1.86 (m, 1 H), 0.23-0.64 (m, 4 H); ES-MS m/z 480.13 [M+H]$^+$, HPLC RT (min) 2.19.

Example 302

Preparation of 1-(4-{3-[4-Amino-5-(2-benzyl-2H-indazol-6-yl)-pyrrolo[2,1-f][1,2,4]triazin-7-yl]-propyl}-piperazin-1-yl)-propan-1-one

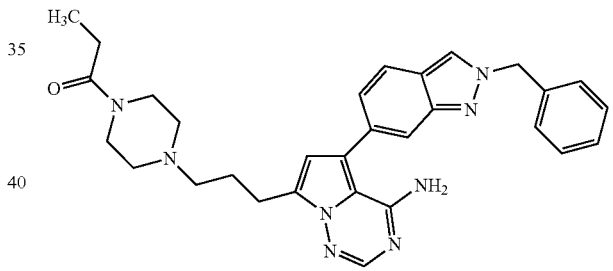

5-(2-benzyl-2H-indazol-6-yl)-7-(3-piperazin-1-yl-propyl)pyrrolo-[2,1-f][1,2,4]triazin-4-ylamine (75 mg, 0.16 mmol) was dissolved in anhydrous DMF (3.2 mL) and treated with EtN(iPr)$_2$ (44 μL, 0.32 mmol) followed by the addition of propionyl chloride (22 μL, 0.24 mmol). The mixture was heated to 50° C. for 18 h, cooled to rt and poured into water. The aqueous layer was extracted with 3×10 mL of EtOAc and the combined organic phases were washed with brine, dried (Na$_2$SO$_4$), filtered and concentrated in vacuo. The crude was purified via preparative HPLC. The product containing fractions were collected, and the TFA from the eluent was removed via filtration through an acidic resin followed by washing with acetonitrile. The product was then eluted with 2M NH$_3$ in MeOH. The filtrate was concentrated and the residue was crystallized from DCM-ether to provide the title compound (35.5 mg, 42%) as a white solid. $^1$H NMR (300 MHz, DMSO-d$_6$) δ 8.54 (s, 1H), 7.88 (s, 1H), 7.79 (d, 1H), 7.57 (s, 1H), 7.36 to 7.28 (m, 5H), 7.13 (dd, 1H), 6.60 (s, 1H), 5.63 (s, 2H), 3.41-3.31 (m, 4H), 2.89 (t, 2H), 2.38 to 2.24 (m, 8H), 1.90 to 1.84 (m, 2H), 0.93 (t, 3H); ES-MS m/z 523.3 [M+H]$^+$, RT (min) 2.15.

Example 303

Preparation of 1-(4-{3-[4-Amino-5-(2-benzyl-2H-indazol-6-yl)-pyrrolo[2,1-f][1,2,4]triazin-7-yl]-propyl}-piperazin-1-yl)-3,3,3-trifluoro-propan-1-one

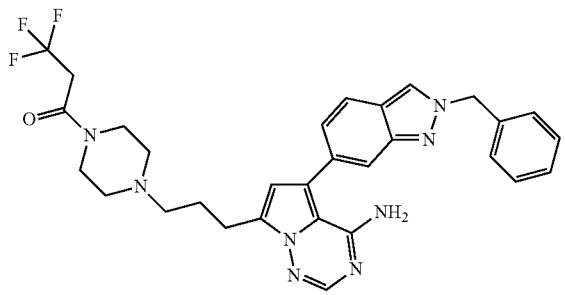 [SMILES: Nc1ncnn2c(CCCN3CCN(C(=O)CC(F)(F)F)CC3)cc(-c3ccc4cn(Cc5ccccc5)nc4c3)c12]

Using the procedure described for the preparation of Example 302 and substituting 3,3,3-trifluoropropionyl chloride for propionyl chloride, the title compound was prepared. $^1$H NMR (300 MHz, DMSO-$d_6$) δ 8.54 (s, 1H), 7.88 (s, 1H), 7.78 (d, 1H), 7.57 (s, 1H), 7.36 to 7.29 (m, 5H), 7.13 (dd, 1H), 6.60 (s, 1H), 5.64 (s, 2H), 3.61 (q, 2H), 3.44-3.37 (m, 4H), 2.89 (t, 2H), 2.39 to 2.30 (m, 6H), 1.88 to 1.84 (m, 2H); ES-MS m/z 577.2 [M+H]$^+$, RT (min) 2.25.

Example 304

Preparation of 1-(4-{3-[4-Amino-5-(2-benzyl-2H-indazol-6-yl)-pyrrolo[2,1-f][1,2,4]triazin-7-yl]-propyl}-piperazin-1-yl)-propan-2-one

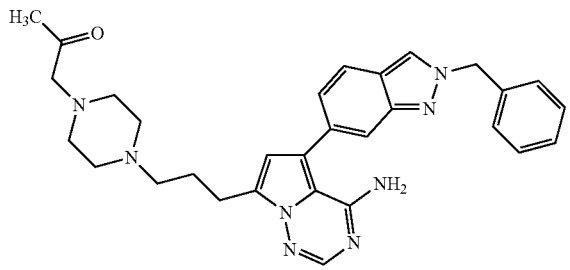 [SMILES: CC(=O)CN1CCN(CCCc2cc(-c3ccc4cn(Cc5ccccc5)nc4c3)c3c(N)ncnn23)CC1]

5-(2-Benzyl-2H-indazol-6-yl)-7-(3-piperazin-1-yl-propyl)pyrrolo-[2,1-f][1,2,4]triazin-4-ylamine (75 mg, 0.16 mmol) was dissolved in anhydrous DMF (3.2 mL) and treated with K$_2$CO$_3$ (33 mg, 0.24 mmol) followed by the addition of chloroacetone (15 µL, 0.19 mmol). The mixture was heated to 50° C. for 18 h, cooled to rt and poured into water. The aqueous layer was extracted with 3×10 mL of EtOAc and the combined organic phases were washed with brine, dried (Na$_2$SO$_4$), filtered and concentrated in vacuo. The crude was purified via preparative HPLC. The product containing fractions were collected, and the TFA from the eluent was removed via filtration through an acidic resin followed by washing with acetonitrile. The product was then eluted with 2M NH$_3$ in MeOH. The filtrate was concentrated and the residue was crystallized from DCM-ether to provide the title compound (10.8 mg, 13%) as a white solid. $^1$H NMR (300 MHz, DMSO-$d_6$) δ 8.54 (s, 1H), 7.87 (s, 1H), 7.79 (d, 1H), 7.57 (s, 1H), 7.36 to 7.29 (m, 5H), 7.13 (d, 1H), 6.59 (s, 1H), 5.64 (s, 2H), 3.27 to 3.24 (m, 1H), 3.09 (s, 2H), 2.87 (t, 2H), 2.36 to 2.23 (m, 9H), 2.04 (s, 3H), 1.88 to 1.79 (m, 2H); ES-MS m/z 523.2 [M+H]$^+$, RT (min) 2.08.

Example 305

Preparation of 4-{3-[5-(2-Benzyl-2H-indazol-6-yl)-4-(3-methyl-ureido)-pyrrolo[2,1-f][1,2,4]triazin-7-yl]-propyl}-piperazine-1-carboxylic acid methylamide

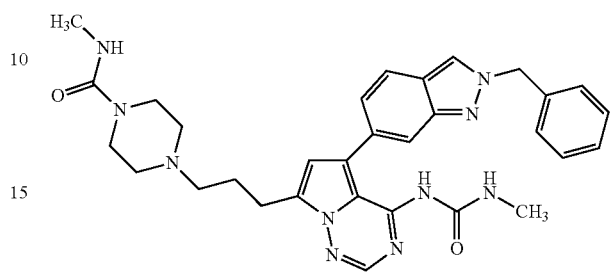

To a heterogeneous mixture of 5-(2-benzyl-2H-indazol-6-yl)-7-(3-piperazin-1-yl-propyl)pyrrolo-[2,1-f][1,2,4]triazin-4-ylamine (138 mg, 0.30 mmol) In anhydrous DCE (5.9 mL) was added N-methylisocyanate (20.2 mg, 0.35 mmol). The mixture was heated to 50° C. for 18 h, cooled to rt and poured into water. The aqueous layer was extracted with 3×25 mL of EtOAc and the combined organic phases were washed with brine, dried (Na$_2$SO$_4$), filtered and concentrated in vacuo. The crude was purified via preparative HPLC. The product containing fractions were collected, and the TFA from the eluent was removed via filtration through an acidic resin followed by washing with acetonitrile. The product was then eluted with 2M NH$_3$ in MeOH. The filtrate was concentrated and the residue was crystallized from DCM-ether to provide the title compound (98.7 mg, 58%) as a white solid. $^1$H NMR (300 MHz, DMSO-$d_6$) δ 9.14 (broad s, 1H), 8.59 (s, 1H), 8.19 (s, 1H), 7.87 (d, 1H), 7.70 (s, 1H), 7.40 (s, 1H), 7.36 to 7.28 (m, 5H), 7.18 (d, 1H), 6.81 (s, 1H), 6.37 to 6.35 (m, 1H), 5.67 (s, 2H), 3.20 (t, 4H), 2.94 (t, 2H), 2.73 (d, 3H), 2.52 (d, 3H), 2.35 (t, 2H), 2.27 (t, 4H), 1.90 to 1.86 (m, 2H); ES-MS m/z 581.3 [M+H]$^+$, RT (min) 2.75.

Example 306

Preparation of 1-[4-Amino-5-(2-benzyl-2H-indazol-6-yl)-pyrrolo[2,1-f][1,2,4]triazin-7-yl]-propan-1-ol

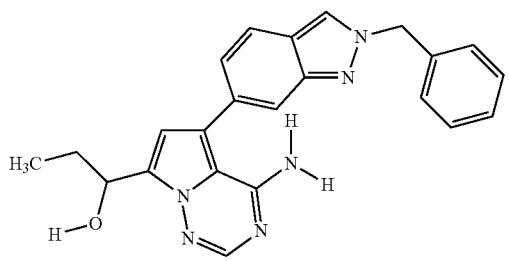 [SMILES: CCC(O)c1cc(-c2ccc3cn(Cc4ccccc4)nc3c2)c2c(N)ncnn12]

Step 1: Preparation of 1-(4-amino-pyrrolo[2,1-f][1,2,4]triazin-7-yl)-propan-1-ol

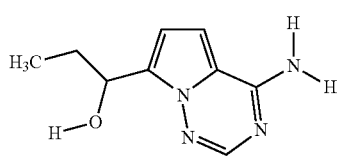

To a stirred suspension of Intermediate B (2.0 g, 9.39 mmol) in anhydrous THF (60 mL) at 0° C. was added 2.0 M isopropylmagnesium chloride in THF (14.0 mL, 28 mmol, 4.5 eq). The reaction mixture was stirred at 50° C. for 2 h. TLC analysis shows ~75% conversion. The reaction was cooled to rt, and an additional 2.0M isopropylmagnesium chloride in THF (7.0 mL, 14 mmol, 1.5 eq) was added. The reaction mixture was stirred at 50° C. for 2 h and then cooled to rt. Propylene oxide (3.0 mL, 42.3 mmol, 4.5 eq) was added, and the reaction mixture was stirred at rt for 16 h and poured into water. The aqueous layer was extracted with 3×200 mL of EtOAc and the combined organic phases were washed with brine, dried ($Na_2SO_4$), filtered and concentrated in vacuo. The residue was purified by MPLC (Biotage®, gradient elution 2-6% EtOH/DCM) and the higher $R_f$ spot was collected to give the title compound (325.9 mg, 18%) as a beige solid. $^1$H NMR (300 MHz, DMSO-$d_6$) δ 7.78 (s, 1H), 7.59 (broad s, 2H), 6.80 (d, 1H), 6.52 (d, 1H), 5.11 (d, 1H), 4.98 to 4.93 (m, 1H), 1,83 to 1.66 (m, 2H), 0.84 (t, 3H); ES-MS m/z 192.9 [M+H]$^+$, RT (min) 1.15.

Step 2: Preparation of 1-(4-Amino-5-bromo-pyrrolo [2,1-f][1,2,4]triazin-7-yl)-propan-1-ol

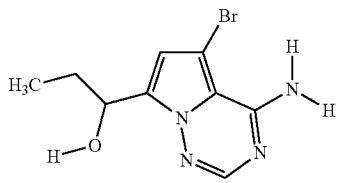

This compound was prepared in a manner similar to the bromination procedure described for the preparation of tert-butyl 4-(4-amino-5-bromopyrrolo[2,1-f][1,2,4]triazin-7-yl) piperidine-1-carboxylate, using 1-(4-amino-pyrrolo[2,1-f] [1,2,4]triazin-7-yl)-propan-1-ol as the starting material. $^1$H NMR (300 MHz, DMSO-$d_6$) δ 7.78 (s, 1H), 7.59 (broad s, 6.80 (d, 1H), 6.52 (d, 1H), 5.11 (d, 1H), 4.98 to 4.93 (m, 1H), 1,83 to 1.66 (m, 2H), 0.84 (t, 3H); ES-MS m/z 271.3/273.1 [M+H]$^+$, RT (min) 1.86.

Step 2: Preparation of the Title Compound

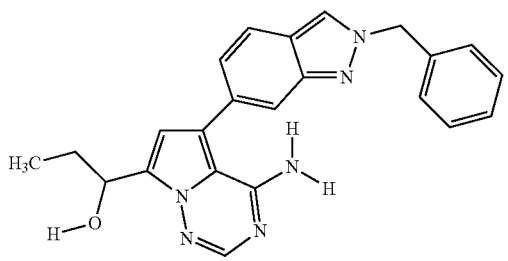 [SMILES: CCC(O)c1cc(-c2ccc3cn(Cc4ccccc4)nc3c2)c2c(N)ncnn12]

1-(4-Amino-5-bromo-pyrrolo[2,1-f][1,2,4]triazin-7-yl)-propan-1-ol (355 mg, 1.31 mmol) and 2-benzyl-6-(4,4,5,5-tetramethyl-[1,3,2]dioxaborolan-2-yl)-2H-indazole (656.4 mg, 1.96 mmol, 1.5 eq) were dissolved in 1:1 EtOH-toluene (11 mL each) and degassed with nitrogen. After 30 minutes [1,1'-bis(diphenylphosphino)ferrocene]dichloropalladium (II) complexed with dichloromethane (95.8 mg, 0.13 mmol, 0.1 eq) followed by 2M sodium carbonate solution (1.31 mL, 2.62 mmol, 2.0 eq) were added. The reaction mixture was stirred at 80° C. for 17 h and cooled to rt. The reaction mixture was partitioned between EtOAc and water and filtered through a pad of Celite® to rid of excess palladium salts. The organic layer was washed with water and brine, dried over $Na_2SO_4$, filtered, and concentrated in vacuo. The crude product was purified using an ISCO® instrument (gradient 1 to 100% [20% MeOH/DCM+1% Et$_3$N]/DCM) and the product containing fractions were concentrated. Trituration with DCM-hexane gave 295.3 mg (57%) of the title compound as beige solid. $^1$H NMR (300 MHz, DMSO-$d_6$) δ 8.54 (s, 1 H), 7.88 (s, 1 H), 7.80 (d, 1 H), 7.57 (s, 1 H), 7.34-7.28 (m, 5 H), 7.13 (dd, 1 H), 6.66 (s, 1 H), 5.65 (s, 2 H), 5.23 (d, 1H), 5.04 to 4.99 (m, 1H), 1.89 to 1.83 (m, 1H), 1.78 to 1.70 (m, 1H), 0.90 (t, 3H); ES-MS m/z 399.3 [M+H]$^+$, RT (min) 2.55.

Example 307

Preparation of 7-{3-[(Azetidin-3-ylmethyl)-amino]-propyl}-5-(2-benzyl-2H-indazol-6-yl)-pyrrolo[2,1-f] [1,2,4]triazin-4-ylamine

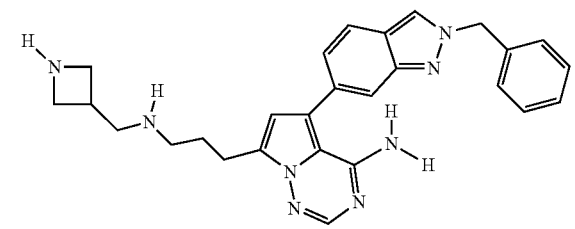 [SMILES: Nc1ncnn2c(CCCNCC3CNC3)cc(-c3ccc4cn(Cc5ccccc5)nc4c3)c12]

To a suspension of 3-({3-[4-amino-5-(2-benzyl-2H-indazol-6-yl)-pyrrolo[2,1-f][1,2,4]triazin-7-yl]-propylamino}-methyl)-azetidine-1-carboxylic acid tert-butyl ester (80 mg, 0.14 mmol) in anhydrous DCM (2.8 mL) was added trifluoroacetic acid (1.4 mL). The mixture was stirred at rt under $N_2$ for 3 days. The reaction mixture was concentrated and the crude was dissolved in EtOAc. The organic layer was washed with aqueous, saturated NaHCO$_3$ solution, water and brine, dried (Na$_2$SO$_4$), filtered and concentrated in vacuo. The crude was purified via preparative HPLC [gradient 15 to 90% ACN/ H$_2$O+0.1% TFA]. The product containing fractions were collected, and the TFA was removed via filtration through an acidic resin followed by washing with acetonitrile. The product was then eluted with 2M NH$_3$ in MeOH. The filtrate was concentrated and the residue was crystallized from DCM-ether to provide the title compound (6 mg, 9%) as a white solid. $^1$H NMR (300 MHz, MeOD). δ 8.39 (s, 1H), 7.85 to 7.82 (m, 2H), 7.65 (s, 1H), 7.36 to 7.33 (m, 5H), 7.24 (d, 1H), 6.56 (s, 1H), 5.67 (s, 2H), 4.02 (t, 2H), 3.78 to 3.75 (m, 2H), 3.05 (t, 3H), 2.87 (d, 2H), 2.70 (t, 2H), 2.02 to 1.98 (m, 2H); ES-MS m/z 467.3 [M+H]$^+$, RT (min) 2.82.

Example 308

Preparation of 4-[4-Amino-5-(2-benzyl-2H-indazol-6-yl)-pyrrolo[2,1-f][1,2,4]triazin-7-yl]-butyronitrile

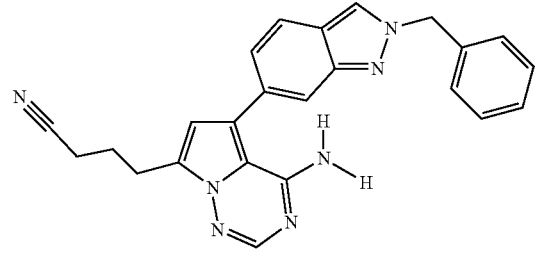 [SMILES: N#CCCCc1cc(-c2ccc3cn(Cc4ccccc4)nc3c2)c2c(N)ncnn12]

A solution of 5-(2-benzyl-2H-indazol-6-yl)-7-(3-bromopropyl)pyrrolo[2,1-f][1,2,4]triazin-4-ylamine (80 mg, 0.173 mmol), sodium cyanide (17 mg, 0.35 mmol, 2.0 eq.), and sodium iodide (2.6 mg, 0.017 mmol, 0.1 eq.) in anhydrous DMF (1.7 mL) was stirred at 100° C. for 16 h. The reaction mixture was cooled to rt and poured into water. The aqueous layer was extracted with 3×25 mL of EtOAc and the combined organic phases were washed with brine, dried (Na₂SO₄), filtered and concentrated in vacuo. The crude was purified via preparative HPLC. The product containing fractions were collected, and the TFA from the eluent was removed via filtration through an acidic resin followed by washing with acetonitrile. The product was then eluted with 2M NH₃ in MeOH. The filtrate was concentrated and the residue was crystallized from DCM-ether to provide the title compound (47.5 mg, 67%) as a white solid. $^1$H NMR (300 MHz, DMSO-d₆) δ 8.54 (s, 1H), 7.91 (s, 1H), 7.80 (d, 1H), 7.59 (s, 1H), 7.36 to 7.30 (m, 5H), 7.15 (dd, 1H), 6.65 (s, 1H), 5.65 (s, 2H), 3.00 (t, 2H), 2.59 (t, 2H), 2.04 to 1.96 (m, 2H); ES-MS m/z 408.3 [M+H]⁺, RT (min) 2.95.

Example 309

Preparation of 2-[4-Amino-5-(2-benzyl-2H-indazol-6-yl)-pyrrolo[2,1-f][1,2,4]triazin-7-yl]-ethanol

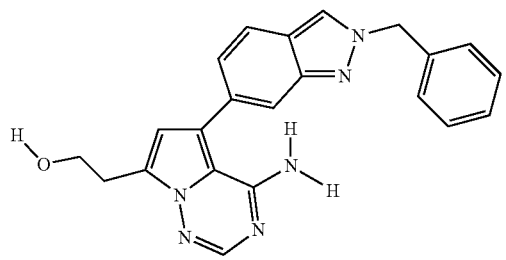 [SMILES: Nc1ncnn2c(CCO)cc(-c3ccc4cn(Cc5ccccc5)nc4c3)c12]

Step 1: Preparation of 2-(4-Amino-pyrrolo[2,1-f][1,2,4]triazin-7-yl)-ethanol

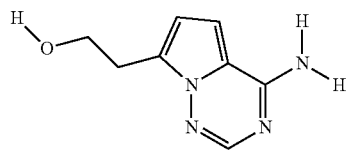 [SMILES: Nc1ncnn2c(CCO)ccc12]

To a stirred suspension of Intermediate B (2.00 g, 9.39 mmol) in anhydrous THF (94 mL) at −78° C. was added 2.5 M n-butyllithium in hexane (16.9 mL, 42.2 mmol, 4.5 eq). After stirring at −78° C. for 30 min, ethylene oxide was bubbled into the reaction mixture for 10 min. The mixture was stirred at rt for 17 h and poured into water. The aqueous layer was extracted with 3×100 mL of EtOAc, and the combined organic phases were washed with brine, dried (Na₂SO₄), filtered and concentrated in vacuo. The residue was purified by MPLC (Biotage®, gradient elution 0-3% MeOH/EtOAc) to give the title compound (204 mg, 12.2%) as a white solid. $^1$H NMR (300 MHz, DMSO-d₆) δ 7.79 (s, 1H), 7.57 (broad s, 2H), 6.78 (d, 1H), 6.44 (d, 1H), 4.71 (t, 1H), 3.68 to 3.63 (m, 2H), 2.98 (t, 2H); ES-MS m/z 179.2 [M+H]⁺, RT (min) 0.25.

Step 2: Preparation of 2-(4-Amino-5-bromo-pyrrolo[2,1-f][1,2,4]triazin-7-yl)-ethanol

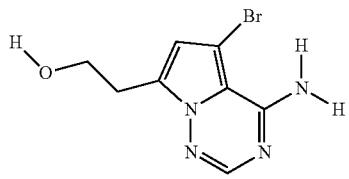 [SMILES: Nc1ncnn2c(CCO)cc(Br)c12]

This compound was prepared in a manner similar to the bromination procedure described for the preparation of tert-butyl 4-(4-amino-5-bromopyrrolo[2,1-f][1,2,4]triazin-7-yl)piperidine-1-carboxylate, using 2-(4-amino-pyrrolo[2,1-f][1,2,4]triazin-7-yl)-ethanol as the starting material. $^1$H NMR (300 MHz, DMSO-d₆) δ 7.83 (s, 1H), 6.64 (s, 1H), 4.75 (t, 1H), 3.65 (q, 2H), 2.96 (t, 2H); ES-MS m/z 257.3/259.2 [M+H]⁺, RT (min) 0.35.

Step 3: Preparation of the Title Compound

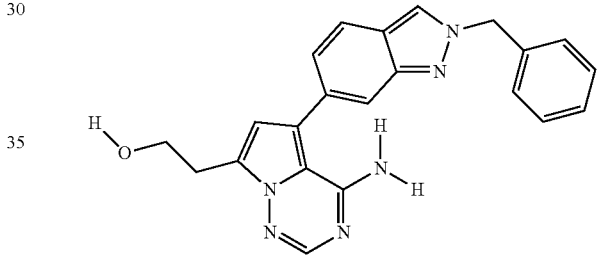

2-(4-Amino-5-bromo-pyrrolo[2,1-f][1,2,4]triazin-7-yl)-ethanol (425 mg, 1.65 mmol) and 2-benzyl-6-(4,4,5,5-tetramethyl-[1,3,2]dioxaborolan-2-yl)-2H-indazole (828.8 mg, 2.48 mmol, 1.5 eq) were dissolved in 1:1 EtOH-toluene (33 mL each) and degassed with nitrogen. After 30 minutes, [1,1'-bis(diphenylphosphino)ferrocene]dichloropalladium (II) complexed with dichloromethane (121 mg, 0.17 mmol, 0.1 eq) followed by 2M aqueous sodium carbonate solution (1.65 mL, 3.31 mmol, 2.0 eq) were added. The reaction mixture was stirred at 80° C. for 17 h and cooled to rt. The reaction mixture was partitioned between EtOAc and water and filtered through a pad of Celite® to remove excess palladium salts. The organic layer was washed with water and brine, dried over Mg₂SO₄, filtered, and concentrated in vacuo. The crude product was purified using an ISCO® instrument (gradient 1 to 100% [20% MeOH/DCM+1% Et₃N]/DCM) and the product containing fractions were concentrated. Trituration with DCM-hexane gave 232.3 mg (36%) of the title compound as beige solid. $^1$H NMR (300 MHz, DMSO-d₆) δ 8.54 (s, 1H), 7.88 (s, 1H), 7.79 (d, 1H), 7.56 (s, 1H), 7.34-7.28 (m, 5H), 7.13 (dd, 1H), 6.62 (s, 1H), 5.64 (s, 2H), 4.76 (t, 1H), 3.72 (q, 2H), 3.04 (t, 2H); ES-MS m/z 385.2 [M+H]⁺, RT (min) 2.25.

Example 310

Preparation of 1-(4-{2-[4-Amino-5-(2-benzyl-2H-indazol-6-yl)-pyrrolo[2,1-f][1,2,4]triazin-7-yl]-ethyl}-piperazin-1-yl)-ethanone

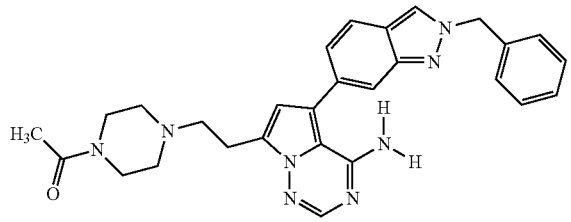 [SMILES: CC(=O)N1CCN(CCc2cc(-c3ccc4cn(Cc5ccccc5)nc4c3)c3c(N)ncnn23)CC1]

Step 1: Preparation of 5-(2-Benzyl-2H-indazol-6-yl)-7-(2-bromo-ethyl)-pyrrolo[2,1-f][1,2,4]-triazin-4-ylamine

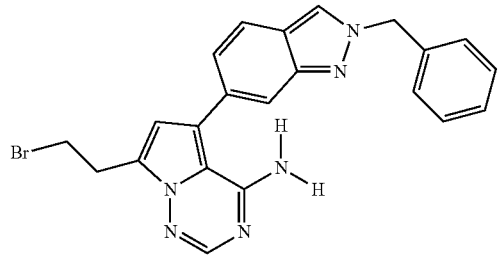 [SMILES: Nc1ncnn2c(CCBr)cc(-c3ccc4cn(Cc5ccccc5)nc4c3)c12]

To a solution of 2-[4-Amino-5-(2-benzyl-2H-indazol-6-yl)-pyrrolo[2,1-f][1,2,4]triazin-7-yl]-ethanol (210 mg, 0.55 mmol) in anhydrous THF (5.5 mL) at 0° C. was added carbon tetrabromide (235.5 mg, 0.71 mmol, 1.3 eq) and triphenylphosphine (157.6 mg, 0.60 mmol, 1.1 eq), and the reaction mixture was stirred at rt for 16 h. The reaction was poured into EtOAc. The organic layer was washed with water and brine, dried over Na$_2$SO$_4$, filtered, and concentrated in vacuo. The crude product was purified by MPLC (Biotage®) eluted with 15% acetone/DCM to give 222.6 mg (91%) of desired product as a white solid. $^1$H-NMR (300 MHz, DMSO-d$_6$) δ 8.55 (s, 1H), 7.93 (s, 1H), 7.81 (d, 1H), 7.58 (s, 1H), 7.36 to 7.15 (m, 5H), 7.13 (d, 1H), 6.73 (s, 1H), 5.65 (s, 2H), 3.82 (t, 2H), 3.46 (t, 2H); ES-MS m/z 447.3/449.2 [M+H]$^+$, RT (min) 2.91.

Step 2: Preparation of the Title Compound

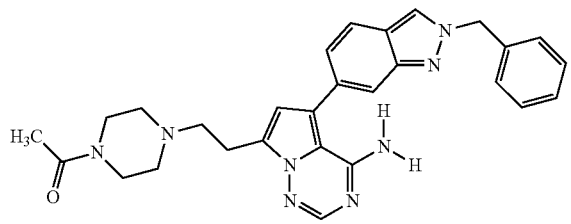 [SMILES: CC(=O)N1CCN(CCc2cc(-c3ccc4cn(Cc5ccccc5)nc4c3)c3c(N)ncnn23)CC1]

A solution of 5-(2-benzyl-2H-indazol-6-yl)-7-(2-bromo-ethyl)-pyrrolo[2,1-f][1,2,4]-triazin-4-ylamine (70 mg, 0.156 mmol), 1-acetyl-piperazine (40.1 mg, 0.313 mmol, 2.0 eq), triethylamine (20.6 mg, 0.20 mmol, 1.3 eq), and sodium iodide (2.3 mg, 0.016 mmol, 0.1 eq) in anhydrous DMF (1.6 mL) was stirred at 50° C. for 15 h. The reaction mixture was partitioned between EtOAc and water, and the organic layer was washed with 50% aqueous brine (3×), dried over Na$_2$SO$_4$, filtered, and concentrated in vacuo. The crude was purified via preparative HPLC. The product containing fractions were collected, and the TFA from the eluent was removed via filtration through an acidic resin followed by washing with acetonitrile. The product was then elided with 2M NH$_3$ in MeOH. The filtrate was concentrated and the residue was crystallized from DCM-hexane to provide the title compound (50.3 mg, 65%) as a white solid. $^1$H NMR (300 MHz, DMSO-d$_6$) δ 8.54 (s, 1H), 7.89 (s, 1H), 7.80 (dd, 1H), 7.57 (s, 1H), 7.36 to 7.30 (m, 5H), 7.13 (dd, 1H), 6.65 (s, 1H), 5.65 (s, 2H), 3.40 (q, 4H), 3.07 (t, 2H), 2.68 (t, 2H), 2.45 (t, 2H), 2.38 (t, 2H), 1.97 (s, 3H); ES-MS m/z 495.3 [M+H]$^+$, RT (min) 2.02.

Example 311

Preparation of 5-(2-Benzyl-2H-inda-zol-6-yl)-7-[2-(4-methanesulfonyl-piperazin-1-yl)-ethyl]-pyrrolo[2,1-f][1,2,4]triazin-4-ylamine

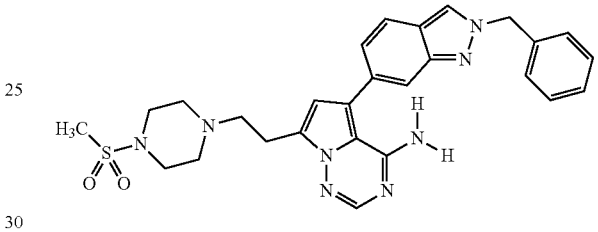

In a manner similar to the procedure described for the preparation of Example 310 and using 4-methanesulfonyl-piperazine as the starting material, 47.6 mg (57.3%) of the desired product was isolated. $^1$H NMR (300 MHz, DMSO-d$_6$) δ: 8.55 (s, 1H), 7.89 (s, 1H), 7.80 (d, 1H), 7.57 (s, 1H), 7.35 to 7.29 (m, 5H), 7.13 (d, 1H), 6.65 (s, 1H), 5.65 (s, 2H), 3.12 to 3.05 (m, 6H), 2.85 (s, 3H), 2.73 (t, 2H), 2.57 to 5.53 (m, 4H). ES-MS m/z 531.2 [M+H]$^+$, RT (min) 2.16.

Example 312

Preparation of 4-{2-[4-Amino-5-(2-benzyl-2H-inda-zol-6-yl)pyrrolo[2,1-f][1,2,4]triazin-7-yl]-ethyl}pipera-zin-2-one

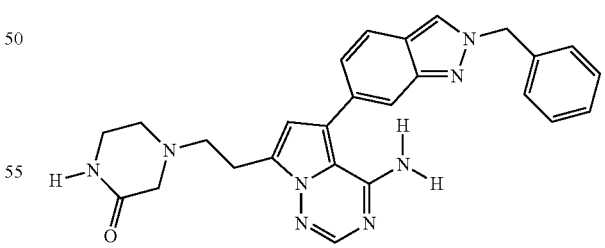

In a manner similar to the procedure described for the preparation of Example 310 and using 2-oxopiperazine as the starting material, 18.7 mg (27.6%) of the desired product was isolated. $^1$H NMR (300 MHz, DMSO-d$_6$) δ; 8.54 (s, 1H), 7.90 (s, 1H), 7.80 (d, 1H), 7.72 (s, 1H), 7.57 (s, 1H), 7.36 to 7.29 (m, 5H), 7.13 (dd, 1H), 6.65 (s, 1H), 5.65 (s, 2H), 3.16 to 3.12 (m, 2H), 3.07 (t, 2H), 2.99 (s, 2H), 2.73 (t, 2H), 2.63 (t, 2H). ES-MS m/z 467.2 [M+H]$^+$, RT (min)=2.05.

Example 313

Preparation of 5-(3-Amino-2-benzyl-2H-indazol-6-yl)-7-(1-cyclopropyl-piperidin-4-yl)-pyrrolo[2,1-f][1,2,4]triazin-4-ylamine

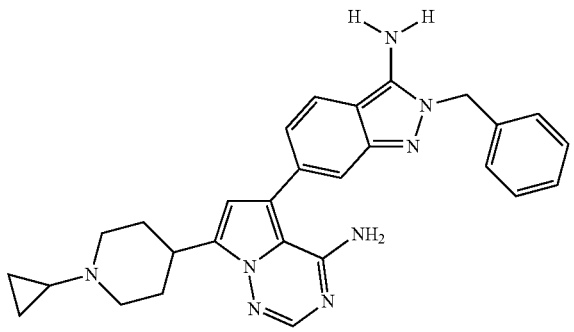 [SMILES: Nc1ncnn2c(C3CCN(C4CC4)CC3)cc(-c3ccc4c(N)n(Cc5ccccc5)nc4c3)c12]

To a solution of 5-(3-amino-2-benzyl-2H-indazol-6-yl)-7-piperidin-4-ylpyrrolo[2,1-f][1,2,4]triazin-4-amine (100 mg, 0.228 mmol) in MeOH (2.3 mL) was added acetic acid (0.13 mL, 2.28 mmol, 10.0 eq), 3 Å molecular sieves (50 mg), [1-(ethoxycyclopropyl)-oxy]timethylsilane (0.28 mL, 1.37 mmol, 6.0 eq), and sodium cyanoborohydride (64.5 mg, 1.03 mmol, 4.5 eq). The reaction mixture was stirred at 60° C. under $N_2$ for 18 h. The mixture was cooled to rt and aqueous, saturated $NaHCO_3$ solution (1.0 mL) was added to quench the reaction. The mixture was partitioned between EtOAc and water. The organic phase was washed with water and brine, dried over $Na_2SO_4$, filtered, and concentrated in vacuo. The crude was purified via preparative HPLC. The product containing fractions were collected, and the TFA from the eluent was removed via filtration through an acidic resin followed by washing with acetonitrile. The product was then eluted with 2M $NH_3$ in MeOH. The MeOH was removed and the residue was crystallized from DCM-ether-hexane to provide the title compound (35.5 mg, 32.5%) as pink solid. $^1H$ NMR (300 MHz, DMSO-$d_5$) δ 7.87 (s, 1H), 7.70 (d, 1H), 7.34 to 7.29 (m, 2H), 7.27 to 7.21 (m, 3H), 7.15 (s, 1H), 6.73 (dd, 1H), 6.52 (s, 1H), 6.37 (s, 2H), 5.38 (s, 2H), 3.12 to 3.00 (m, 3H), 2.28 (t, 2H), 1.96 (d, 2H), 1.67 to 1.56 (m, 3H), 0.43 to 0.39 (m, 2H), 0.31 to 0.27 (m, 21-1); ES-MS m/z 479.2 [M+H]$^+$, RT (min) 1.80.

Example 314

Preparation of N-{6-[4-Amino-7-(1-cyclopropyl-piperidin-4)-pyrrolo[2,1-f][1,2,4]triazin-5-yl]-2-benzyl-2H-indazol-3-yl}-propionamide

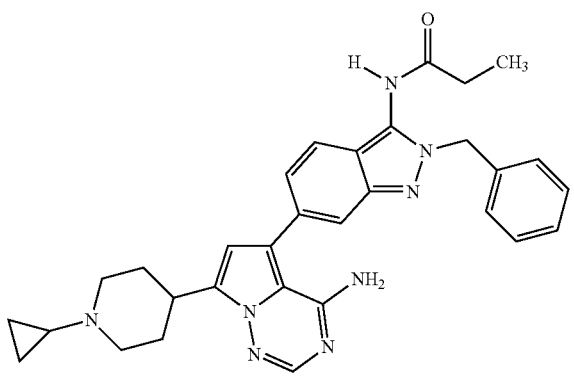 [SMILES: CCC(=O)Nc1c2ccc(-c3cc(C4CCN(C5CC5)CC4)n4ncnc(N)c34)cc2nn1Cc1ccccc1]

To a solution of 5-(3-amino-2-benzyl-2H-indazol-6-yl)-7-piperidin-4-yl-pyrrolo[2,1-f][1,2,4]triazin-4-ylamine (100 mg, 0.228 mmol) in MeOH (2.3 mL) was added acetic acid (0.13 mL, 2.28 mmol, 10.0 eq), 3 Å molecular sieves (50 mg), [1-(ethoxycyclopropyl)-oxy]trimethylsilane (0.28 mL, 1.37 mmol, 6.0 eq), and sodium cyanoborohydride (64.5 mg, 1.03 mmol, 4.5 eq). The reaction mixture was stirred at 60° C. under $N_2$ for 18 h. The mixture was cooled to rt and aqueous, saturated $NaHCO_3$ solution (1.0 mL) was added to quench the reaction. The mixture was partitioned between EtOAc and water. The organic phase was washed with water and brine, dried over $Na_2SO_4$, filtered, and concentrated in vacuo. The crude was purified via preparative HPLC. Fractions from a second peak different from 5-(3-amino-2-benzyl-2H-indazol-6-yl)-7-(1-cyclopropyl-piperidin-4-yl)-pyrrolo[2,1-f][1,2,4]triazin-4-ylamine were collected, and the TFA from the eluent was removed via filtration through an acidic resin followed by washing with acetonitrile. The product was then eluted with 2M $NH_3$ in MeOH. The MeOH was removed and the residue was crystallized from DCM-ether-hexane to provide the title compound (2.1 mg, 1.7%) as pink solid. $^1H$ NMR (300 MHz, DMSO-$d_6$) δ 10.27 (s, 1H), 7.89 (s, 1H), 7.55 (d, 1H), 7.50 (s, 1H), 7.34 to 7.21 (m, 5H), 7.10 (d, 1H), 6.07 (s, 1H), 5.48 (s, 2H), 3.11 (dt, 1H), 3.05 to 3.00 (m, 2H), 2.44 (q, 2H), 2.29 (t, 2H), 1.98 to 1.95 (m, 2H), 1.67 to 1.58 (m, 3H), 1.12 (t, 3H), 0.44 to 0.39 (m, 2H), 0.31 to 0.27 (m, 2H); ES-MS m/z 535.7 [M+H]$^+$, RT (min) 2.05.

Example 315

Preparation of N-{6-[4-Amino-7-(1-methanesulfonyl-piperidin-4-yl)-pyrrolo-[2,1-f][1,2,4]tria-zin-5-yl]-2-benzyl-2H-indazol-3-yl}-acetamide

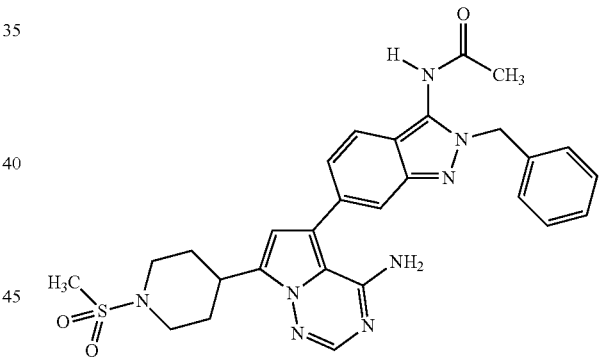

To a suspension of 5-(3-Amino-2-benzyl-2H-indazol-6-yl)-7-(1-methanesulfonyl-piperidin-4-yl)-pyrrolo[2,1-f][1,2,4]triazin-4-ylamine (150 mg, 0.29 mmol) in DCE (2.9 mL) and pyridine (0.29 mL) was added acetyl chloride (20 μl, 0.38 mmol, 1.3 mmol), and the reaction mixture was stirred at rt under $N_2$ for 18 h. The mixture was partitioned between EtOAc and water. The organic phase was washed with water and brine, dried over $Na_2SO_4$, filtered, and concentrated in vacuo. The crude was purified via preparative HPLC. The product containing fractions were collected, and the TFA from the eluent was removed via filtration through an acidic resin followed by washing with acetonitrile. The product was then eluted with 2M $NH_3$ in MeOH. The MeOH was removed and the residue was crystallized from DCM-hexane to provide the title compound (14 mg, 9%) as a solid. $^1H$ NMR (300 MHz, DMSO-$d_6$) δ 10.34 (s, 1H), 7.91 (s, 1H), 7.58 (d, 1H), 7.51 (s, 1H), 7.35 to 7.22 (m, 5H), 7.14 (dd, 1H), 6.65 (s, 1H), 5.49 (s, 2H), 3.68 to 3.64 (m, 2H), 3.26 (dt, 1H), 2.92 to 2.86 (m, 5H), 2.16 to 2.07 (m, 5H), 1.77 to 1.73 (m, 2H); ES-MS m/z 559.4 [M+H]$^+$, RT (min) 2.39.

Example 316

Preparation of 1-{-4-[4-Amino-5-(3-amino-2-benzyl-2H-indazol-6-yl)-pyrrolo[2,1-f][1,2,4]triazin-7-yl]-piperidin-1-yl}-2-methylamino-ethanone

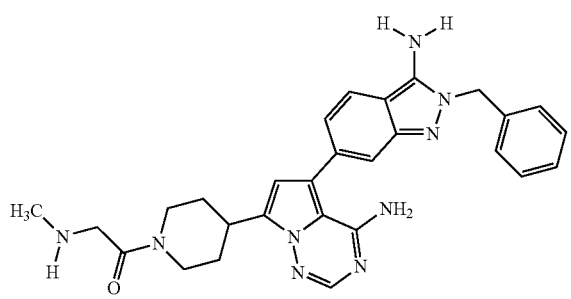 [SMILES: CNCC(=O)N1CCC(c2cc(-c3ccc4c(N)n(Cc5ccccc5)nc4c3)c3c(N)ncnn23)CC1]

Step 1: Preparation of (2-{4-[4-Amino-5-(3-amino-2-benzyl-2H-indazol-6-yl)-pyrrolo[2,1-f][1,2,4]triazin-7-yl]-piperidin-1-yl}-2-oxo-ethyl)-methyl-carbamic acid tert-butyl ester

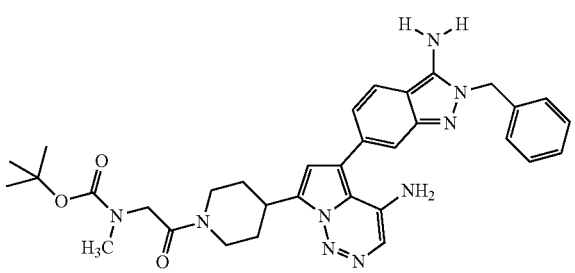 [SMILES: CN(CC(=O)N1CCC(c2cc(-c3ccc4c(N)n(Cc5ccccc5)nc4c3)c3c(N)cnnn23)CC1)C(=O)OC(C)(C)C]

To a stirred solution of N-t-BOC-sarcosine (44.0 mg, 0.233 mmol, 1.2 eq), ByPOP (120 mg, 0.27 mmol, 1.4 eq), and diisopropylethylamine (0.10 mL, 0.58 mmol, 3.0 eq) in anhydrous THF (1.9 mL) and DCE (1.0 mL) was added 5-(3-amino-2-benzyl-2H-indazol-6-yl)-7-piperidin-4-yl-pyrrolo[2,1-f][1,2,4]triazin-4-ylamine (85 mg, 0.194 mmol). The reaction mixture was stirred at 40° C. under $N_2$ for 18 h and cooled to rt. The mixture was cooled and poured into EtOAc. The organic phase was washed with water and brine, dried over $Na_2SO_4$, filtered, and concentrated in vacuo. The residue was dissolved in anhydrous THF (2.0 mL), and 1.0 M sodium methoxide in MeOH (0.5 mL) was added. The reaction mixture was stirred at it for 18 h and poured into EtOAc. The organic layer was washed with water and brine, dried over $Na_2SO_4$, filtered, and concentrated in vacuo. The crude product was purified using an ISCO® instrument (gradient 0 to 25% MeOH/EtOAc) and the product containing fractions were concentrated. Trituration with DCM-hexane afforded 43.9 mg (37.2%) of the title compound as pink solid. $^1$H NMR (300 MHz, DMSO-$d_6$) δ 7.89 (s, 1H), 7.71 (d, 1H), 7.34 to 7.29 (m, 2H), 7.27 to 7.14 (m, 3H), 7.15 (t, 1H), 6.73 (t, 1H), 6.56 (s, 0.5H), 6.48 (s, 0.5H), 6.37 (s, 2H), 5.38 (s, 2H), 4.50 to 4.45 (m, 1H), 4.13 to 3.83 (m, 3H), 3.44 to 3.35 (m, 1H), 3.16 (t, 1H), 2.78 to 2.70 (m, 4H), 2.07 to 2.04 (m, 2H), 1.66 to 1.51 (m, 2H), 1.35 (d, 9H); ES-MS m/z 610.0 [M+H]$^+$, RT (min) 2.55.

Step 2: Preparation of the Title Compound

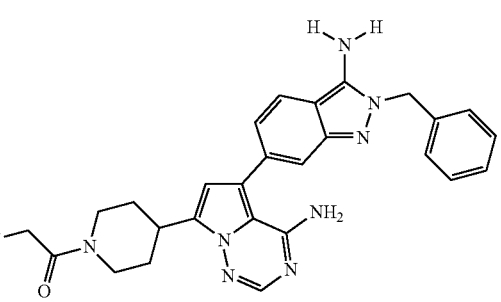

To a suspension of (2-(4-[4-Amino-5-(3-amino-2-benzyl-2H-indazol-6-yl)-pyrrolo[2,1-f][1,2,4]triazin-7-yl]-piperidin-1-yl)-2-oxo-ethyl)-methyl-carbamic acid tart-butyl ester (30 mg, 0.049 mmol) in anhydrous DCM (1.0 mL) was added trifluoroacetic acid (1.0 mL), and the reaction mixture was stirred at rt. After 1 h, the mixture was poured into EtOAc (75 mL), and the organic phase was washed with aqueous, saturated $NaHCO_3$ solution (3×25 mL), water and brine, dried over $Na_2SO_4$, filtered, and concentrated in vacuo. Trituration with DCM-hexane afforded the title compound (24.7 mg, 98.5%) as a pink solid. $^1$H NMR (300 MHz, DMSO-$d_6$) δ 7.88 (s, 1H), 7.71 (d, 1H), 7.34 to 7.29 (m, 2H), 7.27 to 7.21 (m, 3H), 7.15 (s, 1H), 6.73 (dd, 1H), 6.54 (s, 1H), 6.37 (broad s, 2H), 5.38 (s, 2H), 4.50 (d, 1H), 3.90 (d, 1H), 3.42 to 3.27 (m, 3H), 3.13 (t, 1H), 2.76 to 2.66 (m, 1H), 2.26 (s, 3H), 2.05 to 1.99 (m, 3H), 1.68 to 1.49 (m, 2H); ES-MS m/z 510.1 [M+H]$^+$, RT (min) 1.56.

Example 317

Preparation of 1-{4-[4-Amino-5-(3-amino-2-benzyl-2H-indazol-6-yl-pyrrolo[2,1-f][1,2,4]-tria-zin-7-yl]-piperidin-1-yl}-2-dimethylamino-ethanone

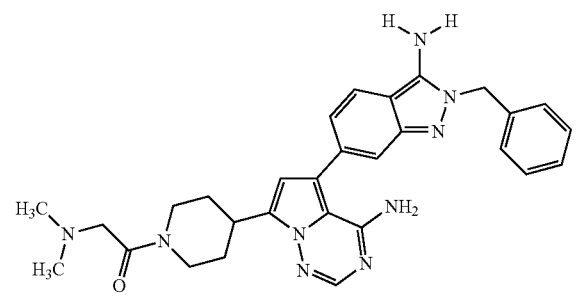 [SMILES: CN(C)CC(=O)N1CCC(c2cc(-c3ccc4c(N)n(Cc5ccccc5)nc4c3)c3c(N)ncnn23)CC1]

In a manner similar to the procedure described for step 1 of Example 316 and using N,N-dimethylglycine hydrochloride as the starting material, 59.1 mg (58.2%) of the desired product was isolated. $^1$H NMR (300 MHz, DMSO-$d_5$) δ 7.88 (s, 1H), 7.71 (d, 1H), 7.33 to 7.29 (m, 2H), 7.27 to 7.21 (m, 3H), 7.15 (s, 1H), 6.74 (dd, 1H), 6.54 (s, 1H), 6.37 (s, 2H), 5.38 (s, 2H), 4.46 (d, 1H), 4.13 (d, 1H), 3.42 to 3.34 (m, 1H), 3.18 to 3.05 (m, 3H), 2.70 (t, 1H), 2.20 (s, 6H), 2.03 (d, 2H), 1.70 to 1.63 (m, 1H), 1.54 to 1.47 (m, 1H); ES-MS m/z 524.2 [M+H]$^+$, RT (min) 1.91.

Example 318

Preparation of 5-(3-Amino-2-benzyl-2H-indazol-6-yl)-7-(1-ethanesulfonyl-piperidin-4-yl)-pyrrolo[2,1,2,4]triazin-4-ylamine

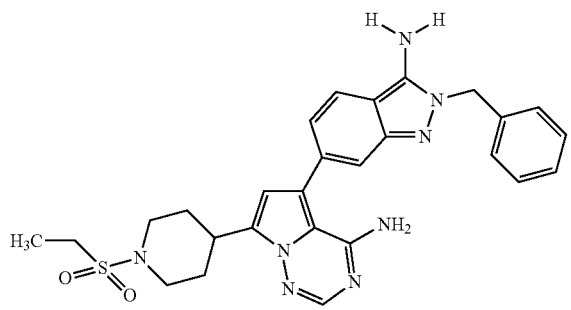 [SMILES: CCS(=O)(=O)N1CCC(c2cc(-c3ccc4c(N)n(Cc5ccccc5)nc4c3)c3c(N)ncnn23)CC1]

5-(3-Amino-2-benzyl-2H-indazol-6-yl)-7-piperidin-4-yl-pyrrolo[2,1-f][1,2,4]triazin-4-ylamine (100 mg, 0.228 mmol) was dissolved in anhydrous DMF (2.3 mL) and treated with EtN(IPr)₂ (117 µL, 0.68 mmol, 3.0 eq) followed by the addition of ethanesulfonyll chloride (31 µL, 0.33 mmol, 1.4 eq). The mixture was stirred at it for 16 h and poured into water. The aqueous layer was extracted with 3×10 mL of EtOAc and the combined organic phases were washed with brine, dried (Na₂SO₄), filtered and concentrated in vacuo. The crude was purified on the ISCO® eluted with 0 to 20% MeOH/EtOAc. Crystallization from DCM—ether—hexane provided the title compound (52.8 mg, 43.6%) as pink solid.

¹H NMR (300 MHz, DMSO-d₆) δ 10.34 (s, 1H), 7.91 (s, 1H), 7.58 (d, 1H), 7.51 (s, 1H), 7.35 to 7.22 (m, 5H), 7.14 (dd, 1H), 6.65 (s, 1H), 5.49 (s, 2H), 3.68 to 3.64 (m, 2H), 3.26 (dt, 1H), 2.92 to 2.86 (m, 5H), 2.16 to 2.07 (m, 5H), 1.77 to 1.73 (m, 2H); ES-MS m/z 531.7 [M+H]⁺, RT (min) 2.21.

Example 319

Preparation of 5-(3-Amino-2-benzyl-2H-indazol-6-yl)-7-(1-cyclopropanesulfonyl-piperidin-4-yl)-pyrrolo[2,1-f][1,2,4]triazin-4-ylamine

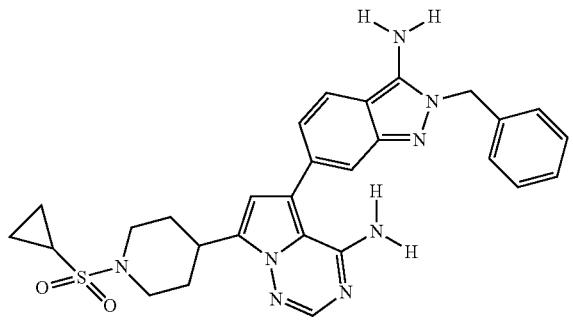 [SMILES: Nc1ncnn2c(C3CCN(S(=O)(=O)C4CC4)CC3)cc(-c3ccc4c(N)n(Cc5ccccc5)nc4c3)c12]

In a manner similar to the procedure described for the preparation of Example 318 and using cyclopropylsulfonyl chloride as the starting material, 35.2 mg (28.4%) of the desired product was isolated. ¹H NMR (300 MHz, DMSO-d₆) δ 7.89 (s, 1H), 7.71 (d, 1H), 7.34 to 7.29 (m, 2H), 7.27 to 7.21 (m, 3H), 7.16 (s, 1H), 6.74 (dd, 1H), 6.60 (s, 1H), 6.38 (s, 2H), 5.39 (s, 2H), 3.71 (d, 2H), 3.31 to 3.23 (m, 1H), 3.01 (t, 2H), 2.66 to 2.58 (m, 1H), 2.11 (d, 2H), 1.79 to 1.69 (m, 2H), 1.02 to 0.97 (m, 2H), 0.96 to 0.91 (m, 2H); ES-MS m/z 543.1 [M+H]⁺, RT (min) 2.36.

Example 320

Preparation of 4-[4-Amino-5-(3-amino-2-benzyl-2H-indazol-6-yl)-pyrrolo[2,1-f][1,2,4]tria-zin-7-yl]-piperidin-1-yl}-cyclopropyl-methanone

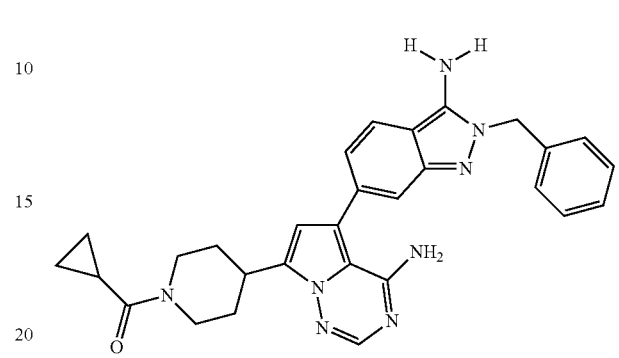

In a manner similar to the procedure described for the preparation of Example 318 and using cyclopropane carboxylic acid chloride as the starting material, 35.6 mg (30.8%) of the desired product was isolated. ¹H NMR (300 MHz, DMSO-d₅) δ 7.89 (s, 1H), 7.71 (d, 1H), 7.34 to 7.21 (m, 5H), 7.16 (s, 1H), 6.74 (dd, 1H), 6.57 (s, 1H), 6.37 (s, 2H), 5.38 (s, 2H), 4.49 (d, 1H), 4.37 (d, 1H), 145 to 3.37 (m, 1H), 3.29 to 3.21 (m, 1H), 2.72 (t, 1H), 2.10 to 1.96 (m, 3H), 1.70 to 1.48 (m, 2H), 0.86 to 0.67 (m, 4H); ES-MS m/z 507.2 [M+H]⁺, RT (min) 2.25.

Example 321

Preparation of 2-{4-[4-Amino-5-(3-amino-2-benzyl-2H-indazol-6-yl)-pyrrolo[2,1-f][1,2,4]-tria-zin-7-yl]-piperidin-1-yl}-ethanol

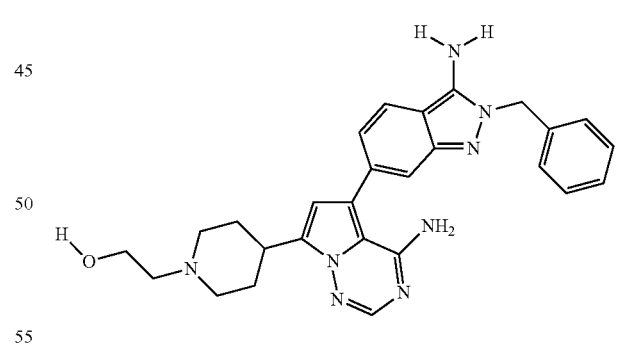

In a manner similar to the procedure described for the preparation of Example 254 and using 5-(3-amino-2-benzyl-2H-indazol-6-yl)-7-piperidin-4-yl-pyrrolo[2,1-f][1,2,4]triazin-4-ylamine as the starting material, 36.7 mg (41.6%) of the desired product was isolated. ¹H-NMR (300 MHz, DMSO-d₆) δ 7.86 (s, 1H), 7.71 (d, 1H), 7.35 to 7.20 (m, 5H), 7.16 (s, 1H), 6.74 (dd, 1H), 6.53 (s, 1H), 6.37 (s, 2H), 5.38 (s, 2H), 4.37 (t, 1H), 3.50 (q, 2H), 3.10 to 3.01 (m, 1H), 2.96 (d, 2H), 2.40 (t, 2H), 2.08 (t, 2H), 1.96 (d, 2H), 1.74 to 1.64 (m, 2H); ES-MS m/z 483.2 [M+H]⁺, RT (min) 1.18.

Example 322

Preparation of {4-[4-Amino-5-(3-amino-2-benzyl-2H-indazol-6-yl)-pyrrolo[2,1-f][1,2,4]-tria-zin-7-yl]-piperidin-1-yl}-(1-amino-cyclopropyl)-methanone

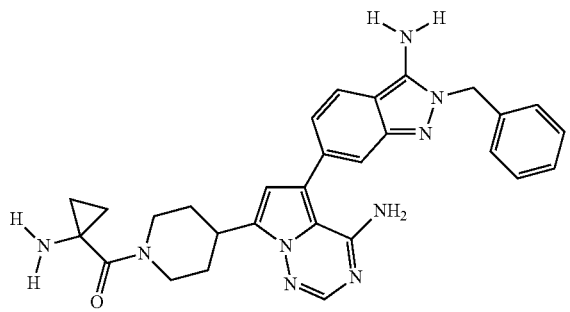 [SMILES: Nc1ncnn2c(C3CCN(C(=O)C4(N)CC4)CC3)cc(-c3ccc4c(N)n(Cc5ccccc5)nc4c3)c12]

In a manner similar to the procedure described for the preparation of Example 238 and using 5-(3-amino-2-benzyl-2H-indazol-6-yl)-7-piperidin-4-yl-pyrrolo[2,1-f][1,2,4]triazin-4-ylamine as the starting material, 50.6 mg (31.3%) of the desired product was isolated. $^1$H NMR (300 MHz, DMSO-d$_6$) δ 7.89 (s, 1H), 7.71 (d, 1H), 7.34 to 7.22 (m, 5H), 7.16 (s, 1H), 6.74 (dd, 1H), 6.56 (s, 1H), 6.37 (s, 2H), 5.38 (s, 2H), 4.43 (d, 2H), 3.43 to 3.36 (m, 1H), 2.95 (broad s, 2H), 2.25 (s, 2H), 2.03 (d, 2H), 1.60 (broad s, 2H), 0.85 to 0.80 (m, 2H), 0.65 to 0.61 (m, 2H); ES-MS m/z 522.2 [M+H]$^+$, RT (min) 1.83.

Example 323

Preparation of 5-(2-Benzyl-5-fluoro-2H-indazol-6-yl)-7-piperidin-4-yl-pyrrolo[2,1-f][1,2,4]-tria-zin-4-ylamine

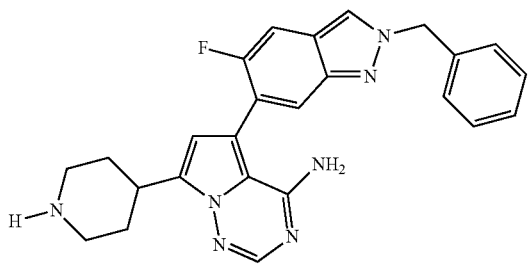 [SMILES: Nc1ncnn2c(C3CCNCC3)cc(-c3cc4nn(Cc5ccccc5)cc4cc3F)c12]

Step 1: Preparation of 4-[4-Amino-5-(2-benzyl-5-fluoro-2H-indazol-6-yl)-Pyrrolo[2,1-f][1,2,4]triazin-7-yl]-piperidine-1-carboxylic acid tert-butyl ester

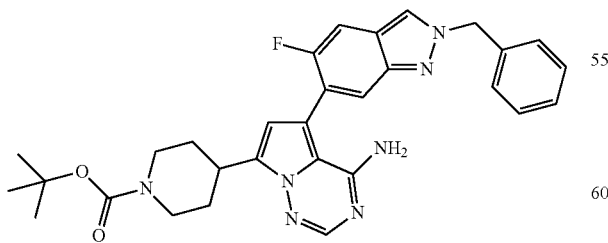

To the microwave vial was added tert-butyl 4-(4-amino-5-bromopyrrolo[2,1-f][1,2,4]triazin-7-yl)piperidine-1-carboxylate (250 mg, 0.63 mmol), 2-benzyl-5-fluoro-6-(4,4,5,5-tetramethyl-[1,3,2]dioxaborolan-2-yl)-2H-indazole (300 mg, 0.85 mmol, 1.35 eq), and tetrakis(trephenylphosphine) palladium (0) (46 mg, 0.063 mmol, 0.1 eq). Degassed, anhydrous DMF (6.3 mL) was added followed by 2.0M sodium carbonate solution (1.0 mL). The vial was capped and the reaction was irradiated in a microwave reactor at 180° C. for 25 min. The mixture was cooled to rt, diluted with EtOAc and filtered through a pad of Celite® to remove excess palladium. The filtrate was washed with 50% aqueous brine (3x), dried over Na$_2$SO$_4$, filtered, and concentrated in vacuo. The residue was purified by ISCO® (gradient elution 0 to 10% MeOH/DCM) to give the product (309.7 mg, 68%) as an oil. $^1$H-NMR (300 MHz, CD$_3$OD) δ 8.35 (s, 1H), 7.84 (s, 1H), 7.63 (d, 1H), 7.56 (d, 1H), 7.38 to 7.31 (m, 5H), 6.59 (s, 1H), 5.65 (s, 2H), 4.23 to 4.17 (m, 2H), 3.48 to 3.39 (m, 1H), 2.95 (broad s, 2H), 2.12 (d, 2H), 1.72 to 1.59 (m, 2H), 1.47 (s, 9H); ES-MS m/z 542.3 [M+H]$^+$, RT (min) 3.10.

Step 2: Preparation of the Title Compound

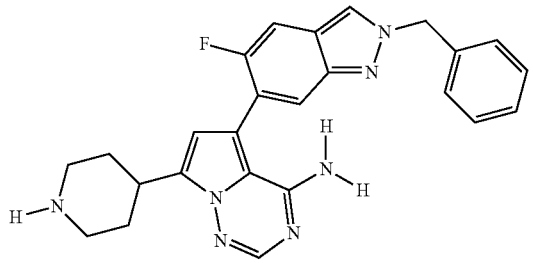 [SMILES: Nc1ncnn2c(C3CCNCC3)cc(-c3cc4nn(Cc5ccccc5)cc4cc3F)c12]

To a solution of 4-[4-amino-5-(2-benzyl-5-fluoro-2H-indazol-6-yl)-pyrrolo[2,1-f][1,2,4]triazin-7-yl]-piperidine-1-carboxylic acid tert-butyl ester (370 mg, 0.68 mmol) in DCM (12 mL) was added trifluoroacetic acid (3 mL). The reaction was stirred at rt under N$_2$ for 18 h and poured into EtOAc. The organic phase was washed with saturated, aqueous NaHCO$_3$ solution, water and brine, dried over Na$_2$SO$_4$, filtered, and concentrated in vacuo. The crude was purified via preparative HPLC. The product containing fractions were collected, and the TFA from the eluent was removed via filtration through an acidic resin followed by washing with acetonitrile. The product was then eluted with 2M NH$_3$ in MeOH. The filtrate was concentrated and the residue was crystallized from DCM-ether-hexane to provide the title compound (166.4 mg, 55.1%) as a white solid. $^1$H NMR (300 MHz, CD$_3$OD) δ 8.36 (s, 1H), 7.85 (s, 1H), 7.63 (d, 1H), 7.52 (d, 1H), 7.37 to 7.54 (m, 5H), 6.63 (s, 1H), 5.66 (s, 2H), 3.52 to 3.46 (m, 1H), 3.36 to 3.30 (m, 2H), 3.28 to 3.25 (m, 1H), 3.00 (dt, 2H), 2.25 (d, 2H), 1.92 to 1.80 (m, 2H); ES-MS m/z 442.2 [M+H]$^+$, RT (min) 2.08.

Example 324

Preparation of 5-(2-Benzyl-5-fluoro-2H-indazol-6-yl)-7-(1-methanesulfonyl-piperidin-4-yl)-pyrrolo[2,1-f][1,2,4]triazin-4-ylamine

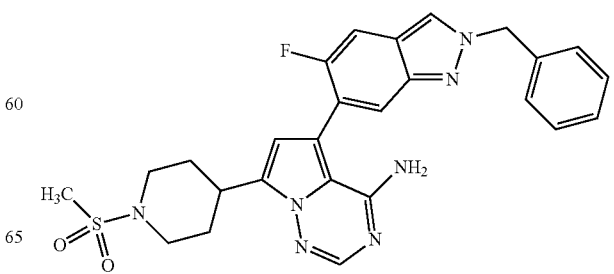

In a manner similar to the procedure described for the preparation of Example 249 and using 5-(2-benzyl-5-fluoro-2H-indazol-6-O-7-piperidin-4-yl-pyrrolo[2,1-f][1,2,4]triazin-4-ylamine as the starting material, 27.1 mg (29%) of the desired product was isolated. $^1$H NMR (300 MHz, DMSO-d$_6$) δ 8.52 (s, 1H), 7.92 (s, 1H), 7.60 to 7.56 (m, 2H), 7.37 to 7.28 (m, 5H), 6.61 (s, 1H), 5.65 (s, 2H), 3.66 (d, 2H), 3.33 to 3.22 (m, 1H), 2.92 to 2.85 (m, 5H), 2.13 (d, 2H), 1.78 to 1.67 (m, 2H); ES-MS m/z 520.3 [M+H]$^+$, RT (min) 3.06.

Example 325

Preparation of 5-(2-Benzyl-5-fluoro-2H-indazol-6-yl)-7-(1-cyclopropyl-piperidin-4-yl)-pyrrolo[2,1-f][1,2,4]triazin-4-ylamine

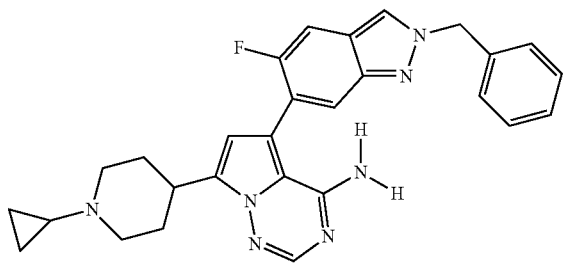 [SMILES: Nc1ncnn2c(C3CCN(C4CC4)CC3)cc(-c3cc4nn(Cc5ccccc5)cc4cc3F)c12]

In a manner similar to the procedure described for the preparation of Example 313 and using 5-(2-benzyl-5-fluoro-2H-indazol-6-yl)-7-piperidin-4-yl-pyrrolo[2,1-f][1,2,4]triazin-4-ylamine as the starting material, 30 mg (34%) of the desired product was isolated. $^1$H NMR (300 MHz, CD$_3$OD) δ 8.30 (s, 1H), 7.81 (s, 1H), 7.61 (d, 1H), 7.46 (d, 1H), 7.34 to 7.29 (m, 5H), 6.55 (s, 1H), 5.62 (s, 2H), 3.28 to 3.19 (m, 1H), 3.14 (d, 2H), 2.38 (dt, 2H), 2.10 (d, 2H), 1.79 to 1.68 (m, 4H), 1.66 to 1.60 (m, 1H), 1.57 to 1.50 (m, 1H), 1.10 to 1.63 (m, 1H); ES-MS m/z 482.2 [M+H]$^+$, RT (min) 2.17.

Example 326

Preparation of 5-(3-Amino-2-phenyl-2H-indazol-6-yl)-7-piperidin-4-yl-pyrrolo[2,1-f][1,2,4]triazin-4-ylamine

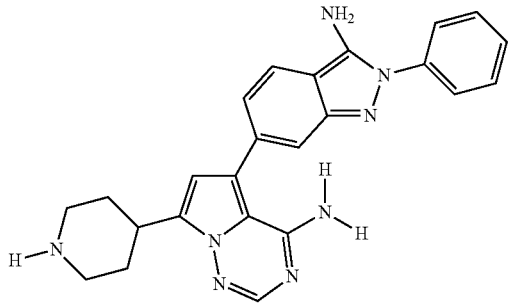 [SMILES: Nc1ncnn2c(C3CCNCC3)cc(-c3ccc4c(N)n(-c5ccccc5)nc4c3)c12]

This compound was prepared in a manner similar to the procedure described for the preparation of Example 1 and using 2-phenyl-6-(4,4,5,5-tetramethyl-[1,3,2]dioxaborolan-2-yl)-2H-indazol-3-ylamine in place of 2-benzyl-6-(4,4,5,5-tetramethyl-[1,3,2]dioxaborolan-2-yl)-2H-indazole.

$^1$H-NMR (300 MHz, DMSO-d$_6$) δ 7.88 (s, 1H), 7.83 (d, 1H), 7.72 (d, 2H), 7.57 (t, 2H), 7.44 (t, 1H), 7.24 (s, 1H), 6.80 (dd, 1H), 6.55 (s, 1H), 6.39 (s, 2H), 3.22 to 3.15 (m, 1H), 3.01 (d, 2H), 2.61 (t, 2H), 1.92 (d, 2H), 1.58 to 1.50 (m, 2H); ES-MS m/z 425.3 [M+H]$^+$, RT (min) 0.24.

Example 327

Preparation of 5-(3-Amino-2-phenyl-2H-indazol-6-yl)-7-(1-methanesulfonyl-piperidin-4-yl)-pyrrolo[2,1-f][1,1,2,4]triazin-4-ylamine

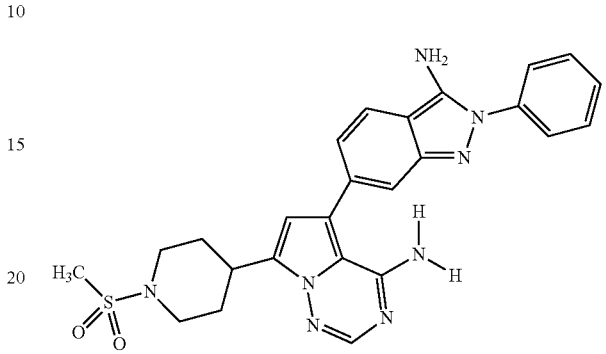

In a manner similar to the procedure described for the preparation of Example 249 and using 5-(3-amino-2-phenyl-2H-indazol-6-O-7-piperidin-4-yl-pyrrolo[2,1-f][1,2,4]triazin-4-ylamine as the starting material, 22 mg (26%) of the desired product was isolated. $^1$H NMR (300 MHz, DMSO-d$_6$) δ 7.91 (s, 1H), 7:83 (d, 1H), 7.73 to 7.71 (m, 2H), 7.59 to 7.54 (m, 2H), 7.46 to 7.42 (m, 1H), 7.24 (s, 1H), 6.81 (dd, 1H), 6.65 (s, 1H), 6.40 (s, 2H), 3.67 (d, 2H), 3.29 to 3.22 (m, 1H), 2.93 to 2.87 (m, 5H), 2.14 (d, 2H), 1.82 to 1.72 (m, 2H); ES-MS m/z 503.2 [M+H]$^+$, RT (min) 2.16.

Example 328

Preparation of 1-{4-[4-Amino-5-(3-amino-2-phenyl-2H-indazol-6-yl)-pyrrolo[2,1-f][1,1,2,4]triazin-7-yl]-piperidin-1-yl}-2-dimethylamino-ethanone

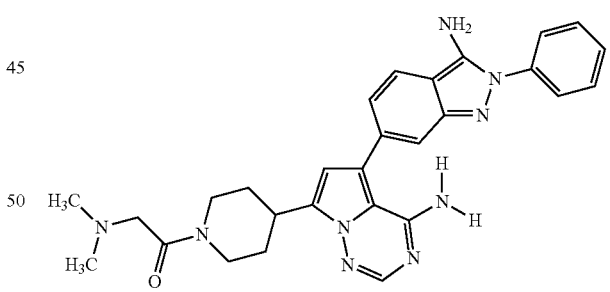

In a manner similar to the procedure described for the preparation of Example 316, step 1, and using 5-(3-amino-2-phenyl-2H-indazol-6-yl)-7-piperidin-4-yl-pyrrolo[2,1-f][1,2,4]triazin-4-ylamine and NJW-dimethylglycine hydrochloride as starting materials, 33.5 mg (37%) of the desired product was isolated. $^1$H NMR (300 MHz, DMSO-d$_6$) δ 7.90 (s, 1H), 7.83 (d, 1H), 7.71 (d, 2H), 7.56 (t, 2H), 7.44 (t, 1H), 7.24 (s, 1H), 6.80 (dd, 1H), 6.59 (s, 1H), 6.38 (s, 2H), 4.47 (d, 1H), 4.16 (d, 1H), 3.43 to 3.35 (m, 1H), 3.18 to 3.01 (m, 3H), 2.68 (t, 1H), 2.18 (s, 6H), 2.05 (d, 2H), 1.71 to 1.63 (m, 1H), 1.56 to 1.45 (m, 1H); ES-MS m/z 510.2 [M+H]$^+$, RT (min) 0.24.

Example 329

Preparation of 2-{4-[4-Amino-5-(3-amino-2-phenyl-2H-indazol-6-yl)-pyrrolo[2,1-f][1,2,4]triazin-7-yl]-piperidin-1-yl}-N-methyl-acetamide

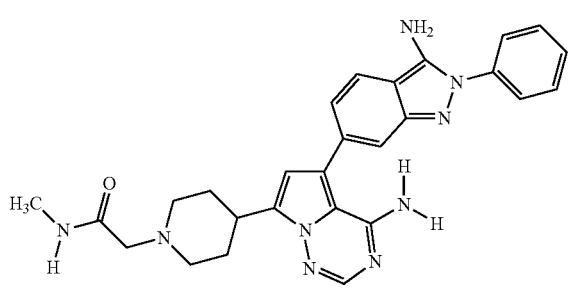 [SMILES: CNC(=O)CN1CCC(c2cc(-c3ccc4c(N)n(-c5ccccc5)nc4c3)c3c(N)ncnn23)CC1]

In a manner similar to the procedure described for the preparation of Example 298 and using 5-(3-amino-2-phenyl-2H-indazol-6-yl)-7-piperidin-4-yl-pyrrolo[2,1-f][1,2,4]triazin-4-ylamine and 2-chloro-N-methylacetamide as starting materials, 42.3 mg (38%) of the desired product was isolated. $^1$H NMR (300 MHz, CD$_3$OD) δ 7.81 to 7.78 (m, 2H), 7.70 to 7.67 (m, 2H), 7.61 (t, 2H), 7.53 to 7.49 (m, 1H), 7.35 (s, 1H), 6.95 (dd, 1H), 6.61 (s, 1H), 3.26 to 3.19 (m, 1H), 3.07 (s, 2H), 2.99 (d, 2H), 2.79 (s, 3H), 2.36 (t, 2H), 2.11 (d, 2H), 1.97 to 1.87 (m, 2H); ES-MS m/z 496.2 [M+H]$^+$, RT (min) 1.25.

Example 330

Preparation of 4-amino-5-(2-benzyl-2H-indazol-6-yl)-7-piperidin-4-ylpyrrolo[2,1-f][1,2,4]triazine-6-carbonitrile

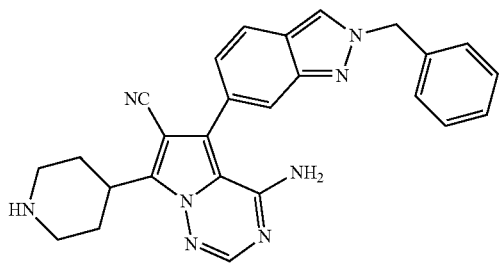 [SMILES: N#Cc1c(-c2ccc3cn(Cc4ccccc4)nc3c2)c2c(N)ncnn2c1C1CCNCC1]

Step 1: Preparation of 1-amino-1H-pyrrole-2,4-dicarbonitrile

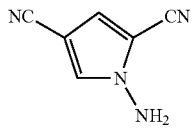

To a stirred solution of 2,4-dicyano-pyrrole (3.00 g, 25.6 mmol) in DMF (300 mL) was added sodium hydride (60% in mineral oil, 1.54 g, 38.4 mmol). The mixture was stirred for 15 min. Diphenylphosphinyl amino ester (8.96 g, 38.4 mmol) was added. The mixture was vigorously stirred while heating at 80° C. for 2 h and then cooled to rt. The mixture was filtered using DCM washings. The filtrate was concentrated to dryness to provide desired product (2.00 g, 59%). LTQ LC-MS: [M+H]$^+$ 133.0, RT 0.96 min. The product was used in the next step without further purification.

Step 2: Preparation 4-aminopyrrolo[2,1-f][1,2,4]triazine-6-carbonitrile

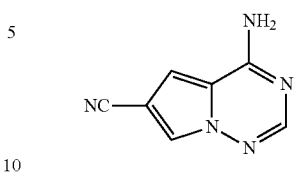

1-Amino-1H-pyrrole-2,4-dicarbonitrile (3.00 g, 22.71 mmol), formamidine acetate (22.71 g, 272.47 mmol) and K$_2$CO$_3$ (43.93 g, 317.88 mmol) were diluted in EtOH (105 mL). The mixture was heated at 80° C. for 2 h and then cooled to rt. EtOAc (200 mL) was added and the organic layer was washed with water (100 mL), dried over MgSO$_4$ and then concentrated to dryness. The crude material was purified by ISCO® chromatography to afford the desired product (2.58 g, 71%). $^1$H NMR (400 MHz, DMF-d$_6$) δ 7.91 (s, 1H), 7.64 (s, 1H), 7.61 (s, 1H), 7.21 (s, 2H); LC-MS m/z [M+H]$^+$ 159.9, RT 1.21 min.

Step 3: Preparation of 4-amino-7-bromopyrrolo[2,1-f][1,1,2,4]triazine-6-carbonitrile

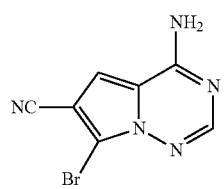 [SMILES: N#Cc1cc2c(N)ncnn2c1Br]

4-Aminopyrrolo[2,1-f][1,2,4]triazine-6-carbonitrile (1.89 g, 11.88 mmol) was dissolved in DMF (38 mL) and N-bromosuccinimide (2.11 g, 11.88 mmol) was added. The mixture was stirred at rt overnight. EtOAc (100 mL) was added, followed by 10% aqueous Na$_2$S$_2$O$_3$ and saturated, aqueous Na$_2$CO$_3$. The organic layer was dried over MgSO$_4$ and then concentrated to dryness. Trituration with acetone afforded 2.7 g (95.4%) product. $^1$H NMR (400 MHz, DMSO-d$_6$) δ 8.61 (s, 2H), 8.28 (s, 1H), 7.79 (s, 1H); LC-MS m/z [M+H]$^+$ 238.3 & 240.2, RT 2.19 min.

Step 4: Preparation of tert-butyl 4-(4-amino-6-cyanopyrrolo[2,1-f][1,2,4]triazin-7-yl)-3,6-dihydropyridine-1(2H)-carboxylate

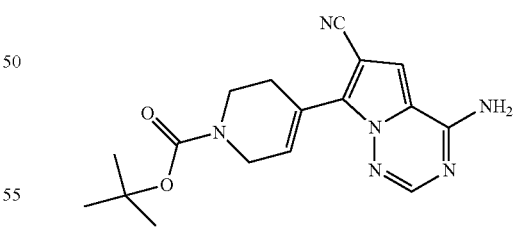

To the solution of 4-amino-7-bromopyrrolo[2,1-f][1,2,4]triazine-6-carbonitrile (1.00 g, 4.20 mmol) and tert-butyl 4-(4,4,5,5-tetramethyl-1,3,2-dioxaborolan-2-yl)-3,6-dihydropyridine-1(2H)-carboxylate (1.95 g, 6.30 mmol) in DMF (50 mL) and DME (6.9 mL), was added sodium carbonate in water (2M, 6.3 mL). The mixture was degassed for 15 min. Dichloro[bis(diphenylphosphino)ferrocene]palladium(II) CH$_2$Cl$_2$ adduct (307 mg, 0.42 mmol) was added. The mixture was stirred at 80° C. under nitrogen overnight then cooled to rt. The mixture was filtered through Celite®, washing with EtOAc (100 mL) then 20% MeOH/DCM (100 mL). The filtrate was concentrated to dryness. ISCO® purification (20% EtOAc/hexane then EtOAc) afforded title compound (1.0 g, 69.4%). $^1$H NMR (400 MHz, DMSO-d$_6$) δ 8.20 (s, 2H), 7.97 (s, 1H), 7.34 (s, 1H), 6.38 (t, 1H), 4.02 (d, 2H), 3.58 (t, 2H), 2.62 (t, 2H), 1.41 (s, 9H); LC-MS m/z [M+H]$^+$ 341.2, RT 3.16 min.

Step 5: Preparation of tert-butyl 4-(4-amino-6-cyanopyrrolo[2,1-f][1,2,4]triazin-7-yl)piperidine-1-carboxylate

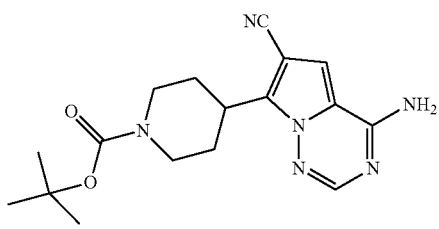 [SMILES: CC(C)(C)OC(=O)N1CCC(c2c(C#N)cc3c(N)ncnn23)CC1]

To a solution of tert-butyl 4-(4-amino-6-cyanopyrrolo[2,1-f][1,2,4]triazin-7-yl)-3,6-dihydropyridine-1(2H)-carboxylate (160 mg, 0.47 mmol) in MeOH (32 mL) and EtOAc (16 mL), was added Pd(OH)$_2$ (164 mg, 0.118 mmol) followed by ammonium formate (592 mg, 9.40 mmol). The mixture was heated at 65° C. for 1.5 h then cooled to rt. The mixture was filtered through Celite® and the cake was washed with EtOAc (10 mL) and MeOH (10 mL). The filtrate was concentrated to dryness. ISCO® purification (50% EtOAc/Hexane) afforded pure product (56.6 mg, 35%). $^1$H NMR (400 MHz, DMSO-d$_6$ δ 8.08 (s, 2H), 7.98 (s, 1H), 7.23 (s, 1H), 4.12-4.04 (m, 4H), 3.59-3.50 (m, 1H), 1.98-1.78 (m, 4H), 1.41 (s, 9H); LC-MS m/z[M+H]$^+$ 343.1, RT 3.05 min.

Step 6: Preparation of tert-butyl 4-(4-amino-5-bromo-6-cyanopyrrolo[2,1-f][1,2,4]triazin-7-yl)piperidine-1-carboxylate

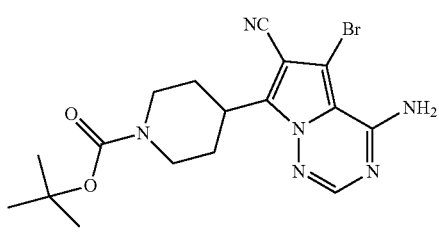 [SMILES: CC(C)(C)OC(=O)N1CCC(c2c(C#N)c(Br)c3c(N)ncnn23)CC1]

To the solution of tert-butyl 4-(4-amino-6-cyanopyrrolo[2,1-f][1,2,4]triazin-7-yl)piperidine-1-carboxylate (54 mg, 0.158 mmol) in DMF (2 mL), NBS (28.07 mg, 0.158 mmol) was added. The mixture was stirred at 0° C. for 2 h. The mixture was concentrated to dryness. Trituration with acetone afforded product (60 mg, 90%). $^1$H NMR (400 MHz, DMF-d$_a$) δ 7.52 (s, 1H), 4.42-4.38 (m, 4H), 4.88-4.78 (m, 1H), 2.20-2.08 (m, 4H), 1.62 (s, 9H); LC-MS m/z [M+H]$^+$ 420.9% 422.9, LC-MS RT 3.24 min.

Step 7: Preparation of tert-butyl 4-[4-amino-5-(2-benzyl-2H-indazol-6-yl)-6-cyanopyrrolo[2,1-f][1,1,2,4]triazin-7-yl]piperidine-1-carboxylate

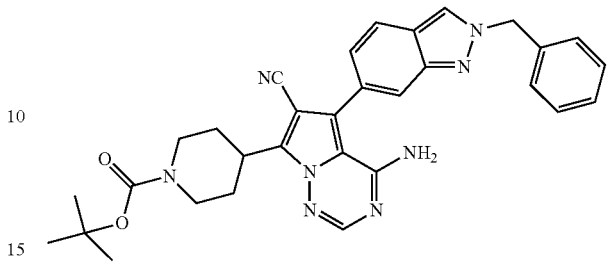

To a stirred, degassed solution of tert-butyl 4-(4-amino-5-bromo-6-cyanopyrrolo[2,1-f][1,2,4]triazin-7-yl)piperidine-1-carboxylate (85 mg, 0.182 mmol), 2-benzyl-6-(4,4,5,5-tetramethyl-[1,3,2]dioxaborolan-2-yl)-2H-indazole (92.89 mg, 0.272 mmol), and tetrakis(triphenylphosphine)palladium(0) (20.98 mg, 0.018 mmol) in DMF (4.25 mL), was added aqueous Na$_2$CO$_3$ solution (2 M, 0.272 mL). The reaction was heated (microwave 15 min at 150° C.) and then cooled to rt. The mixture was filtered. The filtrate was concentrated to dryness. The crude material was purified by ISCO® chromatography using a gradient of 25 to 100% ethyl acetate in hexanes to afford the desired product (70.8 mg, 71%). $^1$H NMR (400 MHz, DMSO-d$_5$) δ 8.60 (s, 1H), 8.20 (d, 2H), 8.01 (s, 1H), 7.87 (d, 1H), 7.70 (s, 1H), 7.40-7.30 (m, 5H), 7.11 (d, 1H), 5.67 (s, 2H), 4.16-4.04 (m, 2H), 3.64-3.58 (m, 1H), 2.98-2.80 (m, 2H), 2.02-1.82 (m, 4H), 1.40 (s, 9H); LC-MS m/z [M+H]$^+$ 549.2, RT 3.64 min.

Step 8: Preparation of the Title Compound

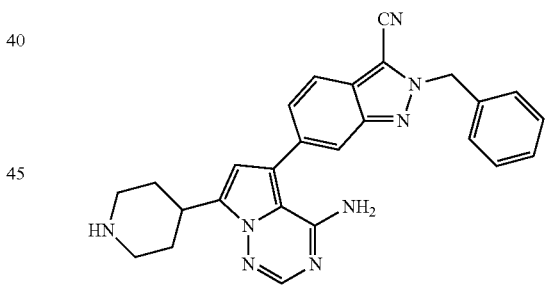

To a solution of tert-butyl 4-[4-amino-5-(2-benzyl-2H-indazol-6-yl)-6-cyanopyrrolo[2,1-f][1,2,4]triazin-7-yl]piperidine-1-carboxylate (90 mg, 0.148 mmol) in dichloromethane (2 mL) was added trifluoroacetic acid (0.3 mL). The reaction was stirred at rt for 17 h. The mixture was made basic (pH 9) with the addition of saturated, aqueous NaHCO$_3$ and the layers were separated. The aqueous phase was extracted with dichloromethane (2×10 mL) and the combined organic layers were washed with brine, dried (Na$_2$SO$_4$), and evaporated. The crude material was purified by ISCO® chromatography using 2N NH$_3$ in MeOH/EtOAc to afford pure product (60 mg, 91%). $^1$H NMR (400 MHz, CD$_3$OD) δ 8.43 (s, 1H), 7.93 (s, 1H), 7.91 (d, 1H), 7.75 (s, 1H), 7.37-7.34 (m, 5H), 7.20 (d, 1H), 5.69 (s, 2H), 4.22-4.20 (m, 2H), 3.76-3.64 (m, 1H), 2.85 (m, 2H), 2.38-2.22 (m, 2H), 2.02-1.98 (m, 2H); LC-MS m/z [M+H]$^+$ 449.2, RT 2.22 min.

Example 331

Preparation of 6-[7-(1-acetylpiperidin-4-yl)-4-aminopyrrolo[2,1-f][1,2,4]triazin-5-yl]-2-benzyl-2H-indazole-3-carbonitrile

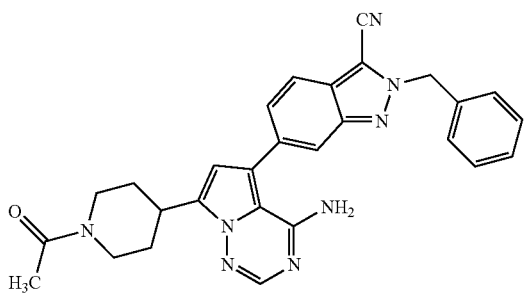 [SMILES: CC(=O)N1CCC(c2cc(-c3ccc4c(C#N)n(Cc5ccccc5)nc4c3)c3c(N)ncnn23)CC1]

To a solution of 4-amino-5-(2-benzyl-2H-indazol-6-yl)-7-piperidin-4-ylpyrrolo[2,1-f][1,2,4]triazine-6-carbonitrile (50 mg, 0.11 mmol) in THF (2 mL) was added. N,N-diisopropylethylamine (39 µL, 0.22 mmol) followed by acetyl chloride (8.8 µL, 0.11 mmol). The mixture was stirred at rt overnight. The mixture was diluted with dichloromethane (25 mL) and was washed with H$_2$O (20 mL), brine, and was dried (Na$_2$SO$_4$) and concentrated. The crude material was purified by ISCO® chromatography to obtain the desired product (20 mg, 37%). $^1$H NMR (400 MHz, DMSO-d$_6$) δ 8.60 (s, 1H), 8.02 (s, 1H), 7.86 (d, 1H), 7.68 (s, 1H), 7.40-7.24 (m, 5H), 7.11 (d, 1H), 5.66 (s, 2H), 4.60-4.56 (m, 1H), 3.00-3.96 (m, 1H), 3.71-3.62 (m, 1H), 3.22-3.18 (m, 1H), 2.66-2.61 (m, 1H), 2.02 (s, 3H), 2.04-1.88 (m, 4H); LC-MS m/z[M+H]$^+$ 491.3, RT 2.83 min.

Example 332

Preparation of 5-(2-benzyl-1,3-benzothiazol-6-yl)-7-piperidin-4-ylpyrrolo[2,1-f][1,2,4]triazin-4-amine

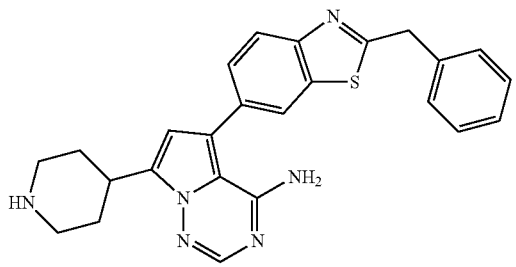 [SMILES: Nc1ncnn2c(C3CCNCC3)cc(-c3ccc4nc(Cc5ccccc5)sc4c3)c12]

Step 1: Preparation of 6-bromo-2-(methylthio)-1,3-benzothiazole

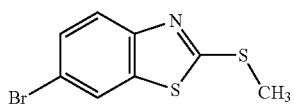

To the solution of 2-(methylthio)-1,3-benzothiazole (5.00 g, 27.58 mmol) in CHCl$_3$ (85 mL) in a NaCl-ice water bath, bromine (4.24 mL, 82.8 mmol) was slowly added dropwise, followed by acetic acid (30 mL). The mixture was stirred at rt overnight. The white solid was filtered and then dissolved in EtOAc (200 mL). Saturated, aqueous Na$_2$CO$_3$ (200 mL) was added and the organic layer was separated, dried over MgSO$_4$ and concentrated to dryness. Desired product (5.0 g, 70%) was obtained. $^1$H NMR (400 MHz, DMSO-d$_6$) δ 8.30 (s, 1H), 7.76 (d, 1H), 7.59 (d, 1H), 2.79 (s, 3H); LC-MS m/z [M+H]$^+$ 260.2 & 262.1, RT 3.65 min.

Step 2: Preparation of 2-benzyl-6-bromo-1,3-benzothiazole

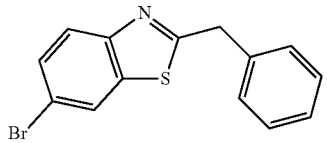 [SMILES: Brc1ccc2nc(Cc3ccccc3)sc2c1]

A degassed mixture of 6-bromo-2-(methylthio)-1,3-benzothiazole (4.20 g, 16.14 mmol), tetrakis(triphenylphosphine)palladium(0) (186 mg, 0.161 mmol) and benzylzinc bromide (0.5 M in THF, 61.34 mL) was heated at 60° C. for 4 hrs. EtOAc (200 mL) was added and the organic layer was washed with saturated, aqueous NaHCO$_3$ (3×150 mL), then water (3×150 mL). The organic layer was dried over MgSO$_4$ and concentrated. The crude material was purified by ISCO® chromatography using 4% EtOAc in hexane to obtain the desired product (1.50 g, 28%). $^1$H NMR (400 MHz, acetone-d$_6$) δ 8.20 (s, 1H), 7.88 (d, 1H), 7.62 (d, 1H), 7.44-7.30 (m, 5H), 4.44 (s, 2H); LC-MS m/z [M+H]$^+$ 304.2 & 306.1, RT 4.02 min.

Step 3: Preparation of 2-benzyl-6-(4,4,5,5-tetramethyl-1,3,2-dioxaborolan-2-yl)-1,3-benzothiazole

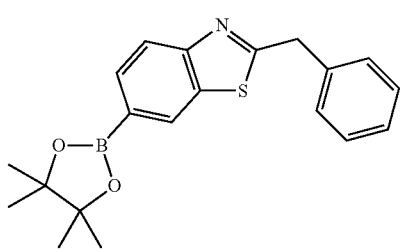 [SMILES: CC1(C)OB(c2ccc3nc(Cc4ccccc4)sc3c2)OC1(C)C]

To the degassed suspension of 2-benzyl-6-bromo-1,3-benzothiazole (1.40 g, 4.14 mmol), bis(pinacolato)diboron (1.61 g, 6.21 mmol) and potassium acetate (1.22 g, 12.43 mmol) in 1,4-dioxane (34 mL), 1-1'-bis(diphenylphosphino)ferrocenepalladium(11)chloride dichloromethane adduct (303 mg, 0.37 mmol) was added. The mixture was heated at 80° C. for 7 h followed by 90° C. for 1 h. The mixture was filtered and the cake was washed with EtOAc, MeOH and DCM. The filtrate was concentrated. The crude material was purified by ISCO® chromatography using 3% EtOAc in hexane to obtain the desired product (0.92 g, 63%). $^1$H NMR (400 MHz, acetone-d$_6$) δ 8.30 (s, 1H), 7.88 (d, 1H), 7.82 (d, 1H), 7.44-7.30 (m, 5H), 4.52 (s, 2H), 1.22 (s, 12H); LC-MS m/z [M+H]+ 352.3, RT 3.88 min.

Step 4: Preparation of tert-butyl 4-[4-amino-5-(2-benzyl-1,3-benzothiazol-6-yl)pyrrolo[2,1-f][1,2,4]triazin-7-yl]piperidine-1-carboxylate

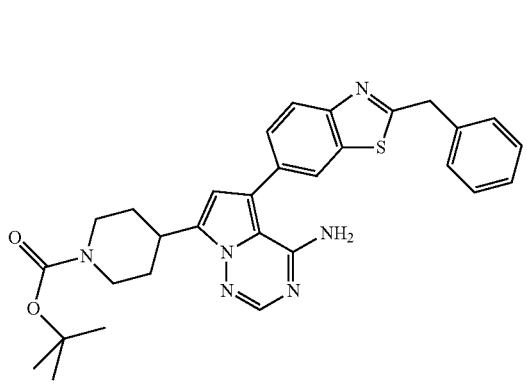 [SMILES: CC(C)(C)OC(=O)N1CCC(c2cc(-c3ccc4nc(Cc5ccccc5)sc4c3)c3c(N)ncnn23)CC1]

In a manner similar to the procedure described for step 7 of the preparation of Example 330 and using tert-butyl 4-(4-amino-5-bromopyrrolo[2,1-f][1,2,4]triazin-7-yl)piperidine-1-carboxylate and 2-benzyl-6-(4,4,5,5-tetramethyl-1,3,2-dioxaborolan-2-yl)-1,3-benzothiazole as starting material, 510 mg (87%) of the desired product was isolated. $^1$H NMR (400 MHz, DMSO-d$_6$) δ 7.99 (s, 1H), 7.97 (d, 1H), 7.81 (s, 1H), 7.51 (d, 1H), 7.38-7.32 (m, 5H), 7.56 (s, 1H), 4.41 (s, 2H), 4.12-4.04 (m, 2H), 3.81 (s, 2H), 3.32-3.28 (m, 1H), 2.88-2.82 (m, 2H), 2.01-1.96 (m, 2H), 1.60-1.52 (m, 2H), 1.38 (s, 9H); LC-MS m/z [M+H]+ 541.1, RT 3.40 min.

Step 5: Preparation of the Title Compound

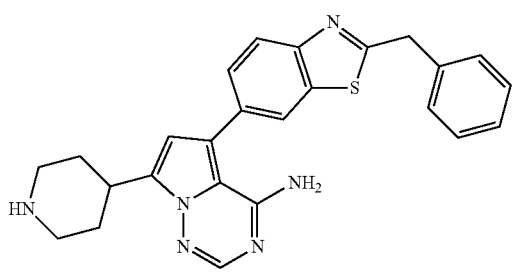 [SMILES: Nc1ncnn2c(C3CCNCC3)cc(-c3ccc4nc(Cc5ccccc5)sc4c3)c12]

In a manner similar to the procedure described for step 8 of the preparation of Example 330 and using tert-butyl 4-[4-amino-5-(2-benzyl-1,3-benzothiazol-6-yl)pyrrolo[2,1-f][1,2,4]triazin-7-yl]piperidine-1-carboxylate as starting material, 80 mg (72.7%) of the desired product was isolated. $^1$H NMR (400 MHz, CD$_2$Cl$_2$) δ 8.05 (d, 1H), 7.94 (s, 1H), 7.91 (s, 1H), 7.59 (d, 1H), 7.48-7.36 (m, 5H), 6.57 (s, 1H), 4.48 (s, 2H), 3.43-3.35 (m, 1H), 3.28-3.18 (m, 2H), 2.88-2.80 (m, 2H), 2.20-2.10 (m, 2H), 1.80-1.68 (m, 2H); LC-MS m/z [M+H]+ 441.2, RT 2.28 min.

Example 333

Preparation of 7-(1-acetylpiperidin-4-yl)-5-(2-benzyl-1,3-benzothiazol-6-yl)pyrrolo[2,1-f][1,2,4]triazin-4-amine

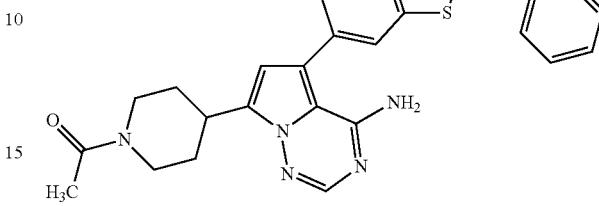

In a manner similar to the procedure described for the preparation of Example 331 and using 5-(2-benzyl-1,3-benzothiazol-6-yl)-7-piperidin-4-ylpyrrolo[2,1-f][1,2,4]triazin-4-amine and acetyl chloride as starting material, 27 mg (54.8%) of the desired product was isolated. $^1$H NMR (400 MHz, CD$_2$Cl$_2$) δ 8.04 (d, 1H), 7.91 (s, 1H), 7.89 (s, 1H), 7.59 (d, 1H), 7.41-7.29 (m, 5H), 7.56 (s, 1H), 4.76-4.68 (m, 1H), 4.44 (s, 2H), 3.96-3.90 (m, 1H), 3.56-3.44 (m, 1H), 3.30-3.24 (m, 1H), 2.70-2.80 (m, 1H), 2.22-2.12 (m, 2H), 2.10 (s, 3H), 1.76-1.60 (m, 2H) LC-MS m/z [M+H]+ 483.3, RT 2.76 min.

Example 334

Preparation of tert-butyl 4-[4-amino-5-(2-benzyl-1,3-benzothiazol-5-yl)pyrrolo[2,1-f][1,2,4]triazin-7-yl]piperidine-1-carboxylate

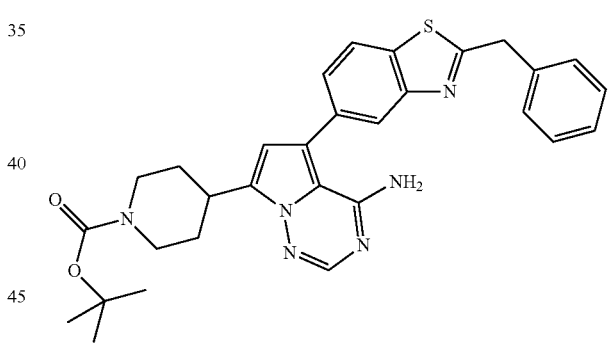

Step 1: Preparation of 5-bromo-2-(methylthio)-1,3-benzothiazole

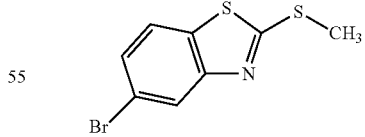

A mixture of 5-bromo-1,3-benzothiazole-2-thiol (3.0 g, 12.19 mmol), dry THF (44 mL), iodomethane (0.80 mL, 12.80 mmol), KOH (0.68 g, 12.19 mmol), and tetra-n-butylammonium bromide (0.39 g, 1.2 mmol) was stirred at rt overnight. The reaction mixture was diluted with EtOAc (100 mL) and washed with saturated, aqueous Na$_2$CO$_3$ (50 mL). The organic layer was dried over MgSO$_4$ and then concentrated. The crude material was purified by ISCO® chromatography using 1-2% EtOAc in hexane to obtain the desired product (2.4 g, 76%). $^1$H NMR (400 MHz, DMSO-d$_6$) δ 8.02

(s, 1H), 8.0 (d, 1H), 7.51 (d, 1H), 2.79 (s, 3H); LC-MS m/z[M+H]+ 260.3 & 262.2, RT 3.82 min.

Step 2: Preparation of 2-benzyl-5-bromo-1,3-benzothiazole

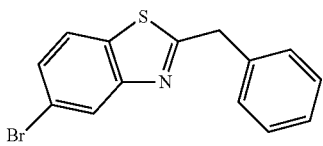 [SMILES: Brc1ccc2sc(Cc3ccccc3)nc2c1]

In a manner similar to the procedure described for Step 2 of the preparation of 5-(2-benzyl-1,3-benzothiazol-6-yl)-7-piperidin-4-ylpyrrolo[2,1-f][1,2,4]triazin-4-amine and using 5-bromo-2-(methylthio)-1,3-benzothiazole and benzylzinc bromide as starting material, 1.30 g (48%) of the desired product was isolated. $^1$H NMR (400 MHz, DMSO-$d_6$) δ 8.18 (s, 1H), 7.99 (d, 1H), 7.56 (d, 1H), 7.40-7.18 (m, 5H), 4.44 (s, 2H); LC-MS m/z [M+H]+304.3 & 306.3, RT 5.16 min.

Step 3: Preparation of 2-benzyl-5-(4,4,5,5-tetramethyl-1,3,2-dioxaborolan-2-yl)-1,3-benzothiazole

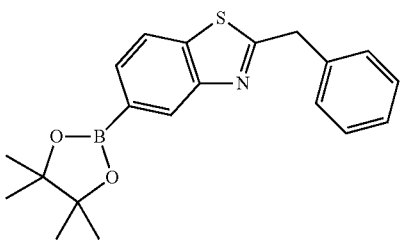 [SMILES: CC1(C)OB(c2ccc3sc(Cc4ccccc4)nc3c2)OC1(C)C]

In a manner similar to the procedure described for Step 3 of the preparation of 5-(2-benzyl-1,3-benzothiazol-6-yl)-7-piperidin-4-ylpyrrolo[2,1-f][1,2,4]triazin-4-amine and using 2-benzyl-5-bromo-1,3-benzothiazole as starting material, 0.48 g mg (66%) of the desired product was isolated. $^1$H NMR (400 MHz, DMSO-$d_6$) δ 8.20 (s, 1H), 8.08 (d, 1H), 7.66 (d, 1H), 7.42-7.36 (m, 2H), 4.52 (s, 2H), 1.38 (s, 12H); LC-MS m/z [M+H]+ 352.4, RT 4.25 min.

Step 4: Preparation of the Title Compound

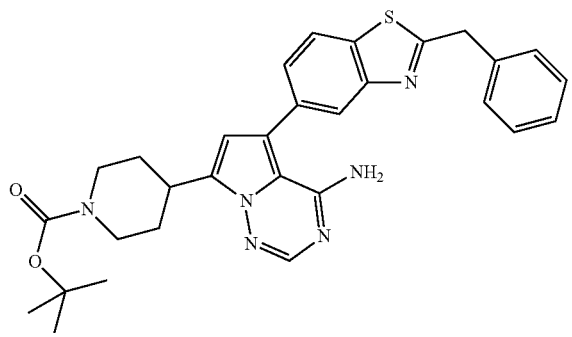 [SMILES: CC(C)(C)OC(=O)N1CCC(c2cc(-c3ccc4sc(Cc5ccccc5)nc4c3)c3c(N)ncnn23)CC1]

In a manner similar to the procedure described for step 7 of the preparation of Example 330 and using 2-benzyl-5-(4,4,5,5-tetramethyl-1,3,2-dioxaborolan-2-yl)-1,3-benzothiazole and tert-butyl 4-(4-amino-5-bromopyrrolo[2,1-f][1,2,4]triazin-7-yl)piperidine-1-carboxylate as starting material, 411 mg (95.6%) of the desired product was isolated. $^1$H NMR (400 MHz, CD$_2$Cl$_2$) δ 8.06 (s, 1H), 8.94 (s, 1H), 8.92 (d, 1 H), 7.49 (d, 1H), 7.37-7.45 (m, 5 H), 6.59 (s, 1H), 4.49 (s, 2 H), 4.25 (m, 2 H), 3.42 (m, 1H), 2.94 (m, 2H), 2.11 (m, 2H), 1.76-1.64 (m, 2 H), 1.48 (s, 9H); LC-MS m/z [M+H]+541.2, RT 3.37 min.

Example 335

Preparation of 5-(2-benzyl-1,3-benzothiazol-5-yl)-7-piperidin-4-ylpyrrolo[2,1-f][1,2,4]triazin-4-amine

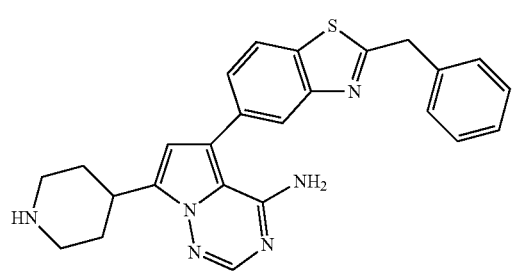 [SMILES: Nc1ncnn2c(C3CCNCC3)cc(-c3ccc4sc(Cc5ccccc5)nc4c3)c12]

In a manner similar to the procedure described for step 8 of the preparation of Example 330 and using tert-butyl 4-[4-amino-5-(2-benzyl-1,3-benzothiazol-5-yl)pyrrolo[2,1-f][1,2,4]triazin-7-yl]piperidine-1-carboxylate as the starting material, 240 mg (77%) of the desired product was isolated. $^1$H NMR (400 MHz, CD$_2$Cl$_2$) δ 8.07 (s, 1H), 7.92 (d, 1H), 7.90 (s, 1H), 7.50 (d, 1H), 7.43-7.36 (m, 5H), 6.58 (s, 1H), 5.43 (s, 2H), 4.47 (s, 2H), 3.41-3.33 (m, 1H), 3.21-3.18 (m, 2H), 2.78-2.87 (m, 2H), 2.11-2.08 (m, 2H), 1.73-1.62 (m, 2H); LC-MS m/z [M+H]+ 441.2, RT 2.25 min.

Example 336

Preparation of 7-(1-acetylpiperidin-4-yl)-5-(2-benzyl-1,3-benzothiazol-5-yl)pyrrolo[2,1-f][1,2,4]triazin-4-amine

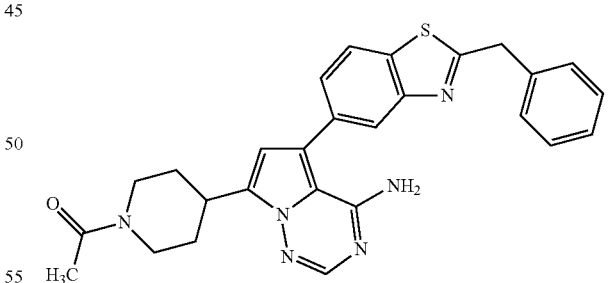

In a manner similar to the procedure described for the preparation of Example 331 and using 5-(2-benzyl-1,3-benzothiazol-5-yl)-7-piperidin-4-ylpyrrolo[2,1-f][1,2,4]triazin-4-amine and acetyl chloride as starting material, 17.5 mg (32%) of the desired product was isolated. $^1$H NMR (400 MHz, CD$_2$Cl$_2$) δ 8.06 (s, 1H), 7.95 (2H), 7.92 (s, 1H), 7.48 (d, 1H), 7.43-7.36 (m, 5H), 6.56 (s, 1H), 5.60 (s, 2H), 4.75-4.69 (m, 1H), 4.47 (s, 2H), 3.98-3.92 (m, 1H), 3.54-3.46 (m, 1H), 3.31-3.28 (m, 1H), 2.80-2.72 (m, 1H), 2.24-2.20 (m, 2H), 2.10 (s, 3H), 1.75-1.64 (m, 2H); LC-MS m/z [M+H]+ 483.2, RT 3.02 min.

Example 337

Preparation of 5-(2-benzyl-1,3-benzothiazol-5-yl)-7-[1-(methylsulfonyl)-piperidin-4-yl]pyrrolo[2,1-f][1,2,4]triazin-4-amine

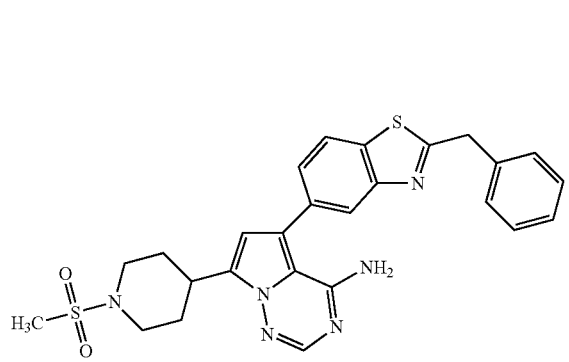 [SMILES: CS(=O)(=O)N1CCC(c2cc(-c3ccc4sc(Cc5ccccc5)nc4c3)c3c(N)ncnn23)CC1]

In a manner similar to the procedure described for the preparation of Example 331 and using 5-(2-benzyl-1,3-benzothiazol-5-yl)-7-piperidin-4-ylpyrrolo[2,1-f][1,2,4]triazin-4-amine and methanesulfonyl chloride as starting material, 20 mg (34%) of the desired product was isolated. $^1$H NMR (400 MHz, CD$_2$Cl$_2$) δ 8.49 (s, 1H), 8.39 (d, 1H), 8.32 (s, 1H), 7.92 (d, 1H), 7.84-7.78 (m, 5H), 7.04 (s, 1H), 4.91 (s, 2H), 4.38-4.33 (m, 2H), 3.84-3.78 (m, 1H), 3.38-3.30 (m, 2H), 3.23 (s, 3H), 2.74-2.69 (m, 2H), 2.38-2.30 (m, 2H); LC-MS m/z [M+H]$^+$ 519.2, RT 3.13 min.

Example 338

Preparation of 2-{4-[4-amino-5-(2-benzyl-1,3-benzothiazol-5-yl)pyrrolo[2,1-f][1,2,4]triazin-7-yl]piperidin-1-yl}-N,N-dimethylacetamide

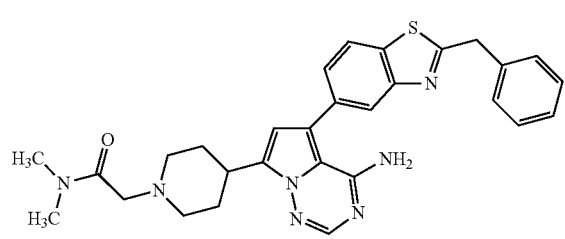 [SMILES: CN(C)C(=O)CN1CCC(c2cc(-c3ccc4sc(Cc5ccccc5)nc4c3)c3c(N)ncnn23)CC1]

In a manner similar to the procedure described for the preparation of Example 355 and using 5-(2-benzyl-1,3-benzothiazol-5-yl)-7-piperidin-4-ylpyrrolo[2,1-f][1,2,4]triazin-4-amine and 2-chloro-N,N-dimethylacetamide as starting material, 21.6 mg (36.2%) of the desired product was isolated. $^1$H NMR (400 MHz, CD$_2$Cl$_2$) δ 8.06 (s, 1H), 7.92 (d, 1H), 7.91 (s, 1H), 7.49 (d, 1H), 7.43-7.36 (m, 5H), 6.59 (s, 1H), 5.43 (s, 2H), 4.47 (s, 2H), 3.32-3.23 (m, 1H), 3.21 (s, 2H), 3.10 (s, 3H), 3.09-3.03 (m, 2H), 2.92 (s, 3H), 2.40-2.32 (m, 2H), 2.16-2.12 (m, 2H), 1.94-1.82 (m, 2H); LC-MS m/z [M+H]$^+$ 526.2, RT 2.30 min.

Example 339

Preparation of 4-[4-amino-5-(2-benzyl-1,3-benzothiazol-5-yl)pyrrolo[2,1-f][1,2,4]triazin-7-yl]-N-ethylpiperidine-1-carboxamide

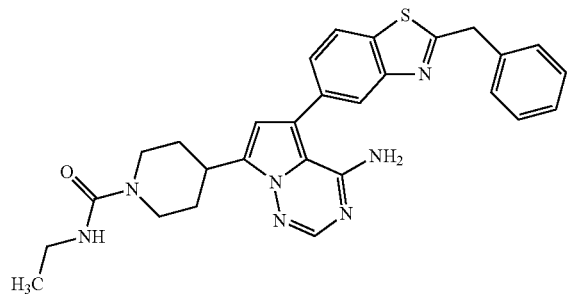 [SMILES: CCNC(=O)N1CCC(c2cc(-c3ccc4sc(Cc5ccccc5)nc4c3)c3c(N)ncnn23)CC1]

In a manner similar to the procedure described for the preparation of Example 331 and using 5-(2-benzyl-1,3-benzothiazol-5-yl)-7-piperidin-4-ylpyrrolo[2,1-f][1,2,4]triazin-4-amine and ethylisocyanate as starting material, 7 mg (12%) of the desired product was isolated.

$^1$H NMR (400 MHz, CD$_2$Cl$_2$) δ 8.04 (s, 1H), 7.92 (d, 1H), 7.91 (s, 1H), 7.48 (d, 1H), 7.42-7.32 (m, 5H), 6.58 (s, 1H), 5.38 (s, 2H), 4.50 (t, 1H), 4.44 (s, 2H), 4.08-4.04 (m, 2H), 3.48-3.40 (m, 1H), 3.28-3.22 (m, 2H), 3.00-2.96 (m, 2H), 2.19-2.16 (m, 2H), 1.78-1.66 (m, 2H), 1.18 (t, 3H); LC-MS m/z [M+H]$^+$ 512.1, RT 3.05 min.

Example 340

Preparation of 5-[3-(benzyloxy)-5-fluorophenyl]-7-piperidin-4-ylpyrrolo[2,1-f][1,2,4]triazin-4-amine

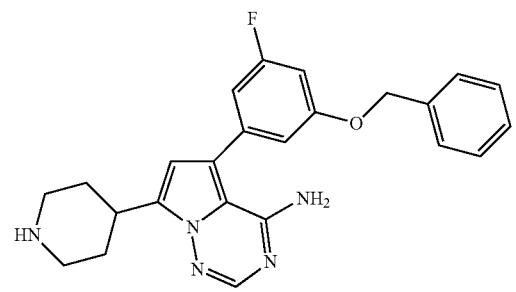 [SMILES: Nc1ncnn2c(C3CCNCC3)cc(-c3cc(F)cc(OCc4ccccc4)c3)c12]

Step 1: Preparation of tert-butyl 4-{4-amino-5-[3-benzyloxy)-5-fluorophenyl]pyrrolo[2,1-f][1,2,4]triazin-7-yl}piperidine-1-carboxylate

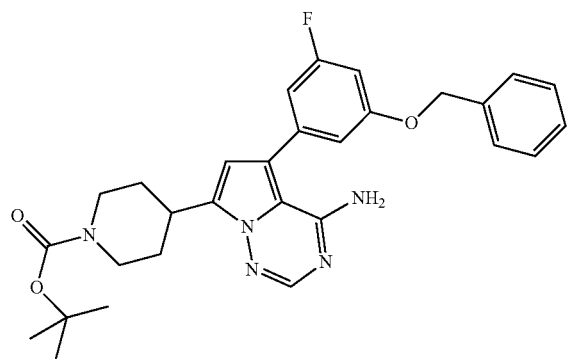 [SMILES: CC(C)(C)OC(=O)N1CCC(c2cc(-c3cc(F)cc(OCc4ccccc4)c3)c3c(N)ncnn23)CC1]

In a manner similar to the procedure described for step 7 of the preparation of Example 330 and using tert-butyl 4-(4-amino-5-bromopyrrolo[2,1-f][1,2,4]triazin-7-yl)piperidine-1-carboxylate and [3-(benzyloxy)-5-fluorophenyl](hydroxymethyl)boronic acid as starting material, 800 mg (76%) of the desired product was isolated. ¹H NMR (400 MHz, CD₃OD) δ 7.82 (s, 1H), 7.46 (m, 5H), 6.92 (s, 1H), 6.82 (s, 1H), 6.78 (s, 1H), 6.58 (s, 1H), 5.17 (s, 2H), 4.22-4.18 (m, 2H), 3.46-3.36 (m, 1H), 3.02-2.92 (m, 2H), 2.14-2.08 (m, 2H), 1.72-1.64 (m, 2H), 1.48 (s, 9H); LC-MS m/z[M+H]⁺ 518.2, RT 3.45 min.

Step 2: Preparation of the Title Compound

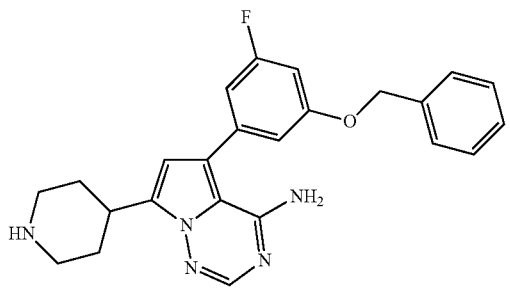 [SMILES: Nc1ncnn2c(C3CCNCC3)cc(-c3cc(F)cc(OCc4ccccc4)c3)c12]

In a manner similar to the procedure described for step 8 of Example 330 and using tort-butyl 4-(4-amino-5-[3-(benzyloxy)-5-fluorophenyl]pyrrolo[2,1-f][1,2,4]triazin-7-yl)piperidine-1-carboxylate as starting material, 600 mg (99%) of the desired product was isolated. ¹H NMR (400 MHz, CD₂Cl₂) δ 7.92 (s, 1H), 7.49-7.37 (m, 5H), 6.90 (s, 1H), 6.84 (d, 1H), 6.79 (d, 1H), 6.56 (s, 1H), 5.45 (s, 2H), 5.15 (s, 2H), 3.68 (s, 1H), 3.52-3.38 (m, 3H), 3.02-2.98 (m, 2H), 2.28-2.22 (m, 2H), 1.97-1.92 (m, 2H); LC-MS m/z[M+H]⁺418.3, RT 2.28 min.

Example 341

Preparation of 2-(4-{4-amino-5-[3-(benzyloxy)-5-fluorophenyl]pyrrolo[2,1-f][1,2,4]triazin-7-yl}piperidin-1-yl)-N,N-dimethylacetamide

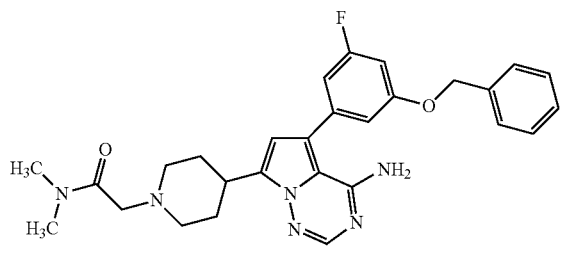 [SMILES: CN(C)C(=O)CN1CCC(c2cc(-c3cc(F)cc(OCc4ccccc4)c3)c3c(N)ncnn23)CC1]

In a manner similar to the procedure described for the preparation of Example 355 and using 5-[3-(benzyloxy)-5-fluorophenyl]-7-piperidin-4-ylpyrrolo[2,1-f][1,2,4]triazin-4-amine and 2-chloro-N,N-dimethylacetamide as starting material, 20 mg (17%) of the desired product was isolated. ¹H NMR (400 MHz, CD₂Cl₂) δ 7.89 (s, 1H), 7.47-7.36 (m, 5H), 6.89 (s, 1H), 6.82 (d, 1H), 6.74 (d, 1H), 6.52 (s, 1H), 5.56 (s, 2H), 5.13 (s, 2H), 3.25-3.20 (m, 1H), 3.18 (s, 2H), 3.10 (s, 3H), 3.02-2.98 (m, 2H), 2.92 (s, 3H), 2.26 (t, 2H), 2.11-2.08 (m, 2H), 1.82-1.78 (m, 2H); LC-MS m/z [M+H]⁺ 503.9, RT 2.77 min.

Example 342

Preparation of 5-[3-(benzyloxy)-5-fluorophenyl]-7-{1-[(dimethylamino)-acetyl]piperidin-4-yl}pyrrolo[2,1-f][1,2,4]triazin-4-amine

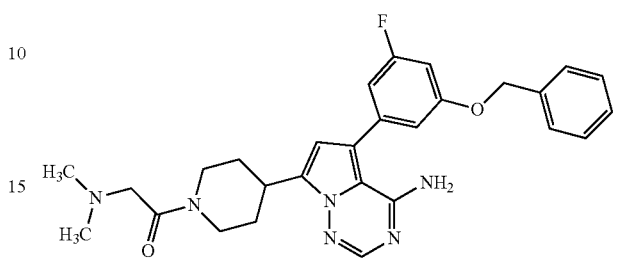

The solution of N,N-dimethylglycine (100 mg, 0.24 mmol) in DCM (1 mL) was treated with N,N-diisopropylethylamine (83 uL, 0.48 mmol), 1-(3-dimethylaminopropyl)-3-ethylcarbodiimide hydrochloride (55 mg, 0.29 mmol) and 1-hydroxybenzotriazole (38.8 mg, 0.29 mmol) followed by 5-[3-(benzyloxy)-5-fluorophenyl]-7-piperidin-4-ylpyrrolo[2,1-f][1,2,4]triazin-4-amine (100 mg, 0.24 mmol). The mixture was stirred at rt overnight then purified by HPLC. 20 mg (17%) of the desired product was isolated. ¹H NMR (400 MHz, CD₂Cl₂) δ 7.91 (s, 1H), 7.47-7.35 (m, 5H), 6.88 (s, 1H), 6.82 (d, 1H), 6.75 (d, 1H), 6.50 (s, 1H), 5.49 (s, 2H), 5.13 (s, 2H), 4.66 (d, 1H), 4.23 (d, 1H), 3.48 (m, 1H), 3.25-3.15 (m, 2H), 3.12-3.04 (m, 1H), 2.76 (td, 1H), 2.29 (s, 6H), 2.17 (s, 2H), 1.72-1.61 (m, 2H); LC-MS m/z [M+H]⁺ 503.3, RT 2.34 min.

Example 343

Preparation of 7-(1-acetylpiperidin-4-yl)-5-[3-(benzyloxy)-5-fluorophenyl]pyrrolo[2,1-f][1,2,4]triazin-4-amine

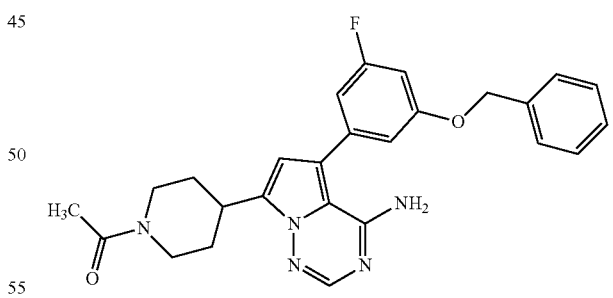

In a manner similar to the procedure described for the preparation of Example 331 and using 5-[3-(benzyloxy)-5-fluorophenyl]-7-piperidin-4-ylpyrrolo[2,1-f][1,2,4]triazin-4-amine and acetyl chloride as starting material, 20 mg (26%) of the desired product was isolated. ¹H NMR (400 MHz, CD₂Cl₂) δ 7.91 (s, 1H), 7.47-7.35 (m, 5H), 6.90 (s, 1H), 6.82 (d, 1H), 6.75 (d, 1H), 6.50 (s, 1H), 5.48 (s, 2H), 5.13 (s, 2H), 4.76-4.71 (m, 1H), 3.97-3.90 (m, 1H), 3.54-3.44 (m, 1H), 3.26 (td, 1H), 2.74 (td, 1H), 2.22-2.15 (m, 2H), 2.09 (s, 3H), 1.72-1.60 (m, 2H); LC-MS m/z[M+H]⁺ 460.4, RT 3.10 min.

Example 344

Preparation of 5-[3-(benzyloxy)phenyl]-7-piperidin-4-ylpyrrolo[2,1-f][1,2,4]triazin-4-amine

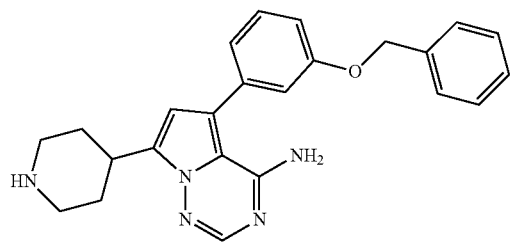 [SMILES: Nc1ncnn2c(C3CCNCC3)cc(-c3cccc(OCc4ccccc4)c3)c12]

Step 1: Preparation of tert-butyl 4-{4-amino-5-[3-(benzyloxy)phenyl]pyrrolo[2,1-f][1,2,4]triazin-7-yl}piperidine-1-carboxylate

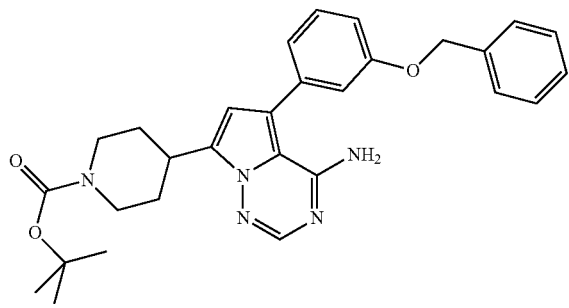 [SMILES: CC(C)(C)OC(=O)N1CCC(c2cc(-c3cccc(OCc4ccccc4)c3)c3c(N)ncnn23)CC1]

In a manner similar to the procedure described for step 7 of Example 330 and using tert-butyl 4-(4-amino-5-bromopyrrolo[2,1-f][1,2,4]triazin-7-yl)piperidine-1-carboxylate and (3-benzyloxyphenyl)boronic acid as starting material, 300 mg (88%) of the desired product was isolated. LC-MS m/z [M+H]⁺500.2, RT 3.47 min.

Step 2: Preparation of the Title Compound

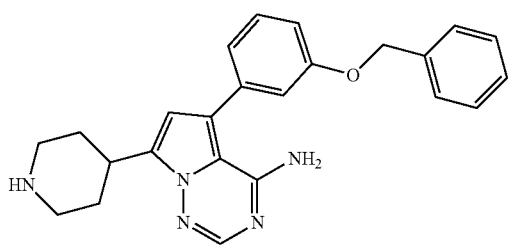 [SMILES: Nc1ncnn2c(C3CCNCC3)cc(-c3cccc(OCc4ccccc4)c3)c12]

In a manner similar to the procedure described for Step 8 of Example 295 and using tert-butyl 4-{4-amino-5-[3-benzyloxyphenyl]pyrrolo[2,1-f][1,2,4]triazin-7-yl}piperidine-1-carboxylate as starting material, 254 mg (88%) of the desired product was isolated. H NMR (400 MHz, CD₃OD) δ 7.80 (s, 1H), 7.45-7.33 (m, 6H), 7.13-7.03 (m, 3H), 6.58 (s, 1H), 5.12 (s, 2H), 3.50-3.41 (m, 3H), 3.28-3.12 (m, 2H), 2.34-2.24 (m, 2H), 1.99-1.88 (m, 2H); LC-MS m/z[M+H]⁺400.2, RT 2.21 min.

Example 345

Preparation of 5-(3-benzyloxyphenyl)-7-{1-[(dimethylamino) acetyl]piperidin-4-yl}pyrrolo[2,1-f][1,2,4]triazin-4-amine

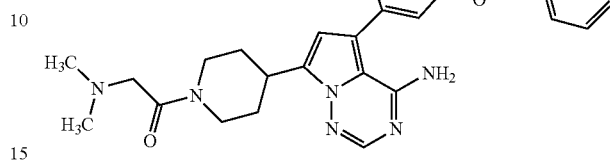

In a manner similar to the procedure described for the preparation of Example 342 and using 5-(3-benzyloxyphenyl)-7-piperidin-4-ylpyrrolo[2,1-f][1,2,4]triazin-4-amine and N,N-dimethylglycine as starting material, 20 mg (24%) of the desired product was isolated. ¹H NMR (400 MHz, DMSO-d₆) δ 7.90 (s, 1H), 7.45-7.30 (m, 6H), 7.10 (s, 1H), 7.05-6.97 (m, 2H), 6.56 (s, 1H), 5.13 (s, 2H), 4.48-4.42 (m, 1H), 4.18-4.12 (m, 1H), 3.41-3.32 (m, 3H), 3.20-3.10 (m, 2H), 3.05-2.97 (m, 1H), 2.76-2.68 (m, 1H), 2.16 (s, 6H), 2.06-1.98 (m, 2H); LC-MS m/z [M+H]⁺ 485.3, RT 2.32 min.

Example 346

Preparation of 2-[4-{4-amino-5-(3-benzyloxyphenyl]pyrrolo[2,1-f][1,2,4]triazin-7-yl}piperidin-1-yl)-N,N-dimethylacetamide

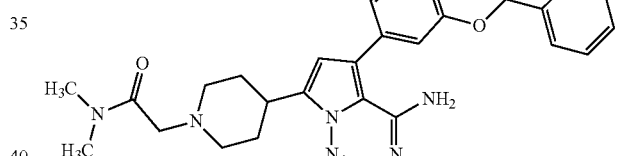

In a manner similar to the procedure described for the preparation of Example 355 and using 5-(3-benzyloxyphenyl)-7-piperidin-4-ylpyrrolo[2,1-f][1,2,4]triazin-4-amine and 2-chloro-N,N-dimethylacetamide as starting material, 20 mg (23.6%) of the desired product was isolated. ¹H NMR (400 MHz, DMSO-d₅) δ 7.90 (s, 1H), 7.44-7.32 (m, 6H), 7.10 (s, 1H), 7.02-6.98 (m, 2H), 6.59 (s, 1H), 5.16 (s, 2H), 3.16 (s, 2H), 3.15-3.04 (m, 1H), 3.03 (s, 3H), 2.97-2.90 (m, 2H), 2.80 (s, 3H), 2.22-2.14 (m, 2H), 1.98-1.92 (m, 2H), 1.74-1.64 (m, 2H); LC-MS m/z [M+H]⁺485.2, RT 2.29 min.

Example 347

Preparation of 3-(4-amino-7-piperidin-4-ylpyrrolo[2,1-f][1,2,4]triazin-5-yl)-N-phenylbenzamide

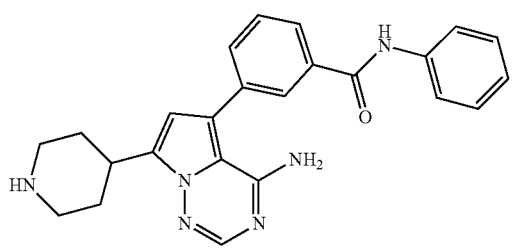 [SMILES: Nc1ncnn2c(C3CCNCC3)cc(-c3cccc(C(=O)Nc4ccccc4)c3)c12]

Step 1: Preparation of tert-butyl 4-{4-amino-5-[3-(anilinocarbonyl)phenyl]pyrrolo[2,1-f][1,2,4]triazin-7-yl}piperidine-1-carboxylate

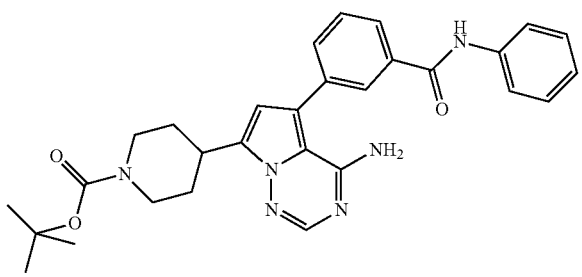 [SMILES: CC(C)(C)OC(=O)N1CCC(c2cc(-c3cccc(C(=O)Nc4ccccc4)c3)c3c(N)ncnn23)CC1]

In a manner similar to the procedure described for the preparation of Example 330 and using tert-butyl 4-{4-amino-5-bromopyrrolo[2,1-f][1,2,4]triazin-7-yl}piperidine-1-carboxylate and (3-phenylaminocarbonylphenyl)boronic acid as starting material, 334 mg (96%) of the desired product was isolated. LC-MS m/z [M+H]+ 513.2, RT 3.13 min.

Step 2: Preparation of the Title Compound

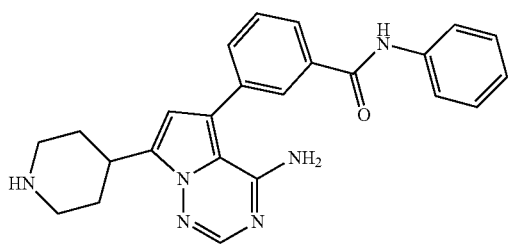 [SMILES: Nc1ncnn2c(C3CCNCC3)cc(-c3cccc(C(=O)Nc4ccccc4)c3)c12]

In a manner similar to the procedure described for step 8 of Example 330 and using tert-butyl 4-{4-amino-5-[3-(anilinocarbonyl)phenyl]pyrrolo[2,1-f][1,2,4]triazin-7-yl}piperidine-1-carboxylate as starting material, 102 mg (43%) of the desired product was isolated. $^1$H NMR (400 MHz, CD$_3$OD) δ 8.06 (s, 1H), 7.98 (d, 1H), 7.87 (s, 1H), 7.69-7.60 (m, 4H), 7.40-7.36 (m, 2H), 7.20-7.16 (t, 1H), 6.69 (s, 1H), 3.60-3.48 (m, 3H), 3.28-3.16 (m, 2H), 2.42-2.36 (m, 2H), 2.06-1.92 (m, 2H); LC-MS m/z [M+H]+413.3, RT 1.86 min.

Example 348

Preparation of 3-{4-amino-7-[1-(N,N-dimethylglycyl)piperidin-4-yl]pyrrolo[2,1-f][1,2,4]triazin-5-yl}-N-phenylbenzamide

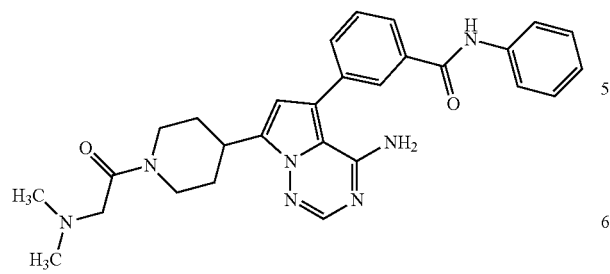

In a manner similar to the procedure described for the preparation of Example 342 using 3-(4-amino-7-piperidin-4-ylpyrrolo[2,1-f][1,2,4]triazin-5-yl)-N-phenylbenzamide and N,N dimethylglycine as starting material, 10 mg (18%) of the desired product was isolated. $^1$H NMR (400 MHz, DMSO-d$_6$) δ10.24 (s, 1H), 8.02 (s, 1H), 7.96 (m, 2H), 7.80-7.76 (m, 2H), 7.64-7.58 (m, 2H), 7.38-7.36 (m, 2H), 7.11-7.09 (m, 1H), 6.64 (s, 1H), 4.52-4.44 (m, 1H), 4.10-4.00 (m, 1H), 3.50-3.38 (m, 1H), 3.37 (s, 2H), 3.22-3.16 (m, 1H), 2.80-2.70 (m, 1H), 2.36 (s, 6H), 2.10-2.04 (m, 2H), 1.78-1.61 (m, 1H), 1.59-1.30 (m, 1H); LC-MS m/z [M+H]+, 498.4, RT 2.11 min.

Example 349

Preparation of 3-[7-(1-acetylpiperidin-4-yl)-4-aminopyrrolo[2,1-f][1,2,4]triazin-5-yl]-N-benzylbenzamide

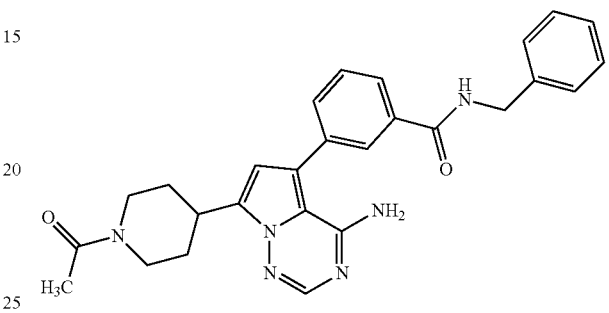

Step 1: Preparation of tert-butyl 4-{4-amino-5-[3-(benzylcarbamoyl)phenyl]pyrrolo[2,1-f][1,2,4]triazin-7-yl}piperidine-1-carboxylate

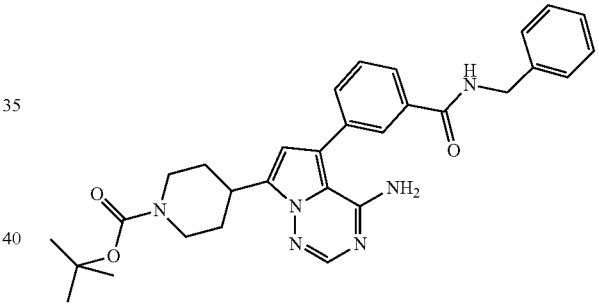

In a manner similar to the procedure described for step 7 of Example 330 and using tert-butyl 4-(4-amino-5-bromopyrrolo[2,1-f][1,2,4]triazin-7-yl)piperidine-1-carboxylate and as starting material, 335 mg (93.5%) of the desired product was isolated. LC-MS m/z [M+H]+,527.2, RT 3.05 min.

Step 2: Preparation of 3-(4-amino-7-piperidin-4-ylpyrrolo[2,1-f][1,2,4]triazin-5-yl)-N-benzylbenzamide

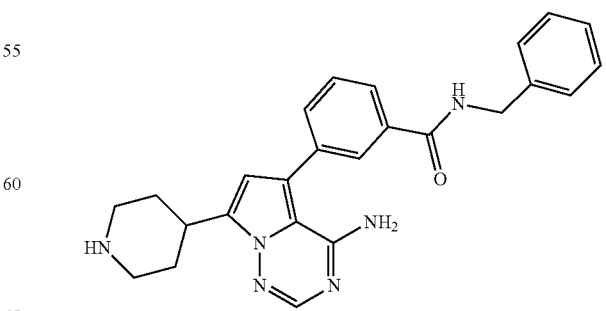

In a manner similar to the procedure described for step 8 of Example 330 and using tert-butyl 4-{4-amino-5-[3-(benzylcarbamoyl)phenyl]pyrrolo[2,1-f][1,2,4]triazin-7-yl}piperidine-1-carboxylate as starting material, 198 mg (82%) of the desired product was isolated. $^1$H NMR (400 MHz, CD$_3$OD) δ 8.00 (s, 1H,), 8.90-8.88 (, m, 2H), 7.70-7.60 (m, 2H), 7.40-7.24 (m, 5H), 6.64 (s, 1H), 4.60 (s, 2H), 3.61-3.51 (m, 3H), 3.32-3.22 (m, 2H), 2.42-2.38 (m, 2H), 2.08-1.98 (m 2H); LC-MS m/z [M+H]$^+$ 427.2, RT 0.57 min.

Step 3: Preparation of the Title Compound

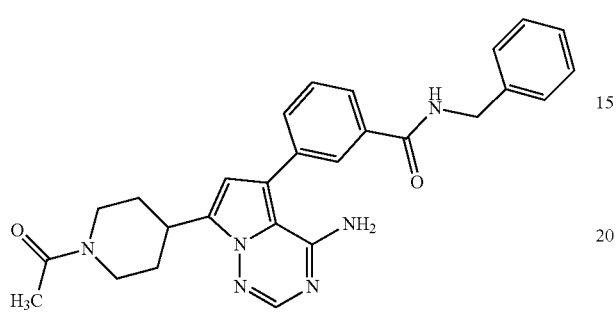

In a manner similar to the procedure described for the preparation of Example 331 and using 3-(4-amino-7-piperidin-4-ylpyrrolo[2,1-f][1,2,4]triazin-5-yl)-N-benzylbenzamide and acetyl chloride as starting material, 20 mg (26.0%) of the desired product was isolated. $^1$H NMR (400 MHz, CD$_3$OD) δ 7.98 (s, 1H), 7.88-7.82 (m 2H), 7.62 (d, 1H), 7.55 (t, 1H), 7.36-7.28 (m, 4H), 7.25-7.20 (m, 1H), 6.58 (s, 1H), 4.67-4.59 (m, 3H), 4.06-3.98 (m, 1H), 3.52-3.43 (m, 1H), 3.33-3.24 (m, 1H), 2.78 (td, 1H), 2.20-2.08 (m, 5H), 1.73-1.63 (m, 2H); LC-MS m/z [M+H]$^+$469.3, RT 2.34 min.

Example 350

Preparation of 3-{4-amino-7-[1-(N,N-dimethylglycyl)piperidin-4-yl]pyrrolo[2,1-f][1,2,4]triazin-5-yl}-N-benzylbenzamide

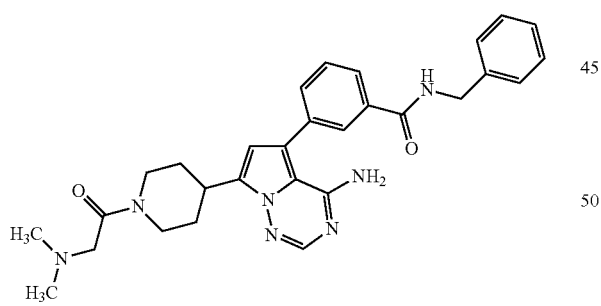

In a manner similar to the procedure described for the preparation of Example 342 and using 3-(4-amino-7-piperidin-4-ylpyrrolo[2,1-f][1,2,4]triazin-5-yl)-N-benzylbenzamide and N,N-dimethylglycine as starting material, 10 mg (18%) of the desired product was isolated. $^1$H NMR (400 MHz, CO$_3$OD) δ 7.98 (s, 1H), 7.85 (d, 1H), 7.82 (s, 1H), 7.62 (d, 1H), 7.55 (t, 1H), 7.36-7.28 (m, 4H), 7.25-7.20 (m, 1H), 6.57 (s, 1H), 4.62-4.57 (m, 3H), 4.18-4.14 (m, 1H), 3.51-3.42 (m, 1H), 3.31-3.16 (m, 5H), 2.82-2.78 (m, 1H), 2.29 (s, 6H), 2.19-2.11 (m, 2H), 1.78-1.59 (m, 2H); 512.3, LC-MS m/z [M+H]$^+$ 512.3, RT 1.96 min.

Example 351

Preparation of 5-(2-benzyl-3-chloro-2H-indazol-6-yl)-7-piperidin-4-ylpyrrolo[2,1-f][1,2,4]triazin-4-amine

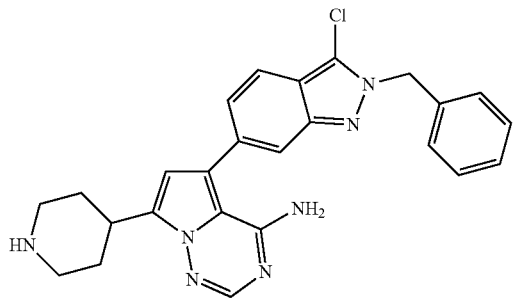 [SMILES: Nc1ncnn2c(C3CCNCC3)cc(-c3ccc4c(Cl)n(Cc5ccccc5)nc4c3)c12]

Step 1: Preparation of 2-benzyl-3-chloro-6-(4,4,5,5-tetramethyl-1,3,2-dioxaborolan-2-yl)-2H-indazole

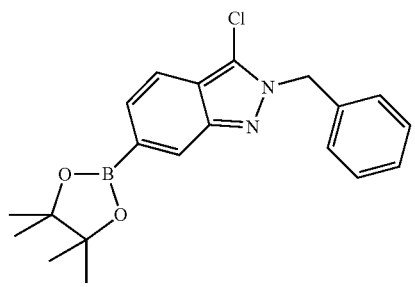 [SMILES: CC1(C)OB(c2ccc3c(Cl)n(Cc4ccccc4)nc3c2)OC1(C)C]

To a solution of 2-benzyl-6-(4,4,5,5-tetramethyl-1,3,2-dioxaborolan-2-yl)-2H-Indazole (200 mg, 0.598 mmol) in THF (2 mL), was added N-chlorosuccinimide (95.9 mg, 0.718 mmol). The mixture was heated at 40° C. for 4 hr, cooled to rt then concentrated to dryness. The crude material was purified by ISCO® chromatography using a gradient of 1-7% EtOAc in hexane to afford the desired product (180.1 mg, 82%). $^1$H NMR (400 MHz, DMF-d$_6$) δ 7.98 (s, 1H), 7.59 (d, 1H), 7.38-7.28 (m, 4H), 7.22-7.19 (m, 2H), 5.74 (s, 2H), 1.34 (s, 12H); LC-MS m/z [M+H]$^+$ 369.2, RT 3.94 min.

Step 2: Preparation of tert-butyl 4-[4-amino-5-(2-benzyl-3-chloro-2H-indazol-6-yl)pyrrolo[2,1-f][1,2,4]triazin-7-yl]piperidine-1-carboxylate

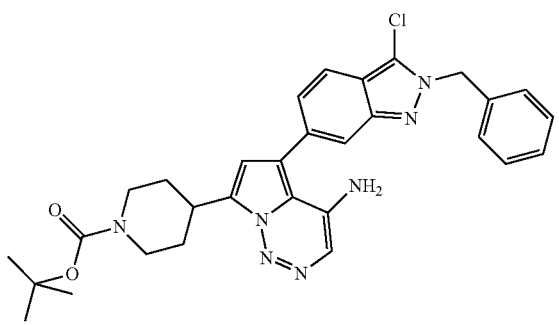 [SMILES: CC(C)(C)OC(=O)N1CCC(c2cc(-c3ccc4c(Cl)n(Cc5ccccc5)nc4c3)c3c(N)cnnn23)CC1]

In a manner similar to the procedure described for step 7 of Example 330 and using tort-butyl 4-(4-amino-5-bromopyrrolo[2,1-f][1,2,4]triazin-7-yl)piperidine-1-carboxylate and 2-benzyl-3-chloro-6-(4,4,5,5-tetramethyl-1,3,2-dioxaborolan-2-yl)-2H-indazole as starting material, 70 mg (56%) of the desired product was isolated. -MS m/z [M+H]⁺ 558.3, RT 3.38 min.

Step 3: Preparation of the Title Compound

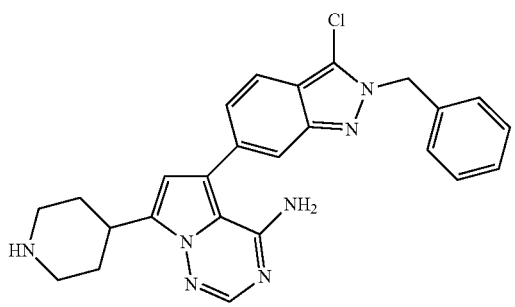 [SMILES: Nc1ncnn2c(C3CCNCC3)cc(-c3ccc4c(Cl)n(Cc5ccccc5)nc4c3)c12]

In a manner similar to the procedure described for step 8 of Example 330 and using tert-butyl 4-[4-amino-5-(2-benzyl-3-chloro-2H-indazol-6-yl)pyrrolo[2,1-f][1,2,4]triazin-7-yl]piperidine-1-carboxylate as starting material, 70 mg (95%) of the desired product was isolated. $^1$H NMR (400 MHz, CD$_3$OD) δ 7.85 (s, 1H), 7.74-7.71 (m, 2H), 7.65 (s, 1H), 7.38-7.28 (m, 5H), 6.67 (s, 1H), 5.72 (s, 2H), 3.58-3.47 (m, 3H), 3.25-3.10 (m, 2H), 2.40-2.30 (m, 2H), 2.05-2.95 (m, 2H); LC-MS m/z [M+H]⁺ 458.4, RT 2.22 min.

Example 352

Preparation of 2-{4-[4-amino-5-(2-benzyl-3-chloro-2H-indazol-6-yl)pyrrolo[2,1-f][1,2,4]triazin-7-yl]piperidin-1-yl}-N,N-dimethylacetamide

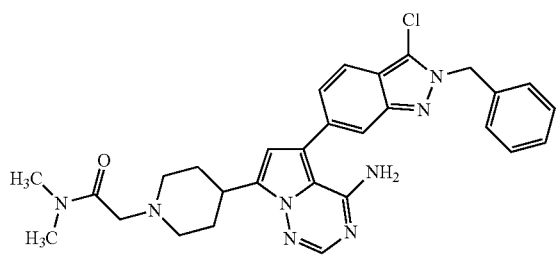 [SMILES: CN(C)C(=O)CN1CCC(c2cc(-c3ccc4c(Cl)n(Cc5ccccc5)nc4c3)c3c(N)ncnn23)CC1]

In a manner similar to the procedure described for the preparation of Example 355 and using 5-(2-benzyl-3-chloro-2H-indazol-6-yl)-7-piperidin-4-ylpyrrolo[2,1-f][1,2,4]triazin-4-amine and 2-chloro-N,N-dimethylacetamide as starting material, 20 mg (24%) of the desired product was isolated. $^1$H NMR (400 MHz, acetone-d$_6$) δ 7.84 (s, 1H), 7.72-7.66 (m, 2H), 7.40-7.30 (m, 6H), 6.60 (s, 1H), 5.78 (s, 2H), 3.28-3.20 (m, 1H), 3.20 (s, 2H), 3.17 (s, 3H), 3.06-3.02 (m, 2H), 2.88 (s, 3H), 2.32-2.22 (m, 2H), 2.18-2.08 (m, 2H), 1.90-1.80 (m, 2H); LC-MS m/z [M+H]⁺543.1, RT 2.32 min.

Example 353

Preparation of 5-(2-benzyl-3-methyl-2H-indazol-6-yl)-7-piperidin-4-ylpyrrolo[2,1-f][1,2,4]triazin-4-amine

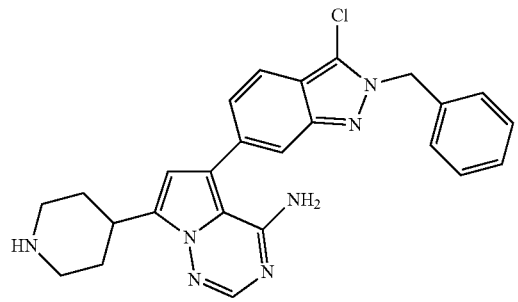 [SMILES: Nc1ncnn2c(C3CCNCC3)cc(-c3ccc4c(Cl)n(Cc5ccccc5)nc4c3)c12]

Step 1: Preparation of tert-butyl 4-[4-amino-5-(2-benzyl-3-methyl-2H-indazol-6-yl)pyrrolo[2,1-f][1,2,4]triazin-7-yl]piperidine-1-carboxylate

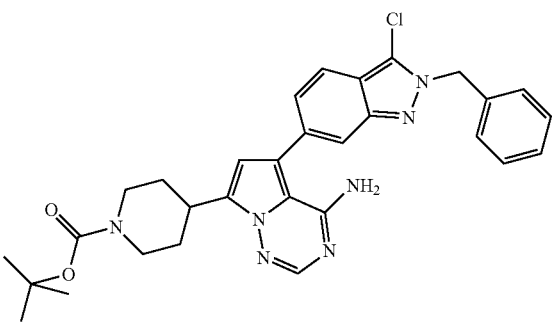

In a manner similar to the procedure described for step 7 of Example 330 and using tent-butyl 4-(4-amino-5-bromopyrrolo[2,1-f][1,2,4]triazin-7-yl)piperidine-1-carboxylate and 2-benzyl-3-methyl-6-(4,4,5,5-tetramethyl-1,3,2-dioxaborolan-2-yl)-2H-indazole as starting material, 70 mg (55%) of the desired product was isolated. LC-MS m/z [M+H]⁺ 538.3, RT 3.06 min.

Step 2: Preparation of the Title Compound

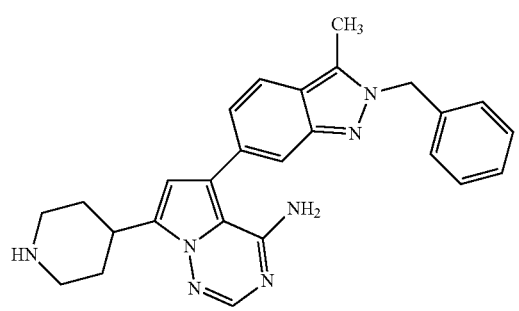 [SMILES: Cc1c2ccc(-c3cc(C4CCNCC4)n4ncnc(N)c34)cc2nn1Cc1ccccc1]

In a manner similar to the procedure described for step 8 of the preparation of Example 330 and using tert-butyl 4-(4-amino-5-(2-benzyl-3-methyl-2H-indazol-6-yl)pyrrolo[2,1-f][1,2,4]triazin-7-yl]piperidine-1-carboxylate as starting material, 90 mg (93%) of the desired product was isolated. $^1$H NMR (400 MHz, CD$_3$OD) δ 7.84 (s, 1H), 7.80 (d, 1H), 7.60 (s, 1H), 7.36-7.25 (m, 3H), 7.20-7.14 (m, 3H), 6.65 (s, 1H), 5.66 (s, 2H), 3.60-3.47 (m, 3H), 3.19-3.11 (m, 2H), 2.64 (s, 3H), 2.37-2.34 (m, 2H), 2.05-1.95 (m, 2H); LC-MS m/z[M+H]$^+$ 438.2, RT 2.13 min.

Example 354

Preparation of 2-{4-[4-amino-5-(2-benzyl-3-methyl-2H-indazol-6-yl)pyrrolo[2,1-f][1,2,4]triazin-7-yl]piperidin-1-yl}-N,N-dimethylacetamide

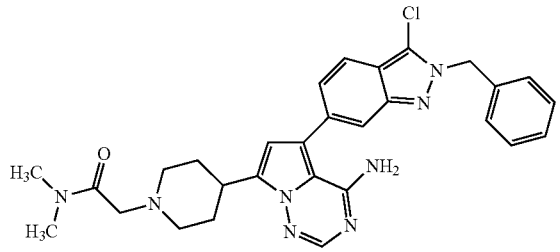 [SMILES: CN(C)C(=O)CN1CCC(c2cc(-c3ccc4c(Cl)n(Cc5ccccc5)nc4c3)c3c(N)ncnn23)CC1]

In a manner similar to the procedure described for the preparation of Example 355 and using 5-(2-benzyl-3-methyl-2H-indazol-6-yl)-7-piperidin-4ylpyrrolo[2,1-f][1,2,4]triazin-4-amine and 2-chloro-N,N-dimethylacetamides starting material, 20 mg (23.6%) of the desired product was isolated. $^1$H NMR (400 MHz, CD$_3$OD) δ 7.79 (s, 1H), 7.73 (d, 1H), 7.59 (s, 1H), 7.34-7.25 (m, 3H), 7.19-7.12 (m, 3H), 6.59 (s, 1H), 5.64 (s, 2H), 3.28 (s, 2H), 3.25-3.17 (m, 1H), 3.10 (s, 3H), 3.05 (m, 2H), 2.93 (s, 3H), 2.62 (s, 3H), 2.30-2.21m, 2H), 2.11-2.04 (m, 2H), 1.90-1.79 (m, 2H); LC-MS m/z[M+H]$^+$ 523.2, RT 2.19 min.

Example 355

Preparation of 2-{4-[4-amino-5-(2-benzyl-2H-indazol-6-yl)pyrrolo[2,1-f][1,2,4]triazin-7-yl]piperidin-1-yl}-N,N-dimethylacetamide

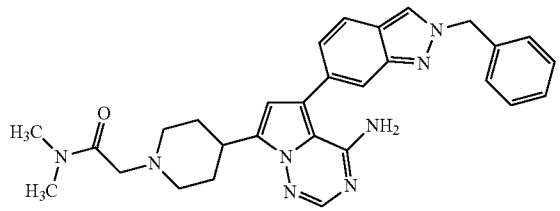 [SMILES: CN(C)C(=O)CN1CCC(c2cc(-c3ccc4cn(Cc5ccccc5)nc4c3)c3c(N)ncnn23)CC1]

The suspension of 5-(2-benzyl-2H-indazol-6-yl)-7-piperidin-4-ylpyrrolo[2,1-f][1,2,4]triazin-4-amine (500 mg, 1.81 mmol) was treated with N,N-diisopropylethylamine (411 uL, 2.36 mmol) followed by 2-chloro-N,N-dimethylacetamide (192 uL, 1.42 mmol). The mixture was heated at 60° C. for 3 h then cooled to rt. The white solid was filtered then purified by ISCO® using 0-10% 2N NH3 in MeOH/EtOAc. 313 mg (52.1%) of the desired product was isolated. $^1$H NMR (400 MHz, CD$_2$Cl$_2$) δ 8.42 (s, 1H), 8.04 (s, 1H), 8.19-8.12 (m, 2H), 7.82-7.70 (m, 5H), 7.62-7.60 (d, 1H), 6.99 (s, 1H), 6.02 (s, 2H), 5.96 (s, 2H), 3.70-3.59 (m, 3H), 3.50 (s, 3H), 3.48-3.40 (m, 2H), 3.36 (s, 3H), 2.79-2.50 (m, 2H), 2.59-2.48 (m, 2H), 2.36-2.24 (m, 2H); LC-MS m/z[M+H]$^+$ 509.2, RT 2.09 min.

Example 356

Preparation of 5-(2-benzyl-2H-indazol-6-yl)-7H-pyrrolo[2,1-f][1,2,4]triazin-4-amine

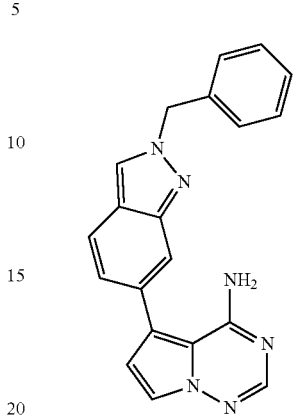

A stirred mixture of 5-bromopyrrolo[2,1-f][1,2,4]triazin-4-amine (100 mg, 0.47 mmol), 2-benzyl-6-(4,4,5,5-tetramethyl-1,3,2-dioxaborolan-2-yl)-2H-indazole (188 mg, 0.56 mmol), sodium carbonate (119 mg, 1.13 mmol), N,N-dimethylformamide (4 mL) and water (0.3 mL) was degassed with nitrogen. Tetrakis(triphenylphosphine)palladium(0) (54 mg, 0.04 mmol) was added, and the reaction was irradiated in a microwave reactor at 150° C. for 15 minutes. The reaction mixture was filtered through Celite®, the pad washed with methanol, and the filtrate concentrated in vacuo. The residue was partitioned between dichloromethane and 1N aqueous hydrochloric acid. The dichloromethane extracts were washed with 5% aqueous sodium bicarbonate solution, then brine, dried (anhydrous sodium sulfate); filtered and concentrated in vacuo to afford 61 mg (38% yield) of yellow solid. $^1$H-NMR (CD$_2$Cl$_2$): δ 8.04 (d, 1 H), 7.86 (s, 1 H), 7.77 (dd, 1 H), 7.75 (d, 1 H), 7.65 (d; 1 H), 7.40-7.32 (m, 5 H), 7.21 (dd, 1 H), 6.77 (d, 1 H), 6.91 (br s, 2 H), 5,61 (s, 2 H). MS: LC/MS (+esi), m/z=341 [M+H]. RT=2.44 min.

Example 357

Preparation of 5-(2-benzyl-2H-indazol-6-yl)-2-methylpyrrolo[2,1-f][1,2,4]triazin-4-amine

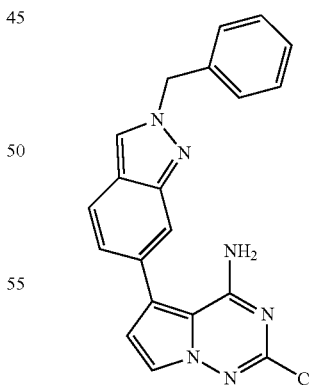

The title compound was prepared in the same manner described for the preparation of Example 356 and substituting 5-bromo-2-methylpyrrolo[2,1-1,2,4]triazin-4-amine for 5-bromopyrrolo[2,1-f][1,2,4]triazin-4-amine. $^1$H-NMR (CD$_2$Cl$_2$): δ 8.04 (d, 1 H), 7.78 (d, 1 H), 7.75 (dd, 1 H), 7.59 (d, 1 H), 7.40-7.32 (m, 5 H), 7.20 (dd, 1 H), 6.72 (d, 1 H), 6.0 (br s, 2 H), 5.80 (s, 2 H), 2.38 (s, 3 H). MS: LC/MS (+esi), m/z=355 [M+H]. RT=2.63 min.

Example 358

Preparation of 5-(2-benzyl-2H-indazol-6-yl)-7-bromo-2-methylpyrrolo[2,1-f][1,2,4]triazin-4-amine

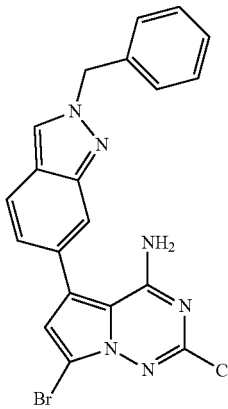

A stirred solution of 5-(2-benzyl-2H-indazol-6-yl)-2-methylpyrrolo[2,1-f][1,2,4]triazin-4-amine (130 mg, 0.367 mmol) in dichloromethane (10 mL) was cooled (−30° C.) under nitrogen atmosphere, and a solution of 1,3-dibromo-5,5-dimethyl-imidazolidine-2,4-dione (52.4 mg, 0.183 mmol) in dichloromethane (10 mL) was added dropwise. After 35 min, the mixture was concentrated in vacuo and purified via MPLC (hexanes/ethyl acetate gradient) to afford 148 mg (93%) of sand-colored solid. $^1$H-NMR (CD$_2$Cl$_2$): δ 8.04 (d, 1 H), 7.77 (dd, 1 H), 7.73 (dd, 1 H), 7.40-7.31 (m, 5 H), 7.18 (dd, 1 H), 6.75 (s, 1 H), 5.61 (s, 2 H), 5.52 (br s, 2 H), 2.41 (s, 3 H). MS: LC/MS (+esi), m/z=433 [M+H]. RT=2.88 min.

Example 359

Preparation of tert-butyl 4-[4-amino-5-(2-benzyl-2H-indazol-6-yl)-2-methylpyrrolo[2,1-f][1,2,4]triazin-7-yl]-3,6-dihydropyridine-1(2H)-carboxylate

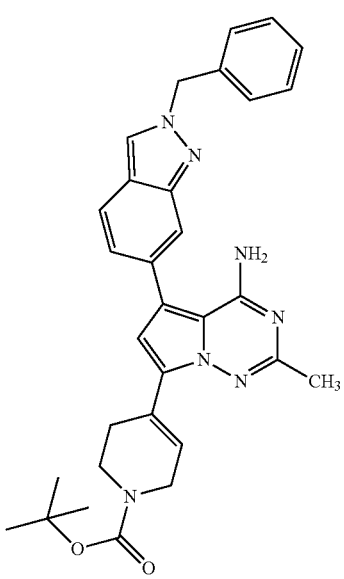 [SMILES: Cc1nc(N)c2c(-c3ccc4cn(Cc5ccccc5)nc4c3)cc(C3=CCN(C(=O)OC(C)(C)C)CC3)n2n1]

The title compound was prepared in the same manner described for step 1 of Example 1 and using 5-(2-benzyl-2H-indazol-6-yl)-7-bromo-2-methylpyrrolo[2,1-f][1,2,4]triazin-4-amine as a starting material. $^1$H-NMR (CD$_3$OD): δ 8.36 (d, 1 H), 7.81 (dd, 1 H), 7.66 (dd, 1 H), 7.36-7.31 (m, 5 H), 7.23 (dd, 1 H), 7.08 (m, 1 H), 6.73 (s, 1 H), 5.65 (s, 2 H), 4.15 (m, 2 H), 3.66 (m, 2 H), 2.67 (m, 2 H), 2.36 (s, 3 H), 1.49 (s, 9 H). MS: LC/MS (+esi), m/z=536 (M+H). RT=3.22 min.

Example 360

Preparation of 5-(2-benzyl-2H-indazol-6-yl)-2-methyl-7-(1,2,3,6-tetrahydropyridin-4-yl)pyrrolo[2,1-f][1,2,4]triazin-4-amine

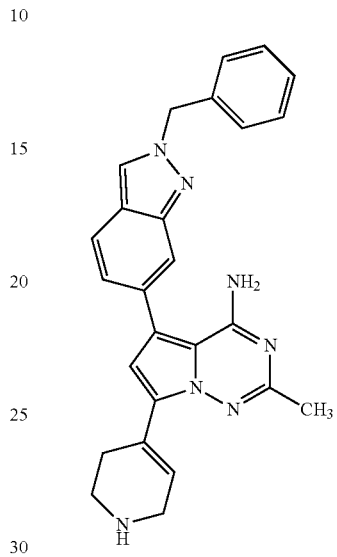

The title compound was prepared in the same manner described for step 5 of Example 1 and substituting tert-butyl 4-[4-amino-5-(2-benzyl-2H-indazol-6-yl)-2-methylpyrrolo[2,1-f][1,2,4]triazin-7-yl]-3,6-dihydropyridine-1(2H)-carboxylate for tert-butyl 4-[4-amino-5-(2-benzyl-2H-indazol-6-yl)pyrrolo[2,1-f][1,2,4]triazin-7-yl]piperidine-1-carboxylate. $^1$H-NMR (DMSO-d$_5$): δ 8.57 (m, 1 H), 7.81 (m, 2 H), 7.62 (m, 1 H), 7.40-7.36 (m, 5 H), 7.17 (m, 1 H), 6.80 (s, 1 H), 5.67 (s, 2 H), 3.72 (m, 2 H), 3.20 (m, 2 H), 2.69 (m, 2 H), 2.31 (s, 3 H). MS: LC/MS (+esi), m/z=436 [M+H]. RT=2.07 min.

Example 361

Preparation of tert-butyl 4-[4-amino-5-(2-benzyl-1,3-benzoxazol-5-yl)-pyrrolo[2,1-f][1,2,4]triazin-7-yl]piperidine-1-carboxylate

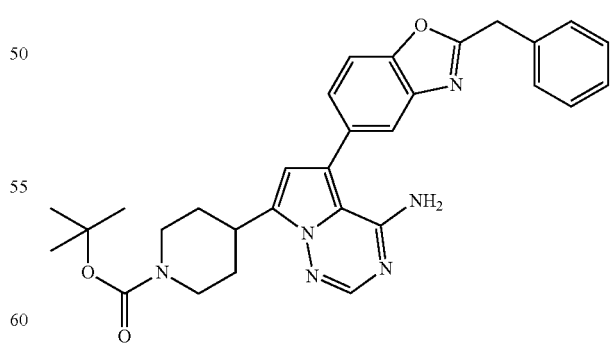

The title compound was prepared in the same manner described for step 4 of Example 1 and substituting 2-benzyl-5-(4,4,5,5-tetramethyl-1,3,2-dioxaborolan-2-yl)-1,3-benzoxazole for 2-benzyl-6-(4,4,5,5-tetramethyl-1,3,2-dioxaborolan-2-yl)-2H-indazole. $^1$H-NMR (CD$_2$Cl$_2$): δ 7.88 (s, 1 H), 7.73 (d, 1 H), 7.56 (d, 1 H), 7.42-7.20 (m, 6 H), 6.50 (s, 1

H), 5.40 (br s, 2 H), 4.30 (s, 2 H), 4.22 (m, 2 H), 3.39 (m, 1 H), 2.91 (m, 2 H), 2.08 (d, 2 H), 1.64 (m, 2 H), 1.45 (s, 9 H). MS: LC/MS (+esi), m/z=525 [M+H]. RT=3.30 min.

Example 362

Preparation of 5-(2-benzyl-1,3-benzoxazol-5-yl)-7-piperidin-4-ylpyrrolo[2,1-f][1,2,4]triazin-4-amine

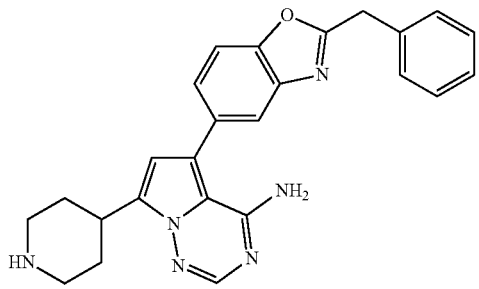 [SMILES: Nc1ncnn2c(C3CCNCC3)cc(-c3ccc4oc(Cc5ccccc5)nc4c3)c12]

The title compound was prepared in the same manner described for step 5 of Example 1 and substituting tert-butyl 4-[4-amino-5-(2-benzyl-1,3-benzoxazol-5-yl)pyrrolo[2,1-f][1,2,4]triazin-7-yl]piperidine-1-carboxylate for tert-butyl 4-[4-amino-5-(2-benzyl-2H-indazol-6-yl)pyrrolo[2,1-f][1,2,4]triazin-7-yl]piperidine-1-carboxylate. $^1$H-NMR (DMSO-$d_6$): δ 7.88 (s, 1 H), 7.72 (dd, 1 H), 7.69 (d, 1 H), 7.40 (d, 1 H), 7.38-7.34 (m, 4 H), 7.26 (m, 1 H), 6.54 (s, 1 H), 4.36 (s, 2 H), 3.19 (m, 1 H), 3.01 (d, 2 H), 2.62 (dd, 2 H), 1.91 (d, 2 H), 1.60-1.50 (m, 2 H). MS: LC/MS (+esi), m/z=425 [M+H]. RT=2.27 min.

Example 363

Preparation of tert-butyl 4-[4-amino-5-(2-benzyl-1,3-benzoxazol-6-yl)pyrrolo[2,1-f][1,2,4]triazin-7-yl]piperidine-1-carboxylate

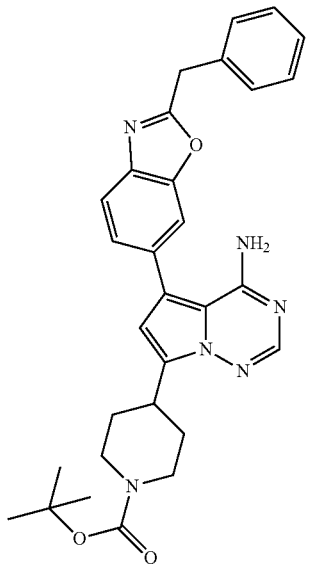 [SMILES: CC(C)(C)OC(=O)N1CCC(c2cc(-c3ccc4nc(Cc5ccccc5)oc4c3)c3c(N)ncnn23)CC1]

The title compound was prepared in the same manner described for step 4 of Example 1 and substituting 2-benzyl-6-(4,4,5,5-tetramethyl-1,3,2-dioxaborolan-2-yl)-1,3-benzoxazole for 2-benzyl-5-(4,4,5,5-tetramethyl-1,3,2-dioxaborolan-2-yl)-2H-indazole. $^1$H-NMR (CD$_2$Cl$_2$): δ 7.88 (s, 1 H), 7.73 (d, 1 H), 7.58 (d, 1 H), 7.43-7.28 (m, 6 H), 6.51 (s, 1 H), 5.56 (br s, 2 H), 4.30 (s, 2 H), 4.21 (m, 2 H), 3.38 (m, 1 H), 2.89 (m, 2 H), 2.08 (dd, 2 H), 1.65 (m, 2 H), 1.45 (s, 9 H). MS: LC/MS (+esi), m/z=525 [M+H]. RT=3.13 min.

Example 364

Preparation of 5-(2-benzyl-1,3-benzoxazol-6-yl)-7-piperidin-4-ylpyrrolo[2,1-f][1,2,4]triazin-4-amine

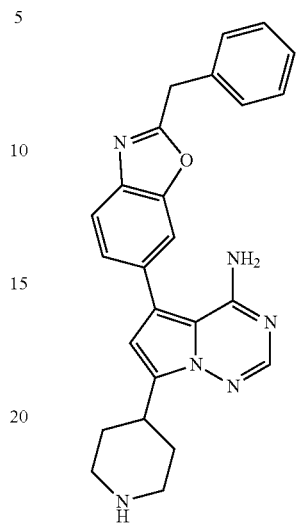

The title compound was prepared in the same manner described for step 5 of Example 1 and substituting tert-butyl 4-[4-amino-5-(2-benzyl-1,3-benzoxazol-6-yl)pyrrolo[2,14][1,2,4]triazin-7-yl]piperidine-1-carboxylate for tert-butyl 4-[4-amino-5-(2-benzyl-2H-indazol-6-yl)pyrrolo[2,1-f][1,2,4]triazin-7-yl]piperidine-1-carboxylate. $^1$H-NMR (DMSO-$d_6$): δ 8.41 (br s, 2 H), 7.92 (s, 1 H), 7.75 (d, 1 H), 7.69 (d, 1 H), 7.41-7.34 (m, 5 H), 7.28 (m, 1 H), 6.61 (s, 1 H), 4.37 (s, 2 H), 3.44-3.33 (m, 3 H), 3.08 (m, 2 H), 2.19 (m, 2 H), 1.82 (m, 2 H); MS: LC/MS (+esi), m/z=425 [M+11]. RT=2.09 min.

Example 365

Preparation of 2-{4-[4-amino-5-(2-benzyl-1,3-benzoxazol-6-yl)pyrrolo[2,1-f][1,2,4]triazin-7-yl]piperidin-1-yl}-N,N-dimethylacetamide

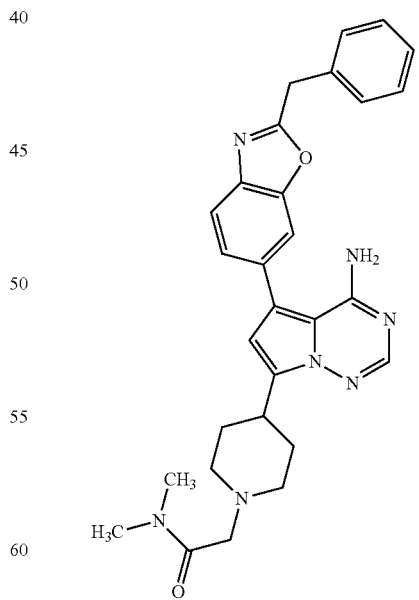

The title compound was prepared in the same manner described for the preparation of Example 355 and substituting 5-(2-benzyl-1,3-benzoxazol-6-yl)-7-piperidin-4-ylpyrrolo[2,1-f][1,2,4]triazin-4-amine for 5-(2-benzyl-2H-indazol-6-yl)-7-piperidin-4-ylpyrrolo[2,1-][1,2,4]triazin-4-amine.

¹H-NMR (CD₃OD): δ 7.85 (s, 1 H), 7.74 (d, 1 H), 7.66 (d, 1 H), 7.47 (dd, 1 H), 7.41-7.33 (m, 4 H), 7.28 (m, 1 H), 6.65 (s, 1 H), 4.34 (s, 2H), 4.27 (s, 2 H), 3.74 (m, 2 H), 3.56 (m, 2 H), 3.02 (s, 3 H), 3.01 (s, 3 H), 2.43 (m, 2 H), 2.17 (m, 2 H); MS: LC/MS (+esi), m/z=510 [M+H]. RT=2.15 min.

Example 366

Preparation of 2-{4-[4-amino-5-(2-benzyl-1,3-benzoxazol-5-yl)pyrrolo[2,1-f][1,2,4]triazin-7-yl]piperidin-1-yl}-N,N-dimethylacetamide

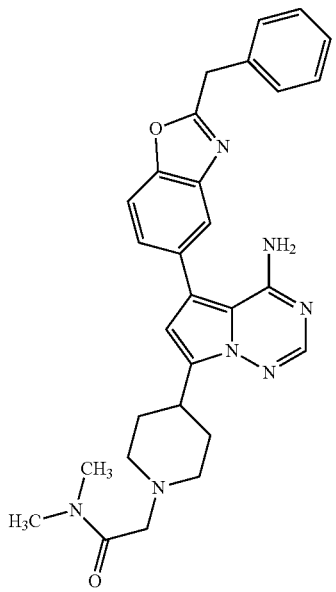 [SMILES: CN(C)C(=O)CN1CCC(c2cc(-c3ccc4oc(Cc5ccccc5)nc4c3)c3c(N)ncnn23)CC1]

The title compound was prepared in the same manner described for the preparation of Example 355 and substituting 5-(2-benzyl-1,3-benzoxazol-5-yl)-7-piperidin-4-ylpyrrolo[2,1-f][1,2,4]triazin-4-amine for 5-(2-benzyl-2H-indazol-6-yl)-7-piperidin-4-ylpyrrolo[2,1-f][1,2,4]triazin-4-amine.
¹H-NMR (DMSO-d₆): δ 7.89 (s, 1 H), 7.72 (d, 1 H), 7.69 (d, 1 H), 7.40 (d, 1 H), 7.39-7.34 (m, 4 H), 7.26 (m, 1 H), 6.58 (s, 1 H), 4.36 (s, 2H), 3.15 (m, 2 H), 3.09 (m, 1 H), 3.03 (s, 3 H), 2.93 (m, 2 H), 2.81 (s, 3 H), 2.20 (m, 2 H), 1.99 (m, 2 H), 1.71 (m, 2 H). MS: LC/MS (+esi), m/z=510 [M+H]. RT=2.18 min.

Example 367

Preparation of tert-butyl 4-[4-amino-5-(3-amino-2-benzyl-2H-indazol-6-yl)-2-methylpyrrolo[2,1-f][1,2,4]triazin-7-yl]piperidine-1-carboxylate

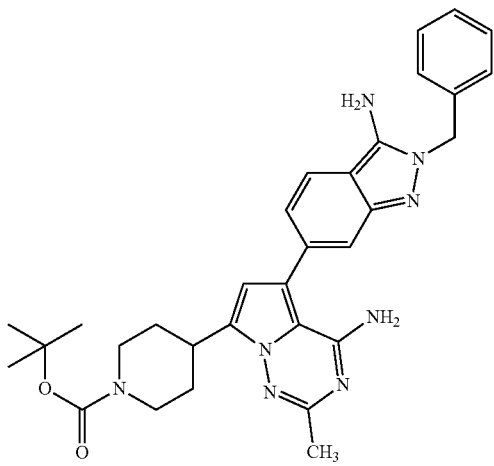 [SMILES: Cc1nc(N)c2c(-c3ccc4c(N)n(Cc5ccccc5)nc4c3)cc(C3CCN(C(=O)OC(C)(C)C)CC3)n2n1]

The title compound was prepared in the same manner described for step 4 of Example 1 and substituting tert-butyl 5-bromo-4-(4-amino-2-methylpyrrolo[2,1-f][1,2,4]triazin-7-yl)piperidine-1-carboxylate for tert-butyl 5-bromo-4-(4-aminopyrrolo[2,1-f][1,2,4]triazin-7-yl)piperidine-1-carboxylate. ¹H-NMR (CD₂Cl₂): δ 7.56 (d, 1 H), 7.49 (s, 1 H), 7.35-7.21 (m, 5 H), 6.99 (dd, 1 H), 6.49 (s, 1 H), 5.80 (br s, 2 H), 5.80 (s, 2 H), 4.20 (m, 2 H), 4.0 (s, 2 H), 3.31 (m, 1 H), 2.91 (m, 2 H), 2.36 (s, 3 H), 2.09 (m, 2 H), 1.64 (m, 2 H), 1.45 (s, 9H). MS: LC/MS (+esi), m/z=525 [M+H]. RT=3.30 min.

Example 368

Preparation of 5-(3-amino-2-benzyl-2H-indazol-6-yl)-2-methyl-7-piperidin-4-ylpyrrolo[2,1-f][1,2,4]triazin-4-amine)

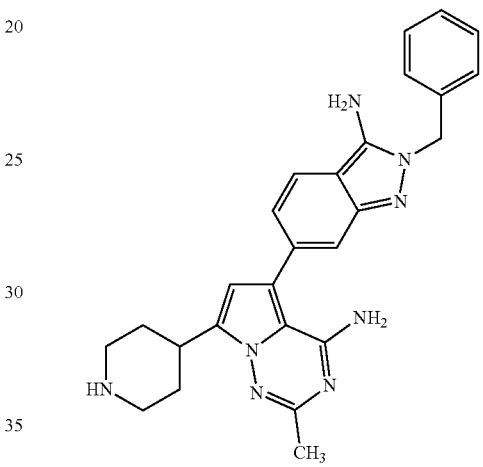

The title compound was prepared in the same manner described for step 5 of Example 1 and substituting tert-butyl 4-[4-amino-5-(3-amino-2-benzyl-2H-indazol-6-yl)-2-methylpyrrolo[2,1-f][1,2,4]triazin-7-yl]piperidine-1-carboxylate for tert-butyl 4-[4-amino-5=(2-benzyl-2H-indazol-6-yl)pyrrolo[2,1-f][1,2,4]triazin-7-yl]piperidine-1-carboxylate.
¹H-NMR (DMSO-d₆): δ 7.71 (m, 1 H), 7.34-7.15 (m, 6 H), 6.73 (m, 1 H), 6.35 (s, 1 H), 5.36 (m, 2 H), 3.27 (m, 2 H), 3.02 (m, 2 H), 2.64 (m, 2 H), 2.25 (s, 3H), 1.91 (m, 2 H), 1.56 (m, 2 H); MS: LC/MS (+esi), m/z=453 [M+H]. RT=1.26 min.

Example 369

Preparation of 2-(4-{4-amino-5-[3-amino-2-(2-fluorobenzyl)-2H-indazol-6-yl]pyrrolo[2,1-f][1,2,4]triazin-7-yl}piperidin-1-yl)-N,N-dimethylacetamide

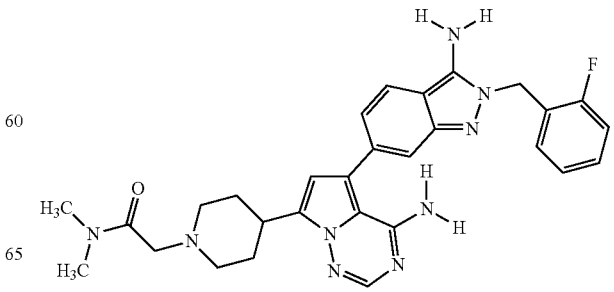

Step 1: Preparation of tert-butyl 2-isopropylidenehydrazinecarboxylate

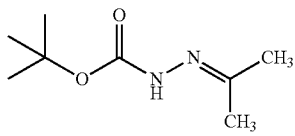

To a solution of tert-butyl hydrazinecarboxylate (25.1 g, 0.190 mol) in acetone (185 mL) was added the magnesium sulfate (6 g) and 12 drops acetic acid. The mixture was heated to reflux for 2.5 h and cooled to rt and filtered. The filtrate was concentrated to give an off-white solid (32 g, 98%) (used in the next step without further purification). LC-MS [M+H]$^+$= 172.9, RT=2.11 min.

Step 2: Preparation of tert-butyl 1-(2-fluorobenzyl)-2-isopropylidenehydrazinecarboxylate

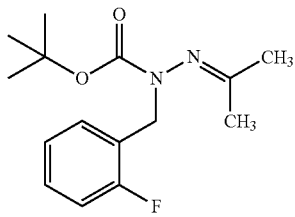 [SMILES: CC(C)=NN(Cc1ccccc1F)C(=O)OC(C)(C)C]

Powdered KOH (4.24 g, 75.48 mmol) and tetrabutylammonium hydrogen sulfate (1.97 g, 5.81 mmol) were added to a solution of tert-butyl 2-isopropylidenehydrazinecarboxylate (10 g, 58.05 mmol) in toluene (150 mL). The mixture was stirred vigorously and heated to 50° C. and 1-(bromomethyl)-2-fluorobenzene (13.17 g, 69.68 mmol) was added slowly. The temperature was increased to 80° C. and maintained for 3 h and cooled to room temperature. The mixture was washed with water until the pH of the aqueous wash was neutral. The organic layer was washed with brine and dried over MgSO$_4$ and concentrated to give a yellow oil (17.11 g) used for the next step without further purification). LC-MS [M+H]$^+$=280.9, RT=3.41 min.

Step 3: Preparation of (2-fluorobenzyl)hydrazine dihydrochloride

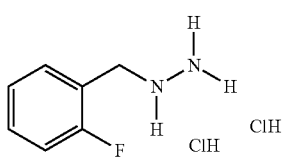

Aqueous hydrochloric acid (3 M, 60.64 mL, 181.92 mmol)I was added to a solution of tert-butyl 1-(2-fluorobenzyl)-2-isopropylidenehydrazinecarboxylate (17 g, 60.64 mmol) in THF (100 mL) and the mixture was heated at reflux for 3 h and concentrated. The residue was taken up in toluene and concentrated, then ether was added to the residue and the suspension was stirred for 30 min and filtered. The filter cake (12.2 g, 94%) was washed with ether and dried on the high vacuum pump. LC-MS [M-2HCl]=141.0, RT=0.25 min.

Step 4: Preparation of 6-bromo-2-(2-fluorobenzyl)-2H-indazol-3-amine

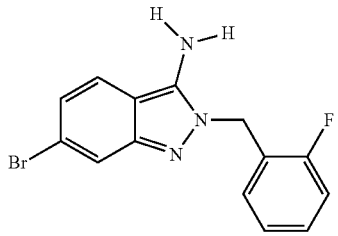 [SMILES: Nc1c2ccc(Br)cc2nn1Cc1ccccc1F]

To a solution of 4-bromo-2-fluorobenzonitrile (3.19 g, 15.64 mmol) and diisopropylamine (13.16 mL, 93.86 mmol) in n-butanol (70 mL) was added (2-fluorobenzyl)hydrazine dihydrochloride (10 g, 46.93 mmol) and the very thick slurry was heated to 125° C. (the mixture became a cloudy solution at 90° C.) for 18 h. The reaction mixture was poured into water and ethyl acetate. The organic layer was isolated and washed with brine, dried over Na$_2$SO$_4$ and concentrated. The resulting light brown solid was taken up in DCM (60 mL) and the suspension stirred for 15 min and filtered. The filter cake was washed with very little DCM and hexanes and dried on a high vacuum pump to give the product as a light brown solid (1.55 g, 31%). LC-MS [M+H]$^+$=320.3, 322.3, RT=2.33 min.

Step 5: Preparation of 2-(2-fluorobenzyl)-6-(4,4,5,5-tetramethyl-1,3,2-dioxaborolan-2-yl)-2H-indazol-3-amine

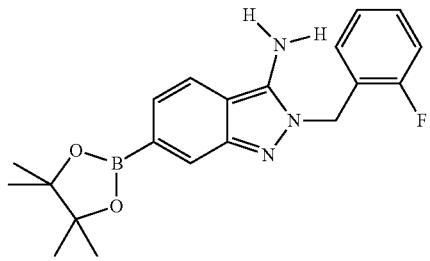 [SMILES: CC1(C)OB(c2ccc3c(N)n(Cc4ccccc4F)nc3c2)OC1(C)C]

A solution of 6-bromo-2-(2-fluorobenzyl)-2H-indazol-3-amine (1.5 g, 4.69 mmol), bis(pinacolato)-diboron (2.38 g, 9.37 mmol) and KOAc (2.76 g, 28.11 mmol) in DMSO (30 mL) was degassed for 5 min, then 1,1'-bis(diphenylphosphino)ferrocenepalladium(II) chloride-complex with CH$_2$Cl$_2$ (0.12 g, 0.141 mmol) was added and the mixture further degassed for 5 min and heated to 85° C. for 2 h and cooled to rt. The mixture was diluted with ethyl acetate and filtered through Celite® and concentrated to remove ethyl acetate. The residue was poured into water (200 mL) and stirred for 10 min. The mixture was filtered through Celite® which was rinsed with water and then ethyl acetate. The filtrate was washed with water and brine, then dried over Na$_2$SO$_4$ and concentrated. The residue was taken up in 20% ethyl acetate in hexanes and the mixture stirred for 30 min and filtered. The brown filter cake was washed with hexanes and dried on the pump (1.17 g, 68%). LC-MS [M+H]$^+$=368.3, RT=2.62 min.

Step 6: Preparation of tert-butyl 4-{4-amino-5-[3-amino-2-(2-fluorobenzyl)-2H-indazol-6-yl]pyrrolo[2,1-f][1,2,4]triazin-7-yl}piperidine-1-carboxylate

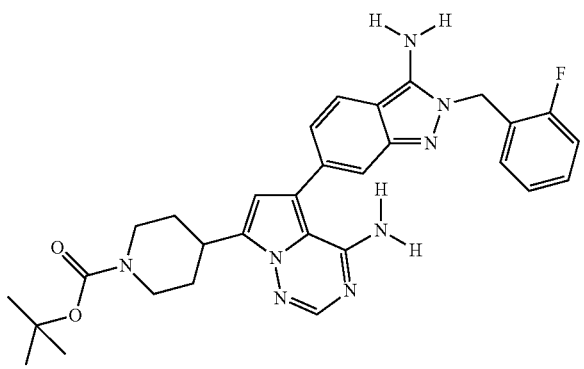 [SMILES: CC(C)(C)OC(=O)N1CCC(c2cc(-c3ccc4c(N)n(Cc5ccccc5F)nc4c3)c3c(N)ncnn23)CC1]

To a solution of tert-butyl 4-(4-amino-5-bromopyrrolo[2,1-f][1,2,4]triazin-7-yl)piperidine-1-carboxylate (0.5 g, 1.26 mmol) in DMF (15 mL) was added 2-(2-fluorobenzyl)-6-(4,4,5,5-tetramethyl-1,3,2-dioxaborolan-2-yl)-2H-indazol-3-amine (0.695 g, 1.89 mmol), solid $Na_2CO_3$ (0.4 g, 3.79 mmol) and water (1.9 mL). The solution was degassed for 10 min and tetrakis(triphenylphosphine)palladium(0) (0.146 g, 0.126 mmol) was added and the mixture was degassed for another 10 min. The mixture was heated at 110° C. for 1 h 15 min and then cooled to rt. The mixture was filtered through a plug of Celite® and the filtrate was concentrated. The crude purified using an ISCO® instrument using 40-100% ethyl acetate in hexanes. LC-MS [M+H]$^+$=557.2, RT=2.65 min.

Step 7: Preparation of 5-[3-amino-2-(2-fluorobenz 1-2H-indazol-6-yl]-7-piperidin-4, ylpyrrolo[2,1-f][1,2,4]triazin-4-amine

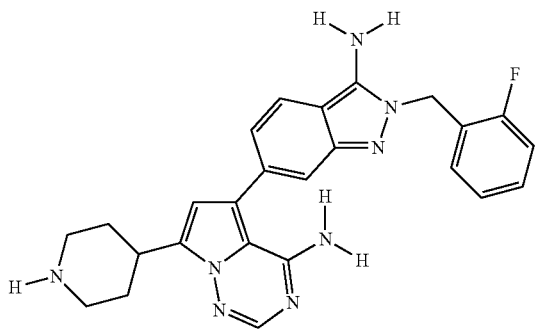 [SMILES: Nc1ncnn2c(C3CCNCC3)cc(-c3ccc4c(N)n(Cc5ccccc5F)nc4c3)c12]

Hydrogen chloride (2.11 mL, 4 M in 1,4-dioxane) was added to a solution of tert-butyl 4-{4-amino-5-[3-amino-2-(2-fluorobenzyl)-2H-indazol-6-yl]pyrrolo[2,1-f][1,2,4]triazin-7-yl}piperidine-1-carboxylate (0.47 g, 0.844 mmol) in 1,4-dioxane (20 mL) and the mixture stirred at rt for 18 h. The suspension was diluted with ethyl acetate and filtered. The filter cake was taken up in ethyl acetate/methanol (8:2) and to the suspension was added saturated aqueous $K_2CO_3$. The mixture was stirred until no solid was observed, then the organic layer was isolated and dried over $Na_2SO_4$, concentrated and the residue purified on by HPLC (2 to 80% acetonitrile) to give the product (0.4 g. 100%). $^1$H NMR (400 MHz, $CD_3OD$) δ 7.71-7.80 (m, 2 H) 7.26-7.34 (m, 2 H) 7.05-7.16 (m, 2 H) 6.84-6.93 (m, 2H) 6.56 (s, 1 H) 5.50 (s, 2 H) 3.30-3.37 (m, 1 H) 3.15 (d, 2 H) 2.79 (dd, 2 H) 2.07 (d, 2 H) 1.65-1.77 (m, 2 H). LC-MS [M+H]$^+$=457.3, RT=0.26 min.

Step 8: Preparation of the Title Compound

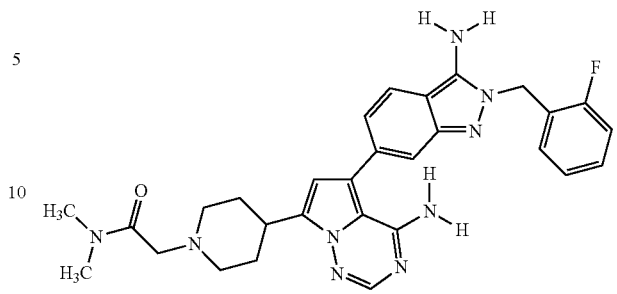

To a suspension of 5-[3-amino-2-(2-fluorobenzyl)-2H-indazol-6-yl]-7-piperidin-4-ylpyrrolo[2,1-f][1,2,4]triazin-4-amine (0.1 g, 0.22 mmol) in THF (2 mL) was added 2-chloro-N,N-dimethylacetamide (0.024 g, 0.2 mmol) and DIEA (0.11 g, 0.88 mmol). The mixture was stirred at room temperature for 18 h, diluted with methanol, and concentrated. The crude product was purified by HPLC (10 to 90% $CH_3CN$). $^1$H NMR (400 MHz, $CD_2Cl_2$) δ 7.87 (s, 1 H) 7.58 (d, 1 H) 7.11-7.35 (m, 5 H) 7.01 (d, 1 H) 6.55 (s, 1 H) 5.50-5.55 (m, 4 H) 4.25 (s, 2 H) 2.90-3.30 (m, 11 H) 2.30 (dt, 2 H) 2.10 (d, 2 H) 1.83 (dt, 2 H). LC-MS [M+H]$^+$=542.3, RT=0.31 min.

Additional compounds illustrated below were prepared by choosing the appropriate starting materials that are readily available and/or the synthesis of which is taught herein, and using the processes of method described herein, or other standard chemical processes known in the art.

Example 370

Preparation of tert-butyl 4-[4-amino-5-(3-amino-2-benzyl-2H-indazol-6-yl)pyrrolo[2,1-f][1,2,4]triazin-7-yl]piperidine-1-carboxylate

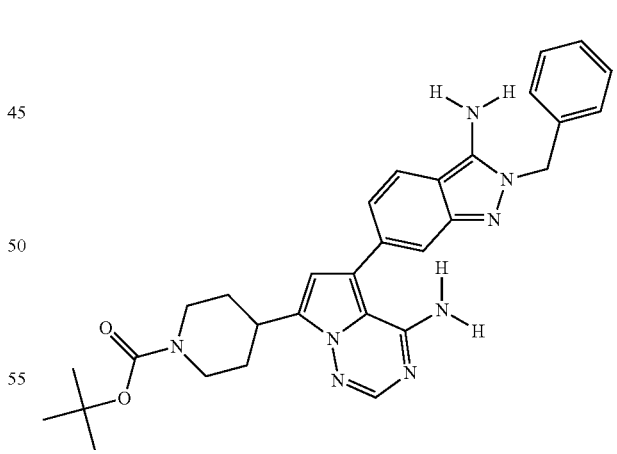

In a manner similar to the procedure described for step 6 of Example 369 and using 2-benzyl-6-(4,4,5,5-tetramethyl-1,3,2-dioxaborolan-2-yl)-2H-indazol-3-amine as starting material, 520 mg (77%) of the desired product was isolated. $^1$H NMR (400 MHz, $CD_3OD$) δ 7.81-7.66 (m, 2.H) 7.24-7.32 (m, 5 H) 6.90 (d, 1 H) 6.58 (s, 1 H) 5.42 (m, 4 H) 4.22 (d, 2 H) 4.19 (s, 1 H) 3.31 (m, 1 H) 2.10 (d, 2 H) 1.65 (m, 2 H) 1.47 (s, 9 H). LC-MS [M+H]$^+$=539.2, RT=2.55 min.

Example 371

Preparation of tert-butyl 4-[4-amino-5-(3-amino-1-benzyl-1H-indazol-6-yl)pyrrolo[2,1-f][1,2,4]triazin-7-yl]piperidine-1-carboxylate

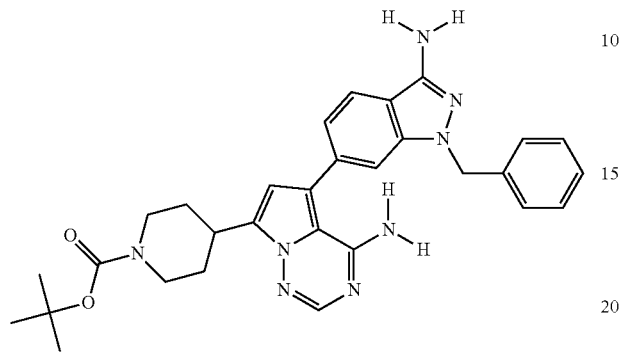

In a manner similar to the procedure described for step 6 of Example 369 and using 1-benzyl-6-(4,4,5,5-tetramethyl-1,3,2-dioxaborolan-2-yl)-1H-indazol-3-amine as starting material, 120 mg (44%) of the desired product was Isolated. $^1$H NMR (400 MHz, CD$_2$Cl$_2$) δ 7.88 (s, 1 H) 7.65 (d, 1 H) 7.24-7.32 (m, 5 H) 7.13-7.23 (m, 4 H) 6.54 (s, 1 H) 4.21 (s, 2 H) 3.35-3.44 (m, 1 H) 2.91 (s, 2 H) 2.08 (s, 2 H) 1.65 (dd, 2 H) 1.46 (s, 9 H). LC-MS [M+H]$^+$=539.0, RT=2.86 min.

Example 372

Preparation of tert-butyl 4-[4-amino-5-(3-amino-2-benzyl-2H-indazol-6-yl)pyrrolo[2,1-f][1,2,4]triazin-7-yl]piperidine-1-carboxylate

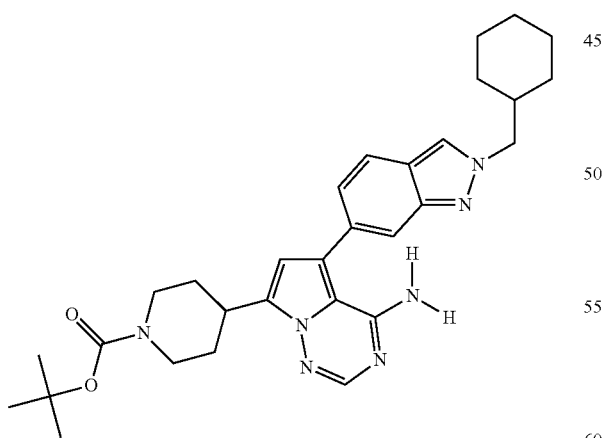

In a manner similar to the procedure described for step 6 of Example 369 and using 2-(cyclohexylmethyl)-6-(4,4,5,5-tetramethyl-1,3,2-dioxaborolan-2-yl)-2H-Indazole as starting material, 390 mg (75%) of the desired product was isolated. LC-MS [M+H]$^+$=530.2, RT=3.31 min.

Example 373

Preparation of 5-(3-amino-2-benzyl-2H-indazol-6-yl)-7-piperidin-4-ylpyrrolo[2,1-f][1,2,4]triazin-4-amine

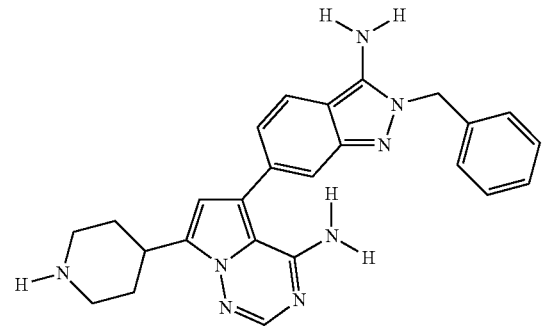 [SMILES: Nc1ncnn2c(C3CCNCC3)cc(-c3ccc4c(N)n(Cc5ccccc5)nc4c3)c12]

In a manner similar to the procedure described for step 7 of Example 369 and using tort-butyl 4-[4-amino-5-(3-amino-2-benzyl-2H-indazol-6-yl)pyrrolo[2,1-f][1,2,4]triazin-7-yl]piperidine-1-carboxylate as starting material, 130 mg (94%) of the desired product was isolated. $^1$H NMR (400 MHz, CD$_3$OD) δ 7.83-7.90 (m, 2 H) 7.12-7.39 (m, 7 H) 6.64 (s, 1 H) 5.40-5.45 (m, 2 H) 3.40-3.61 (m, 3 H) 3.12-3.23 (m, 2 H) 2.34-2.42 (m, 2 H) 1.85-2.03 (m, 2 H). LC-MS [M+H]$^+$=439.3, RT=0.25 min.

Example 374

Preparation of 5-[2-(2-fluorobenzyl)-2H-indazol-6-yl]-7-piperidin-4-ylpyrrolo[2,1-f][1,2,4]triazin-4-amine

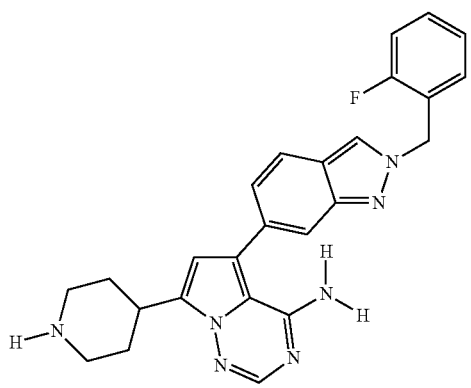 [SMILES: Nc1ncnn2c(C3CCNCC3)cc(-c3ccc4cn(Cc5ccccc5F)nc4c3)c12]

In a manner similar to the procedure described for step 7 of Example 369 and using tert-butyl 4-{4-amino-5-[2-(2-fluorobenzyl)-2H-indazol-6-yl]pyrrolo[2,1-f][1,2,4]triazin-7-yl}piperidine-1-carboxylate as starting material, 430 mg (88%) of the desired product was isolated. $^1$H NMR (400 MHz, CD$_3$OD) δ 8.36 (s, 1 H) 7.78-7.83 (m, 2 H) 7.63 (d, 1 H) 7.15-7.38 (m, 5 H) 6.58 (s, 1 H) 5.72 (s, 2 H) 3.33-3.39 (m, 0.1 H) 3.09-3.19 (m, 2 H) 2.78 (td, 2 H) 2.08 (dd, 2 H) 1.64-1.76 (m, 2 H). LC-MS [M+H]$^+$=442.2, RT=2.04 min.

Example 375

Preparation of 5-[2-(4-fluorobenzyl)-2H-indazol-6-yl]-7-piperidin-4-ylpyrrolo[2,1-f][1,2,4]triazin-4-amine

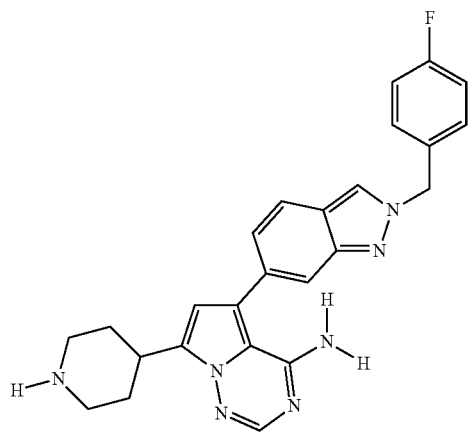 [SMILES: Nc1ncnn2c(C3CCNCC3)cc(-c3ccc4cn(Cc5ccc(F)cc5)nc4c3)c12]

In a manner similar to the procedure described for step 7 of Example 369 and using tort-butyl 4-{4-amino-5-[2-(4-fluorobenzyl)-2H-indazol-6-yl]pyrrolo[2,1-f][1,2,4]triazin-7-yl}piperidine-1-carboxylate as starting material, 10 mg (21%) of the desired product was isolated. LC-MS [M+H]⁺=442.2, RT=1.05 min.

Example 376

Preparation of 5-(2-benzyl-4-fluoro-2H-indazol-6-yl)-7-piperidin-4-ylpyrrolo[2,1-f][1,2,4]triazin-4-amine

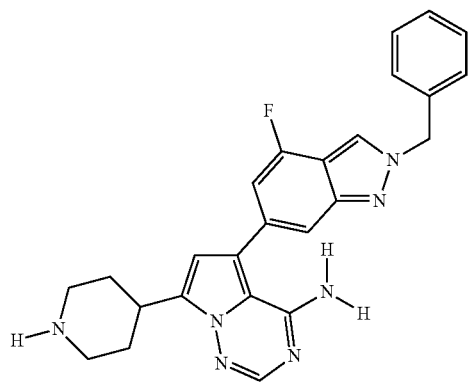 [SMILES: Nc1ncnn2c(C3CCNCC3)cc(-c3cc(F)c4cn(Cc5ccccc5)nc4c3)c12]

In a manner similar to the procedure described for step 7 of Example 369 and using tert-butyl 4-[4-amino-5-(2-benzyl-4-fluoro-2H-indazol-6-yl)pyrrolo[2,1-f][1,2,4]triazin-7-yl]piperidine-1-carboxylate as starting material, 120 mg (76%) of the desired product was isolated. $^1$H NMR (400 MHz, CD$_3$OD) δ 8.48 (s, 1 H) 7.81 (s, 1 H) 7.33-7.45 (m, 7 H) 6.89 (d, 1 H) 6.60 (s, 1 H) 5.65 (s, 2 H) 3.33-3.36 (m, 0.1 H) 3.09-3.19 (m, 2 H) 2.80 (td, 2 H) 2.08 (dd, 2 H) 1.69-1.77 (m, 2 H). LC-MS [M+H]⁺=442.3, RT=1.14 min.

Example 377

Preparation of 7-piperidin-4-yl-5-[2-(pyridin-3-ylmethyl)-2H-indazol-6-yl]pyrrolo[2,1-f][1,2,4]triazin-4-amine

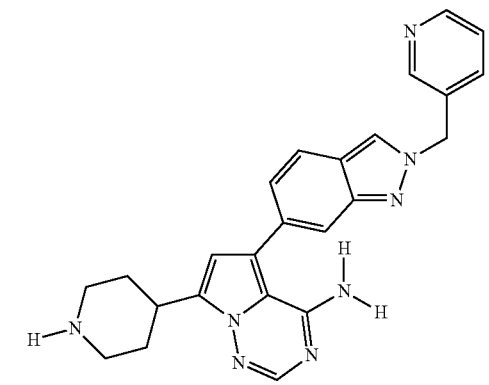 [SMILES: Nc1ncnn2c(C3CCNCC3)cc(-c3ccc4cn(Cc5cccnc5)nc4c3)c12]

In a manner similar to the procedure described for step 7 of Example 369 and using tert-butyl 4-{4-amino-5-[2-(pyridin-3-ylmethyl)-2H-indazol-6-yl]pyrrolo[2,1-f][1,2,4]triazin-7-yl}piperidine-1-carboxylate as starting material, 400 mg (113%) of the desired product was Isolated. NMR (400 MHz, CD$_3$OD) δ 8.58 (d, 1 H) 8.51 (dd, 1 H) 8.49 (d, 1 H) 7.81-7.87 (m, 3 H) 7.64-7.66 (m, 1 H) 7.44 (ddd, 1 H) 7.25 (dd, 1 H) 6.65 (s, 1 H) 5.75 (s, 2 H) 3.48-3.56 (m, 1 H) 3.13-3.23 (m, 2 H) 2.39 (dd, 2 H) 2.34 (d, 2 H) 1.93-2.05 (m, 2 H). LC-MS [M+H]⁺=425.3, RT=1.03 min.

Example 378

Preparation of 7-piperidin-4-yl-5-[2-(pyridin-2-ylmethyl)-2H-indazol-6-yl]pyrrolo[2,1-f][1,1,2,4]triazin-4-amine

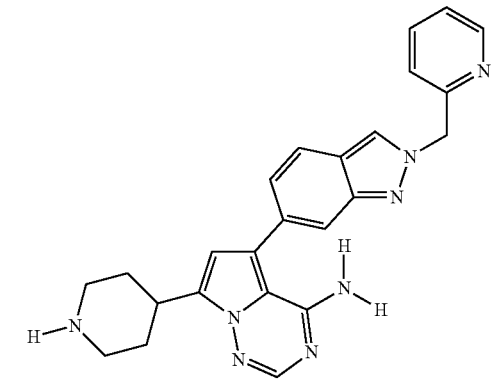 [SMILES: Nc1ncnn2c(C3CCNCC3)cc(-c3ccc4cn(Cc5ccccn5)nc4c3)c12]

In a manner similar to the procedure described for step 7 of Example 369 and using tort-butyl 4-{4-amino-5-[2-(pyridin-2-ylmethyl)-2H-indazol-6-yl]pyrrolo[2,14][1,2,4]triazin-7-yl}piperidine-1-carboxylate as starting material, 370 mg (99%) of the desired product was isolated. $^1$H NMR (400 MHz, CD$_3$OD) δ 8.53 (d, 1 H) 8.46 (s, 1 H) 7.81-7.87 (m, 3 H) 7.65 (s, 1 H) 7.37 (ddd, 1 H) 7.25 (dd, 2 H) 6.60 (s, 1 H) 5.78

(s, 2 H) 3.47-3.52 (m, 1 H) 3.13-3.23 (m, 2 H) 2.78-2.84 (m, 2 H) 1.93-2.05 (m, 2 H) 1.75 (dt, 2 H). LC-MS [M+H]⁺=425.3, RT=1.18 min.

Example 379

Preparation of 5-(2-benzyl-2H-indazol-5-yl)-7-piperidin-4-ylpyrrolo[2,1-f][1,2,4]triazin-4-amine

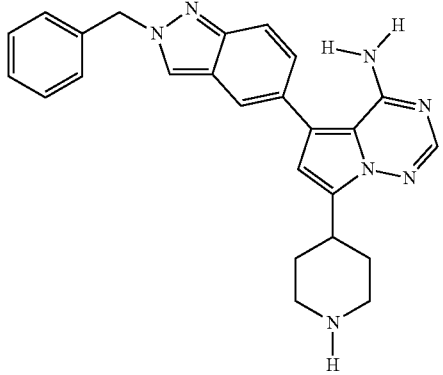 [SMILES: Nc1ncnn2c(C3CCNCC3)cc(-c3ccc4nn(Cc5ccccc5)cc4c3)c12]

In a manner similar to the procedure described for step 7 of Example 369 and using tort-butyl 4-[4-amino-5-(2-benzyl-2H-indazol-5-yl)pyrrolo[2,1-f][1,2,4]triazin-7-yl]piperidine-1-carboxylate as starting material, 100 mg (65%) of the desired product was isolated. ¹H NMR (400 MHz, CD₃OD) δ 8.31 (d, 1 H), 7.71-7.81 (m, 3 H), 7.25-7.45 (m, 6 H), 6.56 (s, 1 H), 5.65 (s, 2 H), 3.19-3.45 (m, 3 H), 2.87-2.91 (m, 2 H), 2.13 (d, 2 H), 1.65-1.79 (s, 2 H). LC-MS [M+H]⁺=425.3, RT=1.18 min.

Example 380

Preparation 5-[2-(cyclohexlmethyl)-2H-indazol-6-yl]-7-piperidin-4-ylpyrrolo[2,1-f][1,2,4]triazin-4-amine

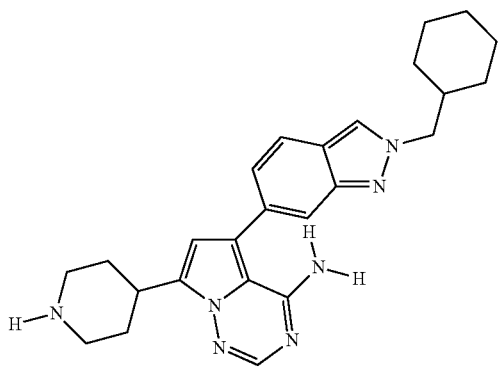 [SMILES: Nc1ncnn2c(C3CCNCC3)cc(-c3ccc4cn(CC5CCCCC5)nc4c3)c12]

TFA was added to a solution of tert-butyl 4-{4-amino-5-[2-(cyclohexylmethyl)-2H-indazol-6-yl]pyrrolo[2,1-f][1,2,4]triazin-7-yl}piperidine-1-carboxylate (0.25 g, 0.472 mmol) in DCM (5 mL) and the mixture stirred for 4.5 h and concentrated. The residue was taken up in DCM, a few drops of triethylamine was added and the mixture was purified using an ISCO® instrument (1% triethylamine and 10% methanol in DCM). The desired fractions were concentrated and the oily residue was purified by HPLC (5 to 90% CH₃CN) to give the product (20 mg, 9%). ¹H NMR (400 MHz, CD₃OD) δ 8.27 (d, 1 H) 7.86 (s, 1 H) 7.83 (dd, 1 H) 7.66 (d, 1 H) 7.22 (dd, 1 H) 6.67 (s, 1 H) 4.29 (d, 2 H) 3.50-3.62 (m, 3 H) 3.19-3.22 (m, 2 H) 2.41 (d, 2 H) 1.98-2.11 (m, 3 H) 145-1.97 (m, 5 H) 0.89-1.36 (m, 5 H). LC-MS [M+H]⁺= 430.4, RT=0.99 min.

Example 381

Preparation of 5-[2-(cyclobutylmethyl)-2H-indazol-6-yl]-7-piperidin-4-ylpyrrolo[2,1-f][1,2,4]triazin-4-amine

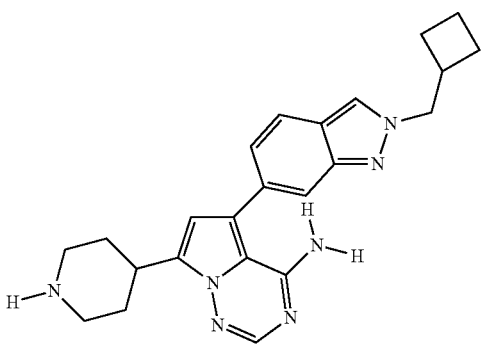 [SMILES: Nc1ncnn2c(C3CCNCC3)cc(-c3ccc4cn(CC5CCC5)nc4c3)c12]

In a manner similar to the procedure described for Example 380 and using tert-butyl 4-{4-amino-5-[2-(cyclobutylmethyl)-2H-indazol-6-yl]pyrrolo[2,1-f][1,2,4]triazin-7-yl}piperidine-1-carboxylate as starting material, 20 mg (40%) of the desired product was isolated. ¹H NMR (400 MHz, CD₃OD) δ 8.29 (d, 1 H) 7.86 (s, 1 H) 7.83 (dd, 1 H) 7.65 (d, 1 H) 7.22 (dd, 1 H) 6.66 (s, 1 H) 4.28 (d, 2 H) 3.50-3.62 (m, 3 H) 3.19-3.22 (m, 2 H) 2.89-3.05 (m, 1 H) 2.41 (d, 2 H) 1.98-2.11 (m, 8 H). LC-MS [M+H]⁺=402.2, RT=1.93 min.

Example 382

Preparation of 5-[2-(cyclopropylmethyl)-2H-indazol-6-yl]-7-piperidin-4-ylpyrrolo[2,1-f][1,2,4]triazin-4-amine

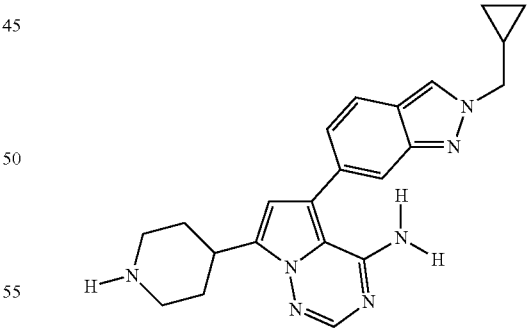

In a manner similar to the procedure described for Example 380 and using tert-butyl 4-{4-amino-5-[2-(cyclopropylmethyl)-2H-indazol-6-yl]pyrrolo[2,1-f][1,2,4]triazin-7-yl}piperidine-1-carboxylate as starting material, 10 mg (6%) of the desired product was isolated. ¹H NMR (400 MHz, CD₃OD) δ 8.37 (s, 1H) 7.81-7.85 (m, 2 H) 7.65 (s, 1 H) 7.24 (d, 1 H) 6.67 (s, 1 H) 4.32 (d, 2 H) 3.41-3.55 (m, 3 H) 3.17-3.26 (m, 2 H) 2.36 (d, 2 H) 1.92-2.03 (m, 2 H) 1.41-1.47 (m, 1 H) 0.65-0.70 (m, 2 H) 0.51 (dt, 2 H) LC-MS [M+H]⁺= 388.3, RT=0.42 min.

Example 383

Preparation of 7-(1-acetylpiperidin-4-yl)-5-[3-amino-2-(2-fluorobenzyl)-2H-Indazol-6-yl]pyrrolo[2,1-f][1,2,4]triazin-4-amine

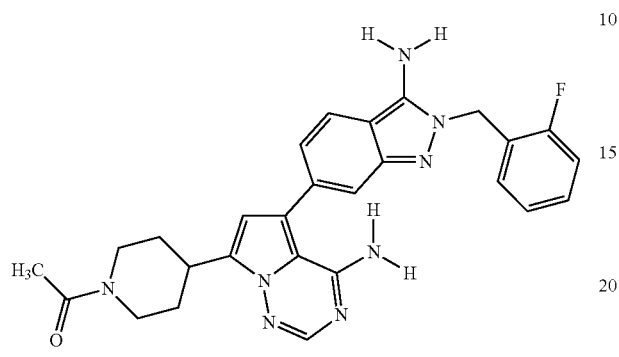

In a manner similar to the procedure described for the preparation of Example 369 and using and substituting acetyl chloride for 2-chloro-N,N-dimethylacetamide as starting material, 40 mg (41%) of the desired product was isolated. $^1$H NMR (400 MHz, CD$_2$Cl$_2$) δ 7.87 (s, 1 H) 7.58 (d, 1 H) 7.47 (s, 1 H) 7.29-7.37 (m, 1 H) 7.10-7.22 (m, 3 H) 6.99 (d, 1H) 6.52 (s, 1 H) 5.71 (br, 2 H) 5.52 (s, 2 H) 4.70 (d, 1 H) 4.32 (br, 2 H) 3.91 (s, 1 H) 3.43-3.53 (m, 1 H) 3.21-3.31 (m, 1 H) 2.74 (d, 1 H) 1.99-2.22 (m, 5 H) 1.62-1.73 (m, 2 H) LC-MS [M+H]P=499.3, RT=2.29 min.

Example 384

Preparation of 2-{4-[4-amino-5-(3-amino-2-benzyl-2H-indazol-6-yl)pyrrolo[2,1-f][1,1,2,4]triazin-7-yl]piperidin-1-yl}-N,N-dimethylacetamide

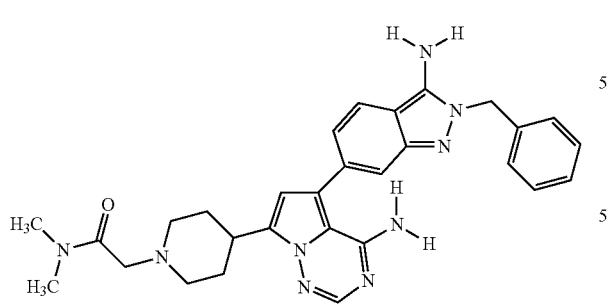

In a manner similar to the procedure described for Example 369 and using 5-(3-amino-2-benzyl-2H-indazol-6-yl)-7-piperidin-4-ylpyrrolo[2,1-f][1,2,4]triazin-4-amine as starting material, 60 mg (41%) of the desired product was isolated. LC-MS [M+H]$^+$=524.3, RT=1.36 min.

Example 385

Preparation of (1-acetylpiperidin-4-yl)-5-(3-amino-2-benzyl-2H-indazol-6-yl)pyrrolo[2,1-f][1,2,4]triazin-4-amine

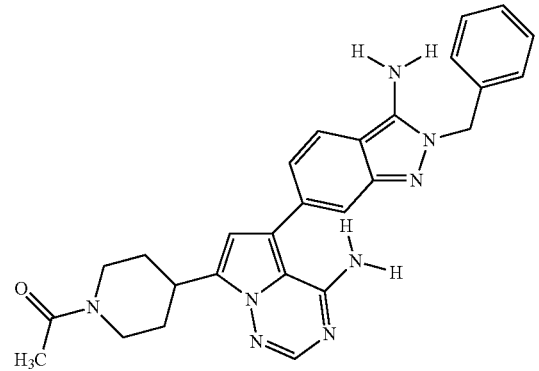 [SMILES: CC(=O)N1CCC(c2cc(-c3ccc4c(N)n(Cc5ccccc5)nc4c3)c3c(N)ncnn23)CC1]

In a manner similar to the procedure described for Example 369 and using 5-(3-amino-2-benzyl-2H-indazol-6-yl)-7-piperidin-4-ylpyrrolo[2,1-f][1,2,4]triazin-4-amine and substituting acetyl chloride for 2-chloro-N,N-dimethylacetamide, 20 mg (38%) of the desired product was isolated. LC-MS [M+H]$^+$=481.3, RT=2.10 min.

Example 386

Preparation of 5-(3-amino-2-benzyl-2H-indazol-6-yl-7-[1-(methylsulfonyl)piperidin-4-yl]pyrrolo[2,1-f][1,2,4]triazin-amine

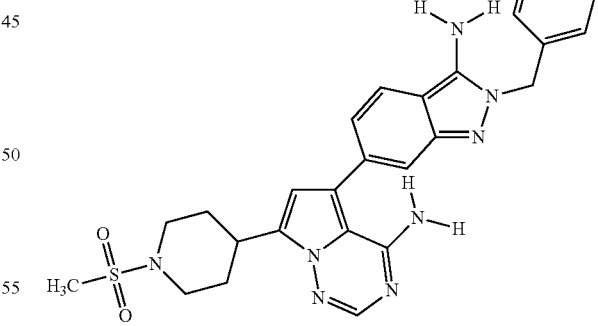

In a manner similar to the procedure described for Example 369 and using 5-(3-amino-2-benzyl-2H-indazol-6-yl)-7-piperidin-4-ylpyrrolo[2,1-f][1,2,4]triazin-4-amine and substituting methyl sulfonyl chloride for 2-chloro-N,N-dimethylacetamide as starting material, 10 mg (15%) of the desired product was isolated. $^1$H NMR (400 MHz, CD$_3$OD) δ 7.82 (s, 1 H) 7.73 (d, 1 H) 7.25-7.36 (m, 6 H) 6.93 (d, 1 H) 6.59 (s, 1 H) 5.44 (s, 2 H) 3.87 (d, 2 H) 3.31 (dt, 1 H) 2.94 (d, 2 H) 2.87 (s, 3 H) 2.25 (d, 2 H) 1.87 (dt, 2 H). LC-MS [M+H]$^+$=517.3, RT=2.21 min.

Example 387

Preparation of 4-[4-amino-5-(3-amino-2-benzyl-2H-indazol-6-yl)pyrrolo[2,1-f][1,2,4]triazin-7-yl]-N,N-dimethylpiperidine-1-carboxamide

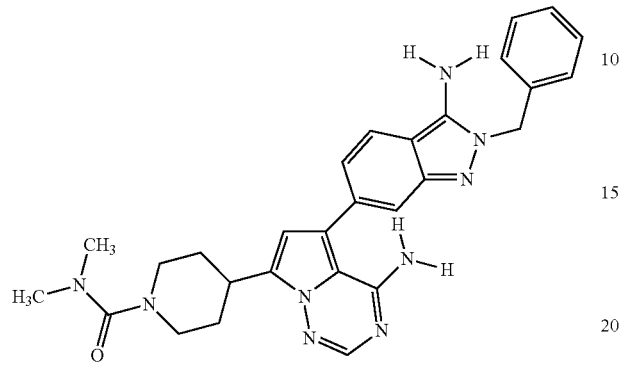

In a manner similar to the procedure described for Example 369 and using 5-(3-amino-2-benzyl-2H-indazol-6-yl)-7-piperidin-4-ylpyrrolo[2,1-f][1,2,4]triazin-4-amine and substituting dimethylcarbamyl chloride for 2-chloro-N,N-dimethylacetamide as starting materials, 40 mg (46%) of the desired product was isolated. $^1$H NMR (400 MHz, CD$_3$OD) δ ppm 7.82 (s, 1 H) 7.71 (d, 1 H) 7.23-7.37 (m, 6 H) 6.96 (d, 1 H) 6.57 (s, 1 H) 5.44 (s, 2 H) 3.79 (d, 2 H) 3.41 (dt, 1 H) 3.01 (d, 2 H) 2.86 (s, 6 H) 2.16 (d, 2 H) 1.77 (dt, 2 H). LC-MS [M+H]$^+$=510.2, RT=2.21 min.

Example 388

Preparation 4-[4-amino-5-(3-amino-2-benzyl-2H-indazol-6-yl)pyrrolo[2,1-f][1,2,4]triazin-7-yl]-N,N-dimethylpiperidine-1-sulfonamide

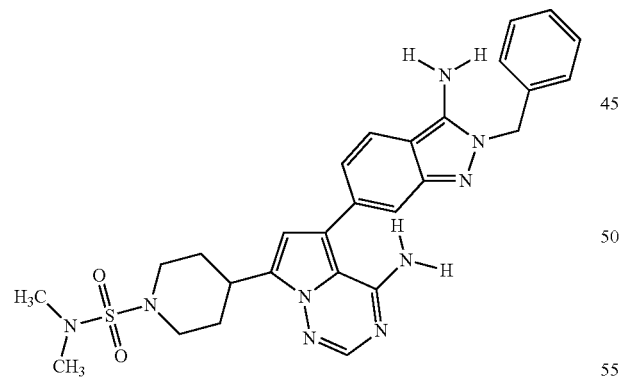

In a manner similar to the procedure described for Example 369 and using 5-(3-amino-2-benzyl-2H-indazol-6-yl)-7-piperidin-4-ylpyrrolo[2,1-f][1,2,4]triazin-4-amine and substituting dimethylsulfomoyl chloride for 2-chloro-N,N-dimethylacetamide as starting materials, 50 mg (52%) of the desired product was isolated. $^1$H NMR (400 MHz, DMSO-d$_6$) δ ppm 7.85 (s, 1 H) 7.71 (d, 1 H) 723-7.37 (m, 6 H) 6.81 (d, 1 H) 6.57 (s, 1 H) 6.16 (s, 2 H, NH$_2$) 5.56 (s, 2 H, NH$_2$) 5.44 (s, 2 H) 3.74 (d, 2 H) 3.31 (dt, 1 H) 3.02 (d, 2 H) 2.82 (d, 6 H) 2.15 (d, 2 H) 1.78 (dt, 2 H). LC-MS [M+H]$^+$=546.3, RT=2.29 min.

Example 389

Preparation 2-{4-[4-amino-5-(3-amino-2-benzyl-2H-indazol-6-yl)pyrrolo[2,1-f][1,2,4]triazin-7-yl]piperidin-1-yl}-N,N-dimethylacetamide

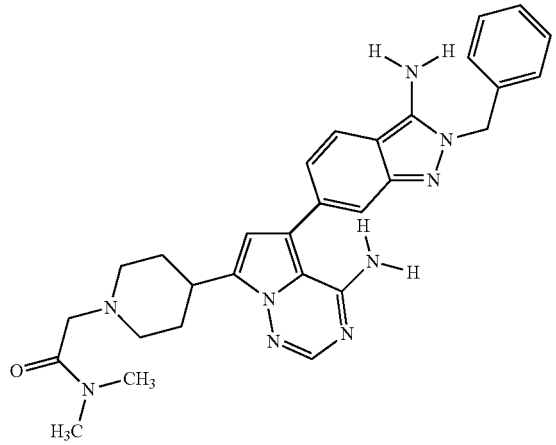 [SMILES: CN(C)C(=O)CN1CCC(c2cc(-c3ccc4c(N)n(Cc5ccccc5)nc4c3)c3c(N)ncnn23)CC1]

In a manner similar to the procedure described for Example 369 and using 5-(3-amino-2-benzyl-2H-indazol-6-yl)-7-piperidin-4-ylpyrrolo[2,1-f][1,2,4]triazin-4-amine as starting material, 30 mg (31%) of the desired product was isolated. $^1$H NMR (400 MHz, CD$_3$OD) 7.79 (s, 1 H) 7.73 (d, 1 H) 7.20-7.33 (m, 6 H) 6.93 (d, 1 H) 6.58 (s, 1 H) 5.49 (s, 2 H) 3.12-3.31 (m, 3 H) 2.94-3.11 (m, 8 H) 2.31 (dt, 2 H) 2.10 (d, 2 H) 1.87 (dt, 2 H). LC-MS [M+H]$^+$=524.3, RT=1.35 min.

Example 390

Preparation-(4-{4-amino-5-[2-(2-fluorobenzyl)-2H-indazol-6-yl]pyrrolo[2,1-f][1,2,4]triazin-7-yl}piperidin-1-yl)-N,N-dimethylacetamide

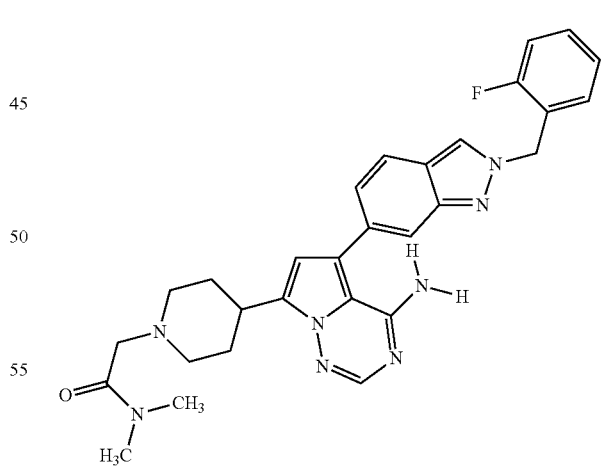

In a manner similar to the procedure described for Example 369 and using 5-[2-(2-fluorobenzyl)-2H-indazol-6-yl]-7-piperidin-4-ylpyrrolo[2,1-f][1,2,4]triazin-4-amine as starting material, 30 mg (31%) of the desired product was Isolated. $^1$H NMR (400 MHz, CD$_3$OD) δ 8.25 (s, 1 H) 7.77-7.81 (m, 2 H) 7.62 (d, 1 H) 7.16-7.40 (m, 5 H) 6.59 (s, 1 H) 5.69 (s, 2 H) 2.93-3.30 (m, 11 H) 2.30 (td, 2 H) 2.09 (s, 2 H) 1.87 (dt, 2 H). LC-MS [M+H]$^+$=527.3, RT=2.01 min.

Example 391

Preparation 4-{4-amino-5-[2-(2-fluorobenzyl)-2H-indazol-6-yl]pyrrolo[2,1-f][2,4]triazin-7-yl}-N,N-dimethylpiperidine-1-carboxamide

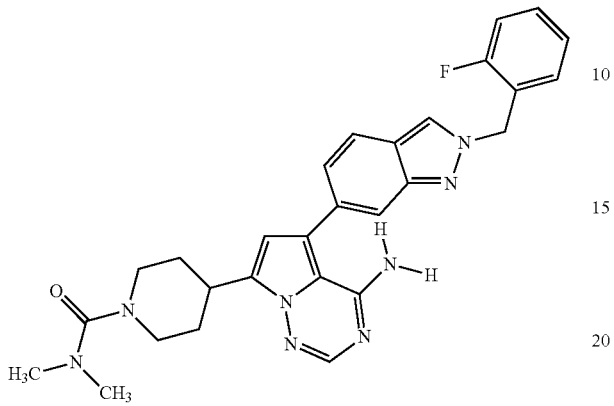

In a manner similar to the procedure described for Example 369 and using 5-[2-(2-fluorobenzyl)-2H-indazol-6-yl]-7-piperidin-4-ylpyrrolo[2,1-f][1,2,4]triazin-4-amine and substituting dimethylcarbamyl chloride for 2-chloro-N,N-dimethylacetamide as starting materials, 30 mg (31%) of the desired product was Isolated. ¹H NMR (400 MHz, CD₃OD) δ 8.35 (s, 1 H) 7.77-7.82 (m, 2 H) 7.63 (d, 1 H) 7.15-7.41 (m, 5 H) 6.59 (s, 1 H) 5.72 (s, 2 H) 3.79 (d, 1 H) 3.39-3.42 (m, 1 H) 2.99 (td, 2 H) 2.85 (s, 6 H) 2.12 (d, 2 H) 1.70-1.81 (m, 2H). LC-MS [M+H]⁺=513.2, RT=2.54 min.

Example 392

Preparation of 7-(1-acetylpiperidin-4-yl)-5-[2-(4-fluorobenzyl)-2H-indazol-6-yl]pyrrolo[2,1-f][1,2,4]triazin-4-amine

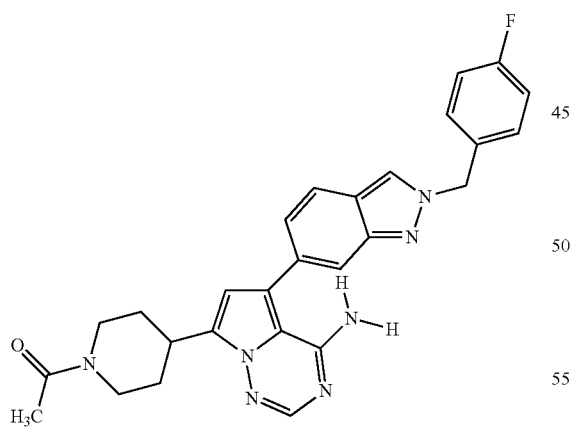

In a manner similar to the procedure described for Example 369 and using 5-[2-(4-fluorobenzyl)-2H-indazol-6-yl]-7-piperidin-4-ylpyrrolo[2,1-f][1,2,4]triazin-4-amine and substituting acetyl chloride for 2-chloro-N,N-dimethylacetamide as starting materials, 30 mg (55%) of the desired product was isolated. ¹H NMR (400 MHz, CD₃OD) δ 8.34 (s, 1 H) 7.81 (s, 1 H) 7.77 (d, 1 H) 7.62 (d, 1 H) 7.32-7.40 (m, 2 H) 7.19 (d, 1 H) 7.03-7.10 (m, 2 H) 6.55 (s, 1 H) 5.61 (s, 2 H) 4.63 (d, 1 H) 4.00 (d, 1 H) 3.45 (tt, 1 H) 3.25 (td, 1 H) 2.75 (td, 1 H) 2.07-2.18 (m, 5 H) 1.62-1.72 (m, 2 H).

Example 393

Preparation of 5-[2-(4-fluorobenzyl)-2H-indazol-6-yl]-7-[1-(methylsulfonyl)piperidin-4-yl]pyrrolo[2,1-f][1,2,4]triazin-4-amine

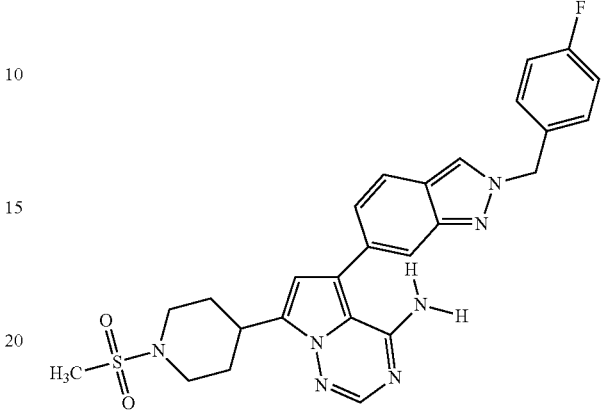

In a manner similar to the procedure described for Example 369 and using 5-[2-(4-fluorobenzyl)-2H-indazol-6-yl]-7-piperidin-4-ylpyrrolo[2,1-f][1,2,4]triazin-4-amine and substituting methane sulfonyl chloride for 2-chloro-N,N-dimethylacetamide as starting materials, 3.2 mg (7%) of the desired product was isolated. ¹H NMR (400 MHz, CD₃OD) δ 8.62 (s, 1H) 8.18 (s, 1 H) 7.91 (d, 1 H) 7.35-7.44 (m, 3 H) 7.17 (dd, 2 H) 6.88 (s, 1 H) 5.75 (s, 2 H) 2.42-2.68 (m, 3 H) 3.00 (d, 1 H) 2.86 (d, 1 H) 2.71 (s, 3 H) 2.37 (d, 5 H) 2.02-2.19 (m, 2 H). LC-MS [M+H]⁺=520.3, RT=2.62 min.

Example 394

Preparation of 4-{4-amino-5-[2-(4-fluorobenzyl)-2H-indazol-6-yl]pyrrolo-[2,1-f][1,2,4]triazin-7-yl}-N,N-dimethylpiperidine-1-carboxamide

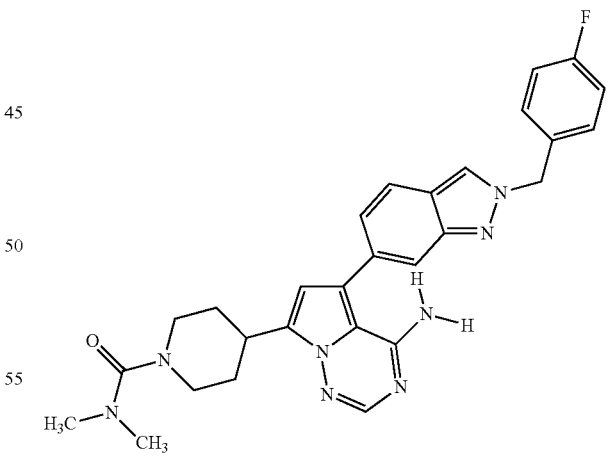

In a manner similar to the procedure described for Example 369 and using 5-[2-(4-fluorobenzyl)-2H-indazol-6-yl]-7-piperidin-4-ylpyrrolo[2,1-f][1,2,4]triazin-4-amine and substituting dimethycarbamyl chloride for 2-chloro-N,N-dimethylacetamide as starting materials, 20 mg (49%) of the desired product was isolated. ¹H NMR (400 MHz, CD₂Cl₂) δ 8.05 (s, 1 H) 7.89 (s, 1 H) 7.78 (d, 1 H) 7.74 (s, 1 H) 7.33-7.39 (m, 2 H) 7.24 (dd, 1 H) 7.10 (ddd, 2 H) 6.59 (s, 1 H) 5.61 (s, 2 H) 3.79 (d, 2 H) 3.38-3.47 (m, 1 H) 2.97 (td, 2 H) 2.84 (s, 6 H)

2.17 (d, 1 H) 2.14 (s, 1 H) 1.76-1.71 (m, 2 H). LC-MS [M+H]⁺=513.1, RT=2.57 min.

Example 395

Preparation of 4-{4-amino-5-[2-(4-fluorobenzyl)-2H-indazol-6-yl]pyrrolo[2,1-f][1,2,4]triazin-7-yl}-N,N-dimethylpiperidine-1-sulfonamide

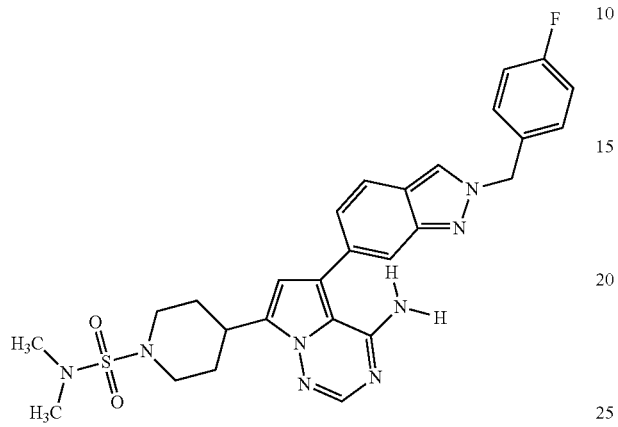

In a manner similar to the procedure described for Example 369 and using 5-[2-(4-fluorobenzyl)-2H-indazol-6-yl]-7-piperidin-4-ylpyrrolo[2,1-f][1,2,4]triazin-4-amine and substituting dimethylsulfomoyl chloride for 2-chloro-N,N-dimethylacetamide as starting materials, 20 mg (46%) of the desired product was isolated. ¹H NMR (400 MHz, CD₂Cl₂) δ 8.06 (s, 1 H) 7.91 (s, 1 H) 7.78 (d, 1 H) 7.75 (s, 1 H) 7.33-7.38 (m, 2 H) 7.24 (dd, 1 H) 7.10 (ddd, 2 H) 6.62 (s, 1 H) 5.61 (s, 2 H) 3.81 (d, 2 H) 3.39 (m, 1 H) 3.05 (td, 2 H) 2.85 (s, 6 H) 2.18 (d, 1 H) 2.15 (s, 1 H) 1.87-1.79 (m, 2 H). LC-MS [M+H]⁺= 549.3, RT=2.74 min.

Example 396

Preparation of 7-{1-[(dimethylamino)acetyl]piperidin-4-yl}-5-[2-(4-fluorobenzyl)-2H-indazol-6-yl]pyrrolo[2,1-f][1,2,4]triazin-4-amine

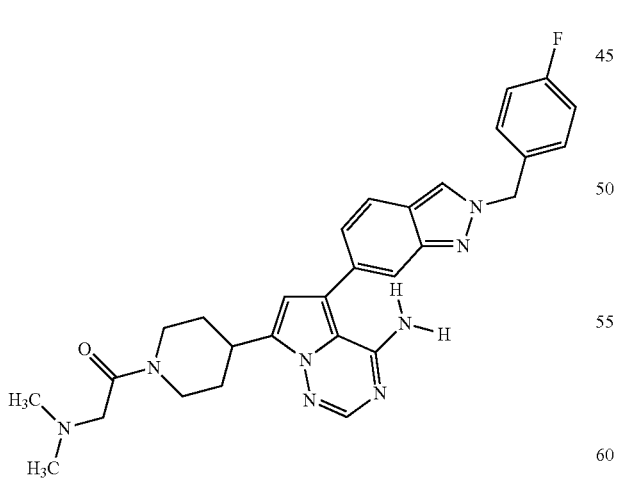

In a manner similar to the procedure described for Example 369 and using 5-[2-(4-fluorobenzyl)-2H-indazol-6-yl]-7-piperidin-4-ylpyrrolo[2,1-f][1,2,4]triazin-4-amine as starting material, 20 mg (40%) of the desired product was isolated. ¹H NMR (400 MHz, CD₃OD) δ 8.31 (s, 1 H) 7.82 (s, 1 H) 7.78 (d, 1 H) 7.63 (s, 1 H) 7.38 (dd, 2 H) 7.22 (d, 1H) 7.08 (t, 2 H) 6.60 (s, 1 H) 5.63 (s, 2 H) 3.26 (s, 3 H) 3.12 (s, 3 H) 3.05 (d, 2 H) 2.97 (s, 3 H) 2.30 (dd, 2 H) 2.12 (d, 2 H) 1.87-1.77 (m, 2 H). LC-MS [M+H]⁺=527.2, RT=2.14 min.

Example 397

Preparation of 7-{1-[(dimethylamino)acetyl]piperidin-4-yl}-5-[2-(4-fluorobenzyl)-2H-indazol-6-yl]pyrrolo[2,1-f][1,2,4]triazin-4-amine

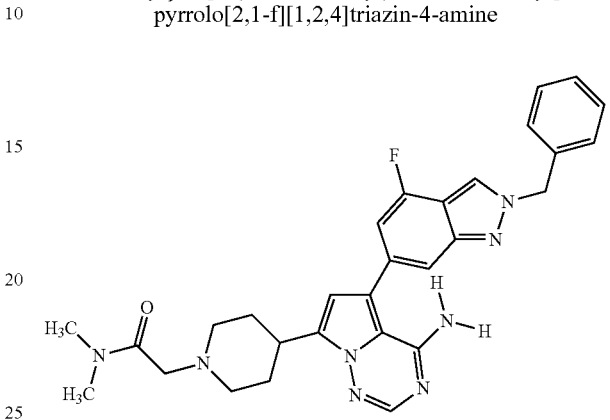

In a manner similar to the procedure described for Example 369 and using 5-(2-benzyl-4-fluoro-2H-indazol-6-yl)-7-piperidin-4-ylpyrrolo[2,1-f][1,2,4]triazin-4-amine as starting material, 40 mg (43%) of the desired product was isolated. ¹H NMR (400 MHz, CD₃OD) 8.44 (s, 1 H) 7.78 (d, 1 H) 7.43 (d, 1 H) 7.19-7.38 (m, 5 H) 6.87 (d, 1 H) 6.57 (s, 1 H) 5.62 (s, 2 H) 2.92-3.31 (m, 11 H) 2.21 (td, 2 H) 2.02 (dd, 2 H) 1.69-1.82 (m, 2 H). LC-MS [M+H]⁺=527.4, RT=2.09 min.

Example 398

Preparation of 7-(1-acetylpiperidin-4-yl)-5-[2-(pyridin-3-ylmethyl)-2H-indazol-6-yl]pyrrolo[2,1-f][1,2,4]triazin-4-amine

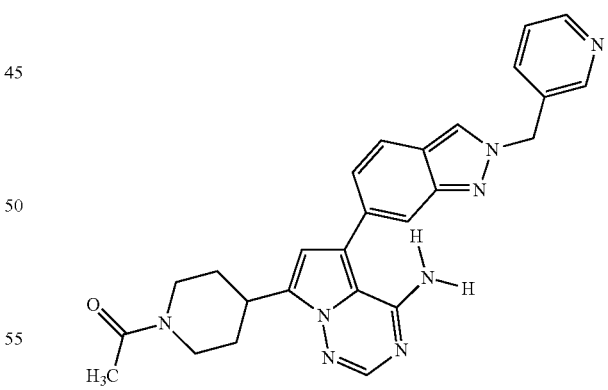

In a manner similar to the procedure described for Example 369 and using 7-piperidin-4-yl-5-[2-(pyridin-3-ylmethyl)-2H-indazol-6-yl]pyrrolo[2,1-f][1,2,4]triazin-4-amine and substituting acetyl chloride for 2-chloro-N,N-dimethylacetamide as starting materials, 20 mg (40%) of the desired product was isolated. ¹H NMR (400 MHz, CD₃OD) δ 8.47 (s, 1 H) 7.47-7.87 (m, 2 H) 7.82-7.86 (m, 3 H) 7.67 (s, 1 H) 7.43 (dd, 1 H) 7.26 (d, 1 H) 6.61 (s, 1 H) 5.75 (s, 2 H) 4.76 (dd, 1 H) 4.02 (dd, 1 H) 3.21-3.50 (m, 2 H) 2.82 (dd, 1 H) 2.14-2.26 (m, 5 H) 1.88 (dt, 2 H). LC-MS [M+H]*=467.4, RT=0.44 min.

Example 399

Preparation of 7-[1-(methylsulfonyl)piperidin-4-yl]-5-[2-(pyridin-3-ylmethyl)-2H-indazol-6-yl]pyrrolo[2,1-f][1,2,4]triazin-4-amine

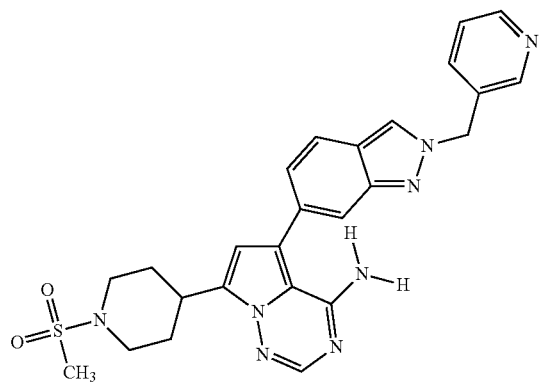 [SMILES: CS(=O)(=O)N1CCC(c2cc(-c3ccc4cn(Cc5cccnc5)nc4c3)c3c(N)ncnn23)CC1]

In a manner similar to the procedure described for Example 369 and using 7-piperidin-4-yl-5-[2-(pyridin-3-ylmethyl)-2H-indazol-6-yl]pyrrolo[2,1-f][1,2,4]triazin-4-amine and substituting methane sulfonyl chloride for 2-chloro-N,N-dimethylacetamide as starting materials, 50 mg (60%) of the desired product was isolated. $^1$H NMR (400 MHz, CD$_3$OD) δ 8.57 (s, 1 H) 8.49 (d, 1 H) 8.35 (s, 1 H) 7.65-7.84 (m, 4 H) 7.41 (dd, 1 H) 7.24 (d, 1 H) 6.59 (s, 1 H) 5.70 (s, 2 H) 3.84 (d, 2 H) 3.34 (m, 1 H) 2.85-2.96 (m, 5 H) 2.24 (dd, 2 H) 1.87 (dt, 2 H). LC-MS [M+H]$^+$=503.3, RT=0.75 min.

Example 400

Preparation of 4-{4-amino-5-[2-(pyridin-3-ylmethyl)-2H-indazol-6-yl]pyrrolo[2,1-f][1,2,4]triazin-7-yl}-N,N-dimethylpiperidine-1-carboxamide

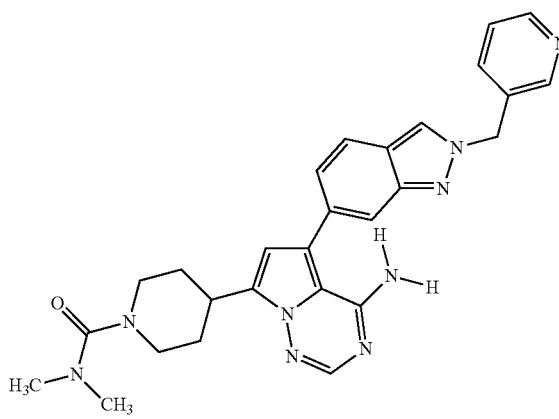 [SMILES: CN(C)C(=O)N1CCC(c2cc(-c3ccc4cn(Cc5ccccn5)nc4c3)c3c(N)ncnn23)CC1]

In a manner similar to the procedure described for Example 369 and using 7-piperidin-4-yl-5-[2-(pyridin-3-ylmethyl)-2H-indazol-6-yl]pyrrolo[2,1-f][1,2,4]triazin-4-amine and substituting dimethylcarbamyll chloride for 2-chloro-N,N-dimethylacetamide as starting material, 50 mg (65%) of the desired product was isolated. $^1$H NMR (400 MHz, CD$_3$OD) δ 8.57 (s, 1 H) 8.49 (d, 1 H) 8.43 (s, 1 H) 7.75-7.80 (m, 3 H) 7.63 (s, 1 H) 7.42 (dd, 1 H) 7.21 (d, 1 H) 6.56 (s, 1 H) 5.71 (s, 2 H) 3.76 (d, 2 H) 3.34 (m, 1 H) 2.94 (dd, 2 H) 2.84 (s, 6 H) 2.06 (dd, 2 H) 1.73 (dt, 2 H). LC-MS [M+H]$^+$=496.4, RT=1.08 min.

Example 401

Preparation of 4-{4-amino-5-[2-(pyridin-3-ylmethyl)-2H-indazol-6-yl]pyrrolo[2,1-f][1,2,4]triazin-7-yl}-N,N-dimethylpiperidine-1-sulfonamide

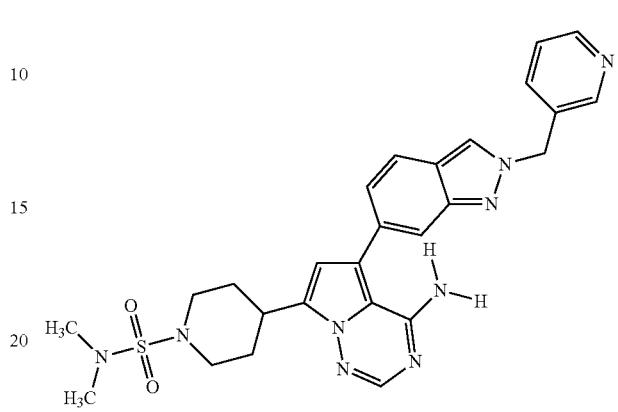

In a manner similar to the procedure described for Example 369 and using 7-piperidin-4-yl-5-[2-(pyridin-3-ylmethyl)-2H-indazol-6-yl]pyrrolo[2,1-f][1,2,4]triazin-4-amine and substituting dimethylsulfomoyl chloride for 2-chloro-N,N-dimethylacetamide as starting materials, 50 mg (60%) of the desired product was isolated. $^1$H NMR (400 MHz, CD$_2$Cl$_2$) δ 8.58 (s, 1H) 8.32 (d, Hz, 1H) 7.72-7.88 (m, 4H) 7.42 (dd, 1H) 7.26 (dd, 1H) 6.64 (s, 1H) 5.71 (s, 2H) 3.82 (d, 1H) 3.31-3.41 (m, 1H) 3.05 (td, 2H) 3.87 (s, 6H) 3.19 (d, 2H) 1.78-1.90 (m, 2H). LC-MS [M+H]$^+$=532.3, RT=1.67 min.

Example 402

Preparation of 2-(4-{4-amino-5-[2-(pyridin-3-ylmethyl)-2H-indazol-6-yl]pyrrolo[2,1-f][1,2,4]triazin-7-yl}piperidin-1-yl)-N,N-dimethylacetamide

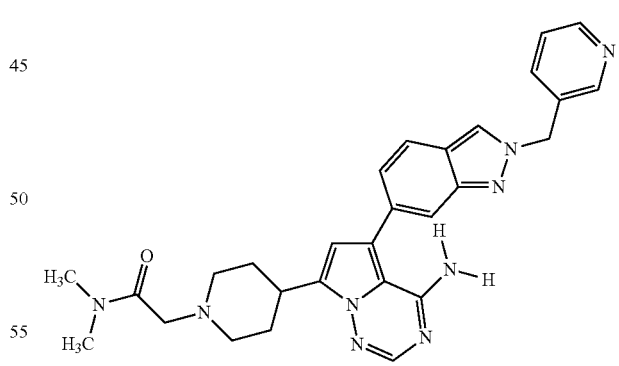

In a manner similar to the procedure described for Example 369 and using 7-piperidin-4-yl-5-[2-(pyridin-3-ylmethyl)-2H-indazol-6-yl]pyrrolo[2,1-f][1,2,4]triazin-4-amine as starting material, 60 mg (65%) of the desired product was isolated. $^1$H NMR (400 MHz, CD$_3$OD) δ 8.60 (s, 1 H) 8.48 (d, 1 H) 8.46 (s, 1 H) 7.78-7.81 (m, 3 H) 7.65 (s, 1 H) 7.44 (dd, 1 H) 7.25 (d, 1 H) 6.60 (s, 1 H) 5.74 (s, 2 H) 3.09-3.35 (m, 8 H) 2.94 (s, 3 H) 2.28 (d, 2 H) 2.06 (dd, 2 H) 1.86 (dt, 2 H). LC-MS [M+H]$^+$=510.3, RT=1.06 min.

Example 403

Preparation of 7-(1-acetylpiperidin-4-yl)-5-[2-(Pyridin-2-ylmethyl)-2H-Indazol-6-yl]pyrrolo[2,1-f][1,2,4]triazin-4-amine

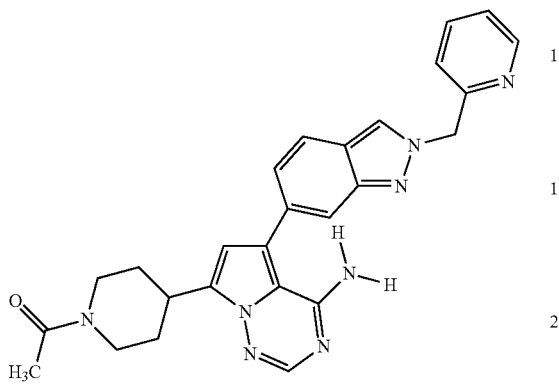

In a manner similar to the procedure described for Example 369 and using 7 7-piperidin-4-yl-5-[2-(pyridin-2-ylmethyl)-2H-indazol-6-yl]pyrrolo[2,1-f][1,2,4]triazin-4-amine and substituting acetyl chloride for 2-chloro-N,N-dimethylacetamide as starting materials, 43 mg (83%) of the desired product was isolated. $^1$H NMR (400 MHz, CD$_2$Cl$_2$) δ 8.58 (d, 1 H) 8.41 (s, 1 H) 7.65-7.81 (m, 3 H) 7.39 (s, 1 H) 7.19-7.26 (m, 3 H) 6.57 (s, 1 H) 5.78 (s, 2 H) 4.68 (d, 1 H) 4.02 (d, 1 H) 3.21-3.41 (m, 2 H) 2.76 (dd, 1 H) 2.01-2.19 (m, 5 H) 1.87 (dt, 2 H) LC-MS [M+H]$^+$=467.4, RT=2.07 min.

Example 404

Preparation of 7-[1-(methylsulfonyl)piperidin-4-yl]-5-[2-(pyridin-2-ylmethyl)-2H-indazol-6-yl]pyrrolo[2,1-f][1,2,4]triazin-4-amine

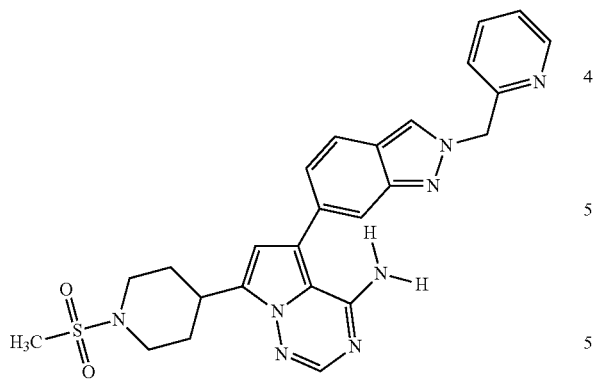

In a manner similar to the procedure described for Example 369 and using 7 7-piperidin-4-yl-5-[2-(pyridin-2-ylmethyl)-2H-indazol-6-yl]pyrrolo[2,1-f][1,2,4]triazin-4-amine and substituting methane sulfonyl chloride for 2-chloro-N,N-dimethylacetamide as starting materials, 30 mg (46%) of the desired product was isolated. $^1$H NMR (400 MHz, CD$_2$Cl$_2$) δ 8.57 (d, 1 H) 8.21 (s, 1 H) 7.83 (s, 1 H) 7.65-7.76 (m, 3 H) 7.19-7.26 (m, 3 H) 6.57 (s, 1 H) 5.72 (s, 2 H) 3.85 (d, 2 H) 3.34 (m, 1 H) 2.85-2.96 (m, 5 H) 2.26 (dd, 2 H) 1.87 (dt, 2 H). LC-MS [M+H]$^+$=503.3, RT=226 min.

Example 405

Preparation of 4-{4-amino-5-[2-(pyridin-2-ylmethyl)-2H-indazol-6-yl]pyrrolo[1,2-f][1,2,4]triazin-7-yl}-N,N-dimethylpiperidine-1-carboxamide

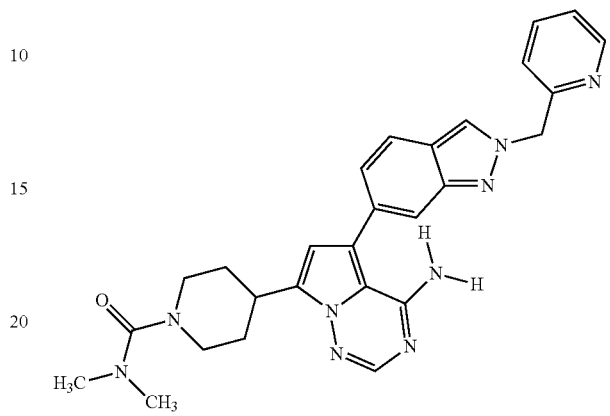

In a manner similar to the procedure described for Example 369 and using 7-piperidin-4-yl-5-[2-(pyridin-2-ylmethyl)-2H-indazol-6-yl]pyrrolo[2,1-f][1,2,4]triazin-4-amine and substituting dimethylcarbamyl chloride for 2-chloro-N,N-dimethylacetamide as starting materials, 50 mg (69%) of the desired product was isolated. $^1$H NMR (400 MHz, CD$_3$OD) δ 8.57 (s, 1 H) 8.49 (d, 1 H) 8.43 (s, 1 H) 7.75-7.80 (m, 3 H) 7.63 (s, 1 H) 7.42 (dd, 1 H) 7.21 (d, 1 H) 6.56 (s, 1 H) 5.71 (s, 2 H) 3.76 (d, 2 H) 3.34 (m, 1 H) 2.94 (dd, 2 H) 2.84 (s, 6 H) 2.06 (dd, 2 H) 1.73 (dt, 2 H). LC-MS [M+H]$^+$=496.2, RT=2.26 min.

Example 406

Preparation of 2-(4-{4-amino-5-[2-(pyridin-2-ylmethyl)-2H-indazol-6-yl]pyrrolo[2,1-f][1,2,4]triazin-7-yl}piperidin-1-yl)-N,N-dimethylacetamide

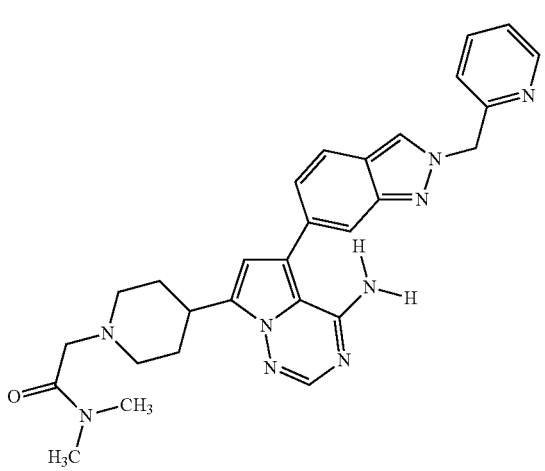 [SMILES: CN(C)C(=O)CN1CCC(c2cc(-c3ccc4cn(Cc5ccccn5)nc4c3)c3c(N)ncnn23)CC1]

In a manner similar to the procedure described for Example 369 and using 7 7-piperidin-4-yl-5-[2-(pyridin-2-ylmethyl)-2H-indazol-6-yl]pyrrolo[2,1-f][1,2,4]triazin-4-amine as starting material, 30 mg (36%) of the desired product was isolated. LC-MS [M+H]$^+$=510.3, RT=1.56 min.

Example 407

Preparation of 7-(1-acetylpiperidin-4-yl)-5-[2-(cyclohexylmethyl)-2H-indazol-6-yl]pyrrolo[2,1-f][1,2,4]triazin-4-amine

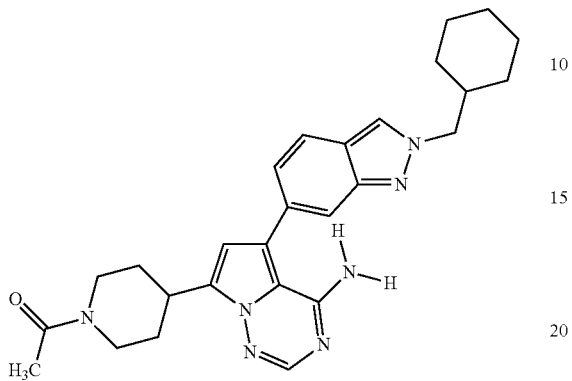

In a manner similar to the procedure described for Example 369 and using 5-[2-(cyclohexylmethyl)-2H-indazol-6-yl]-7-piperidin-4-ylpyrrolo[2,1-f][1,2,4]triazin-4-amine and substituting acetyl chloride for 2-chloro-N,N-dimethylacetamide as starting materials, 13 mg (16%) of the desired product was isolated. $^1$H NMR (400 MHz, CD$_3$OD) δ 8.25 (s, 1 H) 7.82 (s, 1 H) 7.80 (d, 1 H) 7.64 (d, 1 H) 7.21 (dd, 1 H) 6.60 (s, 1 H) 4.65 (dd, 1 H) 4.26-4.31 (m, 2 H) 4.04 (dd, 1 H) 3.50 (dt, 1 H) 3.27 (dd, 1 H) 2.80 (dd, 1 H) 2.12-222 (m, 6H) 1.67-1.77 (m, 7 H) 1.06-1.29 (m, 5 H). LC-MS [M+H]$^+$= 472.3, RT=2.66 min.

Example 408

Preparation of 7-(1-acetylpiperidin-4-yl)-5-[2-(cyclohexylmethyl)-2H-indazol-6-yl]pyrrolo[2,1-f][1,2,4]triazin-4-amine

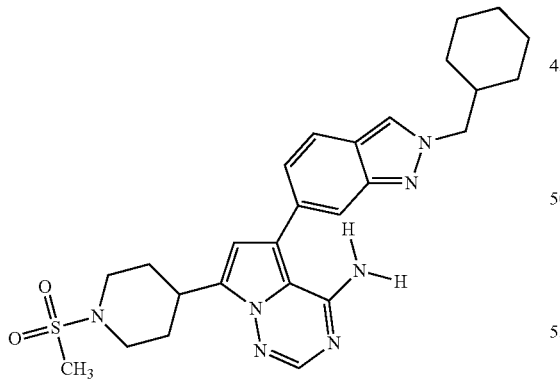

In a manner similar to the procedure described for Example 369 and using 5-[2-(cyclohexylmethyl)-2H-indazol-6-yl]-7-piperidin-4-ylpyrrolo[2,1-f][1,2,4]triazin-4-amine and substituting methane sulfonyl chloride for 2-chloro-N,N-dimethylacetamide as starting materials, 11 mg (16%) of the desired product was isolated. $^1$H NMR (400 MHz, CD$_3$OD) δ 8.25 (s, 1 H) 7.79-7.84 (m, 2 H) 7.65 (s, 1 H) 7.23 (d, 1 H) 6.63 (s, 1 H) 4.29 (d, 2 H) 3.85 (d, 2 H) 3.35-3.40 (m, 1 H) 2.94 (td, 2 H) 2.88 (s, 3 H) 1.58-2.24 (m, 10 H) 1.07-1.30 (m, 5 H). LC-MS [M+H]$^+$=508.3, RT=2.86 min.

Example 409

Preparation of 4-{4-amino-5-[2-(cyclohexylmethyl)-2H-indazol-6-yl]pyrrolo[2,1-f][1,2,4]triazin-7-yl}-N,N-dimethylpiperidine-1-carboxamide

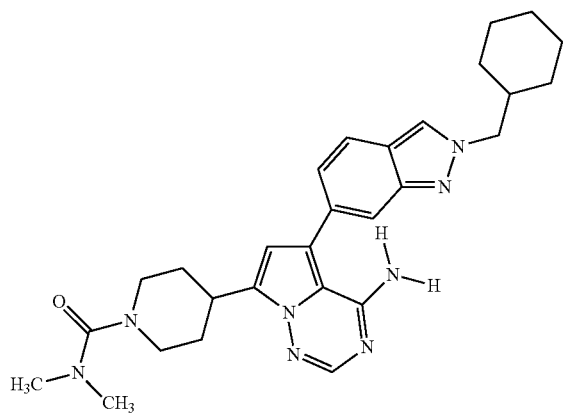 [SMILES: CN(C)C(=O)N1CCC(c2cc(-c3ccc4cn(CC5CCCCC5)nc4c3)c3c(N)ncnn23)CC1]

In a manner similar to the procedure described for Example 369 and using 5-[2-(cyclohexylmethyl)-2H-indazol-6-yl]-7-piperidin-4-ylpyrrolo[2,1-f][1,2,4]triazin-4-amine and substituting dimethylcarbamyl chloride for 2-chloro-N,N-dimethylacetamide as starting materials, 21 mg (31%) of the desired product was isolated. $^1$H NMR (400 MHz, CD$_3$OD) δ 8.25 (s, 1 H) 7.79-7.83 (m, 2 H) 7.65 (s, 1 H) 7.21 (d, 1 H) 6.60 (s, 1 H) 4.28 (d, 2 H) 3.83 (d, 2 H) 3.36-3.41 (m, 1 H) 2.97 (td, 2 H) 2.87 (s, 6 H) 1.99-2.16 (m, 3 H) 1.58-1.85 (m, 7 H) 1.04-1.27 (m, 5 H). LC-MS [M+H]$^+$=501.6, RT=3.04 min.

Example 410

Preparation of 4-{4-amino-5-[2-(cyclohexylmethyl)-2H-indazol-6-yl]pyrrolo[2,1-f][1,2,4]triazin-7-yl}-N,N-dimethylpiperidine-1-sulfonamide

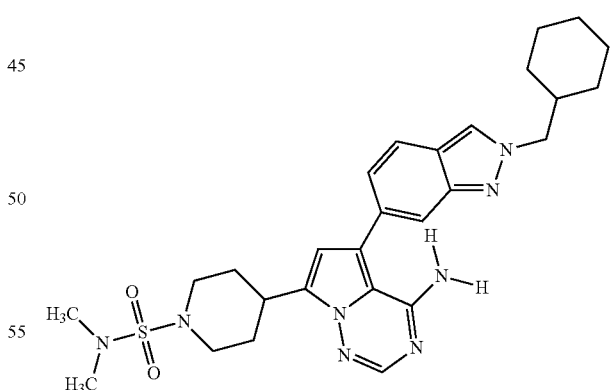

In a manner similar to the procedure described for Example 369 and using 5-[2-(cyclohexylmethyl)-2H-indazol-6-yl]-7-piperidin-4-ylpyrrolo[2,1-f][1,2,4]triazin-4-amine and substituting dimethylsulfomoyl chloride for 2-chloro-N,N-dimethylacetamide as starting materials, 10 mg (16%) of the desired product was isolated. $^1$H NMR (400 MHz, CD$_3$OD) δ 8.11 (s, 1 H) 7.79-7.83 (m, 2 H) 7.62 (s, 1 H) 7.22 (d, 1 H) 6.61 (s, 1 H) 4.27 (d, 2 H) 3.81 (d, 2 H) 3.31-3.45 (m, 1 H) 3.05 (td, 2 H) 2.84 (s, 6 H) 1.99-2.16 (m, 3 H) 1.58-1.85 (m, 7 H)

1.04-1.31 (m, 5 H). LC-MS [M+H]⁺=501.6, RT=3.04 min. LC-MS [M+H]⁺=537.3, RT=2.93 min.

Example 411

Preparation of 2-(4-{4-amino-5-[2-(cyclohexylmethyl)-2H-indazol-6-yl]pyrrolo[2,1-f][1,2,4]triazin-7-yl}piperidin-1-yl)-N,N-dimethylacetamide

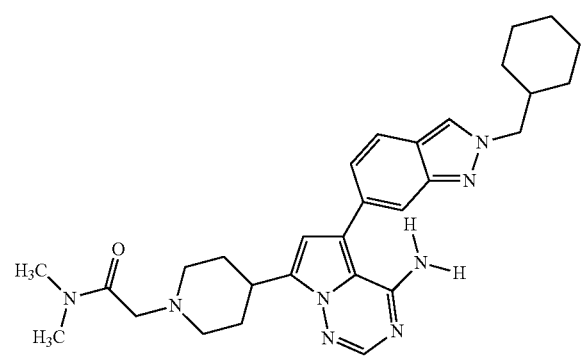 [SMILES: CN(C)C(=O)CN1CCC(c2cc(-c3ccc4cn(CC5CCCCC5)nc4c3)c3c(N)ncnn23)CC1]

In a manner similar to the procedure described for Example 369 and using 5-[2-(cyclohexylmethyl)-2H-indazol-6-yl]-7-piperidin-4-ylpyrrolo[2,1-f][1,2,4]triazin-4-amine as starting material, 10 mg, (14%) of the desired product was isolated. ¹H NMR (400 MHz, CD₃OD) δ p8.26 (s, 1 H) 7.79-7.83 (m, 2 H) 7.65 (s, 1 H) 7.24 (d, 1 H) 6.62 (s, 1 H) 4.30 (d, 2 H) 2.94-3.31 (m, 10 H) 1.58-2.31 (m, 12 H) 1.04-1.31 (m, 6 H). LC-MS [M+H]⁺=501.6, RT=3.04 min. LC-MS [M+H]⁺=515.3, RT=2.26 min.

Example 412

Preparation of 7-(1-acetylpiperidin-4-yl)-5-[2-(cyclobutylmethyl)-2H-indazol-6-yl]pyrrolo[2,1-f][1,2,4]triazin-4-amine

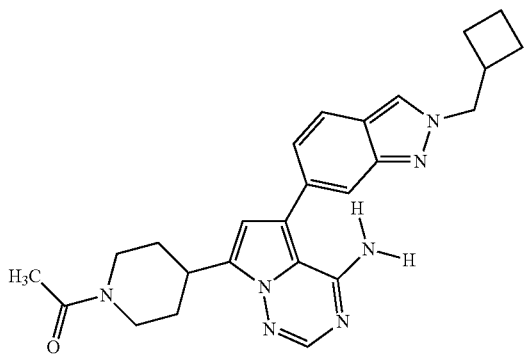 [SMILES: CC(=O)N1CCC(c2cc(-c3ccc4cn(CC5CCC5)nc4c3)c3c(N)ncnn23)CC1]

In a manner similar to the procedure described for Example 369 and using 5-[2-(cyclobutylmethyl)-2H-indazol-6-yl]-7-piperidin-4-ylpyrrolo[2,1-f][1,2,4]triazin-4-amine and substituting acetyl chloride for 2-chloro-N,N-dimethylacetamide as starting materials, 48 mg, (62%) of the desired product was isolated. LC-MS [M+H]⁺=444.3, RT=2.37 min.

Example 413

Preparation of 5-[2-(cyclobutylmethyl)-2H-indazol-6-yl]-7-[1-(methylsulfonyl)piperidin-4-yl]pyrrolo[2,1-f][1,2,4]triazin-4-amine

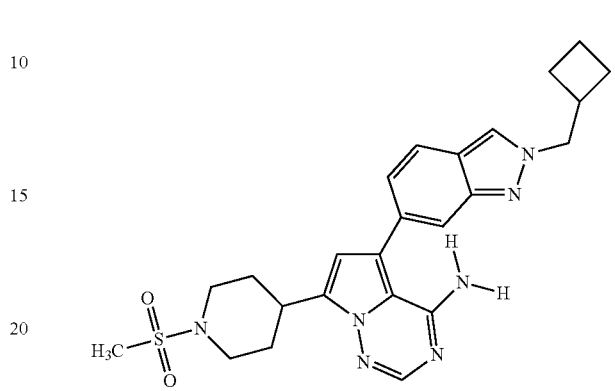

In a manner similar to the procedure described for the preparation of Example 369 and substituting methane sulfonyl chloride for 2-chloro-N,N-dimethylacetamide using 5-[2-(cyclobutylmethyl)-2H-indazol-6-yl]-7-piperidin-4-ylpyrrolo[2,1-f][1,2,4]triazin-4 amine as starting materials, 61 mg (73%) of the desired product was isolated. LC-MS [M+H]⁺=480.3, RT=2.59 min.

Example 414

Preparation of 4-{4-amino-5-[2-(cyclobutylmethyl)-2H-indazol-6-yl]pyrrolo[2,1-f][1,2,4]triazin-7-yl}-N,N-dimethylpiperidine-1-carboxamide

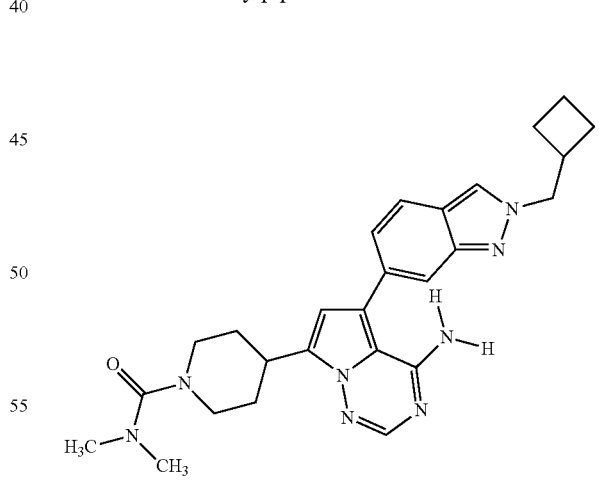

In a manner similar to the procedure described for Example 369 and using 5-[2-(cyclobutylmethyl)-2H-indazol-6-yl]-7-piperidin-4-ylpyrrolo[2,1-f][1,2,4]triazin-4-amine and substituting dimethylcarbamyl chloride for 2-chloro-N,N-dimethylacetamide as starting materials, 60 mg, (85%) of the desired product was isolated. LC-MS [M+H]⁺=473.3, RT=2.55 min.

Example 415

Preparation of 4-{4-amino-5-[2-(cyclobutylmethyl)-2H-indazol-6-yl]pyrrolo[2,1-f][1,2,4]triazin-7-yl}-N,N-dimethylpiperidine-1-carboxamide

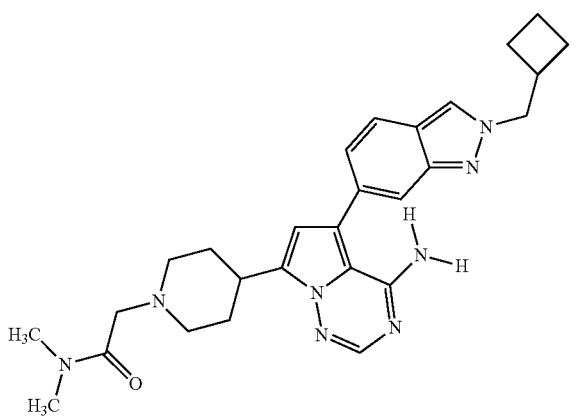 [SMILES: CN(C)C(=O)CN1CCC(c2cc(-c3ccc4cn(CC5CCC5)nc4c3)c3c(N)ncnn23)CC1]

In a manner similar to the procedure described for Example 369 and using 5-[2-(cyclobutylmethyl)-2H-indazol-6-yl]-7-piperidin-4-ylpyrrolo[2,1-f][1,2,4]triazin-4-amine as starting material, 38 mg, (55%) of the desired product was isolated. LC-MS [M+h]$^+$=487.3, RT=1.96 min.

Example 416

Preparation of 3-(2-benzyl-2H-indazol-5-yl)-7-{[4-(trifluoroacetyl)piperazin-1-yl]methyl}pyrrolo[2,1-f][1,2,4]triazin-4-amine

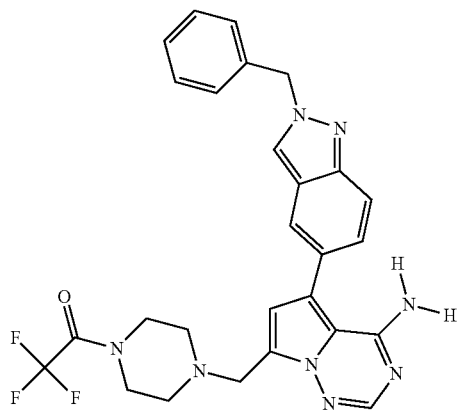 [SMILES: Nc1ncnn2c(CN3CCN(C(=O)C(F)(F)F)CC3)cc(-c3ccc4nn(Cc5ccccc5)cc4c3)c12]

Step 1: Preparation of 5-bromo-1H-indazole

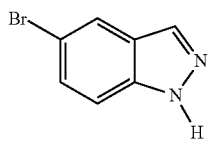

To an orange solution of 5-bromo-2-fluorobenzaldehyde (3.0 g, 14.78 mmol) in n-butanol (6 mL) was added hydrazine hydrate (11.1 g, 10.78 mL, 221.66 mmol) and the thick orange slurry was heated to 125° C. (became clear at 65° C.) in an oil bath for 21 h and cooled to rt. The mixture was poured into water (100 mL) and ethyl acetate (300 mL). The aqueous layer was isolated and extracted with ethyl acetate (100 mL). The combined organics were washed with brine, dried over Na$_2$SO$_4$ and concentrated. The product was isolated by column chromatography (33% ethyl acetate in hexanes) as a cream colored solid (0.86 g, 30%). LC-MS [M+H]$^+$=197.1, RT=2.64 min.

Step 2: Preparation of 2-benzyl-5-bromo-2H-indazole

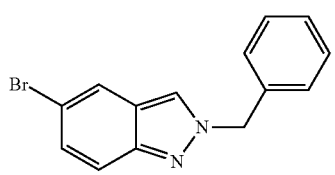 [SMILES: Brc1ccc2nn(Cc3ccccc3)cc2c1]

A mixture of 5-bromo-1H-indazole (5.0 g, 25.38 mmol) and benzyl bromide (5.4 g, 30.45 mmol) in 1,4-dioxane (30 mL) was heated to reflux for 18 h and cooled to room temperature. The slurry was diluted with cold 1,4-dioxane and filtered. The filter cake was washed with cold 1,4-dioxane, followed by cold ether. The filter cake was taken up in DCM/water mixture, followed by the slow addition of solid NaHCO$_3$. The mixture was stirred until the aqueous layer was basic. The organic layer was isolated, washed with brine and dried over Na$_2$SO$_4$ and concentrated. The product (5.57 g, 76%) was Isolated using an ISCO® instrument and using a gradient of 0-65% ethyl acetate in hexanes. LC-MS [M+H]$^+$=288.0, RT=3.46 min.

Step 3: Preparation of 2-benzyl-5-(4,4,5,5-tetramethyl-1,3,2-dioxaborolan-2-yl)-2H-indazole

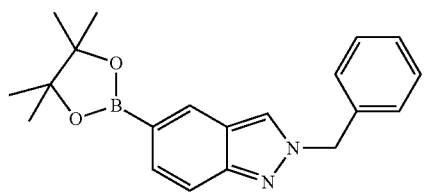 [SMILES: CC1(C)OB(c2ccc3nn(Cc4ccccc4)cc3c2)OC1(C)C]

A solution of 2-benzyl-5-bromo-2H-indazole (0.60 g, 2.09 mmol), bis(pinacolato)-diboron (0.64 g, 2.51 mmol) and KOAc (0.62 g, 6.27 mmol) in 1,4-dioxane (10 mL) was degassed for 5 min, then 1,1'-bis(diphenylphosphino)ferrocenepalladium(11) chloride-complex with CH$_2$Cl$_2$ (0.05 g, 0.063 mmol) was added and the mixture further degassed for 5 min. The mixture was heated to 85° C. for 3 h and cooled to rt. The mixture was diluted with ethyl acetate and filtered through Celite® and the filtrate was concentrated. The residue was passed through a pad of silica gel and eluted with 25% ethyl acetate in hexanes. The desired fractions were concentrated to give the product as a white waxy solid (0.60 g, 86%). LC-MS [M+H]$^+$=335.2, RT=3.76 min.

Step 4: Preparation of 1-(trifluoroacetyl)piperazine

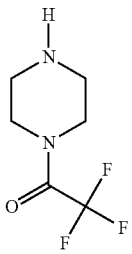

Ethyl trifluoroacetate (34.54 mL, 287.33 mmol) was added to a suspension of piperazine (25.0 g, 287.33 mmol) in THF (250 mL) at room temperature under nitrogen and stirred for 30 min and concentrated to remove solvent. The oily residue was taken up in ether and filtered and the filter cake was washed with ether. The filtrate was concentrated to give a clear oil (24.37 g, 47%). LC-MS [M+H]$^+$=183.1, RT=1.07 min.

Step 5: Preparation of 7-{[4-(trifluoroacetyl)piperazin-1-yl]methyl}pyrrolo[2,1-f][1,2,4]triazin-4-amine

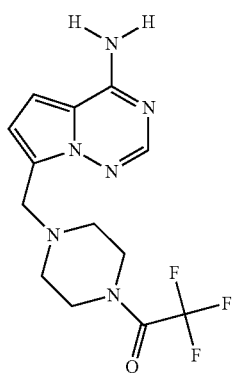 [SMILES: Nc1ncnn2c(CN3CCN(C(=O)C(F)(F)F)CC3)ccc12]

In a manner similar to the procedure described for step 1 of Example 83 and using 1-(trifluoroacetyl)piperazine as starting material, 1.44 g, (48%) of the desired product was isolated. LC-MS [M+H]$^+$=329.0, RT=1.10 min.

Step 6: Preparation of 5-bromo-7-{[4-(trifluoroacetyl)piperazin-1-yl]methyl}pyrrolo[2,1-f][1,2,4]triazin-4-amine

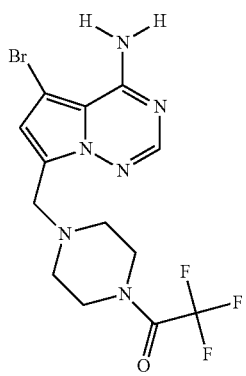 [SMILES: Nc1ncnn2c(CN3CCN(C(=O)C(F)(F)F)CC3)cc(Br)c12]

In a manner similar to the procedure described for step 2 of Example 83 and using 7-{[4-(trifluoroacetyl)piperazin-1-yl]methyl}pyrrolo[2,1-f][1,2,4]triazin-4-amine as starting material, 1.24 g, (65%) of the desired product was isolated. LC-MS [M+H]$^+$=408.0=1.61 min.

Step 7: Preparation of the Title Compound

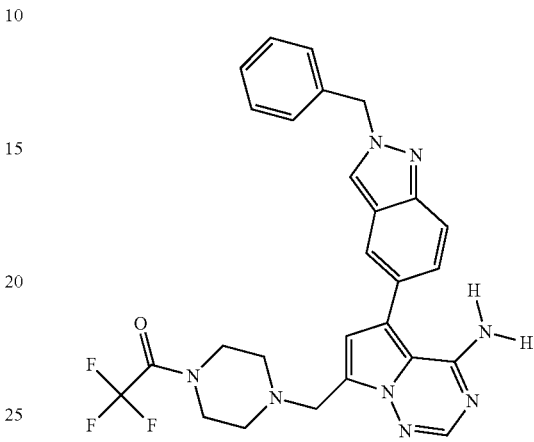

In a manner similar to the procedure described for step 3 of Example 83 and using 5-bromo-7-{[4-(trifluoroacetyl)piperazin-1-yl]methyl}pyrrolo[2,1-f][1,2,4]triazin-4-amine and 2-benzyl-5-(4,4,5,5-tetramethyl-1,3,2-dioxaborolan-2-yl)-2H-indazole as starting materials, 14 mg, (11%) of the desired product was isolated. $^1$H NMR (400 MHz, CD$_2$Cl$_2$) δ 8.05 (s, 1 H) 7.89 (s, 1 H) 7.73-7.81 (m, 2 H) 7.33-7.44 (m, 6 H) 6.68 (s, 1 H) 5.63 (s, 4 H) 4.01 (s, 2 H) 3.59-3.71 (m, 4 H) 2.64 (td, 2.24 Hz, 4 H). LC-MS [M+H]$^+$=5.35.1, RT=2.50 min.

Example 417

Preparation of 5-(2-benzyl-2H-indazol-6-yl)-7-{[4-(trifluoroacetyl)piperazin-1-yl]methyl}pyrrolo[2,1-f][1,2,4]triazin-4-amine

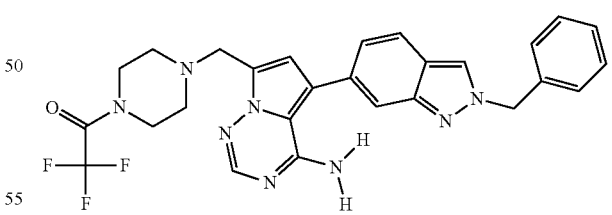

In a manner similar to the procedure described for step 3 of Example 83 and using 5-bromo-7-{[4-(trifluoroacetyl)piperazin-1-yl]methyl}pyrrolo[2,1-f][1,2,4]triazin-4-amine and 2-benzyl-6-(4,4,5,5-tetramethyl-1,3,2-dioxaborolan-2-yl)-2H-indazole as starting materials, 14 mg, (11%) of the desired product was isolated. $^1$H NMR (400 MHz, CD$_2$Cl$_2$) δ 8.05 (s, 1 H) 7.89 (s, 1 H) 7.74-7.81 (m, 2 H) 7.32-7.42 (m, 5 H) 7.24 (dd, 1 H) 6.71 (s, 1 H) 5.80 (br, 2 H) 5.62 (s, 2 H), 4.00 (s, 2 H) 3.59-3.71 (m, 4 H) 2.59-2.69 (m, 4 H). LC-MS [M+H]$^+$=535.2, RT=2.51 min

Example 418

Preparation of 5-(2-benzyl-2H-indazol-6-yl)-7-(piperazin-1-ylmethyl)pyrrolo[2,1-f][1,2,4]triazin-4-amine

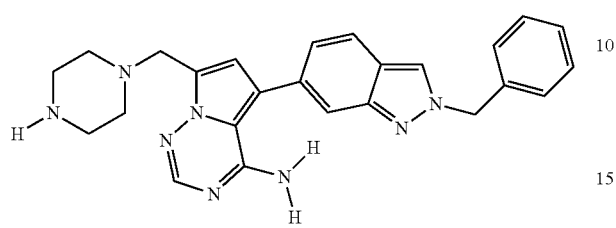

Method A

To a solution of 5-(2-benzyl-2H-indazol-6-yl)-7-{[4-(trifluoroacetyl)piperazin-1-yl]methyl}pyrrolo[2,1-f][1,2,4]triazin-4-amine (0.045 g, 0.084 mmol) in THF (1 mL) was added a mixture of methanol (1 mL) and 6% aqueous KOH (0.5 mL) and the mixture stirred at rt for 18 h and concentrated. The residue purified on the HPLC (10 to 90% $CH_3CN$) as methanol solution; 33 mg (89%). $^1$H NMR (400 MHz, $CD_2Cl_2$) δ 8.04 (s, 1 H) 7.89 (s, 1 H) 7.74-7.80 (m, 2 H) 7.34-7.41 (m, 5 H) 7.19-7.28 (m, 1 H) 6.70 (s, 1 H) 5.79 (br, 2 H) 5.62 (s, 2 H) 3.88-3.94 (m, 2 H) 2.81-2.88 (m, 4 H) 2.51 (s, 4 H). LC-MS [M+H]$^+$=439.0, RT=2.07 min Method B To a stirred solution of 5-(2-benzyl-2H-indazol-6-yl)-7-{[4-(trifluoroacetyl)piperazin-1-yl]methyl}pyrrolo[2,1-f][1,2,4]triazin-4-amine (0.47 g, 0.88 mmol) in $CH_3CN$ (14 ml) was added sodium iodide (0.52 g, 3.47 mmol) then chlorotrimethylsilane (0.38 g, 3.47 mmol). The mixture stirred at rt for 12 h. Saturated, aqueous solution of $K_2CO_3$ (5 mL) was added and stirring was continued for 1 h. The mixture was diluted with ethyl acetate (100 mL) and the layers separated. The organic layer was dried over $K_2CO_3$ and concentrated to give a yellow, foamy solid (0.3 g, 79%). LC-MS [M+H]$^+$=439.0, RT=2.07 min,

Example 419

Preparation of tert-butyl 4-{[4-amino-5-(2-benzyl-2H-indazol-6-yl)pyrrolo[2,1-f][1,2,4]triazin-7-yl]methyl}piperazine-1-carboxylate

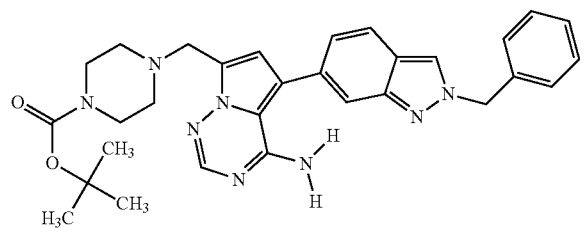 [SMILES: CC(C)(C)OC(=O)N1CCN(Cc2cc(-c3ccc4cn(Cc5ccccc5)nc4c3)c3c(N)ncnn23)CC1]

Step 1: Preparation of 7-(piperazin-1-ylmethyl)pyrrolo[2,1-f][1,2,4]triazin-4-amine

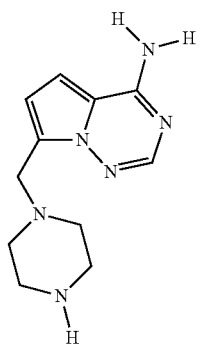 [SMILES: Nc1ncnn2c(CN3CCNCC3)ccc12]

In a manner similar to the procedure described for method A above and using 7-{[4-(trifluoroacetyl)piperazin-1-yl]methyl}pyrrolo[2,1-f][1,2,4]triazin-4-amine as starting materials, 850 mg, (100%) of the desired product was isolated. LC-MS [M+H]$^+$=233.1, RT=1.04 min

Step 2: Preparation of tert-butyl 4-[(4-aminopyrrolo[2,1-f][1,2,4]triazin-7-yl)methyl]piperazine-1-carboxylate

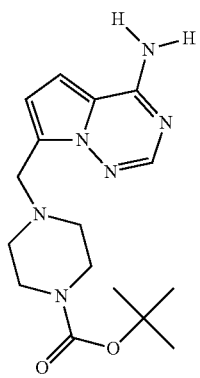 [SMILES: CC(C)(C)OC(=O)N1CCN(Cc2ccc3c(N)ncnn23)CC1]

To a cooled (0° C.) solution of 7-(piperazin-1-ylmethyl)pyrrolo[2,1-f][1,2,4]triazin-4-amine (0.85 g, 3.66 mmol) and triethylamine (0.56 mL, 4.03 mmol) in THF (8.5 mL)/DCM (8.5 mL) was added iii-tert-butyl dicarbonate (0.88 g, 4.03 mmol) and the mixture was allowed to warm to rt and further stirred for 18 h and concentrated. The residue was taken up in ethyl acetate, washed with water and dried over $Na_2SO_4$ and concentrated (used in the next step without further purification). LC-MS [M+H]$^+$=332.8, RT=1.17 min

Step 3: Preparation of tert-butyl 4[(4-amino-5-bromopyrrolo[2,1-f][1,2,4]triazin-7-yl)methyl]piperazine-1-carboxylate

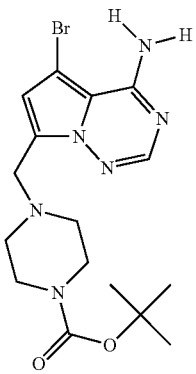 [SMILES: CC(C)(C)OC(=O)N1CCN(Cc2cc(Br)c3c(N)ncnn23)CC1]

In a manner similar to the procedure described for the preparation of Example 4, step 6, and using tert-butyl 4-[(4-aminopyrrolo[2,1-f][1,2,4]triazin-7-yl)methyl]piperazine-1-carboxylate as starting material, 0.60 g, (53%) of the desired product was isolated. LC-MS [M+]$^+$=410.7, RT=1.90 ml

Step 4: Preparation of the Title Compound

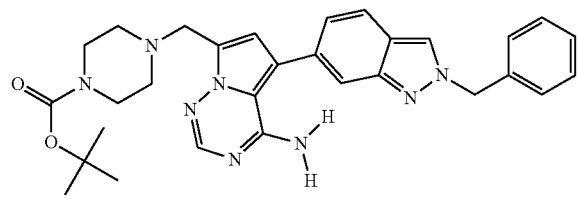 [SMILES: CC(C)(C)OC(=O)N1CCN(Cc2cc(-c3ccc4cn(Cc5ccccc5)nc4c3)c3c(N)ncnn23)CC1]

In a manner similar to the procedure described for step 3 of Example 83 and using tort-butyl 4-[(4-amino-5-bromopyrrolo[2,1-f][1,2,4]triazin-7-yl)methyl]piperazine-1-carboxylate and 2-benzyl-6-(4,4,5,5-tetramethyl-1,3,2-dioxaborolan-2-yl)-2H-indazole as starting materials, 520 mg, (66%) of the desired product was isolated. $^1$H NMR (400 MHz, CD$_2$Cl$_2$) δ 8.06 (s, 1 H) 7.95 (s, 1 H) 7.74-7.81 (m, 2 H) 7.32-7.42 (m, 5 H) 7.24 (dd, 1 H) 6.71 (s, 1 H) 5.63 (s, 2 H) 3.91-3.96 (m, 2 H), 3.44-339 (m, 4 H) 2.46-2.54 (m, 4 H) 1.44 (s, 9 H). LC-MS [M+H]$^+$=438.7, RT=2.42 min

Example 420

Preparation of 5-(2-ethyl-2H-indazol-6-yl)-7-piperidin-4-ylpyrrolo[2,1-f][1,2,4]triazin-4-amine

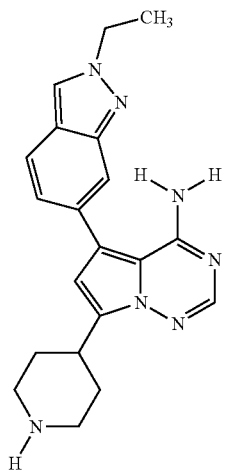 [SMILES: CCn1cc2ccc(-c3cc(C4CCNCC4)n4ncnc(N)c34)cc2n1]

Step 1: Preparation of 6-(4,4,5,5-tetramethyl-1,3,2-dioxaborolan-2-yl)-1H-Indazole

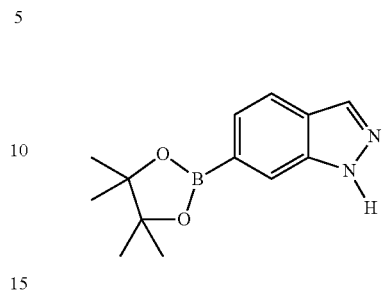

A solution of 6-bromo-1H-indazole (3.0 g, 15.23 mmol), bis(pinacolato)-diboron (5.80 g, 22.84 mmol) and KOAc (8.97 g, 91.35 mmol) in DME (75 mL) was degassed for 5 min, then 1,11-Bis(diphenylphosphino)ferrocenepalladium (11) chloride-complex with CH$_2$Cl$_2$ (0.37 g, 0.457 mmol) was added and the mixture further degassed for 5 min. The mixture was heated to 85° C. for 18 h and cooled to rt. The mixture was diluted with ethyl acetate and filtered through Celite®. The filtrate was washed successively with water and brine, dried over Na$_2$SO$_4$ and concentrated. The residue was purified using an ISCO® instrument using 0-25% ethyl acetate in hexanes. The desired fractions were concentrated to give the product as an off-white waxy solid (2.89 g, 78%). LC-MS [M+H]$^+$=245.2, RT=3.18 min.

Step 2: Preparation of 2-ethyl-6-(4,4,5,5-tetramethyl-1,3,2-dioxaborolan-2-yl)-2H-indazole

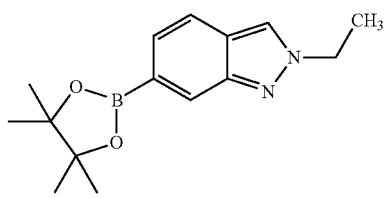 [SMILES: CCn1cc2ccc(B3OC(C)(C)C(C)(C)O3)cc2n1]

To a solution of 6-(4,4,5,5-tetramethyl-1,3,2-dioxaborolan-2-yl)-1H-indazole (0.63 g, 2.56 mmol) in ethyl acetate (7.5 mL) was added triethyloxonium tetrafluoroborate (0.65 g, 3.33 mmol). The mixture was stirred at rt for 5 h under nitrogen (turned to a white suspension after about 0.5 h). The mixture was diluted with ethyl acetate (50 mL) and washed with saturated, aqueous sodium bicarbonate (50 mL). The aqueous layer was extracted with ethyl acetate (2×50 mL), the combined organic layers were dried over MgSO$_4$, filtered and concentrated. The crude purified using an ISCO® instrument using 0-40% ethyl acetate in hexanes. LC-MS [M+H]$^+$= 2732, RT=3.27 min.

Step 3: tert-butyl 4-[4-amino-5-(2-ethyl-2H-indazol-6-yl)pyrrolo[2,1-f][1,2,4]triazin-7-yl]piperidine-1-carboxylate

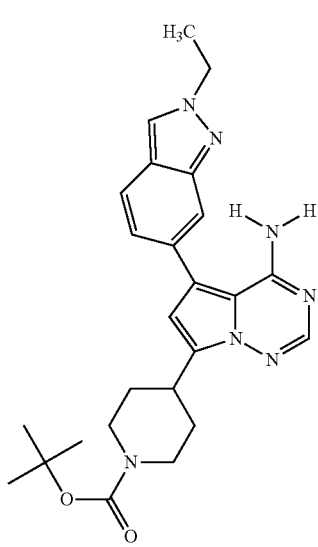 [SMILES: CCn1cc2ccc(-c3cc(C4CCN(C(=O)OC(C)(C)C)CC4)n4ncnc(N)c34)cc2n1]

In a manner similar to the procedure described for step 3 of Example 83 and using 2-ethyl-6-(4,4,5,5-tetramethyl-1,3,2-dioxaborolan-2-yl)-2H-indazole as starting material, 81 mg, (72%) of the desired product was isolated. LC-MS [M+H]$^+$= 462.2, RT=2.84 min.

Step 4: Preparation of the Title Compound

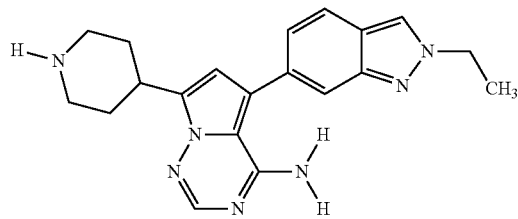 [SMILES: CCn1cc2ccc(-c3cc(C4CCNCC4)n4ncnc(N)c34)cc2n1]

In a manner similar to the procedure described for Example 380 and using tert-butyl 4-[4-amino-5-(2-ethyl-2H-indazol-6-yl)pyrrolo[2,1-f][1,2,4]triazin-7-yl]piperidine-1-carboxylate as the starting material, 30 mg (52%) of the desired product was isolated. $^1$H NMR (400 MHz, CD$_3$OD) δ 8.30 (m, 1 H) 7.80-7.83 (m, 2H) 7.23-35 (m, 2 H) 6:61 (s, 1H) 4.53 (q, 2 H) 3.56 (m, 1 H) 3.25 (d, 2 H) 2.90 (m, 2 H) 2.15 (d, 2 H) 1.66-1.74 (m, 2 H) 1.62 (t, 3H). LC-MS [M+H]$^+$=362.2, RT=0.26 min Example 421

Preparation of the 5-(2-methyl-2H-indazol-6-yl)-7-piperidin-4-ylpyrrolo[2,1-f][1,2,4]triazin-4-amine

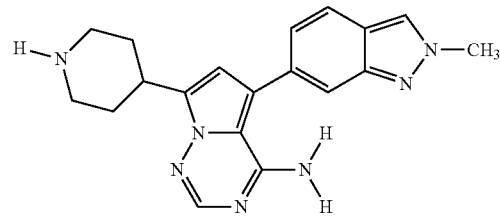 [SMILES: Cn1cc2ccc(-c3cc(C4CCNCC4)n4ncnc(N)c34)cc2n1]

In a manner similar to the procedure described for Example 380 and using tert-butyl 4-[4-amino-5-(2-methyl-2H-indazol-6-yl)pyrrolo[2,1-f][1,2,4]triazin-7-yl]piperidine-1-carboxylate as the starting material, 23 mg (42%) of the desired product was isolated. $^1$H NMR (400 MHz, CD$_3$OD) δ 8.15 (s, 1 H) 7.81 (s, 1 H) 7.78 (dd, 1 H) 7.66 (q, 1 H) 7.22 (dd, 1 H) 6.58 (s, 1 H) 4.22 (s, 3 H) 3.33-3.42 (m, 1 H) 3.13-3.21 (m, 2 H) 2.82 (td, 2 H) 2.13 (d, 2 H) 1.66-1.77 (m, 2 H) LC-MS [M+H]$^+$=348.2, RT=1.20 min Example 422

Preparation of 5-(2-benzyl-1H-benzimidazol-6-yl)-7-piperidin-4-ylpyrrolo[2,1-f][1,2,4]triazin-4-amine

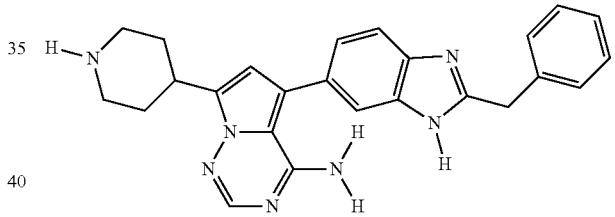

Step 1: tert-butyl 4-[4-amino-5-(2-benzyl-1H-benzimidazol-6-yl)pyrrolo[2,1-f][1,2,4]triazin-7-yl]piperidine-1-carboxylate

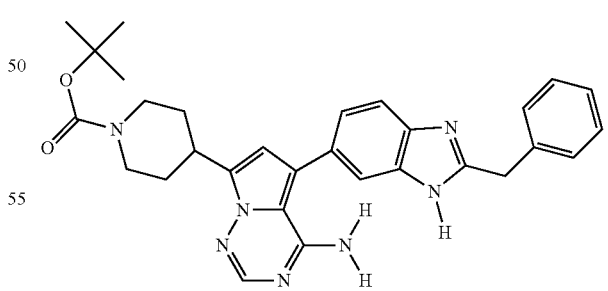

In a manner similar to the procedure described for step 3 of Example 83 and using 2-benzyl-1-methyl-6-(4,4,5,5-tetramethyl-1,3,2-dioxaborolan-2-yl)-1H-benzimidazole as starting material, 210 mg, (32%) of the desired product was isolated. $^1$H NMR (400 MHz, CD$_2$Cl$_2$) δ ppm 7.85 (s, 1 H) 7.57 (s, 2 H) 7.27-7.37 (m, 6 H) 6.49 (s, 1 H) 5.48 (br, 2 H) 4.31 (s, 2 H) 4.22 (s, 2 H) 3.39 (m, 1 H) 2.91 (m, 2 H) 2.10 (d, 2 H) 1.66 (m, 2 H) 1.47 (s, 9 H). LC-MS [M+H]$^+$=524.2, RT=2.54 min.

Step 2: Preparation of the Title Compound

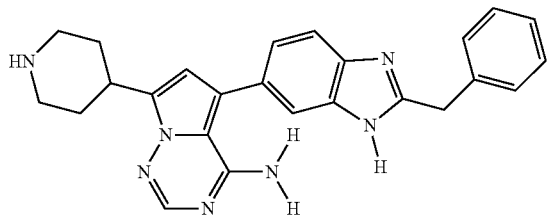 [SMILES: Nc1ncnn2c(C3CCNCC3)cc(-c3ccc4nc(Cc5ccccc5)[nH]c4c3)c12]

In a manner similar to the procedure described for Example 380 and using tert-butyl 4-[4-amino-5-(2-benzyl-1H-benzimidazol-6-yl)pyrrolo[2,1-f][1,2,4]triazin-7-yl]piperidine-1-carboxylate as the starting material, 90 mg (53%) of the desired product was isolated. $^1$H NMR (400 MHz, CD$_3$OD) δ 7.78 (s, 1 H) 7.53-7.62 (m, 2 H) 7.21-7.35 (m, 6 H) 6.45 (s, 1 H) 4.23-4.28 (m, 2 H) 3.38 (m, 1 H) 3.11-3.19 (m, 2 H) 2.79 (td, 2 H)) 2.10 (s, 1 H) 1.98-2.06 (m, 1 H) 1.71 (qd, 2 H). LC-MS [M+H]$^+$=424.2, RT=1.11 min Example 423

Preparation of tert-butyl 4-[4-amino-5-(2-benzyl-1-methyl-1H-benzimidazol-5-yl)pyrrolo[2,1-f][1,2,4]triazin-7-yl]piperidine-1-carboxylate

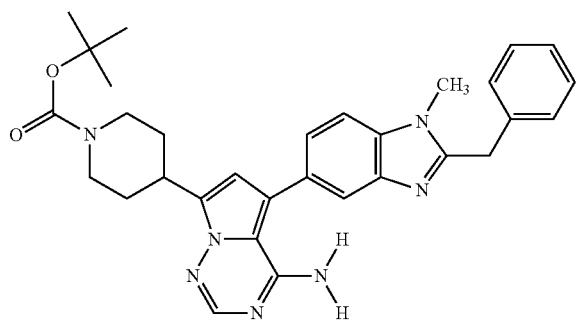 [SMILES: Cn1c(Cc2ccccc2)nc2cc(-c3cc(C4CCN(C(=O)OC(C)(C)C)CC4)n4ncnc(N)c34)ccc21]

In a manner similar to the procedure described for step 3 of Example 83 and using 2-benzyl-1-methyl-5-(4,4,5,5-tetramethyl-1,3,2-dioxaborolan-2-yl)-1H-benzimidazole as starting material, 190 mg, (34%) of the desired product was isolated. $^1$H NMR (400 MHz, CD$_2$Cl$_2$) δ ppm 7.88 (s, 11-1) 7.76 (d, 1 H) 7.32-7.42 (m, 5 H) 7.25-7.30 (m, 2 H) 6.52 (s, 1 H) 5.42 (s, 2 H) 4.34 (s, 2 H) 4.23 (s, 2 H) 3.67 (s, 3 H) 3.40 (m, 1 H) 2.92 (s, 2 H) 2.11 (s, 2 H) 1.68-1.65° (m 2 H) 1.48 (s, 9 H). LC-MS [M+H]$^+$=537.9, RT=2.47 min.

Example 424

Preparation of 5-(2-benzyl-1-methyl-1H-benzimidazol-6-yl)-7-piperidin-4-ylpyrrolo[2,1-f][1,2,4]triazin-4-amine

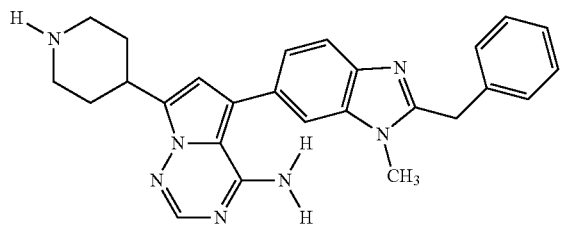 [SMILES: Cn1c(Cc2ccccc2)nc2ccc(-c3cc(C4CCNCC4)n4ncnc(N)c34)cc21]

In a manner similar to the procedure described for step 3 of Example 83 and using tert-butyl 4-[4-amino-5-(2-benzyl-1-methyl-1H-benzimidazol-6-yl)pyrrolo[2,1-f][1,2,4]triazin-7-yl]piperidine-1-carboxylate as the starting material, 90 mg (53%) of the desired product was isolated. $^1$H NMR (400 MHz, CD$_3$OD) δ 7.85 (s, 1 H) 7.75 (d, 1 H) 7.49-7.55 (m, 1 H) 7.24-7.40 (m, 6 H) 6.60-6.62 (m, 1 H) 4.39 (s, 2 H) 3.71 (s, 3 H) 3.49-3.60 (m, 3 H) 3.19 (td, 2 H) 2.38 (d, 2 H) 1.98-2.10 (m, 2 H) LC-MS [M+H]$^+$=438.2, RT=1.22 min Example 425

Preparation of 5-(2-benzyl-1-methyl-1H-benzimidazol-5-yl)-7-piperidin-4-ylpyrrolo[2,1-f][1,2,4]triazin-4-amine

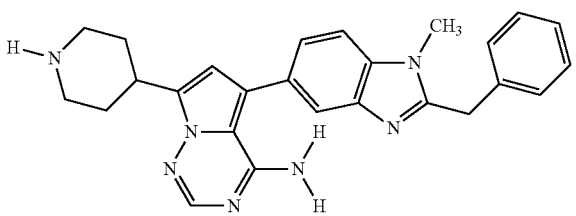 [SMILES: Cn1c(Cc2ccccc2)nc2cc(-c3cc(C4CCNCC4)n4ncnc(N)c34)ccc21]

In a manner similar to the procedure described for Example 380 and using tert-butyl 4-[4-amino-5-(2-benzyl-1-methyl-1H-benzimidazol-5-yl)pyrrolo[2,1-f][1,2,4]triazin-7-yl]piperidine-1-carboxylate as the starting material, 90 mg (53%) of the desired product was isolated. NMR (400 MHz, CD$_3$OD) δ 7.81 (s, 1 H) 7.53-7.62 (m, 2 H) 7.21-7.35 (m, 6 H) 6.45 (s, 1 H) 4.23-4.28 (m, 2 H) 3.67 (s, 3 H) 3.38 (m, 1 H) 3.11-3.19 (m, 2 H) 2.79 (td, 2 H)) 2.10 (s 1 H) 1.98-2.06 (m, 1 H) 1.71 (qd, 2 H). LC-MS [M+H]$^+$=438.0, RT=1.19 min.

Example 426

Preparation of 5-(2-benzyl-2H-indazol-5-yl)-7-(4-pyrrolidin-1-ylbutyl)pyrrolo[2,1-f][1,2,4]triazin-4-amine

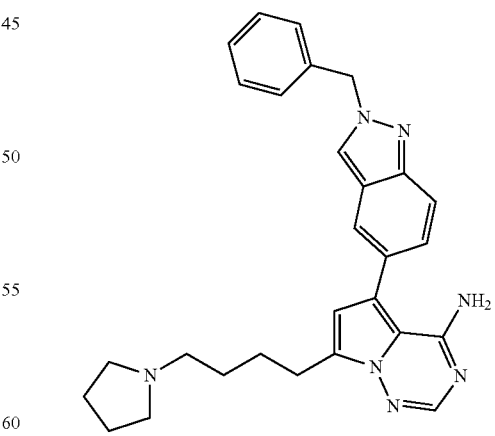

In a manner similar to the procedure described for the preparation of Example 17 and using 5-(2-benzyl-2H-indazol-5-yl)-7-(4-bromobutyl)pyrrolo[2,1-f][1,2,4]triazin-4-amine as starting material, 43 mg (44%) of the desired product was isolated. NMR (400 MHz, CD$_2$Cl$_2$) δ 8.03 (d, 1 H), 7.86 (s, 1 H), 7.71-7.79 (m, 2 H), 7.32-7.43 (m, 6 H), 6.55 (s, 1 H), 5.62 (s, 2 H), 2.95-3.02 (m, 2 H), 2.43-2.51 (m, 6 H), 1.72-1.83 (m, 6 H), 1.62 (qd, 2 H). LC-MS [M+H]$^+$=466.1, RT=2.11 min Example 427

5-(2-benzyl-2H-indazol-5-yl)-7-(4-morpholin-4-ylbutyl)pyrrolo[2,1-f][1,2,4]triazin-4-amine

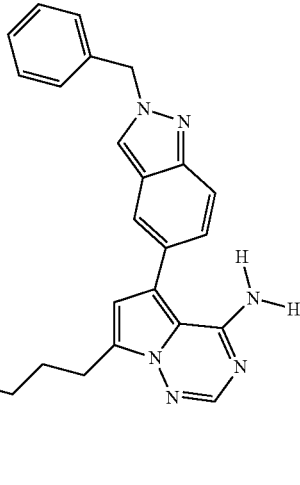

In a manner similar to the procedure described for the preparation of Example 17 and using 5-(2-benzyl-2H-indazol-5-yl)-7-(4-bromobutyl)pyrrolo[2,1-f][1,2,4]triazin-4-amine as starting material, 78 mg (77%) of the desired product was isolated. $^1$H NMR (400 MHz, CD$_2$Cl$_2$) δ 8.03 (d, 1 H), 7.77-7.84 (m, 2 H), 7.66-7.73 (m, 1 H), 7.32-7.44 (m, 6 H), 6.54 (s, 1 H), 5.62 (s, 2 H), 3.61-3.68 (m, 4 H), 2.95-3.01 (m, 2H), 2.33-2.43 (m, 6H), 1.76-1.85 (m, 2 H), 1.55-1.64 (m, 2 H). LC-MS [M+H]$^+$=482.1, RT=2.04 min Example 428

Preparation of 5-(2-Benzyl-2H-indazol-6-yl)-7-[4-(1,4-dioxa-8-aza-spiro[4.5]dec-8-yl)-butyl]-pyrrolo[2,1-f][1,2,4]triazin-4-ylamine

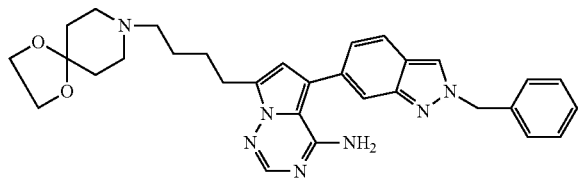 [SMILES: Nc1ncnn2c(CCCCN3CCC4(CC3)OCCO4)cc(-c3ccc4cn(Cc5ccccc5)nc4c3)c12]

1,4-Dioxa-8-azaspiro[4.5]decane (28.6 mg, 0.2 mmol, 2.0 eq), triethylamine (30.3 mg, 0.300 mmol, 3.0 eq), and sodium iodide (0.150 mg, 0.001 mmol, 0.01 eq) was added to a solution of 5-(2-benzyl-2H-indazol-6-O-7-(4-bromobutyl) pyrrolo[2,1-f][1,2,4]triazin-4-amine (47.5 mg, 0.1 mmol, 1 eq.) and 1.5 mL of anhydrous DMF. The reaction mixture was shaken at 55° C. for 17 h. The reaction was filtered and the filtrate was purified by basic HPLC (X-bridge 30×100 column; 10% ACN to 90% H$_2$O) to give 23.20 mg (43%) of desired product. $^1$H-NMR (DMSO-d$_6$) δ 8.53 (s, 2H), 7.88 (s, 4H), 7.58 (s, 3 H), 7.35 (s, 5 H), 7.15 (s, 2 H), 5.65 (s, 4 H), 3.83 (s, 3 H), 2.89 (s, 3 H), 2.33 (s, 1 H), 1.57 (s, 8 H); MS LC-MS [M+H]$^+$=538.3, RT=2.68 min.

Additional compounds illustrated below were prepared as described for the preparation of 5-(2-benzyl-2H-indazol-6-yl)-7-[4-(1,4-dioxa-8-aza-spiro[4.5]dec-8-yl)-butyl]-pyrrolo[2,1-f][1,2,4]triazin-4-ylamine by choosing the appropriate starting materials that are readily available and/or the synthesis of which is taught herein, and using the processes of method described above or other standard chemical processes known in the art. In some instances the NMR signals using flow NMR method are weaker in intensity, broadened, or absent due to solvent suppression.

Example 429

Preparation of 1-{4-[4-Amino-5-(2-benzyl-2H-indazol-6-yl]-pyrrolo[2,1-f][1,2,4]triazin-7-yl]-butyl}-piperidine-3-carboxylic acid diethylamide

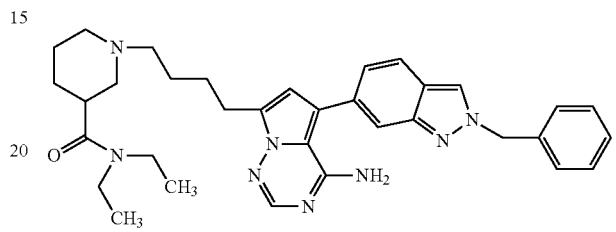

$^1$H-NMR (DMSO-d$_6$) δ 8.53 (s, 2 H) 7.87 (s, 2 H) 7.80 (d, J=8.31 Hz, 2 H) 7.58 (s, 2 H) 7.35 (s, 5 H) 7.14 (d, J=8.07 Hz, 2 H) 5.65 (s, 4 H) 2.89 (s, 3 H) 2.77 (s, 2 H) 1.59 (s, 2 H) 1.49 (s, 5 H) 1.32 (s, 2 H) 1.06 (s, 5 H) 0.95 (s, 3 H); MS LC-MS [M+H]$^+$=579.4, RT=2.72 min.

Example 430

Preparation of (1-{4-[4-amino-5-(2-benzyl-2H-indazol-6-yl)pyrrolo[2,1-f][1,2,4]triazin-7-yl] butyl}piperidin-2-yl)methanol

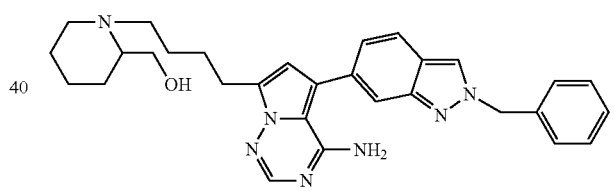

$^1$H NMR (400 MHz, DMSO-d$_6$) δ 8.53 (s, 2 H) 7.88 (s, 1 H) 7.80 (d, J=8.44 Hz, 2 H) 7.58 (s, 2 H) 7.35 (s, 5 H) 7.13 (s, 2 H) 5.65 (s, 3 H) 3.11 (s, 1 H) 2.88 (s, 3 H) 2.74 (s, 2 H) 1.59 (s, 2 H) 1.48 (s, 4 H) 1.32 (s, 1 H) 1.22 (s, 3 H); MS LC-MS [M+H]$^+$=510.3, RT=2.63 min.

Example 431

Preparation of 1-{4-[4-amino-5-(2-benzyl-2H-indazol-6-pyrrolo[2,1-f][1,2,4]triazin-7-yl] butyl}piperidin-3-yl)methanol

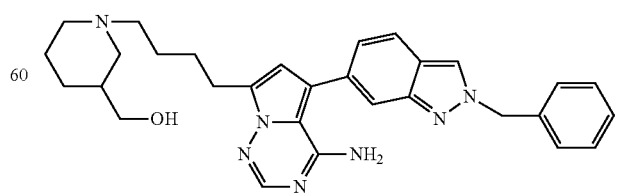

$^1$H NMR (400 MHz, DMSO-d$_6$) δ 7.76 (s, 2 H) 7.47 (s, 1 H) 7.31 (s, 2 H) 5.53 (s, 1 H) 3.47 (s, 18 H) 3.26-3.29 (m, 2 H)

2.76 (s, 1 H) 2.67 (s, 3 H) 1.67 (s, 1 H) 1.43 (s, 4 H); MS LC-MS [M+H]⁺=510.3, RT=2.61 min.

Example 432

Preparation of 1-{4-[4-amino-5-(2-benzyl-2H-indazol-6-yl)pyrrolo[2,1-f][1,2,4]triazin-7-yl]butyl}piperidin-3-ol

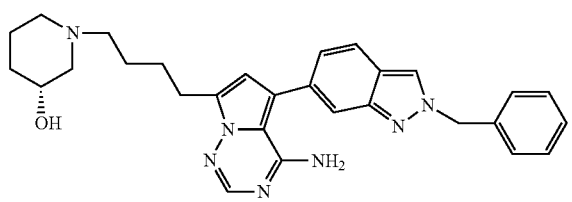 [SMILES: Nc1ncnn2c(CCCCN3CCC[C@@H](O)C3)cc(-c3ccc4cn(Cc5ccccc5)nc4c3)c12]

¹H NMR (400 MHz, DMSO-d₆) δ 8.53 (s, 2 H) 7.88 (s, 4 H) 7.58 (s, 3 H) 7.35 (s, 7 H) 5.65 (s, 3 H) 4.52 (s, 1 H) 3.58 (s, 1 H) 2.89 (s, 4 H) 1.37 (s, 8 H); MS LC-MS [M+H]⁺=496.3, RT=2.60 min.

Example 433

Preparation of 1-{4-[4-Amino-5-(2-benzyl-2H-indazol-6-yl)-pyrrolo[2,1-f][1,2,4]triazin-7-yl]-butyl}-piperidine-4-carboxylic acid methyl ester

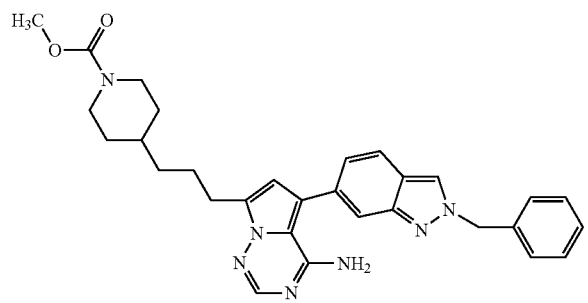 [SMILES: COC(=O)N1CCC(CCCc2cc(-c3ccc4cn(Cc5ccccc5)nc4c3)c3c(N)ncnn23)CC1]

¹H NMR (400 MHz, DMSO-d₆) δ 8.53 (s, 2 H) 7.88 (s, 2 H) 7.80 (d, J=8.44 Hz, 2 H) 7.58 (s, 2 H) 7.35 (s, 9 H) 5.65 (s, 4 H) 3.67 (s, 1 H) 2.88 (s, 5 H) 1.49 (s, 9 H); MS LC-MS [M+H]⁺=540.3, RT=2.67 min.

Example 434

Preparation of 2-(1-{4-[4-amino-5-(2-benzyl-2H-indazol-6-yl)pyrrolo[2,1-f][1,2,4]triazin-7-yl]butyl}piperidin-4-yl)ethanol

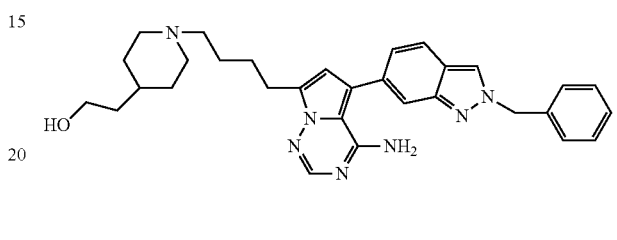

¹H NMR (400 MHz, DMSO-d₆) δ 8.53 (s, 2 H) 7.88 (s, 2 H) 7.80 (d, J=8.19 Hz, 2 H) 7.58 (s, 2 H) 7.35 (s, 5 H) 7.14 (d, J=8.44 Hz, 2 H) 5.65 (s, 3 H) 4.27 (s, 1 H) 2.88 (s, 3 H) 2.78 (s, 2 H) 1.78 (s, 1 H) 1.56 (s, 2 H) 1.49 (s, 3 H) 1.31 (s, 5 H) 1.08 (s, 3 H); MS LC-MS [M+H]⁺=524.3, RT=2.61 min.

Example 435

Preparation of 1-{4-[4-amino-5-(2-benzyl-2H-indazol-6-yl)pyrrolo[2,1-f][1,2,4]triazin-7-yl]butyl}piperidin-4-ol

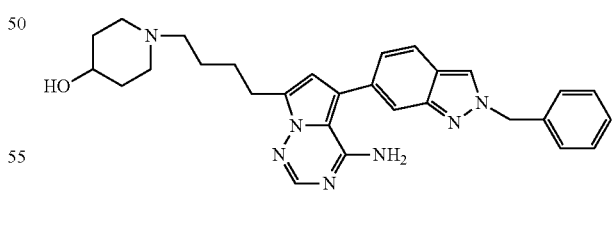

¹H NMR (400 MHz, DMSO-d₆) δ. 8.53 (s, 2 H) 7.88 (s, 4 H) 7.58 (s, 3 H) 7.35 (s, 7 H) 5.65 (s, 4 H) 4.46 (s, 1 H) 3.70 (s, 2 H) 2.85 (s, 3 H) 1.92 (s, 1 H) 1.41 (s, 7 H); MS LC-MS [M+H]⁺=496.3, RT=2.59 min.

Example 436

Preparation of 1-{4-[4-amino-5-(2-benzyl-2H-indazol-6-yl)pyrrolo[2,1-f][1,2,4]triazin-7-yl]butyl}piperidine-4-carboxamide

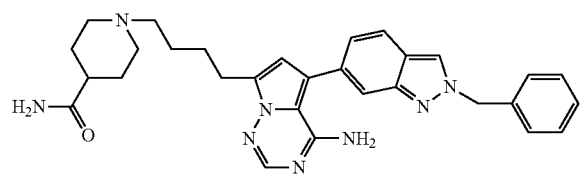 [SMILES: NC(=O)C1CCN(CCCCc2cc(-c3ccc4cn(Cc5ccccc5)nc4c3)c3c(N)ncnn23)CC1]

¹H NMR (400 MHz, DMSO-d₆) δ 8.53 (s, 2 H) 7.88 (s, 1 H) 7.80 (d, J=8.44 Hz, 2 H) 7.58 (s, 2 H) 7.35 (s, 4 H) 7.15 (s, 3 H) 6.65 (s, 1 H) 5.65 (s, 3 H) 3.26 (s, 4 H) 2.89 (s, 4 H) 2.01 (s, 1 H) 1.81 (s, 2 H) 1.62 (s, 1 H) 1.51 (s, 4 H); MS LC-MS [M+H]⁺=523.3, RT=2.61 min.)

Example 437

Preparation of 5-(2-benzyl-2H-indazol-6-yl)-7-[4-(3-methylpiperidin-1-yl)butyl]pyrrolo[2,1-f][1,1,2,4]triazin-4-amine

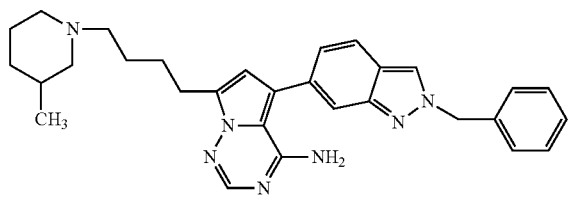 [SMILES: CC1CCCN(CCCCc2cc(-c3ccc4cn(Cc5ccccc5)nc4c3)c3c(N)ncnn23)C1]

¹H NMR (400 MHz, DMSO-d₆) δ 8.53 (s, 2 H) 7.88 (s, 2 H) 7.79 (s, 2 H) 7.58 (s, 2 H) 7.35 (s, 4 H) 7.15 (s, 2 H) 5.65 (s, 3 H) 2.89 (s, 4 H) 1.49 (s, 9 H) 0.79 (d, J=5.26 Hz, 5 H); MS LC-MS [M+H]⁺=494.3, RT=2.69 min.

Example 438

Preparation of 5-(2-benzyl-2H-indazol-6-yl)-7-[4-(4-methylpiperidin-1-yl)butyl]pyrrolo[2,1-f][1,2,4]triazin-4-amine

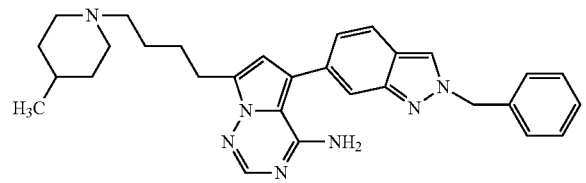 [SMILES: CC1CCN(CCCCc2cc(-c3ccc4cn(Cc5ccccc5)nc4c3)c3c(N)ncnn23)CC1]

¹H NMR (400 MHz, DMSO-d₆) δ 8.58 (s, 2 H) 7.35 (s, 12 H) 5.65 (s, 3 H) 3.59 (s, 2 H) 2.82 (s, 4 H) 1.29 (s, 10 H) 0.73 (s, 1 H); MS LC-MS [M+H]⁺=494.3, RT=2.68 min.

Example 439

Preparation of 5-(2-benzyl-2H-indazol-6-yl)-7-[4-(3,5-dimethylpiperidin-1-yl)butyl]pyrrolo[2,1-f][1,2,4]triazin-4-amine

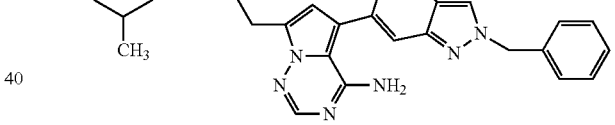

¹H NMR (400 MHz, DMSO-d₆) δ 8.53 (s, 2 H) 7.88 (s, 3 H) 7.58 (s, 2 H) 7.35 (s, 6 H) 5.65 (s, 3 H) 2.89 (s, 4 H) 1.51 (s, 8 H) 0.77 (d, J=6.11 Hz, 9 H); MS LC-MS [M+H]⁺=508.3, RT=2.75 min.

Example 440

Preparation of 5-(2-benzyl-2H-indazol-6-yl)-7-{4-[(2-piperidin-1-ylethyl)amino]butyl}pyrrolo[2,1-f][1,2,4]triazin-4-amine

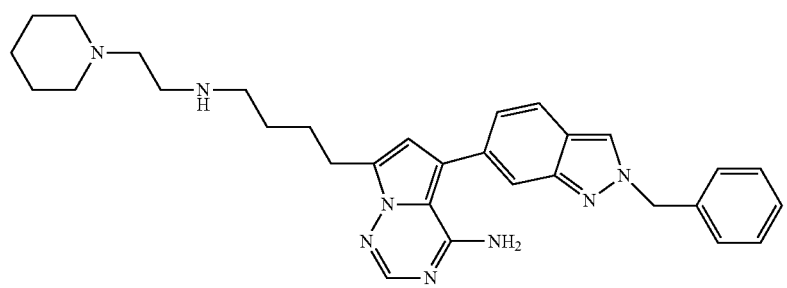 [SMILES: Nc1ncnn2c(CCCCNCCN3CCCCC3)cc(-c3ccc4cn(Cc5ccccc5)nc4c3)c12]

$^1$H NMR (400 MHz, DMSO-d$_6$) δ 8.53 (s, 2 H) 7.88 (s, 4 H) 7.58 (s, 3 H) 7.35 (s, 8 H) 5.65 (s, 4 H) 3.63 (s, 1 H) 2.88 (s, 3 H) 2.26 (s, 1 H) 1.43 (s, 13 H); MS LC-MS [M+H]$^+$=523.3, RT=2.51 min.

Example 441

Preparation of 1-{4-[4-amino-5-(2-benzyl-2H-indazol-6-yl)pyrrolo[2,1-f][1,2,4]triazin-7-yl]butyl}piperidine-3-carboxamide

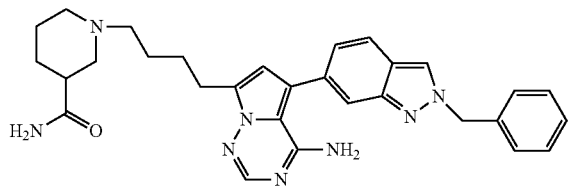 [SMILES: NC(=O)C1CCCN(CCCCc2cc(-c3ccc4cn(Cc5ccccc5)nc4c3)c3c(N)ncnn23)C1]

$^1$H NMR (400 MHz, DMSO-d$_6$) δ 8.53 (s, 2 H) 7.88 (s, 2 H) 7.80 (d, J=8.44 Hz, 2 H) 7.58 (s, 2 H) 7.35 (s, 7 H) 7.14 (d, J=8.44 Hz, 2 H) 6.71 (s, 2 H) 5.65 (s, 4 H) 2.89 (s, 3 H) 2.77 (s, 1 H) 1.94 (s, 1 H) 1.50 (s, 4 H) 1.39 (s, 1 H) 1.30 (s, 2 H); MS LC-MS [M+H]$^+$=523.3, RT=2.61 min.

Example 442

Preparation of 5-(2-benzyl-2H-indazol-6-yl)-7-[4-(4-pyrrolidin-1-ylpiperidin-1-yl)butyl]pyrrolo[2,1-f][1,2,4]triazin-4-amine

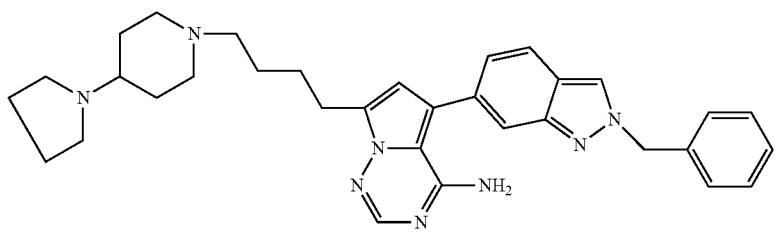 [SMILES: Nc1ncnn2c(CCCCN3CCC(N4CCCC4)CC3)cc(-c3ccc4cn(Cc5ccccc5)nc4c3)c12]

$^1$H NMR (400 MHz, DMSO-d$_6$) δ 8.53 (s, 2 H) 7.88 (s, 1 H) 7.81 (s, 2 H) 7.58 (s, 2 H) 7.35 (s, 6 H) 7.13 (s, 5 H) 5.65 (s, 4 H) 2.88 (s, 6 H) 1.63 (s, 5 H) 1.48 (s, 3 H) 1.33 (s, 4 H); MS LC-MS [M+H]$^+$=549.3, RT=2.50 min.

Example 443

Preparation of 5-(2-benzyl-2H-indazol-6-yl)-7-[4-(3-methoxypiperidin-1-yl)butyl]pyrrolo[2,1-f][1,2,4]triazin-4-amine $^1$H NMR (400 MHz, DMSO-d$_6$) δ 8.53 (s, 2 H) 7.88 (s, 2 H) 7.80 (d, J=8.44 Hz, 2 H) 7.58 (s, 3 H) 7.35 (s, 5 H) 7.14 (d, J=8.56 Hz, 2 H) 5.65 (s, 4 H) 3.63 (s, 1 H) 2.88 (d, J=4.89 Hz, 4 H) 1.50 (s, 9 H); MS LC-MS [M+H]$^+$=510.3, RT=2.63 min.

Example 444

Preparation of 5-(2-benzyl-2H-indazol-6-yl)-7-(4-thiomorpholin-4-ylbutyl)pyrrolo[2,1-f][1,2,4]triazin-4-amine $^1$H NMR (400 MHz, DMSO-d$_6$) δ 8.53 (s, 2 H) 7.88 (s, 2 H) 7.79 (s, 2 H) 7.58 (s, 3 H) 7.35 (s, 6 H) 7.15 (s, 2 H) 5.65 (s, 4 H) 3.62 (s, 1 H) 2.88 (s, 3 H) 2.31 (s, 1 H) 1.49 (s, 4 H); MS LC-MS [M+H]$^+$=498.2, RT=2.64 min.

Example 445

Preparation of 5-(2-benzyl-2H-indazol-6-yl)-7-[4-(4-pyrimidin-2-ylpiperazin-1-yl)butyl]pyrrolo[2,1-f][1,2,4]triazin-4-amine

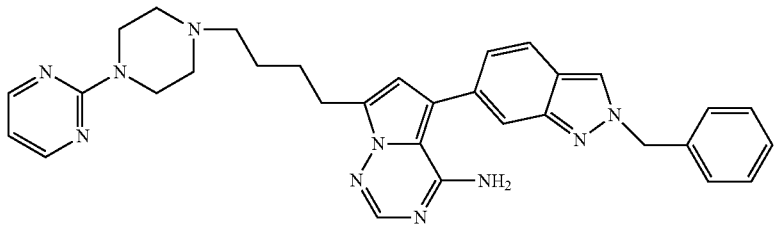 [SMILES: Nc1ncnn2c(CCCCN3CCN(c4ncccn4)CC3)cc(-c3ccc4cn(Cc5ccccc5)nc4c3)c12]

$^1$H NMR (400 MHz, DMSO-d$_6$) δ 8.53 (s, 2 H) 8.32 (d, J=4.03 Hz, 4 H) 7.89 (s, 4 H) 7.59 (s, 2 H) 7.35 (s, 7 H) 6.61 (s, 1 H) 5.65 (s, 3 H) 3.66 (s, 4 H) 2.87 (s, 2 H) 2.32 (s, 1 H) 1.51 (s, 3 H); MS LC-MS [M+H]$^+$=559.3, RT=2.65 min.

Example 446

Preparation of 5-(2-benzyl-2H-indazol-6-yl)-7-[4-(4-ethylpiperazin-1-yl)butyl]pyrrolo[2,1-f][1,2,4]triazin-4-amine

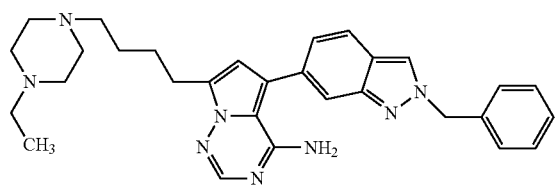 [SMILES: CCN1CCN(CCCCc2cc(-c3ccc4cn(Cc5ccccc5)nc4c3)c3c(N)ncnn23)CC1]

$^1$H NMR (400 MHz, DMSO-d$_6$) δ 8.53 (s, 2 H) 7.88 (s, 2 H) 7.80 (d, J=8.44 Hz, 2 H) 7.58 (s, 3 H) 7.35 (s, 7 H) 7.15 (s, 2 H) 5.65 (s, 4 H) 3.61 (s, 1 H) 2.89 (s, 3 H) 2.26 (s, 2 H) 1.49 (s, 3 H) 0.95 (s, 4 H); MS LC-MS [M+H]$^+$=509.3, RT=2.54 min.

Example 447

Preparation of 5-(2-benzyl-2H-indazol-6-yl)-7-(4-{4-[2-(methylsulfonyl)ethyl]piperazin-1-yl}butyl)pyrrolo[2,1-f][1,2,4]triazin-4-amine

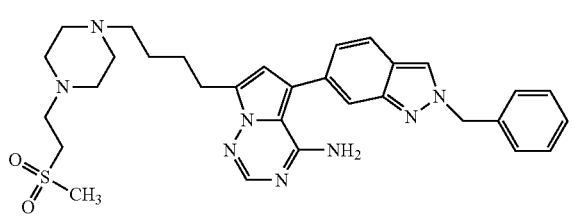 [SMILES: CS(=O)(=O)CCN1CCN(CCCCc2cc(-c3ccc4cn(Cc5ccccc5)nc4c3)c3c(N)ncnn23)CC1]

$^1$H NMR (400 MHz, DMSO-d$_6$) δ 8.53 (s, 2 H) 7.88 (s, 5 H) 7.58 (s, 3 H) 7.35 (s, 9 H) 5.65 (s, 4 H) 3.64 (s, 2 H) 3.00 (s, 4 H) 2.86 (s, 4 H) 2.30 (s, 1 H) 1.46 (s, 4 H); MS LC-MS [M+H]$^+$=587.3, RT=2.53 min.

Example 448

Preparation of 5-(2-benzyl-2H-indazol-6-yl)-7-{4-[(2R,6S)-2,6-dimethylmorpholin-4-yl]butyl}pyrrolo[2,1-f][1,2,4]triazin-4-amine

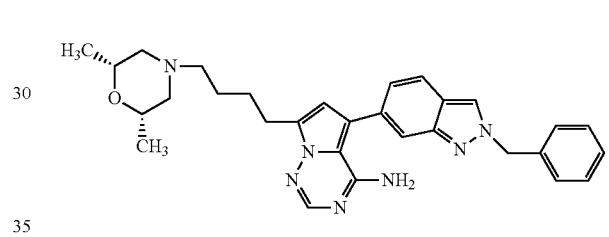

$^1$H NMR (400 MHz, DMSO-d$_6$) δ 8.53 (s, 2 H) 7.88 (s, 2 H) 7.80 (d, J=8.44 Hz, 2 H) 7.58 (s, 2 H) 7.35 (s, 5 H) 7.14 (d, J=8.31 Hz, 2 H) 5.65 (s, 3 H) 3.50 (s, 1 H) 2.89 (s, 3 H) 2.69 (s, 1 H) 1.51 (s, 5 H) 1.00 (d, J=5.62 Hz, 8 H); MS LC-MS [M+H]$^+$=510.3, RT=2.67 min.

Example 449

Preparation of 7-[4-(4-acetylpiperazin-1-yl)butyl]-5-(2-benzyl-2H-indazol-6-yl)pyrrolo[2,1-f][1,2,4]triazin-4-amine

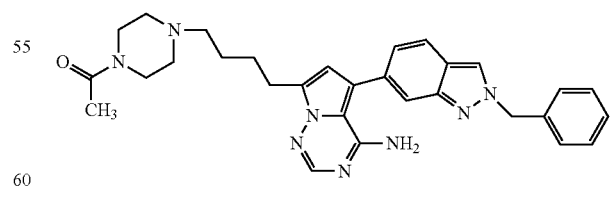

$^1$H NMR (400 MHz, DMSO-d$_6$) δ 8.54 (s, 2 H), 7.89 (s, 2 H), 7.80 (d, J=8.44 Hz, 2 H), 7.58 (s, 2 H), 7.35 (s, 6 H), 7.14 (d, J=8.19 Hz, 3 H), 5.65 (s, 4 H), 2.90 (s, 3 H), 2.31 (s, 3 H), 1.95 (s, 3 H), 1.51 (s, 3 H); MS LC-MS [M+H]$^+$=523.3, RT=2.60 min.

Example 450

Preparation of 5-(2-benzyl-2H-indazol-6-yl)-7-[4-(2-tert-butylpyrrolidin-1-yl)butyl]pyrrolo[2,1-f][1,2,4]triazin-4-amine

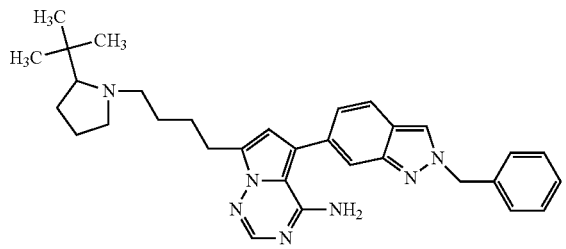 [SMILES: CC(C)(C)C1CCCN1CCCCc1cc(-c2ccc3cn(Cc4ccccc4)nc3c2)c2c(N)ncnn12]

$^1$H NMR (400 MHz, DMSO-d$_6$) δ 8.53 (s, 2 H) 7.88 (s, 2 H) 7.79 (s, 2 H) 7.58 (s, 2 H) 7.35 (s, 6 H) 7.15 (s, 2 H) 5.65 (s, 3 H) 2.89 (s, 4 H) 1.51 (s, 5 H) 0.79 (s, 11 H); MS LC-MS [M+H]$^+$=522.3, RT=2.74 min.

Example 451

Preparation of 5-(2-benzyl-2H-indazol-6-yl)-7-{4-[(3R)-3-(dimethylamino)pyrrolidin-1-yl]butyl}pyrrolo[2,1-f][1,2,4]triazin-4-amine

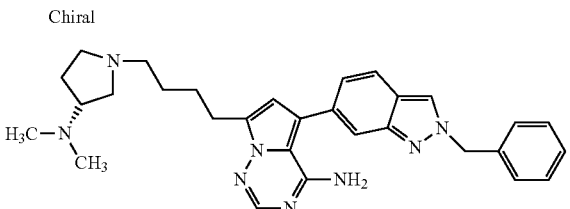

$^1$H NMR (400 MHz, DMSO-d$_6$) δ 8.54 (s, 2 H) 7.88 (s, 4 H) 7.58 (s, 3 H) 7.35 (s, 6 H) 7.14 (s, 2 H) 5.65 (s, 4 H) 3.65 (s, 1 H) 2.89 (d, J=1.34 Hz, 3 H) 2.06 (s, 8 H) 1.50 (s, 5 H); MS LC-MS [M+H]$^+$=509.3, RT=2.49 min.

Example 452

Preparation of 5-(2-benzyl-2H-indazol-6-yl)-7-{4-[ethyl(pyridin-4-ylmethyl)amino]butyl}pyrrolo[2,1-f][1,2,4]triazin-4-amine

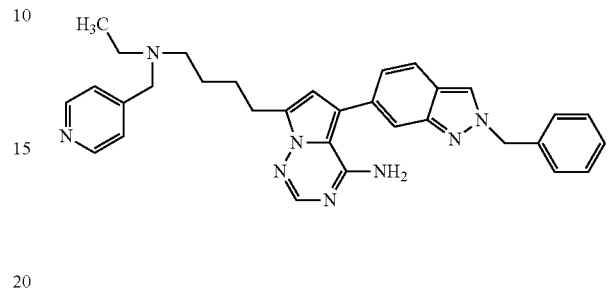

$^1$H NMR (400 MHz, DMSO-d$_6$) δ 8.54 (s, 5 H) 7.35 (s, 16 H) 5.65 (s, 3 H) 3.61 (s, 2 H) 2.86 (s, 2 H) 1.46 (s, 3 H) 0.95 (s, 3 H); MS LC-MS [M+H]$^+$=531.3, RT=2.58 min.

Example 453

Preparation of 5-(2-benzyl-2H-indazol-6-yl)-7-{4-[(1,3-dioxolan-2-ylmethyl)(methyl)amino]butyl}pyrrolo[2,1-f][1,2,4]triazin-4-amine

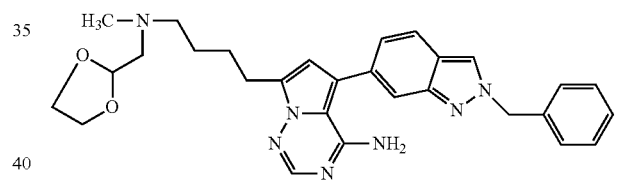

$^1$H NMR (400 MHz, DMSO-d$_6$) δ 8.53 (s, 2 H) 7.88 (s, 2 H) 7.80 (d, J=8.44 Hz, 2 H) 7.58 (s, 2 H) 7.35 (s, 6 H) 7.15 (s, 2 H) 5.65 (s, 4 H) 4.82 (s, 1 H) 3.83 (s, 1 H) 3.72 (s, 2 H) 2.88 (s, 3 H) 2.20 (s, 2 H) 1.47 (s, 3 H); MS LC-MS [M+H]$^+$= 512.3, RT=2.64 min.

Example 454

Preparation of 5-(2-benzyl-2H-indazol-6-yl)-7-{4-[[(1-isopropylpyrrolidin-3-yl)methyl](methy)amino]butyl}pyrrolo[2,1-f][1,2,4]triazin-4-amine

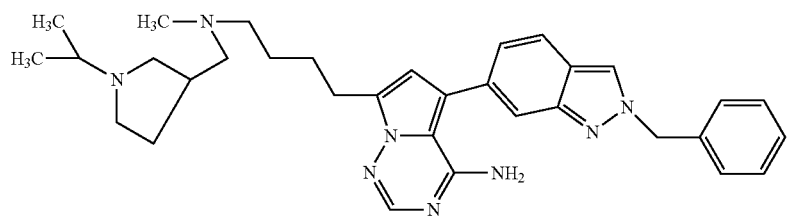 [SMILES: CC(C)N1CCC(CN(C)CCCCc2cc(-c3ccc4cn(Cc5ccccc5)nc4c3)c3c(N)ncnn23)C1]

¹H NMR (400 MHz, DMSO-d₆) δ 8.53 (s, 2 H) 7.88 (s, 4 H) 7.58 (s, 3 H) 7.35 (s, 8 H) 5.65 (s, 4 H) 3.66 (s, 2 H) 2.89 (s, 3 H) 2.09 (s, 5 H) 1.47 (s, 5 H) 0.95 (s, 5 H); MS LC-MS [M+H]⁺=551.3, RT=2.53 min.

Example 455

Preparation of 5-(2-benzyl-2H-indazol-6-yl)-7-{4-[methyl(1-methylpiperidin-4-yl)amino]butyl}pyrrolo[2,1-f][1,2,4]triazin-4-amine

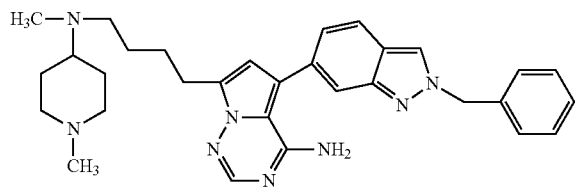 [SMILES: CN1CCC(N(C)CCCCc2cc(-c3ccc4cn(Cc5ccccc5)nc4c3)c3c(N)ncnn23)CC1]

¹H NMR (400 MHz, DMSO-d₆) δ 8.53 (s, 2 H) 7.88 (s, 3 H) 7.58 (s, 2 H) 7.35 (s, 7 H) 6.74 (s, 1 H) 5.65 (s, 3 H) 3.63 (s, 2 H) 2.87 (s, 2 H) 2.73 (s, 2 H) 2.08 (s, 4 H) 1.74 (s, 1 H) 1.38 (s, 8 H); MS LC-MS [M+H]⁺=523.3, RT=2.48 min.

Example 456

Preparation of 5-(2-benzyl-2H-indazol-6-yl)-7-[4-(5-ethyl-2-methylpiperidin-1-yl)butyl]pyrrolo[2,1-f][1,2,4]triazin-4-amine

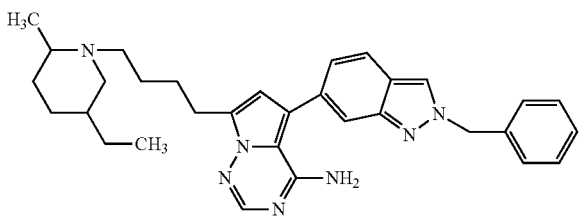 [SMILES: CCC1CCC(C)N(CCCCc2cc(-c3ccc4cn(Cc5ccccc5)nc4c3)c3c(N)ncnn23)C1]

¹H NMR (400 MHz, DMSO-d₆) δ 8.44 (s, 1 H) 7.79 (s, 3 H) 7.49 (s, 3 H) 7.26 (s, 3 H) 7.06 (s, 1 H) 5.56 (s, 2 H) 3.64 (s, 3 H) 3.30 (s, 2 H) 3.28 (d, J=1.59 Hz, 1 H) 2.80 (s, 2 H) 2.57 (s, 4 H) 1.37 (s, 5 H) 1.04 (s, 4 H) 0.89 (s, 2 H) 0.71 (s, 2 H); MS LC-MS [M+H]⁺=522.3, RT=2.77 min.

Example 457

Preparation of 5-(2-benzyl-2H-indazol-6-yl)-7-[4-(2-ethylpiperidin-1-yl)butyl]pyrrolo[2,1-f][1,2,4]triazin-4-amine

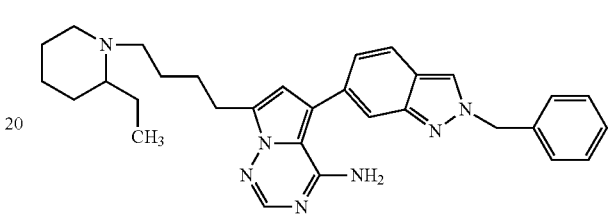

¹H NMR (400 MHz, DMSO-d₆) δ 8.53 (s, 1 H) 7.88 (s, 3 H) 7.58 (s, 2 H) 7.35 (s, 7 H) 5.65 (s, 3 H) 3,62 (s, 1 H) 2.89 (s, 3 H) 2.08 (s, 1 H) 1.46 (s, 9 H) 1.22 (s, 4 H) 0.77 (s, 3 H); MS LC-MS [M+H]⁺=508.3, RT=2.62 min.

Example 458

Preparation of 1-{4-[4-amino-5-(2-benzyl-2H-indazol-6-yl)pyrrolo[2,1-f][1,2,4]triazin-7-yl]butyl}-N,N-diethylpiperidine-4-carboxamide

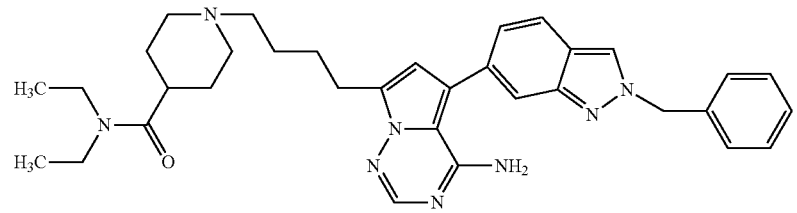 [SMILES: CCN(CC)C(=O)C1CCN(CCCCc2cc(-c3ccc4cn(Cc5ccccc5)nc4c3)c3c(N)ncnn23)CC1]

¹H NMR (400 MHz, DMSO-d₆) δ 8.53 (s, 2 H) 7.88 (s, 2 H) 7.81 (s, 2 H) 7.58 (s, 2 H) 7.35 (s, 7 H) 7.15 (d, J=8.44 Hz, 2 H) 5.65 (s, 3 H) 2.89 (s, 5 H) 1.51 (s, 7 H) 1.08 (s, 5 H) 1.03-0.93 (m, 5 H); MS LC-MS [M+H]⁺=579.3, RT=2.69 min.

Example 459

Preparation of ethyl 1-{4-[4-amino-5-(2-benzyl-2H-indazol-6-yl)pyrrolo[2,1-f][1,2,4]triazin-7-yl]butyl}piperidine-2-carboxylate

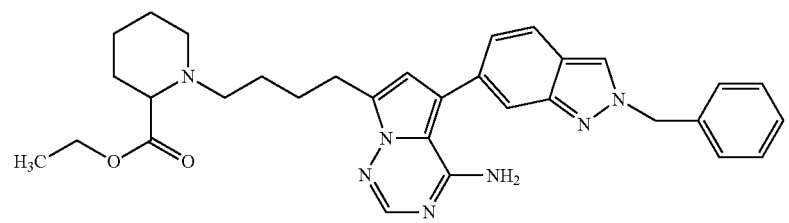 [SMILES: CCOC(=O)C1CCCCN1CCCCc1cc(-c2ccc3cn(Cc4ccccc4)nc3c2)c2c(N)ncnn12]

¹H NMR (400 MHz, DMSO-d₆) δ 8.62 (s, 2 H) 7.35 (s, 13 H) 5.65 (s, 3 H) 3.58 (s, 1 H) 3.05 (s, 2 H) 2.85 (s, 3 H) 1.47 (s, 7 H) 1.13 (s, 5 H); MS LC-MS [M+H]⁺=552.3, RT=2.71 min.

Example 460

Preparation of ethyl 1-{4-[4-amino-5-(2-benzyl-2H-indazol-6-yl)pyrrolo[2,1-f][1,2,4]triazin-7-yl]butyl}piperidine-4-carboxylate

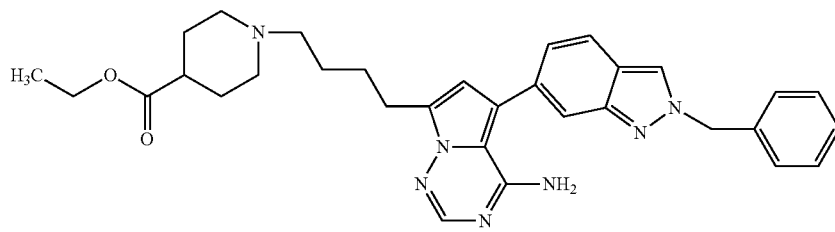 [SMILES: CCOC(=O)C1CCN(CCCCc2cc(-c3ccc4cn(Cc5ccccc5)nc4c3)c3c(N)ncnn23)CC1]

¹H NMR (400 MHz, DMSO-d₆) δ 8.53 (s, 2 H) 7.88 (s, 2 H) 7.80 (d, J=8.44 Hz, 2 H) 7.58 (s, 2 H) 7.35 (s, 6 H) 7.14 (d, J=8.19 Hz, 2 H) 5.65 (s, 3 H) 4.02 (s, 2 H) 2.83-2.92 (m, 3H) 2.75 (s, 2 H) 1.90 (s, 1 H) 1.49 (s, 6 H) 1.15 (t, J=6.91 Hz, 5 H); MS LC-MS [M+H]⁺=552.3, RT=2.70 min.

Example 461

Preparation of 5-(2-benzyl-2H-indazol-6-yl)-7-[4-(4,4-difluoropiperidin-1-yl)butyl]pyrrolo[2,1-f][1,2,4]triazin-4-amine

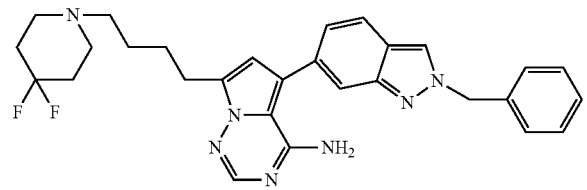 [SMILES: Nc1ncnn2c(CCCCN3CCC(F)(F)CC3)cc(-c3ccc4cn(Cc5ccccc5)nc4c3)c12]

¹H NMR (400 MHz, DMSO-d₆) δ 8.54 (s, 2 H) 7.88 (s, 4 H) 7.58 (s, 2 H) 7.35 (s, 9 H) 5.65 (s, 3 H) 3.68 (s, 2 H) 2.88 (s, 2 H) 1.83 (s, 4 H) 1.45 (s, 3 H); MS LC-MS [M+H]⁺=516.3, RT=2.66 min.

Example 462

Preparation of 5-(2-benzyl-2H-indazol-6-yl)-7-[4-(2,6-dimethylpiperidin-1-yl)butyl]pyrrolo[2,1-f][1,2,4]triazin-4-amine

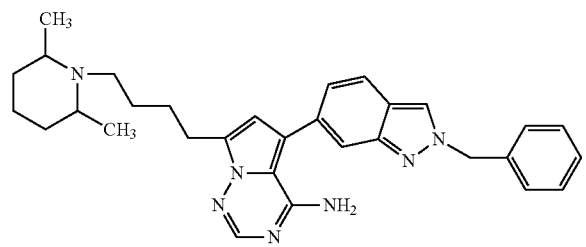 [SMILES: CC1CCCC(C)N1CCCCc1cc(-c2ccc3cn(Cc4ccccc4)nc3c2)c2c(N)ncnn12]

¹H NMR (400 MHz, DMSO-d₆) δ 12.03 (s, 1 H) 8.57 (s, 2 H) 7.84 (s, 3 H) 7.59 (s, 2 H) 7.38 (s, 4 H) 7.16 (s, 2 H) 5.64 (s, 3 H) 3.64 (s, 6 H) 3.04 (s, 1 H) 2.86 (s, 2 H) 1.28 (s, 12H); MS LC-MS [M+H]⁺=508.3, RT=2.70 min.

Example 463

Preparation of 5-(2-benzyl-2H-indazol-6-yl)-7-{4-[methyl(1-pyridin-4-ylethyl)amino]butyl}pyrrolo[2,1-f][1,2,4]triazin-4-amine

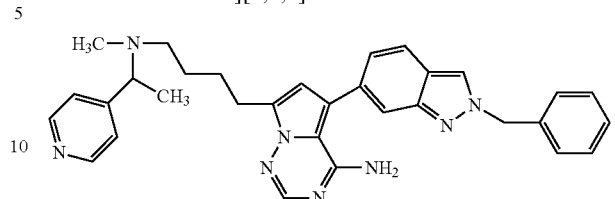

¹H NMR (400 MHz, DMSO-d₆) δ 8.51 (s, 4 H) 7.69 (s, 5 H) 7.26 (s, 8 H) 5.64 (s, 3 H) 3.61 (s, 4 H) 3.05 (s, 2 H) 2.85 (s, 2 H) 2.06 (s, 1 H) 1.50 (s, 2 H) 1.18 (s, 4 H); MS LC-MS [M+H]⁺=531.3, RT=2.59 min.

Example 464

Preparation of 5-(2-benzyl-2H-indazol-6-yl)-7-{4-[methyl(1-pyridin-3-ylethyl)amino]butyl}pyrrolo[2,1-f][1,2,4]triazin-4-amine

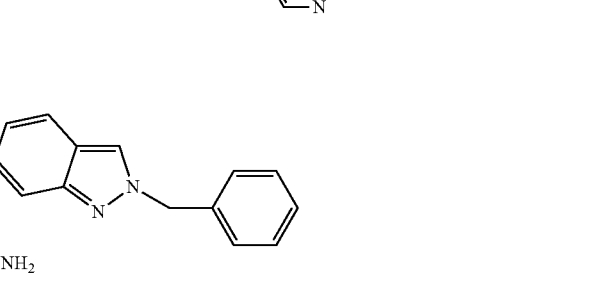

¹H NMR (400 MHz, DMSO-d₆) δ 8.50 (s, 4 H) 7.73 (s, 6 H) 7.30 (s, 7 H) 5.62 (s, 3 H) 3.68 (s, 5 H) 3.05 (s, 1 H) 2.82 (s, 2 H) 2.06 (s, 1 H) 1.48 (s, 2 H) 1.25 (s, 4 H); MS LC-MS [M+H]⁺=531.3, RT=2.60 min.

Example 465

Preparation of 5-(2-benzyl-2H-indazol-6-yl)-7-{4-[methyl(pyrimidin-4-ylmethyl)amino]butyl}pyrrolo[2,1-f][1,2,4]triazin-4-amine

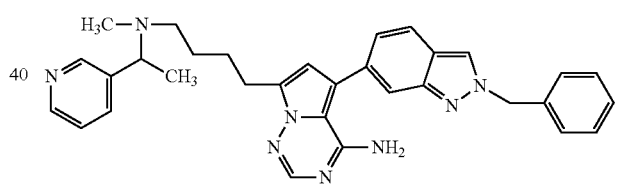

¹H NMR (400 MHz, DMSO-d₆) δ 8.70 (s, 1 H) 8.53 (s, 2 H) 7.83 (s, 3 H) 7.46 (s, 7 H) 7.15 (s, 2 H) 5.60 (s, 3 H) 4.29 (s,

1 H) 3.66 (s, 7 H) 3.04 (s, 1 H) 2.87 (s, 2 H) 2.17 (s, 1 H) 1.54 (s, 2 H); MS LC-MS [M+H]⁺=518.3, RT=2.62 min.

Example 466

Preparation of 5-(2-benzyl-2H-indazol-6-yl)-7-(1-L-prolylpiperidin-4-yl)pyrrolo[2,1-f][1,2,4]triazin-4-amine

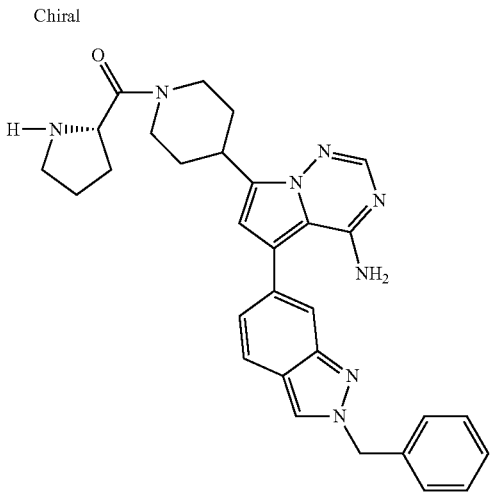 [SMILES: Nc1ncnn2c(C3CCN(C(=O)[C@@H]4CCCN4)CC3)cc(-c3ccc4cn(Cc5ccccc5)nc4c3)c12]

Step 1: Preparation of 2-{4-[4-Amino-5-(2-benzyl-2H-indazol-6-yl)-pyrrolo[2,1-f][1,2,4]triazin-7-yl]-piperidine-1-carbonyl}-pyrrolidine-1-carboxylic acid tert-butyl ester

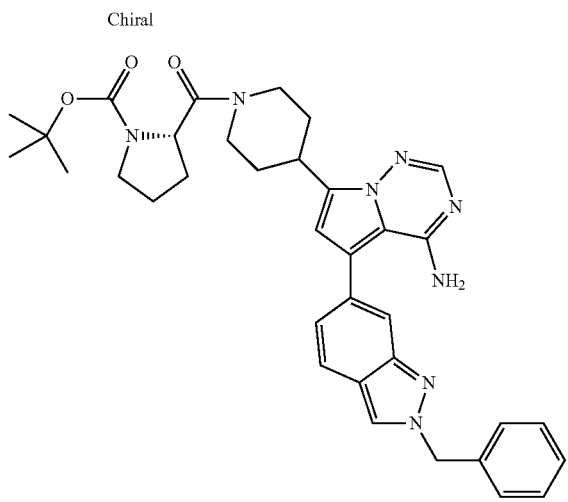 [SMILES: CC(C)(C)OC(=O)N1CCC[C@H]1C(=O)N1CCC(c2cc(-c3ccc4cn(Cc5ccccc5)nc4c3)c3c(N)ncnn23)CC1]

N,N-Diisopropylethylamine (35.0 μL, 0.200 mmol, 2.0 eq.) was added to N-(tert-butoxycarbonyl)-L-proline (23.7 mg, 0.110 mmol, 1.1 eq), 1-(3-dimethylaminopropyl)-3-ethylcarbodiimide hydrochloride (19.2 mg, 0.100 mmol, 1.0 eq), 1-hydroxybenzotriazole (13.5 mg, 0.100 mmol, 1.0 eq) and 1 mL of anhydrous DMF. The reaction was cooled to 0° C. and shaken for 30 minutes. Then to this mixture was added 5-(2-benzyl-2H-indazol-6-yl)-7-piperidin-4-ylpyrrolo[2,1-f][1,2,4]triazin-4-amine (42.3 mg, 0.1 mmol, 1.0 eq.) in 1 mL of anhydrous DMF. The reaction was shaken for 5 minutes at 0° C. The reaction was slowly warmed to rt and shaken over night. The product was purified by acidic HPLC on a Sunfire column (5% to 90%, 12 min).

Step 2: Preparation of the Title Compound

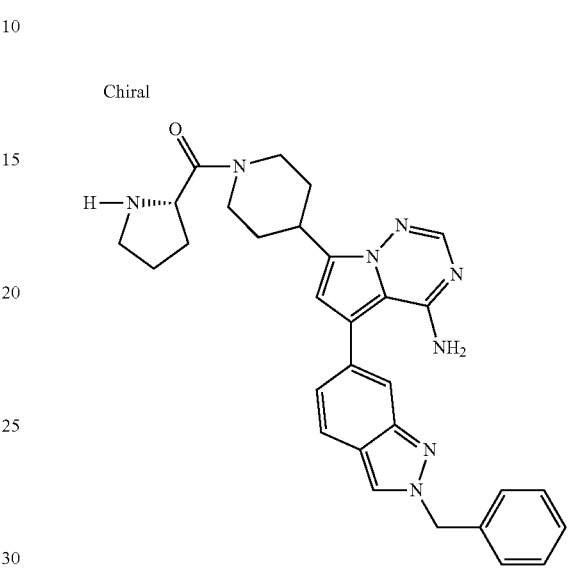

To a solution of 2-{4-[4-Amino-5-(2-benzyl-2H-indazol-6-yl)-pyrrolo[2,1-f][1,2,4]triazin-7-yl]-piperidine-1-carbonyl}-pyrrolidine-1-carboxylic acid tert-butyl ester (73.5 mg, 0.1 mmol) in dichloromethane (2 mL) was added trifluoroacetic acid (0.2 mL). The reaction was stirred at rt for 5 h. The sample was concentrated and the residue taken up in 1.5 mL of methanol, 0.5 mL of acetonitrile and 0.5 mL of water. The sample was then free-based using Phenomenex's Strata-X-C cation mixed mode polymer SPE plate (500 mg/6 mL/well) to give 9.20 mg (17%) of desired product. ¹H NMR (400 MHz, DMSO-d₆) δ 8.54 (s, 1 H), 7.80 (d, J=8.56 Hz, 1 H), 7.60 (s, 1 H), 7.29-7.39 (m, 5 H), 7.15 (d, J=8.56 Hz, 1 H), 6.63 (d, J=11.49 Hz, 1 H), 4.52 (d, J=12.59 Hz, 1 H), 4.05 (d, J=11.62 Hz, 1 H), 2.78 (t, J=12.47 Hz, 1 H), 2.56-2.66 (m, 1 H), 2.17 (s, 1 H), 1.99-2.10 (m, 5 H), 1.77-1.85 (m, 5 H), 1.63-1.69 (m, 2 H), 1.52-1.62 (m, 3 H), 1.17-1.27 (m, 2 H); MS LC-MS [M+H]⁺=521.5, RT=2.96 min.

Additional compounds illustrated below were prepared as described for step 1 and 2 of the preparation of 5-(2-benzyl-2H-indazol-6-yl)-7-(1-L-prolylpiperidin-4-yl)pyrrolo[2,1-f][1,2,4]triazin-4-amine and by choosing the appropriate starting materials that are readily available and/or the synthesis of which is taught herein, and using the processes of method described above or other standard chemical processes known in the art. If compounds did not possess a BOC group, then they were free-based without the need for removal of a BOC group. In some instances the NMR signals using flow NMR method are weaker in intensity, broadened, or absent due to solvent suppression.

Example 467

Preparation of 5-(2-benzyl-2H-indazol-6-yl)-7-(1-D-prolylpiperidin-4-yl)pyrrolo[2,1-f][1,2,4]triazin-4-amine

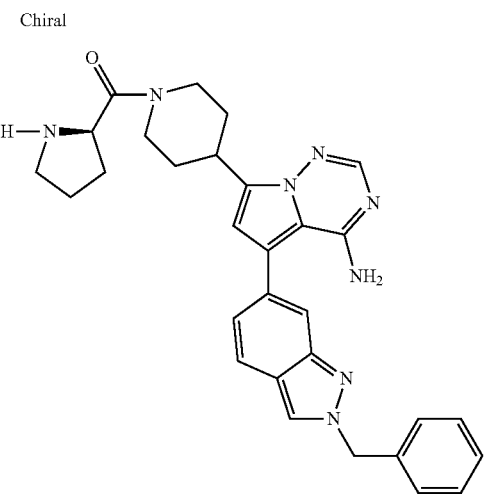 [SMILES: Nc1ncnn2c(C3CCN(C(=O)[C@H]4CCCN4)CC3)cc(-c3ccc4cn(Cc5ccccc5)nc4c3)c12]

¹H NMR (400 MHz, DMSO-d₆) δ 8.54 (s, 1 H), 7.81 (d, J=8.56 Hz, 1 H), 7.55-7.63 (m, 1 H), 7.29-7.39 (m, 5 H), 7.15 (d, J=8.56 Hz, 1 H), 6.63 (d, J=11.49 Hz, 1 H), 4.52 (d, J=12.59 Hz, 1 H), 4.04 (s, 1 H), 2.78 (t, J=12.41 Hz, 1 H), 2.56-2.66 (m, 1 H), 2.17 (s, 1H), 2.00-2.10 (m, 5 H), 1.75-1.86 (m, 5 H), 1.63-1.69 (m, 1 H), 1.52-1.62 (m, 3 H), 1.16-1.27 (m, 2 H); MS LC-MS [M+H]⁺=521.5, RT=2.85 min.

Example 468

Preparation of 7-{1-[(benzylamino)acetyl]piperidin-4-yl}-5-(2-benzyl-2H-indazol-6-yl)pyrrolo[2,1-f][1,2,4]triazin-4-amine

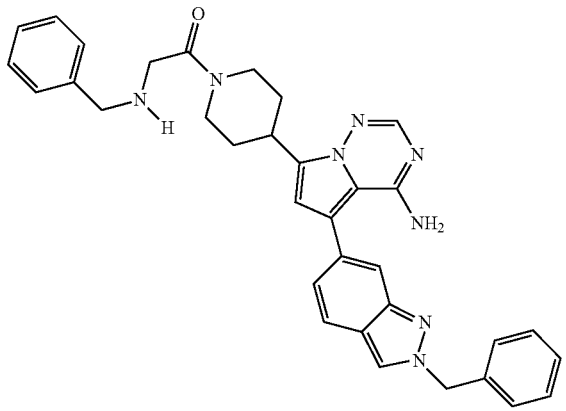 [SMILES: Nc1ncnn2c(C3CCN(C(=O)CNCc4ccccc4)CC3)cc(-c3ccc4cn(Cc5ccccc5)nc4c3)c12]

¹H NMR (400 MHz, DMSO-d₆) δ 8.54 (s, 1 H), 7.91 (s, 1 H), 7.81 (d, 1 H), 7.60 (s, 1 H), 7.37-7.36 (m, 5 H), 7.15 (d, 1 H), 6.59 (d, 1 H), 5.66 (s, 2 H) 4.46-4.56 (m, 1 H) 3.82-3.93 (m, 2 H) 3.77 (s, 1 H) 3.61-3.72 (m, 2 H) 3.51 (s, 2 H) 3.07-3.19 (m, 1 H) 2.98-3.07 (m, 3 H), 2.75 (t, 1 H), 2.12-2.18 (m, 2 H) 2.00-2.10 (m, 4 H) 1.75-1.86 (m, 2 H); MS LC-MS [M+H]⁺=571.6, RT=2.97 min.

Example 469

Preparation of (3)R-5-({4-[4-amino-5-(2-benzyl-2H-indazol-6-yl)pyrrolo[2,1-f][1,2,4]triazin-7-yl]piperidin-1-yl}carbonyl)pyrrolidin-3-ol

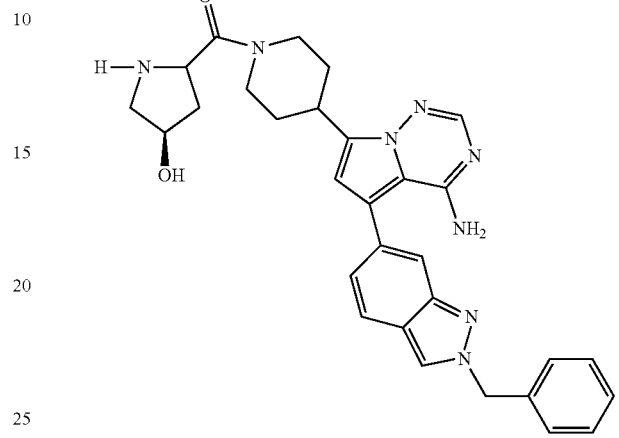

¹H NMR (400 MHz; DMSO-d₆) δ 8.54 (s, 1 H), 7.60 (s, 1 H), 7.30-7.39 (m, 4 H), 7.16 (d, J=8.56 Hz, 1 H), 6.62 (d, J=6.97 Hz, 1 H), 5.66 (s, 1 H), 4.51 (s, 1 H), 4.14 (s, 1 H), 2.81 (s, 1 H), 2.55-2.63 (m, 1 H), 2.20-2.28 (m, 1 H), 2.17 (s, 3 H), 2.03-2.14 (m, 5 H), 1.76-1.88 (m, 5 H), 1.65 (s, 1 H), 1.59 (s, 1 H), 1.47 (s, 1 H); MS LC-MS [M+H]⁺=537.5, RT=2.79 min.

Example 470

Preparation of (3S)-5-({4-[4-amino-5-(2-benzyl-2H-indazol-6-yl)pyrrolo[2,1-f][1,2,4]triazin-7-yl]piperidin-1-yl}carbonyl)pyrrolidin-3-ol

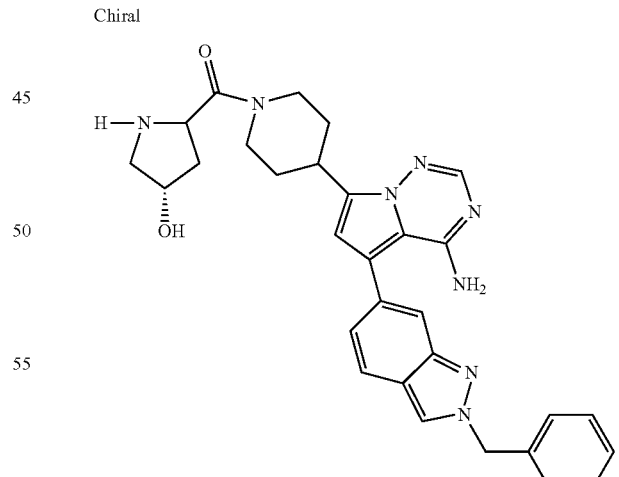

¹H NMR (400 MHz, DMSO-d₆) δ 8.54 (s, 1 H), 7.60 (s, 1 H), 7.30-7.39 (m, 4 H), 7.16 (d, J=8.56 Hz, 1 H), 6.62 (d, J=6.85 Hz, 1 H), 5.66 (s, 1 H), 4.51 (s, 1 H), 4.14 (s, 1 H), 2.81 (s, 1 H), 2.60 (d, J=3.18 Hz, 1 H), 2.20-2.28 (m, 1 H), 2.17 (s, 3 H), 2.02-2.14 (m, 5 H), 1.76-1.88 (m, 5 H), 1.65 (s, 1 H), 1.57 (d, J=10.27 Hz, 2 H); MS LC-MS [M+H]⁺=537.5, RT=2.81 min.

Example 471

Preparation of 5-(2-benzyl-2H-indazol-6-yl)-7-(1-{piperazin-1-yl[4-(trifluoromethyl)phenyl]acetyl}piperidin-4-yl)pyrrolo[2,1-f][1,2,4]triazin-4-amine

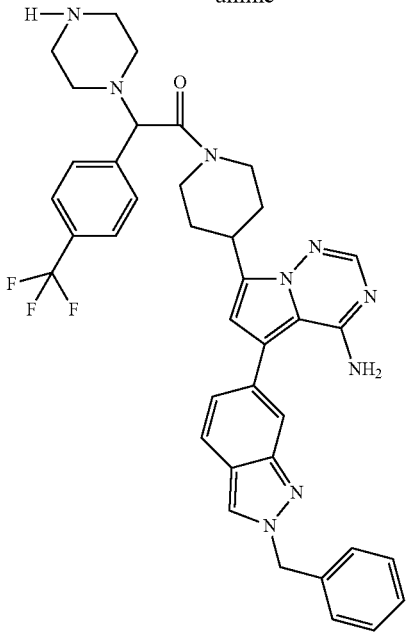

$^1$H NMR (400 MHz, DMSO-d$_6$) δ 8.54 (d, J=2.32 Hz, 1 H), 7.76-7.83 (m, 1 H), 7.64-7.75 (m, 3 H), 7.29-7.38 (m, 5 H), 7.07-7.18 (m, 1 H), 6.53-6.64 (m, 1 H), 5.66 (s, 3 H), 4.51 (s, 1 H), 4.41 (s, 1 H), 2.65-2.76 (m, 4 H), 2.37 (s, 4 H), 2.17 (s, 1 H), 2.02-2.12 (m, 3 H), 1.76-1.85 (m, 5 H), 1.66 (s, 1 H), 0.98 (s, 2 H); MS LC-MS [M+H]$^+$=694.6, RT=3.03 min.

Example 472

Preparation of 5-(2-benzyl-2H-indazol-6-yl)-7-{1-[(6-fluoro-1,2,3,4-tetrahydroisoquinolin-1-yl)carbonyl)piperidin-4-yl}pyrrolo[2,1-f][1,2,4]triazin-4-amine

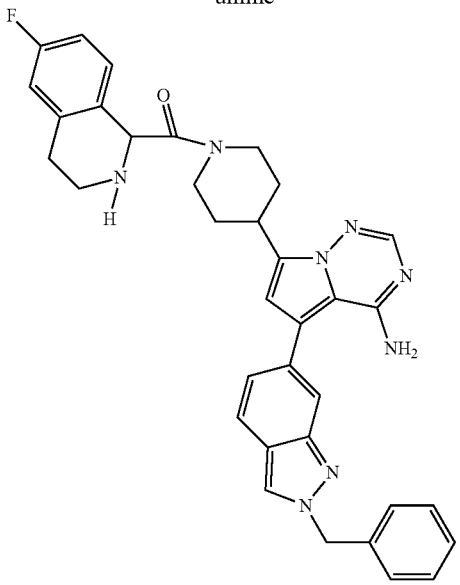

$^1$H NMR (400 MHz, DMSO-d$_6$) δ 8.55 (s, 1 H), 7.29-7.39 (m, 5 H), 7.16 (d, 2 H), 6.90-7.01 (m, 4 H), 5.67 (s, 2 H), 4.95 (s, 1 H), 4.53 (s, 1 H), 4.32-4.44 (m, 1 H); 3.01-3.13 (m, 1 H), 2.77-2.89 (m, 2 H), 2.75 (s, 1 H), 2.68 (s, 1 H), 2.17 (s, 2 H), 2.04-2.14 (m, 4 H), 1.77-1.86 (m, 5 H), 1.58 (d, J=15.65 Hz, 1 H); MS LC-MS [M+H]$^+$ 601.5, RT=2.96 min.

Example 473

Preparation of 5-(2-benzyl-2H-indazol-6-yl)-7-{1-[(6-methoxy-2,3,4,9-tetrahydro-1H-beta-carbolin-1-yl)carbonyl]piperidin-4-yl}pyrrolo[2,1-f][1,2,4]triazin-4-amine

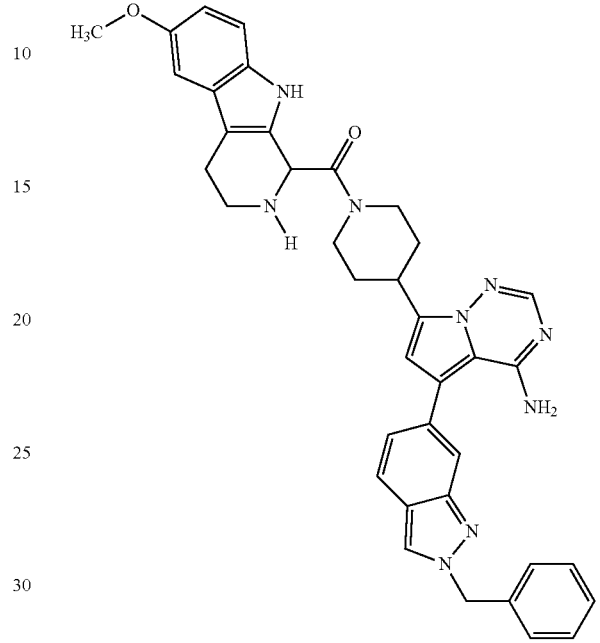

$^1$H NMR (400 MHz, DMSO-d$_6$) δ 8.55 (s, 1 H), 7.55-7.63 (m, 1 H), 7.30-7.39 (m, 6 H), 7.12-7.22 (m, 3 H), 6.80-6.90 (m, 2 H), 6.64 (td, 2 H), 5.67 (s, 2 H), 5.04 (s, 1 H), 3.69-3.80 (m, 2 H), 2.55-2.66 (m, 3 H), 2.15-2.18 (m, 3 H), 2.04-2.12 (m, 4 H), 1.92-2.01 (m, 1 H), 1.77-1.88 (m, 6 H), 1.60 (s, 1 H); MS LC-MS [M+H]$^+$=652.6, RT=3.02 min.

Example 474

Preparation of 1-{4-[4-Amino-5-(2-benzyl-2H-indazol-6-yl)-pyrrolo[2,1-f][1,2,4]triazin-7-yl]-piperidin-1-yl}-2-methylamino-ethanone

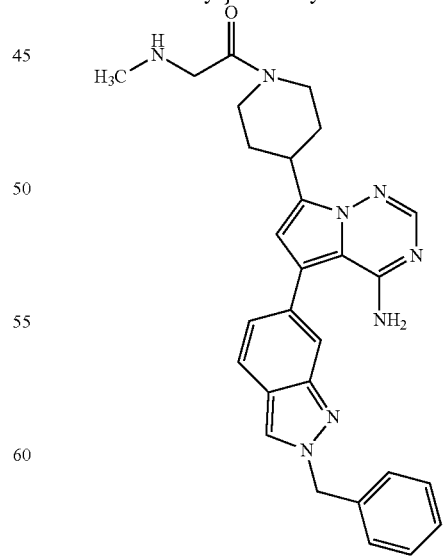

$^1$H NMR (400 MHz, DMSO-d$_6$) δ 8.04 (s, 1 H), 7.87 (s 1H), 7.75 (dd, 1H), 7.73-7.72 (m, 1 H), 7.41-7.36 (m, 2 H), 7.34-7.32 (m, 2 H), 7.21 (dd, 1H), 6.53 (s, 1 H), 5.61 (s, 2 H), 4.71 (d, 1 H), 4.41 (t, 3H), 3.87 (d, 1 H), 3.52-3.46 (m, 1H), 3.20 (t, 1H), 2.79 (t, 1H), 2.42 (s, 3 H), 2.23-2.11 (m, 3 H), 1.91 (s, 1 H), 1.84 (s, 1 H), 1.73-1.63 (m, 2 H); MS LC-MS [M+H]+=495.5, RT=2.20 min.

Example 475

Preparation of 5-(2-benzyl-2H-indazol-6-yl)-7-[1-(2-morpholin-4-ylbutanoyl)piperidin-4-yl]pyrrolo[2,1-f][1,2,4]triazin-4-amine

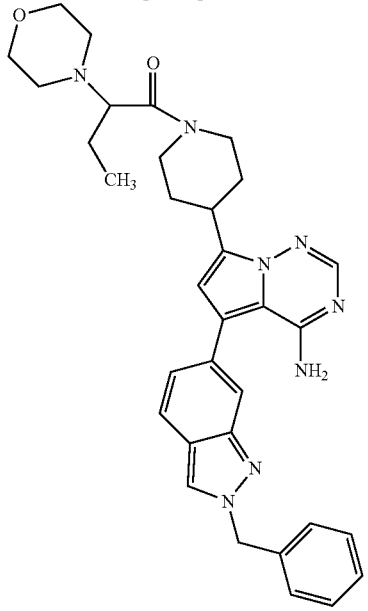 [SMILES: CCC(C(=O)N1CCC(c2cc(-c3ccc4cn(Cc5ccccc5)nc4c3)c3c(N)ncnn23)CC1)N1CCOCC1]

$^1$H NMR (400 MHz, DMSO-d$_6$) δ 8.54 (s, 1 H), 7.59 (s, 1 H), 7.29-7.39 (m, 5 H), 7.15 (dd, 1 H), 6.60 (s, 1 H), 5.66 (s, 1 H), 4.52 (s, 1 H), 3.98 (s, 1 H), 3.50-3.59 (m, 1 H), 2.70 (s, 1 H), 2.25-2.37 (m, 10 H), 2.17 (s, 2 H), 2.01-2.12 (m, 4 H), 1.82 (t, 2 H), 1.60-1.71 (m, 3 H), 1.53 (d, 1 H); MS LC-MS [M+H]+=579.3, RT=2.85 min.

Example 476

Preparation of 2-[(2-{4-[4-amino-5-(2-benzyl-2H-indazol-6-yl)pyrrolo[2,1-f][1,2,4]triazin-7-yl]piperidin-1-yl}-2-oxoethyl)(methyl)amino]ethanol

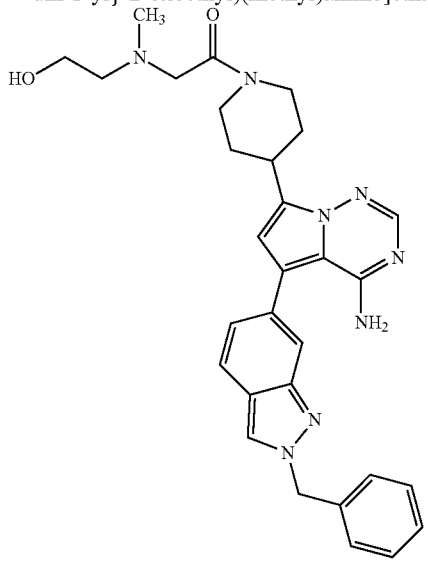

$^1$H NMR (400 MHz, DMSO-d$_6$) δ 8.54 (s, 2 H), 7.81 (d, 2 H), 7.60 (s, 2 H), 7.29-7.39 (m, 8 H), 7.16 (dd, 2 H), 6.54-6.63 (m, 2 H), 3.02 (s, 1 H), 2.64 (t, 2 H), 2.00-2.11 (m, 1 H), 1.94 (d, 3 H), 1.75-1.86 (m, 4 H), 1.57 (qd, 3 H), 1.17-1.25 (m, 2 H); MS LC-MS [M+H]+=539.3, RT=2.81 min.

Example 477

Preparation of 5-(2-benzyl-2H-indazol-6-yl)-7-[1-(2-morpholin-4-ylpropanoyl)piperidin-4-yl]pyrrolo[2,1-f][1,2,4]triazin-4-amine

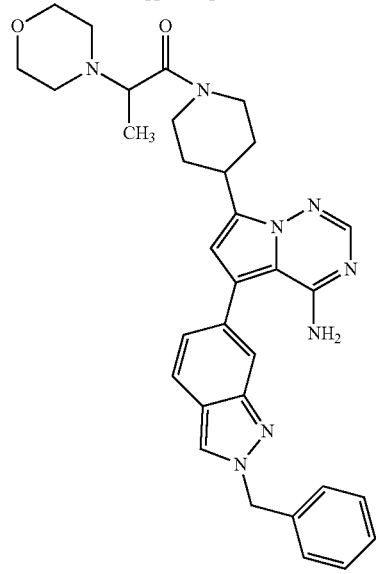 [SMILES: CC(C(=O)N1CCC(c2cc(-c3ccc4cn(Cc5ccccc5)nc4c3)c3c(N)ncnn23)CC1)N1CCOCC1]

$^1$H NMR (400 MHz, DMSO-d$_6$) δ 8.54 (s, 1 H), 7.60 (s, 1 H), 7.29-7.39 (m, 6 H), 7.16 (d, 2 H), 6.56-6.64 (m, 2 H), 5.66 (s, 2 H), 4.55 (d, 2 H), 4.25 (d, 1 H), 3.56 (s, 2 H), 2.66-2.77 (m, 1 H), 2.45 (s, 4 H), 2.17 (s, 2 H), 2.02-2.14 (m, 5 H), 1.77-1.88 (m, 5 H), 1.48-1.60 (m, 1H); MS LC-MS [M+H]+= 565.3, RT=2.83 min.

Example 478

Preparation of 5-(2-benzyl-2H-indazol-6-yl)-7-[1-(2-pyrrolidin-1-ylpropanoyl)piperidin-4-yl]pyrrolo[2,1-f][1,2,4]triazin-4-amine

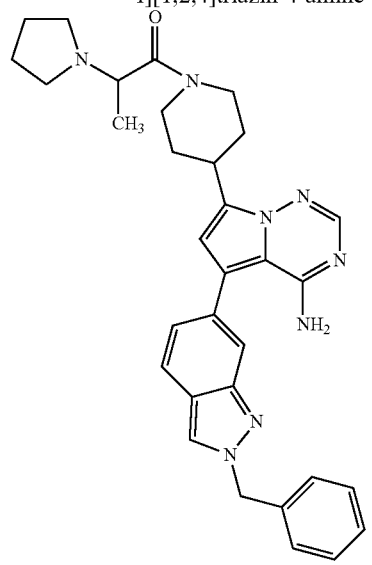

$^1$H NMR (400 MHz, DMSO-d$_6$) δ 8.54 (s, 1 H), 7.60 (s, 1 H), 7.29-7.39 (m, 6 H), 7.15 (dd, 2 H), 6.60 (d, 2 H), 5.66 (s, 2 H), 4.52 (s, 1 H), 4.50 (d, 1 H), 4.42 (s, 1 H), 2.64-2.73 (m, 1 H), 2.17 (s, 1 H), 2.02-2.12 (m, 5 H), 1.76-1.86 (m, 4 H), 1.66 (s, 6 H), 1.58-1.64 (m, 2 H); MS LC-MS [M+H]+=549.3, RT=2.87 min.

Example 479

Preparation of 3-(2-{4-[4-amino-5-(2-benzyl-2H-indazol-6-yl)pyrrolo[2,1-f][1,2,4]triazin-7-yl]piperidin-1-yl}-2-oxoethyl)-5-chloro-1,3-benzoxazol-2(3H)-one

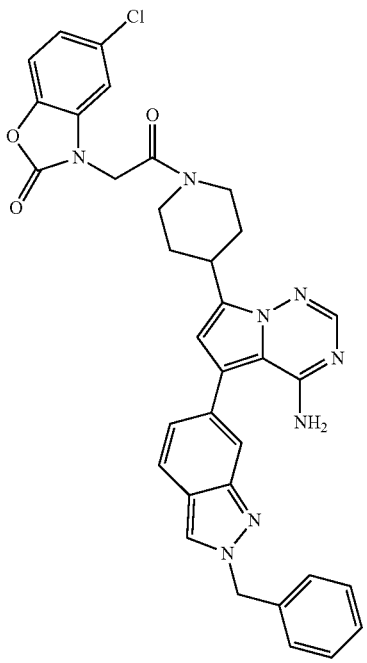 [SMILES: Nc1ncnn2c(C3CCN(C(=O)Cn4c(=O)oc5ccc(Cl)cc54)CC3)cc(-c3ccc4cn(Cc5ccccc5)nc4c3)c12]

$^1$H NMR (400 MHz, DMSO-d$_6$) δ 8.55 (s, 1 H), 7.61 (s, 1 H), 7.49 (d, 1 H), 7.30-7.41 (m, 5 H), 7.12-7.22 (m, 2 H), 6.58-6.67 (m, 1 H), 5.67 (s, 1 H), 4.82-4.92 (m, 2 H), 4.45 (s, 1 H), 4.01 (s, 1 H), 2.85 (t, 1 H), 2.57 (s, 1 H), 2.17 (s, 2 H), 2.05-2.14 (m, 3 H), 1.88-1.98 (m, 1 H), 1.82 (t, 3 H), 1.57-1.68 (m, 1 H); MS LC-MS [M+H]$^+$=633.3, RT=3.52 min.

Example 480

Preparation of 5-(2-benzyl-2H-indazol-6-yl)-7-[1-(piperidin-1-ylacetyl)piperidin-4-yl]pyrrolo[2,1-f][1,2,4]triazin-4-amine

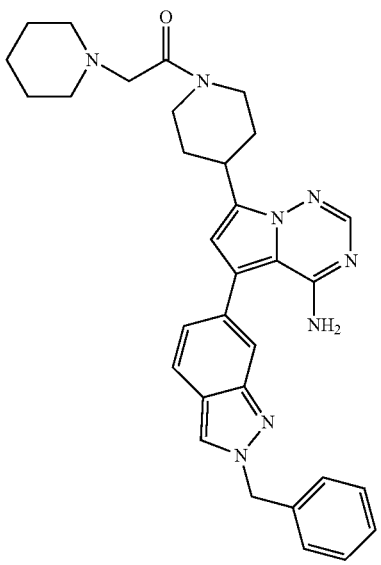 [SMILES: Nc1ncnn2c(C3CCN(C(=O)CN4CCCCC4)CC3)cc(-c3ccc4cn(Cc5ccccc5)nc4c3)c12]

$^1$H NMR (400 MHz, DMSO-d$_6$) δ 8.55 (s, 1 H), 7.60 (s, 1 H), 7.29-7.39 (m, 6 H), 7.15 (dd, 2 H), 6.58 (s, 2 H), 5.66 (s, 2 H), 4.48 (d, 1 H), 4.20 (s, 1 H), 2.72 (t, 1 H), 2.35 (s, 5 H), 2.17 (s, 2 H), 2.02-2.12 (m, 4 H), 1.75-1.86 (m, 3 H), 1.65-1.75 (m, 1 H), 1.45-1.56 (m, 4 H); MS LC-MS [M+H]$^+$=549.3, RT=2.85 min.

Example 481

Preparation of 5-(2-benzyl-2H-indazol-6-yl)-7-[1-(piperidin-2-ylcarbonyl)piperidin-4-yl]pyrrolo[2,1-f][1,2,4]triazin-4-amine

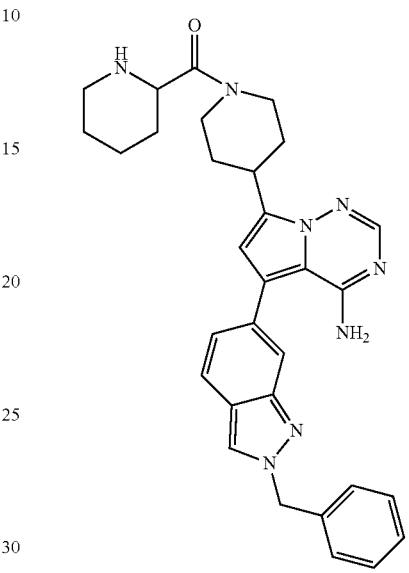

$^1$H NMR (400 MHz, DMSO-d$_6$) δ 8.31 (s, 1 H), 7.58 (d, J=8.56 Hz, 1 H), 7.06-7.16 (m, 4 H), 6.92 (dd, J=8.62, 1.16 Hz, 1 H), 6.39 (d, J=7.34 Hz, 1 H), 5.43 (s, 3 H), 4.27 (s, 1 H), 3.86 (s, 1 H), 2.27 (d, J=1.59 Hz, 3 H), 2.26 (s, 1 H), 1.94 (s, 1 H), 1.79-1.89 (m, 5 H), 1.52-1.64 (m, 6 H), 1.41 (d, 2 H), 1.21-1.32 (m, 2 H), 0.75 (s, 2 H); MS LC-MS [M+H]$^+$=535.3, RT=2.83 min.

Example 482

Preparation of 5-(2-benzyl-2H-indazol-6-yl)-7-[1-(3-piperidin-1-ylpropanoyl)piperidin-4-yl]pyrrolo[2,1-f][1,2,4]triazin-4-amine

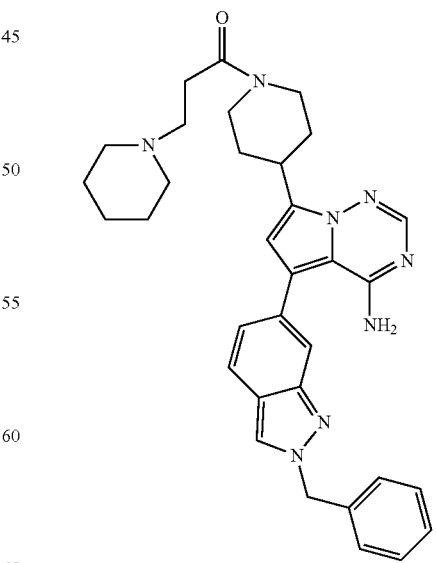

$^1$H NMR (400 MHz, DMSO-d$_6$) δ 8.54 (s, 1 H), 7.81 (d, t H), 7.60 (s, 1 H), 7.29-7.38 (m, 2 H), 7.15 (dd, 1 H), 5.66 (s,

3 H), 4.52 (d, 1 H), 2.08 (dd, 2 H), 1.78-1.87 (m, 1 H), 1.43-1.54 (m, 7 H), 1.31-1.41 (m, 4 H), 1.17-1.25 (m, 4 H), 1.05-1.15 (m, 7 H), 0.98 (s, 2 H); MS LC-MS [M+H]⁺=563.3, RT=2.88 min.

Example 483

Preparation of 5-(2-benzyl-2H-indazol-6-yl)-7-[1-3-pyrrolidin-1-ylpropanoyl)piperidin-4-yl]pyrrolo[2,1-f][]1,2,4]triazin-4-amine

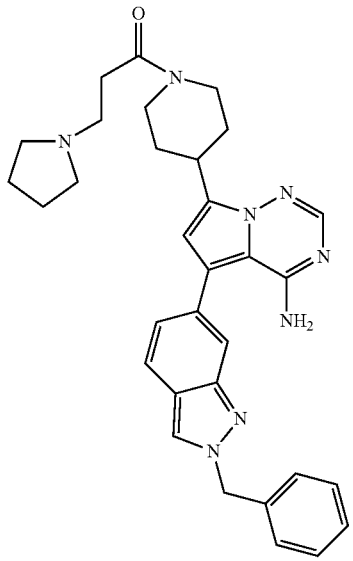 [SMILES: Nc1ncnn2c(C3CCN(C(=O)CCN4CCCC4)CC3)cc(-c3ccc4cn(Cc5ccccc5)nc4c3)c12]

¹H NMR (400 MHz, DMSO-d₆) δ 8.54 (s, 1 H), 7.60 (s, 1 H), 7.29-7.38 (m, 5 H), 7.15 (dd, 2 H), 6.60 (s, 1 H), 5.66 (s, 1 H), 4.51 (s, 1 H), 3.99 (s, 1 H), 2.56-2.67 (m, 3 H), 2.44 (s, 4 H), 2.17 (s, 2 H), 2.01-2.12 (m, 4 H), 1.98 (s, 1 H), 1.77-1.88 (m, 2 H), 1.60-1.71 (m, 4 H), 1.46-1.55 (m, 1 H); MS LC-MS [M+H]⁺=549.3, RT=2.84 min.

Example 484

Preparation of 5-({4-[4-amino-5-(2-benzyl-2H-indazol-6-yl)pyrrolo[2,1-f][1,2,4]triazin-7-yl]piperidin-1-yl}carbonyl)pyrrolidin-2-one

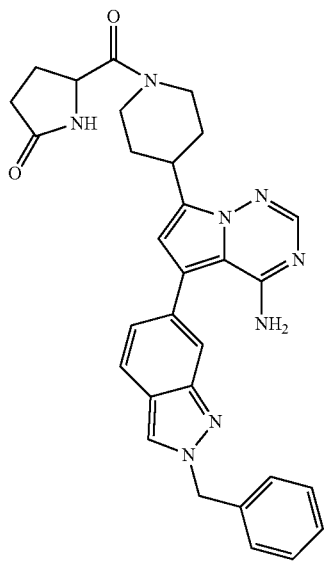 [SMILES: Nc1ncnn2c(C3CCN(C(=O)C4CCC(=O)N4)CC3)cc(-c3ccc4cn(Cc5ccccc5)nc4c3)c12]

¹H NMR (400 MHz, DMSO-d₆) δ 8.55 (s, 1 H), 7.60 (s, 1 H), 7.29-7.39 (m, 5 H), 7.15 (d, 1 H), 5.66 (s, 1 H), 4.51-4.61 (m, 1 H), 4.48 (s, 1 H), 3.99 (s, 1 H), 2.29-2.40 (m, 1 H), 2.17 (s, 2 H), 2.03-2.14 (m, 7 H), 1.77-1.89 (m, 5 H), 1.63 (s, 1 H), 1.58 (d, 1 H); MS LC-MS [M+H]⁺=535.3, RT=2.98 min.

Example 485

Preparation of 5-(2-benzyl-2H-indazol-6-yl)-7-[1-(morpholin-4-ylacetyl)piperidin-4-yl]pyrrolo[2,1-f][]1,2,4]triazin-4-amine

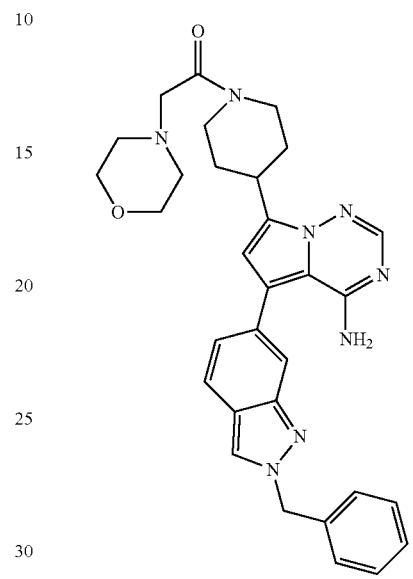

¹H NMR (400 MHz, DMSO-d₆) δ 8.56 (s, 1 H), 7.61 (s, 1 H), 7.30-7.40 (m, 6 H), 7.16 (dd, 1 H), 6.57-6.65 (m, 1 H), 5.67 (s, 2 H), 4.47 (s, 1 H), 4.17 (s, 1 H), 3.53-3.63 (m, 1 H), 2.69-2.79 (m, 1 H), 2.42 (s, 5 H), 2.18 (s, 2 H), 2.03-2.13 (m, 4 H), 1.82-1.87 (m, 2 H), 1.70-1.80 (m, 2 H), 1.47-1.58 (m, 1 H); MS LC-MS [M+H]⁺=551.3, RT=2.82 min.

Example 486

Preparation of 5-(2-benzyl-2H-indazol-6-yl)-7-[1-(pyrrolidin-1-ylacetyl)piperidin-4-yl]pyrrolo[2,1-f][1,2,4]triazin-4-amine

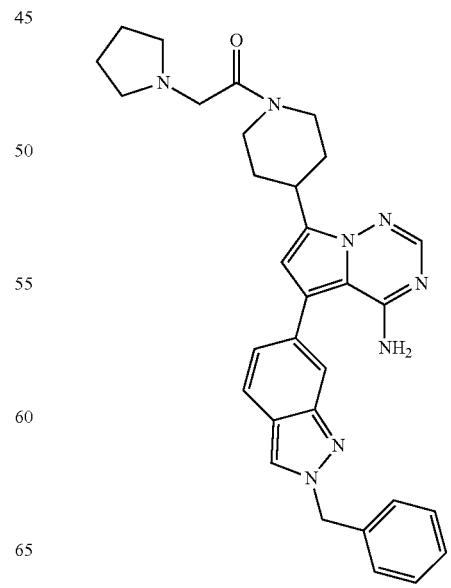

¹H NMR (400 MHz, DMSO-d₆) δ 8.54 (s, 1 H), 7.60 (s, 1 H), 7.29-7.39 (m, 6 H), 7.15 (dd, 2 H), 6.55-6.65 (m, 2 H), 5.66 (s, 2 H), 4.47 (s, 1 H), 4.14 (s, 1 H), 2.72 (s, 1 H), 2.17 (s, 2 H), 2.60-2.11 (m, 5 H), 1.92 (d, 1 H), 1.76-1.87 (m, 3 H), 1.68 (s, 5 H); MS LC-MS [M+H]⁺=535.3, RT=2.84 min.

Example 487

2-{4-[4-Amino-5-(2-benzyl-2H-indazol-6-yl)-pyrrolo[2,1f][1,2,4]triazin-7-yl]-piperidin-1-yl}-N,N-dimethyl-acetamide

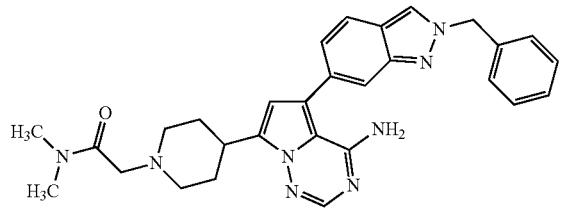 [SMILES: CN(C)C(=O)CN1CCC(c2cc(-c3ccc4cn(Cc5ccccc5)nc4c3)c3c(N)ncnn23)CC1]

Example 1 (150 mg, 0.33 mmol) was dissolved in 1.5 mL of MeOH and treated with EtN(iPr)₂ (0.17 mL, 0.98 mmol) followed by the addition of 2-chloro-N,N-dimethylacetamide (0.040 mL, 0.39 mmol). The mixture was stirred at rt overnight overnight. HPLC analysis shows ~75% conversion. The mixture was heated to 60° C. for 6 hours, cooled to rt and poured into water. The aqueous layer was extracted with 3×10 mL of EtOAc and the combined organic phases were washed with brine, dried (Na₂SO₄), filtered and concentrated in vacuo. The residue was purified using an ISCO® instrument (gradient 5%—40% EtOH (+1% NH₄OH)/EtOAc) and the product containing fractions concentrated to give 64 mg of the title compound as a glass. ¹H NMR (300 MHz, DMSO-d₆) δ 8.58 (s, 1H), 7.89 (s, 1H), 7.78 (d, 1H), 7.40-7.24 (m, 5 H), 7.15 (d, 1 H), 6.60 (s, 1H), 5.63 (s, 2 H), 3.18-3.07 (m, 3 H), 3.05 (s, 3 H) 2.92 (bd, 2 H), 2.79 (s, 3 H), 2.07 (m, 2H), 1.97 (m, 2 H), 1.71 (dd, 2 H); ES-MS m/z 509.3 [M+H]⁺, HPLC RT (min) 2.11.

Example 488

2-{4-[4-Amino-5-(2-benzyl-2H-indazol-6-yl)-pyrrolo[2,1-f][1,2,4]triazin-7-yl]-piperidin-1-yl}-N,N-diethyl-acetamide

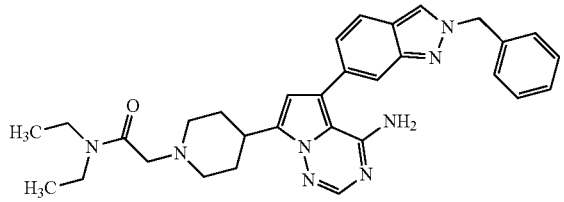 [SMILES: CCN(CC)C(=O)CN1CCC(c2cc(-c3ccc4cn(Cc5ccccc5)nc4c3)c3c(N)ncnn23)CC1]

Using the procedure outlined in Example 487 and substituting 2-chloro-N,N-diethylacetamide for 2-chloro-N,N-dimethylacetamide provided the title compound. ¹H NMR (300 MHz, DMSO-d₆) δ 8.59 (s, 1 H), 7.92 (s, 1 H), 7.74 (d, 1 H), 7.40 (m, 4 H), 7.35 (m, 1H), 7.19 (d, 1 H), 6.63 (s, 1 H), 5.70 (s; 2 H), 3.42 (q, 2H), 3.28 (q, 2H), 3.18 (bs, 2H) 3.13 (m, 1H) 2.95 (bd, 2 H), 2.20 (m, 2H), 2.07 (m, 2H), 1.75 (m, 2H); ES-MS m/z 537.2 [M+H]⁺, HPLC RT (min) 2.351.

Example 489

(R)-5-(2-Benzyl-2H-indazol-6-yl)-7-piperidin-3-yl-pyrrolo[2,1-f][1,2,4]triazin-4-ylamine

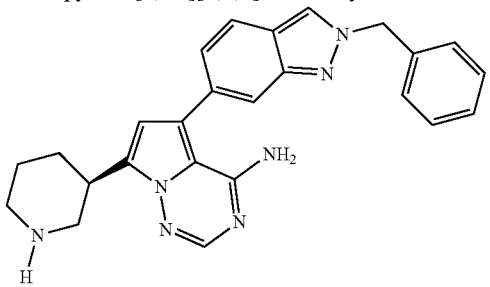

Step 1: Preparation of (R)-3-[4-Amino-5-(2-benzyl-2H-indazol-6-yl)-pyrrolo[2,1-f][1,2,4]triazin-7-yl]-piperidine-1-carboxylic acid benzyl ester

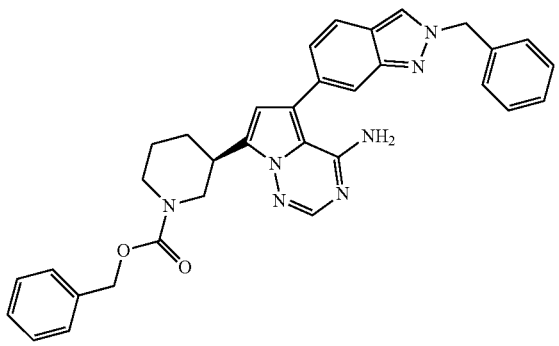 [SMILES: Nc1ncnn2c([C@@H]3CCCN(C(=O)OCc4ccccc4)C3)cc(-c3ccc4cn(Cc5ccccc5)nc4c3)c12]

DMF (4 mL) was degassed by a vacuum purge/N₂ flush procedure and then Intermediate 1 (860 mg, 2.00 mmol) and Intermediate C (902 mg, 2.70 mmol) were added. To this mixture was added 1,1'-bis(diphenylphosphino)ferrocene-palladium(11) chloride (44 mg, 0.06 mmol) followed by the 5 mL of 2M aqueous Na₂CO₃ solution and the mixture was placed in a 110° C. oil bath for 4 h and cooled to rt. The mixture was partitioned between water and EtOAc (25 mL each). The layers were separated and the aq. layer was extracted with 2×25 mL of EtOAc and the combined organic fractions were washed with water and brine, dried, filtered through a 0.5"×1" pad of SiO₂ (pre-wetted with EtOAc) and the pad was washed well with EtOAc and concentrated in vacuo to give a residue that was purified using an ISCO® instrument (Redi-Sep 40, Eluting with 80%—100% EtOAc (and 2% EtOH)/hexanes) to give 597 mg of the desired product. ¹H NMR (300 MHz, DMSO-d₆) δ 8.76 (s, 1H), 7.91 (bs, 1H), 7.81 (d, 1H), 7.69 (s, 1H), 7.43-7.25 (m, 10H), 7.17 (d, 1H), 6.62 (s, 1H), 5.65 (s, 2H), 5.09 (bs, 2H), 4.28 (m, 1H), 3.98 (m, 1H), 3.33 (m, 1H), 3.20-2.88 (m, 2H), 2.08 (m, 1H), 1.77 (m, 2H), 1.53 (m, 1H). ES-MS m/z 558.2 [M+H]⁺, HPLC RT (min) 3.15.

Step 2: Preparation the Title Compound

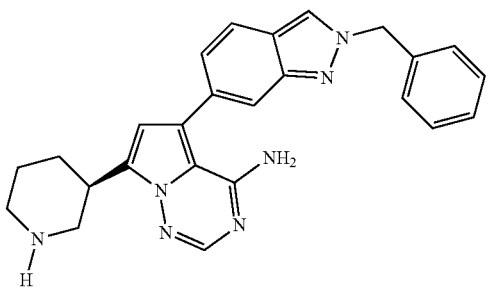 [SMILES: Nc1ncnn2c([C@@H]3CCCNC3)cc(-c3ccc4cn(Cc5ccccc5)nc4c3)c12]

The product from step 1 (256 mg) was mixed with 6N aqueous HCl and heated to reflux for 30 min (HPLC analysis shows complete consumption of SM) and then allowed to cool to rt. The mixture was concentrated in vacuo and then dissolved in water (1 mL) and acetonitrile was added drop wise with stirring (~10 mL). The mixture was stirred and a precipitate began to form. The mixture was stirred for 1 hour and the precipitate was collected by filtration, washed with acetonitrile and dried in a vacuum oven overnight and this fraction (presumably HCl salt) was set aside. The filtrate was concentrated in vacuo and the process repeated (0.5 mL of water and 20 mL of acetonitrile). The mixture was stirred overnight and then cooled in an ice bath for 1 hour and the precipitate was collected by filtration and dried in a vacuum oven (set aside). The filtrate from this process was poured through a column containing an acidic ion exchange resin. The column was washed with acetonitrile and the product eluted by washing the column with 2M $NH_3$ in MeOH. The filtrate was concentrated to give 46 mg of the title compound as a free base. $^1$H NMR (300 MHz, DMSO-$d_6$) δ 8.75 (s, 1H), 7.89 (s, 1H), 7.79 (d, 1H), 7.68 (s, 1H), 7.39-7.23 (m, 5H), 7.14 (d, 1H), 6.58 (s, 1H), 5.63 (s, 2H), 3.30-3.12 (m, 2H), 2.92 (d, 1H), 2.58-2.30 (m, 3H), 2.06 (m, 1H), 1.69-1.43 (m, 2H). ES-MS m/z 424.2 [M+H]$^+$, HPLC RT (min) 2.17. Spectral properties of the HCl salt: $^1$H NMR (300 MHz, DMSO-$d_6$) 9.22 (m, 1H), 9.06 (m, 1H), 8.59 (s, 1H), 8.07 (s, 1H), 7.83 (d, 1H), 7.62 (s, 1H), 7.38-7.25 (m, 5H), 7.13 (d, 1H), 6.78 (s, 1H), 5.62 (s, 2H), 3.64 (m, 1H), 3.52 (d, 1H), 3.31 (d, 1H), 3.09 (dd, 1H), 2.90 (dd, 1H), 2.10 (d, 1H), 1.96-1.69 (m, 3H). ES-MS m/z 424.4 [M+H]$^+$, HPLC RT (min) 2.01.

Example 490

(S)-5-(2-Benzyl-2H-indazol-6-yl)-7-piperidin-3-yl-pyrrolo[2,1-f][1,2,4]triazin-4-ylamine

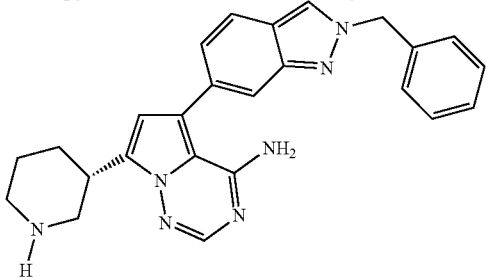 [SMILES: Nc1ncnn2c([C@H]3CCCNC3)cc(-c3ccc4cn(Cc5ccccc5)nc4c3)c12]

Using the procedure described in the above example, but substituting Intermediate E E E for Intermediate D D D, the title compound was prepared. The spectral properties were identical in all aspects with the R-isomer.

Example 491

5-(2-Benzyl-2H-indazol-6-yl)-7-[1-(4,5-dihydro-oxazol-2-yl)-piperidin-3-yl]-pyrrolo[2,1-f][1,2,4]triazin-4-ylamine

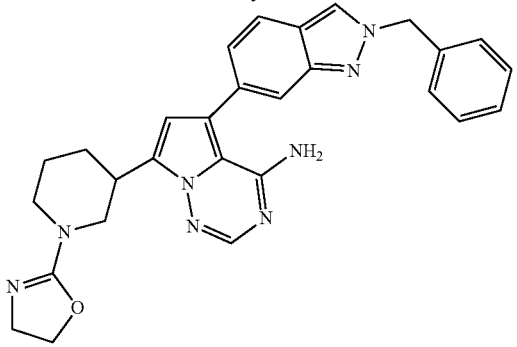 [SMILES: Nc1ncnn2c(C3CCCN(C4=NCCO4)C3)cc(-c3ccc4cn(Cc5ccccc5)nc4c3)c12]

5-(2-Benzyl-2H-indazol-6-yl)-7-piperidin-3-yl-pyrrolo[2,1-f][1,2,4]triazin-4-ylamine (63 mg, 0.15 mmol) was dissolved in 1 mL of acetonitrile and 0.5 ml. DMF and treated with 2-bromoethyl isocyante (0.013 mL, 0.16 mmol) and the mixture was stirred 3 h. The reaction was quenched by the addition of ~0.2 mL water. This mixture was directly injected on to a preparative HPLC. The product containing fractions were collected, and the TFA from the eluate was removed via filtration through an acidic resin followed by washing with acetonitrile. The product was then eluted with 2M $NH_3$ in MeOH. The MeOH was removed and the residue was dried overnight in a vacuum oven at 40° C. to provide the title compound. NMR (300 MHz, DMSO-$d_6$) δ 8.54 (s, 1H), 7.91 (s, 1H), 7.80 (d, 1H), 7.59 (s, 4H), 7.38-7.24 (m, 5H), 7.12 (d, 1H), 6.61 (s, 1H), 5.62 (s, 2H), 4.24 (m, 2H), 4.10 (dd, 1H), 3.83 (dd, 1H), 3.61 (m, 2H), 2.93 (m, 1H), 2.89 (m, 1H), 2.08 (m, 1H) 1.72 (m, 2H), 1.58 (m, 1H). ES-MS m/z 493.2 [M+H]$^+$, HPLC RT (min) 2.29.

B. Physiological activity

The in vitro effect of the compounds according to the invention can be demonstrated in the following assays:

IGF-1R Biochemical Assay: Spa Format (96 Well):

80 µl of kinase reaction buffer (50 mM HEPES pH7.5, 10 mM $MnCl_2$, 1 mM DTT, 0.05% (v/v) Tween 20 and 0.2 mg/mL BSA) containing 2.0 nM of N-terminal His-tagged GST-IGF-1R (amino acids 954-1367) fusion protein (1.6 nM enzyme final concentration) is added to each well of a 96 well white/clear bottom plate (Matrix Cat# 4924). Compounds of the invention, dissolved in DMSO, are added to the wells to generate final concentrations of 10 µM, 2 µM, 0.4 µM, 0.08 µM, 0.016 µM, 0.0032 µM, 0.00064 µM, and 0.000128 µM (1% (v/v) DMSO final concentration) generating an inhibitor compound dose response. The kinase reaction is started by the addition of 20 µL of a biotinylated poly-Glu-Tyr peptide substrate (Schering CIS bio International; Cat. # 61GT0BLB, final concentration at 28 nM) containing $^{33}$P-ATP (Perkin-Elmer-NEN Cat. # NEG 602H, 0.1 µCi per well) and ATP (1.0 µM final concentration). The reaction is incubated at room temperature for 2 hours and is terminated by the addition of 50 µL of stop solution (10 mg/mL Streptavidin Scintillation Proximity (SPA) beads (Amersham Cat. # RPNQ0007) in 150 mM EDTA), for final concentrations of 0.5 mg SPA beads and 50 mM EDTA per well. The plates are incubated at room temperature for 15 minutes and then centrifuged at 2000 rpm for 10 minutes. The $^{33}$P-radiolabel incorporation into the peptide substrate is quantitated on a Microbeta liquid scintillation counter. Staurosporine (Sigma-Aldrich, Cat. # 4400), at a final concentration of 450 nM/well, is used as a positive inhibitor control. Results are expressed as percent Inhibition using the following equation. $IC_{50}$ values and graphical representation were generated using Analyze 5 data analysis software.

% inhibition=$1-(T_{cpm}-B_{cpm})/(P_{cpm}-B_{cpm})\times 100$ $T_{cpm}$=$^{33}$P-cpm in presence of test compound
$B_{cpm}$=$^{33}$P-cpm in background control (no enzyme)

IGF-1R-dependent p-(S473)AKT cytoblot assay

A cytoblot assay was developed in human tumor cell lines to evaluate inhibition of IGF-1R signaling by measuring the inhibition of IGF-1 stimulated AKT phosphorylation on the serine 473 residue [p-(S473)AKT]. Cell lines include A549 and H460 non-small cell lung carcinoma, DU145 prostate carcinoma, MCF-7 breast carcinoma and Colo205 colon carcinoma cell lines. In addition, the assay has been formatted to measure IGF-1 and insulin-induced AKT phosphorylation in the IGF-1 and insulin responsive Chinese hamster ovary (CHO) cell line.

Briefly, log phase growth cells were plated at 50,000 cells/well in 96-well poly-D-lysine coated, clear bottom, black-sided plates in 10 µL of starvation medium (RPMI medium containing 0.1% BSA (w/v)) and incubated overnight at 37° C. in a 5% $CO_2$ incubator. The following day the cells were incubated for 1 hour at 37° C. in 5% $CO_2$ with compounds of the invention (10 mM stock solutions in DMSO). Compounds of the invention were diluted to final concentrations of 0.01 μM, 0.03 μM, 0.1 μM, 0.3 μM, 1.0 μM, 3.0 μM and 10 μM. Compound treated cells were then stimulated with IGF-1 (25 ng/mL) for 10 minutes at 37° C. in 5% $CO_2$ incubator. For CHO cells, 50 ng/mL IGF-1 or 50 ng/mL insulin was used. Control cells were left either unstimulated or stimulated with IGF-1, as described, in the absence of compound to determine basal and maximal signals. After incubation, the media was removed using a vacuum manifold and the cells washed once with Tris-Buffered Saline (TBS). Cells were then fixed by the addition of cold 3.7% (v/v) formaldehyde in TBS (200/well) for 15 minutes at 4° C. After fixation, the formaldehyde was aspirated and the cells permeabilized by the addition of −20° C. methanol (50 μL/well) for 5 minutes. The methanol was aspirated and 200 μL of blocking buffer (1.0% (w/v) BSA in TBS containing 0.05% (v/v) Tween 20 (TBS-T)) was added to each well, to block non-specific antibody binding sites. Plates were then incubated at room temperature for 30 minutes. After removal of the blocking buffer, 50 μL of p-(S473) AKT primary antibody was added at a dilution of 1:250 in blocking buffer and the plate incubated for at least 1 hour (at room temperature), and up to 18 hours at 4° C., depending on antibody source and/or species. All p-(S473)AKT antibodies used are commercially available and include rabbit polyclonal, rabbit monoclonal and mouse monoclonal antibodies from multiple vendors (e.g. Cell Signaling Technology Cat#9277, #9271, #4058, #3787, #4051; Upstate Biotechnology, Inc. Cat#07-310, #05-669). After incubation with primary antibody, the plates were washed 3 times with cold TBS-T. Horseradish Peroxidase (HRP)-conjugated anti-rabbit or anti-mouse secondary antibody was then added to each well (100 μL as a 1:250 dilution in blocking buffer) and the plate incubated at room temperature for 1 hour. After washing four times with ice-cold TBS-T, enhanced chemiluminescence reagent (ECL) was added (100 μL/well) and mixed for 1 minute. The ECL signal was detected using a Perkin-Elmer Victor 5 Multilabel Counter. Results are expressed as percent inhibition using the following equation. $IC_{50}$ values and graphical representation were generated using Analyze 5 data analysis software.

% inhibition=$1-(S_i-S_b)/(S_{wo}-S_b) \times 100$.

$s_i$=signal with inhibitor
$S_b$=background signal (signal in the absence of primary p-(S473)AKT antibody)
$S_{wo}$=signal without inhibitor (maximal p-(S473)AKT signal)

The exemplary compounds were tested and exhibited an $IC_{50} \leq 10$ μM in at least one of the above assays, and are considered to be active.

The in vivo effect of the compounds according to the invention can be demonstrated using human tumor xenograft models, for example Colo205, H460 and the like. The tumor models were established by subcutaneously implanting the tumor cells Into the hind flank region of female athymic NCR mice. Upon implantation, the tumor cells grew and were allowed to reach a predetermined size, usually about 100 $mm^3$, before treatment was initiated. Tumor-bearing mice received the compounds of the invention orally or perenterally in a suitable dosing vehicle at doses from about 0.1 mg/kg to about 500 mg/kg every day until a predetermined end-point was reached, usually from about 9 days to about 45 days. During the period of treatment, the length and width of each tumor was measured using electronic calipers every 2 or 3 days, or daily, and tumor volume ($mm^3$) was calculated at each measuring time-point based on the equation of length× [(width$^2$)/2]. Tumor growth inhibition (TGI %) was used to evaluate the antitumor effect of the compounds of the invention. TGI % was calculated as 100%−(T/C×100), where T=final tumor volume from a treated group, and C=final tumor volume from the vehicle group. A two-tailed student t-test was used for statistic analysis and p≦0.05 was considered significant. A dose which provided a TGI Z 50% was considered as an effective dosage C. Operative Examples Relating to Pharmaceutical Compositions The compounds according to the invention can be converted into pharmaceutical preparations as follows:

Tablet:
Composition:

100 mg of the compound of Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, curvature radius 12 mm.

Preparation:

The mixture of active component, lactose and starch is granulated with a 5% solution (m/m) of the PVP in water. After drying, the granules are mixed with magnesium stearate for 5 min. This mixture is molded using a customary tablet press (tablet format, see above). The molding force applied is typically 15 kN.

Suspension for Oral Administration:
Composition:

1000 mg of the compound of Example 1, 1000 mg of ethanol (96%), 400 mg of Rhodigel (xanthan gum from FMC, Pennsylvania, USA) and 99 g of water.

A single dose of 100 mg of the compound according to the invention is provided by 10 mL of oral suspension.

Preparation:

The Rhodigel is suspended in ethanol and the active component is added to the suspension. The water is added with stirring. Stirring is continued for about 6 h until the swelling of the Rhodigel is complete.

Solution for Intravenous Administration 1:

Composition: 100-200 mg of the compound of Example 1, 15 g polyethylenglykol 400 and 250 g water optionally with up to 15% Cremophor EL, and optionally up to 15% ethyl alcohol, and optionally up to 2 equivalents of a pharmaceutically suitable acid such as citric acid or hydrochloric acid.

Preparation:

The compound of Example 1 and the polyethylenglykol 400 are dissolved in the water with stirring. The solution is sterile filtered (pore size 0.22 μm) and filled into heat sterilized infusion bottles under aseptical conditions. The infusion bottles are being sealed with rubber seals.

Solution for Intravenous Administration 2:

Composition: 100-200 mg of the compound of Example 1, saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid.

Preparation:

The compound of Example 1 is dissolved in the saline solution with stirring. Optionally Cremophor EL, ethyl alcohol or acid are added. The solution is sterile filtered (pore size 0.22 μm) and filled into heat sterilized infusion bottles under aseptical conditions. The infusion bottles are being sealed with rubber seals.

The invention claimed is:
1. A compound of formula (I)

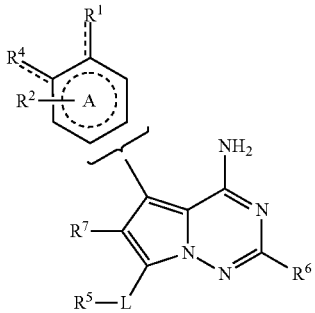

wherein
the dotted lines between ring A and the first atoms of groups $R^1$ and $R^4$, respectively, indicate possible double bonds, if required by the structures of $R^1$ and $R^4$;
the dotted circle in ring A indicates that ring A is aromatic;
the bracket indicates the carbon atoms of ring A to which the pyrrolotriazine may be attached;
$R^1$ represents H or halogen;
$R^2$ represents H, or halogen;
$R^4$ represents
—C(O)—$NR^8R^9$ wherein
$R^8$ represents H or ($C_1$-$C_3$)alkyl; and
$R^9$ represents H, ($C_1$-$C_3$)alkyl, optionally substituted phenyl, or optionally substituted benzyl;
—$OR^{10}$ wherein
$R^{10}$ represents H, ($C_1$-$C_3$)alkyl, optionally substituted phenyl, or optionally substituted benzyl; or

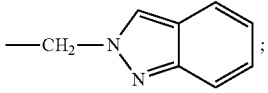

or
$R^1$ and $R^4$ may be joined, and taken together with the carbon atoms to which they are attached, form a fused heterocycle having a partial structure selected from the group consisting of

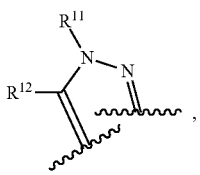 , 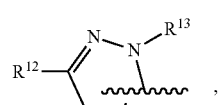 ,

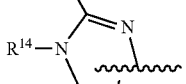 ,  and

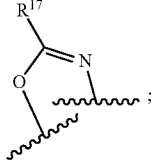 ;

wherein
$R^{11}$ represents H, ($C_1$-$C_3$)alkyl, ($C_3$-$C_6$)cycloalkyl($C_1$-$C_3$)alkyl, pyridyl($C_1$-$C_3$)alkyl, optionally substituted phenyl, or optionally substituted benzyl;
$R^{12}$ represents
H;
($C_1$-$C_4$)alkyl;
halogen;

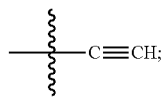

CN; or
$NR^{12a}R^{12b}$ wherein
$R^{12a}$ represents H or ($C_1$-$C_3$)alkyl; and
$R^{12b}$ represents H, ($C_1$-$C_3$)alkyl, benzyl, or —C(O)—($C_1$-$C_4$)alkyl;
$R^{13}$ represents H, ($C_1$-$C_3$)alkyl, or optionally substituted benzyl;
$R^{14}$ represents H, ($C_1$-$C_3$)alkyl, or optionally substituted benzyl;
$R^{15}$ represents H, ($C_1$-$C_3$)alkyl, or optionally substituted benzyl;
$R^{16}$ represents H, ($C_1$-$C_3$)alkyl, or optionally substituted benzyl;
$R^{17}$ represents H, ($C_1$-$C_3$)alkyl, or optionally substituted benzyl;
L represents
a bond;
($C_1$-$C_6$)alkanediyl;
($C_3$-$C_5$)alkenediyl;
($C_3$-$C_5$)alkynediyl;
a carbonyl group;

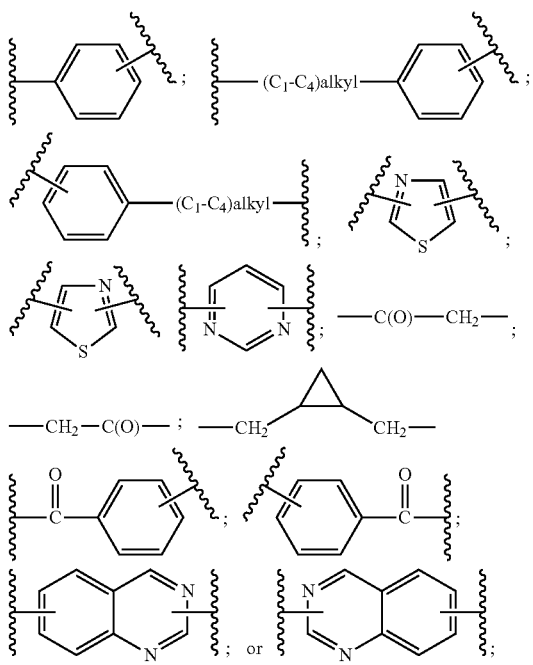

$R^5$ represents

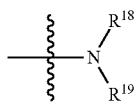

wherein
  $R^{18}$ represents H or $(C_1-C_3)$alkyl;
  $R^{19}$ represents
    H;
    $(C_1-C_3)$alkyl;
    $(C_3-C_7)$cycloalkyl;
    $(CH_2)_a$—$OR^{20}$ wherein
      $R^{20}$ represents H or $(C_1-C_3)$alkyl; and
      subscript "a" represents 2, 3, or 4;
    C(O)—$R^{21}$ wherein
      $R^{21}$ represents $(C_1-C_3)$alkyl, optionally substituted phenyl, or $NR^{22}R^{23}$ wherein
        $R^{22}$ and $R^{23}$ each independently represents H or $(C_1-C_3)$allyl;

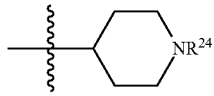

wherein
  $R^{24}$ represents H, $(C_1-C_3)$alkyl, or —C(O)—O$(C_1-C_4)$alkyl;
  $SO_2R^{25}$ wherein
    $R^{25}$ represents $(C_1-C_3)$alkyl or —$NR^{26}R^{27}$ wherein
      $R^{26}$ and $R^{27}$ independently represent H or $(C_1-C_3)$alkyl;

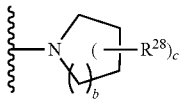

wherein
  subscript "b" represents 0, 1 or 2;
  subscript "c" represents 0, 1, or 2; and
  $R^{28}$ represents
    H;
    $(C_1-C_4)$alkyl optionally substituted with $OR^{29}$ wherein
      $R^{29}$ represents H or $(C_1-C_3)$alkyl;
    $OR^{30}$ wherein
      $R^{30}$ represents H or $(C_1-C_3)$alkyl;
    halogen;
    —C(O)—$R^{31}$ wherein
      $R^{31}$ represents $(C_1-C_3)$alkyl;
    —$NR^{32}R^{33}$ wherein $R^{32}$ and $R^{33}$ independently represent H or $(C_1-C_3)$alkyl, or $R^{32}$ and $R^{33}$ may be joined and taken together with the N to which they are attached form a pyrrolidine or piperidine ring;
    —C(O)—$NR^{34}R^{35}$ wherein $R^{34}$ and $R^{35}$ independently represent H or $(C_1-C_3)$alkyl;

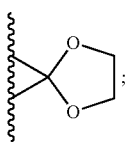

or
  —$CO_2R^{36}$ wherein $R^{36}$ represents $(C_1-C_4)$alkyl;

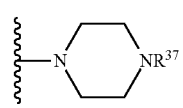

wherein
  $R^{37}$ represents
    H;
    $(C_1-C_4)$alkyl;
    $(CH_2)_d$—$OR^{38}$ wherein
      subscript "d" represents 2, 3, or 4; and
      $R^{38}$ represents H or $(C_1-C_3)$alkyl;
    $(C_3-C_6)$cycloalkyl;
    $(CH_2)_e$—C(O)—$(CH_2)_f$—$NR^{39}R^{40}$ wherein
      subscript "e" represents 0 or 1;
      subscript "f" represents 0, 1, 2, or 3; and
      $R^{39}$ and $R^{40}$ independently represent H or $(C_1-C_3)$alkyl, or $R^{39}$ and $R^{40}$ may be joined and taken together with the N to which the are attached form a 6-membered heterocycle also containing O, S, or $NR^{41}$ wherein $R^{41}$ represents H or $(C_1-C_3)$alkyl;
    C(O)—$OR^{42}$ wherein
      $R^{42}$ represents H or $(C_1-C_4)$alkyl;

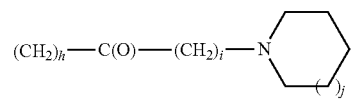

wherein the N-containing ring is optionally substituted with halogen; and
  subscript "h" represents 0 or 1;
  subscript "i" represents 0, 1, 2, or 3;
  subscript "j" represents 0 or 1;
  $(CH_2)_k$—C(O)—$R^{43}$ wherein
    subscript "k" represents 0 or 1; and
    $R^{43}$ represents $(C_1-C_4)$alkyl optionally substituted with halogen, or $(C_3-C_6)$cycloalkyl optionally substituted with halogen;
  $(CH_2)_m$—$SO_2R^{44}$ wherein
    subscript "m" represents 1, 2, or 3; and
    $R^{44}$ represents $(C_1-C_3)$alkyl, $(C_3-C_6)$cycloalkyl, or —$NR^{45}R^{46}$ wherein $R^{45}$ and $R^{46}$ independently represent H or $(C_1-C_3)$alkyl;
  $(CH_2)_n$—CN wherein
    subscript "n" represents 1, 2, or 3;

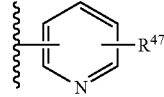

wherein
  $R^{47}$ represents CN or $(C_1-C_3)$alkyl; or

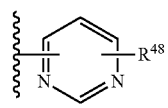

wherein
  $R^{48}$ represents H or $(C_1-C_3)$alkyl;

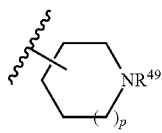

wherein
subscript "p" represents 0, 1, or 2; and
the ring is optionally substituted on carbon with up to two substituents independently selected from halogen, hydroxyl, and $(C_1-C_3)$alkyl;
$R^{49}$ represents
H;
$(C_1-C_4)$alkyl;
$(CH_2)_q$—$OR^{50}$ wherein
subscript "q" represents 2, 3, or 4; and
$R^{50}$ represents H or $(C_1-C_3)$alkyl;
$(C_3-C_6)$cycloalkyl;
$(CH_2)_r$—C(O)—$(CH_2)_s$—$NR^{51}R^{52}$ wherein
subscript "r" represents 0 or 1;
subscript "s" represents 0, 1, 2, or 3; and
$R^{51}$, and $R^{52}$ independently represent H or $(C_1-C_3)$alkyl, or $R^{51}$ and $R^{52}$ may be joined and taken together with the N to which they are attached form a 6-membered heterocycle also containing O, S, or $NR^{53}$ wherein $R^{53}$ represents H or $(C_1-C_3)$alkyl;
C(O)—$(CH_2)_t$—$OR^{54}$ wherein
subscript "t" represents 0, 1, 2, or 3; and
$R^{54}$ represents H or $(C_1-C_4)$alkyl;

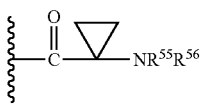

wherein
$R^{55}$ and $R^{56}$ independently represent H or $(C_1-C_3)$alkyl;

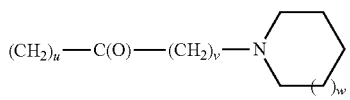

wherein
the ring is optionally substituted with halogen;
subscript "u" represents 0 or 1;
subscript "v" represents 0, 1, 2, or 3; and
subscript "w" represents 0 or 1;
$(CH_2)_x$—C(O)—$R^{57}$ wherein
subscript "x" represents 0 or 1; and
$R^{57}$ represents $(C_1-C_4)$alkyl optionally substituted with halogen, or represents $(C_3-C_6)$cycloalkyl optionally substituted with halogen;

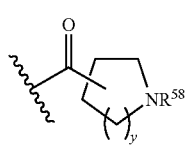

wherein
subscript "y" represents 0 or 1; and
$R^{58}$ represents H or $(C_1-C_3)$alkyl;

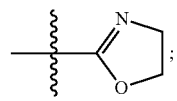

or
—$SO_2R^{59}$ wherein
$R^{59}$ represents $(C_1-C_3)$alkyl, $(C_3-C_6)$cycloalkyl, or —$NR^{60}R^{61}$ wherein $R^{60}$ and $R^{61}$ represent H or $(C_1-C_3)$alkyl;
$OR^{62}$ wherein
$R^{62}$ represents H or $(C_1-C_3)$alkyl;
halogen;
CN;

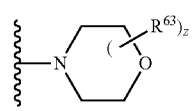

wherein
$R^{63}$ represents $(C_1-C_3)$alkyl optionally substituted with hydroxyl or halogen; and subscript "Z" represents 0, 1, or 2;

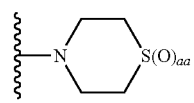

wherein
subscript "aa" represents 0, 1, or 2;

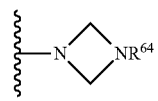

wherein
$R^{64}$ represents
H;
$(C_1-C_3)$alkyl optionally substituted with hydroxyl or halogen;
—C(O)—$(CH_2)_{bb}$—$NR^{65}R^{66}$ wherein
subscript "bb" represents 0, 1, 2, or 3;
$R^{65}$ and $R^{66}$ are independently H or $(C_1-C_3)$alkyl, or $R^{65}$ and $R^{66}$ may be joined and taken together with the N to which they are attached form a pyrrolidine ring;
—C(O)—$(C_1-C_4)$alkyl;
—C(O)-O$(C_1-C_4)$alkyl;
—$SO_2R^{67}$ wherein
$R^{67}$ represents $(C_1-C_3)$alkyl;

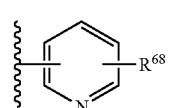

wherein
$R^{68}$ represents $(C_1-C_3)$alkyl;

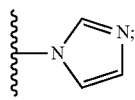

—SO$_2$R$^{69}$ wherein
R$^{69}$ represents (C$_1$-C$_3$)alkyl;
—O—CH$_2$-phenyl;

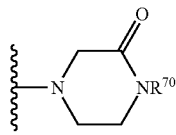

wherein
R$^{70}$ represents H or (C$_1$-C$_3$)alkyl;

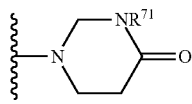

wherein
R$^{71}$ represents H or (C$_1$-C$_3$)alkyl;

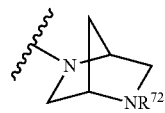

wherein
R$^{72}$ represents H, (C$_1$-C$_3$)alkyl, or —C(O)O(t-butyl);

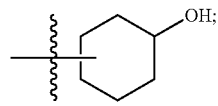

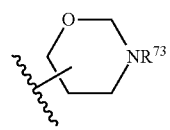

wherein
R$^{73}$ represents
H
(C$_1$-C$_3$)alkyl;

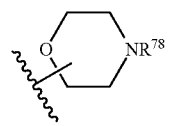

wherein
R$^{78}$ represents
H
(C$_1$-C$_3$)alkyl;
(C$_3$-C$_6$)cycloalkyl;
—SO$_2$R$^{79}$ wherein R$^{79}$ represents H or (C$_1$-C$_3$)alkyl;
—C(O)—(C$_1$-C$_3$)alkyl;
—C(O)-(optionally substituted phenyl);

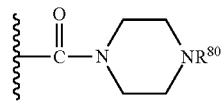

wherein R$^{80}$ represents H or (C$_1$-C$_3$)alkyl;
—(CH$_2$)$_{ee}$—C(O)—(CH$_2$)$_{ff}$—NR$^{81}$R$^{82}$ wherein
subscript "ee" represents 0 or 1;
subscript "ff" represents 0, 1, 2, or 3; and
R$^{81}$ and R$^{82}$ independently represent H or (C$_1$-C$_3$) alkyl

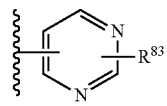

wherein
R$^{83}$ represents H or (C$_1$-C$_3$)alkyl;

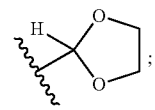

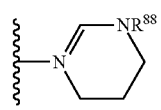

wherein
R$^{85}$ represents H, (C$_1$-C$_3$)alkyl, or —(CH$_2$)$_{ii}$—C(O)—(CH$_2$)$_{jj}$—NR$^{86}$R$^{87}$ wherein
subscript "ii" represents 0 or 1;
subscript "jj" represents 0, 1, 2, or 3; and
R$^{86}$ and R$^{87}$ independently represent H or (C$_1$-C$_3$)alkyl;

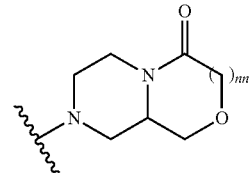

wherein
R$^{88}$ represents H, (C$_1$-C$_3$)alkyl, or —(CH$_2$)$_{kk}$—C(O)—(CH$_2$)$_{mm}$—NR$^{89}$R$^{90}$ wherein
subscript "kk" represents 0 or 1;
subscript "mm" represents 0, 1, 2, or 3; and
R$^{89}$ and R$^{90}$ independently represent H or (C$_1$-C$_3$)alkyl;

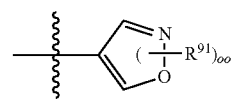

wherein subscript "nn" represents 0 or 1;

wherein
subscript "oo" represents 0, 1, or 2; and
$R^{91}$ represents $(C_1-C_3)$alkyl;

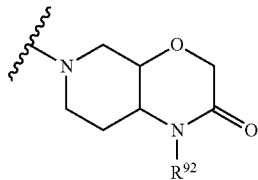

wherein $R^{92}$ represents H or $(C_1-C_3)$alkyl;

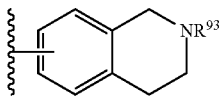

wherein
$R^{93}$ represents
H;
$(CH_2)_{pp}$—$OR^{94}$ wherein
subscript "pp" represents 2 or 3; and
$R^{94}$ represents H or $(C_1-C_3)$alkyl;
$(CH_2)_{qq}$—C(O)—$(CH_2)_{rr}$—$NR^{95}R^{96}$ wherein
subscript "qq" represents 0 or 1;
subscript "rr" represents 0 or 1; and
$R^{95}$ and $R^{96}$ independently represent H or $(C_1-C3)$ alkyl;
C(O)—$R^{97}$ wherein
$R^{97}$ represents H or $(C_1-C_3)$alkyl;
—$SO_2R^{98}$ wherein
$R^{98}$ represents H or $(C_1-C_3)$alkyl;
$(C_3-C_6)$cycloalkyl;
$(CH_2)_{ss}$—$CH(OR^{99})$—$(CH_2)_{tt}R^{100}$ wherein
subscript "ss" represents 0 or 1;
subscript "tt" represents 1, 2, or 3; and
$R^{99}$ and $R^{100}$ each independently represents H or $(C_1-C_3)$alkyl;

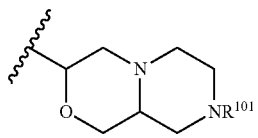

wherein
$R^{101}$ represents
H;
$(C_1-C_3)$alkyl;
$(C_3-C_6)$cycloalkyl;
$(CH_2)_{uu}$—$OR^{102}$ wherein
subscript "uu" represents 2 or 3; and
$R^{102}$ represents H or $(C_1-C_3)$alkyl;
$SO_2R^{103}$ wherein
$R^{103}$ represents $(C_1-C_3)$alkyl;
$(CH_2)_{vv}$—C(O)—$(CH_2)_{ww}$—$NR^{104}R^{105}$ wherein
subscript "v v" represents 0 or 1;
subscript "w w" represents 0 or 1; and
$R^{104}$ and $R^{105}$ independently represent H or $(C_1-C_3)$alkyl;
—C(O)O(t-butyl);
C(O)—$R^{106}$ wherein
$R^{106}$ represents $(C_1-C_3)$alkyl optionally substituted with
$OR^{107}$ wherein
$R^{107}$ represents H or $(C_1-C_3)$alkyl;

$R^6$ represents H or $(C_1-C_3)$alkyl; and
$R^7$ represents H, CN, or $(C_1-C_3)$alkyl;
or a pharmaceutically acceptable salt or stereoisomer thereof.

2. The compound of formula (I) of claim 1

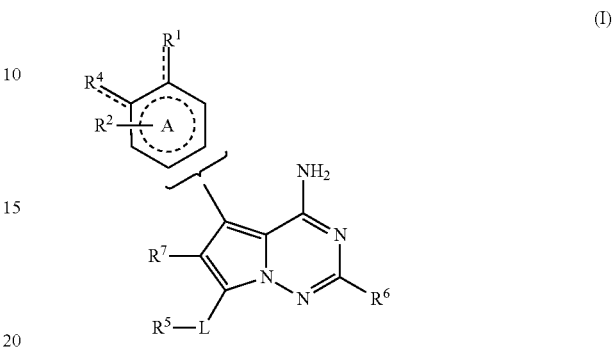

(I)

wherein
the dotted lines between ring A and the first atoms of groups $R^1$ and $R^4$, respectively, indicate possible double bonds, if required by the structures of $R^1$ and $R^4$;
the dotted circle in ring A indicates that ring A is aromatic;
the bracket indicates the carbon atoms of ring A to which the pyrrolotriazine may be attached;
$R^1$ represents H or halogen;
$R^2$ represents H or halogen;
$R^4$ represents
—$OR^{10}$ wherein
$R^{10}$ represents H, $(C_1-C_3)$alkyl, optionally substituted phenyl, or optionally substituted benzyl; or
or
$R^1$ and $R^4$ may be joined, and taken together with the carbon atoms to which they are attached, form a fused heterocycle having a partial structure selected from the group consisting of

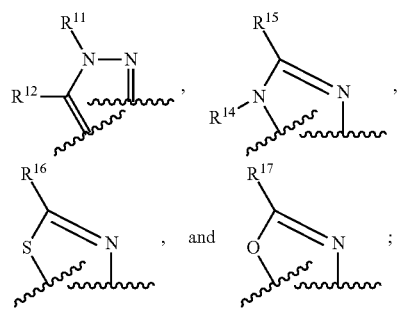

wherein
$R^{11}$ represents H, $(C_1-C_3)$alkyl, $(C_3-C_6)$cycloalkyl$(C_1-C_3)$alkyl, pyridyl$(C_1-C_3)$alkyl, optionally substituted phenyl, or optionally substituted benzyl;
$R^{12}$ represents
H;
$(C_1-C_4)$alkyl;
halogen;

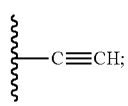

CN; or
$NR^{12a}R^{12b}$ wherein $R^{12a}$ represents H or $(C_1\text{-}C_3)$alkyl; and
$R^{12b}$ represents H, $(C_1\text{-}C_3)$alkyl, benzyl, or —C(O)—$(C_1\text{-}C_4)$alkyl;
$R^{14}$ represents H, $(C_1\text{-}C_3)$alkyl, or optionally substituted benzyl;
$R^{15}$ represents H, $(C_1\text{-}C_3)$alkyl, or optionally substituted benzyl;
$R^{16}$ represents H, $(C_1\text{-}C_3)$alkyl, or optionally substituted benzyl;
$R^{17}$ represents H, $(C_1\text{-}C_3)$alkyl, or optionally substituted benzyl;
L represents
  a bond;
  —$(C_1\text{-}C_6)$alkanediyl;
  a carbonyl group;

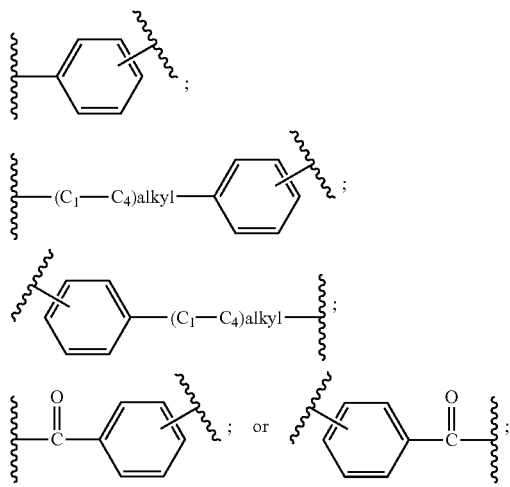

$R^5$ represents

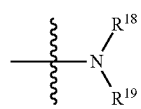

wherein
$R^{18}$ represents H or $(C_1\text{-}C_3)$alkyl;
$R^{19}$ represents
  H;
  $(C_1\text{-}C_3)$alkyl;
  $(C_3\text{-}C_7)$cycloalkyl;
  $(CH_2)_a$—$OR^{20}$ wherein
    $R^{20}$ represents H or $(C_1\text{-}C_3)$alkyl; and
    subscript "a" represents 2, 3, or 4;
  $C(O)$—$R^{21}$ wherein
    $R^{21}$ represents $(C_1\text{-}C_3)$alkyl, optionally substituted phenyl, or $NR^{22}R^{23}$ wherein
      $R^{22}$ and $R^{23}$ each independently represents H or $(C_1\text{-}C_3)$alkyl;
  $SO_2R^{25}$ wherein
    $R^{25}$ represents $(C_1\text{-}C_3)$alkyl or —$NR^{26}R^{27}$ wherein
      $R^{26}$ and $R^{27}$ independently represent H or $(C_1\text{-}C_3)$alkyl;

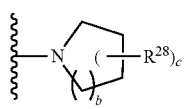

wherein
subscript "b" represents 0, 1 or 2;
subscript "c" represents 0, 1, or 2; and
$R^{28}$ represents
  H;
  $(C_1\text{-}C_4)$alkyl optionally substituted with $OR^{29}$ wherein
    $R^{29}$ represents H or $(C_1\text{-}C_3)$alkyl;
  $OR^{30}$ wherein
    —$R^{30}$ represents H or $(C_1\text{-}C_3)$alkyl;
  halogen;
  —C(O)—$R^{31}$ wherein
    $R^{31}$ represents $(C_1\text{-}C_3)$alkyl;
  —C(O)—$NR^{34}R^{35}$ wherein $R^{34}$ and $R^{35}$ independently represent H or $(C_1\text{-}C_3)$alkyl; or
  —$CO_2R^{36}$ wherein $R^{36}$ represents $(C_1\text{-}C_4)$alkyl;

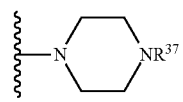

wherein
$R^{37}$ represents
  H;
  $(C_1\text{-}C_4)$alkyl;
  $(CH_2)_d$—$OR^{38}$ wherein
    subscript "d" represents 2, 3, or 4; and
    $R^{38}$ represents H or $(C_1\text{-}C_3)$alkyl;
  $(C_3\text{-}C_6)$cycloalkyl;
  $(CH_2)_e$—C(O)—$(CH_2)_f$—$NR^{39}R^{40}$ wherein
    subscript "e" represents 0 or 1;
    subscript "f" represents 0, 1, 2, or 3; and
    $R^{39}$ and $R^{40}$ independently represent H or $(C_1\text{-}C_3)$alkyl, or $R^{39}$ and $R^{40}$ may be joined and taken together with the N to which they are attached form a 6-membered heterocycle also containing O, S, or $NR^{41}$ wherein $R^{41}$ represents H or $(C_1\text{-}C_3)$alkyl;

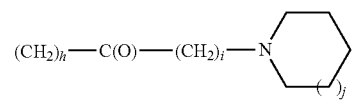

wherein the N-containing ring is optionally substituted with halogen; and
  subscript "h" represents 0 or 1;
  subscript "i" represents 0, 1, 2, or 3;
  subscript "j" represents 0 or 1; or
  $(CH_2)_m$—$SO_2R^{44}$ wherein
    subscript "m" represents 1, 2, or 3; and
    $R^{44}$ represents $(C_1\text{-}C_3)$alkyl, $(C_3\text{-}C_6)$cycloalkyl, or —$NR^{45}R^{46}$ wherein $R^{45}$ and $R^{46}$ independently represent H or $(C_1\text{-}C_3)$alkyl;

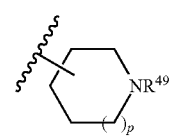

wherein
  subscript "p" represents 0, 1, or 2; and
  the ring is optionally substituted on carbon with up to two substituents independently selected from halogen, hydroxyl, and $(C_1\text{-}C_3)$alkyl;

$R^{49}$ represents
  H;
  $(C_1-C_4)$alkyl;
  $(CH_2)_q$—$OR^{50}$ wherein
    subscript "q" represents 2, 3, or 4; and
    $R^{50}$ represents H or $(C_1-C_3)$alkyl;
  $(C_3-C_6)$cycloalkyl;
  $(CH_2)_r$—$C(O)$—$(CH_2)_s$—$NR^{51}R^{52}$ wherein
    subscript "r" represents 0 or 1;
    subscript "s" represents 0, 1, 2, or 3; and
    $R^{51}$ and $R^{52}$ independently represent H or $(C_1-C_3)$alkyl, or $R^{51}$ and $R^{52}$ may be joined and taken together with the N to which they are attached form a 6-membered heterocycle also containing O, S, or $NR^{53}$ wherein $R^{53}$ represents H or $(C_1-C_3)$alkyl;
  $C(O)$—$(CH_2)_t$—$OR^{54}$ wherein
    subscript "t" represents 0, 1, 2, or 3; and
    $R^{54}$ represents H or $(C_1-C_4)$alkyl;

wherein
    $R^{55}$ and $R^{56}$ independently represent H or $(C_1-C_3)$alkyl;

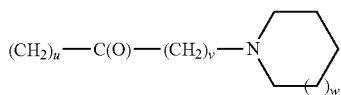

wherein
    the ring is optionally substituted with halogen;
    subscript "u" represents 0 or 1;
    subscript "v" represents 0, 1, 2, or 3; and
    subscript "w" represents 0 or 1;
  $(CH_2)_x$—$C(O)$—$R^{57}$ wherein
    subscript "x" represents 0 or 1; and
    $R^{57}$ represents $(C_1-C_4)$alkyl optionally substituted with halogen, or represents $(C_3-C_6)$cycloalkylv optionally substituted with halogen;

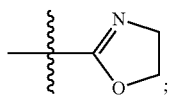

or
  —$SO_2R^{59}$ wherein
    $R^{59}$ represents $(C_1-C_3)$alkyl, $(C_3-C_6)$cycloalkyl, or —$NR^{60}R^{61}$ wherein $R^{60}$ and $R^{61}$ represent H or $(C_1-C_3)$alkyl;
  $OR^{62}$ wherein
    $R^{62}$ represents H or $(C_1-C_3)$alkyl;
  halogen;
  CN;

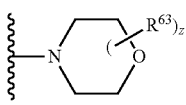

wherein
    $R^{63}$ represents $(C_1-C_3)$alkyl optionally substituted with hydroxyl or halogen; and subscript "z" represents 0, 1, or 2;

wherein
subscript "aa" represents 0, 1, or 2;

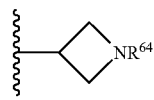

wherein
$R^{64}$ represents
  H;
  $(C_1-C_3)$alkyl optionally substituted with hydroxyl or halogen;
  —$C(O)$—$(CH_2)_{bb}$—$NR^{65}R^{66}$ wherein
    subscript "bb" represents 0, 1, 2, or 3;
    $R^{65}$ and $R^{66}$ are independently H or $(C_1-C_3)$alkyl, or $R^{65}$ and $R^{66}$ may be joined and taken together with the N to which they are attached form a pyrrolidine ring;
  —$C(O)$—$(C_1-C_4)$alkyl;
  —$C(O)$—$O(C_1-C_4)$alkyl;

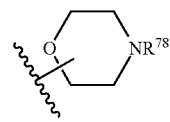

wherein
$R^{78}$ represents
  H
  $(C_1-C_3)$alkyl;
  $(C_3-C_6)$cycloalkyl;
  —$SO_2R^{79}$ wherein $R^{79}$ represents H or $(C_1-C_3)$alkyl;
  —$C(O)$—$(C_1-C_3)$alkyl;
  —$(CH_2)_{ee}$—$C(O)$—$(CH_2)_{ff}$—$NR^{81}R^{82}$ wherein
    subscript "ee" represents 0 or 1;
    subscript "ff" represents 0, 1, 2, or 3; and
    $R^{81}$ and $R^{82}$ independently represent H or $(C_1-C_3)$alkyl;

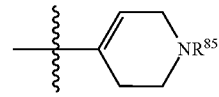

wherein
$R^{85}$ represents H, $(C_1-C_3)$alkyl, or —$(CH_2)_{ii}$—$C(O)$—$(CH_2)_{jj}$—$NR^{86}R^{87}$ wherein
  subscript "ii" represents 0 or 1;
  subscript "jj" represents 0, 1, 2, or 3; and
  $R^{86}$ and $R^{87}$ independently represent H or $(C_1-C_3)$alkyl;

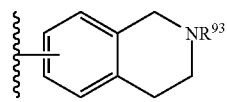

wherein
$R^{93}$ represents
  H;
  $(CH_2)_{pp}$—$OR^{94}$ wherein
    subscript "pp" represents 2 or 3; and
    $R^{94}$ represents H or $(C_1-C_3)$alkyl;

(CH$_2$)$_{qq}$—C(O)—(CH$_2$)$_{rr}$—NR$^{95}$R$^{96}$ wherein
  subscript "qq" represents 0 or 1;
  subscript "rr" represents 0 or 1; and
  R$^{95}$ and R$^{96}$ independently represent H or (C$_1$-C$_3$)alkyl;
C(O)—R$^{97}$ wherein
  R$^{97}$ represents H or (C$_1$-C$_3$)alkyl;
—SO$_2$R$^{98}$ wherein
  R$^{98}$ represents H or (C$_1$-C$_3$)alkyl;

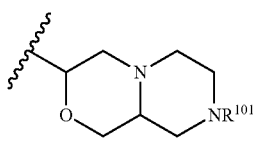

wherein
  R$^{101}$ represents
    H;
    (C$_1$-C$_3$)alkyl;
    (C$_3$-C$_6$)cycloalkyl;
    (CH$_2$)$_{uu}$—OR$^{102}$ wherein
      subscript "uu" represents 2 or 3; and
      R$^{102}$ represents H or (C$_1$-C$_3$)alkyl;
    SO$_2$R$^{103}$ wherein
      R$^{103}$ represents (C$_1$-C$_3$)alkyl;
    (CH$_2$)$_{vv}$—C(O)—(CH$_2$)$_{ww}$—NR$^{104}$R$^{105}$ wherein
      subscript "v v" represents 0 or 1;
      subscript "w w" represents 0 or 1; and
      R$^{104}$ and R$^{105}$ independently represent H or (C$_1$-C$_3$)alkyl;
    C(O)—R$^{106}$ wherein
      R$^{106}$ represents (C$_1$-C$_3$)alkyl optionally substituted with OR$^{107}$ wherein
        R$^{107}$ represents H or (C$_1$-C$_3$)alkyl;
R$^6$ represents H or (C$_1$-C$_3$)alkyl; and
R$^7$ represents H, CN, or (C$_1$-C$_3$)alkyl;
or a pharmaceutically acceptable salt or stereoisomer thereof.

3. The compound of formula (I) of claim 1

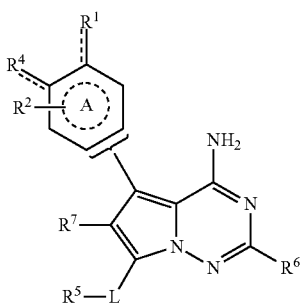

wherein
  the dotted lines between ring A and the first atoms of groups R$^1$ and R$^4$, respectively, indicate possible double bonds, if required by the structures of R$^1$ and R$^4$;
  the dotted circle in ring A indicates that ring A is aromatic;
  the bracket indicates the carbon atoms of ring A to which the pyrrolotriazine may be attached;
  R$^1$ represents H or halogen;
  R$^2$ represents H or halogen;
  R$^4$ represents
    —OR$^{10}$ wherein
      R$^{10}$ represents H, (C$_1$-C$_3$)alkyl, optionally substituted phenyl, or optionally substituted benzyl; or or
R$^1$ and R$^4$ may be joined, and taken together with the carbon atoms to which they are attached, form a fused heterocycle having a partial structure selected from the group consisting of

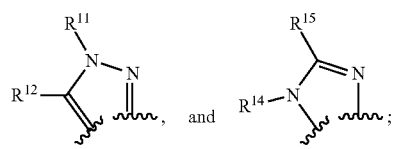

wherein
  R$^{11}$ represents H, (C$_1$-C$_3$)alkyl, (C$_3$-C$_6$)cycloalkyl(C$_1$-C$_3$)alkyl, pyridyl(C$_1$-C$_3$)alkyl, optionally substituted phenyl, or optionally substituted benzyl;
  R$^{12}$ represents
    H;
    (C$_1$-C$_4$)alkyl;
    halogen;

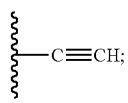

CN; or
    NR$^{12a}$R$^{12b}$ wherein
      R$^{12a}$ represents H or (C$_1$-C$_3$)alkyl; and
      R$^{12b}$ represents H, (C$_1$-C$_3$)alkyl, benzyl, or —C(O)—(C$_1$-C$_4$)alkyl;
  R$^{14}$ represents H, (C$_1$-C$_3$)alkyl, or optionally substituted benzyl;
  R$^{15}$ represents H, (C$_1$-C$_3$)alkyl, or optionally substituted benzyl;
L represents
  a bond; or
  (C$_1$-C$_6$)alkanediyl;
R$^5$ represents

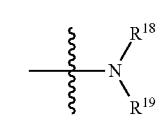

wherein
  R$^{18}$ represents H or (C$_1$-C$_3$)alkyl;
  R$^{19}$ represents
    H;
    (C$_1$-C$_3$)alkyl;
    (C$_3$-C$_7$)cycloalkyl;
    (CH$_2$)$_a$—OR$^{20}$ wherein
      R$^{20}$ represents H or (C$_1$-C$_3$)alkyl; and
      subscript "a" represents 2, 3, or 4;
    C(O)—R$^{21}$ wherein
      R$^{21}$ represents (C$_1$-C$_3$)alkyl, optionally substituted phenyl, or NR$^{22}$R$^{23}$ wherein
        R$^{22}$ and R$^{23}$ each independently represents H or (C$_1$-C$_3$)alkyl;
    SO$_2$R$^{25}$ wherein
      R$^{25}$ represents (C$_1$-C$_3$)alkyl or —NR$^{26}$R$^{27}$ wherein
        R$^{26}$ and R$^{27}$ independently represent H or (C$_1$-C$_3$)alkyl;

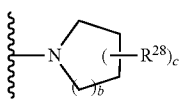

wherein
subscript "b" represents 0, 1 or 2;
subscript "c" represents 0, 1, or 2; and
$R^{28}$ represents
H;
$(C_1-C_4)$alkyl optionally substituted with $OR^{29}$ wherein
$R^{29}$ represents H or $(C_1-C_3)$alkyl;
$OR^{30}$ wherein
$R^{30}$ represents H or $(C_1-C_3)$alkyl;
halogen;
—C(O)—$R^{31}$ wherein
$R^{31}$ represents $(C_1-C_3)$alkyl;
—C(O)—$NR^{34}R^{35}$ wherein $R^{34}$ and $R^{35}$ independently represent H or $(C_1-C_3)$alkyl; or
—$CO_2R^{36}$ wherein $R^{36}$ represents $(C_1-C_4)$alkyl;

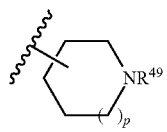

wherein
subscript "p" represents 0, 1, or 2; and
the ring is optionally substituted on carbon with up to two substituents independently selected from halogen, hydroxyl, and $(C_1-C_3)$alkyl;
$R^{49}$ represents
H;
$(C_1-C_4)$alkyl;
$(CH_2)_q$—$OR^{50}$ wherein
subscript "q" represents 2, 3, or 4; and
$R^{50}$ represents H or $(C_1-C_3)$alkyl;
$(C_3-C_6)$cycloalkyl;
$(CH_2)_r$—C(O)—$(CH_2)_s$—$NR^{51}R^{52}$ wherein
subscript "r" represents 0 or 1;
subscript "s" represents 0, 1, 2, or 3; and
$R^{51}$ and $R^{52}$ independently represent H or $(C_1-C_3)$alkyl, or $R^{51}$ and $R^{52}$ may be joined and taken together with the N to which they are attached form a 6-membered heterocycle also containing O, S, or $NR^{53}$ wherein $R^{53}$ represents H or $(C_1-C_3)$alkyl;

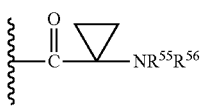

wherein
$R^{55}$ and $R^{56}$ independently represent H or $(C_1-C_3)$alkyl;

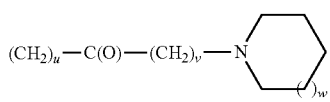

wherein
the ring is optionally substituted with halogen;
subscript "u" represents 0 or 1;
subscript "v" represents 0, 1, 2, or 3; and
subscript "w" represents 0 or 1; or
—$SO_2R^{59}$ wherein
$R^{59}$ represents $(C_1-C_3)$alkyl, $(C_3-C_6)$cycloalkyl, or —$NR^{60}R^{61}$ wherein $R^{60}$ and $R^{61}$ represent H or $(C_1-C_3)$alkyl;

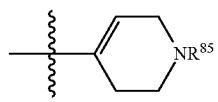

wherein
$R^{85}$ represents H, $(C_1-C_3)$alkyl, or —$(CH_2)_{ii}$—C(O)—$(CH_2)_{jj}$—$NR^{86}R^{87}$ wherein
subscript "ii" represents 0 or 1;
subscript "jj" represents 0, 1, 2, or 3; and
$R^{86}$ and $R^{87}$ independently represent H or $(C_1-C_3)$alkyl;

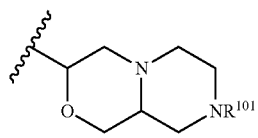

wherein
$R^{101}$ represents
H;
$(C_1-C_3)$alkyl;
$(C_3-C_6)$cycloalkyl;
$(CH_2)_{uu}$—$OR^{102}$ wherein
subscript "uu" represents 2 or 3; and
$R^{102}$ represents H or $(C_1-C_3)$alkyl;
$SO_2R^{103}$ wherein
$R^{103}$ represents $(C_1-C_3)$alkyl;
$(CH_2)_{vv}$—C(O)—$(CH_2)_{ww}$—$NR^{104}R^{105}$ wherein
subscript "v v" represents 0 or 1;
subscript "w w" represents 0 or 1; and
$R^{104}$ and $R^{105}$ independently represent H or $(C_1-C_3)$alkyl;
C(O)—$R^{106}$ wherein
$R^{106}$ represents $(C_1-C_3)$alkyl optionally substituted with $OR^{107}$ wherein
$R^{107}$ represents H or $(C_1-C_3)$alkyl;
$R^6$ represents H or $(C_1-C_3)$alkyl; and
$R^7$ represents H, CN, or $(C_1-C_3)$alkyl;
or a pharmaceutically acceptable salt or stereoisomer thereof.

4. A pharmaceutical composition comprising a compound of formula (I) as defined in claim 1 plus a pharmaceutically acceptable carrier.

5. A pharmaceutical composition comprising a compound of formula (I) as defined in claim 2 plus a pharmaceutically acceptable carrier.

6. A pharmaceutical composition comprising a compound of formula (I) as defined in claim 3 plus a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,431,695 B2 | Page 1 of 1 |
| APPLICATION NO. | : 12/084411 | |
| DATED | : April 30, 2013 | |
| INVENTOR(S) | : O'Connor et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1244 days.

Signed and Sealed this
Thirtieth Day of December, 2014

Michelle K. Lee
*Deputy Director of the United States Patent and Trademark Office*